US011065231B2

(12) United States Patent
Crew et al.

(10) Patent No.: US 11,065,231 B2
(45) Date of Patent: Jul. 20, 2021

(54) COMPOUNDS AND METHODS FOR THE TARGETED DEGRADATION OF INTERLEUKIN-1 RECEPTOR- ASSOCIATED KINASE 4 POLYPEPTIDES

(71) Applicant: Arvinas Operations, Inc., New Haven, CT (US)

(72) Inventors: Andrew P. Crew, Chester, CT (US); Erika Araujo, Woodbridge, CT (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 0 days.

(21) Appl. No.: 16/194,094

(22) Filed: Nov. 16, 2018

(65) Prior Publication Data

US 2019/0151295 A1 May 23, 2019

Related U.S. Application Data

(60) Provisional application No. 62/587,799, filed on Nov. 17, 2017.

(51) Int. Cl.

| | |
|---|---|
| *A61K 31/437* | (2006.01) |
| *A61P 25/00* | (2006.01) |
| *C07D 487/04* | (2006.01) |
| *C07D 417/14* | (2006.01) |
| *A61P 29/00* | (2006.01) |
| *C07D 401/14* | (2006.01) |
| *A61K 47/64* | (2017.01) |
| *A61P 21/04* | (2006.01) |
| *A61P 37/06* | (2006.01) |
| *A61P 35/00* | (2006.01) |
| *A61K 31/422* | (2006.01) |
| *A61K 31/427* | (2006.01) |
| *A61K 31/551* | (2006.01) |
| *A61K 38/20* | (2006.01) |
| *A61K 38/53* | (2006.01) |

(52) U.S. Cl.

CPC .......... *A61K 31/437* (2013.01); *A61K 31/422* (2013.01); *A61K 31/427* (2013.01); *A61K 31/551* (2013.01); *A61K 38/2006* (2013.01); *A61K 38/53* (2013.01); *A61K 47/642* (2017.08); *A61P 21/04* (2018.01); *A61P 25/00* (2018.01); *A61P 29/00* (2018.01); *A61P 35/00* (2018.01); *A61P 37/06* (2018.01); *C07D 401/14* (2013.01); *C07D 417/14* (2013.01); *C07D 487/04* (2013.01)

(58) Field of Classification Search

None

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,132,438 | B2 | 11/2006 | Frenkel et al. |
| 7,208,157 | B2 | 4/2007 | Sakamoto et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0269140 | A1 | 10/2008 | Wang et al. |
| 2010/0203012 | A1 | 8/2010 | Laurent et al. |
| 2011/0195043 | A1 | 8/2011 | Sun et al. |
| 2012/0270800 | A1 | 10/2012 | Verdine et al. |
| 2014/0194404 | A1 | 7/2014 | McElroy et al. |
| 2014/0235629 | A1 | 8/2014 | Bartberger et al. |

(Continued)

FOREIGN PATENT DOCUMENTS

| | | | |
|---|---|---|---|
| CN | 1844118 | A | 10/2006 |
| CN | 103688176 | A | 3/2014 |

(Continued)

OTHER PUBLICATIONS

International Preliminary Report on Patentability for PCT/US2018/061655, dated Mar. 19, 2019.

(Continued)

*Primary Examiner* — Lianko G Garyu

(74) *Attorney, Agent, or Firm* — Bryan D. Zerhusen, Esq.; Cantor Colburn LLP

(57) ABSTRACT

The present disclosure relates to bifunctional compounds, which find utility as modulators of Interleukin-1 Receptor-Associated Kinase 4 (IRAK-4); the target protein). In particular, the present disclosure is directed to bifunctional compounds, which contain on one end a Von Hppel-Lindau, cereblon, ligand which binds to the E3 ubiquitin ligase and on the other end a moiety which binds the target protein, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein are treated or prevented with compounds and compositions of the present disclosure.

24 Claims, 8 Drawing Sheets

(56) References Cited

U.S. PATENT DOCUMENTS

| | | | | |
|---|---|---|---|---|
| 2014/0243372 | A1 | 8/2014 | Rew | |
| 2014/0302523 | A1 | 10/2014 | Crews et al. | |
| 2014/0329799 | A1 | 11/2014 | Seganish et al. | |
| 2014/0356322 | A1 | 12/2014 | Crews et al. | |
| 2015/0011532 | A1 | 1/2015 | Paidi et al. | |
| 2015/0045347 | A1 | 2/2015 | Dodd et al. | |
| 2015/0119435 | A1 | 4/2015 | Crews et al. | |
| 2015/0133451 | A1 | 5/2015 | Yoshida et al. | |
| 2015/0191464 | A1 | 7/2015 | Santella et al. | |
| 2015/0274708 | A1 | 10/2015 | Seganish et al. | |
| 2015/0284405 | A1 | 10/2015 | Trzupek et al. | |
| 2015/0291562 | A1* | 10/2015 | Crew | A61P 3/04 424/94.3 |
| 2015/0344473 | A1 | 10/2015 | Du et al. | |
| 2016/0002265 | A1 | 1/2016 | Jenkins et al. | |
| 2016/0022642 | A1 | 1/2016 | Crews et al. | |
| 2016/0045607 | A1 | 2/2016 | Crew et al. | |
| 2016/0058872 | A1 | 3/2016 | Crew et al. | |
| 2016/0083375 | A1 | 3/2016 | Paidi et al. | |
| 2016/0136230 | A1 | 5/2016 | Campos et al. | |
| 2016/0214972 | A1 | 7/2016 | Jin et al. | |
| 2016/0243247 | A1 | 8/2016 | Bradner et al. | |
| 2016/0272639 | A1 | 9/2016 | Crew et al. | |
| 2016/0326151 | A1 | 11/2016 | Gummadi et al. | |
| 2016/0368911 | A1 | 12/2016 | Campos et al. | |
| 2017/0008904 | A1 | 1/2017 | Crew et al. | |
| 2017/0037004 | A1 | 2/2017 | Crew et al. | |
| 2017/0065719 | A1 | 3/2017 | Qian et al. | |
| 2017/0121321 | A1 | 5/2017 | Crews et al. | |
| 2017/0204093 | A1 | 7/2017 | Chan et al. | |
| 2017/0209446 | A1 | 7/2017 | Altman et al. | |
| 2017/0217981 | A1 | 8/2017 | Altman et al. | |
| 2017/0247388 | A1 | 8/2017 | Altman et al. | |
| 2017/0275297 | A1 | 9/2017 | Altman et al. | |
| 2017/0281784 | A1 | 10/2017 | Wang et al. | |
| 2017/0307614 | A1 | 10/2017 | Crews et al. | |
| 2017/0327469 | A1 | 11/2017 | Crew et al. | |
| 2018/0015087 | A1 | 1/2018 | Liu et al. | |
| 2018/0072711 | A1 | 3/2018 | Crew et al. | |
| 2018/0099940 | A1 | 4/2018 | Crew et al. | |
| 2018/0125821 | A1 | 5/2018 | Crew et al. | |
| 2018/0147202 | A1 | 5/2018 | Crew et al. | |
| 2018/0155322 | A1 | 6/2018 | Crew et al. | |
| 2018/0177750 | A1 | 6/2018 | Crew et al. | |
| 2018/0179183 | A1 | 6/2018 | Crew et al. | |
| 2018/0193470 | A1 | 7/2018 | Crew et al. | |
| 2018/0215731 | A1 | 8/2018 | Crew et al. | |
| 2018/0228907 | A1 | 8/2018 | Crew et al. | |
| 2018/0237418 | A1 | 8/2018 | Crew et al. | |
| 2018/0256586 | A1 | 9/2018 | Crew et al. | |

FOREIGN PATENT DOCUMENTS

| | | | |
|---|---|---|---|
| EP | 2985285 | | 2/2016 |
| JP | A 2004-525889 | | 8/2004 |
| JP | A 2010-502627 | | 1/2010 |
| RU | 2008112221 | A | 10/2009 |
| RU | 2448101 | C2 | 4/2012 |
| RU | 2011121567 | A | 10/2012 |
| RU | 2012138709 | A | 3/2014 |
| WO | WO 1998/003502 | | 1/1998 |
| WO | WO 2000/066119 | | 11/2000 |
| WO | WO 2002/066512 | | 8/2002 |
| WO | WO 2002/100845 | | 12/2002 |
| WO | WO 2005/097791 | | 10/2005 |
| WO | WO 2006/069063 | | 6/2006 |
| WO | WO 2006/113942 | | 10/2006 |
| WO | WO 2007/101347 | | 9/2007 |
| WO | WO 2007/106670 | | 9/2007 |
| WO | WO 2007/130626 | | 11/2007 |
| WO | WO 2008/011392 | | 1/2008 |
| WO | WO 2008/014236 | | 1/2008 |
| WO | WO 2008/109057 | | 9/2008 |
| WO | WO 2008/128121 | | 10/2008 |
| WO | WO 2008/128171 | | 10/2008 |
| WO | WO 2008/134679 | | 11/2008 |
| WO | WO 2009/015254 | | 1/2009 |
| WO | WO 2009/060292 | | 5/2009 |
| WO | WO 2010/107485 | | 9/2010 |
| WO | WO 2010/141805 | | 12/2010 |
| WO | WO 2011/008260 | | 1/2011 |
| WO | WO 2011/043371 | | 4/2011 |
| WO | WO 2012/003281 | | 1/2012 |
| WO | WO 2012/007375 | | 1/2012 |
| WO | WO 2012/040527 | | 3/2012 |
| WO | WO 2012/078559 | | 6/2012 |
| WO | WO 2012/090104 | | 7/2012 |
| WO | WO 2013/042137 | | 3/2013 |
| WO | WO 2013/071035 | | 5/2013 |
| WO | WO 2013/071039 | | 5/2013 |
| WO | WO 2013/106535 | | 7/2013 |
| WO | WO 2013/106643 | | 7/2013 |
| WO | WO 2013/106646 | | 7/2013 |
| WO | WO 2013/170147 | | 11/2013 |
| WO | WO 2013/175417 | | 11/2013 |
| WO | WO 2013/178570 | | 12/2013 |
| WO | WO 2014/011712 | | 1/2014 |
| WO | WO 2014/020502 | | 2/2014 |
| WO | WO 2014/025759 | | 2/2014 |
| WO | WO 2014/038606 | | 3/2014 |
| WO | WO 2014/047024 | | 3/2014 |
| WO | WO 2014/055461 | | 4/2014 |
| WO | WO 2014/058691 | | 4/2014 |
| WO | WO 2014/074658 | | 5/2014 |
| WO | WO 2014/100065 | | 6/2014 |
| WO | WO 2014/100071 | | 6/2014 |
| WO | WO 2014/107713 | | 7/2014 |
| WO | WO 2014/108452 | | 7/2014 |
| WO | WO 2014/123418 | | 8/2014 |
| WO | WO 2014/134201 | | 9/2014 |
| WO | WO 2014/151863 | | 9/2014 |
| WO | WO 2015/000868 | | 1/2015 |
| WO | WO 2015/006181 | | 1/2015 |
| WO | WO 2015/006524 | | 1/2015 |
| WO | WO 2015/104688 | | 7/2015 |
| WO | WO 2015/160845 | | 10/2015 |
| WO | WO 2016/011390 | | 1/2016 |
| WO | WO 2016/053769 | | 4/2016 |
| WO | WO 2016/053770 | | 4/2016 |
| WO | WO 2016/053771 | | 4/2016 |
| WO | WO 2016/053772 | | 4/2016 |
| WO | WO 2016/118666 | | 7/2016 |
| WO | WO 2016/144844 | | 9/2016 |
| WO | WO 2016/144846 | | 9/2016 |
| WO | WO 2016/144847 | | 9/2016 |
| WO | WO 2016/144848 | | 9/2016 |
| WO | WO 2016/144849 | | 9/2016 |
| WO | WO 2016/146985 | | 9/2016 |
| WO | WO 2016/169989 | | 10/2016 |
| WO | WO 2016/172134 | | 10/2016 |
| WO | WO 2016/197114 | | 12/2016 |
| WO | WO 2017/011590 | | 1/2017 |
| WO | WO 2017/030814 | | 2/2017 |
| WO | WO 2017/046036 | | 3/2017 |
| WO | WO 2017/079267 | | 5/2017 |
| WO | WO 2017/161119 | | 9/2017 |
| WO | WO 2017/185036 | | 10/2017 |
| WO | WO 2017/197051 | | 11/2017 |

OTHER PUBLICATIONS

International Preliminary Report on Patentability for PCT/US2018/061655, dated May 19, 2020.

Ahn, et al., "HIF-lalpha peptide derivatives with modifications at the hydroxyproline residue as activators of HIF-lalpha", Bioorg Med Chem Lett. 19(15), 2009, 4403-4405.

Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).

(56) References Cited

OTHER PUBLICATIONS

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).
Bargagna-Mohan, et al., "Use of PROTACS as molecular probes of angiogenesis", Bioorg Med Chem Left. 15(11) 2005, 2724-2727.
Bondeson DP, et al. (2018) "Lessons in PROTAC Design from Selective Degradation with a Promiscuous Warhead." *Cell Chem Biol* 25(1):78-87 e75.
Bondeson, et al., (2017) "Targeted Protein Degradation by Small Molecules." *Annu Rev Pharmacol Toxicol* 57:107-123.
Bondeson, et al., "Catalytic in vivo protein knockdown by small-molecule PROTACS", National Chem Biol. 11(8) Aug. 2015, 611-617.
Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and HIF1a", Angew Chem Int Ed Engl.51(46), Nov. 12, 2012, 11463-11467.
Buckley, et al., "Targeting the von Hippel-Lindau E3 ubiquitin ligase using small molecules to disrupt the VHL/HIF-1$\alpha$ interaction", Journal of the American Chemical Society, Feb. 27, 2012, 134(10): 4465-4468.
Burslem GM, et al. (2018) "The Advantages of Targeted Protein Degradation Over Inhibition: An RTK Case Study." *Cell Chem Biol* 25(1):67-77 e63.
Burslem, et al., (2017) "Small-Molecule Modulation of Protein Homeostasis." *Chem Rev* 117(17):11269-11301.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
CAS Registry No. 1004933-70-3, which entered STN on Feb. 21, 2008.
CAS Registry No. 871986-52-6 entered STN Jan 16, 2006.
Chan, et al., (2018) "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds." *J Med Chem* 61(2):504-513.
CHEMBL256713, PubChem (2009); National Center for Biotechnology Information. PubChem Compound Database; CID-44449334, https://pubchem.ncbi.nlm.nih.gov/compound/44449334.
Chene, P., et al., "Inhibiting the p53-MDM2 interaction: an important target for cancer therapy" Nat. Rev. Cancer (2003), 3, 102-109.
Churcher I (2018) "Protac-Induced Protein Degradation in Drug Discovery: Breaking the Rules or Just Making New Ones?" *J Med Chem* 61(2):444-452.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antogonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crew AP, et al. (2018) "Identification and Characterization of Von Hippel-Lindau-Recruiting Proteolysis Targeting Chimeras (PROTACs) of TANK-Binding Kinase 1." *J Med Chem* 61(2):583-598.
Crews, C. M., "Targeting the undruggable proteome: the small molecules of my dreams", *Chem Biol 17*, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol 13*, 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 (2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Hanisak, et al., "Efforts toward the optimization of a bi-aryl class of potent IRAK4 inhibitors", Bioorg Med Chem Lett 1;26(17) 4250-4255 (2016).
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in H1f-1 alpha by pVHL", Nature 417, Jun. 27, 2002, 975-978.
Huang HT, et al. (2018) "A Chemoproteomic Approach to Query the Degradable Kinome Using a Multi-kinase Degrader." *Cell Chem Biol* 25(1):88-99 e86.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
IRAK-1-4 Inhibitor I, PubChem (2007); National Center for Biotechnology Information. PubChem Compound Database; CID-11983295, https://pubchem.ncbi.nlm.nih.gov/compound/11983295.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.

(56) References Cited

OTHER PUBLICATIONS

Janssens, S., et al. "Functional Diversity and Regulation of Different Interleukin-1 Receptor-Associated Kinase (IRAK) Family Members", Mol. Cell. 11(2), 2003, 293-302.
Kanakaraj, et al, "Interleukin (IL)-1 Receptor-associated Kinase (IRAK) Requirement for Optimal Induction of Multiple IL-1 Signaling Pathways and IL-6 Production", J. Exp. Med. 187(12), 1998, 2073-2079.
Kanakaraj, et al. "Defective Interleukin (IL)-18-mediated Natural Killer and T Helper Cell Type 1 Responses in IL-1 Receptor-associated Kinase (IRAK)-deficient Mice", J. Exp. Med. 189(7), 1999, 1129-1138.
Kawagoe, T, et al. "Essential role of IRAK-4 protein and its kinase activity in Toll-like receptor-mediated immune responses but not in TCR signaling", J. Exp. Med. 204(5): 2007, 1013-1024.
Kim, K.S., "Discovery of tetrahydroisoquinoline-based bivalent heterodimeric IAP antagonists", Bioorg. Med. Chem. Lett. 24(21), 5022-5029 (2014).
Kim, T W, et al., "A critical role for IRAK4 kinase activity in Toll-like receptor-mediated innate immunity", J. Exp Med 204(5), 2007, 1025-1036.
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Koziczak-Holbrom, et al., "IRAK-4 Kinase Activity is Required for Interleukin-1 (IL-1) Receptor-and Toll-like Receptor 7-mediated Signaling and Gene Expression", J. Biol. Chem. 282(18): 2007; 13552-13560.
Kronke, et al, "Lenalidomide Causes Selective Degradation of IKZF1 and IKZF3 in Multiple Myeloma Cells", Science 343, 301-305 (2014).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, et al. "Mutant Cells That do not respond to Interleukin-1 (IL-1) Reveal a Novel Role for IL-1 Receptor-Associated Kinase", Mol. Cell. Biol. 19(7), 1999, 4643-4652.
Li, S., et al. "IRAK-4: A novel member of the IRAK family with the properties of an IRAK-kinase", Proc. Natl. Acad. Sci. USA 99(8), 2002, 5567-5572.
Li, Yan, et al., "Single polymer-drug conjugate carrying two drugs for fixed-dose co-delivery", Medicinal Chemistry, 2014, vol. 4(10): 676-683.
Lim, et al "Discovery of 5-Amino-N-(1H-pyrazol-4-yl)pyrazolo[1,5-a]pyrimidine-3-carboxamide inhibitors of IRAK4", ACS Med Chem Lett 6: 683-688 (2015).
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Lye, E. et al, "The role of interleukin 1 receptor-associated Kinase-4 (IRAK-4) kinase activity in IRAK-4-mediated signaling", J. Biol. Chem. 279(39); 2004, 40653-40658.
Maniaci C, et al. (2017) "Homo-PROTACs: bivalent small-molecule dimerizers of the VHL E3 ubiquitin ligase to induce self-degradation." *Nat Commun* 8(1):830 1-13.
Mannhold, R., et al., "IAP antagonists: promising candidates for cancer therapy", Drug Discov. Today, 15 (5-6), 210-219 (2010).
McElroy, et al., "Discovery and hit-to-lead optimization of 2.6-diaminopyrimidine inhibitors of interleukin-1 receptor-associated kinase 4", Bioorg Med Chem Lett 25(9) 1836-1841 (2015).
McElroy, et al., "Potent and Selective Amidopyrazole Inhibitors of IRAK4 that are Efficacious in a Rodent Model of Inflammation", ACS Med Chem Lett 6: 677-682 (2015).
Medline Plus Trusted Health Information for You, www.nlm.nih.gov/medlineplus/cancer.html pp. 1-10, (2007).
Medvedev, et al. "Distinct Mutations in IRAK-4 confer hyporesponsiveness to lipopolysaccharide and interleukin-1 in a patient with recurrent bacterial infections", J. Exp. Med., 198(4), 2003, 521-531.
Min, Jung-hyun, et al., "Structure of an HIV-1-alpha—pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Ohoka, N. et al. SNIPER(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Perez, HL," Discovery of potent heterodimeric antagonists of inhibitor of apoptosis proteins (IAPs) with sustained antitumor activity", J. Med. Chem. 58(3), 1556-1562 (2015).
Powell, C. E. et al. Chemically Induced Degradation of Anaplastic Lymphoma Kinase (ALK). J. Med. Chem. 61, 4249-4255 (2018).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J

(56) References Cited

OTHER PUBLICATIONS

Med Chem. Dec. 26, 2014;57(24):10499-10511. doi: 10.1021/jm501550p. Epub Dec. 4, 2014. PubMed PMID: 25384157.
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Schenkel, et al., "Discovery of Potent and Highly Selective Thienopyridine Janus Kinase 2 Inhibitors", J Med Chem.54(24), Dec. 22, 2011, 8440-8450.
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Seganish, "Inhibitors of interleukin-1 receptor-associated kinase 4 (IRAK4): a patent review (2012-2015)", Expert Opin Ther Pat 26:8, 917-932 (2016).
Seganish, et al., "Discovery and Structure Enabled Synthesis of 2,6-Diaminopyrimidin-4-one IRAK4 Inhibitors", ACS Med Chem Lett (6) 942-947 (2015).
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stanton, et al., (2018) "Chemically induced proximity in biology and medicine." *Science* 359(6380).
Staschke et al. "IRAK4 kinase activity is required for Th17 differentiation and TH17-mediated disease", The Journal of Immunology, 183(1), 2009, 568-577.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017 "Compounds containing sulfur Chromophores v. Complex cyanines".
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, B. et al. BET protein proteolysis targeting chimera (PROTAC) exerts potent lethal activity against mantle cell lymphoma cells. Leukemia 32, 343-352 (2018).
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Suzuki et al. "Severe impairment of interleukin-1 and toll-like receptor signaling in mice lacking IRAK-4", Nature, 416(6882), 2002, 750-756.
Toure, et al., (2016) "Small-Molecule PROTACS: New Approaches to Protein Degradation." *Angew Chem Int Ed Engl* 55(6):1966-1973.
Tumey, et al., "Identification and optimization of indolo[2,3-c]quinolone inhibitors of IRAK4", Bioorg Med Chem Lett 24(9) 2066-2072 (2014).
Turk, B. E., "Binding of thalidomide to alphal-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor la protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Wietek C., et al, "IRAK-4: a new drug target in inflammation, sepsis, and autoimmunity", Mol. Interv. 2: 2002, 212-215.
Winter, et al., "Phthalimide Conjugation as a strategy for in vivo target protein degradation", Science, 2015 vol. 348 (6241), pp. 1376-1381 [Pub online: May 21, 2015].
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).
Smith, Graham F., et al., Identification of quinazoline based inhibitors of IRAK4 for the treatment of inflammation, Bioorganic & Medical Chemistry Letter, vol. 27., No. 12, Apr. 18, 2017, pp. 2721-2726.

* cited by examiner

IRAK4
Dmax = 71%
DC50 = 9.7nM

IRAK1
No significant degradation

COMPOUNDS AND METHODS FOR THE TARGETED DEGRADATION OF INTERLEUKIN-1 RECEPTOR- ASSOCIATED KINASE 4 POLYPEPTIDES

RELATED APPLICATIONS

The present disclosure claims priority to U.S. Provisional Patent Application No. 62/587,799, filed 17 Nov. 2017, titled COMPOUNDS AND METHODS FOR THE TARGETED DEGRADATION OF INTERLEUKIN-1 RECEPTOR-ASSOCIATED KINASE 4 POLYPEPTIDES, which is incorporated herein by reference in its entirety for all purposes.

INCORPORATION BY REFERENCE

U.S. patent application Ser. No. 15/230,354, filed on Aug. 5, 2016, published as U.S. Patent Application Publication No. 2017/0065719; and U.S. patent application Ser. No. 15/206,497 filed 11 Jul. 2016, published as U.S. Patent Application Publication No. 2017/0008904; and U.S. patent application Ser. No. 15/209,648 filed 13 Jul. 2016, published as U.S. Patent Application Publication No. 2017/0037004; and U.S. patent application Ser. No. 15/730,728, filed on Oct. 11, 2017, published as U.S. Patent Application Publication No. 2018/0099940; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639; and U.S. patent application Ser. No. 15/885,671, filed Jan. 31, 2018, published as U.S. Patent Application Publication No. 2018/0215731 A1; and International Patent Application No. PCT/US2016/023258, filed Mar. 18, 2016, published as International Patent Application Publication No. WO2016/149668, are incorporated herein by reference in their entirety. Furthermore, all references cited herein are incorporated by reference herein in their entirety.

FIELD OF THE INVENTION

The description provides bifunctional compounds comprising a target protein binding moiety and a E3 ubiquitin ligase binding moiety, and associated methods of use. The bifunctional compounds are useful as modulators of targeted ubiquitination, especially with respect to Interleukin-1 receptor-associated kinases-4 (IRAK-4), which is degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Levine, et al. Nature (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from p53/MDM2 auto regulatory system. In other words, p53 regulates MDM2 at the transcription level, and MDM2 regulates p53 at its activity level (A. J. Levine, et al. *Genes Dev.* (1993) 7, 1126-1132).

First, MDM2 binds to N-terminal domain of p53 and blocks expression of p53-responsive genes (J. Momand, et al. *Cell* (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). As such, because MDM2 functions as E3 ligase, recruiting MDM2 to a disease causing protein and effectuating its ubiquitination and degradation is an approach of high interest for drug discovery.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitrochondria-derived activator of caspases or SMAC) and HTRA2 (also known as Omi). Binding of DIABLO and HTRA2 appears to block IAP activity.

SMAC interacts with essentially all known IAPs including XIAP, c-IAP1, c-IAP2, NIL-IAP, Bruce, and survivin. The first four amino acids (AVPI) of mature SMAC bind to a portion of IAPs, which is believed to be essential for blocking the anti-apoptotic effects of IAPs.

Interleukin-1 (IL-1) Receptor-Associated Kinase-4 (IRAK-4) is a serine/threonine kinase enzyme that plays an essential role in signal transduction by Toll/IL-1 receptors (TIRs). Diverse IRAK enzymes are key components in the signal transduction pathways mediated by interleukin-1 receptor (IL-1R) and Toll-like receptors (TLRs) (Janssens, S, et al. Mol. Cell. 11(2), 2003, 293-302). There are four members in the mammalian IRAK family: IRAK-1, IRAK-2, IRAK-M and IRAK-4. These proteins are characterized by a typical N-terminal death domain that mediates interaction with MyD88-family adaptor proteins and a centrally located kinase domain. Upon recruitment of MyD88 and IRAK4 to the Toll-interleukin domain, activation leads to phosphorylation of IRAK1 and/or IRAK2 leading to engagement of TRAF6. Subsequent signaling results in activation of NF-kB and the release of various cytokines and chemokines. The MYD88 L265P mutation occurring in 91% Waldenstrom's macroglobulinemia, 29% ABC DLBCL, 9% MALT lymphomas, and 3% CLL coordinates a constitutively active signalosome in which IRAK4-mediated phosphorylation of IRAKI promotes the assembly of additional signaling proteins driving survival in these cancers.

The IRAK proteins, as well as MyD88, have been shown to play a role in transducing signals other than those originating from IL-1R receptors, including signals triggered by activation of IL-18 receptors (Kanakaraj, et al. J. Exp. Med. 189(7), 1999, 1129-38) and LPS receptors (Yang, et al., J. Immunol. 163(2), 1999, 639-643). Out of four members in the mammalian IRAK family, IRAK-4 is considered to be the "master IRAK". Under overexpression conditions, all IRAKs can mediate the activation of nuclear factor-.kappa.B (NF-κB) and stress-induced mitogen activated protein kinase (MAPK)-signaling cascades. However, only IRAK-1 and IRAK-4 have been shown to have active kinase activity. While IRAK-1 kinase activity could be dispensable for its function in IL-1-induced NF-.kappa.B activation (Kanakaraj et al, J. Exp. Med. 187(12), 1998, 2073-2079) and (Li, et al. Mol. Cell. Biol. 19(7), 1999, 4643-4652), IRAK-4 requires its kinase activity for signal transduction [(Li S, et al. Proc. Natl. Acad. Sci. USA 99(8), 2002, 5567-5572) and (Lye, E et al, J. Biol. Chem. 279(39); 2004, 40653-8)]. Given the central role of IRAK4 in Toll-like/IL-1R signalling and immunological protection, IRAK4 inhibitors have been implicated as valuable therapeutics in inflammatory diseases, sepsis and autoimmune disorders (Wietek C, et al, Mol. Interv. 2: 2002, 212-215).

Mice lacking IRAK-4 are viable and show complete abrogation of inflammatory cytokine production in response to IL-1, IL-18 or LPS (Suzuki et al. *Nature,* 416(6882), 2002, 750-756). Similarly, human patients lacking IRAK-4 are severely immunocompromised and are not responsive to these cytokines (Medvedev et al. *J. Exp. Med.,* 198(4), 2003, 521-531 and Picard et al. *Science* 299(5615), 2003, 2076-2079). Knock-in mice containing inactive IRAK4 were completely resistant to lipopolysaccharide- and CpG-induced shock (Kim T W, et al. *J. Exp. Med* 204(5), 2007, 1025-36) and (Kawagoe T, et al. *J. Exp. Med.* 204(5): 2007, 1013-1024) and illustrated that IRAK4 kinase activity is essential for cytokine production, activation of MAPKs and induction of NF-κB regulated genes in response to TLR ligands (Koziczak-Holbro M, et al. *J. Biol. Chem.* 282(18): 2007; 13552-13560). Inactivation of IRAK4 kinase (IRAK4 KI) in mice leads to resistance to EAE due to reduction in infiltrating inflammatory cells into CNS and reduced antigen specific CD4+ T-cell mediated IL-17 production (Staschke et al. *The Journal of Immunology,* 183(1), 2009, 568-577).

Bifunctional compounds such as those that are described in U.S. Patent Application Publication Nos 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

An ongoing need exists in the art for effective treatments for disease associated with overexpression or aggregation of IRAK-4. However, non-specific effects, and the inability to target and modulate IRAK-4, remain as obstacles to the development of effective treatments. As such, small-molecule therapeutic agents that target IRAK-4 and that leverage or potentiate VHL's, cereblon's, MDM2's, and IAPs' substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, inflammatory diseases/disorders, neurodegenerative diseases, as well as cardiovascular diseases/disorders.

As such, in one aspect the disclosure provides bifunctional or PROTAC compounds, which comprise an E3 ubiquitin ligase binding moiety (i.e., a ligand for an E3 ubquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double miniute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

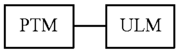

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

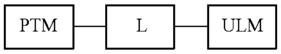

where PTM is a protein/polypeptide targeting moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the biofunctional compound can be depicted as:

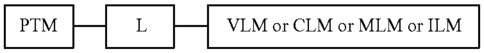

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP;

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Pub. No. 2014-03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication US 2015-0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer, autoimmune diseases/disorder, and/or inflammatory diseases/disorders. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, wherein PTM is coupled to VLM or CLM or MLM or ILM through a linkger to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
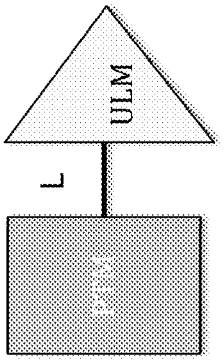
FIGS. 1A and 1B. Illustration of general principle for PROTAC function. (1A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (1B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 1B:
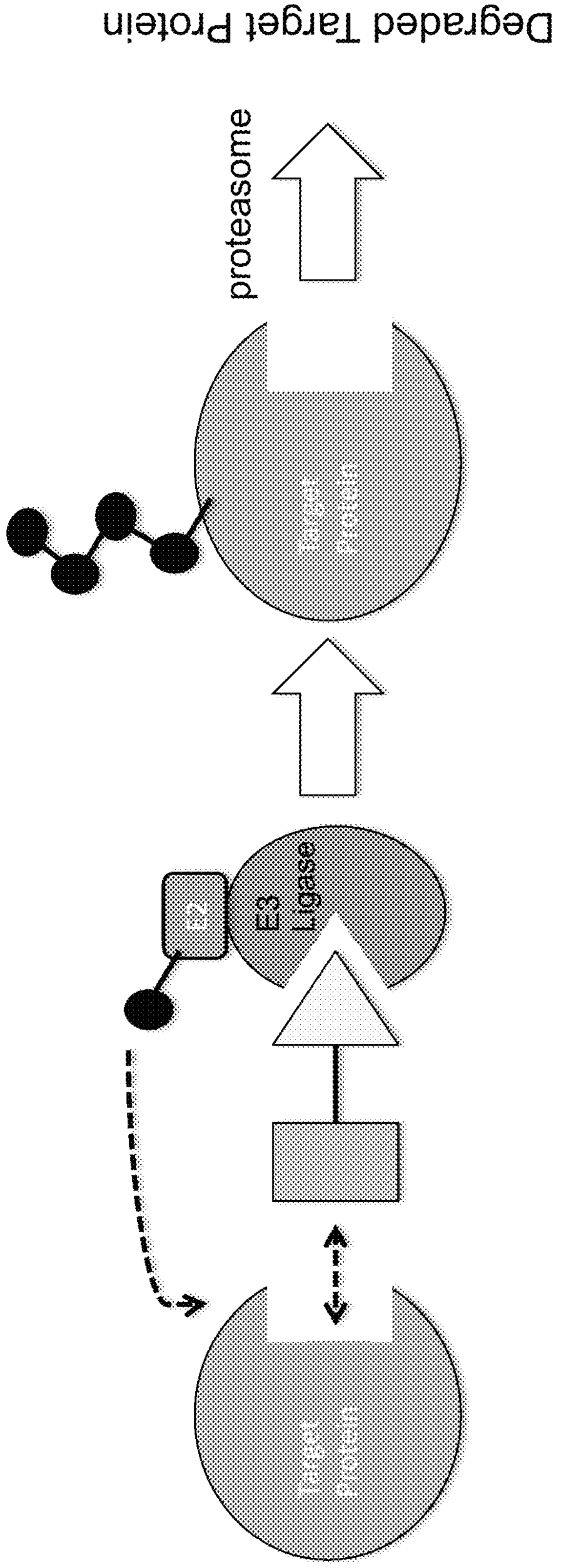

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent or an anti-inflammatory agent. In particularly preferred aspects, the co-administration of compounds results in synergistic activity and/or therapy, including anticancer or anti-inflammatory activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse bould minute 2 homologue (MDM2) E3 ubiquitin ligase binding moiety (MLM). In an exemplary embodiment, the ULM is coupled to a target protein binding moiety (PTM) via a chemical linker (L) according to the structure:

(A) PTM-L-ULM wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitein ligase binding moieties, the term VLM is inclusive of all possible VHL binding moeities, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

(B) PTM-ILM (C) PTM-CLM (D) PTM-VLM (E) PTM-MLM

In certain embodiments, the bifunctional compound further comprises a chemical linker ("L"). For example, the bifunctional compound can be depicted as:

(F) PTM-L-ILM (G) PTM-L-CLM (H) PTM-L-VLM (I) PTM-L-MLM wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 μM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects of embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ILMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

Exemplary ILMs

AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

(I)

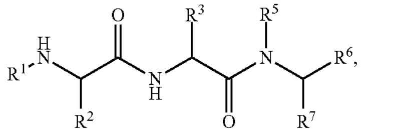

(II)

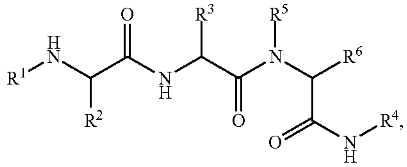

(III)

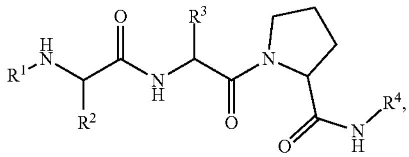

(IV)

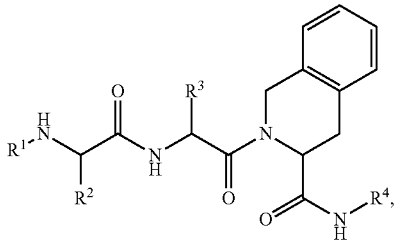

(V)

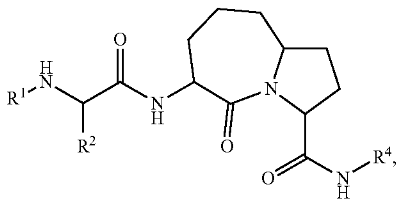

wherein:

$R^1$ for Formulas (I), (II), (III), (IV), and (V) is selected from H or alkyl;

$R^2$ for Formulas (I), (II), (III), (IV), and (V) is selected from H or alkyl;

$R^3$ for Formulas (I), (II), (III), (IV), and (V) is selected from H, alkyl, cycloalkyl and heterocycloalkyl;

$R^5$ and $R^6$ for Formulas (I), (II), (III), (IV), and (V) are independently selected from H, alkyl, cycloalkyl, heterocycloalkyl, or more preferably, $R^5$ and $R^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;

$R^3$ and $R^5$ for Formulas (I), (II), (III), (IV), and (V) taken together can form a 5-8-membered ring further optionally fused to 1-2 cycloalkyl, heterocycloalkyl, aryl or heteroaryl rings;

$R^7$ for Formulas (I), (II), (III), (IV), and (V) is selected from cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or $R^7$ is —C(O)NH—$R^4$; and $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formular (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

(VI)

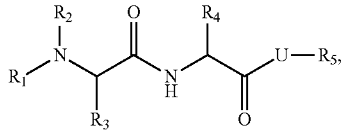

wherein:

$R_1$ of Formula (VI) is, independently selected from H, $C_1$-$C_4$-alky, $C_1$-$C_4$-alkenyl, $C_1$-$C_4$-alkynyl or $C_3$-$C_{10}$-cycloalkyl which are unsubstituted or substituted;

$R_2$ of Formula (VI) is, independently selected from H, $C_1$-$C_4$-alkyl, $C_1$-$C_4$-alkenyl, $C_1$-$C_4$-alkynyl or $C_3$-$C_{10}$-cycloalkyl which are unsubstituted or substituted;

$R_3$ of Formula (VI) is, independently selected from H, —$CF_3$, —$C_2$Hs, $C_1$-$C_4$-alkyl $C_1$-$C_4$-alkenyl, $C_1$-$C_4$-alkynyl, —$CH_2$—Z or any $R_2$ and $R_3$ together form a heterocyclic ring;

each Z of Formula (VI) is, independently selected from H, —OH, F, Cl, —$CH_3$, —$CF_3$, —$CH_2$Cl, —$CH_2$F or —$CH_2$OH;

$R_4$ of Formula (VI) is, independently selected from $C_1$-$C_{16}$ straight or branched alkyl, $C_1$-$C_{16}$-alkenyl, $C_1$-$C_{16}$-alkynyl, $C_3$-$C_{10}$-cycloalkyl, —$(CH_2)_{0-6}$—$Z_1$, —$(CH_2)_{0-6}$-aryl, and —$(CH_2)_{0-6}$-het, wherein alkyl, cycloalkyl, and phenyl are unsubstituted or substituted;

$R_5$ of Formula (VI) is, independently selected from H, $C_{1-10}$-alkyl, aryl, phenyl, $C_{3-7}$-cycloalkyl, —$(CH_2)_{1-6}$—$C_{3-7}$-cycloalkyl, —$C_{1-10}$-alkyl-aryl, —$(CH_2)_{0-6}$—$C_{3-7}$-cycloalkyl-$(CH_2)_{0-6}$-phenyl, —$(CH_2)_{0-4}$—CH[$(CH_2)_{1-4}$-phenyl]$_2$, indanyl, —C(O)—$C_{1-10}$-alkyl, —C(O)—$(CH_2)_{1-6}$—$C_{3-7}$-cycloalkyl, —C(O)—$(CH_2)_{0-6}$-phenyl, —$(CH_2)_{0-6}$—C(O)-phenyl, —$(CH_2)_{0-6}$-het, —C(O)—$(CH_2)_{1-6}$-het, or $R_5$ is selected from a residue of an amino acid, wherein the alkyl, cycloalkyl, phenyl, and aryl substituents are unsubstituted or substituted;

$Z_1$ of Formula (VI) is, independently selected from —N($R_{10}$)—C(O)—$C_{1-10}$-alkyl, —N($R_{10}$)—C(O)—$(CH_2)_{0-6}$—$C_{3-7}$-cycloalkyl, —N($R_{10}$)—C(O)—$(CH_2)_{0-6}$-phenyl, —N($R_{10}$)—C(O)$(CH_2)_{1-6}$-het, —C(O)—N($R_{11}$)($R_{12}$), —C(O)—O—$C_{1-10}$-alkyl, —C(O)—O—$(CH_2)_{1-6}$—$C_{3-7}$-cycloalkyl, —C(O)—O—$(CH_2)_{0-6}$-phenyl, —C(O)—O—$(CH_2)_{1-6}$-het, —O—C(O)—$C_{1-10}$-alkyl, —O—C(O)—$(CH_2)_{1-6}$—$C_{3-7}$-cycloalkyl, —O—C(O)—$(CH_2)_{0-6}$-phenyl, —O—C(O)—$(CH_2)_{1-6}$-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

$R_{10}$ of Formula (VI) is selected from H, —$CH_3$, —$CF_3$, —$CH_2$OH, or —$CH_2$Cl;

$R_{11}$ and $R_{12}$ of Formula (VI) are independently selected from H, $C_{1-4}$-alkyl, $C_{3-7}$-cycloalkyl, —$(CH_2)_{1-6}$—$C_{3-7}$-cycloakyl, $(CH_2)_{0-6}$-phenyl, wherein alkyl, cycloalkyl, and phenyl are unsubstituted or substituted; or $R_{11}$ and $R_{12}$ together with the nitrogen form het, and U of Formula (VI) is, independently, as shown in Formula (VII):

(VII)

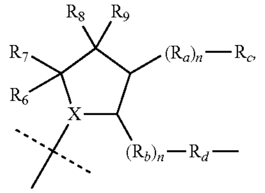

wherein:

each n of Formula (Vii) is, independently selected from 0 to 5;

X of Formula (VII) is selected from the group —CH and N;

$R_a$ and $R_b$, of Formula (VII) are independently selected from the group O, S, or N atom or $C_{0-8}$-alkyl wherein one or more of the carbon atoms in the alkyl chain are optionally replaced by a heteroatom selected from O, S, or N. and where each alkyl is, independently, either unsubstituted or substituted;

$R_d$ of Formula (VII) is selected from the group Re-Q-$(R_f)_p(R_g)_q$, and $Ar_1$-D-$Ar_2$;

$R_e$ of Formula (VII) is selected from the group H or any $R_c$ and $R_d$ together form a cycloalkyl or het; where if $R_c$ and $R_d$ form a cycloalkyl or het, $R_5$ is attached to the formed ring at a C or N atom;

p and q of Formula (VII) are independently selected from 0 or 1;

$R_e$ of Formula (VII) is selected from the group $C_{1-8}$-alkyl and alkylidene, and each Re is either unsubstituted or substituted;

Q is selected from the group N, O, S, S(O), and $S(O)_2$;

$Ar_1$ and $Ar_2$ of Formula (VII) are independently selected from the group of substituted or unsubstituted aryl and het;

$R_f$ and $R_g$ of Formula (VII) are independently selected from H, —C1-10-alkyl, $C_{1-10}$-alkylaryl, —OH, —O—$C_{1-10}$-alkyl, —$(CH_2)_{0-6}$—$C_{3-7}$-cycloalkyl, —O—$(CH_2)_{0-6}$-aryl, phenyl, aryl, phenyl-phenyl, $-(CH_2)_{1-6}$-het, $-O-(CH_2)_{1-6}$-het, $-OR_{13}$, $-C(O)-R_{13}$, $-C(O)-N(R_{13})(R_{14})$, $-N(R_{13})(R_{14})$, $-S-R_{13}$, $-S(O)-R_{13}$, $-S(O)_2-R_{13}$, $-S(O)_2-NR_{13}R_{14}$, $-NR_{13}-S(O)_2-R_{14}$, $-S-C_{1-10}$-alkyl, aryl-$C_{1-4}$-alkyl, or het-$C_{1-4}$-alkyl, wherein alkyl, cycloalkyl, het, and aryl are unsubstituted or substituted, $-SO_2-C_{1-2}$-alkyl, $-SO_2-C_{1-2}$-alkylphenyl, $-O-C_{1-4}$-alkyl, or any $R_g$ and $R_f$ together form a ring selected from het or aryl;

D of Formula (VII) is selected from the group —CO—, $-C(O)-C_{1-7}$-alkylene or arylene, $-CF_2-$, —O—, —S(O), where r is 0-2, 1,3-dioxalane, or $C_{1-7}$-alkyl-OH; where alkyl, alkylene, or arylene are unsubstituted or substituted with one or more halogens, OH, $-O-C_{1-6}$-alkyl, $-S-C_{1-6}$-alkyl, or $-CF_3$; or each D is, independently selected from $N(R_h)$;

Rh is selected from the group H, unsubstituted or substituted $C_{1-7}$-alkyl, aryl, unsubstituted or substituted $-O-(C_{1-7}$-cycloalkyl), $-C(O)-C_{1-10}$-alkyl, $-C(O)-C_{0-10}$-alkyl-aryl, $-C-O-C_{01-10}$-alkyl, $-C-O-C_{0-10}$-alkyl-aryl, $-SO_2-C_{1-10}$-alkyl, or $-SO_2-(C_{0-10}$-alkylaryl);

$R_6$, $R_7$, $R_8$, and $R_9$ of Formula (VII) are, independently, selected from the group H, $-C_{1-10}$-alkyl, $-C_{1-10}$-alkoxy, aryl-$C_{1-10}$-alkoxy, —OH, $-O-C_{1-10}$-alkyl, $-(CH_2)_{0-6}-C_{3-7}$-cycloalkyl, $-O-(CH_2)_{0-6}$-aryl, phenyl, $-(CH_2)_{1-6}$-het, $-O-(CH_2)_{1-6}$-het, $-OR_{13}$, $-C(O)-R_{13}$, $-C(O)-N(R_{13})(R_{14})$, $-N(R_{13})(R_{14})$, $-S-R_{13}$, $-S(O)-R_3$, $-S(O)_2-R_{13}$, $-S(O)_2-NR_{13}R_{14}$, or $-NR_{13}-S(O)_2-R_{14}$; wherein each alkyl, cycloalkyl, and aryl is unsubstituted or substituted; and any $R_6$, $R_7$, $R_8$, and $R_9$ optionally together form a ring system;

$R_{13}$ and $R_{14}$ of Formula (VII) are independently selected from the group H, Co-alkyl, $-(CH_2)_{0-6}-C_{3-7}$-cycloalkyl, $-(CH_2)_{0-6}-(CH)_{0-1}-(aryl)_{1-2}$, $-C(O)-C_{1-10}$-alkyl, $-C(O)-(CH_2)_{1-6}-C_{3-7}$-cycloalkyl, $-C(O)-O-(CH_2)_{0-6}$-aryl, $-C(O)-(CH_2)_{0-6}$-O-fluorenyl, $-C(O)-NH-(CH_2)_{0-6}$-aryl, $-C(O)-(CH_2)_{0-6}$-aryl, $-C(O)-(CH_2)_{0-6}$-het, $-C(S)-C_{1-10}$-alkyl, $-C(S)-(CH_2)_{1-6}-C_{3-7}$-cycloalkyl, $-C(S)-O-(CH_2)_{0-6}$-aryl, $-C(S)-(CH_2)_{0-6}$-O-fluorenyl, $-C(S)-NH-(CH_2)_{0-6}$-aryl, $-C(S)-(CH_2)_{0-6}$-aryl, or $-C(S)-(CH_2)_{1-6}$-het, wherein each alkyl, cycloalkyl, and aryl is unsubstituted or substituted: or any $R_1$ and $R_{14}$ together with a nitrogen atom form het;

wherein alkyl substituents of $R_{13}$ and $R_{14}$ of Formula (VII) are unsubstituted or substituted and when substituted, are substituted by one or more substituents selected from $C_{1-10}$-alkyl, halogen, OH, $-O-C_{1-6}$-alkyl, $-S-C_{1-6}$-alkyl, and $-CF_3$; and substituted phenyl or aryl of $R_{13}$ and $R_{14}$ are substituted by one or more substituents selected from halogen, hydroxyl, $C_{1-4}$-alkyl, $C_{1-4}$-alkoxy, nitro, —CN, $-O-C(O)-C_{1-4}$-alkyl, and $-C(O)-O-C_{1-4}$-aryl; or a pharmaceutically acceptable salt or hydrate thereof.

In certain embodiments, the compound further comprises an independently selected second ILM attached to the ILM of Formula (VI), or an unnatural mimetic thereof, by way of at least one additional independently selected linker group. In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM. In an embodiment, the at least one additional linker group for an ILM of the Formula (VI), or an unnatural mimetic thereof, chemically links groups selected from $R_4$ and $R_5$. For example, an ILM of Formula (VI) and a second ILM of Formula (VI), or an unnatural mimetic thereof, can be linked as shown below:

(A)

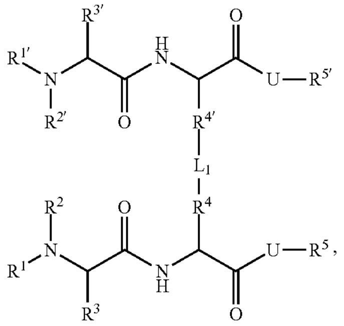

(B)

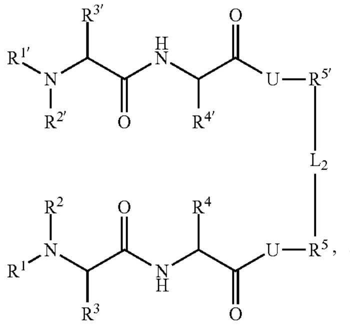

and (C)

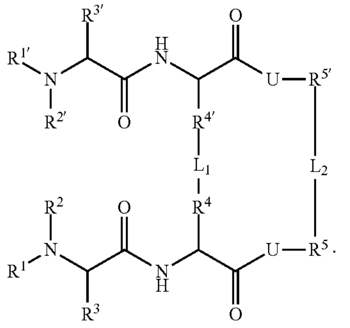

In certain embodiments, the ILM, the at least one additional independently selected linker group L, and the second ILM has a structure selected from the group consisting of:

(A)
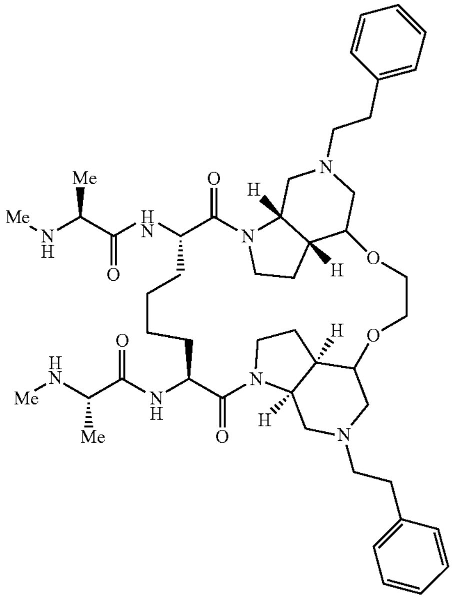
;
(B)
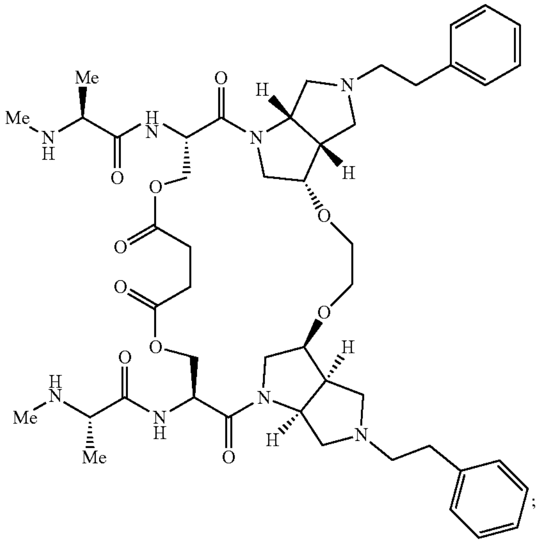
;
(C)
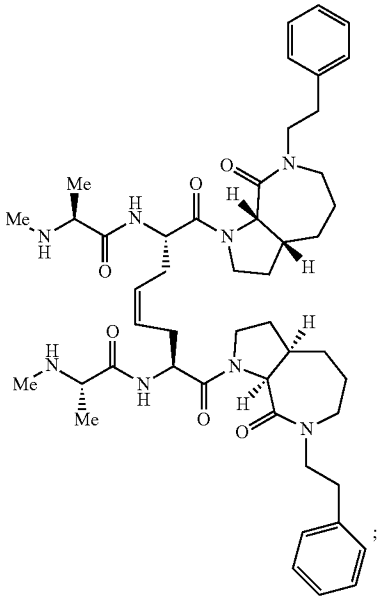
;
(D)
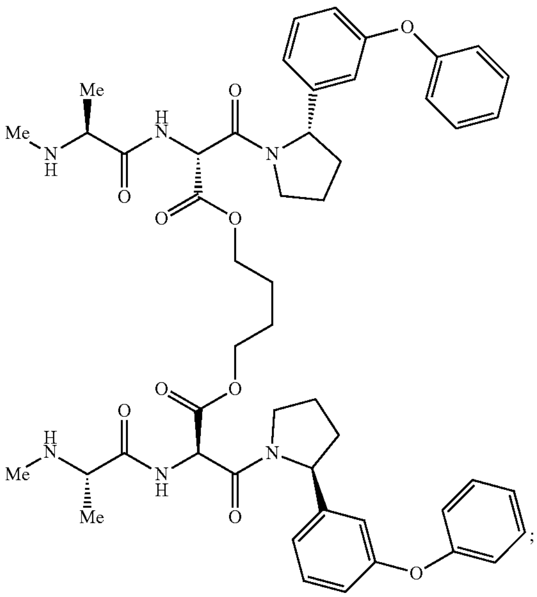
;

-continued
(E)
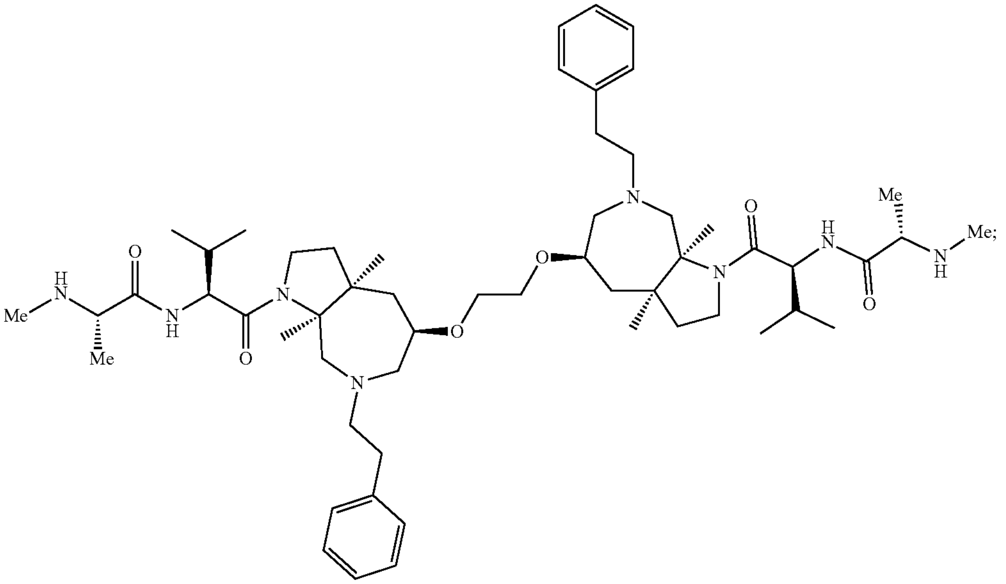
and
(F)
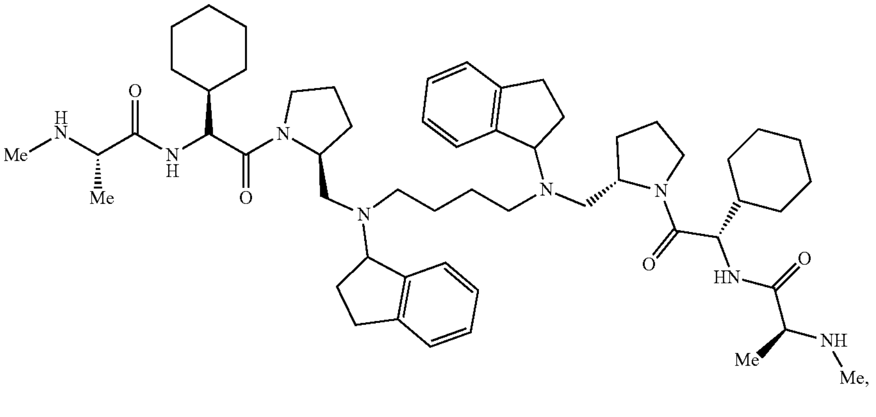

which are derivatives of IAP antagonists described in WO Pub. No. 2008/014236.

In any of the compounds described herein, the ILM can have the structure of Formula (VIII), which is based on the IAP ligrands described in Ndubaku, C., et al. Antagonism of c-IAP and XIAP proteins is required for efficient induction of cell death by small-molecule IAP antagonists, *ACS Chem. Biol.,* 557-566, 4 (7) (2009), or an unnatural mimetic thereof:

(VIII)

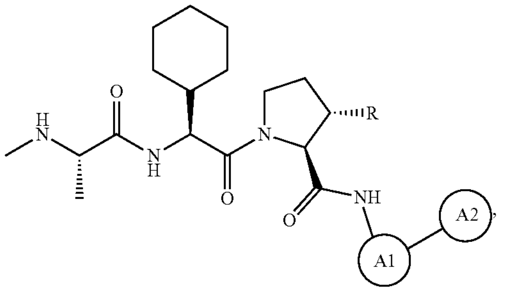

wherein each of A1 and A2 of Formula (VIII) is independently selected from optionally substituted monocyclic, fused rings, aryls and hetoroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of (A)

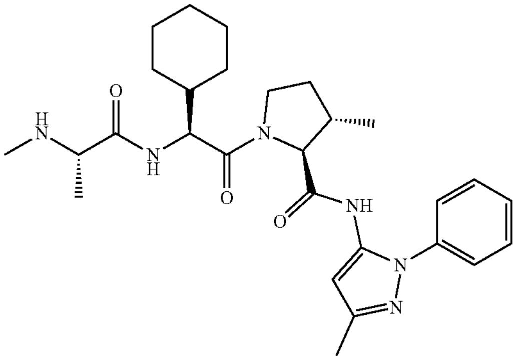

and (B)

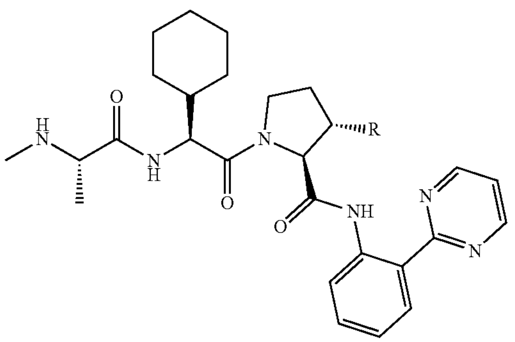

In any of the compounds described herein, the ILM can have the structure of Formula (IX), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(IX)

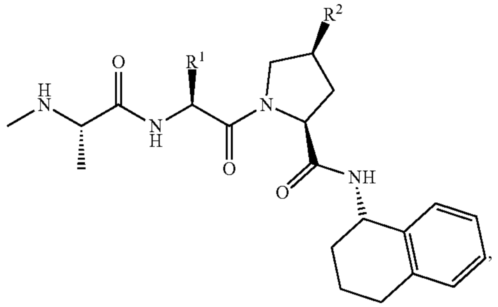

wherein $R^1$ is selected from alkyl, cycloalkyl and heterocycloalkyl and, most preferably, from isopropyl, tert-butyl, cyclohexyl and tetrahydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(X)

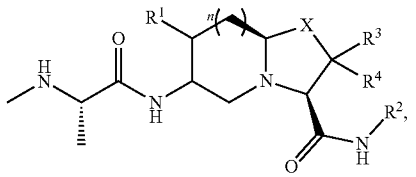

n = 1, 2, 3 wherein:

$R^1$ of Formula (X) is selected from H, $—CH_2OH$, $—CH_2CH_2OH$, $—CH_2NH_2$, $—CH_2CH_2NH_2$;

X of Formula (X) is selected from S or $CH_2$;

$R^2$ of Formula (X) is selected from:

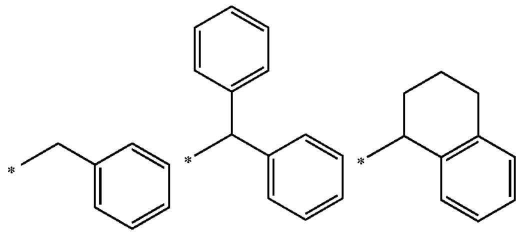

-continued

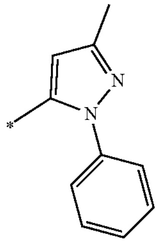

$R^3$ and $R^4$ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(XI)

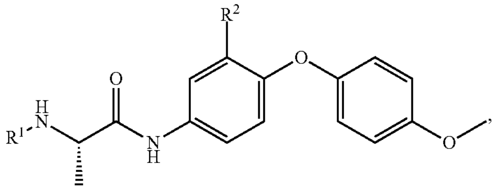

wherein $R^1$ of Formula (XI) is selected from H or Me, and $R^2$ of Formula (XI) is selected from H or

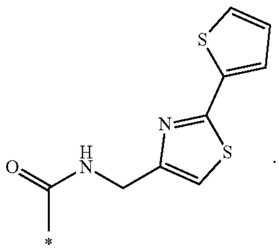

.

In any of the compounds described herein, the ILM can have the structure of Formula (XII), which is derived from the chemotypes cross-referenced in Mannhold, R., et al. IAP antagonists: promising candidates for cancer therapy, *Drug Discov. Today,* 15 (5-6), 210-9 (2010), or an unnatural mimetic thereof:

(XII)

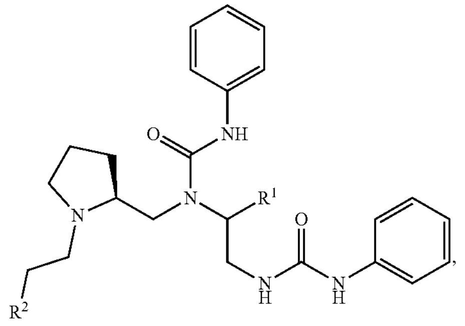

wherein: $R^1$ of Formula (XII) is selected from:

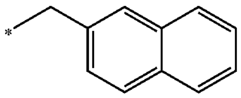

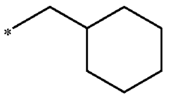

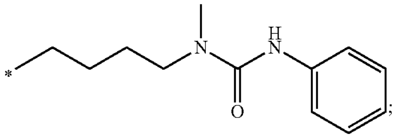

and $R^2$ of Formula (XII) is selected from:

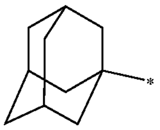

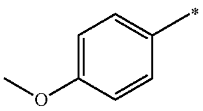

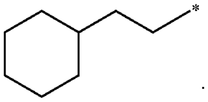

In any of the compounds described herein, the IAP E3 ubiquitin ligase binding moiety is selected from the group consisting of:

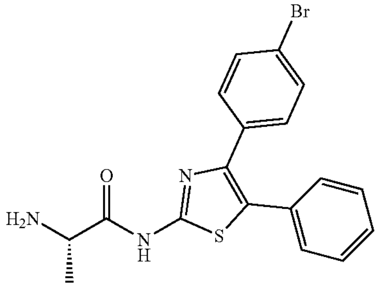

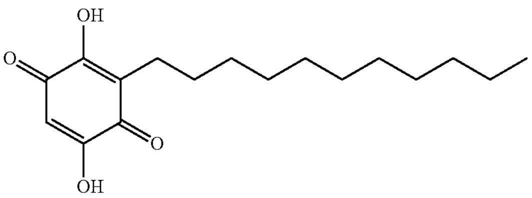

-continued
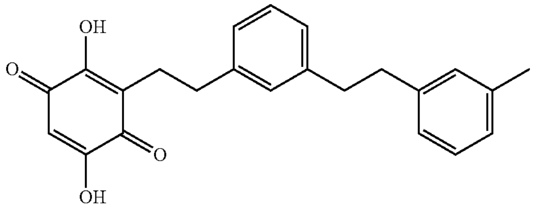
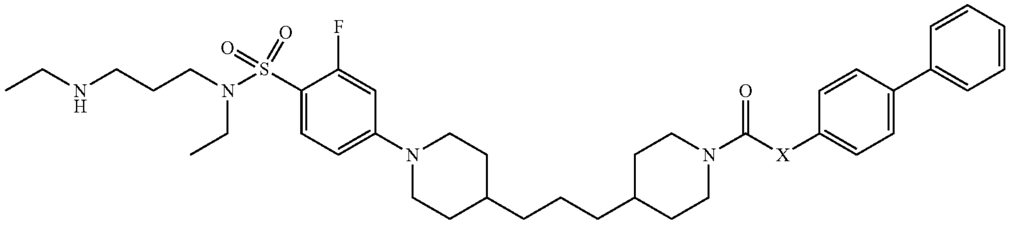
X = NH, bond
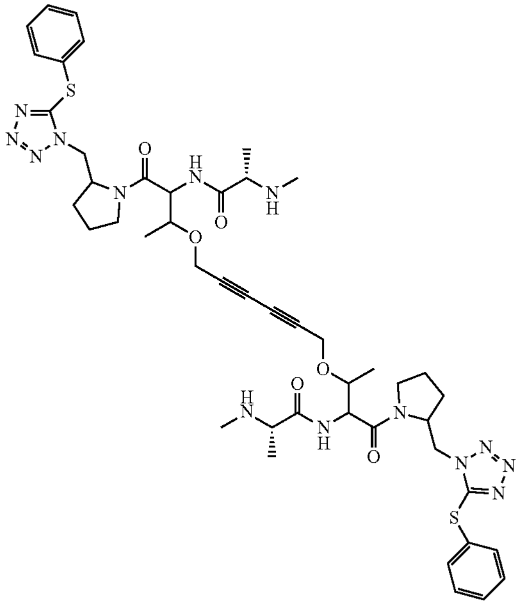
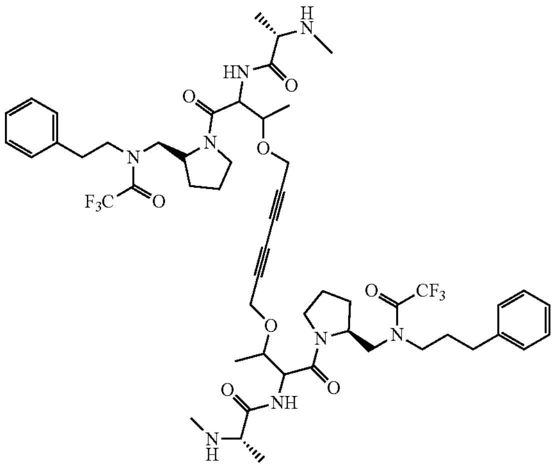
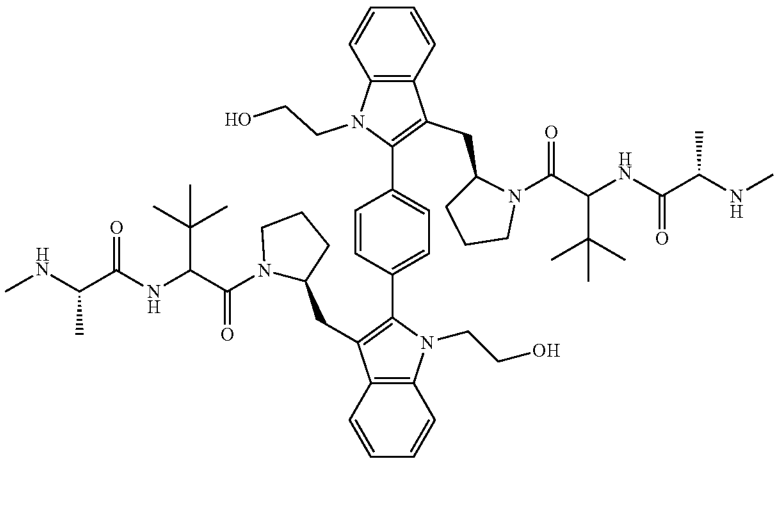

-continued
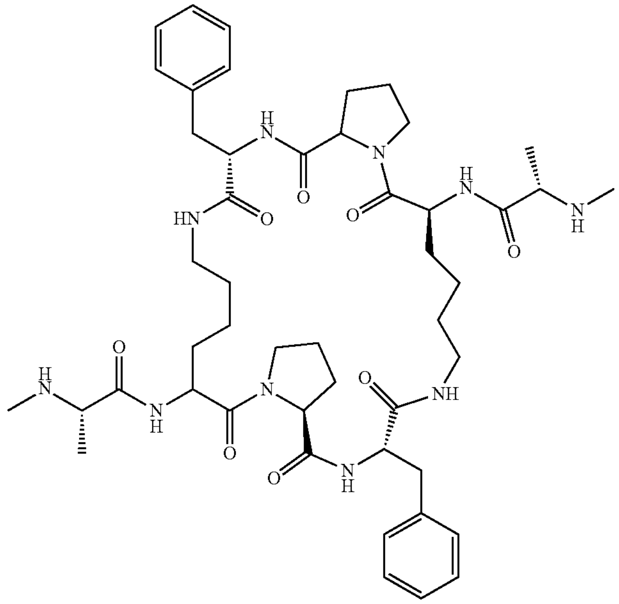
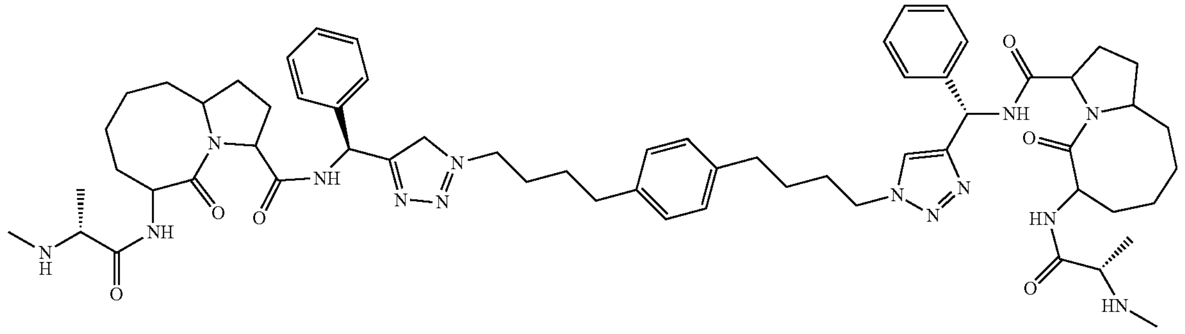
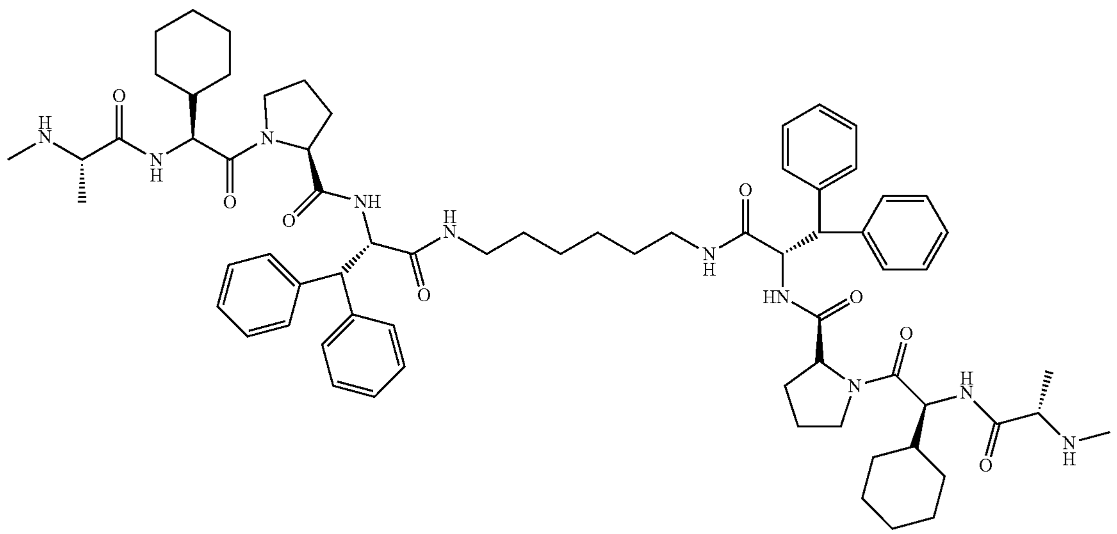
and

-continued

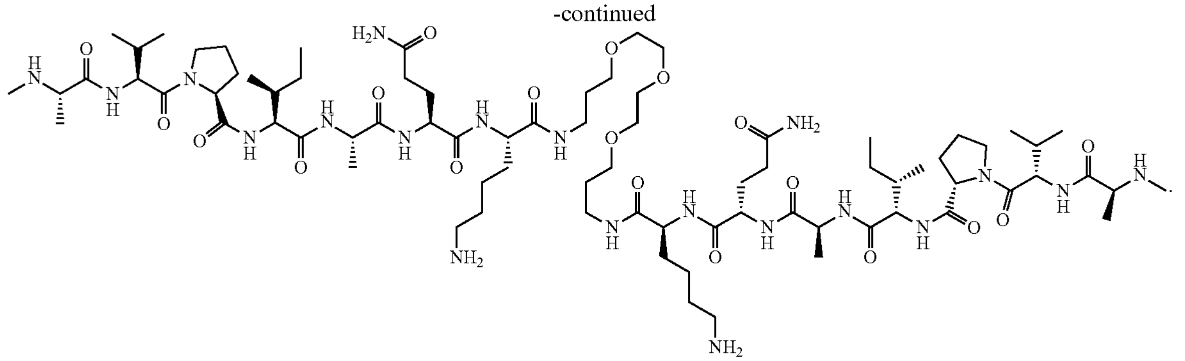

In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.,* 20 (2), 251-67 (2010), or an unnatural mimetic thereof:

(XIII)

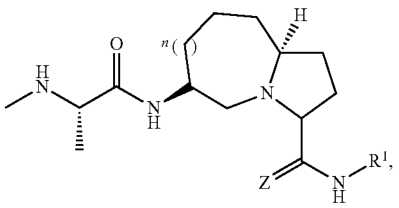

n = 0, 2 or, preferably, 1 wherein:

Z of Formula (XIII) is absent or O;

$R^1$ of Formula (XIII) is selected from:

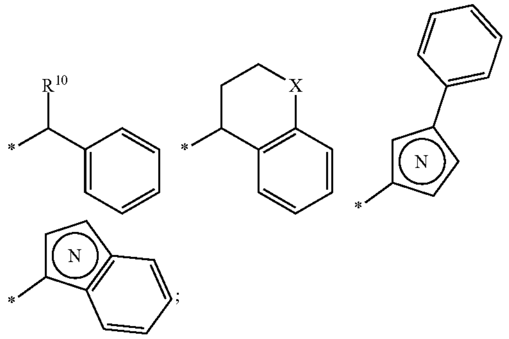

$R^{10}$ of

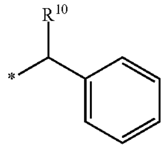

is selected from H, alkyl, or aryl;

X is selected from CH2 and O; and

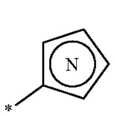

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.,* 20 (2), 251-67 (2010), or an unnatural mimetic thereof:

(XIV)

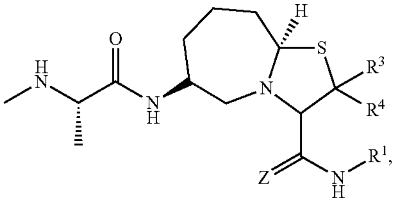

wherein:

Z of Formula (XIV) is absent or O;

$R^3$ and $R^4$ of Formula (XIV) are independently selected from H or Me;

$R^1$ of Formula (XIV) is selected from:

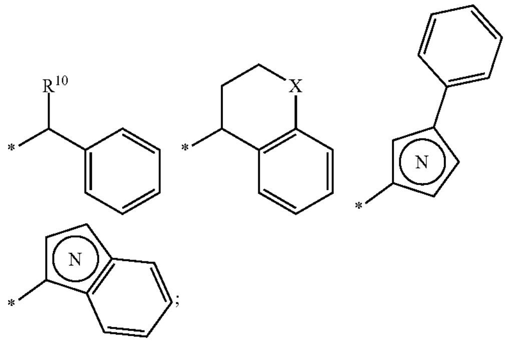

$R^{10}$ of

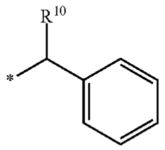

is selected from H, alkyl, or aryl;

X of

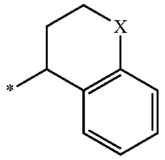

is selected from CH2 and O; and

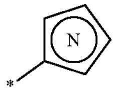

of

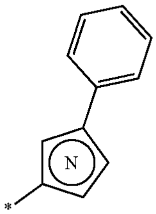

or

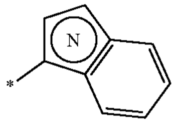

is a nitrogen-containing heterary l.

In any of the compounds described herein, the ILM is selected from the group consisting of:

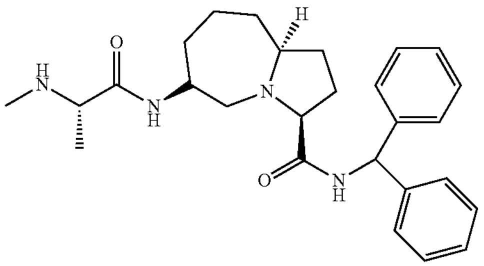

and

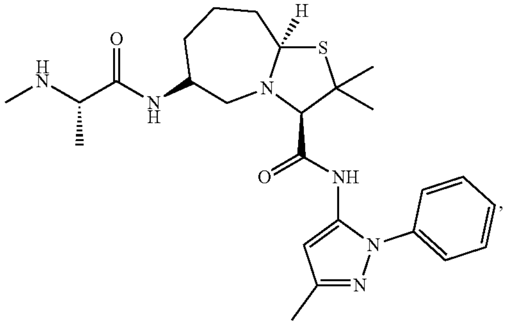

which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

(XV)

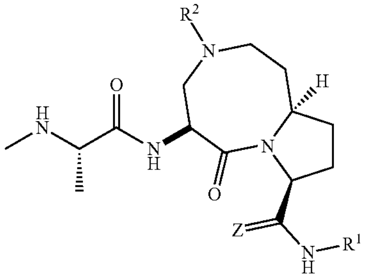

wherein:

Z of Formula (XV) is absent or O;

$R^1$ of Formula (XV) is selected from:

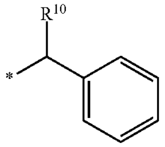

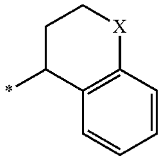

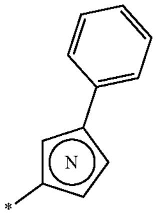

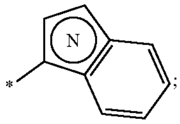

;

$R^{10}$ of

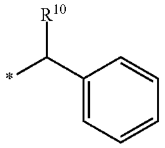

is selected from H, alkyl, or aryl;

X of

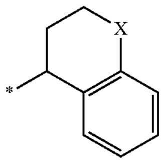

is selected from CH2 and O; and

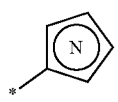
of
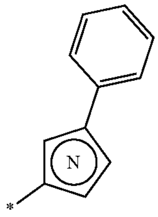
or
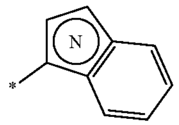

is a nitrogen-containing heterary1; and $R^2$ of Formula (XV) selected from H, alkyl, or acyl;

In a particular embodiment, the ILM has the following structure:

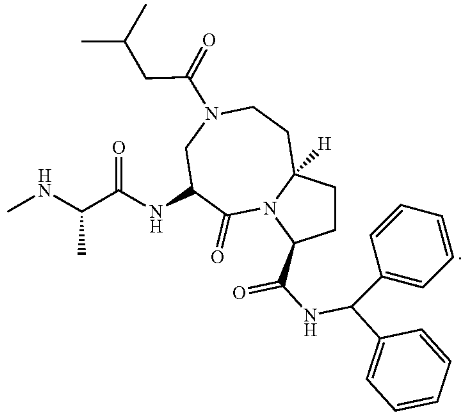

In any of the compounds described herein, the ILM can have the structure of Formula (XVI), which is based on the IAP ligand described in WO Pub. No. 2006/069063, or an unnatural mimetic thereof:

(XVI)

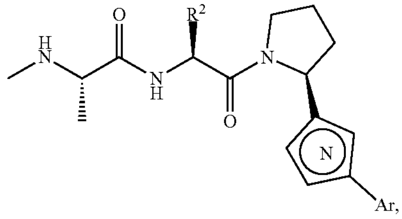

wherein:

$R^2$ of Formula (XVI) is selected from alkyl, cycloalkyl and heterocycloalkyl; more preferably, from isopropyl, tert-butyl, cyclohexyl and tetrahydropyranyl, most preferably from cyclohexyl;

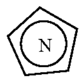

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVII)

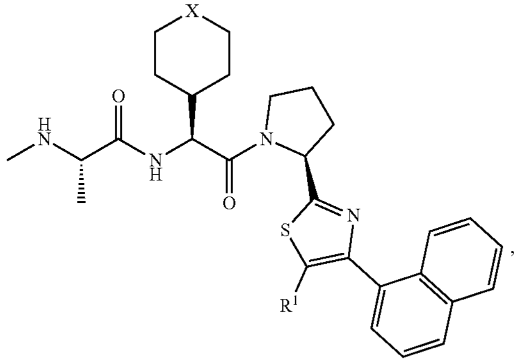

wherein:

$R^1$ of Formula (XVII) is selected from the group halogen (e.g. fluorine), cyano,

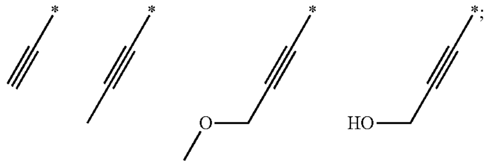

X of Formula (XVII) is selected from the group O or CH2.

In any of the compounds described herein, the ILM can have the structure of Formula (XVIII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVIII)

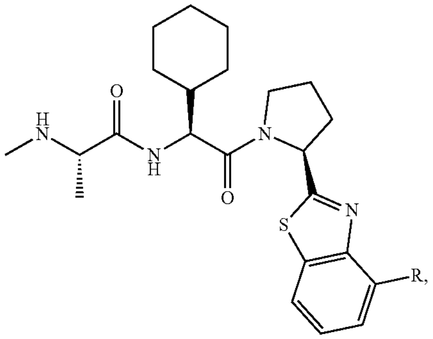

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., *Antogonists of inhibitors of apoptosis proteins based on thiazole amide isosteres*, Bioorg. Med. Chem. Lett., 20(7), 2229-33 (2010), or an unnatural mimetic thereof:

(XIX)

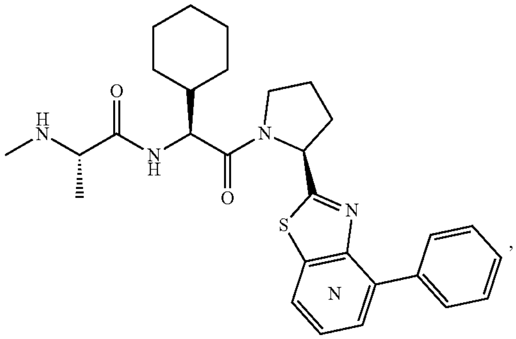

wherein

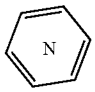

is a 6-member nitrogen heteroaryl.

In a certain embodiment, the ILM of the composition is selected from the group consisting of:

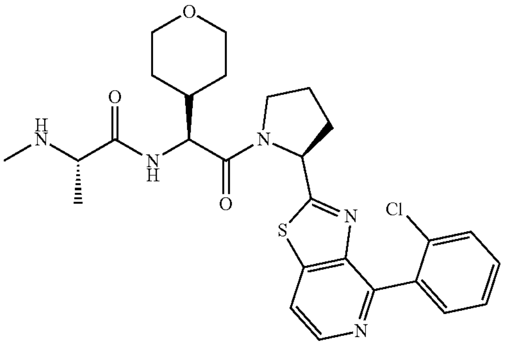

and

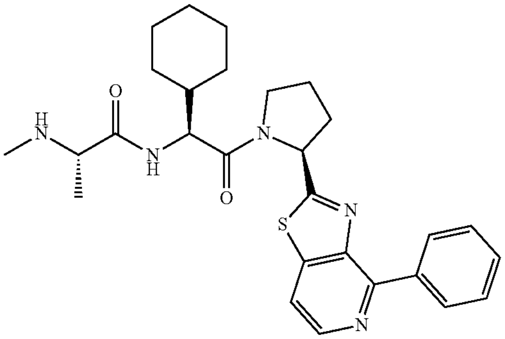

.

In certain embodiments, the ILM of the composition is selected from the group consisting of:

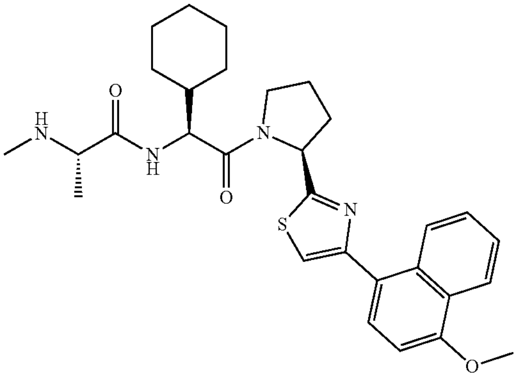

,

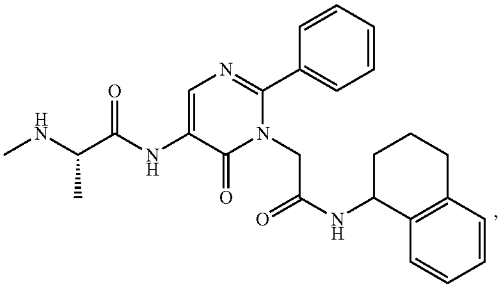

, and

-continued

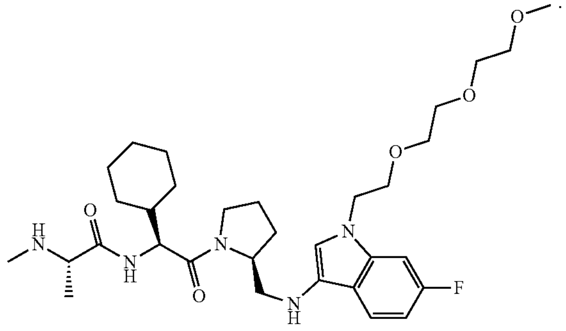

In any of the compounds described herein, the ILM can have the structure of Formula (XX), which is based on the IAP ligands described in WO Pub. No. 2007/101347, or an unnatural mimetic thereof:

(XX)

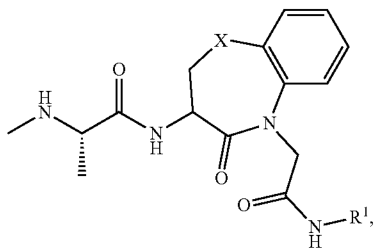

wherein X of Formula (XX) is selected from $CH_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

(XXI)

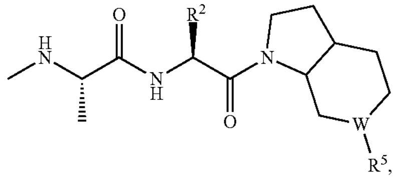

wherein:

$R^2$ of Formula (XXI) is selected from:

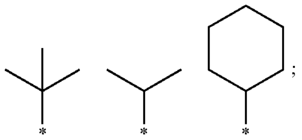

$R^5$ of Formula (XXI) is selected from:

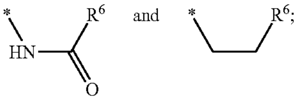

and

W of Formula (XXI) is selected from CH or N; and $R^6$ of

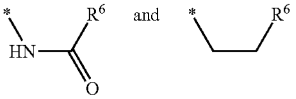

and are independently a mono- or bicyclic fused aryl or heteroaryl.

In certain embodiments, the ILM of the compound is selected from the group consisting of:

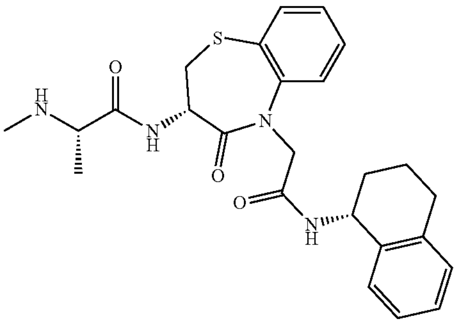

,

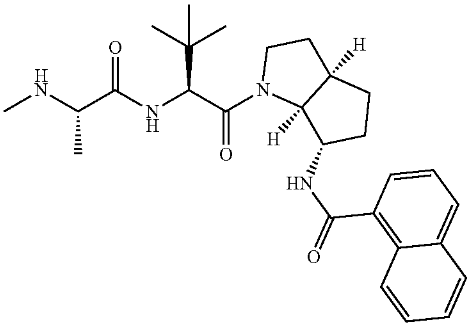

, and

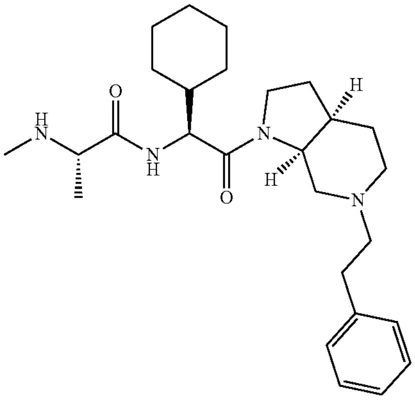

In certain embodiments, the ILM of the compound is selected from the group consisting of:

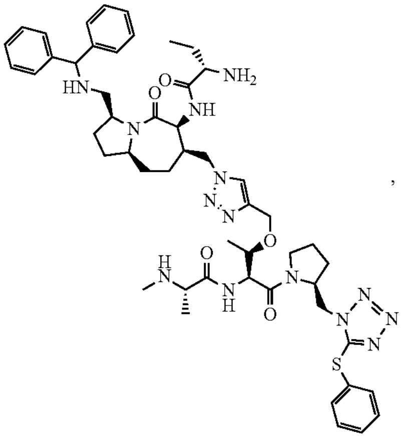
,
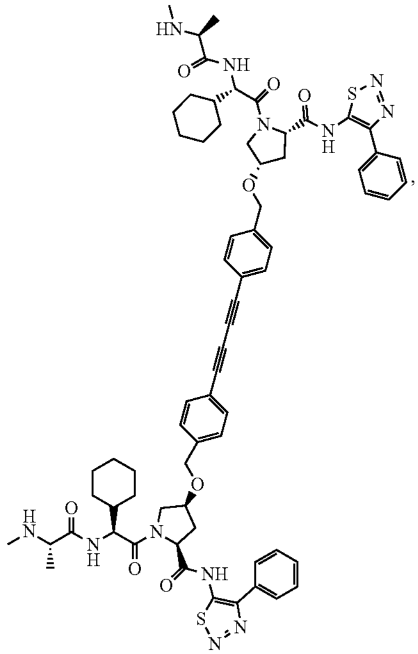
,
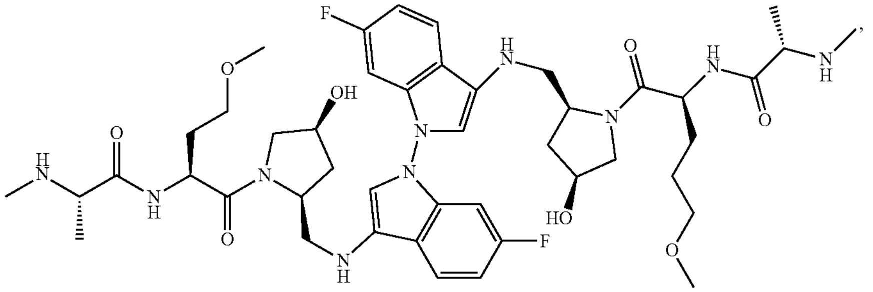
,
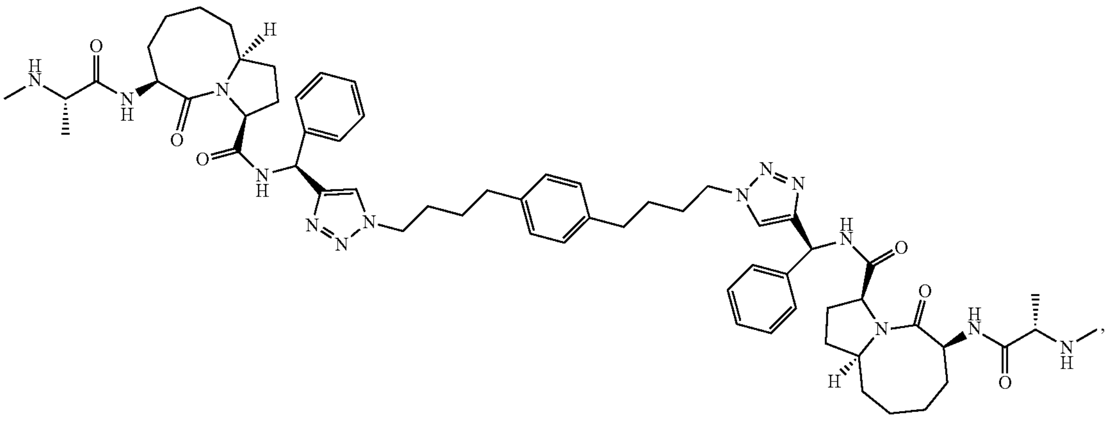
, and

-continued

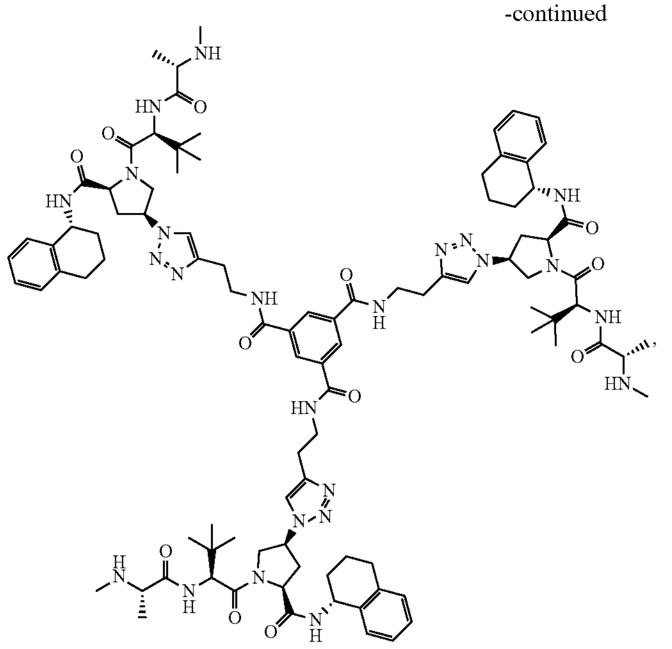

which are described in WO Pub. No. 2009/060292, U.S. Pat. No. 7,517,906, WO Pub. No. 2008/134679, WO Pub. No. 2007/130626, and WO Pub. No. 2008/128121.

In any of the compounds described herein, the ILM can have the structure of Formula (XXII) or (XXIII), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof:

(XXII)

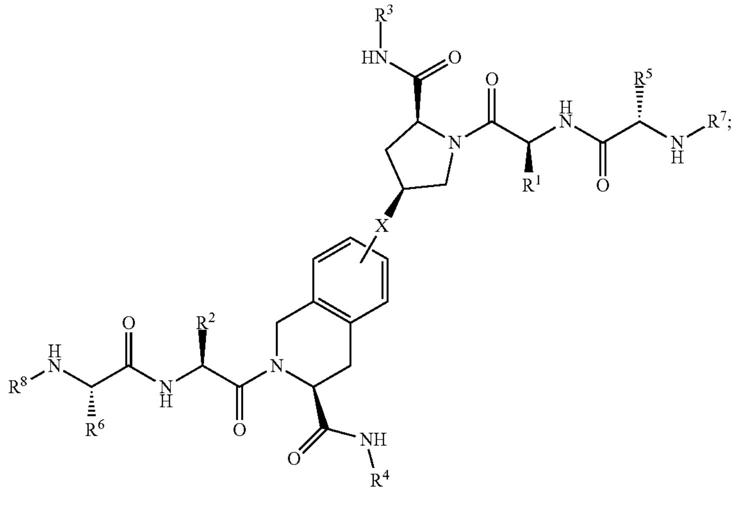

or

-continued (XXIII)

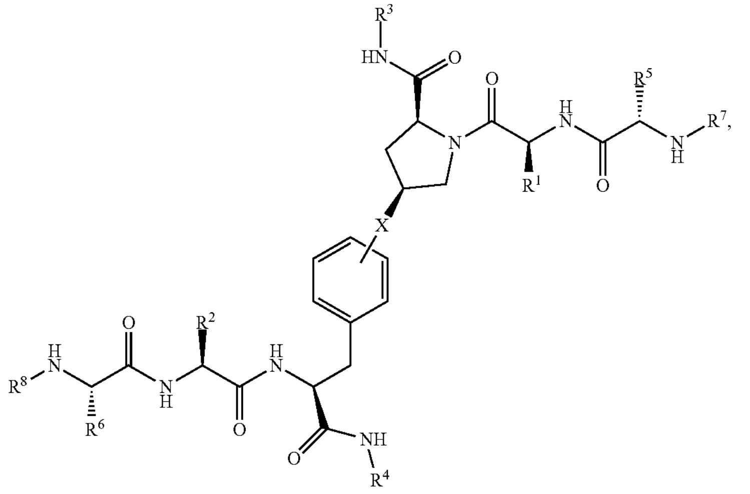

wherein:

$R^1$ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

or alternatively, $R^1$ and $R^2$ of Formula (XXII) or (XXIII) are independently optionally substituted thioalkyl wherein the substituents attached to the S atom of the thioalkyl are optionally substituted alkyl, optionally substituted branched alkyl, optionally substituted heterocyclyl, $—(CH_2)_vCOR^{20}$, $—CH_2CHR^{21}COR^{22}$ or $—CH_2R^{23}$;

wherein:

v is an integer from 1-3;

$R^{20}$ and $R^{22}$ of $—(CH_2)_vCOR^{20}$ and $—CH_2R^{23}$ are independently selected from OH, $NR^{24}R^{25}$ or $OR^{26}$;

$R^{21}$ of $—CH_2CHR^{21}COR^2$ is selected from the group $NR^{24}R^{25}$;

$R^{23}$ of $—CH_2R^{23}$ is selected from optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, $—CH_2(OCH_2CH_2O)_mCH_3$, or a polyamine chain, such as spermine or spermidine;

$R^{26}$ of $OR^{26}$ is selected from optionally substituted alkyl, wherein the optional substituents are OH, halogen or $NH_2$; and m is an integer from 1-8;

$R^3$ and $R^4$ of Formula (XXII) or (XXIII) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXII) or (XXIII) are independently selected from hydrogen, optionally substituted alkyl or optionally substituted cycloalkyl; and X is selected from a bond or a chemical linker group, and/or a pharmaceutically acceptable salt, tautomer or stereoisomer thereof.

In certain embodiments, X is a bond or is selected from the group consisting of:

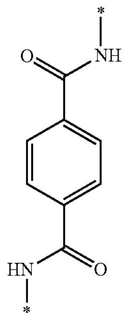

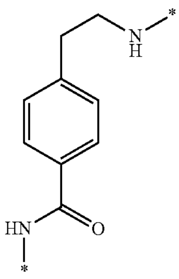

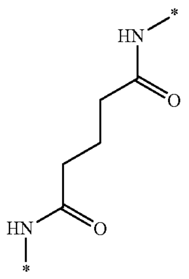

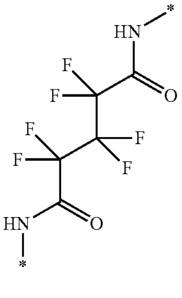

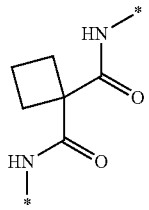

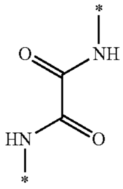

-continued

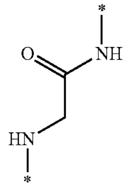
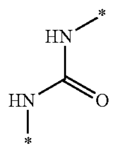
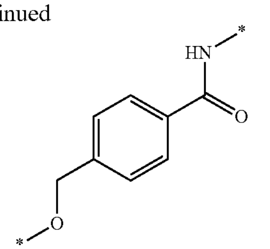
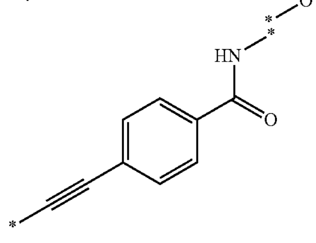

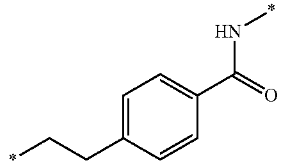

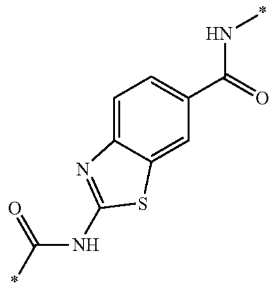
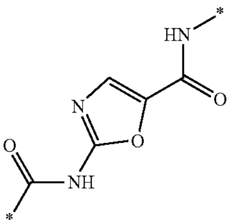

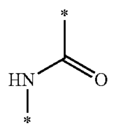
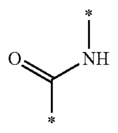
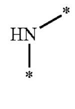
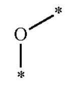

wherein "*" is the point of attachment of a PTM, L or ULM, e.g., an ILM.

In any of the compounds described herein, the ILM can have the structure of Formula (XXIV) or (XXVI), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof, and the chemical linker to linker group L as shown:

(XXIV)

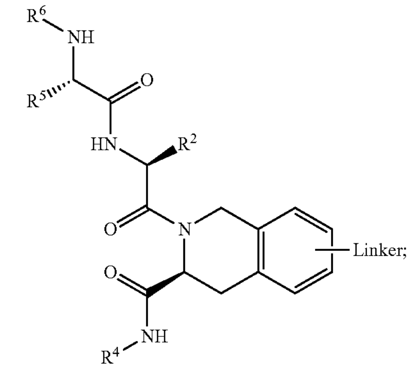

(XXV)

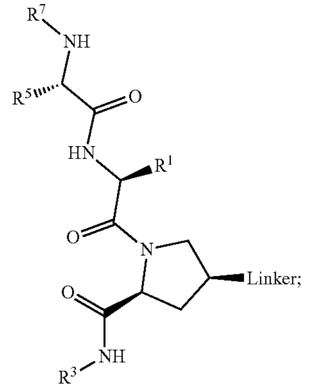

or (XXVI)

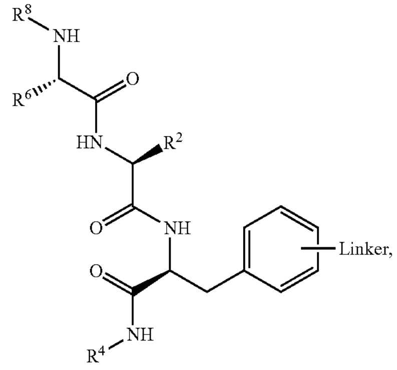

wherein:

$R^1$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl; or alternatively, $R^1$ and $R^2$ of Formula (XXIV), (XXV) or (XXVI) are independently selected from optionally substituted thioalkyl wherein the substituents attached to the S atom of the thioalkyl are optionally substituted alkyl, optionally substituted branched alkyl, optionally substituted heterocyclyl, $-(CH_2)_vCOR^{20}$, $-CH_2CHR^{21}COR^{22}$ or $-CH_2R^{23}$, wherein:

v is an integer from 1-3;

$R^{20}$ and $R^{22}$ of $—(CH_2)_vCOR^{20}$ and $—CH_2R^{23}$ are independently selected from OH, $NR^{24}R^{25}$ or $OR^{26}$;

$R^{21}$ of $—CH_2CHR^{21}COR^2$ is selected from $NR^{24}R^{25}$;

$R^{23}$ of $—CH_2R^{23}$ is selected from optionally substituted aryl or optionally substituted heterocyclyl, wherein the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, $—CH_2(OCH_2CH_2O)_mCH_3$, or a polyamine chain, such as spermine or spermidine;

$R^{26}$ of $OR^{26}$ is selected from optionally substituted alkyl, wherein the optional substituents are OH, halogen or $NH_2$; and m is an integer from 1-8;

$R^3$ and $R^4$ of Formula (XXIV), (XXV) or (XXVI) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXIV), (XXV) or (XXVI) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXVI):

$R^7$ and $R^8$ are selected from the H or Me;

$R^5$ and $R^6$ are selected from the group comprising:

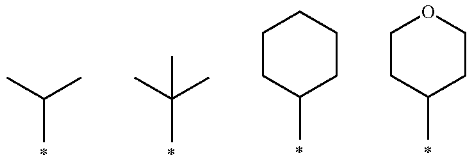

$R^3$ and $R^4$ are selected from the group comprising:

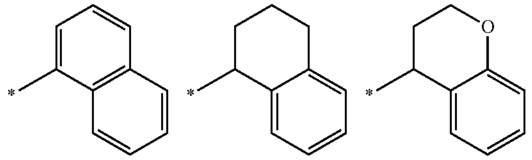

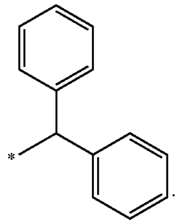

In any of the compounds described herein, the ILM can have the structure of Formula (XXVII) or (XXVII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof:

(XXVII)

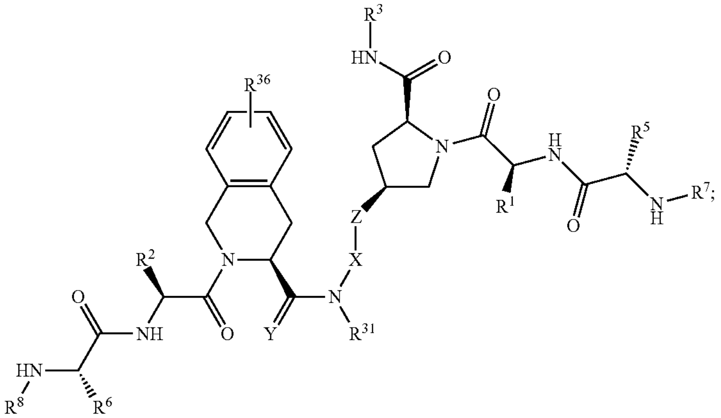

and

-continued (XXVIII)

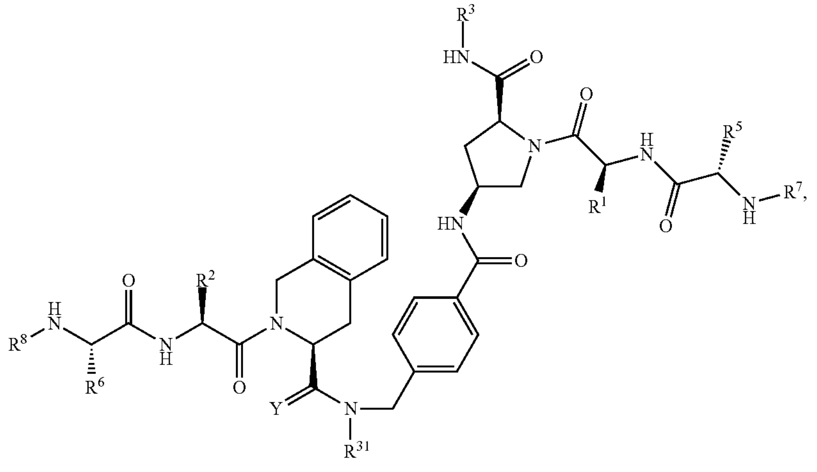

wherein:

$R^{35}$ is 1-2 substituents selected from alkyl, halogen, alkoxy, cyano and haloalkoxy;

$R^1$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl; or alternatively, $R^1$ and $R^2$ of Formula (XXVII) and (XXVIII) are independently selected from an optionally substituted thioalkyl —$CR^{60}R^{61}SR^{70}$, wherein $R^{60}$ and $R^{61}$ are selected from H or methyl, and $R^{70}$ is selected from an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$, wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{21}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]_\psi CH_2CH_2(CH_2)_{\overline{\omega}}$ $NH_2$, such as spermine or spermidine;

wherein $\delta$=0-2, $\psi$=1-3, $\overline{\omega}$=0-2;

$R^{26}$ of $OR^{26}$ is an optionally substituted alkyl, wherein the optional substituents are OH, halogen or $NH_2$; and m is an integer from 1-8, $R^3$ and $R^4$ of Formula (XXVII) and (XXVIII) are independently selected from an optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXVII) and (XXVIII) are independently selected from hydrogen, optionally substituted alkyl or optionally substituted cycloalkyl;

$R^{31}$ of Formulas (XXVII) and (XXVIII) is selected from alkyl, aryl, arylalkyl, heteroaryl or heteroarylalkyl optionally further substituted, preferably selected form the group consisting of:

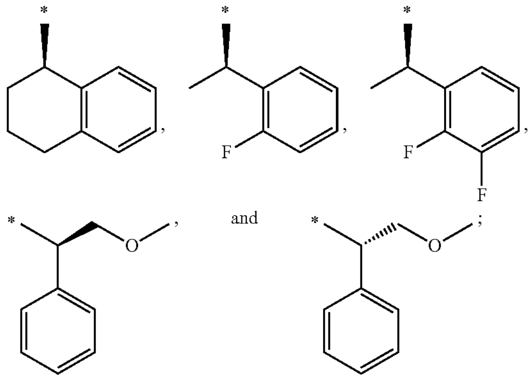

, , , and ;

X of Formulas (XXVII) and (XXVIII) is selected from —$(CR^{81}R^{82})_m$—, optionally substituted heteroaryl or heterocyclyl,

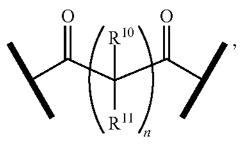

,

-continued

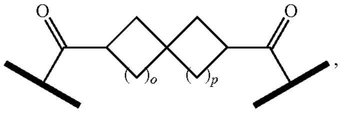,

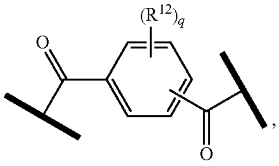,

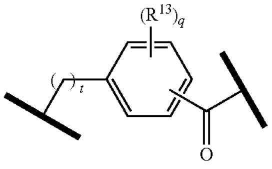

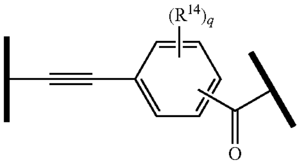, 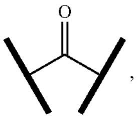,

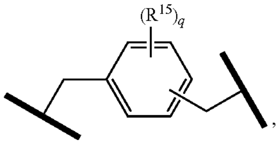,

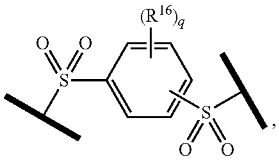,

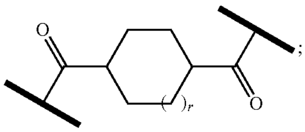;

Z of Formulas (XXVII) is selected from C═O, —O—, —NR, —CONH—, —NHCO—, or may be absent;

$R^{81}$ and $R^{82}$ of $—(CR^{81}R^{82})_m—$ are independently selected from hydrogen, halogen, alkyl or cycloalkyl, or $R^{81}$ and $R^{82}$ can be taken together to form a carbocyclic ring;

$R^{10}$ and $R^{11}$ of

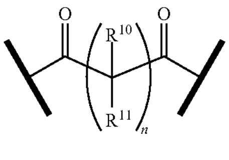

are independently selected from hydrogen, halogen or alkyl;

$R^{12}$, $R^{13}$, $R^{14}$, $R^{15}$ and $R^{16}$ of

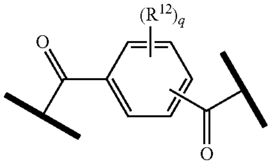,

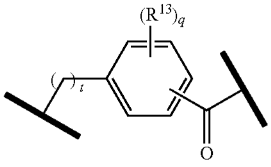,

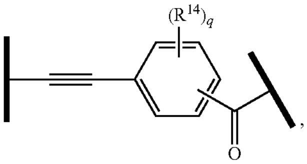,

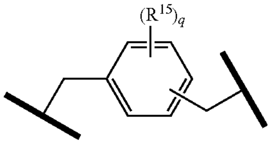, and

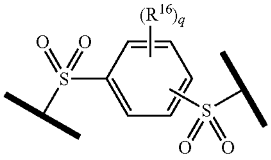, are independently selected from hydrogen, halogen or optionally substituted alkyl or $OR^{17}$;

$R^{17}$ is selected from hydrogen, optionally substituted alkyl or optionally substituted cycloalkyl;

m and n of $—(CR^{21}R^{22})_m—$ and

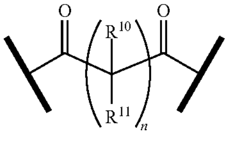

are independently 0, 1, 2, 3, or 4;

o and p of

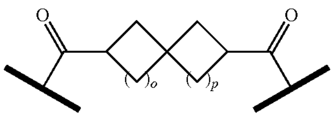

are independently 0, 1, 2 or 3;

q and t of

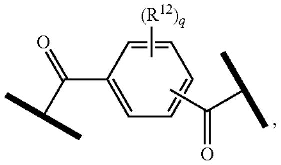

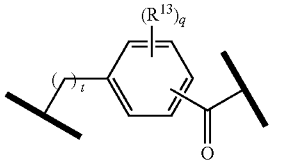

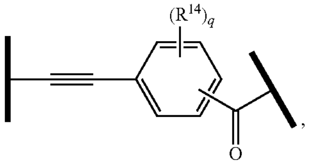

and

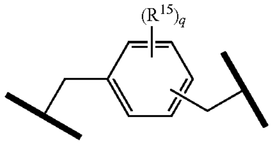

are independently 0, 1, 2, 3, or 4;

r of

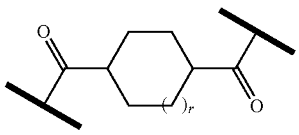

is 0 or 1;

and/or a pharmaceutically acceptable salt, tautomer or stereoisomer thereof.

In any of the compounds described herein, the ILM can have the structure of Formula (XXIX), (XXX), (XXXI), or (XXXII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

(XXIX)

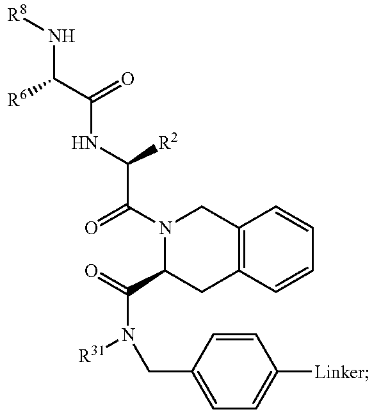

(XXX)

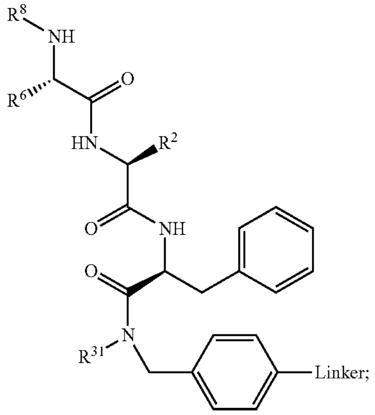

(XXXI)

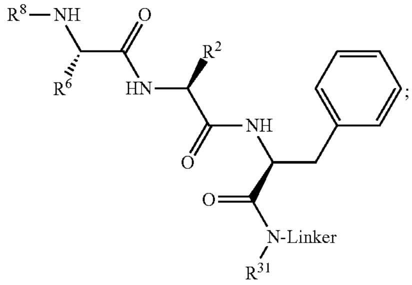

and (XXXII)

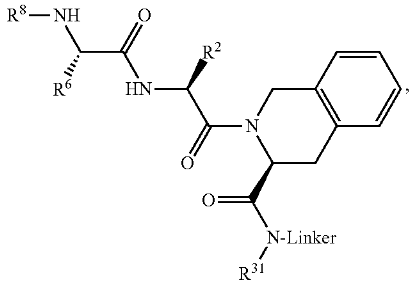

wherein:

$R^2$ of Formula (XXIX) through (XXXII) is selected from H, an optionally substituted alkyl, optionally substituted cycloalkyl, optionally substituted cycloalkylalkyl, optionally substituted heterocyclyl, optionally substituted arylalkyl or optionally substituted aryl; or alternatively;

$R^1$ and $R^2$ of Formula (XXVII) and (XXVIII) are independently selected from H, an optionally substituted thioalkyl $—CR^{60}R^{61}SR^{70}$ wherein $R^{60}$ and $R^{61}$ are selected from H or methyl, and $R^{70}$ is an optionally substituted alkyl, optionally substituted branched alkyl, optionally substituted heterocyclyl, $—(CH_2)_vCOR^{20}$, $—CH_2CHR^{21}COR^{22}$ or $—CH_2R^{23}$;

wherein:

v is an integer from 1-3;

$R^{20}$ and $R^{22}$ of $—(CH_2)_vCOR^{20}$ and $—CH_2CHR^{21}COR^{22}$ are independently selected from OH, $NR^{24}R^{25}$ or $OR^{26}$;

$R^{21}$ of $—CH_2CHR^{21}COR^{22}$ is selected from $NR^{24}R^{25}$;

$R^{23}$ of $—CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, $—CH_2CH_2(OCH_2CH_2)_mCH_3$, or a polyamine chain $—[CH_2CH_2(CH_2)_\delta NH]_\psi CH_2CH_2(CH_2)_{\overline{\omega}}NH_2$, such as spermine or spermidine, wherein $\delta$=0-2, $\psi$=1-3, $\overline{\omega}$=0-2;

$R^{26}$ of $OR^{26}$ is an optionally substituted alkyl, wherein the optional substituents are OH, halogen or $NH_2$;

m is an integer from 1-8;

$R^6$ and $R^8$ of Formula (XXIX) through (XXXII) are independently selected from hydrogen, optionally substituted alkyl or optionally substituted cycloalkyl; and $R^{31}$ of Formulas (XXIX) through (XXXII) is selected from alkyl, aryl, arylalkyl, heteroaryl or heteroarylalkyl optionally further substituted, preferably selected form the group consisting of:

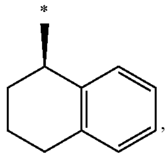,
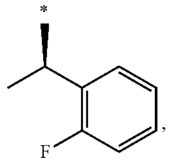,
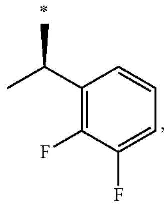,

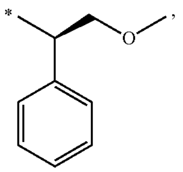,
and
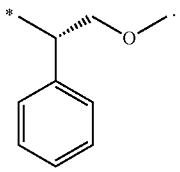

In certain embodiments, the ILM of the compound is:

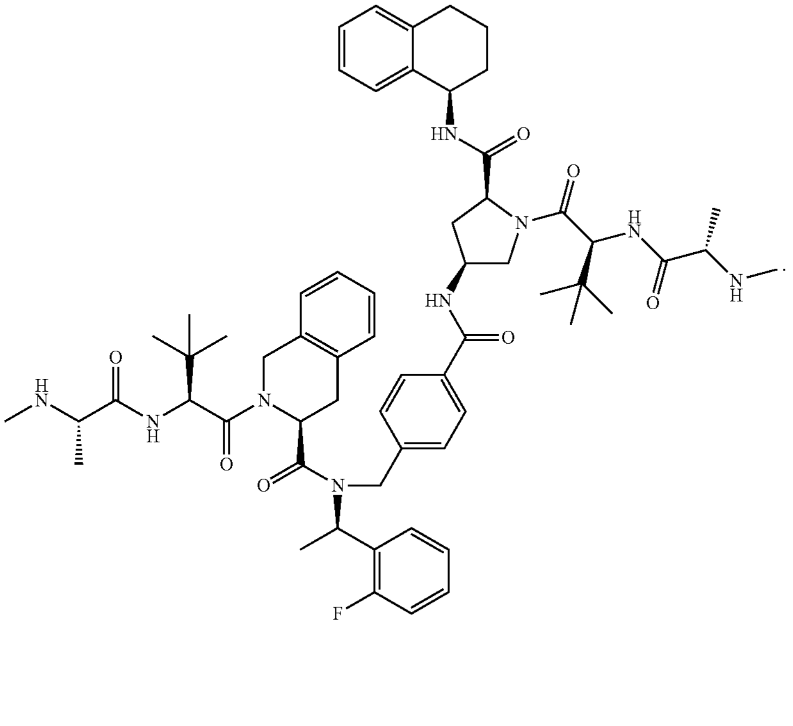

In any of the compounds described herein, the ILM can have the structure of Formula (XXXIII), which are derived from the IAP ligands described in WO Pub. No. 2014/074658 and WO Pub. No. 2013/071035, or an unnatural mimetic thereof:

(XXXIII)

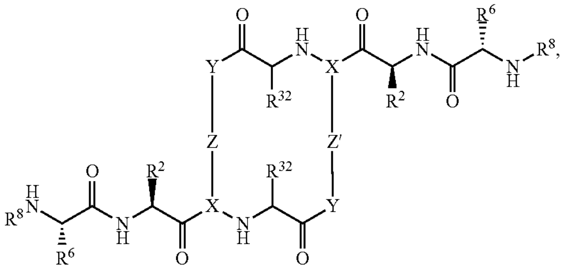

wherein:

$R^2$ of Formula (XXXIII) is selected from H, an optionally substituted alkyl, optionally substituted cycloalkyl, optionally substituted cycloalkylalkyl, optionally substituted heterocyclyl, optionally substituted arylalkyl or optionally substituted aryl;

$R^6$ and $R^8$ of Formula (XXXIII) are independently selected from hydrogen, optionally substituted alkyl or optionally substituted cycloalkyl;

$R^{32}$ of Formula (XXXIII) is selected from (C1-C4 alkylene)-$R^{33}$ wherein $R^{33}$ is selected from hydrogen, aryl, heteroaryl or cycloalkyl optionally further substituted;

X of Formula (XXXIII) is selected from:

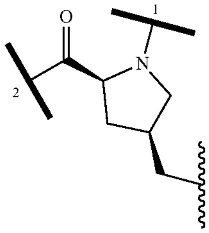,
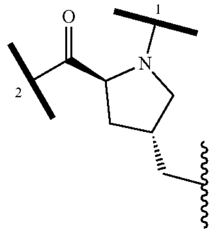,
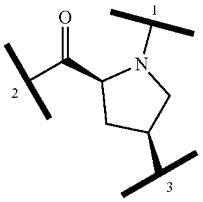,
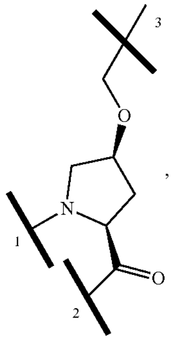,

-continued

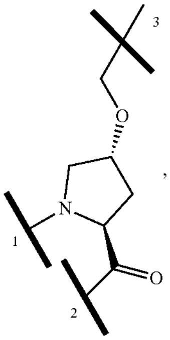,
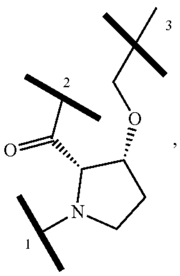,
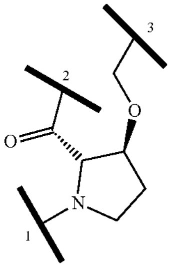,
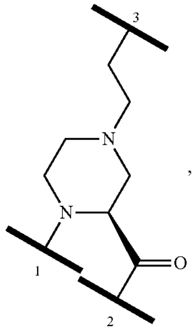,
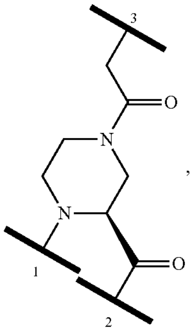, and
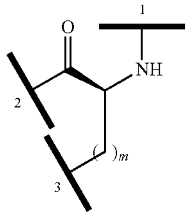;

Z and Z' of Formula (XXXIII) are independently selected from:

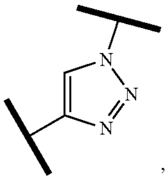,
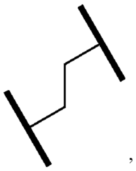,
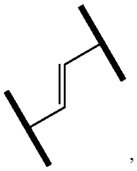,
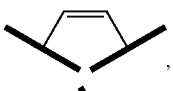,
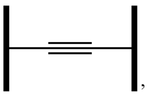,
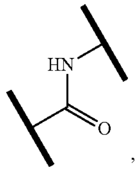,
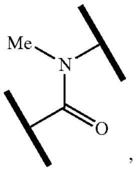,
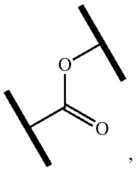,
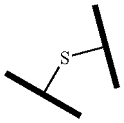, and -continued
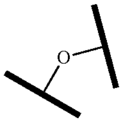
,
wherein each
represents a point of attachment to the compound, and Z and Z' cannot both be
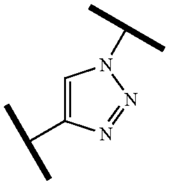
in any given compound;
Y of Formula (XXXIII) is selected from:
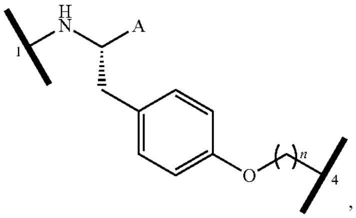
,
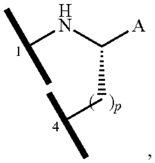
,
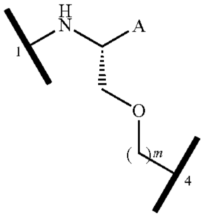
,
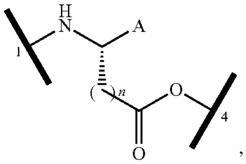
,
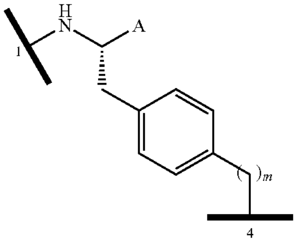
,
-continued
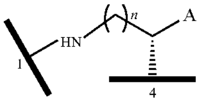
,
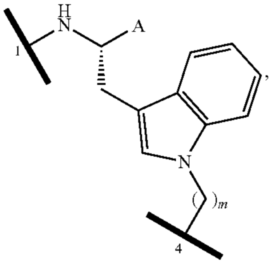
,
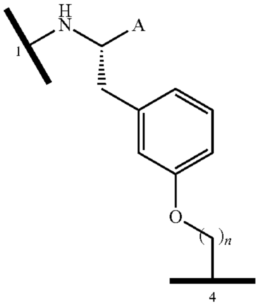
, and
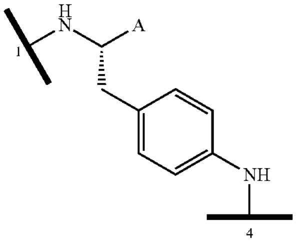
,
wherein Z and Z' of Formula (XXXIII) are the same and Z is
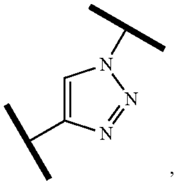
,
wherein each
represents a point of attachment to the compound, X is selected from:
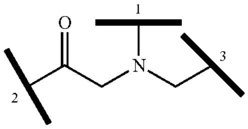
,
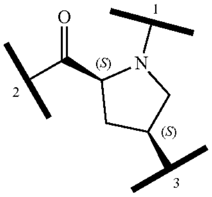
, -continued
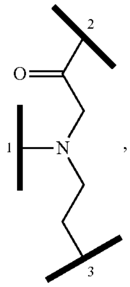
,
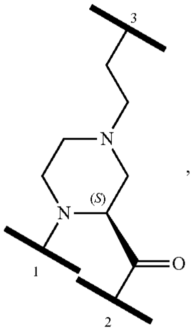
,
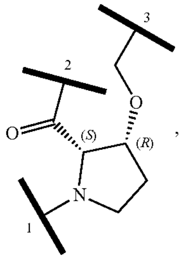
,
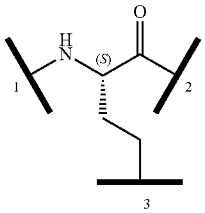
,
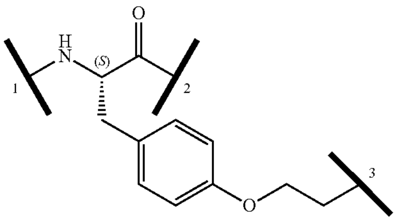
,
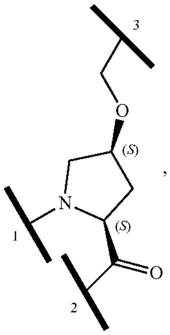
,
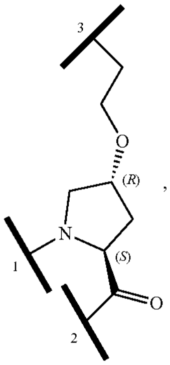
,
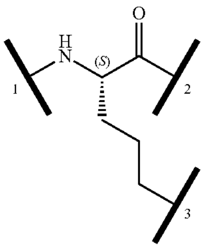
,
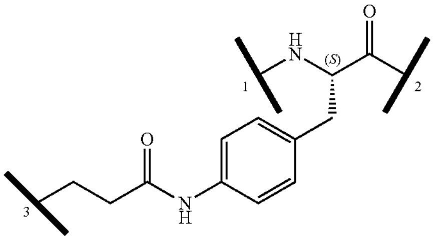
,
-continued
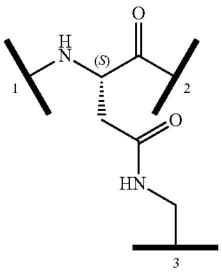
,
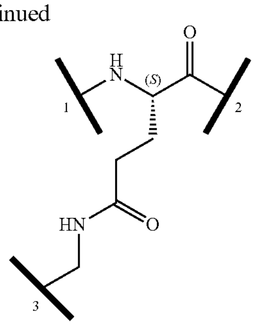
,
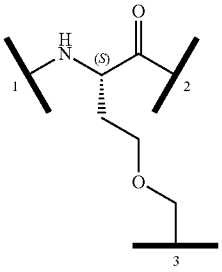
,
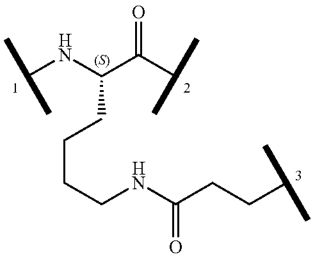
,
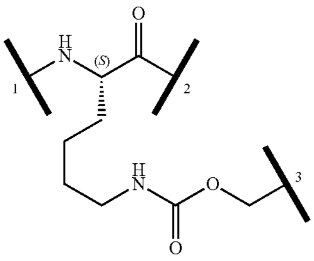
,
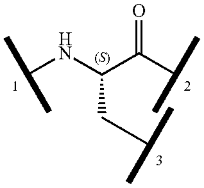
,
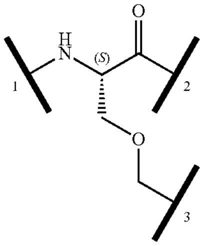
, and
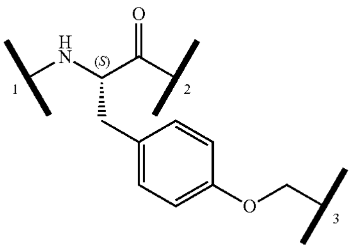
, and
Y of Formula (XXXIII) is independently selected from:
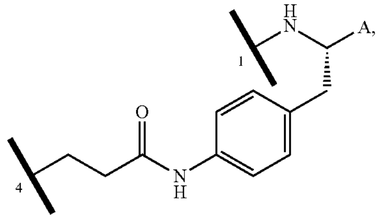
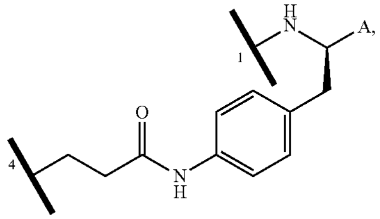
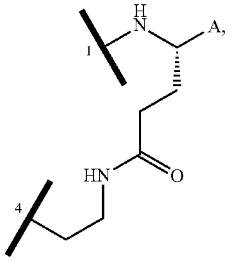
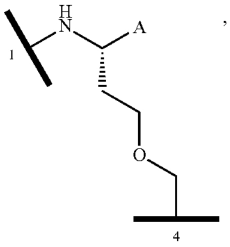
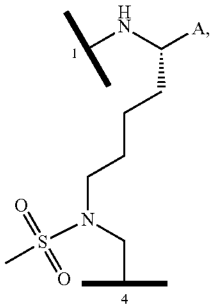
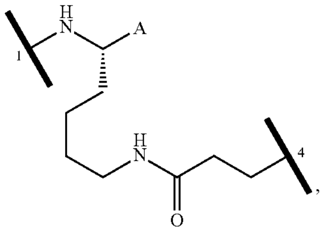
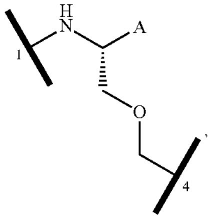
-continued
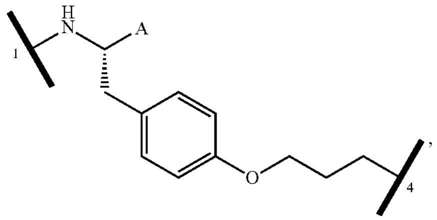
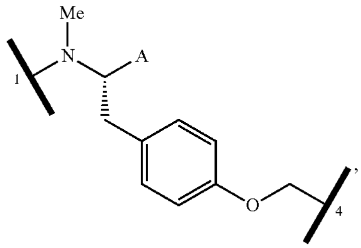
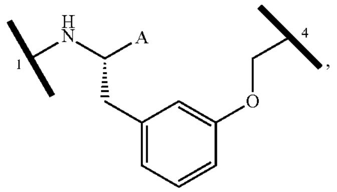
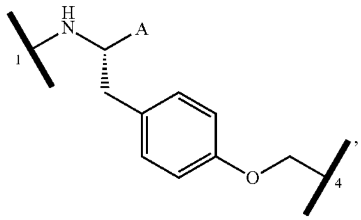
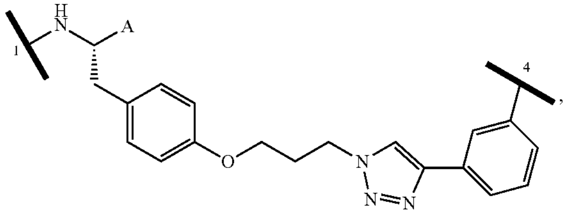
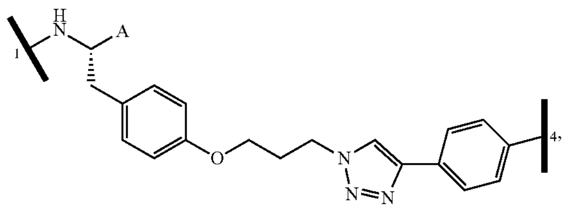
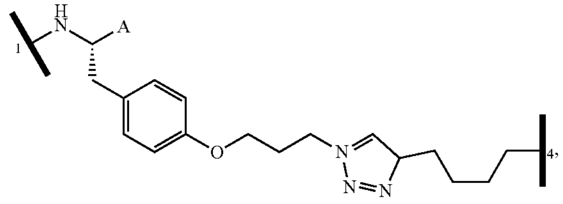
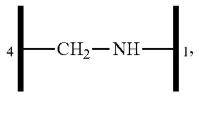
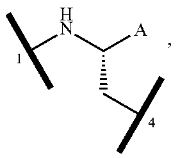

-continued

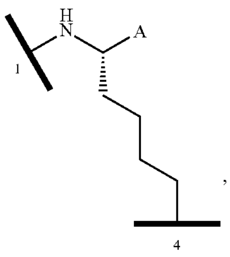

,

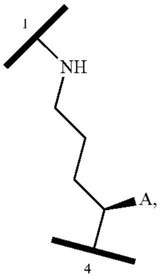

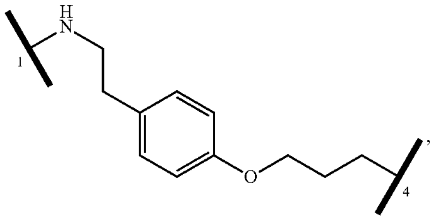

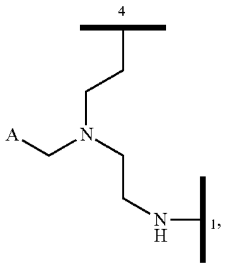

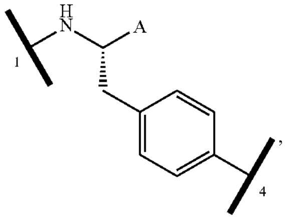

and

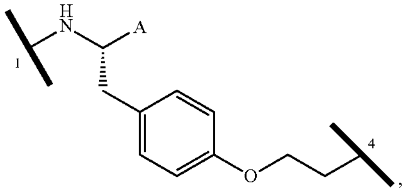

wherein:

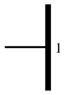

represents a point of attachment to a —C═O portion of the compound;

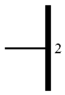

represents a point of attachment to a —NH portion of the compound;

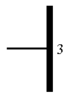

represents a first point of attachment to Z;

m is an integer from 0-3;

n is an integer from 1-3;

p is an integer from 0-4; and

A is —C(O)$R^3$;

$R^3$ is selected from —C(O)$R^3$ is OH, NHCN, $NHSO_2R^{10}$, $NHOR^{11}$ or $N(R^{12})(R^{13})$;

$R^{10}$ and $F^{11}$ of $NHSO_2R^{10}$ and $NHOR^{11}$ are independently selected from hydrogen, optionally substituted —$C_1$-$C_4$ alkyl, cycloalkyl, aryl, heteroaryl, heterocyclyl or heterocycloalkyl;

$R^{12}$ and $R^{13}$ of $N(R^{12})(R^{13})$ are independently selected from hydrogen, —$C_1$-$C_4$ alkyl, —($C_1$-$C_4$) alkylene)-NH—($C_1$-$C_4$ alkyl), and —($C_1$-$C_4$ alkylene)-O—($C_1$-$C_4$ hydroxyalkyl), or $R^{12}$ and $R^{13}$ taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXIV) or (XXXV), which are derived from the IAP ligands described in WO Pub. No. 2014/047024, or an unnatural mimetic thereof:

(XXXIV)

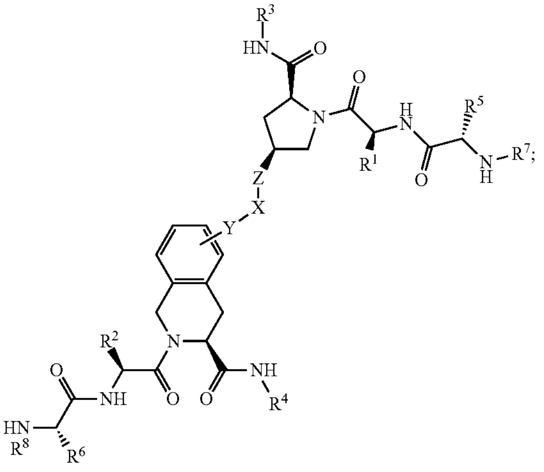

or

-continued (XXXV)

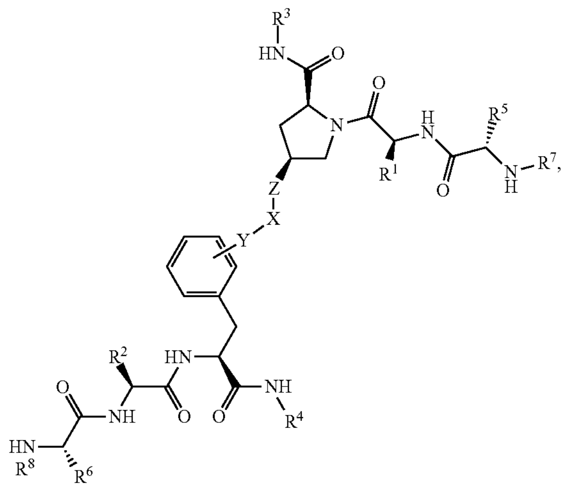

wherein:

X of Formula (XXXIV) or (XXXV) is absent or a group selected from $-(CR^{10}R^{11})_m-$, optionally substituted heteroaryl or optionally substituted heterocyclyl,

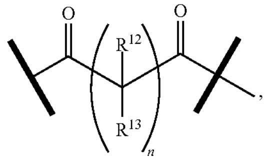
,

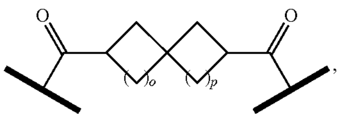
,

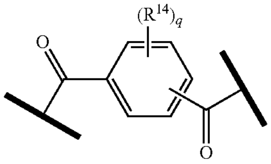
,

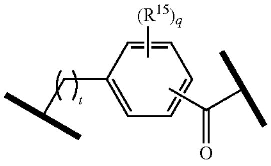
,

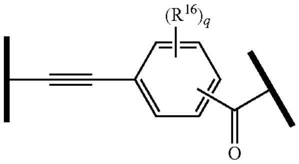
,

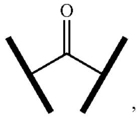
,

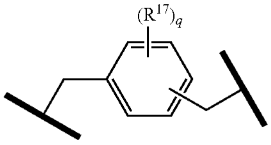
,

-continued

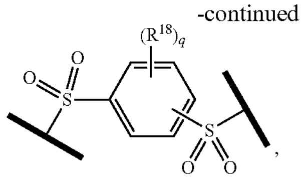
,

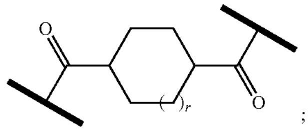
;

Y and Z of Formula (XXXIV) or (XXXV) are independently selected from C═O, —O—, $-NR^9-$, —CONH—, —NHCO— or may be absent;

$R^1$ and $R^2$ of Formula (XXXIV) or (XXXV) are independently selected from an optionally substituted alkyl, optionally substituted cycloalkyl, optionally substituted cycloalkylalkyl, optionally substituted arylalkyl, optionally substituted aryl, or $R^1$ and $R^2$ of Formula (XXXIV) or (XXXV) are independently selected from optionally substituted thioalkyl wherein the substituents attached to the S atom of the thioalkyl are optionally substituted alkyl, optionally substituted branched alkyl, optionally substituted heterocyclyl, $-(CH_2)_vCOR^{20}$, $-CH_2CHR^{21}COR^{22}$ or $-CH_2R^{23}$; wherein v is an integer from 1-3;

$R^{20}$ and $R^{22}$ of $-(CH_2)_vCOR^{20}$ and $-CH_2CHR^{21}COR^{22}$ are independently selected from OH, $NR^{24}R^{25}$ or $OR^{26}$;

$R^{21}$ of $-CH_2CHR^{21}COR^{22}$ is selected from $NR^{24}R^{25}$;

$R^{23}$ of $-CH_2R^{23}$ are selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, $-CH_2(OCH_2CH^{20})_mCH3$, or a polyamine chain;

$R^{26}$ is an optionally substituted alkyl, wherein the optional substituents are OH, halogen or $NH_2$;

m of $-(CR^{10}R^{11})_m-$ is an integer from 1-8;

$R^3$ and $R^4$ of Formula (XXXIV) or (XXXV) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXXIV) or (XXXV) are independently selected from hydrogen, optionally substituted alkyl or optionally substituted cycloalkyl;

$R^{10}$ and $R^{11}$ of $-(CR^{10}R^{11})_m-$ are independently selected from hydrogen, halogen or optionally substituted alkyl;

$R^{12}$ and $R^{13}$ of

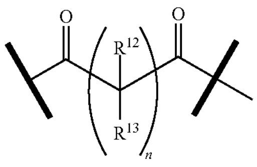

are independently selected from hydrogen, halogen or optionally substituted alkyl, or $R^{12}$ and $R^{13}$ can be taken together to form a carbocyclic ring;

$R^{14}$, $R^{15}$, $R^{16}$, $R^{17}$ and $R^{18}$ of

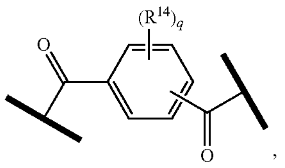

,

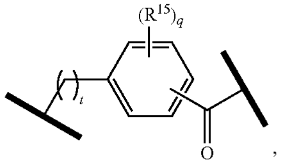

,

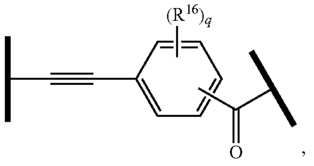

,

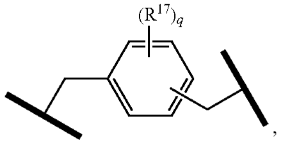

, and

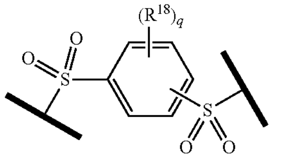

are independently selected from hydrogen, halogen, optionally substituted alkyl or $OR^{19}$;

$R^{19}$ of $OR^{19}$ is selected from hydrogen, optionally substituted alkyl or optionally substituted cycloalkyl;

m and n of $—(CR^{10}R^{11})_m—$ are independently 0, 1, 2, 3, or 4;

o and p of $—(CR^{10}R^{11})_m—$ are independently 0, 1, 2 or 3;

q of $—(CR^{10}R^{11})_m—$ is 0, 1, 2, 3, or 4; r is 0 or 1;

t of $—(CR^{10}R^{11})_m—$ is 1, 2, or 3; and/or a pharmaceutically acceptable salt, tautomer or stereoisomer thereof.

In any of the compounds described herein, the ILM can have the structure of Formula (XXXVI), which are derived from the IAP ligands described in WO Pub. No. 2014/025759, or an unnatural mimetic thereof:

(XXXVI)

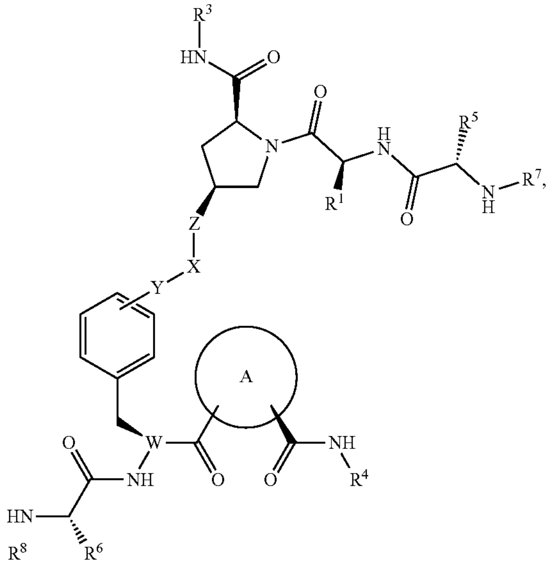

where:

A of Formula (XXXVI) is selected from:

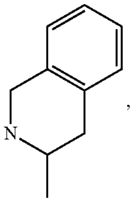

,

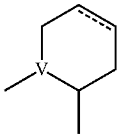

, or

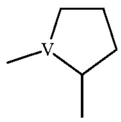

, where the dotted line represents an optional double bond;

X of Formula (XXXVI) is selected from: $—(CR^{21}R^{22})_m—$,

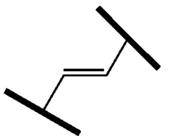

,

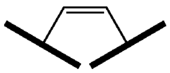

,

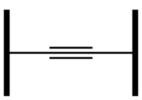

,

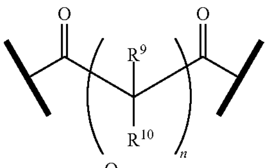

,

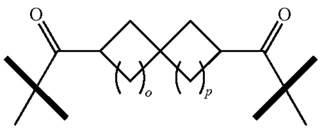

,

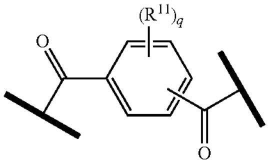

,

-continued

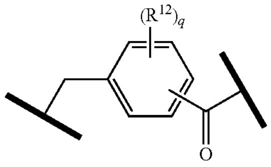

,

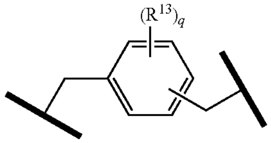

,

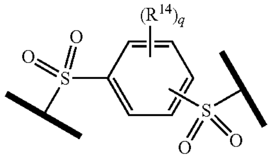

,

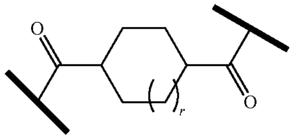

;

Y and Z of Formula (XXXVI) are independently selected from -0-, —$NR^6$— or are absent;

V of Formula (XXXVI) is selected from —N— or —CH—;

W of Formula (XXXVI) is selected from —CH— or —N—;

$R^1$ of Formula (XXXVI) is selected from an optionally substituted alkyl, optionally substituted cycloalkyl, optionally substituted cycloalkylalkyl, optionally substituted arylalkyl or optionally substituted aryl;

$R^3$ and $R^4$ of Formula (XXXVI) are independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

$R^5$, $R^6$, $R^7$ and $R^8$ of Formula (XXIV), (XXV) or (XXVI) are independently selected from hydrogen, optionally substituted alkyl or optionally substituted cycloalkyl, or preferably methyl;

$R^9$ and $R^{10}$ of

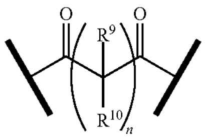

are independently selected from hydrogen, halogen or optionally substituted alkyl, or $R^9$ and $R^{10}$ can be taken together to form a ring;

$R^{11}$, $R^{12}$, $R^{13}$ and $R^{14}$ of

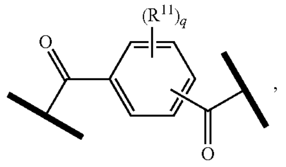

,

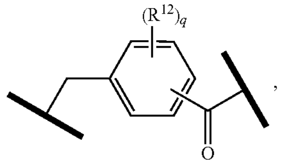

,

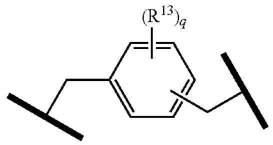

and

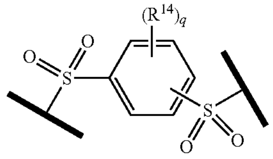

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

m and n of —$(CR^{21}R^{22})_m$— and

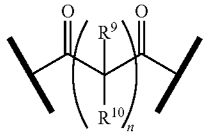

are independently selected from 0, 1, 2, 3, or 4;

o and p of

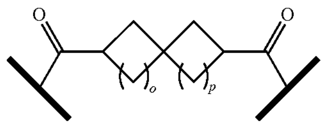

and are independently selected from 0, 1, 2 or 3;

q of

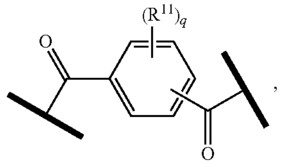

,

-continued

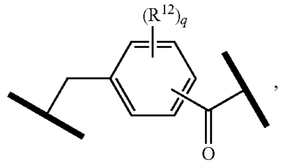

,

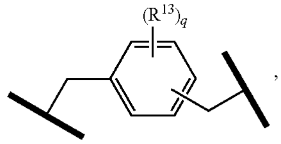

, or

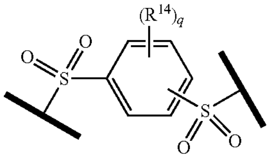

is selected from 0, 1, 2, 3, or 4;

r of

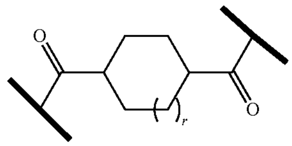

is selected from 0 or 1, and/or or a pharmaceutically acceptable salt, tautomer or stereoisomer thereof.

In any of the compounds described herein, the ILM can have the structure of Formula (XXXVII) or (XXXVIII), which are derived from the IAP ligands described in WO Pub. No. 2014/011712, or an unnatural mimetic thereof:

(XXXVII)

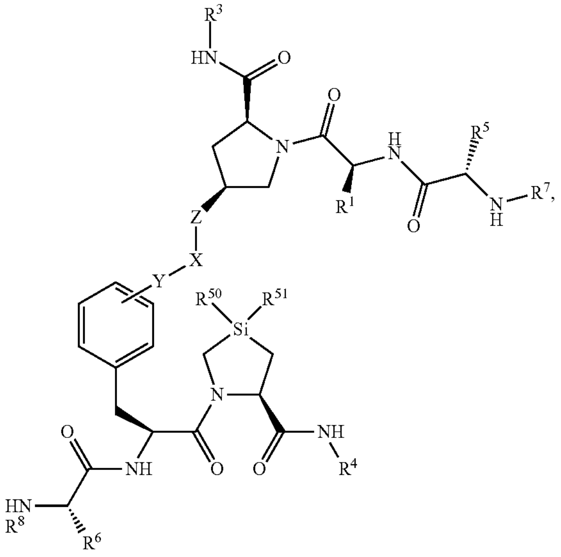

-continued (XXXVIII)

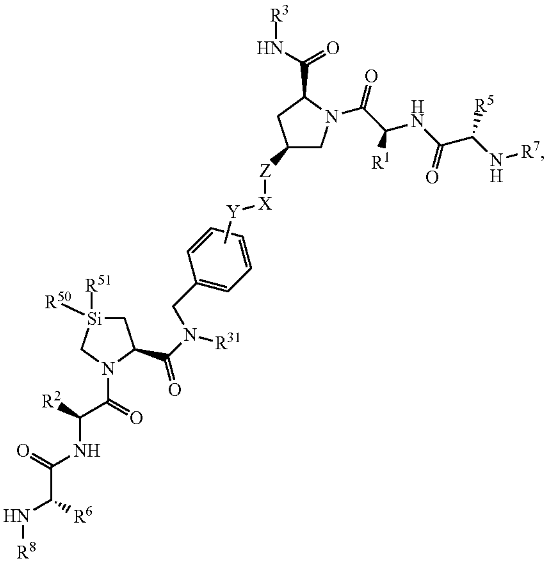

where:

X of Formulas (XXXVII) and (XXXVIII) is $-(CR^{16}R^{17})_m-$,

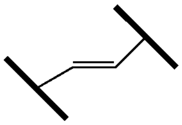

,

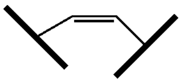

,

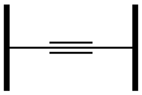

,

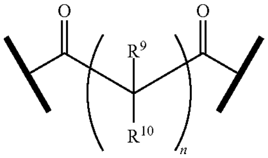

,

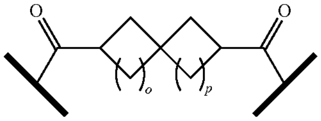

,

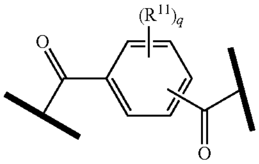

,

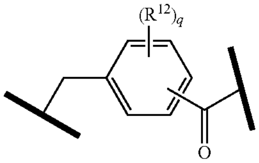

,

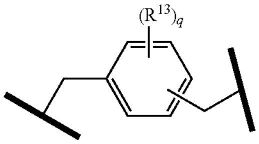

,

-continued

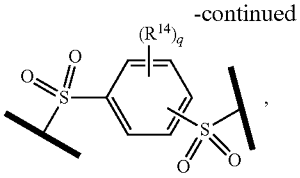

,

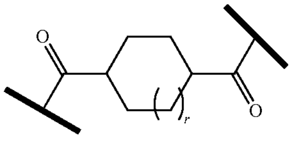

, or absent;

Y and Z of Formula (XXXVII) and (XXXVIII) are independently selected from —O—, C═O, $NR^6$ or are absent;

$R^1$ and $R^2$ of Formula (XXXVII) and (XXXVIII) are selected from optionally substituted alkyl, optionally substituted cycloalkyl, optionally substituted alkylaryl or optionally substituted aryl;

$R^3$ and $R^4$ of Formula (XXXVII) and (XXXVIII) are independently selected from optionally substituted alkyl, optionally substituted cycloalkyl, optionally substituted cycloalkylalkyl, optionally substituted arylalkyl or optionally substituted aryl;

$R^5$ and $R^6$ of Formula (XXXVII) and (XXXVIII) are independently selected from optionally substituted alkyl or optionally substituted cycloalkyl;

$R^7$ and $R^8$ of Formula (XXXVII) and (XXXVIII) are independently selected from hydrogen, optionally substituted alkyl or optionally substituted cycloalkyl, or preferably methyl;

$R^9$ and $R^{10}$ of

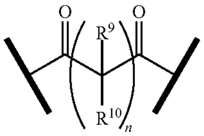

are independently selected from hydrogen, optionally substituted alkyl, or $R^9$ and $R^{10}$ may be taken together to form a ring;

$R^{11}$ to $R^{14}$ of

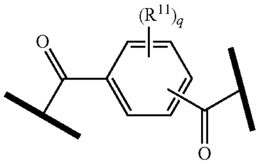

,

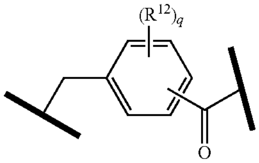

,

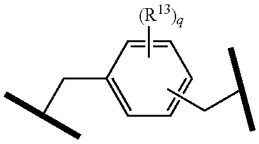

,

-continued

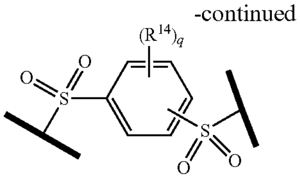

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

$R^{16}$ and $R^{17}$ of $-(CR^{16}R^{17})_m-$ are independently selected from hydrogen, halogen or optionally substituted alkyl;

$R^{50}$ and $R^{51}$ of Formula (XXXVII) and (XXXVIII) are independently selected from optionally substituted alkyl, or $R^{50}$ and $R^{51}$ are taken together to form a ring;

m and n of $-(CR^{16}R^{17})_m-$ and

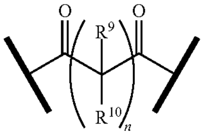

are independently an integer from 0-4;

o and p of

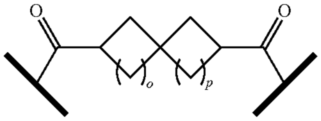

are independently an integer from 0-3;

q of

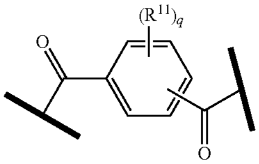

,

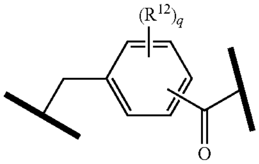

,

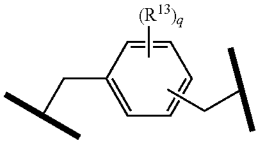

,

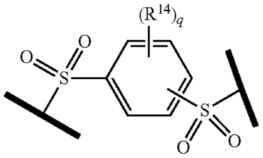

is an integer from 0-4; and r of

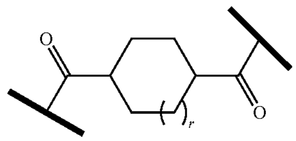

is an integer from 0-1;

or a pharmaceutically acceptable salt, tautomer or stereoisomer thereof.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In any of the compounds described herein, the ILM can have the structure of Formula (XXXIX) or (XL), which are derived from the IAP ligands described in WO Pub. No. 2013/071039, or an unnatural mimetic thereof:

(XXXIX)

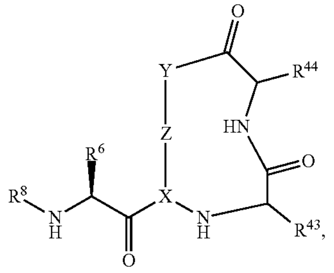

(XL)

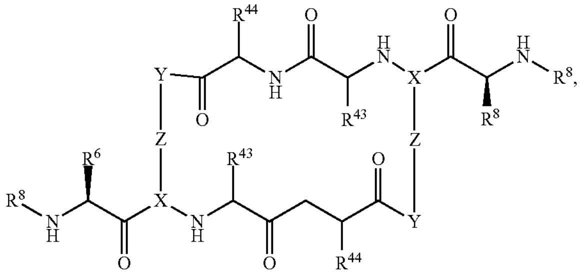

wherein:

$R^{43}$ and $R^{44}$ of Formulas (XXXIX) and (XL) are independently selected from hydrogen, alkyl, aryl, arylalkyl, heteroaryl, heteroarylalkyl, cycloalkyl, cycloalkylalkyl further optionally substituted, and $R^6$ and $R^8$ of Formula (XXXIX) and (XL) are independently selected from hydrogen, optionally substituted alkyl or optionally substituted cycloalkyl.

each X of Formulas (XXXIX) and (XL) is independently selected from:

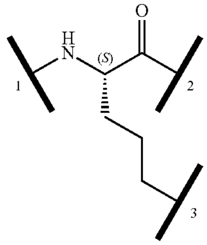

,

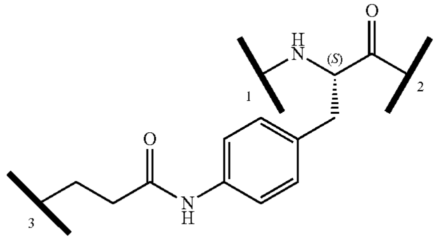

,

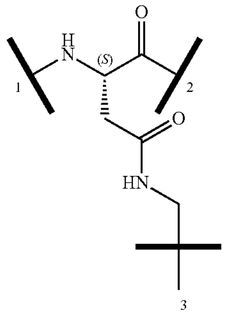

,

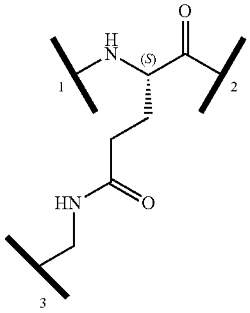

,

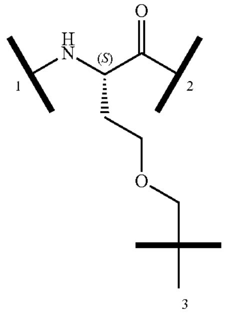

,

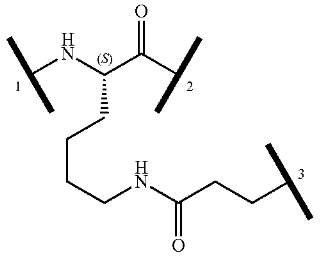

,

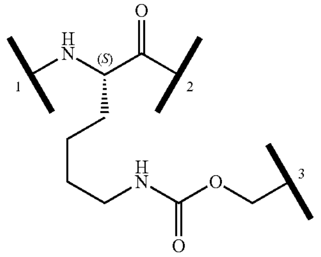

,

-continued
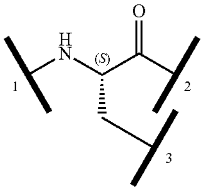 , 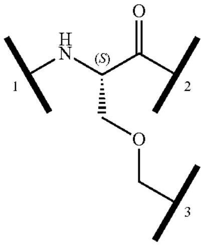 ,
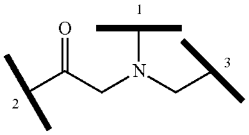 ,
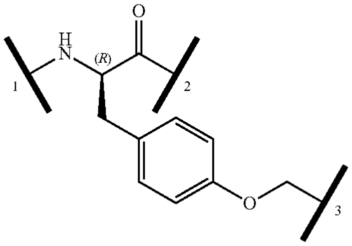 ,
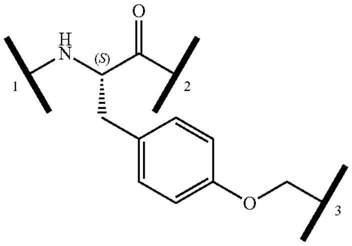 , 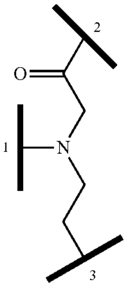 ,
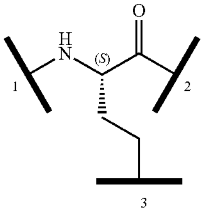 , and
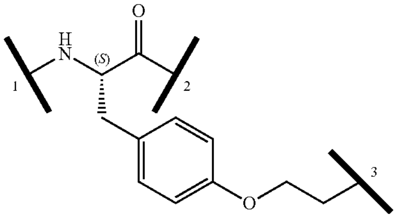 ;
each Z of Formulas (XXXIX) and (XL) is selected from
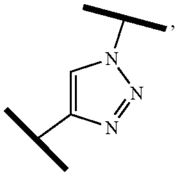 ,
wherein each
represents a point of attachment to the compound; and each Y is selected from:
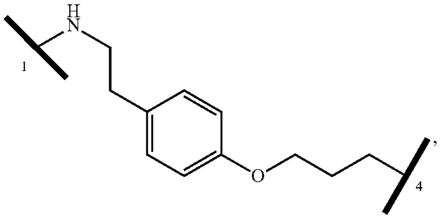 ,
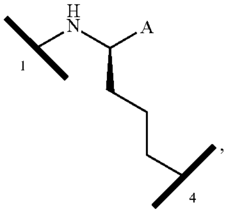 ,
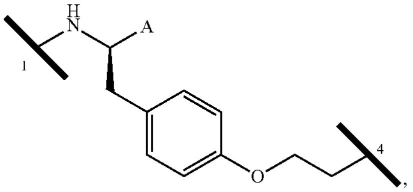 ,
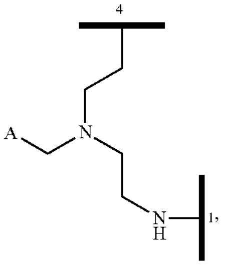 , 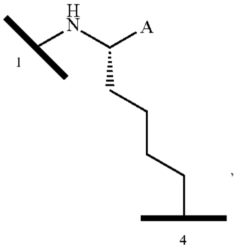 ,
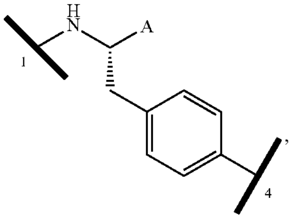 ,
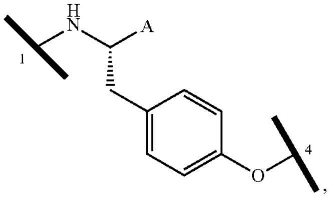 , -continued
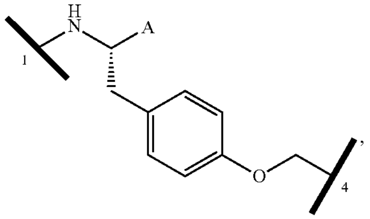
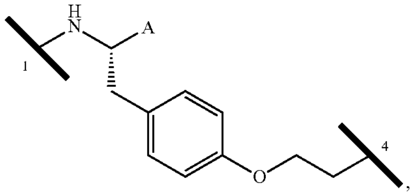
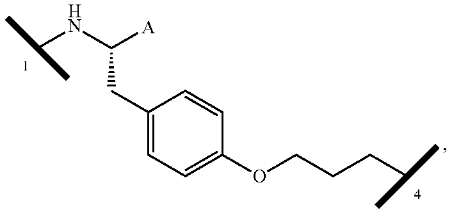
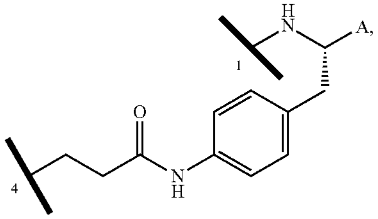
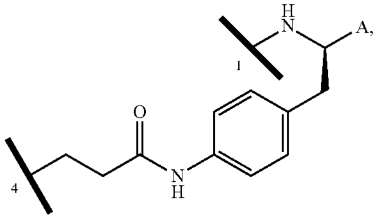
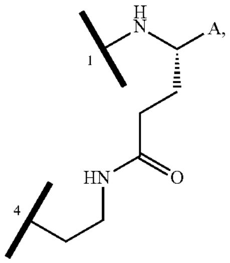
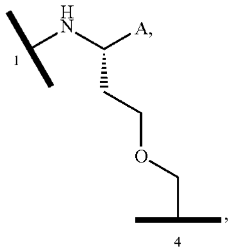
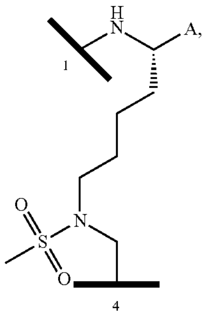
-continued
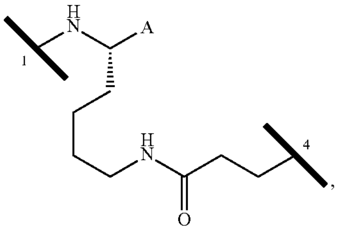
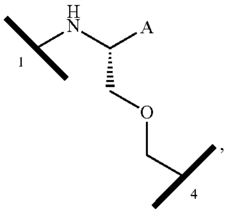
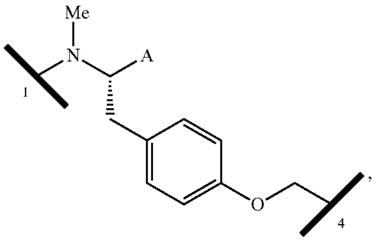
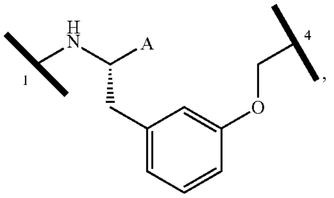
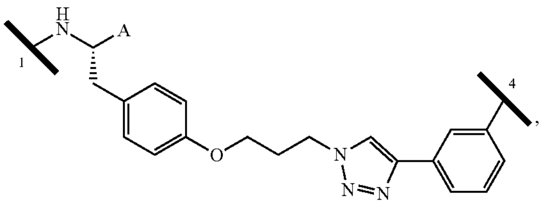
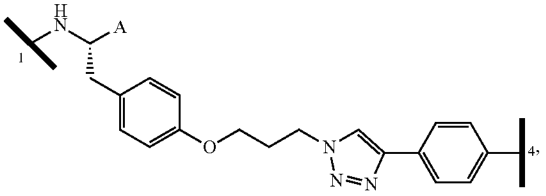
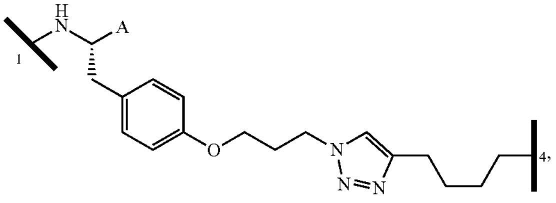
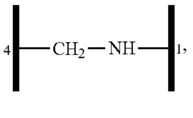
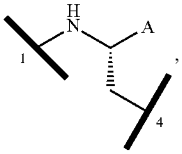
and -continued

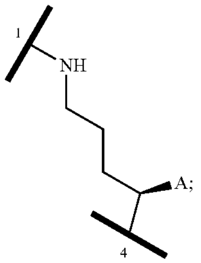

wherein:

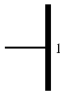

represents a point of attachment to a —C═O portion of the compound;

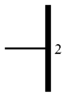

represents a point of attachment to an amino portion of the compound;

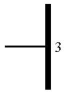

represents a first point of attachment to Z;

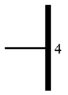

represents a second point of attachment to Z; and

A is selected from —C(O)$R^3$ or

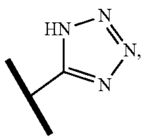 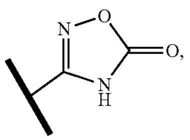

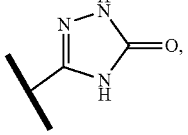 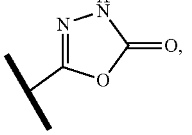

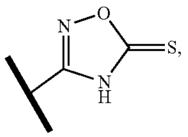 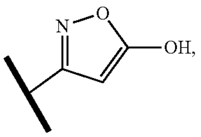

-continued

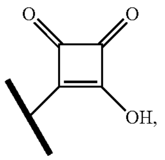 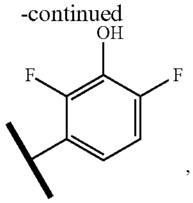

or a tautomeric form of any of the foregoing, wherein:

$R^3$ of —C(O)$R^3$ is selected from OH, NHCN, $NHS0_2R^{10}$, $NHOR^{11}$ or $N(R^{12})(R^{13})$;

$R^{10}$ and $R^{11}$ of $NHS0_2R^{10}$ and $NHOR^{11}$ are independently selected from —$C_1$-$C_4$ alkyl, cycloalkyl, aryl, heteroaryl, or heterocycloalkyl, any of which are optionally substituted, and hydrogen;

each of $R^{12}$ and $R^{13}$ of $N(R^{12})(R^{13})$ are independently selected from hydrogen, —$C_1$-$C_4$ alkyl, —($C_1$-$C_4$ alkylene)-NH—($C_1$-$C_4$ alkyl), benzyl, —($C_1$-$C_4$ alkylene)-C(O)OH, —($C_1$-$C_4$ alkylene)-C(O)$CH_3$, —CH(benzyl)-COOH, —$C_1$-$C_4$ alkoxy, and —($C_1$-$C_4$ alkylene)-O—($C_1$-$C_4$ hydroxyalkyl); or $R^{12}$ and $R^{13}$ of $N(R^{12})(R^{13})$ are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XLI), which are derived from the IAP ligands described in WO Pub. No. 2013/071039, or an unnatural mimetic thereof:

(XLI)

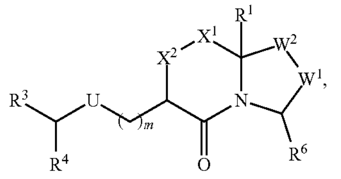

wherein:

$W^1$ of Formula (XLI) is selected from O, S, N—$R^A$, or $C(R^{8a})(R^{8b})$;

$W^2$ of Formula (XLI) is selected from O, S, N—$R^A$, or $C(R^{8c})(R^{8d})$; provided that $W^1$ and $W^2$ are not both O, or both S;

$R^1$ of Formula (XLI) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ is selected from O, N—$R^A$, S, S(O), or $S(O)_2$, then $X^2$ is $C(R^{2a}R^{2b})$;

or:

$X^1$ of Formula (XLI) is selected from $CR^{2c}R^{2d}$ and $X^2$ is $CR^{2a}R^{2b}$, and $R^{2c}$ and $R^{2a}$ together form a bond;

or:

$X^1$ and $X^2$ of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;

or:

$X^1$ of Formula (XLI) is selected from $CH_2$ and $X^2$ is C=0, C═C($R^C$)$_2$, or C═N$R^C$; where each $R^c$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl));

$R^A$ of N—$R^A$ is selected from H, $C_1$-$C_6$alkyl, —C(═O)$C_1$-$C_2$alkyl, substituted or unsubstituted aryl, or substituted or unsubstituted heteroaryl;

$R^2$, $R^{2b}$, $R^{2c}$, $R^{2d}$ of $CR^{2c}R^{2d}$ and $CR^{2a}R^{2b}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted C3-C6cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D$$R^E$;

$R^D$ and $R^E$ of N$R^D$$R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl));

m of Formula (XLI) is selected from 0, 1 or 2;

—U— of Formula (XLI) is selected from —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XLI) is selected from $C_1$-$C_3$alkyl, or $C_1$-$C_3$fluoroalkyl;

$R^4$ of Formula (XLI) is selected from —NH$R^5$, —N($R^5$)2, —N+($R^5$)3 or —O$R^5$;

each $R^5$ of —NH$R^5$, —N($R^5$)2, —N+($R^5$)3 and —O$R^5$ is independently selected from H, $C_1$-$C_3$alkyl, $C_1$-$C_3$haloalkyl, $C_1$-$C_3$heteroalkyl and —$C_1$-$C_3$alkyl-(C3-$C_5$cycloalkyl);

or:

$R^3$ and $R^5$ of Formula (XLI) together with the atoms to which they are attached form a substituted or unsubstituted 5-7 membered ring;

or:

$R^3$ of Formula (XLI) is bonded to a nitrogen atom of U to form a substituted or unsubstituted 5-7 membered ring;

$R^6$ of Formula (XLI) is selected from —NHC(═O)$R^7$, —C(═O)NH$R^7$, —NHS(═O)2$R^7$, —S(═O)$_2$NH$R^7$; —NHC(═O)NH$R^7$, —NHS(═O)$_2$NH$R^7$, —($C_1$-$C_3$alkyl)-NHC(═O)$R^7$, —($C_1$-$C_3$alkyl)-C(═O)NH$R^7$, —($C_1$-$C_3$alkyl)-NHS(═O)2$R^7$, —($C_1$-$C_3$alkyl)-S(═O)2NH$R^7$; —($C_1$-$C_3$alkyl)-NHC(═O)NH$R^7$, —($C_1$-$C_3$alkyl)-NHS(═O)2NH$R^7$, substituted or unsubstituted $C_2$-$C_{10}$heterocycloalkyl, or substituted or unsubstituted heteroaryl;

each $R^7$ of —NHC(═O)$R^7$, —C(═O)NH$R^7$, —NHS(═O)2$R^7$, —S(═O)$_2$NH$R^7$; —NHC(═O)NH$R^7$, —NHS(═O)$_2$NH$R^7$, —($C_1$-$C_3$alkyl)-NHC(═O)$R^7$, —($C_1$-$C_3$alkyl)-C(═O)NH$R^7$, —($C_1$-$C_3$alkyl)-NHS(═O)$_2$$R^7$, —($C_1$-$C_3$alkyl)-S(═O)2NH$R^7$; —($C_1$-$C_3$alkyl)-NHC(═O)NH$R^7$, —($C_1$-$C_3$alkyl)-NHS(═O)2NH$R^7$ is independently selected from $C_1$-$C_6$alkyl, $C_1$-$C_6$haloalkyl, C1-C6heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH2)p-CH(substituted or unsubstituted aryl)2, —$(CH_2)_p$—CH(substituted or unsubstituted heteroaryl)2, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N; where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(═O)OH, —C(═O)$NH_2$, —C(═O)$C_1$-$C_3$alkyl, —S(═O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl. In any of the compounds described herein, the ILM can have the structure of Formula (XLII), which are derived from the IAP ligands described in WO Pub. No. 2013/071039, or an unnatural mimetic thereof:

(XLII)

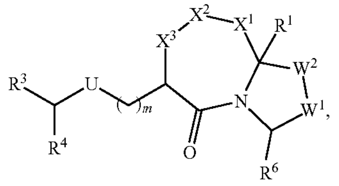

wherein:

$W^1$ of Formula (XLII) is O, S, N—$R^A$, or C($R^{8a}$)($R^{8b}$);

$W^2$ of Formula (XLII) is O, S, N—$R^A$, or C($R^{8c}$)($R^{8d}$); provided that $W^1$ and $W^2$ are not both O, or both S;

$R^1$ of Formula (XLII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XLII) is N—$R^A$, then $X^2$ is C═O, or $CR^{2c}R^{2d}$, and $X^3$ is $CR^{2a}R^{2b}$;

or:

when $X^1$ of Formula (XLII) is selected from S, S(O), or S(O)$_2$, then $X^2$ is $CR^{2c}R^{2d}$, and $X^3$ is $CR^{2a}R^{2b}$.

or:

when $X^1$ of Formula (XLII) is O, then $X^2$ is $CR^{2c}R^{2d}$ and N—$R^A$ and $X^3$ is $CR^{2a}R^{2b}$;

or:

when $X^1$ of Formula (XLII) is $CH_3$, then $X^2$ is selected from O, N—$R^A$, S, S(O), or S(O)$_2$, and $X^3$ is $CR^{2a}R^{2b}$;

when $X^1$ of Formula (XLII) is $CR^{2e}R^{2f}$ and $X^2$ is $CR^{2c}R^{2d}$, and $R^{2e}$ and $R^{2c}$ together form a bond, and $X^3$ of Formula (VLII) is $CR^{2a}R^{2b}$;

or:

$X^1$ and $X^3$ of Formula (XLII) are both $CH_2$ and $X^2$ of Formula (XLII) is C=0, C═C($R^C$)2, or C═N$R^C$; where each $R^C$ is independently selected from H, —CN, —OH, alkoxy, substituted or unsubstituted C1-C6alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;

$R^A$ of N—$R^A$ is selected from H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;

$R^D$ and $R^E$ of N$R^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLII) is selected from 0, 1 or 2;

—U— of Formula (XLII) is selected from —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XLII) is selected from $C_1$-$C_3$alkyl, or $C_1$-$C_3$fluoroalkyl;

$R^4$ of Formula (XLII) is selected from —$NHR^5$, —$N(R^5)_2$, —N+($R^5$)3 or —$OR^5$;

each $R^5$ of —$NHR^5$, —$N(R^5)_2$, —N+$(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLII) together with the atoms to which they are attached form a substituted or unsubstituted 5-7 membered ring;

or:

$R^3$ of Formula (XLII) is bonded to a nitrogen atom of U to form a substituted or unsubstituted 5-7 membered ring;

$R^6$ of Formula (XLII) is selected from —NHC(=O)$R^7$, —C(=O)$NHR^7$, —NHS(=O)2$R^7$, —S(=O)$_2$$NHR^7$; —NHC(=O)$NHR^7$, —NHS(=O)$_2$$NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)$_2$$R^7$, —($C_1$-$C_3$alkyl)-S(=O)$_2$$NHR^7$; —($C_1$-$C_3$alkyl)-NHC(=O)$NHR^7$, —($C_1$-$C_3$alkyl)-NHS(=O)$_2$$NHR^7$, substituted or unsubstituted $C_2$-$C_{10}$heterocycloalkyl, or substituted or unsubstituted heteroaryl;

each $R^7$ of —NHC(=O)$R^7$, —C(=O)$NHR^7$, —NHS(=O)2$R^7$, —S(=O)$_2$$NHR^7$; —NHC(=O)$NHR^7$, —NHS(=O)$_2$$NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)2$R^7$, —($C_1$-$C_3$alkyl)-S(=O)2$NHR^7$; —($C_1$-$C_3$alkyl)-NHC(=O)$NHR^7$, —($C_1$-$C_3$alkyl)-NHS(=O)2$NHR^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH (substituted or unsubstituted aryl)2, —$(CH_2)_p$—CH (substituted or unsubstituted heteroaryl)2, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, $C_1$-$C_4$fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2$$CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIII), which is derived from the IAP ligands described in WO Pub. No. 2013/071039, or an unnatural mimetic thereof:

(XLIII)

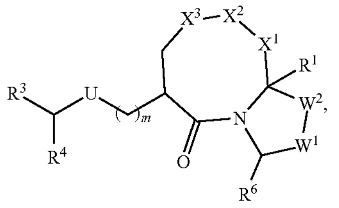

wherein:

$W^1$ of Formula (XLIII) is selected from O, S, N—$R^A$, or C($R^{8a}$)($R^{8b}$);

$W^2$ of Formula (XLIII) is selected from O, S, N—$R^A$, or C($R^{8c}$)($R^{8d}$); provided that $W^1$ and $W^2$ are not both O, or both S;

$R^1$ of Formula (XLIII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XLIII) is selected from N—$R^A$, S, S(O), or S(O)$_2$, then $X^2$ of Formula (XLIII) is $CR^{2c}R^{2d}$, and $X^3$ of Formula (XLIII) is $CR^{2a}R^{2b}$;

or:

when $X^1$ of Formula (XLIII) is O, then $X^2$ of Formula (XLIII) is selected from O, N—$R^A$, S S(O), or S(O)$_2$, and $X^3$ of Formula (XLIII) is $CR^{2a}R^{2b}$;

or:

when $X^1$ of Formula (XLIII) is $CR^{2e}R^{2f}$ and $X^2$ of Formula (XLIII) is $CR^{2c}R^{2d}$, and $R^{2e}$ and $R^{2c}$ together form a bond, and $X^3$ of Formula (XLIII) is $CR^{2a}R^{2b}$;

or:

$X^1$ and $X^2$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIII) is $CR^{2a}R^{2b}$;

or:

$X^2$ and $X^3$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;

$R^A$ of N—$R^A$ is H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLIII) is 0, 1 or 2;

—U— of Formula (XLIII) is —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XLIII) is $C_1$-$C_3$alkyl, or $C_1$-$C_3$fluoroalkyl;

$R^4$ of Formula (XLIII) is —$NHR^5$, —N+$(R^5)_2$, —N+$(R^5)_3$ or —$OR^5$;

each $R^5$ of —$NHR^5$, —N$(R^5)_2$, —N+$(R^5)_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLIII) together with the atoms to which they are attached form a substituted or unsubstituted 5-7 membered ring;

or:

$R^3$ of Formula (XLIII) is bonded to a nitrogen atom of U to form a substituted or unsubstituted 5-7 membered ring;

$R^6$ of Formula (XLIII) is selected from —NHC(═O)$R^7$, —C(═O)$NHR^7$, —NHS(═O)2$R^7$, —S(═O)$_2$$NHR^7$; —NHC(═O)$NHR^7$, —NHS(═O)$_2$$NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)$_2$$R^7$, —($C_1$-$C_3$alkyl)-S(═O)$_2$$NHR^7$; —($C_1$-$C_3$alkyl)-NHC(═O)$NHR^7$, —($C_1$-$C_3$alkyl)-NHS(═O)$_2$$NHR^7$, substituted or unsubstituted $C_2$-$C_{10}$heterocycloalkyl, or substituted or unsubstituted heteroaryl;

each $R^7$ of —NHC(═O)$R^7$, —C(═O)$NHR^7$, —NHS(═O)$_2$$R^7$, —S(═O)$_2$$NHR^7$; —NHC(═O)$NHR^7$, —NHS(═O)$_2$$NHR^7$, —($C_1$-$C_3$alkyl)-NHC(═O)$R^7$, —($C_1$-$C_3$alkyl)-C(═O)$NHR^7$, —($C_1$-$C_3$alkyl)-NHS(═O)2$R^7$, —($C_1$-$C_3$alkyl)-S(═O)$_2$$NHR^7$; —($C_1$-$C_3$alkyl)-NHC(═O)$NHR^7$, —($C_1$-$C_3$alkyl)-NHS(═O)2$NHR^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —($CH_2$)p-CH(substituted or unsubstituted aryl)2, —$(CH_2)_p$—CH(substituted or unsubstituted heteroaryl)2, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is 0, 1 or 2;

$R^{8a}$, $R^{8b}$, $R^{8c}$, and $R^{8a}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond; or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C═O), CN, $C_1$-$C_4$alkyl, $C_1$-$C_4$fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(═O)OH, —C(═O)$NH_2$, —C(═O)$C_1$-$C_3$alkyl, —S(═O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIV), which is derived from the IAP ligands described in WO Pub. No. 2013/071039, or an unnatural mimetic thereof:

(XLIV)

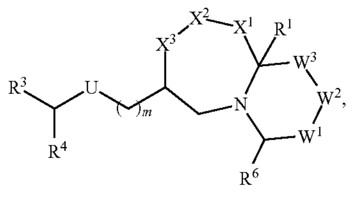

wherein:

$W^1$ of Formula (XLIV) is selected from O, S, N—$R^A$, or C($R^{8a}$)($R^{8b}$);

$W^2$ of Formula (XLIV) is selected from O, S, N—$R^A$, or C($R^{8c}$)($R^{8d}$); provided that $W^1$ and $W^2$ are not both O, or both S;

$W^3$ of Formula (XLIV) is selected from O, S, N—$R^A$, or C($R^{8e}$)($R^{8f}$), providing that the ring comprising $W^1$, $W^2$, and $W^3$ does not comprise two adjacent oxygen atoms or sulfur atoms;

$R^1$ of Formula (XLIV) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ of Formula (XLIV) is O, then $X^2$ of Formula (XLIV) is selected from $CR^{2c}R^{2d}$ and N—$R^A$, and $X^3$ of Formula (XLIV) is $CR^{2a}R^{2b}$;

or:

when $X^1$ of Formula (XLIV) is $CH_2$, then $X^2$ of Formula (XLIV) is selected from O, N—$R^A$, S, S(O), or S(O)$_2$, and $X^3$ of Formula (XLIV) is $CR^{2a}R^{2b}$;

or:

when $X^1$ of Formula (XLIV) is $CR^{2e}R^{2f}$ and $X^2$ of Formula (XLIV) is $CR^{2c}R^{2d}$, and $R^{2e}$ and $R^{2c}$ together form a bond, and $X^3$ of Formula (VLIV) is $CR^{2a}R^{2b}$;

or:

$X^1$ and $X^3$ of Formula (XLIV) are both $CH_2$ and $X^2$ of Formula (XLII) is C=0, C═C($R^C$)2, or C═N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$;

or:

$X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLIV) is $CR^{2e}R^{2f}$;

$R^A$ of N—$R^A$ is selected from H, $C_1$-$C_6$alkyl, —C(═O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(═O)$R^B$;

$R^B$ of —C(═O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;

$R^D$ and $R^E$ of N$R^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLIV) is selected from 0, 1 or 2;

—U— of Formula (XLIV) is selected from —NHC(═O)—, —C(═O)NH—, —NHS(═O)$_2$—, —S(═O)$_2$NH—, —NHC(═O)NH—, —NH(C═O)O—, —O(C═O)NH—, or —NHS(═O)$_2$NH—;

$R^3$ of Formula (XLIV) is selected from $C_1$-$C_3$alkyl, or $C_1$-$C_3$fluoroalkyl;

$R^4$ of Formula (XLIV) is selected from —NHR$^5$, —N(R$^5$)$_2$, —N+(R$^5$)$_3$ or —OR$^5$;

each $R^5$ of —NHR$^5$, —N(R$^5$)$_2$, —N+(R$^5$)$_3$ and —OR$^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLIV) together with the atoms to which they are attached form a substituted or unsubstituted 5-7 membered ring;

or:

$R^3$ of Formula (XLIII) is bonded to a nitrogen atom of U to form a substituted or unsubstituted 5-7 membered ring;

$R^6$ of Formula (XLIII) is selected from —NHC(═O)R$^7$, —C(═O)NHR$^7$, —NHS(═O)2R$^7$, —S(═O)$_2$NHR$^7$; —NHC(═O)NHR$^7$, —NHS(═O)$_2$NHR$^7$, —($C_1$-$C_3$alkyl)-NHC(═O)R$^7$, —($C_1$-$C_3$alkyl)-C(═O)NHR$^7$, —($C_1$-$C_3$alkyl)-NHS(═O)$_2$R$^7$, —($C_1$-$C_3$alkyl)-S(═O)$_2$NHR$^7$; —($C_1$-$C_3$alkyl)-NHC(═O)NHR$^7$, —($C_1$-$C_3$alkyl)-NHS(═O)$_2$NHR$^7$, substituted or unsubstituted $C_2$-$C_{10}$heterocycloalkyl, or substituted or unsubstituted heteroaryl;

each $R^7$ of —NHC(═O)R$^7$, —C(═O)NHR$^7$, —NHS(═O)$_2$R$^7$, —S(═O)$_2$NHR$^7$; —NHC(═O)NHR$^7$, —NHS(═O)$_2$NHR$^7$, —($C_1$-$C_3$alkyl)-NHC(═O)R$^7$, —($C_1$-$C_3$alkyl)-C(═O)NHR$^7$, —($C_1$-$C_3$alkyl)-NHS(═O)2R$^7$, —($C_1$-$C_3$alkyl)-S(═O)$_2$NHR$^7$; —($C_1$-$C_3$alkyl)-NHC(═O)NHR$^7$, —($C_1$-$C_3$alkyl)-NHS(═O)2NHR$^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8c}$ together form a bond;

or:

$R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together form a bond;

or:

$R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$, and $R^{8f}$ of C($R^{8c}$)($R^{8d}$) and C($R^{8e}$)($R^{8f}$) are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$, and $R^{8f}$ of C($R^{8a}$)($R^{8b}$) and C($R^{8e}$)($R^{8f}$) are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ of C($R^{8a}$)($R^{8b}$) and C($R^{8c}$)($R^{8d}$) are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$, $R^{8d}$, $R^{8e}$, and $R^{8f}$ is independently selected from halogen, —OH, —SH, (C═O), CN, $C_1$-$C_4$alkyl, $C_1$-$C_4$fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(═O)OH, —C(=0)NH$_2$, —C(═O)$C_1$-C3alkyl, —S(═O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLV), (XLVI) or (XLVII), which is derived from the IAP ligands described in Vamos, M., et al., *Expedient synthesis of highly potent antagonists of*

*inhibitor of apoptosis proteins* (*IAPs*) *with unique selectivity for ML-IAP*, ACS Chem. Biol., 8(4), 725-32 (2013), or an unnatural mimetic thereof:

(XLV)

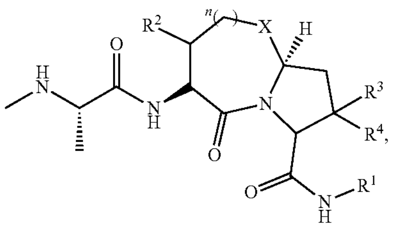

n = 0, 1

(XLVI)

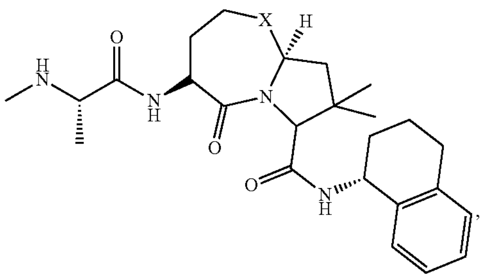

(XLVII)

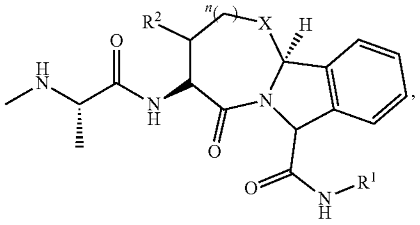

n = 0, 1 wherein:

$R^2$, $R^3$ and $R^4$ of Formula (XLV) are independently selected from H or ME;

X of Formula (XLV) is independently selected from O or S; and $R^1$ of Formula (XLV) is selected from:

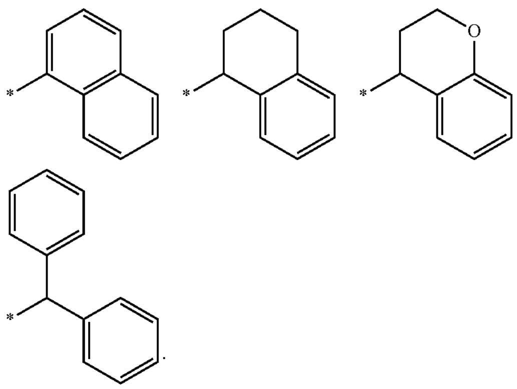

In a particular embodiment, the ILM has a structure according to Formula (XLVIII):

(XLVIII)

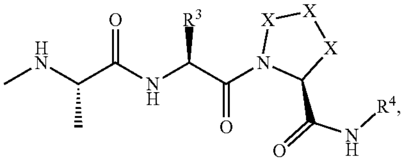

wherein $R^3$ and $R^4$ of Formula (XLVIII) are independently selected from H or ME;

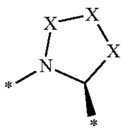

is a 5-member heteocycle selected from:

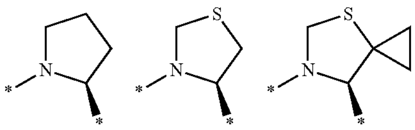

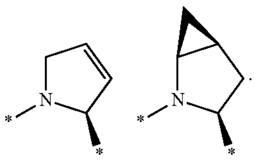

In a particular embodiment, the

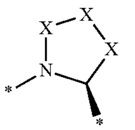

of Formula XLVIII) is

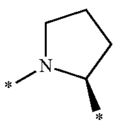 [SMILES: *[C@@H]1CCCN1*]

In a particular embodiment, the ILM has a structure and attached to a linker group L as shown below:

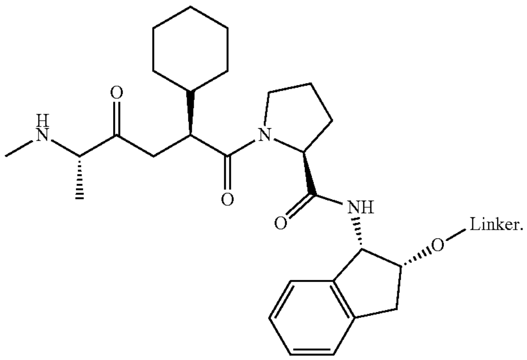
In a particular embodiment, the ILM has a structure according to Formula (XLIX), (L), or (LI):
(XLIX)
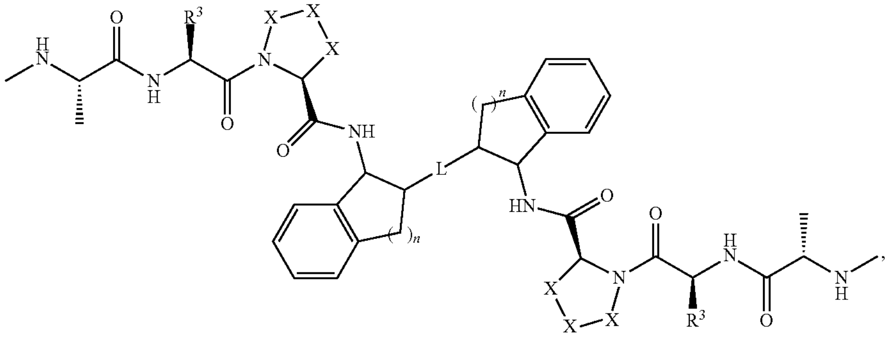
n = 1, 2
(L)
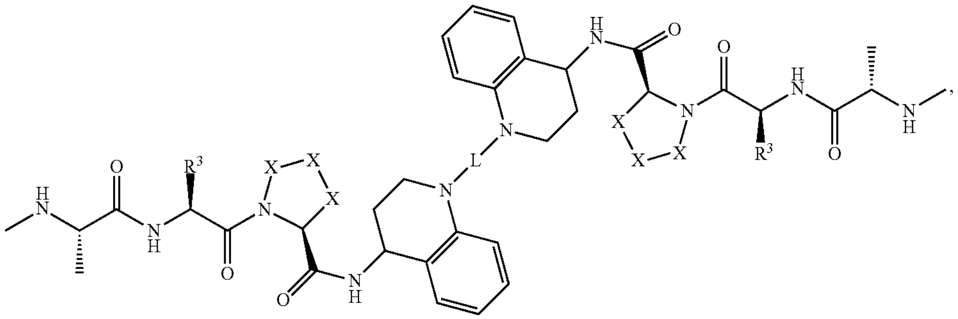
(LI)
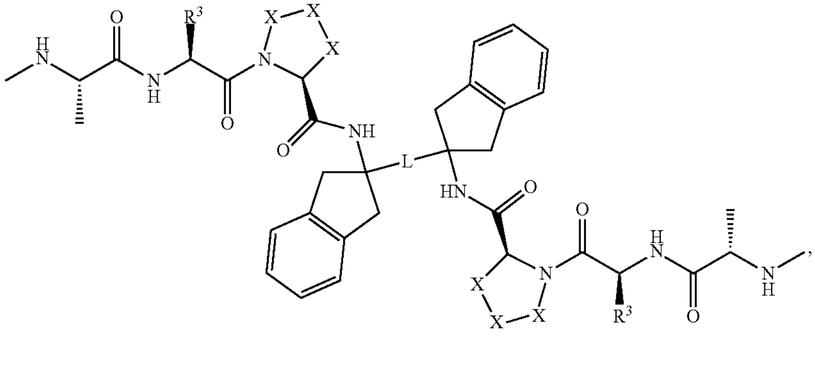

wherein:
$R^3$ of Formula (XLIX), (L) or (LI) are independently selected from H or ME;
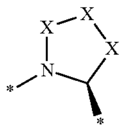
is a 5-member heteocycle selected from:
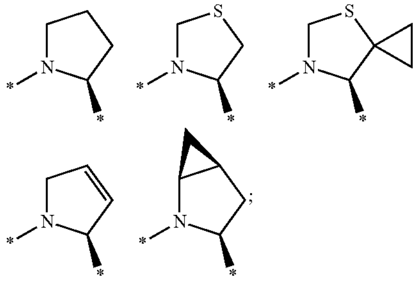
and
L of Formula (XLIX), (L) or (LI) is selected from:
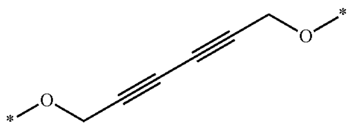
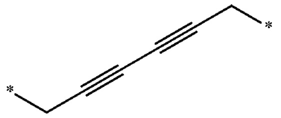
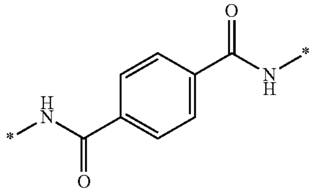
-continued
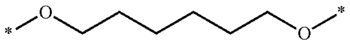
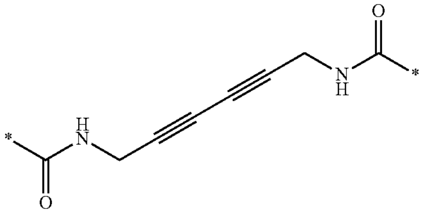
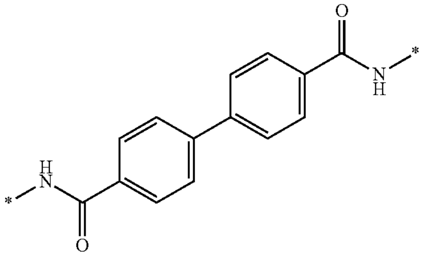
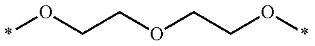
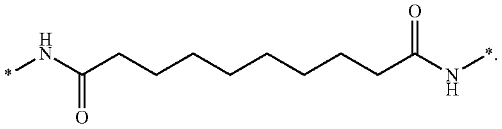
In a particular embodiment, L of Formula (XLIX), (L), or (LI)
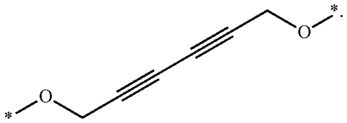
In a particular embodiment, the ILM has a structure according to Formula (LII):
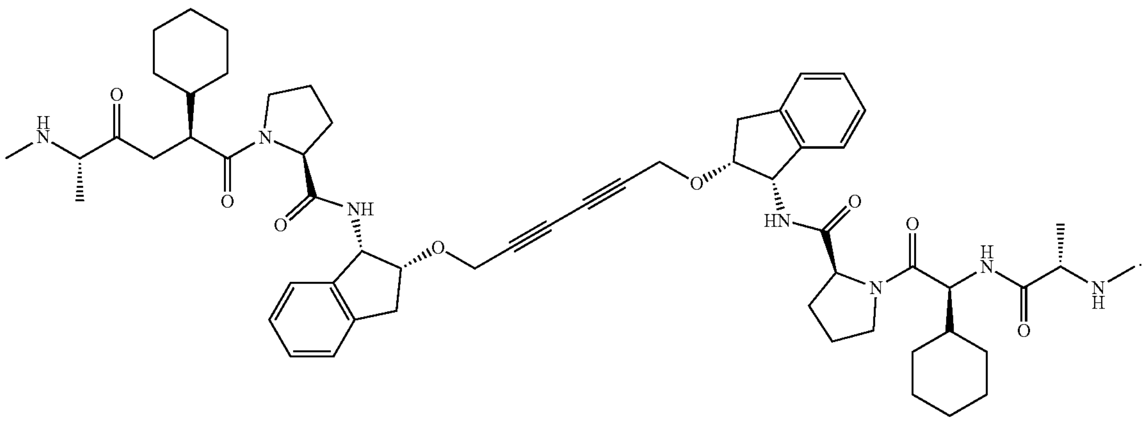

In a particular embodiment, the ILM according to Formula (LII) is chemically linked to the linker group Lin the area denoted with

and as shown below:

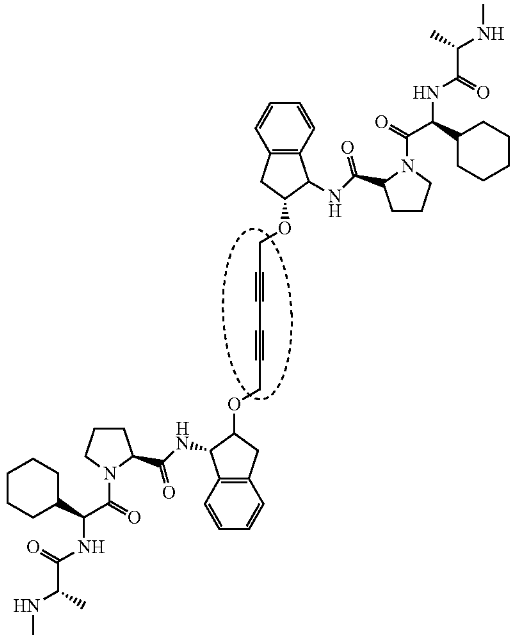

In any of the compounds described herein, the ILM can have the structure of Formula (LIII) or (LIV), which is based on the IAP ligands described in Hennessy, E J, et al., *Discovery of aminopiperidine-based Smac mimetics as IAP antagonists*, Bioorg. Med. Chem. Lett., 22(4), 1960-4 (2012), or an unnatural mimetic thereof:

(LIII)

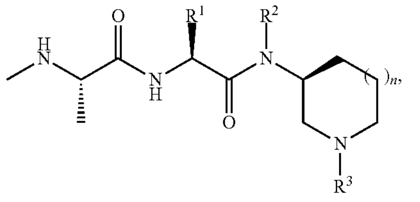

n = 0, 1, 2

(LIV)

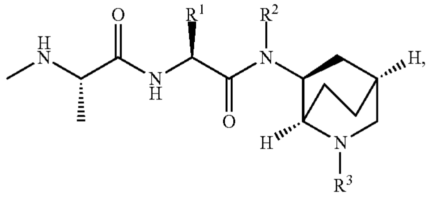

wherein:

$R^1$ of Formulas (LIII) and (LIV) is selected from:

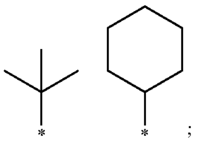

$R^2$ of Formulas (LIII) and (LIV) is selected from H or Me;

$R^3$ of Formulas (LIII) and (LIV) is selected from:

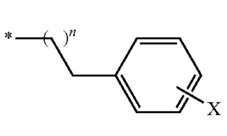

n = 0, 1, 2

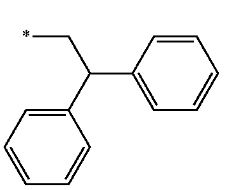

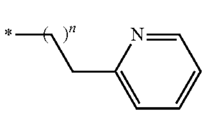

n = 0, 1, 2

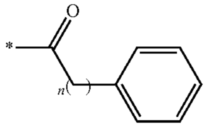

n = 0, 1

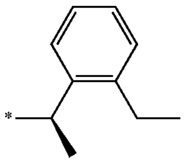

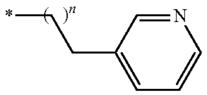

n = 0, 1, 2

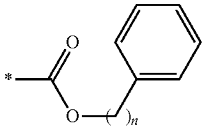

n = 0, 1

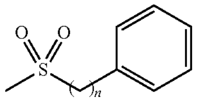

n = 0, 1

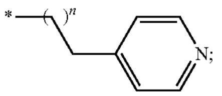

n = 0, 1, 2

X of is selected from H, halogen, methyl, methoxy, hydroxy, nitro or trifluoromethyl.

In any of the compounds described herein, the ILM can have the structure of and be chemically linked to the linker as shown in Formula (LV) or (LVI), or an unnatural mimetic thereof:

(LV)

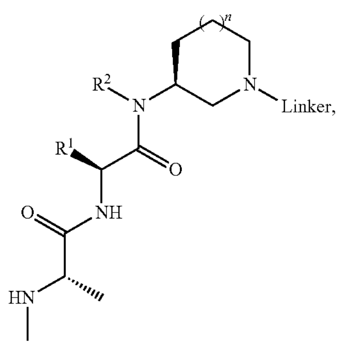

(LVI)

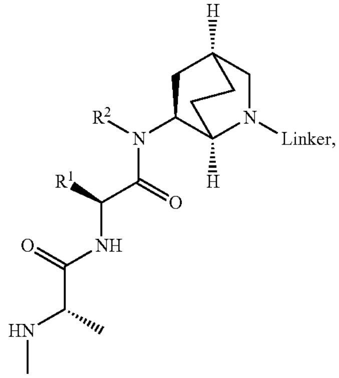

In any of the compounds described herein, the ILM can have the structure of Formula (LVII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

(LVII)

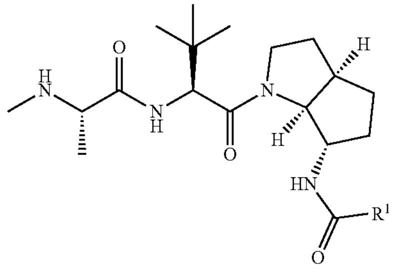

wherein:

R1 of Formulas (LVII) is selected from:

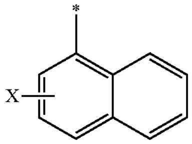

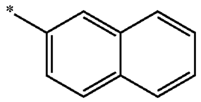

-continued

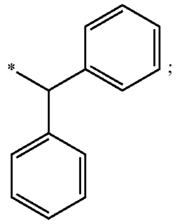

X of

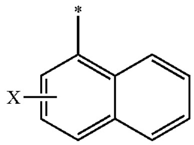

is selected from H, fluoro, methyl or methoxy.

In a particular embodiment, the ILM is represented by the following structure:

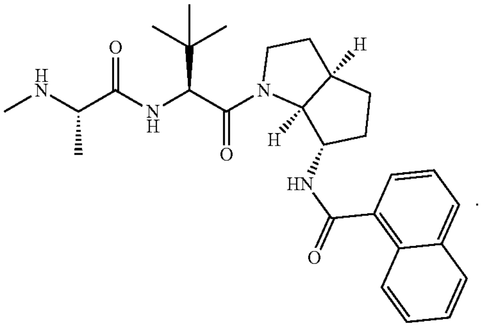 [SMILES: CN[C@@H](C)C(=O)N[C@H](C(=O)N1CC[C@H]2CC[C@H](NC(=O)c3cccc4ccccc34)[C@H]21)C(C)(C)C]

In a particular embodiment, the ILM is selected from the group consisting of, and which the chemical link between the ILM and linker group L is shown:

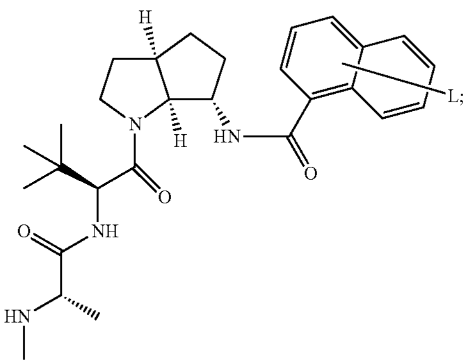

and

-continued

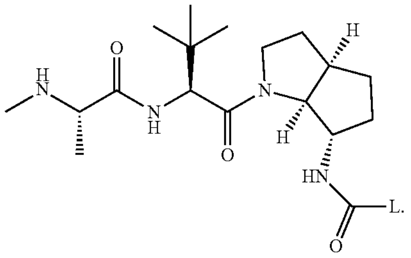

In any of the compounds described herein, the ILM is selected from the group consisting of the structures below, which are based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

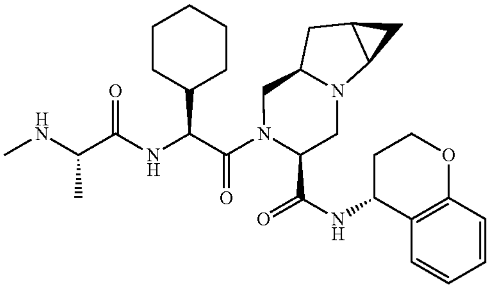

or

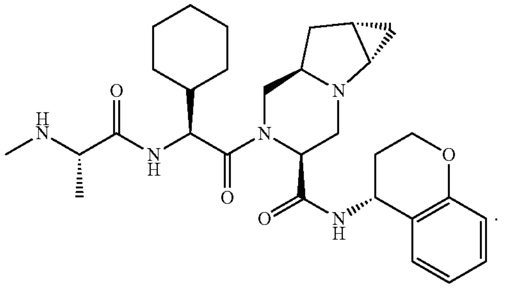

In a particular embodiment, the ILM is selected from the group consisting of, and which the chemical link between the ILM and linker group L is shown:

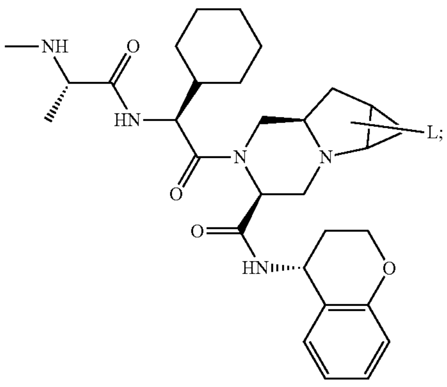

and

-continued

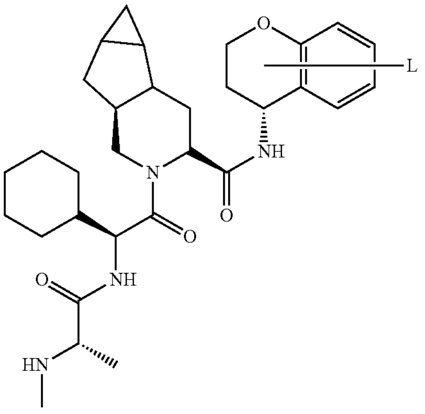

In any of the compounds described herein, the ILM can have the structure of Formula (LVIII), which is based on the IAP ligands described in Asano, M, et al., *Design, steriose-lective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

(LVIII)

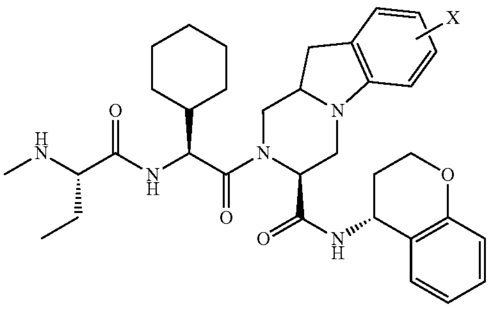

, wherein X of Formula (LVIII) is one or two substituents independently selected from H, halogen or cyano.

In any of the compounds described herein, the ILM can have the structure of and be chemically linked to the linker group L as shown in Formula (LIX) or (LX), or an unnatural mimetic thereof:

(LIX)

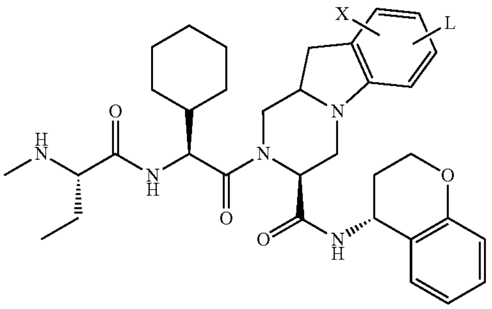

or

-continued (LX)

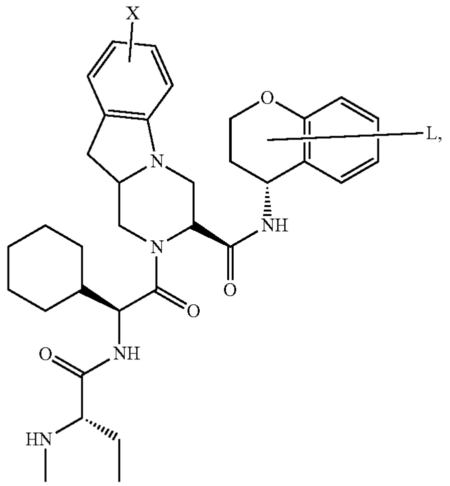

wherein X of Formula (LIX) and (LX) is one or two substituents independently selected from H, halogen or cyano, and; and L of Formulas (LIX) and (LX) is a linker group as described herein.

In any of the compounds described herein, the ILM can have the structure of Formula (LXI), which is based on the IAP ligands described in Ardecky, R J, et al., *Design, synthesis and evaluation of inhibitor of apoptosis (IAP) antagonists that are highly selective for the BIR2 domain of XIAP*, Bioorg. Med. Chem., 23(14): 4253-7 (2013), or an unnatural mimetic thereof:

(LXI)

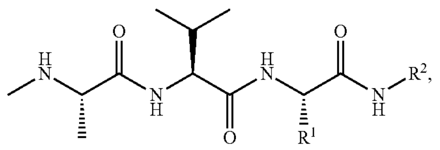

wherein:

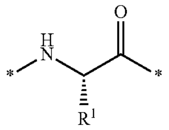

of Formula (LXI) is a natural or unnatural amino acid; and

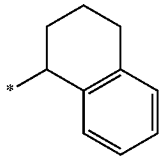

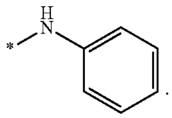

$R^2$ of Formula (LXI) is selected from:

In any of the compounds described herein, the ILM can have the structure of and be chemically linked to the linker group L as shown in Formula (LXII) or (LLXIII), or an unnatural mimetic thereof:

(LXII)

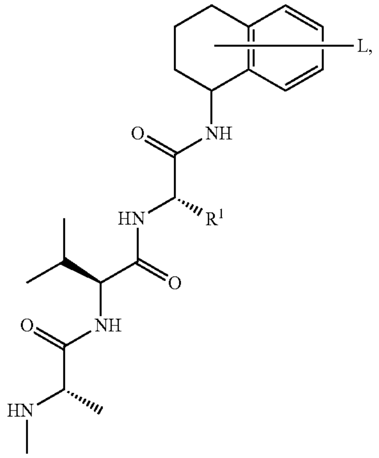

or (LXIII)

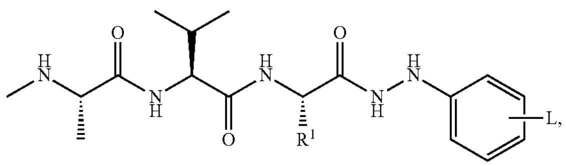

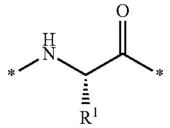

of Formula (LXI) is a natural or unnatural amino acid; and L of Formula (LXI) is a linker group as described herein.

In any of the compounds described herein, the ILM can have the structure selected from the group consisting of, which is based on the TAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

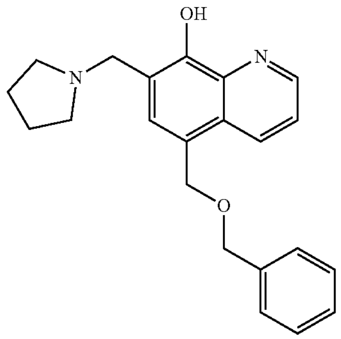

; and

-continued

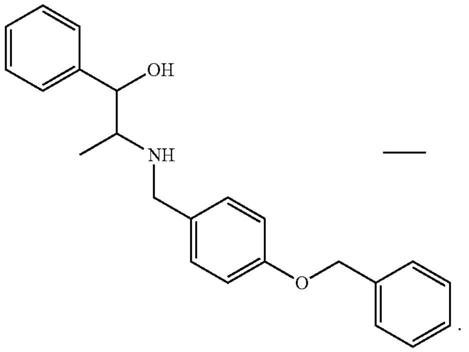

In any of the compounds described herein, the ILM has a structure according to Formula (LXIX), which is based on the IAP ligands described in Hird, A W, et al., Structure-based design and synthesis of tricyclic IAP (Inhibitor*s of Apoptosis Proteins*) *inhibitors*, Bioorg. Med. Chem. Lett., 24(7): 1820-4 (2014), or an unnatural mimetic thereof:

(LXIX)

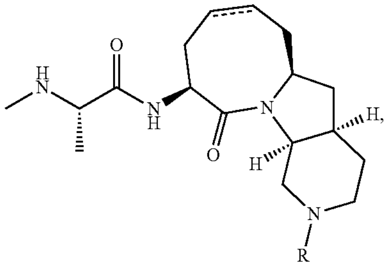

wherein R of Formula LIX is selected from the group consisting of:

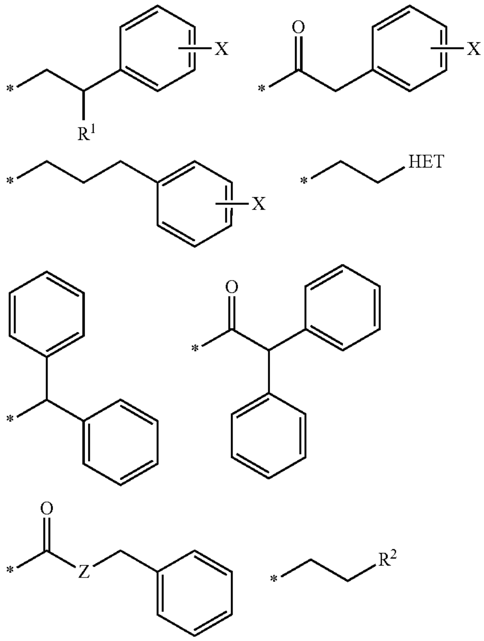

-continued

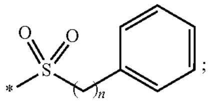

R1 of

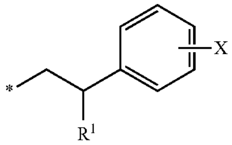

R is selected from H or Me;

R2 of

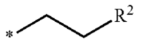

is selected from alkyl or cycloalkyl;

X of

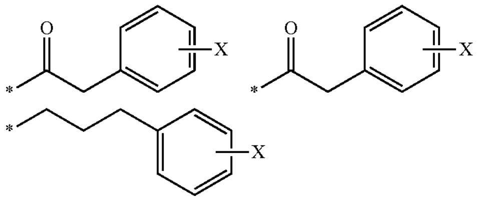

is 1-2 substitutents independently selected from halogen, hydroxy, methoxy, nitro and trifluoromethyl Z of

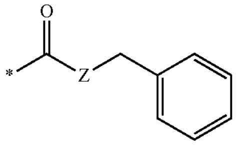

is O or NH;

HET of

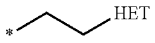

is mono- or fused bicyclic heteroaryl; and

- - - of Formula (LIX) is an optional double bond.

In a particular embodiment, the ILM of the compound has a chemical structure as represented by:

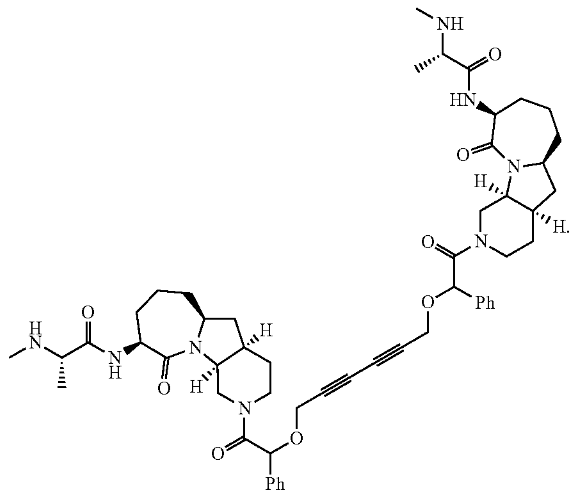

In a particular embodiment, the ILM of the compound has a chemical structure selected from the group consisting of:

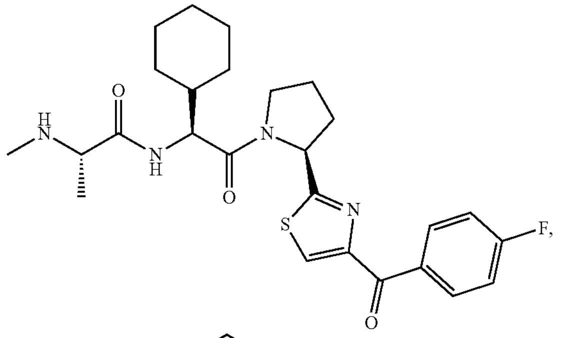

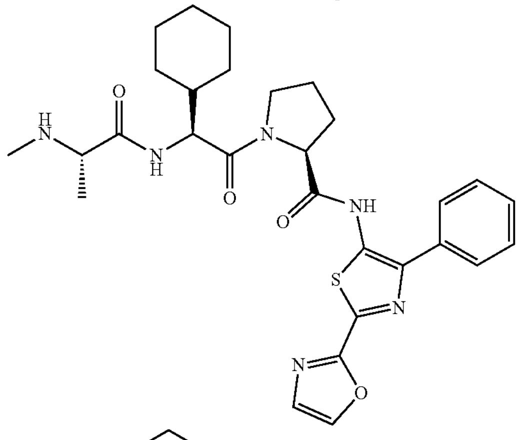

,

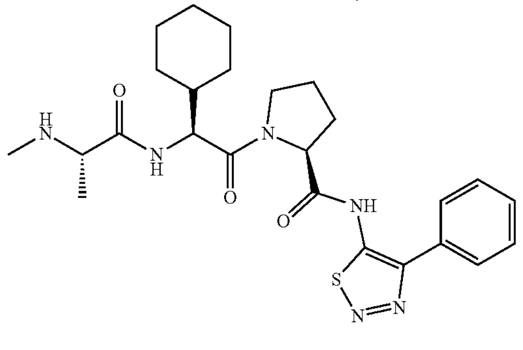

,

-continued

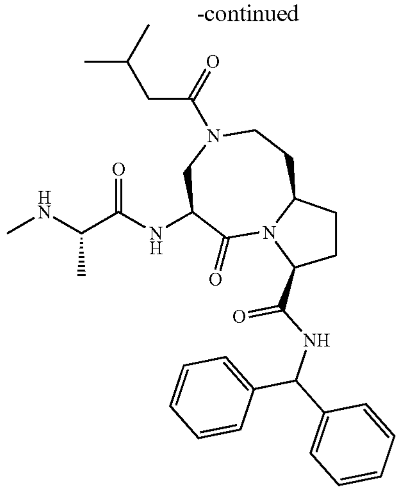

,

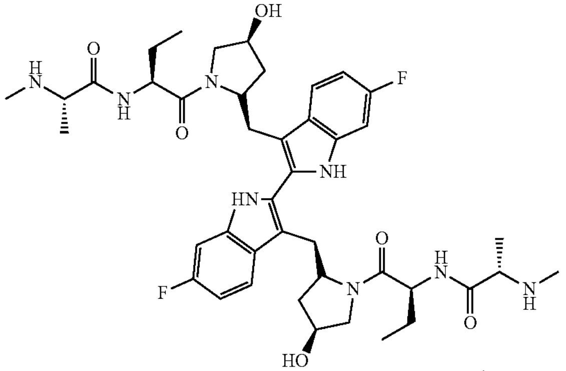

,

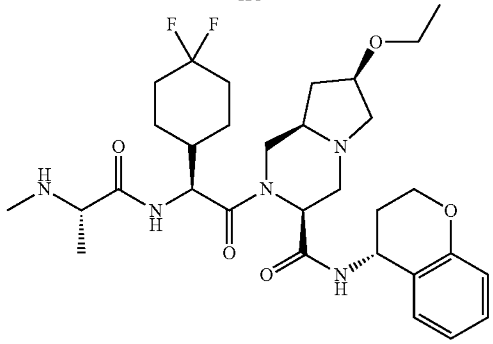

,

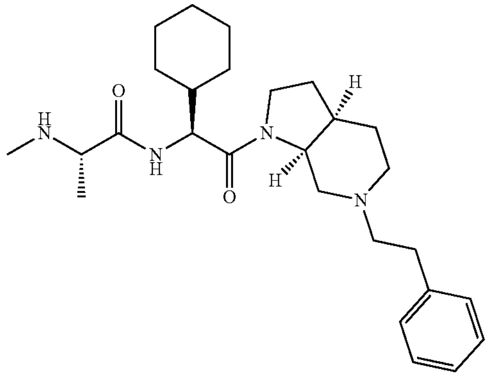

.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C═C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, 0-($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, ═O, $-(CH_2)_m-$ (here, m and n are in context, 1, 2, 3, 4, 5 or 6), $-S-$, $-S(O)-$, $SO_2-$ or $-NH-C(O)-NH-$, $-(CH_2)_nOH$, $-(CH_2)_nSH$, $-(CH_2)_nCOOH$, $C_1$-$C_6$ alkyl, $-(CH_2)_nO-(C_1$-$C_6$ alkyl), $-(CH_2)_nC(O)-(C_1$-$C_6$ alkyl), $-(CH_2)_nOC(O)-(C_1$-$C_6$ alkyl), $-(CH_2)_nC(O)O-(C_1$-$C_6$ alkyl), $-(CH_2)_nNHC(O)-R^1$, $-(CH_2)_nC(O)-NR_1R^2$, $-(OCH_2)_nOH$, $-(CH_2O)_nCOOH$, $C_1$-$C_6$ alkyl, $-(OCH_2)_nO-(C_1$-$C_6$ alkyl), $-(CH_2O)_nC(O)-(C_1$-$C_6$ alkyl), $-(OCH_2)_nNHC(O)-R^1$, $-(CH_2O)_nC(O)-NR_1R_2$, $-S(O)_2-R_S$, $-S(O)-R_S$ ($R_S$ is $C_1$-$C_6$ alkyl or a $-(CH_2)_m-NR_1R_2$ group), $NO_2$, CN or halogen (F, Cl, Br, I, preferably F or Cl), depending on the context of the use of the substituent. R and $R^2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group $O-C(O)-NR_1R_2$ group where $R^1$ and $R^2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: $-(CH_2)_nOH$, $-(CH_2)_n-O-(C_1$-$C_6)$alkyl, $-(CH_2)_n-O-(CH_2)_n-(C_1$-$C_6)$alkyl, $-(CH_2)_n-C(O)(C_0$-$C_6)$ alkyl, $-(CH_2)_n-C(O)O(C_0$-$C_6)$ alkyl, $-(CH_2)_n-OC(O)(C_0$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group $-C(O)OR$, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $-(CH_2)_m-O-C_1$-$C_6$ alkyl group or an optionally substituted $-(CH_2)_m-C(O)-O-C_1$-$C_6$ alkyl group), an optionally substituted pyridine (2-, 3, or 4-pyridine) or a group according to the chemical structure:

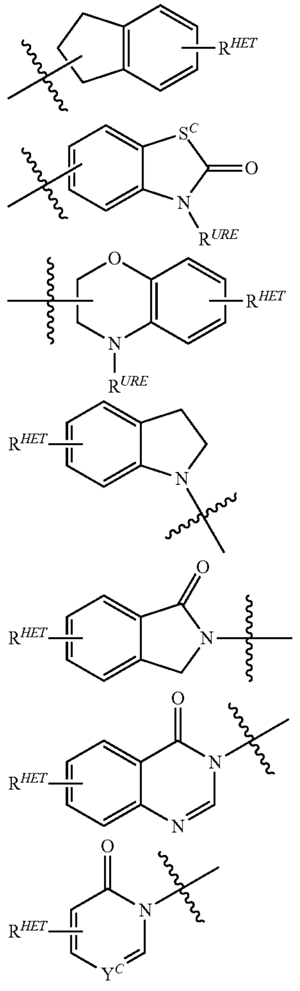

wherein $S^C$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C\equiv C-R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted $O-(C_1$-$C_6$ alkyl) (preferably substituted with one or two hydroxyl groups or up to three halo groups) or an optionally substituted $-C(O)(C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a $-C(O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or $C-R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C\equiv C-R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroinidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO— heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (Br, Cl, F, or I).

The term "lower alkyl" refers to methyl, ethyl or propyl

The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

Formula (A-1)

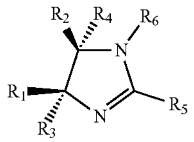

Formula (A-2)

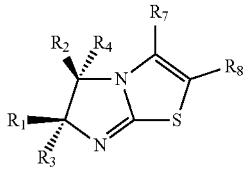

Formula (A-3)

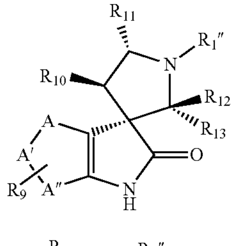

Formula (A-4)

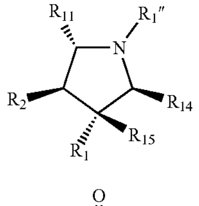

Formula (A-5)

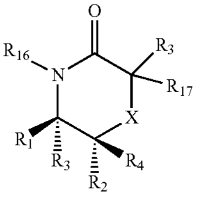

-continued

Formula (A-6)

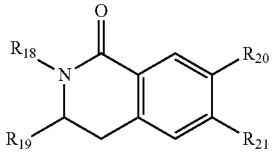

Formula (A-7)

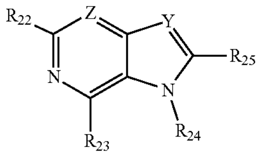

Formula (A-8)

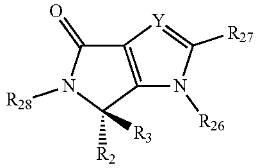

wherein above Formula (A-1) through Formula (A-8),

X of Formula (A-1) through Formula (A-8) is selected from the group consisting of carbon, oxygen, sulfur, sulfoxide, sulfone, and N—$R^a$;

$R^a$ is independently H or an alkyl group with carbon number 1 to 6;

Y and Z of Formula (A-1) through Formula (A-8) are independently carbon or nitrogen;

A, A' and A" of Formula (A-1) through Formula (A-8) are independently selected from C, N, O or S, can also be one or two atoms forming a fused bicyclic ring, or a 6,5- and 5,5-fused aromatic bicyclic group;

$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ of Formula (A-1) through Formula (A-8) are independently selected from the group consisting of H, methyl and C1 to C6 alkyl;

$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R^6$ of Formula (A-1) through Formula (A-8) is H or —C(═O)$R^b$, wherein $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein $R^d$ of Formula (A-1) through Formula (A-8) is selected from the group consisting of alkoxy, alkyl sulfone, alkyl sulfoxide, N-substituted carboxamide, —NHC(O)-alkyl, —NH—$SO_2$-alkyl, aryl, substituted aryl, heteroaryl, substituted heteroaryl;

$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ of Formula (A-1) through Formula (A-8) is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ of Formula (A-1) through Formula (A-8) is an alkylene with 1 to 6 carbons, or a bond;

$R^f$ of Formula (A-1) through Formula (A-8) is a substituted 4- to 7-membered heterocycle;

$R^g$ of Formula (A-1) through Formula (A-8) is selected from the group consisting of aryl, hetero aryl, substituted aryl or heteroaryl, and 4- to 7-membered heterocycle;

$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^i$), wherein $R^h$ and $R^i$ are selected from groups consisting of the following:

H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ of Formula (A-1) through Formula (A-8) are independently selected from the group consisting of H, connected to form a ring, 4-hydroxycyclohehexane; mono- and dihydroxy substituted alkyl (C3 to C6);

3-hydroxycyclobutane; phenyl-4-carboxylic acid, and substituted phenyl-4-carboxylic acid;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of C1-6 alkyl, C2-6 alkenyl, C1-C6 alkyl-C1-C6 cycloalkyl (e.g., C1-C3 alkyl-C3-C6 cycloalky, C1-C6 alkyl-C3-C6 cycloalkyl), C1-6 alkyl or C3-6 cycloalkyl with one or multiple hydrogens replaced by fluorine, alkyl or cycloalkyl with one $CH_2$ replaced by S(═O), —S, or —S(═O)$_2$, alkyl or cycloalkyl with terminal $CH_3$ replaced by S(═O)$_2$N(alkyl)(alkyl), —C(═O)N (alkyl)(alkyl), —N(alkyl)S(═O)$_2$(alkyl), —C(═O)2(allkyl), —O(alkyl), $C_{1-6}$ alkyl or alkyl-cycloalkyl with hydrogen replaced by hydroxyl group, a 3 to 7 membered cycloalkyl or heterocycloalkyl, optionally containing a —(C=0)- group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ of Formula (A-1) through Formula (A-8) is selected from the group consisting of $(CH_2)nC(O)NR^kR^l$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, aklyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N($C_{1-4}$ alkyl)(cycloalkyl), —N($C_{1-4}$ alkyl)alkyl-cycloalkyl, and —N($C_{1-4}$ alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or hetroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydoxylated C1-6 alkoxy, and fluorine substituted $C_{1-6}$ alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O— heteroaryl, —O-alkyl, —O-alkyl-cycloalkyl, —NH-alkyl, —NH-alkyl-cycloalkyl, —N(H)-aryl, —N(H)— heteroaryl, —N(alkyl)-aryl, —N(alkyl)-heteroaryl, the aryl or heteroaryl groups can be substituted with halogen, $C_{1-6}$ alkyl, hydoxylated $C_{1-6}$ alkyl, cycloalkyl, fluorine-substituted $C_{1-6}$ alkyl, CN, alkoxy, alkyl sulfone, amide and sulfonamide;

$R_{24}$ of Formula (A-1) through Formula (A-8) is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydoxylated alkyl, cyano-substituted alkyl, cycloalyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5, 6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH —S(O)$_2$-alkyl, and —S(O)$_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1''}$ of Formula (A-1) through Formula (A-8) is selected from the group consisting of alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperizine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where 'L" is a connector (i.e. a linker group), and "PTM" is a ligand binding to a target protein.

In certain embodiments, the description provides a bifunctional molecule comprising a structure selected from the group consisting of:

Formula (A-9)

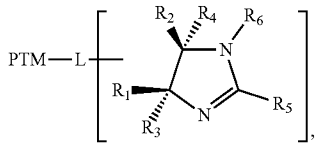

Formula (A-10)

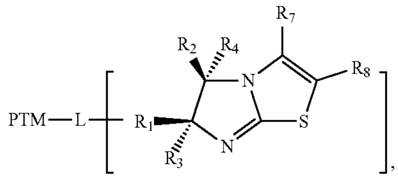

Formula (A-11)

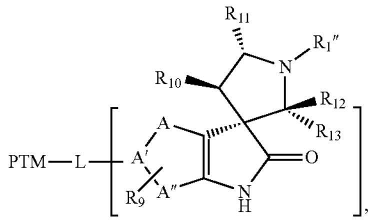

Formula (A-12)

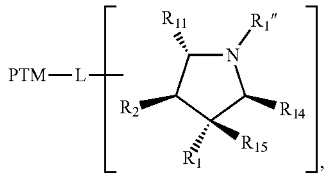

Formula (A-13)

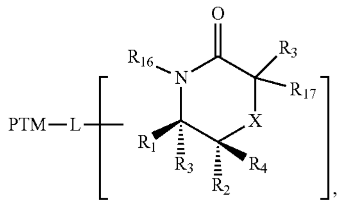

Formula (A-14)

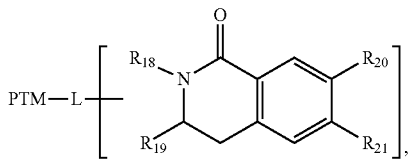

Formula (A-15)

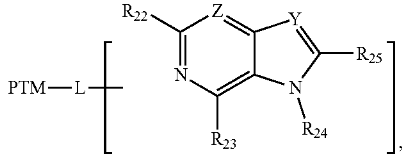

and

-continued

Formula (A-16)

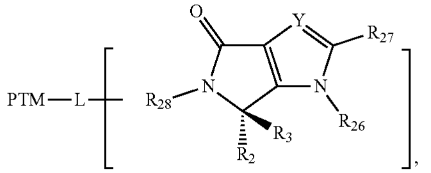

wherein X, $R^a$, Y, Z, A, A', A", $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

A-1-1

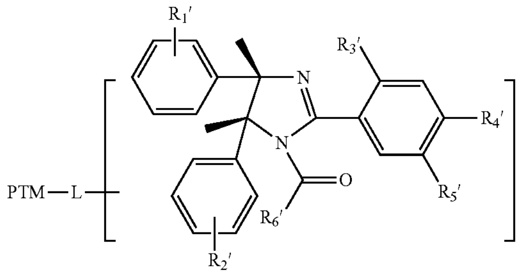

A-1-2

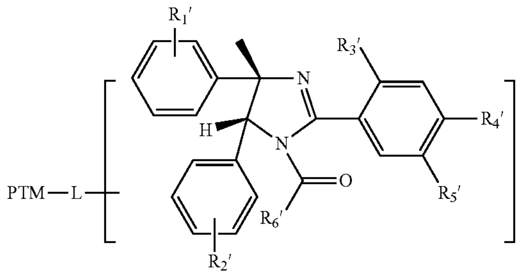

A-1-3

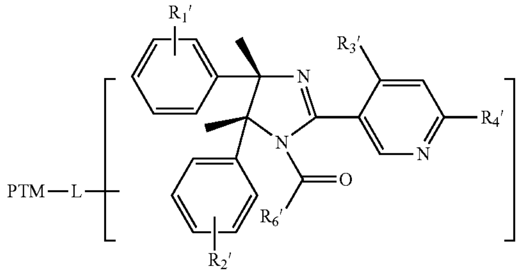

-continued

A-1-4

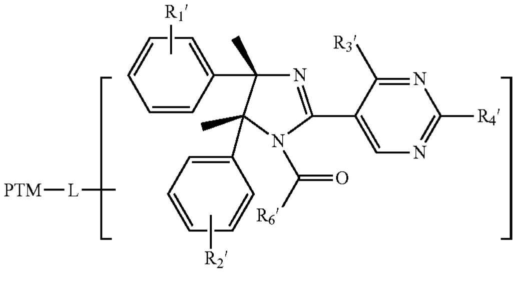

wherein:

R1' and R2' of Formulas A-1-1 through A-1-4 (i.e., A-1-1, A-1-2, A-1-3, and A-1-4) are independently selected from the group consisting of F, Cl, Br, I, acetylene, CN, $CF_3$ and $NO_2$;

R3' is selected from the group consisting of $—OCH_3$, $—OCH_2CH_3$, $—OCH_2CH_2F$, $—OCH_2CH_2OCH_3$, and $—OCH(CH_3)_2$;

R4' of Formulas A-1-1 through A-1-4 is selected from the group consisting of H, halogen, $—CH_3$, $—CF_3$, $—OCH_3$, $—C(CH_3)_3$, $—CH(CH_3)_2$, -cyclopropyl, —CN, $—C(CH_3)_2OH$, $—C(CH_3)_2OCH_2CH_3$, $—C(CH_3)_2CH_2OH$, $—C(CH_3)_2CH_2OCH_2CH_3$, $—C(CH_3)_2CH_2OCH_2CH_2OH$, $—C(CH_3)_2CH_2OCH_2CH_3$, $—C(CH_3)_2CN$, $—C(CH_3)_2C(O)CH_3$, $—C(CH_3)_2C(O)NHCH_3$, $—C(CH_3)_2C(O)N(CH_3)_2$, $—SCH_3$, $—SCH_2CH_3$, $—S(O)_2CH_3$, $—S(O_2)CH_2CH_3$, $—NHC(CH_3)_3$, $—N(CH_3)_2$, pyrrolidinyl, and 4-morpholinyl;

R5' of Formulas A-1-1 through A-1-4 is selected from the group consisting of halogen, -cyclopropyl, $—S(O)_2CH_3$, $—S(O)_2CH_2CH_3$, 1-pyrrolidinyl, $—NH_2$, $—N(CH_3)_2$, and $—NHC(CH_3)_3$; and R6' of Formulas A-1-1 through A-1-4 is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, R6' of Formulas A-1-1 through A-1-4 is independently selected from the group consisting of H,

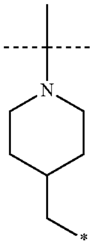

,

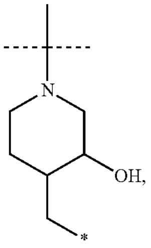

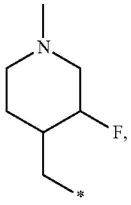

-continued

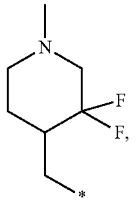

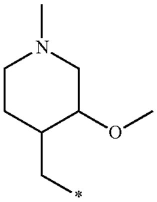

,

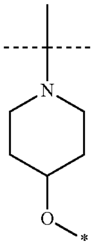

,

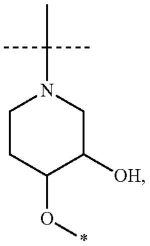

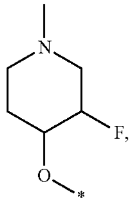

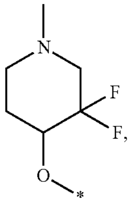

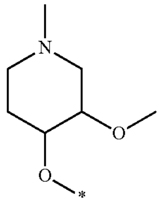

,

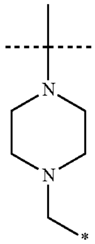

,

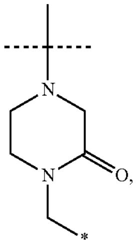

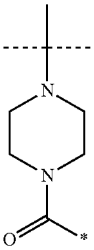

,

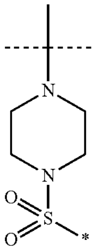

,

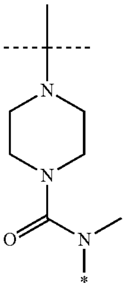

,

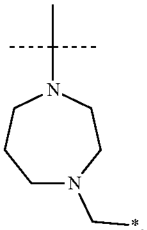

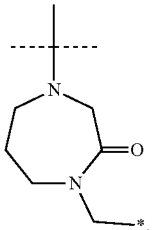

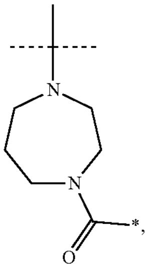

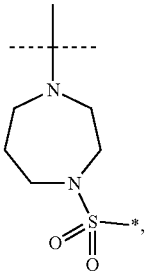

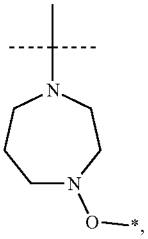

-continued

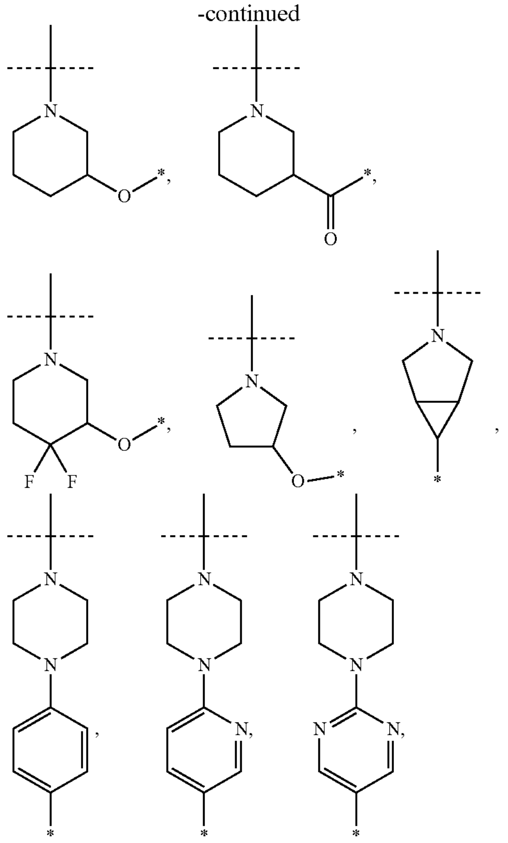

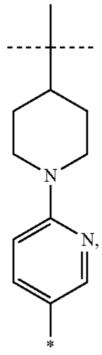

and

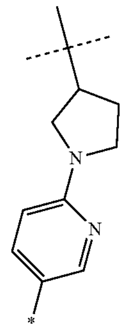

wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

A-4-1

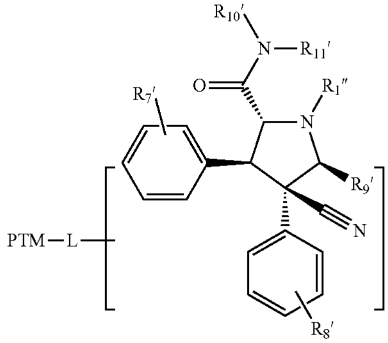

A-4-2

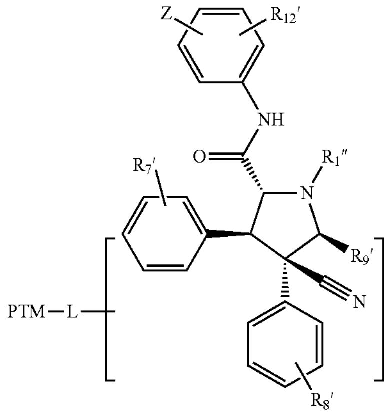

A-4-3

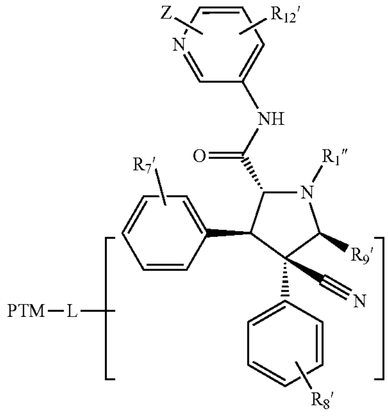

A-4-4

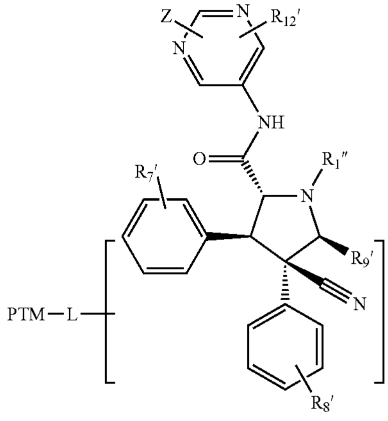

-continued

A-4-5

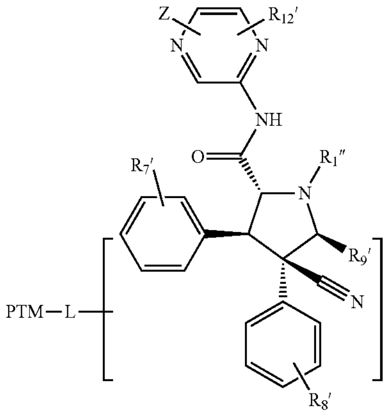

A-4-6

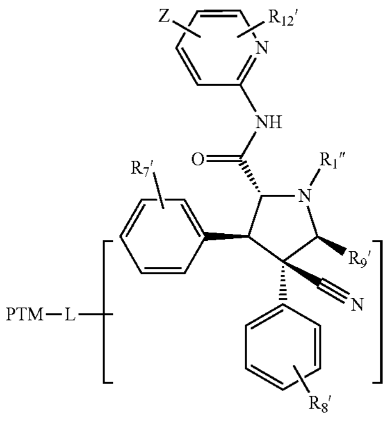

wherein:

R7' of Formula A-4-1 through A-4-6 (i.e., A-4-1, A-4-2, A-4-3, A-4-4, A-4-5, and A-4-6) is a member selected from the group consisting of halogen, mono-, and di- or tri-substituted halogen;

R8' of Formula A-4-1 through A-4-6 is selected from the group consisting of H, —F, —Cl, —Br, —I, —CN, —$NO_2$, ethylnyl, cyclopropyl, methyl, ethyl, isopropyl, vinyl, methoxy, ethoxy, isopropoxy, —OH, other CL-6 alkyl, other $C_{1-6}$ alkenyl, and $C_{1-6}$ alkynyl, mono-, di- or tri-substituted;

R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;

Z of Formula A-4-1 through A-4-6 is selected from the group consisting of H, —$OCH_3$, —$OCH_2CH_3$, and halogen;

R10' and R11' of Formula A-4-1 through A-4-6 are each independently selected from the group consisting of H, $(CH_2)_n$—R', $(CH_2)_n$—NR'R", $(CH_2)_n$—NR'COR", $(CH_2)_n$—NR'$SO_2$R", $(CH_2)_n$—COOH, $(CH_2)_n$—COOR', $(CH)_n$—CONR'R", $(CH_2)_n$—OR', $(CH_2)_n$—SR', $(CH_2)_n$—SOR', $(CH_2)_n$—CH(OH)—R', $(CH_2)_n$—COR', $(CH_2)_n$—$SO_2$R', $(CH_2)_n$—SONR'R", $(CH_2)_n$—$SO_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m$ $(CH_2)_n$—NR'$SO_2$R", $(CH_2CH_2O)_m(CH_2)_n$—COOH, $(CH_2CH_2O)_m(CH_2)_n$—COOR', $(CH_2CH_2O)_m$—$(CH_2)_n$—CONR'R", $(CH_2CH_2O)_m$—$(CH_2)_n$—$SO_2$R', $(CH_2CH_2O)_m$—$(CH_2)_n$—COR', $(CH_2CH_2O)_m$—$(CH_2)_n$—SONR'R", $(CH_2CH_2O)_m$—$(CH_2)_n$—$SO_2$NR'R", $(CH_2)_p$—$(CH_2CH_2O)_m$—$(CH_2)_n$R', $(CH_2)_p$—$(CH_2CH_2O)_m$—$(CH_2)_n$—OH, $(CH_2)_p$—$(CH_2CH_2O)_m$—$(CH_2)_n$—OR', $(CH_2)_p$—$(CH_2CH_2O)_m$—$(CH_2)_n$—NR'R", $(CH_2)_p$—$(CH_2CH_2O)_m$—$(CH_2)_n$—NR'COR", $(CH_2)_p$—$(CH_2CH_2O)$ m-$(CH_2)_n$—NR'$SO_2$R", $(CH_2)_p$—$(CH_2CH_2O)_m$—$(CH_2)_n$—COOH, $(CH_2)_p$—$(CH_2CH_2O)_m$—$(CH_2)_n$—COOR', $(CH_2)_p$—$(CH_2CH_2O)_m$—$(CH_2)_n$—CONR'R", $(CH_2)_p$—$(CH_2CH_2O)_m$—$(CH_2)_n$—$SO_2$R', $(CH_2)_p$—$(CH_2CH_2O)_m$—$(CH_2)_n$—COR', $(CH_2)_p$—$(CH_2CH_2O)_m$—$(CH_2)_n$—SONR'R", $(CH_2)_p$—$(CH_2CH_2O)_m$—$(CH_2)_n$—$SO_2$NR'R", Aryl-$(CH_2)_n$—COOH, and heteroaryl-alkyl-CO-alkyl-NR'R"m, wherein the alkyl may be substituted with OR', and heteroaryl-$(CH_2)_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), N(alkyl)$_2$, oxo, carboxy, clcloalkyl and heteroaryl;

m, n, and p are independently 0 to 6;

R12' of Formula A-4-1 through A-4-6 is selected from the group consisting of —O-(alkyl), —O-(alkyl)-akoxy, —C(O)-(alkyl), —C(OH)-alkyl-alkoxy, —C(O)—NH-(alkyl), —C(O)—N-(alkyl)$_2$, —S(O)-(alkyl), S(O)$_2$-(alkyl), —C(O)-(cyclic amine), and —O-aryl-(alkyl), —O-aryl-(alkoxy);

R1" of Formula A-4-1 through A-4-6 is selected from the group consisting of alkyl, aryl substituted alkyl, aloxy substituted alkyl, cycloalkyl, ary-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", $R^{12}$", or $R^{1}$".

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

Exemplary MDM2 binding moieties include, but not limited, the following:

The HDM2/MDM2 inhibitors identified in Vassilev, et al., In vivo activation of the p53 pathway by small-molecule antagonists of MDM2, *SCIENCE* vol:303, pag:844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

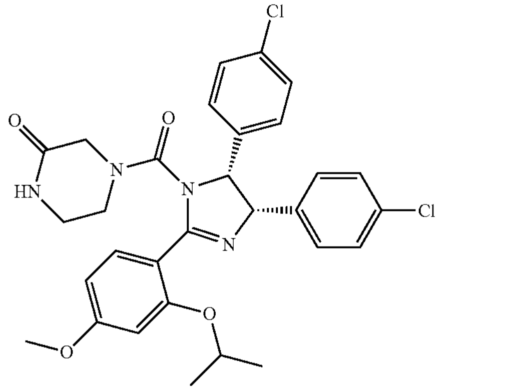 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

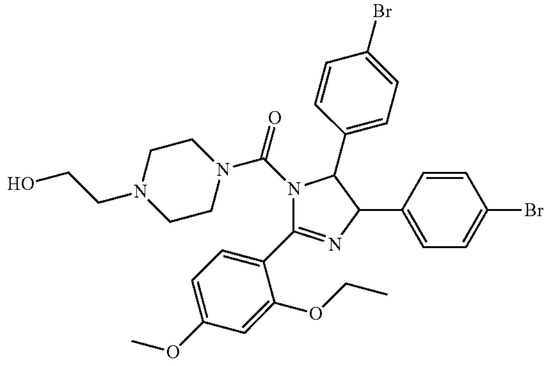 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group); and

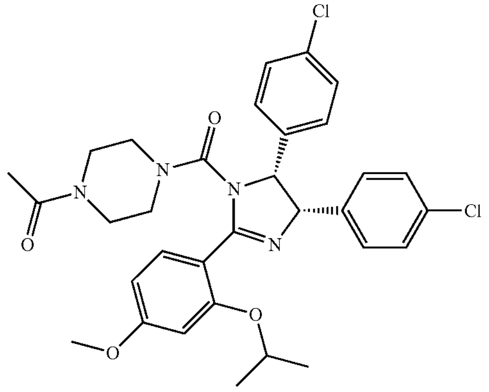 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group).

Exemplary CLMs

Neo-Imide Compounds

In one aspect the description provides compounds useful for binding and/or inhibiting cereblon. In certain embodiments, the compound is selected from the group consisting of chemical structures:

(a)

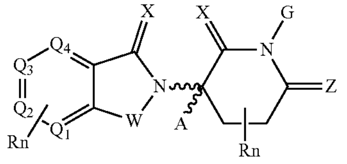

(b)

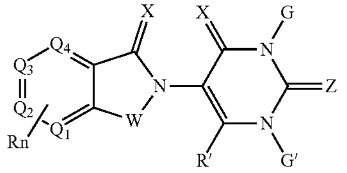

(c)

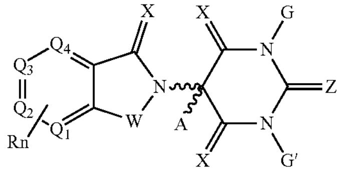

(d)

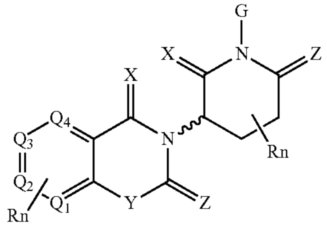

(e)

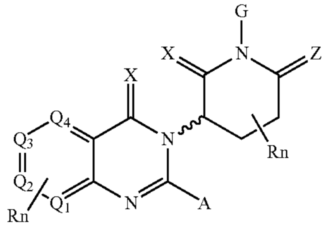

and (f)

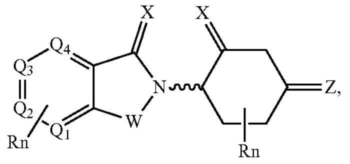

wherein:

W of Formulas (a) through (e) is independently selected from the group $CH_2$, CHR, C═O, $SO_2$, NH, and N-alkyl;

X of Formulas (a) through (e) is independently selected from the group O, S and $H_2$;

Y of Formulas (a) through (e) is independently selected from the group $CH_2$, —C═CR', NH, N-alkyl, N-aryl, N-hetaryl, N-cycloalkyl, N-heterocyclyl, O, and S;

Z of Formulas (a) through (e) is independently selected from the group O, and S or $H_2$ except that both X and Z cannot be $H_2$;

G and G' of Formulas (a) through (e) are independently selected from the group H, optionally substituted linear or branched alkyl, OH, R'OCOOR, R'OCONRR", $CH_2$-heterocyclyl optionally substituted with R', and benzyl optionally substituted with R';

Q1-Q4 of Formulas (a) through (e) represent a carbon C substituted with a group independently selected from R', N or N-oxide;

A of Formulas (a) through (e) is independently selected from the group consisting of H, optionally substituted linear or branched alkyl, cycloalkyl, Cl and F;

R of Formulas (a) through (e) comprises, but is not limited to: —CONR'R", —OR', —NR'R", —SR', —SO2R', —$SO_2$NR'R", —CR'R"—, —CR'NR'R"—, (—CR'O) 'R", -aryl, -hetaryl, optionally substituted linear or branched-alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$ and —$OCF_3$ R' and R" of Formulas (a) through (e) are independently selected from a bond, H, alkyl, cycloalkyl, aryl, heteroaryl, heterocyclic, —C(═O)R, heterocyclyl, each of which is optionally substituted;

N' of Formulas (a) through (e) is an integer from 1-10 (e.g., 1-4, 1, 2, 3, 4, 5, 6, 7, 8, 9, or 10);

〰 of Formulas (a) through (e) represents a bond that may be stereospecific ((R) or (S)) or non-stereospecific; and $R_n$ of Formulas (a) through (e) comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy.

Exemplary CLMs

In any of the compounds described herein, the CLM comprises a chemical structure selected from the group:

(a)

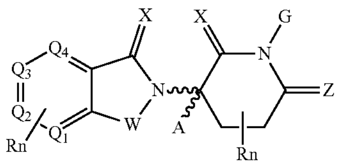

(b)

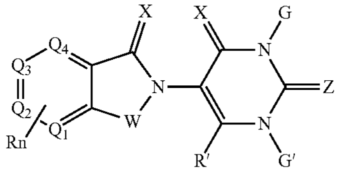

(c)

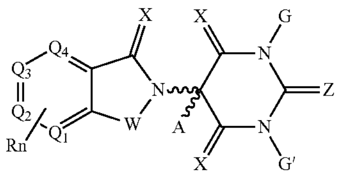

-continued (d)

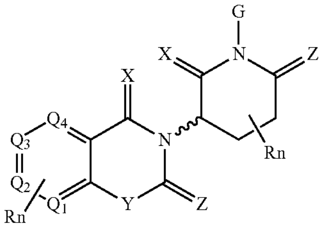

(e)

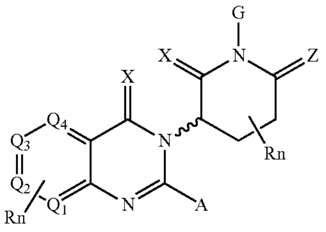

and (f)

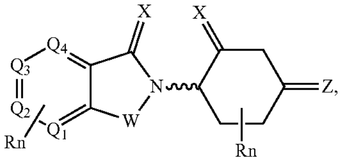

, (e) and (f), wherein:

W of Formulas (a) through (e) is independently selected from the group $CH_2$, CHR, C═O, $SO_2$, NH, and N-alkyl;

X of Formulas (a) through (e) is independently selected from the group O, S and $H_2$;

Y of Formulas (a) through (e) is independently selected from the group $CH_2$, —C═CR', NH, N-alkyl, N-aryl, N-hetaryl, N-cycloalkyl, N-heterocyclyl, O, and S;

Z of Formulas (a) through (e) is independently selected from the group O, and S or $H_2$ except that both X and Z cannot be $H_2$;

G and G' of Formulas (a) through (e) are independently selected from the group H, optionally substituted linear or branched alkyl, OH, R'OCOOR, R'OCONRR", $CH_2$-heterocyclyl optionally substituted with R', and benzyl optionally substituted with R';

Q1-Q4 of Formulas (a) through (e) represent a carbon C substituted with a group independently selected from R', N or N-oxide;

A of Formulas (a) through (e) is independently selected from the group consisting of a H, optionally substituted linear or branched alkyl, cycloalkyl, Cl and F;

R of Formulas (a) through (e) comprises, but is not limited to: —CONR'R", —OR', —NR'R", —SR', —SO2R', —SO2NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$and —$OCF_3$ R' and R" of Formulas (a) through (e) are independently selected from a bond, H, alkyl, cycloalkyl, aryl, heteroaryl, heterocyclic, —C(=O)R, heterocyclyl, each of which is optionally substituted;

n of Formulas (a) through (e) is an integer from 1-10 (e.g., 1-4, 1, 2, 3, 4, 5, 6, 7, 8, 9, or 10);

~ of Formulas (a) through (e) represents a bond that may be stereospecific ((R) or (S)) or non-stereospecific; and Rn of Formulas (a) through (e) comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

Formula (g)

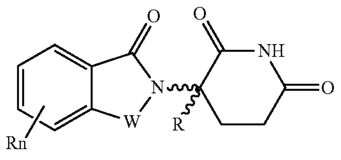

wherein:

W of Formula (g) is independently selected from the group $CH_2$, C=O, NH, and N-alkyl;

R of Formula (g) is independently selected from a H, methyl, or optionally substituted linear or branched alkyl (e.g., optionally substituted linear or branched C1-C6 alkyl);

~ of Formula (g) represents a bond that may be stereospecific ((R) or (S)) or non-stereospecific; and Rn of Formula (g) comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

More specifically, non-limiting examples of CLMs include those shown below as well as those "hybrid" molecules that arise from the combination of 1 or more of the different features shown in the molecules below.

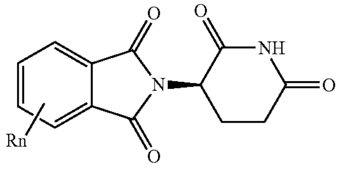

-continued

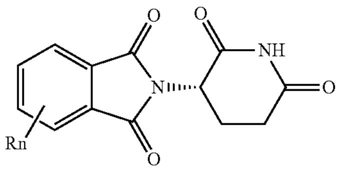

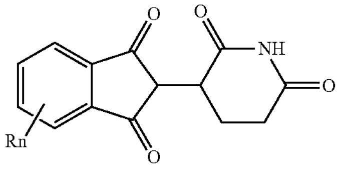

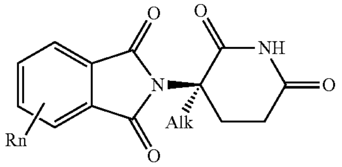

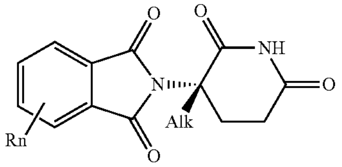

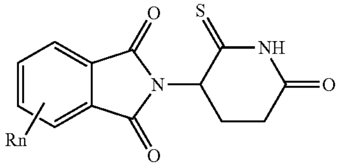

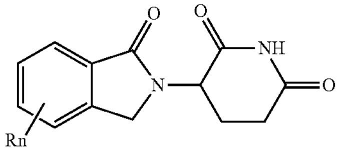

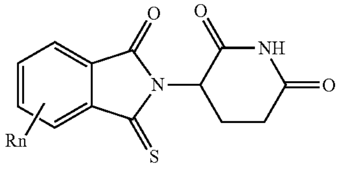

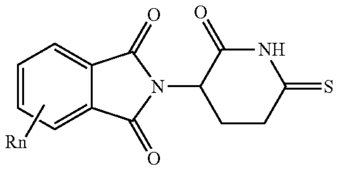

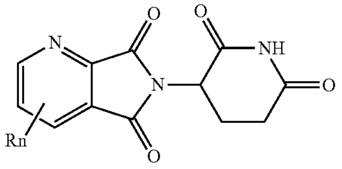

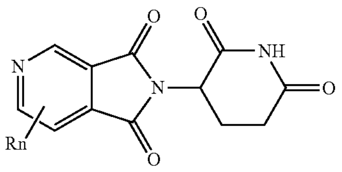

-continued
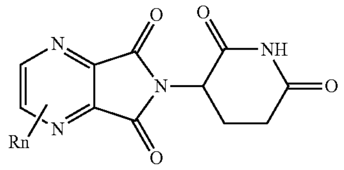
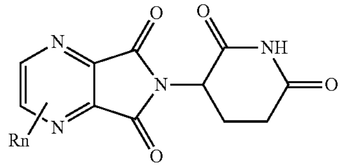
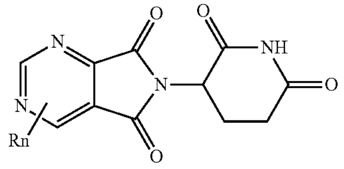
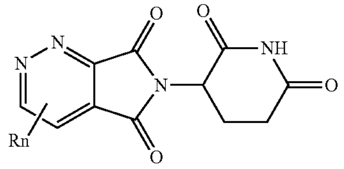
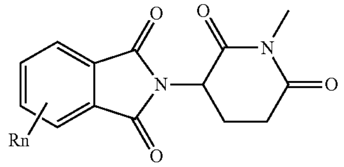
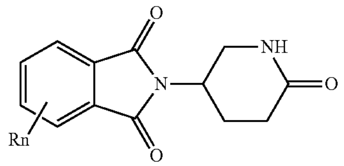
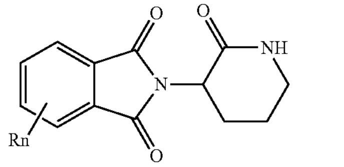
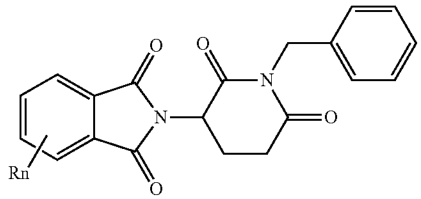
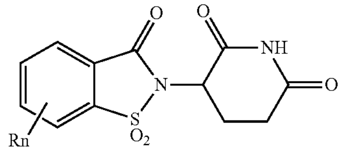
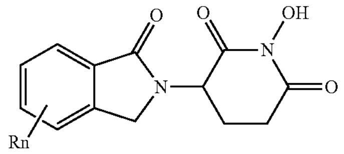
-continued
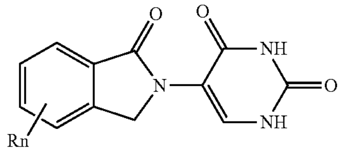
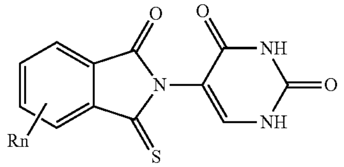
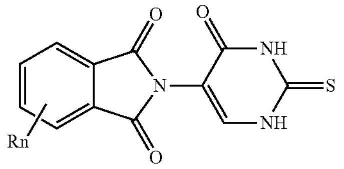
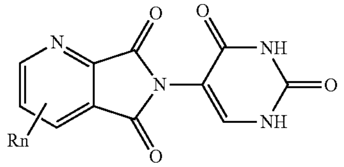
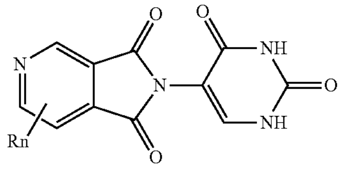
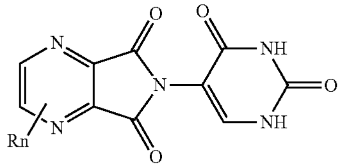
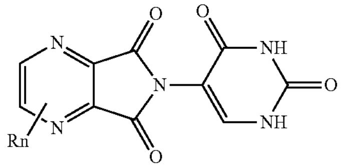
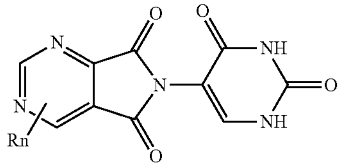
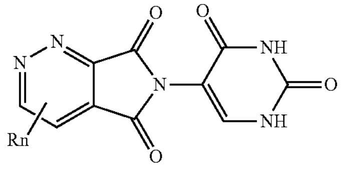
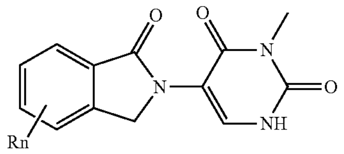

-continued
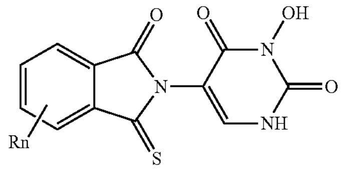
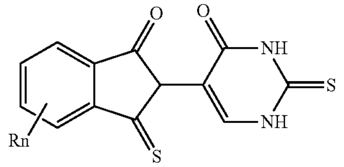
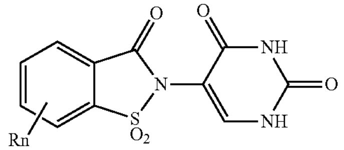
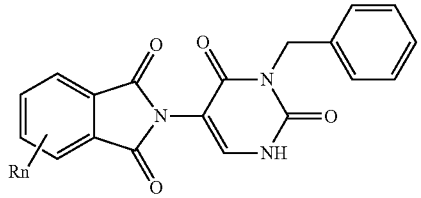
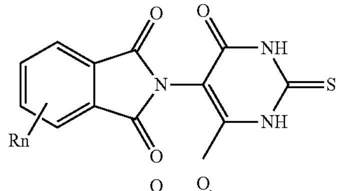
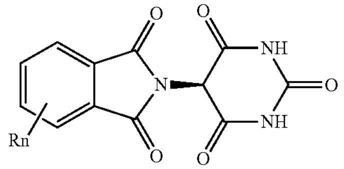
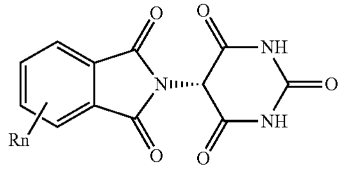
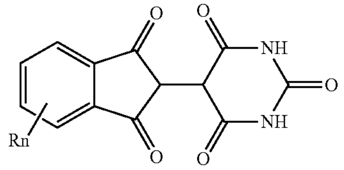
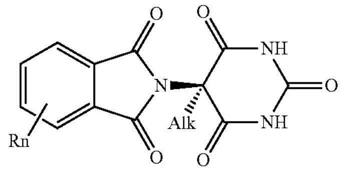
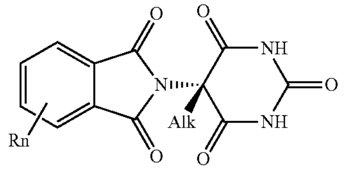
-continued
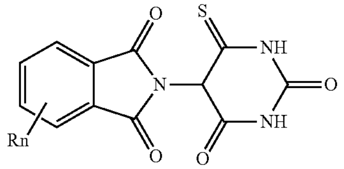
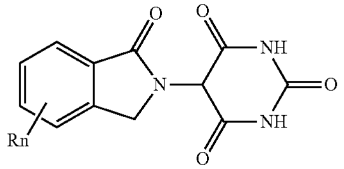
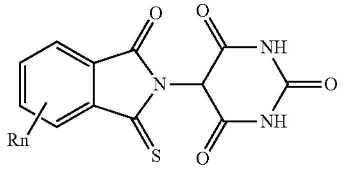
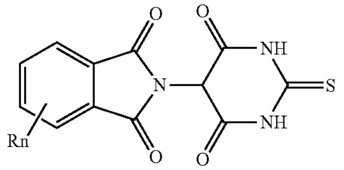
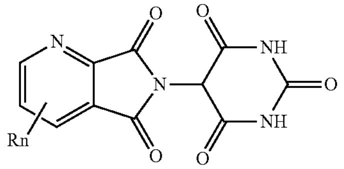
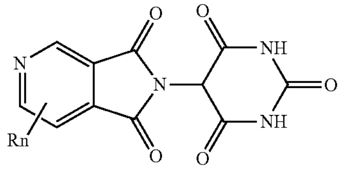
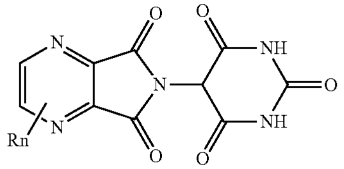
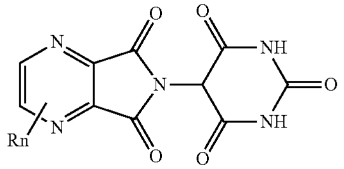
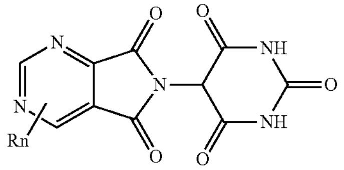
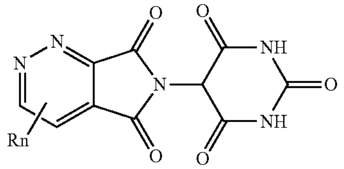

-continued
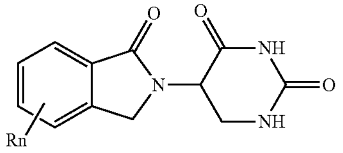
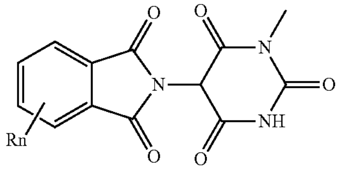
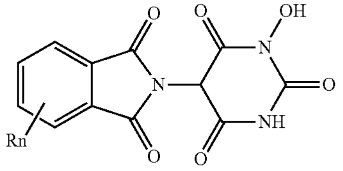
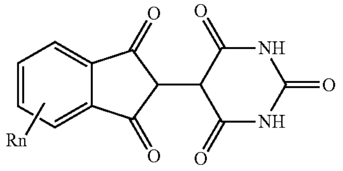
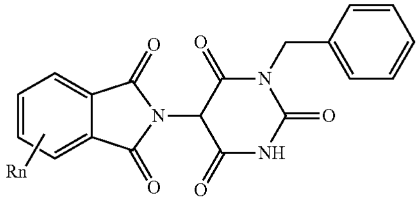
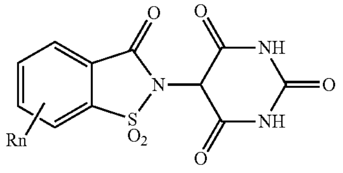
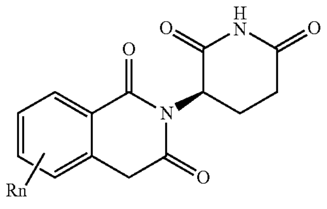
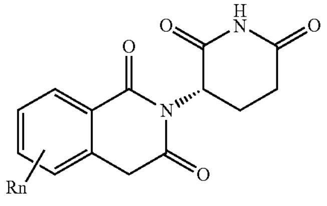
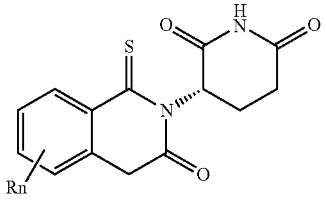
-continued
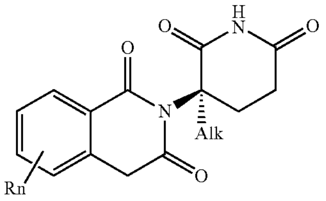
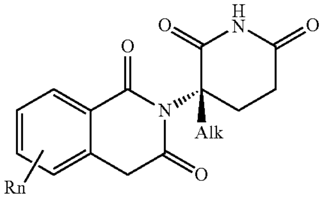
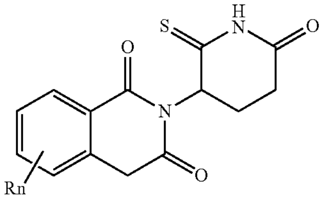
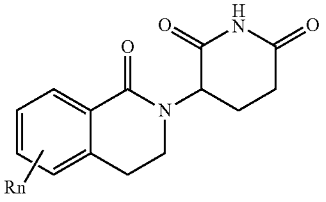
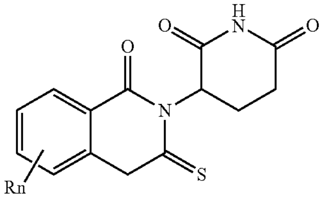
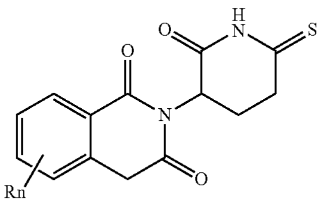
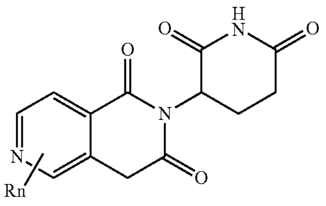
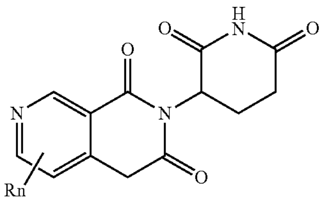

-continued
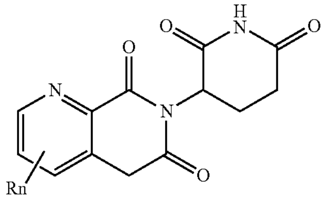
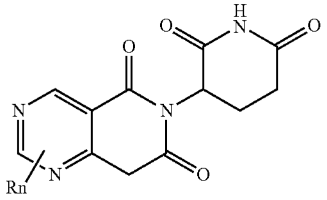
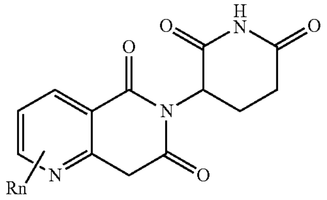
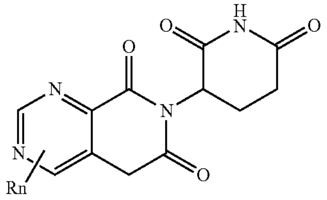
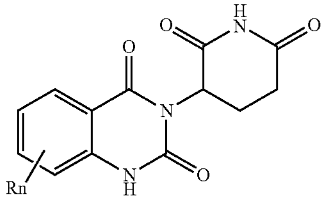
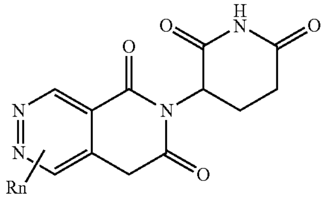
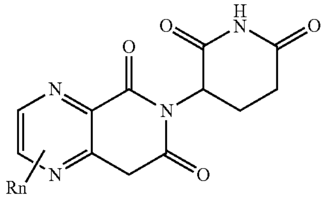
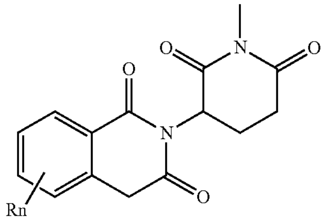
-continued
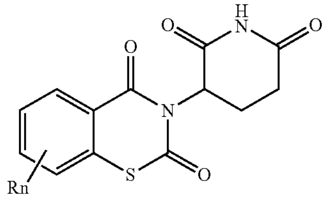
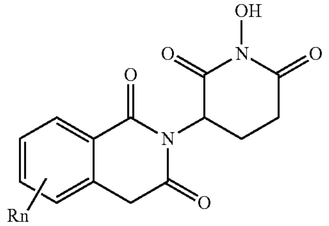
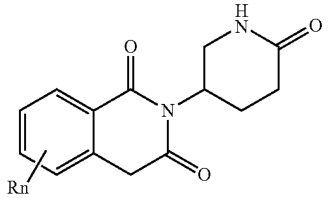
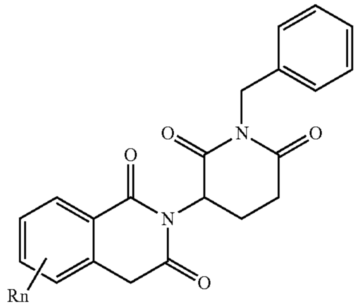
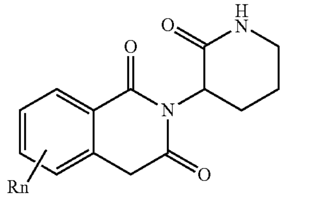
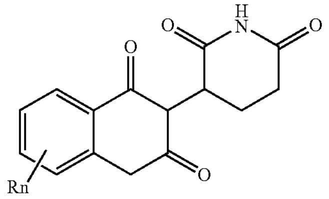
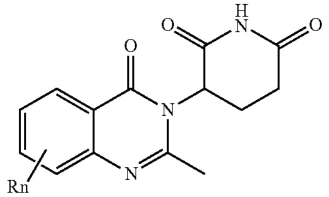
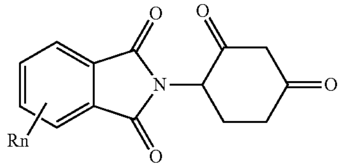

-continued
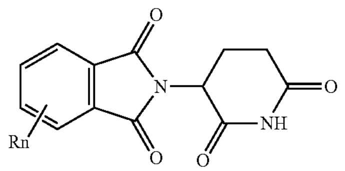
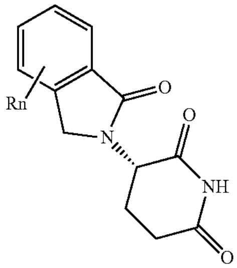
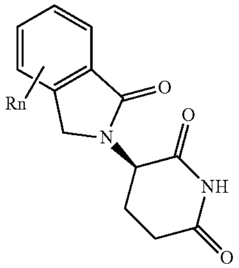
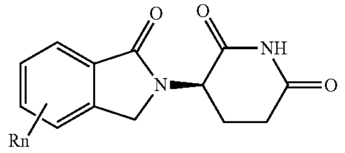
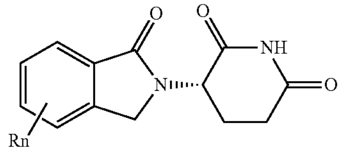
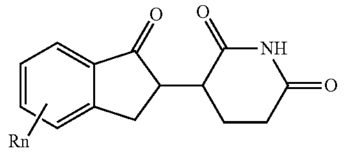
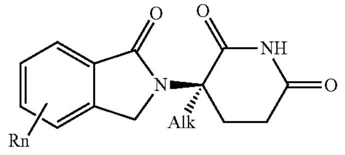
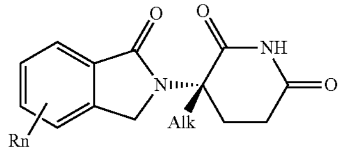
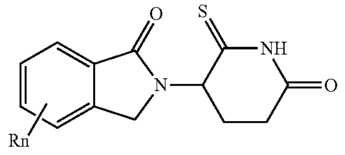
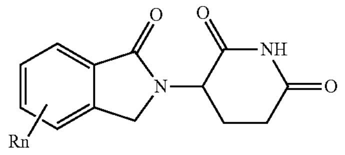
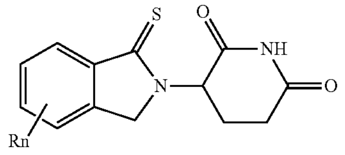
-continued
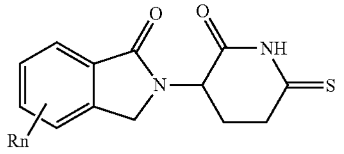
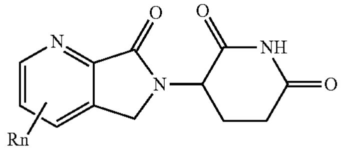
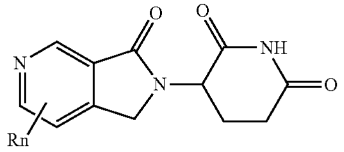
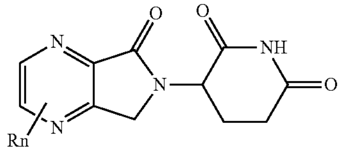
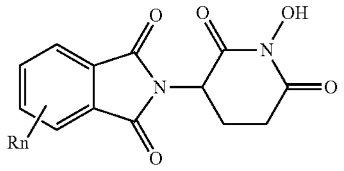
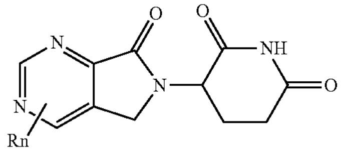
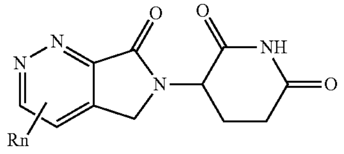
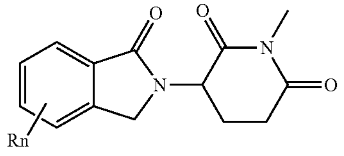
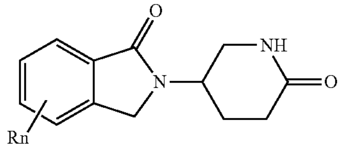
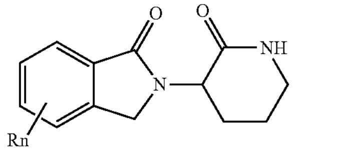
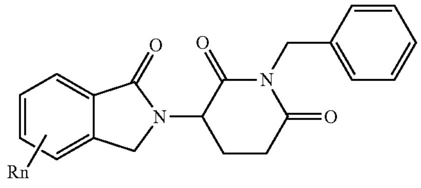

-continued
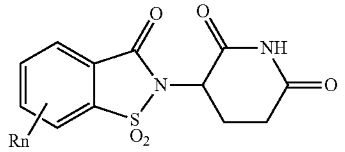
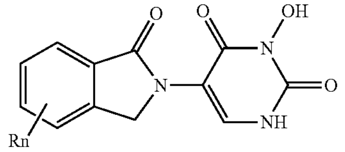
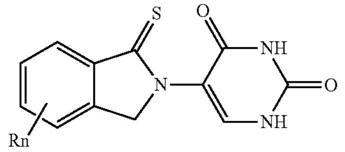
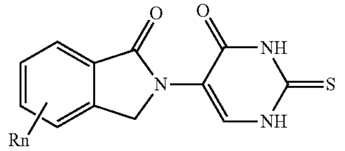
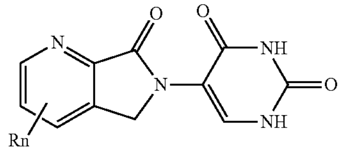
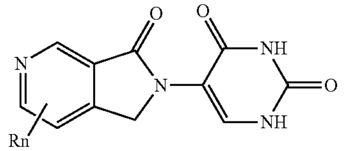
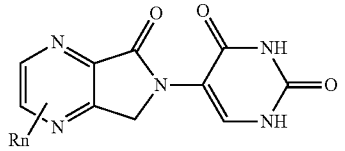
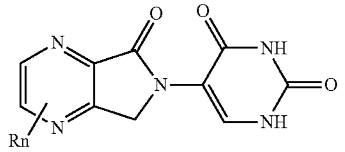
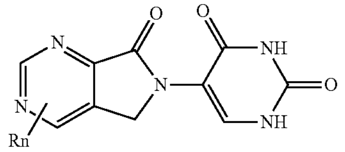
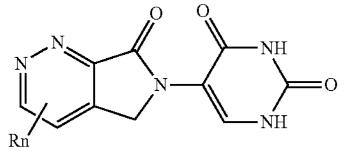
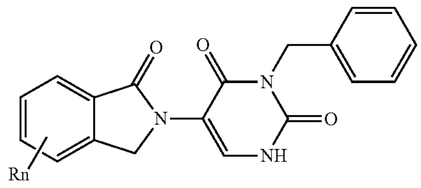
-continued
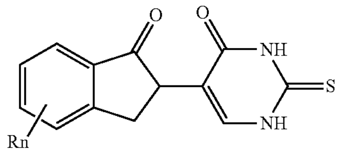
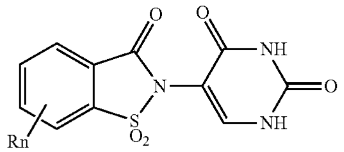
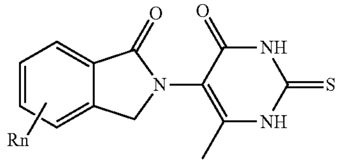
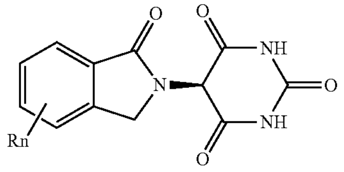
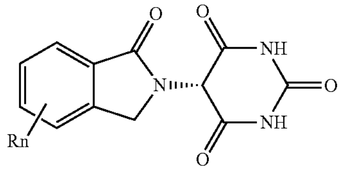
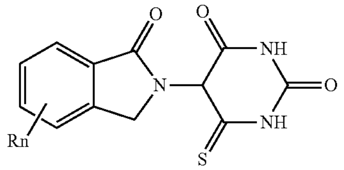
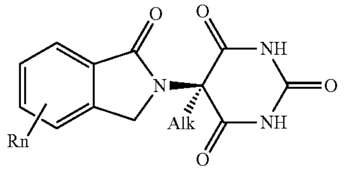
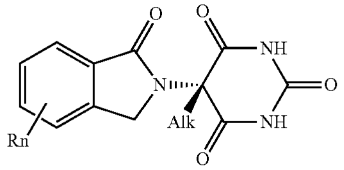
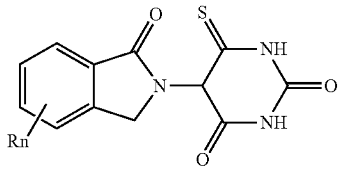
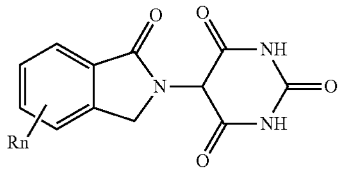

-continued
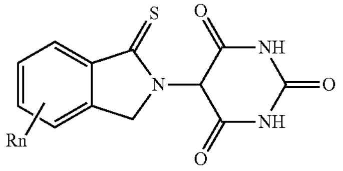
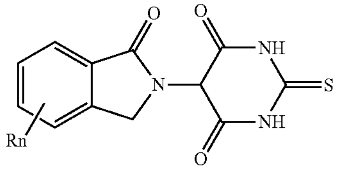
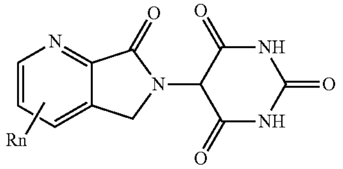
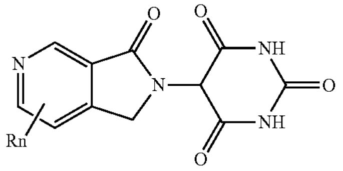
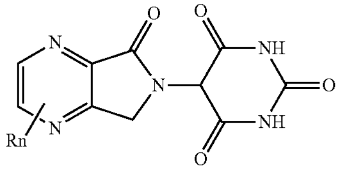
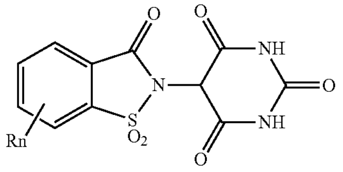
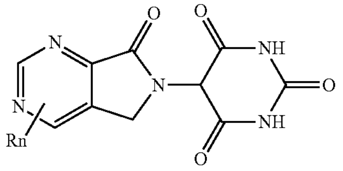
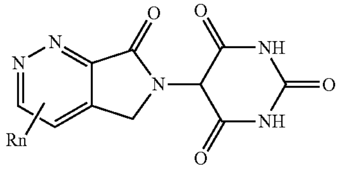
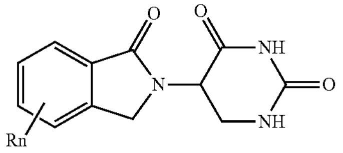
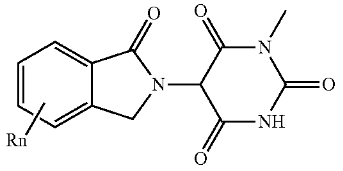
-continued
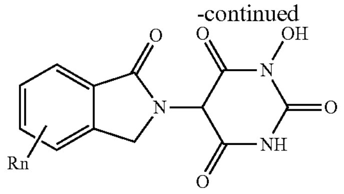
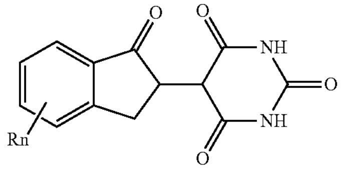
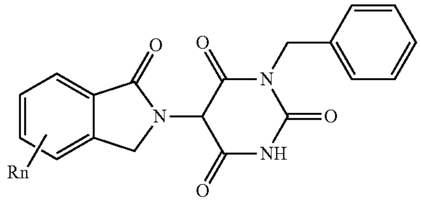
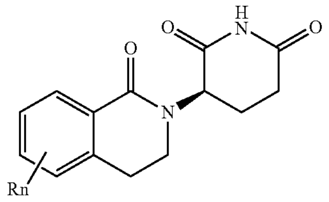
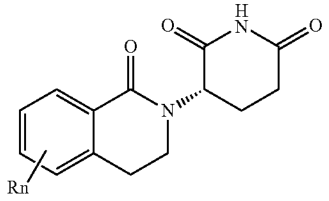
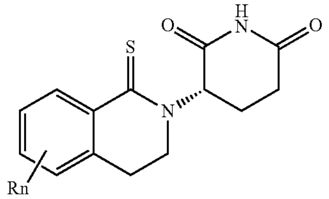
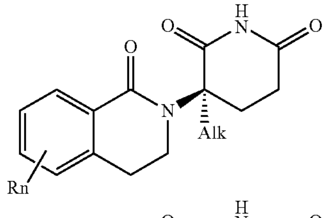
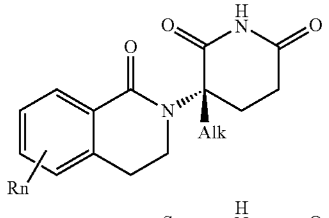
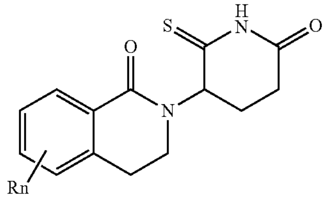

-continued
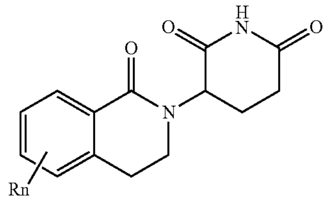
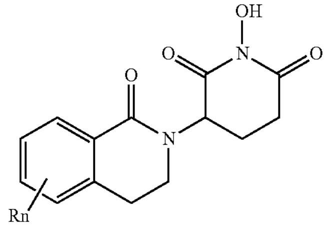
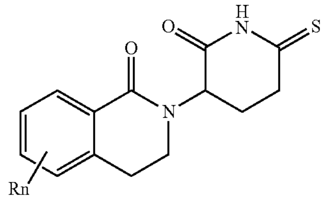
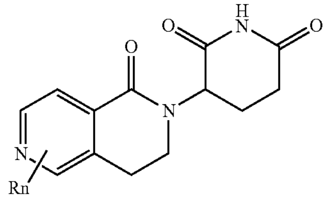
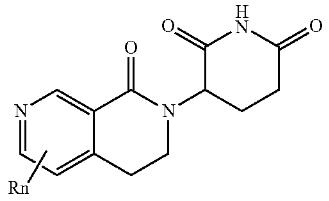
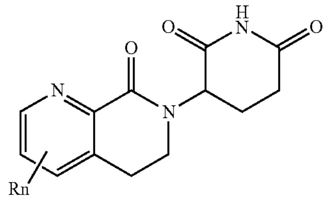
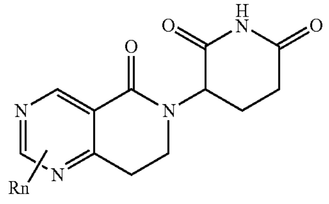
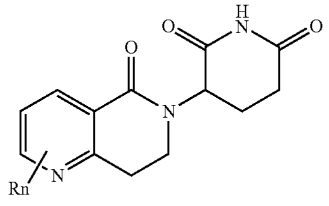
-continued
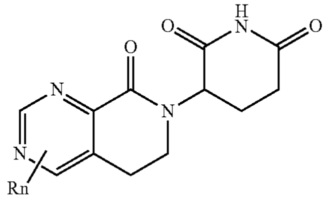
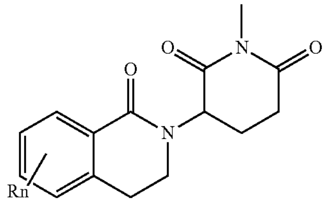
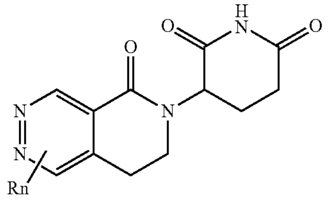
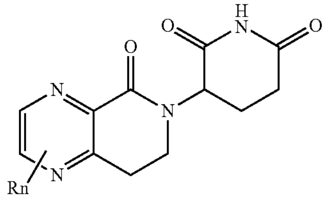
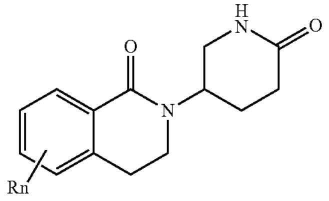
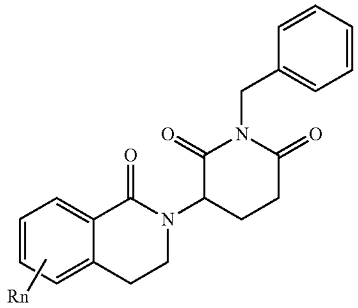
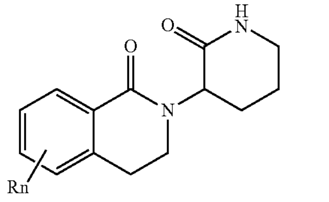
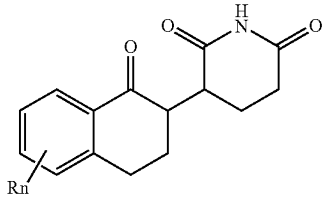

-continued
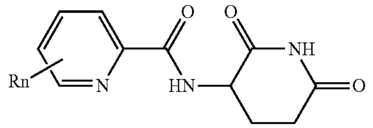
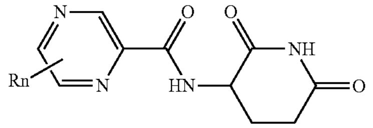
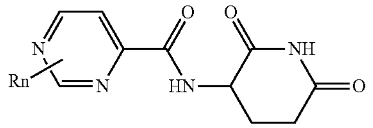
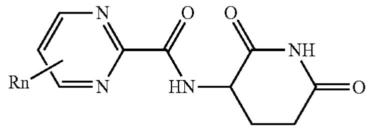
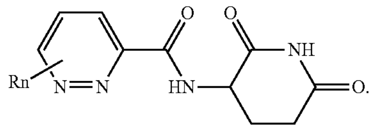
In any of the compounds described herein, the CLM comprises a chemical structure selected from the group:
(h)
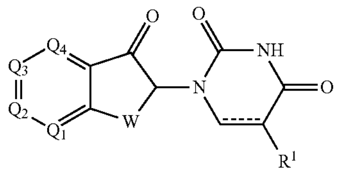
(i)
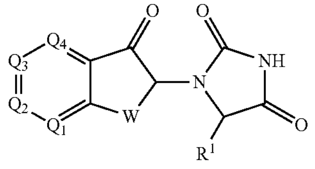
(j)
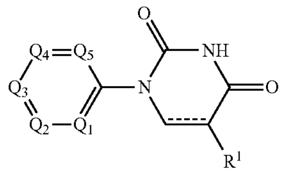
(k)
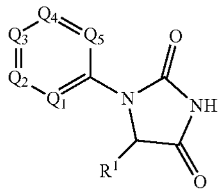
-continued
(l)
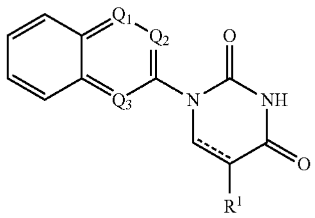
(m)
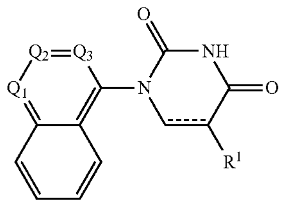
(n)
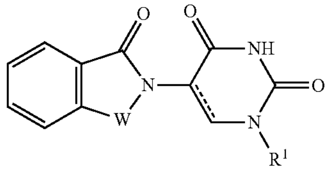
(o)
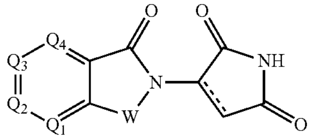
(p)
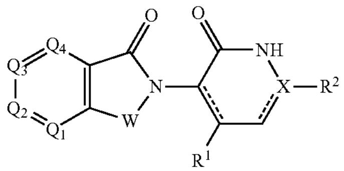
(q)
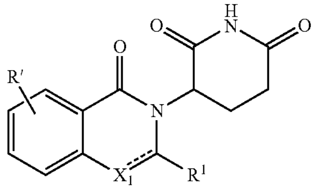
(r)
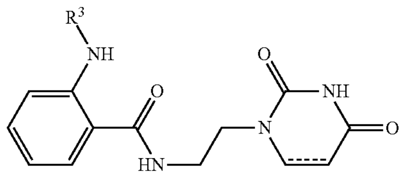
(s)
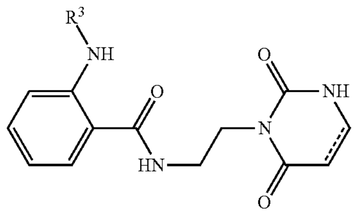

-continued
(t)
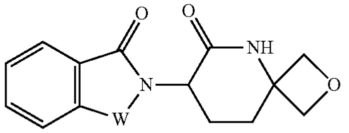
(u)
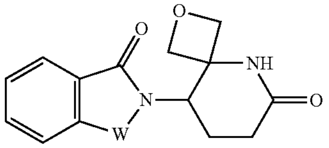
(v)
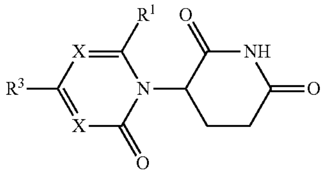
(w)
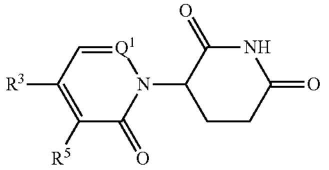
(x)
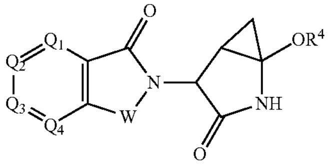
(y)
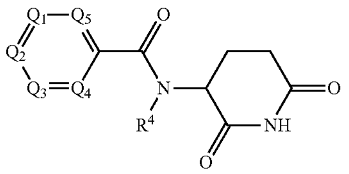
(z)
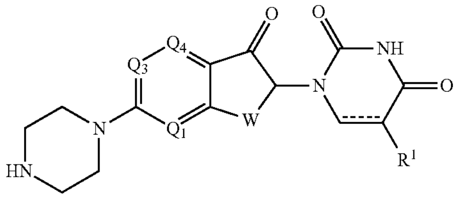
(aa)
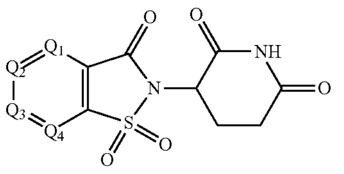
(ab)
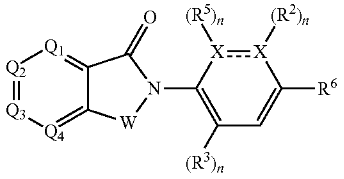
-continued
(ac)
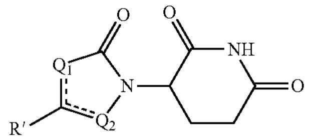
(ad)
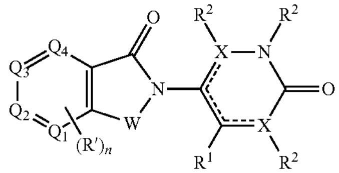
(ae)
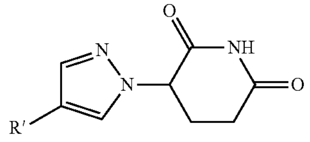
(af)
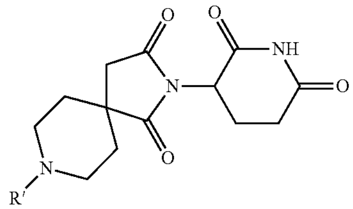
(ag)
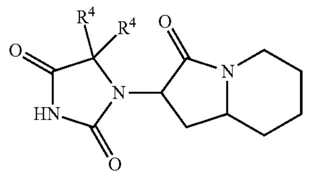
(ah)
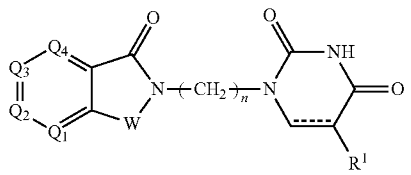
(ai)
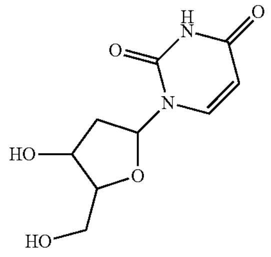
(aj)
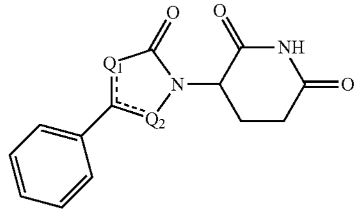

-continued (ak)

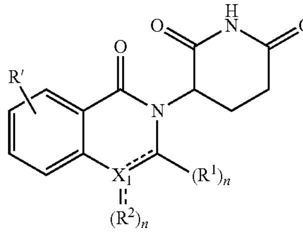

(al)

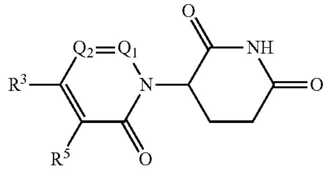

(am)

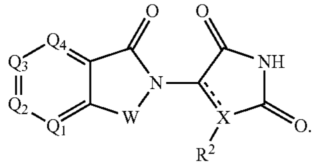

wherein:

W is independently selected from $CH_2$, CHR, C═O, $SO_2$, NH, and N-alkyl;

$Q_1$, $Q_2$, $Q_3$, $Q_4$, $Q_5$ are each independently represent a carbon C or N substituted with a group independently selected from R', N or N-oxide;

$R^1$ is selected from absent, H, OH, CN, $C_1$-$C_3$ alkyl, C═O;

$R^2$ is selected from the group absent, H, OH, CN, $C_1$-$C_3$ alkyl, $CHF_2$, $CF_3$, CHO, C(═O)$NH_2$;

$R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);

$R^4$ is selected from H, alkyl, substituted alkyl;

$R^5$ and $R^6$ are each independently H, halogen, C(═O)R', CN, OH, $CF_3$;

X is C, CH, C═O, or N;

$X_1$ is C═O, N, CH, or $CH_2$;

R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(═O)$OR^2$, optionally substituted phenyl;

n is 0-4;

⋰ is a single or double bond; and the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$.

In any of the embodiments described herein, the W, X, $R^1$, $R^2$, $R^3$, $R^4$, R', $Q_1$, $Q_2$, $Q_3$, $Q_4$, and $Q_5$ can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

(an)

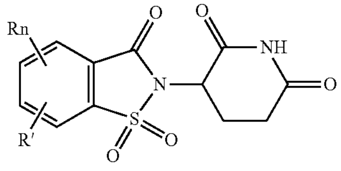

(ao)

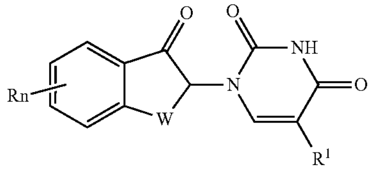

(ap)

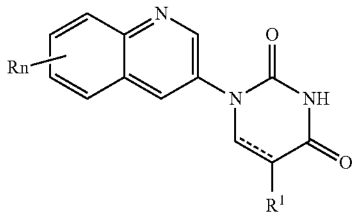

(aq)

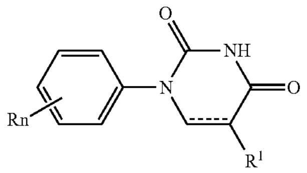

(ar)

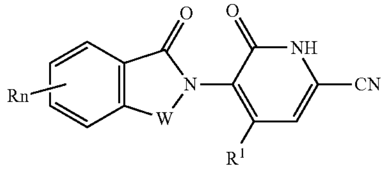

(as)

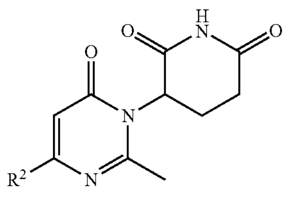

(at)

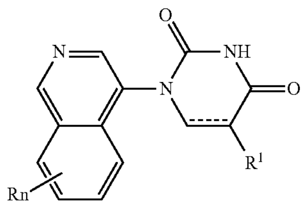

-continued (au)

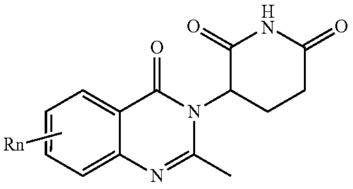

(av)

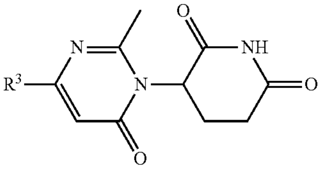

(aw)

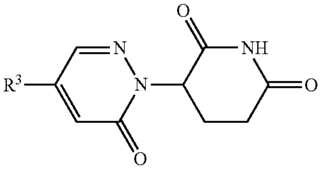

(ax)

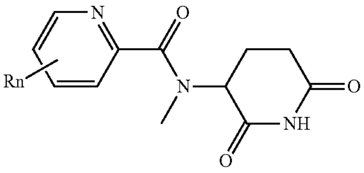

(ay)

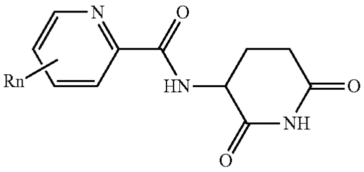

(az)

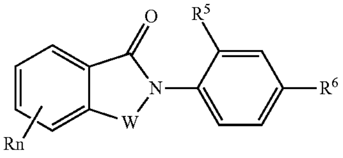

(ba)

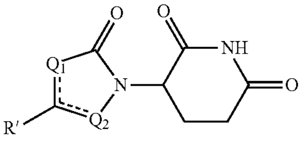

(bb)

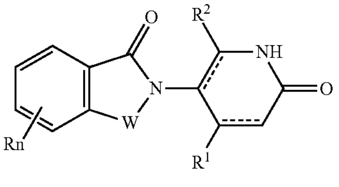

(bc)

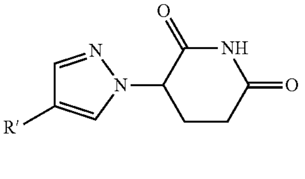

-continued (bd)

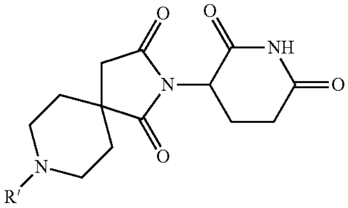

(be)

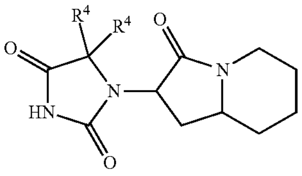

(bf)

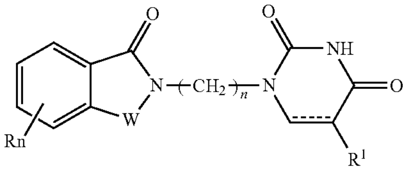

(bg)

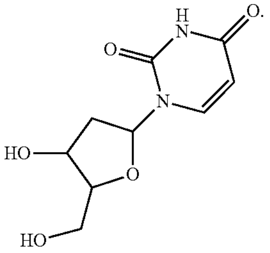

wherein:

W is independently selected from the group $CH_2$, CHR, C═O, $SO_2$, NH, and N-alkyl;

$R^1$ is selected from the group absent, H, CH, CN, C1-C3 alkyl;

$R^2$ is H or a C1-C3 alkyl;

$R^3$ is selected from H, alkyl, substituted alkyl, alkoxy, substituted alkoxy;

$R^4$ is methyl or ethyl;

$R^5$ is H or halo;

$R^6$ is H or halo;

R of the CLM is H;

R' is H or an attachment point for a PTM, a PTM', a chemical linker group (L), a ULM, a CLM, a CLM', $Q_1$ and $Q_2$ are each independently C or N substituted with a group independently selected from H or C1-C3 alkyl;

 is a single or double bond; and

Rn comprises a functional group or an atom.

In any of the embodiments described herein, the W, $R^1$, $R^2$, $Q_1$, $Q_2$, $Q_3$, $Q_4$, and Rn can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn can independently be covalently coupled to a linker and/or a linker to which is attached one or more PTM, ULM, ULM', CLM or CLM' groups.

In any aspect or embodiment described herein, R, is modified to be covalently joined to the linker group (L), a PTM, a ULM, a second CLM having the same chemical structure as the CLM, a CLM', a second linker, or any multiple or combination thereof.
In any aspect or embodiment described herein, the CLM is selected from:
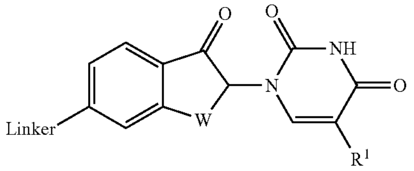
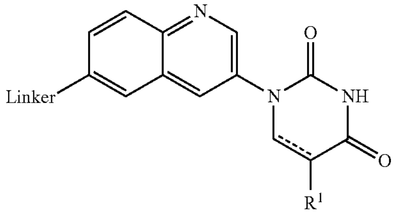
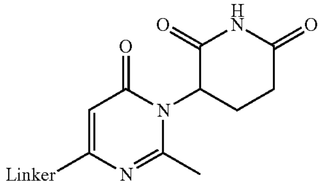
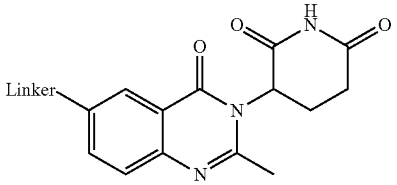
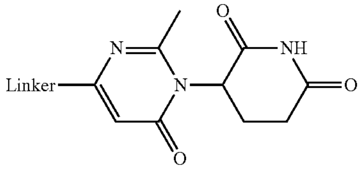
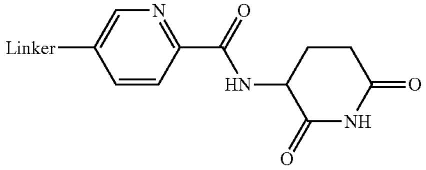
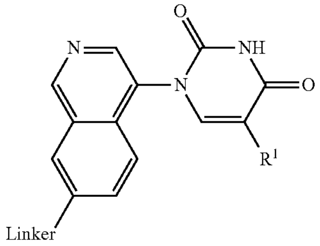
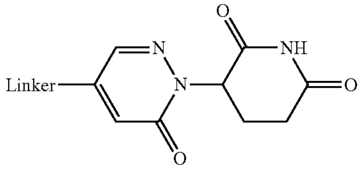
-continued
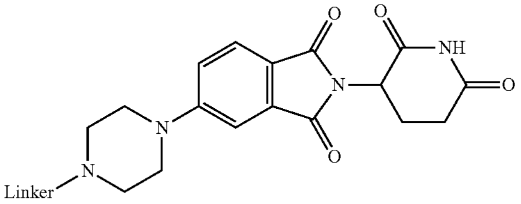
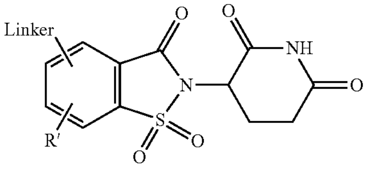
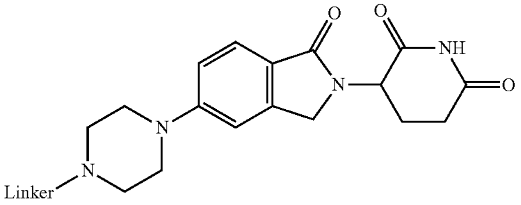
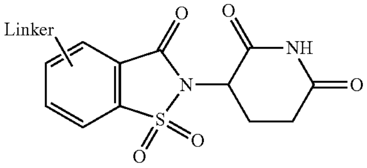
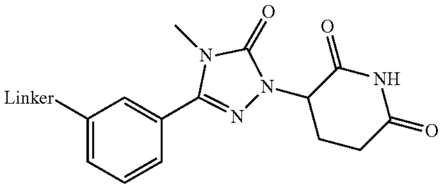
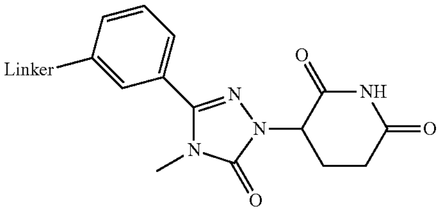
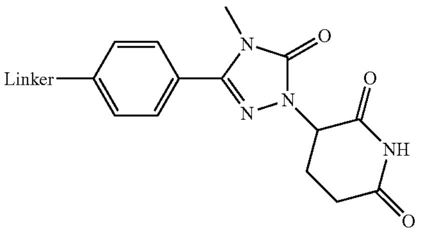
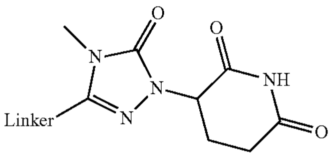
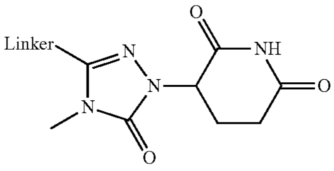

-continued

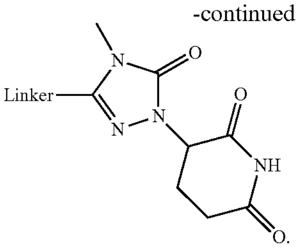

wherein R' is a halogen and $R^1$ is as described in any aspect or embodiment described herein.

In certain cases, "CLM" can be imides that bind to cereblon E3 ligase. These imides and linker attachment point can be but not limited to the following structures:

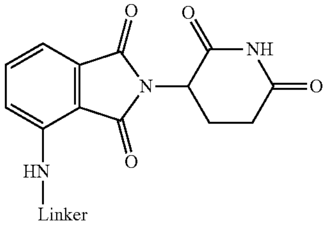

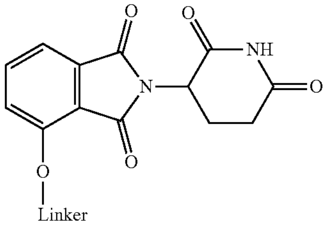

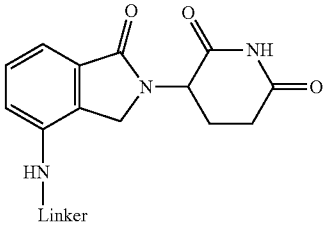

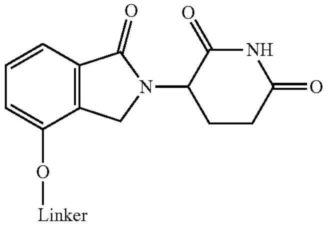

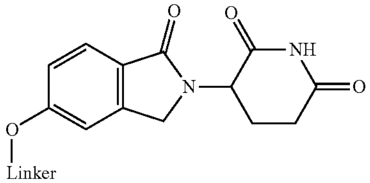

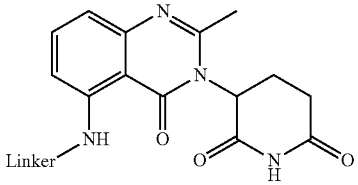

-continued

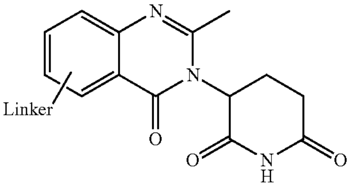

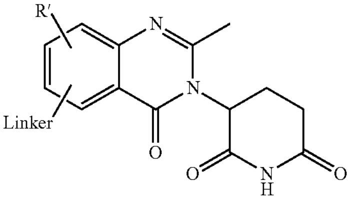

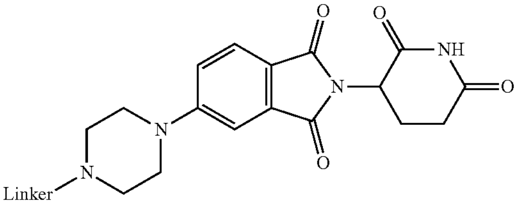

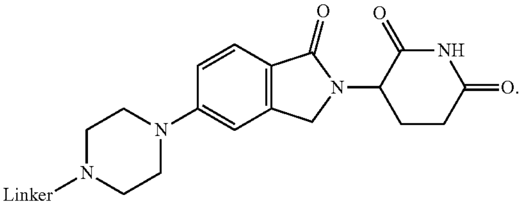

Exemplary VLMs

In certain embodiments of the compounds as described herein, ULM is VLM and comprises a chemical structure selected from the group ULM-a:

ULM-a

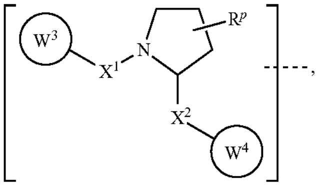

wherein:

where a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;

$X^1$, $X^2$ of Formula ULM-a are each independently selected from the group of a bond, O, $NR^{Y3}$, $CR^{Y3}R^{Y4}$, C═O, C═S, SO, and $SO_2$;

$R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 1-3 $R^P$ groups);

$R^P$ of Formula ULM-a is 1, 2, or 3 groups, each independently selected from the group H, halo, —OH, $C_{1-3}$ alkyl, C═O;

$W^3$ of Formula ULM-a is selected from the group of an optionally substituted T, an optionally substituted -T-N $(R^{1a}R^{1b})X^3$, optionally substituted -T-N($R^{1a}R^{1b}$), optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR^1$-T-Aryl, an optionally substituted —$NR^1$-T-Heteroaryl or an optionally substituted —$NR^1$-T-Heterocycle;

$X^3$ of Formula ULM-a is C═O, $R^1$, $R^{1a}$, $R^{1b}$;

each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}C$═O, $R^{Y3}C$═S, $R^{Y3}SO$, $R^{Y3}SO_2$, $N(R^{Y3}R^{Y4})C$═O, $N(R^{Y3}R^{Y4})C$═S, $N(R^{Y3}R^{Y4})SO$, and $N(R^{Y3}R^{Y4})SO_2$;

T of Formula ULM-a is selected from the group of an optionally substituted alkyl, —$(CH_2)_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocycle, or —OH groups or an amino acid side chain optionally substituted;

$W^4$ of Formula ULM-a is an optionally substituted —NR1-T-Aryl wherein the aryl group may be optionally substituted with an optionally substituted 5-6 membered heteroaryl, an optionally substituted -NR1-T-Heteroaryl group or an optionally substituted -NR1-T-Heterocycle, where —NR1 is covalently bonded to $X^2$ and $R^1$ is H or $CH_3$, preferably H.

In any of the embodiments described herein, T is selected from the group of an optionally substituted alkyl, —$(CH_2)_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocycle, or —OH groups or an amino acid side chain optionally substituted; and n is 0 to 6, often 0, 1, 2, or 3, preferably 0 or 1.

In certain embodiments, $W^4$ of Formula ULM-a is

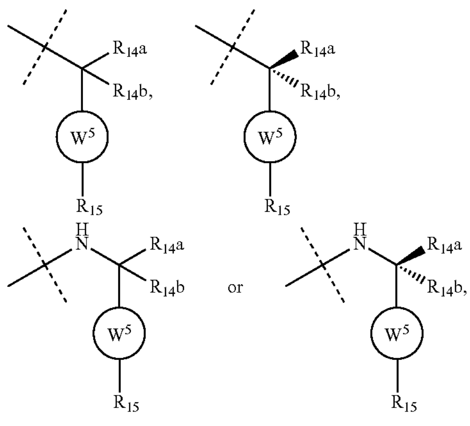

wherein $R_{14a}$, $R_{14b}$, are each independently selected from the group of H, haloalkyl, or optionally substituted alkyl;

In any of the embodiments, $W^5$ of Formula ULM-a is selected from the group of a phenyl or a 5-10 membered heteroaryl, $R_{15}$ of Formula ULM-a is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C═O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

ULM-b

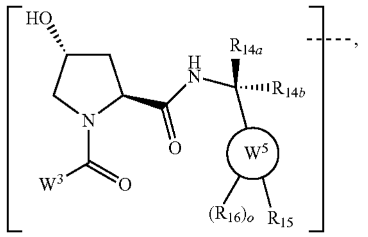

wherein:

$W^3$ of Formula ULM-b is selected from the group of an optionally substituted aryl, optionally substituted heteroaryl, or

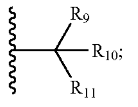

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclic, optionally substituted alkoxy, optionally substituted heteroaryl, optionally substituted aryl,

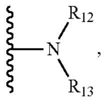,
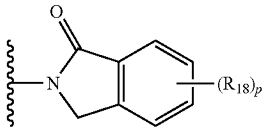 or
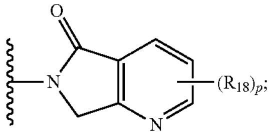

$R_{12}$ of Formula ULM-b is selected from the group of H or optionally substituted alkyl;

$R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula ULM-b, are each independently selected from the group of H, haloalkyl, or optionally substituted alkyl;

$W^5$ of Formula ULM-b is selected from the group of a phenyl or a 5-10 membered heteroaryl, $R_{15}$ of Formula ULM-b is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

$R_{16}$ of Formula ULM-b is independently selected from the group consisting of halo, optionally substituted alkyl, optionally substituted haloalkyl, hydroxy, or optionally substituted haloalkoxy;

o of Formula ULM-b is 0, 1, 2, 3, or 4;

$R_{18}$ of Formula ULM-b is independently selected from the group consisting of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ of Formula ULM-b is

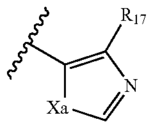

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ of Formula ULM-b is selected from the group methyl, ethyl, isopropyl, and cyclopropyl.

In certain additional embodiments, $R_{15}$ of Formula ULM-b is selected from the group consisting of:

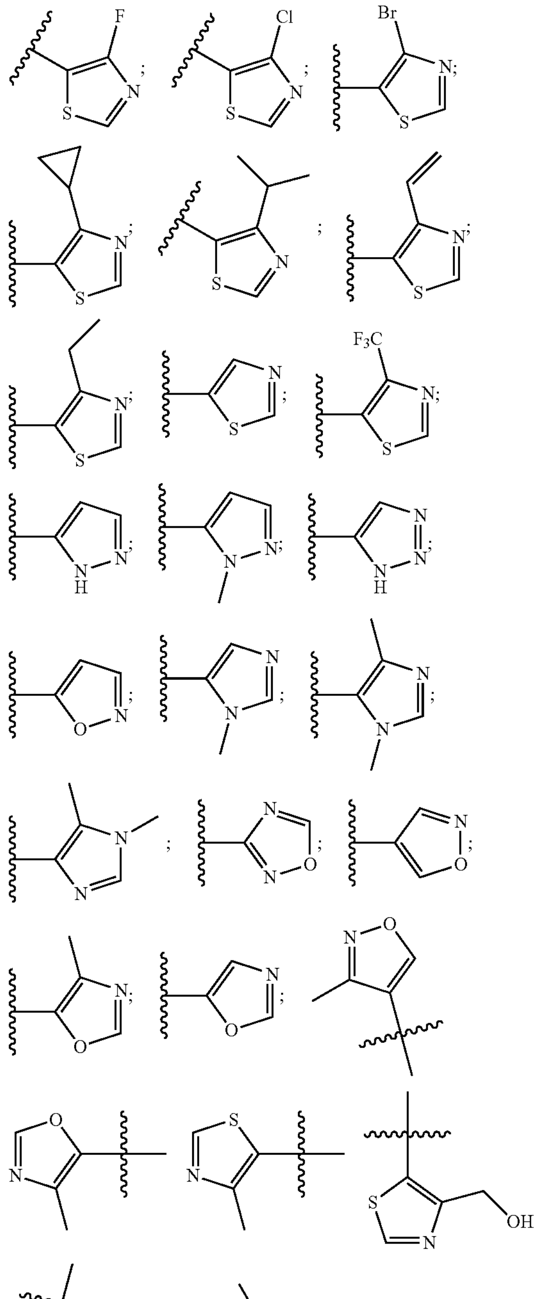

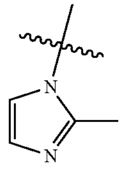 and 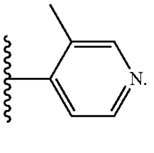

In certain embodiments, $R_{11}$ of Formula ULM-b is selected from the group consisting of:

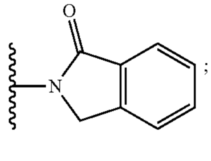 ; 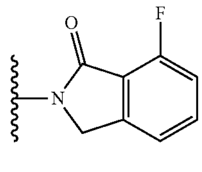 ;

-continued

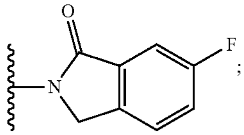 ; 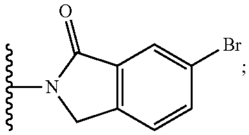 ;

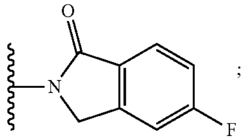 ; 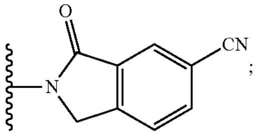 ;

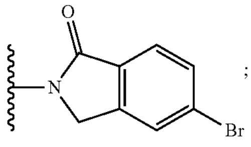 ; 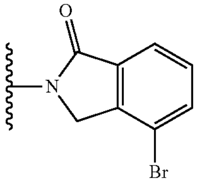 ;

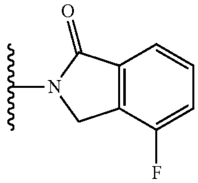 ; 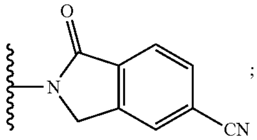 ;

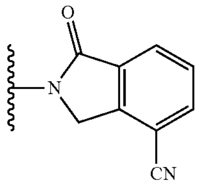 ; 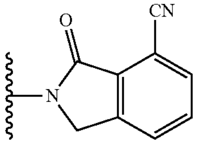 ;

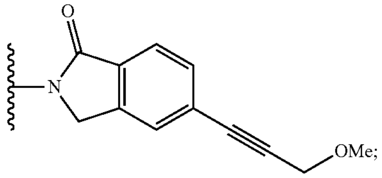

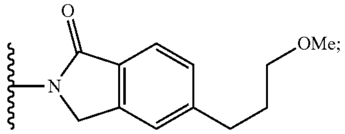

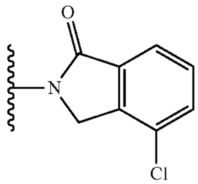 ; 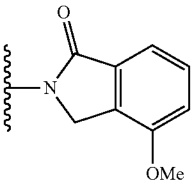 ;

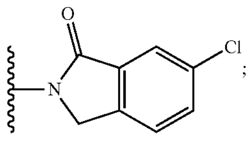 ; and 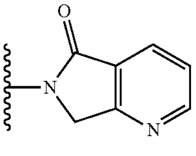 .

In certain embodiments, ULM has a chemical structure selected from the group of:

ULM-c

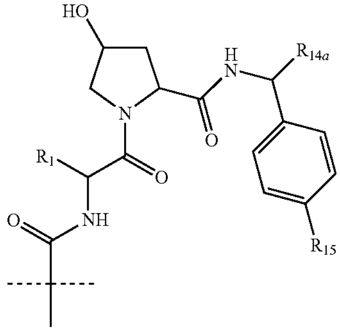

ULM-d

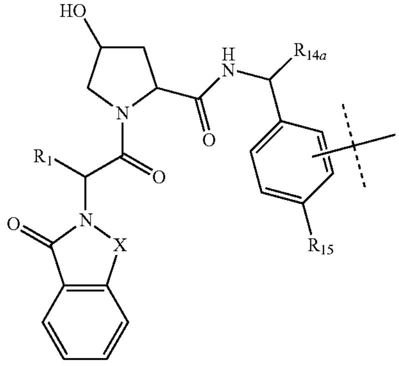

ULM-e

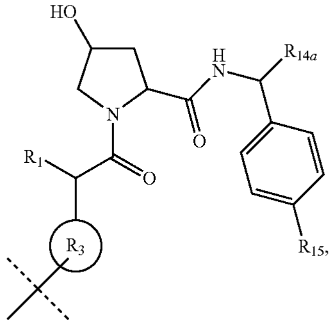

wherein:

$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, $NO_2$, optionally substituted heteroaryl, optionally substituted aryl, optionally substituted alkyl, optionally substituted haloalkyl, optionally substituted haloalkoxy, cycloalkyl, or cycloheteroalkyl;

X of Formulas ULM-c, ULM-d, and ULM-e is C, $CH_2$, or C═O $R_3$ of Formulas ULM-c, ULM-d, and ULM-e is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

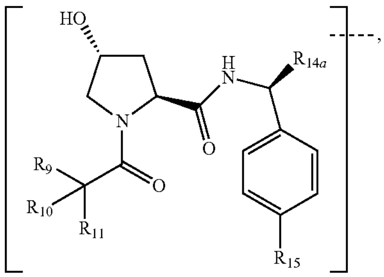

ULM-f wherein $R_{14a}$ of Formula ULM-f is H, haloalkyl, optionally substituted alkyl, methyl, fluoromethyl, hydroxymethyl, ethyl, isopropyl, or cyclopropyl;

$R_9$ of Formula ULM-f is H;

$R_{10}$ of Formula ULM-f is H, ethyl, isopropyl, tert-butyl, sec-butyl, cyclopropyl, cyclobutyl, cyclopentyl, or cyclohexyl;

$R_{11}$ of Formula ULM-f is

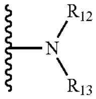 ; 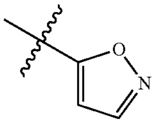 ; 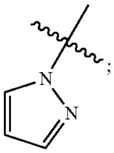 ;

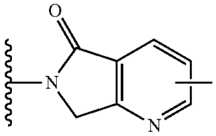 ;

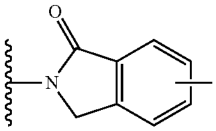 ; 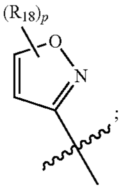 ;

or optionally substituted heteroaryl;

p of Formula ULM-f is 0, 1, 2, 3, or 4;

each $R_{18}$ of Formula ULM-f is independently halo, optionally substituted alkoxy, cyano, optionally substituted alkyl, haloalkyl, haloalkoxy or a linker;

$R_{12}$ of Formula ULM-f is H, C═O;

$R_{13}$ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ of Formula ULM-f is selected from the group consisting of H, halogen, Cl, CN, OH, $NO_2$, optionally substituted heteroaryl, optionally substituted aryl;

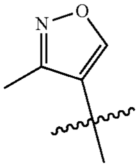 ; 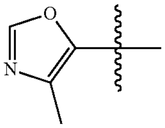 ; 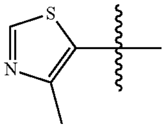 ;

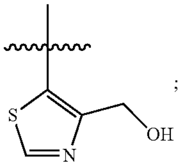 ; 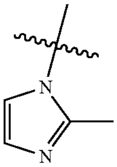 ; 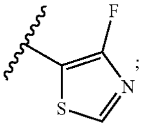 ;

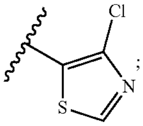 ; 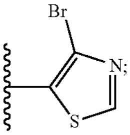 ; 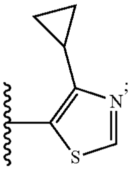 ;

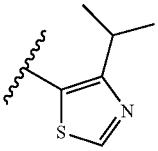 ; 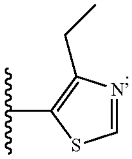 ; 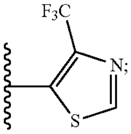 ;

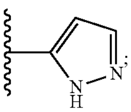 ; 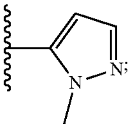 ; 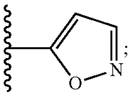 ;

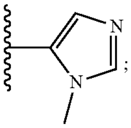 ; 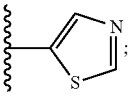 ; 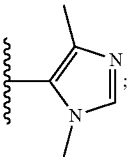 ;

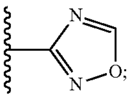 ; and and wherein the dashed line of Formula ULM-f indicates the site of attachment of at least one PTM, another ULM (ULM') or a chemical linker moiety coupling at least one PTM or a ULM' or both to ULM.

In certain embodiments, the ULM is selected from the following structures:

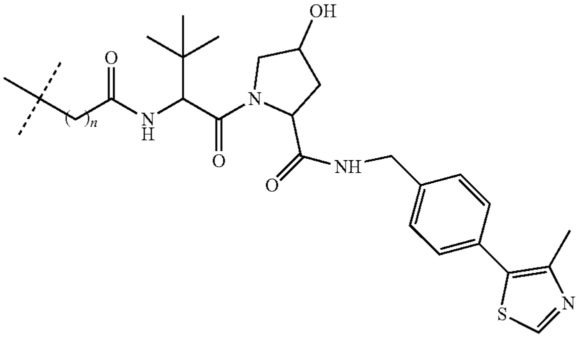

-continued
ULM-a2
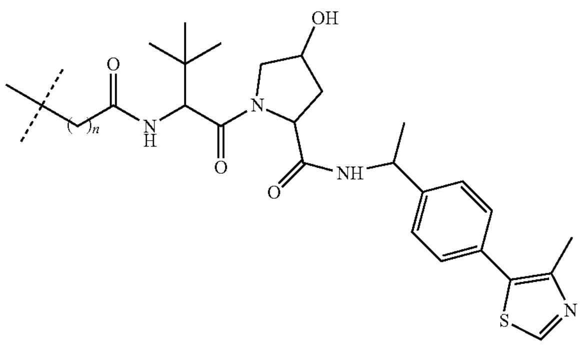
ULM-a3
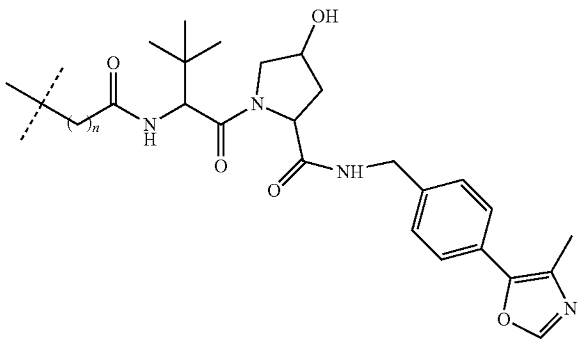
ULM-a4
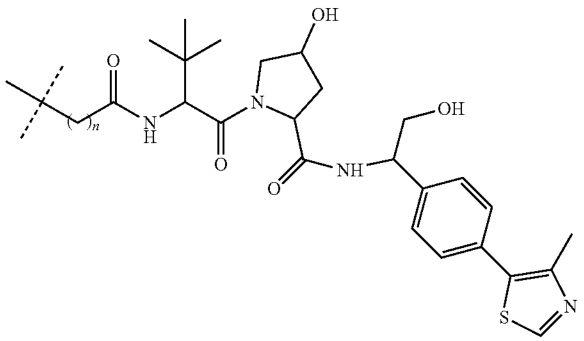
ULM-a5
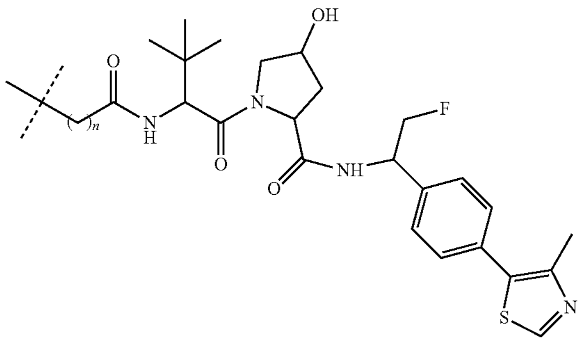
-continued
ULM-a6
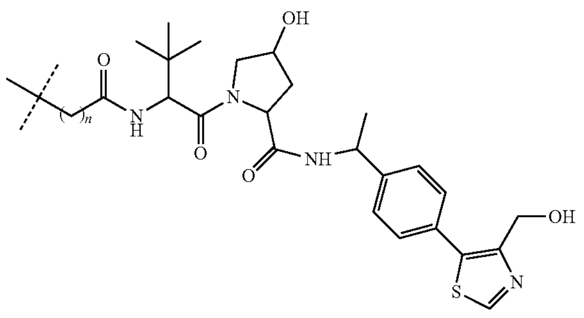
ULM-a7
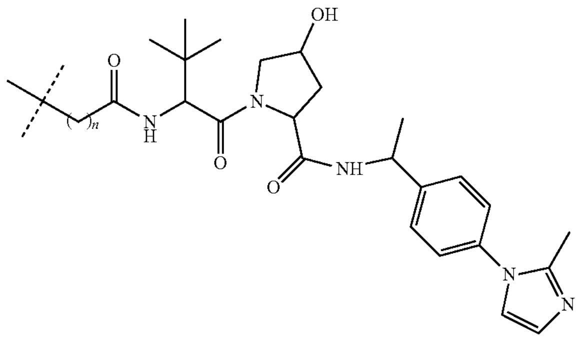
ULM-a8
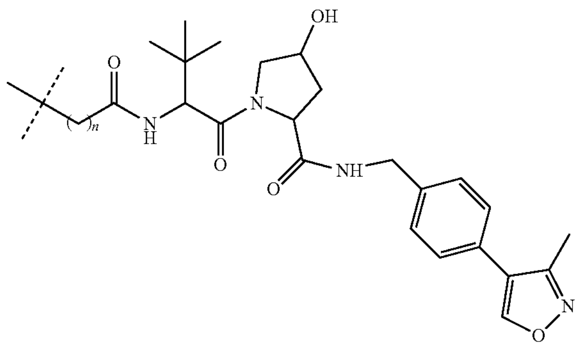
ULM-a9
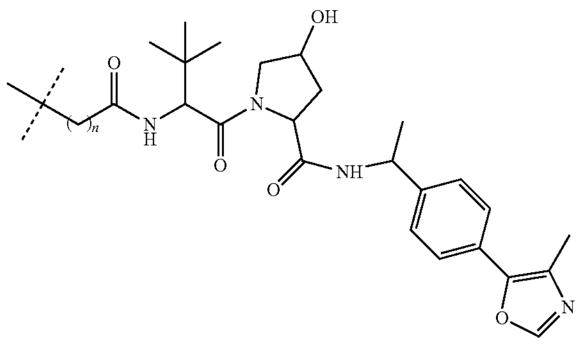

-continued
ULM-a10
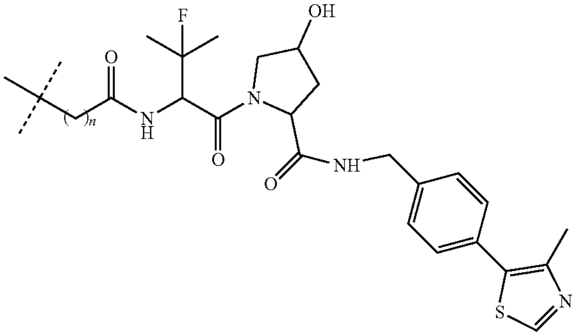
ULM-a11
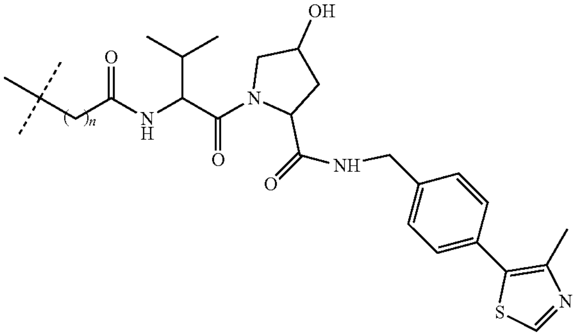
ULM-a12
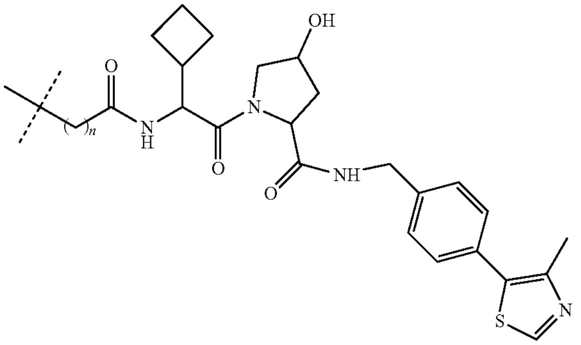
ULM-a13
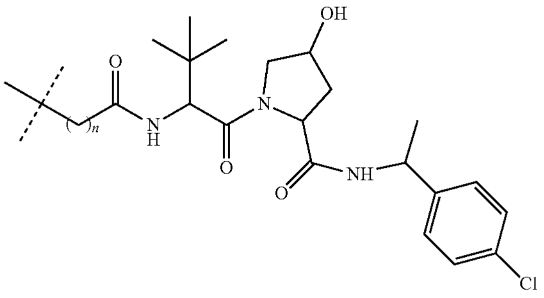
-continued
ULM-a14
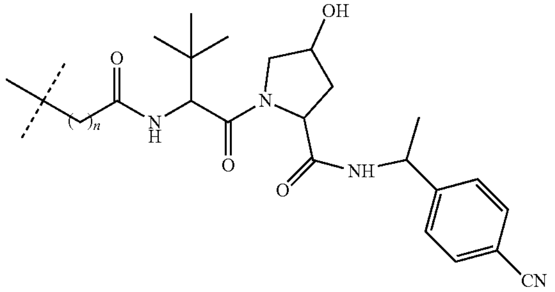
ULM-a15
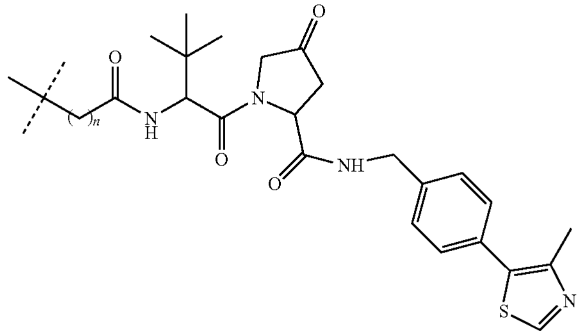
where n is 0 or 1.
In certain embodiments, the ULM is selected from the following structures:
ULM-b1
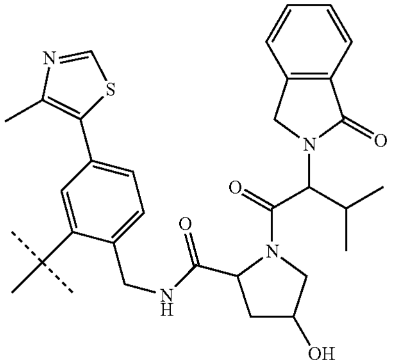
ULM-b2
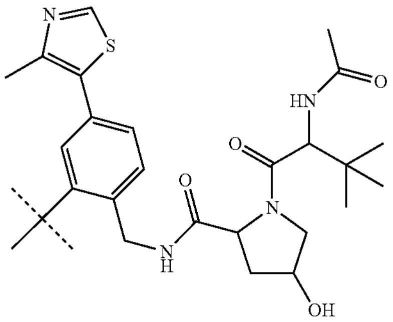

-continued
ULM-b3
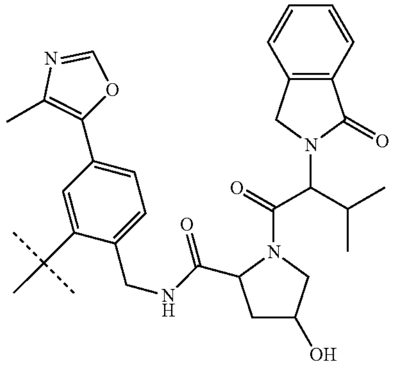
ULM-b4
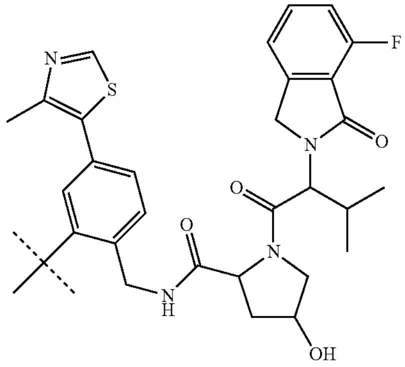
ULM-b5
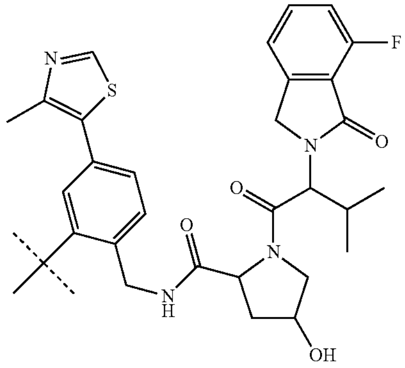
ULM-b6
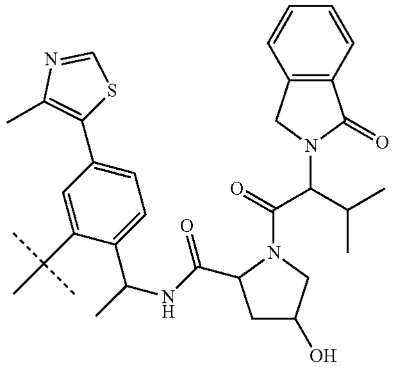
-continued
ULM-b7
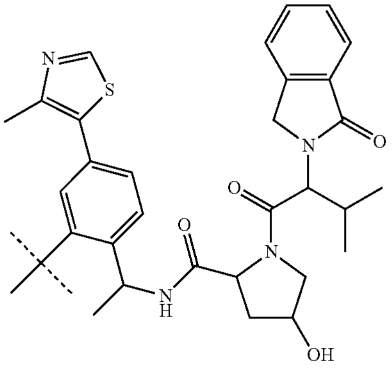
ULM-b8
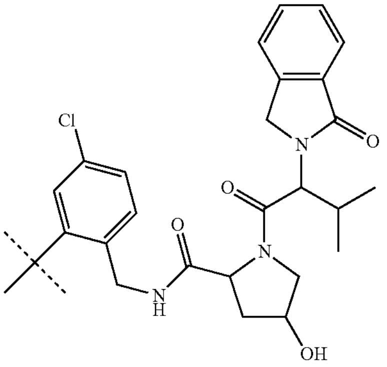
ULM-b9
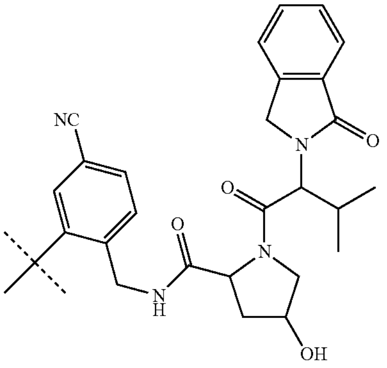
ULM-b7
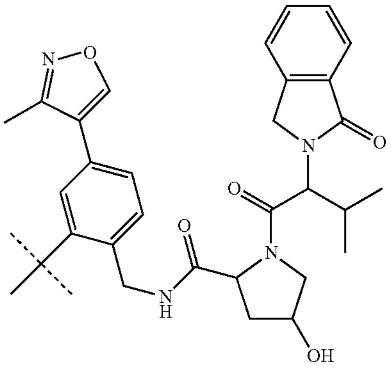

-continued
ULM-b8
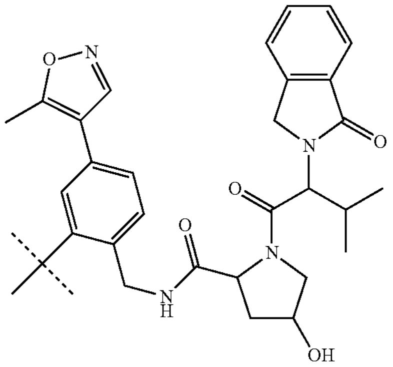
ULM-b9
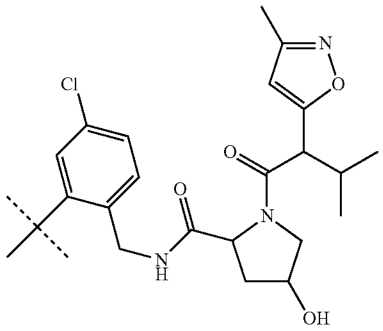
ULM-c1
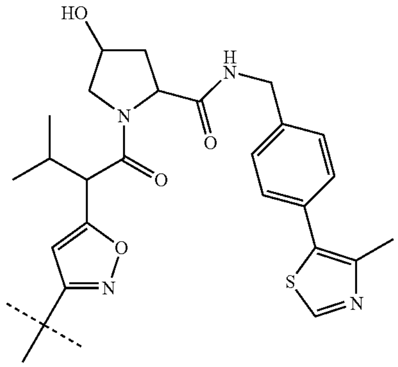
ULM-c2
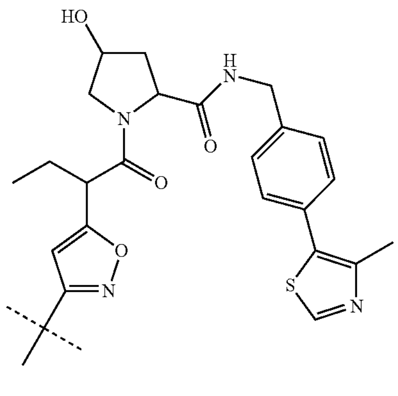
-continued
ULM-c3
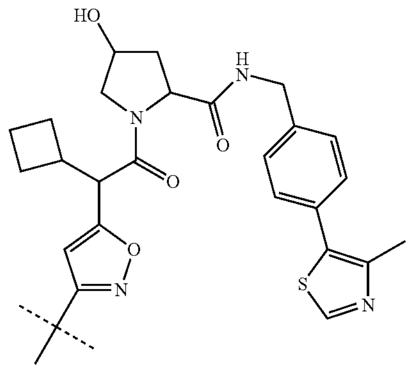
ULM-c4
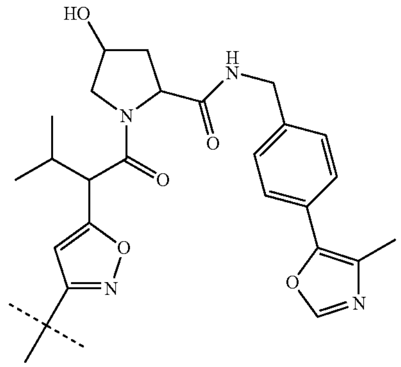
ULM-c5
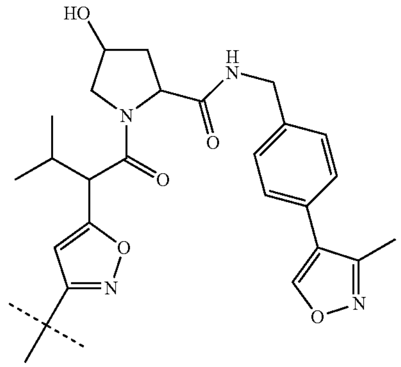
ULM-c6
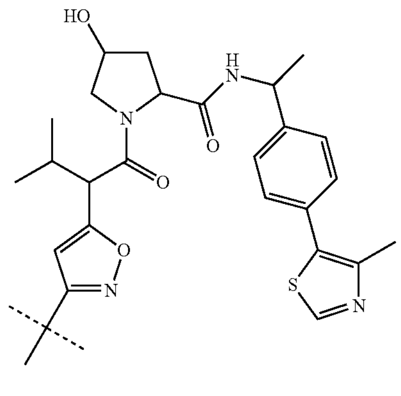

-continued
ULM-c7
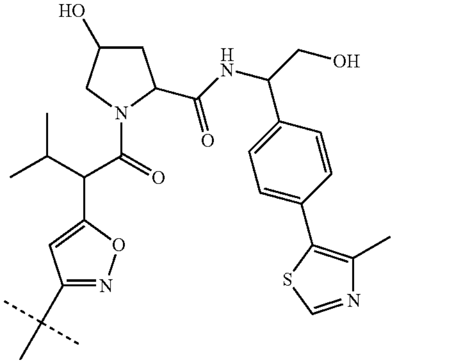
ULM-c8
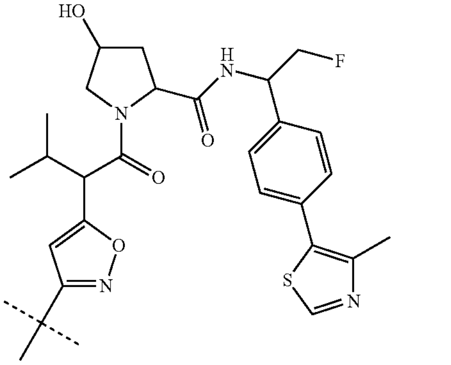
ULM-c9
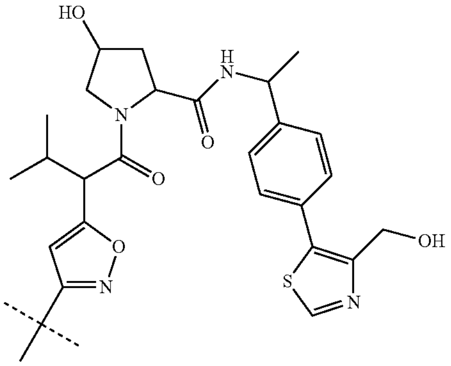
ULM-c10
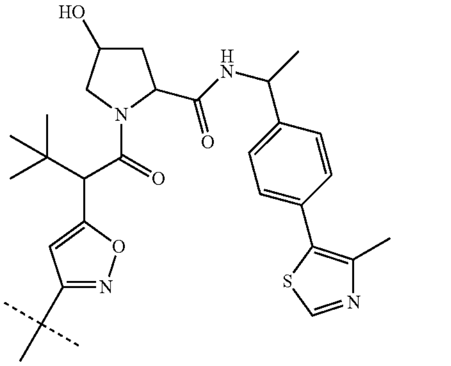
-continued
ULM-c11
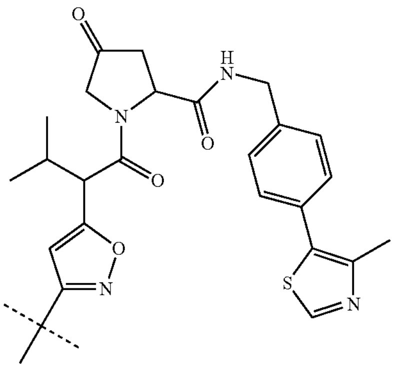
ULM-c12
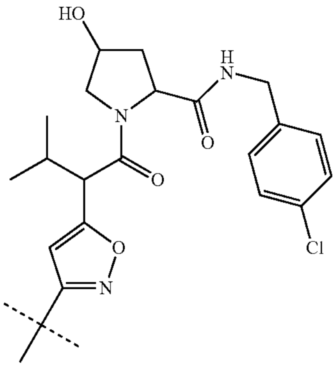
ULM-c13
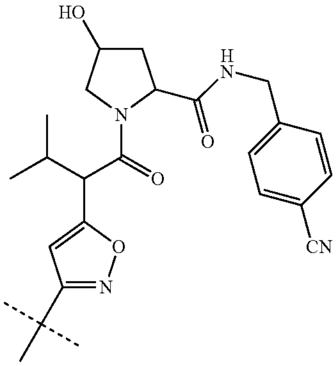
ULM-c14
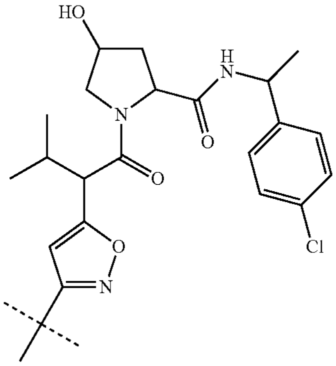

-continued
ULM-c15
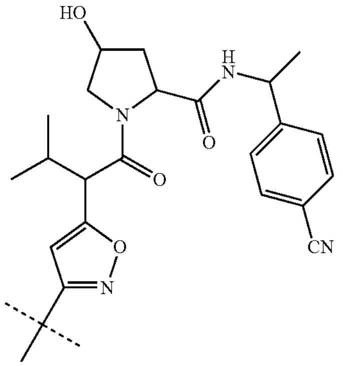
ULM-d1
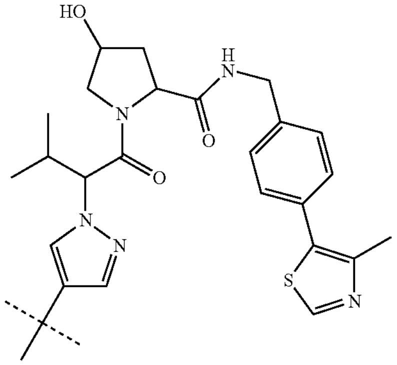
ULM-d2
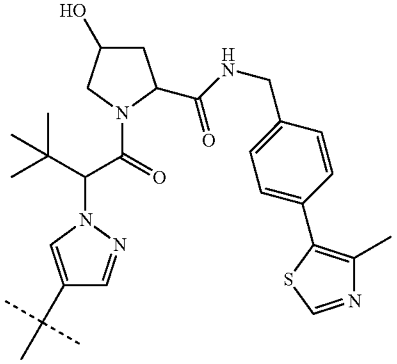
ULM-d3
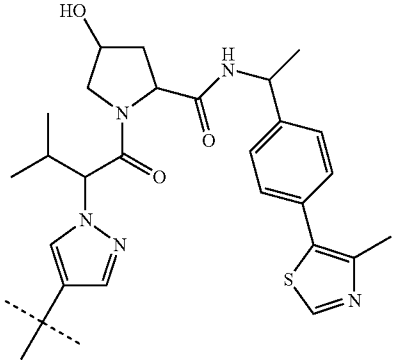
-continued
ULM-d4
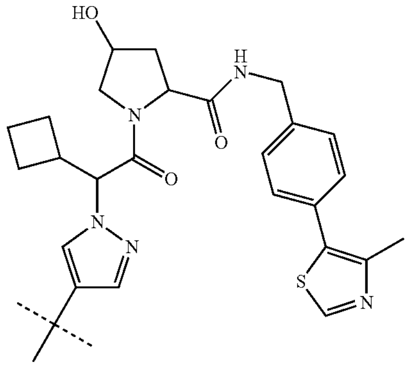
ULM-d5
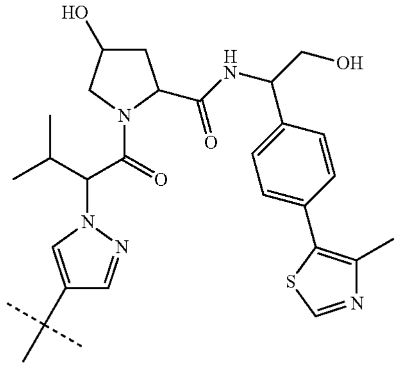
ULM-d6
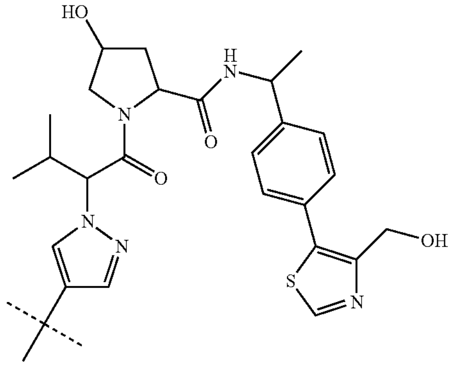
ULM-d7
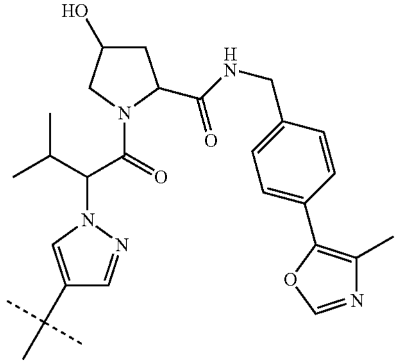

-continued

ULM-d8

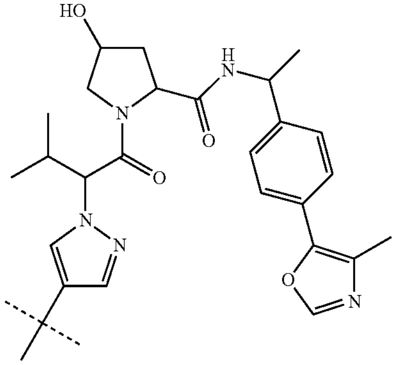

ULM-d9

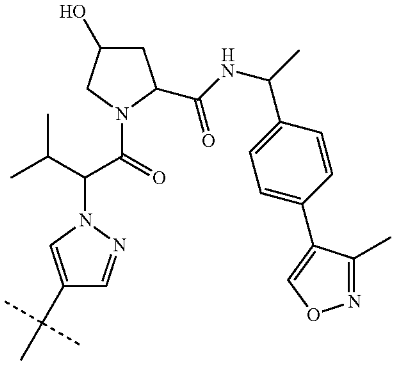

wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-al through ULM-a15, ULM-b1 through ULM-b12, ULM-c1 through ULM-c15 and ULM-dl through ULM-d9 can be functionalized as the ester to make it a part of the prodrug.

In certain embodiments, the hydroxyl group on the pyrrolidine ring of ULM-al through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

ULM-g

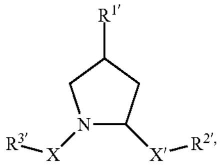

wherein:

$R^{1'}$ of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—WCOCW—$(C_0$-$C_6)$alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—$(C_1$-$C_6$alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—$(C_1$-$C_6$ alkyl), an optionally substituted —$(CH_2)_n$C(O)—O—$(C_1$-$C_6$ alkyl), an optionally substituted —$(CH_2O)_n$COOH, an optionally substituted —$(OCH_2)_n$O—$(C_1$-$C_6$ alkyl), an optionally substituted —$(CH_2O)_n$C(O)—$(C_1$-$C_6$ alkyl), an optionally substituted —$(OCH_2)_n$NHC(O)—$R^1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—$(C_1$-$C_6$ alkyl), an optionally substituted —$(CH_2CH_2O)_n$C(O)—$(C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);

$R_1$ and $R_2$ of ULM-g are each independently H or a $C_1$-$C_6$ alkyl group which may be optionally substituted with one or two hydroxyl groups or up to three halogen groups (preferably fluorine);

$R_S$ of ULM-g is a $C_1$-$C_6$ alkyl group, an optionally substituted aryl, heteroaryl or heterocycle group or a —$(CH_2)_m$$NR_1R_2$ group;

X and X' of ULM-g are each independently C═O, C═S, —S(O), $S(O)_2$, (preferably X and X' are both C═O);

$R^{2'}$ of ULM-g is an optionally substituted —$(CH_2)_n$—$(C{=}O)_u(NR_1)_v(SO_2)_w$alkyl group, an optionally substituted —$(CH_2)_n$—$(C{=}O)_u(NR_1)_v(SO_2)_w NR_{1N}NR_{2N}$ group, an optionally substituted —$(CH_2)_n$—$(C{=}O)_u(NR_1)_v(SO_2)_w$-Aryl, an optionally substituted —$(CH_2)_n$—$(C{=}O)_u(NR_1)_v(SO_2)_w$-Heteroaryl, an optionally substituted —$(CH_2)_n$—$(C{=}O)_u(NR_1)_v(SO_2)_w$-Heterocycle, an optionally substituted —$(CH_2)_n$—$C(O)_u(NR_1)_v(SO_2)_w$-alkyl, an optionally substituted —$NR^1$—$(CH_2)_n$—$C(O)_u(NR_1)_v(SO_2)_w$—$NR_{1N}R_{2N}$, an optionally substituted —$NR^1$—$(CH_2)_n$—$C(O)_u(NR_1)_v(SO_2)_w$—$NR_1C(O)R_{1N}$, an optionally substituted —$NR^1$—$(CH_2)_r$—$(C{=}O)_u(NR_1)_v(SO_2)_w$-Aryl, an optionally substituted —$NR^1$—$(CH_2)_n$—$(C{=}O)_u(NR_1)_v(SO_2)_w$-Heteroaryl or an optionally substituted —$NR^1$—$(CH_2)_n$—$(C{=}O)_vNR_1(SO_2)_w$-Heterocycle, an optionally substituted —$X^{R2'}$-alkyl group; an optionally substituted —$X^{R2'}$-Aryl group; an optionally substituted —$X^{R2'}$-Heteroaryl group; an optionally substituted —$X^{R2'}$-Heterocycle group; an optionally substituted;

$R^{3'}$ of ULM-g is an optionally substituted alkyl, an optionally substituted —$(CH_2)$—$(O)_u(NR_1)_v(SO_2)_w$-alkyl, an optionally substituted —$(CH_2)_n$—$C(O)_u(NR_1)_v(SO_2)_w$—$NR_{1N}R_{2N}$, an optionally substituted —$(CH_2)_n$—$C(O)_u(NR_1)_v(SO_2)_w$—$NR_1C(O)R_{1N}$, an optionally substituted —$(CH_2)_n$—$C(O)_u(NR_1)_v(SO_2)_w$—$C(O)NR_1R_2$, an optionally substituted —$(CH_2)_n$—$C(O)_u(NR_1)_v(SO_2)_w$-Aryl, an optionally substituted —$(CH_2)_n$—$C(O)_u(NR_1)_v(SO_2)_w$-Heteroaryl, an optionally substituted —$(CH_2)_n$—$C(O)_u(NR_1)_v(SO_2)_w$-Heterocycle, an optionally substituted —$NR^1$—$(CH_2)_n$—$C(O)_u(NR_1)_v(SO_2)_w$-alkyl, an optionally substituted —$NR^1$—$(CH_2)_n$—$C(O)_u(NR_1)_v$ $(SO_2)_w$— $NR_{1N}R_{2N}$, an optionally substituted —NR—$(CH_2)_n$—$C(O)_u(NR_1)_v(SO_2)_w$—$NR_1C(O)R_{1N}$, an optionally substituted —$NR^1$—$(CH_2)_n$—$C(O)_u(NR_1)_v(SO_2)_w$-Aryl, an optionally substituted —NR—$(CH_2)_n$—$C(O)_u(NR_1)_v(SO_2)_w$-Heteroaryl, an optionally substituted —$NR^1$—$(CH_2)_n$—$C(O)_u(NR_1)_v(SO_2)_w$-Heterocycle, an optionally substituted —O—$(CH_2)_n$—$(C{=}O)_u(NR_1)_v(SO_2)_w$-alkyl, an optionally substituted —O—$(CH_2)$n-$(C{=}O)_u(NR_1)_v(SO_2)_w$—$NR_{1N}R_{2N}$, an optionally substituted —O—$(CH_2)$n-$(C{=}O)_u(NR_1)_v(SO_2)_w$—$NR_1C(O)R_{1N}$, an optionally substituted —O—$(CH_2)$n-$(C{=}O)_u(NR_1)_v(SO_2)_w$-Aryl, an optionally substituted —O—$(CH_2)_n$—$(C{=}O)_u(NR_1)_v(SO_2)_w$-Heteroaryl or an optionally substituted —O—$(CH_2)_n$—$(C{=}O)_u(NR_1)_v(SO_2)_w$-Heterocycle; —$(CH_2)_n$—$(V)_{n'}$—$(CH_2)_n$—$(V)_{n'}$-alkyl group, an optionally substituted —$(CH_2)_n$—$(V)_{n'}$—$(CH_2)_n$—$(V)_{n'}$-Aryl group, an optionally substituted —$(CH_2)_n$—$(V)_{n'}$—$(CH_2)_n$—$(V)_{n'}$-Heteroaryl group, an optionally substituted —$(CH_2)_n$—$(V)_{n'}$—$(CH_2)_n$—$(V)_{n'}$-Heterocycle group, an optionally substituted —$(CH_2)_n$—$N(R_{1'})(C{=}O)_{m'}$—$(V)_{n'}$-alkyl group, an optionally substituted —$(CH_2)_n$—$N(R_{1'})(C{=}O)_{m'}$—$(V)_{n'}$-Aryl group, an optionally substituted —$(CH_2)_n$—$N(R')(C{=}O)_{m'}$—$(V)_{n'}$-Heteroaryl group, an optionally substituted —$(CH_2)_n$—$N(R_{1'})(C{=}O)_{m'}$—$(V)_{n'}$-Heterocycle group, an optionally substituted —$X^{R3'}$-alkyl group; an optionally substituted —$X^{R3'}$-Aryl group; an optionally substituted —$X^{R3'}$-Heteroaryl group; an optionally substituted —$X^{R3'}$-Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocycle group;

V of ULM-g is O, S or $NR_1$;

$R_1$ of ULM-g is the same as above;

$R^1$ and $R_{1'}$ of ULM-g are each independently H or a $C_1$-$C_3$ alkyl group;

$X^{R2'}$ and $X^{R3'}$ of ULM-g are each independently an optionally substituted —$CH_2)_n$—, $CH_2)_n$—$CH(X_v)$=$CH(X_v)$— (cis or trans), —$CH_2)_n$—CH≡CH—, —$(CH_2CH_2O)_n$— or a $C_3$-$C_6$ cycloalkyl group, where $X_v$ is H, a halo or a $C_1$-$C_3$ alkyl group which is optionally substituted;

each m of ULM-g is independently 0, 1, 2, 3, 4, 5, 6;

each m' of ULM-g is independently 0 or 1;

each n of ULM-g is independently 0, 1, 2, 3, 4, 5, 6;

each n' of ULM-g is independently 0 or 1;

each u of ULM-g is independently 0 or 1;

each v of ULM-g is independently 0 or 1;

each w of ULM-g is independently 0 or 1; and any one or more of $R^{1'}$, $R^{2'}$, $R^{3'}$, X and X' of ULM-g is optionally modified to be covalently bonded to the PTM group through a linker group when PTM is not ULM', or when PTM is ULM', any one or more of $R^{1'}$, $R^{2'}$, $R^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

ULM-h

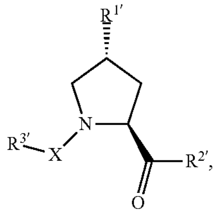

wherein:

each of $R^{1'}$, $R^{2'}$ and $R^{3'}$ of ULM-h are the same as above and X is C=O, C=S, —S(O) group or a $S(O)_2$ group, more preferably a C=O group, and any one or more of $R^{1'}$, $R^{2'}$ and $R^{3'}$ of ULM-h are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

ULM-i

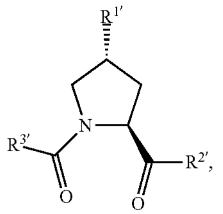

wherein:

any one or more of $R^{1'}$, $R^{2'}$ and $R^{3'}$ of ULM-I are optionally modified to bind a linker group to which is further covalently bonded to the PTM group when PTM is not ULM', or when PTM is ULM', any one or more of $R^{1'}$, $R^{2'}$, $R^{3'}$ of each of ULM and ULM' are optionally modified to be covalently bonded to each other directly or through a linker group, or a pharmaceutically acceptable salt, enantiomer, diastereomer, solvate or polymorph thereof.

In further preferred aspects of the invention, R of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, —$(CH_2)_n$OH, $(CH_2)_n$—O—($C_1$-$C_6$) alkyl group, —$(CH_2)_n$COOH, —$(CH_2O)_n$H, an optionally substituted —$(CH_2)_n$OC(O)—($C_1$-$C_6$ alkyl), or an optionally substituted —$(CH_2)_n$C(O)—O—($C_1$-$C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a $S(O)_2$ group, more preferably a C=O group;

$R^{2'}$ of ULM-g through ULM-i is preferably an optionally substituted —$NR^1$-T-Aryl, an optionally substituted —$NR^1$-T-Heteroaryl group or an optionally substituted —$NR^1$-T-Heterocycle, where $R^1$ is H or $CH_3$, preferably H and T is an optionally substituted —$(CH_2)_n$— group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6, often 0, 1, 2 or 3, preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, all of which groups are optionally substituted.

Preferred Aryl groups for $R^{2'}$ of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

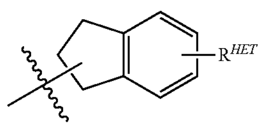

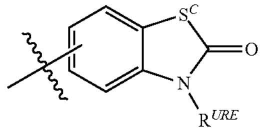

-continued

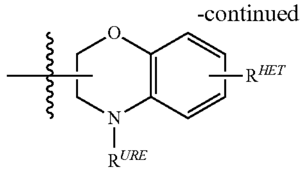

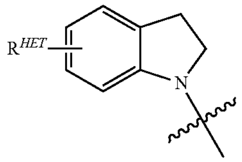

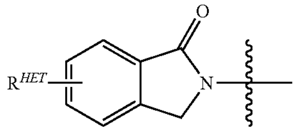

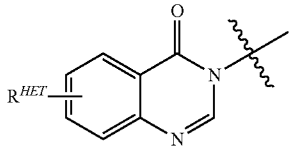

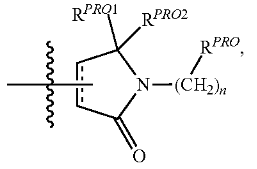

wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2\ of\ ULM\text{-}g\ through\ ULM\text{-}i}$ are each independently H, an optionally substituted $C_1$-$C_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally attached to a PTM group (including a ULM' group) via a linker group.

In certain preferred aspects,

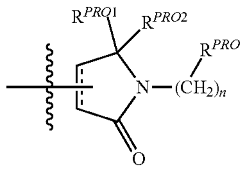

of ULM-g through ULM-i is a

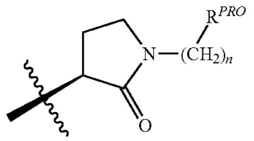

or

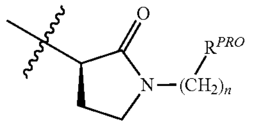

group, where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

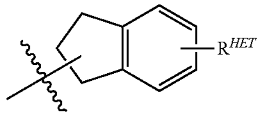

-continued

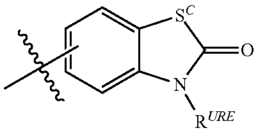

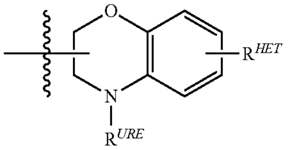

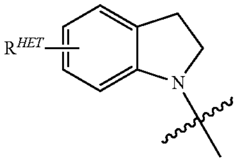

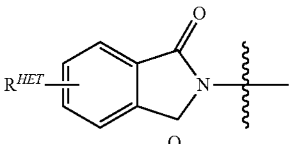

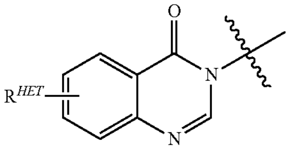

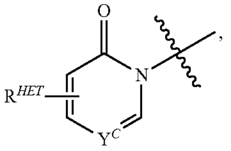

wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1\text{-}C_6$ alkyl) (preferably substituted with one or two hydroxyl groups or up to three halo groups) or an optionally substituted acetylenic group —C≡C—$R_a$ where $R_a$ is H or a $C_1\text{-}C_6$ alkyl group (preferably $C_1\text{-}C_3$ alkyl), each of which groups may be optionally connected to a PTM group (including a ULM' group) via a linker group.

Preferred heterocycle groups for $R^{2'}$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

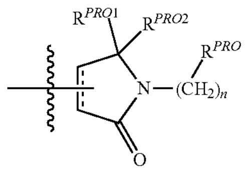

or

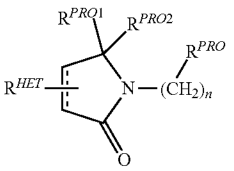

preferably, a

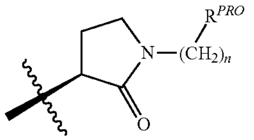

or

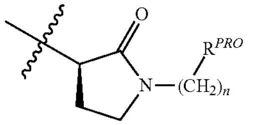

group, wherein:

$R^{PRO}$ of ULM-g through ULM-i is H, optionally substituted $C_1\text{-}C_6$ alkyl or an optionally substituted aryl, heteroaryl or heterocyclic group;

$R^{PRO1}$ and $R^{PRO2}$ of ULM-g through ULM-i are each independently H, an optionally substituted $C_1\text{-}C_3$ alkyl group or together form a keto group and each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted-T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle, where $R^1$ is H or a $C_1\text{-}C_3$ alkyl group, preferably H or $CH_3$, T is an optionally substituted —$(CH_2)_n$— group, wherein each one of the methylene groups may be optionally substituted with one or two substituents, preferably selected from halogen, a $C_1\text{-}C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a —$(CH_2)_m$—$NR_1C(O)R^2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a $C_1\text{-}C_6$ alkyl group, an optionally substituted aryl, heteroaryl or heterocycle group or a —$(CH_2)_mNR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

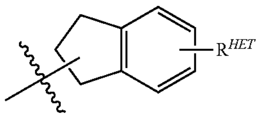

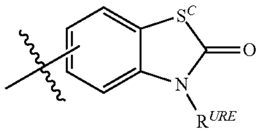

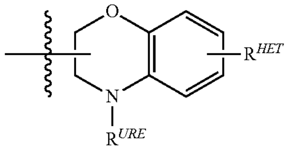

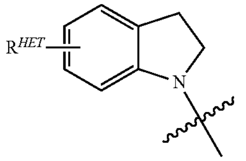

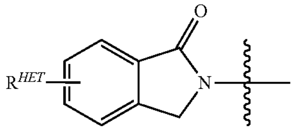

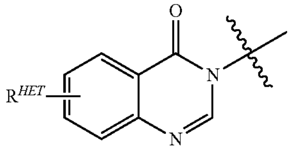

or

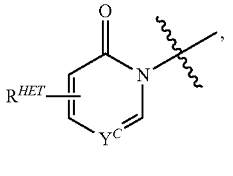

wherein:

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl); $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

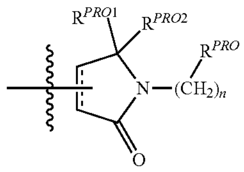

or

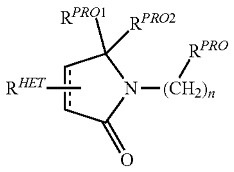

, preferably, a

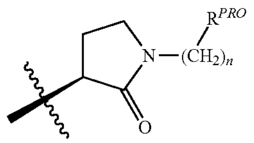

or

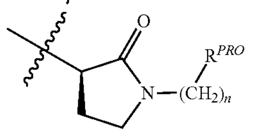

group, wherein:

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is 0, 1, 2, 3, 4, 5, or 6 (preferably 0 or 1), wherein each of said Heteocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted $—NR_1—X^{R2'}$-alkyl group, $—NR_1—X^{R2'}$-Aryl group; an optionally substituted $—NR_1—X^{R2'}$-HET, an optionally substituted $—NR_1—X^{R2'}$-Aryl-HET or an optionally substituted $—NR_1—X^{R2'}$-HET-Aryl, wherein:

$R_1$ of ULM-g through ULM-i is H or a $C_1$-$C_3$ alkyl group (preferably H);

$X^{R2'}$ of ULM-g through ULM-i is an optionally substituted $—CH_2)_n—$, $—CH_2)_n—CH(X_v)═CH(X_v)—$ (cis or trans), $—(CH_2)_n—CH≡CH—$, $—(CH_2CH_2O)_n—$ or a $C_3$-$C_6$ cycloalkyl group; and $X_v$ of ULM-g through ULM-i is H, a halo or a $C_1$-$C_3$ alkyl group which is optionally substituted with one or two hydroxyl groups or up to three halogen groups;

Alkyl of ULM-g through ULM-i is an optionally substituted C1-$C_{10}$ alkyl (preferably a $C_1$-$C_6$ alkyl) group (in certain preferred embodiments, the alkyl group is end-capped with a halo group, often a Cl or Br);

Aryl of ULM-g through ULM-i is an optionally substituted phenyl or naphthyl group (preferably, a phenyl group); and HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

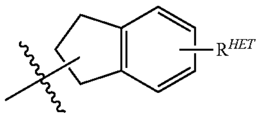

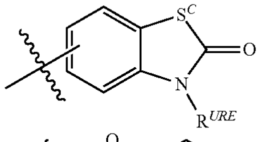

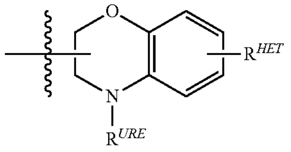

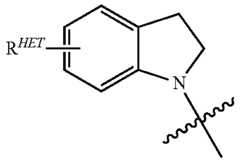

-continued

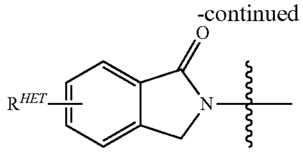

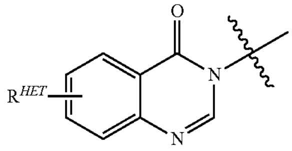

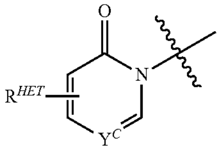

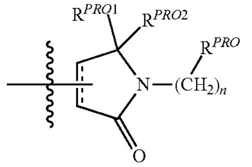

or

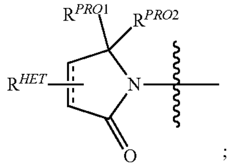

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C≡C—R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted $O—(C_1$-$C_6$ alkyl) (preferably substituted with one or two hydroxyl groups or up to three halo groups) or an optionally substituted $—C(O)(C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a $—C(O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or $C—R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C≡C—R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present invention, $R^{3'}$ of ULM-g through ULM-i is an optionally substituted $—(CH_2)_{n'}—(V)_{n'}—(CH_2)_{n'}—(V)_{n'}—R^{S3'}$ group, an optionally substituted-$(CH_2)_{n'}—N(R_{1'})(C{=}O)_{m'}—(V)_{n'}—R^{S3'}$ group, an optionally substituted $—X^{R3'}$-alkyl group, an optionally substituted $—X^{R3'}$-Aryl group; an optionally substituted $—X^{R3'}$-HET group, an optionally substituted $—X^{R3'}$-Aryl-HET group or an optionally substituted $—X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is $—(CH_2)_n—$, $—(CH_2CH_2O)_n—$, $—CH_2)_n—CH(X_v){=}CH(X_v)—$ (cis or trans), $—CH_2)_n—CH{\equiv}CH—$, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

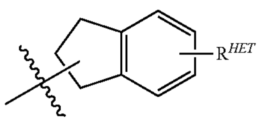

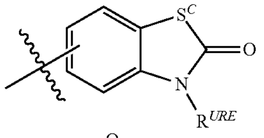

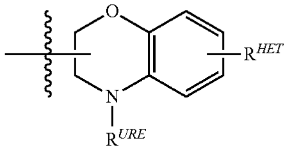

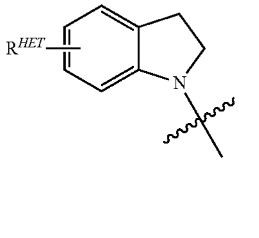

-continued

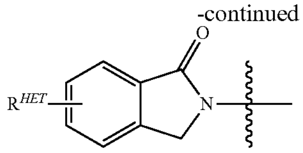

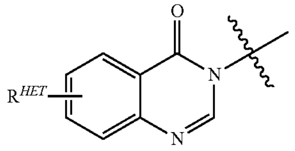

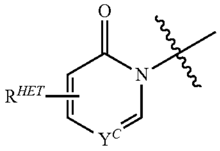

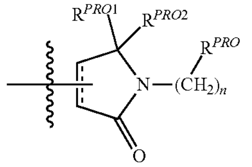

or

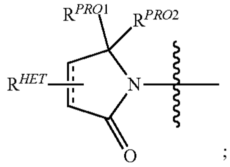

;

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C{\equiv}C—R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted $O—(C_1$-$C_6$ alkyl) (preferably substituted with one or two hydroxyl groups or up to three halo groups) or an optionally substituted $—C(O)(C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a $—C(O)(C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or $C—R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C{\equiv}C—R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker.

In alternative embodiments, $R^{3'}$ of ULM-g through ULM-i is $—(CH_2)_n$-Aryl, $—(CH_2CH_2O)_n$-Aryl, $—(CH_2)_n$-HET or $—(CH_2CH_2O)_n$-HET, wherein:

said Aryl of ULM-g through ULM-i is phenyl which is optionally substituted with one or two substitutents, wherein said substituent(s) is preferably selected from $—(CH_2)_nOH$, $C_1$-$C_6$ alkyl which itself is further optionally substituted with CN, halo (up to three halo groups), OH, $—(CH_2)_nO(C_1$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with $—(CH_2)_nOH$, $—(CH_2)_n—O—(C_1$-$C_6)$alkyl, $—(CH_2)_n—O—(CH_2)_n—(C_1$-$C_6)$alkyl, $—(CH_2)_n—C(O)(C_0$-$C_6)$ alkyl, $—(CH_2)_n—C(O)O(C_0$-$C_6)$alkyl, $—(CH_2)_n—OC(O)(C_1$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted $—(CH_2)_n—(V)_m—CH_2)_n—(V)_m—(C_1$-$C_6)$alkyl group, a $—(V)_{m'}—(CH_2CH_2O)_{n'}—R^{PEG}$ group where V is O, S or $NR_{1'}$, $R_{1'}$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

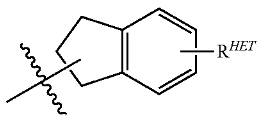

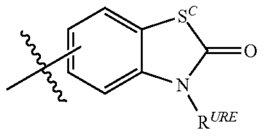

-continued

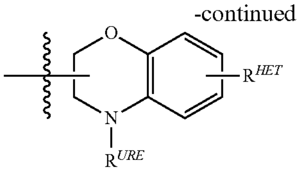

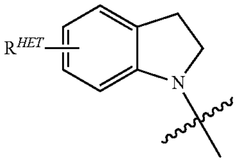

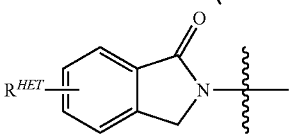

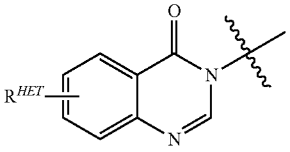

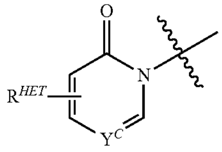

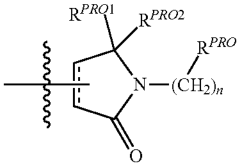

or

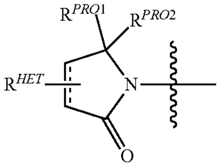

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $—C≡C—R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted $O—(C_1$-$C_6$ alkyl) (preferably substituted with one or two hydroxyl groups or up to three halo groups) or an optionally substituted $—C(O)(C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a $—C(O)(C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or $C—R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

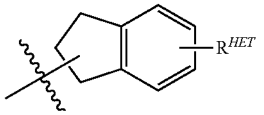

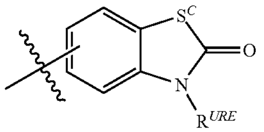

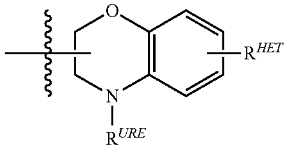

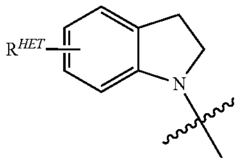

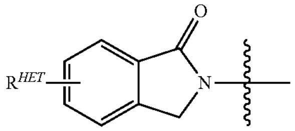

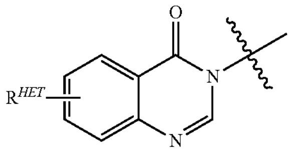

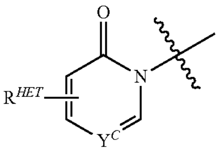

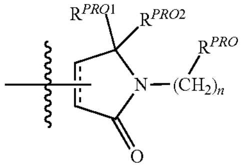

or

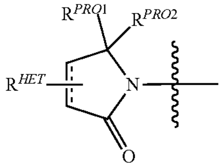

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl); $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

ULM-i

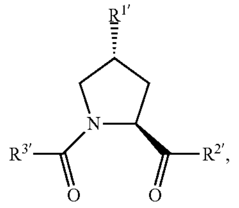

wherein:

$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^{3'}$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —$(CH_2)_nOCH_3$ group where n is 1 or 2 (preferably 2), or a

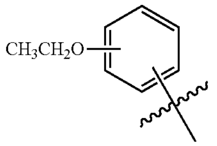

group (the ethyl ether group is preferably meta-substituted on the phenyl moiety), a morpholino group (linked to the carbonyl at the 2- or 3-position;

$R^{3P2}$ of ULM-i is a

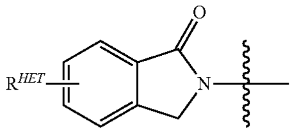

group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

ULM-j

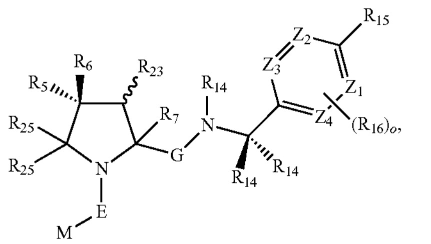

wherein:

each $R_5$ and $R_6$ of ULM-j is independently OH, SH, or optionally substituted alkyl or $R_5$, $R_6$, and the carbon atom to which they are attached form a carbonyl;

$R_7$ of ULM-j is H or optionally substituted alkyl;

E of ULM-j is a bond, C═O, or C═S;

G of ULM-j is a bond, optionally substituted alkyl, —COOH or C=J;

J of ULM-j is O or N—$R_8$;

$R_8$ of ULM-j is H, CN, optionally substituted alkyl or optionally substituted alkoxy;

M of ULM-j is optionally substituted aryl, optionally substituted heteroaryl, optionally substituted heterocyclic or

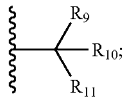

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

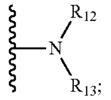

$R_{12}$ of ULM-j is H or optionally substituted alkyl;

$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate, each $R_{14}$ of ULM-j is independently H, haloalkyl, optionally substituted cycloalkyl, optionally substituted alkyl or optionally substituted heterocycloalkyl;

$R_{15}$ of ULM-j is H, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C═O and M is

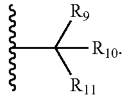

In certain embodiments, wherein E of ULM-j is C═O, Rn is optionally substituted heterocyclic or

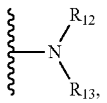

and M is

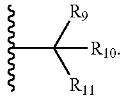

In certain embodiments, wherein E of ULM-j is C═O, M is

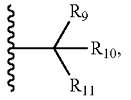

and $R_{11}$ is

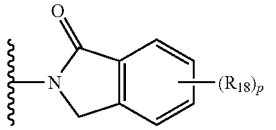

or

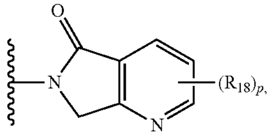

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

ULM-k

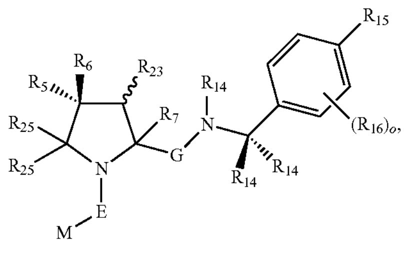

wherein:

G of ULM-k is C=J, J is O;

$R_7$ of ULM-k is H;

each $R_{14}$ of ULM-k is H;

o of ULM-k is 0;

$R_{15}$ of ULM-k is

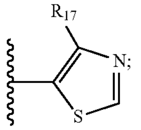

and $R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

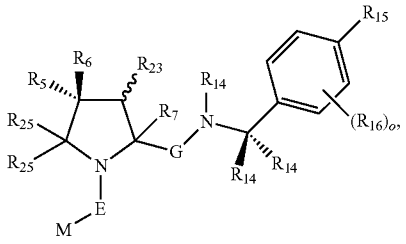

wherein:

G of ULM-k is C=J, J is O;

$R_7$ of ULM-k is H;

each $R_{14}$ of ULM-k is H;

o of ULM-k is 0; and $R_{15}$ of ULM-k is selected from the group consisting of:

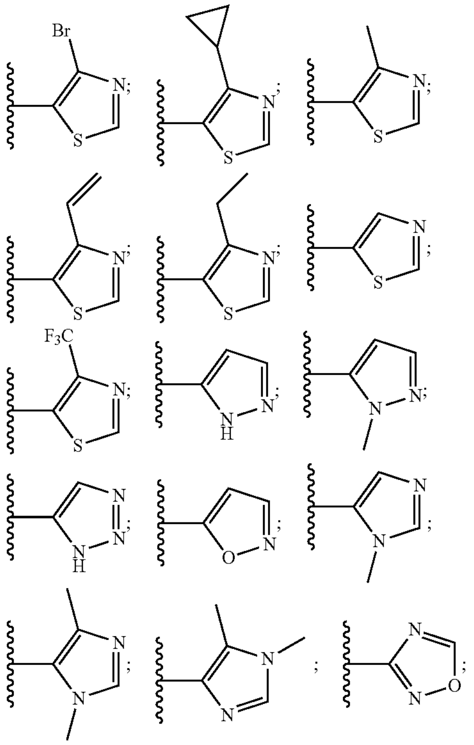

-continued
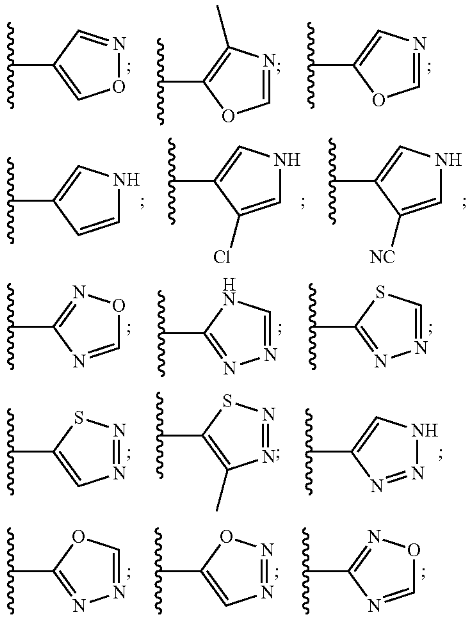
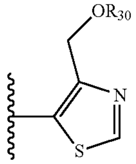
and
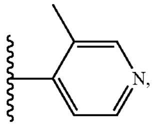
wherein $R_{30}$ of ULM-k is H or an optionally substituted alkyl.
In other embodiments, ULM and where present, ULM', are each independently a group according to the chemical structure:
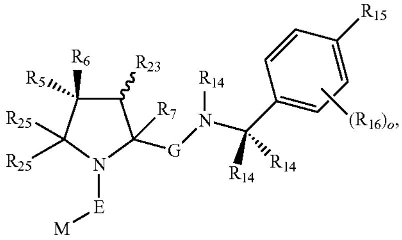
ULM-k
wherein:
E of ULM-k is C=O;
M of ULM-k is
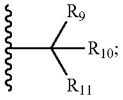
and
$R_{11}$ of ULM-k is selected from the group consisting of
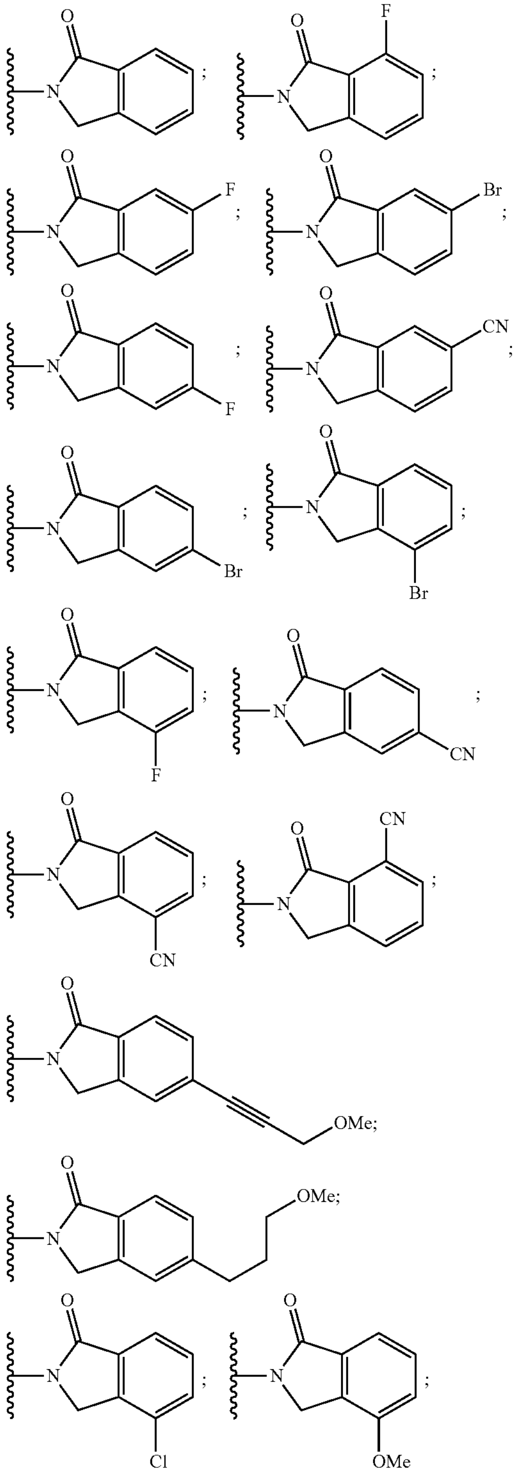
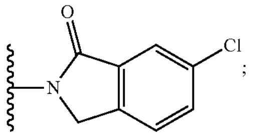
and
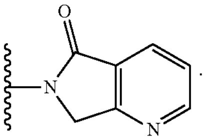

In still other embodiments, a compound of the chemical structure,

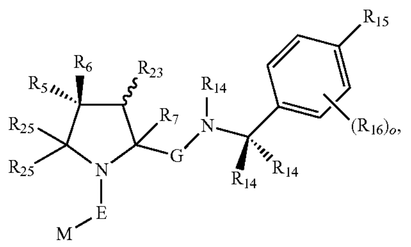

ULM-k wherein E of ULM-k is C═O;

$R_{11}$ of ULM-k is

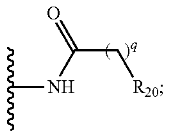

and

M of ULM-k is

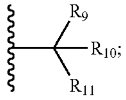

q of ULM-k is 1 or 2;

$R_{20}$ of ULM-k is H, optionally substituted alkyl, optionally substituted cycloalkyl, optionally substituted aryl, or

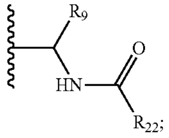

$R_{21}$ of ULM-k is H or optionally substituted alkyl; and $R_{22}$ of ULM-k is H, optionally substituted alkyl, optionally substituted alkoxy, or haloalkyl.

In any embodiment described herein, $R_{11}$ of ULM-j or ULM-k is selected from the group consisting of:

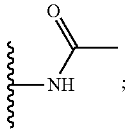 ; 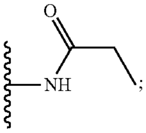 ; 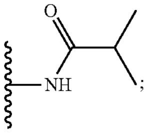 ;

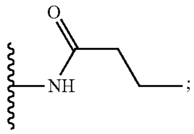 ; 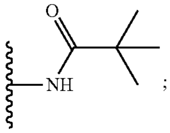 ;

-continued

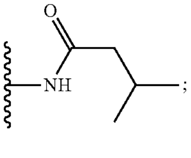 ; 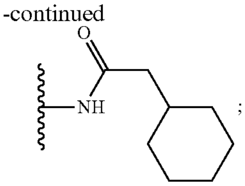 ;

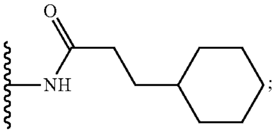 ; 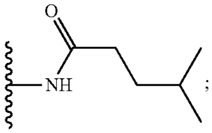 ;

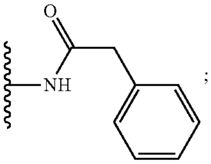 ; 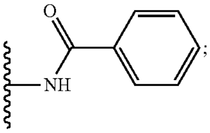 ;

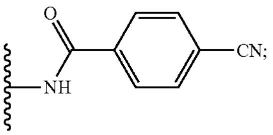 ; 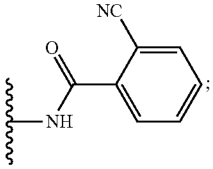 ;

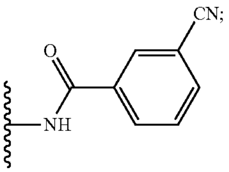 ; 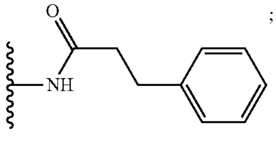 ;

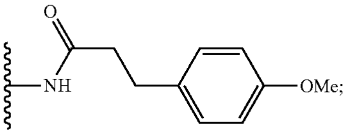

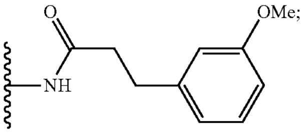

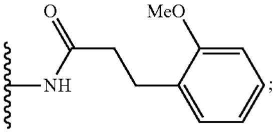

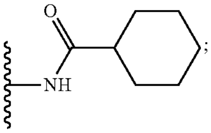 ; 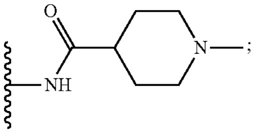 ;

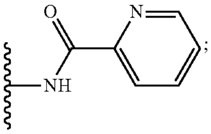 ; 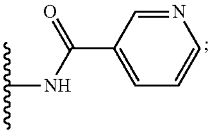 ;

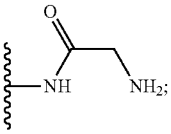 ; 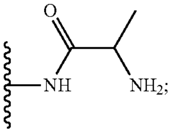 ; 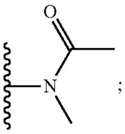 ;

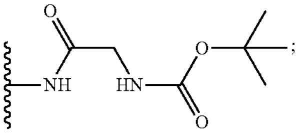 ;

-continued
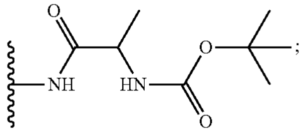
;
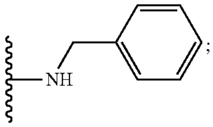
;
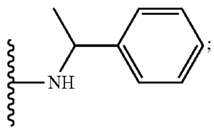
;
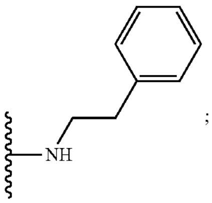
;
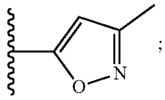
;
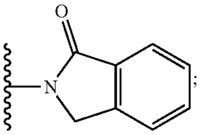
;
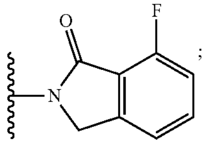
;
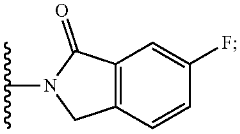
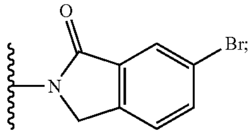
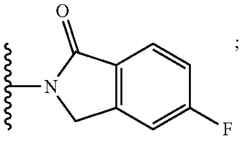
;
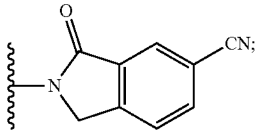
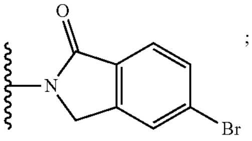
;
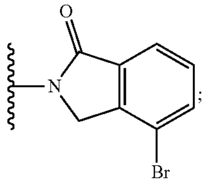
;
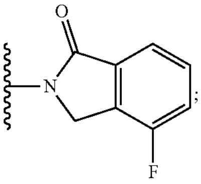
;
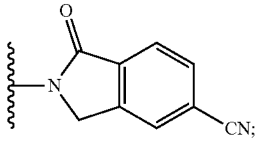
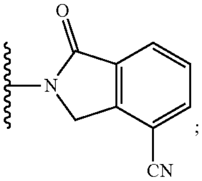
;
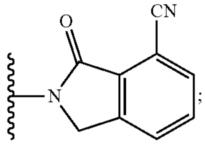
;
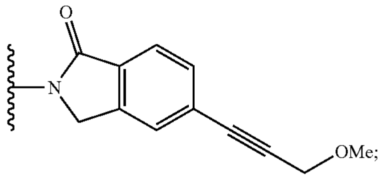
;
-continued
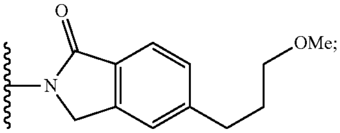
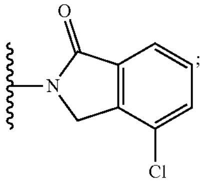
;
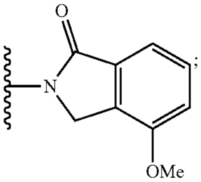
;
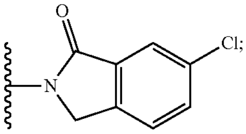
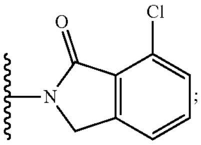
;
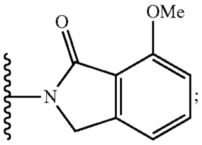
;
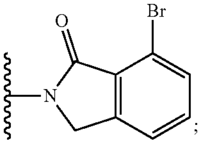
;
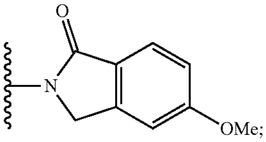
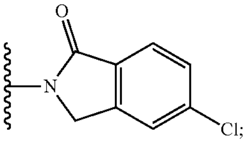
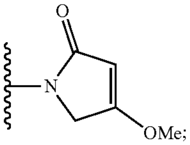
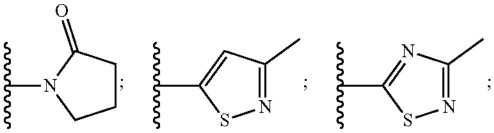
;
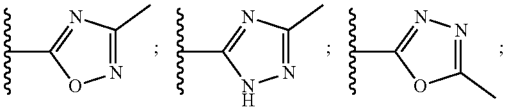
;
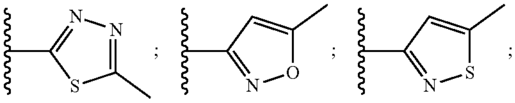
;
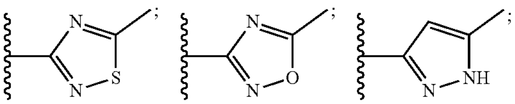
;
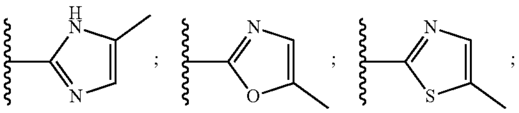
;
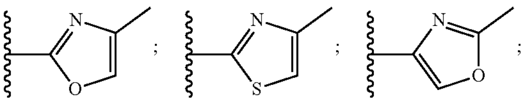
;
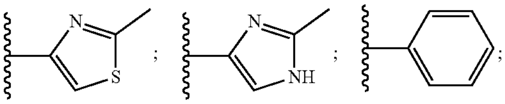
;
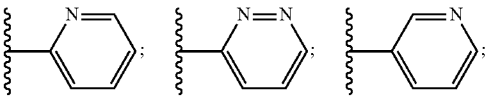
;

-continued
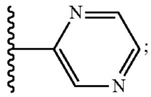 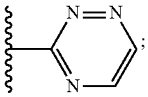 and
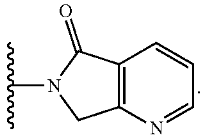
In certain embodiments, $R_{11}$ of ULM-j or ULM-k is selected from the group consisting of:
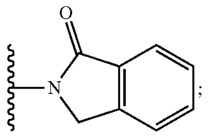 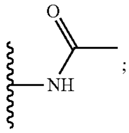
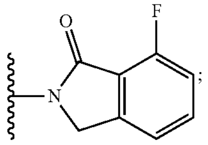 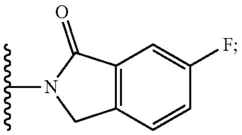
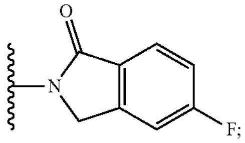 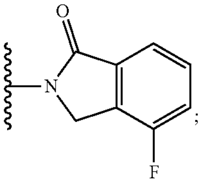
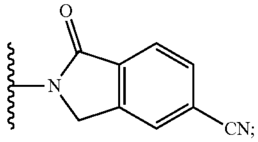 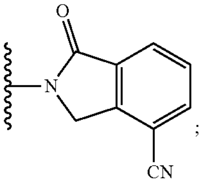
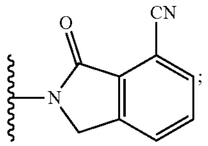 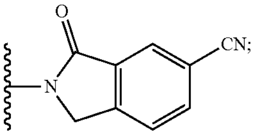
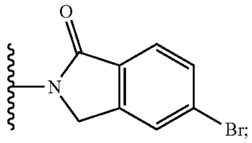 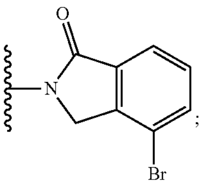
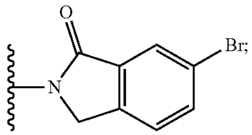 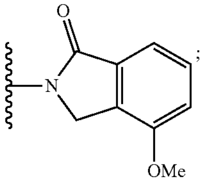
-continued
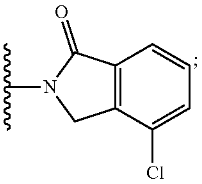 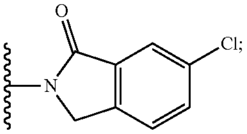
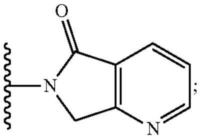
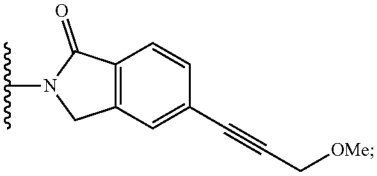
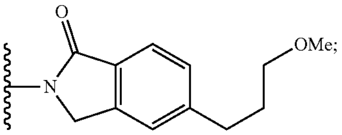 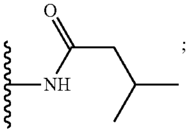
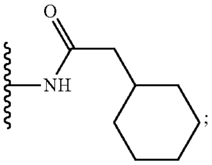 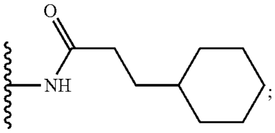
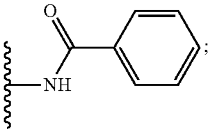 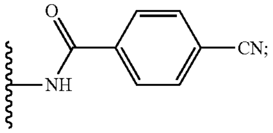
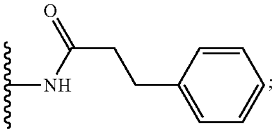
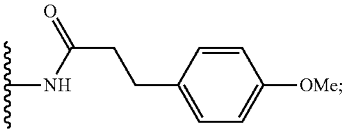
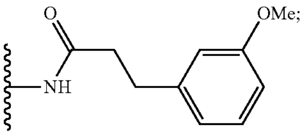
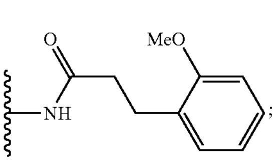 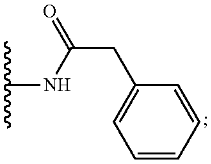
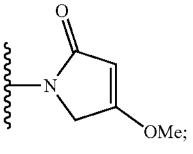 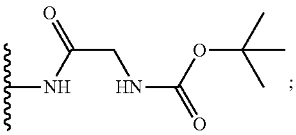

-continued

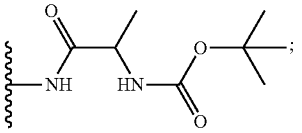

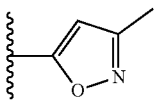

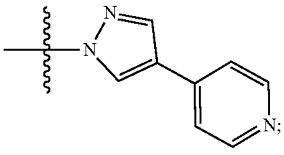

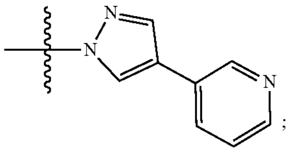

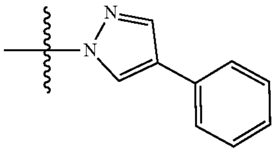

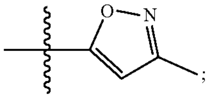

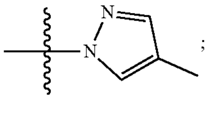

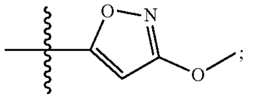

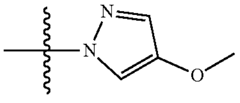

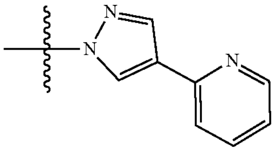

and

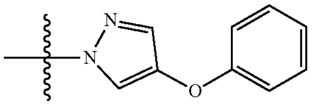

In certain embodiments, ULM (or when present ULM') is a group according to the chemical structure:

ULM-1

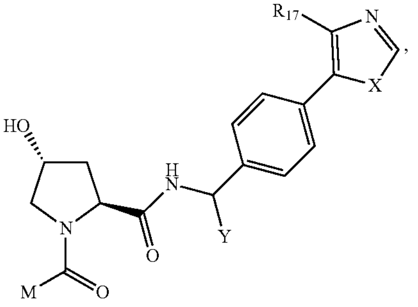

wherein:

X of ULM-1 is O or S;

Y of ULM-1 is H, methyl or ethyl;

$R_{17}$ of ULM-1 is H, methyl, ethyl, hydoxymethyl or cyclopropyl;

M of ULM-1 is optionally substituted aryl, optionally substituted heteroaryl, or

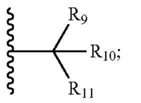

$R_{9\ of\ ULM\text{-}1}$ is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

R11 of ULM-1 is optionally substituted heteroaromatic, optionally substituted heterocyclic, optionally substituted aryl or

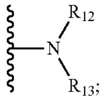

$R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

ULM-m

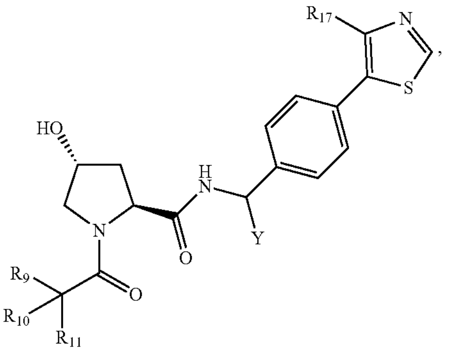

wherein:

Y of ULM-m is H, methyol or ethyl $R_9$ of ULM-m is H;

$R_{10}$ is isopropyl, tert-butyl, sec-butyl, cyclopentyl, or cyclohexyl;

$R_{11}$ of ULM-m is optionally substituted amide, optionally substituted isoindolinone, optionally substituted isooxazole, optionally substituted heterocycles.

In other preferred embodiments of the invention, ULM and where present, ULM', are each independently a group according to the chemical structure:

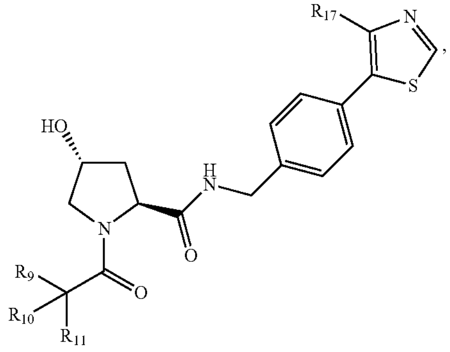

ULM-n

Wherein:

$R_{17}$ of ULM-n is methyl, ethyl, or cyclopropyl; and $R_9$, $R_{10}$, and $R_{11}$ of ULM-n are as defined above. In other instances, $R_9$ is H; and $R_{10}$ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the invention, the ULM moiety is selected from the group consisting of:

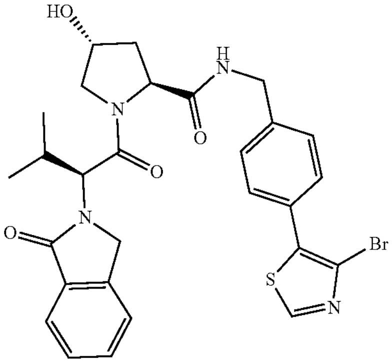

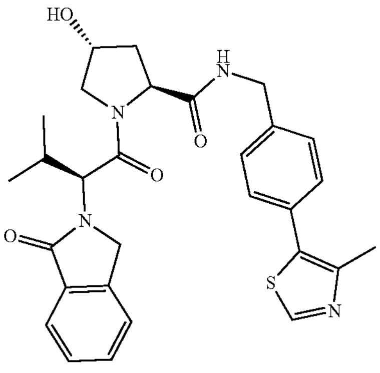

-continued

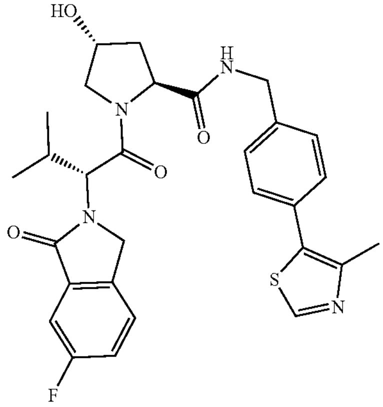

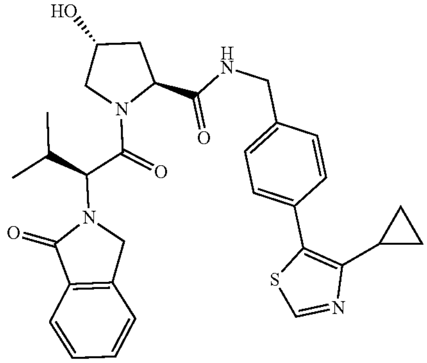

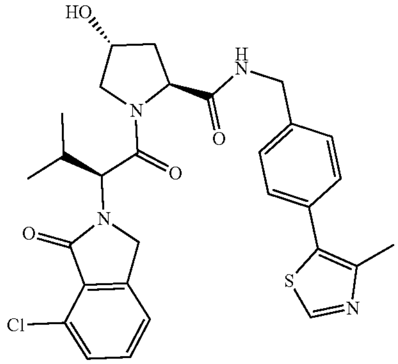

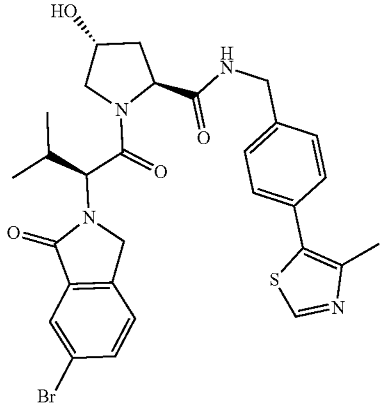

-continued
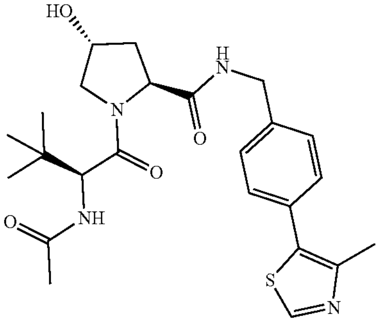
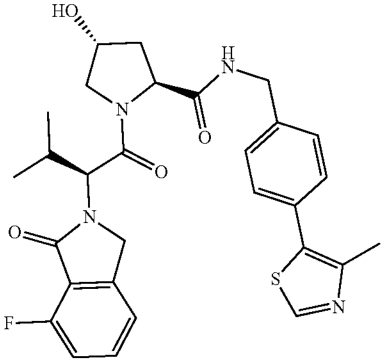
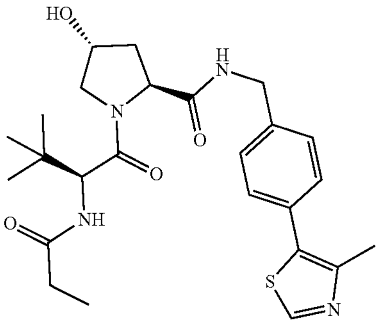
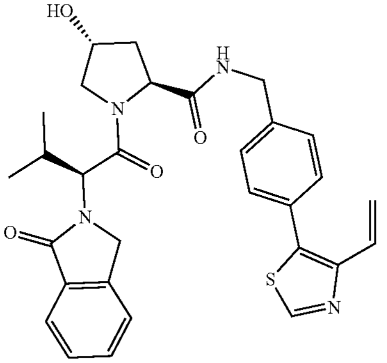
-continued
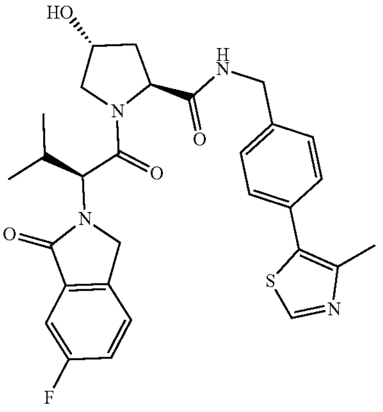
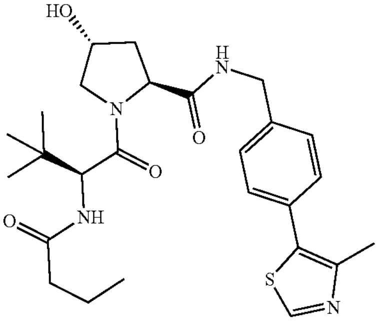
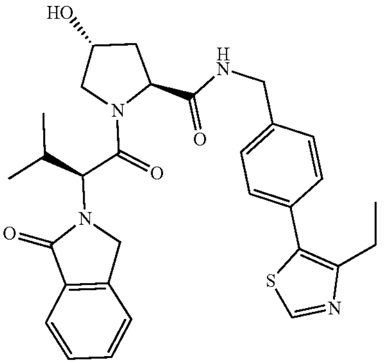
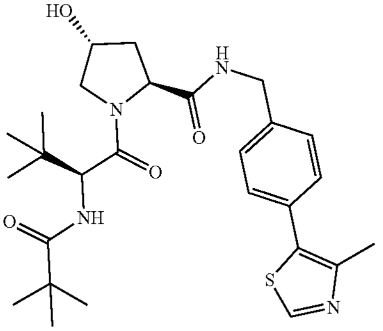

-continued
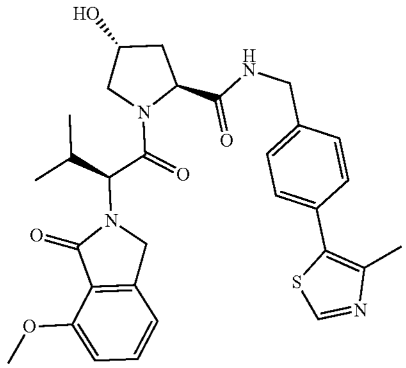
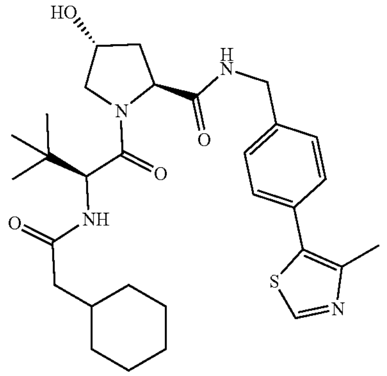
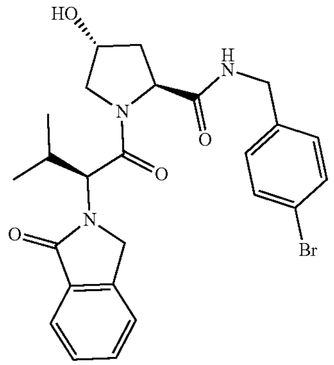
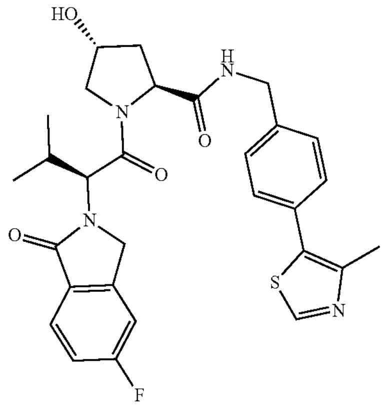
-continued
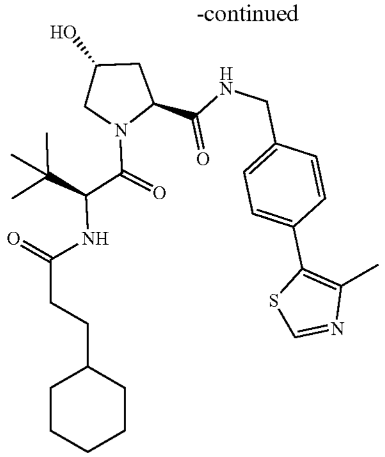
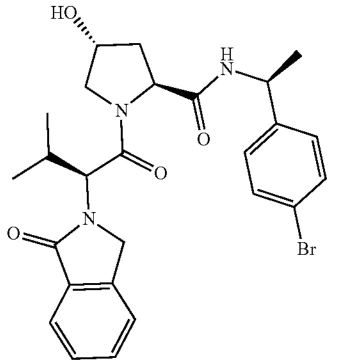
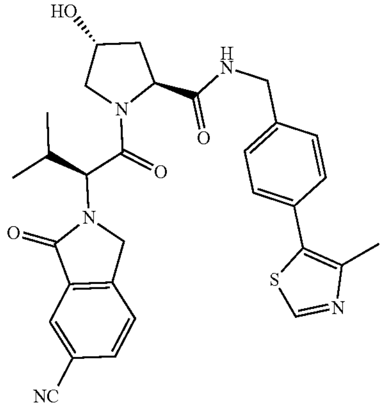
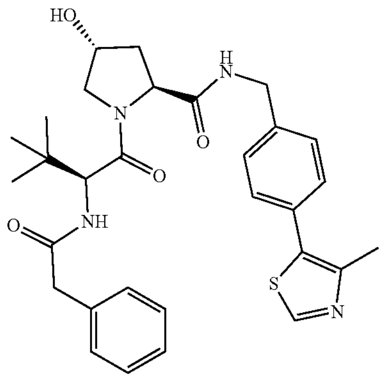

-continued
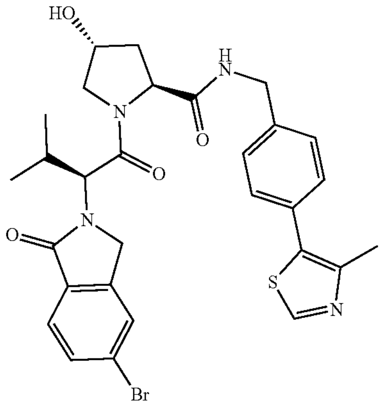
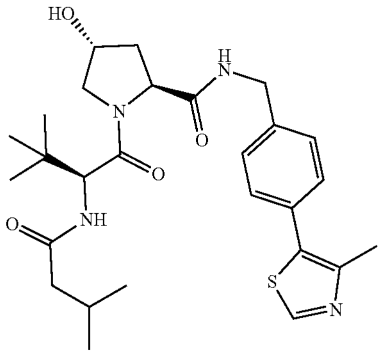
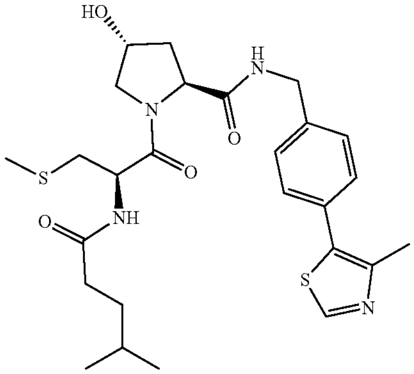
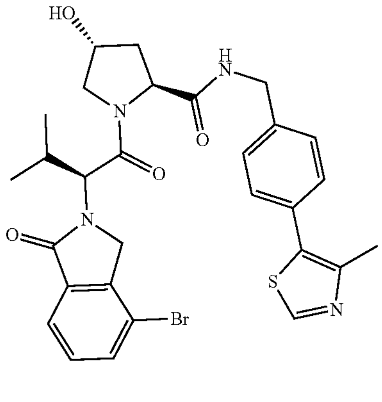
-continued
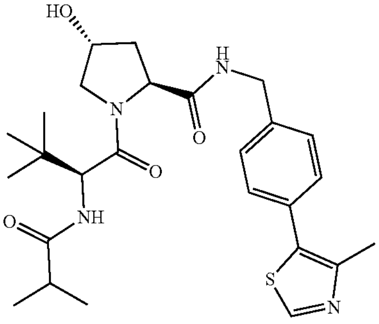
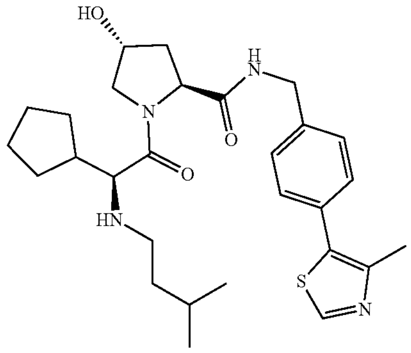
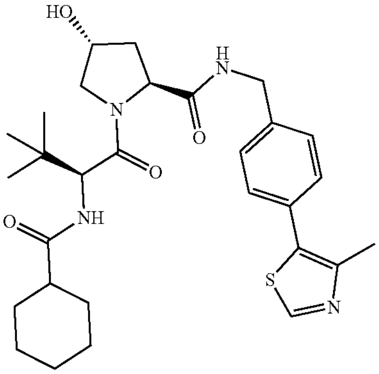
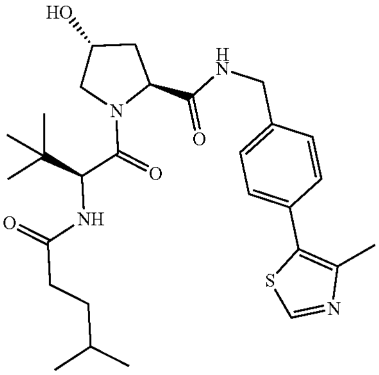

-continued
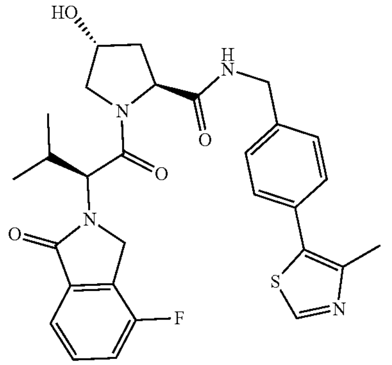
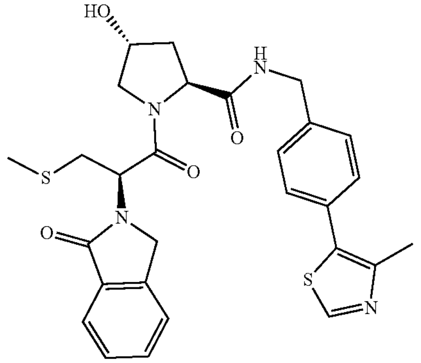
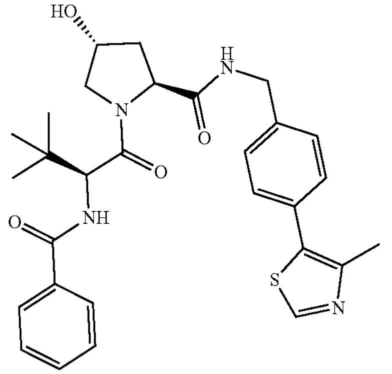
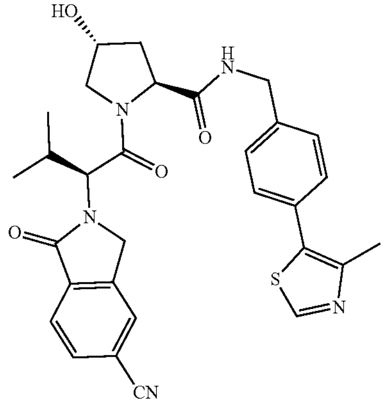
-continued
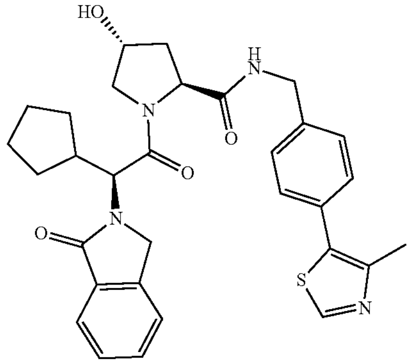
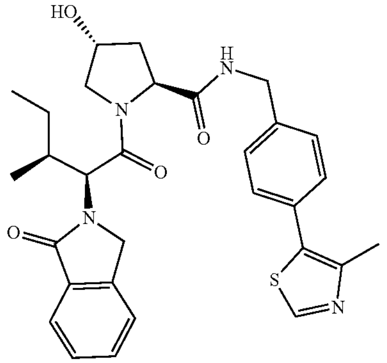
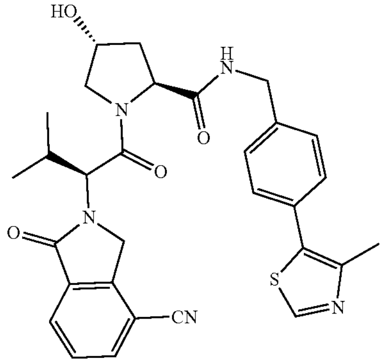
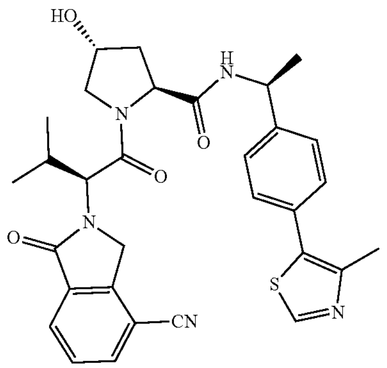

-continued
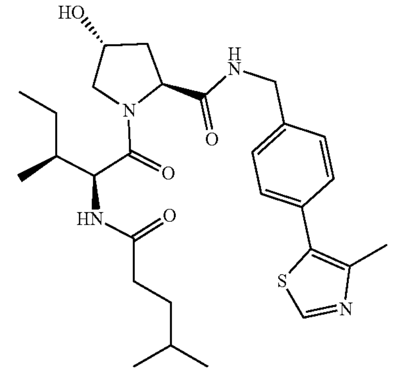
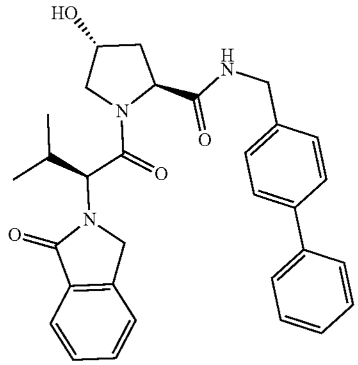
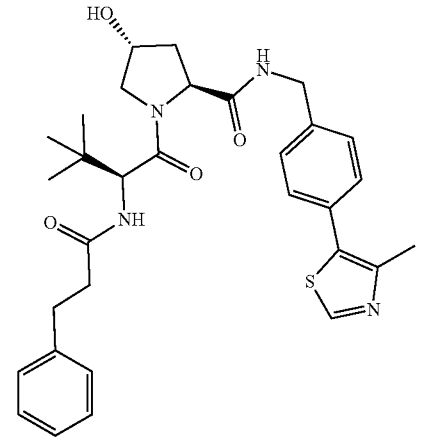
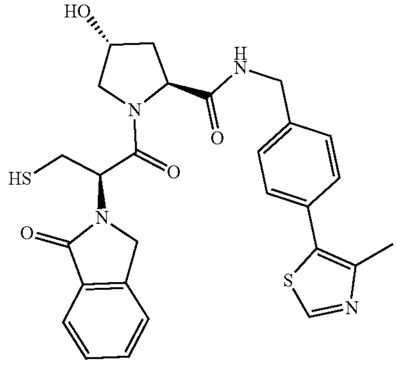
-continued
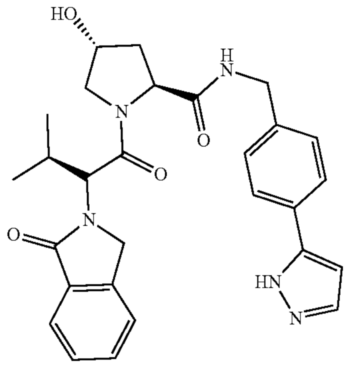
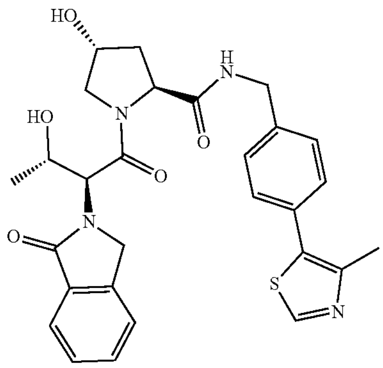
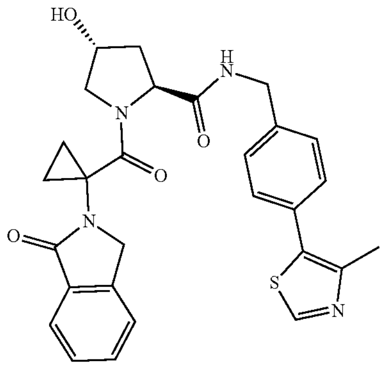
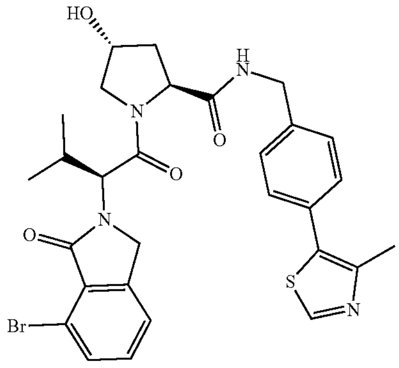

-continued
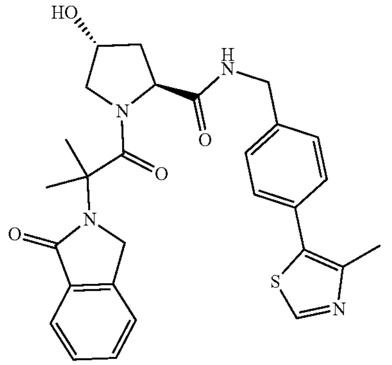
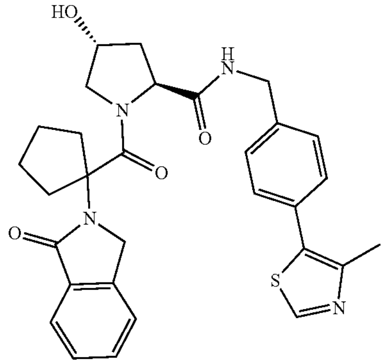
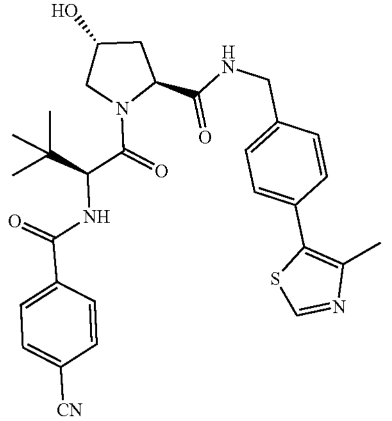
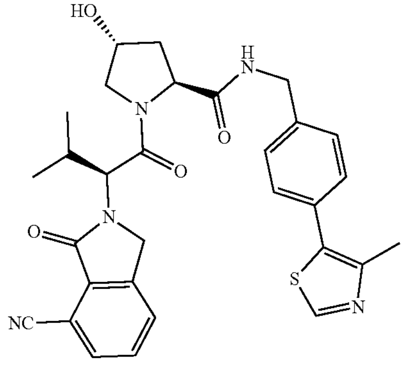
-continued
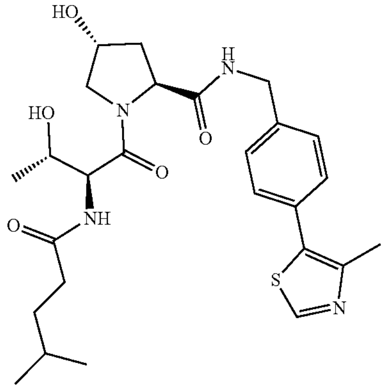
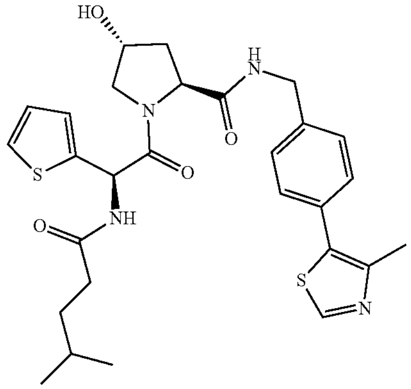
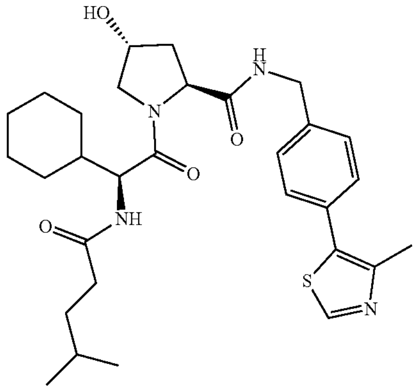
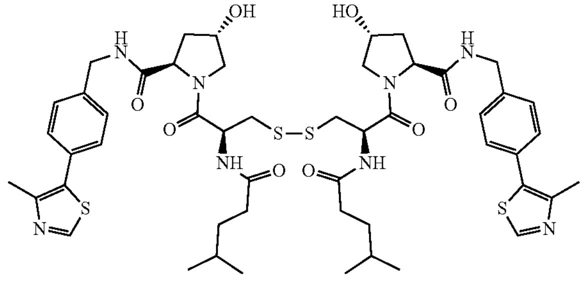

-continued
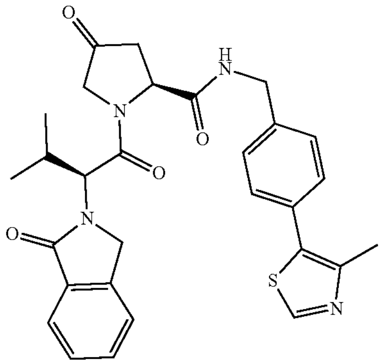
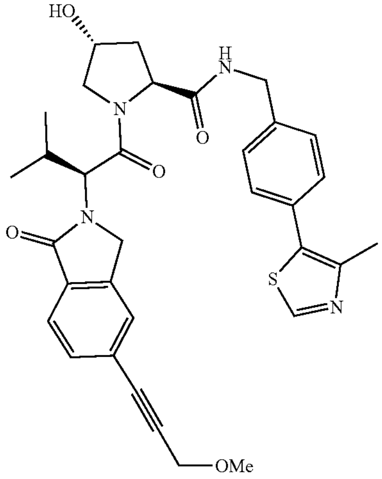
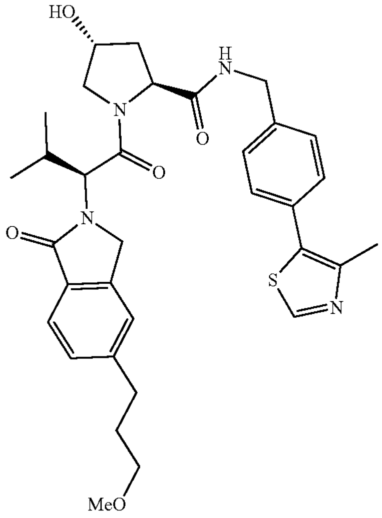
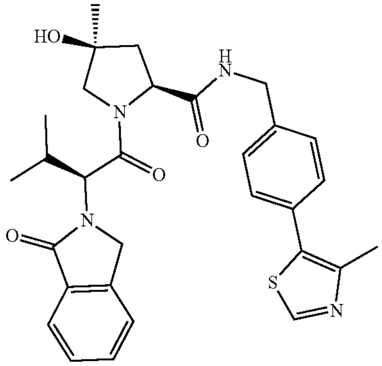
-continued
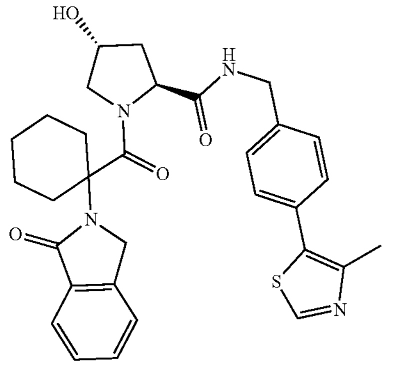
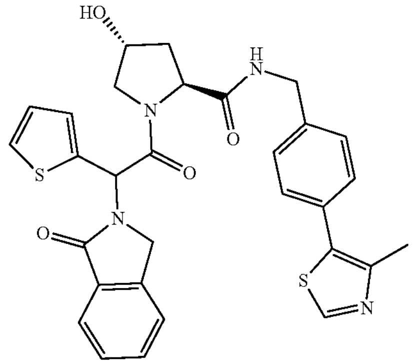
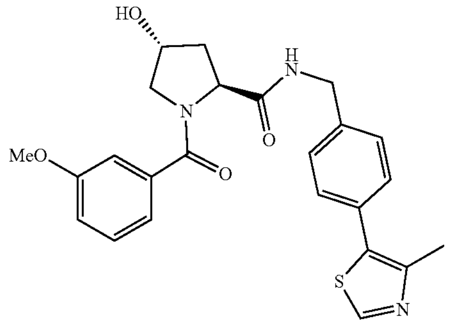
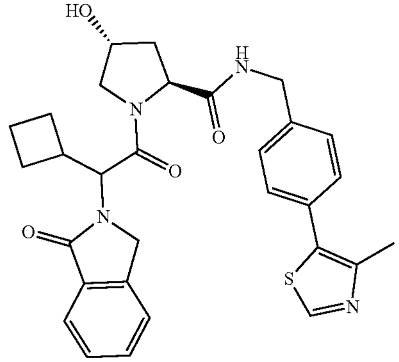

-continued
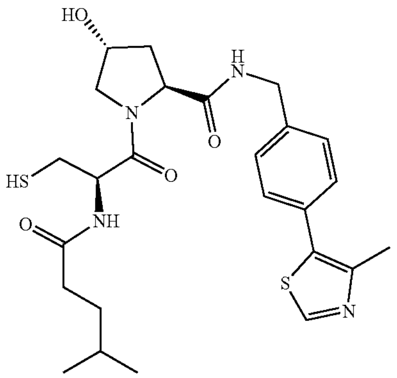
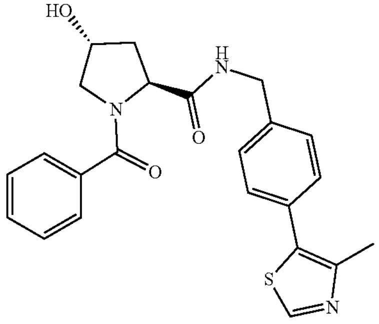
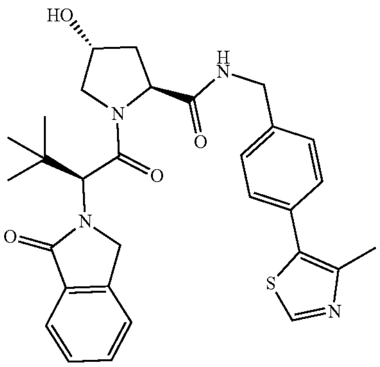
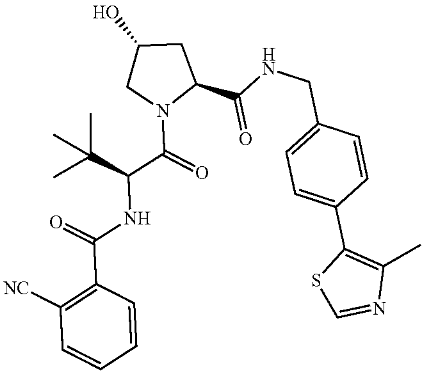
-continued
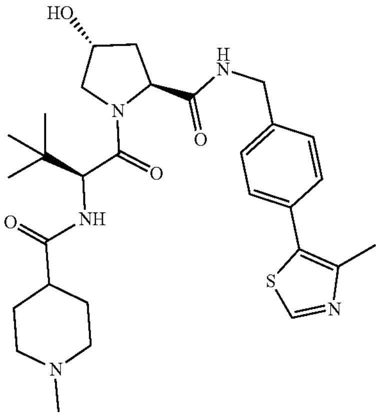
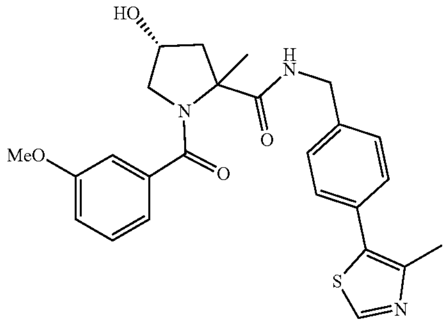
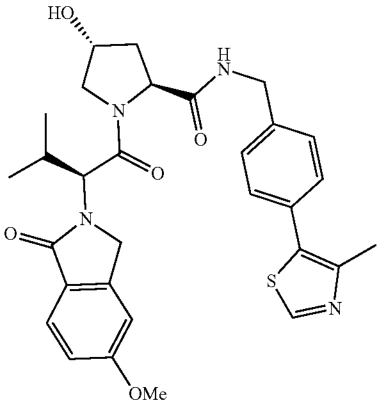
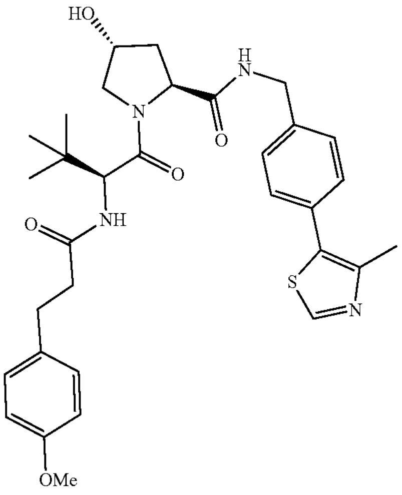

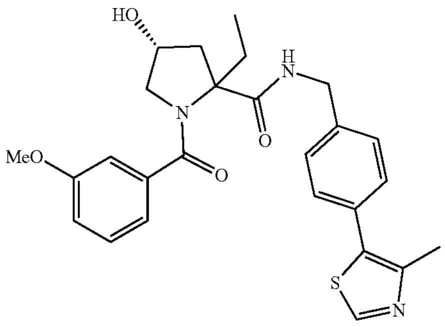
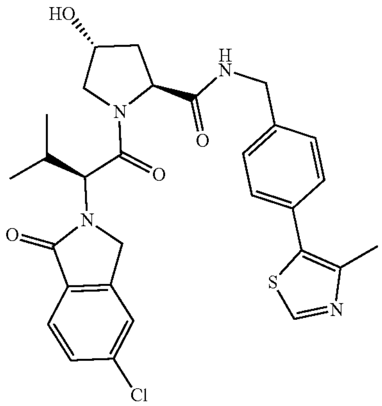
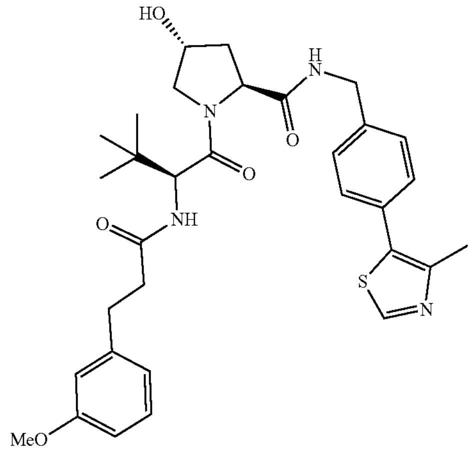
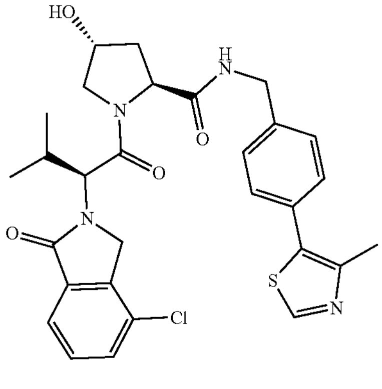
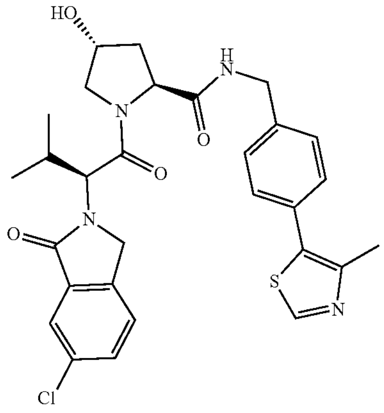
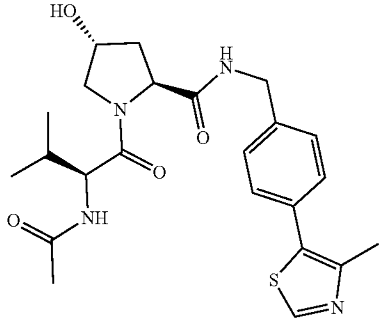
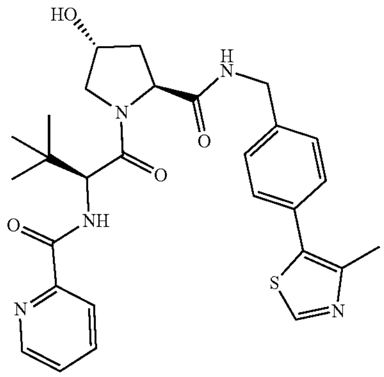
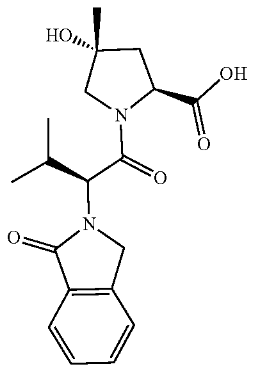

-continued
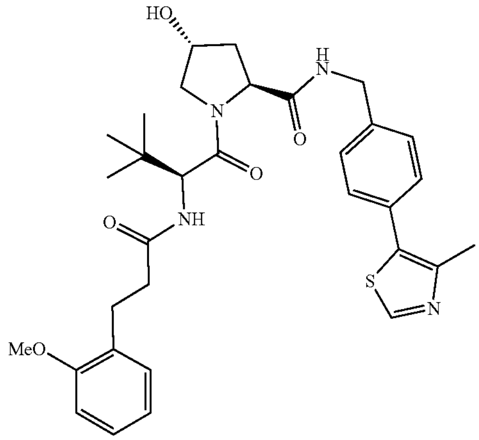
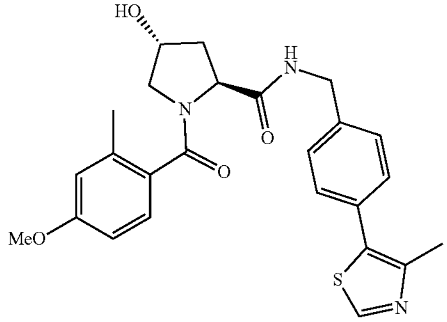
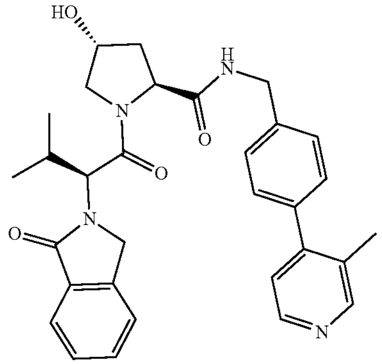
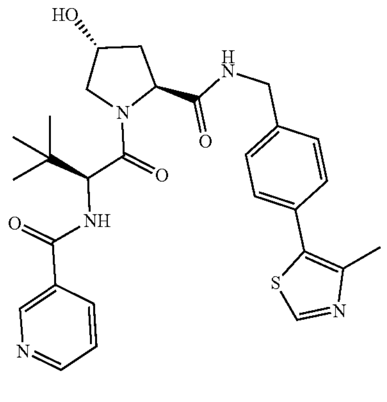
-continued
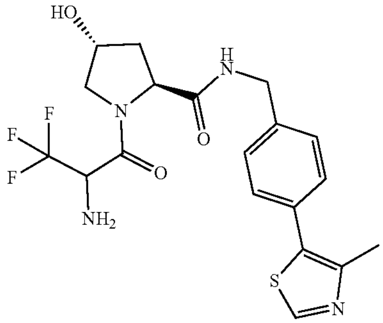
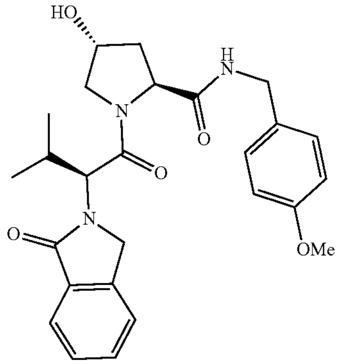
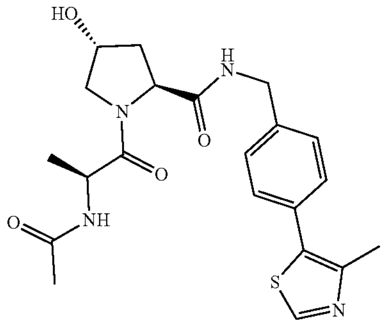
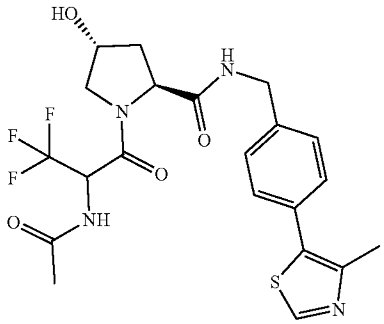
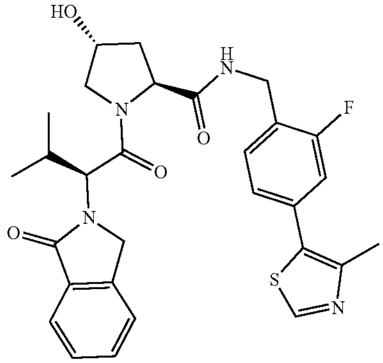

-continued
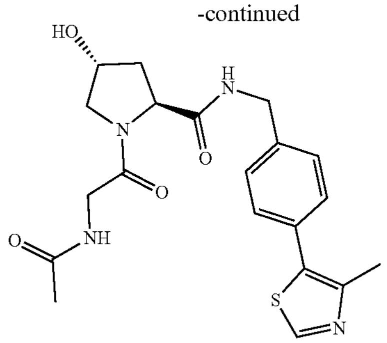
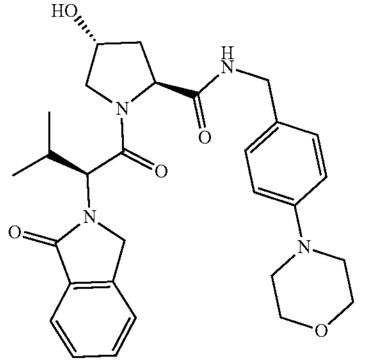
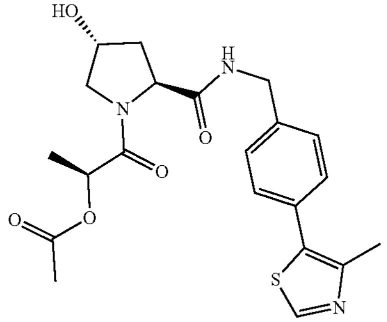
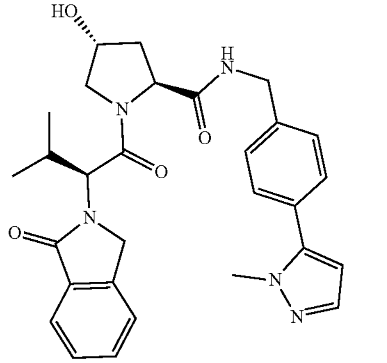
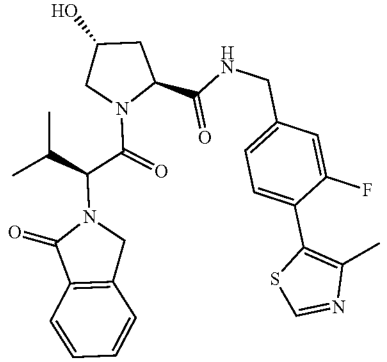
-continued
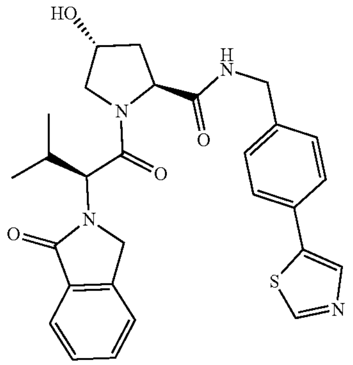
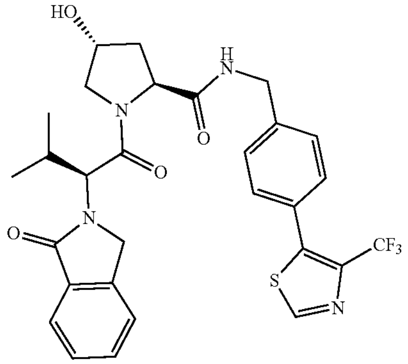
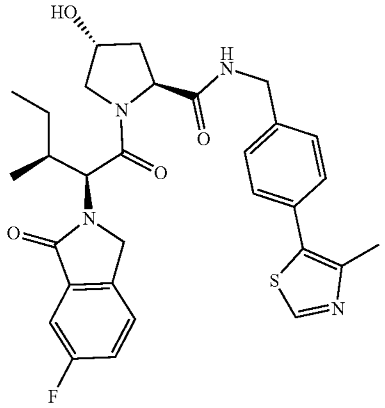
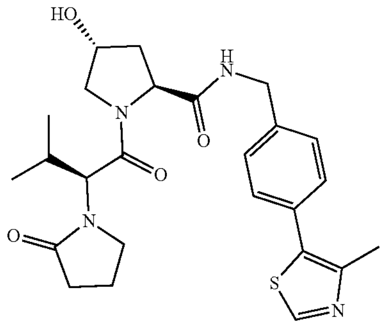

-continued
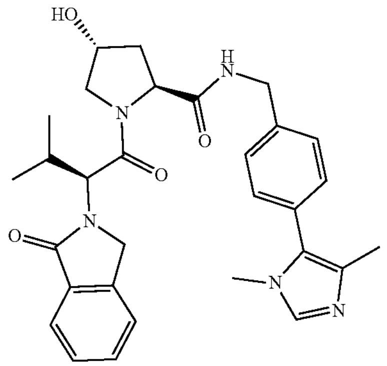
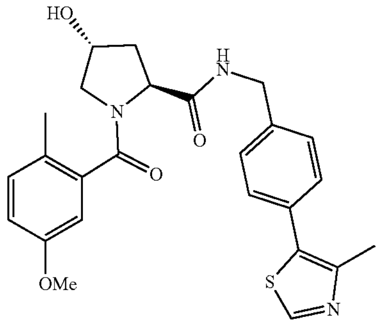
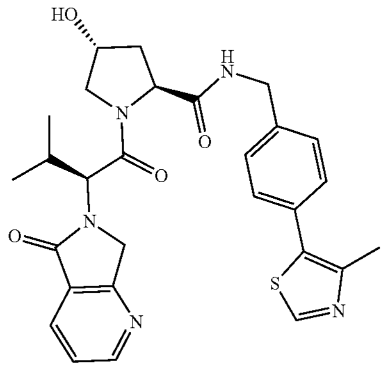
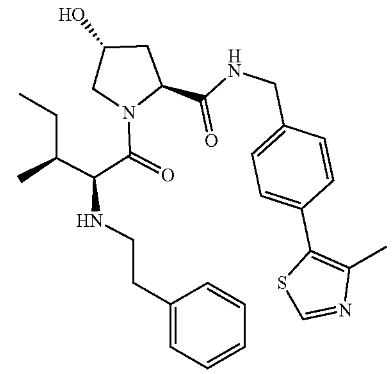
-continued
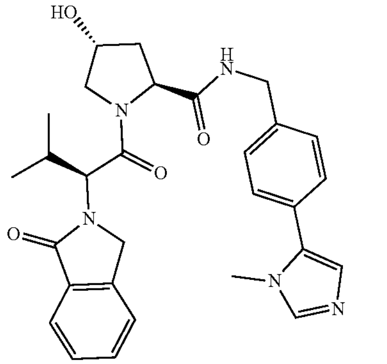
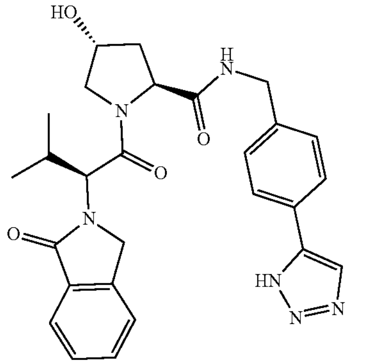
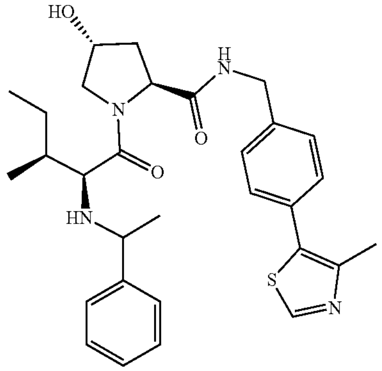
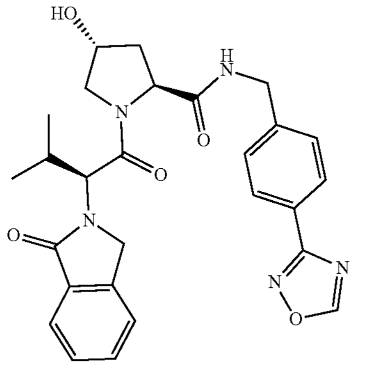

-continued
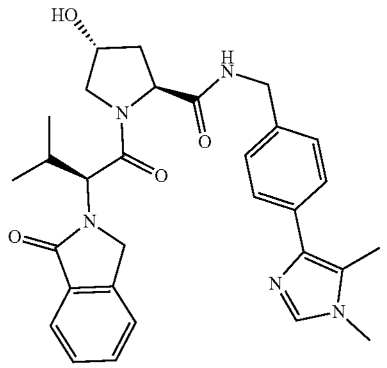
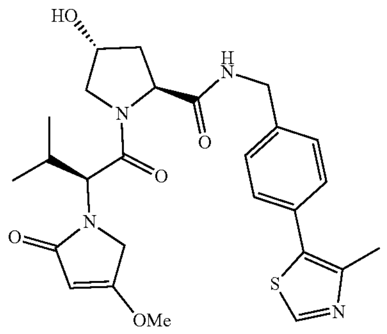
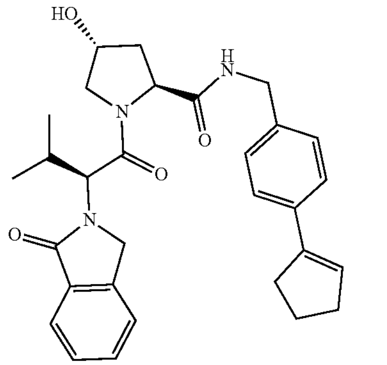
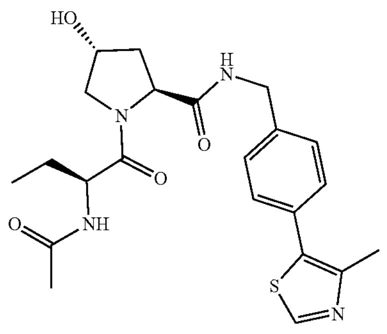
-continued
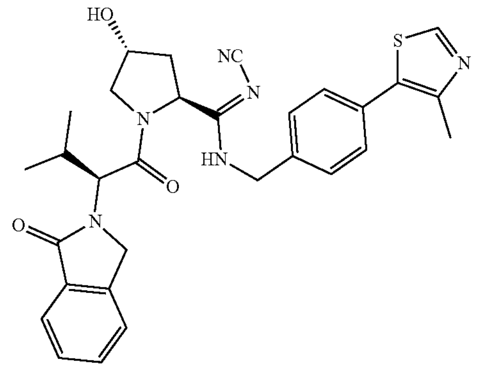
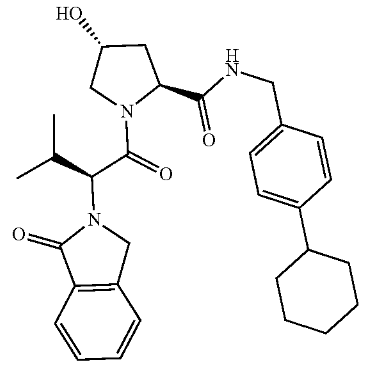
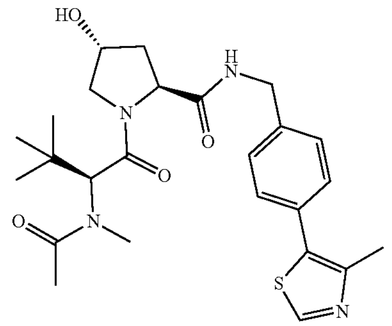
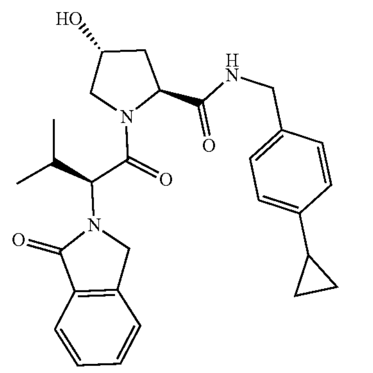

-continued
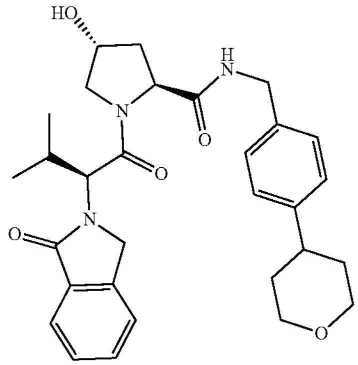
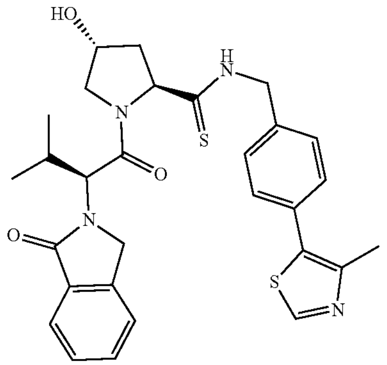
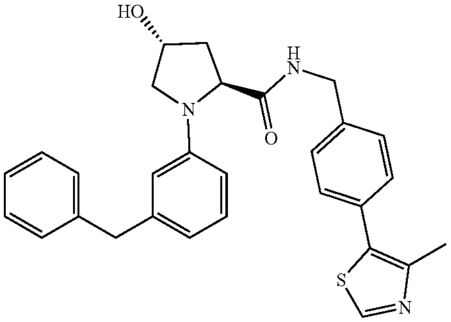
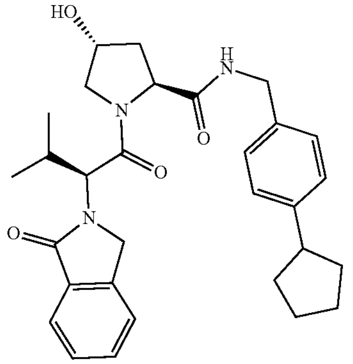
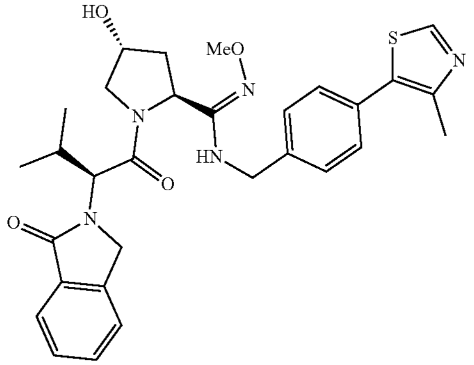
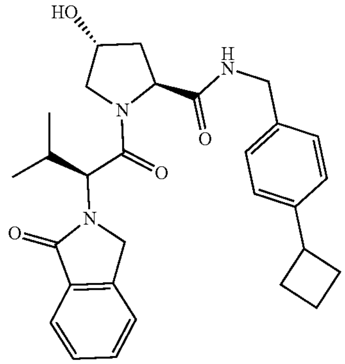
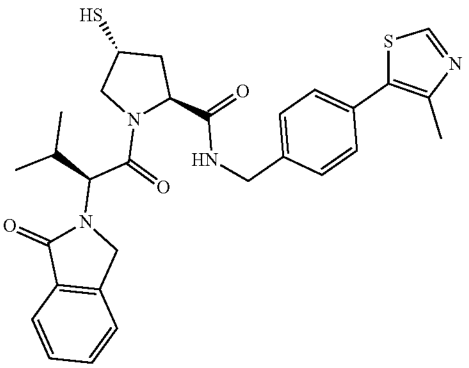
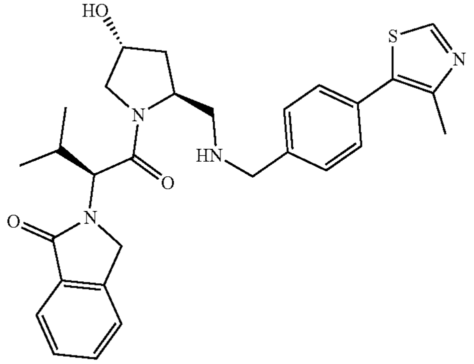
-continued -continued
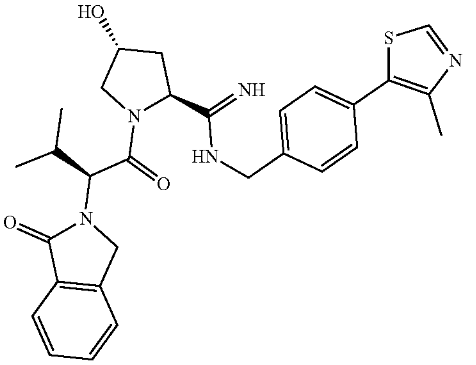
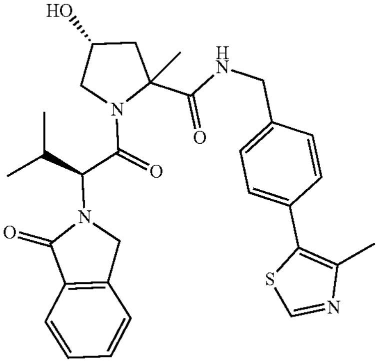
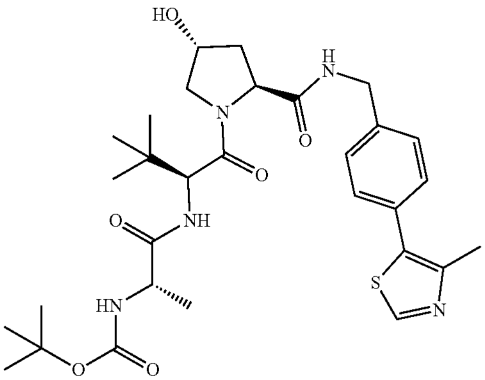
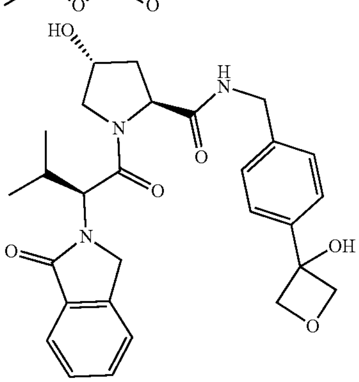
-continued
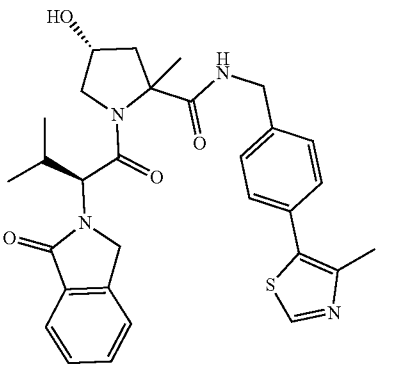
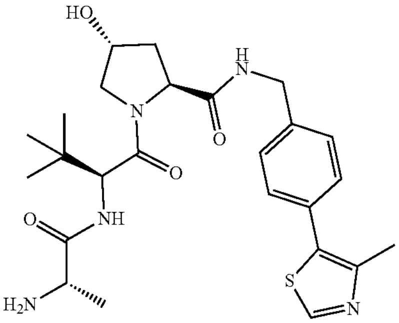
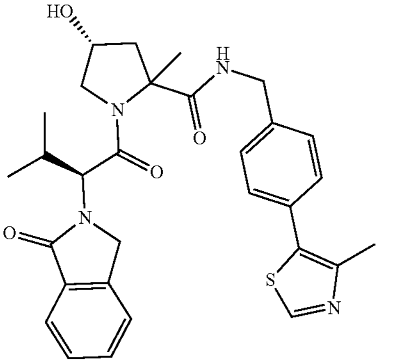
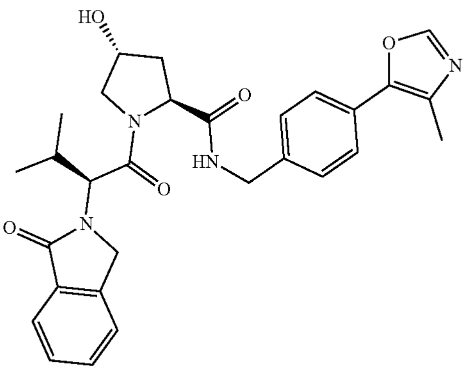

-continued
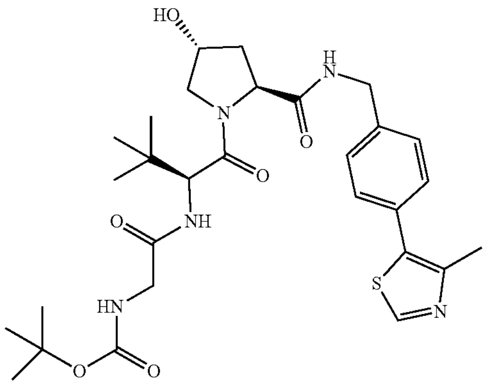
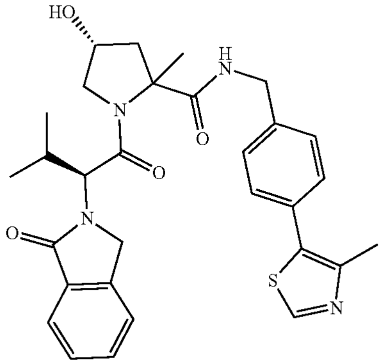
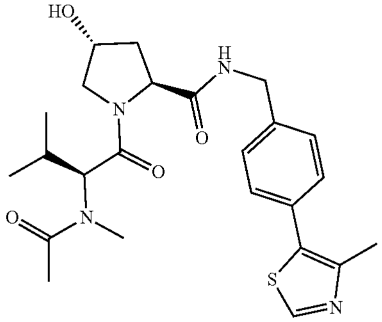
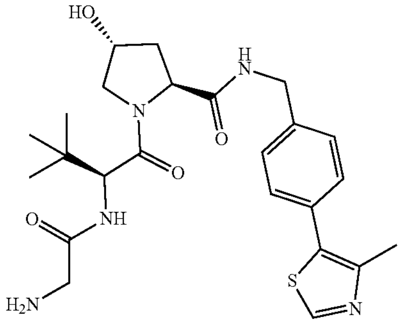
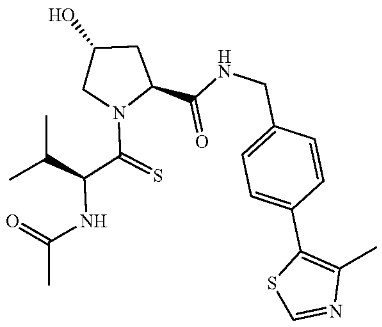
-continued
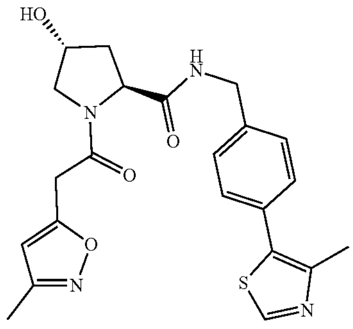
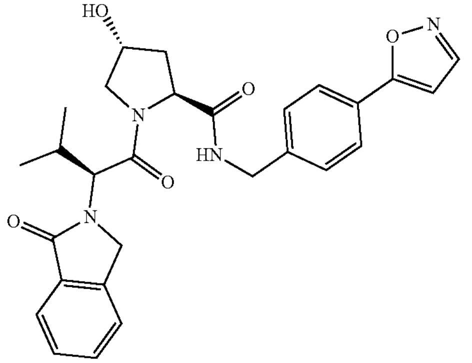
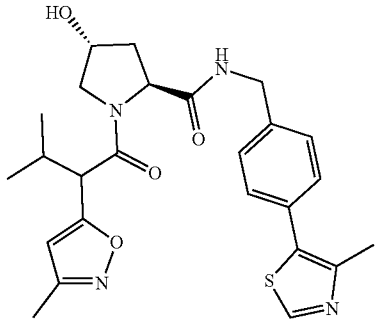
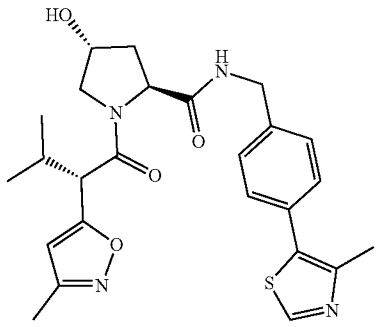
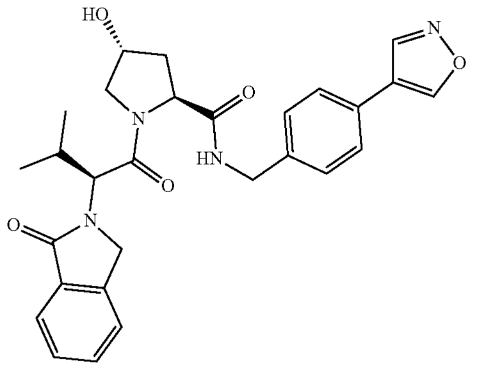

-continued
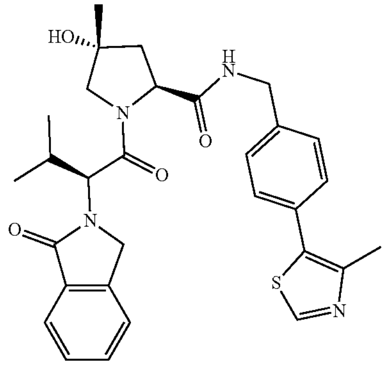
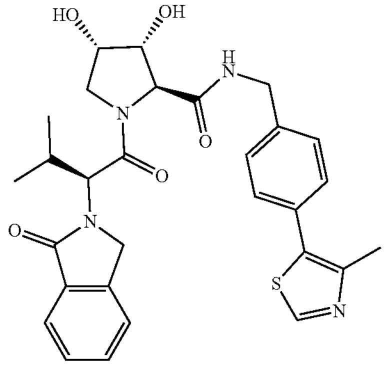
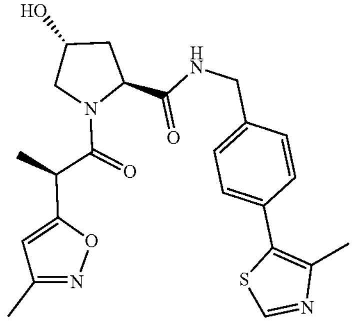
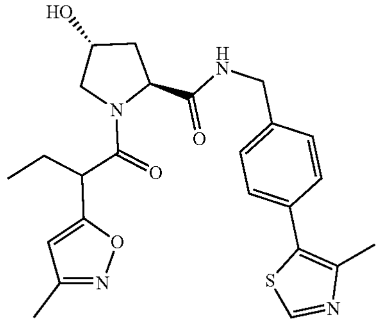
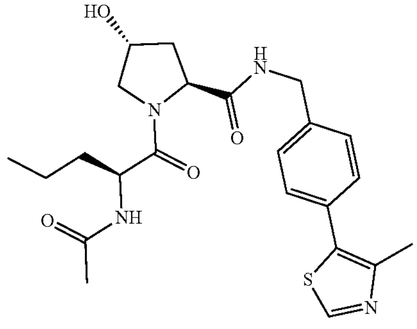
-continued
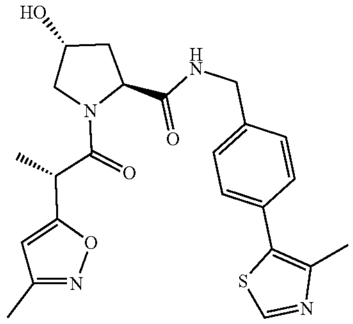
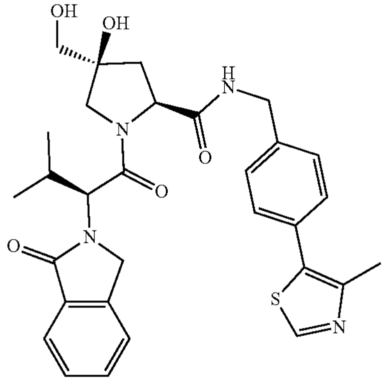
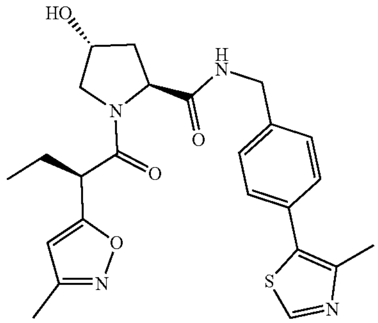
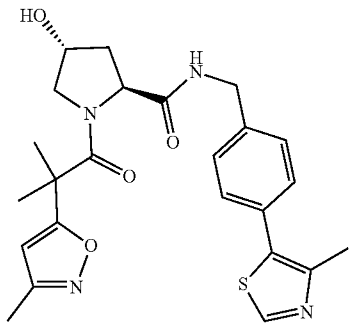
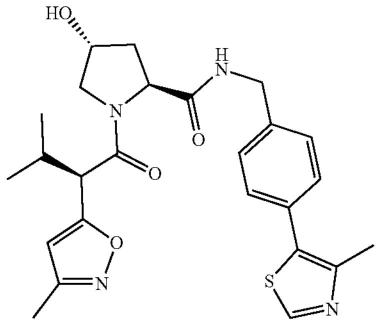

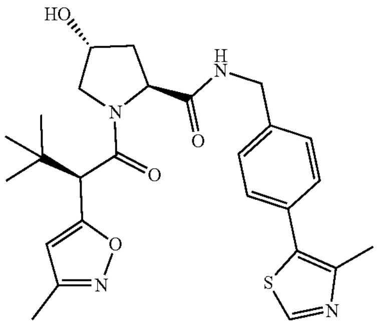
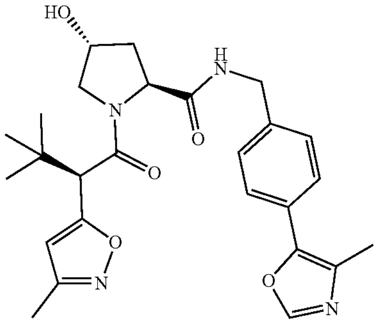
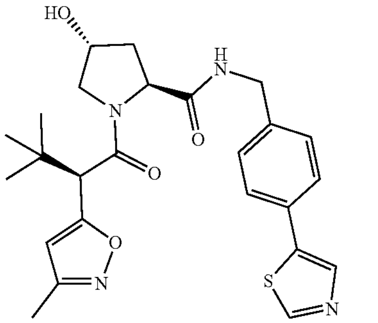
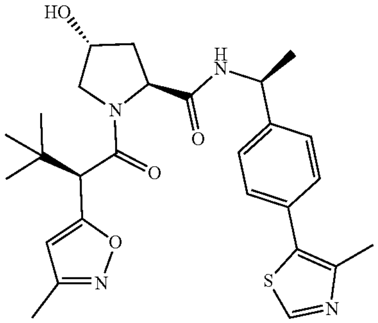
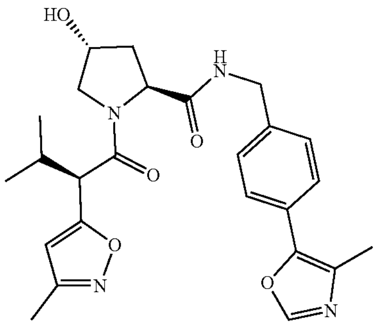
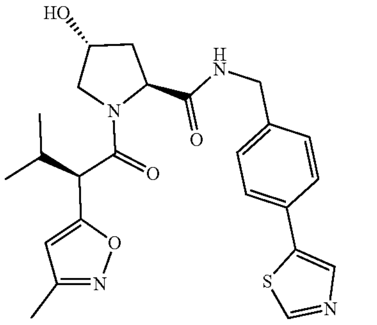
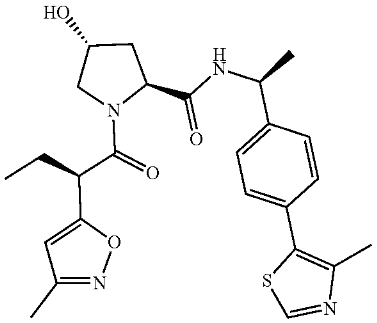
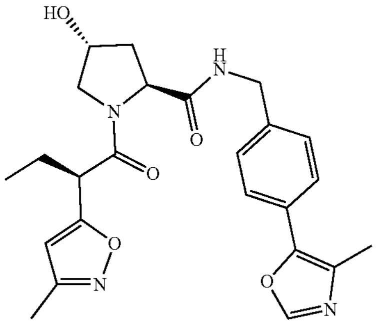
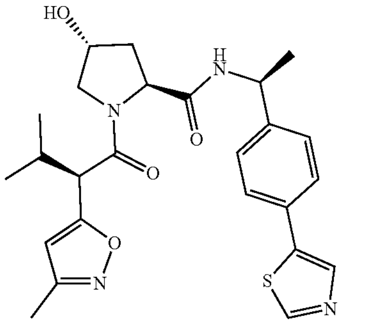
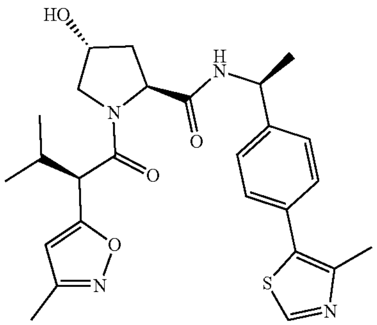

-continued
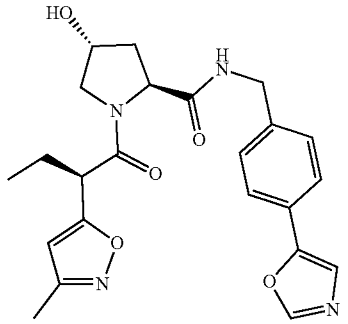
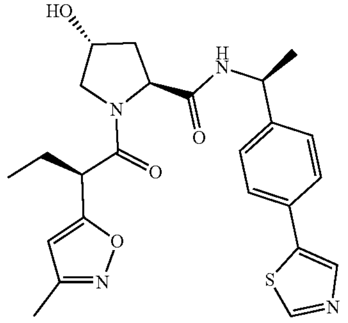
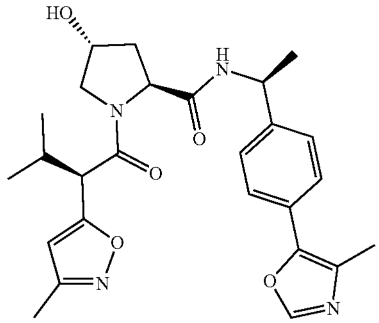
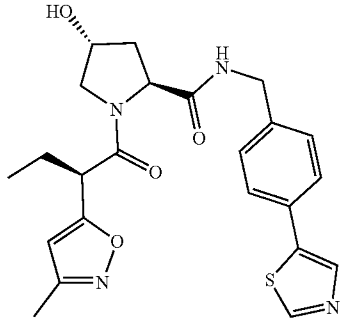
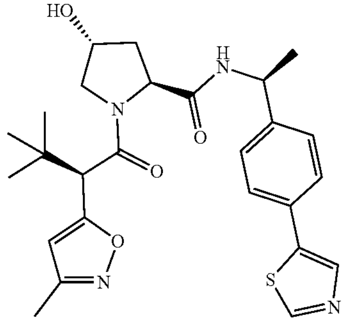
-continued
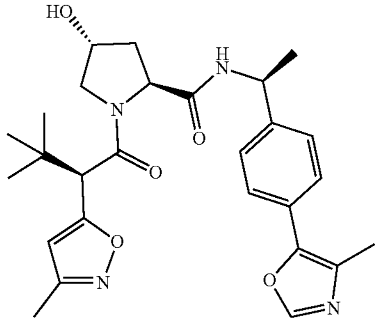
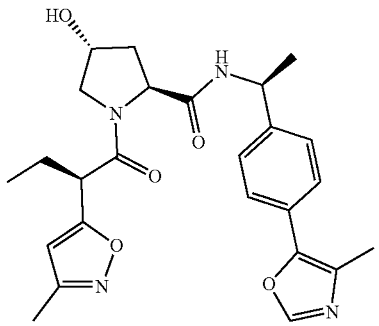
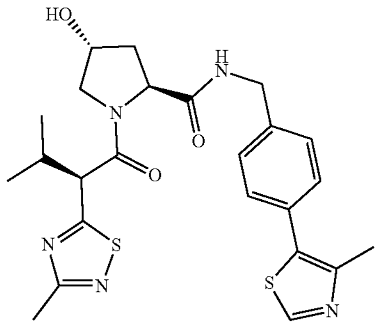
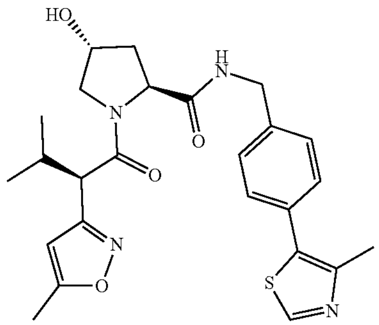
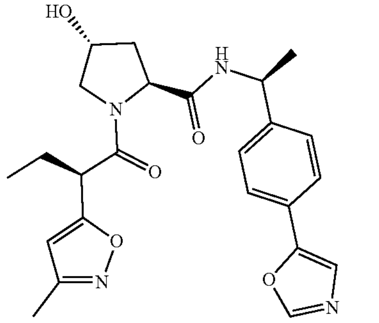

-continued
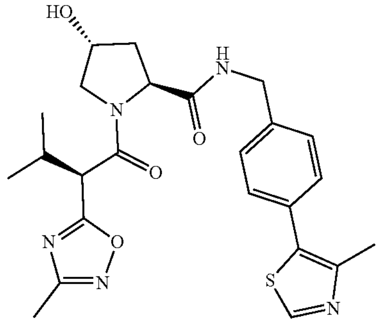
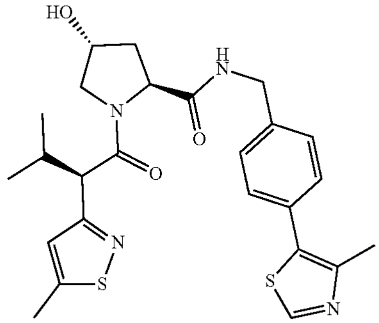
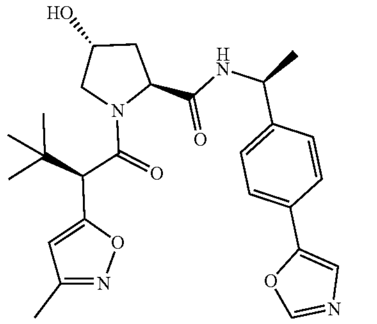
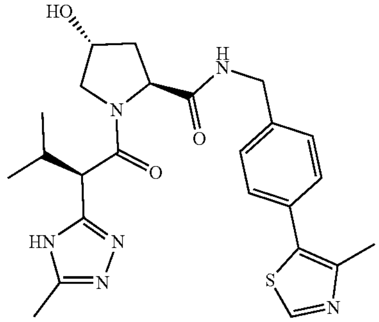
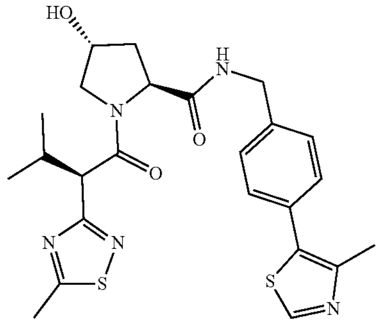
-continued
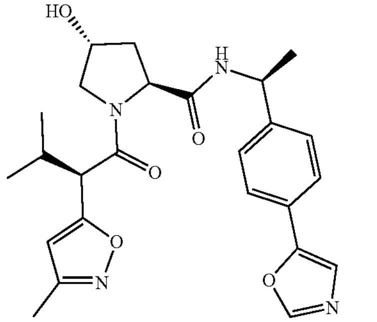
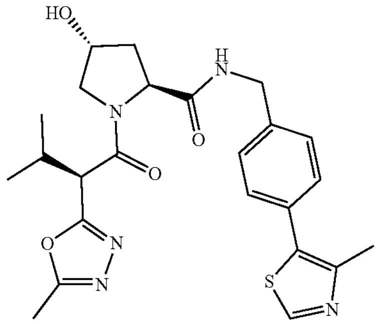
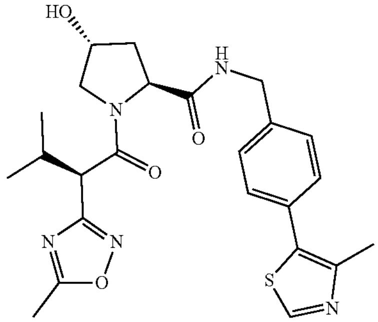
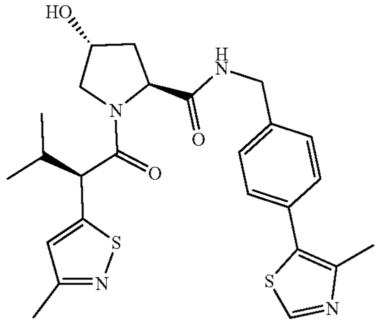
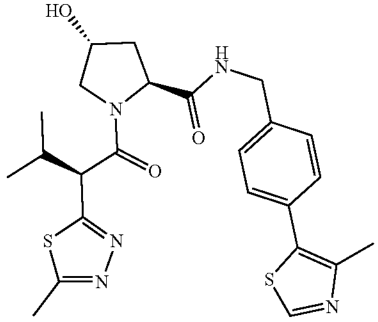

-continued
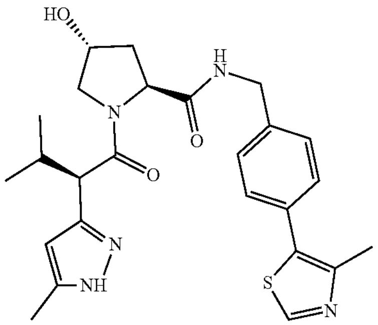
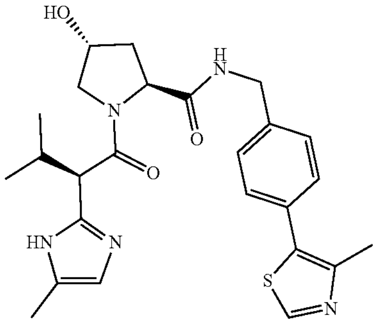
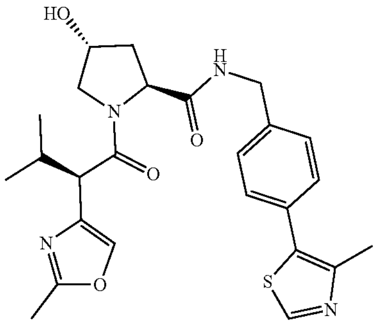
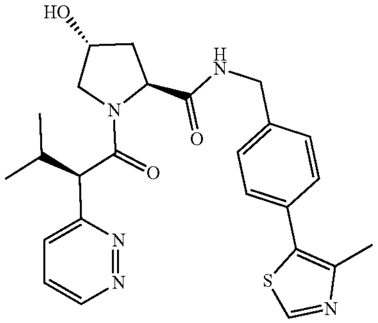
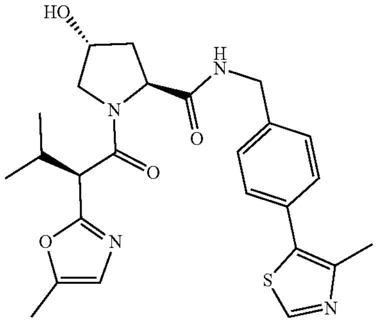
-continued
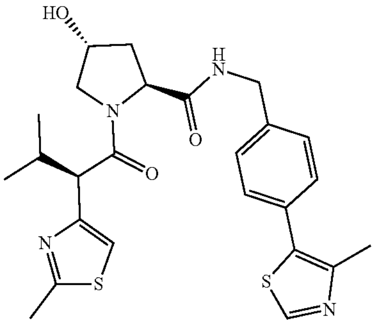
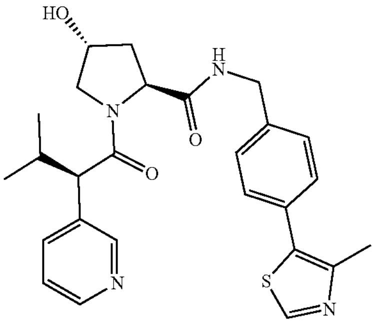
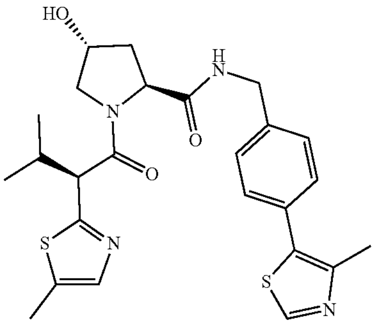
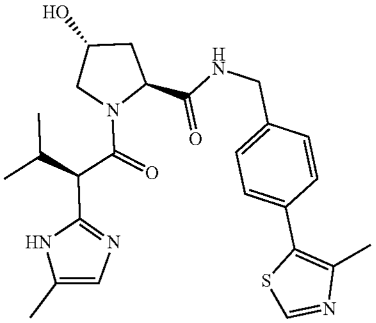
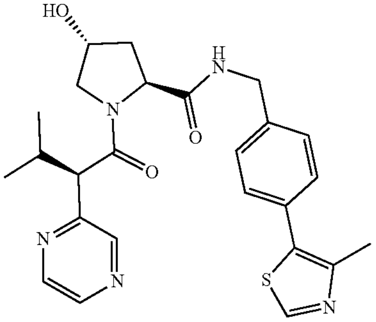

-continued
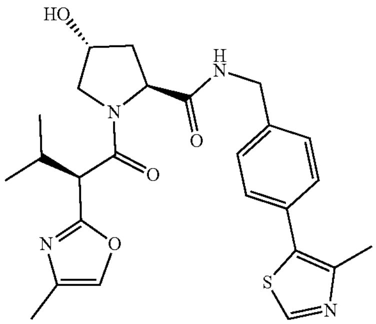
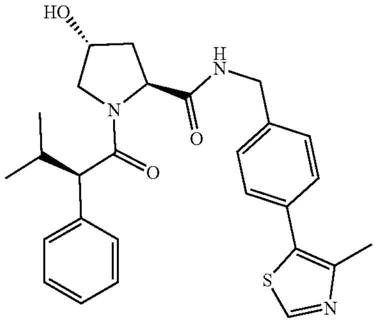
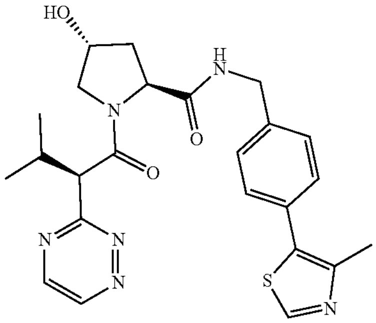
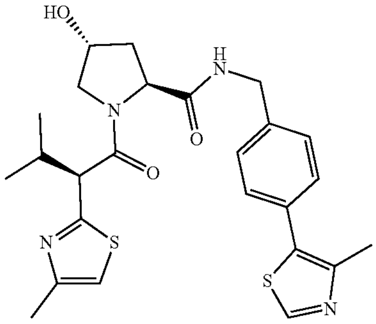
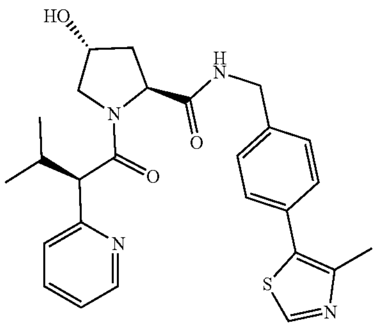
-continued
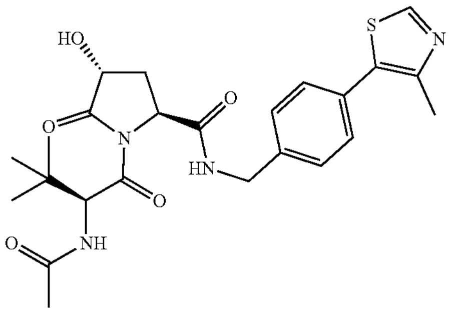
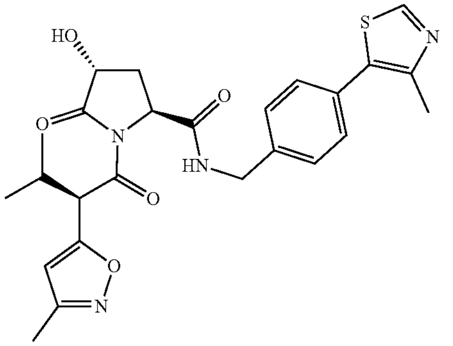
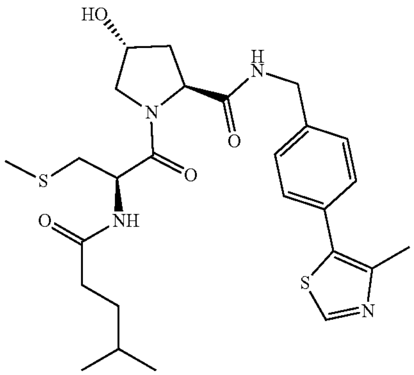
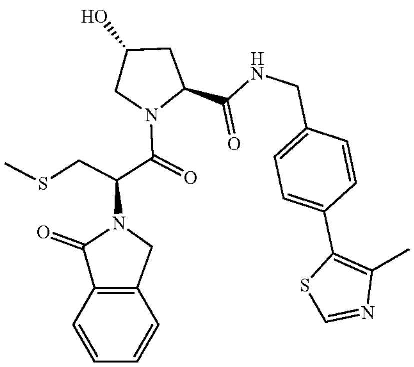

-continued
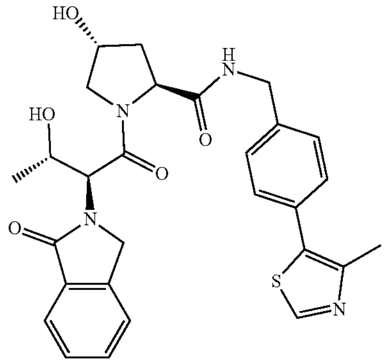
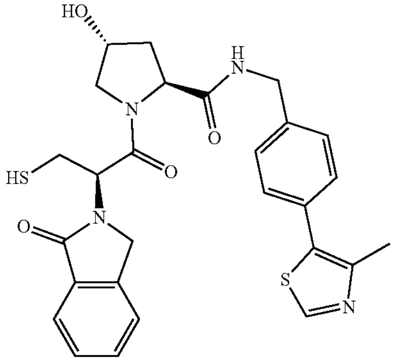
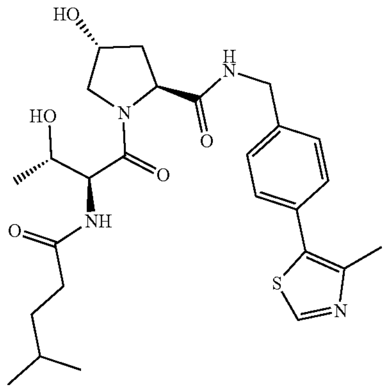
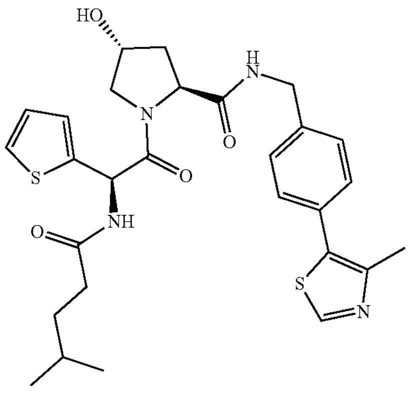
-continued
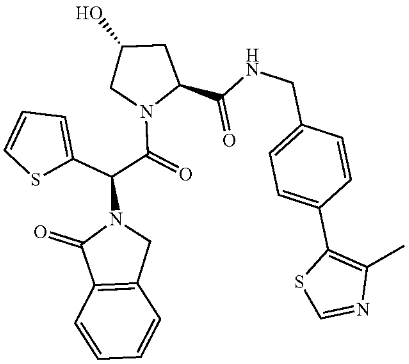
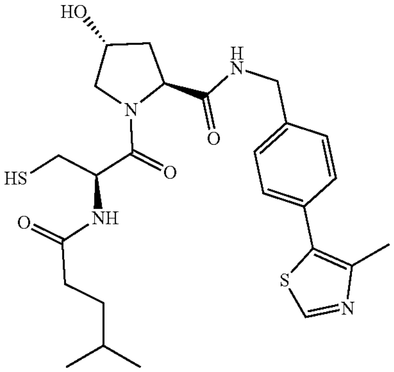
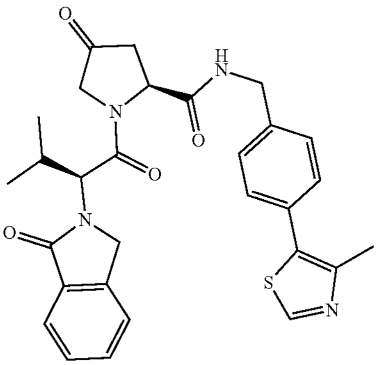
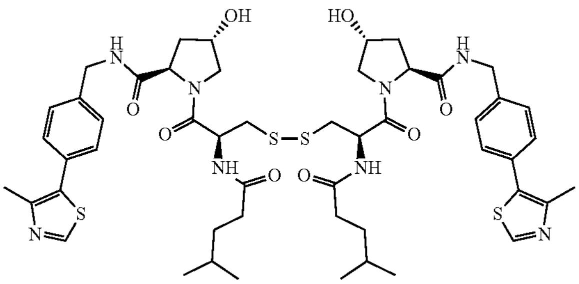

-continued
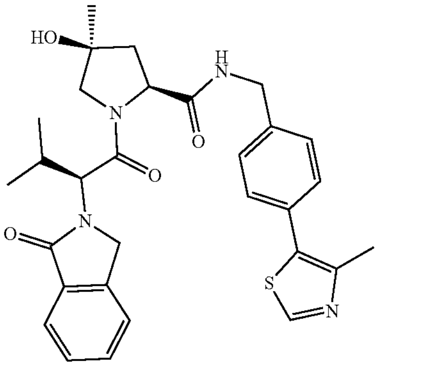
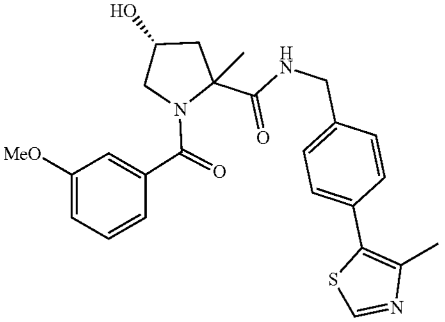
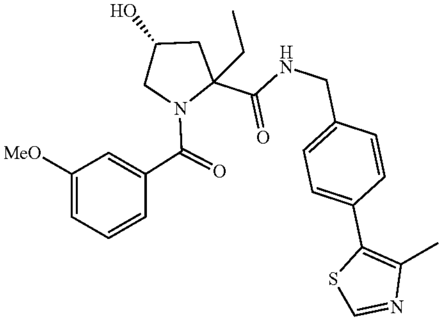
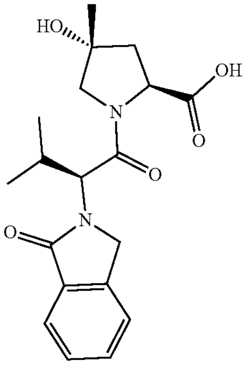
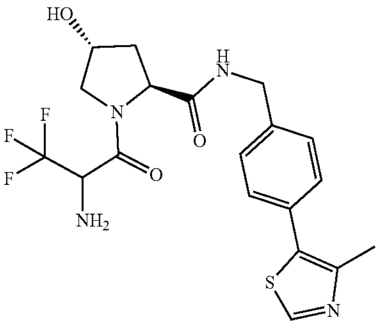
-continued
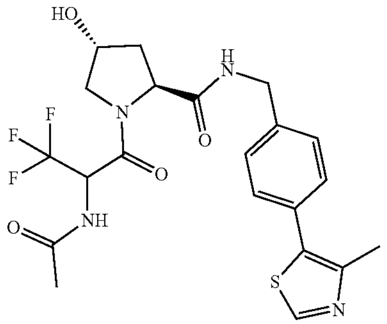
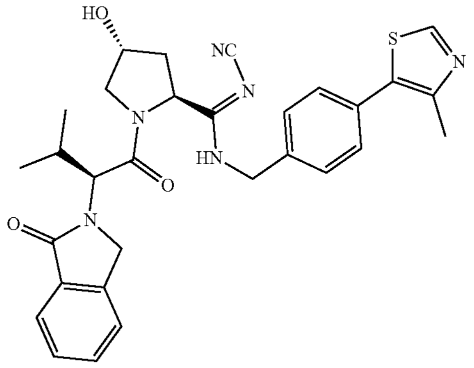
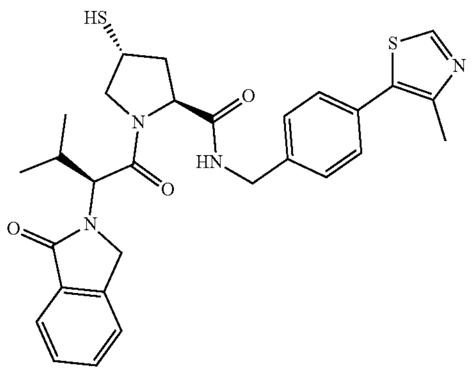
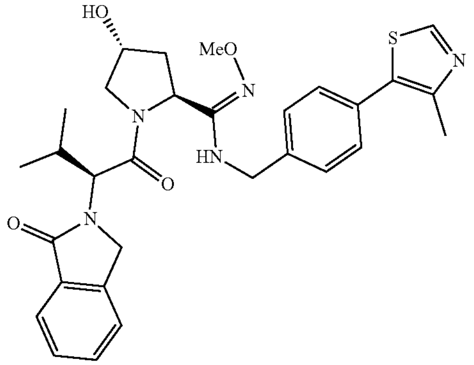

-continued
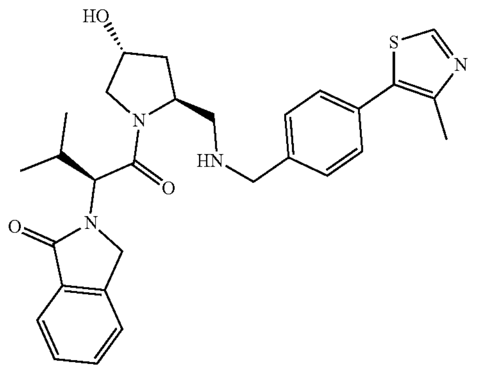
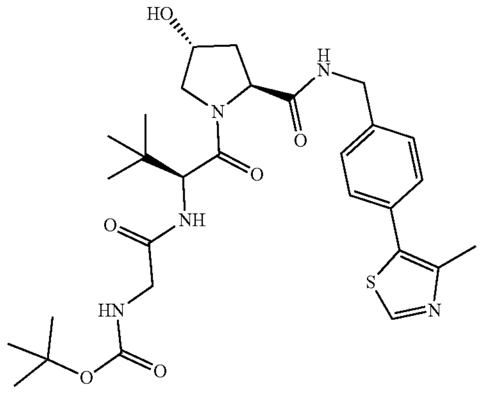
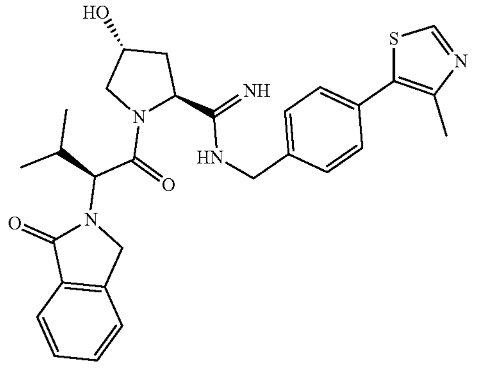
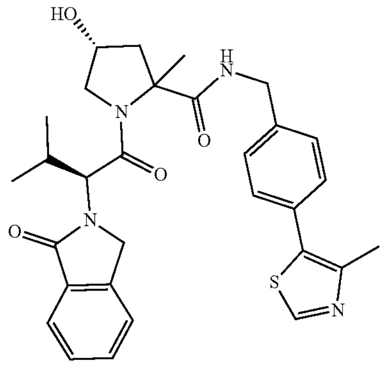
-continued
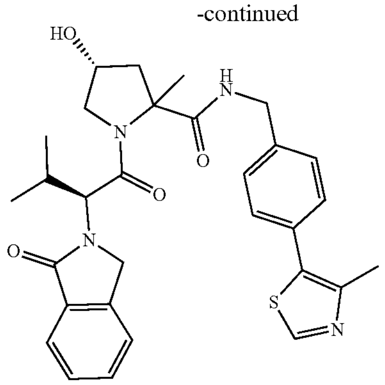
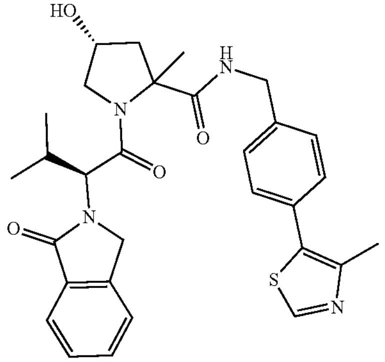
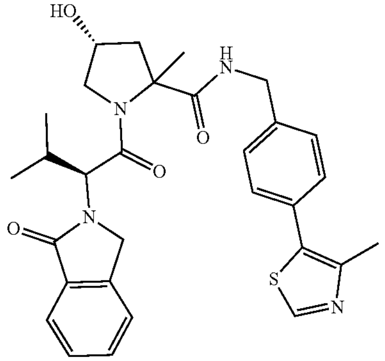
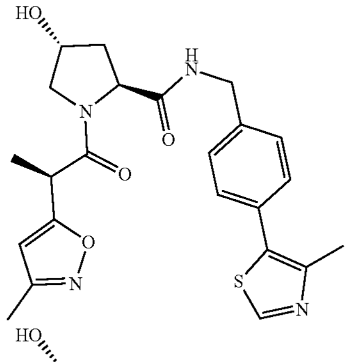
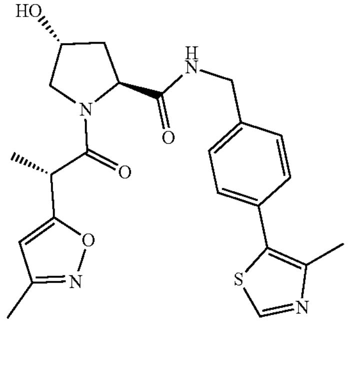

-continued
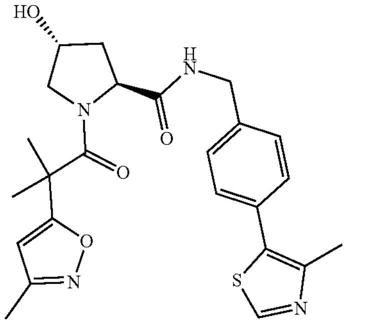
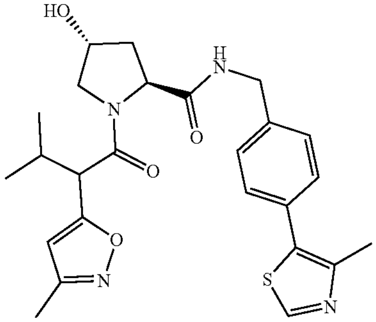
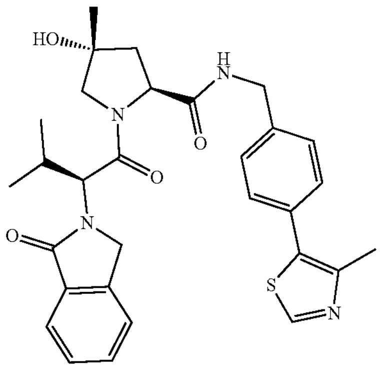
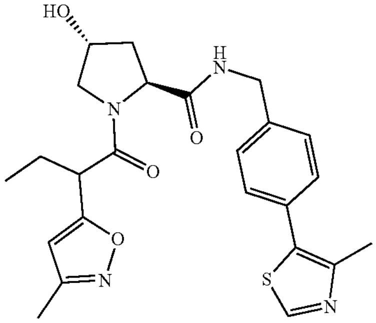
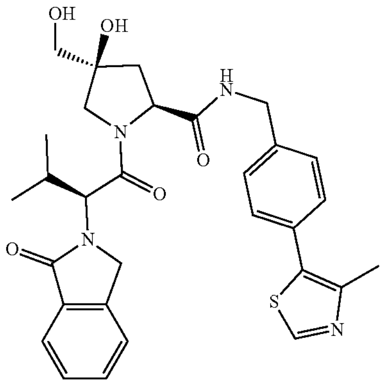
-continued
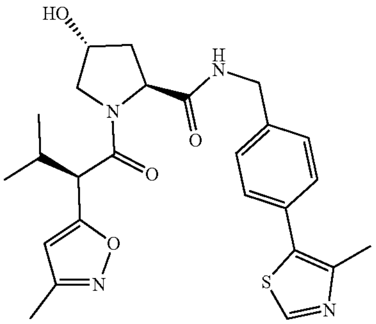
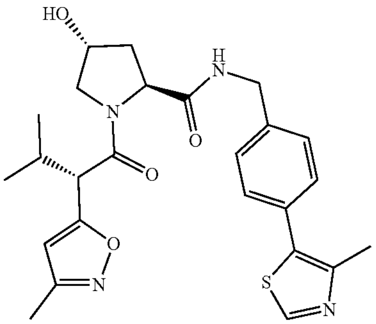
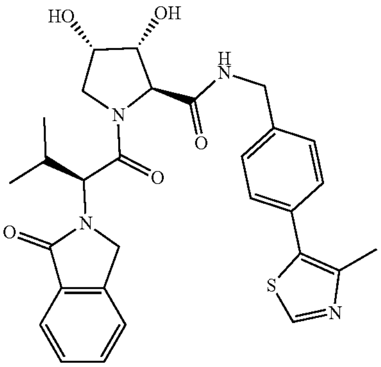
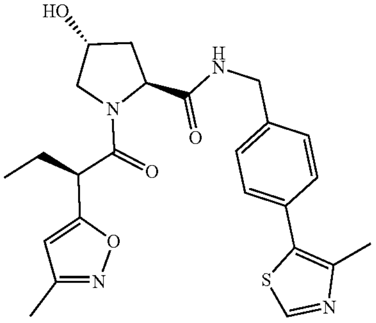
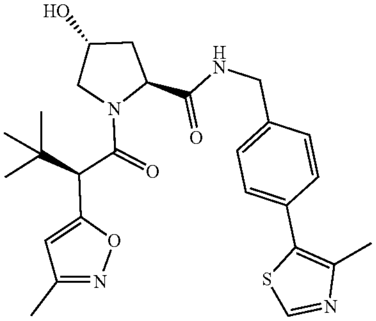

-continued
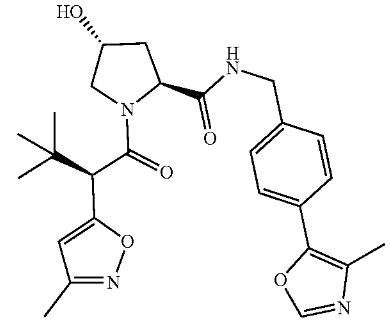
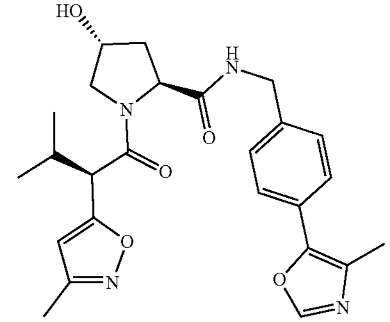
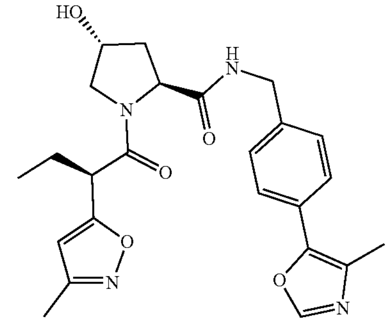
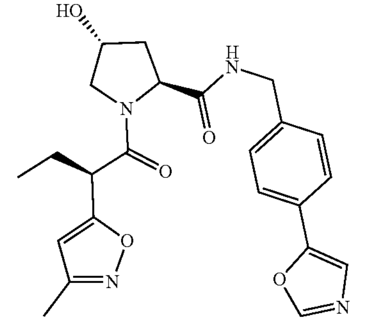
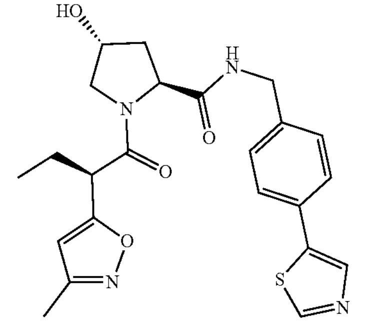
-continued
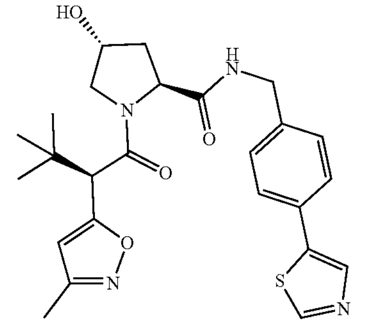
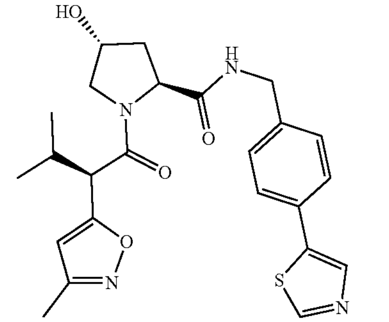
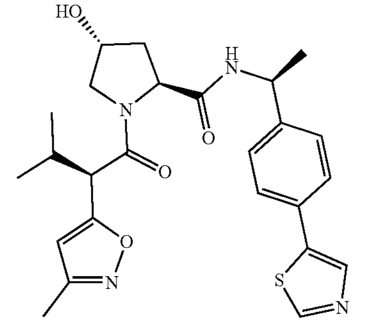
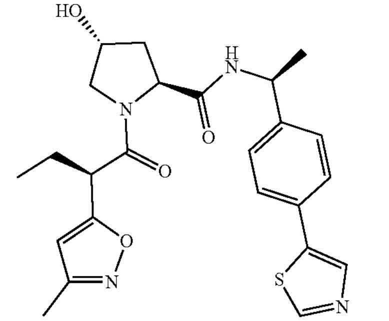
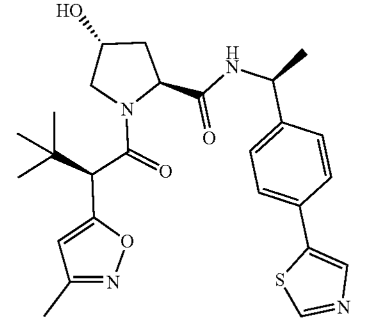

-continued
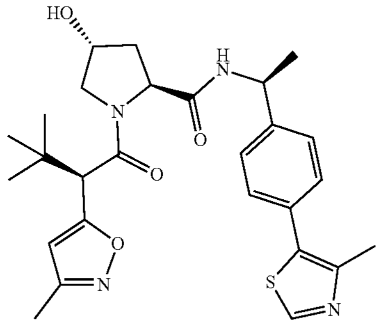
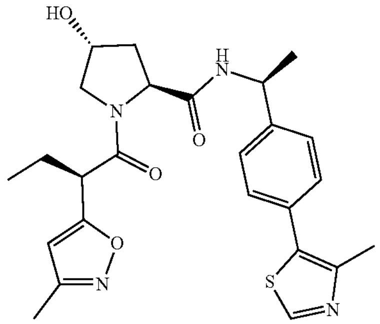
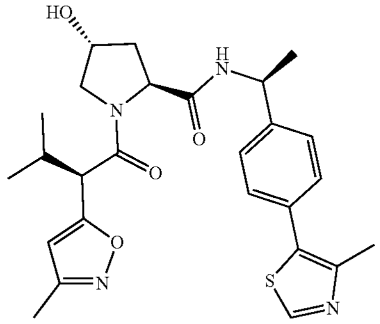
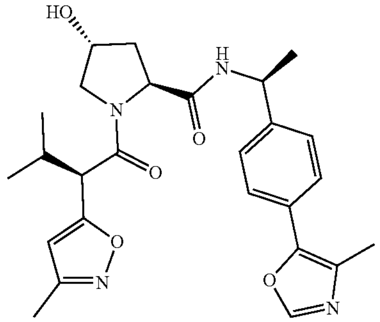
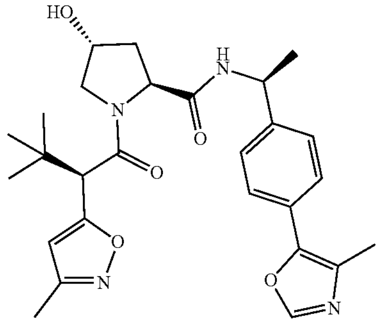
-continued
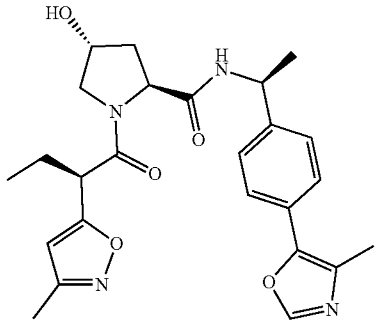
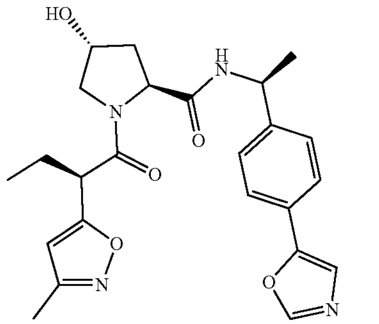
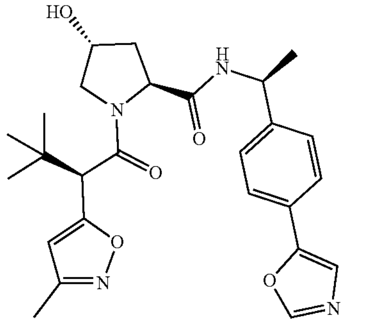
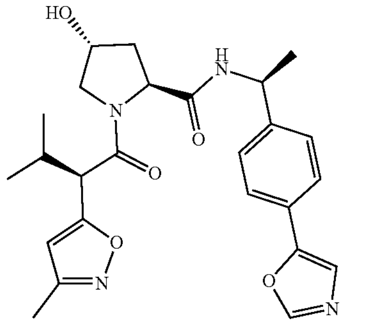
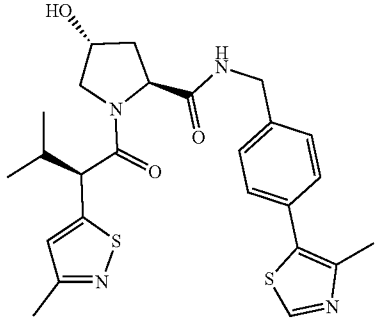

-continued
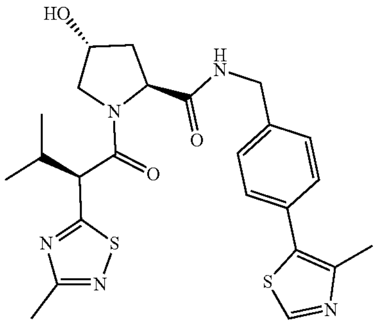
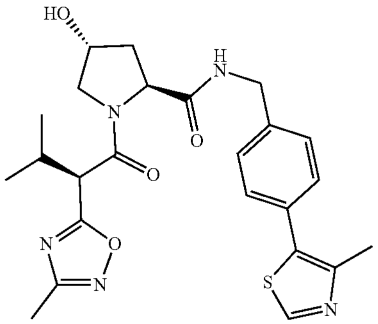
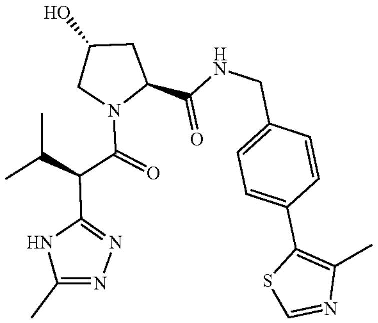
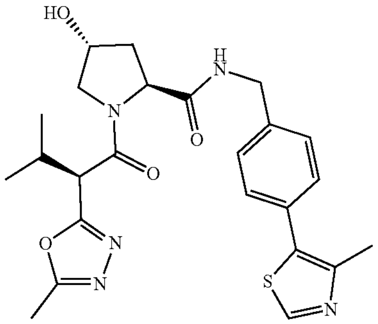
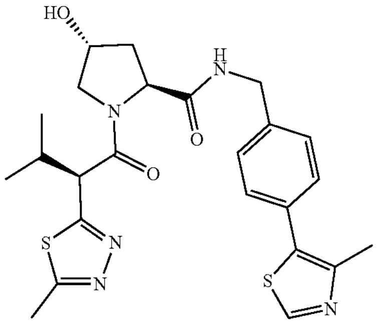
-continued
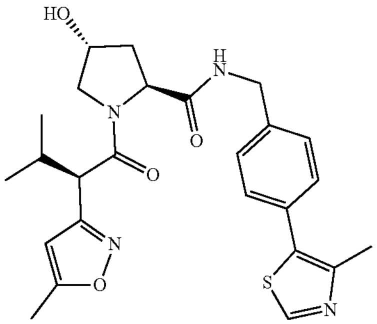
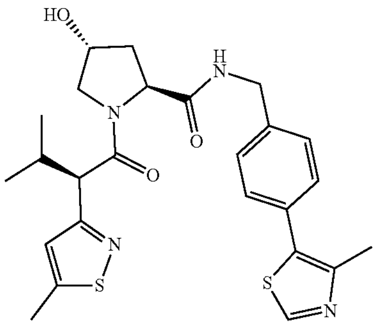
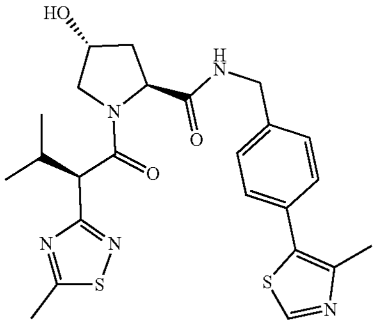
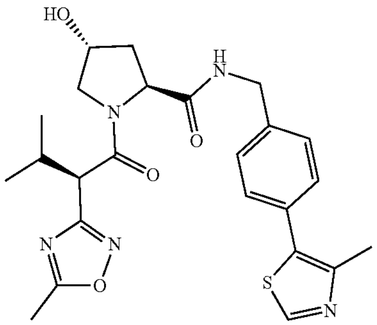
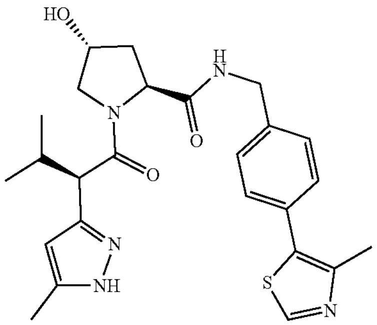

-continued
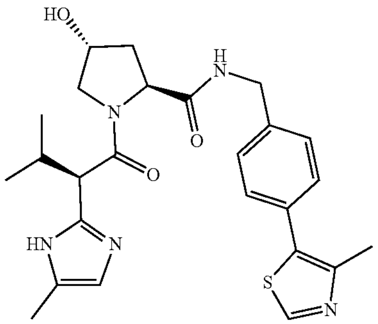
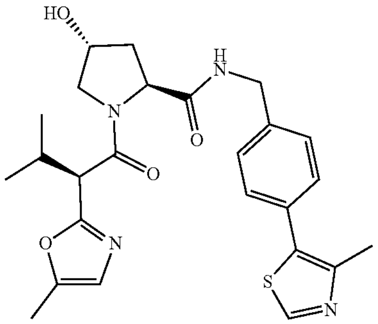
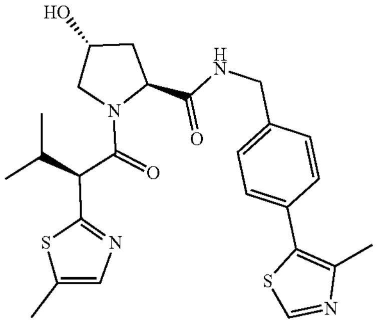
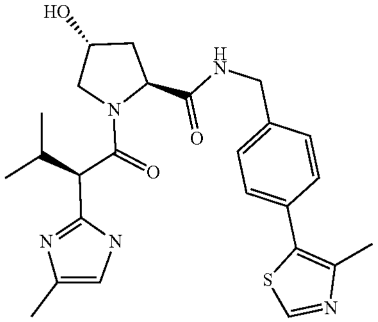
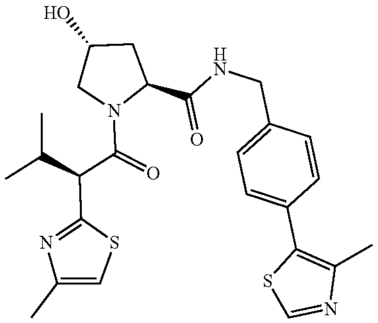
-continued
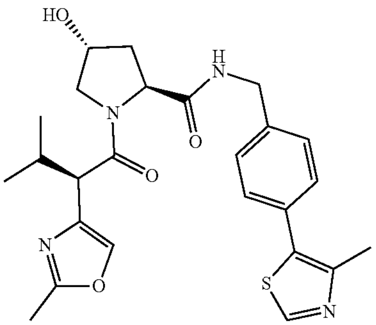
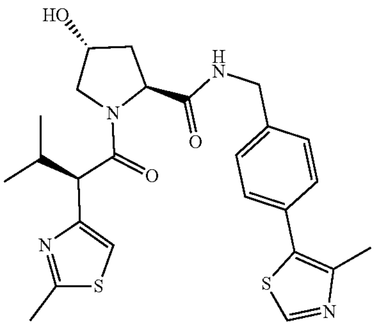
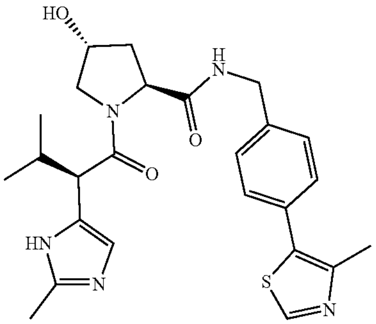
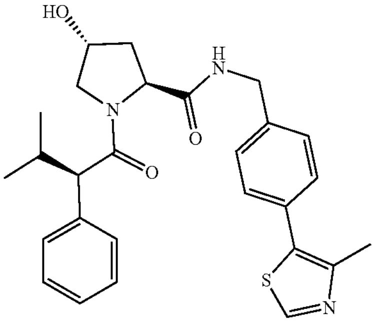
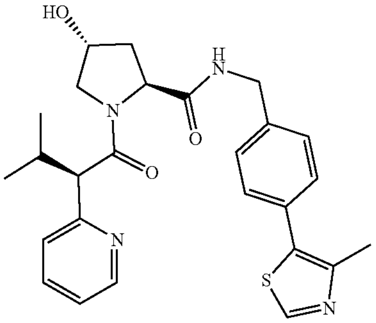

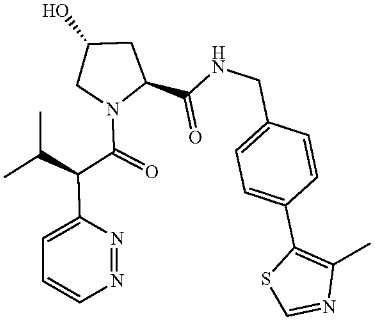
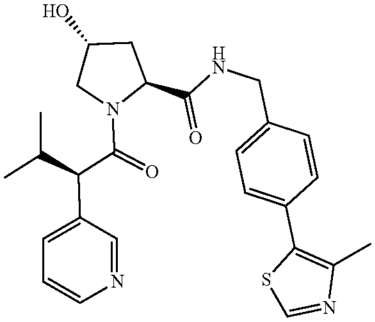
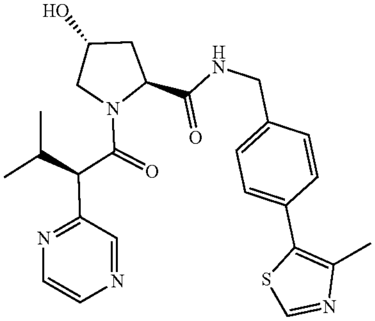
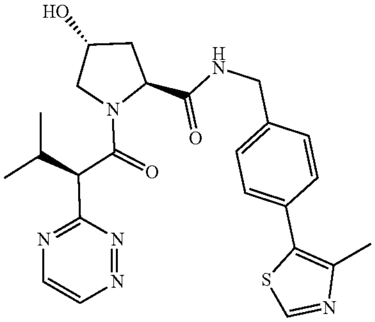
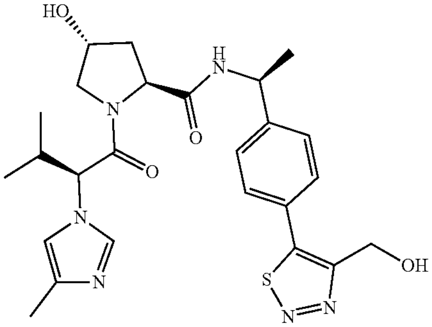
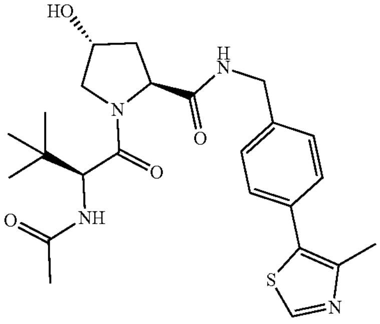
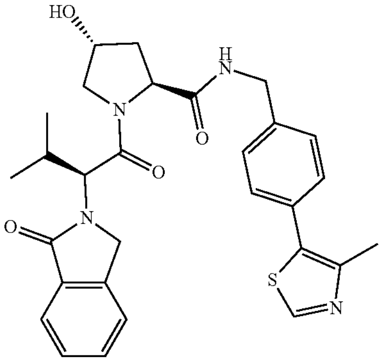
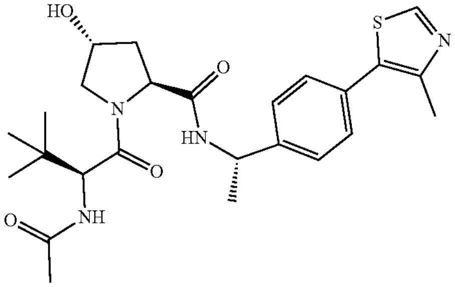
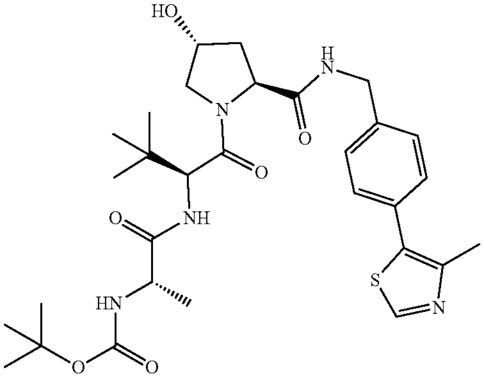
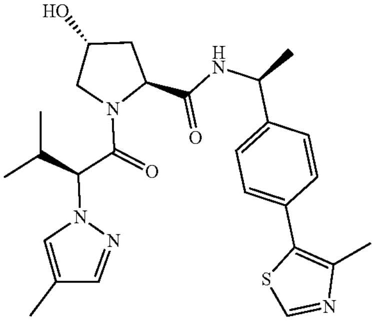

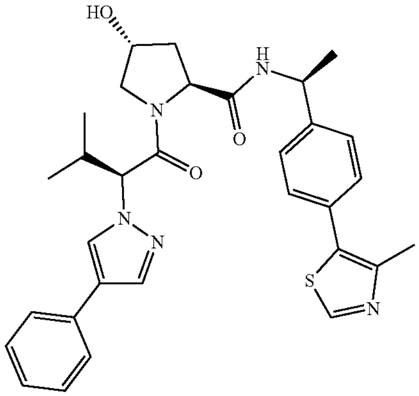
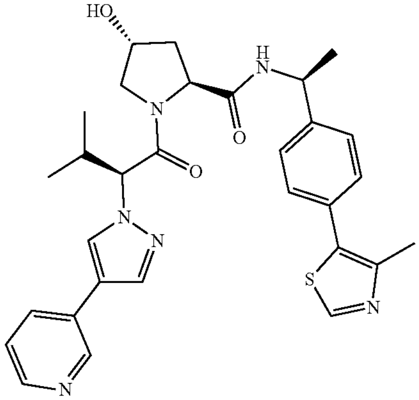
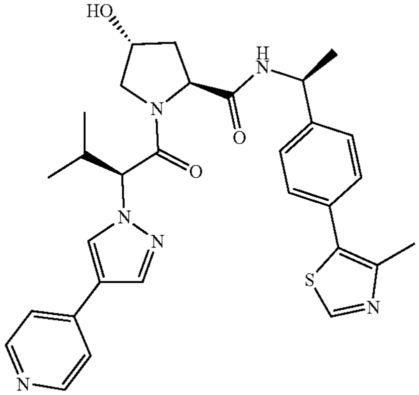
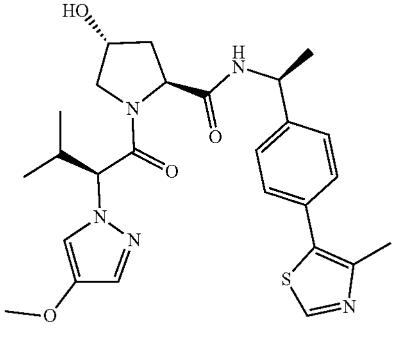
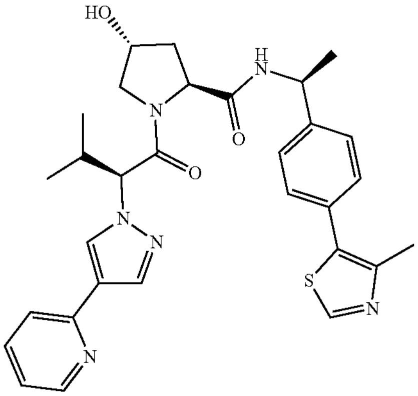
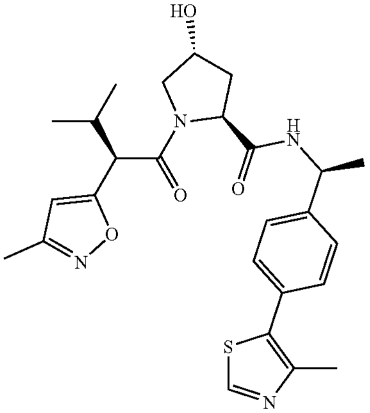
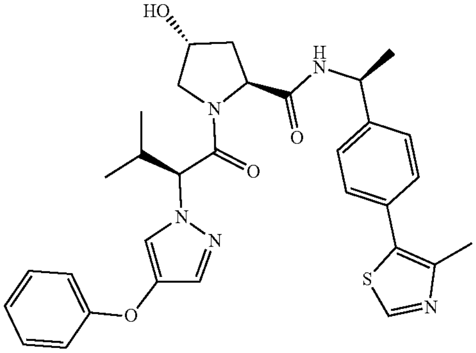
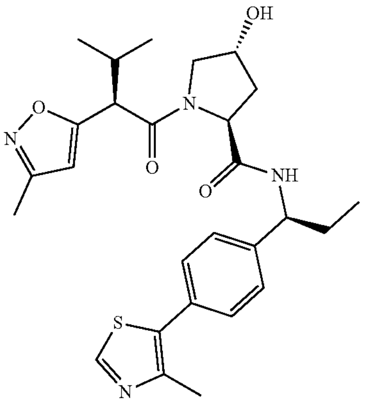
and -continued

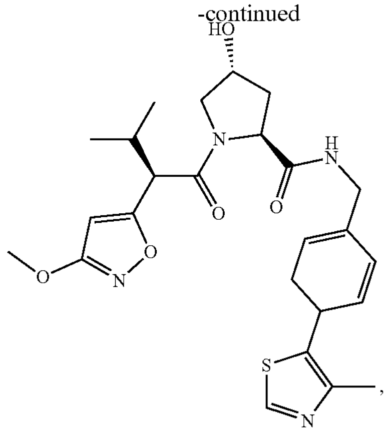

wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A^{L}_{1} \ldots (A^{L})_{q}-$ or $-(A^{L})_{q}-$), wherein $A_1$ is a group coupled to PTM, and $(A^{L})_{q}$ is a group coupled to ULM.

In any aspect or embodiment described herein, the linker group L is a bond or a chemical linker group represented by the formula $-(A^{L})_{q}-$, wherein A is a chemical moiety and q is an integer from 1-100, and wherein L is covalently bound to the PTM and the ULM, and provides for sufficient binding of the PTM to the protein target and the ULM to an E3 ubiquitin ligase to result in target protein ubiquitination.

In certain embodiments, the linker group L is $-(A^{L})_{q}-$, wherein:

- $(A^{L})_{q}$ is a group which is connected to at least one of a ULM moiety, a PTM moiety, or a combination thereof;
- q of the linker is an integer greater than or equal to 1;
- each $A^{L}$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and
- $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC{-}C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)\ SO_2N(C_{1-8}alkyl)_2$, $NH\ SO_2NH(C_{1-8}alkyl)$, $NH\ SO_2N(C_{1-8}alkyl)_2$, $NH\ SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^{L})_{q}$ is a group which is connected to ULM, and $A_{L1}$ and $(A^{L})_{q}$ are connected via structural units of the linker (L).

In certain embodiments, e.g., where q of the linker is 2, $(A^{L})_{q}$ is a group which is connected to $A^{L}_{1}$ and to a ULM.

In certain embodiments, e.g., where q of the linker is 1, the structure of the linker group L is $-A^{L}_{1}-$, and $A^{L}_{1}$ is a group which is connected to a ULM moiety and a PTM moiety.

In certain embodiments, the linker (L) comprises a group represented by a general structure selected from the group consisting of:

—$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —$NR(CH_2)_n$-(cycloalkyl)-(lower alkyl)-$OCH_2$—, —$NR(CH_2)_n$-(hetero cycloalkyl)-, —$NR(CH_2CH_2O)_n$-(lower alkyl)-O—$CH_2$—, —$NR(CH_2CH_2O)_n$-(hetero cycloalkyl)-O—$CH_2$—, —$NR(CH_2CH_2O)_n$-Aryl-O—$CH_2$—, —$NR(CH_2CH_2O)_n$-(hetero aryl)-O—$CH_2$—, —$NR(CH_2CH_2O)_n$-(cyclo alkyl)-O-(hetero aryl)-O—$CH_2$—, —$NR(CH_2CH_2O)_n$-(cyclo alkyl)-O-Aryl-O—$CH_2$—, —$NR(CH_2CH_2O)$-(lower alkyl)-NH-Aryl-O—$CH_2$—, —$NR(CH_2CH_2O)_n$-(lower alkyl)-O-Aryl-$CH_2$, —$NR(CH_2CH_2O)_n$-cycloalkyl-O-Aryl-, —$NR(CH_2CH_2O)_n$-cycloalkyl-O-(hetero aryl)l-, —NR(CH2CH2)n-(cycloalkyl)-O-(heterocycle)-$CH_2$, —NR(CH2CH2)n-(heterocycle)-(heterocycle)-$CH_2$, —N(R1R2)-(heterocycle)-CH2; where n of the linker can be 0 to 10;

R of the linker can be H, lower alkyl;

R1 and R2 of the linker can form a ring with the connecting N.

In certain embodiments, the linker (L) comprises a group represented by a general structure selected from the group consisting of:

—N(R)—$(CH2)_m$-$O(CH2)_n$-$O(CH2)_o$-$O(CH2)_p$-$O(CH2)_q$-$O(CH2)_r$-OCH2-,

O—$(CH2)_m$-$O(CH2)_n$-$O(CH2)_o$-$O(CH2)_p$-$O(CH2)_q$-$O(CH2)_r$-OCH2-,

O—$(CH2)_m$-$O(CH2)_n$-$O(CH2)_o$-$O(CH2)_p$-$O(CH2)_q$-$O(CH2)_r$-O—;

—N(R)—$(CH2)_m$-$O(CH2)_n$-$O(CH2)_o$-$O(CH2)_p$-$O(CH2)_q$-$O(CH2)_r$-O—;

$(CH2)_m$-$O(CH2)_n$-$O(CH2)_o$-$O(CH2)_p$-$O(CH2)_q$-$O(CH2)_r$-O—;

$(CH2)_m$-$O(CH2)_n$-$O(CH2)_o$-$O(CH2)_p$-$O(CH2)_q$-$O(CH2)_r$-OCH2-;

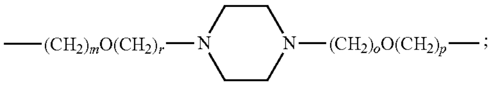
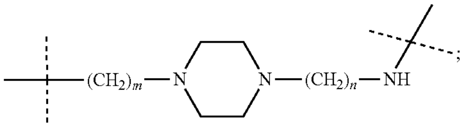
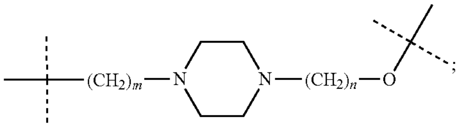
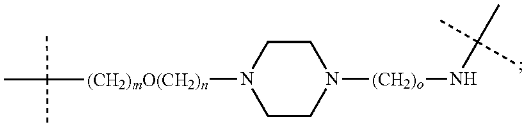
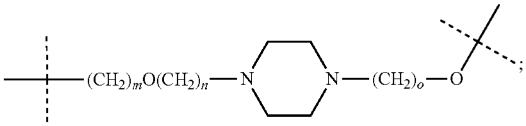
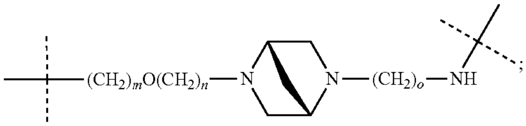
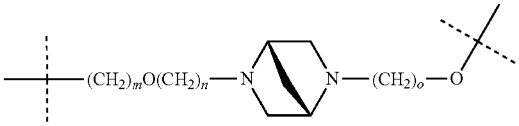
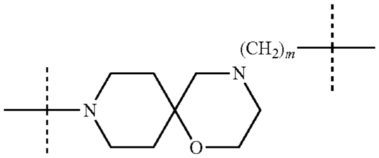
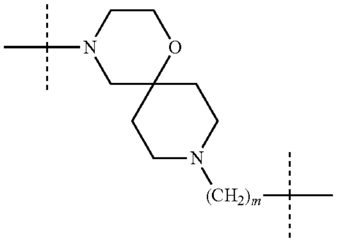
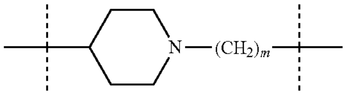
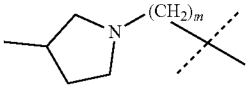
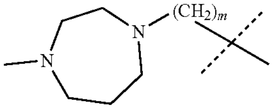
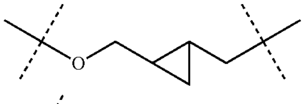
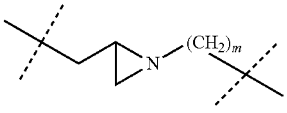
-continued
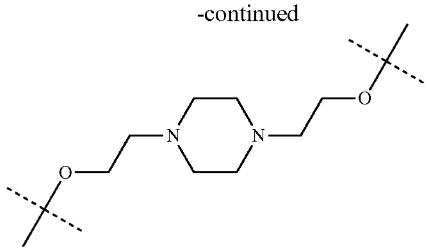
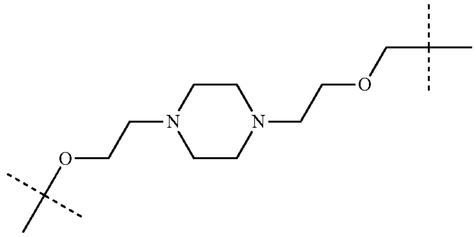
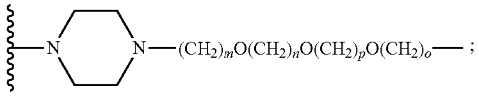
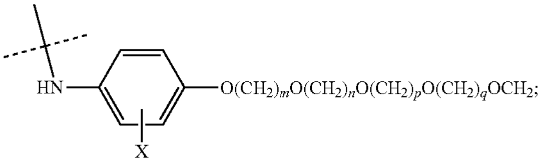
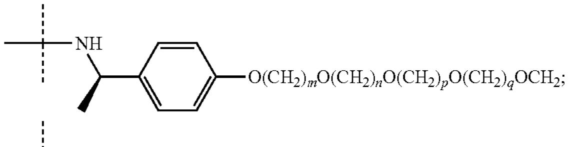
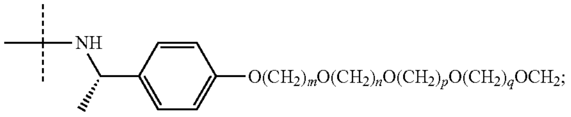
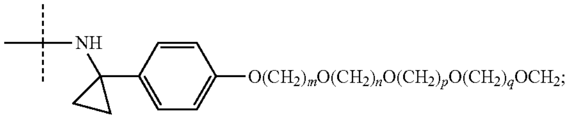
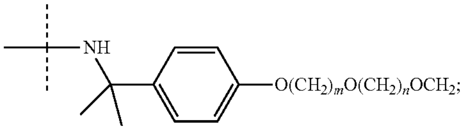
and
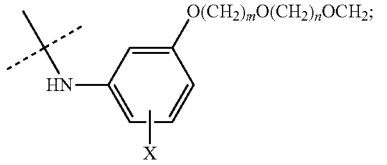
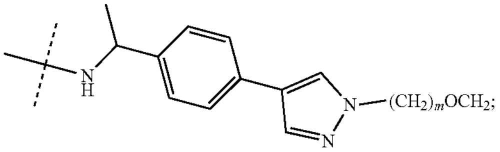
wherein
m, n, o, p, q, and r of the linker are independently 0, 1, 2, 3, 4, 5, 6;
when the number is zero, there is no N—O or O—O bond
R of the linker is H, methyl and ethyl;
X of the linker is H and F

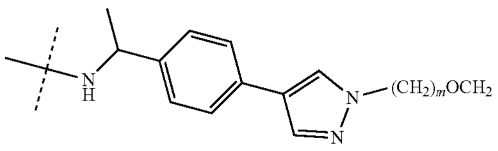
where m of the linker can be 2, 3, 4, 5
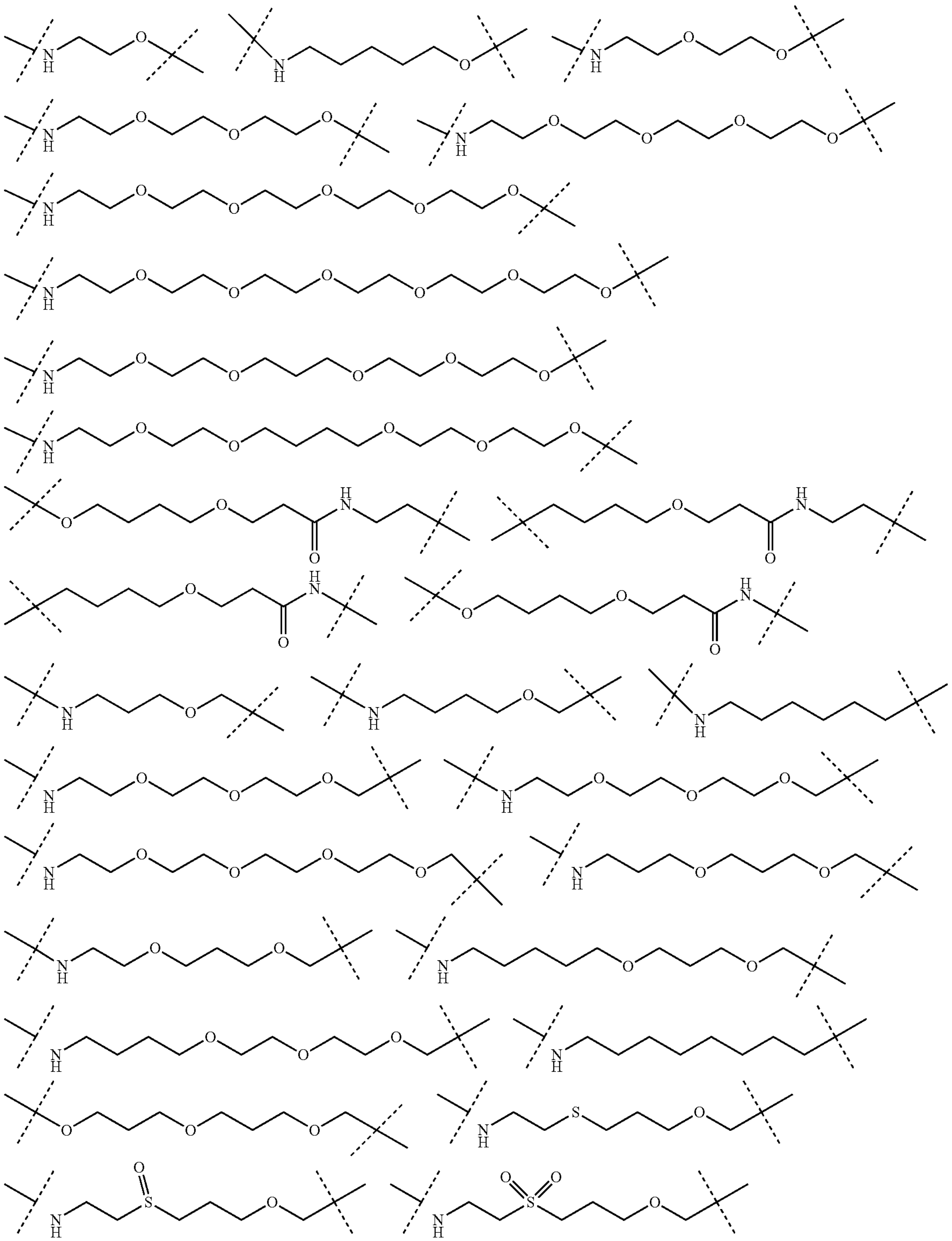

-continued
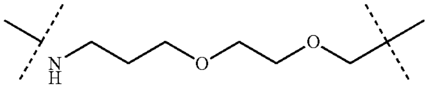
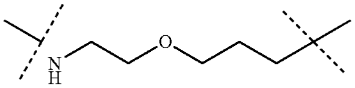
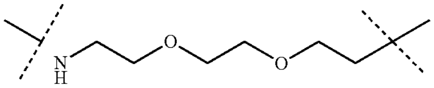
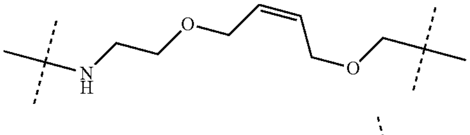
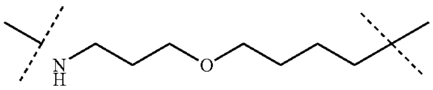
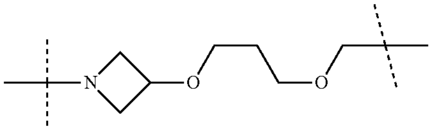
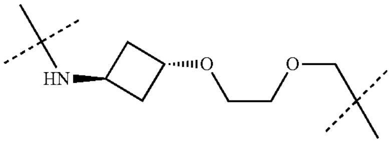
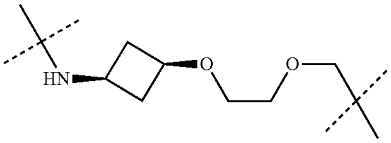
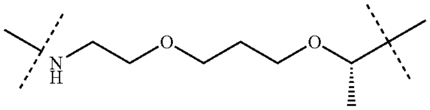
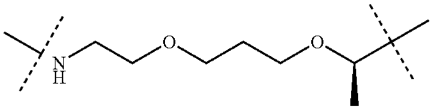
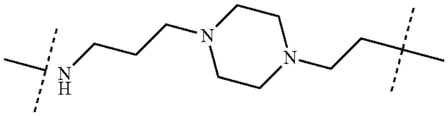
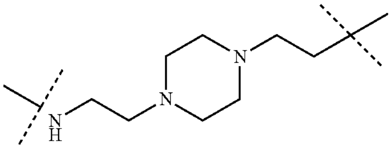
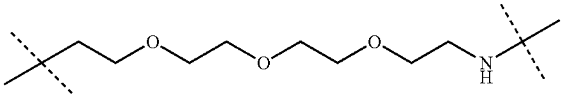
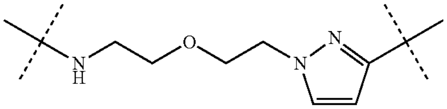
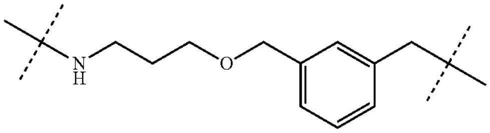
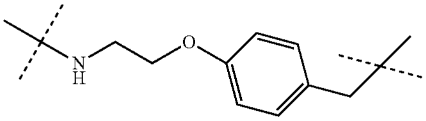
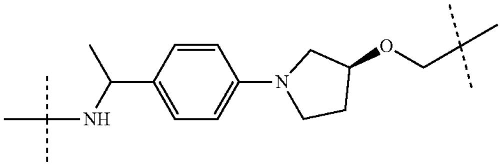
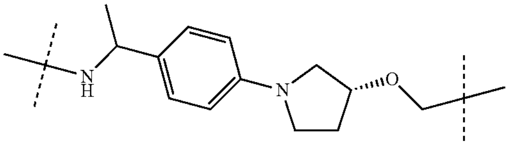
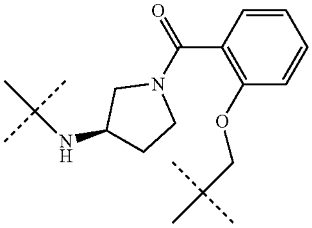
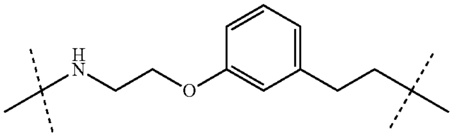
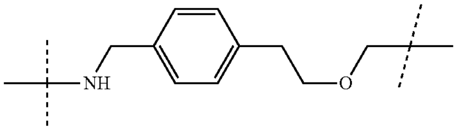
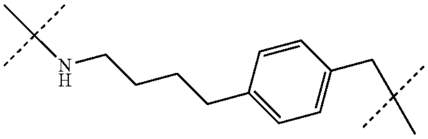
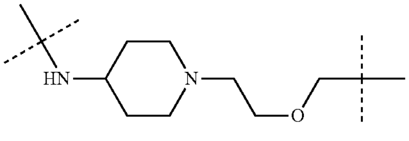
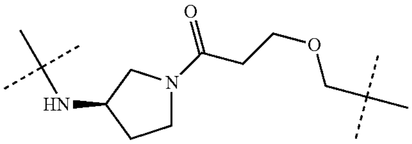

-continued
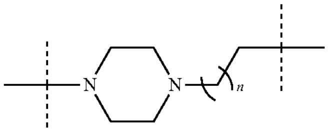 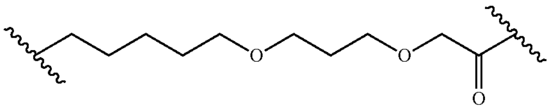;
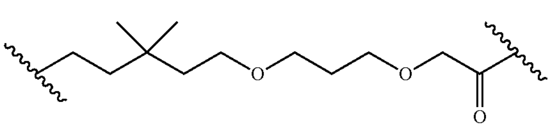; 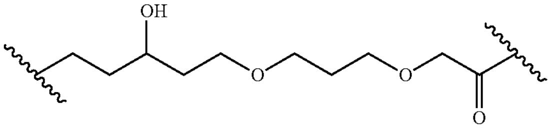;
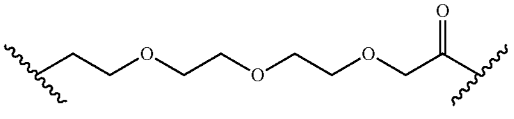; 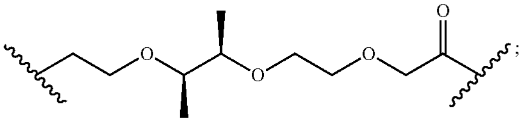;
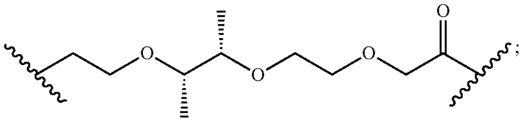; 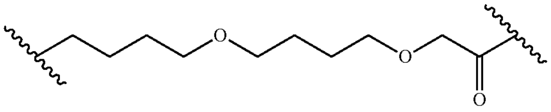;
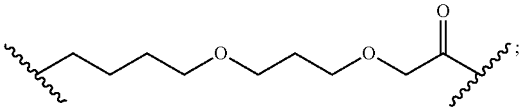; 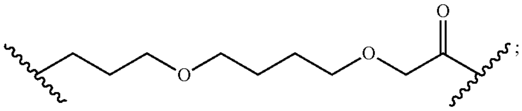;
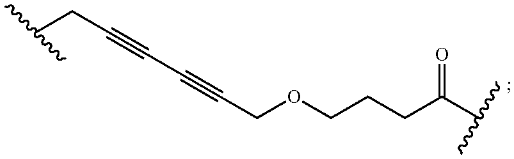; 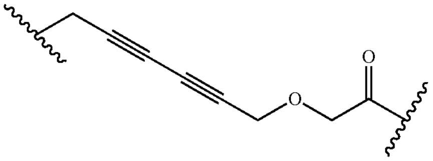;
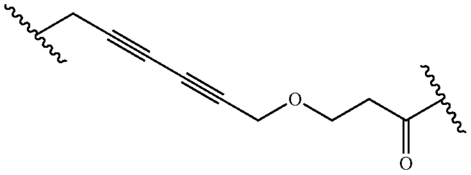; 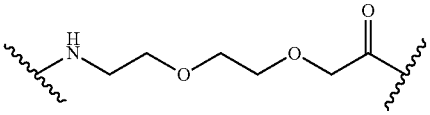;
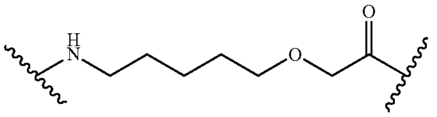; 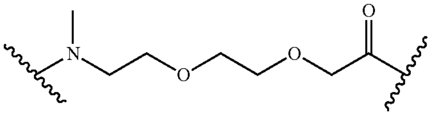;
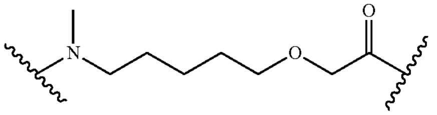; 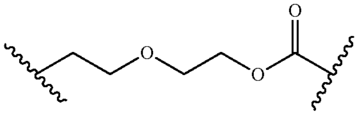;
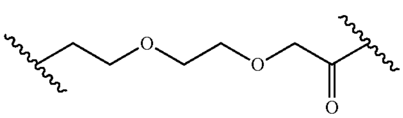; 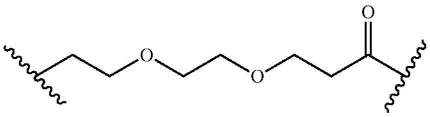;
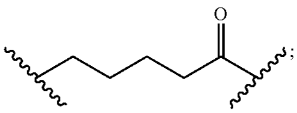; 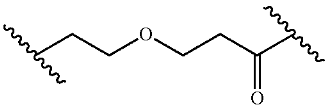; 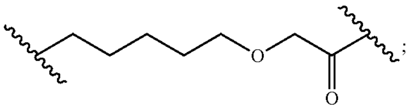;
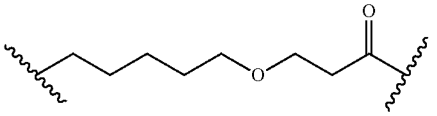; 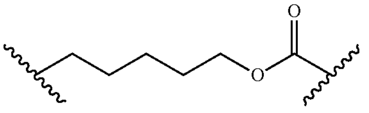;
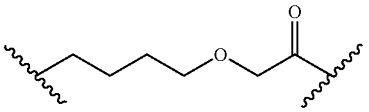; 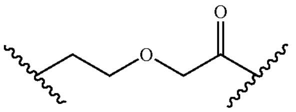;

-continued
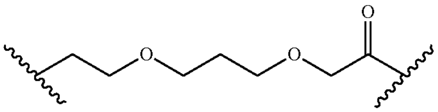
;
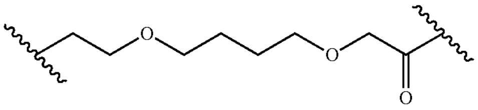
;
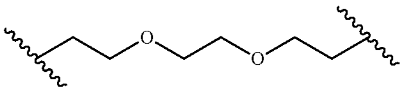
;
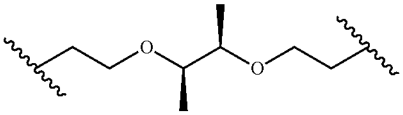
;
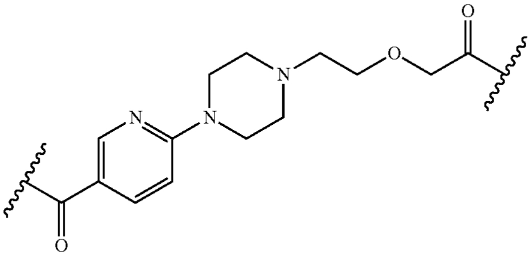
;
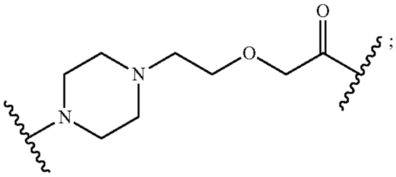
;
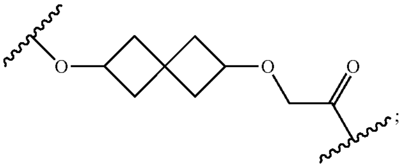
;
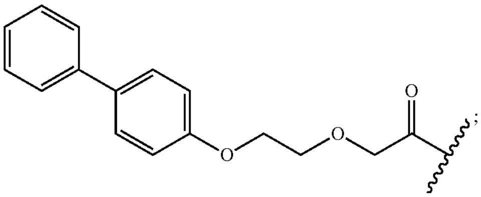
;
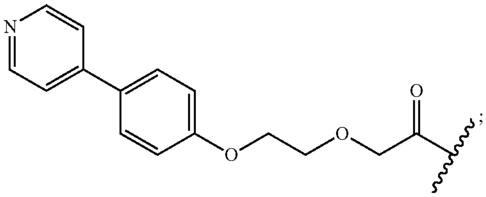
;
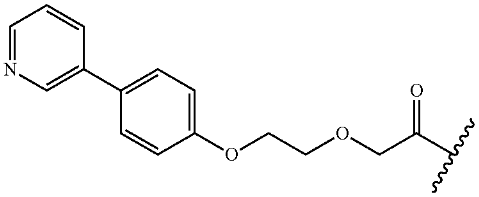
;
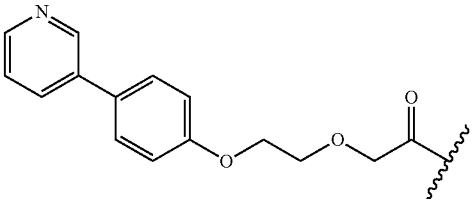
;
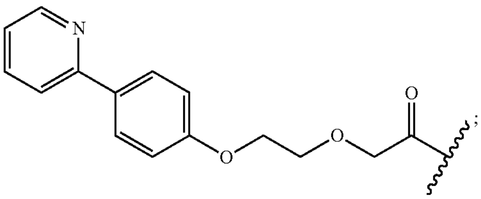
;
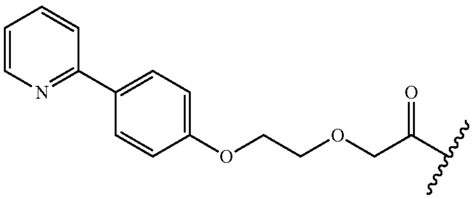
;
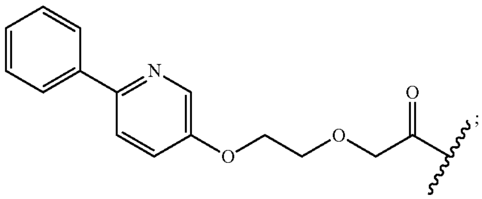
;
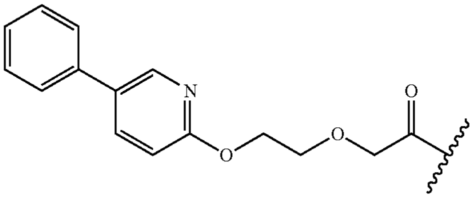
;
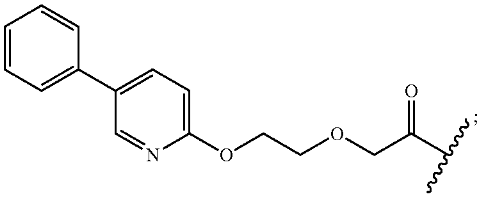
;
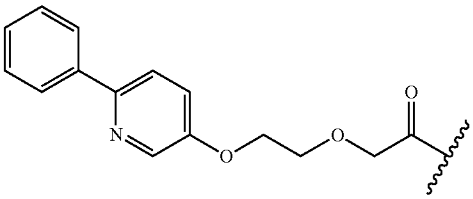
;
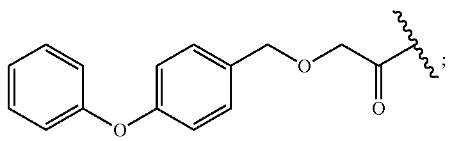
;

-continued
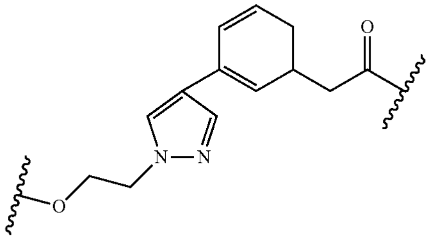
;
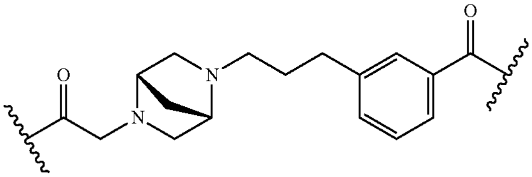
;
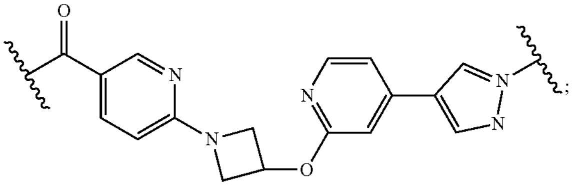
;
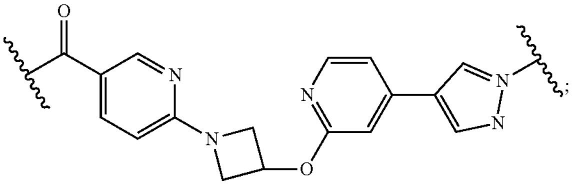
;
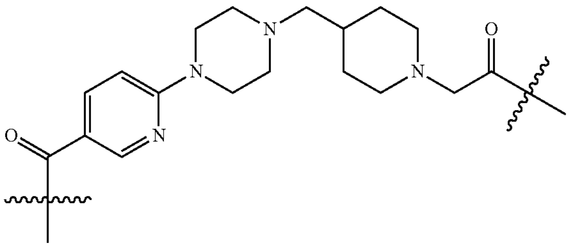
;
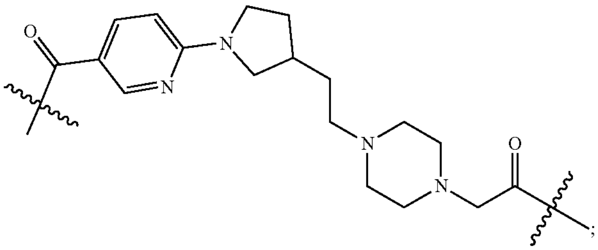
;
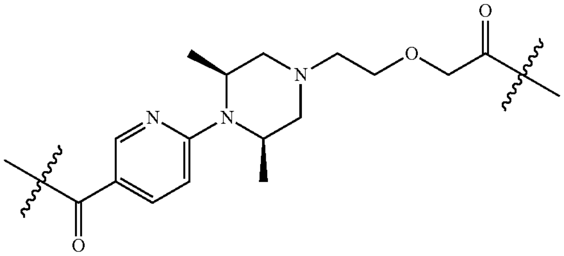
;
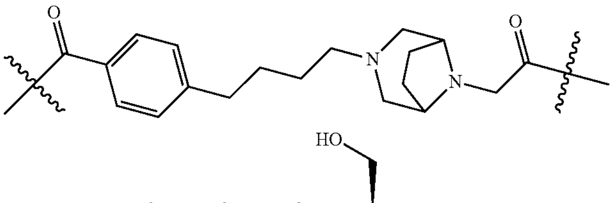
;
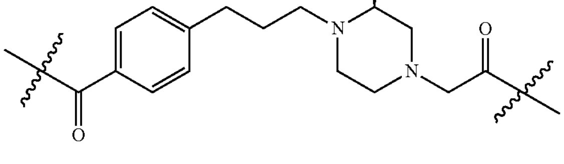
;

-continued
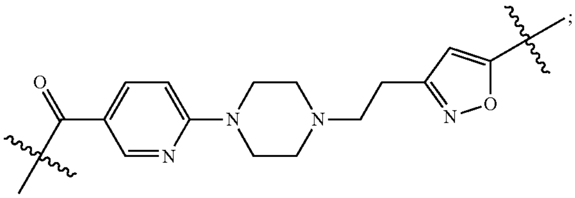
;
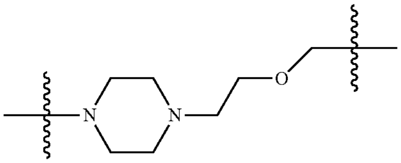
;
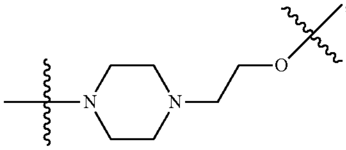
;
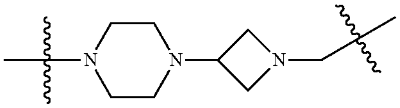
;
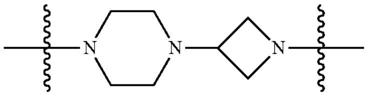
;
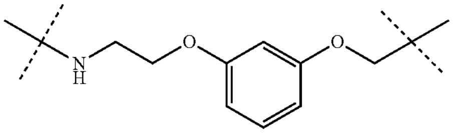
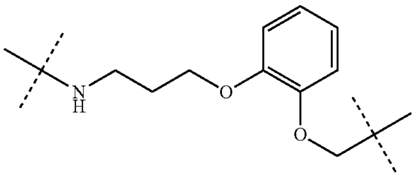
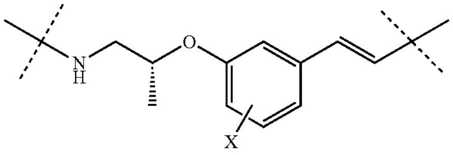
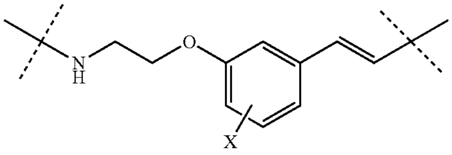
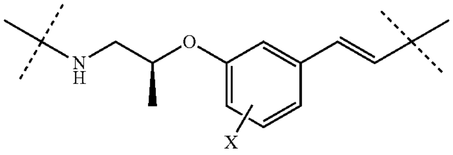
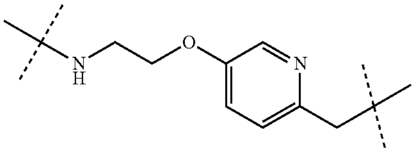
X = H, F
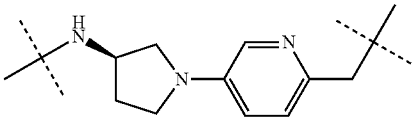
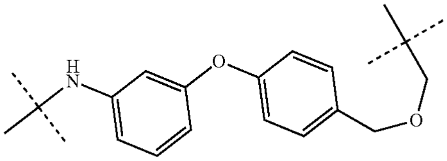
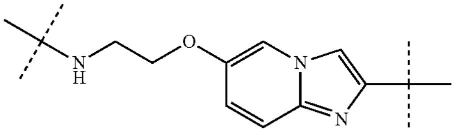
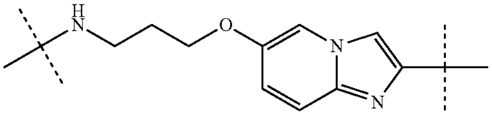
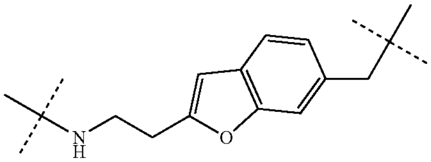
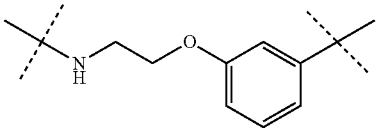
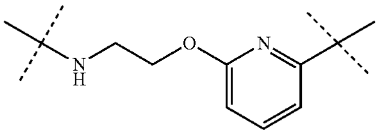
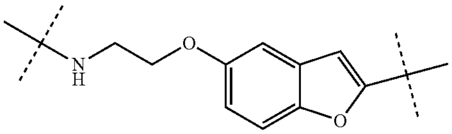
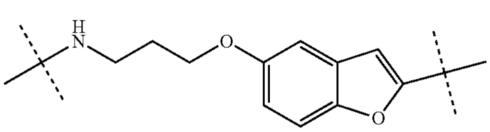
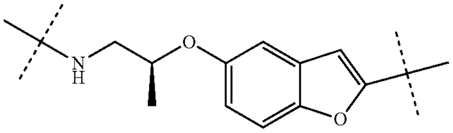

-continued
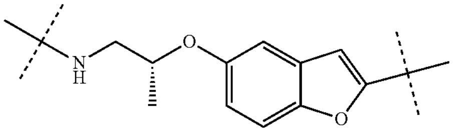
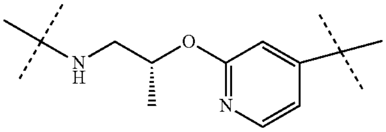
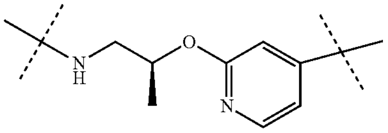
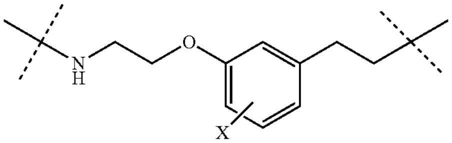
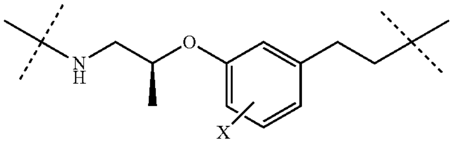
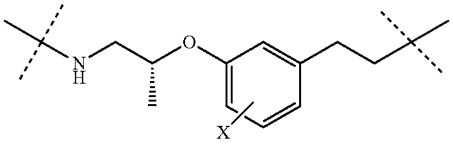
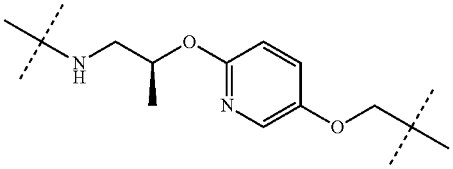
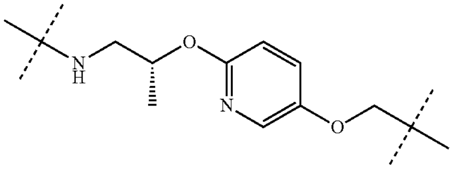
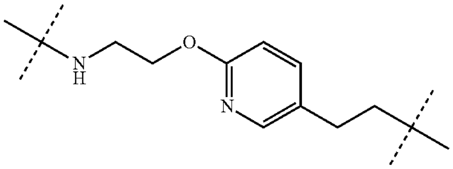
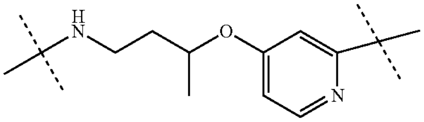
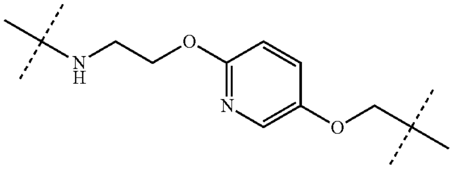
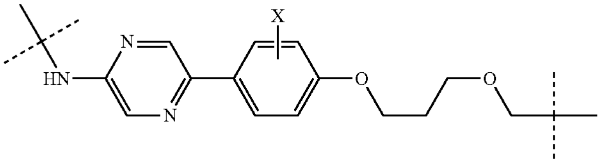
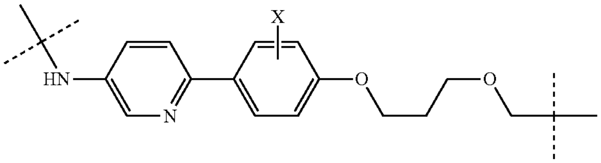
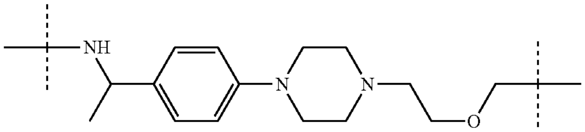
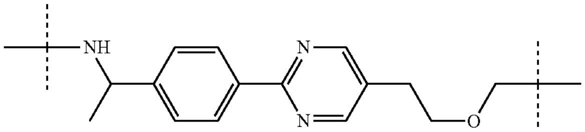
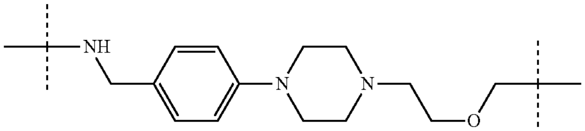
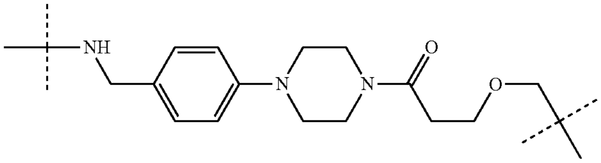

-continued
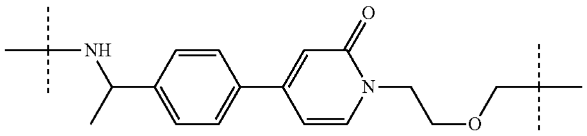
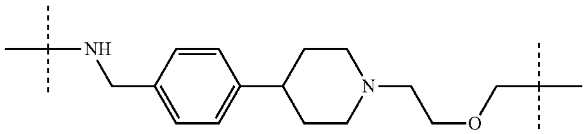
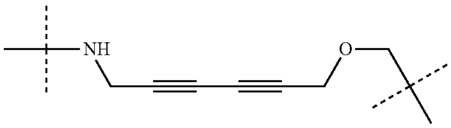
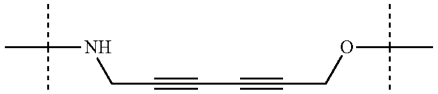
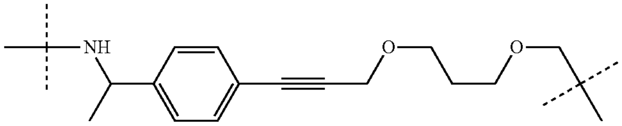
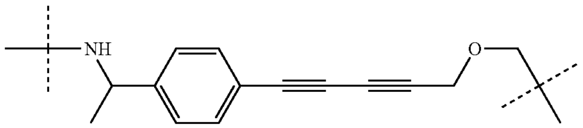
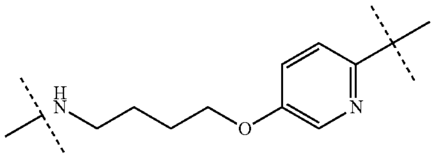
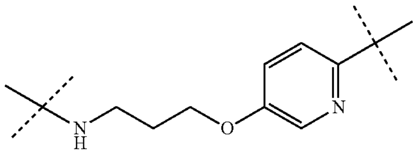
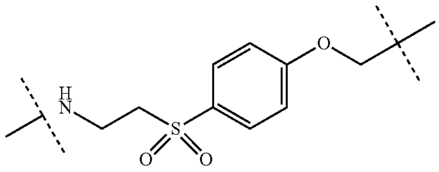
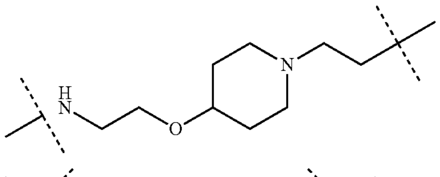
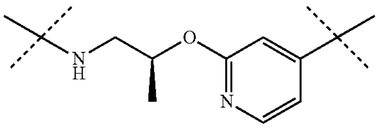
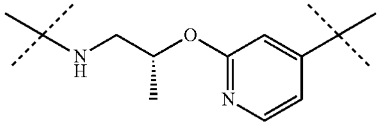
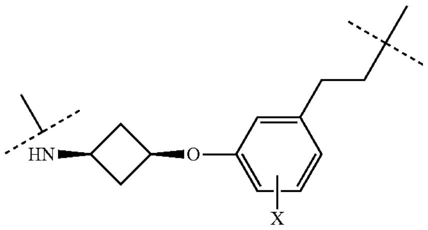
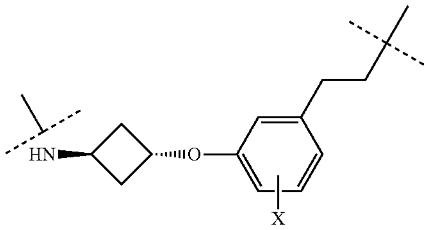
X = H, F
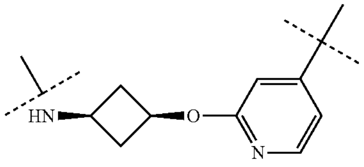
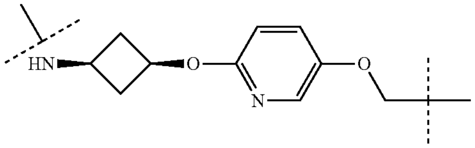
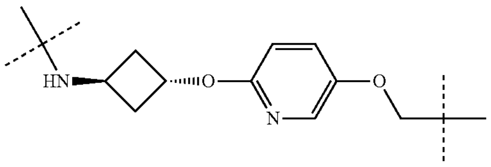
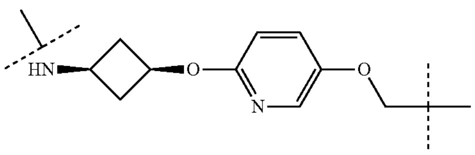

-continued
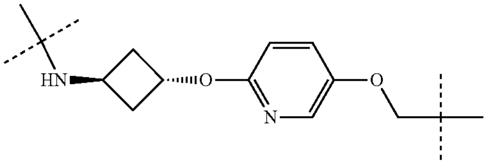
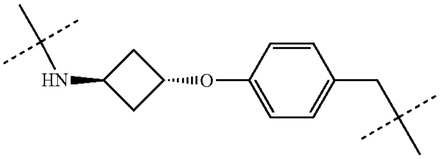
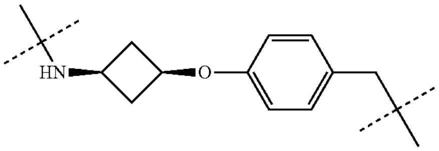
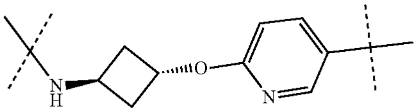
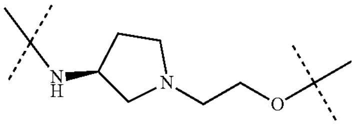
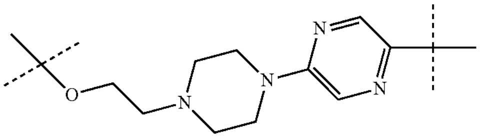
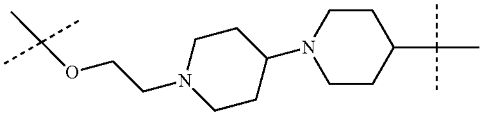
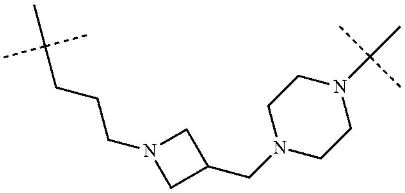
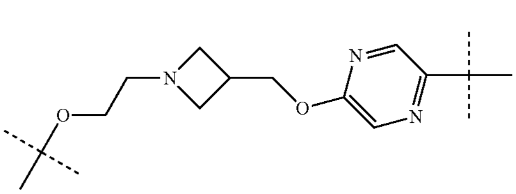
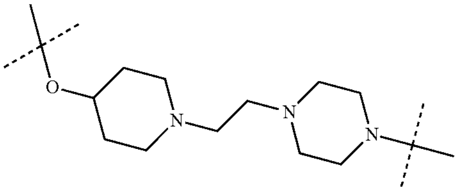
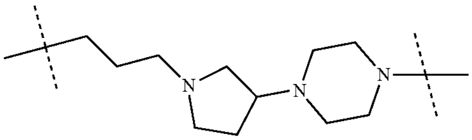
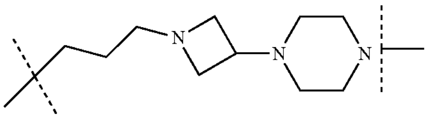
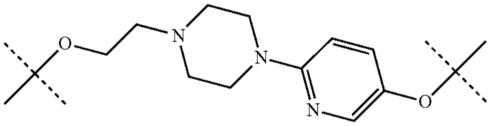
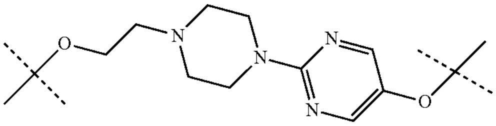
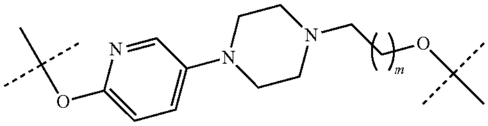
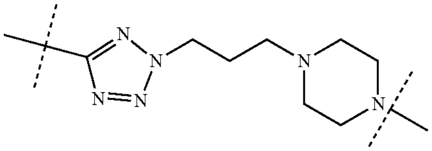
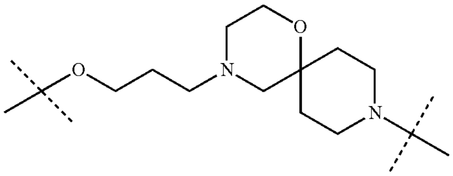
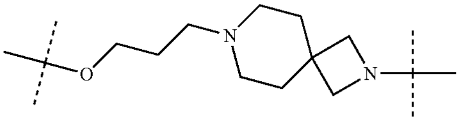
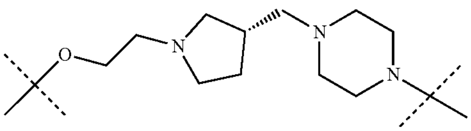
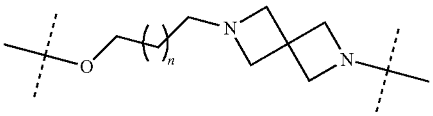
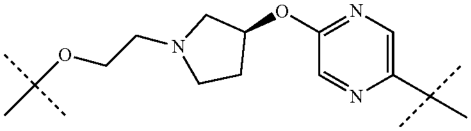
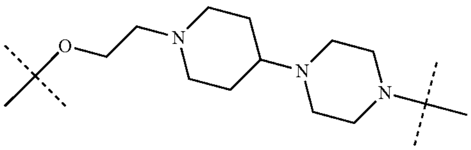

-continued
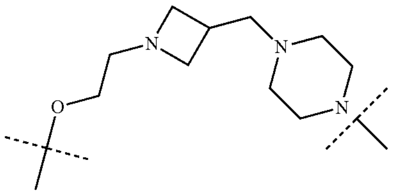
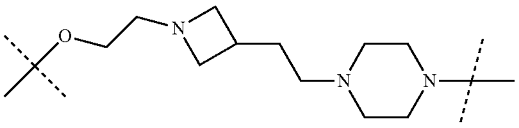
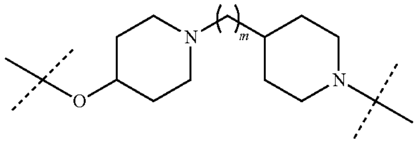
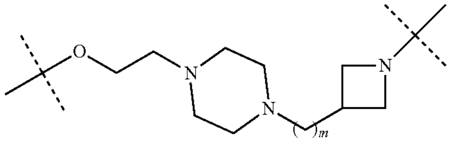
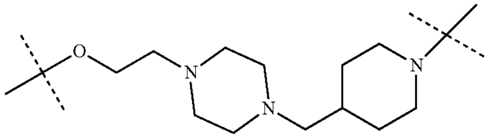
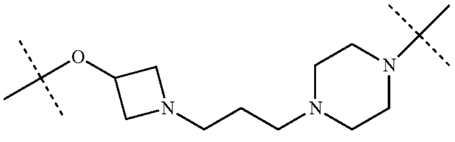
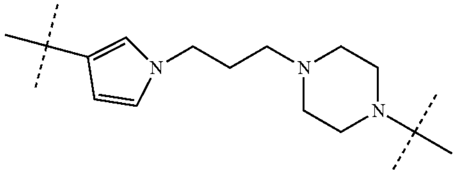
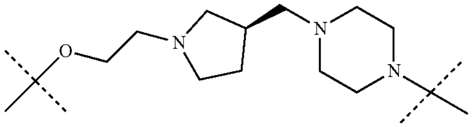
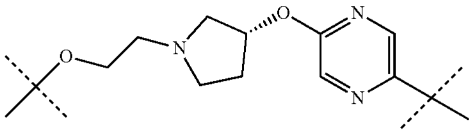
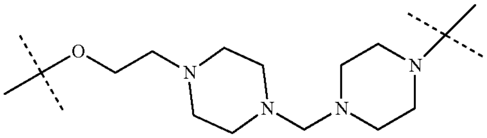
m = 1, 2; n = 0, 1
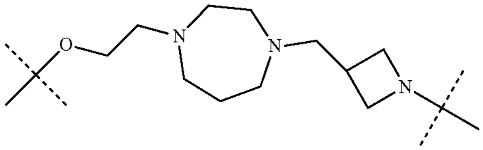
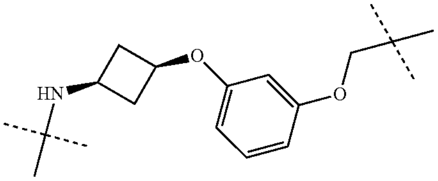
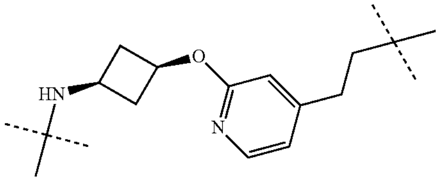
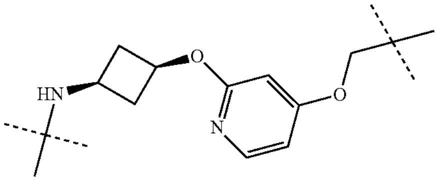
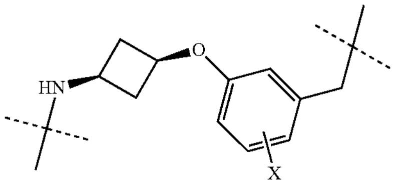
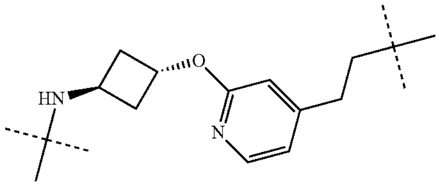
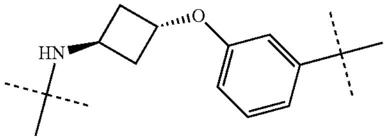
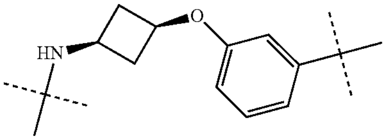
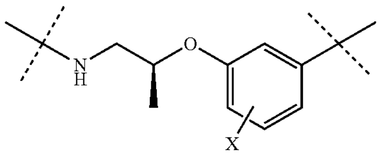
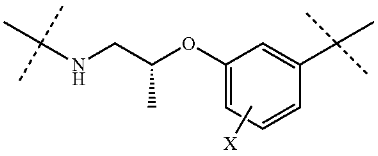

-continued
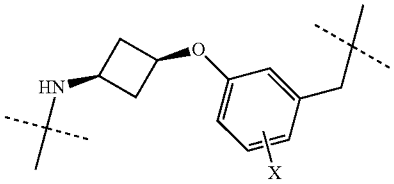
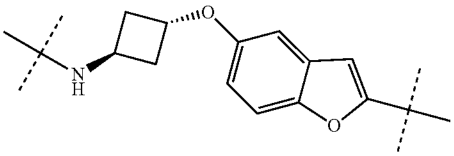
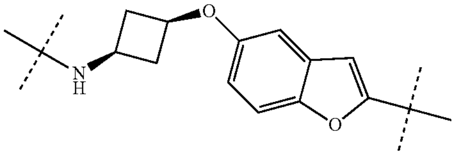
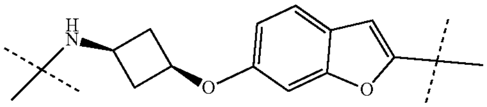
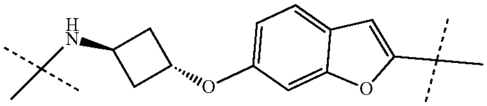
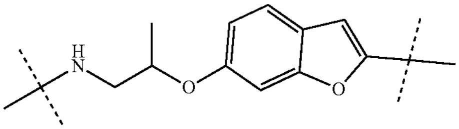
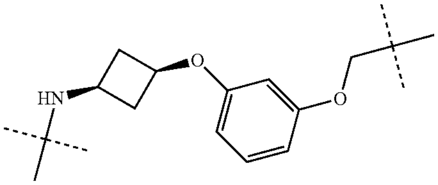
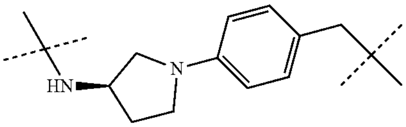
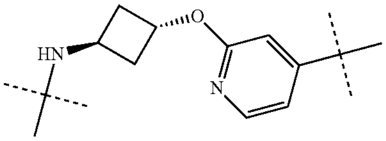
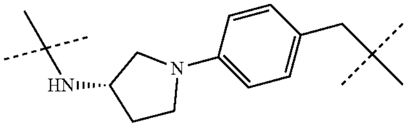
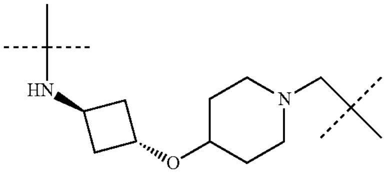
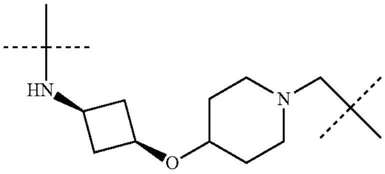
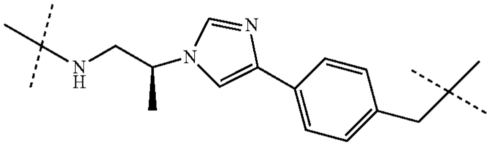
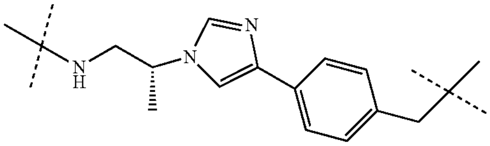
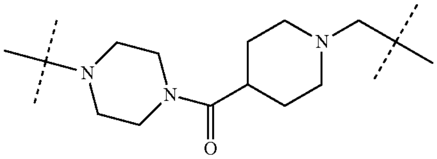
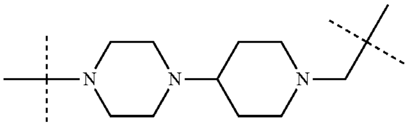
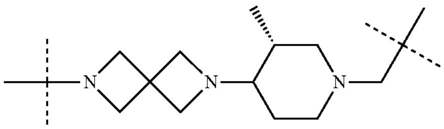
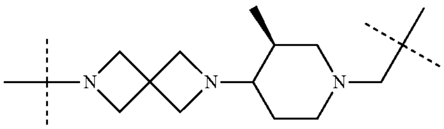
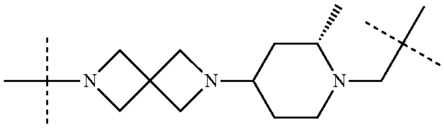
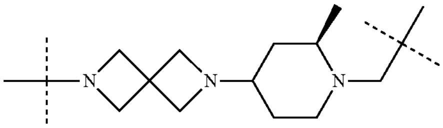
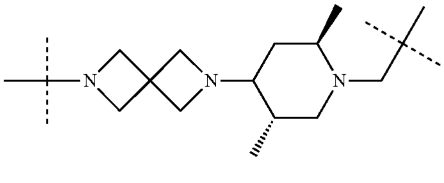
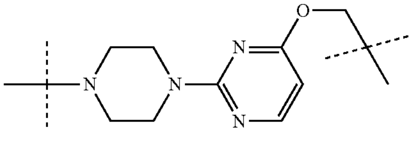

-continued
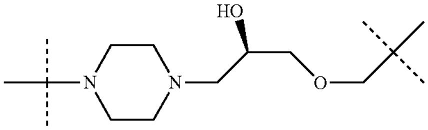
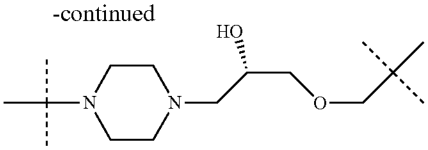
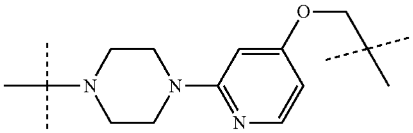
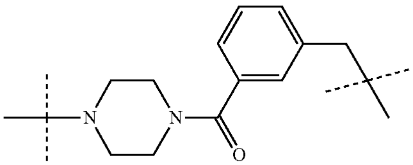
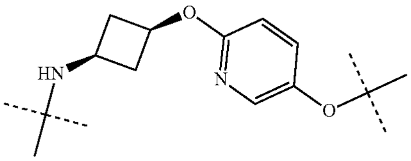
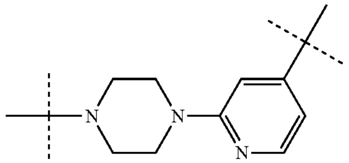
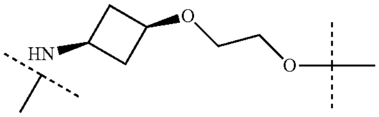
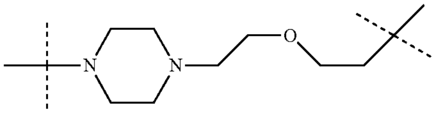
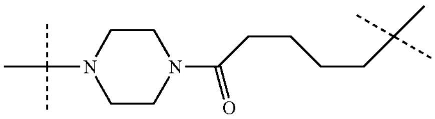
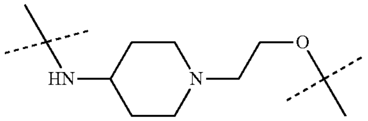
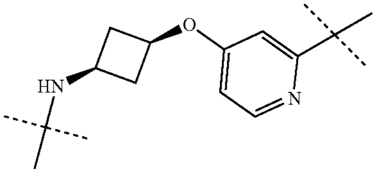
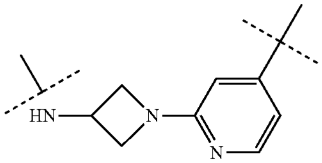
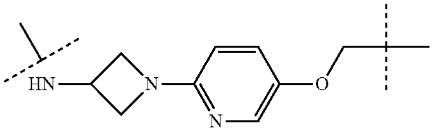
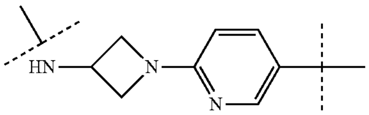
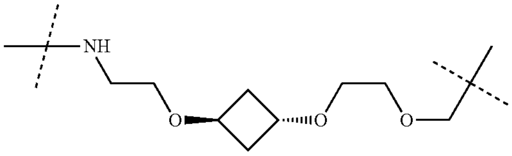
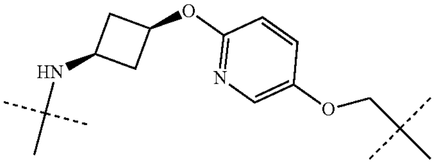
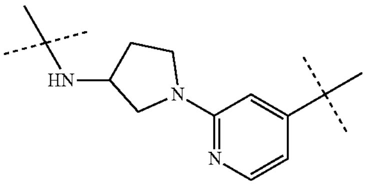
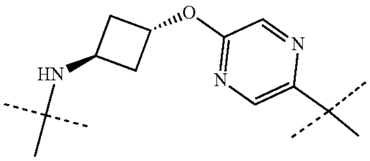
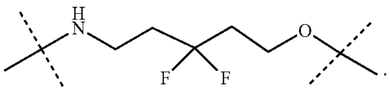
where each n and m of the linker can independently be 0, 1, 2, 3, 4, 5, 6.
In any aspect or embodiment described herein, the linker (L) is selected from the group consisting of:

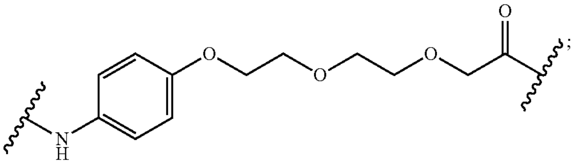
;
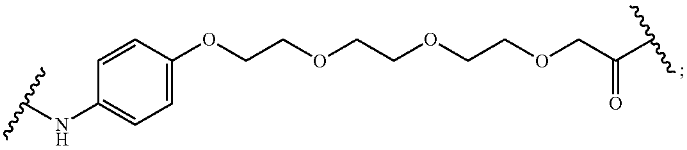
;
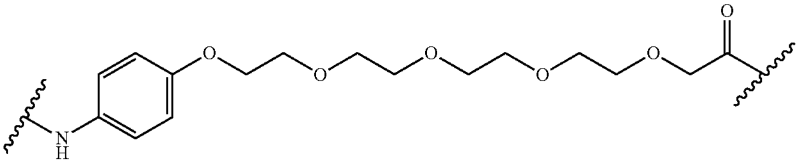
;
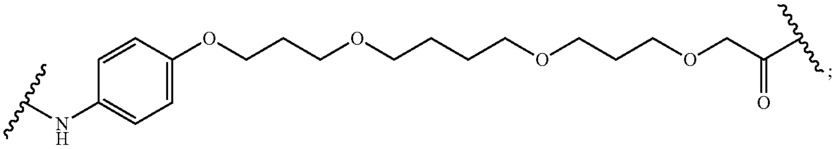
;
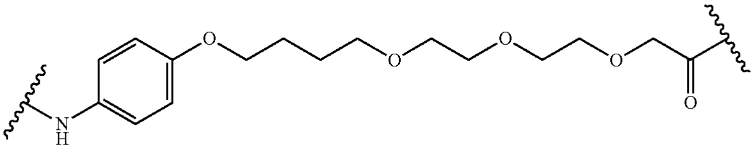
;
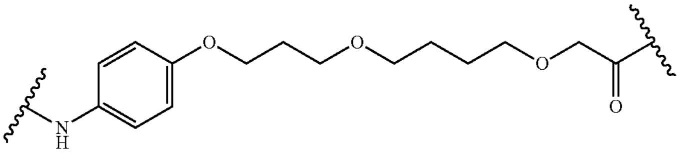
;
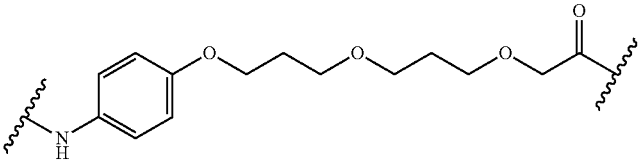
;
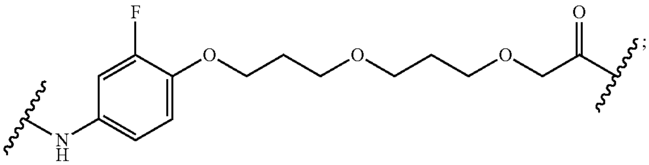
;
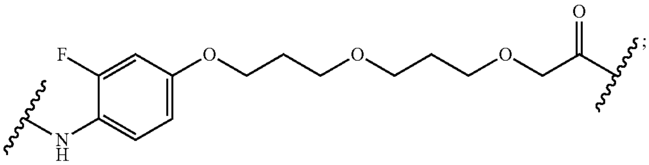
;
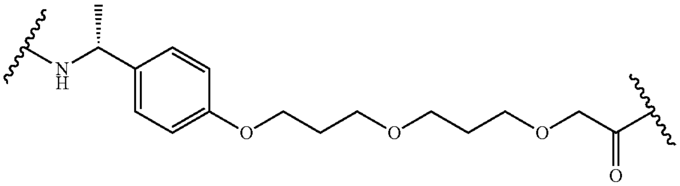
;

-continued
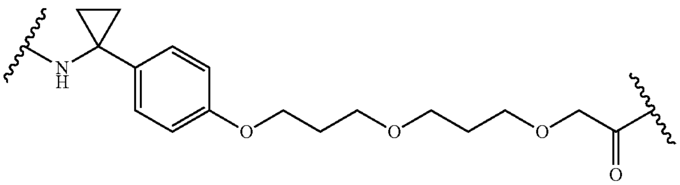
;
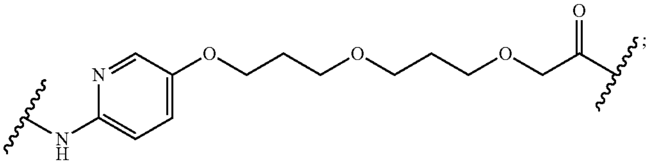
;
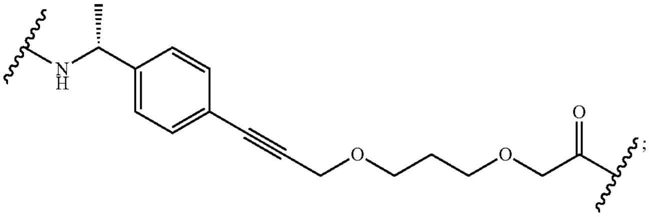
;
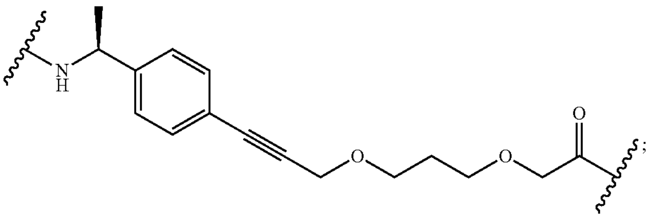
;
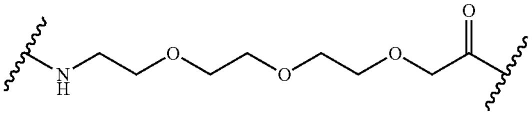
;
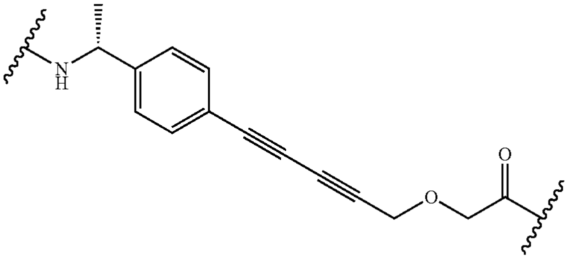
;
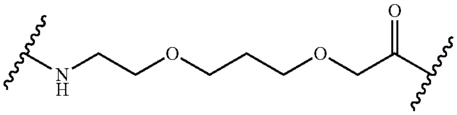
;
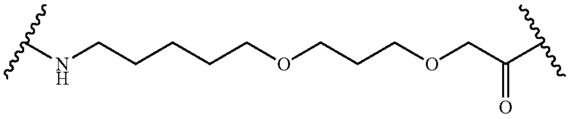
;
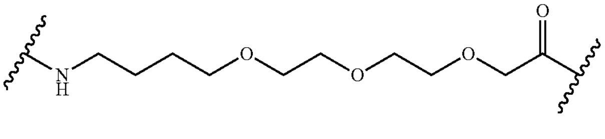
;
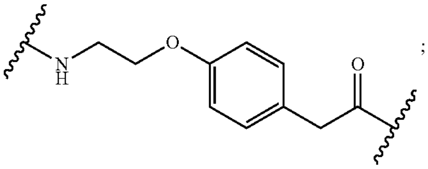
;
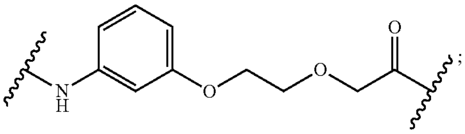
;
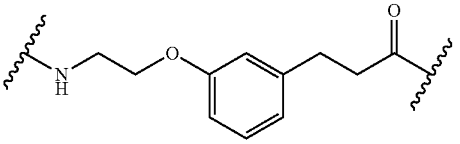
;
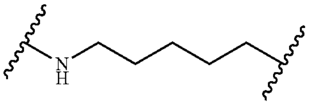
;
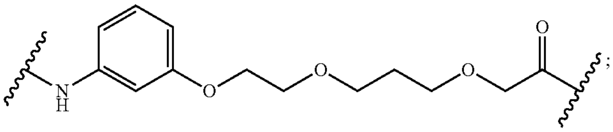
;

-continued
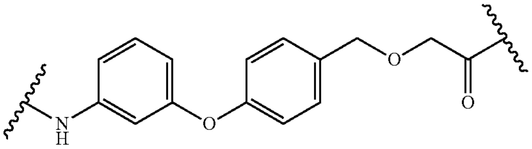
;
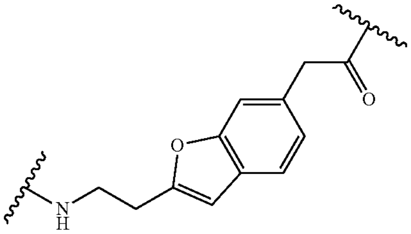
;
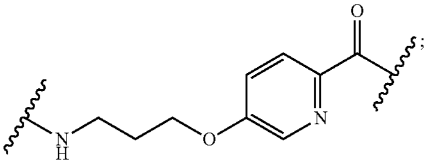
;
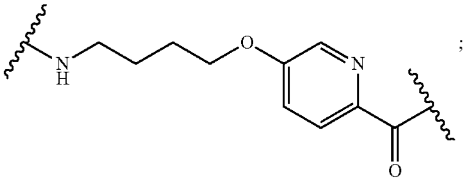
;
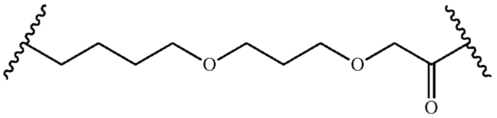
;
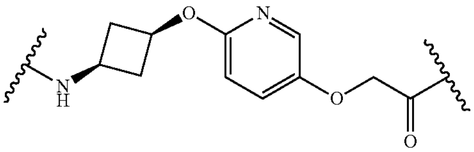
;
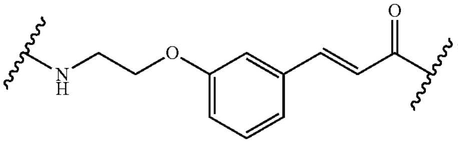
;
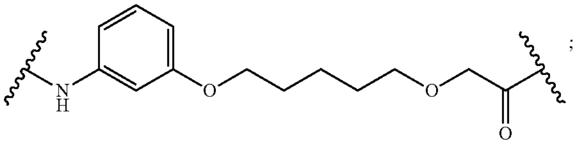
;
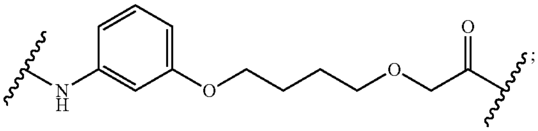
;
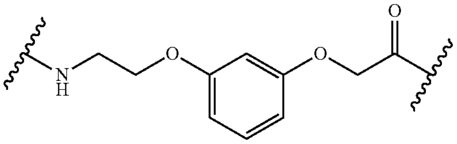
;
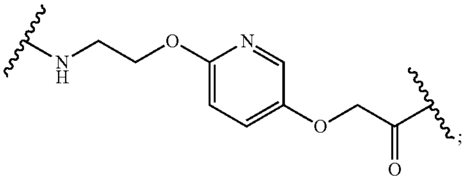
;
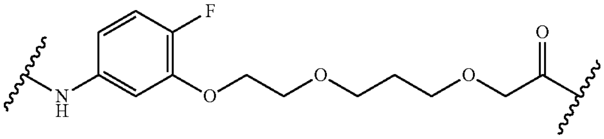
;
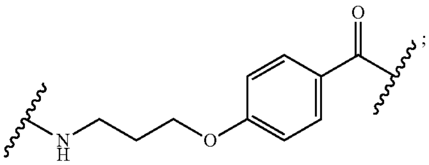
;
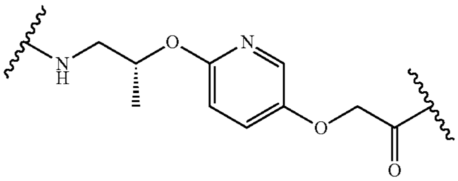
;
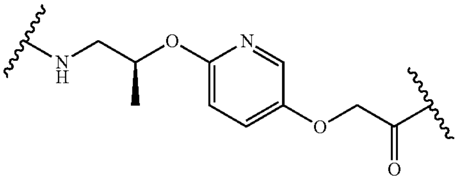
;
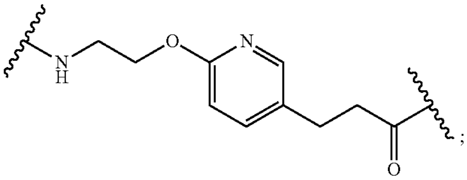
;
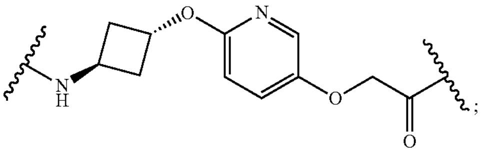
;
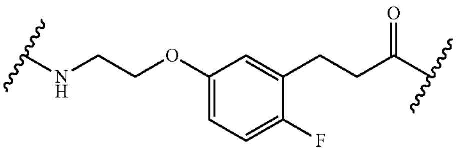
;
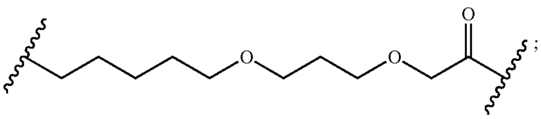
;
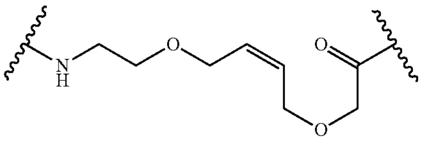
;

-continued
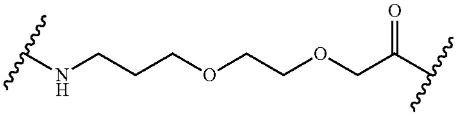
;
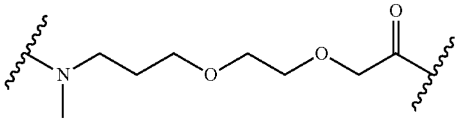
;
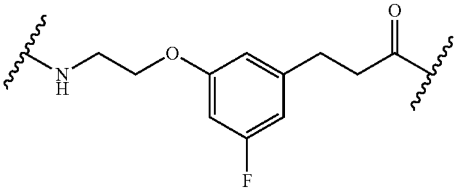
;
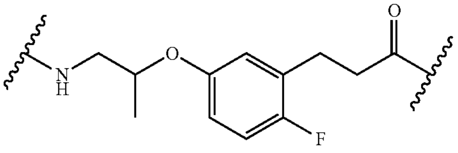
;
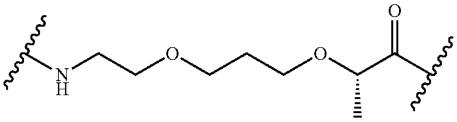
;
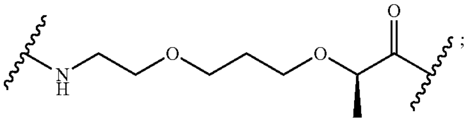
;
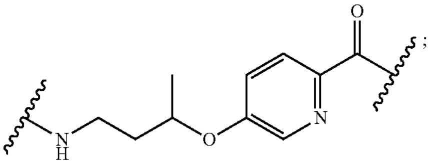
;
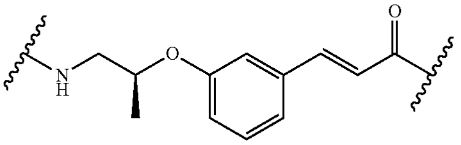
;
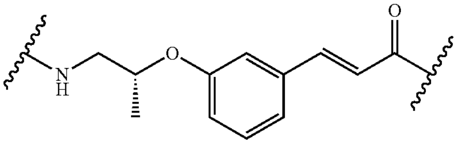
;
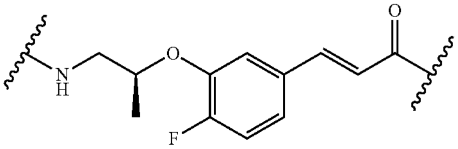
;
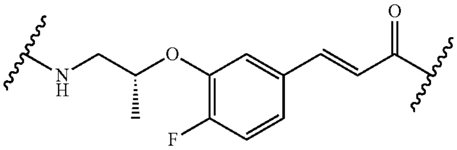
;
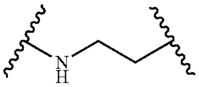
;
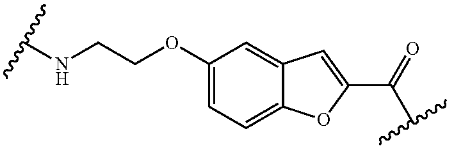
;
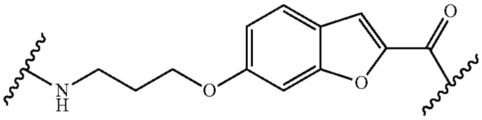
;
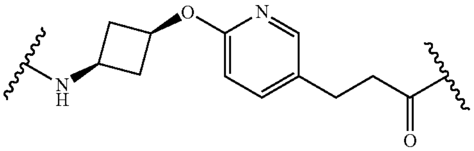
;
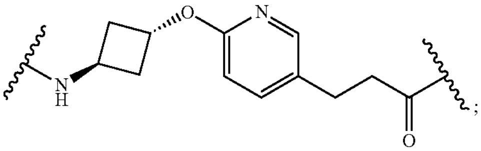
;
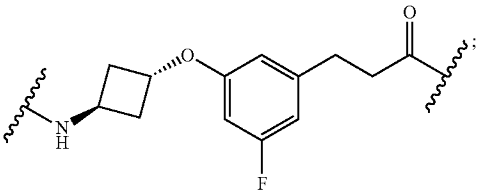
;
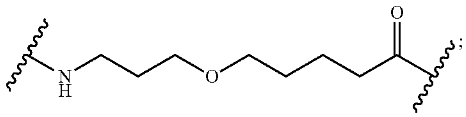
;
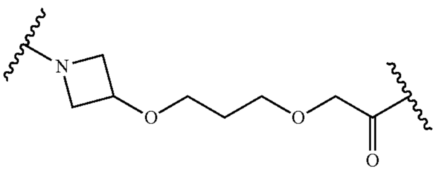
;
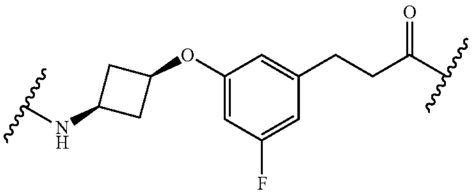
;

-continued
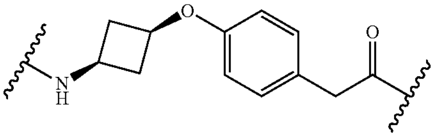
;
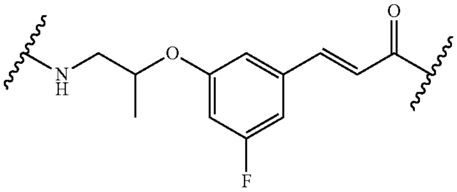
;
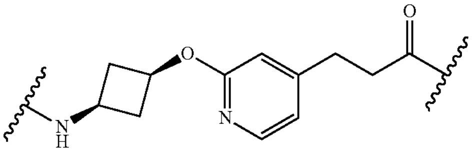
;
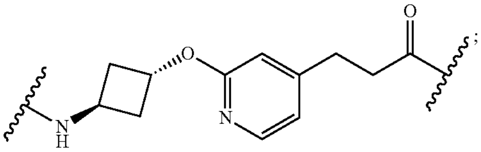
;
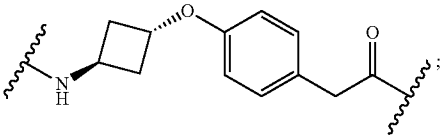
;
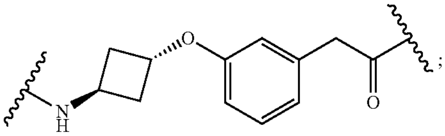
;
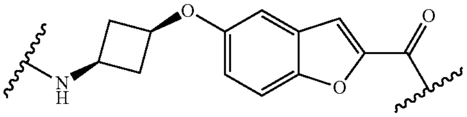
;
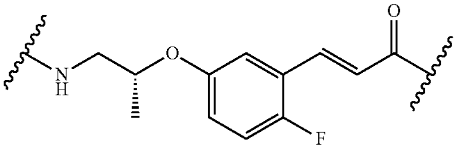
;
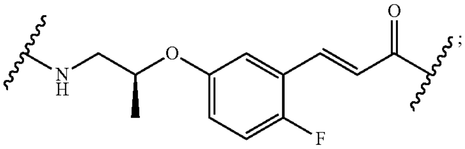
;
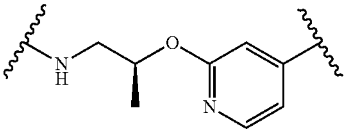
;
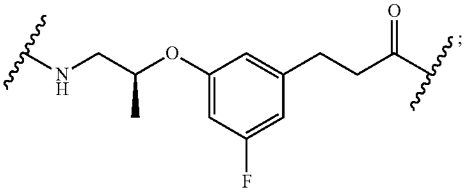
;
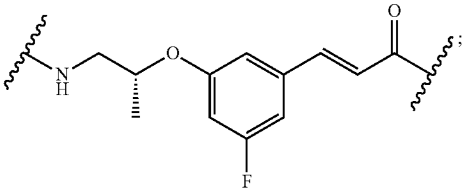
;
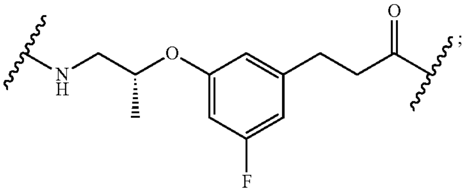
;
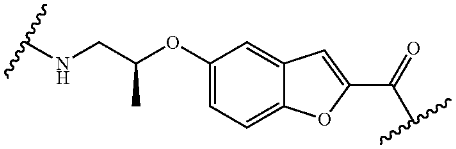
;
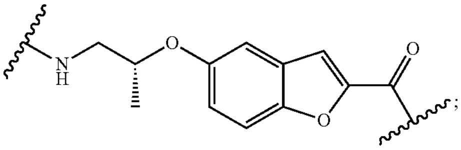
;
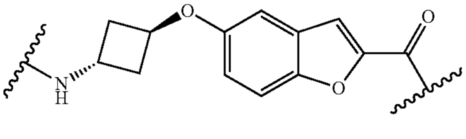
;
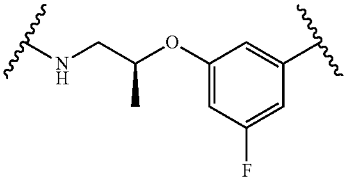
;
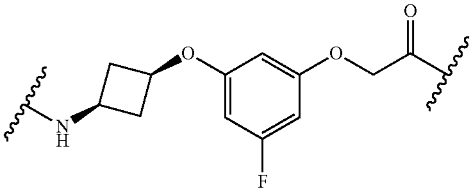
;
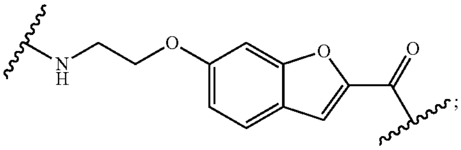
;
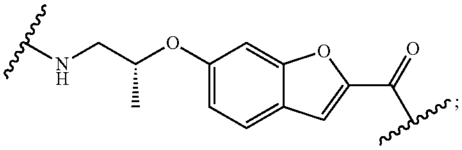
;

-continued
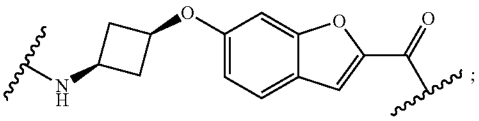 ; 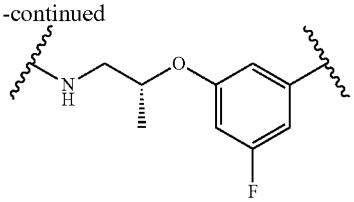 ;
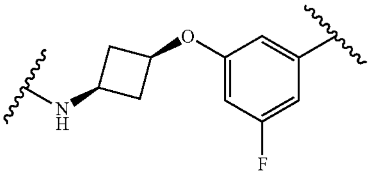 ; 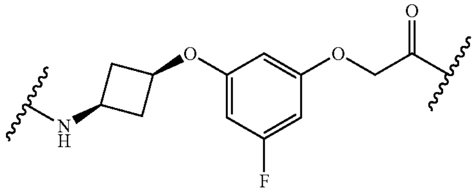 ;
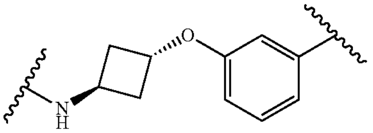 ; 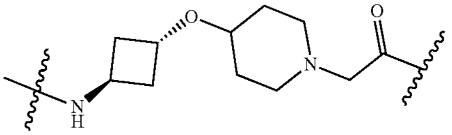 ;
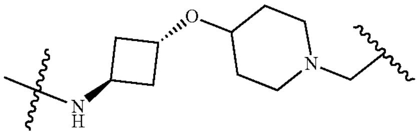 and 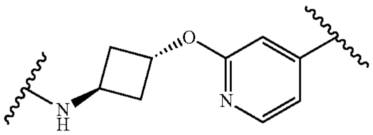 .
In any aspect or embodiment described herein, the linker (L) is selected from the group consisting of:
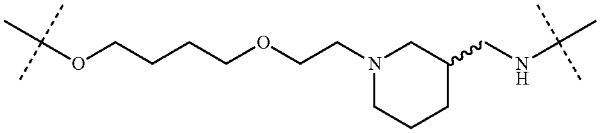 ;
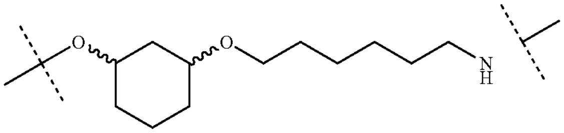 ; 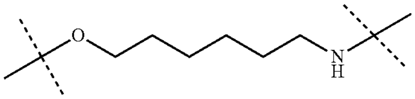 ;
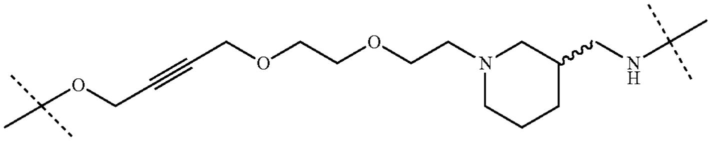 ;
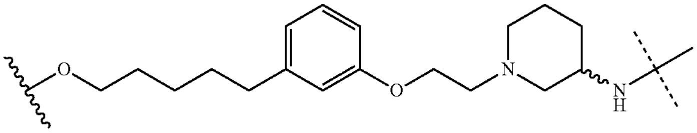 ;
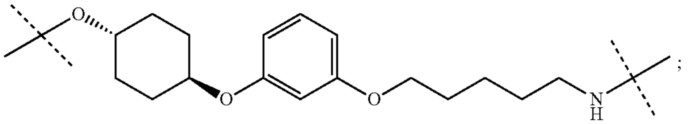 ;
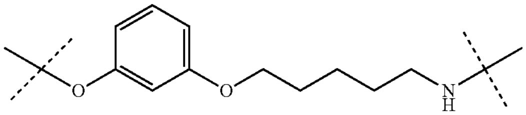 ; 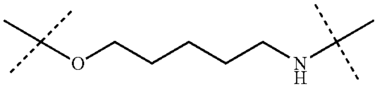 ;
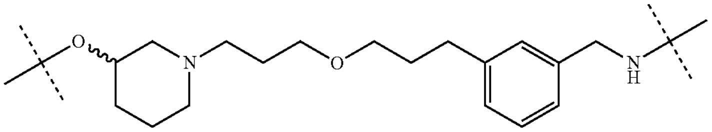 ;

-continued
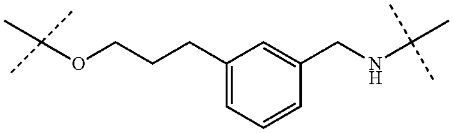
;
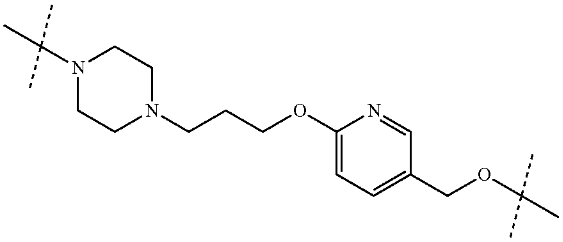
;
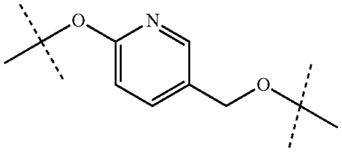
;
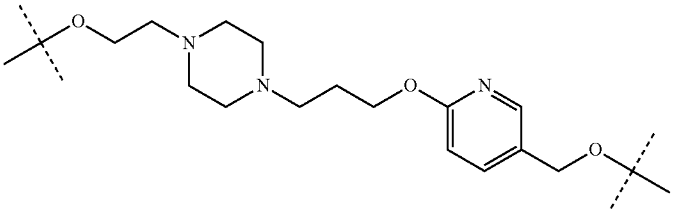
;
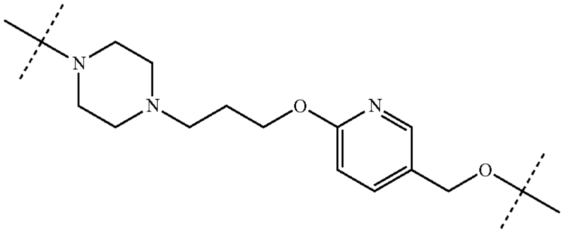
;
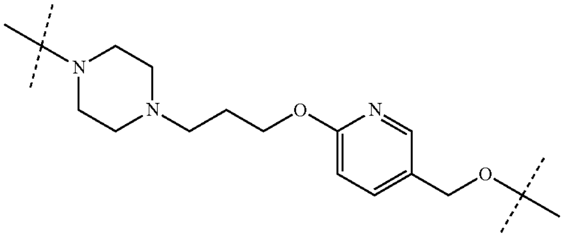
;
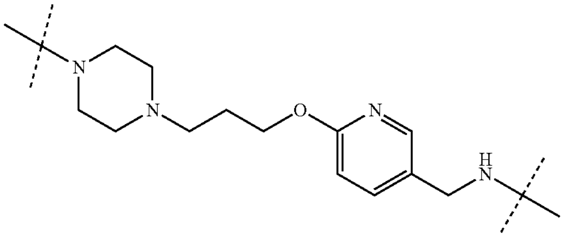
;
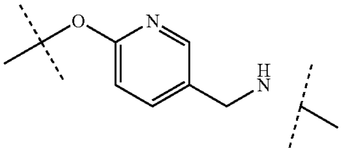
;
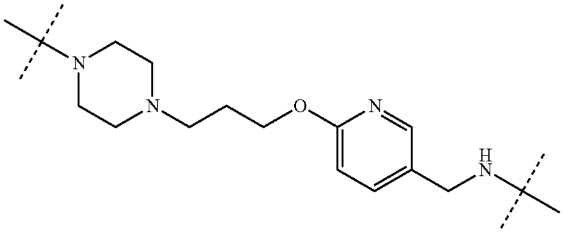
;
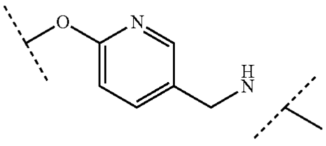
;
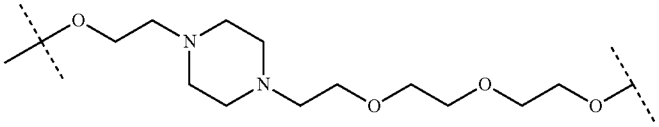
;
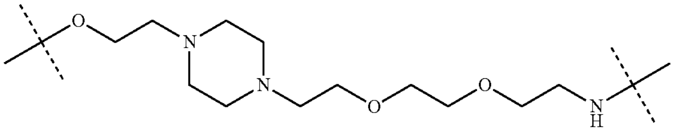
;

-continued
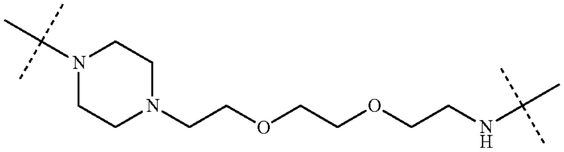
;
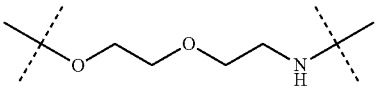
;
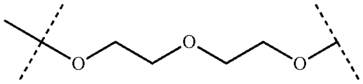
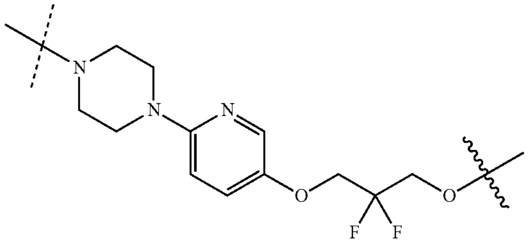
;
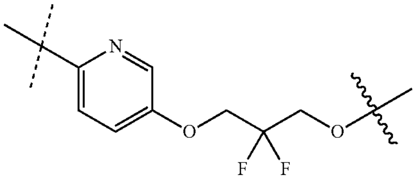
;
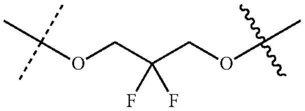
;
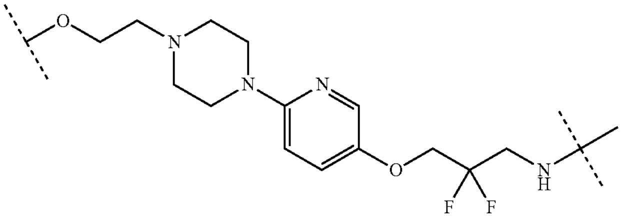
;
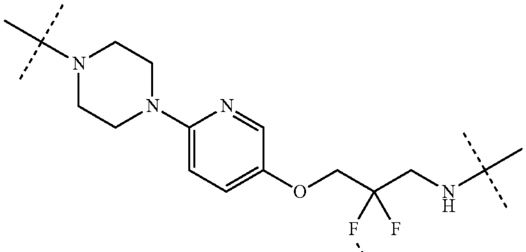
;
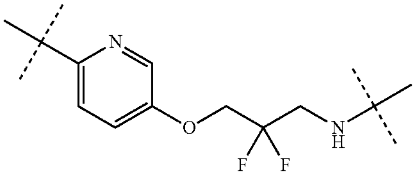
;
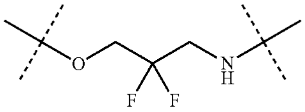
;
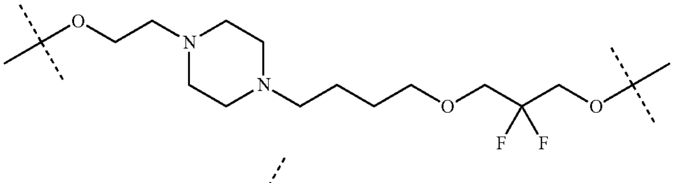
;
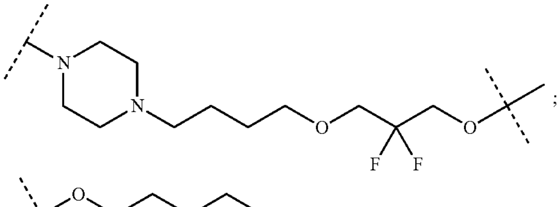
;
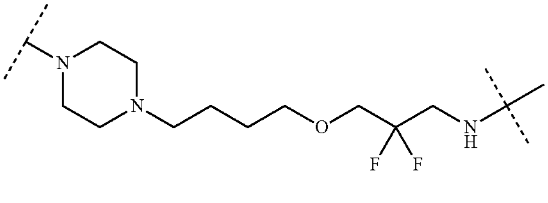
;
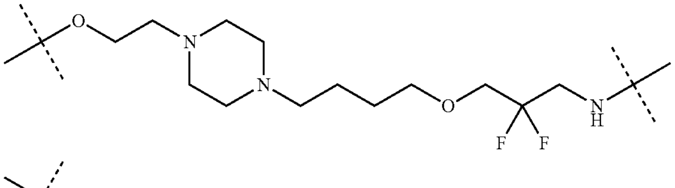
;
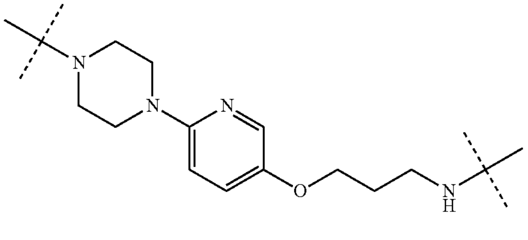
;
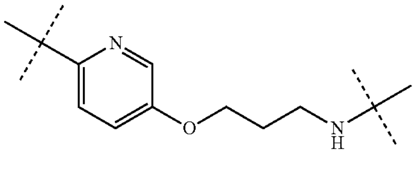
;

-continued
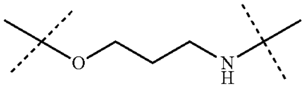 ; 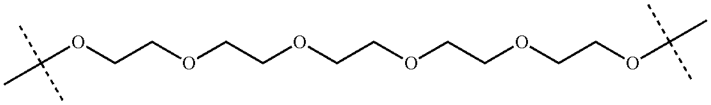 ;
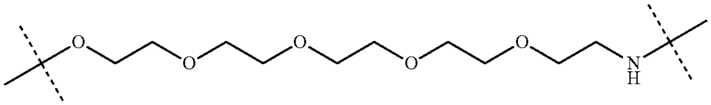 ;
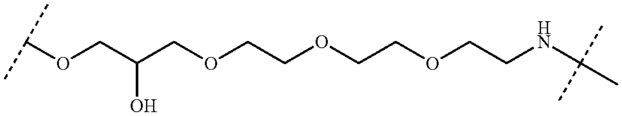 ;
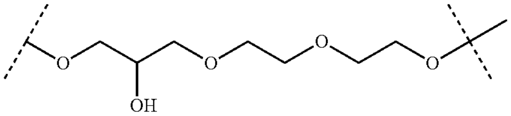 ;
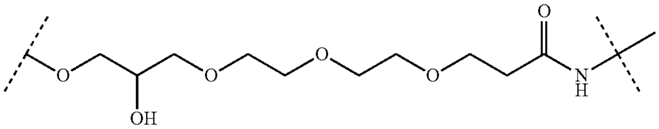 ;
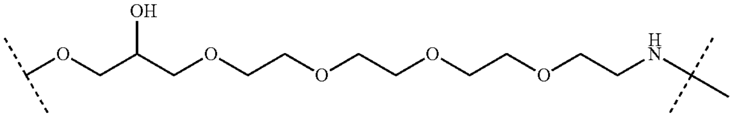 ;
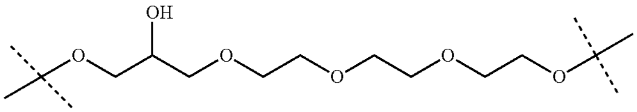 ;
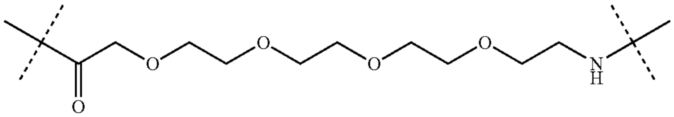 ;
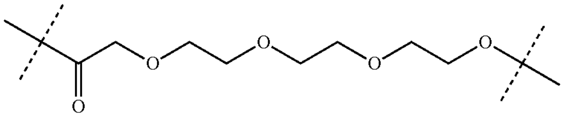 ;
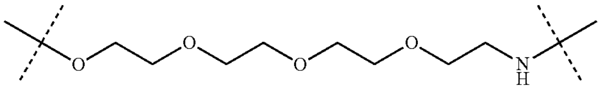 ;
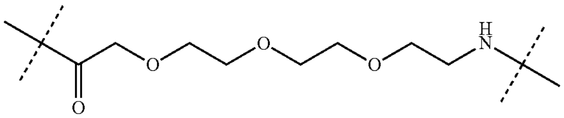 ; 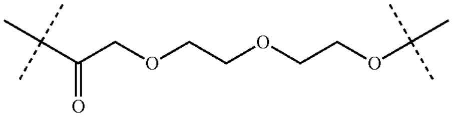 ;
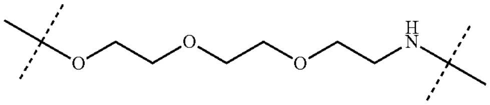 ;
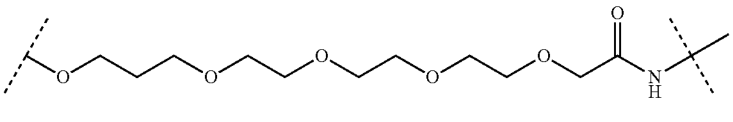 ;
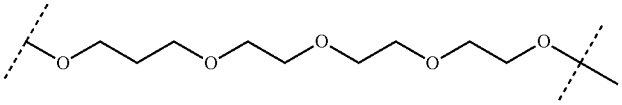 ; 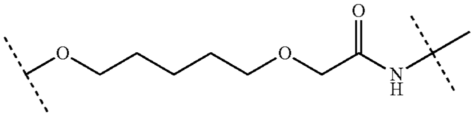 ;
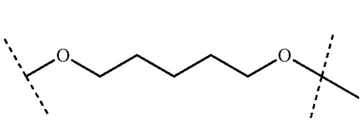 ; 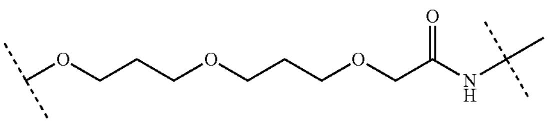 ;

-continued
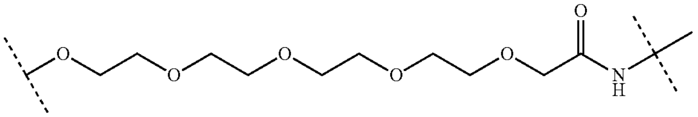 ;
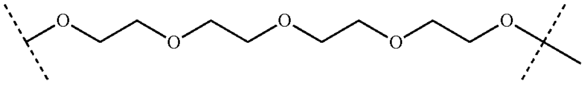 ; 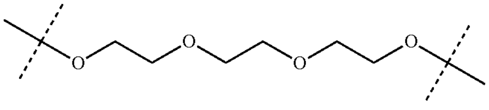 ;
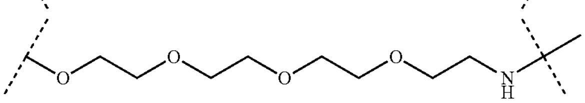 ; 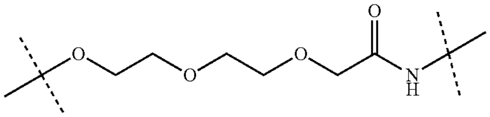 ;
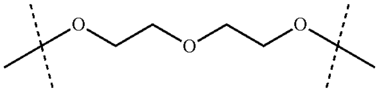 ; 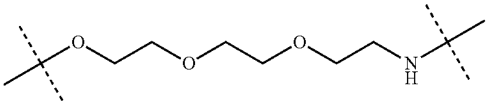 ;
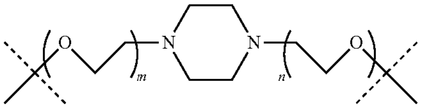 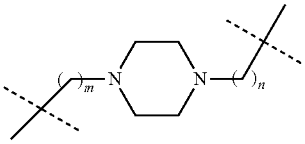 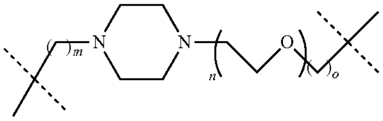
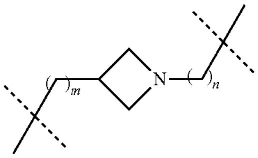 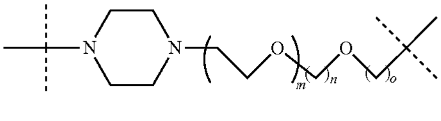 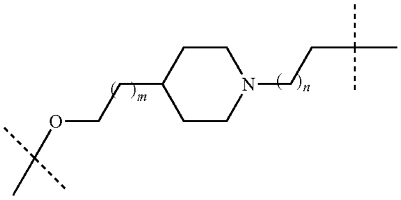
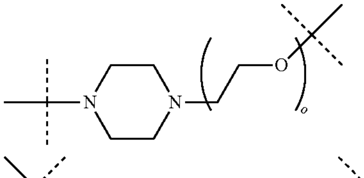 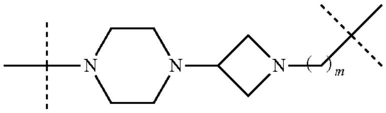
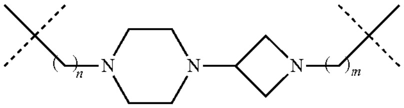 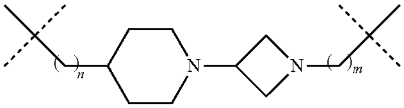
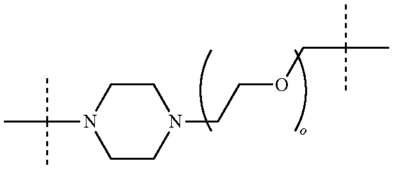 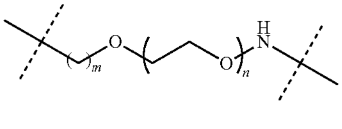 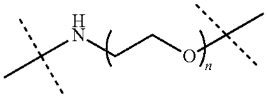
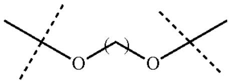 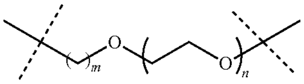 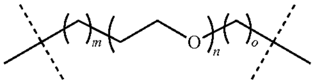
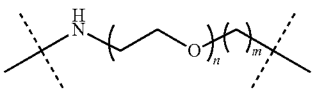 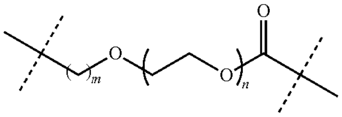 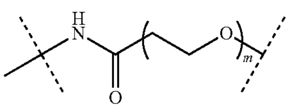
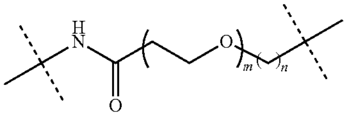 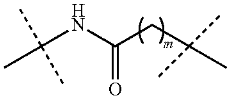 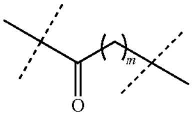 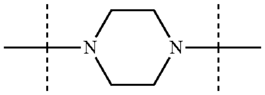
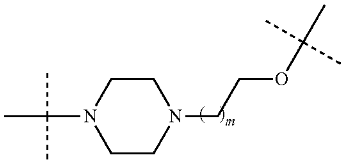 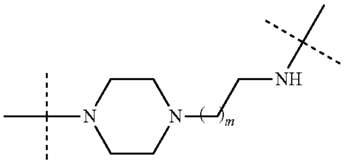 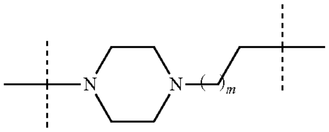

-continued
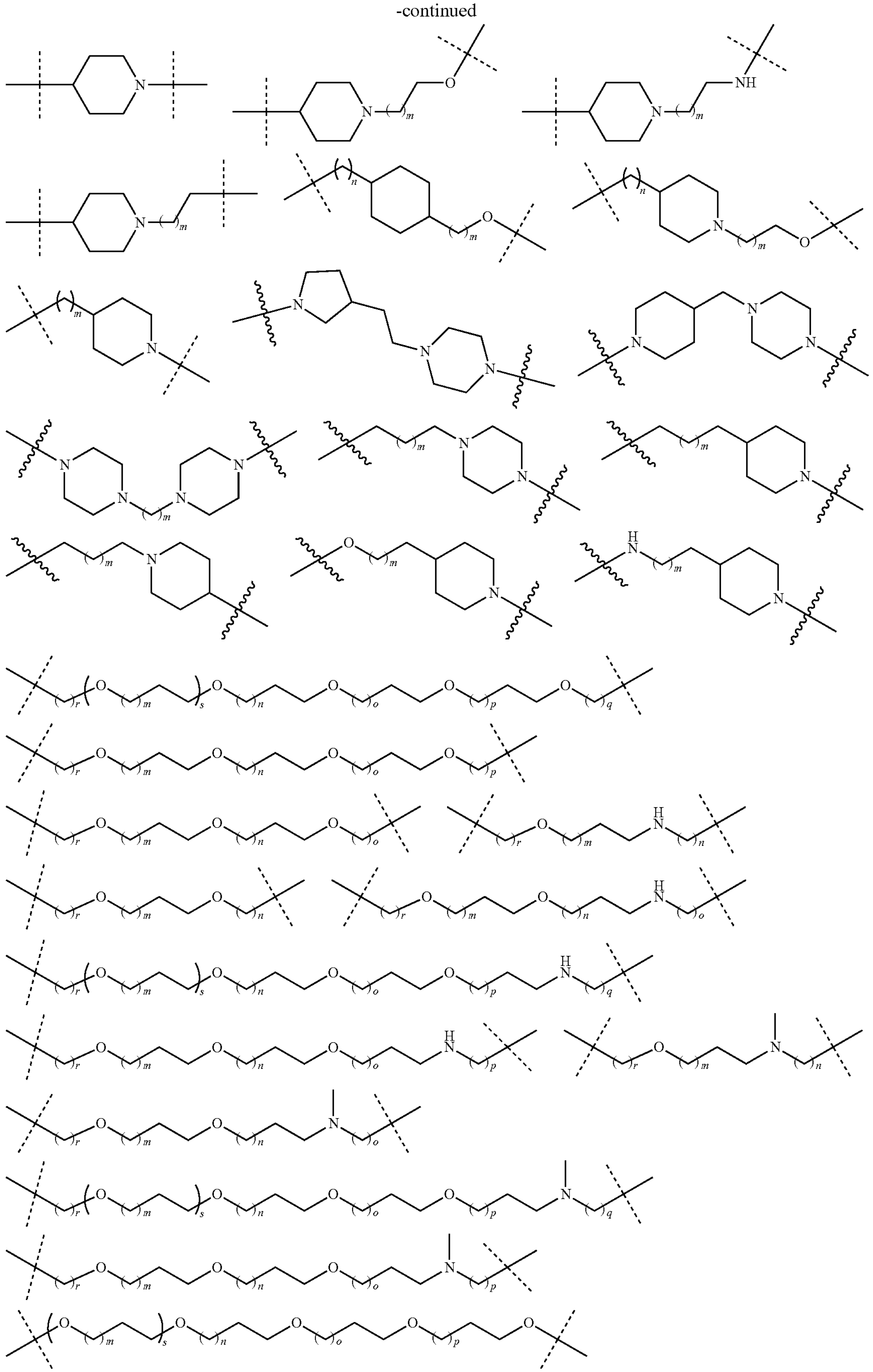

-continued
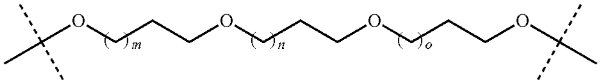 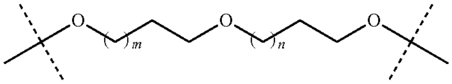
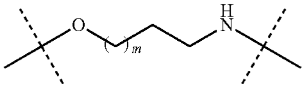 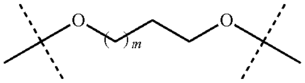 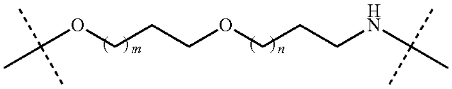
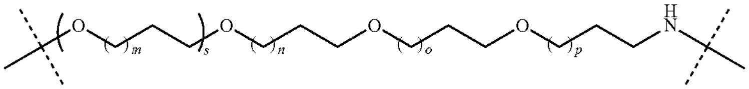
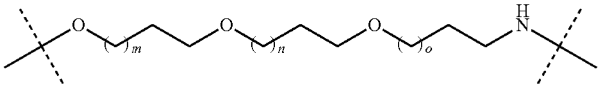
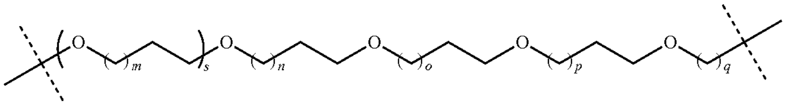
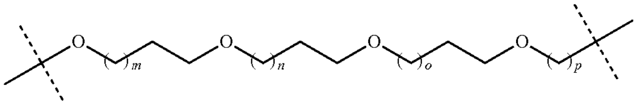 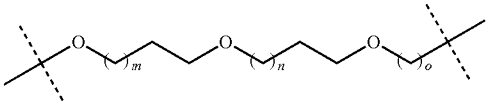
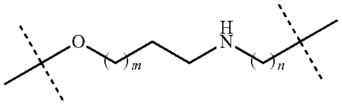 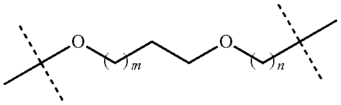
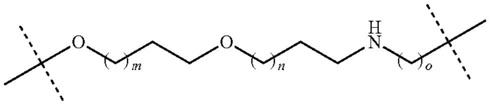
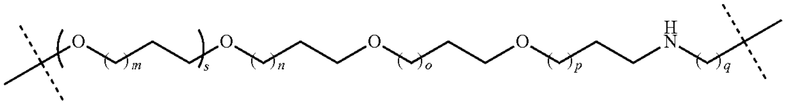
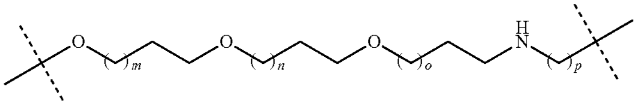
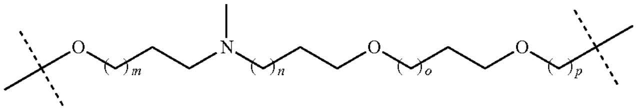 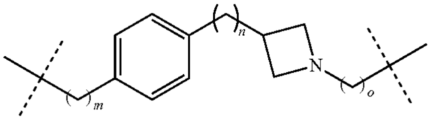
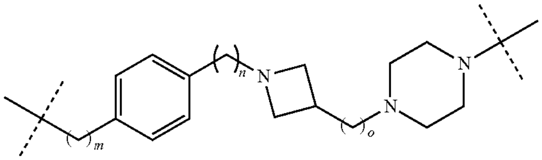 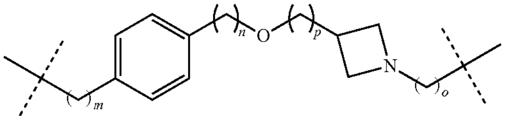
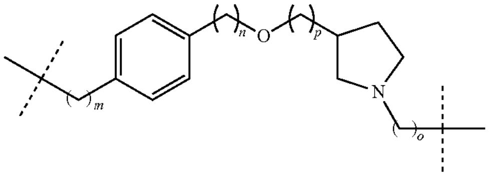 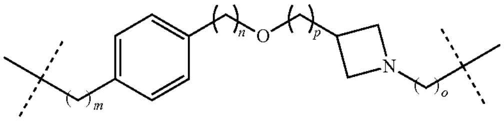
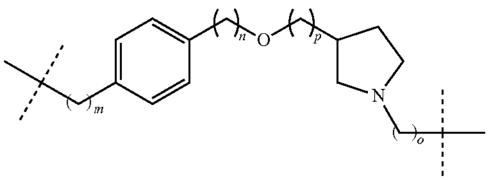 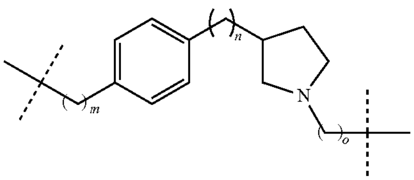

-continued
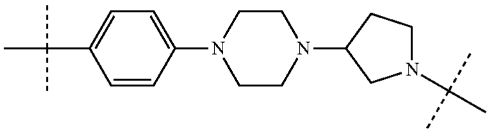
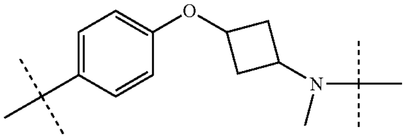
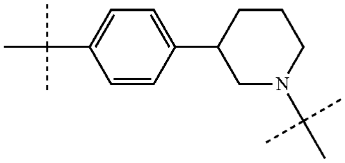
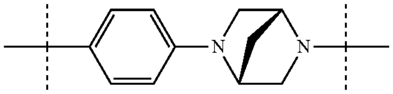
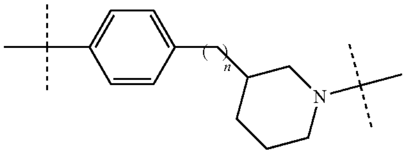
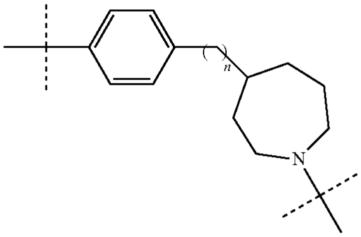
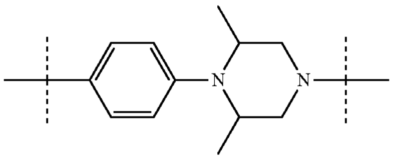
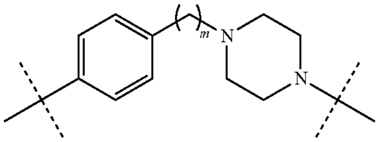
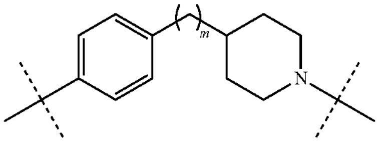
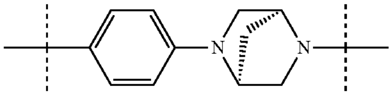
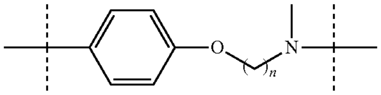
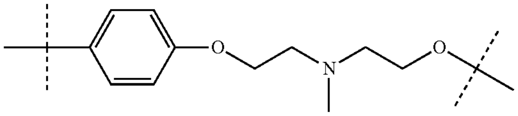
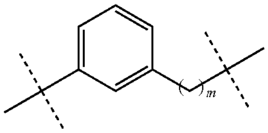
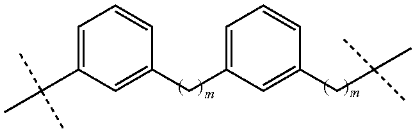
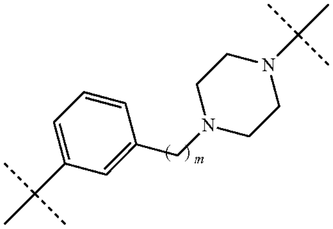
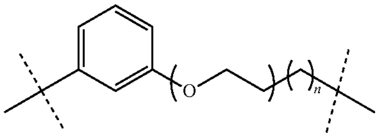
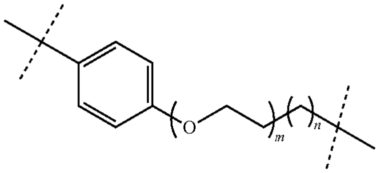
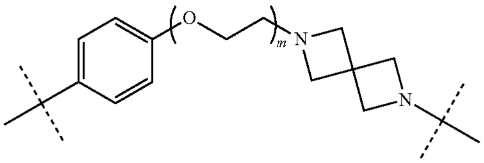
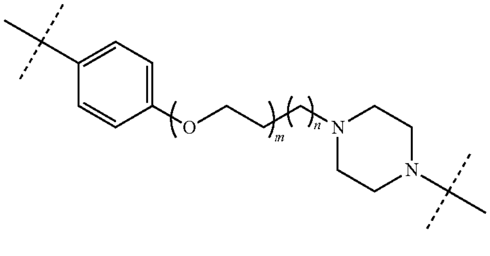

-continued
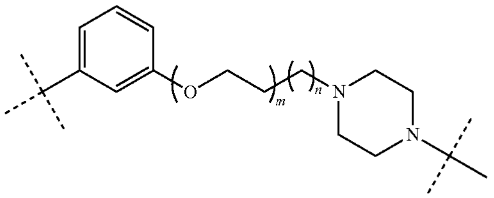
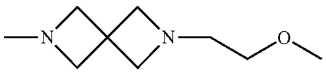
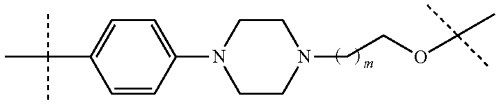
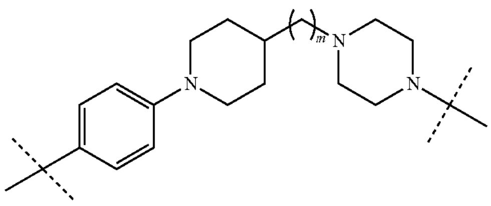
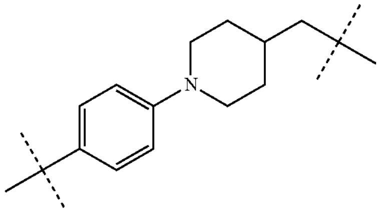
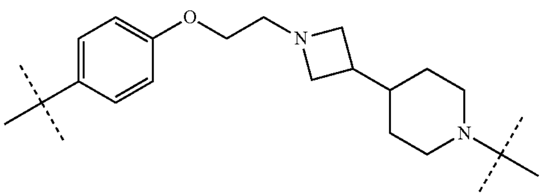
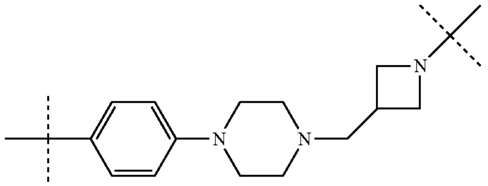
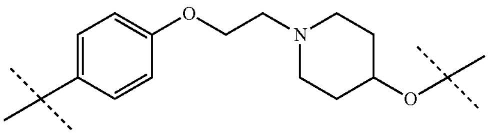
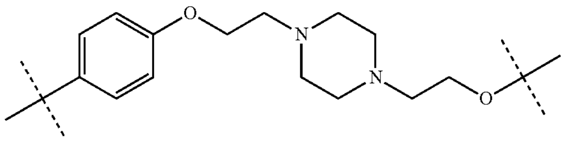
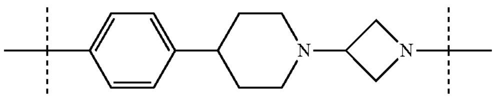
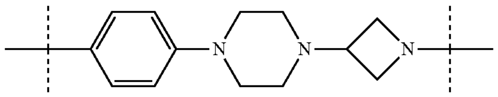
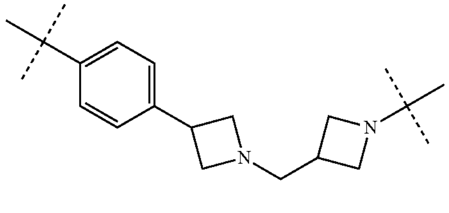
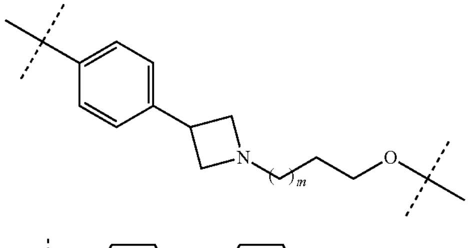
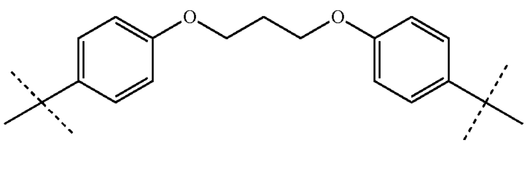
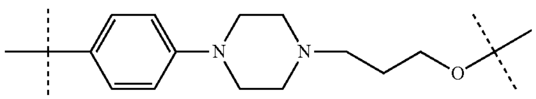
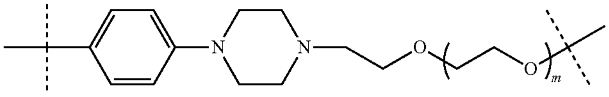
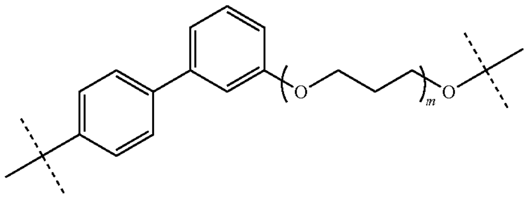
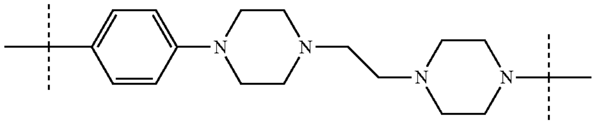

-continued
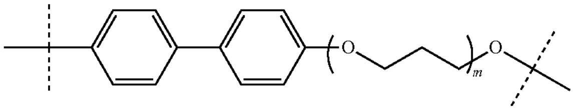
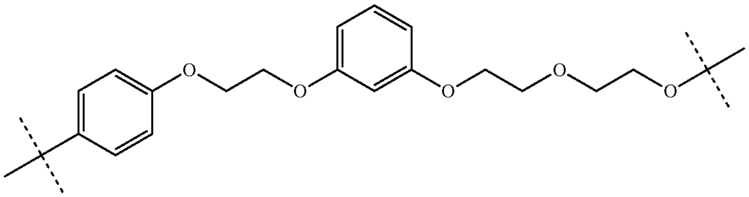
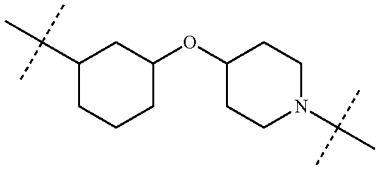
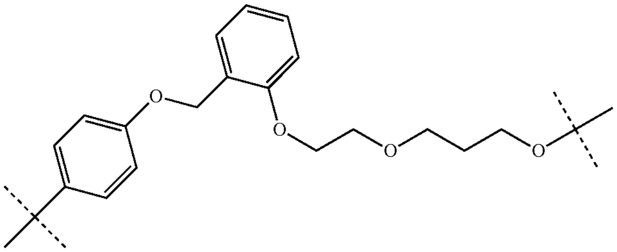
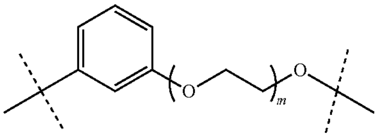
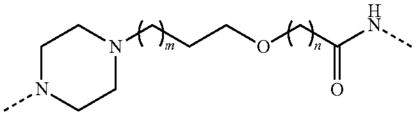
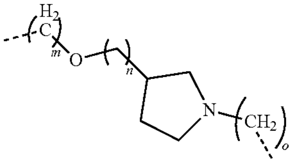
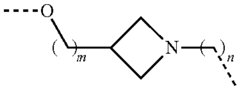
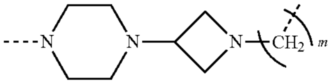
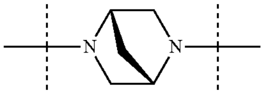
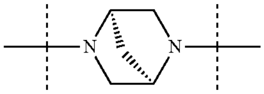
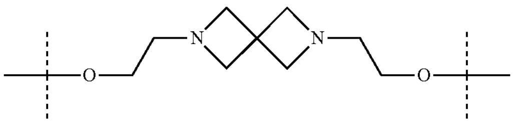
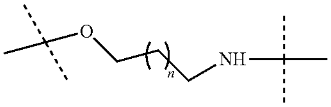
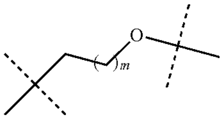
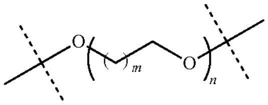
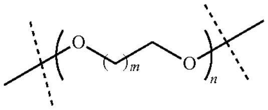
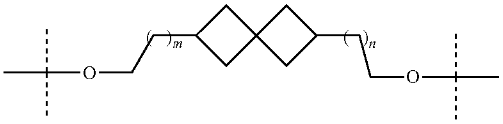
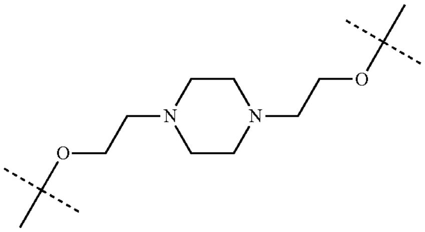
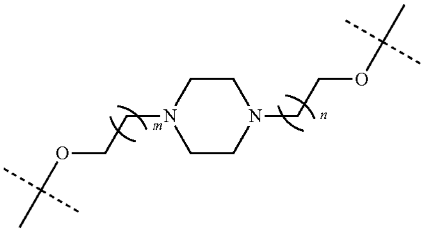
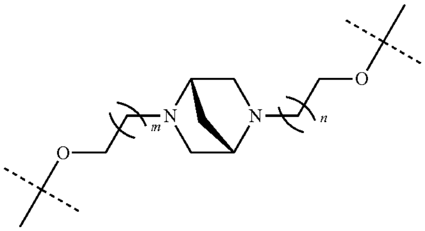
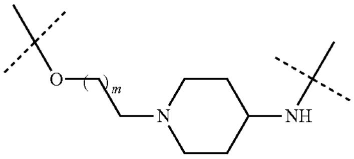

-continued
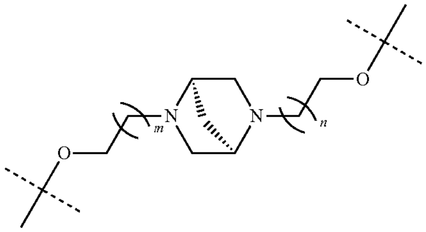
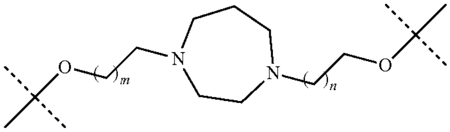
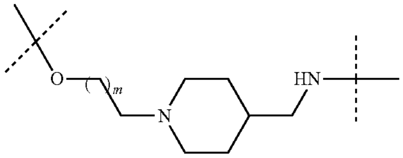
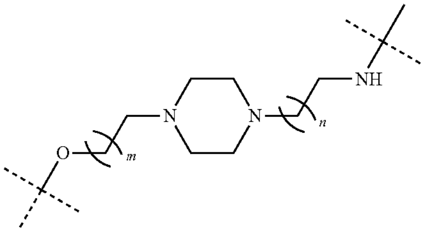
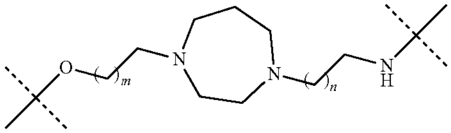
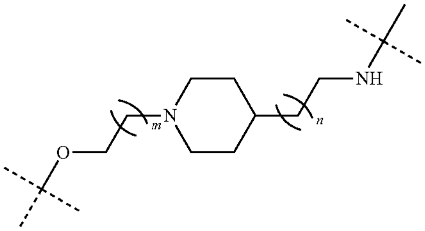
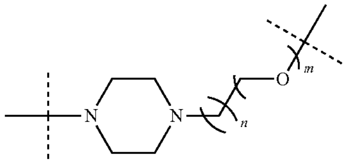
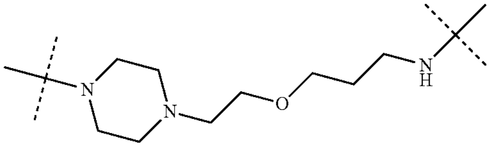
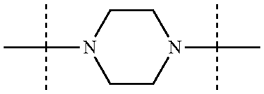
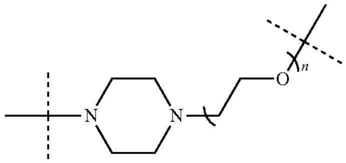
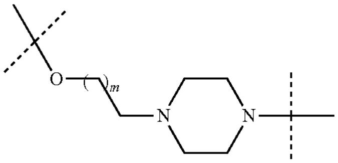
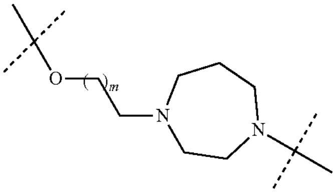
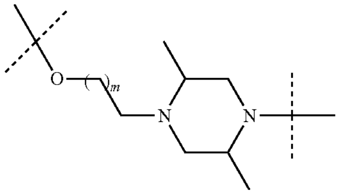
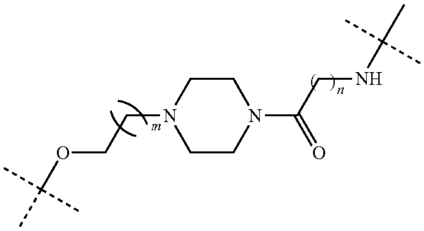
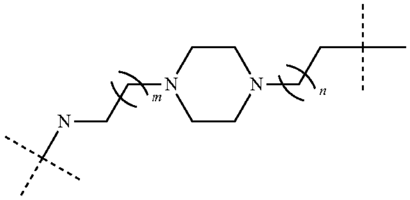
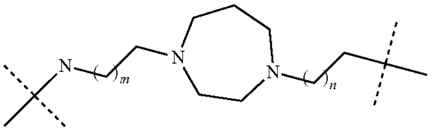
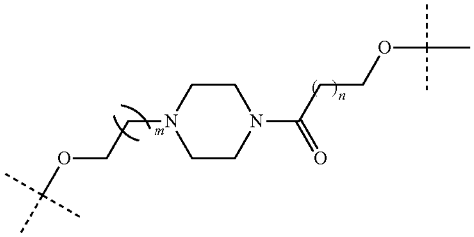
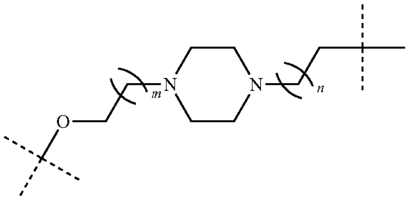

-continued
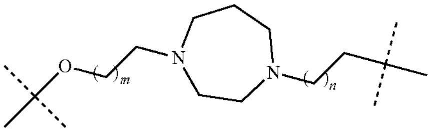
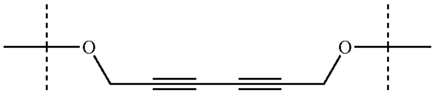
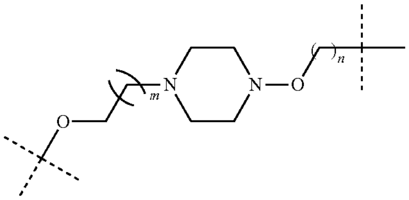
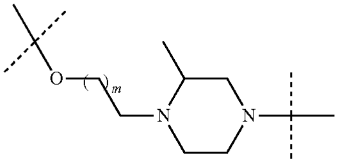
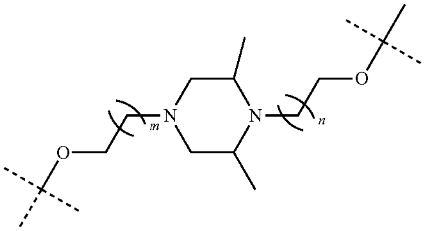
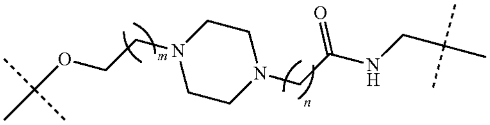
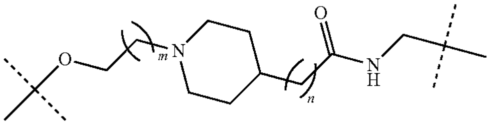
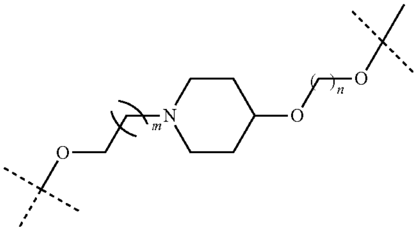
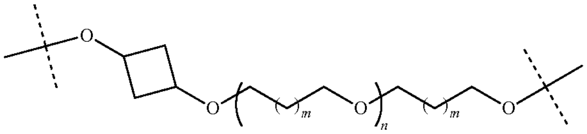
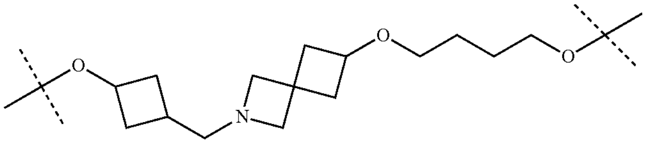
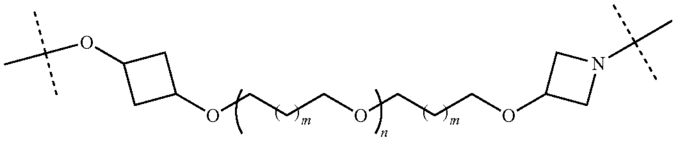
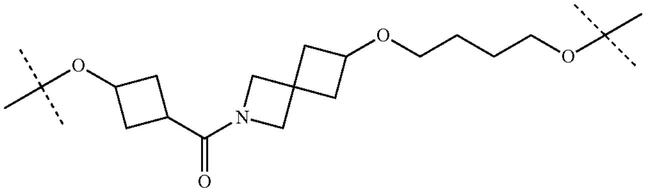
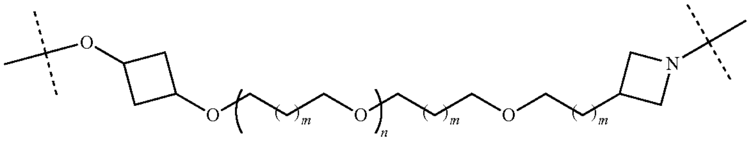
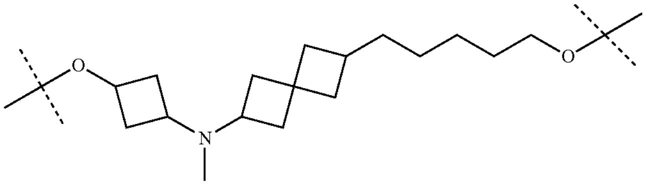

-continued
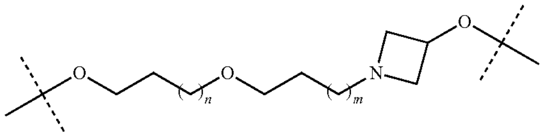
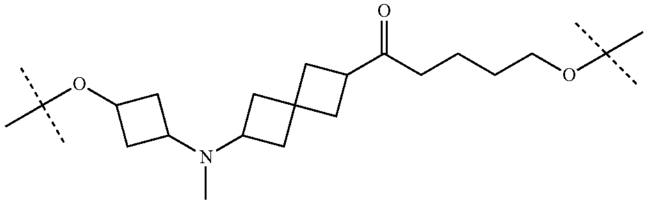
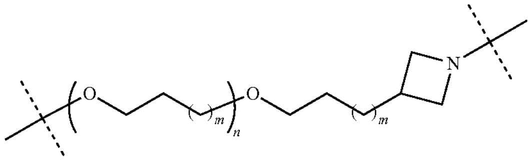
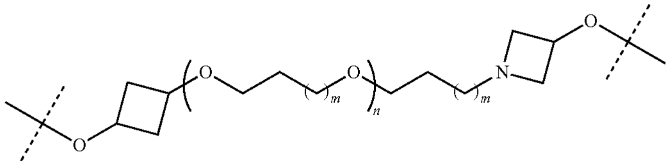
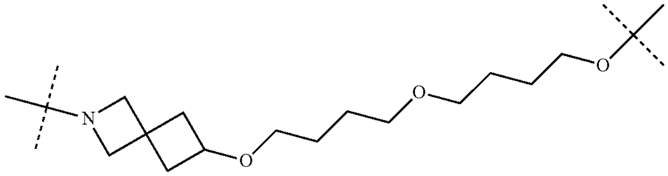
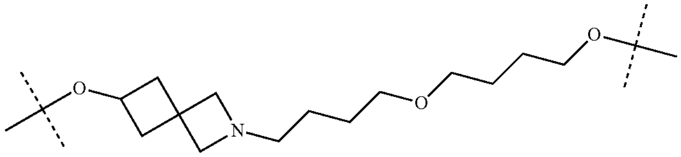
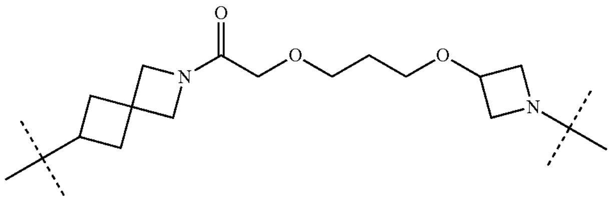
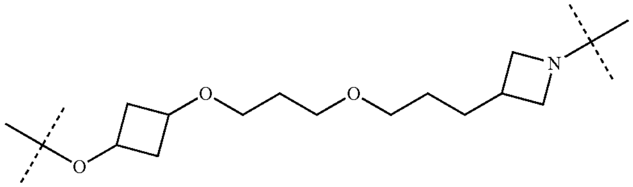
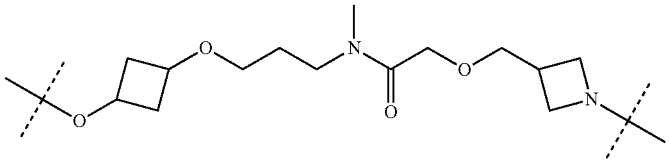
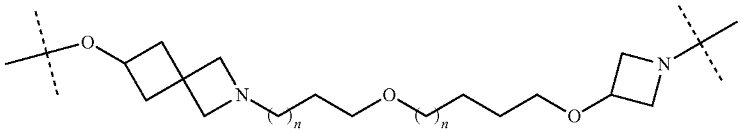

-continued
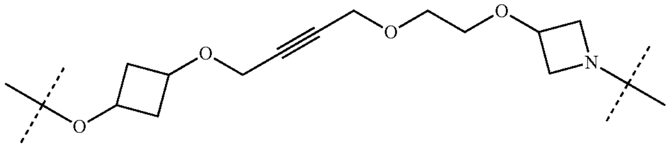
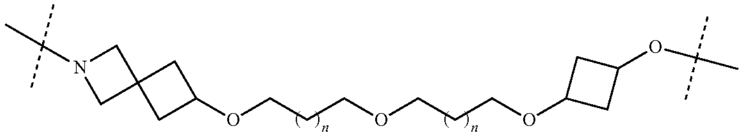
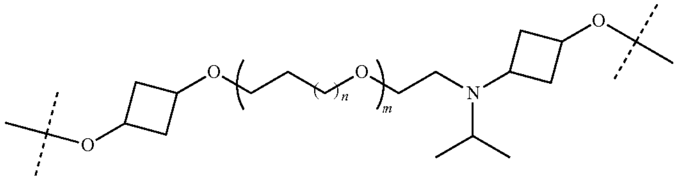
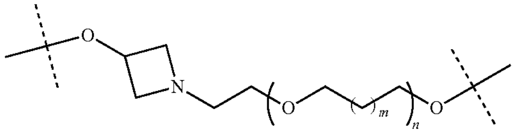
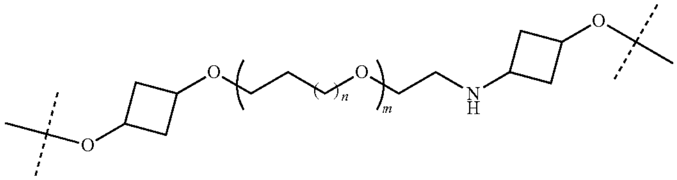
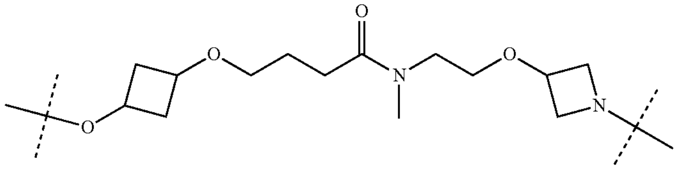
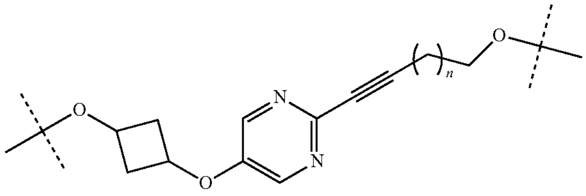
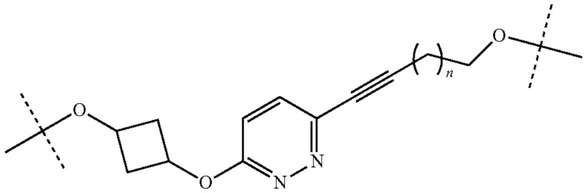
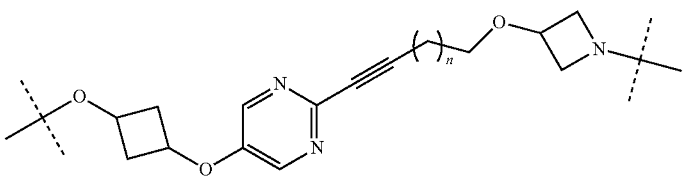
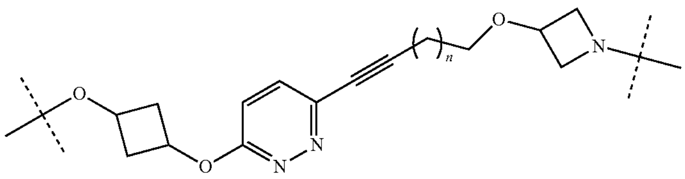

-continued
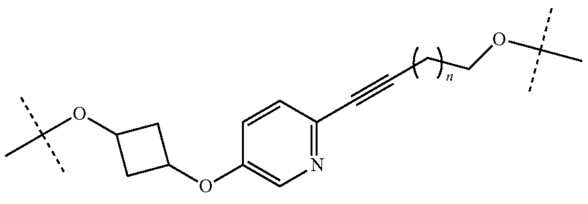
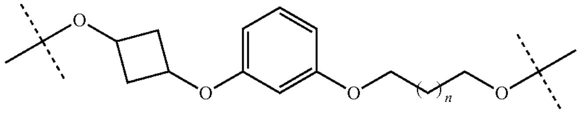
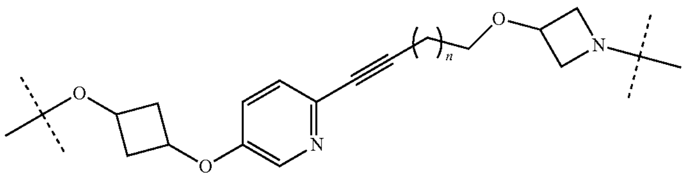
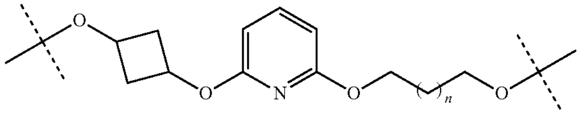
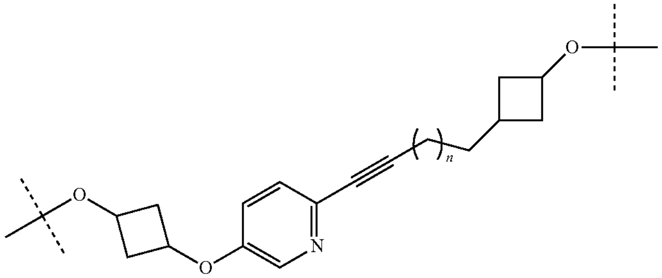
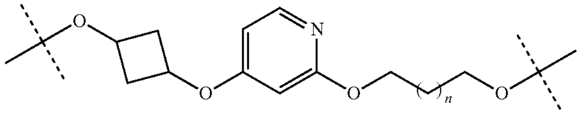
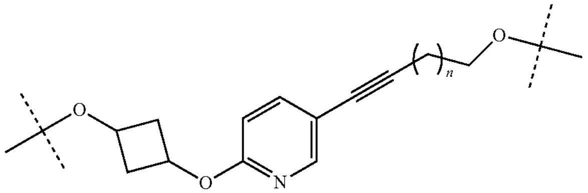
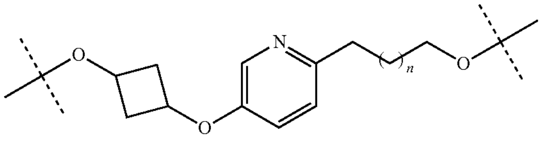
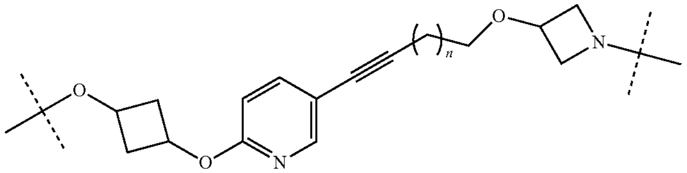
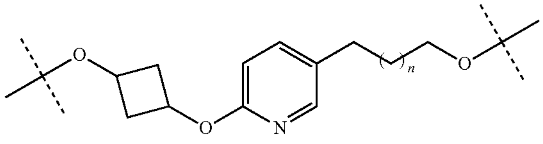
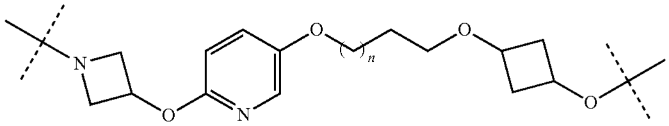

-continued
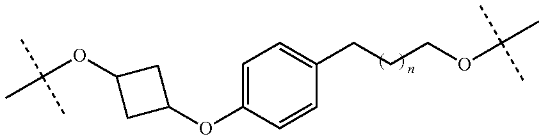
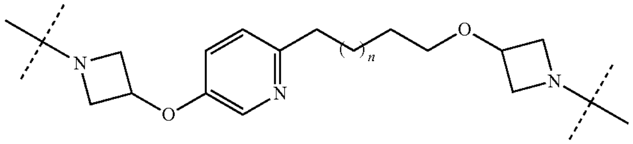
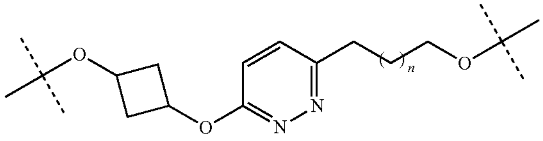
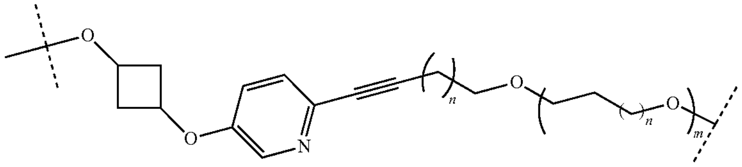
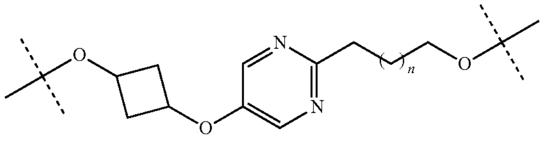
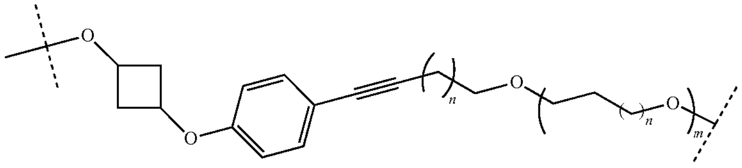
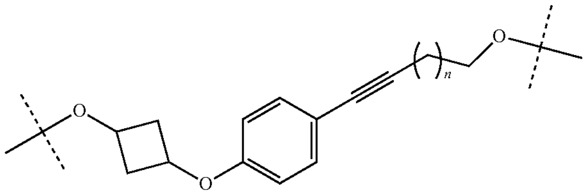
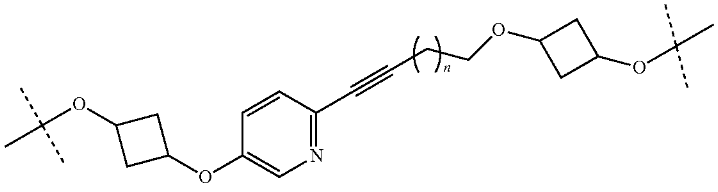
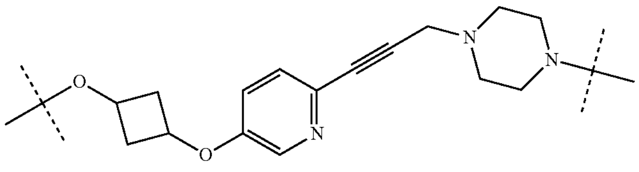
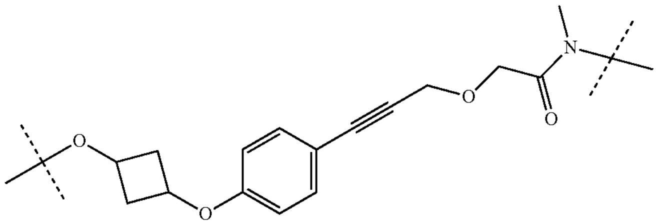

-continued
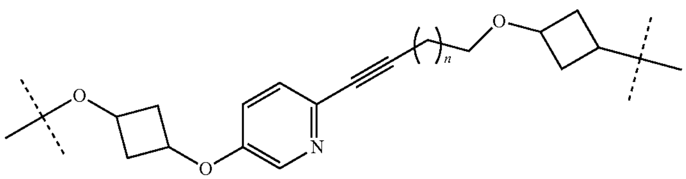
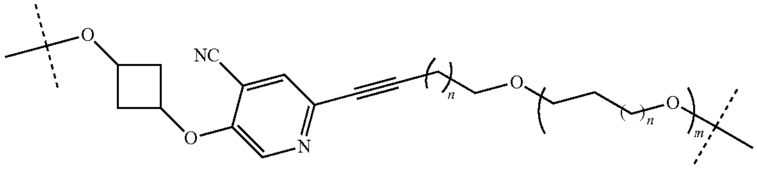
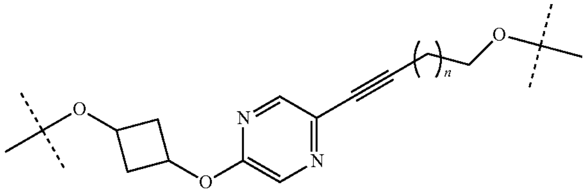
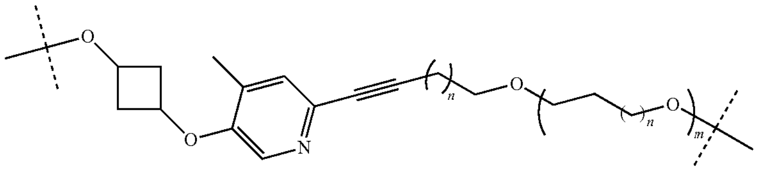
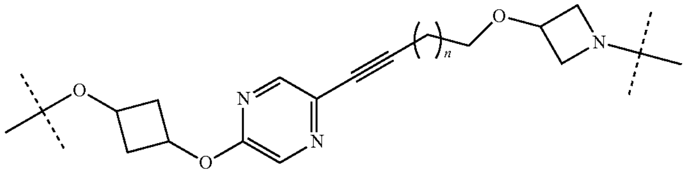
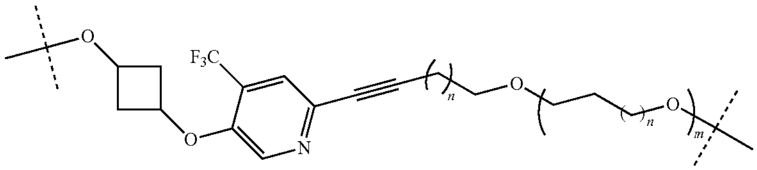
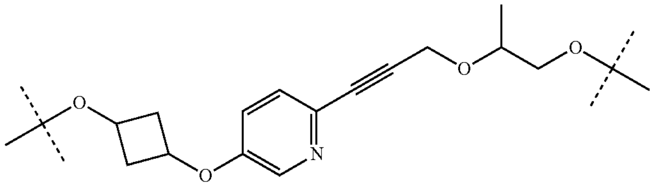
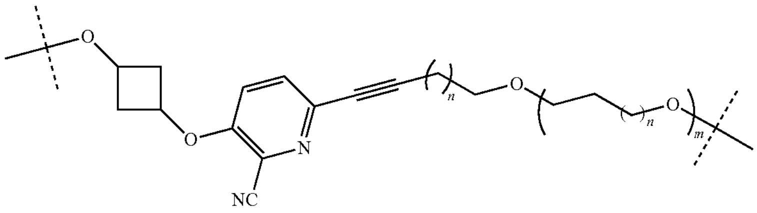
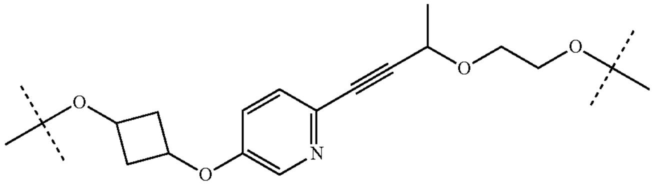

-continued
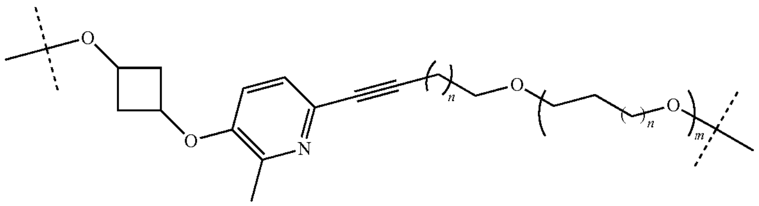
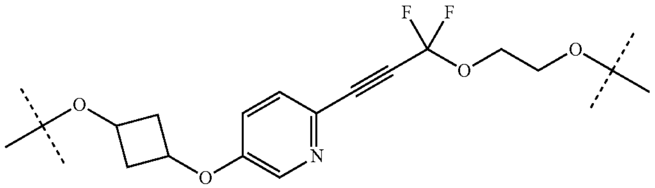
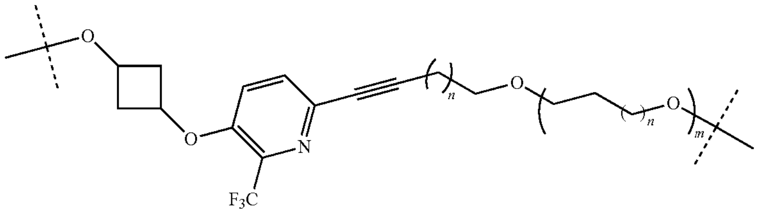
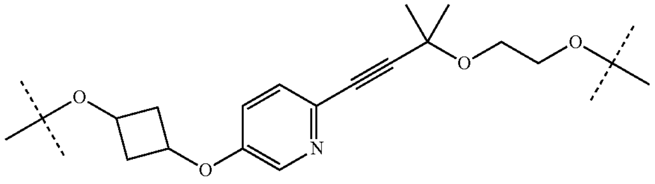
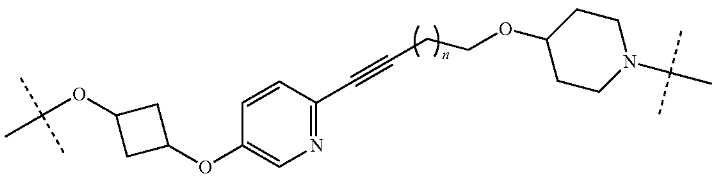
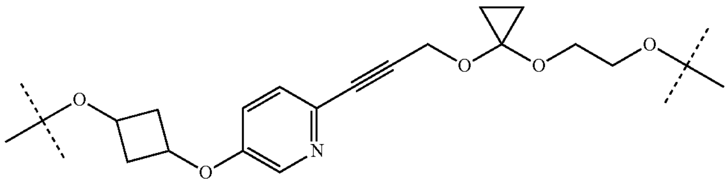
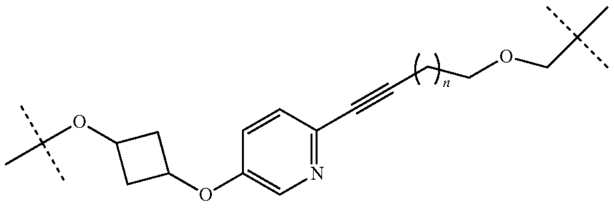
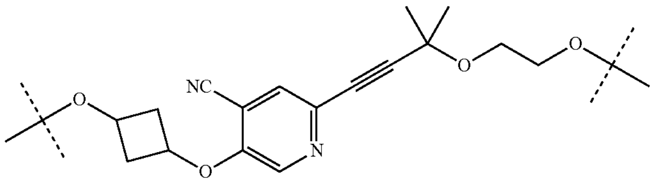
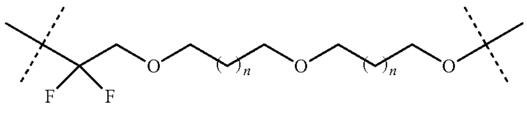

-continued
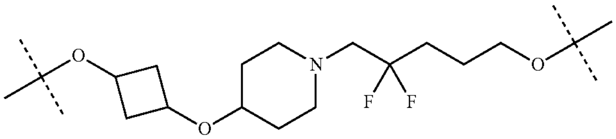
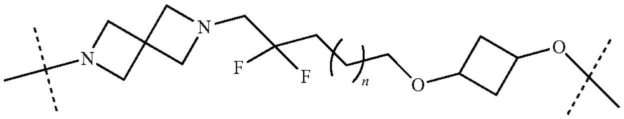
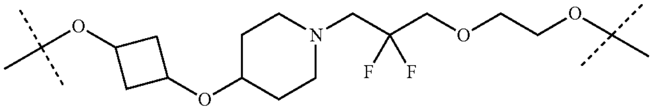
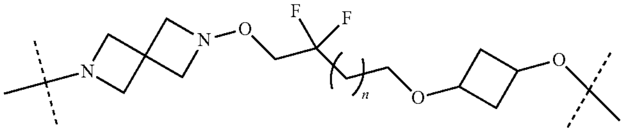
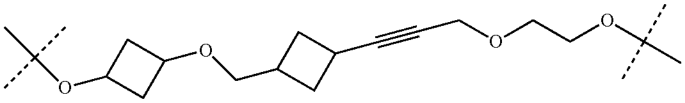
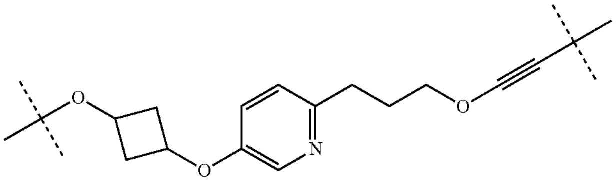
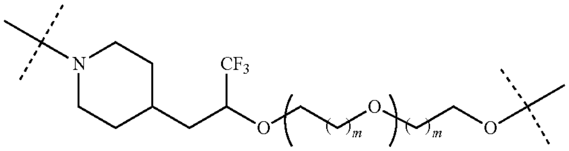
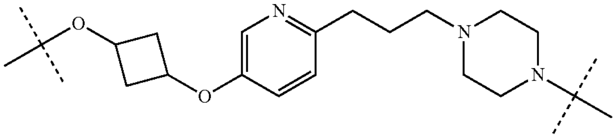
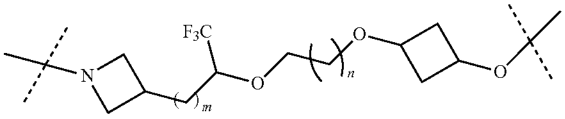
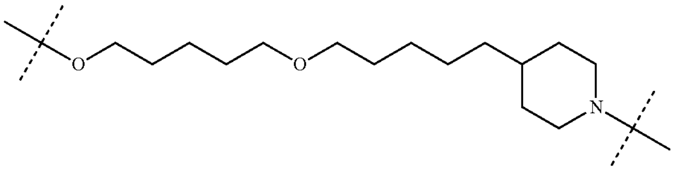
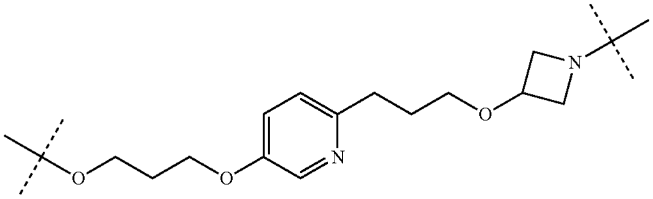

-continued
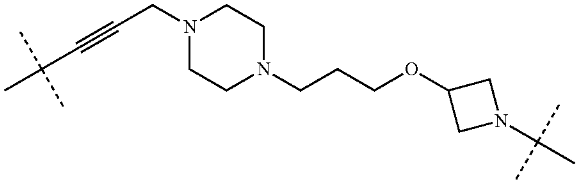
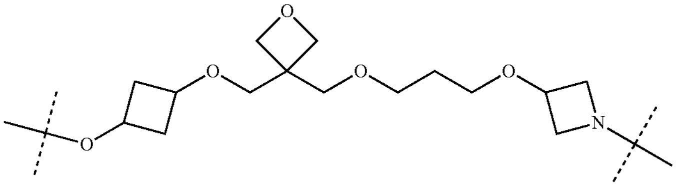
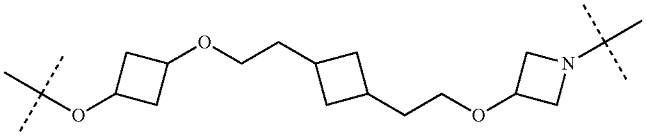
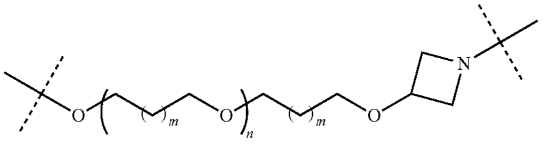
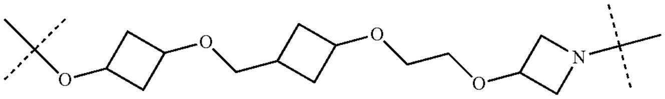
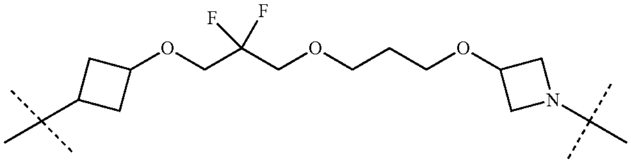
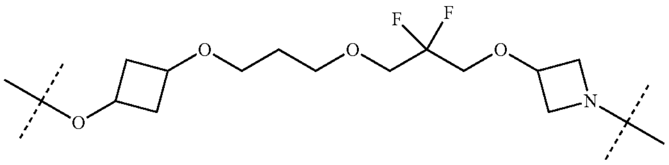
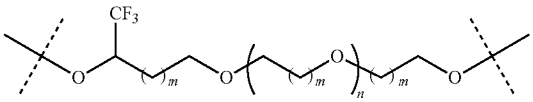
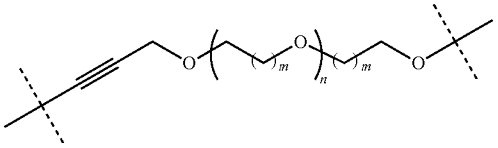
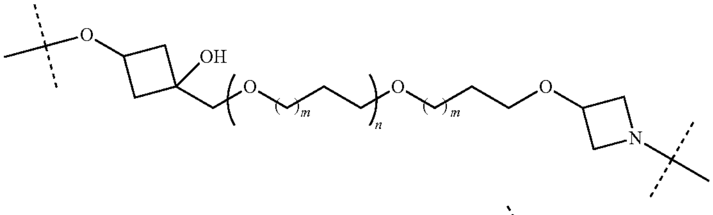
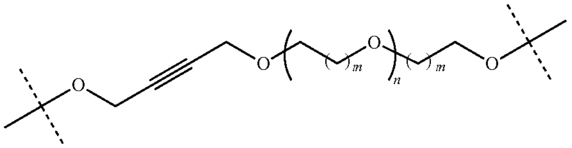
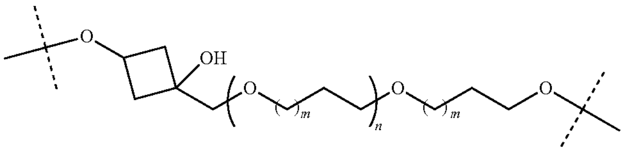

-continued
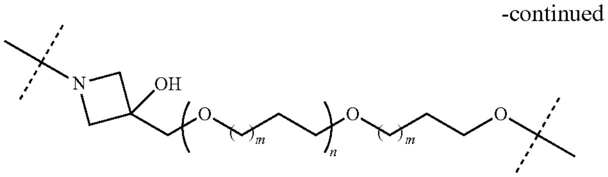
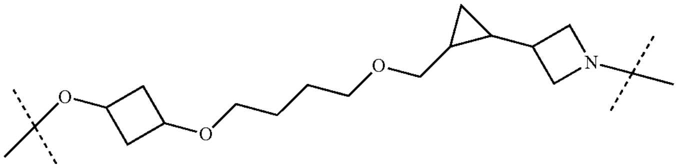
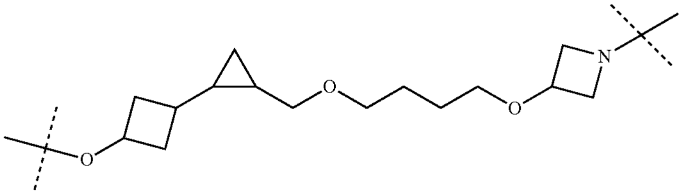
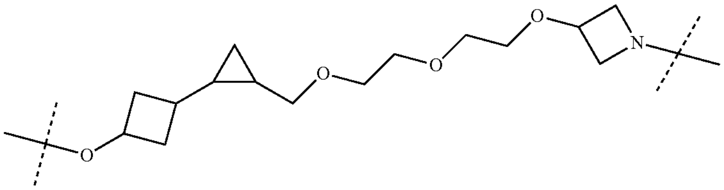
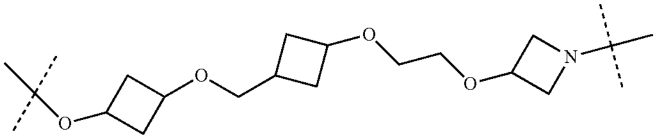
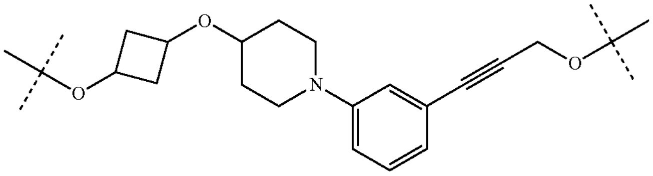
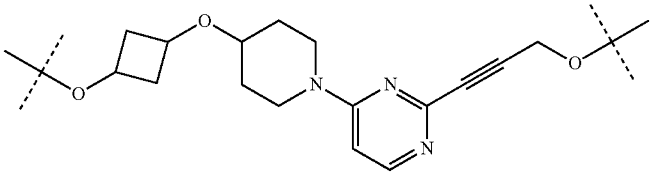
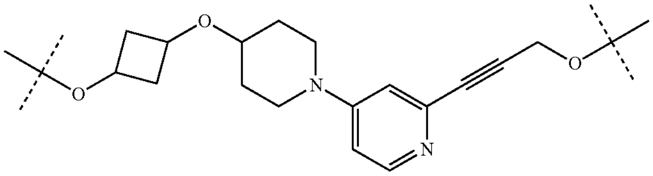
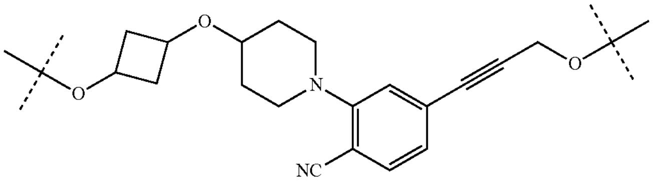
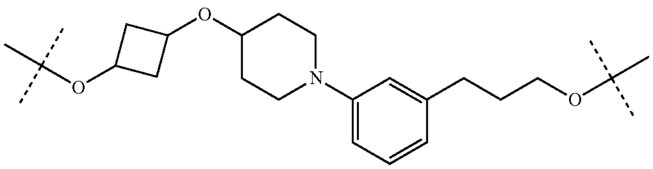

-continued
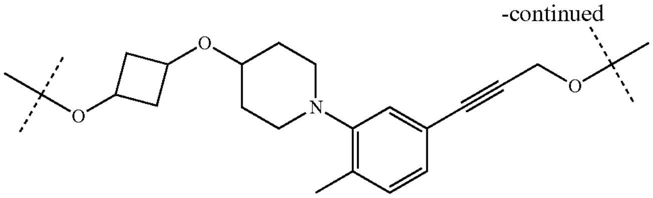
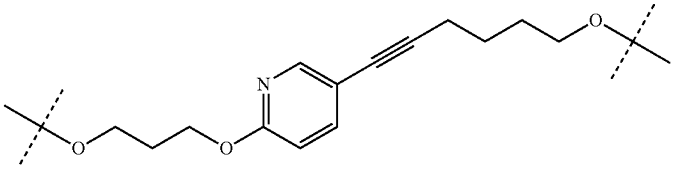
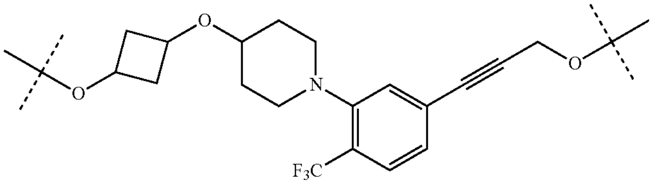
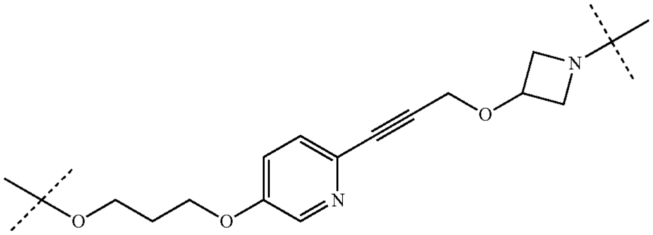
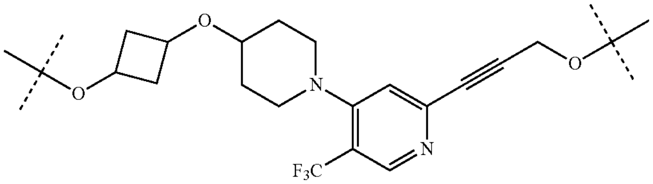
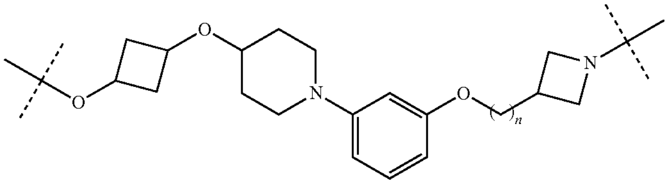
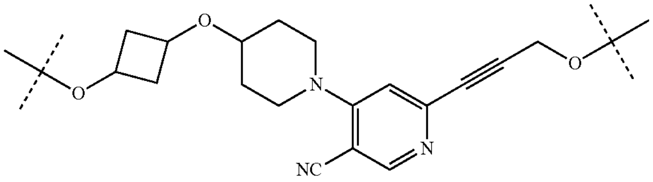
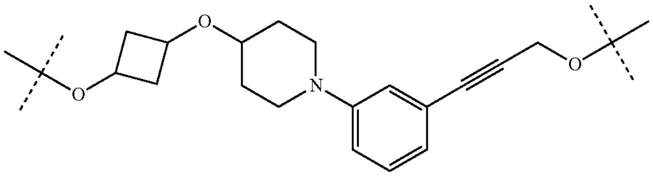
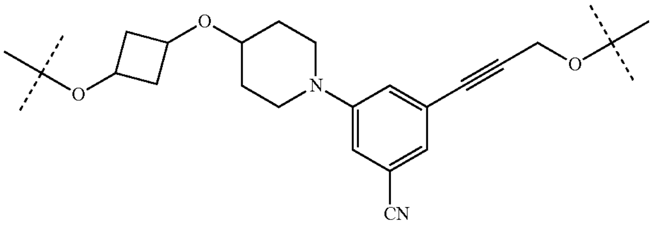

-continued
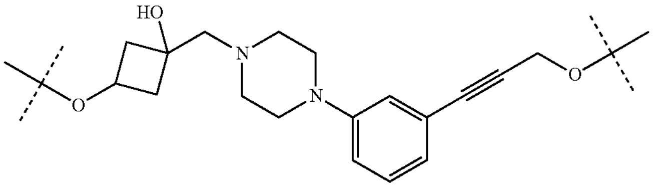
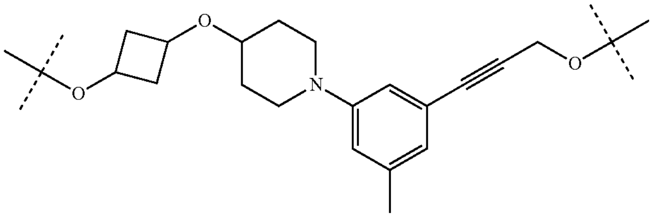
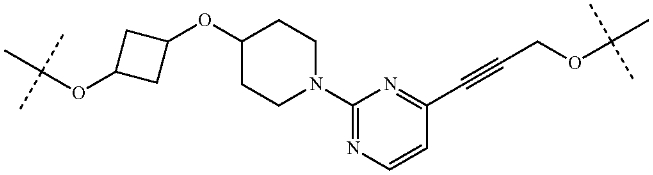
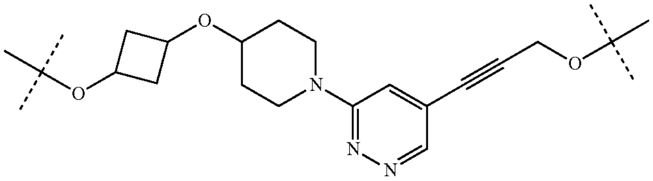
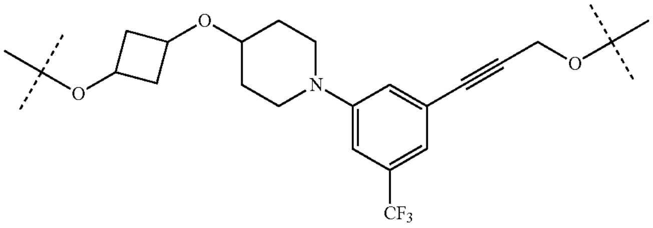
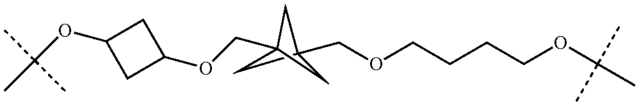
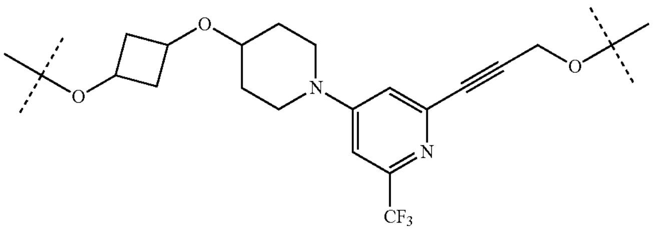
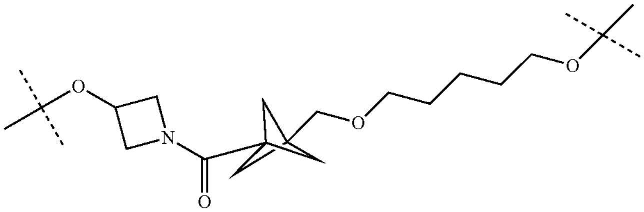

-continued
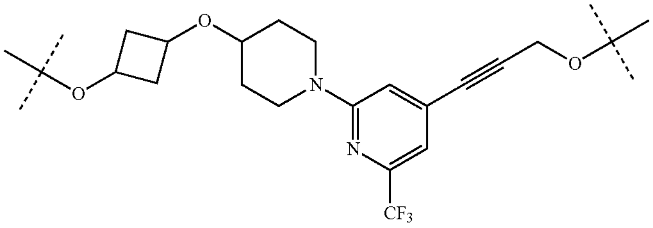
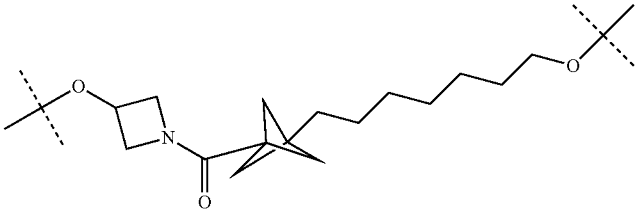
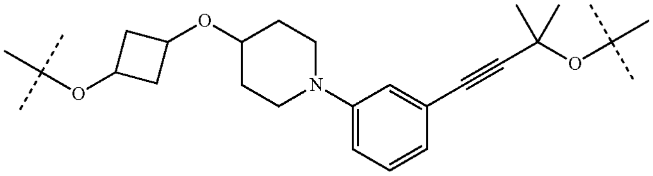
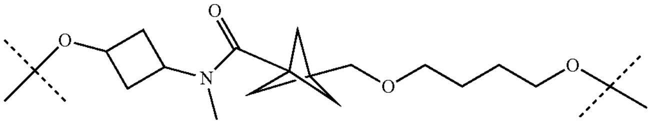
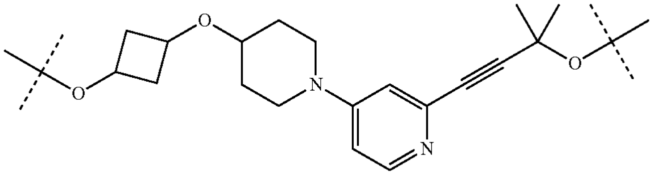
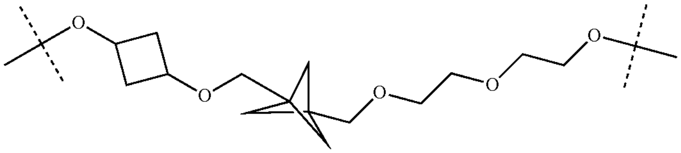
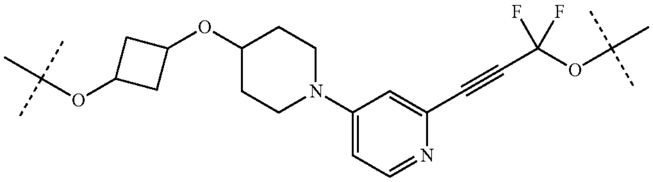
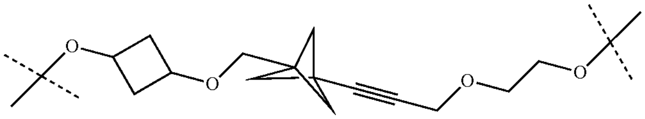
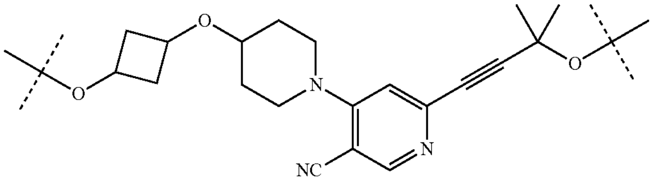
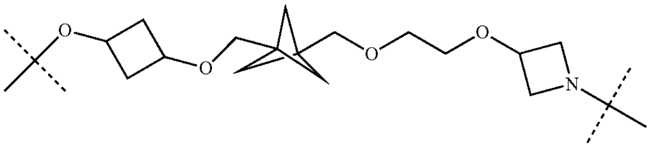

-continued
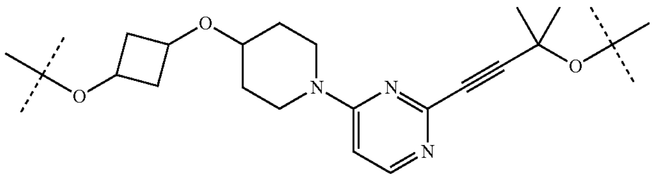
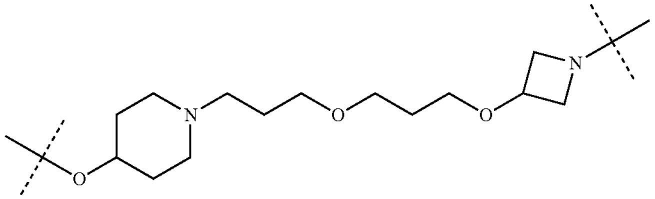
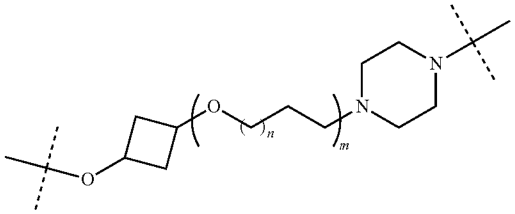
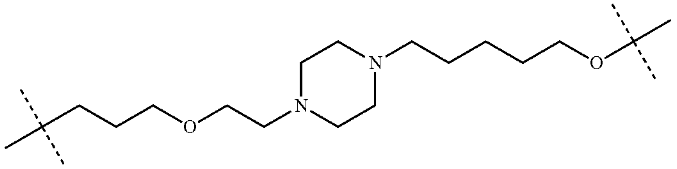
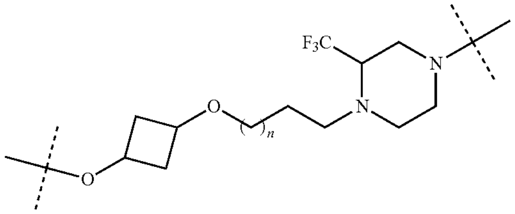
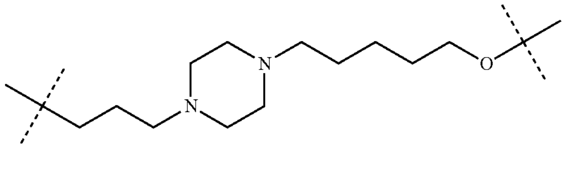
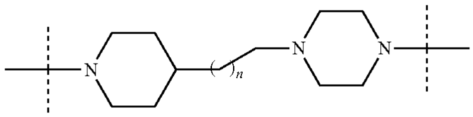
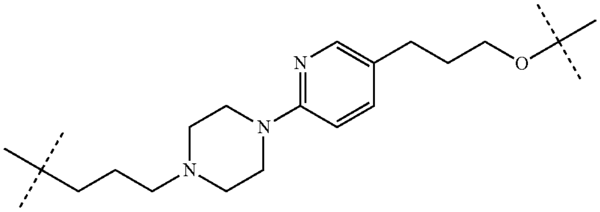
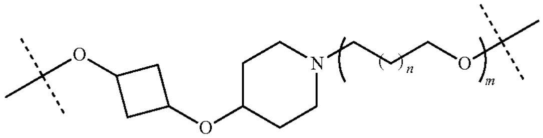
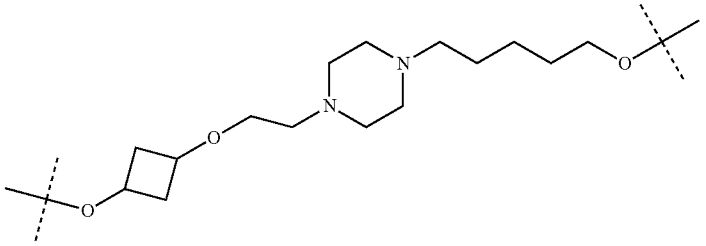
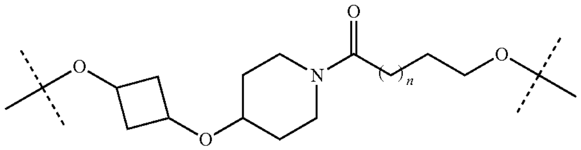

-continued
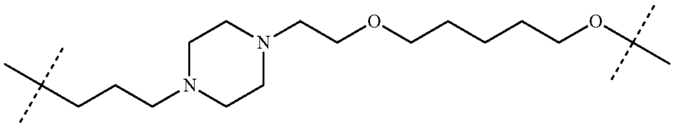
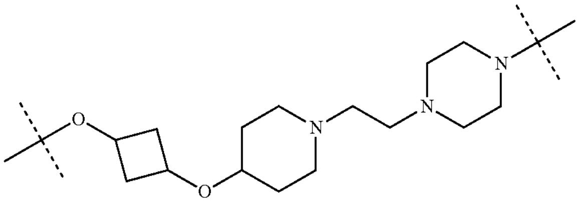
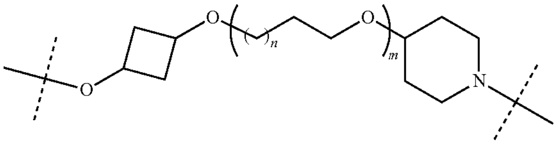
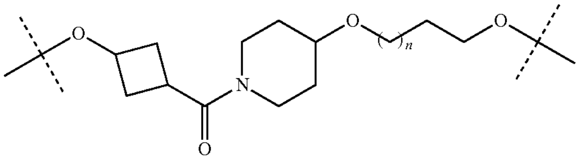
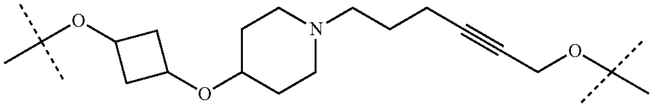
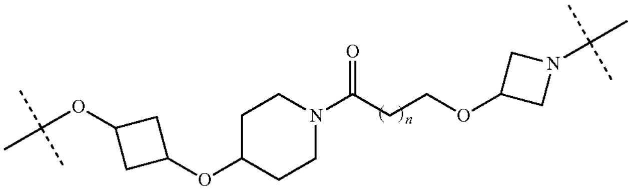
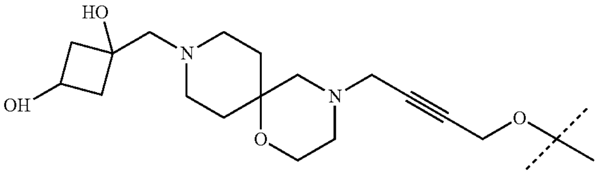
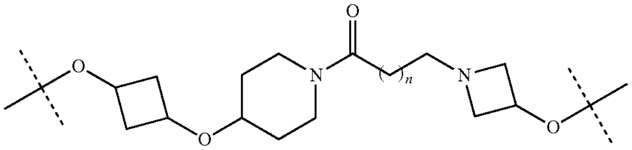
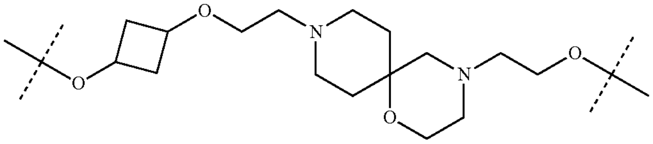
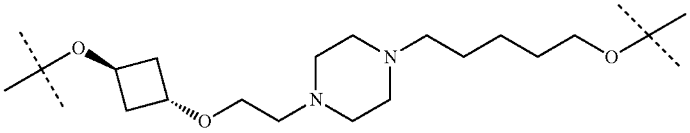
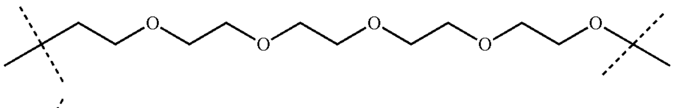
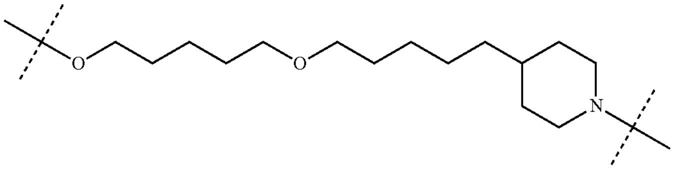

-continued
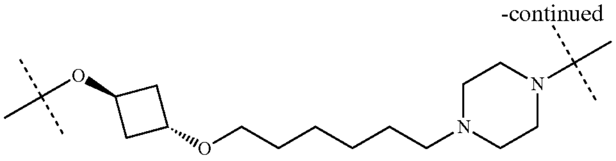
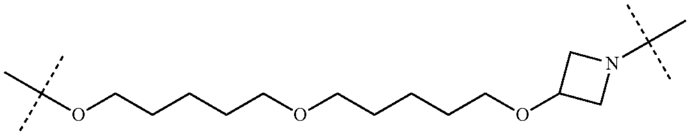
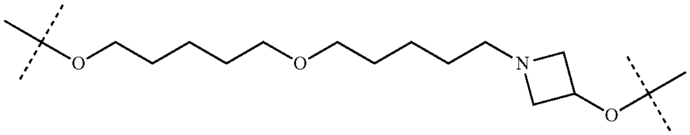
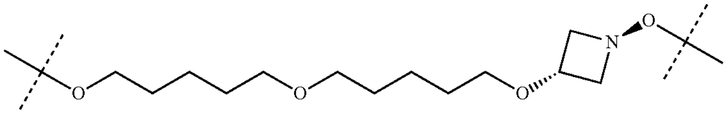
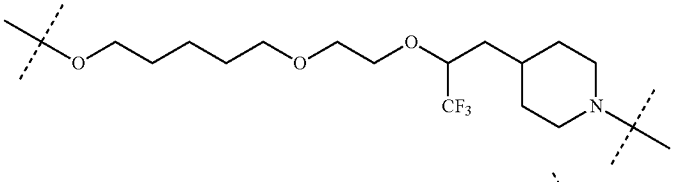
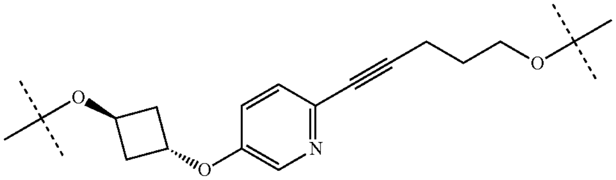,
wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, L is selected from the group consisting of:
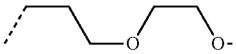;
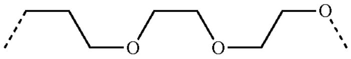;
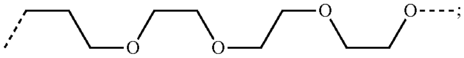;
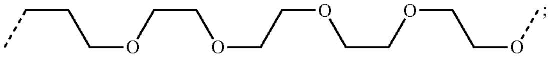;
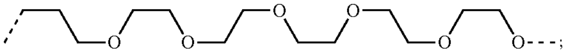;
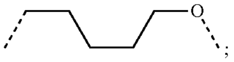; 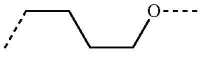;
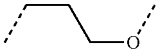; 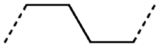; 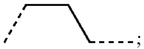;
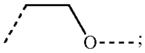; 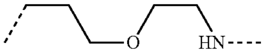;
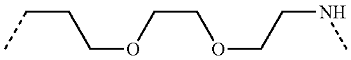;
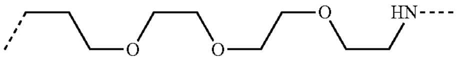;
-continued
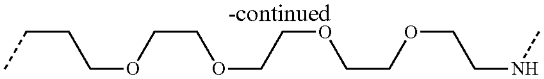;
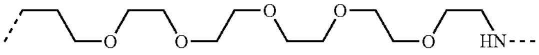;
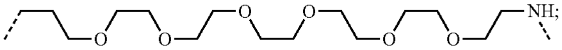;
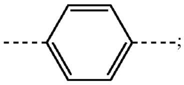; 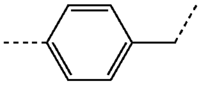;
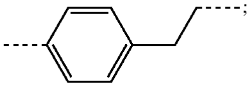;
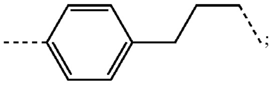;
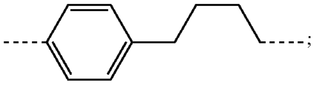;
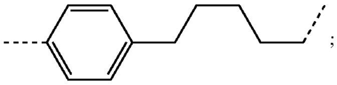;
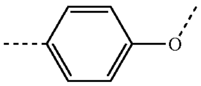; 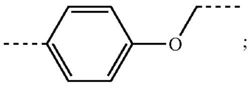;
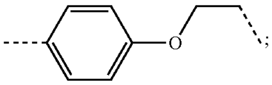;

-continued
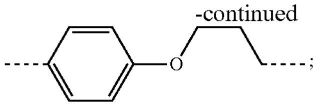
;
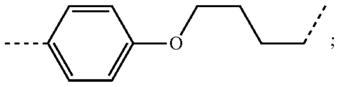
;
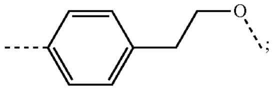
;
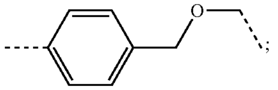
;
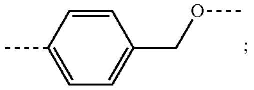
;
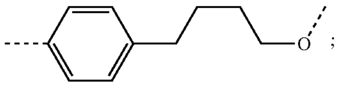
;
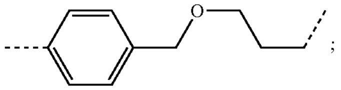
;
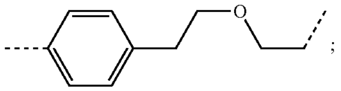
;
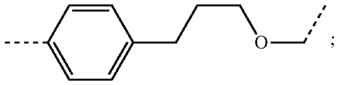
;
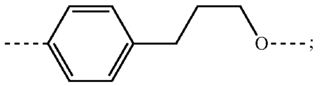
;
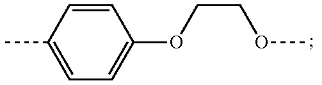
;
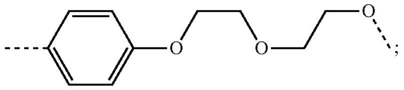
;
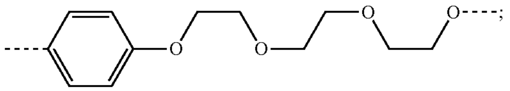
;
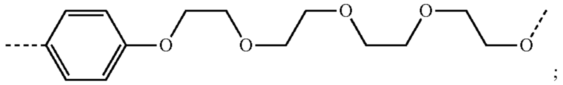
;
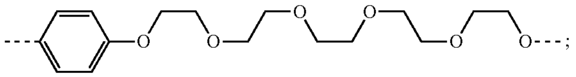
;
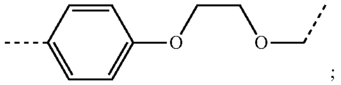
;
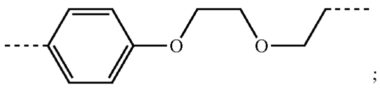
;
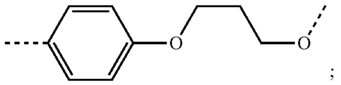
;
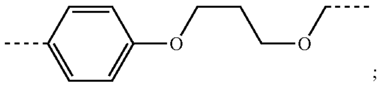
;
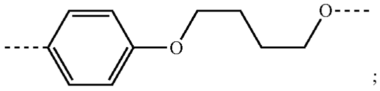
;
-continued
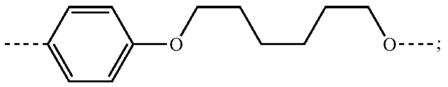
;
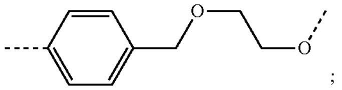
;
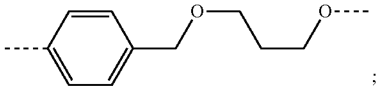
;
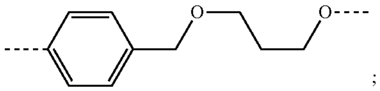
;
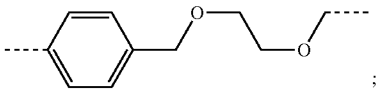
;
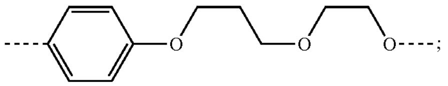
;
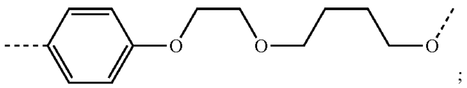
;
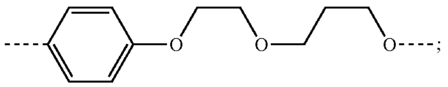
;
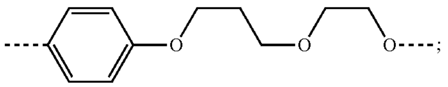
;
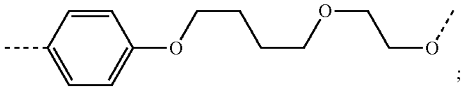
;
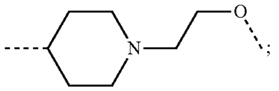
;
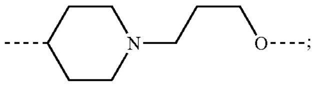
;
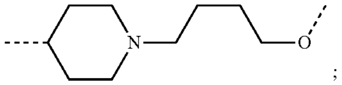
;
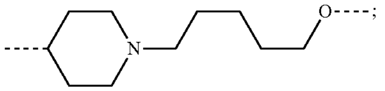
;
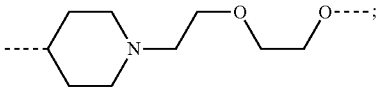
;
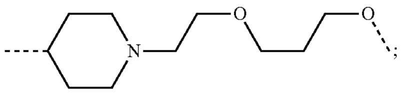
;
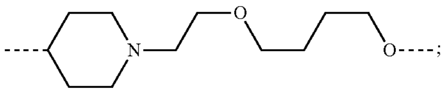
;
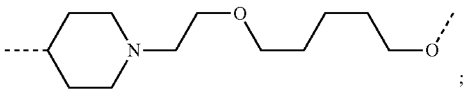
;
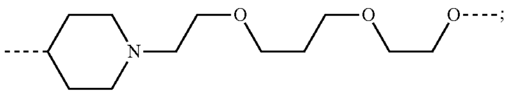
;

-continued
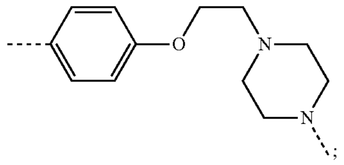
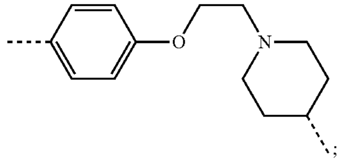
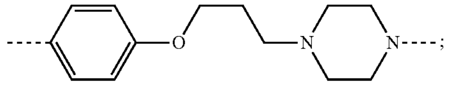
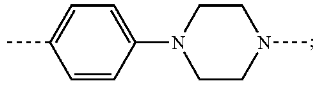
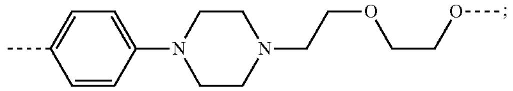
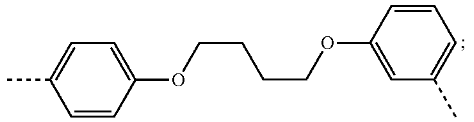
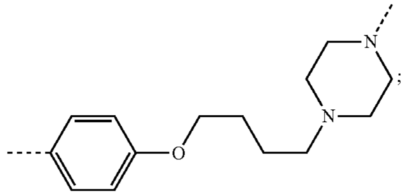
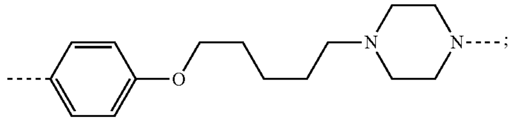
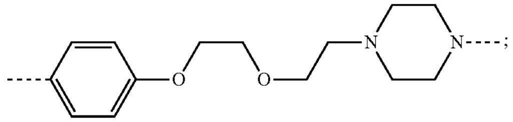
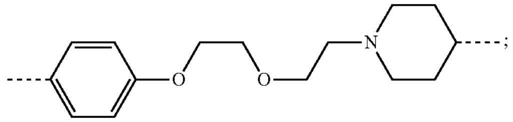
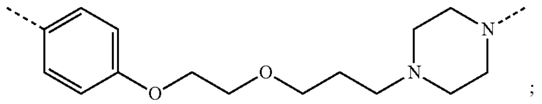
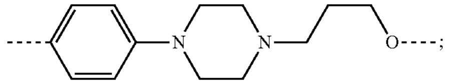
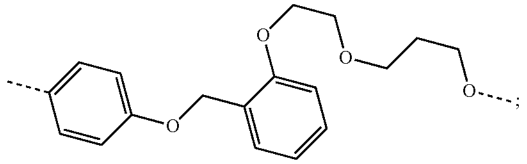
-continued
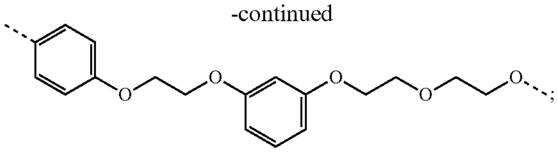
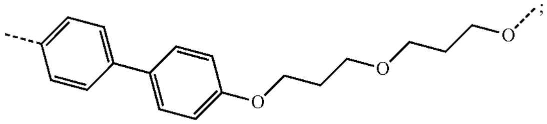
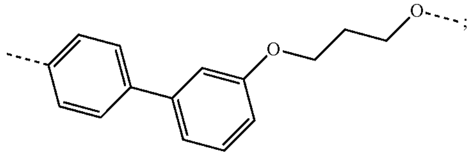
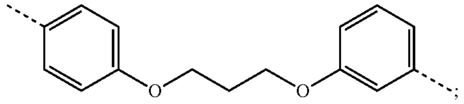
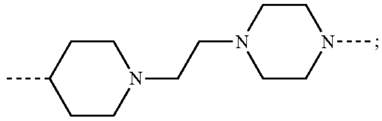
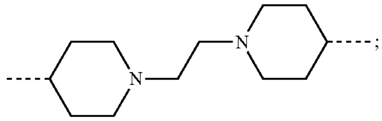
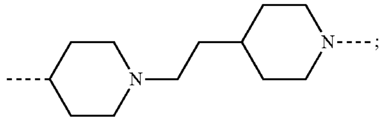
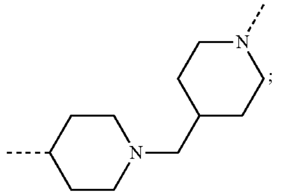
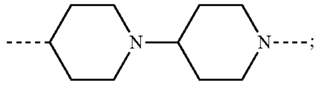
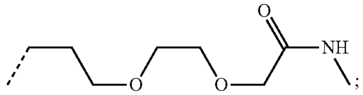
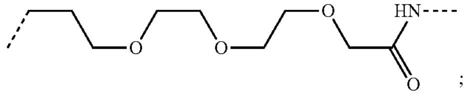
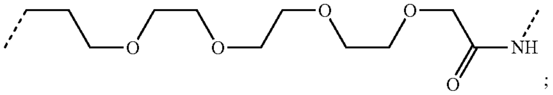
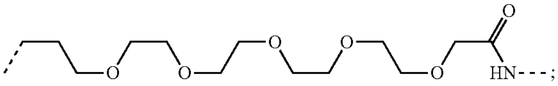
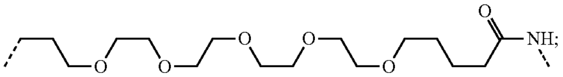
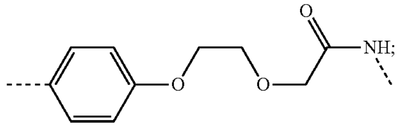

-continued
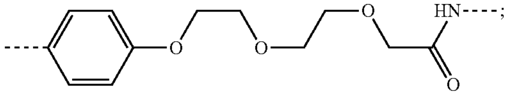
;
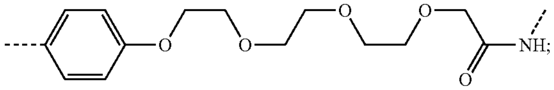
;
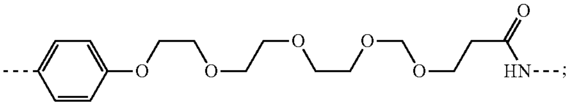
;
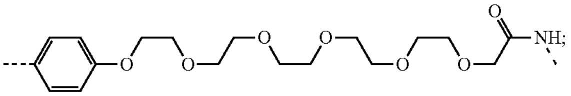
;
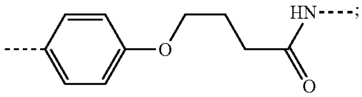
;
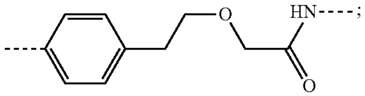
;
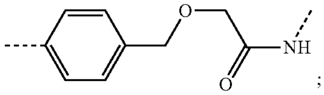
;
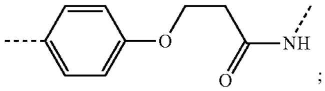
;
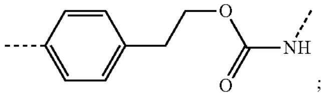
;
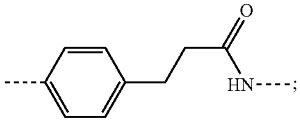
;
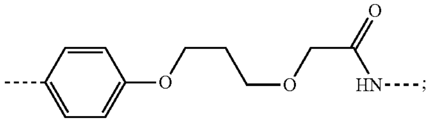
;
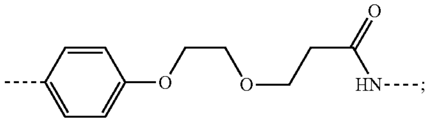
;
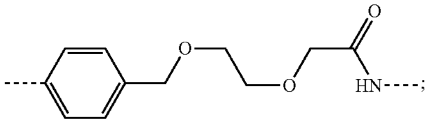
;
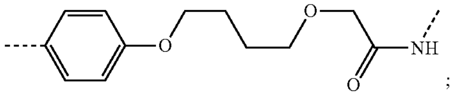
;
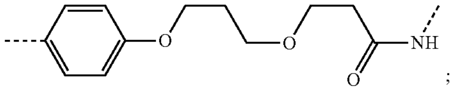
;
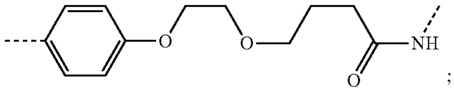
;
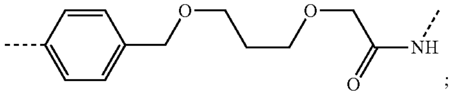
;
-continued
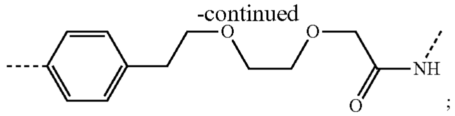
;
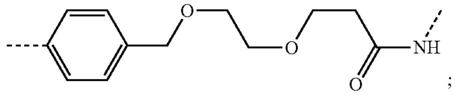
;
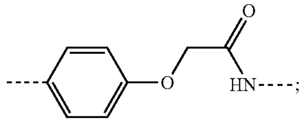
;
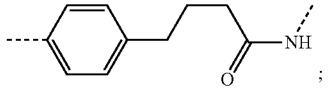
;
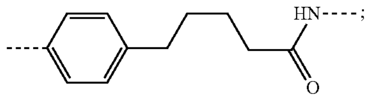
;
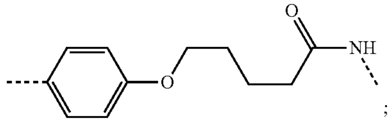
;
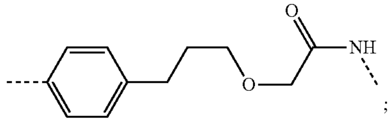
;
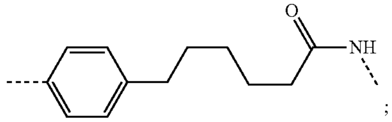
;
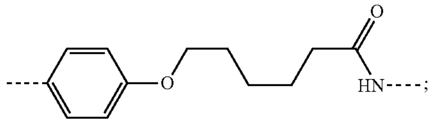
;
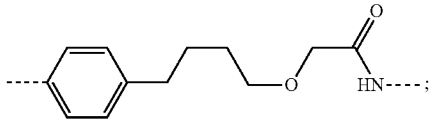
;
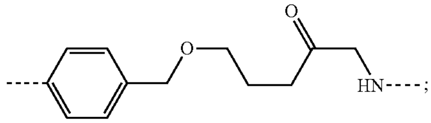
;
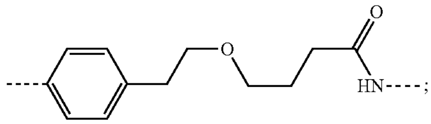
;
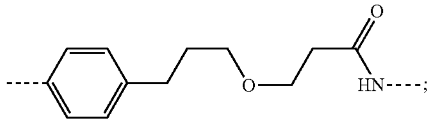
;
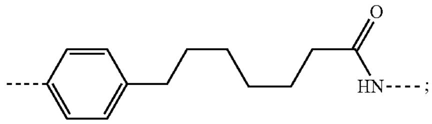
;
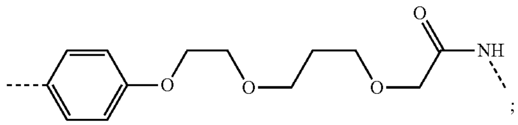
;

-continued
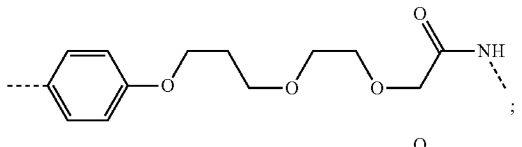
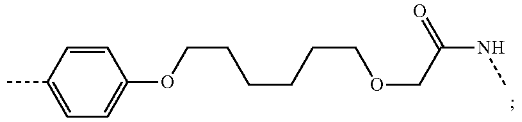
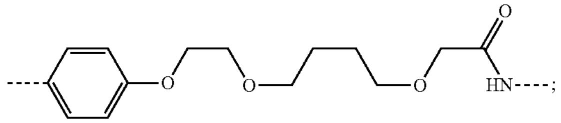
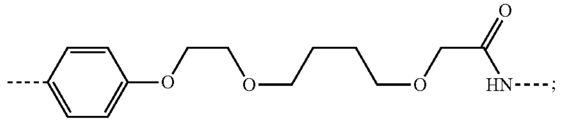
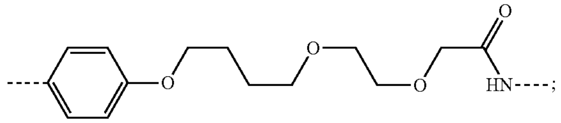
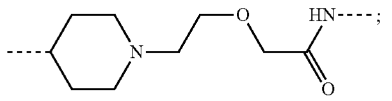
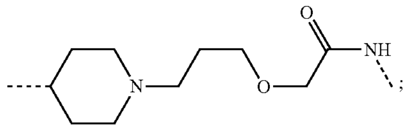
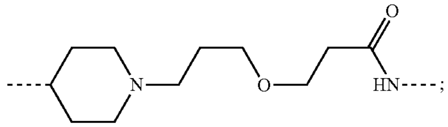
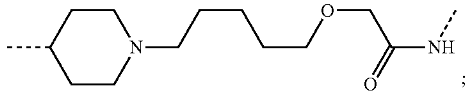
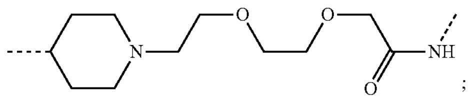
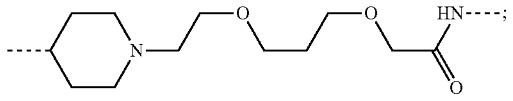
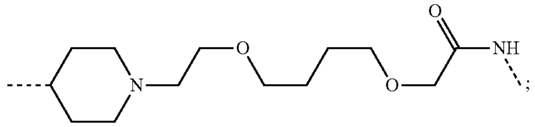
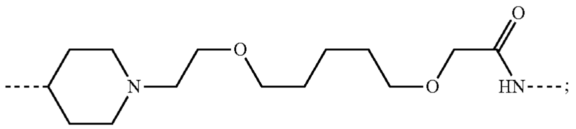
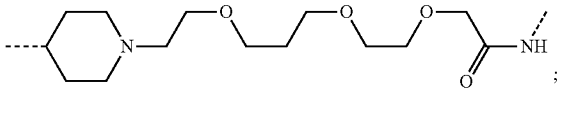
-continued
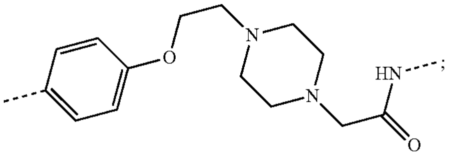
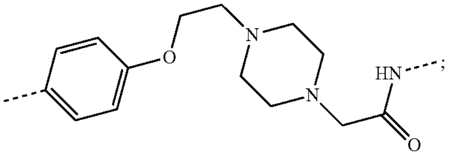
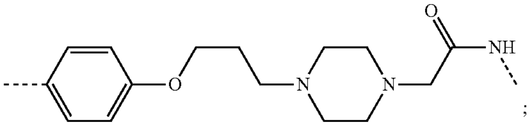
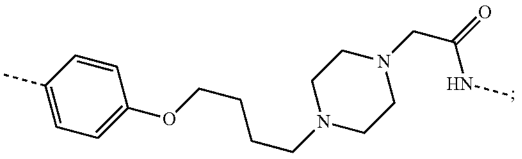
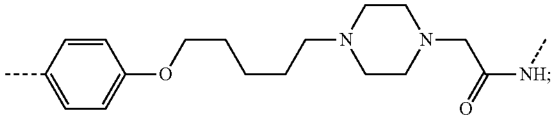
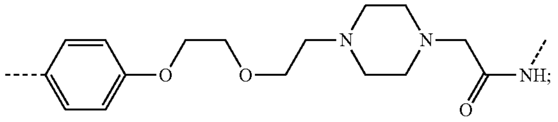
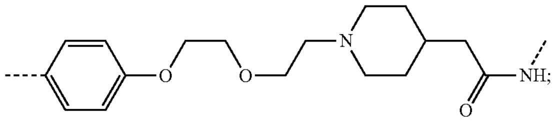
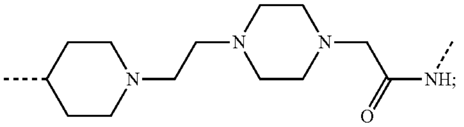
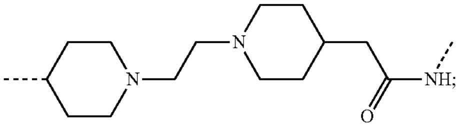
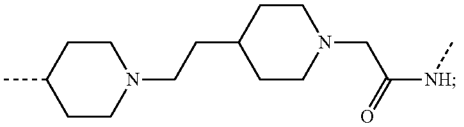
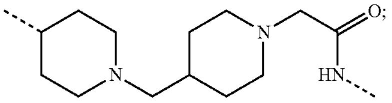
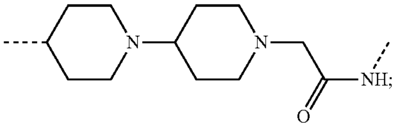
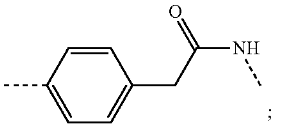

-continued
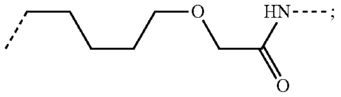;
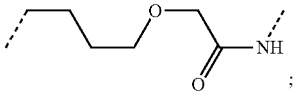;
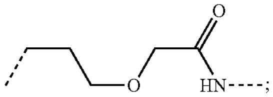;
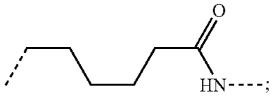; 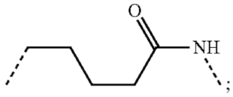;
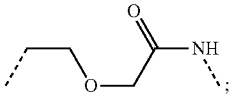;
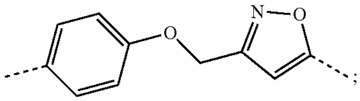;
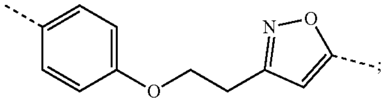;
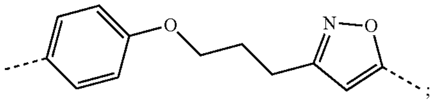;
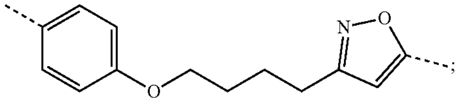;
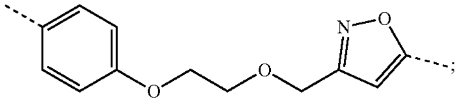;
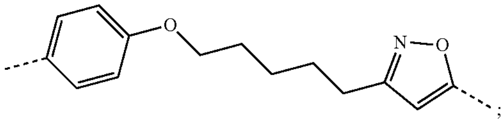;
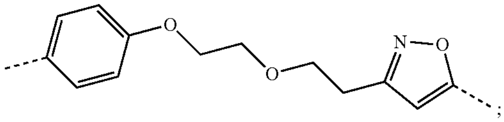;
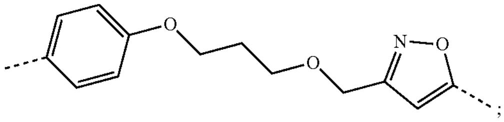;
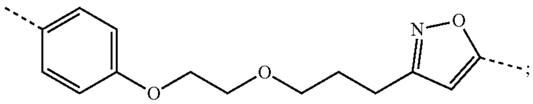;
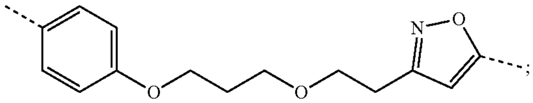;
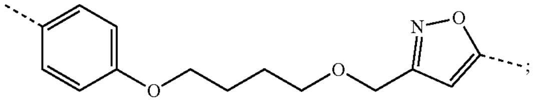;
-continued
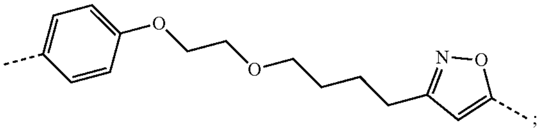;
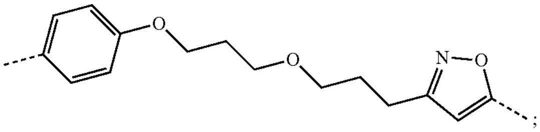;
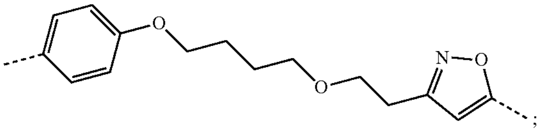;
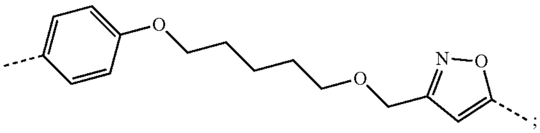;
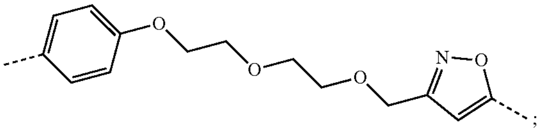;
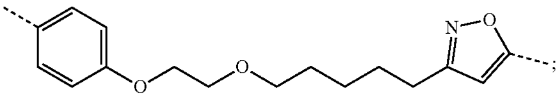;
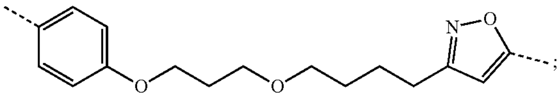;
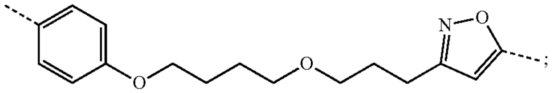;
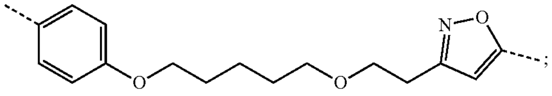;
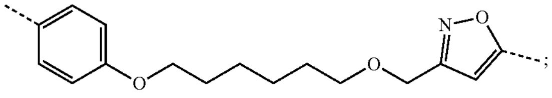;
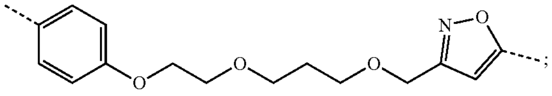;
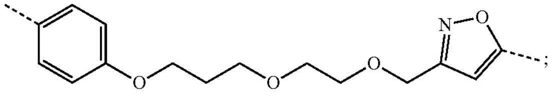;
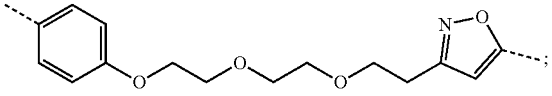;
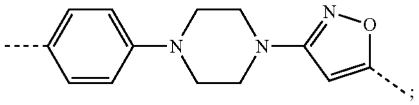;
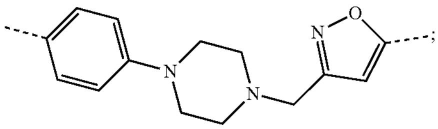;

-continued
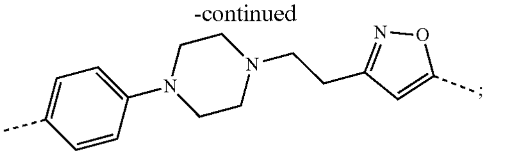
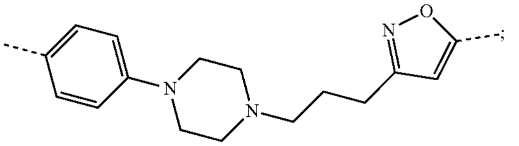
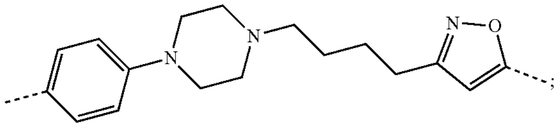
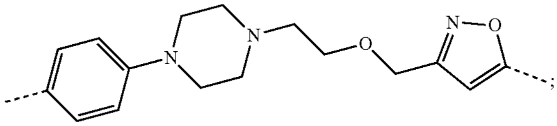
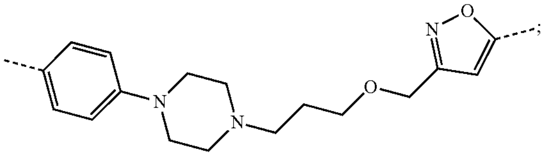
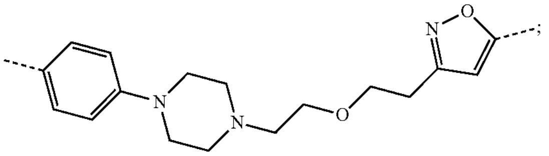
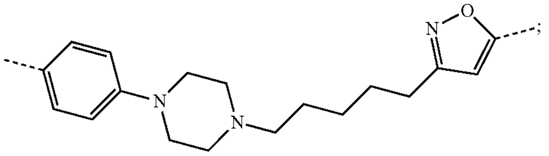
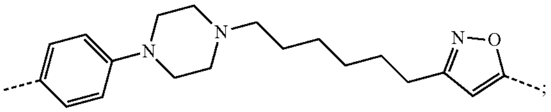
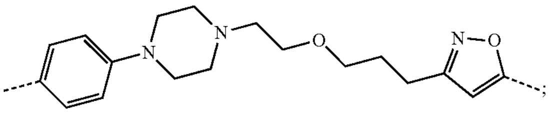
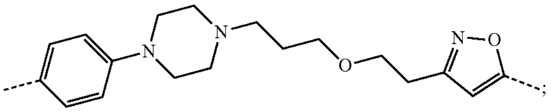
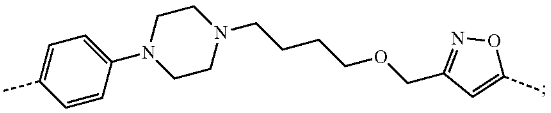
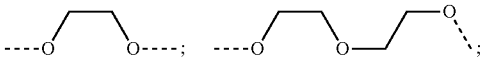
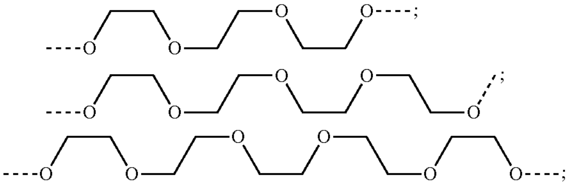
-continued
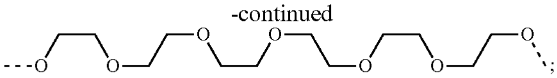
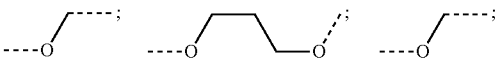
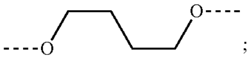
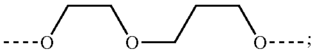
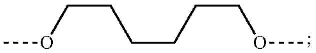
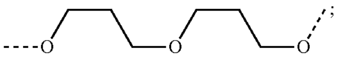
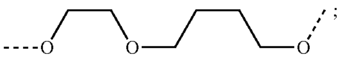
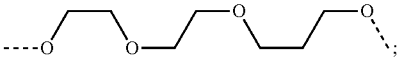
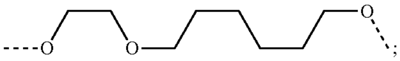
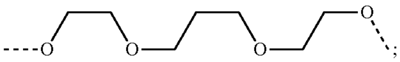
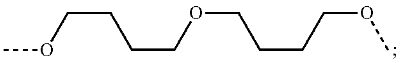
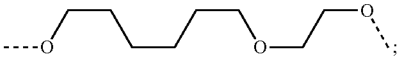
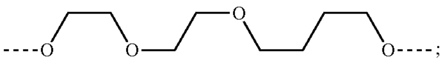
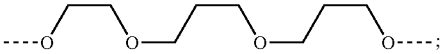
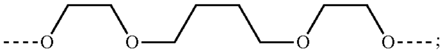
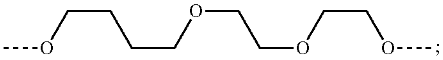
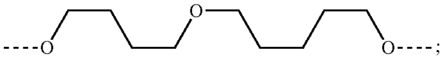
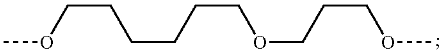
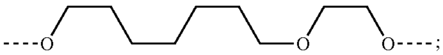
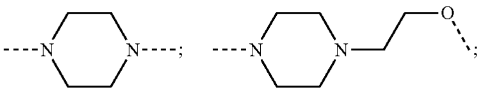
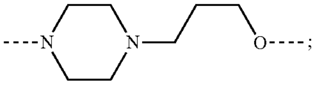
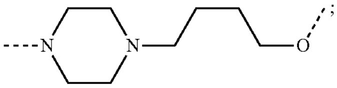
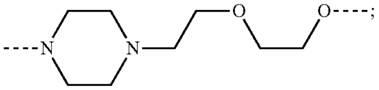
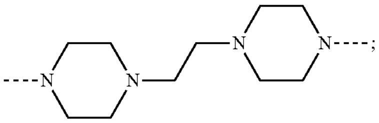
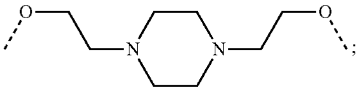

-continued
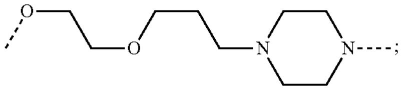
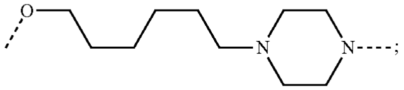
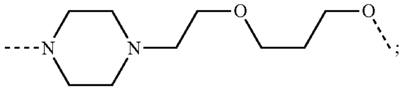
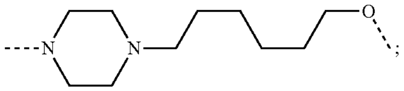
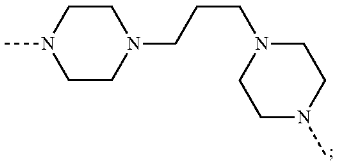
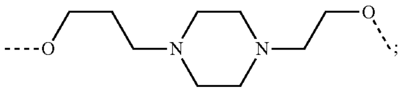
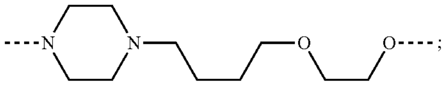
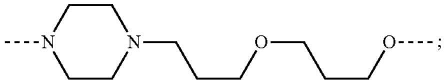
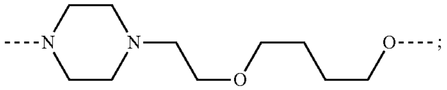
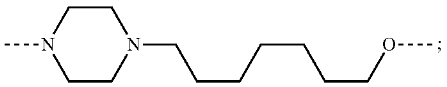
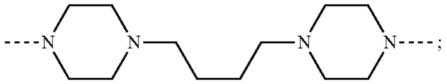
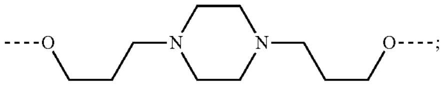
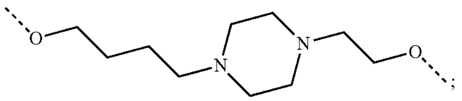
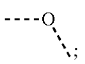
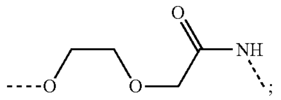
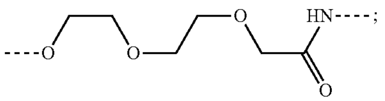
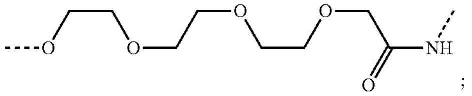
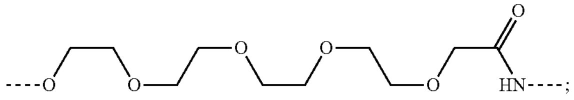
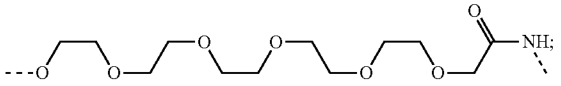
-continued
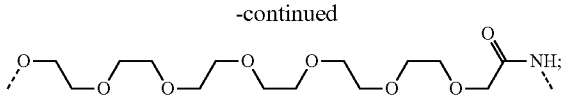
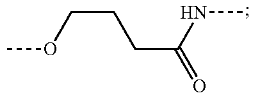
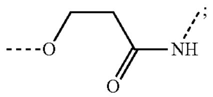
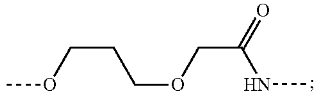
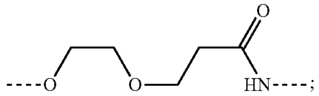
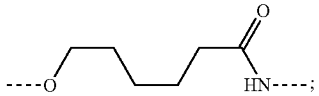
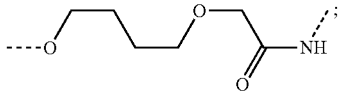
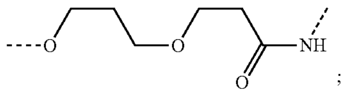
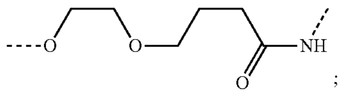
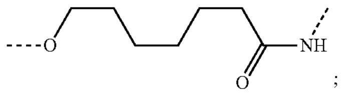
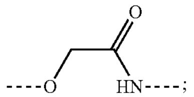
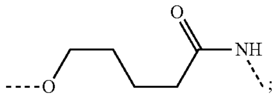
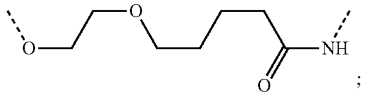
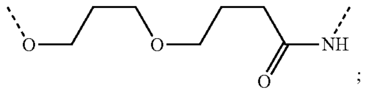
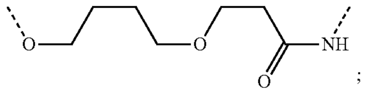
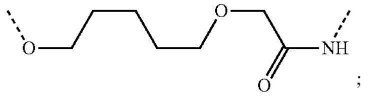
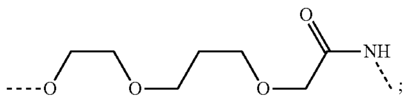
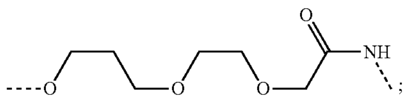
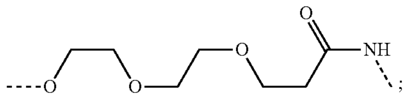
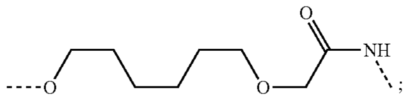

-continued
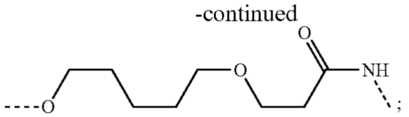
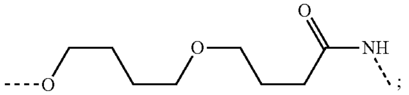
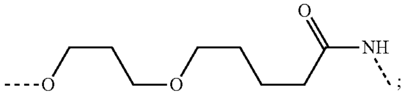
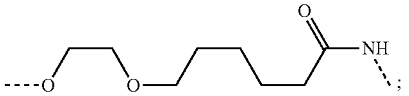
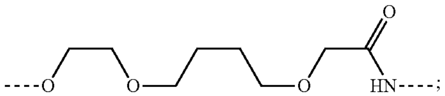
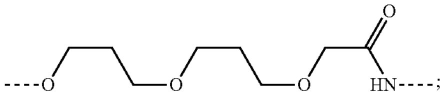
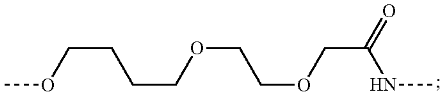
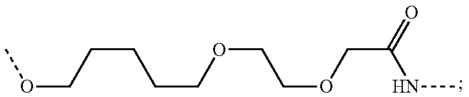
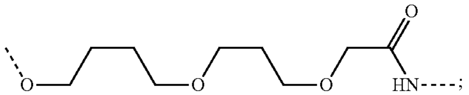
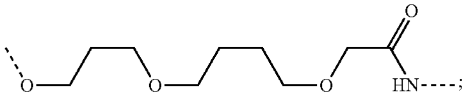
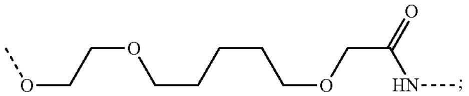
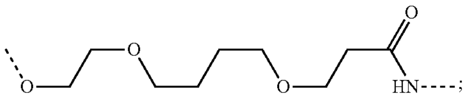
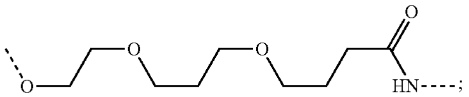
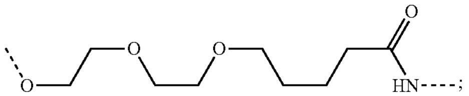
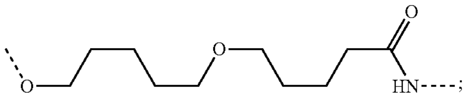
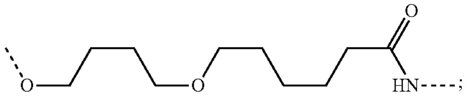
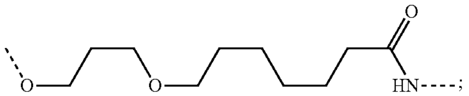
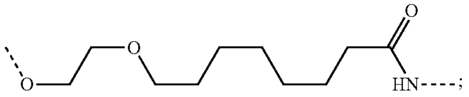
-continued
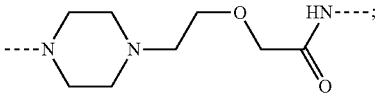
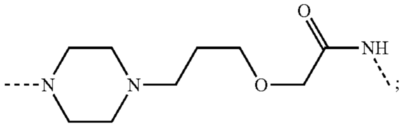
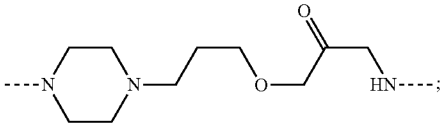
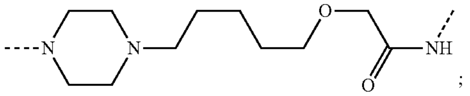
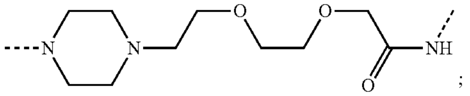
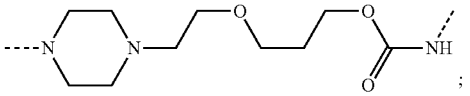
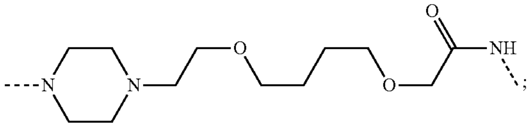
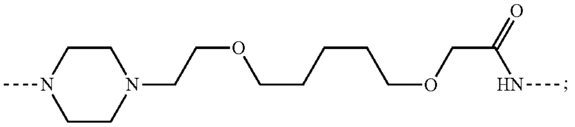
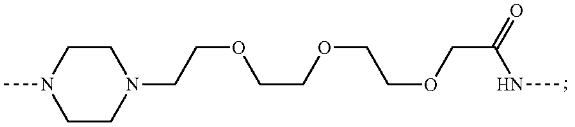
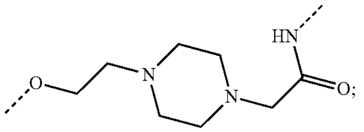
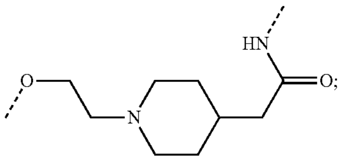
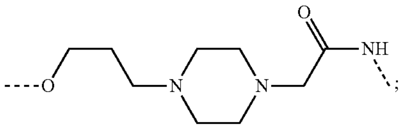
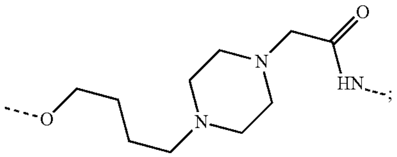
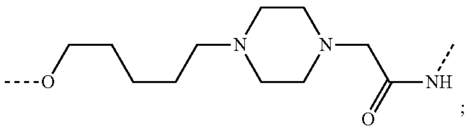

-continued
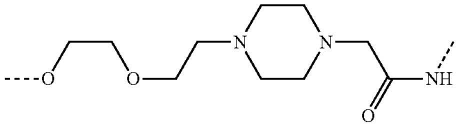
;
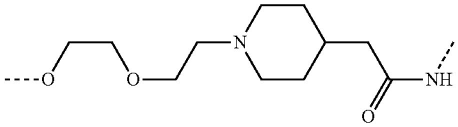
;
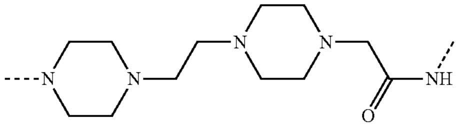
;
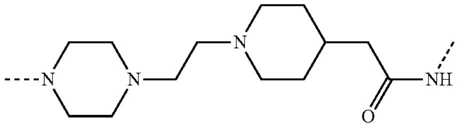
;
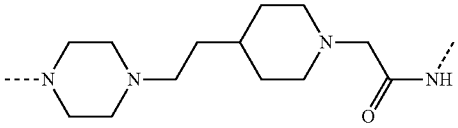
;
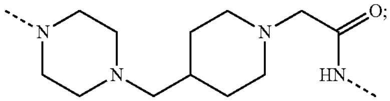
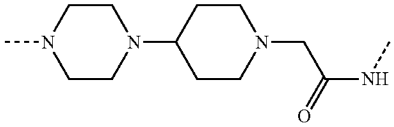
;
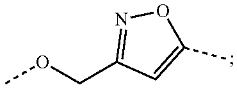
;
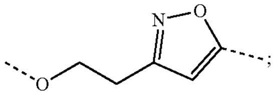
;
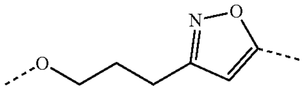
;
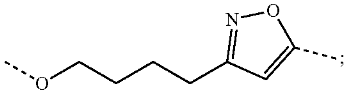
;
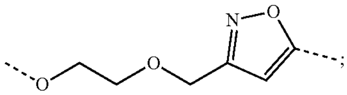
;
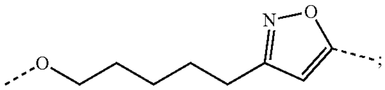
;
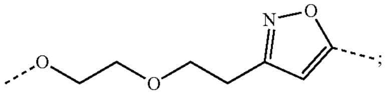
;
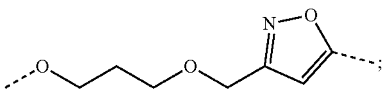
;
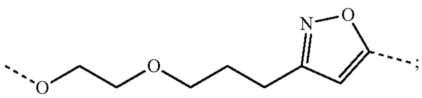
;
-continued
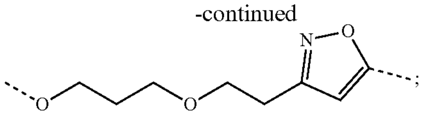
;
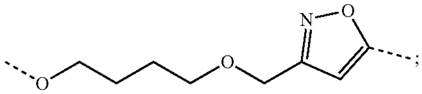
;
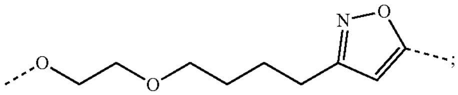
;
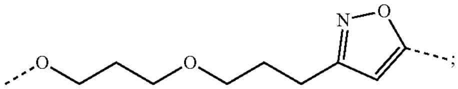
;
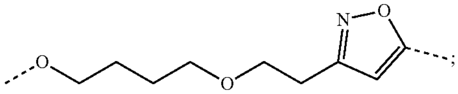
;
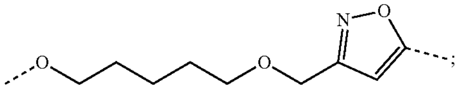
;
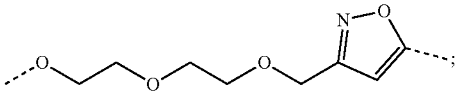
;
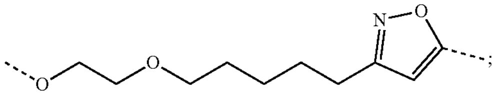
;
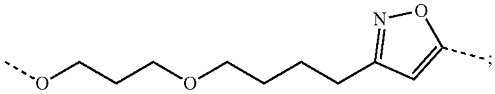
;
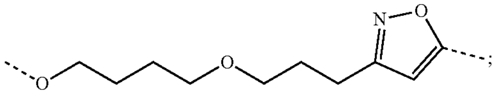
;
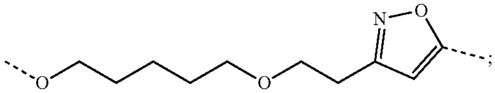
;
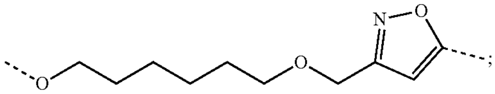
;
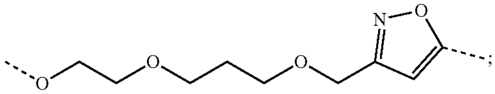
;
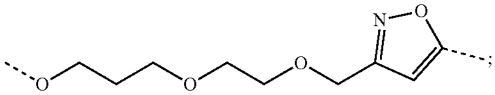
;
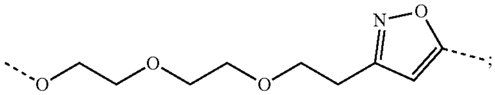
;
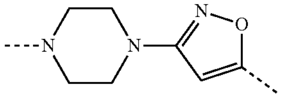
;
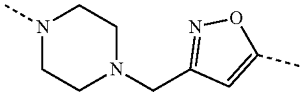
;
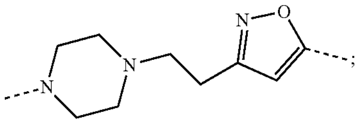
;

-continued

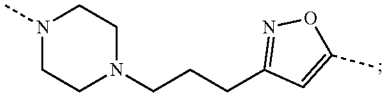
;

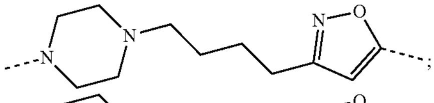
;

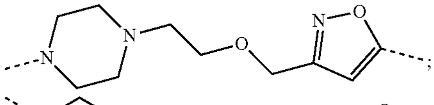
;

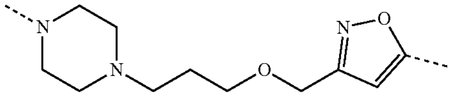
;

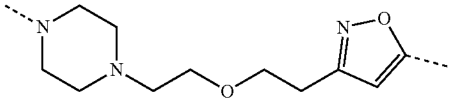
;

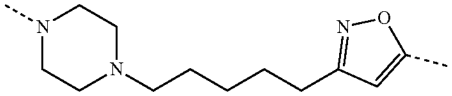
;

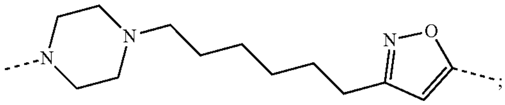
;

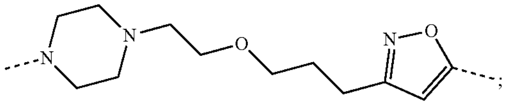
;

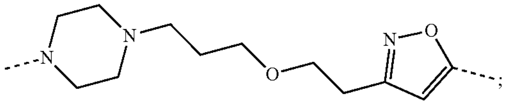
;

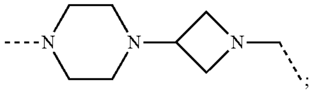
; and

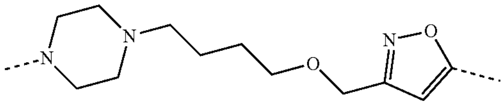
.

In additional embodiments, the linker (L) comprises a structure selected from, but not limited to the structure shown below, where a dashed line indicates the attachment point to the PTM or ULM moieties.

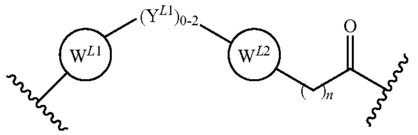
or

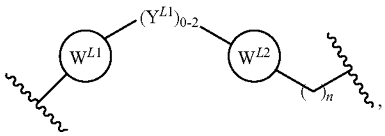
, wherein:

$W^{L1}$ and $W^{L2}$ are each independently a 4-8 membered ring with 0-4 heteroatoms, optionally substituted with $R^Q$, each $R^Q$ is independently a H, halo, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;

$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);

n is 0-10; and a dashed line indicates the attachment point to the PTM or ULM moieties.

In additional embodiments, the linker (L) comprises a structure selected from, but not limited to the structure shown below, where a dashed line indicates the attachment point to the PTM or ULM moieties.

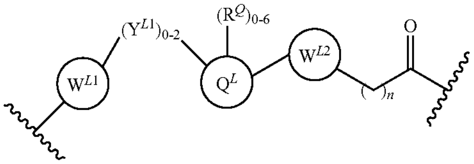
or

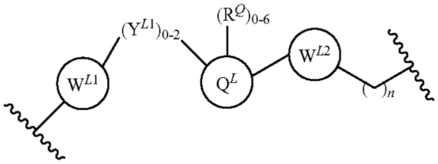
, wherein:

$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In additional embodiments, the linker group is optionally substituted (poly)ethyleneglycol having between 1 and about 100 ethylene glycol units (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, etc., ethylene glycol units), between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency. For example, in any aspect or embodiment described herein, the linker (L) has a chemical structure selected from:

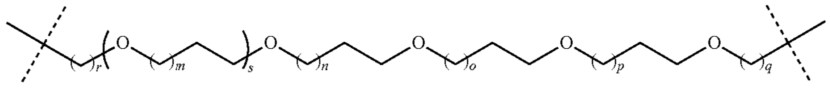

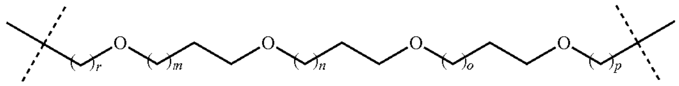

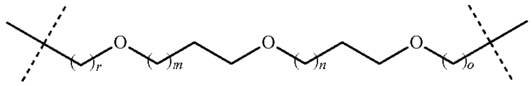
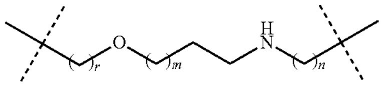

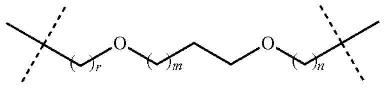
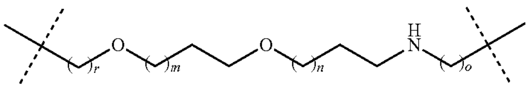

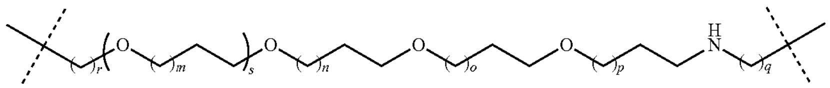

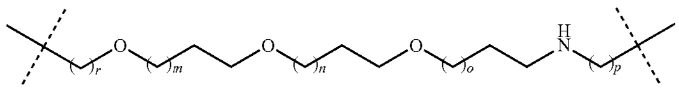

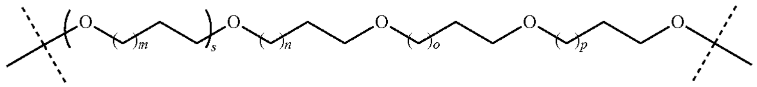

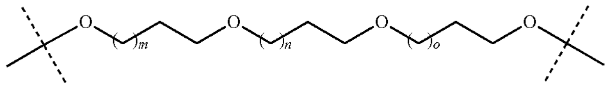
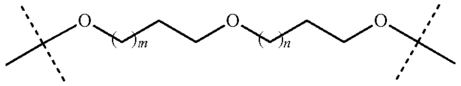

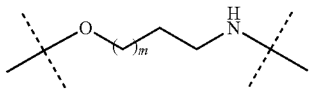
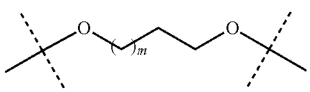

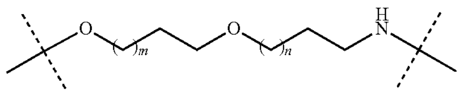

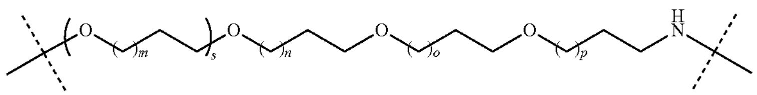

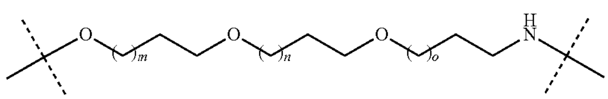

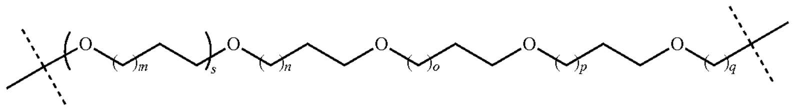

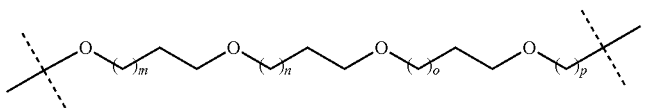
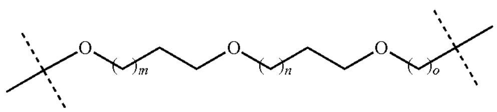

-continued

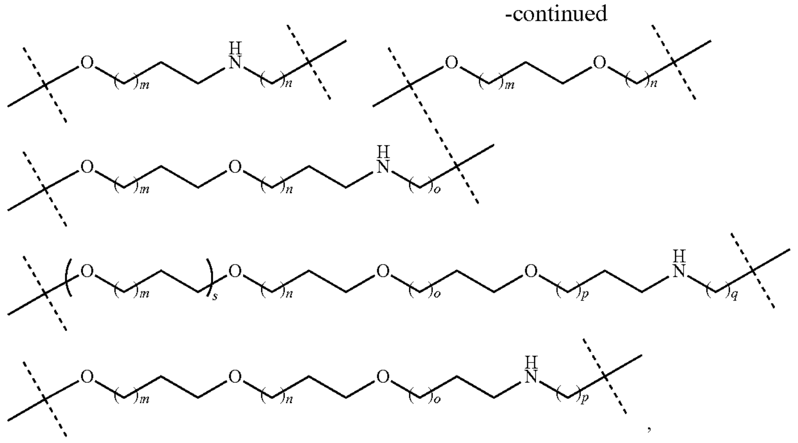

wherein carbon or oxygen may be substituted with a heteroatom selected from N, S, P, or Si atoms with an appropriate number of hydrogens to complete valency.

In another embodiment, the present disclosure is directed to a compound which comprises a PTM group as described above, which binds to a target protein (e.g., IRAK-4) or polypeptide, which is ubiquitinated by an ubiquitin ligase and is chemically linked directly to the ULM group or through a linker moiety L, or PTM is alternatively a ULM' group which is also an ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

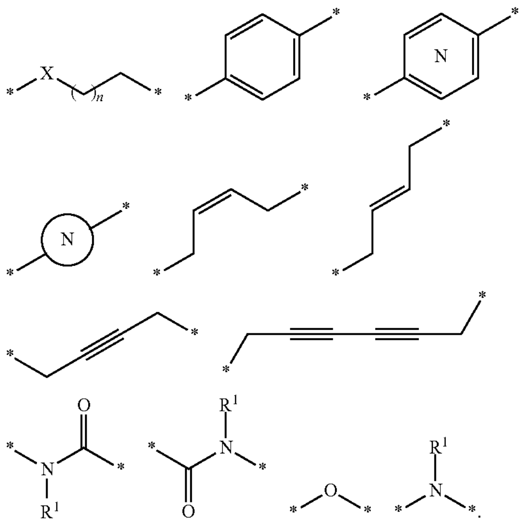

The X is selected from the group consisting of O, N, S, S(O) and $SO_2$; n is integer from 1-5, 5; $R^{L1}$ is hydrogen or alkyl,

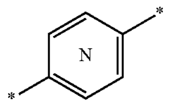

is a mono- or bicyclic aryl or heteroaryl optionally substituted with 1-3 substituents selected from alkyl, halogen, haloalkyl, hydroxy, alkoxy or cyano;

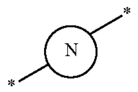

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group.

The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein.

PTM groups according to the present disclosure include, for example, any moiety which binds to IRAK-4 specifically (binds to a target protein). The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

The present disclosure may be used to treat a number of disease states and/or conditions, including any disease state and/or condition in which IRAK-4 is dysregulated and where a patient would benefit from the degradation or inhibition of IRAK-4.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer, inflammatory diseases/disorders, autoimmune diseases/disorders, neurodegenerative diseases, and/or cardiovascular diseases/disorders.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, inflammatory diseases/disorders, autoimmune diseases/disorders, neurodegenerative diseases, as well as cardiovascular diseases/disorders, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include IRAK-4, including fragments thereof, analogues thereof, and/or homologues thereof.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include IRAK-4, among numerous others. The compositions described below exemplify some of the members of the small molecule target proteins.

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any aspect or embodiment described herein, the PTM is represented by Formula PTM-I (which correspond to Formula I from U.S. Patent Application Publication No. 2014/0329799 A1, which is incorporated herein in its entirety for all purposes):

PTM-I

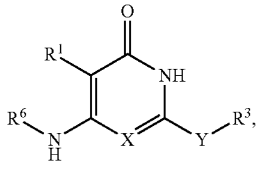

wherein:

X of PTM-I is —N═ or —CH═;

Y of PTM-I is selected from the group consisting of $—NR^2—$, $—CH_2—$ and —O—; or when Y is $—NR^2—$, $R^2$ and $R^3$ together with the nitrogen to which they are attached optionally form a 4- to 6-membered heterocyclic ring, wherein the 4- to 6-membered heterocyclic ring is optionally substituted with 1 to 3 substituents independently selected from $R^7$ groups;

$R^1$ of PTM-I is selected from the group consisting of: hydrogen, $C_{1-10}$ alkyl, $C_{3-8}$ cycloalkyl, aryl, heterocyclyl halogen, —COOR$^7$, —NR$^7$, —SR$^7$, —OR$^7$, —SO$_2$R$^7$, —COR$^7$, —NCOR$^7$, and —CONR$^7$;

$R^2$ of PTM-I is selected from the group consisting of: hydrogen, $C_{1-10}$ alkyl, and $C_{3-4}$ cycloalkyl;

$R^3$ of PTM-I is selected from the group consisting of: hydrogen, $C_{1-10}$ alkyl, $C_{3-4}$ cycloalkyl, aryl, heterocyclyl, and —COOR$^7$;

$R^6$ of PTM-I is selected from the group consisting of: $C_{1-10}$ alkyl, $C_{3-4}$ cycloalkyl, aryl, heterocyclyl, —COOR$^7$, —SO$_2$R$^7$, —COR$^7$; and $R^7$ of PTM-I is selected from the group consisting of: hydrogen, $C_{1-10}$ alkyl, $C_{3-4}$ cycloalkyl, aryl, and heteroaryl;

wherein each of the $C_{1-10}$ alkyl, $C_{3-4}$ cycloalkyl, aryl and heterocyclyl of $R^1$, $R^3$, $R^6$ and $R^7$ is optionally substituted with 1-4 substituents independently selected from the group consisting of $C_{1-4}$ alkyl, $C_{1-4}$ alkoxy, halogen, —SO2R$^8$ and —OR$^8$;

$R^8$ of PTM-I is selected from the group consisting of hydrogen, and $C_{1-6}$ alkyl; and the PTM-I is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-I is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, $R^5$, $R^6$, $R^7$, or $R^8$).

In any aspect or embodiment described herein, PTM-I may comprise:

X of PTM-I is —N═;

Y of PTM-I is —NH—;

$R^1$ of PTM-I is selected from the group consisting of: $C_{1-6}$ alkyl, $C_{3-6}$ cycloalkyl, aryl, and heterocyclyl;

$R^2$ of PTM-I is selected from the group consisting of: hydrogen, and $C_{1-4}$ alkyl;

$R^3$ of PTM-I is selected from the group consisting of: hydrogen, $C_{1-6}$ alkyl, $C_{3-6}$ cycloalkyl, aryl, and heterocyclyl;

$R^6$ of PTM-I is selected from the group consisting of: $C_{1-6}$ alkyl, $C_{3-6}$ cycloalkyl, aryl, and heterocyclyl; and $R^7$ of PTM-I is selected from the group consisting of: hydrogen, $C_{1-6}$ alkyl, $C_{3-6}$ cycloalkyl, aryl, and heteroaryl;

wherein each of the $C_{1-6}$ alkyl, $C_{3-6}$ cycloalkyl, aryl and heterocyclyl of $R^1$, $R^3$, $R^6$ and $R^7$ is optionally substituted with 1-3 substituents independently selected from the group consisting of $C_{1-4}$ alkyl, $C_{1-4}$ alkoxy, halogen, —SO$_2$R$^8$ and —OR$^8$; and $R^8$ of PTM-I is selected from the group consisting of hydrogen, methyl, and ethyl.

In any aspect or embodiment described herein, PTM-I may comprise:

X of PTM-I is —N═;

Y of PTM-I is —NH—;

$R^1$ of PTM-I is selected from the group consisting of: $C_{1-6}$ alkyl, $C_{3-6}$ cycloalkyl, aryl, and heterocyclyl;

$R^2$ of PTM-I is selected from the group consisting of: hydrogen, and $C_{1-4}$ alkyl;

$R^3$ of PTM-I is selected from the group consisting of: hydrogen, $C_{1-6}$ alkyl, $C_{3-6}$ cycloalkyl, aryl, and heterocyclyl;

$R^6$ of PTM-I is selected from the group consisting of: $C_{1-6}$ alkyl, $C_{3-6}$ cycloalkyl, aryl, and heterocyclyl; and $R^7$ of PTM-I is selected from the group consisting of: hydrogen, $C_{1-6}$ alkyl, $C_{3-6}$ cycloalkyl, aryl, and heteroaryl;

wherein each of the $C_{1-6}$ alkyl, $C_{3-6}$ cycloalkyl, aryl and heterocyclyl of $R^1$, $R^3$, $R^6$ and $R^7$ of PTM-I is optionally substituted with 1-3 substituents independently selected from the group consisting of $C_{1-4}$ alkyl, $C_{1-4}$ alkoxy, oxo, halogen, —SO$_2$R$^8$ and —OR$^8$; and $R^8$ of PTM-I is selected from the group consisting of hydrogen, methyl, and ethyl.

In any aspect or embodiment described herein, $R^1$ of PTM-I is phenyl or heterocyclyl. For example, $R^1$ of PTM-I is selected from the group consisting of phenyl, pyridinyl, pyrimidinyl,

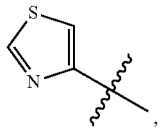
,
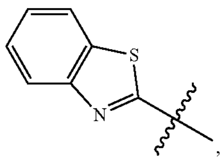
,
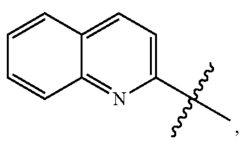
, and
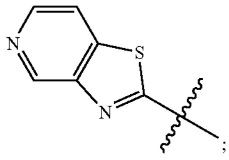
;

wherein each of the foregoing $R^1$ group is optionally substituted with 1-3 substituents independently selected from methyl, ethyl, propyl, hydroxy, halogen, methoxy, ethoxy, oxo, phenyl optionally substituted with 1 or 2 groups independently selected from methyl and halogen.

In any aspect or embodiment described herein, $R^3$ of PTM-I is $C_{1-6}$ alkyl, $C_{3-6}$ cycloalkyl, aryl, a 4-7 membered mono-cyclic ring containing 1-3 hetero atoms selected from O, N and S, heteroaryl; wherein each of the foregoing $R^3$group is optionally substituted with 1-3 substituents independently selected from methyl, ethyl, propyl, hydroxy, halogen, methoxy, ethoxy, oxo, —SO2-methyl, heteroaryl and phenyl optionally substituted with 1 or 2 groups independently selected from methyl and halogen.

In any aspect or embodiment described herein, $R^3$ of PTM-I is selected from the group consisting of methyl, ethyl, propyl, butyl, cyclopropyl, cyclobutyl, cyclopentyl, cyclohexyl, phenyl, pyridinyl, pyrimidinyl,

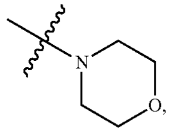
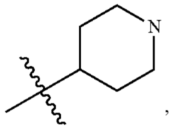
,
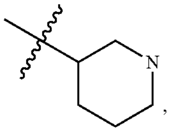
,
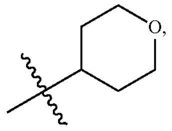
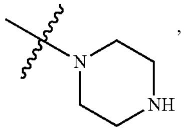
,
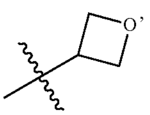

-continued

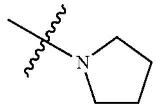 and 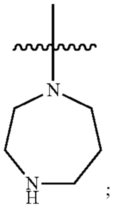 ;

wherein each of the foregoing $R^3$ group is optionally substituted with 1-3 substituents independently selected from methyl, ethyl, propyl, hydroxy, halogen, methoxy, ethoxy, oxo, —$SO_2$-methyl, heteroaryl and phenyl optionally substituted with 1 or 2 groups independently selected from methyl and halogen.

In any aspect or embodiment described herein, $R^6$ of PTM-I is selected from the group consisting of $C_{1-6}$ alkyl, $C_{3-6}$ cycloalkyl, aryl and heteroaryl; wherein each of the foregoing $R^6$ group is optionally substituted with 1-3 substituents independently selected from methyl, ethyl, propyl, hydroxy, halogen, methoxy, ethoxy, oxo, —SO2-methyl, heteroaryl and phenyl optionally substituted with 1 or 2 groups independently selected from methyl and halogen.

In any aspect or embodiment described herein, $R^6$ of PTM-I is selected from the group consisting of methyl, ethyl, propyl, butyl, cyclopropyl, cyclobutyl, cyclopentyl, cyclohexyl, phenyl, pyridinyl, pyrimidinyl,

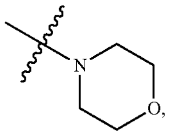 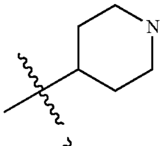 , 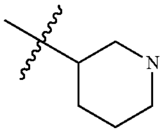 ,

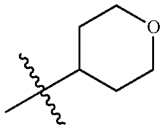 , 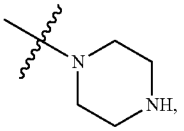

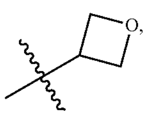 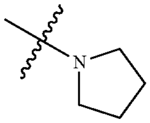 , 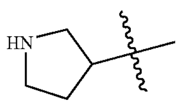 ,

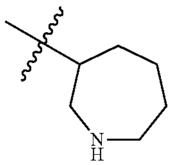 and 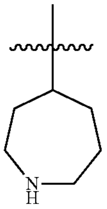 ;

wherein each of the foregoing $R^6$ group is optionally substituted with 1-3 substituents independently selected from methyl, ethyl, propyl, hydroxy, halogen, methoxy, ethoxy, oxo, —$SO_2$-methyl, heteroaryl and phenyl optionally substituted with 1 or 2 groups independently selected from methyl and halogen.

In any aspect or embodiment described herein, $R^6$ of PTM-I is selected from the group consisting of cyclopropyl, cyclobutyl, cyclopentyl, cyclohexyl, phenyl, pyridinyl, pyrimidinyl,

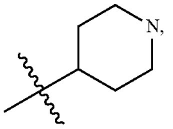 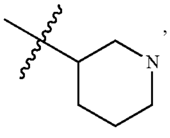 , 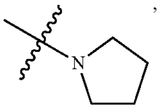 ,

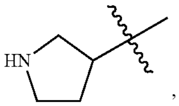 , 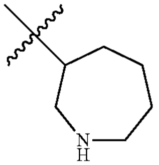 and

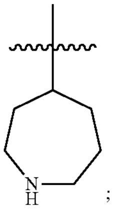 ;

wherein each of the foregoing $R^6$ group is optionally substituted with 1-3 substituents independently selected from methyl, ethyl, propyl, hydroxy, halogen, methoxy, ethoxy, oxo, heteroaryl and phenyl optionally substituted with 1 or 2 groups independently selected from methyl and halogen.

In any aspect or embodiment described herein, the PTM of PTM-I is selected from the group consisting of (R)-2-(2-morpholino-6-oxo-4-(piperidin-3-ylamino)-1,6-dihydropyrimidin-5-yl)benzo[d]thiazole-5-carbonitrile (PTM-I-1), (R)-5-(benzo[d]thiazol-2-yl)-2-morpholino-6-(piperidin-3-ylamino)pyrimidin-4(3H)-one (PTM-I-2), 6-(((1R,2S,3R,4R)-2,3-dihydroxy-4-(hydroxymethyl)cyclopentyl)amino)-5-(4-(4-fluorophenyl)thiazol-2-yl)-2-morpholinopyrimidin-4(3H)-one (PTM-1-3), (R)-5-(benzo[d]thiazol-2-yl)-2-(4-(3-chloro-5-(trifluoromethyl)pyridin-2-yl)piperazin-1-yl)-6-(piperidin-3-ylamino)pyrimidin-4(3H)-one (PTM-I-4), 5-(benzo[d]thiazol-2-yl)-6-(((1R,2S,3R,4R)-2,3-dihydroxy-4-(hydroxymethyl)cyclopentyl)amino)-2-(4-(pyridin-3-yl)piperazin-1-yl)pyrimidin-4(3H)-one (PTM-I-5), 5-(benzo[d]thiazol-2-yl)-6-(((1R,2S,3R,4R)-2,3-dihydroxy-4-(hydroxymethyl)cyclopentyl)amino)-2-(4-(pyrimidin-5-yl)piperidin-1-yl)pyrimidin-4(3H)-one (PTM-I-6), (R)-5-(benzo[d]thiazol-2-yl)-6-(piperidin-3-ylamino)-2-(4-(5-(trifluoromethyl)pyridin-2-yl)piperazin-1-yl)pyrimidin-4(3H)-one (PTM-I-7, 8-(5-(benzo[d]thiazol-2-yl)-4-(((1R,2S,3R,4R)-2,3-dihydroxy-4-(hydroxymethyl)cyclopentyl)amino)-6-oxo-1,6-dihydropyrimidin-2-yl)-2-methyl-2,8-diazaspiro[4.5]decan-1-one(PTM-1-8), and (R)-5-(benzo[d]thiazol-2-yl)-2-(4-(4-chloropyridin-2-yl)piperazin-1-yl)-6-(piperidin-3-ylamino)pyrimidin-4(3H)-one (PTM-I-9).

In any aspect or embodiment described herein, the PTM is represented by Formula PTM-II (which correspond to Formula I from U.S. Patent Application Publication No. 2014/0194404 A1, which is incorporated herein in its entirety for all purposes):

PTM-II

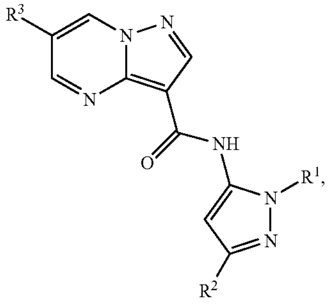

wherein:

$R^1$ of PTM-II is aryl, heteroaryl, heterocyclyl or ($C_{1-6}$ alkyl)$R^6$, wherein said aryl, heteroaryl, and heterocyclyl groups are optionally substituted with one or two substituents selected from the group consisting of halo, cyano, $R^4$, $C_{1-3}$ aminoalkyl, $C_{1-3}$ hydroxyalkyl, $C_{3-4}$ cycloalkyl, $OR^4$, $NR^4R^5$, $NR^4COR^6$, $NR^4SO_2R^6$, $SO_2NR^4R^5$, $CONR^4R^5$;

$R^2$ of PTM-II of PTM-II is aryl, heteroaryl, $C_{3-8}$ cycloalkyl, heterocyclyl or ($C_{1-6}$ alkyl)$R^6$, wherein said aryl, heteroaryl, cycloalkyl and heterocyclyl groups are optionally substituted with one or two substituents selected from the group consisting of halo, cyano, oxo, hydroxyl, imino, hydroxyimino, $R^4$, $OR^4$, O($C_{3-8}$ cycloalkyl), (C═O)$OR^4$, $SO_mR^6$, $SO_mR^4$, $NR^4R^5$, $SO_2NR^4R^5$ and $NR^4SO_2R^6$;

$R^3$ of PTM-II is a halo, cyano, oxo, hydroxyl, imino, hydroxyimino, $R^4$, $OR^4$, $C_{3-8}$ cycloalkyl, $SO_mR^6$, $SO_mR^4NR^4R^5$, or (C═O)$NR^4R^5$, $NR^4$(CO)$R^6$, $SO_mNR^4R^5$ and $NR^4SO_2R^6$;

$R^4$ of PTM-II is independently hydrogen or $C_{1-6}$ alkyl, wherein said alkyl is optionally substituted with one to three halo or hydroxyl;

$R^5$ of PTM-II is independently hydrogen or $C_{1-6}$ alkyl, wherein said alkyl is optionally substituted with halo or hydroxyl;

$R^6$ of PTM-II is independently aryl, heteroaryl, $C_{3-8}$ cycloalkyl or heterocyclyl;

m of PTM-II is an integer from zero to two; and the PTM-II is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-II is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, $R^5$, or $R^6$).

In any aspect or embodiment described herein, $R^1$ of PTM-II is an aryl, wherein said aryl group is optionally substituted with one or two substituents selected from the group consisting of halo, cyano, $R^4$, $C_{3-8}$ cycloalkyl, $C_{1-3}$ aminoalkyl, $C_{1-3}$ hydroxyalkyl, $OR^4$, $NR^4R^5$, $NR^4COR^6$, $NR^4SO_2R^6$, $SO_2NR^4R^5$, $CONR^4R^5$ and $CONR^4R^5$. In a subclass of the invention, $R^1$ is aryl, wherein said aryl group is optionally substituted with $R^4$ or $OR^4$. In a further subclass of the invention, $R^1$ is phenyl, wherein said phenyl group is optionally substituted with $R^4$ or $OR^4$.

In any aspect or embodiment described herein, $R^2$ of PTM-II is a heteroaryl, wherein said heteroaryl group is optionally substituted with one or two substituents selected from the group consisting of halo, cyano, oxo, hydroxyl, imino, hydroxyimino, $R^4$, $OR^4$, O($C_{3-8}$ cycloalkyl), (C═O) $OR^4$, $SO_mR^6$, $SO_mR^4$, $NR^4R^5$, $SO_2NR^4R^5$ and $NR^4SO_2R^6$. In a subclass of the invention, $R^2$ is heteroaryl, wherein said heteroaryl group is optionally substituted with one or two substituents selected from the group consisting of halo, cyano, oxo, hydroxyl, imino, hydroxyimino, $R^4$, $OR^4$, O($C_{3-8}$ cycloalkyl), (C═O)$OR^4$, $SO_mR^6$, $SO_mR^4$, $NR^4R^5$, $SO_2NR^4R^5$ and $NR_4SO_2R^6$.

In any aspect or embodiment described herein, the PTM of PTM-II is selected from the group consisting of: N-(3-(4-oxocyclohexyl)-1-(p-tolyl)-1H-pyrazol-5-yl)pyrazolo[1,5-a]pyrimidine-3-carboxamide (PTM-II-1); N-(3-(4-(hydroxyimino)cyclohexyl)-1-(p-tolyl)-1H-pyrazol-5-yl) pyrazolo[1,5-a]pyrimidine-3-carboxamide (PTM-II-2); N-(3-(4-(methoxyimino)cyclohexyl)-1-(p-tolyl)-1H-pyrazol-5-yl)pyrazolo[1,5-a]pyrimidine-3-carboxamide (PTM-II-3); N-(3-(7-oxoazepan-4-yl)-1-(p-tolyl)-1H-pyrazol-5-yl) pyrazolo[1,5-a]pyrimidine-3-carboxamide (PTM-II-4); N-(3-(4-(dimethylamino)cyclohexyl)-1-(p-tolyl)-1,4-pyrazol-5-yl)pyrazolo[1,5-a]pyrimidine-3-carboxamide (PTM-II-5); N-(3-(4-hydroxycyclohexyl)-1-(p-tolyl)-1H-pyrazol-5-yl)pyrazolo[1,5-a]pyrimidine-3-carboxamide (PTM-II-6); N-(3-(piperidin-4-yl)-1-(p-tolyl)-1H-pyrazol-5-yl)pyrazolo [1,5-a]pyrimidine-3-carboxamide (PTM-II-7); N-(1-(4-methoxyphenyl)-3-(piperidin-4-yl)-1H-pyrazol-5-yl)pyrazolo[1,5-a]pyrimidine-3-carboxamide (PTM-II-8); N-(1-(4-chlorophenyl)-3-(piperidin-4-yl)-1H-pyrazol-5-yl)pyrazolo [1,5-a]pyrimidine-3-carboxamide (PTM-II-9); N-(1-(4-fluorophenyl)-3-(piperidin-4-yl)-1H-pyrazol-5-yl)pyrazolo [1,5-a]pyrimidine-3-carboxamide (PTM-II-10); N-(3-(piperidin-4-yl)-1-(4-(trifluoromethyl)phenyl)-1H-pyrazol-5-yl)pyrazolo[1,5-a]pyrimidine-3-carboxamide (PTM-II-11); N-(1-(4-cyanophenyl)-3-(piperidin-4-yl)-1H-pyrazol-5-yl)pyrazolo[1,5-a]pyrimidine-3-carboxamide (PTM-II-12); N-(3-(piperidin-4-yl)-1-(4-(trifluoromethoxy)phenyl)-1H-pyrazol-5-yl)pyrazolo[1,5-a]pyrimidine-3-carboxamide (PTM-II-13); N-(3-(piperidin-4-yl)-1-(o-tolyl)-1H-pyrazol-5-yl)pyrazolo[1,5-a]pyrimidine-3-carboxamide (PTM-II-14); N-(3-(piperidin-4-yl)-1-(m-tolyl)-1H-pyrazol-5-yl) pyrazolo[1,5-a]pyrimidine-3-carboxamide (PTM-II-15); N-(1-(4-methoxyphenyl)-3-(1-(methylsulfonyl)piperidin-4-yl)-1H-pyrazol-5-yl)pyrazolo[1,5-a]pyrimidine-3-carboxamide (PTM-II-16); N-(3-(1-(methylsulfonyl)piperidin-4-yl)-1-(m-tolyl)-1H-pyrazol-5-yl)pyrazolo[1,5-a]pyrimidine-3-carboxamide (PTM-II-17); N-(3-(1-(methylsulfonyl) piperidin-4-yl)-1-(p-tolyl)-1H-pyrazol-5-yl)pyrazolo[1,5-a] pyrimidine-3-carboxamide (PTM-II-18); N-(3-(1-(cyclopropylsulfonyl)piperidin-4-yl)-1-(4-(trifluoromethoxy)phenyl)-1H-pyrazol-5-yl)pyrazolo[1,5-a] pyrimidine-3-carboxamide (PTM-II-19); N-(3-(1-(methylsulfonyl)piperidin-4-yl)-1-phenyl-1H-pyrazol-5-yl) pyrazolo[1,5-a]pyrimidine-3-carboxamide (PTM-II-20); N-(3-(1-(cyclopropylsulfonyl)piperidin-4-yl)-1-(m-tolyl)-1H-pyrazol-5-yl)pyrazolo[1,5-a]pyrimidine-3-carboxamide (PTM-II-21); N-(3-(1-(cyclopropylsulfonyl)piperidin-4-yl)-1-(4-fluorophenyl)-1H-pyrazol-5-yl)pyrazolo[1,5-a]pyrimidine-3-carboxamide (PTM-II-22); N-(3-(1-(isopropylsulfonyl)piperidin-4-yl)-1-(4-methoxyphenyl)-1H-pyrazol-5-yl) pyrazolo[1,5-a]pyrimidine-3-carboxamide (PTM-II-23); N-(3-(1-(cyclopropylsulfonyl)piperidin-4-yl)-1-(4-methoxyphenyl)-1H-pyrazol-5-yl)pyrazolo[1,5-a]pyrimidine-3-carboxamide (PTM-II-24); N-(3-(1-(cyclopentylsulfonyl)piperidin-4-yl)-1-(p-tolyl)-1H-pyrazol-5-yl) pyrazolo[1,5-a]pyrimidine-3-carboxamide (PTM-II-25); N-(3-(1-(cyclopropylsulfonyl)piperidin-4-yl)-1-(p-tolyl)-1H-pyrazol-5-yl)pyrazolo[1,5-a]pyrimidine-3-carboxamide (PTM-II-26); N-(3-(1-(cyclopropylsulfonyl)piperidin-4-yl)-

1-(4-(trifluoromethoxy)phenyl)-1H-pyrazol-5-yl)pyrazolo[1,5-a]pyrimidine-3-carboxamide (PTM-II-27); N-(1-(2,4-difluorophenyl)-3-(4-(N-methylsulfamoyl)phenyl)-1H-pyrazol-5-yl)pyrazolo[1,5-a]pyrimidine-3-carboxamide (PTM-II-28); N-(1-(4-chloro-2-fluorophenyl)-3-(1-(methylsulfonyl)piperidin-4-yl)-1H-pyrazol-5-yl)pyrazolo[1,5-a]pyrimidine-3-carboxamide (PTM-II-29); N-(1-(4-methoxyphenyl)-3-(1-((trifluoromethyl)sulfonyl)piperidin-4-yl)-1H-pyrazol-5-yl)pyrazolo[1,5-a]pyrimidine-3-carboxamide (PTM-II-30); N-(3-(1-acetylpiperidin-4-yl)-1-(p-tolyl)-1H-pyrazol-5-yl)pyrazolo[1,5-a]pyrimidine-3-carboxamide (PTM-II-31); methyl 4-(1-(4-methoxyphenyl)-5-(pyrazolo[1,5-a]pyrimidine-3-carboxamido)-1H-pyrazol-3-yl)piperidine-1-carboxylate (PTM-II-32); N-(3-(1-(cyclopropanecarbonyl)piperidin-4-yl)-1-(4-methoxyphenyl)-1H-pyrazol-5-yl)pyrazolo[1,5-a]pyrimidine-3-carboxamide (PTM-II-33); N-(1-(2,4-difluorophenyl)-3-(4-(N-methylsulfamoyl)phenyl)-1H-pyrazol-5-yl)pyrazolo[1,5-a]pyrimidine-3-carboxamide (PTM-II-34); N-(3-(1-carbamoylpiperidin-4-yl)-1-(p-tolyl)-1H-pyrazol-5-yl)pyrazolo[1,5-a]pyrimidine-3-carboxamide (PTM-II-35); N-(3-(1-methylpiperidin-4-yl)-1-(p-tolyl)-1H-pyrazol-5-yl)pyrazolo[1,5-a]pyrimidine-3-carboxamide (PTM-II-36); N-(3-(1-isopropylpiperidin-4-yl)-1-(p-tolyl)-1H-pyrazol-5-yl)pyrazolo[1,5-a]pyrimidine-3-carboxamide (PTM-II-37); N-(3-(1-cyclobutylpiperidin-4-yl)-1-(p-tolyl)-1H-pyrazol-5-yl)pyrazolo[1,5-a]pyrimidine-3-carboxamide (PTM-II-38); N-(3-(1-cyclopentylpiperidin-4-yl)-1-(p-tolyl)-1H-pyrazol-5-yl)pyrazolo[1,5-a]pyrimidine-3-carboxamide (PTM-II-39); N-(3-(1-cyclopropylpiperidin-4-yl)-1-(p-tolyl)-1H-pyrazol-5-yl)pyrazolo[1,5-a]pyrimidine-3-carboxamide (PTM-II-40); N-(1-(p-tolyl)-3-(1-(2,2,2-trifluoroethyl)piperidin-4-yl)-1H-pyrazol-5-yl)pyrazolo[1,5-a]pyrimidine-3-carboxamide (PTM-II-41); N-(3-(piperidin-3-yl)-1-(p-tolyl)-1H-pyrazol-5-yl)pyrazolo[1,5-a]pyrimidine-3-carboxamide (PTM-II-42); N-(3-(1-(methylsulfonyl)piperidin-3-yl)-1-(p-tolyl)-1H-pyrazol-5-yl)pyrazolo[1,5-a]pyrimidine-3-carboxamide (PTM-II-43); N-(3-(1-(cyclopropylsulfonyl)piperidin-3-yl)-1-(p-tolyl)-1H-pyrazol-5-yl)pyrazolo[1,5-a]pyrimidine-3-carboxamide (PTM-II-44); N-(3-((tetrahydro-2H-pyran-4-yl)methyl)-1-(p-tolyl)-1H-pyrazol-5-yl)pyrazolo[1,5-a]pyrimidine-3-carboxamide (PTM-II-45); N-(3-(tetrahydro-2H-pyran-4-yl)-1-(p-tolyl)-1H-pyrazol-5-yl)pyrazolo[1,5-a]pyrimidine-3-carboxamide (PTM-II-46); N-(3-(1-isopropylpiperidin-4-yl)-1-(4-methoxyphenyl)-1H-pyrazol-5-yl)pyrazolo[1,5-a]pyrimidine-3-carboxamide (PTM-II-47); N-(1-(2,4-difluorophenyl)-3-(1-methylpiperidin-4-yl)-1H-pyrazol-5-yl)pyrazolo[1,5-a]pyrimidine-3-carboxamide (PTM-II-48); N-(3-(1-cyclobutylpiperidin-4-yl)-1-(2,4-difluorophenyl)-1H-pyrazol-5-yl)pyrazolo[1,5-a]pyrimidine-3-carboxamide (PTM-II-49); N-(1-(4-chloro-2-fluorophenyl)-3-(1-methylpiperidin-4-yl)-1H-pyrazol-5-yl)pyrazolo[1,5-a]pyrimidine-3-carboxamide (PTM-II-50); N-(1-(4-chloro-2-fluorophenyl)-3-(1-cyclobutylpiperidin-4-yl)-1H-pyrazol-5-yl)pyrazolo[1,5-a]pyrimidine-3-carboxamide (PTM-II-51); N-(1-(4-cyclopropylphenyl)-3-(piperidin-4-yl)-1H-pyrazol-5-yl)pyrazolo[1,5-a]pyrimidine-3-carboxamide (PTM-II-52); N-(1-(4-cyclopropylphenyl)-3-(1-(methylsulfonyl)piperidin-4-yl)-1H-pyrazol-5-yl)pyrazolo[1,5-a]pyrimidine-3-carboxamide (PTM-II-53); N-(1-(4-cyclopropylphenyl)-3-(1-(cyclopropylsulfonyl)piperidin-4-yl)-1H-pyrazol-5-yl)pyrazolo[1,5-a]pyrimidine-3-carboxamide (PTM-II-54); N-(1-(4-cyclopropylphenyl)-3-(1-isopropylpiperidin-4-yl)-1H-pyrazol-5-yl)pyrazolo[1,5-a]pyrimidine-3-carboxamide (PTM-II-55); N-(1-(2-fluoro-4-methylphenyl)-3-(piperidin-4-yl)-1H-pyrazol-5-yl)pyrazolo[1,5-a]pyrimidine-3-carboxamide (PTM-II-56); N-(1-(2-fluoro-4-methylphenyl)-3-(1-(methylsulfonyl)piperidin-4-yl)-1H-pyrazol-5-yl)pyrazolo[1,5-a]pyrimidine-3-carboxamide (PTM-II-57); N-(1-(2-fluoro-4-methylphenyl)-3-(1-isopropylpiperidin-4-yl)-1H-pyrazol-5-yl)pyrazolo[1,5-a]pyrimidine-3-carboxamide (PTM-II-58); N-(3-(1-cyclobutylpiperidin-4-yl)-1-(2-fluoro-4-methylphenyl)-1H-pyrazol-5-yl)pyrazolo[1,5-a]pyrimidine-3-carboxamide (PTM-II-59); N-(1-(2-fluoro-4-methylphenyl)-3-(1-methylpiperidin-4-yl)-1H-pyrazol-5-yl)pyrazolo[1,5-a]pyrimidine-3-carboxamide (PTM-II-60); N-(1-(2-fluoro-4-methoxyphenyl)-3-(piperidin-4-yl)-1H-pyrazol-5-yl)pyrazolo[1,5-a]pyrimidine-3-carboxamide (PTM-II-61); N-(1-(2-fluoro-4-methoxyphenyl)-3-(1-isopropylpiperidin-4-yl)-1H-pyrazol-5-yl)pyrazolo[1,5-a]pyrimidine-3-carboxamide (PTM-II-62); N-(3-(1-(cyclopropylsulfonyl)piperidin-4-yl)-1-(2-fluoro-4-methoxyphenyl)-1H-pyrazol-5-yl)pyrazolo[1,5-a]pyrimidine-3-carboxamide (PTM-II-63); N-(1-(2-fluoro-4-methoxyphenyl)-3-(1-(methylsulfonyl)piperidin-4-yl)-1H-pyrazol-5-yl)pyrazolo[1,5-a]pyrimidine-3-carboxamide (PTM-II-64); N-(1-(2-chloro-4-methylphenyl)-3-(piperidin-4-yl)-1H-pyrazol-5-yl)pyrazolo[1,5-a]pyrimidine-3-carboxamide (PTM-II-65); N-(1-(2-chloro-4-methylphenyl)-3-(1-isopropylpiperidin-4-yl)-1H-pyrazol-5-yl)pyrazolo[1,5-a]pyrimidine-3-carboxamide (PTM-II-66); N-(1-(3,5-difluorophenyl)-3-(piperidin-4-yl)-1H-pyrazol-5-yl)pyrazolo[1,5-a]pyrimidine-3-carboxamide (PTM-II-67); N-(1-(4-fluoro-2-methylphenyl)-3-(piperidin-4-yl)-1H-pyrazol-5-yl)pyrazolo[1,5-a]pyrimidine-3-carboxamide (PTM-II-68); N-(1-(4-fluoro-2-methylphenyl)-3-(1-isopropylpiperidin-4-yl)-1H-pyrazol-5-yl)pyrazolo[1,5-a]pyrimidine-3-carboxamide (PTM-II-69); N-(1-(4-bromo-2-fluorophenyl)-3-(piperidin-4-yl)-1H-pyrazol-5-yl)pyrazolo[1,5-a]pyrimidine-3-carboxamide (PTM-II-70); N-(1-(4-bromo-2-fluorophenyl)-3-(1-(methylsulfonyl)piperidin-4-yl)-1H-pyrazol-5-yl)pyrazolo[1,5-a]pyrimidine-3-carboxamide (PTM-II-71); N-(1-(4-cyclopropyl-2-fluorophenyl)-3-(piperidin-4-yl)-1H-pyrazol-5-yl)pyrazolo[1,5-a]pyrimidine-3-carboxamide (PTM-II-72); N-(1-(4-cyclopropyl-2-fluorophenyl)-3-(1-(methylsulfonyl)piperidin-4-yl)-1H-pyrazol-5-yl)pyrazolo[1,5-a]pyrimidine-3-carboxamide (PTM-II-73); N-(1-(4-cyclopropyl-2-fluorophenyl)-3-(1-isopropylpiperidin-4-yl)-1H-pyrazol-5-yl)pyrazolo[1,5-a]pyrimidine-3-carboxamide (PTM-II-74); N-(3-(1-cyclobutylpiperidin-4-yl)-1-(4-cyclopropyl-2-fluorophenyl)-1H-pyrazol-5-yl)pyrazolo[1,5-a]pyrimidine-3-carboxamide (PTM-II-75); N-(1-(4-cyclopropyl-2-fluorophenyl)-3-(1-(2,2,2-trifluoroethyl)piperidin-4-yl)-1H-pyrazol-5-yl)pyrazolo[1,5-a]pyrimidine-3-carboxamide (PTM-II-76); N-(1-(4-cyclopropyl-2,6-difluorophenyl)-3-(piperidin-4-yl)-1H-pyrazol-5-yl)pyrazolo[1,5-a]pyrimidine-3-carboxamide (PTM-II-77); N-(3-(piperidin-4-yl)-1-(tetrahydro-2H-pyran-4-yl)-11'-pyrazol-5-yl)pyrazolo[1,5-a]pyrimidine-3-carboxamide (PTM-II-78); N-(3-(morpholin-3-yl)-1-(p-tolyl)-1H-pyrazol-5-yl)pyrazolo[1,5-a]pyrimidine-3-carboxamide (PTM-II-79); N-(3-(pyrrolidin-3-yl)-1-(p-tolyl)-1H-pyrazol-5-yl)pyrazolo[1,5-a]pyrimidine-3-carboxamide (PTM-II-80); N-(3-(1-(methylsulfonyl)pyrrolidin-3-yl)-1-(p-tolyl)-1H-pyrazol-5-yl)pyrazolo[1,5-a]pyrimidine-3-carboxamide (PTM-II-81); N-(3-(azetidin-3-yl)-1-(p-tolyl)-1H-pyrazol-5-yl)pyrazolo[1,5-a]pyrimidine-3-carboxamide (PTM-II-82); N-(3-(1-(methylsulfonyl)azetidin-3-yl)-1-(p-tolyl)-1H-pyrazol-5-yl)pyrazolo[1,5-a]pyrimidine-3-carboxamide (PTM-II-83); N-(3-(1-(cyclopropylsulfonyl)azetidin-3-yl)-1-(p-tolyl)-1H-pyrazol-5-yl)pyrazolo([1,5-a]pyrimidine-3-carboxamide (PTM-II-84); N-(3-(1-(cyclopentylsulfonyl)azetidin-3-yl)-1-(p-tolyl)-1H-pyrazol-5-yl)pyrazolo[1,5-a]pyrimidine-3- carboxamide (PTM-II-85); N-(3-(1-((2-methoxyethyl)sulfonyl)azetidin-3-yl)-1-(p-tolyl)-1H-pyrazol-5-yl)pyrazolo[1,5-a]pyrimidine-3-carboxamide (PTM-II-86); N-(3-(azetidin-3-yl)-1-(4-cyclopropyl-2-fluorophenyl)-1H-pyrazol-5-yl)pyrazolo[1,5-a]pyrimidine-3-carboxamide (PTM-II-87); N-(1-(4-cyclopropyl-2-fluorophenyl)-3-(1-isopropylazetidin-3-yl)-1H-pyrazol-5-yl)pyrazolo[1,5-a]pyrimidine-3-carboxamide (PTM-II-88); N-(3-(1-cyclobutylazetidin-3-yl)-1-(4-cyclopropyl-2-fluorophenyl)-1H-pyrazol-5-yl)pyrazolo[1,5-a]pyrimidine-3-carboxamide (PTM-II-89); N-(1-(4-acetylphenyl)-3-(1-(methylsulfonyl)piperidin-4-yl)-1H-pyrazol-5-yl)pyrazolo[1,5-a]pyrimidine-3-carboxamide (PTM-II-90); N-(3-(4-methylpiperidin-4-yl)-1-(p-tolyl)-1H-pyrazol-5-yl)pyrazolo[1,5-a]pyrimidine-3-carboxamide (PTM-II-91); N-(3-(4-methyl-1-(methylsulfonyl)piperidin-4-yl)-1-(p-tolyl)-1H-pyrazol-5-yl)pyrazolo[1,5-a]pyrimidine-3-carboxamide (PTM-II-92); methyl 4-(5-(pyrazolo[1,5-a]pyrimidine-3-carboxamido)-1-(p-tolyl)-1H-pyrazol-3-yl)cyclohexanecarboxylate (PTM-II-93); 4-(5-(pyrazolo[1,5-]pyrimidine-3-carboxamido)-1-(p-tolyl)-1H-pyrazol-3-yl)cyclohexanecarboxylic acid (PTM-II-94); N-(3-(4-carbamoylcyclohexyl)-1-(p-tolyl)-1H-pyrazol-5-yl)pyrazolo[1,5-a]pyrimidine-3-carboxamide (PTM-II-95); N-(3-(4-(dimethylcarbamoyl)cyclohexyl)-1-(p-tolyl)-1H-pyrazol-5-yl)pyrazolo[1,5-a]pyrimidine-3-carboxamide (PTM-II-96); N-(1-(p-tolyl)-3-(4-(trifluoromethyl)cyclohexyl)-1H-pyrazol-5-yl)pyrazolo[1,5-a]pyrimidine-3-carboxamide (PTM-II-97); N-(3-(1,1-dioxidotetrahydro-2H-thiopyran-4-yl)-1-(p-tolyl)-1H-pyrazol-5-yl)pyrazolo[1,5-a]pyrimidine-3-carboxamide (PTM-II-98); N-(3-(4-sulfamoylphenyl)-1-(p-tolyl)-1H-pyrazol-5-yl)pyrazolo[1,5-a]pyrimidine-3-carboxamide (PTM-II-99); N-(1-(2-fluoro-4-methylphenyl)-3-(4-(N-methylsulfamoyl)phenyl)-1H-pyrazol-5-yl)pyrazolo[1,5-a]pyrimidine-3-carboxamide (PTM-II-100); N-(1-(4-cyclopropyl-2-fluorophenyl)-3-(4-(N-methylsulfamoyl)phenyl)-1H-pyrazol-5-yl)pyrazolo[1,5-a]pyrimidine-3-carboxamide (PTM-II-101); N-(3-(4-aminophenyl)-1-(p-tolyl)-1H-pyrazol-5-yl)pyrazolo[1,5-a]pyrimidine-3-carboxamide (PTM-II-102); N-(3-(4-(methylsulfonamido)phenyl)-1-(p-tolyl)-1H-pyrazol-5-yl)pyrazolo[1,5-a]pyrimidine-3-carboxamide (PTM-II-103); 6-bromo-N-(1-(4-methoxyphenyl)-3-(piperidin-4-yl)-1H-pyrazol-5-yl)pyrazolo[1,5-a]pyrimidine-3-carboxamide (PTM-II-104); N3-(1-(4-methoxyphenyl)-3-(piperidin-4-yl)-1H-pyrazol-5-yl)pyrazolo[1,5-a]pyrimidine-3,6-dicarboxamide (PTM-II-105); 6-cyclopropyl-N-(1-(4-methoxyphenyl)-3-(piperidin-4-yl)-1H-pyrazol-5-yl)pyrazolo[1,5-a]pyrimidine-3-carboxamide (PTM-II-106); 6-bromo-N-(3-(piperidin-4-yl)-1-(p-tolyl)-1H-pyrazol-5-yl)pyrazolo[1,5-a]pyrimidine-3-carboxamide (PTM-II-107); 6-bromo-N-(3-(1-isopropylpiperidin-4-yl)-1-(p-tolyl)-1H-pyrazol-5-yl)pyrazolo[1,5-a]pyrimidine-3-carboxamide (PTM-II-108); 6-bromo-N-(3-(1-(tetrahydro-2H-pyran-3-yl)piperidin-4-yl)-1-(p-tolyl)-1H-pyrazol-5-yl)pyrazolo[1,5-a]pyrimidine-3-carboxamide (PTM-II-109); 6-bromo-N-(3-(1-(tetrahydro-2H-pyran-4-yl)piperidin-4-yl)-1-(p-tolyl)-1H-pyrazol-5-yl)pyrazolo[1,5-a]pyrimidine-3-carboxamide (PTM-II-110); 6-bromo-N-(3-(1-methylpiperidin-4-yl)-1-(p-tolyl)-1H-pyrazol-5-yl)pyrazolo[1,5-a]pyrimidine-3-carboxamide (PTM-II-111); 6-bromo-N-(3-(1-(2-hydroxyacetyl)piperidin-4-yl)-1-(p-tolyl)-1H-pyrazol-5-yl)pyrazolo[1,5-a]pyrimidine-3-carboxamide (PTM-II-112); 6-bromo-N-(3-(1-(3-(dimethylamino)propanoyl)piperidin-4-yl)-1-(p-tolyl)-1H-pyrazol-5-yl)pyrazolo[1,5-a]pyrimidine-3-carboxamide (PTM-II-113); 6-bromo-N-(3-(1-(3-(diethylamino)propanoyl)piperidin-4-yl)-1-(p-tolyl)-1H-pyrazol-5-yl)pyrazolo[1,5-a]pyrimidine-3-carboxamide (PTM-II-114); N-(3-(1-(2-amino-2-oxoethyl)piperidin-4-yl)-1-(p-tolyl)-1H-pyrazol-5-yl)-6-bromopyrazolo[1,5-a]pyrimidine-3-carboxamide (PTM-II-115); 6-bromo-N-(3-(1-(1-hydroxycyclobutanecarbonyl)piperidin-4-yl)-1-(p-tolyl)-1H-pyrazol-5-yl)pyrazolo[1,5-a]pyrimidine-3-carboxamide (PTM-II-116); 6-bromo-N-(3-(1-(4-methylmorpholine-2-carbonyl)piperidin-4-yl)-1-(p-tolyl)-1H-pyrazol-5-yl)pyrazolo[1,5-a]pyrimidine-3-carboxamide (PTM-II-117); methyl 4-(5-(6-bromopyrazolo[1,5-a]pyrimidine-3-carboxamido)-1-(p-tolyl)-1H-pyrazol-3-yl)piperidine-1-carboxylate (PTM-II-118); 6-bromo-N-(3-(1-(methylsulfonyl)piperidin-4-yl)-1-(p-tolyl)-1H-pyrazol-5-yl)pyrazolo[1,5-a]pyrimidine-3-carboxamide (PTM-II-119); N3-(3-(1-(methylsulfonyl)piperidin-4-yl)-1-(p-tolyl)-1H-pyrazol-5-yl)pyrazolo[1,5-a]pyrimidine-3,6-dicarboxamide (PTM-II-120); 6-cyano-N-(3-(1-(methylsulfonyl)piperidin-4-yl)-1-(p-tolyl)-1H-pyrazol-5-yl)pyrazolo[1,5-a]pyrimidine-3-carboxamide (PTM-II-121); 6-methyl-N-(3-(1-(methylsulfonyl)piperidin-4-yl)-1-(p-tolyl)-1H-pyrazol-5-yl)pyrazolo[1,5-a]pyrimidine-3-carboxamide (PTM-II-122); N-(3-(pyridin-3-yl)-1-(p-tolyl)-1H-pyrazol-5-yl)pyrazolo[1,5-a]pyrimidine-3-carboxamide (PTM-II-123); N-(3-(6-methoxypyridin-3-yl)-1-(p-tolyl)-1H-pyrazol-5-yl)pyrazolo[1,5-a]pyrimidine-3-carboxamide (PTM-II-124); N-(3-(pyridin-4-yl)-1-(p-tolyl)-1H-pyrazol-5-yl)pyrazolo[1,5-a]pyrimidine-3-carboxamide (PTM-II-125); N-(1-(4-fluorophenyl)-3-(pyridin-4-yl)-1H-pyrazol-5-yl)pyrazolo[1,5-a]pyrimidine-3-carboxamide (PTM-II-126); N-(1-(4-methoxyphenyl)-3-(pyridin-4-yl)-1H-pyrazol-5-yl)pyrazolo[1,5-a]pyrimidine-3-carboxamide (PTM-II-127); N-(1-(3-fluoro-4-methylphenyl)-3-(pyridin-4-yl)-1H-pyrazol-5-yl)pyrazolo[1,5-a]pyrimidine-3-carboxamide (PTM-II-128); N-(3-(2-methoxypyridin-4-yl)-1-(p-tolyl)-1H-pyrazol-5-yl)pyrazolo[1,5-a]pyrimidine-3-carboxamide (PTM-II-129); N-(3-cyclopropyl-1-(p-tolyl)-1H-pyrazol-5-yl)pyrazolo[1,5-a]pyrimidine-3-carboxamide (PTM-II-130); N-(3-(4-methoxyphenyl)-1-(p-tolyl)-1H-pyrazol-5-yl)pyrazolo[1,5-a]pyrimidine-3-carboxamide (PTM-II-131); N-(1-(3-fluorophenyl)-3-(4-methoxyphenyl)-1H-pyrazol-5-yl)pyrazolo [1,5-a]pyrimidine-3-carboxamide (PTM-II-132); N-(3-(3,4-dimethoxyphenyl)-1-(p-tolyl)-1H-pyrazol-5-yl)pyrazolo[1,5-a]pyrimidine-3-carboxamide (PTM-II-133); N-(3-(4-(methylsulfonyl)phenyl)-1-(p-tolyl)-1H-pyrazol-5-yl)pyrazolo[1,5-a]pyrimidine-3-carboxamide (PTM-II-134); N-(3-(4-fluorophenyl)-1-(p-tolyl)-1H-pyrazol-5-yl)pyrazolo[1,5-a]pyrimidine-3-carboxamide (PTM-II-135); N-(3-(5-fluoropyridin-3-yl)-1-(p-tolyl)-1H-pyrazol-5-yl)pyrazolo[1,5-a]pyrimidine-3-carboxamide (PTM-II-136); N-(3-(pyrimidin-5-yl)-1-(p-tolyl)-1H-pyrazol-5-yl)pyrazolo[1,5-a]pyrimidine-3-carboxamide (PTM-II-137); N-(3-(1,2,3,6-tetrahydropyridin-4-yl)-1-(p-tolyl)-1H-pyrazol-5-yl)pyrazolo[1,5-a]pyrimidine-3-carboxamide (PTM-II-138); N-(3-(1-(methylsulfonyl)-1,2,3,6-tetrahydropyridin-4-yl)-1-(p-tolyl)-1H-pyrazol-5-yl)pyrazolo[1,5-a]pyrimidine-3-carboxamide (PTM-II-139); N-(3-(1-methyl-1,2,3,6-tetrahydropyridin-4-yl)-1-(p-tolyl)-1H-pyrazol-5-yl)pyrazolo[1,5-a]pyrimidine-3-carboxamide (PTM-II-140); N-(3-(4-(morpholinosulfonyl)phenyl)-1-(p-tolyl)-1H-pyrazol-5-yl)pyrazolo[1,5-a]pyrimidine-3-carboxamide (PTM-II-141); N-(3-(pyrrolidin-1-ylmethyl)-1-(p-tolyl)-1,4-pyrazol-5-yl)pyrazolo[1,5-a]pyrimidine-3-carboxamide (PTM-II-142); N-(3-(4-(pyrrolidin-1-ylmethyl)phenyl)-1-(p-tolyl)-1H-pyrazol-5-yl)pyrazolo[1,5-a]pyrimidine-3-carboxamide (PTM-II-143); N-(3-(4-((4-methylpiperazin-1-yl)methyl)phenyl)-1-(p-tolyl)-1H-pyrazol-5-yl)pyrazolo[1,5-a]pyrimidine-3-carboxamide (PTM-II-144); N-(3-(4-(morpholinomethyl)phenyl)-1-(p-tolyl)-1H-pyrazol-5-yl)pyrazolo[1, 5-a]pyrimidine-3-carboxamide (PTM-II-145); N-(1-(4-cyclopropylphenyl)-3-(piperidin-4-yl)-1H-pyrazol-5-yl)pyrazolo[1,5-a]pyrimidine-3-carboxamide (PTM-II-146); N-(1-(5-cyclopropylpyridin-2-yl)-3-(1-methylpiperidin-4-yl)-1H-pyrazol-5-yl)pyrazolo[1,5-a]pyrimidine-3-carboxamide (PTM-II-147); N-(3-(1-cyclobutylpiperidin-4-yl)-1-(5-cyclopropylpyridin-2-yl)-1H-pyrazol-5-yl)pyrazolo[1,5-a]pyrimidine-3-carboxamide (PTM-II-148); N-(1-(5-cyclopropylpyridin-2-yl)-3-(1-(methylsulfonyl)piperidin-4-yl)-1H-pyrazol-5-yl)pyrazolo[1,5-a]pyrimidine-3-carboxamide (PTM-II-149); N-(1-(5-cyclopropylpyridin-2-yl)-3-(1-(cyclopropylsulfonyl)piperidin-4-yl)-1H-pyrazol-5-yl)pyrazolo[1,5-a]pyrimidine-3-carboxamide (PTM-II-150); N-(1-(5-cyclopropylpyridin-2-yl)-3-(4-(N-methylsulfamoyl)phenyl)-1H-pyrazol-5-yl)pyrazolo[1,5-a]pyrimidine-3-carboxamide (PTM-II-151); N-(1-(5-methylpyridin-2-yl)-3-(piperidin-4-yl)-1H-pyrazol-5-yl)pyrazolo[1,5-a]pyrimidine-3-carboxamide (PTM-II-152); N-(1-(5-methylpyridin-2-yl)-3-(1-(methylsulfonyl)piperidin-4-yl)-1H-pyrazol-5-yl)pyrazolo[1,5-a]pyrimidine-3-carboxamide (PTM-II-153); N-(3-(1-(cyclopropylsulfonyl)piperidin-4-yl)-1-(5-methylpyridin-2-yl)-1H-pyrazol-5-yl)pyrazolo[1,5-a]pyrimidine-3-carboxamide (PTM-II-154); N-(1-(5-trideuteromethylpyridin-2-yl)-3-(1-(methylsulfonyl)piperidin-4-yl)-1H-pyrazol-5-yl)pyrazolo[1,5-a]pyrimidine-3-carboxamide (PTM-II-155); N-(1-(5-methoxypyridin-2-yl)-3-(1-(methylsulfonyl)piperidin-4-yl)-1H-pyrazol-5-yl)pyrazolo[1,5-a]pyrimidine-3-carboxamide (PTM-II-156); N-(1-(5-(aminomethyl)pyridin-2-yl)-3-(1-(methylsulfonyl)piperidin-4-yl)-1H-pyrazol-5-yl)pyrazolo[1,5-a]pyrimidine-3-carboxamide (PTM-II-157); N-(1-(5-(1-amino-2-methylpropan-2-yl)pyridin-2-yl)-3-(1-(methylsulfonyl)piperidin-4-yl)-1H-pyrazol-5-yl)pyrazolo[1,5-a]pyrimidine-3-carboxamide (PTM-II-158); N-(1-(5-(2-aminopropan-2-yl)pyridin-2-yl)-3-(1-(methylsulfonyl)piperidin-4-yl)-1H-pyrazol-5-yl)pyrazolo[1,5-a]pyrimidine-3-carboxamide (PTM-II-159); N-(1-(5-carbamoylpyridin-2-yl)-3-(piperidin-4-yl)-1H-pyrazol-5-yl)pyrazolo[1,5-a]pyrimidine-3-carboxamide (160); N-(1-(5-(1-(methylamino)ethyl)pyridin-2-yl)-3-(1-(methylsulfonyl)piperidin-4-yl)-1H-pyrazol-5-yl)pyrazolo[1,5-a]pyrimidine-3-carboxamide (PTM-II-161); N-(1-(5-(hydroxymethyl)pyridin-2-yl)-3-(1-(methylsulfonyl)piperidin-4-yl)-1H-pyrazol-5-yl)pyrazolo[1,5-a]pyrimidine-3-carboxamide (PTM-II-162); (R)—N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide (PTM-II-163); (S)—N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide (PTM-II-164); N-(1-(5-formylpyridine-2-yl)-3-(1-(methylsulfonyl)piperidin-4-yl)-1H-pyrazol-5-yl)pyrazolo[1,5-a]pyrimidine-3-carboxamide (PTM-II-165); N-(1-(5-methylpyridin-2-yl)-3-(morpholin-3-yl)-1H-pyrazol-5-yl)pyrazolo[1,5-a]pyrimidine-3-carboxamide (PTM-II-166); N-(1-(6-methylpyridin-3-yl)-3-(piperidin-4-yl)-1H-pyrazol-5-yl)pyrazolo[1,5-a]pyrimidine-3-carboxamide (PTM-II-167); N-(1-(6-methylpyridin-3-yl)-3-(1-(methylsulfonyl)piperidin-4-yl)-1H-pyrazol-5-yl)pyrazolo[1,5-a]pyrimidine-3-carboxamide (PTM-II-168); N-(1-(5-methylpyrimidin-2-yl)-3-(piperidin-4-yl)-1H-pyrazol-5-yl)pyrazolo[1,5-a]pyrimidine-3-carboxamide (PTM-II-169); N-(1-(5-methylpyrimidin-2-yl)-3-(1-(methylsulfonyl)piperidin-4-yl)-1H-pyrazol-5-yl)pyrazolo[1,5-a]pyrimidine-3-carboxamide (PTM-II-170); N-(3-(1-(cyclopropylsulfonyl)piperidin-4-yl)-1-(5-methylpyrimidin-2-yl)-1H-pyrazol-5-yl)pyrazolo[1,5-a]pyrimidine-3-carboxamide (PTM-II-171); N-(1-(5-methylpyrazin-2-yl)-3-(1-(methylsulfonyl)piperidin-4-yl)-1H-pyrazol-5-yl)pyrazolo[1,5-a]pyrimidine-3-carboxamide (PTM-II-172); N-(3-(1-(methylsulfonyl)piperidin-4-yl)-1-(pyridin-2-yl)-1H-pyrazol-5-yl)pyrazolo[1,5-a]pyrimidine-3-carboxamide (PTM-II-173); N-(1-(5,6-dimethylpyridin-2-yl)-3-(1-(methylsulfonyl)piperidin-4-yl)-1H-pyrazol-5-yl)pyrazolo[1,5-a]pyrimidine-3-carboxamide (PTM-II-174); N-(1-(1,3-dimethyl-1H-pyrazolo[3,4-b]pyridin-6-yl)-3-(1-(methylsulfonyl)piperidin-4-yl)-1H-pyrazol-5-yl)pyrazolo[1,5-a]pyrimidine-3-carboxamide (175); N-(1-(5-(aminomethyl)pyridin-2-yl)-3-(1-methylcyclopropyl)-1H-pyrazol-5-yl)pyrazolo[1,5-a]pyrimidine-3-carboxamide (PTM-II-176); N-(1-(5-methylpyridin-2-yl)-3-(4-(morpholinosulfonyl)phenyl)-1H-pyrazol-5-yl)pyrazolo[1,5-a]pyrimidine-3-carboxamide (PTM-II-177); N-(3-(4-((4-methylpiperazin-1-yl)sulfonyl)phenyl)-1-(5-methylpyridin-2-yl)-1H-pyrazol-5-yl)pyrazolo[1,5-a]pyrimidine-3-carboxamide (PTM-II-178); N-(1-(5-methylpyridin-2-yl)-3-(4-(methylsulfonyl)phenyl)-1H-pyrazol-5-yl)pyrazolo[1,5-a]pyrimidine-3-carboxamide (PTM-II-179); N-(3-cyclopropyl-1-(5-methylpyridin-2-yl)-1H-pyrazol-5-yl)pyrazolo[1,5-a]pyrimidine-3-carboxamide (PTM-II-180); N-(3-(1-methylcyclopropyl)-1-(5-methylpyridin-2-yl)-1H-pyrazol-5-yl)pyrazolo[1,5-a]pyrimidine-3-carboxamide (PTM-II-181); N-(3-methoxy-1-(5-methylpyridin-2-yl)-1H-pyrazol-5-yl)pyrazolo[1,5-a]pyrimidine-3-carboxamide (PTM-II-182); methyl((4-(5-(pyrazolo[1,5-a]pyrimidine-3-carboxamido)-1-(p-tolyl)-1H-pyrazol-3-yl)cyclohexyl)methyl)carbamate (PTM-II-183); N-(3-(4-(aminomethyl)cyclohexyl)-1-(p-tolyl)-1H-pyrazol-5-yl)pyrazolo[1,5-a]pyrimidine-3-carboxamide (PTM-II-184); N-(3-(4-aminocyclohexyl)-1-(5-methylpyridin-2-yl)-1H-pyrazol-5-yl)pyrazolo[1,5-a]pyrimidine-3-carboxamide (PTM-II-185); N-(1-(2-aminoethyl)-3-(1-(methylsulfonyl)piperidin-4-yl)-1H-pyrazol-5-yl)pyrazolo[1,5-a]pyrimidine-3-carboxamide (PTM-II-186); N-(1-(1H-imidazol-2-yl)-3-(1-isopropylpiperidin-4-yl)-1H-pyrazol-5-yl)pyrazolo[1,5-a]pyrimidine-3-carboxamide (PTM-II-187); N-(1-(1-(methylsulfonyl)-1H-imidazol-2-yl)-3-(1-(methylsulfonyl)piperidin-4-yl)-1H-pyrazol-5-yl)pyrazolo[1,5-a]pyrimidine-3-carboxamide (PTM-II-188); N-(3-(piperidin-4-yl)-1-(thiazol-2-yl)-1H-pyrazol-5-yl)pyrazolo[1,5-a]pyrimidine-3-carboxamide (PTM-II-189); 6-bromo-N-(1-(5-methylpyridin-2-yl)-3-(1-(methylsulfonyl)piperidin-4-yl)-1H-pyrazol-5-yl)pyrazolo[1,5-a]pyrimidine-3-carboxamide (PTM-II-190); 6-cyano-N-(1-(5-methylpyridin-2-yl)-3-(1-(methylsulfonyl)piperidin-4-yl)-1H-pyrazol-5-yl)pyrazolo[1,5-a]pyrimidine-3-carboxamide (PTM-II-191); N3-(3-(1-(methylsulfonyl)piperidin-4-yl)-1-(p-tolyl)-1H-pyrazol-5-yl)pyrazolo[1,5-a]pyrimidine-3,6-dicarboxamide (PTM-II-192); 6-ethynyl-N-(1-(5-methylpyridin-2-yl)-3-(1-(methylsulfonyl)piperidin-4-yl)-1H-pyrazol-5-yl)pyrazolo[1,5-a]pyrimidine-3-carboxamide (PTM-II-193); 6-bromo-N-(1-(5-methylpyridin-2-yl)-3-(4-(N-methylsulfamoyl)phenyl)-1H-pyrazol-5-yl)pyrazolo[1,5-a]pyrimidine-3-carboxamide (PTM-II-194); 6-cyclopropyl-N-(1-(5-methylpyridin-2-yl)-3-(4-(N-methylsulfamoyl)phenyl)-1H-pyrazol-5-yl)pyrazolo[1,5-a]pyrimidine-3-carboxamide (PTM-II-195); 6-chloro-N-(1-(5-methylpyridin-2-yl)-3-(4-(N-methylsulfamoyl)phenyl)-1H-pyrazol-5-yl)pyrazolo[1,5-a]pyrimidine-3-carboxamide (PTM-II-196); N-(3-(4-methylpiperazin-1-yl)-1-(5-methylpyridin-2-yl)-1H-pyrazol-5-yl)pyrazolo[1,5-a]pyrimidine-3-carboxamide (PTM-II-197); N-(3-(4-methylpiperazin-1-yl)-1-(5-trideuteromethylpyridin-2-yl)-1H-pyrazol-5-yl)pyrazolo[1,5-a]pyrimidine-3-carboxamide (PTM-II-198); N-(1-(5-methylpyridin-2-yl)-3-(4-(methylsulfonyl)piperazin-1-yl)-1H-pyrazol-5-yl)pyrazolo[1,5-a]pyrimidine-3-carboxamide (PTM-II-199); N-(1-(5-trideuteromethylpyridin-2-yl)-3-(4-(methylsulfonyl)piperazin-1-yl)-1H-pyrazol-5-yl)pyrazolo[1,5-a]pyrimidine-3-carboxamide (PTM-II-200); N-(1-(5-cyclopropylpyridin-2-yl)-3-(4-methylpiperazin-1-yl)-1H-pyrazol-5-yl)pyrazolo[1,5-a]pyrimidine-3-carboxamide (PTM-II-201); N-(1-(5-methylpyridin-2-yl)-3-morpholino-1H-pyrazol-5-yl)pyrazolo[1,5-a]pyrimidine-3-carboxamide (PTM-II-202); N-[3-(1'-acetyl-1,4'-bipiperidin-4-yl)-1-(4-methylphenyl)-1H-pyrazol-5-yl]pyrazolo[1,5-a]pyrimidine-3-carboxamide (PTM-II-203); N-[3-(1-cyclohexylpiperidin-4-yl)-1-(4-methylphenyl)-1H-pyrazol-5-yl]pyrazolo[1,5-a]pyrimidine-3-carboxamide (PTM-II-204); N-[3-(1-cyclobutylpiperidin-4-yl)-1-(4-methylphenyl)-1H-pyrazol-5-yl]pyrazolo[1,5-a]pyrimidine-3-carboxamide (PTM-II-205); N-[3-(1'-methyl-1,4'-bipiperidin-4-yl)-1-(4-methylphenyl)-1H-pyrazol-5-yl]pyrazolo[1,5-a]pyrimidine-3-carboxamide (PTM-II-206); N-{1-(4-methylphenyl)-3-[1-(tetrahydro-2H-pyran-4-yl)piperidin-4-yl]-1H-pyrazol-5-yl}pyrazolo[1,5-a]pyrimidine-3-carboxamide (PTM-II-207); ethyl 4-{1-(4-methylphenyl)-5-[(pyrazolo[1,5-a]pyrimidin-3-ylcarbonyl)amino]-1H-pyrazol-3-yl}-1,4'-bipiperidine-1'-carboxylate (PTM-II-208); N-(3-(1-(3-methylbutan-2-yl)piperidin-4-yl)-1-(p-tolyl)-1H-pyrazol-5-yl)pyrazolo[1,5-a]pyrimidine-3-carboxamide (PTM-II-209); N-(3-(1-(sec-butyl)piperidin-4-yl)-1-(p-tolyl)-1H-pyrazol-5-yl)pyrazolo[1,5-a]pyrimidine-3-carboxamide (PTM-II-210); N-(3-(1-(1-methoxypropan-2-yl)piperidin-4-yl)-1-(p-tolyl)-1H-pyrazol-5-yl)pyrazolo[1,5-a]pyrimidine-3-carboxamide (PTM-II-211): N-(3-(1-(1-(3-fluoropyridin-2-yl)ethyl)piperidin-4-yl)-1-(p-tolyl)-1H-pyrazol-5-yl)pyrazolo[1,5-a]pyrimidine-3-carboxamide (PTM-II-212); N-(3-(1-(1-oxo-1-(piperidin-1-yl)propan-2-yl)piperidin-4-yl)-1-(p-tolyl)-1H-pyrazol-5-yl)pyrazolo[1,5-a]pyrimidine-3-carboxamide (PTM-II-213); N-(3-(1-(1-oxo-1-(pyrrolidin-1-yl)propan-2-yl)piperidin-4-yl)-1-(p-tolyl)-1H-pyrazol-5-yl)pyrazolo[1,5-a]pyrimidine-3-carboxamide (PTM-II-214); N-(3-(1-(1-(6-fluoropyridin-2-yl)ethyl)piperidin-4-yl)-1-(p-tolyl)-1H-pyrazol-5-yl)pyrazolo[1,5-a]pyrimidine-3-carboxamide (PTM-II-215); N-[3-(1t-cyclopropyl-1,4'-bipiperidin-4-yl)-1-(4-methylphenyl)-1H-pyrazol-5-yl]pyrazolo[1,5-a]pyrimidine-3-carboxamide (PTM-II-216); N-[1-(4-methylphenyl)-3-{1-[1-(1,3-thiazol-2-yl)ethyl]piperidin-4-yl}-1H-pyrazol-5-yl]pyrazolo[1,5-a]pyrimidine-3-carboxamide (PTM-II-217); N-[3-(1-benzylpiperidin-4-yl)-1-(4-methylphenyl)-1H-pyrazol-5-yl]pyrazolo[1,5-a]pyrimidine-3-carboxamide (PTM-II-218); N-{1-(4-methylphenyl)-3-[1-(2-methylpropyl)piperidin-4-yl]-1H-pyrazol-5-yl}pyrazolo[1,5-a]pyrimidine-3-carboxamide (PTM-II-219); N-[1-(4-methylphenyl)-3-(1-propylpiperidin-4-yl)-1H-pyrazol-5-yl]pyrazolo[1,5-a]pyrimidine-3-carboxamide (PTM-II-220); N-{3-[1-(cyclopropylmethyl)piperidin-4-yl]-1-(4-methylphenyl)-1H-pyrazol-5-yl}pyrazolo[1,5-a]pyrimidine-3-carboxamide (PTM-II-221); N-{1-(4-methylphenyl)-3-[1-(1,3-thiazol-2-ylmethyl)piperidin-4-yl]-1H-pyrazol-5-yl}pyrazolo[1,5-a]pyrimidine-3-carboxamide (PTM-II-222); N-{1-(4-methylphenyl)-3-[1-(thiophen-3-ylmethyl)piperidin-4-yl]-1H-pyrazol-5-yl}pyrazolo[1,5-a]pyrimidine-3-carboxamide (PTM-II-223); N-(3-(1-(pyridin-4-ylmethyl)piperidin-4-yl)-1-(p-tolyl)-1H-pyrazol-5-yl)pyrazolo[1,5-a]pyrimidine-3-carboxamide (PTM-II-224); N-{1-(4-methylphenyl)-3-[1-(pyridin-3-ylmethyl)piperidin-4-yl]-1H-pyrazol-5-yl}pyrazolo[1,5-a]pyrimidine-3-carboxamide (PTM-II-225); N-{1-(4-methylphenyl)-3-[1-(pyridin-2-ylmethyl)piperidin-4-yl]-1H-pyrazol-5-yl}pyrazolo[1,5-a]pyrimidine-3-carboxamide (PTM-II-226); N-[3-{1-[(6-methoxypyridin-3-yl)methyl]piperidin-4-yl}-1-(4-methylphenyl)-1H-pyrazol-5-yl]pyrazolo[1,5-a]pyrimidine-3-carboxamide (PTM-II-227); N-{1-(4-methylphenyl)-3-[1-(tetrahydrofuran-3-ylmethyl)piperidin-4-yl]-1H-pyrazol-5-yl}pyrazolo[1,5-a]pyrimidine-3-carboxamide (PTM-II-228); N-{1-(4-methylphenyl)-3-[1-(1,3-thiazol-5-ylmethyl)piperidin-4-yl]-1H-pyrazol-5-yl}pyrazolo[1,5-a]pyrimidine-3-carboxamide (PTM-II-229); N-{1-(4-methylphenyl)-3-[1-(1H-pyrazol-5-ylmethyl)piperidin-4-yl]-1H-pyrazol-5-yl}pyrazolo[1,5-a]pyrimidine-3-carboxamide (PTM-II-230); N-{1-(4-methylphenyl)-3-[1-(1,3-thiazol-4-ylmethyl)piperidin-4-yl]-1H-pyrazol-5-yl}pyrazolo[1,5-a]pyrimidine-3-carboxamide (PTM-II-231); N-{1-(4-methylphenyl)-3-[1-(1,3-oxazol-2-ylmethyl)piperidin-4-yl]-1H-pyrazol-5-yl}pyrazolo[1,5-a]pyrimidine-3-carboxamide (PTM-II-232); N-{1-(4-methylphenyl)-3-[1-(1H-pyrazol-4-ylmethyl)piperidin-4-yl]-1H-pyrazol-5-yl}pyrazolo[1,5-a]pyrimidine-3-carboxamide (PTM-II-233); N-[3-(1-azetidin-3-ylpiperidin-4-yl)-1-(4-m ethylphenyl)-1H-pyrazol-5-yl]pyrazolo[1,5-a]pyrimidine-3-carboxamide (PTM-II-234); N-[3-(1-{1-[(1-methylethyl)carbamoyl]azetidin-3-yl}piperidin-4-yl)-1-(4-methylphenyl)-1H-pyrazol-5-yl]pyrazolo[1,5-a]pyrimidine-3-carboxamide (PTM-II-235); N-[3-{1-[1-(tert-butylcarbamoyl)azetidin-3-yl]piperidin-4-yl]-1-(4-methylphenyl)-1H-pyrazol-5-yl}pyrazolo[1,5-a]pyrimidine-3-carboxamide (PTM-II-236); N-[3-{1-[1-(ethylcarbamoyl)azetidin-3-yl]piperidin-4-yl}-1-(4-methylphenyl)-1H-pyrazol-5-yl]pyrazolo[1,5-a]pyrimidine-3-carboxamide (PTM-II-237); methyl 3-(4-{1'-(4-methylphenyl)-5-[(pyrazolo[1,5-a]pyrimidin-3-ylcarbonyl)amino]-1H-pyrazol-3-yl}piperidin-1-yl)azetidine-1-carboxylate (PTM-II-238); ethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (PTM-II-239); 1-methylethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (PTM-II-240); 2-fluoroethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (PTM-II-241); 2-methoxyethyl 3-(4-{I-(4-methylphenyl)-5-[(pyrazolo[1,5-a]pyrimidin-3-ylcarbonyl)amino]-1H-pyrazol-3-yl}piperidin-1-yl)azetidine-1-carboxylate (PTM-II-242); N-[3-{1-[1-(ethylsulfonyl)azetidin-3-yl]piperidin-4-yl}-1-(4-methylphenyl)-1H-pyrazol-5-yl]pyrazolo[1,5-a]pyrimidine-3-carboxamide (PTM-II-243); N-[1-(4-methylphenyl)-3-{1-[1-(methylsulfonyl)azetidin-3-yl]piperidin-4-yl}-1H-pyrazol-5-yl]pyrazolo[1,5-a]pyrimidine-3-carboxamide (PTM-II-244); N-[3-{1-[1-(cyclopropylsulfonyl)azetidin-3-yl]piperidin-4-yl]-1-(4-methylphenyl)-1H-pyrazol-5-yl}pyrazolo[1,5-a]pyrimidine-3-carboxamide (PTM-II-245); N-[3-(1-{1-[(1-methylethyl)sulfonyl] azetidin-3-yl}piperidin-4-yl)-1-(4-methylphenyl)-1H-pyrazol-5-yl]pyrazolo[1,5-a]pyrimidine-3-carboxamide (PTM-II-246); N-[3-(1-{1-[(fluoromethyl)sulfonyl]azetidin-3-yl]piperidin-4-yl)-1-(4-methylphenyl)-1H-pyrazol-5-yl}pyrazolo[1,5-a]pyrimidine-3-carboxamide (PTM-II-247); N-{3-[1-(1-acetylazetidin-3-yl)piperidin-4-yl]-1-(4-methylphenyl)-1H-pyrazol-5-yl}pyrazolo pyrimidine-3-carboxamide (PTM-II-248); N-{1-(4-methylphenyl)-3-[1-(1-propanoylazetidin-3-yl)piperidin-4-yl]-1H-pyrazol-5-yl}pyrazolo[1,5-a]pyrimidine-3-carboxamide (PTM-II-249); N-[1-(4-methylphenyl)-3-{1-[4-(trifluoromethyl)cyclohexyl]piperidin-4-yl}-1H-pyrazol-5-yl]pyrazolo[1,5-a]pyrimidine-3-carboxamide (PTM-II-250); N-[3-(1-{4-[methyl(methylsulfonyl)amino]cyclohexyl}piperidin-4-yl)-1-(4-methylphenyl)-1H-pyrazol-5-yl]pyrazolo[1,5-a]

pyrimidine-3-carboxamide (PTM-II-251); N-[1-(4-methylphenyl)-3-(1-{4-[(methylsulfonyl)amino]cyclohexyl}piperidin-4-yl)-1H-pyrazol-5-yl]pyrazolo[1,5-a]pyrimidine-3-carboxamide (PTM-II-252); N-{3-[1-(4-cyanocyclohexyl)piperidin-4-yl]-1-(4-methylphenyl)-1H-pyrazol-5-yl}pyrazolo[1,5-a]pyrimidine-3-carboxamide (PTM-II-253); N-[3-(1-bicyclo[3.1.0]hex-2-ylpiperidin-4-yl)-1-(4-methylphenyl)-1H-pyrazol-5-yl]pyrazolo[1,5-a]pyrimidine-3-carboxamide (PTM-II-254); N-{1-(4-methylphenyl)-3-[1-(2-oxo-1-azaspiro[4.5]dec-8-yl)piperidin-4-yl]-1H-pyrazol-5-yl}pyrazolo[1,5-a]pyrimidine-3-carboxamide (PTM-II-255); N-{3-[1-(3-tert-butylcyclobutyl)piperidin-4-yl]-1-(4-methylphenyl)-1H-pyrazol-5-yl}pyrazolo[1,5-a]pyrimidine-3-carboxamide (PTM-II-256); N-[1-(4-methylphenyl)-3-(1-spiro[3.4]oct-2-ylpiperidin-4-yl)-1H-pyrazol-5-yl]pyrazolo[1,5-a]pyrimidine-3-carboxamide (PTM-II-257); N-{3-[1-(3-cyanocyclobutyl)piperidin-4-yl]-1-(4-methylphenyl)-1H-pyrazol-5-yl}pyrazolo[1,5-a]pyrimidine-3-carboxamide (PTM-II-258); N-{3-[1-(4,4-difluorocyclohexyl)piperidin-4-yl]-1-(4-methylphenyl)-1H-pyrazol-5-yl}pyrazolo[1,5-a]pyrimidine-3-carboxamide (PTM-II-259); N-{1-(4-methylphenyl)-3-[1-(3,3,3-trifluoro-1-methylpropyl)piperidin-4-yl]-1H-pyrazol-5-yl}pyrazolo[1,5-a]pyrimidine-3-carboxamide (PTM-II-260); tert-butyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (PTM-II-261); N-[3-(1-{4-[methyl(methylsulfonyl)amino]cyclohexyl}piperidin-4-yl)-1-(5-methylpyridin-2-yl)-1H-pyrazol-5-yl]pyrazolo[1,5-a]pyrimidine-3-carboxamide (PTM-II-262); N-[1-(5-methylpyridin-2-yl)-3-(1-{4-[(methylsulfonyl)amino]cyclohexyl]piperidin-4-yl)-1H-pyrazol-5-yl}pyrazolo[1,5-a]pyrimidine-3-carboxamide (PTM-II-263); N-{1-(5-methylpyridin-2-yl)-3-[1-(tetrahydro-2H-pyran-3-yl)piperidin-4-yl]-1H-pyrazol-5-yl}pyrazolo[1,5-a]pyrimidine-3-carboxamide (PTM-II-264); N-{3-[1-(4-cyanocyclohexyl)piperidin-4-yl]-1-(5-methylpyridin-2-yl)-1H-pyrazol-5-yl}pyrazolo[1,5-a]pyrimidine-3-carboxamide (PTM-II-265); N-[3-{1-[1-(4-fluorophenyl)pyrrolidin-3-yl]piperidin-4-yl]-1-(5-methylpyridin-2-yl)-1H-pyrazol-5-yl}pyrazolo-[1,5-a]pyrimidine-3-carboxamide (PTM-II-266); N-[3-(1'-cyclopropyl-1,4'-bipiperidin-4-yl)-1-(5-methylpyridin-2-yl)-1H-pyrazol-5-yl]pyrazolo[1,5-a]pyrimidine-3-carboxamide (PTM-II-267); N-{1-(5-methylpyridin-2-yl)-3-[1-(5,6,7,8-tetrahydroisoquinolin-7-yl)piperidin-4-yl]-1H-pyrazol-5-yl}pyrazolo[1,5-a]pyrimidine-3-carboxamide (PTM-II-268); N-[3-{1-[3-(dimethylamino)cyclobutyl]piperidin-4-yl}-1-(5-methylpyridin-2-yl)-1H-pyrazol-5-yl]pyrazolo[1,5-a]pyrimidine-3-carboxamide (PTM-II-269); N-{3-[1-(1-methylethyl)piperidin-4-yl]-1-(5-methylpyridin-2-yl)-1H-pyrazol-5-yl}pyrazolo[1,5-a]pyrimidine-3-carboxamide (PTM-II-270); N-[L-(5-methylpyridin-2-yl)-3-{1-[4-(trifluoromethyl)cyclohexyl]piperidin-4-yl}-1H-pyrazol-5-yl]pyrazolo[1,5-a]pyrimidine-3-carboxamide (PTM-II-271); N-{3-[1-(3-methylcyclopentyl)piperidin-4-yl]-1-(5-methylpyridin-2-yl)-1H-pyrazol-5-yl}pyrazolo[1,5-a]pyrimidine-3-carboxamide (PTM-II-272); N-[3-{1-[(3R)-3-methylcyclopentyl]piperidin-4-yl}-1-(5-methylpyridin-2-yl)-1H-pyrazol-5-yl]pyrazolo[1,5-a]pyrimidine-3-carboxamide (PTM-II-273); N-[3-(1-cyclobutylpiperidin-4-yl)-1-(5-methylpyridin-2-yl)-1H-pyrazol-5-yl]pyrazolo[1,5-a]pyrimidine-3-carboxamide (PTM-II-274); N-[3-(1'-methyl-1,4'-bipiperidin-4-yl)-1-(5-methylpyridin-2-yl)-1H-pyrazol-5-yl]pyrazolo[1,5-a]pyrimidine-3-carboxamide (PTM-II-275); ethyl 4-{1-(5-methylpyridin-2-yl)-5-[(pyrazolo[1,5-a]pyrimidin-3-ylcarbonyl)amino]-1H-pyrazol-3-yl}-1,4'-bipiperidine-1'-carboxylate (PTM-II-276); N-{3-[1-(3-methylcyclohexyl)piperidin-4-yl]-1-(5-methylpyridin-2-yl)-1H-pyrazol-5-yl}pyrazolo[1,5-a]pyrimidine-3-carboxamide (PTM-II-277); N-{3-[1-(2-methylpropyl)piperidin-4-yl]-1-(5-methylpyridin-2-yl)-1H-pyrazol-5-yl}pyrazolo[1,5-a]pyrimidine-3-carboxamide (PTM-II-278); N-[3-(1'-ethyl-1,4'-bipiperidin-4-yl)-1-(5-methylpyridin-2-yl)-1H-pyrazol-5-yl]pyrazolo[1,5-a]pyrimidine-3-carboxamide (PTM-II-279); N-[1-(5-methylpyridin-2-yl)-3-(1-propylpiperidin-4-yl)-1H-pyrazol-5-yl]pyrazolo[1,5-a]pyrimidine-3-carboxamide (PTM-II-280); N-{3-[1-(cyclopropylmethyl)piperidin-4-yl]-1-(5-methylpyridin-2-yl)-1H-pyrazol-5-yl}pyrazolo[1,5-a]pyrimidine-3-carboxamide (PTM-II-281); N-{3-[1-(2,3-dihydro-1H-inden-2-yl)piperidin-4-yl]-1-(5-methylpyridin-2-yl)-1H-pyrazol-5-yl}pyrazolo[1,5-a]pyrimidine-3-carboxamide (PTM-II-282); N-{1-(4-methylphenyl)-3-[1-(tetrahydrofuran-3-ylmethyl)piperidin-3-yl]-1H-pyrazol-5-yl}pyrazolo[1,5-a]pyrimidine-3-carboxamide (PTM-II-283); N-{1-(4-methylphenyl)-3-[1-(1,3-thiazol-5-ylmethyl)piperidin-3-yl]-1H-pyrazol-5-yl}pyrazolo[1,5-a]pyrimidine-3-carboxamide (PTM-II-284); N-[1-(4-methylphenyl)-3-{1-[(3-oxo-2,3-dihydro-1H-isoindol-5-yl)methyl]piperidin-3-yl}-1H-pyrazol-5-yl]pyrazolo[1,5-a]pyrimidine-3-carboxamide (PTM-II-285); N-[3-(1-{[2-(dimethylamino)-1,3-thiazol-5-yl]methyl}piperidin-3-yl)-1-(4-methylphenyl)-1H-pyrazol-5-yl]pyrazolo[1,5-a]pyrimidine-3-carboxamide (PTM-II-286); N-{1-(4-methylphenyl)-3-[1-(1H-pyrazol-5-ylmethyl)piperidin-3-yl]-1H-pyrazol-5-yl}pyrazolo[1,5-a]pyrimidine-3-carboxamide (PTM-II-287); N-{1-(4-methylphenyl)-3-[1-(1,3-thiazol-4-ylmethyl)piperidin-3-yl]-1H-pyrazol-5-yl}pyrazolo[1,5-a]pyrimidine-3-carboxamide (PTM-II-288); N-{1-(4-methylphenyl)-3-[1-(1,3-oxazol-2-ylmethyl)piperidin-3-yl]-1H-pyrazol-5-yl}pyrazolo[1,5-a]pyrimidine-3-carboxamide (PTM-II-289); N-[3-{1-[(2-fluoropyridin-3-yl)methyl]piperidin-3-yl}-1-(4-methylphenyl)-1H-pyrazol-5-yl]pyrazolo[1,5-a]pyrimidine-3-carboxamide (PTM-II-290); N-[3-{1-[(2-methoxypyrimidin-5-yl)methyl]piperidin-3-yl}-1-(4-methylphenyl)-1H-pyrazol-5-yl]pyrazolo[1,5-a]pyrimidine-3-carboxamide (PTM-II-291); N-[3-{1-[(5-fluoropyridin-2-yl)methyl]piperidin-3-yl}-1-(4-methylphenyl)-1H-pyrazol-5-yl]pyrazolo[1,5-a]pyrimidine-3-carboxamide (PTM-II-292); N-[3-{1-[4-(3-cyanooxetan-3-3/1)benzyl]piperidin-3-yl}-1-(4-methylphenyl)-1H-pyrazol-5-yl]pyrazolo[1,5-a]pyrimidine-3-carboxamide (PTM-II-293); N-{1-(4-methylphenyl)-3-[1-(1H-pyrazol-4-ylmethyl)piperidin-3-yl]-1H-pyrazol-5-yl}pyrazolo[1,5-a]pyrimidine-3-carboxamide (PTM-II-294); N-[1-(4-methylphenyl)-3-{1-[(1-oxo-2,3-dihydro-1H-isoindol-4-yl)methyl]piperidin-3-yl}-1H-pyrazol-5-yl]pyrazolo[1,5-a]pyrimidine-3-carboxamide (PTM-II-295); N-[1-(4-methylphenyl)-3-{1-[4-(methylsulfonyl)benzyl]piperidin-3-yl}-1H-pyrazol-5-yl]pyrazolo[1,5-a]pyrimidine-3-carboxamide (PTM-II-296); N-{3-[1-(cyclopropylmethyl)piperidin-3-yl]-1-(4-methylphenyl)-1H-pyrazol-5-yl}pyrazolo[1,5-a]pyrimidine-3-carboxamide (PTM-II-297); N-{1-(4-methylphenyl)-3-[1-(1,3-thiazol-2-ylmethyl)piperidin-3-yl]-1H-pyrazol-5-yl}pyrazolo[1,5-a]pyrimidine-3-carboxamide (PTM-II-298); N-{1-(4-methylphenyl)-3-[1-(pyridin-4-ylmethyl)piperidin-3-yl]-1H-pyrazol-5-yl}pyrazolo[1,5-a]pyrimidine-3-carboxamide (PTM-II-299); N-{1-(4-methylphenyl)-3-[1-(pyridin-3-ylmethyl)piperidin-3-yl]-1H-pyrazol-5-yl}pyrazolo[1,5-a]pyrimidine-3-carboxamide (PTM-II-300); N-{1-(4-methylphenyl)-3-[1-(pyridin-2-ylmethyl)piperidin-3-yl]-

1H-pyrazol-5-yl}pyrazolo[1,5-a]pyrimidine-3-carboxamide (PTM-II-301); N-[3-{1-[(6-methoxypyridin-3-yl)methyl]piperidin-3-yl}-1-(4-methylphenyl)-1H-pyrazol-5-yl]pyrazolo[1,5-a]pyrimidine-3-carboxamide (PTM-II-302); N-[3-{1-[(1-ethyl-1H-pyrazol-5-yl)methyl]piperidin-3-yl}-1-(4-methylphenyl)-1H-pyrazol-5-yl]pyrazolo[1,5-a]pyrimidine-3-carboxamide (PTM-II-303); N-{1-(4-methylphenyl)-3-[1-(pyrazin-2-ylmethyl)azetidin-3-yl]-1H-pyrazol-5-yl}pyrazolo[1,5-a]pyrimidine-3-carboxamide (PTM-II-304); N-{1-(4-methylphenyl)-3-[1-(1H-pyrazol-4-ylmethyl)azetidin-3-yl]-1H-pyrazol-5-yl}pyrazolo[1,5-a]pyrimidine-3-carboxamide (PTM-II-305); N-{1-(4-methylphenyl)-3-[1-(1H-pyrazol-5-ylmethyl)azetidin-3-yl]-1H-pyrazol-5-yl}pyrazolo[1,5-a]pyrimidine-3-carboxamide (PTM-II-306); N-{1-(4-methylphenyl)-3-[1-(1,3-thiazol-2-ylmethyl)azetidin-3-yl]-1H-pyrazol-5-yl}pyrazolo[1,5-a]pyrimidine-3-carboxamide (PTM-II-307); N-{1-(4-methylphenyl)-3-[1-(pyridin-2-ylmethyl)azetidin-3-yl]-1H-pyrazol-5-yl}pyrazolo[1,5-a]pyrimidine-3-carboxamide (PTM-II-308); N-{1-(4-methylphenyl)-3-[1-(pyridin-4-ylmethyl)azetidin-3-yl]-1H-pyrazol-5-yl}pyrazolo[1,5-a]pyrimidine-3-carboxamide (PTM-II-309); N-{1-(4-methylphenyl)-3-[1-(pyrimidin-5-ylmethyl)azetidin-3-yl]-1H-pyrazol-5-yl}pyrazolo[1,5-a]pyrimidine-3-carboxamide (PTM-II-310); N-[3-{1-[(5-methylisoxazol-3-yl)methyl]azetidin-3-yl]-1-(4-methylphenyl)-1H-pyrazol-5-yl}pyrazolo[1,5-a]pyrimidine-3-carboxamide (PTM-II-311); N-{1-(4-methylphenyl)-3-[1-(1,3-thiazol-5-ylmethyl)azetidin-3-yl]-1H-pyrazol-5-yl}pyrazolo[1,5-a]pyrimidine-3-carboxamide (PTM-II-312); N-[3-{1-[(2-methoxypyridin-3-yl)methyl]azetidin-3-yl}-1-(4-methylphenyl)-1H-pyrazol-5-yl]pyrazolo[1,5-a]pyrimidine-3-carboxamide (PTM-II-313); N-{1-(4-methylphenyl)-3-[1-(pyridin-3-ylmethyl)azetidin-3-yl]-1H-pyrazol-5-yl}pyrazolo[1,5-a]pyrimidine-3-carboxamide (PTM-II-314); N-[3-{1-[(6-methoxypyridin-2-yl)methyl]azetidin-3-yl}-1-(4-methylphenyl)-1H-pyrazol-5-yl]pyrazolo pyrimidine-3-carboxamide (PTM-II-315); N-{1-(4-methylphenyl)-3-[1-(1,3-oxazol-2-ylmethyl)azetidin-3-yl]-1H-pyrazol-5-yl}pyrazolo[1,5-a]pyrimidine-3-carboxamide (PTM-II-316); N-[3-{1-[(2-methoxypyrimidin-5-yl)methyl]azetidin-3-yl}-1-(4-methylphenyl)-1H-pyrazol-5-yl]pyrazolo[1,5-a]pyrimidine-3-carboxamide (PTM-II-317); N-{1-(4-methylphenyl)-3-[1-(1,3-oxazol-4-ylmethyl)azetidin-3-yl]-1H-pyrazol-5-yl}pyrazolo[1,5-a]pyrimidine-3-carboxamide (PTM-II-318); N-[3-(4-cyclohexylpiperazin-1-yl)-1-(5-methylpyridin-2-yl)-1H-pyrazol-5-yl]pyrazolo[1,5-a]pyrimidine-3-carboxamide (PTM-II-319); N-[3-(4-cyclobutylpiperazin-1-yl)-1-(5-methylpyridin-2-yl)-1H-pyrazol-5-yl]pyrazolo[1,5-a]pyrimidine-3-carboxamide (PTM-II-320); N-{1-(5-methylpyridin-2-yl)-3-[4-(tetrahydro-2H-pyran-4-yl)piperazin-1-yl]-1H-pyrazol-5-yl}pyrazolo[1,5-a]pyrimidine-3-carboxamide (PTM-II-321); N-[3-(4-cycloheptylpiperazin-1-yl)-1-(5-methylpyridin-2-yl)-1H-pyrazol-5-yl]pyrazolo[1,5-a]pyrimidine-3-carboxamide (PTM-II-322); N-[3-(4-cyclopentylpiperazin-1-yl)-1-(5-methylpyridin-2-yl)-1H-pyrazol-5-yl]pyrazolo[1,5-a]pyrimidine-3-carboxamide (PTM-II-323); N-{3-[4-(2-methylpropyl)piperazin-1-yl]-1-(5-methylpyridin-2-yl)-1H-pyrazol-5-yl}pyrazolo[1,5-a]pyrimidine-3-carboxamide (PTM-II-324); N-(3-(1-cyclopentylpiperidin-4-yl)-1-(p-tolyl)-1H-pyrazol-5-yl)pyrazolo[1,5-a]pyrimidine-3-carboxamide (PTM-II-325); N-[1'-methyl-1-(4-methylphenyl)-1H,1'H-3,4'-bipyrazol-5-]pyrazolo[1,5-a]pyrimidine-3-carboxamide (PTM-II-326); N-{1-(4-methylphenyl)-3-[5-(4-methylpiperazin-1-yl)pyridin-3-yl]-1H-pyrazol-5-yl}pyrazolo[1,5-a]pyrimidine-3-carboxamide (PTM-II-327); N-{1-(4-methylphenyl)-3-[2-(piperidin-1-ylmethyl)pyridin-4-yl]-1H-pyrazol-5-yl}pyrazolo[1,5-a]pyrimidine-3-carboxamide (PTM-II-328); N-{3-[2-(hydroxymethyl)pyridin-4-yl]-1-(4-methylphenyl)-1H-pyrazol-5-yl}pyrazolo[1,5-a]pyrimidine-3-carboxamide (PTM-II-329); N-{3-[6-(hydroxymethyl)pyridin-3-yl]-1-(4-methylphenyl)-1H-pyrazol-5-yl}pyrazolo[1,5-a]pyrimidine-3-carboxamide (PTM-II-330); N-[2'-methyl-1-(4-methylphenyl)-1H,2'H-3,3'-bipyrazol-5-yl]pyrazolo[1,5-a]pyrimidine-3-carboxamide (PTM-II-331); N-{3-[5-(hydroxymethyl)pyridin-3-yl]-1-(4-methylphenyl)-1H-pyrazol-5-yl}pyrazolo[1,5-a]pyrimidine-3-carboxamide (PTM-II-332); N-{1-(4-methylphenyl)-1'-[2-(methylsulfonyl)ethyl]-1H,1'H-3,4'-bipyrazol-5-yl}pyrazolo[1,5-a]pyrimidine-3-carboxamide (PTM-II-333); N-[3-(3-methylisoxazol-4-yl)-1-(4-methylphenyl)-1H-pyrazol-5-yl]pyrazolo[1,5-a]pyrimidine-3-carboxamide (PTM-II-334); N-[1-(4-methylphenyl)-3-(2-morpholin-4-yl-1,3-thiazol-4-yl)-1H-pyrazol-5-yl]pyrazolo[1,5-a]pyrimidine-3-carboxamide (PTM-II-335); N-{3-[4-(cyclopropylsulfonyl)phenyl]-1-(4-methylphenyl)-1H-pyrazol-5-yl}pyrazolo[1,5-a]pyrimidine-3-carboxamide (PTM-II-336); N-[3-(1-methyl-6-oxo-1,6-dihydropyridin-3-yl)-1-(4-methylphenyl)-1H-pyrazol-5-yl]pyrazolo[1,5-a]pyrimidine-3-carboxamide (PTM-II-337); N-{1-(4-methylphenyl)-3-[4-(methylsulfonyl)-2-(trifluoromethyl)phenyl]-1H-pyrazol-5-yl}pyrazolo[1,5-a]pyrimidine-3-carboxamide (PTM-II-338); N-{3-[2-(benzyloxy)-6-fluorophenyl]-1-(4-methylphenyl)-1H-pyrazol-5-yl}pyrazolo[1,5-a]pyrimidine-3-carboxamide (PTM-II-339); N-{3-[4-(diethylsulfamoyl)-2-methylphenyl]-1-(4-methylphenyl)-1H-pyrazol-5-yl}pyrazolo[1,5-a]pyrimidine-3-carboxamide (PTM-II-340); N-[3-{4-[(1-methylethyl)sulfonyl]phenyl}-1-(4-methylphenyl)-1H-pyrazol-5-yl]pyrazolo[1,5-a]pyrimidine-3-carboxamide (PTM-II-341); N-[1-(4-methylphenyl)-3-{4-[(4-methylpiperazin-1-yl)sulfonyl]phenyl}-1H-pyrazol-5-yl]pyrazolo[1,5-a]pyrimidine-3-carboxamide (PTM-II-342); N-{3-[4-(diethylsulfamoyl)phenyl]-1-(4-methylphenyl)-1H-pyrazol-5-yl}pyrazolo[1,5-a]pyrimidine-3-carboxamide (PTM-II-343); N-{3-[4-(azetidin-1-ylsulfonyl)phenyl]-1-(4-methylphenyl)-1H-pyrazol-5-yl}pyrazolo[1,5-a]pyrimidine-3-carboxamide (PTM-II-344); N-{3-[4-(dimethylsulfamoyl)-2-methylphenyl]-1-(4-methylphenyl)-1H-pyrazol-5-yl}pyrazolo[1,5-a]pyrimidine-3-carboxamide (PTM-II-345); N-[1-(4-methylphenyl)-3-{3-[(methylsulfonyl)amino]phenyl}-1H-pyrazol-5-yl]pyrazolo[1,5-a]pyrimidine-3-carboxamide (PTM-II-346); N-{1-(4-methylphenyl)-3-[4-(methylsulfamoyl)phenyl]-1H-pyrazol-5-yl}pyrazolo[1,5-a]pyrimidine-3-carboxamide (PTM-II-347); N-{3-[4-(methylcarbamoyl)phenyl]-1-(4-methylphenyl)-1H-pyrazol-5-yl}pyrazolo[1,5-a]pyrimidine-3-carboxamide (PTM-II-348); N-{3-[4-(dimethylcarbamoyl)phenyl]-1-(4-methylphenyl)-1H-pyrazol-5-yl}pyrazolo[1,5-a]pyrimidine-3-carboxamide (PTM-II-349); N-{3-[3-(methylcarbamoyl)phenyl]-1-(4-methylphenyl)-1H-pyrazol-5-yl}pyrazolo[1,5-a]pyrimidine-3-carboxamide (PTM-II-350); N-{1-(4-methylphenyl)-3-[6-(methylsulfonyl)pyridin-3-yl]-1H-pyrazol-5-yl}pyrazolo[1,5-a]pyrimidine-3-carboxamide (PTM-II-351); N-{3-[4-(ethylsulfonyl)phenyl]-1-(4-methylphenyl)-1H-pyrazol-5-yl}pyrazolo[1,5-a]pyrimidine-3-carboxamide (PTM-II-352); N-{3-[4-(dimethylsulfamoyl)phenyl]-1-(4-methylphenyl)-1H-pyrazol-5-yl}pyrazolo[1,5-a]pyrimidine-3-carboxamide (PTM-II-353); N-[3-(1-methyl-6-oxo-1,2,3,6-tetrahydropyridin-4-yl)-1-(4-methylphenyl)-1H-pyrazol-5-yl]pyrazolo[1,5-a]pyrimidine-3-carboxamide (PTM-II-354); N-[3-(2-aminopyridin-4-yl)-1-(4-methylphenyl)-1H-pyrazol-5-yl]pyrazolo[1,5-a]pyrimidine-3-carboxamide (PTM-II-355); N-[3-{1-[(1,2-benzisoxazol-3-ylmethyl)sulfonyl]piperidin-4-yl}-1-(4-methylphenyl)-1H-pyrazol-5-yl]pyrazolo[1,5-a]pyrimidine-3-carboxamide (PTM-II-356); N-{1-(4-methylphenyl)-3-[1-(naphthalen-1-ylsulfonyl)piperidin-4-yl]-1H-pyrazol-5-yl}pyrazolo[1,5-a]pyrimidine-3-carboxamide (PTM-II-357); N-[1-(4-methylphenyl)-3-{1-[(pyridin-4-ylmethyl)sulfonyl]piperidin-4-yl}-1H-pyrazol-5-yl]pyrazolo[1,5-a]pyrimidine-3-carboxamide (PTM-II-358); N-[3-{1-[(3,4-dimethoxyphenyl)sulfonyl]piperidin-4-yl}-1-(4-methylphenyl)-1H-pyrazol-5-yl]pyrazolo[1,5-a]pyrimidine-3-carboxamide (PTM-II-359); N-[3-{1-[(3,5-difluorophenyl)sulfonyl]piperidin-4-yl}-1-(4-methylphenyl)-1H-pyrazol-5-yl]pyrazolo[1,5-a]pyrimidine-3-carboxamide (PTM-II-360); N-{1-(4-methylphenyl)-3-[1-(propylsulfonyl)piperidin-4-yl]-1H-pyrazol-5-yl}pyrazolo[1,5-a]pyrimidine-3-carboxamide (PTM-II-361); N-[3-{1-[(2-cyanophenyl)sulfonyl]piperidin-4-yl}-1-(4-methylphenyl)-1H-pyrazol-5-yl]pyrazolo[1,5-a]pyrimidine-3-carboxamide (PTM-II-362); N-[1-(4-methylphenyl)-3-{1-[(3,3,3-trifluoropropyl)sulfonyl]piperidin-4-yl}-1H-pyrazol-5-yl]pyrazolo[1,5-a]pyrimidine-3-carboxamide (PTM-II-363); N-[3-{1-[(2,4-dimethyl-1,3-thiazol-5-yl)sulfonyl]piperidin-4-yl}-1-(4-methylphenyl)-1H-pyrazol-5-yl]pyrazolo[1,5-a]pyrimidine-3-carboxamide (PTM-II-364); N-3-{1-[(3,4-difluorophenyl)sulfonyl]piperidin-4-yl}-1-(4-methylphenyl)-1H-pyrazol-5-yl)pyrazolo[1,5-a]pyrimidine-3-carboxamide (PTM-II-365); N-[3-{1[(4-fluorophenyl)sulfonyl]piperidin-4-yl}-1-(4-methylphenyl)-1H-pyrazol-5-yl]pyrazolo[1,5-a]pyrimidine-3-carboxamide (PTM-II-366); N-[3-{1-[(4-methoxyphenyl)sulfonyl]piperidin-4-yl}-1-(4-methylphenyl)-1H-pyrazol-5-yl]pyrazolo[1,5-a]pyrimidine-3-carboxamide (PTM-II-367); N-[3-{1-[(1-methylethyl)sulfonyl]piperidin-4-yl}-1-(4-methylphenyl)-1H-pyrazol-5-yl]pyrazolo[1,5-a]pyrimidine-3-carboxamide (PTM-II-368); N-{3-[1-(butylsulfonyl)piperidin-4-yl]-1-(4-methylphenyl)-1H-pyrazol-5-yl}pyrazolo[1,5-a]pyrimidine-3-carboxamide (PTM-II-369); N-[3-{1-[(2,4-difluorophenyl)sulfonyl]piperidin-4-yl}-1-(4-methylphenyl)-1H-pyrazol-5-yl]pyrazolo[1,5-a]pyrimidine-3-carboxamide (PTM-II-370); N-[1-(4-methylphenyl)-3-(1-{[3-(trifluoromethyl)phenyl]sulfonyl}piperidin-4-yl)-1H-pyrazol-5-yl]pyrazolo[1,5-a]pyrimidine-3-carboxamide (PTM-II-371); N-[3-{1-[(2,4-dimethoxyphenyl)sulfonyl]piperidin-4-yl}-1-(4-methylphenyl)-1H-pyrazol-5-yl]pyrazolo[1,5-a]pyrimidine-3-carboxamide (PTM-II-372); N-{3-[1-(cyclohexylsulfonyl)piperidin-4-yl]-1-(4-methylphenyl)-1H-pyrazol-5-yl}pyrazolo[1,5-a]pyrimidine-3-carboxamide (PTM-II-373); N-[3-{1-[(3-cyanophenyl)sulfonyl]piperidin-4-yl}-1-(4-methylphenyl)-1H-pyrazol-5-yl]pyrazolo[1,5-a]pyrimidine-3-carboxamide (PTM-II-374); N-[1-(4-methylphenyl)-3-{1-[(1-methyl-1H-pyrazol-4-yl)sulfonyl]piperidin-4-yl}-1H-pyrazol-5-yl]pyrazolo[1,5-a]pyrimidine-3-carboxamide (PTM-II-375); N-[3-{1-[(1-methyl-1H-imidazol-4-yl)sulfonyl]piperidin-4-yl}-1-(4-methylphenyl)-1H-pyrazol-5-yl]pyrazolo[1,5-a]pyrimidine-3-carboxamide (PTM-II-376); N-{1-(4-methylphenyl)-3-[1-(naphthalen-2-ylsulfonyl)piperidin-4-yl]-1H-pyrazol-5-yl}pyrazolo[1,5-a]pyrimidine-3-carboxamide (PTM-II-377); N-[3-{1-[(2-fluorophenyl)sulfonyl]piperidin-4-yl}-1-(4-methylphenyl)-1H-pyrazol-5-yl]pyrazolo[1,5-a]pyrimidine-3-carboxamide (PTM-II-378); N-[3-{1-[(3-fluorophenyl)sulfonyl]piperidin-4-yl}-1-(4-methylphenyl)-1H-pyrazol-5-yl]pyrazolo[1,5-a]pyrimidine-3-carboxamide (PTM-II-379); N-[3-{1-[(4-cyanophenyl)sulfonyl]piperidin-4-yl}-1-(4-methylphenyl)-1H-pyrazol-5-yl]pyrazolo[1,5-a]pyrimidine-3-carboxamide (PTM-II-380); N-[1-(4-methylphenyl)-3-(1-{[4-(trifluoromethyl)phenyl]sulfonyl}piperidin-4-yl)-1H-pyrazol-5-yl]pyrazolo[1,5-a]pyrimidine-3-carboxamide (PTM-II-381); N-[3-{1-[(4-chloropyridin-3-yl)sulfonyl]piperidin-4-yl}-1-(4-methylphenyl)-1H-pyrazol-5-yl]pyrazolo[1,5-a]pyrimidine-3-carboxamide (PTM-II-382); N-[1-(4-methylphenyl)-3-{1-[(6-morpholin-4-ylpyridin-3-yl)sulfonyl]piperidin-4-yl}-1H-pyrazol-5-yl]pyrazolo[1,5-a]pyrimidine-3-carboxamide (PTM-II-383); N-{3-[1-(1,3-benzothiazol-6-ylsulfonyl)piperidin-4-yl]-1-(4-methylphenyl)-1H-pyrazol-5-yl}pyrazolo[1,5-a]pyrimidine-3-carboxamide (PTM-II-384); N-[3-{1-[(3-methoxyphenyl)sulfonyl]piperidin-4-yl}-1-(4-methylphenyl)-1H-pyrazol-5-yl]pyrazolo[1,5-a]pyrimidine-3-carboxamide (PTM-II-385); N-[3-{1-[(1,2-dimethyl-1H-imidazol-4-yl)sulfonyl]piperidin-4-yl}-1-(4-methylphenyl)-1H-pyrazol-5-yl]pyrazolo[1,5-a]pyrimidine-3-carboxamide (PTM-II-386); N-{3-[1-(benzylsulfonyl)piperidin-4-yl]-1-(4-methylphenyl)-1H-pyrazol-5-yl}pyrazolo[1,5-a]pyrimidine-3-carboxamide (PTM-II-387); N-[3-{1-[(2-chloropyridin-3-yl)sulfonyl]piperidin-4-yl}-1-(4-methylphenyl)-1H-pyrazol-5-yl]pyrazolo[1,5-a]pyrimidine-3-carboxamide (PTM-II-388); N-[3-{1-[(6-methoxypyridin-3-yl)sulfonyl]piperidin-4-yl}-1-(4-methylphenyl)-1H-pyrazol-5-yl]pyrazolo[1,5-a]pyrimidine-3-carboxamide (PTM-II-389); N-[3-{1-[(2,6-dichlorophenyl)sulfonyl]piperidin-4-yl}-1-(4-methylphenyl)-1H-pyrazol-5-yl]pyrazolo[1,5-a]pyrimidine-3-carboxamide (PTM-II-390); N-[3-{1[(2,4-dichlorophenyl)sulfonyl]piperidin-4-yl}-1-(4-methylphenyl)-1H-pyrazol-5-yl]pyrazolo[1,5-a]pyrimidine-3-carboxamide (PTM-II-391); N-[1-(4-methylphenyl)-3-{1-[(pyridin-3-ylmethyl)sulfonyl]piperidin-4-yl}-1H-pyrazol-5-yl]pyrazolo[1,5-a]pyrimidine-3-carboxamide (PTM-II-392); N-[3-{1-[(5-chlorothiophen-2-yl)sulfonyl]piperidin-4-yl}-1-(4-methylphenyl)-1H-pyrazol-5-yl]pyrazolo[1,5-a]pyrimidine-3-carboxamide (PTM-II-393); N-[1-(4-methylphenyl)-3-(1-{[6-(trifluoromethyl)pyridin-2-yl]sulfonyl}piperidin-4-yl)-1H-pyrazol-5-yl]pyrazolo[1,5-a]pyrimidine-3-carboxamide (PTM-II-394); N-[1-(4-methylphenyl)-3-{1-[(2-phenylethyl)sulfonyl]piperidin-4-yl}-1H-pyrazol-5-yl]pyrazolo[1,5-a]pyrimidine-3-carboxamide (PTM-II-395); N-{1-(4-methylphenyl)-3-[1-(quinolin-8-ylsulfonyl)piperidin-4-yl]-1H-pyrazol-5-yl}pyrazolo[1,5-a]pyrimidine-3-carboxamide (PTM-II-396); N-[1-(4-methylphenyl)-3-{1-[(pyridin-2-ylmethyl)sulfonyl]piperidin-4-yl}-1H-pyrazol-5-yl]pyrazolo[1,5-a]pyrimidine-3-carboxamide (PTM-II-397); N-(1-(4-cyclopropyl-2-fluorophenyl)-3-(1-methylpiperidin-4-yl)-1H-pyrazol-5-yl)pyrazolo[1,5-a]pyrimidine-3-carboxamide (PTM-II-398); and N-(3-(1-methylpiperidin-4-yl)-1-(5-methylpyridin-2-yl)-1H-pyrazol-5-yl)pyrazolo[1,5-a]pyrimidine-3-carboxamide (PTM-II-399).

In any aspect or embodiment described herein, the PTM is represented by Formula PTM-III (which correspond to Formula I from U.S. Patent Application Publication No. 2015/0133451 A1, which is incorporated herein in its entirety for all purposes):

PTM-III

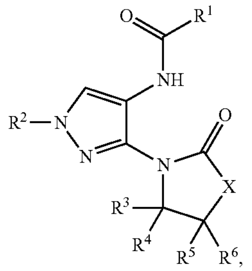

wherein $R^1$ of PTM-III is an optionally substituted aromatic heterocyclic group or an optionally substituted $C_{6-14}$ aryl group;

$R^2$ of PTM-III is a hydrogen atom or a substituent;

$R^3$ and $R^4$ of PTM-III are independently a hydrogen atom or a substituent, or $R^3$ and $R^4$ in combination optionally form an optionally substituted ring;

$R^5$ and $R^6$ of PTM-III are independently a hydrogen atom or a substituent, or $R^5$ and $R^6$ in combination optionally form an optionally substituted ring;

X of PTM-III is $CR^7R^8$, $NR^9$, O or S;

$R^7$ and $R^8$ of PTM-III are independently a hydrogen atom or a substituent, or $R^7$ and $R^8$ in combination optionally form an optionally substituted ring;

$R^9$ of PTM-III is a hydrogen atom or a substituent; and the PTM-III is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-I is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, $R^1$, $R^6$, $R^7$, $R^8$, or $R^9$).

In any aspect or embodiment described herein, the "substituent" of PTM-II may include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group. Furthermore, the substituent may be independently selected from the group consisting of: a halogen atom, a nitro group, a cyano group, an oxo group, a hydroxy group, an optionally halogenated $C_{1-6}$ alkoxy group, a $C_{6-14}$ aryloxy group (e.g., phenoxy, naphthoxy), a $C_{7-16}$ aralkyloxy group (e.g., benzyloxy), a 5- to 14-membered aromatic heterocyclyloxy group (e.g., pyridyloxy), a 3- to 14-membered non-aromatic heterocyclyloxy group (e.g., morpholinyloxy, piperidinyloxy), a $C_{1-6}$ alkyl-carbonyloxy group (e.g., acetoxy, propanoyloxy), a $C_{6-14}$ aryl-carbonyloxy group (e.g., benzoyloxy, naphthoyloxy, 2-naphthoyloxy), a $C_{1-6}$ alkoxy-carbonyloxy group (e.g., methoxycarbonyloxy, ethoxycarbonyloxy, propoxycarbonyloxy, butoxycarbonyloxy), a mono- or di-$C_{1-6}$ alkyl-carbamoyloxy group (e.g., methylcarbamoyloxy, ethylcarbamoyloxy, dimethylcarbamoyloxy, diethylcarbamoyloxy), a $C_{6-14}$ aryl-carbamoyloxy group (e.g., phenylcarbamoyloxy, naphthylcarbamoyloxy), a 5- to 14-membered aromatic heterocyclylcarbonyloxy group (e.g., nicotinoyloxy), a 3- to 14-membered non-aromatic heterocyclylcarbonyloxy group (e.g., morpholinylcarbonyloxy, piperidinylcarbonyloxy), an optionally halogenated $C_{1-6}$ alkylsulfonyloxy group (e.g., methylsulfonyloxy, trifluoromethylsulfonyloxy), a $C_{6-14}$ arylsulfonyloxy group optionally substituted by a $C_{1-6}$ alkyl group (e.g., phenylsulfonyloxy, toluenesulfonyloxy), an optionally halogenated $C_{1-6}$ alkylthio group, a 5- to 14-membered aromatic heterocyclic group, a 3- to 14-membered non-aromatic heterocyclic group, a formyl group, a carboxy group, an optionally halogenated $C_{1-6}$ alkyl-carbonyl group, a $C_{6-14}$ aryl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, 1-naphthyloxycarbonyl, 2-naphthyloxycarbonyl), a $C_{7-16}$ aralkyloxy-carbonyl group (e.g., benzyloxycarbonyl, phenethyloxycarbonyl), a carbamoyl group, a thiocarbamoyl group, a mono- or di-$C_{1-6}$ alkyl-carbamoyl group, a $C_{6-14}$ aryl-carbamoyl group (e.g., phenylcarbamoyl), a 5- to 14-membered aromatic heterocyclylcarbamoyl group (e.g., pyridylcarbamoyl, thienylcarbamoyl), a 3- to 14-membered non-aromatic heterocyclylcarbamoyl group (e.g., morpholinylcarbamoyl, piperidinylcarbamoyl), an optionally halogenated $C_{1-6}$ alkylsulfonyl group, a $C_{6-14}$ arylsulfonyl group, a 5- to 14-membered aromatic heterocyclylsulfonyl group (e.g., pyridylsulfonyl, thienylsulfonyl), an optionally halogenated $C_{1-6}$ alkylsulfinyl group, a $C_{6-14}$ arylsulfinyl group (e.g., phenylsulfinyl, 1-naphthylsulfinyl, 2-naphthylsulfinyl), a 5- to 14-membered aromatic heterocyclylsulfinyl group (e.g., pyridylsulfinyl, thienylsulfinyl), an amino group, a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino), a mono- or di-$C_{6-14}$ arylamino group (e.g., phenylamino), a 5- to 14-membered aromatic heterocyclylamino group (e.g., pyridylamino), a $C_{7-16}$ aralkylamino group (e.g., benzylamino), a formylamino group, a $C_{1-6}$ alkyl-carbonylamino group (e.g., acetylamino, propanoylamino, butanoylamino), a ($C_{1-6}$ alkyl) ($C_{1-6}$ alkyl-carbonyl)amino group (e.g., N-acetyl-N-methylamino), a $C_{6-14}$ aryl-carbonylamino group (e.g., phenylcarbonylamino, naphthylcarbonylamino), a $C_{1-6}$ alkoxy-carbonylamino group (e.g., methoxycarbonylamino, ethoxycarbonylamino, propoxycarbonylamino, butoxycarbonylamino, tert-butoxycarbonylamino), a $C_{7-16}$ aralkyloxy-carbonylamino group (e.g., benzyloxycarbonylamino), a $C_{1-6}$ alkylsulfonylamino group (e.g., methylsulfonylamino, ethylsulfonylamino), a $C_{6-14}$ arylsulfonylamino group optionally substituted by a $C_{1-6}$ alkyl group (e.g., phenylsulfonylamino, toluenesulfonylamino), an optionally halogenated $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group and a $C_{6-14}$ aryl group.

The term "optionally substituted hydrocarbon group" of PTM-III includes a hydrocarbon group optionally having substituent(s) independently selected from the group consisting of: a halogen atom, a nitro group, a cyano group, an oxo group, a hydroxy group, an optionally halogenated $C_{1-6}$ alkoxy group, a $C_{6-14}$ aryloxy group (e.g., phenoxy, naphthoxy), a $C_{7-16}$ aralkyloxy group (e.g., benzyloxy), a 5- to 14-membered aromatic heterocyclyloxy group (e.g., pyridyloxy), a 3- to 14-membered non-aromatic heterocyclyloxy group (e.g., morpholinyloxy, piperidinyloxy), a $C_{1-6}$ alkyl-carbonyloxy group (e.g., acetoxy, propanoyloxy), a $C_{6-14}$ aryl-carbonyloxy group (e.g., benzoyloxy, naphthoyloxy, 2-naphthoyloxy), a $C_{1-6}$ alkoxy-carbonyloxy group (e.g., methoxycarbonyloxy, ethoxycarbonyloxy, propoxycarbonyloxy, butoxycarbonyloxy), a mono- or di-$C_{1-6}$ alkyl-carbamoyloxy group (e.g., methylcarbamoyloxy, ethylcarbamoyloxy, dimethylcarbamoyloxy, diethylcarbamoyloxy), a $C_{6-14}$ aryl-carbamoyloxy group (e.g., phenylcarbamoyloxy, naphthylcarbamoyloxy), a 5- to 14-membered aromatic heterocyclylcarbonyloxy group (e.g., nicotinoyloxy), a 3- to 14-membered non-aromatic heterocyclylcarbonyloxy group (e.g., morpholinylcarbonyloxy, piperidinylcarbonyloxy), an optionally halogenated $C_{1-6}$ alkylsulfonyloxy group (e.g., methylsulfonyloxy, trifluoromethylsulfonyloxy), a $C_{6-14}$ arylsulfonyloxy group optionally substituted by a $C_{1-6}$ alkyl group (e.g., phenylsulfonyloxy, toluenesulfonyloxy), an optionally halogenated $C_{1-6}$ alkylthio group, a 5- to 14-membered aromatic heterocyclic group, a 3- to 14-membered non-aromatic heterocyclic group, a formyl group, a carboxy group, an optionally halogenated $C_{1-6}$ alkyl-carbonyl group, a $C_{6-14}$ aryl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, 1-naphthyloxycarbonyl, 2-naphthyloxycarbonyl), a $C_{7-16}$ aralkyloxy-carbonyl group (e.g., benzyloxycarbonyl, phenethyloxycarbonyl), a carbamoyl group, a thiocarbamoyl group, a mono- or di-$C_{1-6}$ alkyl-carbamoyl group, a $C_{6-14}$ aryl-carbamoyl group (e.g., phenylcarbamoyl), a 5- to 14-membered aromatic heterocyclylcarbamoyl group (e.g., pyridylcarbamoyl, thienylcarbamoyl), a 3- to 14-membered non-aromatic heterocyclylcarbamoyl group (e.g., morpholinylcarbamoyl, piperidinylcarbamoyl), an optionally halogenated $C_{1-6}$ alkylsulfonyl group, a $C_{6-14}$ arylsulfonyl group, a 5- to 14-membered aromatic heterocyclylsulfonyl group (e.g., pyridylsulfonyl, thienylsulfonyl), an optionally halogenated $C_{1-6}$ alkylsulfinyl group, a $C_{6-14}$ arylsulfinyl group (e.g., phenylsulfinyl, 1-naphthylsulfinyl, 2-naphthylsulfinyl), a 5- to 14-membered aromatic heterocyclylsulfinyl group (e.g., pyridylsulfinyl, thienylsulfinyl), an amino group, a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino), a mono- or di-$C_{6-14}$ arylamino group (e.g., phenylamino), a 5- to 14-membered aromatic heterocyclylamino group (e.g., pyridylamino), a $C_{7-16}$ aralkylamino group (e.g., benzylamino), a formylamino group, a $C_{1-6}$ alkyl-carbonylamino group (e.g., acetylamino, propanoylamino, butanoylamino), a ($C_{1-6}$ alkyl) ($C_{1-6}$ alkyl-carbonyl)amino group (e.g., N-acetyl-N-methylamino), a $C_{6-14}$ aryl-carbonylamino group (e.g., phenylcarbonylamino, naphthylcarbonylamino), a $C_{1-6}$ alkoxy-carbonylamino group (e.g., methoxycarbonylamino, ethoxycarbonylamino, propoxycarbonylamino, butoxycarbonylamino, tert-butoxycarbonylamino), a $C_{7-16}$ aralkyloxy-carbonylamino group (e.g., benzyloxycarbonylamino), a $C_{1-6}$ alkylsulfonylamino group (e.g., methylsulfonylamino, ethylsulfonylamino), a $C_{6-14}$ arylsulfonylamino group optionally substituted by a $C_{1-6}$ alkyl group (e.g., phenylsulfonylamino, toluenesulfonylamino), an optionally halogenated $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group and a $C_{6-14}$ aryl group.

In any aspect or embodiments described herein, the PTM of PTM-III comprises at least one of:

$R^1$ of PTM-III is an aromatic, heterocyclic group or a $C_{6-14}$ aryl group, each of which is optionally substituted by 1 to 3 substituents selected from a halogen atom, an optionally substituted $C_{1-6}$ alkyl group, an optionally substituted $C_{6-14}$ aryl group, an optionally substituted heterocyclic group, a $C_{3-10}$ cycloalkylsulfonyl group, a $C_{1-6}$ alkyl-carbonyl group, an aromatic heterocyclylsulfonyl group and a halogenated sulfanyl group;

$R^2$ of PTM-III is an optionally substituted $C_{1-6}$ alkyl group, an optionally substituted $C_{3-10}$ cycloalkyl group or an optionally substituted non-aromatic heterocyclic group;

$R^3$ and $R^4$ of PTM-III are independently a hydrogen atom or an optionally substituted $C_{1-6}$ alkyl group;

$R^5$ and $R^6$ of PTM-III are independently (1) a hydrogen atom, (2) a hydroxy group, (3) an optionally substituted $C_{1-6}$ alkyl group, (4) an optionally substituted $C_{1-6}$ alkoxy group, (5) an amino group optionally mono- or di-substituted by substituent(s) selected from (i) an optionally substituted $C_{1-6}$ alkyl group, (ii) an optionally substituted $C_{1-6}$ alkyl-carbonyl group, and (iii) an optionally substituted $C_{1-6}$ alkylsulfonyl group, (6) an optionally substituted non-aromatic heterocyclic group, (7) a carboxy group, or (8) a carbamoyl group optionally mono- or di-substituted by $C_{1-6}$ alkyl group(s), or $R^5$ and $R^6$ in combination optionally form an optionally substituted non-aromatic heterocycle or an optionally substituted $C_{3-10}$ cycloalkane;

X of PTM-III is $CR^7R^8$, $NR^9$, O or S;

$R^7$ and $R^8$ of PTM-III are independently a hydrogen atom, a cyano group, an optionally substituted $C_{1-6}$ alkyl group or a hydroxy group, or $R^7$ and $R^8$ in combination optionally form an optionally substituted $C_{3-10}$ cycloalkane or an optionally substituted non-aromatic heterocycle; and $R^9$ of PTM-III is a hydrogen atom, an optionally substituted $C_{1-6}$ alkyl group, an optionally substituted $C_{2-6}$ alkenyl group or an optionally substituted $C_{7-16}$ aralkyl group.

In any aspect or embodiment described herein, the PTM of PTM-III comprises at least one of: X is $CR^7R^8$ or $NR^9$; and $R^3$ and $R^4$ are both hydrogen atoms.

In any aspect or embodiment described herein, the PTM of PTM-III is selected from the group consisting of: N-(3-(3-(2-Hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide (PTM-III-1); N-(1-Methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide (PTM-III-2); and N-(1-Methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide (PTM-III-3).

In any aspect or embodiment described herein, the PTM is represented by Formula PTM-IV (which correspond to Formula I from U.S. Patent Application Publication No. 2015/0191464 A1, which is incorporated herein in its entirety for all purposes):

PTM-IV

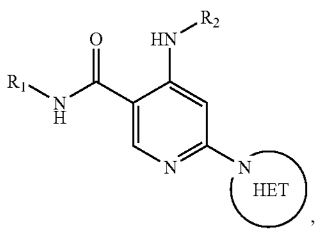

, wherein:

HET of PTM-IV is a heteroaryl selected from pyrazolyl, indolyl, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$;

$R_a$ of PTM-IV is H, F, Cl, Br, —CN, —OH, C alkyl, C fluoroalkyl, $C_{1-4}$ hydroxyalkyl, $C_{1-4}$ alkoxy, —$NH_2$, —NH($C_{1-4}$ alkyl), —N($C_{1-4}$ alkyl)$_2$, —NH($C_{1-4}$ hydroxyalkyl), —NH($C_{1-4}$ fluoroalkyl), —NH($C_{1-6}$ hydroxy-fluoroalkyl), —C(O)$NH_2$, —$CH_2$NHC(O)($C_{1-6}$ alkyl), —$CH_2$NHC(O)($C_{1-6}$ hydroxyalkyl), —$CH_2$NHC(O)NH($C_{1-6}$ alkyl), —$CH_2$NHC(O)NH$CH_2$(phenyl), —$CH_2$NHC(O)N($C_{1-4}$ alkyl)$_2$, —$CH_2$NHC(O)O($C_{1-4}$ alkyl), —$CH_2$NHC(O)($C_{3-6}$ cycloalkyl), —$CH_2$NHC(O)(tetrahydrofuranyl), —$CH_2$NHC(O)$CH_2$($C_{3-6}$ cycloalkyl), —$CH_2$NHC(O)$CH_2$(tetrahydropyranyl), —$CH_2$NHC(O)$CH_2$(phenyl), —NHC(O)($C_{1-4}$ alkyl), pyrrolidinyl, hydroxypyrrolidinyl, or pyridazinyl;

$R_b$ of PTM-IV is H or —$NH_2$;

$R_1$ of PTM-IV is: (i) $C_{1-6}$ alkyl, $C_{1-6}$ fluoroalkyl, $C_{1-6}$ hydroxyalkyl, $C_{1-8}$ hydroxy-fluoroalkyl, —($C_{1-6}$ alkylenyl)O($C_{1-4}$ alkyl), —($C_{1-6}$ alkylenyl)O($C_{1-4}$ fluoroalkyl), —($C_{1-6}$ fluoroalkylenyl)O($C_{1-4}$ alkyl), —($C_{1-6}$ fluoroalkylenyl)O($C_{1-4}$ deuteroalkyl), —($C_{1-6}$ fluoroalkylenyl)O($C_{1-4}$ fluoroalkyl), —($C_{1-4}$ fluoroalkylenyl)C($C_{3-6}$ cycloalkyl)$_2$(OH), —($C_{1-4}$ alkylenyl)NHC(O)($C_{1-4}$ alkylenyl)OC(O)($C_{1-3}$ alkyl), —($C_{1-6}$ alkylenyl)NHS(O)$_2$($C_{1-4}$ alkyl), —($C_{1-6}$ alkylenyl)P(O)($C_{1-4}$ alkoxy)$_2$, —($C_{1-6}$ fluoroalkylenyl)NH($C_{1-4}$ alkyl), —($C_{1-6}$ alkylenyl)C(O)NH($C_{1-4}$ alkyl), —($C_{1-6}$ fluoroalkylenyl)C(O)NH($C_{1-4}$ alkyl), —($C_{1-6}$ fluoroalkylenyl)C(O)NH($C_{1-4}$ hydroxyalkyl), or —($C_{1-6}$ fluoroalkylenyl)OP(O)(OH)$_2$; (ii) —($C_{1-3}$ alkylenyl)$R_x$, —($C_{1-3}$ fluoroalkylenyl)$R_x$, —($C_{1-3}$ alkylenyl)C(O)$R_x$, —($C_{1-3}$ alkylenyl)C(O)NH$R_x$, —($C_{1-3}$ fluoroalkylenyl)C(O)$R_x$, or —$CH_2$CF=(tetrahydropyranyl), wherein $R_x$ is a cyclic group selected from $C_{3-6}$ cycloalkyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —$CH_3$, —C($CH_2$)$_2$OH, —$OCH_3$, —C(O)$CH_2$CN, —S(O)$_2CH_3$, —S(O)$_2NH_2$, —NHC(O)$CH_3$, —N(S(O)$_2CH_3$)$_2$, —$CH_2CH_2$(acetamidophenyl), —$CH_2CH_2$(methoxyphenyl), —$CH_2CH_2$ (sulfamoylphenyl), oxetanyl, benzyl, and morpholinyl; (iii) C3-6 cycloalkyl or C4-6 cycloalkenyl, each substituted with zero to 3 substituents independently selected from F, —OH, —CN, C1-3 alkyl, C1-3 alkoxy, —S(C1-3 alkyl), —NO2, —S(O)2(C1-3 alkyl), C1-4 hydroxyalkyl, —C(C1-3 alkyl)(OH)(C3-6 cycloalkyl), —CH2C(O)NH(C1-3 alkyl), —NHC(O)(C1-3 alkyl), NHC(O)(C1-4 hydroxyalkyl), C(O)NH(C1-3 alkyl), —C(O)NH(C1-3 deuteroalkyl), —C(O)NH(C3-6 cycloalkyl), —NHC(O)O(C1-3 alkyl), —NHS(O)2(C1-3 alkyl), pyridinyl, imidazolyl, pyrazolyl, methylimidazolyl, methylpyrazolyl, and thiazolyl; (iv) tetrahydropyranyl, piperidinyl, pyrazolyl, phenyl, pyridinyl, or pyrimidinyl, each substituted with zero to 1 substituent selected from —OH, C1-3 alkyl, C1-3 fluoroalkyl, C1-4 hydroxyalkyl, C1-3 alkoxy, —C(O)($C_{1-4}$ alkyl), —S(O)2(C1-4 alkyl), —S(O)2NH(C1-4 alkyl), —NH(C1-3 alkyl), —N(C1-3 alkyl)$_2$, —O(C1-3 alkylenyl)N(C1-3 alkyl)2, —CH2(morpholinyl), azetidinyl, oxetanyl, tetrahydropyranyl, morpholinyl, piperazinyl, piperidinyl, methylpiperazinyl, methoxypiperidinyl, pyridinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione;

$R_2$ is: (i) $C_{1-7}$ alkyl or $C_{2-6}$ alkenyl, each substituted with zero to three substituents independently selected from F, —OH, and —CN; —($C_{1-4}$ alkylenyl)O($C_{1-4}$ alkyl), —($C_{1-4}$ alkylenyl)O($C_{1-4}$ fluoroalkyl), —($C_{1-6}$ alkylenyl)$NH_2$, —($C_{1-6}$ alkylenyl)S(O)$_2$($C_{1-3}$ alkyl), —($C_{1-6}$ fluoroalkylenyl)NH($C_{1-3}$ alkyl), or —($C_{1-6}$ alkylenyl)NHC(O)($C_{1-4}$ fluoroalkyl); (ii) —($C_{1-4}$ alkylenyl)$R_y$, wherein $R_y$ is $C_{3-6}$ cycloalkyl, azetidinyl, oxetanyl, oxazolyl, pyridinyl, tetrahydropyranyl, or morpholinyl, each substituted with zero to 2 substituents independently selected from F, —OH, and $C_{1-3}$ alkyl; (iii) $C_{3-6}$ cycloalkyl, azetidinyl, oxetanyl, furanyl, tetrahydrofuranyl, pyrrolidinyl, piperidinyl, or tetrahydropyranyl, each substituted with zero to 3 substituents independently selected from F, —OH, $C_{1-3}$ alkyl, $C_{1-3}$ hydroxyalkyl, —C(O)($C_{1-3}$ alkyl), —C(O)($C_{1-3}$ fluoroalkyl), —C(O)($C_{1-3}$ cyanoalkyl), —C(O)O($C_{1-3}$ alkyl), —C(O)$NH_2$, —C(O)NH($C_{1-3}$ alkyl), —C(O)(difluorophenyl), —$NH_2$, —NH($C_{1-3}$ alkyl), —NH($C_{1-3}$ fluoroalkyl), —NH(oxetanyl), —NHC(O)($C_{1-3}$ alkyl), —NHC(O)($C_{1-3}$ fluoroalkyl), —NHC(O)($C_{3-6}$ cycloalkyl), —NHC(O)(fluorophenyl), —S(O)$_2$($C_{1-3}$ alkyl), imidazolyl, phenyl, pyrimidinyl, fluoropyrimidinyl, choropyrimidinyl, and methoxypyrimidinyl; (iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxybicyclo[2.2.1]heptanyl; or (v) phenyl, pyrazolyl, thiazolyl, thiadiazolyl, or indazolyl, each substituted with 0 to 2 substituents independently selected from F, Cl, —OH, —CN, Cia alkyl, $C_{1-4}$ hydroxyalkyl, $C_{1-4}$ fluoroalkyl, Cia cyanoalkyl, $C_{1-3}$ alkoxy, $C_{3-6}$ cycloalkyl, —($C_{1-3}$ alkylenyl)O($C_{1-3}$ alkyl), —($C_{1-3}$ alkylenyl)O($C_{1-3}$ fluoroalkyl), —C(O)$NH_2$, —C(O)NH($C_{1-3}$ alkyl), —NHC(O)($C_{1-3}$ alkyl), —NHC(O)S(O)$_2$($C_{1-3}$ alkyl), —S(O)$_2NH_2$, —S(O)$_2$($C_{1-3}$ alkyl), pyrazolyl, methyl pyrazolyl, imidazolyl, triazolyl, methyl tetrazolyl, ethyl tetrazolyl, phenyl, pyrimidinyl, fluoropyrimidinyl, and tetrahydropyranyl; and the PTM-IV is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-IV is covalently joined to a ULM, a chemical linker group (L), a CLM, an ILM, a VLM, MLM, a ULM', a CLM', a ILM', a VLM', a MLM', or combination thereof via an R group (e.g., $R_1$, $R_2$, $R_a$ or $R_b$).

In any aspect or embodiment described herein, the HET group of PTM-IV is a heteroaryl group having at least one nitrogen heteroatom, wherein one nitrogen heteroatom of the HET group forms a bond to a carbon atom adjacent to the nitrogen heteroatom in the pyridine ring. For example, the HET may be a heteroaryl selected from

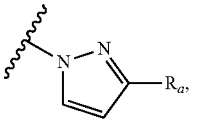

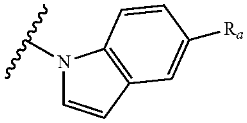

,

-continued

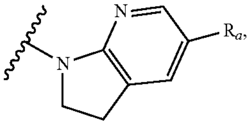

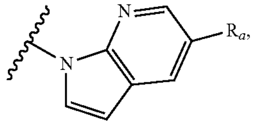

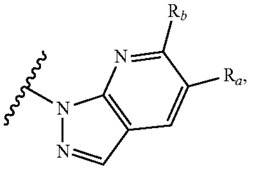

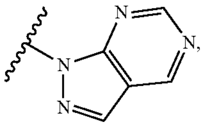

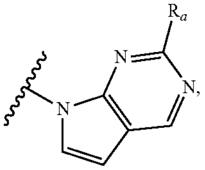

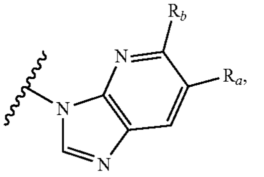

and

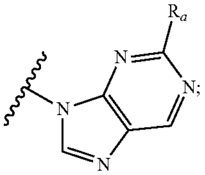

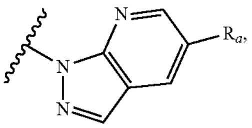

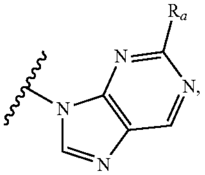

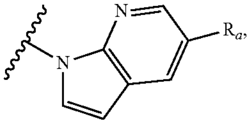

wherein:

$R_a$ of PTM-IV is H, F, Cl, Br, —CN, —OH, —$CH_3$, —$CHF_2$, —$OCH_3$, —$NH_2$, —$N(CH_3)_2$, —$NHCH_2CH_2OH$, —$NHCH_2C(CH_3)_2H$, —$NHCH_2CHFC(CH_3)_2OH$, —$C(O)NH_2$, —$CH_2NHC(O)CH_2CH_2CH_3$, —$CH_2NHC(O)CH(CH_3)_2$, —$CH_2NHC(O)CH_2CH(CH_3)_2$, —$CH_2NHC(O)CH_2C(CH_3)_3$, —$CH_2NHC(O)CH_2CH_2CH(CH_3)_2$, —$CH_2NHC(O)CH_2C(CH_3)_2OH$, —$CH_2NHC(O)NHCH_2CH_2CH_3$, —$CH_2NHC(O)NHCH_2CH_2CH_2CH_3$, —$CH_2NHC(O)NHCH_2$(phenyl), —$CH_2NHC(O)N(CH_2CH_3)_2$, —$CH_2NHC(O)OCH_2CH_3$, —$CH_2NHC(O)OCH_2CH(CH_3)_2$, —$CH_2NHC(O)$(cyclopropyl), —$CH_2NHC(O)$(tetrahydrofuranyl), —$CH_2NHC(O)CH_2$(cyclopentyl), —$CH_2NHC(O)CH_2$(cyclohexyl), —$CH_2NHC(O)CH_2$(tetrahydropyranyl), —$CH_2NHC(O)CH_2$(phenyl), —$NHC(O)CH_3$, hydroxypyrrolidinyl, or pyridazinyl; and $R_b$ of PTM-IV is H or —$NH_2$.

In any aspect or embodiment described herein, at least one of:

$R_1$ of PTM-IV is: (i) —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2CH_2CH(CH_3)_2$, —$CH_2CHFCH_3$, —$CH_2CH_2CF_2CH_3$, —$CH_2CHFCH(CH_3)_2$, —$CH_2CH_2C(CH_3)_2F$, —$CH_2CHFC(CH_3)_2F$, —$CH_2CH_2CH(OH)CH_3$, —$CH_2CH_2C(CH_3)_2OH$, —$CH_2CHFCH(CH_3)OH$, —$CH_2CHFC(CH_3)_2OH$, —$CH_2CF_2C(CH_3)_2OH$, —$CH_2CHFC(CH_2CH_3)_2OH$, —$CH_2CHFC$(cyclopropyl)$_2$(OH), —$CH_2CHFCH(OH)CH(CH_3)_2$, —$CH_2CH_2OCH_2CH_3$, —$(CH_2)_3OCH(CH_3)_2$, —$(CH_2)_3OC(CH_3)_3$, —$CH_2CHFCH_2OCH_3$, —$CH_2CHFC(CH_3)_2OCH_3$, —$CH_2CHFC(CH_3)_2OCD_3$, —$CH_2CHFC(CH_3)_2OCHF_2$, —$CH_2CHFC(CH_3)_2OCH_2CH_3$, —$CH_2CH_2C(O)OCH_3$, —$CH_2CH_2NHC(O)C(CH_3)_2OC(O)CH_3$, —$CH_2CH_2NHS(O)_2CH_3$, —$CH_2CH_2CH(CH_3)NHS(O)_2CH_3$, —$CH_2CH_2C(CH_3)_2NHS(O)_2CH_3$, —$CH_2CH_2P(O)(OCH_2CH_3)_2$, —$CH_2CHFCH(CH_3)NHCH(CH_3)_2$, —$CH_2CHFC(O)NHCH_3$, —$CH_2CH_2C(O)NHCH_2CH_3$, —$CH_2CHFC(O)NHCH(CH_3)_2$, —$CH_2CHFC(O)NHCH(CH_3)CH_2OH$, or —$CH_2CHFC(CH_3)_2OP(O)(OH)_2$; (ii) —($C_{1-3}$ alkylenyl)$R_x$, —($C_{1-2}$ fluoroalkylenyl)$R_x$, —($C_{1-2}$alkylenyl)C(O)$R_x$, —$CH_2C(O)NHR_x$, —$CH_2CHFC(O)R_x$, or —$CH_2CF$=(tetrahydropyranyl), wherein $R_x$ is a cyclic group selected from cyclopropyl, cyclopentyl, cyclohexyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —$CH_3$, —$C(CH_2)_2OH$, —$OCH_3$, —$C(O)CH_2CN$, —$S(O)_2CH_3$, —$S(O)_2NH_2$, —$NHC(O)CH_3$, —$N(S(O)_2CH_3)_2$, —$CH_2CH_2$(acetamidophenyl), —$CH_2CH_2$(methoxyphenyl), —$CH_2CH_2$(sulfamoylphenyl), oxetanyl, benzyl, and morpholinyl; (iii) cyclopropyl, cyclopentyl, cyclopentenyl, or cyclohexyl, each substituted with zero to 2 substituents independently selected from F, —OH, —CN, —$CH_3$, —$OCH_3$, —$SCH_3$, —$NO_2$, —$S(O)_2CH_3$, —$C(CH_3)_2OH$, —$C(CH_3)(OH)$(cyclopropyl), —$CH_2C(O)NHCH_3$, —$NHC(O)CH(OH)CH_3$, —$C(O)NHCD_3$, —$C(O)NHCH_3$, —$C(O)NHCH_2CH_3$, —$C(O)NH$(cyclopropyl), —$NHC(O)CH_3$, —$NHC(O)OCH_3$, —$NHS(O)_2CH_3$, pyridinyl, methylimidazolyl, methylpyrazolyl, and thiazolyl; (iv) tetrahydropyranyl, piperidinyl, pyrazolyl, phenyl, pyridinyl, or pyrimidinyl, each substituted with zero to 1 substituent selected from —OH, —$OCH_3$, —$CH_2CHF_2$, —$C(CH_3)_2OH$, —$CH_2C(CH_3)_2OH$, —$C(O)CH(CH_3)_2$, —$S(O)_2CH_3$, —$S(O)_2CH_2CH_3$, —$S(O)_2CH(CH_3)_2$, —$S(O)_2NHCH_3$, —$S(O)_2NHCH(CH_3)_2$, —$N(CH_3)_2$, —$OCH_2CH_2N(CH_3)_2$, —$CH_2$(morpholinyl), oxetanyl, tetrahydropyranyl, morpholinyl, piperazinyl, methylpiperazinyl, methoxypiperidinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and $R_2$ of PTM-IV is: (i) —$CH_2CH_3$, —$CH_2CH_2CH_3$, —$CH(CH_3)_2$, —$C(CH_3)_3$, —$CH_2C(CH_3)_3$, —$CH(CH_3)CH_2CH_3$, —$CH_2CH_2CH(CH_3)_2$, —$CH(CH_3)CH_2CH(CH_3)_2$, —$CH(CH_3)CH_2OH$, —$CH_2CH_2CH(CH_3)OH$, —$CH(CH_3)CH_2CH_2OH$, —$CH_2C(CH_3)_2OH$, —$C(CH_3)_2CH_2OH$, —$CH(CH_3)CH(OH)CH_2CH(CH_3)_2$, —$CH_2CH(OH)CH(CH_3)_2$, —$CH(CH_2OH)CH_2CH_3$, —$CH(CH_2OH)CH(CH_3)_2$, —$CH{=}CHC(CH_3)_2OH$, —$CH_2CH_2CN$, —$CH_2CHF_2$, —$CH_2CF_3$, —$CH_2CHFCH_3$, —$CH(CH_3)CF_3$, —$CH_2CH_2CF_3$, —$CH(CH_3)CH_2F$, —$CH_2CH_2CH_2F$, —$CH_2CHFCH_2CH_3$, —$CH_2CH_2CHFCH_3$, —$CH(CH_3)CHFCH_3$, $CH(CH_3)CH_2CH_2F$, —$CH_2CH_2C(CH_3)_2F$, —$CH_2CHFC(CH_3)_2OH$, —$CH_2CF_2C(CH_3)_2OH$, —$CH_2C(CH_3)FCH_2OH$, —$CH(CH_2F)CH_2OH$, —$CH_2CH_2OCHF_2$, —$CH_2C(CH_3)OCHF_2$, —$CH_2C(CH_3)_2OCHF_2$, —$CH_2C(CH_3)_2OCH_3$, —$CH_2C(CH_3)_2CH_2NH_2$, —$CH_2CHFC(O)NHCH$ $(CH_3)_2$, $—CH_2CH_2NHS(O)_2CH_3$, or $—CH_2CH_2NHC(O)OC(CH_3)_2CF_3$; (ii) $—CH_2$(azetidinyl), $—CH_2$(cyclopropyl), $—CH_2$(fluorocyclobutyl), $—CH_2$(hydroxycyclobutyl), $—CH_2$(oxetanyl), $—CH_2$(methyloxetanyl), $—CH_2$(oxazolyl), $—CH_2$(methylpyridinyl), $—CH_2$(tetrahydropyranyl), $—CH_2CH_2$(methylmorpholinyl) $—CH(CH_3)$(cyclopropyl), $—CH_2CH_2$(morpholinyl), $—CH_2CH(CH_3)$(morpholinyl), or $—CH_2C(CH_3)_2$(morpholinyl); (iii) $C_{3-6}$ cycloalkyl substituted with zero to 3 substituents independently selected from F, —OH, $—CH_3$, $—CH_2H$, $—C(CH_3)_2OH$, $—C(O)NH_2$, $—C(O)NHCH(CH_3)_2$, $—NH_2$, $—NHCH_2CF_3$, —NH(oxetanyl), $—NHC(O)CHF_2$, —NHC(O)(cyclopropyl), —NHC(O)(fluorophenyl), and imidazolyl; azetidinyl substituted with $—C(O)CH_3$, $—C(O)OCH_3$, $—C(O)OCH_2CH_3$, $—C(O)OC(CH_3)_3$, $—S(O)_2CH_3$, fluoropyrimidinyl, or chloropyrimidinyl; tetrahydrofuranyl substituted with zero to 2 substituents independently selected from F and —OH; pyrrolidinyl substituted with zero to 1 substituent selected from $—C(O)CH_3$, $—C(O)CH_2CF_3$, $—C(O)CH_2CN$, $—C(O)OCH_3$, $—S(O)_2CH_3$, —C(O)(difluorophenyl), pyrimidinyl, fluoropyrimidinyl, and methoxypyrimidinyl; piperidinyl substituted with $—S(O)_2CH_3$, phenyl, or fluoropyrimidinyl; tetrahydropyranyl, fluorotetrahydropyranyl, or oxetanyl; (iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxybicyclo[2.2.1]heptanyl; or (v) phenyl substituted with 1 to 2 substituents independently selected from F, —OH, —CN, $—CH_2OH$, $—C(CH_3)_2OH$, $—OCH_3$, $—C(O)NH_2$, $—C(O)NHCH_3$, $—NHC(O)CH_3$, $—NHC(O)S(O)_2CH_3$, $—S(O)_2NH_2$, pyrazolyl, methyl pyrazolyl, imidazolyl, triazolyl, methyl tetrazolyl, and ethyl tetrazolyl; pyrazolyl substituted with 1 to 2 substituents independently selected from $—CH_3$, $—CH_2CH_3$, $—CH_2CH_2CH_3$, $—CH(CH_3)_2$, $—CHF_2$, $—CH_2CHF_2$, $—CH_2CF_3$, $—CH_2CHFCH_3$, $—CH_2CH_2CH_2F$, $—CH_2C(CH_3)_2F$, $—CH_2CF_2CH_3$, $—CH_2C(CH_3)_2OH$, $—CH_2CH_2OCH_3$, $—CH_2CH(CH_3)OCHF_2$, $—CH_2CH_2CN$, $—C(O)NHCH_2CH_3$, $—S(O)_2CH_3$, cyclopropyl, oxetanyl, phenyl, pyrimidinyl, fluoropyrimidinyl, and tetrahydropyranyl; methyl thiadiazolyl, hydroxypropyl thiazolyl, or indazolyl.

In any aspect or embodiment described herein, the Het of PTM-IV is a heteroaryl selected from:

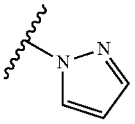,
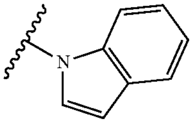,
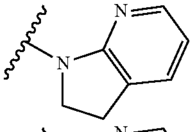,
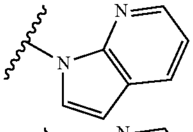,
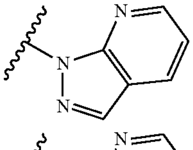,
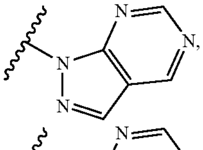
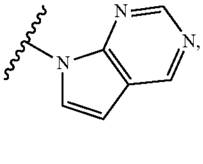
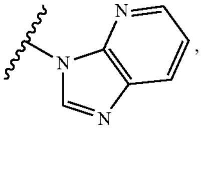, -continued

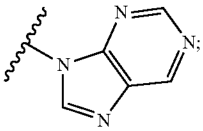
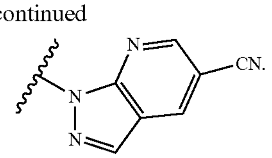

In any aspect or embodiment described herein, Q of PTM-IV is selected from:

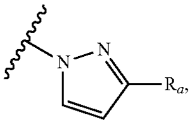
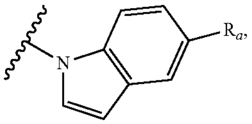
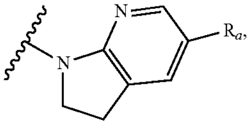
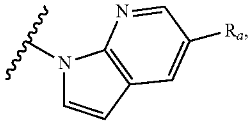
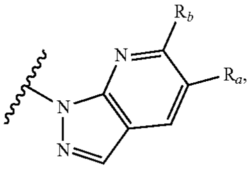
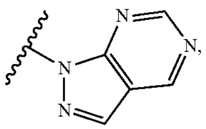
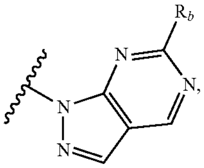
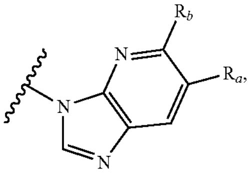 and
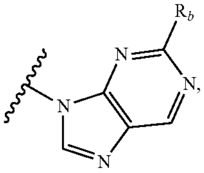
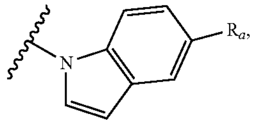
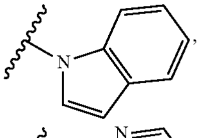
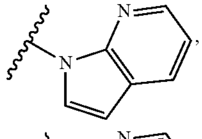
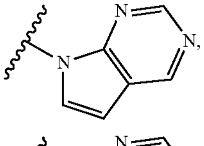
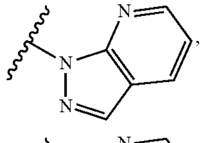
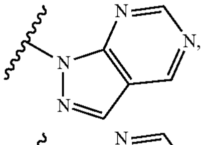
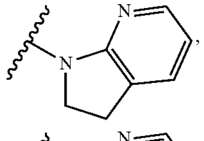
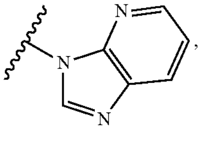
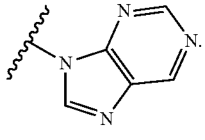

In any aspect or embodiment described herein, the PTM of PTM-IV is selected from: (R)-6-(5-cyano-1H-indol-1-yl)-N-(2-fluoro-3-hydroxy-3-methylbutyl)-4-(isopropylamino)nicotinamide (PTM-IV-1); (R)-6-(5-cyano-1H-pyrrolo[2,3- b]pyridin-1-yl)-4-(cyclopropylamino)-N-(2-fluoro-3-hydroxy-3-methylbutyl)nicotinamide (PTM-IV-2); (R)-6-(5-cyano-1H-pyrrolo[2,3-b]pyridin-1-yl)-N-(2-fluoro-3-hydroxy-3-methylbutyl)-4-((tetrahydro-2H-pyran-4-yl)amino)nicotinamide (PTM-IV-3); (R)-6-(5-cyano-1H-pyrrolo[2,3-b]pyridin-1-yl)-4-(ethylamino)-N-(2-fluoro-3-hydroxy-3-methylbutyl) nicotinamide (PTM-IV-4); (R)-6-(5-cyano-1H-pyrrolo[2,3-b]pyridin-1-yl)-N-(2-fluoro-3-hydroxy-3-methylbutyl)-4-(2,2,2-trifluoroethyl)amino) nicotinamide (PTM-IV-5); (R)-6-(5-cyano-1H-pyrrolo[2,3-b]pyridin-1-yl)-4-(cyclobutylamino)-N-(2-fluoro-3-hydroxy-3-methylbutyl) nicotinamide (PTM-IV-6); 6-(5-cyano-1H-pyrrolo[2,3-b]pyridin-1-yl)-N—((R)-2-fluoro-3-hydroxy-3-methylbutyl)-4-((tetrahydro-2H-pyran-3-yl)amino)nicotinamide (PTM-IV-7); 6-(5-cyano-1H-pyrrolo[2,3-b]pyridin-1-yl)-N—((S)-2-fluoro-3-hydroxy-3-methylbutyl)-4-((tetrahydro-2H-pyran-3-yl)amino) nicotinamide (PTM-IV-8); 6-(5-cyano-1H-pyrrolo[2,3-b]pyridin-1-yl)-N—((R)-2-fluoro-3-hydroxy-3-methylbutyl)-4-(((S)-1-hydroxypropan-2-yl)amino) nicotinamide (PTM-IV-9); (R)-6-(5-cyano-1H-pyrrolo[2,3-b]pyridin-1-yl)-4-(cyclopentylamino)-N-(2-fluoro-3-hydroxy-3-methylbutyl) nicotinamide (PTM-IV-10); 6-(5-cyano-1H-pyrrolo[2,3-b]pyridin-1-yl)-N-(3-hydroxy-3-methylbutyl)-4-(isopropylamino)nicotinamide (PTM-IV-11); 6-(5-cyano-1H-pyrrolo[2,3-b]pyridin-1-yl)-N-(3-hydroxy-3-methylbutyl)-4-((tetrahydro-2H-pyran-4-yl)amino) nicotinamide (PTM-IV-12); 4-((1s,3S)-adamantan-1-ylamino)-6-(5-cyano-1H-pyrrolo[2,3-b]pyridin-1-yl)-N—((R)-2-fluoro-3-hydroxy-3-methylbutyl)nicotinamide (PTM-IV-13); 6-(5-cyano-1H-pyrrolo[2,3-b]pyridin-1-yl)-N-(4-hydroxybicyclo[2.2.1]heptan-1-yl)-4-(isopropylamino)nicotinamide (PTM-IV-14); N-(3-(tert-butoxy)propyl)-6-(5-cyano-1H-pyrrolo[2,3-b]pyridin-1-yl)-4-(isopropylamino)nicotinamide (PTM-IV-15); (R)-6-(5-cyano-1H-pyrrolo[2,3-b]pyridin-1-yl)-N-(2-fluoro-3-hydroxy-3-methylbutyl)-4-((4-hydroxybicyclo[2.2.1]heptan-1-yl)amino)nicotinamide (PTM-IV-16); (R)-6-(5-cyano-1H-pyrrolo[2,3-b]pyridin-1-yl)-N-(2-fluoro-3-hydroxy-3-methylbutyl)-4-((1-methylcyclopropyl)amino) nicotinamide (PTM-IV-17); (R)-6-(5-cyano-1H-pyrrolo[2,3-b]pyridin-1-yl)-N-(2-fluoro-3-hydroxy-3-methylbutyl)-4-((1-methylcyclopropyl)amino)nicotinamide (PTM-IV-18); (R)-6-(5-cyano-1H-pyrrolo[2,3-b]pyridin-1-yl)-N-(2-fluoro-3-hydroxy-3-methylbutyl)-4-(isopentylamino) nicotinamide (19); (R)-6-(5-cyano-1H-pyrrolo[2,3-b]pyridin-1-yl)-N-(2-fluoro-3-hydroxy-3-methylbutyl)-4-(((3-methyloxetan-3-yl)methyl)amino)nicotinamide (PTM-IV-20); 6-(5-cyano-1H-pyrrolo[2,3-b]pyridin-1-yl)-N—((R)-2-fluoro-3-hydroxy-3-methylbutyl)-4-((4-hydroxybutan-2-yl)amino)nicotinamide (PTM-IV-21); 6-(5-cyano-1H-pyrrolo[2,3-b]pyridin-1-yl)-N—((S)-2-fluoro-3-hydroxy-3-methylbutyl)-4-((4-hydroxybutan-2-yl)amino)nicotinamide (PTM-IV-22); (S)-6-(5-cyano-1H-pyrrolo[2,3-b]pyridin-1-yl)-N-(2-fluoro-3-hydroxy-3-methylbutyl)-4-(isopropylamino)nicotinamide (PTM-IV-23); 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (PTM-IV-24); diastereomer 1; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (PTM-IV-25); diastereomer 2; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (PTM-IV-26); diastereomer 3; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (PTM-IV-27); diastereomer 4; (R)-6-(5-cyano-1H-pyrrolo[2,3-b]pyridin-1-yl)-N-(2-fluoro-3-hydroxy-3-methylbutyl)-4-(((1-hydroxycyclobutyl)methyl)amino) nicotinamide (PTM-IV-28); (R)-6-(5-cyano-1H-pyrrolo[2,3-b]pyridin-1-yl)-N-(2-fluoro-3-hydroxy-3-methylbutyl)-4-((oxetan-3-ylmethyl)amino) nicotinamide (29); 6-(5-cyano-1H-pyrrolo[2,3-b]pyridin-1-yl)-N—((R)-2-fluoro-3-hydroxy-3-methylbutyl)-4-(((1R,2R)-2-hydroxycyclopentyl)amino)nicotinamide (PTM-IV-30); (R)-6-(5-chloro-1H-pyrrolo[2,3-b]pyridin-1-yl)-4-(cyclobutylamino)-N-(2-fluoro-3-hydroxy-3-methylbutyl)nicotinamide (PTM-IV-31); (R)-6-(5-chloro-1H-pyrrolo[2,3-b]pyridin-1-yl)-N-(2-fluoro-3-hydroxy-3-methylbutyl)-4-((tetrahydro-2H-pyran-4-yl)amino) nicotinamide (PTM-IV-32); (R)-6-(5-chloro-1H-pyrrolo[2,3-b]pyridin-1-yl)-4-(ethylamino)-N-(2-fluoro-3-hydroxy-3-methylbutyl) nicotinamide (PTM-IV-33); (R)-6-(5-chloro-1H-pyrrolo[2,3-b]pyridin-1-yl)-4-(cyclopropylamino)-N-(2-fluoro-3-hydroxy-3-methylbutyl)nicotinamide (PTM-IV-34); (R)-6-(5-chloro-1H-pyrrolo[2,3-b]pyridin-1-yl)-N-(2-fluoro-3-hydroxy-3-methylbutyl)-4-((2-hydroxy-2-methylpropyl)amino)nicotinamide (PTM-IV-35); 6-(5-chloro-1H-pyrrolo[2,3-b]pyridin-1-yl)-N-(3-hydroxy-3-methylbutyl)-4-((tetrahydro-2H-pyran-4-yl)amino)nicotinamide (PTM-IV-36); (R)-6-(5-chloro-1H-indol-1-yl)-N-(2-fluoro-3-hydroxy-3-methylbutyl)-4-(isopropylamino)nicotinamide (PTM-IV-37); (R)-6-(5-fluoro-1H-pyrrolo[2,3-b]pyridin-1-yl)-N-(2-fluoro-3-hydroxy-3-methylbutyl)-4-(isopropylamino)nicotinamide (PTM-IV-38); (R)—N-(2-fluoro-3-hydroxy-3-methylbutyl)-4-(isopropylamino)-6-(7H-pyrrolo[2,3-d]pyrimidin-7-yl)nicotinamide (PTM-IV-39); (R)—N-(2-fluoro-3-hydroxy-3-methylbutyl)-6-(7H-pyrrolo[2,3-d]pyrimidin-7-yl)-4-((tetrahydro-2H-pyran-4-yl)amino) nicotinamide (PTM-IV-40); (R)-4-(cyclopropylamino)-N-(2-fluoro-3-hydroxy-3-methylbutyl)-6-(7H-pyrrolo[2,3-d]pyrimidin-7-yl)nicotinamide (PTM-IV-41); (R)—N-(2-fluoro-3-hydroxy-3-methylbutyl)-4-((2-hydroxy-2-methylpropyl)amino)-6-(7H-pyrrolo[2,3-d]pyrimidin-7-yl) nicotinamide (PTM-IV-42); N-(3-hydroxy-3-methylbutyl)-6-(7H-pyrrolo[2,3-d]pyrimidin-7-yl)-4-((tetrahydro-2H-pyran-4-yl)amino)nicotinamide (PTM-IV-43); N-(3-hydroxy-3-methylbutyl)-4-(isopropylamino)-6-(7H-pyrrolo[2,3-d]pyrimidin-7-yl)nicotinamide (PTM-IV-44); (R)-6-(5-acetamido-1H-pyrrolo[2,3-b]pyridin-1-yl)-N-(2-fluoro-3-hydroxy-3-methylbutyl)-4-(isopropylamino)nicotinamide (PTM-IV-45); (R)-6-(5-cyano-1H-pyrrolo[2,3-b]pyridin-1-yl)-N-(2-fluoro-3-hydroxy-3-methylbutyl)-4-((3-hydroxyphenyl)amino)nicotinamide (PTM-IV-46); 6-(5-cyano-1H-pyrrolo[2,3-b]pyridin-1-yl)-N-(3-isopropoxypropyl)-4-(isopropylamino) nicotinamide (PTM-IV-47); 6-(5-cyano-1H-pyrrolo[2,3-b]pyridin-1-yl)-N-((2R)-2-fluoro-3-hydroxybutyl)-4-(isopropylamino)nicotinamide (PTM-IV-48); 6-(5-cyano-1H-pyrrolo[2,3-b]pyridin-1-yl)-N-((2S)-2-fluoro-3-hydroxybutyl)-4-(isopropylamino)nicotinamide (PTM-IV-49); (R)-6-(5-cyano-1H-pyrrolo[2,3-b]pyridin-1-yl)-N-(2-fluoro-3-hydroxy-3-methylbutyl)-4-((3-sulfamoylphenyl)amino)nicotinamide (PTM-IV-50); (R)-6-(5-cyano-1H-pyrrolo[2,3-b]pyridin-1-yl)-N-(2-fluoro-3-hydroxy-3-methylbutyl)-4-((3-methoxyphenyl)amino) nicotinamide (PTM-IV-51); 6-(5-cyano-1H-pyrrolo[2,3-b]pyridin-1-yl)-N—((R)-2-fluoro-3-hydroxy-3-methylbutyl)-4-(((R)-2-fluoro-3-hydroxy-3-methylbutyl)amino) nicotinamide (PTM-IV-52); (R)-6-(5-cyano-1H-pyrrolo[2,3-b]pyridin-1-yl)-4-((3,3-difluorocyclobutyl)amino)-N-(2-fluoro-3-hydroxy-3-methylbutyl)nicotinamide (PTM-IV-53); (R)-4-((3-acetamidophenyl)amino)-6-(5-cyano-1H-pyrrolo[2,3-b]pyridin-1-yl)-N-(2-fluoro-3-hydroxy-3- methylbutyl) nicotinamide (PTM-IV-54); (R)-6-(5-cyano-1H-pyrrolo[2,3-b]pyridin-1-yl)-N-(2-fluoro-3-hydroxy-3-methylbutyl)-4-((3-(methylcarbamoyl)phenyl)amino) nicotinamide (PTM-IV-55); (R)-4-((3-carbamoylphenyl) amino)-6-(5-cyano-1H-pyrrolo[2,3-b]pyridin-1-yl)-N-(2-fluoro-3-hydroxy-3-methylbutyl)nicotinamide (PTM-IV-56); (R)-6-(5-cyano-1H-pyrrolo[2,3-b]pyridin-1-yl)-N-(2-fluoro-3-hydroxy-3-methylbutyl)-4-((3-(methylsulfonamido)phenyl)amino) nicotinamide (PTM-IV-57); 6-(5-cyano-1H-pyrrolo[2,3-b]pyridin-1-yl)-4-(isopropylamino)-N-(4-sulfamoylphenethyl)nicotinamide (PTM-IV-58); (R)-6-(5-cyano-1H-pyrrolo[2,3-b]pyridin-1-yl)-N-(2-fluoro-3-hydroxy-3-methylbutyl)-4-((3-(2-hydroxypropan-2-yl)phenyl)amino) nicotinamide (PTM-IV-59); (R)-4-((4-carbamoylphenyl)amino)-6-(5-cyano-1H-pyrrolo[2,3-b]pyridin-1-yl)-N-(2-fluoro-3-hydroxy-3-methylbutyl)nicotinamide (PTM-IV-60); 6-(5-cyano-1H-pyrrolo[2,3-b]pyridin-1-yl)-N—((R)-2-fluoro-3-hydroxy-3-methylbutyl)-4-(((1s,4S)-4-hydroxy-4-methylcyclohexyl) amino)nicotinamide (PTM-IV-61); 6-(5-cyano-1H-pyrrolo [2,3-b]pyridin-1-yl)-N—((R)-2-fluoro-3-hydroxy-3-methylbutyl)-4-(((trans)-4-hydroxy-4-methylcyclohexyl) amino)nicotinamide (PTM-IV-62); 6-(5-cyano-1H-pyrrolo [2,3-b]pyridin-1-yl)-4-(isopropylamino)-N-(2-(methylsulfonamido)ethyl)nicotinamide (PTM-IV-63); (R)-4-(benzo[d]thiazol-6-ylamino)-6-(5-cyano-1H-pyrrolo[2,3-b]pyridin-1-yl)-N-(2-fluoro-3-hydroxy-3-methylbutyl) nicotinamide (PTM-IV-64); (R)-6-(5-cyano-1H-pyrrolo[2,3-b]pyridin-1-yl)-N-(2-fluoro-3-hydroxy-3-methylbutyl)-4-(((1-fluorocyclobutyl)methyl)amino) nicotinamide (PTM-IV-65); (R)-6-(5-cyano-1H-pyrrolo[2,3-b]pyridin-1-yl)-4-((3-cyanophenyl)amino)-N-(2-fluoro-3-hydroxy-3-methylbutyl)nicotinamide (PTM-IV-66); (R)-4-((4-(1H-1,2,4-triazol-1-yl)phenyl)amino)-6-(5-cyano-1H-pyrrolo[2,3-b] pyridin-1-yl)-N-(2-fluoro-3-hydroxy-3-methylbutyl) nicotinamide (PTM-IV-67); (R)-6-(5-cyano-1H-pyrrolo[2,3-b]pyridin-1-yl)-N-(2-fluoro-3-hydroxy-3-methylbutyl)-4-((4-(1-methyl-1H-tetrazol-5-yl)phenyl)amino)nicotinamide (PTM-IV-68); (R)-6-(5-cyano-1H-pyrrolo[2,3-b]pyridin-1-yl)-N-(2-fluoro-3-hydroxy-3-methylbutyl)-4-((4-(1-methyl-1H-tetrazol-5-yl)phenyl)amino)nicotinamide (PTM-IV-69); 6-(5-cyano-1H-pyrrolo[2,3-b]pyridin-1-yl)-N-(2-(1,1-dioxidotetrahydrothiophen-3-yl)amino)-2-oxoethyl)-4-(isopropylamino)nicotinamide (PTM-IV-70); (R)-6-(5-cyano-1H-pyrrolo[2,3-b]pyridin-1-yl)-N-(2-fluoro-3-hydroxy-3-methylbutyl)-4-((3-(hydroxymethyl)phenyl)amino) nicotinamide (PTM-IV-71); 6-(5-cyano-1H-pyrrolo[2,3-b] pyridin-1-yl)-N—((R)-2-fluoro-3-hydroxy-3-methylbutyl)-4-(((2S)-3-fluorobutan-2-yl)amino) nicotinamide (PTM-IV-72); N-(2-amino-4,5,6,7-tetrahydrobenzo[d]thiazol-6-yl)-6-(5-cyano-1H-pyrrolo[2,3-b]pyridin-1-yl)-4-(isopropylamino)nicotinamide (PTM-IV-73); (R)—N-(2-fluoro-3-hydroxy-3-methylbutyl)-4-(isopropylamino)-6-(1H-pyrrolo[2,3-b]pyridin-1-yl)nicotinamide (PTM-IV-74); (R)-6-(5-cyano-1H-pyrrolo[2,3-b]pyridin-1-yl)-N-(2-fluoro-3-hydroxy-3-methylbutyl)-4-(isopropylamino)nicotinamide (PTM-IV-75); (R)-6-(5-chloro-1H-pyrrolo[2,3-b] pyridin-1-yl)-N-(2-fluoro-3-hydroxy-3-methylbutyl)-4-(isopropylamino) nicotinamide (PTM-IV-76); (R)-6-(5-cyano-1H-pyrrolo[2,3-b]pyridin-1-yl)-N-(2-fluoro-3-hydroxy-3-methylbutyl)-4-((2-hydroxy-2-methylpropyl) amino)nicotinamide (PTM-IV-77); 6-(5-cyano-1H-pyrrolo [2,3-b]pyridin-1-yl)-N—((R)-2-fluoro-3-hydroxy-3-methylbutyl)-4-((1-fluoropropan-2-yl)amino)nicotinamide (PTM-IV-78); 6-(5-cyano-1H-indol-1-yl)-4-(isopropylamino)-N-((trans)-4-(methylcarbamoyl)cyclohexyl)nicotinamide (PTM-IV-79); 6-(5-cyano-1H-pyrrolo[2,3-b]pyridin-1-yl)-4-(isopropylamino)-N-((trans)-4-(methylcarbamoyl)cyclohexyl)nicotinamide (PTM-IV-80); 4-(isopropylamino)-N-((trans)-4-(methylcarbamoyl)cyclohexyl)-6-(7H-pyrrolo[2,3-d]pyrimidin-7-yl)nicotinamide (PTM-IV-81); N-((trans)-4-(methylcarbamoyl)cyclohexyl)-6-(7H-pyrrolo[2,3-d]pyrimidin-7-yl)-4-((tetrahydro-2H-pyran-4-yl)amino)nicotinamide (PTM-IV-82); N-((trans)-4-acetamidocyclohexyl)-6-(7H-pyrrolo[2,3-d]pyrimidin-7-yl)-4-((tetrahydro-2H-pyran-4-yl)amino)nicotinamide (PTM-IV-83); N-((trans)-4-acetamidocyclohexyl)-4-(isopropylamino)-6-(7H-pyrrolo[2,3-d]pyrimidin-7-yl)nicotinamide (PTM-IV-84); 6-(5-cyano-1H-pyrrolo[2,3-b]pyridin-1-yl)-4-(cyclopropylamino)-N-((trans)-4-(methylcarbamoyl)cyclohexyl) nicotinamide (PTM-IV-85); 6-(5-cyano-1H-pyrrolo[2,3-b]pyridin-1-yl)-N-((trans)-4-(methylcarbamoyl)cyclohexyl)-4-((tetrahydro-2H-pyran-4-yl)amino)nicotinamide (PTM-IV-86); N-((trans)-4-acetamidocyclohexyl)-6-(5-cyano-1H-pyrrolo[2,3-b]pyridin-1-yl)-4-(cyclopropylamino)nicotinamide (PTM-IV-87); N-((trans)-4-acetamidocyclohexyl)-6-(5-cyano-1H-pyrrolo [2,3-b]pyridin-1-yl)-4-((tetrahydro-2H-pyran-4-yl)amino) nicotinamide (PTM-IV-88); 6-(5-cyano-1H-pyrrolo[2,3-b] pyridin-1-yl)-4-(((S)-1-hydroxypropan-2-yl)amino)-N-((1r,4S)-4-(methylcarbamoyl)cyclohexyl)nicotinamide (PTM-IV-89); 6-(5-cyano-1H-pyrrolo[2,3-b]pyridin-1-yl)-4-(isopropylamino)-N-((trans)-4-(isopropylcarbamoyl) cyclohexyl) nicotinamide (PTM-IV-90); 6-(5-cyano-1H-pyrrolo[2,3-b]pyridin-1-yl)-N-((trans)-4-(cyclopropylcarbamoyl)cyclohexyl)-4-(isopropylamino) nicotinamide (PTM-IV-91); 6-(5-cyano-1H-pyrrolo[2,3-b] pyridin-1-yl)-N-((trans)-4-(ethylcarbamoyl)cyclohexyl)-4-(isopropylamino)nicotinamide (PTM-IV-92); 6-(5-cyano-1H-pyrrolo[2,3-b]pyridin-1-yl)-4-((2-hydroxy-2-methylpropyl)amino)-N-((trans)-4-(methylcarbamoyl) cyclohexyl) nicotinamide (PTM-IV-93); 6-(5-cyano-1H-pyrrolo[2,3-b]pyridin-1-yl)-4-((2-hydroxy-2-methylpropyl) amino)-N-((trans)-4-(($^{2}H_{3}$)methylcarbamoyl)cyclohexyl) nicotinamide (PTM-IV-94); 6-(5-cyano-1H-pyrrolo[2,3-b] pyridin-1-yl)-4-(isopropylamino)-N-((trans)-4-nitrocyclohexyl)nicotinamide (PTM-IV-95); 6-(5-cyano-1H-pyrrolo[2,3-b]pyridin-1-yl)-N-((trans)-4-(2-hydroxypropan-2-yl)cyclohexyl)-4-(isopropylamino) nicotinamide (PTM-IV-96); methyl((trans)-4-(6-(5-cyano-1H-pyrrolo[2,3-b]pyridin-1-yl)-4-(isopropylamino) nicotinamido)cyclohexyl)carbamate (PTM-IV-97); 6-(5-cyano-1H-pyrrolo[2,3-b]pyridin-1-yl)-N-((trans)-4-hydroxycyclohexyl)-4-(isopropylamino)nicotinamide (PTM-IV-98); 6-(5-cyano-1H-pyrrolo[2,3-b]pyridin-1-yl)-N-((trans)-4-hydroxy-4-methylcyclohexyl)-4-(isopropylamino)nicotinamide (PTM-IV-99); 6-(5-cyano-1H-pyrrolo[2,3-b]pyridin-1-yl)-4-(ethylamino)-N-((trans)-4-(2-hydroxypropan-2-yl)cyclohexyl)nicotinamide (PTM-IV-100); 6-(5-cyano-1H-pyrrolo[2,3-b]pyridin-1-yl)-4-(isopropylamino)-N-((trans)-4-(methylthio)cyclohexyl) nicotinamide (PTM-IV-101); 6-(5-cyano-1H-pyrrolo[2,3-b] pyridin-1-yl)-4-(isopropylamino)-N-((trans)-4-(methylsulfonyl)cyclohexyl)nicotinamide (PTM-IV-102); 6-(5-cyano-1H-pyrrolo[2,3-b]pyridin-1-yl)-N-((trans)-4-(methylsulfonyl)cyclohexyl)-4-((tetrahydro-2H-pyran-4-yl) amino)nicotinamide (PTM-IV-103); 6-(5-cyano-1H-pyrrolo [2,3-b]pyridin-1-yl)-4-(cyclopropylamino)-N-((trans)-4-(methylsulfonyl)cyclohexyl) nicotinamide (PTM-IV-104); 4-((3-carbamoylphenyl)amino)-6-(5-cyano-1H-pyrrolo[2,3-b]pyridin-1-yl)-N-((trans)-4-(methylsulfonyl)cyclohexyl) nicotinamide (PTM-IV-105); 6-(5-cyano-1H-pyrrolo[2,3-b] pyridin-1-yl)-N—((R)-2-fluoro-3-hydroxy-3-methylbutyl)-4-((3-fluorotetrahydro-2H-pyran-4-yl)amino)nicotinamide (PTM-IV-106); 6-(5-cyano-1H-pyrrolo[2,3-b]pyridin-1-yl)-N—((R)-2-fluoro-3-hydroxy-3-methylbutyl)-4-((3-fluoro-tetrahydro-2H-pyran-4-yl)amino)nicotinamide (PTM-IV-107); 6-(5-cyano-1H-pyrrolo[2,3-b]pyridin-1-yl)-N—((S)-2-fluoro-3-hydroxy-3-methylbutyl)-4-((3-fluorotetrahydro-2H-pyran-4-yl)amino) nicotinamide (PTM-IV-108); 6-(5-cyano-1H-pyrrolo[2,3-b]pyridin-1-yl)-N—((R)-2-fluoro-3-hydroxy-3-methylbutyl)-4-((3-fluorocyclopentyl)amino) nicotinamide (PTM-IV-109); 6-(5-cyano-1H-pyrrolo[2,3-b] pyridin-1-yl)-N—((S)-2-fluoro-3-hydroxy-3-methylbutyl)-4-((3-fluorocyclopentyl)amino)nicotinamide (PTM-IV-110); 6-(5-cyano-1H-pyrrolo[2,3-b]pyridin-1-yl)-4-((3,3-difluoro-2-hydroxycyclohexyl)amino)-N—((R)-2-fluoro-3-hydroxy-3-methylbutyl) nicotinamide (PTM-IV-111); 6-(5-cyano-1H-pyrrolo[2,3-b]pyridin-1-yl)-4-((3,3-difluoro-2-hydroxycyclohexyl)amino)-N—((R)-2-fluoro-3-hydroxy-3-methylbutyl)nicotinamide (PTM-IV-112); N—((R)-2-fluoro-3-hydroxy-3-methylbutyl)-4-((1-fluoropropan-2-yl) amino)-6-(7H-pyrrolo[2,3-d]pyrimidin-7-yl)nicotinamide (PTM-IV-113); 6-(5-cyano-1H-pyrazolo[3,4-b]pyridin-1-yl)-N—((R)-2-fluoro-3-hydroxy-3-methylbutyl)-4-(((R)-1-fluoropropan-2-yl)amino) nicotinamide (PTM-IV-114); N—((R)-2-fluoro-3-hydroxy-3-methylbutyl)-4-(((R)-1-fluoropropan-2-yl)amino)-6-(7H-pyrrolo[2,3-d]pyrimidin-7-yl)nicotinamide (PTM-IV-115); N—((R)-2-fluoro-3-hydroxy-3-methylbutyl)-4-(((S)-1-fluoropropan-2-yl)amino)-6-(7H-pyrrolo[2,3-d]pyrimidin-7-yl)nicotinamide (PTM-IV-116); 6-(5-cyano-1H-pyrrolo[2,3-b]pyridin-1-yl)-N—((R)-2-fluoro-3-hydroxy-3-methylbutyl)-4-(((S)-1-fluoropropan-2-yl)amino)nicotinamide (PTM-IV-117); 6-(5-cyano-1H-pyrrolo[2,3-b]pyridin-1-yl)-N—((R)-2-fluoro-3-hydroxy-3-methylbutyl)-4-(((R)-1-fluoropropan-2-yl) amino)nicotinamide (PTM-IV-118); (S)-6-(5-cyano-1H-pyrrolo[2,3-b]pyridin-1-yl)-4-((1-fluoropropan-2-yl) amino)-N-(3-hydroxy-3-methylbutyl)nicotinamide (PTM-IV-119); (R)-6-(5-cyano-1H-pyrrolo[2,3-b]pyridin-1-yl)-4-((1-fluoropropan-2-yl)amino)-N-(3-hydroxy-3-methylbutyl)nicotinamide (PTM-IV-120); 6-(5-cyano-1H-pyrazolo[3,4-b]pyridin-1-yl)-N—((R)-2-fluoro-3-hydroxy-3-methylbutyl)-4-(((S)-1-fluoropropan-2-yl)amino) nicotinamide (PTM-IV-121); 6-(5-cyano-1H-pyrazolo[3,4-b]pyridin-1-yl)-4-(((S)-1-fluoropropan-2-yl)amino)-N-((1r, 4S)-4-(methylcarbamoyl)cyclohexyl)nicotinamide (PTM-IV-122); (R)-1-(4-(ethylamino)-5-(2-fluoro-3-hydroxy-3-methylbutyl)carbamoyl)pyridin-2-yl)-1H-pyrrolo[2,3-b] pyridine-5-carboxamide (PTM-IV-123); (R)-1-(4-(cyclobutylamino)-5-((2-fluoro-3-hydroxy-3-methylbutyl) carbamoyl)pyridin-2-yl)-1H-pyrrolo[2,3-b]pyridine-5-carboxamide (PTM-IV-124); 1-((2-(6-(5-cyano-1H-pyrrolo [2,3-b]pyridin-1-yl)-4-(isopropylamino) nicotinamido) ethyl)amino)-2-methyl-1-oxopropan-2-yl acetate (PTM-IV-125); 6-(5-cyano-1H-pyrrolo[2,3-b]pyridin-1-yl)-N-(2-(2-hydroxy-2-methylpropanamido)ethyl)-4-(isopropylamino) nicotinamide (PTM-IV-126); (R)-6-(5-cyano-1H-pyrrolo[2,3-b]pyridin-1-yl)-N-(2-fluoro-3-methoxypropyl)-4-(isopropylamino)nicotinamide (PTM-IV-127); (R)-6-(5-cyano-1H-pyrazolo[3,4-b]pyridin-1-yl)-N-(2-fluoro-3-methoxypropyl)-4-(isopropylamino) nicotinamide (PTM-IV-128); 6-(5-cyano-1H-pyrrolo[2,3-b]pyridin-1-yl)-N-((2R)-2-fluoro-3-(isopropylamino)butyl)-4-(isopropylamino)nicotinamide (PTM-IV-129); 6-(5-cyano-1H-pyrrolo[2,3-b]pyridin-1-yl)-N-((2R)-2-fluoro-3-(isopropylamino)butyl)-4-(isopropylamino) nicotinamide (PTM-IV-130); 6-(5-cyano-1H-pyrrolo[2,3-b]pyridin-1-yl)-N—((R)-2-fluoro-3-hydroxy-3-methylbutyl)-4-((1-fluoro-3-hydroxypropan-2-yl)amino)nicotinamide (PTM-IV-131); (R)-6-(5-cyano-1H-pyrrolo[2,3-b]pyridin-1-yl)-4-(cyclopropylamino)-N-(2-fluoro-3-(methylamino)-3-oxopropyl) nicotinamide (PTM-IV-132); (R)-6-(5-cyano-1H-pyrazolo [3,4-b]pyridin-1-yl)-N-(2-fluoro-3-hydroxy-3-methylbutyl)-4-(isopropylamino)nicotinamide (PTM-IV-133); (R)-4-(cyclopropylamino)-N-(2-fluoro-3-hydroxy-3-methylbutyl)-6-(1H-pyrazolo[3,4-d]pyrimidin-1-yl) nicotinamide (PTM-IV-134); (R)-6-(5-chloro-1H-pyrazolo [3,4-b]pyridin-1-yl)-N-(2-fluoro-3-hydroxy-3-methylbutyl)-4-((tetrahydro-2H-pyran-4-yl)amino) nicotinamide (PTM-IV-135); (R)-6-(5-chloro-1H-pyrazolo [3,4-b]pyridin-1-yl)-4-(cyclopropylamino)-N-(2-fluoro-3-hydroxy-3-methylbutyl)nicotinamide (PTM-IV-136); (R)-6-(5-chloro-1H-pyrazolo[3,4-b]pyridin-1-yl)-N-(2-fluoro-3-hydroxy-3-methylbutyl)-4-(isopropylamino)nicotinamide (PTM-IV-137); (R)-6-(5-cyano-1H-pyrazolo[3,4-b]pyridin-1-yl)-4-(ethylamino)-N-(2-fluoro-3-hydroxy-3-methylbutyl)nicotinamide (PTM-IV-138); (R)-6-(5-cyano-1H-pyrazolo[3,4-b]pyridin-1-yl)-4-(cyclopropylamino)-N-(2-fluoro-3-hydroxy-3-methylbutyl)nicotinamide (PTM-IV-139); 6-(5-cyano-1H-pyrazolo[3,4-b]pyridin-1-yl)-4-(cyclopropylamino)-N-((trans)-4-(methylcarbamoyl) cyclohexyl)nicotinamide (PTM-IV-140); (R)-6-(5-cyano-1H-pyrazolo[3,4-b]pyridin-1-yl)-N-(2-fluoro-3-hydroxy-3-methylbutyl)-4-((tetrahydro-2H-pyran-4-yl)amino) nicotinamide (PTM-IV-141); 6-(5-cyano-1H-pyrazolo[3,4-b]pyridin-1-yl)-N—((R)-2-fluoro-3-hydroxy-3-methylbutyl)-4-((tetrahydro-2H-pyran-3-yl)amino) nicotinamide, diastereomer 1 (PTM-IV-142); 6-(5-cyano-1H-pyrazolo[3,4-b]pyridin-1-yl)-N—((S)-2-fluoro-3-hydroxy-3-methylbutyl)-4-((tetrahydro-2H-pyran-3-yl) amino) nicotinamide, diastereomer 2 (PTM-IV-143); (R)—N-(2-fluoro-3-hydroxy-3-methylbutyl)-4-(isopropylamino)-6-(1H-pyrazolo[3,4-d]pyrimidin-1-yl)nicotinamide (PTM-IV-144); (R)-6-(5-cyano-1H-pyrazolo[3,4-b]pyridin-1-yl)-4-(cyclobutylamino)-N-(2-fluoro-3-hydroxy-3-methylbutyl)nicotinamide (PTM-IV-145); 6-(5-cyano-1H-pyrazolo[3,4-b]pyridin-1-yl)-N-(3-hydroxy-3-methylbutyl)-4-(isopropylamino)nicotinamide (PTM-IV-146); (R)-6-(5-cyano-1H-pyrazolo[3,4-b]pyridin-1-yl)-N-(2-fluoro-3-hydroxy-3-methylbutyl)-4-(2,2,2-trifluoroethyl)amino) nicotinamide (PTM-IV-147); 6-(5-cyano-1H-pyrazolo[3,4-b]pyridin-1-yl)-N-((trans)-4-(2-hydroxypropan-2-yl) cyclohexyl)-4-(isopropylamino)nicotinamide (PTM-IV-148); (R)—N-(3-ethyl-2-fluoro-3-hydroxypentyl)-4-(isopropylamino)-6-(1H-pyrazolo[3,4-d]pyrimidin-1-yl) nicotinamide (PTM-IV-149); 6-(5-chloro-1H-pyrazolo[3,4-b]pyridin-1-yl)-N-((trans)-4-(2-hydroxypropan-2-yl) cyclohexyl)-4-(isopropylamino)nicotinamide (PTM-IV-150); 6-(5-cyano-1H-pyrazolo[3,4-b]pyridin-1-yl)-N-(3-hydroxy-3-methylbutyl)-4-((tetrahydro-2H-pyran-4-yl) amino)nicotinamide (PTM-IV-151); 6-(5-chloro-1H-pyrazolo[3,4-b]pyridin-1-yl)-4-(isopropylamino)-N-((trans)-4-(methylcarbamoyl)cyclohexyl)nicotinamide (PTM-IV-152); (R)—N-(2-fluoro-3-hydroxy-3-methylbutyl)-6-(5-hydroxy-1H-pyrazolo[3,4-b]pyridin-1-yl)-4-(isopropylamino)nicotinamide (PTM-IV-153); 6-(5-chloro-1H-pyrazolo[3,4-b]pyridin-1-yl)-4-(isopropylamino)-N-(2-morpholinoethyl)nicotinamide (PTM-IV-154); (R)—N-(2-fluoro-3-hydroxy-3-methylbutyl)-4-(isopropylamino)-6-(5-methyl-1H-pyrazolo[3,4-b]pyridin-1-yl)nicotinamide (PTM-IV-155); (R)-4-(cyclopropylamino)-6-(5-fluoro-1H-pyrazolo[3,4-b]pyridin-1-yl)-N-(2-fluoro-3-hydroxy-3-methylbutyl)nicotinamide (PTM-IV-156); (R)-6-(5-fluoro-1H-pyrazolo[3,4-b]pyridin-1-yl)-N-(2-fluoro-3-hydroxy-3-methylbutyl)-4-(isopropylamino) nicotinamide (PTM-IV-157); (R)-6-(5-bromo-1H-pyrazolo[3,4-b]pyridin-1-yl)-N-(2-fluoro-3-hydroxy-3-methylbutyl)-4-(isopropylamino)

nicotinamide (PTM-IV-158); 6-(5-cyano-1H-pyrazolo[3,4-b]pyridin-1-yl)-N—((R)-2-fluoro-3-hydroxy-3-methylbutyl)-4-(((trans)-4-hydroxycyclohexyl)amino) nicotinamide (PTM-IV-159); 6-(5-cyano-1H-pyrazolo[3,4-b]pyridin-1-yl)-4-(isopropylamino)-N-((trans)-4-(methylcarbamoyl)cyclohexyl)nicotinamide (PTM-IV-160); 6-(5-cyano-1H-pyrazolo[3,4-b]pyridin-1-yl)-4-(isopropylamino)-N-((trans)-4-(methylsulfonyl)cyclohexyl)nicotinamide (161); 6-(5-cyano-1H-pyrazolo[3,4-b]pyridin-1-yl)-4-(isopropylamino)-N-((trans)-4-(($^2H_3$)methylcarbamoyl) cyclohexyl)nicotinamide (PTM-IV-162); (R)-6-(5-cyano-1H-pyrazolo[3,4-b]pyridin-1-yl)-N-(2-fluoro-3-hydroxy-3-methylbutyl)-4-((4-fluorocyclohexyl)amino)nicotinamide (PTM-IV-163); N-((trans)-4-acetamidocyclohexyl)-6-(5-cyano-1H-pyrazolo[3,4-b]pyridin-1-yl)-4-(isopropylamino) nicotinamide (PTM-IV-164); N-(2-amino-4,5,6,7-tetrahydrobenzo[d]thiazol-6-yl)-6-(5-cyano-1H-pyrazolo[3,4-b] pyridin-1-yl)-4-(isopropylamino)nicotinamide (PTM-IV-165); 6-(5-cyano-1H-pyrazolo[3,4-b]pyridin-1-yl)-4-(isopropylamino)-N-((trans)-4-(methylsulfonamido) cyclohexyl)nicotinamide (PTM-IV-166); 6-(5-cyano-1H-pyrazolo[3,4-b]pyridin-1-yl)-N-(2,2-difluoro-3-hydroxy-3-methylbutyl)-4-(isopropylamino)nicotinamide (PTM-IV-167); (R)—N-(2-fluoro-3-hydroxy-3-methylbutyl)-4-(isopropylamino)-6-(3-(pyridazin-4-yl)-1H-pyrazol-1-yl) nicotinamide (PTM-IV-168); (R)-6-(5-cyano-1H-pyrazolo[3,4-b]pyridin-1-yl)-4-(2,2-difluoro-3-hydroxy-3-methylbutyl)amino)-N-(2-fluoro-3-hydroxy-3-methylbutyl) nicotinamide (PTM-IV-169); (R)—N-(2-fluoro-3-hydroxy-3-methylbutyl)-4-(isopropylamino)-6-(9H-purin-9-yl)nicotinamide (PTM-IV-170); (R)-6-(2-amino-9H-purin-9-yl)-N-(2-fluoro-3-hydroxy-3-methylbutyl)-4-(isopropylamino) nicotinamide (PTM-IV-171); (R)—N-(2-fluoro-3-hydroxy-3-methylbutyl)-6-(2-((2-hydroxyethyl)amino)-9H-purin-9-yl)-4-(isopropylamino)nicotinamide (PTM-IV-172); 6-(5-cyano-1H-pyrrolo[2,3-b]pyridin-1-yl)-N-((1s,4s)-4-hydroxy-4-((1-methyl-1H-pyrazol-5-yl)cyclohexyl)-4-(isopropylamino) nicotinamide (PTM-IV-173); 6-(5-cyano-1H-pyrrolo[2,3-b]pyridin-1-yl)-N-((1s,4s)-4-fluoro-4-((1-methyl-1H-pyrazol-5-yl)cyclohexyl)-4-(isopropylamino) nicotinamide (PTM-IV-174); 6-(5-cyano-1H-pyrrolo[2,3-b] pyridin-1-yl)-N-((1s,4s)-4-hydroxy-4-(thiazol-2-yl) cyclohexyl)-4-(isopropylamino)nicotinamide (PTM-IV-175); 6-(5-cyano-1H-pyrrolo[2,3-b]pyridin-1-yl)-N-((1s,4s)-4-hydroxy-4-((1-methyl-1H-imidazol-2-yl)cyclohexyl)-4-(isopropylamino) nicotinamide (PTM-IV-176); 6-(5-cyano-1H-pyrrolo[2,3-b]pyridin-1-yl)-N-((1s,4s)-4-hydroxy-4-(pyridin-3-yl)cyclohexyl)-4-(isopropylamino) nicotinamide (PTM-IV-177); 6-(5-cyano-1H-pyrrolo[2,3-b] pyridin-1-yl)-N-((1s,4s)-4-hydroxy-4-(pyridin-2-yl) cyclohexyl)-4-(isopropylamino)nicotinamide (PTM-IV-178); 6-(5-cyano-1H-pyrrolo[2,3-b]pyridin-1-yl)-N-((1s,4s)-4-hydroxy-4-(pyridin-4-yl)cyclohexyl)-4-(isopropylamino)nicotinamide (PTM-IV-179); 6-(5-cyano-1H-pyrrolo[2,3-b]pyridin-1-yl)-N-((1s,4s)-4-fluoro-4-(thiazol-2-yl)cyclohexyl)-4-(isopropylamino)nicotinamide (PTM-IV-180); 6-(5-cyano-1H-pyrrolo[2,3-b]pyridin-1-yl)-N-((1s,4s)-4-fluoro-4-((1-methyl-1H-imidazol-2-yl)cyclohexyl)-4-(isopropylamino) nicotinamide (PTM-IV-181); 6-(5-cyano-1H-pyrrolo[2,3-b]pyridin-1-yl)-N-((trans)-4-fluoro-4-((1-methyl-1H-imidazol-2-yl)cyclohexyl)-4-(isopropylamino)nicotinamide (PTM-IV-182); 6-(5-cyano-1H-pyrrolo[2,3-b]pyridin-1-yl)-N-(2,4-dioxo-1,3-diazaspiro [4.5]decan-8-yl)-4-(isopropylamino)nicotinamide (PTM-IV-183); (S)-6-(5-cyano-1H-pyrrolo[2,3-b]pyridin-1-yl)-4-(isopropylamino)-N-(4-(pyridin-4-yl)cyclohex-3-en-1-yl) nicotinamide (PTM-IV-184); (R)-6-(2-(dimethylamino)-7H-pyrrolo[2,3-d]pyrimidin-7-yl)-N-(2-fluoro-3-hydroxy-3-methylbutyl)-4-(isopropylamino)nicotinamide (PTM-IV-185); (R)-6-(2-amino-7H-pyrrolo[2,3-d]pyrimidin-7-yl)-N-(2-fluoro-3-hydroxy-3-methylbutyl)-4-(isopropylamino) nicotinamide (PTM-IV-186); (R)—N-(2-fluoro-3-hydroxy-3-methylbutyl)-6-(2-(2-hydroxy-2-methylpropyl)amino)-7H-pyrrolo[2,3-d]pyrimidin-7-yl)-4-(isopropylamino)nicotinamide (PTM-IV-187); (R)—N-(2-fluoro-3-hydroxy-3-methylbutyl)-6-(2-((2-hydroxyethyl)amino)-7H-pyrrolo[2,3-d]pyrimidin-7-yl)-4-(isopropylamino)nicotinamide (PTM-IV-188); N—((R)-2-fluoro-3-hydroxy-3-methylbutyl)-6-(2-((S)-3-hydroxypyrrolidin-1-yl)-7H-pyrrolo[2,3-d]pyrimidin-7-yl)-4-(isopropylamino)nicotinamide (PTM-IV-189); N—((R)-2-fluoro-3-hydroxy-3-methylbutyl)-6-(2-((R)-3-hydroxypyrrolidin-1-yl)-7H-pyrrolo[2,3-d] pyrimidin-7-yl)-4-(isopropylamino)nicotinamide (PTM-IV-190); (R)-4-(6-(5-cyano-1H-pyrazolo[3,4-b]pyridin-1-yl)-4-(isopropylamino)nicotinamido)-3-fluoro-2-methylbutan-2-yl dihydrogen phosphate (PTM-IV-191); R)-6-(5-cyano-1H-pyrazolo[3,4-b]pyridin-1-yl)-N-(2-fluoro-3-hydroxy-3-methylbutyl)-4-(isopropylamino)nicotinamide, hydrochloride (PTM-IV-192); (R)-4-(sec-butylamino)-6-(5-cyano-1H-pyrazolo[3,4-b]pyridin-1-yl)-N-(3-hydroxy-3-methylbutyl) nicotinamide (PTM-IV-193); (R)—N-(2-fluoro-3-hydroxy-3-methylbutyl)-6-(5-hydroxy-1H-pyrazolo[3,4-b]pyridin-1-yl)-4-(isopropylamino) nicotinamide (PTM-IV-194); (R)—N-(2-fluoro-3-hydroxy-3-methylbutyl)-4-(isopropylamino)-6-(5-methoxy-1H-pyrazolo[3,4-b]pyridin-1-yl)nicotinamide (PTM-IV-195); (S)-6-(5-cyano-1H-pyrazolo[3,4-b]pyridin-1-yl)-N-(2-fluoro-3-hydroxy-3-methylbutyl)-4-(isopropylamino)nicotinamide (PTM-IV-196); (R)-6-(5-cyano-1H-pyrazolo[3,4-b] pyridin-1-yl)-N-(2-fluoro-3-(isopropylamino)-3-oxopropyl)-4-(isopropylamino)nicotinamide (PTM-IV-197); 6-(5-cyano-1H-pyrazolo[3,4-b]pyridin-1-yl)-4-(isopropylamino)-N-(4-methoxycyclohexyl)nicotinamide (PTM-IV-198); N-butyl-6-(5-cyano-1H-pyrazolo[3,4-b] pyridin-1-yl)-4-(isopropylamino)nicotinamide (PTM-IV-199); (R)-6-(5-cyano-1H-pyrazolo[3,4-b]pyridin-1-yl)-N-(2-fluoro-3-methoxy-3-methylbutyl)-4-(isopropylamino) nicotinamide (PTM-IV-200); 6-(5-cyano-1H-pyrazolo[3,4-b]pyridin-1-yl)-4-(isopropylamino)-N-(3-morpholinopropyl)nicotinamide (PTM-IV-201); 6-(5-cyano-1H-pyrazolo [3,4-b]pyridin-1-yl)-N—((R)-2-fluoro-3-hydroxy-3-methylbutyl)-4-(((2S)-3-fluorobutan-2-yl)amino) nicotinamide (202); 6-(5-cyano-1H-pyrazolo[3,4-b]pyridin-1-yl)-N—((R)-2-fluoro-3-hydroxy-3-methylbutyl)-4-(((2S)-3-fluorobutan-2-yl)amino)nicotinamide (203); 6-(5-cyano-1H-pyrazolo[3,4-b]pyridin-1-yl)-4-(isopropylamino)-N-(2-morpholinoethyl)nicotinamide (204); 6-(5-cyano-1H-pyrazolo[3,4-b]pyridin-1-yl)-N—((R)-2-fluoro-3-hydroxy-3-methylbutyl)-4-((4-fluorobutan-2-yl)amino)nicotinamide (205); 6-(5-cyano-1H-pyrazolo[3,4-b]pyridin-1-yl)-4-(isopropylamino)-N-(2-morpholino-2-oxoethyl) nicotinamide (206); methyl 3-(6-(5-cyano-1H-pyrazolo[3,4-b]pyridin-1-yl)-4-(isopropylamino)nicotinamido)propanoate (207); diethyl(2-(6-(5-cyano-1H-pyrazolo[3,4-b]pyridin-1-yl)-4-(isopropylamino)nicotinamido)ethyl)phosphonate (208); 6-(5-cyano-1H-pyrazolo[3,4-b]pyridin-1-yl)-N-((1,1-dioxidotetrahydrothiophen-3-yl)methyl)-4-(isopropylamino) nicotinamide (209); (R)-6-(5-cyano-1H-pyrazolo[3,4-b] pyridin-1-yl)-N-(2-fluoro-3-trideuteromethoxy-3-methylbutyl)-4-(isopropylamino)nicotinamide (210); 6-(5-cyano-1H-pyrazolo[3,4-b]pyridin-1-yl)-N-(2-(1,1-dioxidothiomorpholino)ethyl)-4-(isopropylamino) nicotinamide (211); 6-(5-cyano-1H-pyrazolo[3,4-b]pyridin-1-yl)-N-(3-(ethylamino)-3-oxopropyl)-4-(isopropylamino)

nicotinamide (212); N-(3-(1H-1,2,4-triazol-5-yl)propyl)-6-(5-cyano-1H-pyrazolo[3,4-b]pyridin-1-yl)-4-(isopropylamino) nicotinamide (213); N-((1R,4R)-4-(2-hydroxypropan-2-yl)cyclohexyl)-4-(isopropylamino)-6-(5-methyl-1H-pyrazolo[3,4-b]pyridin-1-yl)nicotinamide (214); (R)-6-(5-cyano-1H-pyrazolo[3,4-b]pyridin-1-yl)-N-(3-ethoxy-2-fluoro-3-methylbutyl)-4-(isopropylamino)nicotinamide (215); 6-(5-cyano-1H-pyrazolo[3,4-b]pyridin-1-yl)-4-(isopropylamino)-N-(6-morpholinopyridin-3-yl) nicotinamide (216); 6-(5-cyano-1H-pyrazolo[3,4-b]pyridin-1-yl)-N-(5-hydroxypyridin-2-yl)-4-(isopropylamino) nicotinamide (217); 6-(5-cyano-1H-pyrazolo[3,4-b]pyridin-1-yl)-4-(isopropylamino)-N-((1R,4R)-4-((2-(methylamino)-2-oxoethyl)cyclohexyl)nicotinamide (218); 6-(5-cyano-1H-pyrazolo[3,4-b]pyridin-1-yl)-4-(isopropylamino)-N-(2-(methylsulfonamido)ethyl)nicotinamide (219); 6-(5-cyano-1H-pyrazolo[3,4-b]pyridin-1-yl)-4-(isopropylamino)-N-(2-(tetrahydro-2H-pyran-2-yl)ethyl)nicotinamide (220); 6-(5-cyano-1H-pyrazolo[3,4-b]pyridin-1-yl)-4-(isopropylamino)-N-(5-morpholinopyridin-2-yl) nicotinamide (221); 6-(5-cyano-1H-pyrazolo[3,4-b]pyridin-1-yl)-4-(isopropylamino)-N-(4-morpholinophenyl) nicotinamide (222); 6-(5-cyano-1H-pyrazolo[3,4-b]pyridin-1-yl)-4-(isopropylamino)-N-(1H-pyrrolo[2,3-c]pyridin-5-yl)nicotinamide (223); 6-(5-cyano-1H-pyrazolo[3,4-b]pyridin-1-yl)-4-(isopropylamino)-N-(2-morpholinopyrimidin-5-yl)nicotinamide (224); 6-(5-cyano-1H-pyrazolo[3,4-b]pyridin-1-yl)-N-(5-(2-(dimethylamino)ethoxy)pyridin-2-yl)-4-(isopropylamino)nicotinamide (225); 6-(5-cyano-1H-pyrazolo[3,4-b]pyridin-1-yl)-4-(isopropylamino)-N-(4-(morpholinomethyl)phenyl)nicotinamide (226); 6-(5-cyano-1H-pyrazolo[3,4-b]pyridin-1-yl)-4-(isopropylamino)-N-(6-(piperazin-1-yl)pyridin-3-yl) nicotinamide (227); 6-(5-cyano-1H-pyrazolo[3,4-b]pyridin-1-yl)-N-(6-(dimethylamino)pyridin-3-yl)-4-(isopropylamino)nicotinamide (228); (R)-6-(5-cyano-1H-pyrazolo[3,4-b]pyridin-1-yl)-N-(2-fluoro-3-(methylamino)-3-oxopropyl)-4-(isopropylamino)nicotinamide (229); 6-(5-cyano-1H-pyrazolo[3,4-b]pyridin-1-yl)-N—((R)-2-fluoro-3-(((S)-1-hydroxypropan-2-yl)amino)-3-oxopropyl)-4-(isopropylamino) nicotinamide (230); (R)-6-(5-(difluoromethyl)-1H-pyrazolo[3,4-b]pyridin-1-yl)-N-(2-fluoro-3-hydroxy-3-methylbutyl)-4-(isopropylamino) nicotinamide (231); 6-(5-cyano-1H-pyrazolo[3,4-b]pyridin-1-yl)-N-((2R)-2-fluoro-3-hydroxy-4-methylpentyl)-4-(isopropylamino)nicotinamide (232); 6-(5-cyano-1H-pyrazolo[3,4-b]pyridin-1-yl)-N-((2R)-2-fluoro-3-hydroxy-4-methylpentyl)-4-(isopropylamino)nicotinamide (233); (R)-6-(5-cyano-1H-pyrazolo[3,4-b]pyridin-1-yl)-N-(2-fluoro-3-hydroxy-3-methylbutyl)-4-((1-hydroxy-2-methylpropan-2-yl)amino)nicotinamide (234); 6-(5-cyano-1H-pyrazolo[3,4-b]pyridin-1-yl)-N-(2-(4-hydroxytetrahydro-2H-pyran-4-yl)ethyl)-4-(isopropylamino) nicotinamide (235); 6-(5-cyano-1H-pyrazolo[3,4-b]pyridin-1-yl)-N-(5-(2-hydroxypropan-2-yl)pyridin-2-yl)-4-(isopropylamino) nicotinamide (236); 6-(5-cyano-1H-pyrazolo[3,4-b]pyridin-1-yl)-N-(2-(3-hydroxytetrahydrofuran-3-yl)ethyl)-4-(isopropylamino) nicotinamide (237); 6-(5-cyano-1H-pyrazolo[3,4-b]pyridin-1-yl)-N-(3-hydroxybutyl)-4-(isopropylamino)nicotinamide (23.8); 6-(5-cyano-1H-pyrazolo[3,4-b]pyridin-1-yl)-N-(3-hydroxybutyl)-4-(isopropylamino)nicotinamide (239); 6-(5-cyano-1H-pyrazolo[3,4-b]pyridin-1-yl)-4-(isopropylamino)-N-(1-(pyrimidin-2-yl)piperidin-4-yl)nicotinamide (240); 6-(5-cyano-1H-pyrazolo[3,4-b]pyridin-1-yl)-4-(isopropylamino)-N-(5-(4-methylpiperazin-1-yl)pyridin-2-yl)nicotinamide (241); 6-(5-cyano-1H-pyrazolo[3,4-b]pyridin-1-yl)-4-(isopropylamino)-N-(3-(4-methylpiperazin-1-yl)-3-oxopropyl) nicotinamide (242); 6-(5-cyano-1H-pyrazolo[3,4-b]pyridin-1-yl)-N-(2-fluoro-2-(3-hydroxyoxetan-3-yl)ethyl)-4-(isopropylamino) nicotinamide, racemic (243); 6-(5-cyano-1H-pyrazolo[3,4-b]pyridin-1-yl)-N-((1S,3 S)-3-(2-hydroxypropan-2-yl) cyclopentyl)-4-(isopropylamino)nicotinamide (244); (R)-6-(5-cyano-1H-pyrazolo[3,4-b]pyridin-1-yl)-4-(isopropylamino)-N-(1-(methylsulfonyl)piperidin-3-yl) nicotinamide (245); (S)-6-(5-cyano-1H-pyrazolo[3,4-b]pyridin-1-yl)-4-(isopropylamino)-N-(1-(methylsulfonyl) piperidin-3-yl)nicotinamide (246); 6-(5-cyano-1H-pyrazolo[3,4-b]pyridin-1-yl)-4-(isopropylamino)-N-(6-(4-methoxypiperidin-1-yl)pyridin-3-yl)nicotinamide (247); 6-(5-cyano-1H-pyrazolo[3,4-b]pyridin-1-yl)-N-(2-fluoro-2-(3-hydroxyoxetan-3-yl)ethyl)-4-(isopropylamino)nicotinamide (248); 6-(5-cyano-1H-pyrazolo[3,4-b]pyridin-1-yl)-N-(2-fluoro-2-(3-hydroxyoxetan-3-yl)ethyl)-4-(isopropylamino)nicotinamide (249); 6-(5-cyano-1H-pyrazolo[3,4-b]pyridin-1-yl)-N-(2-(4-hydroxy-1-methylpiperidin-4-yl)ethyl)-4-(isopropylamino) nicotinamide (250); 6-(5-cyano-1H-pyrazolo[3,4-b]pyridin-1-yl)-4-(isopropylamino)-N-(4-sulfamoylphenethyl) nicotinamide (251); 6-(5-cyano-1H-pyrazolo[3,4-b]pyridin-1-yl)-N-(2-(1-hydroxycyclopentyl)ethyl)-4-(isopropylamino)nicotinamide (252); 6-(5-cyano-1H-pyrazolo[3,4-b]pyridin-1-yl)-N-(2-(4-hydroxy-1-(oxetan-3-yl)piperidin-4-yl)ethyl)-4-(isopropylamino)nicotinamide (253); 6-(5-cyano-1H-pyrazolo[3,4-b]pyridin-1-yl)-4-(isopropylamino)-N-(5-(4-methoxypiperidin-1-yl)pyridin-2-yl) nicotinamide (254); 6-(5-cyano-1H-pyrazolo[3,4-b]pyridin-1-yl)-N-(2-(3-hydroxypyrrolidin-3-yl)ethyl)-4-(isopropylamino)nicotinamide (255); (R)-6-(5-cyano-1H-pyrazolo[3,4-b]pyridin-1-yl)-N-(2-fluoro-3-morpholino-3-oxopropyl)-4-(isopropylamino)nicotinamide (256); (R)-6-(5-cyano-1H-pyrazolo[3,4-b]pyridin-1-yl)-N-(2-fluoro-3-(4-(methylsulfonyl)piperazin-1-yl)-3-oxopropyl)-4-(isopropylamino) nicotinamide (257); 6-(5-chloro-1H-pyrazolo[3,4-b]pyridin-1-yl)-N-(2-fluoro-2-(3-hydroxyoxetan-3-yl)ethyl)-4-(isopropylamino)nicotinamide (258); 6-(5-cyano-1H-pyrazolo[3,4-b]pyridin-1-yl)-4-(isopropylamino)-N-(2-(pyridin-4-yl)ethyl)nicotinamide (259); 6-(5-cyano-1H-pyrazolo[3,4-b]pyridin-1-yl)-N-(4-fluorophenethyl)-4-(isopropylamino)nicotinamide (260); 6-(5-cyano-1H-pyrazolo[3,4-b]pyridin-1-yl)-4-(isopropylamino)-N-(4-methoxyphenethyl)nicotinamide (261); (R)-6-(6-amino-5-cyano-1H-pyrazolo[3,4-b]pyridin-1-yl)-N-(2-fluoro-3-hydroxy-3-methylbutyl)-4-(isopropylamino) nicotinamide (262); 6-(6-amino-5-cyano-1H-pyrazolo[3,4-b]pyridin-1-yl)-N-((2-(2-hydroxypropan-2-yl)cyclopropyl) methyl)-4-(isopropylamino)nicotinamide (263); 6-(5-cyano-1H-pyrazolo[3,4-b]pyridin-1-yl)-4-(isopropylamino)-N-(3-(methylsulfonamido)butyl)nicotinamide (264); 6-(5-cyano-1H-pyrazolo[3,4-b]pyridin-1-yl)-4-(isopropylamino)-N-(3-(methylsulfonamido)butyl)nicotinamide (265); 6-(5-cyano-1H-pyrazolo[3,4-b]pyridin-1-yl)-4-(isopropylamino)-N-(2-(1-methylpiperidin-4-yl)ethyl)nicotinamide (266); N-((3-benzyl-1,2,4-oxadiazol-5-yl)methyl)-6-(5-cyano-1H-pyrazolo[3,4-b]pyridin-1-yl)-4-(isopropylamino) nicotinamide (267); 6-(5-cyano-1H-pyrazolo[3,4-b]pyridin-1-yl)-4-(isopropylamino)-N-(1-(oxetan-3-yl)-1H-pyrazol-4-yl)nicotinamide (268); 6-(5-cyano-1H-pyrazolo[3,4-b]pyridin-1-yl)-4-(isopropylamino)-N-(4-(N-(methylsulfonyl) methylsulfonamido)phenethyl)nicotinamide (269); N-(4-acetamidophenethyl)-6-(5-cyano-1H-pyrazolo[3,4-b]pyridin-1-yl)-4-(isopropylamino) nicotinamide (270); 6-(5-cyano-1H-pyrazolo[3,4-b]pyridin-1-yl)-4-

(isopropylamino)-N-(1-(tetrahydro-2H-pyran-4-yl)-1H-pyrazol-4-yl)nicotinamide (271); 6-(5-cyano-1H-pyrazolo[3,4-b]pyridin-1-yl)-4-(isopropylamino)-N-(1-(isopropylsulfonyl)piperidin-4-yl)nicotinamide (272); 6-(5-cyano-1H-pyrazolo[3,4-b]pyridin-1-yl)-N-(1-isobutyrylpiperidin-4-yl)-4-(isopropylamino)nicotinamide (273); 6-(5-cyano-1H-pyrazolo[3,4-b]pyridin-1-yl)-N-((1S,4R)-4-((S)-2-hydroxypropanamido)cyclohexyl)-4-(isopropylamino)nicotinamide (274); 6-(5-cyano-1H-pyrazolo[3,4-b]pyridin-1-yl)-N-(2-(1-(2-cyanoacetyl)piperidin-4-yl)ethyl)-4-(isopropylamino)nicotinamide (275); 6-(5-cyano-1H-pyrazolo[3,4-b]pyridin-1-yl)-4-(isopropylamino)-N-(2-(pyridin-3-yl)ethyl)nicotinamide (276); 6-(5-cyano-1H-pyrazolo[3,4-b]pyridin-1-yl)-N-(2-(1,4-dihydroxy-4-methylcyclohexyl)ethyl)-4-(isopropylamino)nicotinamide (277); 6-(5-cyano-1H-pyrazolo[3,4-b]pyridin-1-yl)-4-(isopropylamino)-N-(1-(1-(methylsulfonyl) azetidine-3-carbonyl)piperidin-4-yl)nicotinamide (278); 6-(5-cyano-1H-pyrazolo[3,4-b]pyridin-1-yl)-N-(2-(4,4-difluoro-1-hydroxycyclohexyl)ethyl)-4-(isopropylamino) nicotinamide (279); (R)—N-(2-fluoro-3-hydroxy-3-methylbutyl)-4-(isopropylamino)-6-(5-((3-methylbutanamido)methyl)-1H-pyrazolo[3,4-b]pyridin-1-yl)nicotinamide (280); 6-(5-cyano-1H-pyrazolo[3,4-b]pyridin-1-yl)-4-(isopropylamino)-N-(1-(1-(methylsulfonyl) azetidin-3-yl)-11H-pyrazol-4-yl)nicotinamide (281); (R)-6-(6-amino-5-chloro-1H-pyrazolo[3,4-b]pyridin-1-yl)-N-(2-fluoro-3-hydroxy-3-methylbutyl)-4-(isopropylamino) nicotinamide (282); 4-((R)-sec-butylamino)-6-(5-cyano-1H-pyrazolo[3,4-b]pyridin-1-yl)-N—((R)-2-fluoro-3-hydroxy-3-methylbutyl)nicotinamide (283); 6-(6-amino-5-cyano-1H-pyrazolo[3,4-b]pyridin-1-yl)-4((S)-sec-butylamino)-N—((R)-2-fluoro-3-hydroxy-3-methylbutyl)nicotinamide (284); 6-(5-cyano-1H-pyrazolo[3,4-b]pyridin-1-yl)-N-(1-(2,2-difluoroethyl)-1H-pyrazol-4-yl)-4-(isopropylamino) nicotinamide (285); (R)-4-(tert-butylamino)-6-(5-cyano-1H-pyrazolo[3,4-b]pyridin-1-yl)-N-(2-fluoro-3-hydroxy-3-methylbutyl)nicotinamide (286); 6-(5-cyano-1H-pyrazolo[3,4-b]pyridin-1-yl)-N-((1R,4R)-4-((R)-2-hydroxypropanamido)cyclohexyl)-4-(isopropylamino) nicotinamide (287); 4-(tert-butylamino)-6-(5-cyano-1H-pyrazolo[3,4-b]pyridin-1-yl)-N-(3-fluoro-3-methylbutyl) nicotinamide (288); 4-((S)-sec-butylamino)-6-(5-cyano-1H-pyrazolo[3,4-b]pyridin-1-yl)-N—((R)-2-fluoro-3-hydroxy-3-methylbutyl)nicotinamide (289); 6-(5-cyano-1H-pyrazolo[3,4-b]pyridin-1-yl)-N-(1-(ethylsulfonyl)piperidin-4-yl)-4-(isopropylamino) nicotinamide (290); 6-(5-cyano-1H-pyrazolo[3,4-b]pyridin-1-yl)-N-(2-(1-hydroxy-4-methoxycyclohexyl)ethyl)-4-(isopropylamino)nicotinamide (291); (R)-6-(5-cyano-1H-pyrazolo[3,4-b]pyridin-1-yl)-N-(2-fluoro-3-hydroxy-3-methylbutyl)-4-((1-methylcyclopropyl)amino)nicotinamide (292); (R)-6-(6-amino-5-cyano-1H-pyrazolo[3,4-b]pyridin-1-yl)-4-(tert-butylamino)-N-(2-fluoro-3-hydroxy-3-methylbutyl) nicotinamide (293); 6-(5-cyano-1H-pyrazolo[3,4-b]pyridin-1-yl)-N-(2-(dihydro-2H-pyran-4(3H)-ylidene)-2-fluoroethyl)-4-(isopropylamino) nicotinamide (294); (R)-6-(6-amino-5-cyano-1H-pyrazolo[3,4-b]pyridin-1-yl)-N-(2,3-difluoro-3-methylbutyl)-4-(isopropylamino)nicotinamide (295); 6-(5-cyano-1H-pyrazolo[3,4-b]pyridin-1-yl)-N-((3R,6S)-6-(2-hydroxypropan-2-yl)tetrahydro-2H-pyran-3-yl)-4-(isopropylamino) nicotinamide (296); 6-(5-cyano-1H-pyrazolo[3,4-b]pyridin-1-yl)-N—((R)-2-fluoro-3-hydroxy-3-methylbutyl)-4-((1,1,1-trifluoropropan-2-yl)amino) nicotinamide (297); 6-(5-cyano-1H-pyrazolo[3,4-b]pyridin-1-yl)-N-isopentyl-4-(isopropylamino)nicotinamide (298); 6-(6-amino-5-cyano-1H-pyrazolo[3,4-b]pyridin-1-yl)-N-(2-cyclopropylethyl)-4-(isopropylamino)nicotinamide (299); 6-(6-amino-5-cyano-1H-pyrazolo[3,4-b]pyridin-1-yl)-4-((R)-sec-butylamino)-N—((R)-2-fluoro-3-hydroxy-3-methylbutyl)nicotinamide (300); 6-(6-amino-5-cyano-1H-pyrazolo[3,4-b]pyridin-1-yl)-N—((R)-2-fluoro-3-hydroxy-3-methylbutyl)-4-((1,1,1-trifluoropropan-2-yl)amino) nicotinamide (301); 6-(5-cyano-1H-pyrazolo[3,4-b]pyridin-1-yl)-N-(2-cyclopropylethyl)-4-(isopropylamino) nicotinamide (302); 6-(6-amino-5-cyano-1H-pyrazolo[3,4-b]pyridin-1-yl)-N-isopentyl-4-(isopropylamino) nicotinamide (303); 6-(5-cyano-1H-pyrazolo[3,4-b]pyridin-1-yl)-N-(1-(2-hydroxy-2-methylpropyl)-1H-pyrazol-4-yl)-4-(isopropylamino)nicotinamide (304); 6-(6-amino-5-cyano-1H-pyrazolo[3,4-b]pyridin-1-yl)-4-(isopropylamino)-N-methylnicotinamide (305); 6-(5-cyano-1H-pyrazolo[3,4-b]pyridin-1-yl)-4-(isopropylamino)-N-(3-methyl-3-(methylsulfonamido)butyl)nicotinamide (306); 6-(6-amino-5-cyano-1H-pyrazolo[3,4-b]pyridin-1-yl)-N-(3-fluoro-3-methylbutyl)-4-(isopropylamino)nicotinamide (307); (R)-6-(5-cyano-1H-pyrazolo[3,4-b]pyridin-1-yl)-N-(2,3-difluoro-3-methylbutyl)-4-(isopropylamino)nicotinamide (308); 6-(5-cyano-1H-pyrazolo[3,4-b]pyridin-1-yl)-4-(isopropylamino)-N-(1-(N-isopropylsulfamoyl)piperidin-4-yl)nicotinamide (309); 6-(5-cyano-1H-pyrazolo[3,4-b]pyridin-1-yl)-4-(isopropylamino)-N-(2-(tetrahydro-2H-pyran-4-yl)ethyl)nicotinamide (310); N-(2-(1H-imidazol-4-yl)ethyl)-6-(5-cyano-1H-pyrazolo[3,4-b]pyridin-1-yl)-4-(isopropylamino) nicotinamide (311); (S)-6-(5-cyano-1H-pyrazolo[3,4-b]pyridin-1-yl)-N-(2-fluoro-3-methylbutyl)-4-(isopropylamino)nicotinamide (312); 6-(5-cyano-1H-pyrazolo[3,4-b]pyridin-1-yl)-4-(isopropylamino)-N-(1-(N-methylsulfamoyl)piperidin-4-yl)nicotinamide (313); (R)-6-(5-cyano-1H-pyrazolo[3,4-b]pyridin-1-yl)-N-(3-(difluoromethoxy)-2-fluoro-3-methylbutyl)-4-(isopropylamino)nicotinamide (314); (R)-6-(5-cyano-1H-pyrazolo[3,4-b]pyridin-1-yl)-N-(3,3-dicyclopropyl-2-fluoro-3-hydroxypropyl)-4-(isopropylamino) nicotinamide (315); 6-(5-cyano-1H-pyrazolo[3,4-b]pyridin-1-yl)-4-(isopropylamino)-N-((1R,4R)-4-(methylcarbamoyl)cyclohexyl) nicotinamide (316); N-((1R,4R)-4-acetamidocyclohexyl)-6-(6-amino-5-cyano-1H-pyrazolo[3,4-b]pyridin-1-yl)-4-(isopropylamino)nicotinamide (317); (S)-6-(5-cyano-1H-pyrazolo[3,4-b]pyridin-1-yl)-N-(2-cyclopropylethyl)-4-((1-hydroxypropan-2-yl)amino)nicotinamide (318); (S)—N-butyl-6-(5-cyano-1H-pyrazolo[3,4-b]pyridin-1-yl)-4-((1-hydroxypropan-2-yl)amino) nicotinamide (319); (S)-6-(5-cyano-1H-pyrazolo[3,4-b]pyridin-1-yl)-4-((1-hydroxypropan-2-yl)amino)-N-isopentylnicotinamide (320); (R)-6-(6-amino-5-cyano-1H-pyrazolo[3,4-b]pyridin-1-yl)-N-(2-fluoro-3-methoxy-3-methylbutyl)-4-(isopropylamino) nicotinamide (321); 6-(6-amino-5-cyano-1H-pyrazolo[3,4-b]pyridin-1-yl)-4-(isopropylamino)-N-(1-methylcyclopropyl)nicotinamide (322); (R)-6-(6-amino-5-cyano-1H-pyrazolo[3,4-b]pyridin-1-yl)-N-(1-cyclopropylethyl)-4-(isopropylamino)nicotinamide (323); 6-(6-amino-5-cyano-1H-pyrazolo[3,4-b]pyridin-1-yl)-N-cyclohexyl-4-(isopropylamino)nicotinamide (324); 6-(6-amino-5-cyano-1H-pyrazolo[3,4-b]pyridin-1-yl)-N-(1-cyanocyclopropyl)-4-(isopropylamino)nicotinamide (325); 6-(6-amino-5-cyano-1H-pyrazolo[3,4-b]pyridin-1-yl)-4-(isopropylamino)-N-propylnicotinamide (326); 6-(6-amino-5-cyano-1H-pyrazolo[3,4-b]pyridin-1-yl)-N-(cyclopent-2-en-1-yl)-4-(isopropylamino)nicotinamide (327); (R)-6-(6-amino-5-cyano-1H-pyrazolo[3,4-b]pyridin-1-yl)-N-(2-fluoropropyl)-4-(isopropylamino)nicotinamide (328); 6-(5-cyano-1H-pyrazolo[3,4-b]pyridin-1-yl)-N-(2-fluoro-2-(tetrahydro-2H-pyran-4-yl)ethyl)-4-(isopropylamino)

nicotinamide (329); (R)-6-(5-chloro-1H-pyrazolo[3,4-b]pyridin-1-yl)-N-(2,3-difluoro-3-methylbutyl)-4-(isopropylamino)nicotinamide (330); 6-(5-cyano-1H-pyrazolo[3,4-b]pyridin-1-yl)-N-(2-(1-hydroxycyclopropyl)ethyl)-4-(isopropylamino) nicotinamide (331); 6-(5-cyano-1H-pyrazolo[3,4-b]pyridin-1-yl)-N-(3,3-difluorobutyl)-4-(isopropylamino)nicotinamide (332); (R)-6-(6-cyano-3H-imidazo[4,5-b]pyridin-3-yl)-N-(2-fluoro-3-hydroxy-3-methylbutyl)-4-(oxetan-3-ylamino)nicotinamide (333); N—((R)-2-fluoro-3-hydroxy-3-methylbutyl)-6-(2-(((R)-2-fluoro-3-hydroxy-3-methylbutyl)amino)-9H-purin-9-yl)-4-(isopropylamino)nicotinamide (334); (R)-6-(6-cyano-3H-imidazo[4,5-b]pyridin-3-yl)-N-(2-fluoro-3-hydroxy-3-methylbutyl)-4-(isopropylamino) nicotinamide (335); (R)-6-(6-cyano-3H-imidazo[4,5-b]pyridin-3-yl)-4-(cyclopropylamino)-N-(2-fluoro-3-hydroxy-3-methylbutyl) nicotinamide (336); (R)-6-(6-cyano-3H-imidazo[4,5-b]pyridin-3-yl)-N-(2-fluoro-3-hydroxy-3-methylbutyl)-4-(propylamino)nicotinamide (337); (R)-6-(6-cyano-3H-imidazo[4,5-b]pyridin-3-yl)-4-(cyclobutylamino)-N-(2-fluoro-3-hydroxy-3-methylbutyl)nicotinamide (338); (R)-6-(6-chloro-3H-imidazo[4,5-b]pyridin-3-yl)-N-(2-fluoro-3-hydroxy-3-methylbutyl)-4-(isopropylamino)nicotinamide (339); (R)-6-(6-chloro-3H-imidazo[4,5-b]pyridin-3-yl)-N-(2-fluoro-3-hydroxy-3-methylbutyl)-4-(oxetan-3-ylamino) nicotinamide (340); (R)-6-(5-amino-6-cyano-3H-imidazo[4,5-b]pyridin-3-yl)-N-(2-fluoro-3-hydroxy-3-methylbutyl)-4-(isopropylamino)nicotinamide (341); (R)-6-(6-cyano-3H-imidazo[4,5-b]pyridin-3-yl)-N-(2,3-difluoro-3-methylbutyl)-4-(isopropylamino)nicotinamide (342); (R)-6-(6-cyano-3H-imidazo[4,5-b]pyridin-3-yl)-N-(2-fluoro-3-hydroxy-3-methylbutyl)-4-((1-methylcyclopropyl)amino) nicotinamide (343); (R)-6-(6-cyano-3H-imidazo[4,5-b]pyridin-3-yl)-N-(2,3-difluoro-3-methylbutyl)-4-(oxetan-3-ylamino)nicotinamide (344); (R)-6-(6-cyano-3H-imidazo[4,5-b]pyridin-3-yl)-N-(2-fluoro-3-hydroxy-3-methylbutyl)-4-((tetrahydro-2H-pyran-4-yl)amino)nicotinamide (345); (R)-6-(2-amino-9H-purin-9-yl)-N-(2,3-difluoro-3-methylbutyl)-4-(isopropylamino)nicotinamide (346); (R)-6-(5-cyano-1H-pyrazolo[3,4-b]pyridin-1-yl)-4-((1-(2,2-difluoroethyl)-1H-pyrazol-4-yl)amino)-N-(2-fluoro-3-hydroxy-3-methylbutyl) nicotinamide (347); (R)-6-(5-cyano-1H-pyrazolo[3,4-b]pyridin-1-yl)-N-(2-fluoro-3-hydroxy-3-methylbutyl)-4-((1-(oxetan-3-yl)-1H-pyrazol-4-yl)amino)nicotinamide (348); (R)-6-(5-cyano-1H-pyrazolo[3,4-b]pyridin-1-yl)-N-(2-fluoro-3-hydroxy-3-methylbutyl)-4-((1-(tetrahydro-2H-pyran-4-yl)-1H-pyrazol-4-yl)amino)nicotinamide (349); (R)-6-(5-cyano-1H-pyrazolo[3,4-b]pyridin-1-yl)-N-(2-fluoro-3-hydroxy-3-methylbutyl)-4-((1-(2-hydroxy-2-methylpropyl)-1H-pyrazol-4-yl)amino)nicotinamide (350); (R)-6-(5-chloro-1H-pyrazolo[3,4-b]pyridin-1-yl)-4-((1-(2,2-difluoroethyl)-1H-pyrazol-4-yl)amino)-N-(2-fluoro-3-hydroxy-3-methylbutyl) nicotinamide (351); (R)-6-(5-chloro-1H-pyrazolo[3,4-b]pyridin-1-yl)-N-(2-fluoro-3-hydroxy-3-methylbutyl)-4-((1-(tetrahydro-2H-pyran-4-yl)-1H-pyrazol-4-yl)amino) nicotinamide (352); (R)-6-(5-cyano-1H-pyrazolo[3,4-b]pyridin-1-yl)-N-(2-fluoro-3-hydroxy-3-methylbutyl)-4-((1-(2,2,2-trifluoroethyl)-1H-pyrazol-4-yl)amino)nicotinamide (353); (R)-6-(5-chloro-1H-pyrazolo[3,4-b]pyridin-1-yl)-N-(2-fluoro-3-hydroxy-3-methylbutyl)-4-((1-(2,2,2-trifluoroethyl)-1H-pyrazol-4-yl) amino)nicotinamide (354); (R)-6-(5-cyano-1H-pyrazolo[3,4-b]pyridin-1-yl)-4-((1-ethyl-1H-pyrazol-4-yl)amino)-N-(2-fluoro-3-hydroxy-3-methylbutyl)nicotinamide (355); (R)-6-(5-cyano-1H-pyrazolo[3,4-b]pyridin-1-yl)-4-((1-(2-fluoro-2-methylpropyl)-1H-pyrazol-4-yl)amino)-N-(2-fluoro-3-hydroxy-3-methylbutyl)nicotinamide (356); (R)-6-(5-chloro-1H-pyrazolo[3,4-b]pyridin-1-yl)-4((1-ethyl-1H-pyrazol-4-yl)amino)-N-(2-fluoro-3-hydroxy-3-methylbutyl) nicotinamide (357); (R)-6-(5-chloro-1H-pyrazolo[3,4-b]pyridin-1-yl)-N-(2-fluoro-3-hydroxy-3-methylbutyl)-4-((1-isopropyl-1H-pyrazol-4-yl)amino)nicotinamide (358); (R)-6-(6-chloro-3H-imidazo[4,5-b]pyridin-3-yl)-4-((1-(2,2-difluoroethyl)-1H-pyrazol-4-yl)amino)-N-(2-fluoro-3-hydroxy-3-methylbutyl)nicotinamide (359); (R)-6-(6-chloro-3H-imidazo[4,5-b]pyridin-3-yl)-N-(2-fluoro-3-hydroxy-3-methylbutyl)-4-((1-(2,2,2-trifluoroethyl)-1H-pyrazol-4-yl)amino)nicotinamide (360); (R)-6-(6-chloro-3H-imidazo[4,5-b]pyridin-3-yl)-4-((1-ethyl-1H-pyrazol-4-yl)amino)-N-(2-fluoro-3-hydroxy-3-methylbutyl) nicotinamide (361); (R)-6-(6-chloro-3H-imidazo[4,5-b]pyridin-3-yl)-N-(2-fluoro-3-hydroxy-3-methylbutyl)-4-((1-isopropyl-1H-pyrazol-4-yl)amino)nicotinamide (362); (R)-6-(5-cyano-1H-pyrazolo[3,4-b]pyridin-1-yl)-N-(2-fluoro-3-hydroxy-3-methylbutyl)-4-((1-(2-methoxyethyl)-1H-pyrazol-4-yl)amino)nicotinamide (363); (R)-6-(5-chloro-1H-pyrazolo[3,4-b]pyridin-1-yl)-N-(2-fluoro-3-hydroxy-3-methylbutyl)-4-((1-(2-methoxyethyl)-1H-pyrazol-4-yl) amino)nicotinamide (364); (R)-6-(5-cyano-1H-pyrazolo[3,4-b]pyridin-1-yl)-4-((1-(2,2-difluoropropyl)-1H-pyrazol-4-yl)amino)-N-(2-fluoro-3-hydroxy-3-methylbutyl) nicotinamide (365); (R)-6-(6-chloro-3H-imidazo[4,5-b]pyridin-3-yl)-N-(2-fluoro-3-hydroxy-3-methylbutyl)-4-((1-(2-methoxyethyl)-1H-pyrazol-4-yl)amino)nicotinamide (366); (R)-6-(5-chloro-1H-pyrazolo[3,4-b]pyridin-1-yl)-N-(2-fluoro-3-hydroxy-3-methylbutyl)-4-((1-(3-fluoropropyl)-1H-pyrazol-4-yl)amino) nicotinamide (367); (R)-6-(5-cyano-1H-pyrazolo[3,4-b]pyridin-1-yl)-N-(2-fluoro-3-hydroxy-3-methylbutyl)-4-((1-(3-fluoropropyl)-1H-pyrazol-4-yl)amino)nicotinamide (368); (R)-6-(5-chloro-1H-pyrazolo[3,4-b]pyridin-1-yl)-4-((1-(2,2-difluoropropyl)-1H-pyrazol-4-yl)amino)-N-(2-fluoro-3-hydroxy-3-methylbutyl)nicotinamide (369); (R)-6-(6-chloro-3H-imidazo[4,5-b]pyridin-3-yl)-N-(2-fluoro-3-hydroxy-3-methylbutyl)-4-((1-(3-fluoropropyl)-1H-pyrazol-4-yl)amino)nicotinamide (370); (R)-6-(5-cyano-1H-pyrrolo[2,3-b]pyridin-1-yl)-N-(2-fluoro-3-hydroxy-3-methylbutyl)-4-((1-(2,2,2-trifluoroethyl)-1H-pyrazol-4-yl) amino)nicotinamide (371); (R)-6-(5-cyano-1H-pyrrolo[2,3-b]pyridin-1-yl)-4-((1-ethyl-1H-pyrazol-4-yl)amino)-N-(2-fluoro-3-hydroxy-3-methylbutyl) nicotinamide (372); (R)-6-(5-cyano-1H-pyrrolo[2,3-b]pyridin-1-yl)-N-(2-fluoro-3-hydroxy-3-methylbutyl)-4-((1-(tetrahydro-2H-pyran-4-yl)-1H-pyrazol-4-yl)amino) nicotinamide (373); (R)-6-(6-chloro-3H-imidazo[4,5-b]pyridin-3-yl)-4-((1-(2-cyanoethyl)-1H-pyrazol-4-yl)amino)-N-(2-fluoro-3-hydroxy-3-methylbutyl)nicotinamide (374); (R)-6-(6-cyano-3H-imidazo[4,5-b]pyridin-3-yl)-4-((1-(2,2-difluoroethyl)-1H-pyrazol-4-yl)amino)-N-(2-fluoro-3-hydroxy-3-methylbutyl)nicotinamide (375); (R)-6-(5-cyano-1H-pyrazolo[3,4-b]pyridin-1-yl)-4-((1-(2-cyanoethyl)-1H-pyrazol-4-yl)amino)-N-(2-fluoro-3-hydroxy-3-methylbutyl)nicotinamide (376); (R)-6-(5-chloro-1H-pyrazolo[3,4-b]pyridin-1-yl)-4-((1-(2-cyanoethyl)-1H-pyrazol-4-yl)amino)-N-(2-fluoro-3-hydroxy-3-methylbutyl)nicotinamide (377); 6-(6-cyano-3H-imidazo[4,5-b]pyridin-3-yl)-N—((R)-2-fluoro-3-hydroxy-3-methylbutyl)-4-((1-(2-fluoropropyl)-1H-pyrazol-4-yl) amino)nicotinamide, racemic (378); 6-(6-cyano-3H-imidazo[4,5-b]pyridin-3-yl)-4-((1-(2-(difluoromethoxy) propyl)-1H-pyrazol-4-yl)amino)-N—((R)-2-fluoro-3-hydroxy-3-methylbutyl)nicotinamide (379); (R)-6-(5-cyano-1H-pyrazolo[3,4-b]pyridin-1-yl)-N-(2-fluoro-3-hydroxy-3-methylbutyl)-4-((1-propyl-1H-pyrazol-4-yl)

amino)nicotinamide (380); (R)-6-(5-chloro-1H-pyrazolo[3,4-b]pyridin-1-yl)-N-(2-fluoro-3-hydroxy-3-methylbutyl)-4 ((1-propyl-1H-pyrazol-4-yl)amino)nicotinamide (381); (R)-6-(6-chloro-3H-imidazo[4,5-b]pyridin-3-yl)-N-(2-fluoro-3-hydroxy-3-methylbutyl)-4-((1-propyl-1H-pyrazol-4-yl) amino)nicotinamide (382); (R)-6-(5-cyano-1H-pyrrolo[2,3-b]pyridin-1-yl)-N-(2-fluoro-3-hydroxy-3-methylbutyl)-4-((1-propyl-1H-pyrazol-4-yl)amino)nicotinamide (383); (R)-4-((1-(2,2-difluoroethyl)-1H-pyrazol-4-yl)amino)-6-(5-fluoro-1H-pyrazolo[3,4-b]pyridin-1-yl)-N-(2-fluoro-3-hydroxy-3-methylbutyl)nicotinamide (384); (R)-6-(5-cyano-1H-pyrazolo[3,4-b]pyridin-1-yl)-N-(2-fluoro-3-hydroxy-3-methylbutyl)-4-((1-(methylsulfonyl)-1H-pyrazol-4-yl)amino)nicotinamide (385); (R)-6-(5-cyano-1H-pyrazolo[3,4-b]pyridin-1-yl)-4-((1-(ethylcarbamoyl)-1H-pyrazol-4-yl)amino)-N-(2-fluoro-3-hydroxy-3-methylbutyl)nicotinamide (386); (R)-6-(5-cyano-1H-pyrazolo[3,4-b]pyridin-1-yl)-N-(2-fluoro-3-hydroxy-3-methylbutyl)-4-((1-methyl-1H-pyrazol-4-yl)amino) nicotinamide (387); 6-(5-cyano-1H-pyrazolo[3,4-b]pyridin-1-yl)-4-((1-(2,2-difluoroethyl)-1H-pyrazol-4-yl)amino)-N-isopropylnicotinamide (388); 6-(5-cyano-1H-pyrazolo[3,4-b]pyridin-1-yl)-4-((1-(2,2-difluoroethyl)-1H-pyrazol-4-yl) amino)-N-propylnicotinamide (389); N-(tert-butyl)-6-(5-cyano-1H-pyrazolo[3,4-b]pyridin-1-yl)-4-((1-(2,2-difluoroethyl)-1H-pyrazol-4-yl)amino)nicotinamide (390); 6-(5-cyano-1H-pyrazolo[3,4-b]pyridin-1-yl)-4-((1-(2,2-difluoroethyl)-1H-pyrazol-4-yl)amino)-N-isobutylnicotinamide (391); 6-(5-cyano-1H-pyrazolo[3,4-b]pyridin-1-yl)-4-((1-(2,2-difluoroethyl)-1H-pyrazol-4-yl)amino)-N-(2-ethoxyethyl)nicotinamide (392); 6-(5-cyano-1H-pyrazolo[3,4-b]pyridin-1-yl)-4-((1-(2,2-difluoroethyl)-1H-pyrazol-4-yl)amino)-N-ethylnicotinamide (393); (R)-6-(5-chloro-1H-pyrazolo[3,4-b]pyridin-1-yl)-4-((1-(difluoromethyl)-1H-pyrazol-4-yl)amino)-N-(2-fluoro-3-hydroxy-3-methylbutyl) nicotinamide (394); (R)-6-(5-cyano-1H-pyrazolo[3,4-b]pyridin-1-yl)-N-(2,3-difluoro-3-methylbutyl)-4-((1-(2,2-difluoroethyl)-1H-pyrazol-4-yl)amino)nicotinamide (395); 6-(5-cyano-1H-pyrazolo[3,4-b]pyridin-1-yl)-4-((1-(2,2-difluoroethyl)-1H-pyrazol-4-yl)amino)-N-((1R,4R)-4-(2-hydroxypropan-2-yl)cyclohexyl)nicotinamide (396); 6-(5-cyano-1H-pyrazolo[3,4-b]pyridin-1-yl)-N-(2,2-difluoro-3-hydroxy-3-methylbutyl)-4-((1-(2,2-difluoroethyl)-1H-pyrazol-4-yl)amino)nicotinamide (397); (R)-6-(6-chloro-3H-imidazo[4,5-b]pyridin-3-yl)-N-(2-fluoro-3-hydroxy-3-methylbutyl)-4-((1-methyl-1H-pyrazol-4-yl)amino) nicotinamide (398); (R)-6-(5-cyano-1H-pyrrolo[2,3-b]pyridin-1-yl)-N-(2-fluoro-3-hydroxy-3-methylbutyl)-4-((1-methyl-1H-pyrazol-4-yl)amino) nicotinamide (399); (R)-6-(6-chloro-3H-imidazo[4,5-b]pyridin-3-yl)-4-((1-(difluoromethyl)-1H-pyrazol-4-yl)amino)-N-(2-fluoro-3-hydroxy-3-methylbutyl) nicotinamide (400); (R)-6-(6-cyano-3H-imidazo[4,5-b]pyridin-3-yl)-4-((1-(difluoromethyl)-1H-pyrazol-4-yl)amino)-N-(2-fluoro-3-hydroxy-3-methylbutyl) nicotinamide (401); (R)-6-(6-chloro-3H-imidazo[4,5-b]pyridin-3-yl)-N-(2,3-difluoro-3-methylbutyl)-4-((1-(2,2-difluoroethyl)-1H-pyrazol-4-yl) amino)nicotinamide (402); (R)-6-(6-cyano-3H-imidazo[4,5-b]pyridin-3-yl)-N-(2,3-difluoro-3-methylbutyl)-4-((1-(2,2-difluoroethyl)-1H-pyrazol-4-yl)amino)nicotinamide (403); (R)-6-(5-cyano-1H-pyrazolo[3,4-b]pyridin-1-yl)-4-((3-cyclopropyl-1H-pyrazol-5-yl)amino)-N-(2-fluoro-3-hydroxy-3-methylbutyl)nicotinamide (404); (R)-6-(5-cyano-1H-pyrazolo[3,4-b]pyridin-1-yl)-N-(2-fluoro-3-hydroxy-3-methylbutyl)-4-((3-methyl-1H-pyrazol-5-yl)amino) nicotinamide (405); (R)-6-(5-cyano-1H-pyrazolo[3,4-b]pyridin-1-yl)-N-(2-fluoro-3-hydroxy-3-methylbutyl)-4-((3-isopropyl-1H-pyrazol-5-yl)amino)nicotinamide (406); (R)-6-(5-cyano-1H-pyrazolo[3,4-b]pyridin-1-yl)-4-((1-(2,2-difluoroethyl)-1H-pyrazol-3-yl)amino)-N-(2-fluoro-3-hydroxy-3-methylbutyl)nicotinamide (407); (R)-6-(5-cyano-1H-pyrazolo[3,4-b]pyridin-1-yl)-N-(2-fluoro-3-hydroxy-3-methylbutyl)-4-((1-(2,2,2-trifluoroethyl)-1H-pyrazol-3-yl)amino)nicotinamide (408); (R)-6-(5-cyano-1H-pyrazolo[3,4-b]pyridin-1-yl)-N-(2-fluoro-3-hydroxy-3-methylbutyl)-4-((1-methyl-1H-pyrazol-5-yl)amino) nicotinamide (409); (R)-6-(5-cyano-1H-pyrazolo[3,4-b] pyridin-1-yl)-N-(2-fluoro-3-hydroxy-3-methylbutyl)-4-((1-(pyrimidin-2-yl)-1H-pyrazol-4-yl)amino) nicotinamide (410); (R)-6-(5-cyano-1H-pyrazolo[3,4-b]pyridin-1-yl)-N-(2-fluoro-3-hydroxy-3-methylbutyl)-4-((1-(5-fluoropyrimidin-2-yl)-1H-pyrazol-4-yl)amino) nicotinamide (411); (R)-6-(5-cyano-1H-pyrazolo[3,4-b]pyridin-1-yl)-N-(2-fluoro-3-hydroxy-3-methylbutyl)-4-((3-phenyl-1H-pyrazol-5-yl) amino)nicotinamide (412); (R)-6-(5-cyano-1H-pyrazolo[3,4-b]pyridin-1-yl)-4-((1,3-dimethyl-1H-pyrazol-5-yl) amino)-N-(2-fluoro-3-hydroxy-3-methylbutyl)nicotinamide (413); 6-(5-cyano-1H-indol-1-yl)-N-((1R,4R)-4-(2-hydroxypropan-2-yl)cyclohexyl)-4-(isopropylamino)nicotinamide (414); 6-(5-cyano-1H-pyrrolo[2,3-b]pyridin-1-yl)-N-(4-hydroxybicyclo[2.2.1]heptan-1-yl)-4-(isopropylamino) nicotinamide (415); (R)-6-(5-cyano-1H-pyrrolo[2,3-b] pyridin-1-yl)-N-(2-fluoro-3-hydroxy-3-methylbutyl)-4-((3-sulfamoylphenyl)amino)nicotinamide (416); N-(3-(tert-butoxy)propyl)-6-(5-cyano-1H-pyrrolo[2,3-b]pyridin-1-yl)-4-(isopropylamino) nicotinamide (417); (R)-6-(5-cyano-1H-pyrrolo[2,3-b]pyridin-1-yl)-N-(2-fluoro-3-hydroxy-3-methylbutyl)-4-((3-methoxyphenyl)amino)nicotinamide (418); (R,E)-6-(5-cyano-1H-pyrrolo[2,3-b]pyridin-1-yl)-N-(2-fluoro-3-hydroxy-3-methylbutyl)-4-((3-hydroxy-3-methylbut-1-en-1-yl)amino)nicotinamide (419); 6-(5-cyano-1H-pyrrolo[2,3-b]pyridin-1-yl)-N-((1R,4R)-4-fluoro-4-((1-methyl-1H-imidazol-2-yl)cyclohexyl)-4-(isopropylamino) nicotinamide (420); (R)-4-(benzo[d]oxazol-6-ylamino)-6-(5-cyano-1H-pyrrolo[2,3-b]pyridin-1-yl)-N-(2-fluoro-3-hydroxy-3-methylbutyl)nicotinamide (421); 6-(5-cyano-1H-pyrrolo[2,3-b]pyridin-1-yl)-N—((R)-2-fluoro-3-hydroxy-3-methylbutyl)-4-((3-hydroxybutyl)amino)nicotinamide (422); (R)-6-(5-cyano-1H-pyrrolo[2,3-b]pyridin-1-yl)-N-(2-fluoro-3-hydroxy-3-methylbutyl)-4-(((6-methylpyridin-3-yl)methyl)amino) nicotinamide (423); (R)-6-(5-cyano-1H-pyrrolo[2,3-b]pyridin-1-yl)-N-(2-fluoro-3-hydroxy-3-methylbutyl)-4-((1-methyl-1H-pyrazol-5-yl)amino) nicotinamide (424); (R)-6-(5-cyano-1H-pyrrolo[2,3-b] pyridin-1-yl)-N-(2-fluoro-3-hydroxy-3-methylbutyl)-4-((3,3,3-trifluoropropyl)amino)nicotinamide (425); 6-(5-cyano-1H-pyrrolo[2,3-b]pyridin-1-yl)-N—((R)-2-fluoro-3-hydroxy-3-methylbutyl)-4-((4-fluorobutan-2-yl)amino) nicotinamide (426); 6-(5-cyano-1H-pyrrolo[2,3-b]pyridin-1-yl)-N—((R)-2-fluoro-3-hydroxy-3-methylbutyl)-4-((4-fluorobutan-2-yl)amino)nicotinamide (427); 4-(cyclopropylamino)-6-(5-fluoro-1H-pyrrolo[2,3-b]pyridin-1-yl)-N-((1R,4R)-4-((2-hydroxypropan-2-yl)cyclohexyl) nicotinamide (428); 6-(5-cyano-1H-pyrrolo[2,3-b]pyridin-1-yl)-4-(cyclopropylamino)-N-((1R,4R)-4-(2-hydroxypropan-2-yl)cyclohexyl) nicotinamide (429); (R)-6-(5-cyano-1H-pyrrolo[2,3-b]pyridin-1-yl)-4-((3-cyano-2-fluorophenyl)amino)-N-(2-fluoro-3-hydroxy-3-methylbutyl)nicotinamide (430); (R)-4-((3-(1H-imidazol-2-yl)phenyl)amino)-6-(5-cyano-1H-pyrrolo[2,3-b]pyridin-1-yl)-N-(2-fluoro-3-hydroxy-3-methylbutyl)nicotinamide (431); 6-(5-fluoro-1H-pyrrolo[2,3-b]pyridin-1-yl)-4-(((S)-1-hydroxypropan-2-yl)amino)-N-((1R,4S)-4-(2-hydroxypropan-2-yl)cyclohexyl)nicotinamide (432); (R)-6-(5- cyano-1H-pyrrolo[2,3-b]pyridin-1-yl)-4-((4-(1-ethyl-1H-tetrazol-5-yl)phenyl)amino)-N-(2-fluoro-3-hydroxy-3-methylbutyl) nicotinamide (433); (R)-6-(5-cyano-1H-pyrrolo[2,3-b]pyridin-1-yl)-N-(2-fluoro-3-methoxy-3-methylbutyl)-4-(isopropylamino)nicotinamide (434); 6-(5-cyano-1H-pyrrolo[2,3-b]pyridin-1-yl)-4-(((R)-2-fluoro-3-(isopropylamino)-3-oxopropyl)amino)-N—((R)-2-fluoro-3-hydroxy-3-methylbutyl)nicotinamide (435); (R)-4-((1H-benzo[d][1,2,3]triazol-6-yl)amino)-6-(5-cyano-1H-pyrrolo[2,3-b]pyridin-1-yl)-N-(2-fluoro-3-hydroxy-3-methylbutyl) nicotinamide (436); (R)-6-(5-cyano-1H-pyrrolo[2,3-b]pyridin-1-yl)-N-(2-fluoro-3-hydroxy-3-methylbutyl)-4-(oxetan-3-ylamino)nicotinamide (437); (R)-4-((1H-indazol-5-yl)amino)-6-(5-cyano-1H-pyrrolo[2,3-b]pyridin-1-yl)-N-(2-fluoro-3-hydroxy-3-methylbutyl)nicotinamide (438); (R)-4-((1H-benzo[d]imidazol-6-yl)amino)-6-(5-cyano-1H-pyrrolo[2,3-b]pyridin-1-yl)-N-(2-fluoro-3-hydroxy-3-methylbutyl) nicotinamide (439); 6-(5-cyano-1H-pyrrolo[2,3-b]pyridin-1-yl)-N—((R)-2-fluoro-3-hydroxy-3-methylbutyl)-4-(((R)-tetrahydrofuran-3-yl)amino)nicotinamide (440); 6-(5-cyano-1H-pyrrolo[2,3-b]pyridin-1-yl)-N—((R)-2-fluoro-3-hydroxy-3-methylbutyl)-4-(((S)-tetrahydrofuran-3-yl)amino)nicotinamide (441); (R)-6-(5-cyano-1H-pyrrolo[2,3-b]pyridin-1-yl)-N-(2-fluoro-3-trideuteromethoxy-3-methylbutyl)-4-(isopropylamino) nicotinamide (442); 6-(5-cyano-1H-pyrrolo[2,3-b]pyridin-1-yl)-N—((R)-2-fluoro-3-trideuteromethoxy-3-methylbutyl)-4-((3-(hydroxymethyl) cyclohexyl)amino)nicotinamide (443); 6-(5-cyano-1H-pyrrolo[2,3-b]pyridin-1-yl)-N-(4-(1-cyclopropyl-1-hydroxyethyl)cyclohexyl)-4-(isopropylamino)nicotinamide (444); 6-(5-cyano-1H-pyrrolo[2,3-b]pyridin-1-yl)-N—((R)-2-fluoro-3-hydroxy-3-methylbutyl)-4-((3-(hydroxymethyl) cyclohexyl)amino)nicotinamide (445); 6-(5-cyano-1H-pyrrolo[2,3-b]pyridin-1-yl)-N-(4-(1-cyclopropyl-1-hydroxyethyl)cyclohexyl)-4-(isopropylamino)nicotinamide (446); 6-(5-cyano-1H-pyrrolo[2,3-b]pyridin-1-yl)-4-(isopropylamino)-N-(1-(methylsulfonyl) piperidin-4-yl)nicotinamide (447); (R)-6-(5-cyano-1H-pyrrolo[2,3-b]pyridin-1-yl)-N-(3-ethoxy-2-fluoro-3-methylbutyl)-4-(isopropylamino)nicotinamide (448); 6-(5-cyano-1H-pyrrolo[2,3-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (449); 6-(5-cyano-1H-pyrrolo[2,3-b]pyridin-1-yl)-4-(((R)-1-cyclopropylethyl)amino)-N—((R)-2-fluoro-3-hydroxy-3-methylbutyl)nicotinamide (450); 6-(5-cyano-1H-pyrrolo[2,3-b]pyridin-1-yl)-4-(((S)-1-cyclopropylethyl)amino)-N—((R)-2-fluoro-3-hydroxy-3-methylbutyl)nicotinamide (451); 6-(5-cyano-1H-pyrrolo[2,3-b]pyridin-1-yl)-4-(isopropylamino)-N-(2-(morpholine-4-sulfonamido)ethyl)nicotinamide (452); 6-(5-cyano-1H-pyrrolo[2,3-b]pyridin-1-yl)-4-(cyclopropylamino)-N-(2-(methylsulfonamido)ethyl)nicotinamide (453); 6-(5-cyano-1H-pyrrolo[2,3-b]pyridin-1-yl)-N—((R)-2-fluoro-3-hydroxy-3-methylbutyl)-4-((4-methylpentan-2-yl)amino) nicotinamide (454); 6-(5-cyano-1H-pyrrolo[2,3-b]pyridin-1-yl)-N—((R)-2-fluoro-3-hydroxy-3-methylbutyl)-4-(((3R,4S)-4-hydroxytetrahydrofuran-3-yl)amino)nicotinamide (455); 6-(5-cyano-1H-pyrrolo[2,3-b]pyridin-1-yl)-N—((R)-2-fluoro-3-hydroxy-3-methylbutyl)-4-(((3R,4S)-4-hydroxytetrahydrofuran-3-yl)amino) nicotinamide (456); (R)-tert-butyl 3-((2-(5-cyano-1H-pyrrolo[2,3-b]pyridin-1-yl)-5-((2-fluoro-3-hydroxy-3-methylbutyl)carbamoyl)pyridin-4-yl)amino)azetidine-1-carboxylate (457); 6-(5-cyano-1H-pyrrolo[2,3-b]pyridin-1-yl)-N—((R)-2-fluoro-3-hydroxy-3-methylbutyl)-4-(((3R,4S)-4-fluorotetrahydrofuran-3-yl) amino)nicotinamide (458); 6-(5-cyano-1H-pyrrolo[2,3-b]pyridin-1-yl)-N—((R)-2-fluoro-3-hydroxy-3-methylbutyl)-4-(((3R,4S)-4-fluorotetrahydrofuran-3-yl)amino)nicotinamide (459); 4-((2-(1H-imidazol-4-yl)cyclopropyl)amino)-6-(5-cyano-1H-pyrrolo[2,3-b]pyridin-1-yl)-N—((R)-2-fluoro-3-hydroxy-3-methylbutyl)nicotinamide (460); 6-(5-cyano-1H-pyrrolo[2,3-b]pyridin-1-yl)-N—((R)-2-fluoro-3-hydroxy-3-methylbutyl)-4-((3-hydroxybutyl)amino) nicotinamide (461); 6-(5-cyano-1H-pyrrolo[2,3-b]pyridin-1-yl)-N—((R)-2-fluoro-3-hydroxy-3-methylbutyl)-4-((3-hydroxybutyl)amino)nicotinamide (462); (R)-6-(5-cyano-1H-pyrrolo[2,3-b]pyridin-1-yl)-N-(2-fluoro-3-hydroxy-3-methylbutyl)-4-((1-(methylsulfonyl) piperidin-4-yl)amino) nicotinamide (463); (R)-6-(5-cyano-1H-pyrrolo[2,3-b]pyridin-1-yl)-N-(2-fluoro-3-hydroxy-3-methylbutyl)-4-((1-phenylpiperidin-4-yl)amino)nicotinamide (464); 6-(5-cyano-1H-pyrrolo[2,3-b]pyridin-1-yl)-N—((R)-2-fluoro-3-hydroxy-3-methylbutyl)-4-(((R)-1-(methylsulfonyl) pyrrolidin-3-yl)amino)nicotinamide (465); 6-(5-cyano-1H-pyrrolo[2,3-b]pyridin-1-yl)-N—((R)-2-fluoro-3-hydroxy-3-methylbutyl)-4-((R)-pyrrolidin-3-ylamino)nicotinamide (466); 6-(5-cyano-1H-pyrrolo[2,3-b]pyridin-1-yl)-4-(isopropylamino)-N-(2-(4-methylpiperazin-1-yl)-2-oxoethyl) nicotinamide (467); (R)-4-((1-acetylazetidin-3-yl)amino)-6-(5-cyano-1H-pyrrolo[2,3-b]pyridin-1-yl)-N-(2-fluoro-3-hydroxy-3-methylbutyl)nicotinamide (468); 4-(((R)-1-acetylpyrrolidin-3-yl)amino)-6-(5-cyano-1H-pyrrolo[2,3-b]pyridin-1-yl)-N—((R)-2-fluoro-3-hydroxy-3-methylbutyl) nicotinamide (469); (R)-4-((1-acetylpiperidin-4-yl)amino)-6-(5-cyano-1H-pyrrolo[2,3-b]pyridin-1-yl)-N-(2-fluoro-3-hydroxy-3-methylbutyl)nicotinamide (470); (R)-4-((4-(1H-imidazol-1-yl)phenyl)amino)-6-(5-cyano-1H-pyrrolo[2,3-b]pyridin-1-yl)-N-(2-fluoro-3-hydroxy-3-methylbutyl) nicotinamide (471); (R)-6-(5-cyano-1H-pyrrolo[2,3-b]pyridin-1-yl)-N-(2-fluoro-3-hydroxy-3-methylbutyl)-4-((1-(5-fluoropyrimidin-2-yl)azetidin-3-yl)amino)nicotinamide (472); 6-(5-cyano-1H-pyrrolo[2,3-b]pyridin-1-yl)-N—((R)-2-fluoro-3-hydroxy-3-methylbutyl)-4-(((R)-1-(3,3,3-trifluoropropanoyl)pyrrolidin-3-yl)amino)nicotinamide (473); (R)-methyl 3-((2-(5-cyano-1H-pyrrolo[2,3-b]pyridin-1-yl)-5-(((R)-2-fluoro-3-hydroxy-3-methylbutyl)carbamoyl)pyridin-4-yl)amino)pyrrolidine-1-carboxylate (474); (R)-1-(4-((azetidin-3-ylmethyl)amino)-5-(2-fluoro-3-hydroxy-3-methylbutyl)carbamoyl)pyridin-2-yl)-1H-pyrrolo[2,3-b] pyridine-5-carboxamide (475); (R)-6-(5-cyano-1H-pyrrolo[2,3-b]pyridin-1-yl)-N-(2-fluoro-3-hydroxy-3-methylbutyl)-4-((1-(methylsulfonyl)azetidin-3-yl)amino) nicotinamide (476); 6-(5-cyano-1H-pyrrolo[2,3-b]pyridin-1-yl)-4-(((R)-1-(2-cyanoacetyl)pyrrolidin-3-yl)amino)-N—((R)-2-fluoro-3-hydroxy-3-methylbutyl)nicotinamide (477); (S)-6-(5-cyano-1H-pyrrolo[2,3-b]pyridin-1-yl)-4-((1-hydroxypropan-2-yl)amino)-N-(2-(methylsulfonamido)ethyl) nicotinamide (478); 6-(5-cyano-1H-pyrrolo[2,3-b]pyridin-1-yl)-N-(2-(methylsulfonamido)ethyl)-4-((tetrahydro-2H-pyran-4-yl)amino)nicotinamide (479); (R)-6-(5-cyano-1H-pyrrolo[2,3-b]pyridin-1-yl)-N-(2-fluoro-3-hydroxy-3-methylbutyl)-4-((2-morpholinoethyl)amino)nicotinamide (480); (R)-methyl 3-((2-(5-cyano-1H-pyrrolo[2,3-b]pyridin-1-yl)-5-((2-fluoro-3-hydroxy-3-methylbutyl)carbamoyl) pyridin-4-yl)amino)azetidine-1-carboxylate (481); (R)-6-(5-cyano-1H-pyrrolo[2,3-b]pyridin-1-yl)-N-(2-fluoro-3-hydroxy-3-methylbutyl)-4-(((tetrahydro-2H-pyran-4-yl) methyl)amino)nicotinamide (482); 6-(5-cyano-1H-pyrrolo[2,3-b]pyridin-1-yl)-N—((R)-2-fluoro-3-hydroxy-3-methylbutyl)-4-((2-(3-methylmorpholino)ethyl)amino) nicotinamide (483); 6-(5-cyano-1H-pyrrolo[2,3-b]pyridin-1-yl)-4-(4,4-difluorotetrahydrofuran-3-yl)amino)-N—((R)-2-fluoro-3-hydroxy-3-methylbutyl)nicotinamide (484); 6-(5-cyano-1H-pyrrolo[2,3-b]pyridin-1-yl)-4-(4,4-difluorotetrahydrofuran-3-yl)amino)-N—((R)-2-fluoro-3-hydroxy-3-methylbutyl)nicotinamide (485); 4-(((1R,4R)-4-carbamoylcyclohexyl)amino)-6-(5-cyano-1H-pyrrolo[2,3-b]pyridin-1-yl)-N—((R)-2-fluoro-3-hydroxy-3-methylbutyl)nicotinamide (486); 6-(5-cyano-1H-pyrrolo[2,3-b]pyridin-1-yl)-N-(2-(1-hydroxycyclopentyl)ethyl)-4-(isopropylamino)nicotinamide (487); 6-(5-cyano-1H-pyrrolo[2,3-b]pyridin-1-yl)-N—((R)-2-fluoro-3-hydroxy-3-methylbutyl)-4-((3-((2,2,2-trifluoroethyl)amino)cyclopentyl)amino)nicotinamide (488); 6-(5-cyano-1H-pyrrolo [2,3-b]pyridin-1-yl)-N—((R)-2-fluoro-3-hydroxy-3-methylbutyl)-4-((3-((2,2,2-trifluoroethyl)amino)cyclopentyl)amino)nicotinamide (489); 4-((3-aminocyclopentyl)amino)-6-(5-cyano-1H-pyrrolo[2,3-b]pyridin-1-yl)-N—((R)-2-fluoro-3-hydroxy-3-methylbutyl)nicotinamide (490); 4-((3-aminocyclopentyl)amino)-6-(5-cyano-1H-pyrrolo[2,3-b]pyridin-1-yl)-N—((R)-2-fluoro-3-hydroxy-3-methylbutyl)nicotinamide (491); 4-((3-aminocyclopentyl)amino)-6-(5-cyano-1H-pyrrolo[2,3-b]pyridin-1-yl)-N—((R)-2-fluoro-3-hydroxy-3-methylbutyl)nicotinamide (492); 4-((3-aminocyclopentyl)amino)-6-(5-cyano-1H-pyrrolo[2,3-b]pyridin-1-yl)-N—((R)-2-fluoro-3-hydroxy-3-methylbutyl)nicotinamide (493); 6-(5-cyano-1H-pyrrolo[2,3-b]pyridin-1-yl)-N-(2-fluoro-2-(3-hydroxyoxetan-3-yl)ethyl)-4-(isopropylamino)nicotinamide (494); 6-(5-cyano-1H-pyrrolo[2,3-b]pyridin-1-yl)-N-(2-fluoro-2-(3-hydroxyoxetan-3-yl)ethyl)-4-(isopropylamino)nicotinamide (495); 6-(5-cyano-1H-pyrrolo[2,3-b]pyridin-1-yl)-N—((R)-2-fluoro-3-hydroxy-3-methylbutyl)-4-(((2S)-3-hydroxy-5-methylhexan-2-yl)amino) nicotinamide (496); 6-(5-cyano-1H-pyrrolo[2,3-b]pyridin-1-yl)-N-((1S,3S)-3-(2-hydroxypropan-2-yl)cyclopentyl)-4-(isopropylamino)nicotinamide (497); (R)-isobutyl((1-(5-((2-fluoro-3-hydroxy-3-methylbutyl)carbamoyl)-4-(isopropylamino)pyridin-2-yl)-1H-pyrrolo[2,3-b]pyridin-5-yl)methyl)carbamate (498); (R)—N-(2-fluoro-3-hydroxy-3-methylbutyl)-6-(5-(3-hydroxy-3-methylbutanamido)methyl)-1H-pyrrolo[2,3-b]pyridin-1-yl)-4-(isopropylamino)nicotinamide (499); (R)-6-(5-((3,3-diethylureido)methyl)-1H-pyrrolo[2,3-b]pyridin-1-yl)-N-(2-fluoro-3-hydroxy-3-methylbutyl)-4-(isopropylamino) nicotinamide (500); (R)-ethyl((1-(5-((2-fluoro-3-hydroxy-3-methylbutyl)carbamoyl)-4-(isopropylamino)pyridin-2-yl)-1H-pyrrolo[2,3-b]pyridin-5-yl)methyl)carbamate (501); (R)-isopropyl((1-(5-((2-fluoro-3-hydroxy-3-methylbutyl)carbamoyl)-4-(isopropylamino) pyridin-2-yl)-1H-pyrrolo[2,3-b]pyridin-5-yl)methyl)carbamate (502); (R)—N-(2-fluoro-3-hydroxy-3-methylbutyl)-4-(isopropylamino)-6-(5-((3-methylbutanamido)methyl)-1H-pyrrolo[2,3-b]pyridin-1-yl)nicotinamide (503); (R)-6-(5-((2-cyclopentylacetamido)methyl)-1H-pyrrolo[2,3-b]pyridin-1-yl)-N-(2-fluoro-3-hydroxy-3-methylbutyl)-4-(isopropylamino)nicotinamide (504); (R)-6-(5-(cyclopropanecarboxamidomethyl)-1H-pyrrolo[2,3-b]pyridin-1-yl)-N-(2-fluoro-3-hydroxy-3-methylbutyl)-4-(isopropylamino) nicotinamide (505); 6-(5-cyano-1H-pyrrolo[2,3-b]pyridin-1-yl)-N—((R)-2-fluoro-3-hydroxy-3-methylbutyl)-4-(((R)-2-fluoropropyl)amino)nicotinamide (506); 6-(5-cyano-1H-pyrrolo[2,3-b]pyridin-1-yl)-N—((R)-2-fluoro-3-hydroxy-3-methylbutyl)-4-(((S)-2-fluoropropyl)amino)nicotinamide (507); (R)-propyl((1-(5-((2-fluoro-3-hydroxy-3-methylbutyl)carbamoyl)-4-(isopropylamino)pyridin-2-yl)-1H-pyrrolo[2,3-b]pyridin-5-yl)methyl)carbamate (508); 6-(5-cyano-1H-pyrrolo[2,3-b]pyridin-1-yl)-N—((R)-2-fluoro-3-hydroxy-3-methylbutyl)-4-(((1R,3R)-3-(2-hydroxypropan-2-yl)cyclobutyl)amino)nicotinamide (509); (R)-6-(5-(butyramidomethyl)-1H-pyrrolo[2,3-b]pyridin-1-yl)-N-(2-fluoro-3-hydroxy-3-methylbutyl)-4-(isopropylamino)nicotinamide (510); (R)-6-(5-((2-cyclohexylacetamido)methyl)-1H-pyrrolo[2,3-b]pyridin-1-yl)-N-(2-fluoro-3-hydroxy-3-methylbutyl)-4-(isopropylamino)nicotinamide (511); (R)—N-(2-fluoro-3-hydroxy-3-methylbutyl)-4-(isopropylamino)-6-(5-((4-methylpentanamido)methyl)-1H-pyrrolo[2,3-b]pyridin-1-yl)nicotinamide (512); (R)—N-(2-fluoro-3-hydroxy-3-methylbutyl)-4-(isopropylamino)-6-(5-((3-propylureido)methyl)-1H-pyrrolo[2,3-b]pyridin-1-yl)nicotinamide (513); (R)-6-(5-((3-benzylureido)methyl)-1H-pyrrolo[2,3-b]pyridin-1-yl)-N-(2-fluoro-3-hydroxy-3-methylbutyl)-4-(isopropylamino)nicotinamide (514); (R)—N-(2-fluoro-3-hydroxy-3-methylbutyl)-4-(isopropylamino)-6-(5-((2-phenylacetamido)methyl)-1H-pyrrolo[2,3-b]pyridin-1-yl)nicotinamide (515); (R)-6-(5-((3-butylureido)methyl)-1H-pyrrolo[2,3-b]pyridin-1-yl)-N-(2-fluoro-3-hydroxy-3-methylbutyl)-4-(isopropylamino)nicotinamide (516); (R)-6-(5-cyano-1H-pyrrolo[2,3-b]pyridin-1-yl)-N-(2,3-difluoro-3-methylbutyl)-4-((3-hydroxyphenyl)amino)nicotinamide (517); (R)—N-(2-fluoro-3-hydroxy-3-methylbutyl)-4-(isopropylamino)-6-(5-((2-(tetrahydro-2H-pyran-4-yl)acetamido)methyl)-1H-pyrrolo[2,3-b]pyridin-1-yl)nicotinamide (518); (R)-6-(5-((3,3-dimethylbutanamido)methyl)-1H-pyrrolo[2,3-b]pyridin-1-yl)-N-(2-fluoro-3-hydroxy-3-methylbutyl)-4-(isopropylamino)nicotinamide (519); N—((R)-2-fluoro-3-hydroxy-3-methylbutyl)-4-(isopropylamino)-6-(5-((tetrahydrofuran-3-carboxamido)methyl)-1H-pyrrolo[2,3-b]pyridin-1-yl)nicotinamide (520); (R)-6-(5-cyano-1H-pyrazolo[3,4-b]pyridin-1-yl)-N-(2-fluoro-3-hydroxy-3-methylbutyl)-4-((5-(2-hydroxypropan-2-yl)thiazol-2-yl)amino)nicotinamide (521); (R)-6-(5-cyano-1H-pyrazolo[3,4-b]pyridin-1-yl)-4-((3-cyanophenyl)amino)-N-(2-fluoro-3-hydroxy-3-methylbutyl)nicotinamide (522); (R)-6-(5-cyano-1H-pyrazolo[3,4-b]pyridin-1-yl)-4-((4-cyanophenyl)amino)-N-(2-fluoro-3-hydroxy-3-methylbutyl)nicotinamide (523); (R)-4-(benzo[d]thiazol-6-ylamino)-6-(5-cyano-1H-pyrazolo[3,4-b]pyridin-1-yl)-N-(2-fluoro-3-hydroxy-3-methylbutyl)nicotinamide (524); (R)-1-(4-(benzo[d]oxazol-6-ylamino)-5-(2-fluoro-3-hydroxy-3-methylbutyl)carbamoyl)pyridin-2-yl)-1H-pyrazolo[3,4-b]pyridine-5-carboxamide (525); (R)-4-((4-(1H-1,2,4-triazol-1-yl)phenyl)amino)-6-(5-cyano-1H-pyrazolo[3,4-b]pyridin-1-yl)-N-(2-fluoro-3-hydroxy-3-methylbutyl)nicotinamide (526); (R)-6-(5-cyano-1H-pyrazolo[3,4-b]pyridin-1-yl)-N-(2-fluoro-3-hydroxy-3-methylbutyl)-4-((4-(1-methyl-1H-tetrazol-5-yl)phenyl)amino)nicotinamide (527); (R)-6-(5-cyano-1H-pyrazolo[3,4-b]pyridin-1-yl)-4-((3-cyano-2-fluorophenyl)amino)-N-(2-fluoro-3-hydroxy-3-methylbutyl)nicotinamide (528); (R)-6-(5-cyano-1H-pyrazolo[3,4-b]pyridin-1-yl)-N-(2,3-difluoro-3-methylbutyl)-4-((4-(1-methyl-1H-tetrazol-5-yl)phenyl)amino) nicotinamide (529); (R)-6-(5-cyano-1H-pyrazolo[3,4-b]pyridin-1-yl)-N-(2-fluoro-3-hydroxy-3-methylbutyl)-4-(5-methyl-1,3,4-thiadiazol-2-yl)amino)nicotinamide (530); (R)-6-(5-cyano-1H-pyrazolo[3,4-b]pyridin-1-yl)-N-(2-fluoro-3-hydroxy-3-methylbutyl)-4-((4-(1-methyl-H-pyrazol-4-yl)phenyl)amino)nicotinamide (531); 6-(5-cyano-1H-pyrazolo[3,4-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (532); 6-(5-cyano-1H-pyrazolo[3,4-b]pyridin-1-yl)-N—((R)-2-fluoro-3-hydroxy-3-methylbutyl)-4-(((S)-1-(5-fluoropyrimidin-2-yl)pyrrolidin-3-yl)amino)nicotinamide (533); 6-(5-cyano-1H-pyrazolo[3,4-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (534); (R)-6-(5-cyano-1H-pyrazolo[3,4-b]pyridin-1-yl)-N-(2-fluoro-3-hydroxy-3- methylbutyl)-4-((1-phenylpiperidin-4-yl)amino) nicotinamide (535); 6-(5-cyano-1H-pyrazolo[3,4-b]pyridin-1-yl)-N—((R)-2-fluoro-3-hydroxy-3-methylbutyl)-4-(((R)-1-(5-methoxypyrimidin-2-yl)pyrrolidin-3-yl)amino) nicotinamide (536); 6-(5-cyano-1H-pyrazolo[3,4-b]pyridin-1-yl)-N—((R)-2-fluoro-3-hydroxy-3-methylbutyl)-4-(((R)-1-(pyrimidin-2-yl)pyrrolidin-3-yl)amino)nicotinamide (537); 6-(5-cyano-1H-pyrazolo[3,4-b]pyridin-1-yl)-4-(((R)-1-(2,4-difluorobenzoyl)pyrrolidin-3-yl)amino)-N—((R)-2-fluoro-3-hydroxy-3-methylbutyl) nicotinamide (538); (R)-6-(5-cyano-1H-pyrazolo[3,4-b]pyridin-1-yl)-N-(2-fluoro-3-hydroxy-3-methylbutyl)-4-((1-(5-fluoropyrimidin-2-yl)azetidin-3-yl)amino)nicotinamide (539); (R)-6-(5-cyano-1H-pyrazolo[3,4-b]pyridin-1-yl)-N-(2-fluoro-3-hydroxy-3-methylbutyl)-4-((1-(5-fluoropyrimidin-2-yl)piperidin-4-yl)amino)nicotinamide (540); (R)-4-((1-(5-chloropyrimidin-2-yl)azetidin-3-yl)amino)-6-(5-cyano-1H-pyrazolo[3,4-b]pyridin-1-yl)-N-(2-fluoro-3-hydroxy-3-methylbutyl) nicotinamide (541); (R)-methyl 3-((2-(5-cyano-1H-pyrazolo[3,4-b]pyridin-1-yl)-5-((2-fluoro-3-hydroxy-3-methylbutyl)carbamoyl)pyridin-4-yl)amino)azetidine-1-carboxylate (542); (R)-ethyl 3-((2-(5-cyano-1H-pyrazolo[3,4-b]pyridin-1-yl)-5-((2-fluoro-3-hydroxy-3-methylbutyl)carbamoyl)pyridin-4-yl)amino)azetidine-1-carboxylate (543); 6-(5-cyano-1H-pyrazolo[3,4-b]pyridin-1-yl)-N—((R)-2-fluoro-3-hydroxy-3-methylbutyl)-4-(((R)-tetrahydrofuran-3-yl)amino)nicotinamide, TFA salt (544); 6-(5-cyano-1H-pyrazolo[3,4-b]pyridin-1-yl)-N—((R)-2-fluoro-3-hydroxy-3-methylbutyl)-4-(((S)-tetrahydrofuran-3-yl)amino)nicotinamide, TFA salt (545); (R)-6-(5-cyano-1H-pyrazolo[3,4-b]pyridin-1-yl)-N-(2-fluoro-3-hydroxy-3-methylbutyl)-4-(oxetan-3-ylamino)nicotinamide (546); 6-(5-fluoro-1H-pyrazolo[3,4-b]pyridin-1-yl)-N—((R)-2-fluoro-3-hydroxy-3-methylbutyl)-4-((tetrahydro-2H-pyran-3-yl)amino)nicotinamide (547); 6-(6-cyano-3H-imidazo[4,5-b]pyridin-3-yl)-N—((R)-2-fluoro-3-hydroxy-3-methylbutyl)-4-(((R)-tetrahydrofuran-3-yl)amino)nicotinamide (548); (R)-6-(5-cyano-2,3-dihydro-1H-pyrrolo[2,3-b]pyridin-1-yl)-N-(2-fluoro-3-hydroxy-3-methylbutyl)-4-(oxetan-3-ylamino)nicotinamide (549); (R)-6-(5-fluoro-1H-pyrazolo[3,4-b]pyridin-1-yl)-N-(2-fluoro-3-hydroxy-3-methylbutyl)-4-(oxetan-3-ylamino)nicotinamide (550); (R)-6-(5-chloro-1H-pyrazolo[3,4-b]pyridin-1-yl)-N-(2-fluoro-3-hydroxy-3-methylbutyl)-4-(oxetan-3-ylamino) nicotinamide (551); 6-(5-cyano-1H-pyrazolo[3,4-b]pyridin-1-yl)-N-((1R,4R)-4-methoxycyclohexyl)-4-(oxetan-3-ylamino)nicotinamide (552); 6-(5-cyano-1H-pyrazolo[3,4-b]pyridin-1-yl)-N-(3-hydroxy-3-methylbutyl)-4-(oxetan-3-ylamino)nicotinamide (553); 6-(5-cyano-1H-pyrazolo[3,4-b]pyridin-1-yl)-4-(4,4-difluorotetrahydrofuran-3-yl)amino)-N—((R)-2-fluoro-3-hydroxy-3-methylbutyl)nicotinamide (554); 6-(5-cyano-1H-pyrazolo[3,4-b]pyridin-1-yl)-N-((1R,4R)-4-(2-hydroxypropan-2-yl)cyclohexyl)-4-(oxetan-3-ylamino)nicotinamide (555); 6-(5-chloro-1H-pyrazolo[3,4-b]pyridin-1-yl)-N-((1R,4R)-4-(2-hydroxypropan-2-yl)cyclohexyl)-4-(oxetan-3-ylamino)nicotinamide (556); 6-(5-cyano-1H-pyrazolo[3,4-b]pyridin-1-yl)-N-isopentyl-4-(oxetan-3-ylamino)nicotinamide (557); 6-(6-amino-5-cyano-1H-pyrazolo[3,4-b]pyridin-1-yl)-N-(2-cyclopropylethyl)-4-(oxetan-3-ylamino) nicotinamide (558); 6-(6-amino-5-cyano-1H-pyrazolo[3,4-b]pyridin-1-yl)-N-butyl-4-(oxetan-3-ylamino)nicotinamide (559); 6-(6-amino-5-cyano-1H-pyrazolo[3,4-b]pyridin-1-yl)-N-isopentyl-4-(oxetan-3-ylamino)nicotinamide (560); N-butyl-6-(5-cyano-1H-pyrazolo[3,4-b]pyridin-1-yl)-4-(oxetan-3-ylamino)nicotinamide (561); (R)-6-(5-fluoro-1H-pyrazolo[3,4-b]pyridin-1-yl)-N-(2-fluoro-3-hydroxy-3-methylbutyl)-4-((tetrahydro-2H-pyran-4-yl)amino) nicotinamide (562); (R)-6-(5-cyano-1H-pyrazolo[3,4-b]pyridin-1-yl)-N-(2-fluoro-3-hydroxy-3-methylbutyl)-4-((3,3,3-trifluoropropyl)amino)nicotinamide (563); 6-(5-cyano-1H-pyrazolo[3,4-b]pyridin-1-yl)-4-(isopropylamino)-N-(5-methoxypyrazin-2-yl)nicotinamide (564); N—((R)-2-fluoro-3-hydroxy-3-methylbutyl)-4-((2-morpholinopropyl)amino)-6-(7H-pyrrolo[2,3-d]pyrimidin-7-yl)nicotinamide (565); N-((2H-tetrazol-5-yl)methyl)-6-(5-cyano-1H-pyrazolo[3,4-b]pyridin-1-yl)-4-(isopropylamino)nicotinamide (566); (R)-6-(5-cyano-2,3-dihydro-1H-pyrrolo[2,3-b]pyridin-1-yl)-N-(2-fluoro-3-hydroxy-3-methylbutyl)-4-(isopropylamino)nicotinamide (567); (R)-6-(6-cyano-3H-imidazo[4,5-b]pyridin-3-yl)-4-(ethylamino)-N-(2-fluoro-3-hydroxy-3-methylbutyl)nicotinamide (568); 6-(5-cyano-1H-pyrazolo[3,4-b]pyridin-1-yl)-N—((R)-2-fluoro-3-hydroxy-3-methylbutyl)-4-(((S)-1-hydroxy-3-methylbutan-2-yl)amino) nicotinamide (569); (R)-6-(5-cyano-1H-pyrazolo[3,4-b]pyridin-1-yl)-N-(2-fluoro-3-hydroxy-3-methylbutyl)-4-((2-methyl-2-morpholinopropyl)amino)nicotinamide (570); (R)-6-(5-cyano-1H-pyrazolo[3,4-b]pyridin-1-yl)-N-(2-fluoro-3-hydroxy-3-methylbutyl)-4-((oxazol-4-ylmethyl)amino)nicotinamide (571); 6-(5-cyano-1H-pyrazolo[3,4-b]pyridin-1-yl)-N—((R)-2-fluoro-3-hydroxy-3-methylbutyl)-4-(((R)-3-hydroxybutyl)amino) nicotinamide (572); 6-(5-cyano-1H-pyrazolo[3,4-b]pyridin-1-yl)-N—((R)-2-fluoro-3-hydroxy-3-methylbutyl)-4-(((R)-3-hydroxybutyl)amino) nicotinamide (573); (R)-6-(5-cyano-1H-pyrazolo[3,4-b]pyridin-1-yl)-4-((2,2-difluoroethyl)amino)-N-(2-fluoro-3-hydroxy-3-methylbutyl)nicotinamide (574); 6-(5-cyano-1H-pyrazolo[3,4-b]pyridin-1-yl)-4-((2-fluoro-3-hydroxy-2-methylpropyl)amino)-N—((R)-2-fluoro-3-hydroxy-3-methylbutyl)nicotinamide (575); (R)-6-(5-cyano-1H-pyrazolo[3,4-b]pyridin-1-yl)-N-(2-fluoro-3-hydroxy-3-methylbutyl)-4-(neopentylamino)nicotinamide (576); (R)-6-(6-amino-5-cyano-1H-pyrazolo[3,4-b]pyridin-1-yl)-4-(ethylamino)-N-(2-fluoro-3-hydroxy-3-methylbutyl) nicotinamide (577); (R)-6-(6-amino-5-cyano-1H-pyrazolo[3,4-b]pyridin-1-yl)-N-(2-fluoro-3-hydroxy-3-methylbutyl)-4-(propylamino)nicotinamide (578); (R)-6-(6-amino-1H-pyrazolo[3,4-d]pyrimidin-1-yl)-N-(2-fluoro-3-hydroxy-3-methylbutyl)-4-(isopropylamino)nicotinamide (579); (R)-6-(6-amino-1H-pyrazolo[3,4-d]pyrimidin-1-yl)-4-(ethylamino)-N-(2-fluoro-3-hydroxy-3-methylbutyl)nicotinamide (580); (R)-6-(5-cyano-1H-pyrazolo[3,4-b]pyridin-1-yl)-N-(2-fluoro-3-hydroxy-3-methylbutyl)-4-(((1-fluorocyclobutyl)methyl)amino)nicotinamide (581); 6-(5-cyano-1H-pyrazolo[3,4-b]pyridin-1-yl)-N—((R)-2-fluoro-3-hydroxy-3-methylbutyl)-4-(((R)-2-fluoropropyl)amino) nicotinamide (582); 6-(5-cyano-1H-pyrazolo[3,4-b]pyridin-1-yl)-N—(R)-2-fluoro-3-hydroxy-3-methylbutyl)-4-(((S)-2-fluoropropyl)amino)nicotinamide (583); 6-(5-cyano-1H-pyrazolo[3,4-b]pyridin-1-yl)-4-(isopropylamino)-N-(1-(1-(methylsulfonyl)azetidine-3-carbonyl)piperidin-4-yl) nicotinamide (584); (R)-4-((3-amino-2,2-dimethylpropyl)amino)-6-(5-cyano-1H-pyrazolo[3,4-b]pyridin-1-yl)-N-(2-fluoro-3-hydroxy-3-methylbutyl)nicotinamide (585); (R)-6-(5-cyano-1H-pyrazolo[3,4-b]pyridin-1-yl)-N-(2-fluoro-3-hydroxy-3-methylbutyl)-4-((2-(methylsulfonamido)ethyl)amino)nicotinamide (586); (R)-1,1,1-trifluoro-2-methylpropan-2-yl(2-((2-(5-cyano-1H-pyrazolo[3,4-b]pyridin-1-yl)-5-(2-fluoro-3-hydroxy-3-methylbutyl)carbamoyl)pyridin-4-yl)amino)ethyl) carbamate (587); 6-(5-cyano-1H-pyrazolo[3,4-b]pyridin-1-yl)-N—((R)-2-fluoro-3-hydroxy-3-methylbutyl)-4-(((S)-1-hydroxybutan-2-yl)amino)nicotinamide (588); 6-(5-chloro-1H-pyrazolo[3,4-b]pyridin-1-yl)-N—((R)-2-fluoro-3-hydroxy-3- methylbutyl)-4-(((S)-1-hydroxybutan-2-yl)amino) nicotinamide (589); 6-(6-amino-5-cyano-1H-pyrazolo[3,4-b]pyridin-1-yl)-N—((R)-2-fluoro-3-hydroxy-3-methylbutyl)-4-(((S)-2-fluoropropyl)amino)nicotinamide (590); 6-(6-amino-5-cyano-1H-pyrazolo[3,4-b]pyridin-1-yl)-N—((R)-2-fluoro-3-hydroxy-3-methylbutyl)-4-(((R)-2-fluoropropyl)amino)nicotinamide (591); (R)-6-(5-cyano-1H-pyrazolo[3,4-b]pyridin-1-yl)-N-(2-fluoro-3-hydroxy-3-methylbutyl)-4-(propylamino)nicotinamide (592); (R)-6-(5-cyano-1H-pyrazolo[3,4-b]pyridin-1-yl)-N-(2-fluoro-3-hydroxy-3-methylbutyl)-4-((2-methoxy-2-methylpropyl)amino)nicotinamide (593); 6-(5-chloro-1H-pyrazolo[3,4-b]pyridin-1-yl)-N—((R)-2-fluoro-3-hydroxy-3-methylbutyl)-4-((2-hydroxy-3-methylbutyl)amino)nicotinamide (594); (R)-6-(5-cyano-1H-pyrazolo[3,4-b]pyridin-1-yl)-N-(2-fluoro-3-hydroxy-3-methylbutyl)-4-((3-fluoropropyl)amino)nicotinamide (595); 6-(5-chloro-1H-pyrazolo[3,4-b]pyridin-1-yl)-N—((R)-2-fluoro-3-hydroxy-3-methylbutyl)-4-((2-hydroxy-3-methylbutyl)amino) nicotinamide (596); 6-(5-cyano-1H-pyrazolo[3,4-b]pyridin-1-yl)-N—((R)-2-fluoro-3-hydroxy-3-methylbutyl)-4-((2-hydroxy-3-methylbutyl)amino)nicotinamide (597); (R)-6-(5-cyano-1H-pyrazolo[3,4-b]pyridin-1-yl)-4-((2-(difluoromethoxy)ethyl)amino)-N-(2-fluoro-3-hydroxy-3-methylbutyl)nicotinamide (598); (R)-6-(6-amino-5-cyano-1H-pyrazolo[3,4-b]pyridin-1-yl)-N-(2-fluoro-3-hydroxy-3-methylbutyl)-4-((3-fluoro-3-methylbutyl)amino)nicotinamide (599); (R)-6-(5-cyano-1H-pyrazolo[3,4-b]pyridin-1-yl)-N-(2-fluoro-3-hydroxy-3-methylbutyl)-4-((3-fluoro-3-methylbutyl)amino) nicotinamide (600); (R)-6-(5-cyano-1H-pyrazolo[3,4-b]pyridin-1-yl)-4-((2-(difluoromethoxy)-2-methylpropyl)amino)-N-(2-fluoro-3-hydroxy-3-methylbutyl)nicotinamide (601); 6-(5-chloro-1H-pyrazolo[3,4-b]pyridin-1-yl)-N—((R)-2-fluoro-3-hydroxy-3-methylbutyl)-4-(((R)-2-fluorobutyl)amino)nicotinamide (602); (R)-6-(5-chloro-1H-pyrazolo[3,4-b]pyridin-1-yl)-4-((2-(difluoromethoxy)-2-methylpropyl)amino)-N-(2-fluoro-3-hydroxy-3-methylbutyl)nicotinamide (603); 6-(5-cyano-1H-pyrazolo[3,4-b]pyridin-1-yl)-N—((R)-2-fluoro-3-hydroxy-3-methylbutyl)-4-((3-fluorobutyl)amino)nicotinamide (604); (R)-6-(5-cyano-1H-pyrazolo[3,4-b]pyridin-1-yl)-4-((cyclopropylmethyl)amino)-N-(2-fluoro-3-hydroxy-3-methylbutyl)nicotinamide (605); 6-(5-cyano-1H-pyrazolo[3,4-b]pyridin-1-yl)-N—((R)-2-fluoro-3-hydroxy-3-methylbutyl)-4-(((1R,4R)-4-(2-hydroxypropan-2-yl)cyclohexyl)amino) nicotinamide (606); 6-(5-cyano-1H-pyrazolo[3,4-b]pyridin-1-yl)-N—((R)-2-fluoro-3-hydroxy-3-methylbutyl)-4-(((1s,4S)-4-hydroxy-4-methylcyclohexyl)amino)nicotinamide (607); 6-(5-cyano-1H-pyrazolo[3,4-b]pyridin-1-yl)-N—((R)-2-fluoro-3-hydroxy-3-methylbutyl)-4-(((1R,4R)-4-hydroxy-4-methylcyclohexyl)amino) nicotinamide (608); 6-(5-fluoro-1H-pyrazolo[3,4-b]pyridin-1-yl)-N—((R)-2-fluoro-3-hydroxy-3-methylbutyl)-4-((3-hydroxycyclopentyl)amino)nicotinamide (609); 6-(5-fluoro-1H-pyrazolo[3,4-b]pyridin-1-yl)-N—((R)-2-fluoro-3-hydroxy-3-methylbutyl)-4-((3-hydroxycyclopentyl)amino) nicotinamide (610); 6-(5-fluoro-1H-pyrazolo[3,4-b]pyridin-1-yl)-N—((R)-2-fluoro-3-hydroxy-3-methylbutyl)-4-((3-hydroxycyclopentyl)amino) nicotinamide (611); 6-(5-cyano-1H-pyrazolo[3,4-b]pyridin-1-yl)-N—((R)-2-fluoro-3-hydroxy-3-methylbutyl)-4-(((1R,3S)-3-(2-hydroxypropan-2-yl)cyclohexyl)amino) nicotinamide (612); (R)-6-(5-cyano-1H-pyrazolo[3,4-b]pyridin-1-yl)-N-(2-fluoro-3-hydroxy-3-methylbutyl)-4-((4-hydroxybicyclo[2.2.1]heptan-1-yl)amino)nicotinamide (613); 6-(5-cyano-1H-pyrazolo[3,4-b]pyridin-1-yl)-4-((3,3-difluorocyclopentyl)amino)-N—((R)-2-fluoro-3-hydroxy-3-methylbutyl)nicotinamide (614); 6-(5-cyano-1H-pyrazolo[3,4-b]pyridin-1-yl)-4-((3,3-difluorocyclopentyl)amino)-N—((R)-2-fluoro-3-hydroxy-3-methylbutyl)nicotinamide (615); (R)-6-(5-cyano-2,3-dihydro-1H-pyrrolo[2,3-b]pyridin-1-yl)-4-(cyclopropylamino)-N-(2-fluoro-3-hydroxy-3-methylbutyl)nicotinamide (616); 6-(5-cyano-1H-pyrazolo[3,4-b]pyridin-1-yl)-N—((R)-2-fluoro-3-hydroxy-3-methylbutyl)-4-(((1S,3S)-3-(2-hydroxypropan-2-yl)cyclopentyl)amino)nicotinamide (617); 6-(5-fluoro-1H-pyrazolo[3,4-b]pyridin-1-yl)-N—((R)-2-fluoro-3-hydroxy-3-methylbutyl)-4-((3-fluorocyclopentyl)amino) nicotinamide (618); 6-(5-fluoro-1H-pyrazolo[3,4-b]pyridin-1-yl)-N—((R)-2-fluoro-3-hydroxy-3-methylbutyl)-4-((3-fluorocyclopentyl)amino) nicotinamide (619); 6-(5-fluoro-1H-pyrazolo[3,4-b]pyridin-1-yl)-N—((R)-2-fluoro-3-hydroxy-3-methylbutyl)-4-((3-fluorocyclopentyl)amino) nicotinamide (620); 6-(5-fluoro-1H-pyrazolo[3,4-b]pyridin-1-yl)-N—((R)-2-fluoro-3-hydroxy-3-methylbutyl)-4-((3-fluorocyclopentyl)amino)nicotinamide (621); 6-(5-cyano-1H-pyrazolo[3,4-b]pyridin-1-yl)-N—((R)-2-fluoro-3-hydroxy-3-methylbutyl)-4-(((1R,4R)-4-(oxetan-3-ylamino)cyclohexyl)amino)nicotinamide (622); 6-(5-cyano-1H-pyrazolo[3,4-b]pyridin-1-yl)-4-(((1R,4R)-4-(cyclopropanecarboxamido)cyclohexyl)amino)-N—((R)-2-fluoro-3-hydroxy-3-methylbutyl)nicotinamide (623); 6-(5-cyano-1H-pyrazolo[3,4-b]pyridin-1-yl)-N—((R)-2-fluoro-3-hydroxy-3-methylbutyl)-4-(((1R,5S)-3-hydroxyadamantan-1-yl)amino) nicotinamide (624); 6-(5-cyano-1H-pyrazolo[3,4-b]pyridin-1-yl)-N—((R)-2-fluoro-3-hydroxy-3-methylbutyl)-4-((3-fluorocyclopentyl)amino) nicotinamide (625); 6-(5-cyano-1H-pyrazolo[3,4-b]pyridin-1-yl)-N—((R)-2-fluoro-3-hydroxy-3-methylbutyl)-4-((3-fluorocyclopentyl)amino)nicotinamide (626); 6-(5-cyano-1H-pyrazolo[3,4-b]pyridin-1-yl)-N—((R)-2-fluoro-3-hydroxy-3-methylbutyl)-4-((3-fluorocyclopentyl)amino) nicotinamide (627); 6-(5-chloro-1H-pyrazolo[3,4-b]pyridin-1-yl)-N—((R)-2-fluoro-3-hydroxy-3-methylbutyl)-4-(((1S,3S)-3-(2-hydroxypropan-2-yl)cyclopentyl)amino) nicotinamide (628); 6-(6-amino-5-cyano-1H-pyrazolo[3,4-b]pyridin-1-yl)-4-(((1R,2R)-2-fluorocyclohexyl)amino)-N-((1R,4R)-4-(methylcarbamoyl)cyclohexyl)nicotinamide (629); 6-(6-amino-5-cyano-1H-pyrazolo[3,4-b]pyridin-1-yl)-4-(((1S,2S)-2-fluorocyclohexyl)amino)-N-((1R,4S)-4-(methylcarbamoyl)cyclohexyl)nicotinamide (630); (R)-6-(6-amino-5-cyano-1H-pyrazolo[3,4-b]pyridin-1-yl)-4-(cyclopropylamino)-N-(2-fluoro-3-hydroxy-3-methylbutyl) nicotinamide (631); 6-(6-amino-5-cyano-1H-pyrazolo[3,4-b]pyridin-1-yl)-N—((R)-2-fluoro-3-hydroxy-3-methylbutyl)-4-(((1R,5S)-3-hydroxyadamantan-1-yl)amino)nicotinamide (632); 6-(5-cyano-1H-pyrazolo[3,4-b]pyridin-1-yl)-4-(((1R,4R)-4-(2,2-difluoroacetamido)cyclohexyl)amino)-N—((R)-2-fluoro-3-hydroxy-3-methylbutyl)nicotinamide (633); 6-(5-cyano-1H-pyrazolo[3,4-b]pyridin-1-yl)-N—((R)-2-fluoro-3-hydroxy-3-methylbutyl)-4-(((1R,4R)-4-((2-fluorobenzamido)cyclohexyl)amino)nicotinamide (634); (R)-4-(bicyclo[1.1.1]pentan-2-ylamino)-6-(5-cyano-1H-pyrazolo[3,4-b]pyridin-1-yl)-N-(2-fluoro-3-hydroxy-3-methylbutyl) nicotinamide (635); 6-(5-cyano-1H-pyrazolo[3,4-b]pyridin-1-yl)-N—((R)-2,3-difluoro-3-methylbutyl)-4-(((1R,5S)-3-hydroxyadamantan-1-yl)amino)nicotinamide (636); (R)-6-(6-amino-5-cyano-1H-pyrazolo[3,4-b]pyridin-1-yl)-4-(bicyclo[1.1.1]pentan-1-ylamino)-N-(2-fluoro-3-hydroxy-3-methylbutyl)nicotinamide (637); 4-((3-aminocyclopentyl)amino)-6-(5-cyano-1H-pyrazolo[3,4-b]pyridin-1-yl)-N—((R)-2-fluoro-3-hydroxy-3-methylbutyl) nicotinamide (638); 4-((3-aminocyclopentyl)amino)-6-(5-cyano-1H- pyrazolo[3,4-b]pyridin-1-yl)-N—((R)-2-fluoro-3-hydroxy-3-methylbutyl)nicotinamide (639); 4-((3-aminocyclopentyl)amino)-6-(5-cyano-1H-pyrazolo[3,4-b]pyridin-1-yl)-N—((R)-2-fluoro-3-hydroxy-3-methylbutyl)nicotinamide (640); 6-(5-cyano-1H-pyrazolo[3,4-b]pyridin-1-yl)-N—((R)-2-fluoro-3-hydroxy-3-methylbutyl)-4-(((1R,4R)-4-(isopropylcarbamoyl)cyclohexyl)amino)nicotinamide (641); 6-(5-cyano-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino)nicotinamide (642); 6-(5-cyano-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino) nicotinamide (643); (R)-6-(5-cyano-1H-pyrazolo[3,4-b]pyridin-1-yl)-4-((3,3-difluorocyclobutyl)amino)-N-(2-fluoro-3-hydroxy-3-methylbutyl)nicotinamide (644); 6-(5-chloro-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino)nicotinamide (645); and 6-(5-chloro-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino)nicotinamide (646).

In any aspect or embodiment described herein, the PTM is represented by Formula PTM-Va (which related to Formula I from International Publication No. 2013/042137 A1 and Formula I from International Publication No. 2015/104688 A1, which are incorporated herein in their entirety for all purposes) or PTM-Vb:

PTM-Va

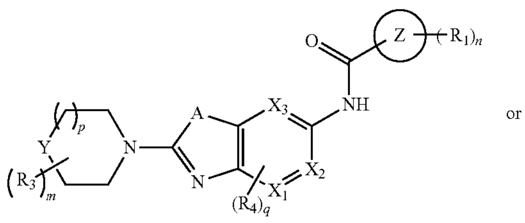

or

PTM-Vb

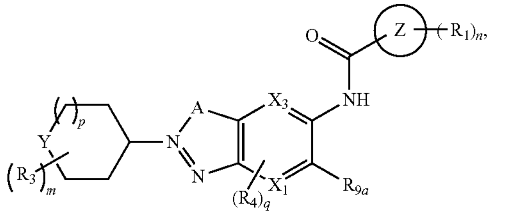

wherein:

- $X_1$ and $X_3$ of PTM-Va or PTM-Vb independently are CH or N; $X_2$ of PTM-V is $CR_2$ or N;
  - provided one and not more than one of $X_1$, X2 or X3 is N;
- Y of PTM-Va or PTM-Vb is —$CH_2$— or O;
- Ring Z of PTM-Va or PTM-Vb is aryl, heteroaryl, or heterocyclyl;
- A of PTM-Va or PTM-Vb is O, S, or NH;
- $R_1$ of PTM-Va or PTM-Vb at each occurrence, is independently hydrogen, cyano, halo, hydroxy, —$NO_2$, —$NR_5R_6$, optionally substituted alkyl, optionally substituted aryl, optionally substituted cycloalkyl, optionally substituted heterocycloalkyl, optionally substituted heterocyclyl or optionally substituted heteroaryl, wherein the substituent, in each occurrence, is independently selected from alkyl, alkoxy, haloalkyl, cyano, aminoalkyl, halo, hydroxyl, hydroxyalkyl, —$NR^7R^8$, or $COOR^9$;
- $R_2$ of PTM-Va or PTM-Vb is hydrogen, optionally substituted cycloalkyl, optionally substituted aryl, optionally substituted heterocyclyl or —$NR_aR_b$; wherein the substituent is alkyl, amino, halo or hydroxyl;
- $R_3$ of PTM-Va or PTM-Vb at each occurrence is independently selected from hydrogen, carboxy, cyano, hydroxy, hydroxyalkyl, alkyl, aryl, heteroaryl, —$SO_2R_7$, hydroxyl or oxo;
- $R_4$ of PTM-Va or PTM-Vb at each occurrence is independently selected from hydrogen, halogen, alkyl, aryl, heterocycloalkyl, heterocycloalkylalkyl, heteroaryl, Y-arylalkyl or —Y-cycloalkyl; wherein cycloalkyl, aryl, heterocycloalkyl, heterocycloalkylalkyl, heteroaryl and arylalkyl can be optionally substituted with hydroxy, alkyl, haloalkyl, cyano or halo;
- $Y_1$ of PTM-Va or PTM-Vb is selected from direct bond, O, —C(O)— or $NR^9$;
- $R_5$ and $R_6$ of PTM-Va or PTM-Vb are independently selected from hydrogen, hydroxyalkyl, aminoalkyl, acyl, optionally substituted alkyl, optionally substituted heterocyclyl, optionally substituted aryl; wherein the optional substituent, in each occurrence, is independently selected from halo, haloalkyl or —$COOR_9$;
- $R_7$ and $R_8$ of PTM-Va or PTM-Vb are independently hydrogen, alkyl, acyl, heterocyclyl, —$COR_9$ or —$COOR_9$;
- $R_9$ of PTM-Va or PTM-Vb at each occurrence is independently selected from hydrogen or alkyl;
- $R_{9a}$ of PTM-Vb is selected from hydrogen, halo, optionally substituted alkoxy (e.g., optionally substituted $C_1$-$C_4$ alkoxy), optionally substituted alkyl (e.g., $C_1$-$C_4$ alkyl optionally substituted with halo or hydroxy), hydroxyalkyl (e.g. $C_1$-$C_4$ hydroxyalkyl), or haloalkyl (e.g., $C_1$-$C_4$ haloalkyl);
- "m", "n" and "q" of PTM-Va or PTM-Vb are independently selected from 0, 1, 2, or 3;
- "p" of PTM-Va or PTM-Vb is 0 or 1; and
- the PTM-Va or PTM-Vb is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-V is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, $R^5$, $R^6$, $R^7$, $R^8$, $R^9$, $9^a$, $R^a$, or $R^b$).

In any aspect or embodiment described herein, the PTM of PTM-Va or PTM-Vb may comprise at least one of:

- $X_1$, $X_2$ and $X_3$ of PTM-Va or PTM-Vb are CH;
- Y of PTM-Va or PTM-Vb is O;
- Ring Z of PTM-Va or PTM-Vb is aryl or heteroaryl;
- A of PTM-Va or PTM-Vb is O, S, or NH;
- $R_1$ of PTM-Va or PTM-Vb, at each occurrence, is independently hydrogen, cyano, halo, hydroxy, —NO2, —$NR_5R_6$, optionally substituted alkyl, optionally substituted aryl, optionally substituted cycloalkyl, optionally substituted heterocycloalkyl, or optionally substituted heteroaryl, wherein the substituent, in each occurrence, is independently selected from is alkyl, haloalkyl, halo, cyano, —$NR_7R_8$, or $COOR_9$;
- $R_3$ of PTM-Va or PTM-Vb, at each occurrence, is independently selected from hydrogen, carboxy, cyano, hydroxy, hydroxyalkyl, alkyl, aryl, heteroaryl, —$SO_2R_7$ or oxo;

$R_4$ of PTM-Va or PTM-Vb at each occurrence is independently selected from hydrogen, halogen, alkyl, aryl, heterocycloalkyl, heterocycloalkylalkyl, heteroaryl, $Y_1$-arylalkyl or —$Y_1$-cycloalkyl; wherein cycloalkyl, aryl, heterocycloalkyl, heterocycloalkylalkyl, heteroaryl and arylalkyl can be optionally substituted with hydroxy, alkyl, haloalkyl, cyano or halo;

$Y_1$ of PTM-Va or PTM-Vb is selected from direct bond, O, —C(O)— or $NR^9$;

$R_5$ and $R_6$ of PTM-Va or PTM-Vb are independently selected from hydrogen, hydroxyalkyl, aminoalkyl, acyl, optionally substituted alkyl, optionally substituted heterocyclyl, optionally substituted aryl; wherein the optional substituent, in each occurrence, is independently selected from halo, haloalkyl or —$COOR^9$;

$R_7$ and $R_8$ of PTM-Va or PTM-Vb are independently hydrogen, alkyl, acyl, heterocyclyl, —$COR^9$ or —$COOR^9$;

$R_9$ of PTM-Va or PTM-Vb at each occurrence is independently selected from hydrogen or alkyl;

"m", "n" and "q" of PTM-Va or PTM-Vb are independently selected from 0, 1, 2, or 3; and "p" of PTM-Va or PTM-Vb is 0 or 1.

In any aspect or embodiment described herein, Ring Z of PTM-Va or PTM-Vb is pyridine or phenyl.

In any aspect or embodiment described herein, $R_1$ of PTM-Va or PTM-Vb is optionally substituted heteroaryl (for example pyrazole, pyridine, pyrimidine, quinoline, indazole or 7-azaindole).

In any aspect or embodiment described herein, $R_4$ of PTM-Va or PTM-Vb is hydrogen, alkyl (for example $C_{1-4}$ alkyl), heterocycloalkyl (for example piperidine, pyrrolidine or morpholine), heterocycloalkylalkyl (for example pyrrolidin-1-ylmethyl), $Y_1$-cycloalkyl (for example $Y_1$ is a bond, NH or $NCH_3$ and cycloalkyl is cyclopropyl), aryl (for example phenyl) or heteroaryl (for example pyridine).

In any aspect or embodiment described herein, the PTM of PTM-V is selected from (PTM-$V_A$-1) N-(2-morpholino-5-(piperidin-1-yl)benzo[d]oxazol-6-yl)-6-(1H-pyrazol-5-yl) picolinamide; (PTM-$V_A$-2) N-(2-morpholino-5-phenylbenzo[d]oxazol-6-yl)-6-(1H-pyrrolo[2,3-b]pyridin-5-yl) picolinamide; (PTM-$V_A$-3) 6'-amino-N-(2-morpholino-5-phenylbenzo[d]oxazol-6-yl)-[2,3'-bipyridine]-6-carboxamide; (PTM-$V_A$-4) N-(2-morpholino-5-(piperidin-1-yl)benzo[d]oxazol-6-yl)-6-(1H-pyrazol-4-yl) picolinamide; (PTM-$V_A$-5) N-(2-morpholino-5-(pyrrolidin-1-yl)benzo[d]oxazol-6-yl)-6-(1H-pyrrolo[2,3-b]pyridin-5-yl)picolinamide; (PTM-$V_A$-6) 6'-amino-N-(5-(cyclopropylamino)-2-morpholinobenzo[d]oxazol-6-yl)-[2,3'-bipyridine]-6-carboxamide; (PTM-$V_A$-7) 6'-amino-N-(5-(4-hydroxypiperidin-1-yl)-2-morpholinobenzo[d]oxazol-6-yl)-[2,3'-bipyridine]-6-carboxamide; (PTM-VA-8) 6'-amino-N-(5-(3-hydroxypyrrolidin-1-yl)-2-morpholinobenzo [d]oxazol-6-yl)-[2,3'-bipyridine]-6-carboxamide; (PTM-$V_A$-9) 6'-amino-N-(5-(benzyloxy)-2-morpholinobenzo[d]oxazol-6-yl)-[2,3'-bipyridine]-6-carboxamide; (PTM-$V_A$-10) N-(5-(4-hydroxypiperidin-1-yl)-2-morpholinobenzo[d]oxazol-6-yl)-6-(1H-pyrazol-5-yl)picolinamide; (PTM-VA-11) N-(5-(3-hydroxypyrrolidin-1-yl)-2-morpholinobenzo[d]oxazol-6-yl)-6-(1H-pyrazol-5-yl) picolinamide; (PTM-$V_A$-12) N-(5-(benzyloxy)-2-morpholinobenzo[d]oxazol-6-yl)-6-(1H-pyrazol-5-yl) picolinamide; (PTM-$V_A$-13) 6'-amino-N-(2-morpholino-5-(piperidin-1-yl)benzo[d]thiazol-6-yl)-[2,3'-bipyridine]-6-carboxamide; (PTM-$V_A$-14) N-(2-morpholino-5-(piperidin-1-yl)benzo[d]thiazol-6-yl)-6-(1H-pyrazol-5-yl) picolinamide; (PTM-VA-15) 6'-amino-N-(2-morpholino-5-(piperidin-1-yl)benzo[d]oxazol-6-yl)-[2,3'-bipyridine]-6-carboxamide; (PTM-VA-16) 6'-amino-N-(5-(2-hydroxyphenyl)-2-morpholinobenzo[d]oxazol-6-yl)-[2,3'-bipyridine]-6-carboxamide; (PTM-$V_A$-17) N-(5-cyclopropyl-2-morpholinobenzo[d]oxazol-6-yl)-6-(1H-pyrazol-5-yl)picolinamide; (PTM-$V_A$-18) 5-bromo-N-(2-morpholino-5-(piperidin-1-yl)benzo[d]oxazol-6-yl)-1H-pyrrolo[2,3-b]pyridine-1-carboxamide; (PTM-VA-19) N-(2-morpholino-5-(piperidin-1-yl)benzo[d]oxazol-6-yl)-6-(1H-pyrrolo[2,3-b]pyridin-5-yl)picolinamide; (PTM-VA-20) N-(7-methyl-2-morpholinobenzo[d]oxazol-6-yl)-6-(1H-pyrrolo[2,3-b]pyridin-5-yl)picolinamide; (PTM-$V_A$-21) N-(7-methyl-2-morpholinobenzo[d]oxazol-6-yl)-[2,4'-bipyridine]-6-carboxamide; (PTM-$V_A$-22) N-(7-isobutyl-2-morpholinobenzo[d]oxazol-6-yl)-[2,4'-bipyridine]-6-carboxamide; (PTM-VA-23) N-(7-isobutyl-2-morpholinobenzo [d]oxazol-6-yl)-6-(1H-pyrrolo[2,3-b]pyridin-5-yl) picolinamide; (PTM-$V_A$-24) N-(2-morpholino-4-phenylbenzo[d]oxazol-6-yl)-6-(1H-pyrrolo[2,3-b]pyridin-5-yl)picolinamide; (PTM-$V_A$-25) 6'-amino-N-(2-morpholino-4-phenylbenzo[d]oxazol-6-yl)-[2,3'-bipyridine]-6-carboxamide; (PTM-$V_A$-26) N-(2-morpholino-4-(pyridin-4-yl)benzo[d]oxazol-6-yl)-[2,4'-bipyridine]-6-carboxamide; (PTM-$V_A$-27) 6'-amino-N-(2-morpholino-4-(pyridin-4-yl)benzo[d]oxazol-6-yl)-[2,3'-bipyridine]-6-carboxamide; (PTM-$V_A$-28) N-(2, -dimorpholinobenzo[d]thiazol-6-yl)-6-(1H-pyrrolo[2,3-b] pyridin-5-yl)picolinamide; (PTM-VA-29) 6'-amino-N-(5-cyclopropyl-2-morpholinobenzo[d]thiazol-6-yl)-[2,3'-bipyridine]-6-carboxamide; (PTM-VA-30) N-(5-cyclopropyl-2-morpholinobenzo[d]thiazol-6-yl)-6-(1H-pyrazol-5-yl) picolinamide; (PTM-$V_A$-31) N-(5-(cyclopropyl(methyl) amino)-2-morpholinobenzo[d]thiazol-6-yl)-6-(1H-pyrazol-5-yl)picolinamide; (PTM-$V_A$-32) 6'-amino-N-(5-isobutyl-2-morpholinobenzo[d]thiazol-6-yl)-[2,3'-bipyridine]-6-carboxamide; (PTM-$V_A$-33) 6'-amino-N-(2-morpholino-5-(pyrrolidin-1-ylmethyl)benzo[d]thiazol-6-yl)-[2,3'-bipyridine]-6-carboxamide; (PTM-$V_A$-34) tert-butyl (1-(6-((2-morpholinobenzo[d]oxazol-6-yl)carbamoyl)pyridin-2-yl)pyrrolidin-3-yl)carbamate; (PTM-$V_A$-35)$_6$-(3-aminopyrrolidin-1-yl)-N-(2-morpholinobenzo[d]oxazol-6-yl)picolinamide; (PTM-$V_A$-36) 2'-fluoro-N-(2-morpholinobenzo[d]oxazol-6-yl)-[2,4'-bipyridine]-6-carboxamide; (PTM-$V_A$-37) N-(2-morpholinobenzo[d] oxazol-6-yl)-[2,3'-bipyridine]-6-carboxamide; (PTM-$V_A$-38) N-(2-morpholinobenzo[d]oxazol-6-yl)-6-(pyrimidin-5-yl)picolinamide; (PTM-$V_A$-39) N-(2-morpholinobenzo[d] oxazol-6-yl)-[2,4'-bipyridine]-6-carboxamide; (PTM-$V_A$-40) 6-(2-aminopyrimidin-5-yl)-N-(2-morpholinobenzo[d] oxazol-6-yl)picolinamide; (PTM-$V_A$-41) 6'-amino-N-(2-morpholinobenzo[d]oxazol-6-yl)-[2,3'-bipyridine]-6-carboxamide; (PTM-$V_A$-42) 6'-acetamido-N-(2-morpholinobenzo[d]oxazol-6-yl)-[2,3'-bipyridine]-6-carboxamide; (PTM-$V_A$-43) 6-(1-indazol-5-yl)-N-(2-morpholinobenzo[d]oxazol-6-yl)picolinamide; (PTM-$V_A$-44) N-(2-morpholinobenzo[d]oxazol-6-yl)-6-(quinolin-6-yl)picolinamide; (PTM-$V_A$-45) N-(2-morpholinobenzo[d] oxazol-6-yl)-6-(1H-pyrrolo[2,3-b]pyridin-5-y picolinamide; (PTM-$V_A$-46) N-(2-moφpholinobenzo[d]oxazol-6-yl)-6-(1H-pyrazol-5-yl)picolinamide; (PTM-$V_A$-47) N-(5-chloro-2-morpholinobenzo[d]oxazol-6-yl)-6-(1-pyrrolo[2,3-b]pyridin-5-yl)picolinamide; (PTM-$V_A$-48) 6'-amino-N-(2-morpholino-1H-benzo[d]imidazol-6-yl)-[2,3'-bipyridine]-6-carboxamide; (PTM-$V_A$-49) 6'-amino-N-(2-morpholinobenzo[d]thiazol-6-yl)-[2,3'-bipyridine]-6-carboxamide; (PTM-$V_A$-50) tert-butyl 4-((6-((2-morpholinobenzo[d]oxazol-6-yl)carbamoyl)pyridin-2-yl)

amino)piperidine-1-carboxylate; (PTM-$V_A$-51) tert-butyl 3-((6-((2-moφpholinobenzo[d]oxazol-6-yl)carbamoyl)pyridin-2-yl) amino)pyrrolidine-1-carboxylate; (PTM-$V_A$-52) N-(2-morpholinobenzo[d]oxazol-6-yl)-6-((3-(trifluoromethyl)phenyl)amino)picolinamide; (PTM-$V_A$-53) 6-((2-aminoethyl)amino)-N-(2-moφpholinobenzo[d]oxazol-6-yl)picolinamide; (PTM-$V_A$-54) 6-((2-hydroxyethyl)amino)-N-(2-moφpholinobenzo[d]o azol-6-yl)picolinamide; (PTM-$V_A$-55) 6-((2-aminoethyl)amino)-N-(2-rrlOφpholinobenzo[d]thiazol-6-yl)picolinamide; (PTM-$V_A$-56) 6-((2-hydroxyethyl)amino)-N-(2-moφholinobenzo[d]thiazol-6-yl)picolinamide; (PTM-$V_A$-57) N-(2-moφpholinobenzo[d]oxazol-6-yl)-3-nitrobenzamide; and (PTM-$V_A$-58) N-(2-(2,6-dimethylrno holino)benzo[d]oxazol-6-yl)-[2,4'-bipyridine]-6-carboxamide.

In any aspect or embodiment described herein, the PTM of PTM-Va or PTM-Vb may comprise at least one of:

$X_1$ and $X_3$ of PTM-Va or PTM-Vb independently are CH or N; X2 of PTM-V is $CR^2$ or N; provided one and not more than one of $X_1$, $X_2$ or $X_3$ is N;

Y of PTM-Va or PTM-Vb is —$CH_2$— or O;

Ring Z of PTM-Va or PTM-Vb is aryl or heterocyclyl;

A of PTM-Va or PTM-Vb is O or S;

$R_1$ of PTM-Va or PTM-Vb, at each occurrence, is independently halo or optionally substituted heterocyclyl, wherein the substituent, in each occurrence, is independently selected from alkyl, alkoxy, aminoalkyl, halo, hydroxyl, hydroxyalkyl or —$NR^7R^8$;

$R_2$ of PTM-Va or PTM-Vb is hydrogen, optionally substituted cycloalkyl, optionally substituted aryl, optionally substituted heterocyclyl or —$NR^5R^6$; wherein the substituent is alkyl, amino, halo or hydroxyl;

$R^3$, of PTM-Va or PTM-Vb at each occurrence, is independently selected from alkyl or hydroxyl;

$R_4$ of PTM-Va or PTM-Vb at each occurrence is independently selected from hydrogen, halogen, alkyl, aryl, heterocycloalkyl, heterocycloalkylalkyl, heteroaryl, Y-arylalkyl or —Y-cycloalkyl; wherein cycloalkyl, aryl, heterocycloalkyl, heterocycloalkylalkyl, heteroaryl and arylalkyl can be optionally substituted with hydroxy, alkyl, haloalkyl, cyano or halo;

$Y_1$ of PTM-Va or PTM-Vb is selected from direct bond, O, —C(O)— or $NR^9$;

$R_5$ and $R_6$ of PTM-Va or PTM-Vb are independently selected from hydrogen, optionally substituted alkyl, optionally substituted acyl, or optionally substituted heterocyclyl, optionally substituted aryl;

$R^9$ of PTM-Va or PTM-Vb at each occurrence is independently selected from hydrogen or alkyl;

"m" and "n" of PTM-Va or PTM-Vb are independently selected from 0, 1, or 2; and

"q" of PTM-Va or PTM-Vb is 0; and

"p" of PTM-Va or PTM-Vb is 0 or 1.

In any aspect or embodiment described herein, the group

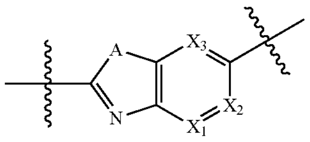

of PTM-V is

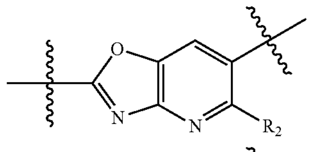

,

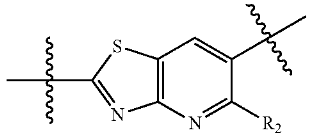

,

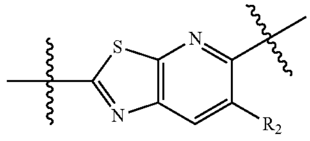

,

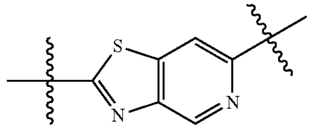

or

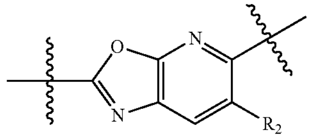

;

wherein $R_2$ is as defined in Formula PTM-Va.

In any aspect or embodiment described herein, the Ring Z of PTM-Va or PTM-Vb is aryl or 5- or 6-membered heterocyclyl. In any aspect or embodiment described herein, Ring Z of PTM-V is phenyl, furanyl, thienyl, pyrrolyl, pyrazolyl, imidazolyl, oxazolyl, isoxazolyl, thiazolyl, isothiazolyl, 1H-tetrazolyl, oxadiazolyl, triazolyl, pyridyl, pyrimidinyl, pyrazinyl, pyridazinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl or dihydropyranyl; wherein each of which is optionally substituted with alkyl, alkoxy, halo, hydroxyl, hydroxyalkyl or —$NR^5R^6$; $R^5$ and $R^6$ are independently hydrogen, alkyl or acyl.

In any aspect or embodiment described herein, the Ring Z of PTM-Va or PTM-Vb is phenyl, oxazolyl, furanyl, thienyl or pyridyl; each of which is optionally substituted with one or more $R_1$.

In any aspect or embodiment described herein, the

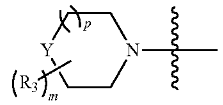

of PTM-Va is

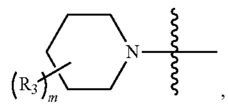

,

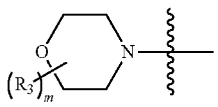

or

-continued

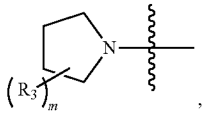

, wherein $R_3$ and "m" are as defined for PTM-Va.

In any aspect or embodiment described herein, the

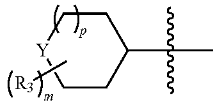

of PTM-Vb is

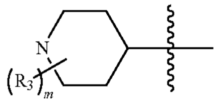 or 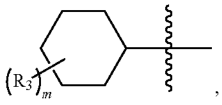 , wherein $R_3$ and "m" are as defined for PTM-Vb.

In any aspect or embodiment described herein, the PTM of PTM-Va is selected from: (PTM-$V_B$-1) 6'-amino-N-(2-morpholinooxazolo[4,5-b]pyridin-6-yl)-[2,3'-bipyridine]-6-carboxamide; (PTM-$V_B$-2) 6'-amino-N-(5-cyclopropyl-2-morpholinooxazolo[4,5-b]pyridin-6-yl)-[2,3'-bipyridine]-6-carboxamide hydrochloride; (PTM-$V_B$-3) N-(5-cyclopropyl-2-morpholinooxazolo[4,5-b]pyridin-6-yl)-2-(2-methylpyridin-4-yl)oxazole-4-carboxamide hydrochloride; (PTM-$V_B$-4) N-(2,5-di(piperidin-1-yl)oxazolo[4,5-b]pyridin-6-yl)-6-(1H-pyrazol-4-yl)picolinamide hydrochloride; (PTM-$V_B$-5) N-(2,5-di(piperidin-1-yl)oxazolo[4,5-b]pyridin-6-yl)-2-(2-methylpyridin-4-yl)oxazole-4-carboxamide; (PTM-$V_B$-6) N-(2-morpholino-5-(piperidin-1-yl)oxazolo[4,5-b]pyridin-6-yl)-6-(1H-pyrazol-4-yl) picolinamide; (PTM-$V_B$-7) 2-(2-methylpyridin-4-yl)-N-(2-morpholino-5-(piperidin-1-yl)oxazolo[4,5-b]pyridin-6-yl) oxazole-4-carboxamide; (PTM-$V_B$-8) 6-chloro-N-(2-morpholino-5-(piperidin-1-yl)oxazolo[4,5-b]pyridin-6-yl) picolinamide; (PTM-$V_B$-9) N-(2,5-di(piperidin-1-ypoxazolo[4,5-b]pyridin-6-yl)-6-(1-methyl-1H-pyrazol-4-yl)picolinamide; (PTM-$V_B$-10) 2-(2-chloropyridin-4-yl)-N-(2,5-di(piperidin-1-yl)oxazolo[4,5-b]pyridin-6-yl)oxazole-4-carboxamide; (PTM-$V_B$-11) (S)-2-(2-methylpyridin-4-yl)-N-(2-morpholino-5-(pyrrolidin-3-ylamino)oxazolo[4,5-b]pyridin-6-yl)oxazole-4-carboxamide; (PTM-$V_B$-12) 6'-amino-N-(2-morpholinooxazolo[5,4-b]pyridin-5-yl)-[2,31-bipyridine]-6-carboxamide; (PTM-$V_B$-13) 6'-amino-N-(2-morpholinothiazolo[4,5-c]pyridin-6-yl)-[2,3'-bipyridine]-6-carboxamide; (PTM-$V_B$-14) 6'-amino-N-(2-morpholinothiazolo[5,4-b]pyridin-5-yl)-[2,3'-bipyridine]-6-carboxamide; (PTM-$V_B$-15) 2-(2-methylpyridin-4-yl)-N-(2-morpholinothiazolo[4,5-b]pyridin-6-yl)oxazole-4-carboxamide; (PTM-$V_B$-16) 6'-amino-N-(2-morpholinothiazolo[4,5-b]pyridin-6-yl)-[2,3'-bipyridine]-6-carboxamide; (PTM-$V_B$-17) N-(2-morpholinothiazolo[4,5-b]pyridin-6-yl)-6-(1H-pyrazol-4-yl)picolinamide; (PTM-$V_B$-18) 3-(4-(aminomethyl)piperidin-1-yl)-5-fluoro-N-(2-morpholinothiazolo[4,5-b]pyridin-6-yl)benzamide; (PTM-$V_B$-19) 2-(4-(aminomethyl)piperidin-1-yl)-5-fluoro-N-(2-morpholinothiazolo[4,5-b]pyridin-6-yl)benzamide; (PTM-$V_B$-20) 2-(2-methylpyridin-4-yl)-N-(2-morpholino-5-(piperidin-1-yl)thiazolo[4,5-b]pyridin-6-yl)oxazole-4-carboxamide; (PTM-$V_B$-21) N-(2-morpholino-5-(piperidin-1-yl)thiazolo[4,5-b]pyridin-6-yl)-6-(1H-pyrazol-4-yl)picolinamide; (PTM-$V_B$-22) N-(2,5-di(piperidin-1-yl)thiazolo [4,5-b]pyridin-6-yl)-6-(1H-pyrazol-4-yl)picolinamide; (PTM-$V_B$-23) N-(2,5-di(piperidin-1-yl)thiazolo[4,5-b]pyridin-6-yl)-2-(2-methylpyridin-4-yl)oxazole-4-carboxamide; (PTM-$V_B$-24) N-(2,5-dimorpholinooxazolo[4,5-b]pyridin-6-yl)-2-(2-methylpyridin-4-yl)oxazole-4-carboxamide; (PTM-$V_B$-25) N-(5-(4-methylpiperazin-1-yl)-2-morpholinooxazolo[4,5-b]pyridin-6-yl)-2-(2-methylpyridin-4-yl) oxazole-4-carboxamide; (PTM-$V_B$-26) N-(2,5-di(piperidin-1-yl)oxazolo[4,5-b]pyridin-6-yl)-2-(6-methoxypyridin-3-yl)oxazole-4-carboxamide; (PTM-$V_B$-27) N-(2,5-di (piperidin-1-ypoxazolo[4,5-b]pyridin-6-yl)-2-(2-methylpyridin-3-yl)oxazole-4-carboxamide; (PTM-$V_B$-28) N-(2,5-di(piperidin-1-yl)oxazolo[4,5-b]pyridin-6-yl)-2-(2-hydroxypyridin-3-yl)oxazole-4-carboxamide; (PTM-$V_B$-29) 2-(2-hydroxypyridin-3-yl)-N-(2-morpholino-5-(piperidin-1-yl)oxazolo [4,5-b]pyridin-6-yl)oxazole-4-carboxamide; (PTM-$V_B$-30) N-(2,5-di(piperidin-1-yl)oxazolo[4,5-b]pyridin-6-yl)-2-(6-hydroxypyridin-3-yl)oxazole-4-carboxamide; (PTM-$V_B$-31) 2-(2-methoxypyridin-4-yl)-N-(2-morpholino-5-(piperidin-1-yl)oxazolo[4,5-b]pyridin-6-yl) oxazole-4-carboxamide; (PTM-$V_B$-32) 2-(2-methylpyridin-3-yl)-N-(2-morpholino-5-(piperidin-1-yl)oxazolo [4,5-b] pyridin-6-yl)oxazole-4-carboxamide; (PTM-$V_B$-33) 2-(3-methylpyridin-4-yl)-N-(2-morpholino-5-(piperidin-1-yl) oxazolo [4,5-b]pyridin-6-yl)oxazole-4-carboxamide; (PTM-$V_B$-34) N-(2,5-di(piperidin-1-ypoxazolo[4,5-b]pyridin-6-yl)-2-(3-methylpyridin-4-yl)oxazole-4-carboxamide; (PTM-$V_B$-35) 2-(6-methylpyridin-3-yl)-N-(2-morpholino-5-(piperidin-1-yl)oxazolo [4,5-b]pyridin-6-yl)oxazole-4-carboxamide; (PTM-$V_B$-36) 6-(1-methyl-1H-pyrazol-4-yl)-N-(2-morpholino-5-(piperidin-1-yl)oxazolo [4,5-b]pyridin-6-yl)picolinamide; (PTM-$V_B$-37) N-(2,5-di(piperidin-1-ypoxazolo[4,5-b]pyridin-6-yl)-2-(6-methylpyridin-3-yl) oxazole-4-carboxamide; (PTM-$V_B$-38) (S)—N-(5-(3-aminopyrrolidin-1-yl)-2-morpholinooxazolo[4,5-b]pyridin-6-yl)-2-(2-methylpyridin-4-yl)oxazole-4-carboxamide; (PTM-$V_B$-39) (S)—N-(5-(3-hydroxypyrrolidin-1-yl)-2-morpholinooxazolo [4,5-b]pyridin-6-yl)-2-(2-methylpyridin-4-yl)oxazole-4-carboxamide; (PTM-$V_B$-40) (R)—N-(5-(3-aminopyrrolidin-1-yl)-2-morpholinooxazolo[4,5-b] pyridin-6-yl)-2-(2-methylpyridin-4-yl)oxazole-4-carboxamide; (PTM-$V_B$-41) (R)—N-(5-(3-hydroxypyrrolidin-1-yl)-2-morpholinooxazolo[4,5-b] pyridin-6-yl)-2-(2-methylpyridin-4-yl)oxazole-4-carboxamide; (PTM-$V_B$-42) (S)-2-(3-aminopyrrolidin-1-yl)-N-(2-morpholino-5-(piperidin-1-yl)oxazolo[4,5-b] pyridin-6-yl)oxazole-4-carboxamide; (PTM-$V_B$-43) (S)-6-(3-hydroxypyrrolidin-1-yl)-N-(2-morpholino-5-(piperidin-1-yl)oxazolo[4,5-b]pyridin-6-yl)picolinamide; (PTM-$V_B$-44) (S)-6-(3-aminopyrrolidin-1-yl)-N-(2-morpholino-5-(piperidin-1-yl)oxazolo[4,5-b]pyridin-6-yl)picolinamide; (PTM-$V_B$-45) (S)-2-(3-hydroxypyrrolidin-1-yl)-N-(2-morpholino-5-(piperidin-1-yl)oxazolo[4,5-b]pyridin-6-yl)oxazole-4-carboxamide; (PTM-$V_B$-46) (5)-N-(5-cyclopropyl-2-morpholinooxazolo[4,5-b]pyridin-6-yl)-2-(3-hydroxypyrrolidin-1-yl)oxazole-4-carboxamide; (PTM-$V_B$-47) (S)-2-(3-aminopyrrolidin-1-yl)-N-(5-cyclopropyl-2-morpholinooxazolo[4,5-b]pyridin-6-yl)oxazole-4-carboxamide; (PTM-$V_B$-48) 2-(2-methylpyridin-4-yl)-N-(5-(piperidin-1-yl)-2-(pyrrolidin-1-yl)oxazolo[4,5-b]pyridin-6-yl)oxazole-4-carboxamide hydrochloride; (PTM-$V_B$-49) N-(2-(2,6-dimethylmorpholino)-5-(piperidin-1-yl)oxazolo [4,5-b]pyridin-6-yl)-2-(2-methylpyridin-4-yl)oxazole-4-carboxamide hydrochloride; (PTM-$V_B$-50) N-(2,5-di(piperidin-1-ypthiazolo[4,5-b]pyridin-6-yl)-6-(1-methyl-1H-pyrazol-4-yl)picolinamide hydrochloride; (PTM-$V_B$-51) 6-(1-methyl-H-pyrazol-4-yl)-N-(2-morpholino-5-(piperidin-1-yl)thiazolo [4,5-b]pyridin-6-yl)picolinamide; (PTM-$V_B$-52) N-(2,5-di(piperidin-1-yl)thiazolo[4,5-b]pyridin-6-yl)-2-(2-methylpyridin-3-yl)oxazole-4-carboxamide hydrochloride; (PTM-$V_B$-53) N-(2-((2S,6R)-2,6-dimethylmorpholino)-5-(piperidin-1-yl)thiazolo[4,5-b]pyridin-6-yl)-2-(2-methylpyridin-4-yl)oxazole-4-carboxamide; (PTM-$V_B$-54) 2-(2-methylpyridin-3-yl)-N-(2-morpholino-5-(piperidin-1-yl)thiazolo[4,5-b]pyridin-6-yl)oxazole-4-carboxamide; (PTM-$V_B$-55) 2-(2-hydroxypyridin-3-yl)-N-(2-morpholino-5-(piperidin-1-yl)thiazolo[4,5-b]pyridin-6-yl)oxazole-4-carboxamide; (PTM-$V_B$-56) N-(2,5-di (piperidin-1-yl)thiazolo[4,5-b]pyridin-6-yl)-2-(2-methoxypyridin-4-yl)oxazole-4-carboxamide; (PTM-$V_B$-57) 2-(6-methoxypyridin-3-yl)-N-(2-morpholino-5-(piperidin-1-yl)thiazolo[4,5-b]pyridin-6-yl)oxazole-4-carboxamide; (PTM-$V_B$-58) 2-(2-methoxypyridin-4-yl)-N-(2-morpholino-5-(piperidin-1-yl)thiazolo[4,5-b]pyridin-6-yl)oxazole-4-carboxamide; (PTM-$V_B$-59) (S)—N-(5-(3-fluoropiperidin-1-yl)-2-morpholinothiazolo[4,5-b]pyridin-6-yl)-2-(2-methylpyridin-4-yl)oxazole-4-carboxamide; (PTM-$V_B$-60) 2-(6-methylpyridin-3-yl)-N-(2-morpholino-5-(piperidin-1-yl)thiazolo[4,5-b]pyridin-6-yl)oxazole-4-carboxamide; (PTM-$V_B$-61) 2-(3-methylpyridin-4-yl)-N-(2-morpholino-5-(piperidin-1-yl)thiazolo[4,5-b]pyridin-6-yl) oxazole-4-carboxamide; (PTM-$V_B$-62) (S)-6-(3-aminopyrrolidin-1-yl)-N-(2-morpholino-5-(piperidin-1-yl) thiazolo[4,5-b]pyridin-6-yl)picolinamide; (PTM-$V_B$-63) (S)-6-(3-hydroxypyrrolidin-1-yl)-N-(2-morpholino-5-(piperidin-1-yl)thiazolo[4,5-b]pyridin-6-yl)picolinamide; (PTM-$V_B$-64) (S)-6-(3-aminopyrrolidin-1-yl)-N-(2,5-di(piperidin-1-yl)thiazolo[4,5-b]pyridin-6-yl)picolinamide; (PTM-$V_B$-65) (S)—N-(2,5-di(piperidin-1-yl)thiazolo[4,5-b]pyridin-6-yl)-6-(3-hydroxypyrrolidin-1-yl)picolinamide; (PTM-$V_B$-66) (S)-2-(3-aminopyrrolidin-1-yl)-N-(2-morpholino-5-(piperidin-1-yl)thiazolo[4,5-b]pyridin-6-yl)oxazole-4-carboxamide; (PTM-$V_B$-67) (S)—N-(5-(3-aminopyrrolidin-1-yl)-2-morpholinothiazolo[4,5-b]pyridin-6-yl)-2-(2-methylpyridin-4-yl)oxazole-4-carboxamide; (PTM-$V_B$-68) (S)-2-(3-aminopyrrolidin-1-yl)-N-(5-cyclopropyl-2-morpholinothiazolo[4,5-b]pyridin-6-yl)oxazole-4-carboxamide; (PTM-$V_B$-69) N-(5-cyclopropyl-2-morpholinothiazolo[4,5-b]pyridin-6-yl)-2-(2-methylpyridin-4-yl)oxazole-4-carboxamide; (PTM-$V_B$-70) (S)-2-(3-hydroxypyrrolidin-1-yl)-N-(2-morpholino-5-(piperidin-1-yl)thiazolo[4,5-b]pyridin-6-yl)oxazole-4-carboxamide; (PTM-$V_B$-71) (S)—N-(5-(3-hydroxypyrrolidin-1-yl)-2-morpholinothiazolo[4,5-b]pyridin-6-yl)-2-(2-methylpyridin-4-yl)oxazole-4-carboxamide; (PTM-$V_B$-72) (5)-N-(5-cyclopropyl-2-morpholinothiazolo[4,5-b]pyridin-6-yl)-6-(3-hydroxypyrrolidin-1-yl)picolinamide; (PTM-$V_B$-73) (S)—N-(5-cyclopropyl-2-morpholinothiazolo[4,5-b]pyridin-6-yl)-2-(3-hydroxypyrrolidin-1-yl)oxazole-4-carboxamide; (PTM-$V_B$-74) (S)—N-(5-cyclopropyl-2-morpholinothiazolo[4,5-b]pyridin-6-yl)-6-(1-(2-hydroxypropyl)-1H-pyrazol-4-yl)picolinamide; (PTM-$V_B$-75) (S)—N-(5-cyclopropyl-2-morpholinothiazolo[4,5-b]pyridin-6-yl)-2-(1-(2-hydroxypropyl)-1H-pyrazol-4-yl) oxazole-4-carboxamide; (PTM-$V_B$-76) N-(5-(3-hydroxypyrrolidin-1-yl)-2-morpholinothiazolo[4,5-b]pyridin-6-yl)-2-(6-methoxypyridin-3-yl)oxazole-4-carboxamide; (PTM-$V_B$-77) (S)—N-(5-(3-hydroxypyrrolidin-1-yl)-2-morpholinothiazolo[4,5-b]pyridin-6-yl)-2-(6-methoxypyridin-3-yl)oxazole-4-carboxamide; (PTM-$V_B$-78) (R)—N-(5-(3-hydroxypyrrolidin-1-yl)-2-morpholinothiazolo[4,5-b]pyridin-6-yl)-2-(6-methoxypyridin-3-yl)oxazole-4-carboxamide; (PTM-$V_B$-79) (S)—N-(5-(azetidin-1-yl)-2-morpholinothiazolo[4,5-b]pyridin-6-yl)-6-(3-hydroxypyrrolidin-1-yl)picolinamide; (PTM-$V_B$-80) N-(5-(3-hydroxyazetidin-1-yl)-2-morpholinothiazolo[4,5-b]pyridin-6-yl)-2-(2-methylpyridin-4-yl)oxazole-4-carboxamide; (PTM-$V_B$-81) (S)—N-(5-(3-hydroxypyrrolidin-1-yl)-2-morpholinothiazolo[4,5-b]pyridin-6-yl)-5-(2-methylpyridin-4-yl)thiophene-2-carboxamide; (PTM-$V_B$-82) (S)—N-(5-(3-hydroxypyrrolidin-1-yl)-2-morpholinothiazolo[4,5-b]pyridin-6-yl)-5-(2-methylpyridin-4-yl)furan-2-carboxamide; (PTM-$V_B$-83) (S)—N-(5-(3-hydroxypiperidin-1-yl)-2-morpholinothiazolo[4,5-b]pyridin-6-yl)-2-(2-methylpyridin-4-yl)oxazole-4-carboxamide; (PTM-$V_B$-84) N-(5-(4-hydroxypiperidin-1-yl)-2-morpholinothiazolo[4,5-b]pyridin-6-yl)-2-(2-methylpyridin-4-yl)oxazole-4-carboxamide; (PTM-$V_B$-85) (R)—N-(5-(3-hydroxypyrrolidin-1-yl)-2-morpholinothiazolo[4,5-b]pyridin-6-yl)-2-(2-methylpyridin-4-yl)oxazole-4-carboxamide; (PTM-$V_B$-86) N-(5-(4-hydroxypiperidin-1-yl)-2-morpholinothiazolo[4,5-b]pyridin-6-yl)-5-(2-methylpyridin-4-yl)furan-2-carboxamide; (PTM-$V_B$-87) N-(5-(azetidin-1-yl)-2-(piperidin-1-yl)thiazolo[4,5-b]pyridin-6-yl)-2-(2-methylpyridin-4-yl)oxazole-4-carboxamide; (PTM-$V_B$-88) 2-(2-methylpyridin-4-yl)-N-(2-(piperidin-1-yl)-5-(pyrrolidin-1-yl)thiazolo[4,5-b]pyridin-6-yl)oxazole-4-carboxamide; (PTM-$V_B$-89) 2-(2-methylpyridin-4-yl)-N-(2-morpholino-5-(pyrrolidin-1-yl)thiazolo[4,5-b]pyridin-6-yl)oxazole-4-carboxamide; (PTM-$V_B$-90) 5-(2-methylpyridin-4-yl)-N-(2-morpholino-5-(piperidin-1-yl) thiazolo[4,5-b]pyridin-6-yl)furan-2-carboxamide; (PTM-$V_B$-91) N-(5-(azepan-1-yl)-2-morpholinothiazolo[4,5-b]pyridin-6-yl)-2-(2-methylpyridin-4-yl)oxazole-4-carboxamide; (PTM-$V_B$-92) 2-(2-aminopyridin-4-yl)-N-(2-morpholino-5-(piperidin-1-yl)thiazolo[4,5-b]pyridin-6-yl) oxazole-4-carboxamide hydrochloride; (PTM-$V_B$-93) N-(5-(azetidin-1-yl)-2-morpholinothiazolo[4,5-b]pyridin-6-yl)-2-(2-methylpyridin-4-yl)oxazole-4-carboxamide; (PTM-$V_B$-94) (R)—N-(5-(3-hydroxypiperidin-1-yl)-2-morpholinothiazolo[4,5-b]pyridin-6-yl)-2-(2-methylpyridin-4-yl)oxazole-4-carboxamide; (PTM-$V_B$-95) (R)—N-(5-(3-hydroxypiperidin-1-yl)-2-morpholinothiazolo [4,5-b]pyridin-6-yl)-5-(2-methylpyridin-4-yl)furan-2-carboxamide; (PTM-$V_B$-96) (S)-6-(1-(2-hydroxypropyl)-1H-pyrazol-4-yl)-N-(2-morpholino-5-(piperidin-1-yl)thiazolo [4,5-b]pyridin-6-yl)picolinamide; (PTM-$V_B$-97) N-(5-(4-fluoropiperidin-1-yl)-2-morpholinothiazolo[4,5-b]pyridin-6-yl)-5-(2-methylpyridin-4-yl)furan-2-carboxamide; (PTM-$V_B$-98) N-(5-(4-fluoropiperidin-1-yl)-2-morpholinothiazolo [4,5-b]pyridin-6-yl)-2-(2-methylpyridin-4-yl)oxazole-4-carboxamide hydrochloride; (PTM-$V_B$-99) N-(5-(1-methyl-1H-pyrazol-4-yl)-2-morpholinothiazolo[4,5-b]pyridin-6-yl)-2-(2-methylpyridin-4-yl)oxazole-4-carboxamide; (PTM-$V_B$-100) N-(5-(3-fluorophenyl)-2-morpholinothiazolo[4,5-b]pyridin-6-yl)-2-(2-methylpyridin-4-yl)oxazole-4-carboxamide; (PTM-$V_B$-101) N-(5-(4-hydroxypiperidin-1-yl)-2-morpholinothiazolo[4,5-b]pyridin-6-yl)-5-(2-methylpyridin-4-yl)furan-2-carboxamide; (PTM-$V_B$-102) N-(5-(3-fluoropiperidin-1-yl)-2-morpholinothiazolo[4,5-b]pyridin-6-yl)-5-(2-methylpyridin-4-yl)furan-2-carboxamide; (PTM-$V_B$-103) (S)—N-(5-(3-hydroxypyrrolidin-1-yl)-2-morpholinooxazolo[4,5-b]pyridin-6-yl)-2-(6-methoxypyridin-3-yl)oxazole-4-carboxamide; (PTM-$V_B$-104) N-(5-(3-hydroxypyrrolidin-1-yl)-2- morpholinooxazolo[4,5-b]pyridin-6-yl)-2-(2-methylpyridin-4-yl)oxazole-4-carboxamide; (PTM-$V_B$-105) (R)—N-(5-(3-hydroxypyrrolidin-1-yl)-2-morpholinooxazolo[4,5-b]pyridin-6-yl)-2-(6-methoxypyridin-3-yl)oxazole-4-carboxamide; (PTM-$V_B$-106) N-(5-(3-hydroxypyrrolidin-1-yl)-2-morpholinooxazolo[4,5-b]pyridin-6-yl)-2-(6-methoxypyridin-3-yl)oxazole-4-carboxamide; (PTM-$V_B$-107) (S)—N-(5-(3-hydroxypyrrolidin-1-yl)-2-morpholinooxazolo[4,5-b]pyridin-6-yl)-5-(2-methylpyridin-4-yl)furan-2-carboxamide; (PTM-$V_B$-108) (S)—N-(5-(3-hydroxypyrrolidin-1-yl)-2-morpholinooxazolo[4,5-b]pyridin-6-yl)-5-(2-methylpyridin-4-yl)thiophene-2-carboxamide; (PTM-$V_B$-109) N-(5-(azetidin-1-yl)-2-(piperidin-1-yl)oxazolo[4,5-b]pyridin-6-yl)-2-(2-methylpyridin-4-yl)oxazole-4-carboxamide; (PTM-$V_B$-110) 2-(2-methylpyridin-4-yl)-N-(2-(piperidin-1-yl)-5-(pyrrolidin-1-yl)oxazolo[4,5-b]pyridin-6-yl)oxazole-4-carboxamide; (PTM-$V_B$-111) 5-(2-methylpyridin-4-yl)-N-(2-morpholino-5-(piperidin-1-yl)oxazolo[4,5-b]pyridin-6-yl)furan-2-carboxamide; (PTM-$V_B$-112) N-(5-(azetidin-1-yl)-2-morpholinooxazolo[4,5-b]pyridin-6-yl)-2-(2-methylpyridin-4-yl)oxazole-4-carboxamide; (PTM-$V_B$-113) 2-(2-methylpyridin-4-yl)-N-(2-morpholino-5-(pyrrolidin-1-yl)oxazolo[4,5-b]pyridin-6-yl)oxazole-4-carboxamide; (PTM-$V_B$-114) N-(5-(4-hydroxypiperidin-1-yl)-2-morpholinooxazolo[4,5-b]pyridin-6-yl)-5-(2-methylpyridin-4-yl)furan-2-carboxamide; (PTM-$V_B$-115) (R)—N-(5-(3-hydroxypiperidin-1-yl)-2-morpholinooxazolo[4,5-b]pyridin-6-yl)-5-(2-methylpyridin-4-yl)furan-2-carboxamide; (PTM-$V_B$-116) N-(5-(furan-3-yl)-2-morpholinooxazolo[4,5-b]pyridin-6-yl)-2-(2-methylpyridin-4-yl)oxazole-4-carboxamide; (PTM-$V_B$-117) N-(5-(3-fluoropiperidin-1-yl)-2-morpholinooxazolo[4,5-b]pyridin-6-yl)-2-(2-methylpyridin-4-yl)oxazole-4-carboxamide; (PTM-$V_B$-118) N-(5-(4-hydroxypiperidin-1-yl)-2-morpholinooxazolo[4,5-b]pyridin-6-yl)-2-(2-methylpyridin-4-yl)oxazole-4-carboxamide; (PTM-$V_B$-119) N-(5-(4-fluoropiperidin-1-yl)-2-morpholinooxazolo[4,5-b]pyridin-6-yl)-2-(2-methylpyridin-4-yl)oxazole-4-carboxamide; (PTM-$V_B$-120) (S)—N-(5-(3-aminopiperidin-1-yl)-2-morpholinothiazolo[4,5-b]pyridin-6-yl)-2-(2-methylpyridin-4-yl)oxazole-4-carboxamide; (PTM-$V_B$-121) 2-(2-methylpyridin-4-yl)-N-(2-morpholino-5-(1H-pyrazol-4-yl)thiazolo[4,5-b]pyridin-6-yl)oxazole-4-carboxamide; (PTM-$V_B$-122) N-(5-(6-fluoropyridin-3-yl)-2-morpholinothiazolo[4,5-b]pyridin-6-yl)-2-(2-methylpyridin-4-yl)oxazole-4-carboxamide; (PTM-$V_B$-123) N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide; (PTM-$V_B$-124) N-(2-(3-hydroxypiperidin-1-yl)-5-(piperidin-1-yl)thiazolo[4,5-b]pyridin-6-yl)-2-(2-methylpyridin-4-yl)oxazole-4-carboxamide; (PTM-$V_B$-125) 2-(2-acetamidopyridin-4-yl)-N-(5-(4-hydroxypiperidin-1-yl)-2-morpholinothiazolo[4,5-b]pyridin-6-yl)oxazole-4-carboxamide; (PTM-$V_B$-126) N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide; (PTM-$V_B$-127) 2-(2-acetamidopyridin-4-yl)-N-(5-(3-hydroxypiperidin-1-yl)-2-morpholinothiazolo[4,5-b]pyridin-6-yl)oxazole-4-carboxamide; (PTM-$V_B$-128) 2-(2-aminopyridin-4-yl)-N-(5-(3-hydroxypiperidin-1-yl)-2-morpholinothiazolo[4,5-b]pyridin-6-yl)oxazole-4-carboxamide hydrochloride; (PTM-$V_B$-129) 5-(2-aminopyridin-4-yl)-N-(5-(4-hydroxypiperidin-1-yl)-2-morpholinothiazolo[4,5-b]pyridin-6-yl)furan-3-carboxamide hydrochloride; (PTM-$V_B$-130) 2-(2-aminopyridin-4-yl)-N-(5-(4-hydroxypiperidin-1-yl)-2-morpholinothiazolo[4,5-b]pyridin-6-yl)oxazole-4-carboxamide hydrochloride; (PTM-$V_B$-131) 2-(2-aminopyridin-4-yl)-N-(5-(4-fluoropiperidin-1-yl)-2-morpholinothiazolo[4,5-b]pyridin-6-yl)oxazole-4-carboxamide hydrochloride; (PTM-$V_B$-132) N-(5-(2-fluoropyridin-4-yl)-2-morpholinothiazolo[4,5-b]pyridin-6-yl)-2-(2-methylpyridin-4-yl)oxazole-4-carboxamide; (PTM-$V_B$-133) N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide; (PTM-$V_B$-134) N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide hydrochloride; and (PTM-$V_B$-135) N-(5-(2-hydroxypyridin-4-yl)-2-morpholinothiazolo[4,5-b]pyridin-6-yl)-2-(2-methylpyridin-4-yl)oxazole-4-carboxamide hydrochloride.

In any aspect or embodiment described herein, the PTM is represented by Formula PTM-VI (i.e., Formula PTM-VIa, Formula PTM-VIb, and/or Formula PTM-VIc, which correspond to Formula I, II, and III, respectively, from U.S. Patent Application Publication No. 2015/0274708 A1, which is incorporated herein in its entirety for all purposes):

PTM-VIa

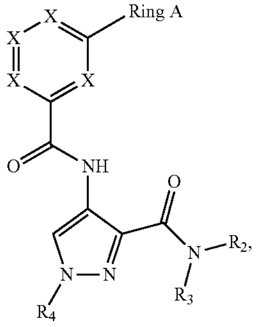

PTM-VIb

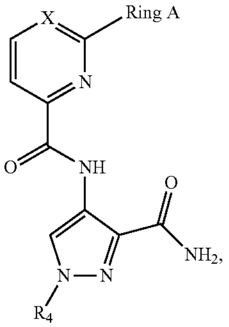

or

PTM-VIc

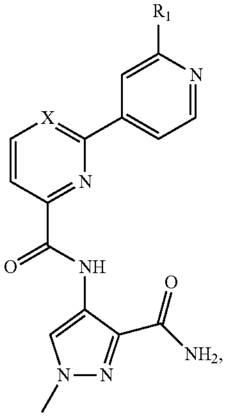

wherein:
X of PTM-VI is CH or N;
a of PTM-VI is 0 or 1;
b of PTM-VI is 0 or 1;
m of PTM-VI is 0, 1 or 2;
Ring A is of PTM-VI $(C_3-C_5)$cycloalkyl, $(C_3-C_8)$cycloalkenyl, aryl or heterocycle optionally substituted with one to three substituents independently selected from $R_1$;
$R_1$ of PTM-VI is selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$fluoroalkyl, $(C=O)_aNR_5R_6$, CN, $(C=O)_aO_b(C_3-C_8)$cycloalkyl, $S(O)_mNR_5R_6$, SH, $S(O)_m-(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;
$R_2$ and $R_3$ of PTM-VI are independently selected from: H, $(C=O)_aO_bC_1-C_{10}$ alkyl, $(C=O)_aO_b$aryl, $C_2-C_{10}$ alkenyl, $C_2-C_{10}$ alkynyl, $(C=O)_aO_b$ heterocyclyl, $CO_2H$, CN, $O_bC_1-C_6$ fluoroalkyl, $O_a(C=O)_bNR_5R_6$, CHO, $(N=O)R_5R_6$, $S(O)_mNR_5R_6$, SH, $S(O)_m-(C_1-C_{10})$alkyl, $(C=O)_aO_bC_3-C_8$ cycloalkyl, optionally substituted with one or more substituents selected from $R_1$; or $R_2$ and $R_3$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R_1$;
$R_4$ of PTM-VI is selected from: $(C_1-C_6)$alkyl and $(C_3-C_6)$cycloalkyl, optionally substituted with $R_a$;
$R_5$ and $R_6$ of PTM-VI are independently selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, $O_b(C_1-C_6)$fluoroalkyl, $(C=O)_aN(R_a)_2$, CN, $(C=O)_aO_b(C_3-C_8)$cycloalkyl, $S(O)_m N(R_a)_2$, SH, $S(O)_m-(C_1-C_{10})$alkyl and $(C=O)_aO_b$-heterocyclyl, said alkyl, aryl, alkenyl, alkynyl, cycloalkyl, and heterocyclyl are optionally substituted with one or more substituents selected from $R_a$;
$R_a$ of PTM-VI is independently selected from $R_b$, OH, $(C_1-C_6)$alkoxy, halogen, cyclopropyl, $CO_2H$, CN, $O_a(C=O)_b(C_1-C_6)$alkyl, oxo, and $N(R_b)_2$;
$R_b$ of PTM-VI is independently selected from H and $(C_1-C_6)$alkyl; and
the PTM-VI is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-VI is covalently joined to a ULM, a chemical linker group (L), a CLM, an ILM, a VLM, MLM, a ULM', a CLM', a ILM', a VLM', a MLM', or combination thereof via an R group (e.g., $R_1$, $R_2$, $R_3$, $R_4$, $R_5$, $R_6$, $R_a$, or $R_b$).

In any aspect or embodiment described herein, the PTM of PTM-VI is selected from the group consisting of: N-(3-carbamoyl-1-methyl-1H-pyrazol-4-yl)-2'-((cyclopropylmethyl)amino)-[2,4'-bipyridine]-6-carboxamide (PTM-VI-1); N-(3-carbamoyl-1-methyl-1H-pyrazol-4-yl)-6-(1H-pyrrol-1-yl)picolinamide (PTM-VI-2); 4-(3-(2-(cyclopropylmethylamino)pyridin-4-yl)benzamido)-1-methyl-1H-pyrazole-3-carboxamide (PTM-VI-3); tert-butyl(6-((3-carbamoyl-1-methyl-1H-pyrazol-4-yl)carbamoyl)-[2,4'-bipyridin-2'-yl) carbamate (PTM-VI-4); N-(3-carbamoyl-1-methyl-1H-pyrazol-4-yl)-2'-(cyclopropylmethylamino)-2,4'-bipyridine-4-carboxamide (PTM-VI-5); 2'-amino-N-(3-carbamoyl-1-methyl-1H-pyrazol-4-yl)-[2,4'-bipyridine]-6-carboxamide (PTM-VI-6); N-(3-carbamoyl-1-methyl-1H-pyrazol-4-yl)-2'-(cyclopropylmethylamino)-3,4'-bipyridine-5-carboxamide (PTM-VI-7); N-(5-carbamoyl-1-methyl-1H-pyrazol-4-yl)-2'-(cyclopropylmethylamino)-2,4'-bipyridine-6-carboxamide (PTM-VI-8); N-(3-carbamoyl-1-methyl-1H-pyrazol-4-yl)-6-morpholinopicolinamide (PTM-VI-9); N-(3-carbamoyl-1-methyl-1H-pyrazol-4-yl)-6-(piperazin-1-yl)picolinamide (PTM-VI-10); N-(3-carbamoyl-1-methyl-1H-pyrazol-4-yl)-2,4'-bipyridine-6-carboxamide (PTM-VI-11); N-(3-carbamoyl-1-methyl-1H-pyrazol-4-yl)-[2,3'-bipyridine]-6-carboxamide (PTM-VI-12); N-(3-carbamoyl-1-methyl-1H-pyrazol-4-yl)-6-(3-methoxyphenyl)picolinamide (PTM-VI-13); N-(3-carbamoyl-1-methyl-1H-pyrazol-4-yl)-6-phenylpicolinamide (PTM-VI-14); N-(3-carbamoyl-1-methyl-1H-pyrazol-4-yl)-2'-((2-methoxyethyl)amino)-[2,4'-bipyridine]-6-carboxamide (PTM-VI-15); N-(3-carbamoyl-1-methyl-1H-pyrazol-4-yl)-2'-((2,2-difluoroethyl)amino)-[2,4'-bipyridine]-6-carboxamide (PTM-VI-16); N-(3-carbamoyl-1-methyl-1H-pyrazol-4-yl)-2'-(((tetrahydro-2H-pyran-4-yl)methyl)amino)-[2,4'-bipyridine]-6-carboxamide (PTM-VI-17); N-(3-carbamoyl-1-methyl-1H-pyrazol-4-yl)-2'-((2,2-trifluoroethyl)amino)-[2,4'-bipyridine]-6-carboxamide (PTM-VI-18); N-(3-carbamoyl-1-methyl-1H-pyrazol-4-yl)-2-(2-((cyclopropylmethyl)amino)pyridin-4-yl)pyrimidine-4-carboxamide (PTM-VI-19); N-(3-carbamoyl-1-methyl-1H-pyrazol-4-yl)-2'-methoxy-[2,3'-bipyridine]-6-carboxamide (PTM-VI-20); N-(3-carbamoyl-1-methyl-1H-pyrazol-4-yl)-6-(3-(trifluoromethoxy)phenyl)picolinamide (PTM-V1-21); N-(3-carbamoyl-1-methyl-1H-pyrazol-4-yl)-6-(thiophen-3-yl)picolinamide (PTM-VI-22); N-(3-carbamoyl-1-methyl-1H-pyrazol-4-yl)-6'-morpholino-[2,3'-bipyridine]-6-carboxamide (PTM-VI-23); N-(3-carbamoyl-1-methyl-1H-pyrazol-4-yl)-6-(3-(methylcarbamoyl)phenyl)picolinamide (PTM-VI-24); N-(3-carbamoyl-1-methyl-1H-pyrazol-4-yl)-6-(1-methyl-1H-pyrazol-4-yl)picolinamide (PTM-VI-25); N-(3-carbamoyl-1-methyl-1H-pyrazol-4-yl)-6-(1,1-dioxido-3,6-dihydro-2H-thiopyran-4-yl)picolinamide (PTM-V1-26); N-(3-carbamoyl-1-methyl-1H-pyrazol-4-yl)-6-(5,6-dihydro-2H-pyran-3-yl)picolinamide (PTM-VI-27); N-(3-carbamoyl-1-methyl-1H-pyrazol-4-yl)-6'-cyclopropyl-[2,3'-bipyridine]-6-carboxamide (PTM-VI-28); N-3-carbamoyl-1-methyl-1H-pyrazol-4-yl)-5'-chloro-[2,3'-bipyridine]-6-carboxamide (PTM-VI-29); N-(3-carbamoyl-1-methyl-1H-pyrazol-4-yl)-6-(3,6-dihydro-2H-pyran-4-yl)picolinamide (PTM-VI-30); N-(3-carbamoyl-1-methyl-1H-pyrazol-4-yl)-4'-chloro-[2,3'-bipyridine]-6-carboxamide (PTM-VI-31); N-(3-carbamoyl-1-methyl-1H-pyrazol-4-yl)-1'-methyl-6'-oxo-1',2',3',6'-tetrahydro-[2,4'-bipyridine]-6-carboxamide (PTM-VI-32); N-(3-carbamoyl-1-methyl-1H-pyrazol-4-yl)-1'-methyl-1',2',5',6'-tetrahydro-[2,3'-bipyridine]-6-carboxamide (PTM-VI-33); 2'-((cyclopropylmethyl)amino)-N-(1-methyl-3-(((1-methylpyrrolidin-3-yl)methyl)carbamoyl)-1H-pyrazol-4-yl)-[2,4'-bipyridine]-6-carboxamide (PTM-VI-34); 2'-((cyclopropylmethyl)amino)-N-(1-methyl-3-((2-(pyrrolidin-1-yl)ethyl)carbamoyl)-1H-pyrazol-4-yl)-[2,4'-bipyridine]-6-carboxamide (PTM-VI-35); N-(3-(((1H-imidazol-2-yl)methyl)carbamoyl)-1-methyl-1H-pyrazol-4-yl)-2'-((cyclopropylmethyl)amino)-[2,4'-bipyridine]-6-carboxamide (PTM-VI-36); 2'-((cyclopropylmethyl)amino)-N-(3-((5-(dimethylamino)pentyl)carbamoyl)-1-methyl-1Hl-pyrazol-4-yl)-[2,4'-bipyridine]-6-carboxamide (PTM-VI-37); 2'-((cyclopropylmethyl)amino)-N-(1-methyl- 3-((2-(pyridin-2-yl)ethyl)carbamoyl)-1H-pyrazol-4-yl)-2,4'-bipyridine]-6-carboxamide (PTM-VI-38); 2'-((cyclopropylmethyl)amino)-N-(1-methyl-3-(4-methylpiperazine-1-carbonyl)-1H-pyrazol-4-yl)-[2,4'-bipyridine]-6-carboxamide (PTM-VI-39); 2'-((cyclopropylmethyl)amino)-N-(3-((3-(dimethylamino)propyl)carbamoyl)-methyl-1H-pyrazol-4-yl)-[2,4'-bipyridine]-6-carboxamide (PTM-VI-40); 2'-((cyclopropylmethyl)amino)-N-(1-methyl-3-(morpholine-4-carbonyl)-1H-pyrazol-4-yl)-[2,4'-bipyridine]-6-carboxamide (PTM-VI-41); N-(3-(3-(aminomethyl)azetidine-1-carbonyl)-1-methyl-1H-pyrazol-4-yl)-2'-((cyclopropylmethyl)amino)-[2,4'-bipyridine]-6-carboxamide (PTM-VI-42); 2'-((cyclopropylmethyl)amino)-N-(1-methyl-3-(pyrimidin-5-ylcarbamoyl)-1H-pyrazol-4-yl)-[2,4'-bipyridine]-6-carboxamide (PTM-VI-43); 2'-((cyclopropylmethyl)amino)-N-(1-methyl-3-((2-(pyrazin-2-yl)ethyl)carbamoyl)-1H-pyrazol-4-yl)-[2,4'-bipyridine]-6-carboxamide (PTM-VI-44); 2'-((cyclopropylmethyl)amino)-N-(3-(((1,1-dioxidotetrahydrothiophen-3-yl)methyl)carbamoyl)-1-methyl-1H-pyrazol-4-yl)-[2,4'-bipyridine]-6-carboxamide (PTM-VI-45); 2'-((cyclopropylmethyl)amino)-N-(3-((3S,4S)-3-(dimethylamino)-4-hydroxypyrrolidine-1-carbonyl)-1-methyl-1H-pyrazol-4-yl)-[2,4'-bipyridine]-6-carboxamide (PTM-VI-46); 2'-((cyclopropylmethyl)amino)-N-(1-methyl-3-((pyrimidin-4-ylmethyl)carbamoyl)-1H-pyrazol-4-yl)-[2,4'-bipyridine]-6-carboxamide (PTM-VI-47); N-(3-((1,3,4-thiadiazol-2-yl)methyl)carbamoyl)-1-methyl-1H-pyrazol-4-yl)-2'-((cyclopropylmethyl)amino)-[2,4'-bipyridine]-6-carboxamide (PTM-VI-48); 2'-((cyclopropylmethyl)amino)-N-(1-methyl-3-(((1-methylpiperidin-3-yl)methyl)carbamoyl)-1H-pyrazol-4-yl)-[2,4'-bipyridine]-6-carboxamide (PTM-VI-49); N-(3-((2-(1H-pyrazol-1-yl)ethyl)carbamoyl)-1-methyl-1H-pyrazol-4-yl)-2'-((cyclopropylmethyl)amino)-[2,4'-bipyridine]-6-carboxamide (PTM-VI-50); and 2'-((cyclopropylmethyl)amino)-N-(1-methyl-3-((tetrahydrofuran-3-yl)carbamoyl)-1H-pyrazol-4-yl)-[2,4'-bipyridine]-6-carboxamide (PTM-VI-51).

In any aspect or embodiment described herein, the PTM of PTM-VI is selected from the group consisting of: N-(3-carbamoyl-1-methyl-1H-pyrazol-4-yl)-2'-((cyclopropylmethyl)amino)-[2,4'-bipyridine]-6-carboxamide (PTM-VI-1); N-(3-carbamoyl-1-methyl-1H-pyrazol-4-yl)-[2,3'-bipyridine]-6-carboxamide (PTM-VI-12); N-(3-carbamoyl-1-methyl-1H-pyrazol-4-yl)-2'-((2-methoxyethyl)amino)-[2,4'-bipyridine]-6-carboxamide (PTM-VI-15); N-(3-carbamoyl-1-methyl-1H-pyrazol-4-yl)-2'-((2,2-difluoroethyl)amino)-[2,4'-bipyridine]-6-carboxamide(PTM-VI-16); N-(3-carbamoyl-1-methyl-1H-pyrazol-4-yl)-2'-((2,2,2-trifluoroethyl)amino)-[2,4'-bipyridine]-6-carboxamide (PTM-VI-18); N-(3-carbamoyl-1-methyl-1H-pyrazol-4-yl)-6-(thiophen-3-yl)picolinamide (PTM-VI-22); N-(3-carbamoyl-1-methyl-1H-pyrazol-4-yl)-6'-cyclopropyl-[2,3'-bipyridine]-6-carboxamide(PTM-VI-28); N-(3-carbamoyl-1-methyl-1H-pyrazol-4-yl)-1'-methyl-6'-oxo-1',2',3',6'-tetrahydro-[2,4'-bipyridine]-6-carboxamide (PTM-VI-32); N-(3-(3-(aminomethyl)azetidine-i-carbonyl)-1-methyl-1H-pyrazol-4-yl)-2'-((cyclopropylmethyl)amino)-[2,4'-bipyridine]-6-carboxamide (PTM-VI-42); and 2'-((cyclopropylmethyl)amino)-N-(1-methyl-3-(((1-methylpiperidin-3-yl)methyl)carbamoyl)-1H-pyrazol-4-yl)-[2,4'-bipyridine]-6-carboxamide(PTM-VI-49).

In any aspect or embodiment described herein, the heterocyclyl of PTM-VI is independently selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, optionally substituted with one to three substituents independently selected from $R_a$.

In any aspect or embodiment described herein, the Ring A of PTM-VI is aryl, heteroaryl or heterocycle optionally substituted with one to three substituents independently selected from $R_1$. For example, Ring A may be selected from the group consisting of phenyl, benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl, which are optionally substituted with one to three substituents independently selected from $R_1$.

In any aspect or embodiment described herein, the $R_1$ of PTM-VI is independently selected from: H, oxo, $(C{=}O)_a(C_1\text{-}C_{10})$alkyl, $(C{=}O)_a$-aryl, $CO_2H$, halo, OH, $O_b(C_1\text{-}C_6)$fluoroalkyl, $(C{=}O)_aNR_5R_6$, CN, $(C{=}O)_a(C_3\text{-}C_8)$cycloalkyl and $(C{=}O)_aO_b$-heterocyclyl, said alkyl, aryl, cycloalkyl, and heterocyclyl are optionally substituted with one or more substituents selected from $R_a$.

In any aspect or embodiment described herein, the $R_2$ and $R_3$ of PTM-VI are independently selected from: H and $C_1\text{-}C_6$ alkyl, optionally substituted with one or more substituents selected from $R_1$; or $R_2$ and $R_3$ can be taken together with the nitrogen to which they are attached to form a monocyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R_1$.

In any aspect or embodiment described herein, the $R_4$ of PTM-VI is selected from $(C_1\text{-}C_6)$alkyl optionally substituted with OH, methoxy and halogen.

In any aspect or embodiment described herein, the $R_5$ and $R_6$ of PTM-VI are independently selected from: H, $(C{=}O)_a(C_1\text{-}C_{10})$alkyl, $(C{=}O)_a(C_3\text{-}C_8)$cycloalkyl, $(C{=}O)_a$-aryl, $(C{=}O)_a$-heterocyclyl and $(C{=}O)_aN(R_a)_2$.

In any aspect or embodiment described herein, the $R_a$ of PTM-VI is independently selected from $R_b$, OH, ($C_1$-$C_6$) alkoxy, halogen, cyclopropyl, $CO_2H$, CN, $O_a(C{=}O)_b$($C_1$-$C_6$)alkyl, oxo, and $N(R_b)_2$.

In any aspect or embodiment described herein, the $R_b$ of PTM-VI is independently selected from H and methyl.

In an embodiment, the PTM is represented by Formula PTM-VII (i.e., Formulas PTM-VIIa, PTM-VIIb, PTM-VIIc, PTM-VIId, PTM-VIIe, PTM-VIIf, PTM-VIIg, PTM-VIIh, PTM-VIIi, PTM-VIIj, PTM-VIk and/or PTM-VIIm, which correspond to Formulas Ia, Ib, Ic, IIa, IIb, IIc, IId, IIe, IIf, IIg, III, and IIIa respectively, from U.S. Patent Application Publication No. 2015/0284405 A1, which is incorporated herein in its entirety for all purposes):

PTM-VIIa

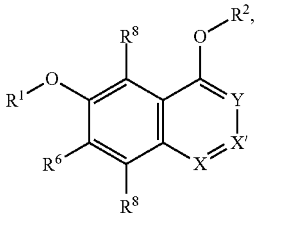

PTM-VIIb

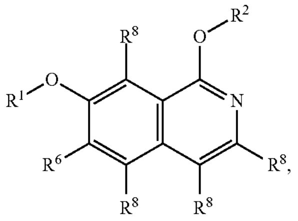

PTM-VIIc

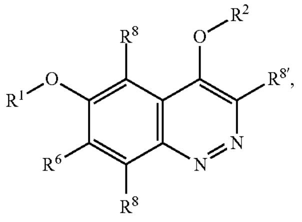

PTM-VIId

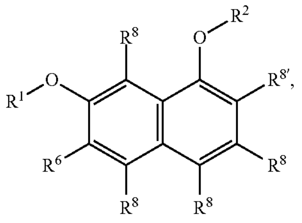

PTM-VIIe

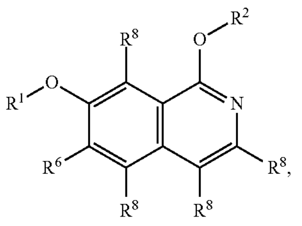

-continued

PTM-VIIf

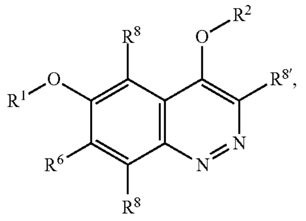

PTM-VIIg

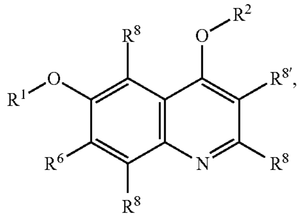

PTM-VIIh

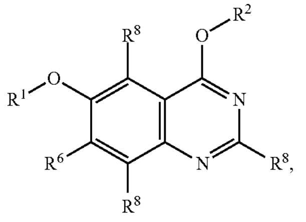

PTM-VIIi

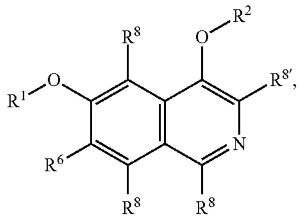

PTM-VIIj

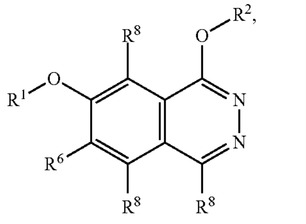

PTM-VIIk

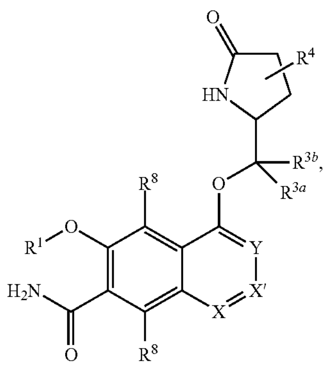

or

-continued

PTM-VIIm

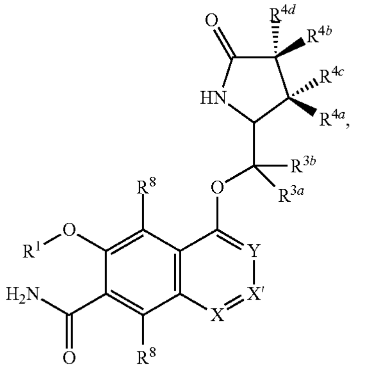

wherein:

X and X' of PTM-VII are each independently $CR^8$, N or —N+—O—; Y is independently N, —N+—O− or $CR^{8'}$; provided that at least one of X, X' or Y is neither N nor —N+—O− and that no more than one of X, X' or Y is —N+—O−;

$R^1$ of PTM-VII is $C_1$-$C_6$alkyl; $C_2$-$C_6$alkenyl; $C_2$-$C_6$alkynyl; —$(CR^{3a}R^{3b})_m$-(3- to 7-membered cycloalkyl); —$(CR^{3a}R^{3b})_m$-(3- to 7-membered heterocycloalkyl) having one to three heteroatoms; —$(CR^{3a}R^{3b})_m$-(5- to 10-membered heteroaryl), having one to three heteroatoms; or —$(CR^{3a}R^{3b})_m$—$C_6$-$C_{12}$aryl; wherein said alkyl, alkenyl, alkynyl, cycloalkyl, heterocycloalkyl, heteroaryl or aryl is optionally substituted with one to five halogen, deuterium, —$OR^5$, —$SR^5$, —$NR^{11a}R^{11b}$, cyano, $C_1$-$C_6$alkyl, $C_3$-$C_6$cycloalkyl or —$C_1$-$C_6$alkoxy;

$R^2$ of PTM-VII is —$(CR^{3a}R^{3b})_m$-(3- to 10-membered cycloalkyl); —$(CR^{3a}R^{3b})_m$-(3- to 10-membered heterocycloalkyl) having one to three heteroatoms; —$(CR^{3a}R^{3b})_m$-(5- to 10 membered heteroaryl) having one to three heteroatoms; or —$(CR^{3a}R^{3b})_m$—$C_6$-$C_{12}$aryl; wherein said cycloalkyl, heterocycloalkyl, heteroaryl or aryl is optionally substituted with one to five $R^4$; and wherein, if the heteroatom on said heterocycloalkyl and heteroaryl is N, said N is optionally substituted with $R^{4'}$; or $R^2$ is $C_1$-$C_6$alkyl, wherein said alkyl is optionally substituted with $NH_2$, OH or cyano;

$R^{3a}$ and $R^{3b}$ of PTM-VII for each occurrence are independently hydrogen or $C_1$-$C_3$alkyl;

$R^4$ of PTM-VII for each occurrence is independently a bond, deuterium, halogen, cyano, $C_1$-$C_6$alkyl, $C_2$-$C_6$alkenyl, oxo, —$OR^5$, —$SR^5$, —$S(O)R^9$, —$S(O)_2R^9$, —$NR^{11a}R^{11b}$, —$C(O)R^{10}$, —$(CR^{3a}R^{3b})_n$-(3- to 7-membered cycloalkyl), —$(CR^{3a}R^{3b})_n$-(4- to 10-membered heterocycloalkyl), having one to three heteroatoms, —$(CR^{3a}R^{3b})_n$-(5- to 10 membered heteroaryl), having one to three heteroatoms, or —$(CR^{3a}R^{3b})_n$—$C_6$-$C_{12}$aryl wherein said alkyl, cycloalkyl, heterocycloalkyl, heteroaryl or aryl is each optionally and independently substituted with one to five deuterium, halogen, —$OR^5$, —$SR^5$, —$NR^{11a}R^{11b}$, cyano, $C_1$-$C_6$alkyl, $C_3$-$C_6$cycloalkyl or $C_1$-$C_6$alkoxy; or two $R^4$ taken together with the respective carbons to which each are bonded form a 3- to 6-membered cycloalkyl or 4- to 6-membered heterocycloalkyl, wherein said cycloalkyl or heterocycloalkyl is optionally substituted with one to three halogen, deuterium, —$OR^5$, —$SR^5$, —$NR^{11a}R^{11b}$, cyano or $C_1$-$C_6$alkyl or $C_1$-$C_6$alkoxy, wherein the alkyl or alkoxy is optionally substituted with halogen, deuterium, —$OR^5$, —$SR^5$, —$NR^{11a}R^{11b}$ or cyano; and wherein, if a heteroatom on said heterocycloalkyl is N, said N is optionally substituted with $R^{4'}$;

$R^{4'}$ of PTM-VII is independently $C_1$-$C_6$alkyl, $C_2$-$C_6$alkenyl, —$C(O)R^{10}$, —$S(O)_2R^9$, —$(CR^{3a}R^{3b})_n$-(3- to 7-membered cycloalkyl), —$(CR^{3a}R^{3b})_n$-(4- to 10-membered heterocycloalkyl) or $C(O)(CH_2)_tCN$; wherein said alkyl, alkenyl, cycloalkyl, or heterocycloalkyl is each optionally and independently substituted with one to five deuterium, halogen, OH, cyano or $C_1$-$C_6$alkoxy; or $R^4$ and $R^{4'}$ taken together with the respective atoms to which each are bonded form a 3- to 6-membered cycloalkyl or 4- to 6-membered heterocycloalkyl, wherein said cycloalkyl or heterocycloalkyl is optionally substituted with one to three halogen, deuterium, —$OR^5$, —$SR^5$, cyano, $C_1$-$C_6$alkyl or $C_1$-$C_6$alkoxy, wherein the alkyl or alkoxy is optionally substituted with halogen, deuterium, —$OR^5$, —$SR^5$, —$NR^{11a}R^{11b}$, or cyano;

$R^{4a}$ and $R^{4b}$ of PTM-VII are each independently hydrogen, deuterium, fluoro, OH, —OR, methyl, ethyl, vinyl, cyclopropyl or propyl, optionally substituted with one to five deuterium, fluoro, methoxy or OH;

$R^{4c}$ and $R^{4d}$ of PTM-VII for each occurrence are independently and optionally halogen, OH, deuterium, $C_1$-$C_6$alkyl, $C_2$-$C_6$alkenyl, —$OR^5$, —$(CR^{3a}R^{3b})_n$-(3- to 6-membered cycloalkyl), or —$(CR^{3a}R^{3b})_n$-(4- to 6-membered heterocycloalkyl) wherein said alkyl, cycloalkyl and heterocycloalkyl are each optionally and independently substituted with one to five deuterium, halogen, OH, cyano, or $C_1$-$C_6$alkoxy; $NH_2$; or $R^{4c}$ and $R^{4d}$ taken together with the carbons to which they are bonded form a 4- to 7-membered heterocycloalkyl or a 3- to 7-membered cycloalkyl, wherein said heterocycloalkyl or cycloalkyl is optionally substituted with one to three fluoro, $C_1$-$C_3$alkyl or $C_1$-$C_3$fluoroalkyl;

or $R^{4a}$ and $R^{4c}$ of PTM-VII taken together with the carbon to which they are bonded form a 4- to 7-membered heterocycloalkyl or a 3- to 7-membered cycloalkyl, wherein said heterocycloalkyl or cycloalkyl is optionally substituted with one to three fluoro, $C_1$-$C_3$alkyl or $C_1$-$C_3$fluoroalkyl;

$R^5$ of PTM-VII is independently hydrogen or $C_1$-$C_6$alkyl, wherein said alkyl is optionally substituted with halogen, deuterium, $C_1$-$C_6$alkoxy, $C_1$-$C_6$alkylthiolyl, —$NR^{11a}R^{11b}$, cyano, $C_1$-$C_6$alkyl or $C_3$-$C_6$cycloalkyl; or two $R^5$ taken together with the oxygen atoms to which they are bonded form a 5- or 6-membered heterocycloalkyl;

$R^6$ of PTM-VII is —$C(O)NHR^7$, $CO_2R^7$ or cyano;

$R^7$ of PTM-VII is hydrogen or $C_1$-$C_6$alkyl;

each $R^8$ of PTM-VII is independently hydrogen, halogen, cyano, —$OR^5$, —$SR^5$, —$C_1$-$C_6$alkyl, $C_3$-$C_6$cycloalkyl, 3- to 10-membered heterocycloalkyl or 5- to 6-membered heteroaryl or aryl, wherein said alkyl, cycloalkyl, heterocycloalkyl, heteroaryl or aryl is optionally substituted with one to three halogen, —$NR^{11a}R^{11e}$, —OR', —$SR^5$, cyano, $C_1$-$C_3$ alkyl, —$C(O)R^{10}$ or oxo;

$R^{8'}$ of PTM-VII is hydrogen, deuterium, halogen, cyano, —$OR^5$, —$SR^5$ or —$NR^{11a}NR^{11b}$;

$R^9$ of PTM-VII is —$(CR^{3a}R^{3b})_p(C_1$-$C_3$alkyl), —$(CR^{3a}R^{3b})_p$(4- to 6-membered cycloalkyl), —$(CR^{3a}R^{3b})_p$(4- to 6-membered heterocycloalkyl) or —$(CR^{3a}R^{3b})_p(C_5$-$C_9$aryl), wherein said alkyl, cycloalkyl, heterocycloalkyl or aryl is each optionally substituted with fluoro or $C_1$-$C_3$alkyl;

$R^{10}$ of PTM-VII is $C_1$-$C_6$alkyl, wherein said alkyl is optionally substituted with deuterium, halogen, OH, $C_1$-$C_6$alkoxy or cyano;

$R^{11a}$ and $R^{11b}$ of PTM-VII are each independently hydrogen or $C_1$-$C_6$alkyl, wherein said alkyl is optionally substituted with deuterium, $C_1$-$C_6$alkoxy or cyano; and if $C_2$-$C_6$alkyl, said alkyl is optionally substituted with deuterium, $C_1$-$C_6$alkoxy, cyano, halogen or OH;

m of PTM-VII is independently 0, 1, 2 or 3;

n of PTM-VII is independently 0, 1, 2 or 3;

p of PTM-VII is independently 0 or 1;

t of PTM-VII is 1, 2 or 3; and the PTM-VII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-VII is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^{3a}$, $R^{3b}$, $R^4$, $R^{4'}$, $R^{4a}$, $R^{4b}$, $R^{4c}$, $R^{4d}$, $R^5$, $R^6$, $R^7$, $R^8$, $R^{8'}$, $R^9$, $R^{10}$, $R^{11a}$, or $R^{11b}$).

In any aspect or embodiment described herein, the PTM of PTM-VII comprises one of the following combinations: X is N, X' is $CR^8$ and Y is $CR^{8'}$; X is N, X' is N and Y is $CR^{8'}$; X is N, X' is $CR^8$ and Y is N; X is $CR^8$, X' and Y are N; X and X' are CR and Y is N; X is $CR^8$ and Y is $CR^{8'}$ and X' is N; or X and X' are $CR^8$ and Y is $CR^{8'}$. In any aspect or embodiments described herein, $R^6$ of PTM-VII is —C(O)NHR$^7$, —$CO_2R^7$ or cyano; and $R^7$ is hydrogen In any aspect or embodiment described herein, the PTM of PTM-VII (e.g., PTM-VIId, PTM-VIIe, PTM-VIIf, PTM-VIIg, PTM-VIIh, PTM-VIIi, PTM-VIIj) comprise at least one of:

$R^1$ of PTM-VII is $C_1$-$C_6$alkyl; $C_2$-$C_6$alkenyl; $C_2$-$C_6$alkynyl; —$(CR^{3a}R^{3b})_m$-(3- to 7-membered cycloalkyl); or —$(CR^{3a}R^{3b})_m$-(3- to 7-membered heterocycloalkyl) having one to three heteroatoms; wherein said alkyl, alkenyl, alkynyl, cycloalkyl or heterocycloalkyl is optionally substituted with one to five halogen, deuterium, —$OR^5$, —$SR^5$, —$NR^{11a}R^{11b}$, cyano, $C_1$-$C_6$alkyl, $C_3$-$C_6$cycloalkyl or $C_1$-$C_6$alkoxy;

$R^2$ of PTM-VII is —$(CR^{3a}R^{3b})_m$-(3- to 7-membered cycloalkyl), wherein said cycloalkyl is optionally substituted with one to four $R^4$; —$(CR^{3a}R^{3b})_m$-(3- to 7-membered heterocycloalkyl) having one to three heteroatoms, wherein said heterocycloalkyl is optionally substituted at a carbon atom with one to five $R^4$ and wherein, if the heteroatom is N, said N is optionally substituted with $R^{4'}$; or $R^2$ is $C_1$-$C_6$alkyl, wherein said alkyl is optionally substituted with $NH_2$, cyano or halogen;

$R^{3a}$ and $R^{3b}$ of PTM-VII are each independently hydrogen or $C_1$-$C_3$alkyl;

$R^4$ of PTM-VII for each occurrence is independently and optionally halogen, cyano, $C_1$-$C_6$alkyl, $C_2$-$C_6$alkenyl, oxo, —$OR^5$, —$SR^5$, —S(O)$R^9$, —S(O)$_2R^9$, —C(O)$R^{10}$, —$(CR^{3a}R^{3b})_n$-(3- to 7-membered cycloalkyl) or —$(CR^{3a}R^{3b})_n$-(4- to 7-membered heterocycloalkyl) wherein said alkyl, cycloalkyl or heterocycloalkyl is each optionally and independently substituted with one to five deuterium, halogen, —$OR^5$, —$SR^5$, —$NR^{11a}R^{11b}$, cyano, $C_1$-$C_6$alkyl, $C_3$-$C_6$cycloalkyl, $C_1$-$C_6$alkoxy or $NR^{11a}R^{11b}$; or two $R^4$ taken together with the respective carbons to which each are bonded form a 3- to 6-membered cycloalkyl or 4- to 6-membered heterocycloalkyl, wherein said cycloalkyl or heterocycloalkyl is optionally substituted with one to three halogen, deuterium, —$OR^5$, —$SR^5$, —$NR^{11a}R^{11b}$, cyano or $C_1$-$C_6$alkyl or $C_1$-$C_6$alkoxy, wherein the alkyl or alkoxy is optionally substituted with halogen, deuterium, —$OR^5$, —$NR^{11a}R^{11b}$, or cyano; and wherein, if a heteroatom on said heterocycloalkyl is N, said N is optionally substituted with $R^{4'}$;

$R^{4'}$ of PTM-VII is independently $C_1$-$C_6$alkyl, $C_2$-$C_6$alkenyl, —S(O)$R^9$, —S(O)$_2R^9$, —C(O)$R^{10}$, C(O)(CH$_2$)$_t$CN; wherein said alkyl is optionally substituted with $NH_2$, cyano or halogen —$(CR^{3a}R^{3b})_n$-(3- to 7-membered cycloalkyl), or $(CR^{3a}R^{3b})_n$-(4- to 10-membered heterocycloalkyl), wherein said alkyl, alkenyl, cycloalkyl, or heterocycloalkyl is each optionally and independently substituted with one to five deuterium, halogen, OH, cyano or $C_1$-$C_6$alkoxy; or $R^4$ and $R^{4'}$ taken together with the respective atoms to which each are bonded form a 3- to 6-membered cycloalkyl or 4- to 6-membered heterocycloalkyl, wherein said cycloalkyl or heterocycloalkyl is optionally substituted with one to three halogen, deuterium, —$OR^5$, —SR, —$NR^{11}R^{11b}$, cyano, $C_1$-$C_6$alkyl or $C_1$-$C_6$alkoxy, wherein the alkyl or alkoxy is optionally substituted with halogen, deuterium, —$OR^5$, —$SR^5$, —$NR^{11a}R^{11b}$ or cyano;

$R^5$ of PTM-VII is hydrogen or $C_1$-$C_6$alkyl, wherein said alkyl is optionally substituted with halogen;

$R^6$ of PTM-VII is —C(O)NHR$^7$ or cyano;

$R^7$ of PTM-VII is hydrogen or $C_1$-$C_6$alkyl;

$R^8$ of PTM-VII is independently hydrogen, halogen, cyano, —$NR^{11a}R^{11b}$, $C_1$-$C_6$alkyl, 5- to 6-membered heteroaryl or 5- to 6-membered aryl, wherein said alkyl or heteroaryl or aryl is optionally substituted with one to three halogen, —$NR^{11a}R^{11b}$, $C_1$-$C_3$ alkyl or oxo;

$R^{8'}$ of PTM-VII is hydrogen, deuterium, halogen, cyano, —$OR^5$ or $NR^{11a}NR^{11b}$;

$R^9$ of PTM-VII is —$(CR^{3a}R^{3b})_p$($C_1$-$C_3$alkyl), —$(CR^{3a}R^{3b})_p$(4- to 6-membered cycloalkyl), —$(CR^{3a}R^{3b})_p$(4- to 6-membered heterocycloalkyl) or —$(CR^{3a}R^{3b})_p$($C_6$-$C_9$aryl), wherein said alkyl, cycloalkyl, heterocycloalkyl or aryl is each optionally substituted with fluoro or $C_1$-$C_3$alkyl;

$R^{10}$ of PTM-VII is $C_1$-$C_6$alkyl, wherein said alkyl is optionally substituted with fluoro or cyano;

$R^{11a}$ and $R^{11b}$ of PTM-VII are each independently hydrogen or $C_1$-$C_6$alkyl, wherein said alkyl is optionally substituted with OH;

m of PTM-VII is independently 0, 1 or 2;

n of PTM-VII is independently 0 or 1;

p of PTM-VII is independently 0 or 1;

t of PTM-VII is 0, 1, 2 or 3;

or a combination thereof.

In any aspect or embodiment described herein, the $R^1$ of PTM-VII is fluoromethyl; difluoromethyl; trifluoromethyl; methyl, ethyl, propyl or isopropyl, each optionally substituted with one to three fluoro or deuterium; allene, propargyl, cyclopropyl, cyclobutyl, cyclopentyl, cyclopropylmethyl, oxetane or tetrahydrofuran, each of which is optionally substituted with fluoro or $C_1$-$C_3$ alkyl.

In any aspect or embodiment described herein, the $R^2$ of PTM-VII is selected from pyrrolidinyl, pyrrolidin-2-onyl, piperidinyl, piperidin-2-onyl, octahydro-1H-pyrrolo[3,4-c]pyridinyl, oxazolidinyl, oxazolidin-2-onyl, 1,3-oxazinan-2-onyl, imidazolidinyl, imidazolidin-2-onyl, morpholinyl, morpholin-3-onyl, thiazyl, isothiazyl, isothiazolidine-1,1- dioxidyl, 1,2-thiazinane 1,1-dioxidyl, hexahydrocyclopenta[b]pyrrol-2(1H)-onyl, octahydrocyclopenta[c]pyrrolyl, azetidinyl, hexahydro-1H-indol-2(3H)-onyl, octahydro-1H-isoindolyl, azepanyl, tetrahydrofuranyl, 1,3-dioxolanyl, oxetanyl, cyclopropyl, cyclobutyl, cyclopentyl, cyclohexyl, 4-azepanyl, 1,4-oxazepanyl, tetrahydro-2H-pyranyl, 6,7-dihydro-5H-pyrrolo[1,2-a]imidazolyl, cyclohex-2-enyl, or 1,2,3,4-tetrahydroisoquinolinyl; wherein said alkyl, cycloalkyl or heterocycloalkyl is optionally substituted with one to four $R^4$.

In any aspect or embodiment described herein, the $R^4$ of PTM-VII is selected from F, Cl, OH; $C_1$-$C_3$alkyl, optionally substituted with one to five deuterium, Cl, F, OH, $C_1$-$C_3$alkyl, $C_1$-$C_3$alkoxy; or two $R^4$ taken together with the respective carbons to which each are bonded form a cyclopropyl, cyclobutyl or cyclopentyl, wherein said cyclopropyl, cyclobutyl or cyclopentyl are optionally substituted with one to three Cl, F, OH, methyl, ethyl, propyl, $C_1$-$C_3$fluoroalkyl, $C_1$-$C_3$hydroxyalkyl, methoxy or ethoxy; or two $R^4$ taken together with the respective carbons to which each are bonded form a 4- to 6-membered heterocycloalkyl, wherein said heterocycloalkyl is optionally substituted with one to three fluoro, $C_1$-$C_3$alkyl, $C_1$-$C_3$fluoroalkyl, —C(O)$(CH_2)_t$CN; or a pharmaceutically acceptable salt thereof or a tautomer of said compound or said salt.

In any aspect or embodiment described herein, the PTM of PTM-VII comprises at least one of: R is methyl, ethyl, propyl or isopropyl wherein each of said $R^1$ moieties are optionally substituted with deuterium, fluoro or methoxy; $R^4$ is independently and optionally selected from fluoro, OH, methyl, ethyl, vinyl, propyl, wherein said methyl, ethyl, vinyl or propyl are optionally substituted with one, two or three fluoro, OH or methoxy; or two $R^4$ taken together with the carbons to which they are bonded form a cyclopropyl, cyclobutyl or cyclopentyl, wherein said cyclopropyl, cyclobutyl or cyclopentyl are optionally substituted with one to three Cl, F, OH, methyl, fluoromethyl, difluoromethyl, trifluoromethyl, ethyl, methoxymethyl, propyl, $C_1$-$C_3$haloalkyl, $C_1$-$C_3$dihaloalkyl, $C_1$-$C_3$trihaloalkyl, $C_1$-$C_3$hydroxyalkyl, methoxy, or ethoxy; $R^8$ is independently hydrogen, halogen or $C_1$-$C_6$alkyl, wherein said alkyl is optionally substituted with fluoro; or a combination thereof.

In any aspect or embodiments described herein, the PTM of PTM-VII is selected from the group consisting of: 5-{[(2S)-5-oxopyrrolidin-2-yl]methoxy}-3-(propan-2-yloxy)naphthalene-2-carboxamide; 1-{[(2S)-4,4-difluoro-5-oxopyrrolidin-2-yl]methoxy}-7-(propan-2-yloxy)isoquinoline-6-carboxamide; 1-{[(2S,4S)-4-ethyl-4-fluoro-5-oxopyrrolidin-2-yl]methoxy}-7-(propan-2-yloxy)isoquinoline-6-carboxamide; 1-{[(2S,4S)-4-ethyl-5-oxopyrrolidin-2-yl]methoxy}-7-(propan-2-yloxy)isoquinoline-6-carboxamide; 1-{[(2S,4S)-4-fluoro-5-oxopyrrolidin-2-yl]methoxy}-7-(propan-2-yloxy)isoquinoline-6-carboxamide; 1-{[(2S)-4,4-difluoro-5-oxopyrrolidin-2-yl]methoxy}-7-methoxyisoquinoline-6-carboxamide; 1-{[(2S,4S)-5-oxo-4-(2,2,2-trifluoroethyl)pyrrolidin-2-yl]methoxy}-7-(propan-2-yloxy)isoquinoline-6-carboxamide; 1-{[(2S,3S,4R)-4-fluoro-3-methyl-5-oxopyrrolidin-2-yl]methoxy}-7-(propan-2-yloxy)isoquinoline-6-carboxamide; 3-methoxy-5-{[(2S)-5-oxopyrrolidin-2-yl]methoxy}naphthalene-2-carboxamide; 1-{[(2S,4S)-4-fluoro-4-methyl-5-oxopyrrolidin-2-yl]methoxy}-7-methoxyisoquinoline-6-carboxamide; 1-{[(2S,3S)-4,4-difluoro-3-methyl-5-oxopyrrolidin-2-yl]methoxy}-7-(propan-2-yloxy)isoquinoline-6-carboxamide; 1-{[(2S,3S,4S)-4-fluoro-3-methyl-5-oxopyrrolidin-2-yl]methoxy}-7-(propan-2-yloxy)isoquinoline-6-carboxamide; 1-{[(2S,3S,4R)-4-fluoro-3-methyl-5-oxopyrrolidin-2-yl]methoxy}-7-methoxyisoquinoline-6-carboxamide; 1-{[(2S,3S,4S)-4-fluoro-3-methyl-5-oxopyrrolidin-2-yl]methoxy}-7-methoxyisoquinoline-6-carboxamide; 5-{[(2S,4S)-4-fluoro-4-methyl-5-oxopyrrolidin-2-yl]methoxy}-3-methoxynaphthalene-2-carboxamide; 1-{[(2R,3R,4S)-3-ethyl-4-fluoro-3-hydroxy-5-oxopyrrolidin-2-yl]methoxy}-7-methoxyisoquinoline-6-carboxamide; 1-{[(2S,3S)-3-ethyl-4,4-difluoro-5-oxopyrrolidin-2-yl]methoxy}-7-(propan-2-yloxy)isoquinoline-6-carboxamide; 5-{[(2S,4R)-4-fluoro-4-(hydroxymethyl)-5-oxopyrrolidin-2-yl]methoxy}-3-methoxynaphthalene-2-carboxamide; 7-methoxy-1-{[(2S,3R)-3-methyl-5-oxopyrrolidin-2-yl]methoxy}isoquinoline-6-carboxamide; 1-{[(2S,4S)-4-fluoro-4-(fluoromethyl)-5-oxopyrrolidin-2-yl]methoxy}-7-methoxyisoquinoline-6-carboxamide; 3-methoxy-5-{[(2S,3R)-3-methyl-5-oxopyrrolidin-2-yl]methoxy}naphthalene-2-carboxamide; 5-{[(2S,3S,4S)-4-fluoro-3-methyl-5-oxopyrrolidin-2-yl]methoxy}-3-methoxynaphthalene-2-carboxamide; 8-fluoro-5-{[(2S,3S,4S)-4-fluoro-3-methyl-5-oxopyrrolidin-2-yl]methoxy}-3-methoxynaphthalene-2-carboxamide; 5-{[(2S,4R)-4-fluoro-5-oxo-4-(2,2,2-trifluoroethyl)pyrrolidin-2-yl]methoxy}-3-methoxynaphthalene-2-carboxamide; 1-{[(2S,3S)-3-ethyl-5-oxopyrrolidin-2-yl]methoxy}-7-methoxyisoquinoline-6-carboxamide; 1-{[(2S,3R)-3-ethyl-5-oxopyrrolidin-2-yl]methoxy}-7-methoxyisoquinoline-6-carboxamide; 4-{[(2S,3S,4S)-4-fluoro-3-methyl-5-oxopyrrolidin-2-yl]methoxy}-6-methoxyquinoline-7-carboxamide; 1-{[(2S,3S)-3-ethenyl-5-oxopyrrolidin-2-yl]methoxy}-7-methoxyisoquinoline-6-carboxamide; 1-{[(2S,4S)-4-fluoro-5-oxopyrrolidin-2-yl]methoxy}-7-methoxyisoquinoline-6-carboxamide; 1-{[(2S,4S)-4-ethyl-4-fluoro-5-oxopyrrolidin-2-yl]methoxy}-7-methoxyisoquinoline-6-carboxamide; 4-{[(2S,4S)-4-ethyl-4-fluoro-5-oxopyrrolidin-2-yl]methoxy}-6-methoxyquinoline-7-carboxamide; 7-methoxy-1-{[(1S,2S,5R)-4-oxo-3-azabicyclo[3.1.0]hex-2-yl]methoxy}isoquinoline-6-carboxamide; 4-{[(2S,4S)-4-fluoro-4-methyl-5-oxopyrrolidin-2-yl]methoxy}-6-(propan-2-yloxy)quinoline-7-carboxamide; 7-methoxy-1-{[(1S,2S,5R)-6-methyl-4-oxo-3-azabicyclo[3.1.0]hex-2-yl]methoxy}isoquinoline-6-carboxamide; 7-ethoxy-1-{[(2S,3S,4S)-4-fluoro-3-methyl-5-oxopyrrolidin-2-yl]methoxy}isoquinoline-6-carboxamide; 7-ethoxy-1-{[(2S,4S)-4-fluoro-4-(fluoromethyl)-5-oxopyrrolidin-2-yl]methoxy}isoquinoline-6-carboxamide; 7-methoxy-1-{[(S,2S,5R)-1-methyl-4-oxo-3-azabicyclo[3.1.0]hex-2-yl]methoxy}isoquinoline-6-carboxamide; 1-{[(2S,3S,4S)-3-ethyl-4-fluoro-5-oxopyrrolidin-2-yl]methoxy}-7-methoxyisoquinoline-6-carboxamide; 1-{[(1S,2S,5R)-1-ethyl-4-oxo-3-azabicyclo[3.1.0]hex-2-yl]methoxy}-7-methoxyisoquinoline-6-carboxamide; 1-{[(1R,2S,5S)-6-(fluoromethyl)-4-oxo-3-azabicyclo[3.1.0]hex-2-yl]methoxy}-7-methoxyisoquinoline-6-carboxamide; 1-{[(2S,3S)-3-cyclopropyl-5-oxopyrrolidin-2-yl]methoxy}-7-methoxyisoquinoline-6-carboxamide; 1-{[(1R,2S,5S)-5-fluoro-6-methyl-4-oxo-3-azabicyclo[3.1.0]hex-2-yl]methoxy}-7-methoxyisoquinoline-6-carboxamide; 7-methoxy-1-{[(2S,3R)-5-oxo-3-propylpyrrolidin-2-yl]methoxy}isoquinoline-6-carboxamide; 1-{[(1S,2S,5R)-6-fluoro-4-oxo-3-azabicyclo[3.1.0]hex-2-yl]methoxy}-7-methoxyisoquinoline-6-carboxamide; 4-{[(2S,3S,4S)-3-ethyl-4-fluoro-5-oxopyrrolidin-2-yl]methoxy}-6-methoxyquinoline-7-carboxamide; 1-{[(1R,2S,5S)-5-fluoro-4-oxo-3-azabicyclo[3.1.0]hex-2-yl]methoxy}-7- methoxyisoquinoline-6-carboxamide; 1-{[(1R,2S,5S)-6-(difluoromethyl)-4-oxo-3-azabicyclo[3.1.0]hex-2-yl]methoxy}-7-methoxyisoquinoline-6-carboxamide; 1-{[(1R,2S,5S)-5-fluoro-4-oxo-3-azabicyclo[3.2.0]hept-2-yl]methoxy}-7-methoxyisoquinoline-6-carboxamide; 4-{[(1R,2S,5S)-5-fluoro-6-methyl-4-oxo-3-azabicyclo[3.1.0]hex-2-yl]methoxy}-6-methoxyquinoline-7-carboxamide; 4-{[(1S,2S,5R)-6-fluoro-4-oxo-3-azabicyclo[3.1.0]hex-2-yl]methoxy}-6-methoxyquinoline-7-carboxamide; 4-{[(1R,2S,5S)-5-fluoro-4-oxo-3-azabicyclo[3.1.0]hex-2-yl]methoxy}-6-methoxyquinoline-7-carboxamide; 7-methoxy-1-{[(4S)-6-oxo-5-azaspiro[2.4]hept-4-yl]methoxy}isoquinoline-6-carboxamide; 4-{[(-1R,2S,5S)-6-(fluoromethyl)-4-oxo-3-azabicyclo[3.1.0]hex-2-yl]methoxy}-6-methoxyquinoline-7-carboxamide; 1-{[(2S,3S,4R)-3-ethyl-4-fluoro-5-oxopyrrolidin-2-yl]methoxy}-7-methoxyisoquinoline-6-carboxamide; 1-{[(2S,3S,4S)-3-ethyl-4-fluoro-5-oxopyrrolidin-2-yl]methoxy}-7-[(trideuterium)methyloxy]isoquinoline-6-carboxamide; 4-{[(2S,3S,4S)-3-ethyl-4-fluoro-5-oxopyrrolidin-2-yl]methoxy}-6-methoxyquinazoline-7-carboxamide; 1-{[(2S,3S,4R)-3-ethyl-4-methoxy-5-oxopyrrolidin-2-yl]methoxy}-7-methoxyisoquinoline-6-carboxamide; 1-{[(2S,3S,4S)-3-(pentadeuterium)ethyl-4-fluoro-5-oxopyrrolidin-2-yl]methoxy}-7-methoxyisoquinoline-6-carboxamide; 1-{[(2S,3S)-3-ethyl-4,4-difluoro-5-oxopyrrolidin-2-yl]methoxy}-7-methoxyisoquinoline-6-carboxamide; 1-{[(2S,3R,4R)-3-ethyl-4-fluoro-5-oxopyrrolidin-2-yl]methoxy}-7-methoxyisoquinoline-6-carboxamide; 1-{[(2S,3R)-4,4-difluoro-3-(methoxymethyl)-5-oxopyrrolidin-2-yl]methoxy}-7-methoxyisoquinoline-6-carboxamide; 1-{[(2S,3R,4S)-4-fluoro-3-(methoxymethyl)-5-oxopyrrolidin-2-yl]methoxy}-7-methoxyisoquinoline-6-carboxamide; 7-methoxy-1-{[(2S,3S,4R)-4-methoxy-3-methyl-5-oxopyrrolidin-2-yl]methoxy}isoquinoline-6-carboxamide; 1-{[(2S,3R,4R)-4-fluoro-3-(methoxymethyl)-5-oxopyrrolidin-2-yl]methoxy}-7-methoxyisoquinoline-6-carboxamide; 1-{[(2S,3S,4R)-3-ethyl-4-hydroxy-5-oxopyrrolidin-2-yl]methoxy}-7-methoxyisoquinoline-6-carboxamide; 1-{[(2S,3S)-3-(2-fluoroethyl)-5-oxopyrrolidin-2-yl]methoxy}-7-methoxyisoquinoline-6-carboxamide; 1-{[(2S,3S,4S)-3-ethyl-4-fluoro-5-oxopyrrolidin-2-yl]methoxy}-7-(propan-2-yloxy)isoquinoline-6-carboxamide; 7-ethoxy-1-{[(2S,3S,4S)-3-ethyl-4-fluoro-5-oxopyrrolidin-2-yl]methoxy}isoquinoline-6-carboxamide; 1-{[(2S,3S,4S)-3-ethyl-4-fluoro-5-oxopyrrolidin-2-yl]methoxy}-4-fluoro-7-methoxyisoquinoline-6-carboxamide; 1-{[(2S,3S,4S)-3-ethyl-4-fluoro-5-oxopyrrolidin-2-yl]methoxy}-8-fluoro-7-methoxyisoquinoline-6-carboxamide; 1-{[(2S,3R)-3-ethyl-5-oxopyrrolidin-2-yl]methoxy}-4-fluoro-7-methoxyisoquinoline-6-carboxamide; 1-{[(2S,3R)-3-ethyl-5-oxopyrrolidin-2-yl]methoxy}-8-fluoro-7-methoxyisoquinoline-6-carboxamide; 4-fluoro-7-methoxy-1-{[(1S,2S,5R)-6-methyl-4-oxo-3-azabicyclo[3.1.0]hex-2-yl]methoxy}isoquinoline-6-carboxamide; 8-fluoro-7-methoxy-1-{[(1S,2S,5R)-6-methyl-4-oxo-3-azabicyclo[3.1.0]hex-2-yl]methoxy}isoquinoline-6-carboxamide; 1-{[(2S,3R)-3-(fluoromethyl)-5-oxopyrrolidin-2-yl]methoxy}-7-methoxyisoquinoline-6-carboxamide; 1-{[(2S,3R,4S)-4-fluoro-3-(fluoromethyl)-5-oxopyrrolidin-2-yl]methoxy}-7-methoxyisoquinoline-6-carboxamide; 1-{[(2S,3S,4S)-3-cyclopropyl-4-fluoro-5-oxopyrrolidin-2-yl]methoxy}-7-methoxyisoquinoline-6-carboxamide; 1-{[(2S,3S,4R)-3-cyclopropyl-4-fluoro-5-oxopyrrolidin-2-yl]methoxy}-7-methoxyisoquinoline-6-carboxamide; 1-{[(2S,3S,4S)-4-fluoro-3-(2-fluoroethyl)-5-oxopyrrolidin-2-yl]methoxy}-7-methoxyisoquinoline-6-carboxamide; 4-(1-methyl-1H-imidazol-4-yl)-1-{[(2S)-5-oxopyrrolidin-2-yl]methoxy}-7-(propan-2-yloxy)isoquinoline-6-carboxamide; 4-(1,2-dimethyl-1H-imidazol-4-yl)-1-{[(2S)-5-oxopyrrolidin-2-yl]methoxy}-7-(propan-2-yloxy)isoquinoline-6-carboxamide; 4-(2-methyl-1H-imidazol-4-yl)-1-{[(2S)-5-oxopyrrolidin-2-yl]methoxy}-7-(propan-2-yloxy)isoquinoline-6-carboxamide; 4-(2-methyl-1H-imidazol-4-yl)-1-{[(2S)-5-oxopyrrolidin-2-yl]methoxy}-7-(propan-2-yloxy)isoquinoline-6-carboxamide; 1-{[(2S,3S,4S)-3-ethyl-4-fluoro-5-oxo(3,4-bisdeuterium)pyrrolidin-2-yl]methoxy}-7-methoxyisoquinoline-6-carboxamide; 4-{[(2S,3S,4S)-3-ethyl-4-fluoro-5-oxopyrrolidin-2-yl]methoxy}-6-methoxyquinoline-7-carboxamide; and 1-{[(2S,3R,4R)-4-fluoro-3-(fluoromethyl)-5-oxopyrrolidin-2-yl]methoxy}-7-methoxyisoquinoline-6-carboxamide;

In any aspect or embodiment described herein, the PTM is represented by Formula PTM-VIII (i.e., Formulas PTM-VIIIa, PTM-VIIIb, PTM-VIIIc, PTM-VIIId, PTM-VIIIe, and/or PTM-VIIIf, which correspond to Formulas I, II, III, IV, VI, and VIII, respectively, from U.S. Patent Application Publication No. 2016/0002265 A1, which is incorporated herein in its entirety for all purposes):

PTM-VIIIa

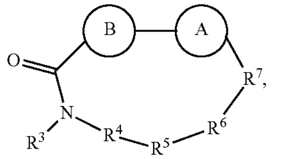

PTM-VIIIb

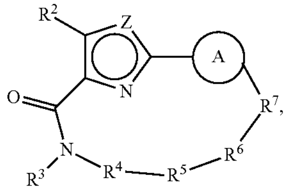

PTM-VIIIc

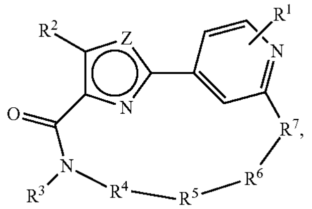

PTM-VIIId

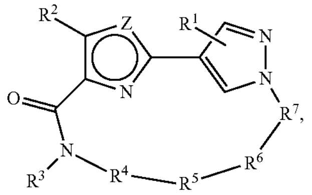

PTM-VIIIe

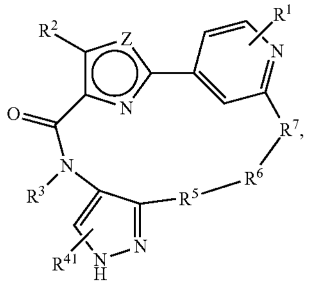

or

-continued

PTMVIIIf

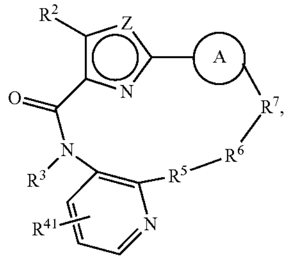

wherein:

Ring A of PTM-VIII is phenylene or 5- to 6-membered heteroarylene containing 1-3 heteroatoms chosen from O, S, and N, wherein ring A is optionally substituted with lower alkyl that is further optionally substituted;

Ring B of PTM-VIII is phenylene, 5- to 6-membered heterocycloalkylene containing 1-3 heteroatoms chosen from O, S, and N, or 5- to 6-membered heteroarylene containing 1-3 heteroatoms chosen from O, S, and N, wherein ring B is optionally substituted with lower alkyl or lower alkyloxyalkyl, either of which is further optionally substituted;

$R^2$ of PTM-VIII is chosen from hydrogen and lower alkyl;

$R^3$ of PTM-VIII is chosen from hydrogen, lower alkyl optionally substituted with alkoxy, amino, N-(alkyl)amino, N,N-(dialkyl)amino, or phenyl, heterocycloalkyl, and heteroaryl, wherein phenyl, heterocycloalkyl, and heteroaryl are optionally substituted with one or two groups independently chosen from lower alkyl and wherein alkoxy is optionally substituted with tri(alkyl)silyl;

$R^4$ of PTM-VIII is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent;

$R^5$ of PTM-VIII is chosen from $C(O)NR^{51}$, $NR^{52}$, and O, or $R^5$ is absent, provided that if $R^4$ is absent, then $R^5$ is absent;

$R^6$ of PTM-VIII is an alkylene or alkenylene chain having one or two double bonds, wherein the alkylene or alkenylene chain has 2 to 10 carbon atoms, the alkylene or alkenylene chain is optionally substituted with one or two groups independently chosen from lower alkyl, cycloalkyl and phenyl, each of which groups is optionally substituted with hydroxyl, alkoxy, $—C(O)OR^{85}$, $—C(O)NR^{82}R^{83}$, benzoyl, and benzyl, further wherein one or two of the carbon atoms in the alkylene or alkenylene chain is optionally replaced by an O, S, SO, $SO_2$, $C(O)NR^{51}$, or $NR^{61}$, and wherein one of the carbon atoms in the alkylene or alkenylene chain, is optionally connected by the nitrogen atom of $C(O)NR^{51}$ or $NR^{61}$ to form a 5- to 7-membered ring, which may further be substituted with oxo, wherein two of the carbon atoms in the alkylene or alkenylene chain, are optionally connected by a two or three carbon atom alkylene or alkenylene chain to form a 5- to 7-membered ring;

$R^7$ of PTM-VIII is chosen from $NR^{71}$ and O, or $R^7$ is absent;

$R^{21}$ of PTM-VIII is chosen from hydrogen and lower alkyl optionally substituted with lower alkoxy, wherein lower alkoxy is optionally substituted with tri(alkyl)silyl;

$R^{41}$ of PTM-VIII is independently chosen from heterocycloalkyl, lower alkyl optionally substituted with $—C(O)OR^9$, amino, N-(alkyl)amino, N,N-(dialkyl)amino, cycloalkyl, or heterocycloalkyl, $—C(O)OR^9$, hydroxyl, and $—C(O)NR^{10}R^{11}$, wherein $R^9$ is chosen from hydrogen and lower alkyl, $R^{10}$ and $R^{11}$ are independently hydrogen and lower alkyl, or $R^{10}$ and $R^{11}$, together with the nitrogen to which they are bound form a heterocycloalkyl, and each lower alkyl, cycloalkyl and heterocycloalkyl is optionally substituted with one, two, or three groups independently chosen from $—C(O)OR^9$, lower alkyl, lower alkoxy, hydroxyl, halogen, amino, N-(alkyl)amino, N,N-(dialkyl)amino, and heterocycloalkyl;

$R^{51}$ of PTM-VIII is chosen from hydrogen and lower alkyl;

$R^{52}$ of PTM-VIII is chosen from hydrogen, lower alkyl, and $—C(O)OR^{81}$;

$R^{61}$ of PTM-VIII is chosen from hydrogen, lower alkyl, $—(CH_2)_nC(O)OR^{81}$, $—(CH_2)_nC(O)NR^{82}R^{83}$, $—C(O)R^{84}$, $—C(O)(CH_2)_pNR^{82}C(O)OR^{81}$, $—C(O)(CH_2)_pNR^{82}R^{83}$;

$R^{71}$ of PTM-VIII is chosen from hydrogen, lower alkyl, and $—C(O)OR^{81}$;

$R^{81}$ of PTM-VIII is hydrogen or lower alkyl;

$R^{82}$ of PTM-VIII is hydrogen or lower alkyl, $R^{83}$ of PTM-VIII is hydrogen or lower alkyl, $R^{84}$ of PTM-VIII is hydrogen, lower alkyl, $C_3$-$C_6$cycloalkyl or tetrahydropyran, wherein the lower alkyl is optionally substituted with hydroxy or $—C(O)OR^{81}$;

$R^{85}$ of PTM-VIII is hydrogen, lower alkyl, or benzyl, n of PTM-VIII is 0, 1, 2, or 3;

p of PTM-VIII is 1 or 2;

Z of PTM-VIII is chosen from O, S, and $NR^{21}$; and the PTM-VIII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-I is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, $R^5$, $R^6$, $R^7$, $R^8$, $R^9$, $R^{10}$, $R^{11}$, $R^{21}$, $R^{41}$, $R^{51}$, $R^{52}$, $R^{61}$, $R^{71}$, $R^{81}$, $R^{82}$, $R^{83}$, $R^{84}$, or $R^{85}$).

In any aspect or embodiment described herein, the Ring A of PTM-VIII is selected from the group consisting of:

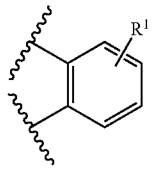

,

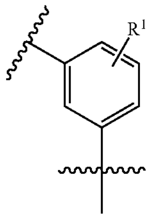

,

-continued

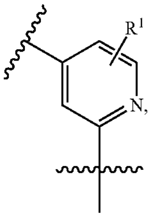

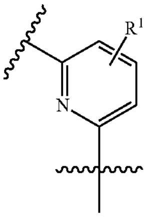
,

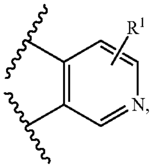

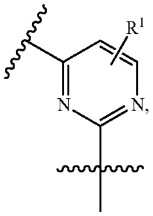

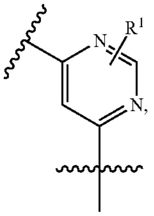

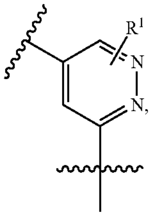

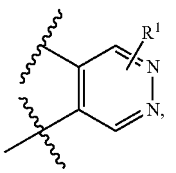

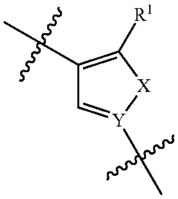
,

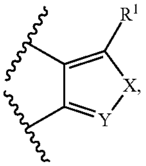

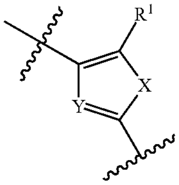
, or

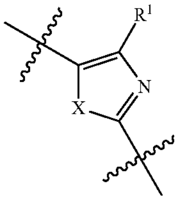
, wherein $R^1$ is hydrogen or lower alkyl, X is O, S, or $NR^{11}$, and $R^{11}$ is hydrogen or lower alkyl, and Y is C, CH, or N.

In any aspect or embodiment described herein, the Ring B of PTM-VIII is selected from the group consisting of:

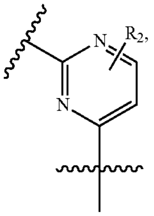

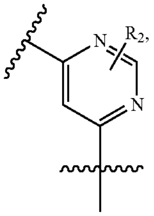

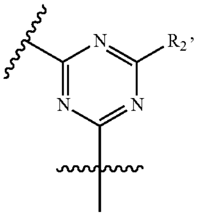

-continued

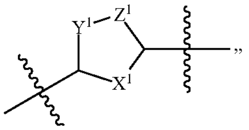
,

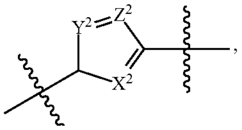
,

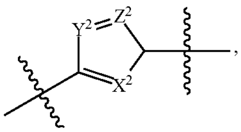
,

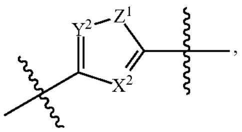
,

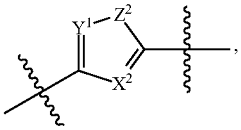
, and

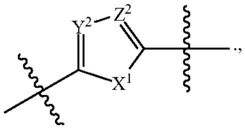
, wherein: $X^1$, $Y^1$, and $Z^1$ are independently chosen from $NR^{21}$, O, $C(R^{21})_2$, and S; $X^2$, $Y^2$, and $Z^2$ are independently chosen from N and $CR^{21}$; and $R^2$ is chosen from hydrogen and lower alkyl, wherein for each occurrence, $R^{21}$ is independently chosen from hydrogen and lower alkyl optionally substituted with lower alkoxy, wherein lower alkoxy is optionally substituted with tri(alkyl)silyl.

In any aspect or embodiment described herein, the Ring B of PTM-VIII is

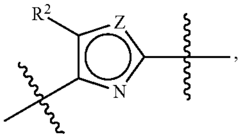
, wherein: Z is chosen from O, S, and $NR^{21}$; and $R^2$ is chosen from hydrogen and lower alkyl, if present, $R^{21}$ is chosen from hydrogen and lower alkyl optionally substituted with lower alkoxy, wherein lower alkoxy is optionally substituted with tri(alkyl)silyl.

In any aspect or embodiment described herein, the $R^4$ of PTM-VIII is arylene optionally substituted with one or more $R^{42}$ wherein for each occurrence, $R^{42}$ is independently chosen from: heterocycloalkyl; lower alkyl optionally substituted with —C(O)OR$^9$, amino, N-(alkyl)amino, N,N-(dialkyl)amino, cycloalkyl, or heterocycloalkyl; —C(O)OR$^9$; hydroxyl; and —C(O)NR$^{10}$R$^{11}$, wherein $R^9$ is chosen from hydrogen and lower alkyl, $R^{10}$ and R are independently hydrogen and lower alkyl, or $R^9$ and $R^{10}$, together with the nitrogen to which they are bound form a heterocycloalkyl, and each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

In any aspect or embodiment described herein, the $R^4$ of the PTM-VIII is selected from the group consisting of

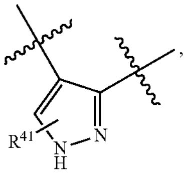
,
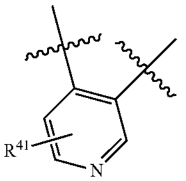
,
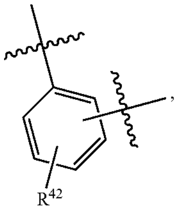
,
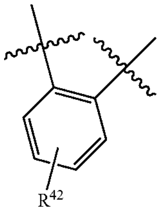
, and
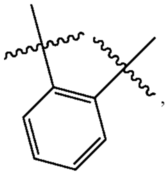
, wherein.

In any aspect or embodiment described herein, the $R^4$ of PTM-VIII is heteroarylene optionally substituted with one or more $R^{41}$.

In any aspect or embodiment described herein, the $R^{41}$ of PTM-VIII is heterocycloalkyl chosen from tetrahydropyranyl, piperidinyl, hexahydropyrimidinyl, and morpholinyl, each of which is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

In any aspect or embodiment described herein, $R^3$ and $R^4$ of PTM-VIII taken together with the nitrogen to which they are bound, form a 3- to 7-membered heterocycloalkyl ring optionally substituted with one or more $R^{44}$ wherein for each occurrence, $R^{44}$ is independently chosen from: heterocycloalkyl; lower alkyl optionally substituted with —C(O)OR$^9$, amino, N-(alkyl)amino, N,N-(dialkyl)amino, cycloalkyl, or heterocycloalkyl; —C(O)OR$^9$; hydroxyl; and —C(O)NR$^{10}$R$^{11}$, wherein $R^9$ is chosen from hydrogen and lower alkyl, $R^{10}$ and $R^{11}$ are independently hydrogen and lower alkyl, or $R^9$ and $R^{10}$, together with the nitrogen to which they are bound form a heterocycloalkyl, and each lower alkyl, cycloalkyl and heterocycloalkyl is optionally substituted with one, two, or three groups independently chosen from —C(O)OR$_9$, lower alkyl, lower alkoxy, hydroxyl, halogen, amino, N-(alkyl)amino, N,N-(dialkyl)amino, and heterocycloalkyl.

In any aspect or embodiment described herein, $R^3$ and $R^4$ of PTM-VIII taken together with the nitrogen to which they are bound, for a 3- to 7-membered hereocycloalkyl ring of

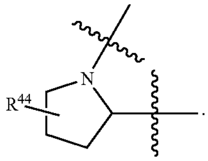
.

In any aspect or embodiment described herein, $R^4$ of PTM-VII is absent.

In any aspect or embodiment described herein, the PTM is represented by Formula PTM-IX (i.e., Formulas PTM-IXa, PTM-IXb, PTM-IXc, PTM-IXd, and/or PTM-IXe, which correspond to Formulas I, II, III, IV, and the structure produced on page 20, respectively, from International Patent Application Publication WO 2016/011390 A1, which is incorporated herein in its entirety for all purposes, PTM-IXf, PTM-IXg, PTM-IXh, PTM-IXi, PTM-IXj, PTM-IXk, PTM-IXl, and/or PTM-IXm):

PTM-IXa

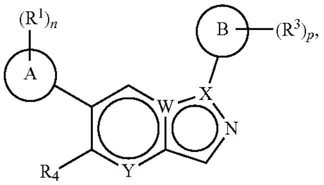

PTM-IXb

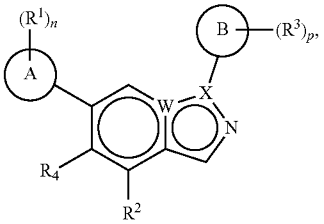

PTM-IXc

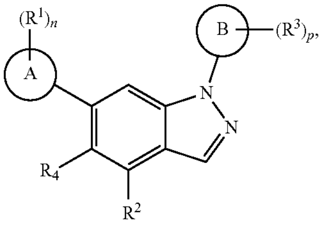

PTM-IXd

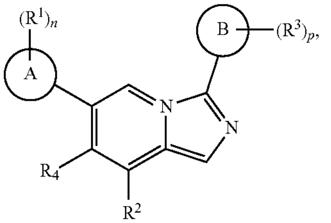
or

PTM-IXe

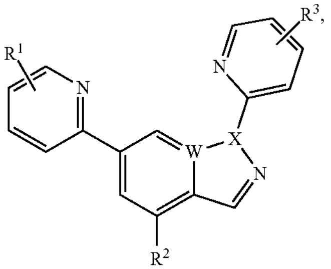

-continued

PTM-IXf

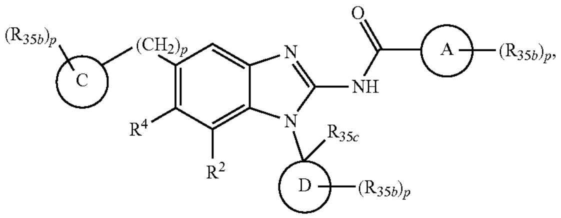

PTM-IXg

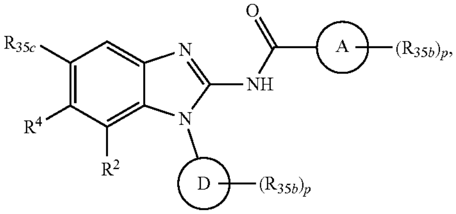

PTM-IXh

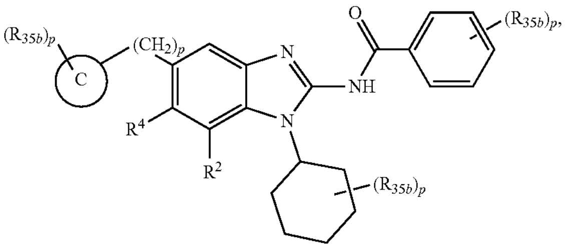

PTM-IXi

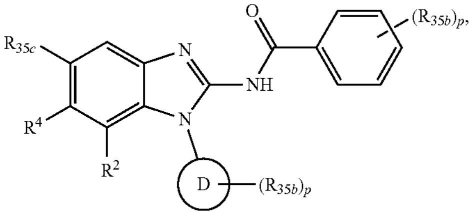

PTM-IXj

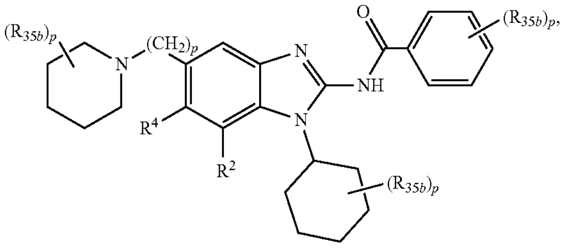

PTM-IXk

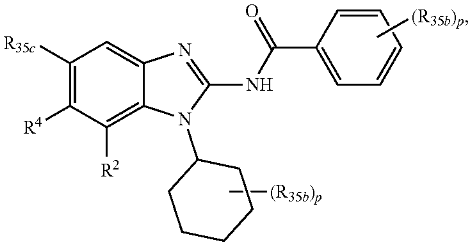

-continued

PTM-IXl

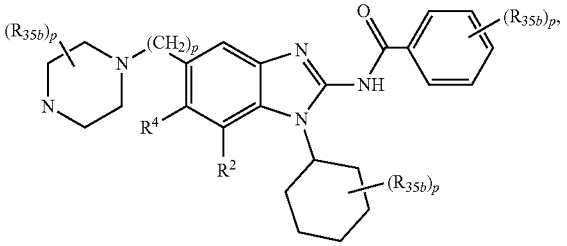

PTM-IXm

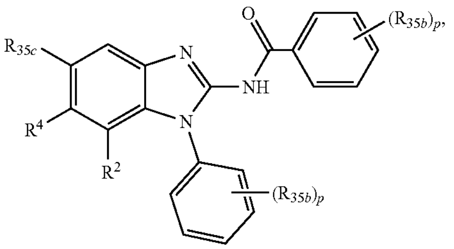

PTM-IXn

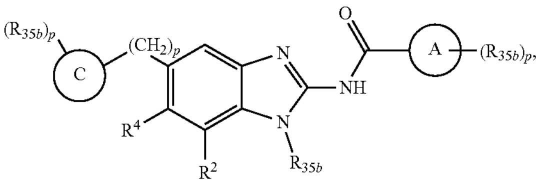

wherein:

Ring A of PTM-IX is selected from phenyl and 5- or 6-membered heteroaryl;

Ring B of PTM-IX is selected from phenyl and 5- or 6-membered heteroaryl;

Ring C of PTM-IX is selected from a 5- or 6-membered cycloalkyl or cycloheteroalkyl;

Rind D of PTM-IX selected from phenyl, 5-membered aryl or heteroaryl, 6-member aryl or heteroaryl, 5-membered cycloalkyl or cycloheteroalkyl, or 6-membered cycloalkyl or cycloheteroalkyl;

n of PTM-IX is 0, 1, or 2;

p of PTM-IX is 0, 1, or 2;

one of W and X of PTM-IX is N, and the other of W and X is C;

Y of PTM-IX is N or C—$R^2$;

$R^1$ of PTM-IX is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{1a}$)═NR(O$R^{1a}$), —C($R^{1a}$)═N($R^{1a}$), —C(O)$R^{1a}$, —C(O)$_2R^{1a}$, —C(O)N($R^{1a}$)$_2$, —$NO_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^1$;

$R^{1a}$ of PTM-IX in each occurrence is independently selected from H, $C_{1-6}$alkyl, $C_{2-6}$alkenyl, $C_{2-6}$alkynyl, 3- to 6-membered monocyclic carbocyclyl, and 3- to 6-membered monocyclic heterocyclyl wherein said $C_{1-6}$alkyl, $C_{2-6}$alkenyl, $C_{2-6}$alkynyl, 3- to 6-membered monocyclic carbocyclyl, and 3- to 6-membered monocyclic heterocyclyl in each occurrence are optionally and independently substituted with one or more $R^{10}$;

$R^{10}$ of PTM-IX in each occurrence is independently selected from C^aUcyl, $C_{2-6}$alkenyl, $C_{2-6}$alkynyl, 3- to 6-membered carbocyclyl, 3- to 6-membered heterocyclyl, halo, —CN, —$C(R^{10a})$═$NR(OR^{10a})$, —$C(R^{10a})$═$N(R^{10a})$, —$C(O)R^{10a}$, —$C(O)_2R^{10a}$, —$C(O)N(R^{10a})_2$, —$NO_2$, —$N(R^{10a})_2$, —$N(R^{10a})C(O)R^{10a}$, —$N(R^{10a})C(O)_2R^{10a}$, —$N(R^{10a})C(O)N(R^{10a})_2$, —$N(R^{10a})S(O)_2R^{10a}$, —$OR^{10a}$, —$OC(O)R^{10a}$, —$OC(O)N(R^{10a})_2$, —$SR^{10a}$, —$S(O)R^{10a}$, —$S(O)_2R^{10a}$, —$S(O)N(R^{10a})_2$, and —$S(O)_2N(R^{10a})_2$;

$R^{10a}$ of PTM-IX in each occurrence is independently selected from H and $C_{1-6}$alkyl, wherein said $C_{1-6}$alkyl is optionally substituted with one or more halo;

$R^{15}$ of PTM-IX in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —$C(R^{15a})$═$NR(OR^{15a})$, —$C(R^{15a})$═$N(R^{15a})$, —$C(O)R^{15a}$, —$C(O)_2R^{15a}$, —$C(O)N(R^{15a})_2$, —$NO_2$, —$N(R^{15a})_2$, —$N(R^{15a})C(O)R^{15a}$, —$N(R^{15a})C(O)_2R^{15a}$, —$N(R^{15a})C(O)N(R^{15a})_2$, —$N(R^{15a})S(O)_2R^{15a}$, —$OR^{15a}$, —$OC(O)R^{15a}$, —$OC(O)N(R^{15a})_2$, —$SR^{15a}$, —$S(O)R^{15a}$, —$S(O)_2R^{15a}$, —$S(O)N(R^{15a})_2$, and —$S(O)_2N(R^{15a})_2$;

$R^{15a}$ of PTM-IX in each occurrence is independently selected from H and $C_{1-6}$alkyl, wherein said $C_{1-6}$alkyl is optionally substituted with one or more halo;

$R^2$ of PTM-IX is selected from H, $C_{1-6}$alkyl, $C_{2-6}$alkenyl, $C_{2-6}$alkynyl, 3- to 7-membered carbocyclyl, 3- to 7-membered heterocyclyl, halo, —CN, —$C(R^{2a})$═$NR(OR^{2a})$, —$C(R^{2a})$═$N(R^{2a})$, —$C(O)R^{2a}$, —$C(O)_2R^{2a}$, —$C(O)N(R^{2a})_2$, —$NO_2$, —$N(R^{2a})_2$, —$N(R^{2a})C(O)R^{2a}$, —$N(R^{2a})C(O)_2R^{2a}$, —$N(R^{2a})C(O)N(R^{2a})_2$, —$N(R^{2a})S(O)_2R^{2a}$, —$OR^{2a}$, —$OC(O)R^{2a}$, —$OC(O)N(R^{2a})_2$, —$SR^{2a}$, —$S(O)R^{2a}$, —$S(O)_2R^{2a}$, —$S(O)N(R^{2a})_2$, and —$S(O)_2N(R^{2a})_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one or more $R^{20}$;

$R^{2a}$ of PTM-IX in each occurrence is independently selected from H and $C_{1-6}$alkyl, wherein said $C_{1-6}$alkyl in each occurrence is optionally and independently substituted with one or more $R^{20}$;

$R^{20}$ of PTM-IX in each occurrence is independently selected from $C_{1-6}$alkyl, $C_{2-6}$alkenyl, $C_{2-6}$alkynyl, $C_{3-7}$cycloalkyl, 3- to 7-membered saturated heterocyclyl, halo, —CN, —$C(R^{20a})$═$NR(OR^{20a})$, —$C(R^{20a})$═$N(R^{20a})$, —$C(O)R^{20a}$, —$C(O)_2R^{20a}$, —$C(O)N(R^{20a})_2$, —$NO_2$, —$N(R^{20a})_2$, —$N(R^{20a})C(O)R^{20a}$, —$N(R^{20a})C(O)_2R^{20a}$, —$N(R^{20a})C(O)N(R^{2a})_2$, —$N(R^{20a})S(O)_2R^{20a}$, —$OR^{20a}$, —$OC(O)R^{20a}$, —$OC(O)N(R^{20a})_2$, —$SR^{20a}$, —$S(O)R^{20a}$, —$S(O)_2R^{2a}$, —$S(O)N(R^{20a})_2$, and —$S(0)_2N(R)_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one or more $R^{25}$;

$R^{20a}$ of PTM-IX in each occurrence is independently selected from H and $C_{1-6}$alkyl, wherein said $C_{1-6}$alkyl is optionally substituted with $R^{25}$;

$R^{25}$ of PTM-IX is selected from halo and —$OR^{25a}$;

$R^{25a}$ of PTM-IX is selected from H and $C_{1-6}$alkyl;

$R^3$ of PTM-IX is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —$C(R^{3a})$═$NR(OR^{3a})$, —$C(R^{3a})$═$N(R^{3a})$, —$C(O)R^{3a}$, —$C(O)_2R^{3a}$, —$C(O)N(R^{3a})_2$, —$NO_2$, —$N(R^{3a})_2$, —$N(R^{3a})C(O)R^{3a}$, —$N(R^{3a})C(O)_2R^{3a}$, —$N(R^{3a})C(O)N(R^{3a})_2$, —$N(R^{3a})S(O)_2R^{3a}$, —$OR^{3a}$, —$OC(O)R^{3a}$, —$OC(O)N(R^{3a})_2$, —$SR^{3a}$, —$S(O)R^{3a}$, —$S(O)_2R^{3a}$, —$S(O)N(R^{3a})_2$, and —$S(O)_2N(R^{3a})_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{30}$.

$R^{3a}$ of PTM-IX in each occurrence is independently selected from H, $C_{1-6}$alkyl, 3- to 6-membered carbocyclyl, and 3- to 6-membered heterocyclyl, wherein said $C_{1-6}$alkyl, 3- to 6-membered carbocyclyl, and 3- to 6-membered heterocyclyl in each occurrence are optionally and independently substituted with one or more $R^{30}$;

$R^{30}$ of PTM-IX in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —$C(R^{30a})$═$NR(OR^{30a})$, —$C(R^{30a})$═$N(R^{30a})$, —$C(O)R^{30a}$, —$C(O)_2R^{30a}$, —$C(O)N(R^{30a})_2$, —$NO_2$, —$N(R^{30a})_2$, —$N(R^{30a})C(O)R^{30a}$, —$N(R^{30a})C(O)_2R^{30a}$, —$N(R^{30a})C(O)N(R^{30a})_2$, —$N(R^{30a})S(O)_2R^{30a}$, —$OR^{30a}$, —$OC(O)R^{30a}$, —$OC(O)N(R^{30a})_2$, —$SR^{30a}$, —$S(O)R^{30a}$, —$S(O)_2R^{30a}$, —$S(O)N(R^{30a})_2$, and —$S(O)_2N(R^{30a})_2$, wherein said $C_{1-3}$alkyl, $C_{2-6}$alkenyl, $C_{2-6}$alkynyl, 3-6 membered carboyclyl, 3- to 6-membered heterocyclyl in each occurrence are optionally and independently substituted with one or more $R^{35}$;

$R^{30a}$ of PTM-IX in each occurrence is independently selected from H and $C_{1-6}$alkyl, wherein said $C_{1-6}$alkyl is optionally substituted with one or more $R^3$;

$R^{35}$ of PTM-IX in each occurrence is independently selected from halo and —$OR^{35}$a;

$R^{35a}$ of PTM-IX in each occurrence is independently selected from H and $C_{1-6}$alkyl;

$R^{35b}$ of PTM-IX in each occurrence is independently selected from H, halo, optionally substituted alkoxy (e.g., optionally substituted C1-C4 alkoxy), optionally substituted alkyl (e.g., C1-C4 alkyl optionally substituted with halo or hydroxy), hydroxyalkyl (e.g. C1-C4 hydroxyalkyl), or haloalkyl (e.g., C1-C4 haloalkyl);

$R^{35c}$ of PTM-IX in each occurrence is independently selected from halo or haloalkyl (e.g., C1-C4 haloalkyl);

$R^4$ of PTM-IX is selected from H, halo, $C_{1-6}$alkyl, $N(R^{4a})_2$, and —$OR^{4a}$;

$R^{4a}$ of PTM-IX in each occurrence is independently selected from H and $C_{1-6}$alkyl; and the PTM-IX is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-IX is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^{1a}$, $R^2$, $R^{2a}$, $R^3$, $R^{3a}$, $R^4$, $R^{4a}$, $R^{10}$, $R^{10a}$, $R^{15}$, $R^{15a}$, $R^{20}$, $R^{20a}$, $R^{25}$, $R^{25a}$, $R^{30}$, $R^{30a}$, $R^{35}$, $R^{35a}$, $R^{35b}$, or $R^{35c}$).

In any aspect or embodiment described herein, the PTM of PTM-IX comprises R is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{1a}$)═NR($OR^{1a}$), —C($R^{1a}$)═N($R^{1a}$), —C(O)$R^{1a}$, —C$(O)_2R^{1a}$, —C(O)N$(R^{1a})_2$, —N$(R^{1a})_2$, —N($R^{1a}$)C(O)$R^{1a}$, —N($R^{1a}$)C$(o)_2R^{1a}$, —N($R^{1a}$)C(O)N$(R^{1a})_2$, —N($R^{1a}$)S$(O)_2R^{1a}$, —$OR^{1a}$, —OC(O)$R^{1a}$, —OC(O)N$(R^{1a})_2$, —$SR^{1a}$, —S(O)$R^{1a}$, —S$(O)_2R^{1a}$, —S(O)N$(R^{1a})_2$, and —S$(O)_2$N$(R^{1a})_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^{15}$.

In any aspect or embodiment described herein, wherein: Ring A of PTM-IX is 5- or 6-membered heteroaryl and Ring B of PTM-IX is 5- or 6-membered heteroaryl; Ring A of PTM-IX is a 5- or 6-membered heteroaryl and the Ring B of PTM-IX is phenyl; Ring A of PTM-IX is a phenyl and Ring B of PTM-IX is a 5- or 6-membered heteroaryl; and Ring A is a phenyl and Ring B is phenyl, wherein the 5- or 6-membered heteroaryl in each occurrence may be independently selected from pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, or tetrazinyl.

In any aspect or embodiment described herein, the PTM of PTM-IX is selected from the group consisting of: 6-(1-(6-methylpyridin-2-yl)-1H-indazol-6-yl)pyridin-2-amine; 2-(1-(6-methylpyridin-2-yl)-1H-indazol-6-yl)pyrimidin-4-amine; 2-(1-(6-methylpyridin-2-yl)-1H-indazol-6-yl)pyridin-4-amine; (6-(1-(6-methylpyridin-2-yl)-1H-indazol-6-yl)pyridin-2-yl)methanamine; (2-(1-(6-methylpyridin-2-yl)-1H-indazol-6-yl)pyridin-4-yl)methanamine; 4-(1-(6-methylpyridin-2-yl)-1H-indazol-6-yl)pyridin-2-amine; 5-(1-(6-methylpyridin-2-yl)-1H-indazol-6-yl)pyridin-3-amine; 3-(1-(6-methylpyridin-2-yl)-1H-indazol-6-yl)aniline; (2-(1-(6-methylpyridin-2-yl)-1H-indazol-6-yl)pyrimidin-4-yl)methanamine; 4-methyl-5-(1-(6-methylpyridin-2-yl)-1H-indazol-6-yl)pyridin-3-amine; 3-(1-(6-methylpyridin-2-yl)-1H-indazol-6-yl)-5-nitropyridin-2-ol; 3-amino-5-(1-(6-methylpyridin-2-yl)-1H-indazol-6-yl)pyridin-4-ol; N-methyl-5-(1-(6-methylpyridin-2-yl)-1H-indazol-6-yl)pyridin-3-amine; N,N-dimethyl-1-(6-(1-(6-methylpyridin-2-yl)-1H-indazol-6-yl)pyridin-2-yl)methanamine; 5-(1-(6-methylpyridin-2-yl)-1H-indazol-6-yl)-1,2,3,4-tetrahydroisoquinoline; 2-methyl-5-(1-(6-methylpyridin-2-yl)-1H-indazol-6-yl)-1,2,3,4-tetrahydroisoquinoline; 6-(2-methylisoindolin-4-yl)-1-(6-methylpyridin-2-yl)-1H-indazole; N-methyl-1-(3-(1-(6-methylpyridin-2-yl)-1H-indazol-6-yl)phenyl)methanamine; 3-(6-(3-aminophenyl)-1H-indazol-1-yl)benzonitrile; 3-(1-(pyridin-2-yl)-1H-indazol-6-yl)aniline; 6-(6-(3-aminophenyl)-1H-indazol-1-yl)picolinonitrile; 3-(1-(4,6-dimethylpyridin-2-yl)-1H-indazol-6-yl)aniline; 3-(1-(5,6-dimethylpyridin-2-yl)-1H-indazol-6-yl)aniline; 3-(1-(6-(trifluoromethyl)pyridin-2-yl)-1H-indazol-6-yl)aniline; 5-(1-(6-cyclopropylpyridin-2-yl)-1H-indazol-6-yl)pyridin-3-amine; 5-(1-(6-cyclobutylpyridin-2-yl)-1H-indazol-6-yl)pyridin-3-amine; 6-(6-(5-aminopyridin-3-yl)-1H-indazol-1-yl)picolinonitrile; 6-(6-(5-aminopyridin-3-yl)-1H-indazol-1-yl)picolinic acid; 6-(6-(5-aminopyridin-3-yl)-1H-indazol-1-yl)picolinamide; 6-(6-(5-aminopyridin-3-yl)-1H-indazol-1-yl)-N-methylpicolinamide; 3-(6-(5-aminopyridin-3-yl)-1H-indazol-1-yl)benzonitrile; 2-(6-(5-aminopyridin-3-yl)-1H-indazol-1-yl)-6-methylisonicotinonitrile; 2-(6-(5-aminopyridin-3-yl)-1H-indazol-1-yl)isonicotinonitrile; 5-(1-(4-methylpyrimidin-2-yl)-1H-indazol-6-yl)pyridin-3-amine; 2-(6-(5-aminopyridin-3-yl)-1H-indazol-1-yl)pyrimidine-4-carbonitrile; 5-(1-(3-chloro-6-methylpyridin-2-yl)-1H-indazol-6-yl)pyridin-3-amine; 5-(1-(4-methylpyridin-2-yl)-1H-indazol-6-yl)pyridin-3-amine; 5-(1-(6-(trifluoromethyl)pyridin-2-yl)-1H-indazol-6-yl)pyridin-3-amine; 5-(3-(6-methylpyridin-2-yl)imidazo[1,5-a]pyridin-6-yl)pyridin-3-amine; 3-(3-(6-methylpyridin-2-yl)imidazo[1,5-a]pyridin-6-yl)aniline; 5-(5-fluoro-1-(6-methylpyridin-2-yl)-1H-indazol-6-yl)pyridin-3-amine; 5-(5-methyl-1-(6-methylpyridin-2-yl)-1H-indazol-6-yl)pyridin-3-amine; 6-(6-(6-(aminomethyl)pyridin-2-yl)-1H-indazol-1-yl)picolinonitrile; 6-(6-(6-(aminomethyl)pyridin-2-yl)-1H-indazol-1-yl)picolinamide; (6-(1-(6-(trifluoromethyl)pyridin-2-yl)-1H-indazol-6-yl)pyridin-2-yl)methanamine; methyl 6-(5-aminopyridin-3-yl)-1-(6-cyanopyridin-2-yl)-1H-indazole-4-carboxylate; methyl 6-(5-aminopyridin-3-yl)-1-(6-(trifluoromethyl)pyridin-2-yl)-1H-indazole-4-carboxylate; 6-(5-aminopyridin-3-yl)-1-(6-(trifluoromethyl)pyridin-2-yl)-1H-indazole-4-carboxylic acid; 6-(5-aminopyridin-3-yl)-1-(6-(trifluoromethyl)pyridin-2-yl)-1H-indazole-4-carboxamide; 5-(4-(aminomethyl)-1-(6-(trifluoromethyl)pyridin-2-yl)-1H-indazol-6-yl)pyridin-3-amine; (6-(5-aminopyridin-3-yl)-1-(6-(trifluoromethyl)pyridin-2-yl)-1H-indazol-4-yl)methanol; 1-(6-(1-(6-methylpyridin-2-yl)-1H-indazol-6-yl)pyridin-2-yl)ethanamine; methyl 6-(6-(1-aminoethyl)pyridin-2-yl)-1-(6-(trifluoromethyl)pyridin-2-yl)-1H-indazole-4-carboxylate; (6-(6-(1-aminoethyl)pyridin-2-yl)-1-(6-(trifluoromethyl)pyridin-2-yl)-1H-indazol-4-yl)methanol; 6-(6-(1-aminoethyl)pyridin-2-yl)-N,N-dimethyl-1-(6-(trifluoromethyl)pyridin-2-yl)-1H-indazole-4-carboxamide; 6-(6-(1-aminoethyl)pyridin-2-yl)-N-methyl-1-(6-(trifluoromethyl)pyridin-2-yl)-1H-indazole-4-carboxamide; 6-(5-aminopyridin-3-yl)-N,N-dimethyl-1-(6-(trifluoromethyl)pyridin-2-yl)-1H-indazole-4-carboxamide; 6-(5-aminopyridin-3-yl)-N-methyl-1-(6-(trifluoromethyl)pyridin-2-yl)-1H-indazole-4-carboxamide; 2-(1-(6-(trifluoromethyl)pyridin-2-yl)-1H-indazol-6-yl)-6,7-dihydro-5H-cyclopenta[b] pyridin-7-amine ; 2-(1-(6-(trifluoromethyl)pyridin-2-yl)-1H-indazol-6-yl)-5,6,7,8-tetrahydroquinolin-8-amine; 6-(6-(5-aminopyridin-3-yl)-1H-indazol-1-yl)-N,N-dimethylpicolinamide; 6-(6-(5-aminopyridin-3-yl)-1H-indazol-1-yl)-N-(2-hydroxyethyl)picolinamide; 6-(6-(5-aminopyridin-3-yl)-1H-indazol-1-yl)-N-(3-hydroxypropyl)picolinamide; 6-(6-(5-aminopyridin-3-yl)-1H-indazol-1-yl)-N-(2-hydroxypropyl)picolinamide; (6-(6-(5-aminopyridin-3-yl)-1H-indazol-1-yl)pyridin-2-yl)(3-hydroxyazetidin-1-yl)methanone; 6-(6-(5-aminopyridin-3-yl)-1H-indazol-1-yl)-N-(2-(dimethylamino)ethyl)picolinamide; 6-(6-(5-aminopyridin-3-yl)-1H-indazol-1-yl)-N-(2-cyanoethyl)picolinamide; 6-(6-(5-aminopyridin-3-yl)-1H-indazol-1-yl)-N-(3-cyanopropyl)picolinamide; N-(2-aminoethyl)-6-(6-(5-aminopyridin-3-yl)-1H-indazol-1-yl)picolinamide; 6-(6-(5-aminopyridin-3-yl)-1H-indazol-1-yl)-N-(cyanomethyl)picolinamide; 6-(6-(5-aminopyridin-3-yl)-1H-indazol-1-yl)-N-(2-(methylsulfonyl)ethyl)picolinamide; 3-(6-(5-aminopyridin-3-yl)imidazo[1,5-a]pyridin-3-yl)benzonitrile; 6-(6-(5-aminopyridin-3-yl)imidazo[1,5-a]pyridin-3-yl)picolinonitrile; 6-(6-(5-aminopyridin-3-yl)imidazo[1,5-a]pyridin-3-yl)picolinamide; 5-(3-(6-(trifluoromethyl)pyridin-2-yl)imidazo[1,5-a]pyridin-6-yl)pyridin-3-amine; 1-(6-(3-(6-(trifluoromethyl)pyridin-2-yl)imidazo[1,5-a]pyridin-6-yl)pyridin-2-yl)ethanamine; 2-(aminomethyl)-6-(1-(6-(trifluoromethyl)pyridin-2-yl)-1H-indazol-6-yl)pyridin-4-amine; 2-(6-(6-(5-aminopyridin-3-yl)-1H-indazol-1- yl)pyridin-2-yl)acetonitrile; 2-(6-(6-(5-aminopyridin-3-yl)-1H-indazol-1-yl)pyridin-2-yl)acetic acid; 1-(6-(1-(6-(trifluoromethyl)pyridin-2-yl)-1H-indazol-6-yl)pyridin-2-yl)ethanamine; 3-amino-5-(1-(6-(trifluoromethyl)pyridin-2-yl)-1H-indazol-6-yl)benzoic acid; 3-amino-N-(cyanomethyl)-5-(1-(6-(trifluoromethyl)pyridin-2-yl)-1H-indazol-6-yl)benzamide; 6-amino-N-(cyanomethyl)-4-(1-(6-(trifluoromethyl)pyridin-2-yl)-1H-indazol-6-yl)picolinamide; 3-amino-N-(2-aminoethyl)-5-(1-(6-(trifluoromethyl)pyridin-2-yl)-1H-indazol-6-yl)benzamide; 1-(3-(1-(6-(trifluoromethyl)pyridin-2-yl)-1H-indazol-6-yl)phenyl)ethanamine; 1-(5-(1-(6-(trifluoromethyl)pyridin-2-yl)-1H-indazol-6-yl)pyridin-3-yl)ethanamine; 1-(4-(1-(6-(trifluoromethyl)pyridin-2-yl)-1H-indazol-6-yl)pyridin-2-yl)ethanamine; 6-(1-(6-(trifluoromethyl)pyridin-2-yl)-1H-indazol-6-yl)pyrazine-2-carbonitrile; (6-(1-(6-(trifluoromethyl)pyridin-2-yl)-1H-indazol-6-yl)pyrazin-2-yl)methanamine; 4-(1-(6-(trifluoromethyl)pyridin-2-yl)-1H-indazol-6-yl)pyrimidine-2-carbonitrile; (4-(1-(6-(trifluoromethyl)pyridin-2-yl)-1H-indazol-6-yl)pyrimidin-2-yl)methanamine; 6-(1-(6-(trifluoromethyl)pyridin-2-yl)-1H-indazol-6-yl)pyrazin-2-amine; 6-(6-(pyrrolidin-2-yl)pyridin-2-yl)-1-(6-(trifluoromethyl)pyridin-2-yl)-1H-indazole; 6-(6-(1-methylpyrrolidin-2-yl)pyridin-2-yl)-1-(6-(trifluoromethyl)pyridin-2-yl)-1H-indazole; 1-(6-(3-(6-methylpyridin-2-yl)imidazo[1,5-a]pyridin-6-yl)pyridin-2-yl)ethanamine; 6-(6-(1-aminoethyl)pyridin-2-yl)-1-(6-methylpyridin-2-yl)-1H-indazol-4-amine; 6-(6-(1-aminoethyl)pyridin-2-yl)-N-methyl-1-(6-methylpyridin-2-yl)-1H-indazol-4-amine; 6-(6-(1-aminoethyl)pyridin-2-yl)-N,N-dimethyl-1-(6-methylpyridin-2-yl)-1H-indazol-4-amine; N-(6-(6-(1-aminoethyl)pyridin-2-yl)-1-(6-methylpyridin-2-yl)-1H-indazol-4-yl)acetamide; 1-(6-(4-(aminomethyl)-1-(6-methylpyridin-2-yl)-1H-indazol-6-yl)pyridin-2-yl)ethanamine; N-((6-(6-(1-aminoethyl)pyridin-2-yl)-1-(6-methylpyridin-2-yl)-1H-indazol-4-yl)methyl)acetamide; 1-(6-(4-chloro-1-(6-methylpyridin-2-yl)-1H-indazol-6-yl)pyridin-2-yl)ethanamine; 1-(6-(4-cyclopropyl-1-(6-methylpyridin-2-yl)-1H-indazol-6-yl)pyridin-2-yl)ethanamine; 1-(6-(1-(6-methylpyridin-2-yl)-4-(prop-1-en-2-yl)-1H-indazol-6-yl)pyridin-2-yl)ethanamine; 1-(6-(4-ethyl-1-(6-methylpyridin-2-yl)-1H-indazol-6-yl)pyridin-2-yl)ethanamine; 1-(6-(4-isopropyl-1-(6-methylpyridin-2-yl)-1H-indazol-6-yl)pyridin-2-yl)ethanamine; 1-(6-(1-(6-methylpyridin-2-yl)-4-(trifluoromethyl)-1H-indazol-6-yl)pyridin-2-yl)ethanamine; methyl 6-(6-(1-aminoethyl)pyridin-2-yl)-1-(6-methylpyridin-2-yl)-1H-indazole-4-carboxylate; 6-(6-(1-aminoethyl)pyridin-2-yl)-1-(6-methylpyridin-2-yl)-1H-indazole-4-carboxylic acid; 6-(6-(1-aminoethyl)pyridin-2-yl)-1-(6-methylpyridin-2-yl)-1H-indazol-4-yl)methanol; 6-(6-(1-aminoethyl)pyridin-2-yl)-N-methyl-1-(6-methylpyridin-2-yl)-1H-indazole-4-carboxamide; N-methyl-1-(6-(1-(6-methylpyridin-2-yl)-1H-indazol-6-yl)pyridin-2-yl)ethanamine; N-methyl-1-(6-(1-(6-(trifluoromethyl)pyridin-2-yl)-1H-indazol-6-yl)pyridin-2-yl)ethanamine; 1-(6-(1-(6-cyclopropylpyridin-2-yl)-1H-indazol-6-yl)pyridin-2-yl)ethanamine; 1-(6-(1-(6-ethylpyridin-2-yl)-1H-indazol-6-yl)pyridin-2-yl)ethanamine; 1-(6-(1-(6-isopropylpyridin-2-yl)-1H-indazol-6-yl)pyridin-2-yl)ethanamine; 1-(6-(1-(pyridin-2-yl)-1H-indazol-6-yl)pyridin-2-yl)ethanamine; (6-(6-(6-(1-aminoethyl)pyridin-2-yl)-1H-indazol-1-yl)pyridin-2-yl)methanol; 1-(4-methyl-6-(1-(6-methylpyridin-2-yl)-1H-indazol-6-yl)pyridin-2-yl)ethanamine; 1-(6-(1-(6-methylpyridin-2-yl)-1H-indazol-6-yl)-4-(trifluoromethyl)pyridin-2-yl)ethanamine; 6-(6-(6-(1-aminoethyl)pyridin-2-yl)-1H-indazol-1-yl)picolinamide; 1-(6-(1-(6-(trifluoromethyl)pyridin-2-yl)-1H-indazol-6-yl)pyridin-2-yl)propan-1-amine; cyclopropyl(6-(1-(6-(trifluoromethyl)pyridin-2-yl)-1H-indazol-6-yl)pyridin-2-yl)methanamine; 2-(6-(1-(6-(trifluoromethyl)pyridin-2-yl)-1H-indazol-6-yl)pyridin-2-yl)propan-2-amine; 1-(6-(1-(6-methylpyridin-2-yl)-1H-indazol-6-yl)pyridin-2-yl)ethanol; cyclopropyl(6-(1-(6-methylpyridin-2-yl)-1H-indazol-6-yl)pyridin-2-yl)methanamine; 1-(6-(1-(6-methylpyridin-2-yl)-1H-indazol-6-yl)pyridin-2-yl)butan-1-amine; 1-(6-(1-(4-methylthiazol-2-yl)-1H-indazol-6-yl)pyridin-2-yl)ethanamine; 1-(6-(1-(5-methylthiazol-2-yl)-1H-indazol-6-yl)pyridin-2-yl)ethanamine; 1-(6-(1-(2-methylthiazol-4-yl)-1H-indazol-6-yl)pyridin-2-yl)ethanamine; 1-(6-(1-(1-methyl-1H-pyrazol-3-yl)-1H-indazol-6-yl)pyridin-2-yl)ethanamine; 1-(6-(1-(1-methyl-1H-imidazol-4-yl)-1H-indazol-6-yl)pyridin-2-yl)ethanamine; (2-(1-(6-methylpyridin-2-yl)-1H-indazol-6-yl)thiazol-4-yl)methanamine; (2-(1-(6-methylpyridin-2-yl)-1H-indazol-6-yl)thiazol-5-yl)methanamine; (R)-1-(6-(1-(6-methylpyridin-2-yl)-1H-indazol-6-yl)pyridin-2-yl)ethanamine; (S)-1-(6-(1-(6-methylpyridin-2-yl)-1H-indazol-6-yl)pyridin-2-yl)ethanamine; (S)-(6-(6-(6-(1-aminoethyl)pyridin-2-yl)-1H-indazol-1-yl)pyridin-2-yl)methanol; (R)-(6-(6-(6-(1-aminoethyl)pyridin-2-yl)-1H-indazol-1-yl)pyridin-2-yl)methanol; (S)-(6-(6-(6-(1-aminobutyl)pyridin-2-yl)-1H-indazol-1-yl)pyridin-2-yl)methanol; (R)-(6-(6-(6-(1-aminobutyl)pyridin-2-yl)-1H-indazol-1-yl)pyridin-2-yl)methanol; 1-(6-methylpyridin-2-yl)-1H-pyrazolo[4,3-c]pyridin-7-amine; 2-(1-(6-methylpyridin-2-yl)-1H-indazol-6-yl)isonicotinamide; N,N-dimethyl-5-(1-(6-methylpyridin-2-yl)-1H-indazol-6-yl)pyridin-3-amine; 1-(6-methylpyridin-2-yl)-6-(5-(pyrrolidin-1-yl)pyridin-3-yl)-1H-indazole; 6-methyl-5-(1-(6-methylpyridin-2-yl)-1H-indazol-6-yl)pyridin-3-amine; 5-(1-(6-cyclopentylpyridin-2-yl)-1H-indazol-6-yl)pyridin-3-amine; 5-(1-(6-methylpyridin-2-yl)-1H-indazol-6-yl)-3,4-dihydroisoquinolin-1(2H)-one; 1-(6-(4-fluoro-1-(6-(trifluoromethyl)pyridin-2-yl)-1H-indazol-6-yl)pyridin-2-yl)ethanone; N-(5-(4-cyano-1-(6-(trifluoromethyl)pyridin-2-yl)-1H-indazol-6-yl)pyridin-3-yl)-2,2,2-trifluoroacetamide; 1-(6-(1-(6-(trifluoromethyl)pyridin-2-yl)-1H-indazol-6-yl)pyridin-2-yl)ethanamine; 2-(1-(6-(trifluoromethyl)pyridin-2-yl)-1H-indazol-6-yl)-5H-cyclopenta[b]pyridin-7(6H)-one; 6-(1-(6-(trifluoromethyl)pyridin-2-yl)-1H-indazol-6-yl)picolinonitrile; 2-(1-(6-(trifluoromethyl)pyridin-2-yl)-1H-indazol-6-yl)-6,7-dihydroquinolin-8(5H)-one; 6-amino-4-(1-(6-(trifluoromethyl)pyridin-2-yl)-1H-indazol-6-yl)picolinic acid; 6-(6-(1-aminoethyl)pyridin-2-yl)-1-(6-methylpyridin-2-yl)-1H-indazole-4-carbonitrile; 1-(6-(4-(aminomethyl)-2-(6-methylpyridin-2-yl)-2H-indazol-6-yl)pyridin-2-yl)ethanamine; N,N-dimethyl-1-(6-(1-(6-(trifluoromethyl)pyridin-2-yl)-1H-indazol-6-yl)pyridin-2-yl)ethanamine; N-((6-(6-(1-aminoethyl)pyridin-2-yl)-2-(6-methylpyridin-2-yl)-2H-indazol-4-yl)methyl)acetamide; 1-(6-(4-chloro-1-(6-methylpyridin-2-yl)-1H-indazol-6-yl)pyridin-2-yl)ethanone; (Z)-1-(6-(4-chloro-1-(6-methylpyridin-2-yl)-1H-indazol-6-yl)pyridin-2-yl)ethanone oxime; N,N-dimethyl-1-(6-(1-(6-methylpyridin-2-yl)-1H-indazol-6-yl)pyridin-2-yl)ethanamine; N,N-dimethyl-1-(6-(1-(6-(trifluoromethyl)pyridin-2-yl)-1H-indazol-6-yl)pyridin-2-yl)ethanamine; 1-(6-(3-(6-(trifluoromethyl)pyridin-2-yl)imidazo[1,5-a]pyridin-6-yl)pyridin-2-yl)ethanamine; 1-(6-(3-(6-(trifluoromethyl)pyridin-2-yl)imidazo[1,5-a]pyridin-6-yl)pyridin-2-yl)ethanamine; (Z)-1-(6-(3-(6-(trifluoromethyl)pyridin-2-yl)imidazo[1,5-a]pyridin-6-yl)pyridin-2-yl)ethanone oxime;

tert-butyl (6-(6-acetylpyridin-2-yl)-1-(6-methylpyridin-2-yl)-1H-indazol-4-yl)(methyl)carbamate; (Z)-tert-butyl (6-

(6-(1-(hydroxyimino)ethyl)pyridin-2-yl)-1-(6-methylpyridin-2-yl)-1H-indazol-4-yl)(methyl)carbamate; (Z)-1-(6-(4-(methylamino)-1-(6-methylpyridin-2-yl)-1H-indazol-6-yl)pyridin-2-yl)ethanone oxime; 1-(6-(1-(6-ethylpyridin-2-yl)-1H-indazol-6-yl)pyridin-2-yl)ethanone; 1-(6-(1-(pyridin-2-yl)-1H-indazol-6-yl)pyridin-2-yl)ethanone; (E)-1-(6-(1-(pyridin-2-yl)-1H-indazol-6-yl)pyridin-2-yl)ethanone oxime; 2-(aminomethyl)-6-(1-(6-methylpyridin-2-yl)-1H-indazol-6-yl)pyridin-4-amine; N,N-dimethyl-1-(6-(1-(6-methylpyridin-2-yl)-1H-indazol-6-yl)pyridin-2-yl)ethanamine; 1-(6-(4-(dimethylamino)-1-(6-methylpyridin-2-yl)-1H-indazol-6-yl)pyridin-2-yl)ethanone; (E)-1-(6-(4-(dimethylamino)-1-(6-methylpyridin-2-yl)-1H-indazol-6-yl)pyridin-2-yl)ethanone oxime; (E)-1-(6-(1-(6-ethylpyridin-2-yl)-1H-indazol-6-yl)pyridin-2-yl)ethanone oxime; 6-(6-(6-acetylpyridin-2-yl)-1H-indazol-1-yl)picolinonitrile; (E)-methyl 6-(6-(6-(1-(hydroxyimino)ethyl)pyridin-2-yl)-1H-indazol-1-yl)picolinate; 1-(6-(1-(4-methylthiazol-2-yl)-1H-indazol-6-yl)pyridin-2-yl)ethanone; 1-(6-(4-fluoro-1-(6-(trifluoromethyl)pyridin-2-yl)-1H-indazol-6-yl)pyridin-2-yl)ethanamine; (S)-1-(6-(1-(6-methylpyridin-2-yl)-1H-indazol-6-yl)pyridin-2-yl)ethanamine; 1-(3-fluoro-6-(1-(6-methylpyridin-2-yl)-1H-indazol-6-yl)pyridin-2-yl)ethanamine; methyl 3-amino-6-(1-(6-methylpyridin-2-yl)-1H-indazol-6-yl)picolinate; 2,2,2-trifluoro-1-(6-(1-(6-methylpyridin-2-yl)-1H-indazol-6-yl)pyridin-2-yl)ethanol; 1-(6-(4-ethoxy-1-(6-methylpyridin-2-yl)-1H-indazol-6-yl)pyridin-2-yl)ethanamine; 1-(6-(4-methoxy-1-(6-methylpyridin-2-yl)-1H-indazol-6-yl)pyridin-2-yl)ethanamine; 3-amino-3-(6-(1-(6-methylpyridin-2-yl)-1H-indazol-6-yl)pyridin-2-yl)propan-1-ol; 6-(1-(6-methylpyridin-2-yl)-1H-indazol-6-yl)picolinamide; 2-(6-(1-(6-methylpyridin-2-yl)-1H-indazol-6-yl)pyridin-2-yl)acetonitrile; 6-(6-(1-aminoethyl)pyridin-2-yl)-1-(6-methylpyridin-2-yl)-1H-indazol-4-ol; 1-(6-(4-(cyclopropylmethoxy)-1-(6-methylpyridin-2-yl)-1H-indazol-6-yl)pyridin-2-yl)ethanamine; (4-(1-(6-methylpyridin-2-yl)-1H-indazol-6-yl)thiazol-2-yl)methanamine; N-((6-(1-(6-methylpyridin-2-yl)-1H-indazol-6-yl)pyridin-2-yl)methyl)acetamide; 2-(6-(1-(6-methylpyridin-2-yl)-1H-indazol-6-yl)pyridin-2-yl)ethanamine; 1-(6-(1-(6-methylpyridin-2-yl)-1H-indazol-6-yl)-3-(trifluoromethyl)pyridin-2-yl)ethanamine; 2-(1-aminoethyl)-6-(1-(6-methylpyridin-2-yl)-1H-indazol-6-yl)pyridin-4-amine; (1-methyl-4-(1-(6-methylpyridin-2-yl)-1H-indazol-6-yl)-1H-imidazol-2-yl)methanol; 2-amino-2-(6-(1-(6-methylpyridin-2-yl)-1H-indazol-6-yl)pyridin-2-yl)acetonitrile; 2,2,2-trifluoro-1-(6-(1-(6-methylpyridin-2-yl)-1H-indazol-6-yl)pyridin-2-yl)ethanamine; 3-amino-3-(6-(1-(6-methylpyridin-2-yl)-1H-indazol-6-yl)pyridin-2-yl)propanoic acid; methyl 3-amino-3-(6-(1-(6-methylpyridin-2-yl)-1H-indazol-6-yl)pyridin-2-yl)propanoate; 1-(6-(1-(6-methylpyridin-2-yl)-1H-indazol-6-yl)pyridin-2-yl)cyclopropanamine; 1-(6-(1-(6-methylpyridin-2-yl)-1H-indazol-6-yl)pyridin-2-yl)propan-1-amine; (R)-1-(6-(1-(6-methylpyridin-2-yl)-1H-indazol-6-yl)pyridin-2-yl)butan-1-amine; (S)-1-(6-(1-(6-methylpyridin-2-yl)-1H-indazol-6-yl)pyridin-2-yl)butan-1-amine; 1-(3-chloro-6-(1-(6-methylpyridin-2-yl)-1H-indazol-6-yl)pyridin-2-yl)ethanamine; 2-amino-2-(6-(1-(6-methylpyridin-2-yl)-1H-indazol-6-yl)pyridin-2-yl)acetamide; 1-(6-(1-(6-(trifluoromethyl)pyridin-2-yl)-1H-indazol-6-yl)pyridin-2-yl)butan-1-amine; 6-(6-(6-(1-aminopropyl)pyridin-2-yl)-1H-indazol-1-yl)picolinamide; 2-(l-aminoethyl)-6-(1-(6-(trifluoromethyl)pyridin-2-yl)-1H-indazol-6-yl)pyridin-4-amine; 2-amino-2-(6-(1-(6-methylpyridin-2-yl)-1H-indazol-6-yl)pyridin-2-yl)ethanol; methyl 2-amino-2-(6-(1-(6-methylpyridin-2-yl)-1H-indazol-6-yl)pyridin-2-yl)acetate; 2-amino-2-(6-(1-(6-methylpyridin-2-yl)-1H-indazol-6-yl)pyridin-2-yl)acetic acid; 6-(6-(6-(1-aminobutyl)pyridin-2-yl)-1H-indazol-1-yl)picolinamide; 1-(6-(3-(6-methylpyridin-2-yl)imidazo[1,5-a]pyridin-6-yl)pyridin-2-yl)propan-1-amine; 1-(6-(3-(6-methylpyridin-2-yl)imidazo[1,5-a]pyridin-6-yl)pyridin-2-yl)butan-1-amine; 2-(6-(6-(6-(1-aminoethyl)pyridin-2-yl)-1H-indazol-1-yl)pyridin-2-yl)propan-2-ol; 1-(6-(1-(6-(methoxymethyl)pyridin-2-yl)-1H-indazol-6-yl)pyridin-2-yl)ethanamine; (6-(6-(6-(1-aminobutyl)pyridin-2-yl)-1H-indazol-1-yl)pyridin-2-yl)methanol; 1-(3-methyl-6-(1-(6-methylpyridin-2-yl)-1H-indazol-6-yl)pyridin-2-yl)ethanamine; 1-(6-(1-(4-methylthiophen-2-yl)-1H-indazol-6-yl)pyridin-2-yl)ethanamine; 1-(6-(1-(6-propylpyridin-2-yl)-1H-indazol-6-yl)pyridin-2-yl)ethanamine; 1-(6-(6-(6-(1-aminoethyl)pyridin-2-yl)-1H-indazol-1-yl)pyridin-2-yl)ethanol; (4-(1-(6-methylpyridin-2-yl)-1H-indazol-6-yl)oxazol-2-yl)methanamine; 1-(6-(1-(6-(ieri-butyl)pyridin-2-yl)-1H-indazol-6-yl)pyridin-2-yl)ethanamine; 1-(6-(1-(6-(aminomethyl)pyridin-2-yl)-1H-indazol-6-yl)pyridin-2-yl)ethanamine; 2-(6-(6-(6-(1-aminoethyl)pyridin-2-yl)-1H-indazol-1-yl)pyridin-2-yl)-2-methylpropanenitrile; 1-(6-(1-(6-(2-(methylsulfonyl)propan-2-yl)pyridin-2-yl)-1H-indazol-6-yl)pyridin-2-yl)ethanamine; 1-(6-(6-(6-(1-aminoethyl)pyridin-2-yl)-1H-indazol-1-yl)pyridin-2-yl)cyclopropanecarbonitrile; (6-(6-(6-(aminomethyl)pyridin-2-yl)-1H-indazol-1-yl)pyridin-2-yl)methanol; 2-(6-(6-(6-(1-aminoethyl)pyridin-2-yl)-1H-indazol-1-yl)pyridin-2-yl)propan-2-amine; 1-(6-(3-(6-ethylpyridin-2-yl)imidazo[1,5-a]pyridin-6-yl)pyridin-2-yl)ethanamine; (6-(6-(6-(1-aminopropyl)pyridin-2-yl)-1H-indazol-1-yl)pyridin-2-yl)methanol; 1-(6-(4-(1H-imidazol-2-yl)-1-(6-methylpyridin-2-yl)-1H-indazol-6-yl)pyridin-2-yl)ethanamine; 1-(6-(1-(4-methylpyrimidin-2-yl)-1H-indazol-6-yl)pyridin-2-yl)ethanamine; 1-(6-(1-(4-(trifluoromethyl)pyrimidin-2-yl)-1H-indazol-6-yl)pyridin-2-yl)ethanamine; 2-(6-(1-(6-methylpyridin-2-yl)-1H-indazol-6-yl)pyridin-2-yl)propan-2-amine; 1-(1-methyl-4-(1-(6-methylpyridin-2-yl)-1H-indazol-6-yl)-1H-imidazol-2-yl)ethanol; (1-methyl-4-(1-(6-methylpyridin-2-yl)-1H-indazol-6-yl)-1H-imidazol-2-yl)methanamine; 2-(6-(6-(6-(1-aminoethyl)pyridin-2-yl)-1H-indazol-1-yl)pyridin-2-yl)-2-methylpropanamide; (6-(6-(6-(1-aminoethyl)pyridin-2-yl)imidazo[1,5-a]pyridin-3-yl)pyridin-2-yl)methanol; 1-(6-(1-(6-methylpyridin-2-yl)-4-(thiazol-2-yl)-1H-indazol-6-yl)pyridin-2-yl)ethanamine; 1-(6-(1-(6-methylpyridin-2-yl)-1H-indazol-6-yl)pyridin-2-yl)cyclobutanecarbonitrile; 1-(1-methyl-4-(1-(6-methylpyridin-2-yl)-1H-indazol-6-yl)-1H-imidazol-2-yl)ethanamine; 1-(6-methylpyridin-2-yl)-6-(pyridin-2-yl)-1H-indazole; (6-(6-(6-(1-aminoethyl)pyridin-2-yl)-4-methoxy-1H-indazol-1-yl)pyridin-2-yl)methanol; 2-(1-(6-methylpyridin-2-yl)-1H-indazol-6-yl)-6,7,8,9-tetrahydro-5H-cyclohepta[b]pyridin-9-amine; (6-(6-(1-aminoethyl)pyridin-2-yl)-1-(6-(hydroxymethyl)pyridin-2-yl)-1H-indazol-4-yl)methanol; 1-(4-(1-(6-methylpyridin-2-yl)-1H-indazol-6-yl)thiazol-2-yl)ethanamine; 1-(6-(8-chloro-3-(6-(trifluoromethyl)pyridin-2-yl)imidazo[1,5-a]pyridin-6-yl)pyridin-2-yl)ethanamine; 1-(6-(1-(6-methylpyridin-2-yl)-1H-indazol-6-yl)pyridin-2-yl)cyclobutanecarboxamide; 1-(6-methylpyridin-2-yl)-6-(6-(3,3,3-trifluoropropyl)pyridin-2-yl)-1H-indazole; 2-(6-(6-(6-(1-aminoethyl)pyridin-2-yl)-1H-indazol-1-yl)pyridin-2-yl)ethanol; 1-(6-(1-(4,6-dimethylpyridin-2-yl)-1H-indazol-6-yl)pyridin-2-yl)ethanamine; 6-(6-(1-aminoethyl)pyridin-2-yl)-1-(6-(hydroxymethyl)pyridin-2-yl)-N-methyl-1H-indazole-4-carboxamide; 1-(6-(8-fluoro-3-(6-(trifluoromethyl)pyridin-2-yl)imidazo[1,5-a]pyridin-6-yl)pyridin-2-yl)ethanamine;

(S)-(6-(6-(6-(1-aminopropyl)pyridin-2-yl)-1H-indazol-1-yl)pyridin-2-yl)methanol; 1-(6-(1-(6-methylpyridin-2-yl)-4-(1H-pyrazol-3-yl)-1H-indazol-6-yl)pyridin-2-yl)ethanamine; (4-(1-(6-methylpyridin-2-yl)-1H-indazol-6-yl)thiazol-2-yl)methanol; (6-(6-(6-(1-aminoethyl)pyridin-2-yl)-4-fluoro-1H-indazol-1-yl)pyridin-2-yl)methanol; (R)-(6-(6-(6-(1-aminopropyl)pyridin-2-yl)-1H-indazol-1-yl)pyridin-2-yl)methanol; 6-(1-methyl-1H-imidazol-4-yl)-1-(6-methylpyridin-2-yl)-1H-indazole; (6-(6-(6-ethylpyridin-2-yl)-4-(5-methyl-1,3,4-oxadiazol-2-yl)-1H-indazol-1-yl)pyridin-2-yl)methanol; 1-(6-(6-((S)-1-aminobutyl)pyridin-2-yl)-1-(6-(hydroxymethyl)pyridin-2-yl)-1H-indazol-4-yl)pyrrolidin-3-ol; (S)-(6-(6-(6-(1-aminopropyl)pyridin-2-yl)-1H-indazol-1-yl)pyrazin-2-yl)methanol; (1-(6-(6-((S)-1-aminobutyl)pyridin-2-yl)-1-(6-(hydroxymethyl)pyridin-2-yl)-1H-indazol-4-yl)pyrrolidin-2-yl)methanol; (S)-(6-(6-(6-(1-aminobutyl)pyridin-2-yl)-4-(methylamino)-1H-indazol-1-yl)pyridin-2-yl)methanol; (S)-(6-(6-(6-(1-aminoethyl)pyridin-2-yl)-4-(oxazol-2-yl)-1H-indazol-1-yl)pyridin-2-yl)methanol; (S)-(6-(6-(6-(1-aminobutyl)pyridin-2-yl)-1H-indazol-1-yl)pyrazin-2-yl)methanol; (S)-(6-(6-(6-(1-aminopropyl)pyridin-2-yl)-4-(1-methyl-1H-pyrazol-3-yl)-1H-indazol-1-yl)pyridin-2-yl)methanol; (S)-(6-(6-(6-(1-aminobutyl)pyridin-2-yl)-4-(2-methoxyethoxy)-1H-indazol-1-yl)pyridin-2-yl)methanol; (6-(6-(6-((1R,2R)-1-amino-2-fluorobutyl)pyridin-2-yl)-4-(2-methoxyethoxy)-1H-indazol-1-yl)pyridin-2-yl)methanol; (S)-(6-(6-(6-(1-aminobutyl)pyridin-2-yl)-4-(ethylamino)-1H-indazol-1-yl)pyridin-2-yl)methanol; (S)-(6-(6-(6-(1-aminobutyl)pyridin-2-yl)-4-(1-methyl-1H-pyrazol-3-yl)-1H-indazol-1-yl)pyridin-2-yl)methanol; (S)-1-(6-(6-(1-aminobutyl)pyridin-2-yl)-1-(6-(hydroxymethyl)pyridin-2-yl)-1H-indazol-4-yl)piperidin-4-ol; 1-(6-(6-((S)-1-aminobutyl)pyridin-2-yl)-1-(6-(hydroxymethyl)pyridin-2-yl)-1H-indazol-4-yl)piperidin-3-ol; (S)-(6-(6-(6-(1-aminoethyl)pyridin-2-yl)-1H-indazol-1-yl)pyrazin-2-yl)methanol; (S)-(6-(6-(6-(1-aminobutyl)pyridin-2-yl)-4-(3,3-difluoroazetidin-1-yl)-1H-indazol-1-yl)pyridin-2-yl)methanol; (S)-(6-(6-(6-(1-aminopropyl)pyridin-2-yl)-4-(methylamino)-1H-indazol-1-yl)pyridin-2-yl)methanol; (S)-1-(6-(1-(4-(difluoromethyl)pyrimidin-2-yl)-1H-indazol-6-yl)pyridin-2-yl)butan-1-amine; (S)-(6-(6-(6-(1-aminoethyl)pyridin-2-yl)-4-(1-methyl-1H-pyrazol-4-yl)-1H-indazol-1-yl)pyridin-2-yl)methanol; (S)-(6-(6-(6-(1-aminobutyl)pyridin-2-yl)-4-(fluoromethyl)-1H-indazol-1-yl)pyridin-2-yl)methanol; (S)-1-(4-(6-(6-(1-aminobutyl)pyridin-2-yl)-1-(6-(hydroxymethyl)pyridin-2-yl)-1H-indazol-4-yl)-5,6-dihydropyridin-1 (2H)-yl)ethanone; (S)-(6-(6-(6-(1-aminobutyl)pyridin-2-yl)-4-methoxy-1H-indazol-1-yl)pyrazin-2-yl)methanol; (S)-(6-(6-(6-(1-aminoethyl)pyridin-2-yl)-4-(5-methyl-1,3,4-thiadiazol-2-yl)-1H-indazol-1-yl)pyridin-2-yl)methanol; (S)-(6-(6-(6-(l-aminobutyl)pyridin-2-yl)-4-chloro-1H-indazol-1-yl)pyridin-2-yl)methanol; (S)-(1-(6-(6-(1-aminobutyl)pyridin-2-yl)-1-(6-(hydroxymethyl)pyridin-2-yl)-1H-indazol-4-yl)-3-(chloromethyl)azetidin-3-yl)methanol; (S) 6 6-(6-(1-aminoethyl)pyridin-2-yl)-4-(1-methy-1H-midazol-4-yl)-1H-indazol-1-yl)pyridin-2-yl)methanol; (S)-(6-(6-(6-(1-aminobutyl)pyridin-2-yl)-4-(3,3-difluoropyrrolidin-1-yl)-1H-indazol-1-yl)pyridin-2-yl)methanol; (6-(6-(6-((S)-1-aminobutyl)pyridin-2-yl)-4-(2-methylmorpholino)-1H-indazol-1-yl)pyridin yl)methanol; (S)-(6-(6-(6-(1-aminobutyl)pyridin-2-yl)-4-(1-methyl-1,2,3,6-tetrahydropyridin-4-yl)-1H-indazol-1-yl)pyridin-2-yl)methanol; (6-(6-(6-((1R,2S)-1-amino-2-fluorobutyl)pyridin-2-yl)-4-(2-methoxyethoxy)-1H-indazol-1-yl)pyridin-2-yl)methanol; (S)-(6-(6-(6-(1-aminoethyl)pyridin-2-yl)-4-(pyrimidin-2-yl)-1H-indazol-1-yl)pyridin-2-yl)methanol; (S)-(6-(6-(6-(1-aminobutyl)pyridin-2-yl)-4-(difluoromethyl)-1H-indazol-1-yl)pyridin-2-yl)methanol; (S)-(6-(6-(1-aminobutyl)pyridin-2-yl)-1-(6-(hydroxymethyl)pyridin-2-yl)-1H-indazol-4-yl)methanol; (S)-(6-(6-(6-(1-aminobutyl)pyridin-2-yl)-4-(3-methoxypropoxy)-1H-indazol-1-yl)pyridin-2-yl)methanol; (S)-(6-(6-(6-(1-aminopentyl)pyridin-2-yl)-1H-indazol-1-yl)pyridin-2-yl)methanol; (S)-(6-(6-(6-(1-aminoethyl)pyridin-2-yl)-4-(1H-imidazol-1-yl)-1H-indazol-1-yl)pyridin-2-yl)methanol; (S)-(6-(6-(6-(1-aminobutyl)pyridin-2-yl)-4-(3,6-dihydro-2H-pyran-4-yl)-1H-indazol-1-yl)pyridin-2-yl)methanol; (S)-(6-(6-(6-(1-aminopropyl)pyridin-2-yl)-4-(3-methoxypropoxy)-1H-indazol-1-yl)pyridin-2-yl)methanol; (S)-(6-(6-(6-(1-aminoethyl)pyridin-2-yl)-4-(1,5-dimethyl-1H-pyrazol-3-yl)-1H-indazol-1-yl)pyridin-2-yl)methanol; (S)-(6-(6-(6-(1-aminoethyl)pyridin-2-yl)-4-(5-methyl-1H-pyrazol-3-yl)-1H-indazol-1-yl)pyridin-2-yl)methanol; (S)-(6-(6-(6-(1-aminobutyl)pyridin-2-yl)-4-(methoxymethyl)-1H-indazol-1-yl)pyridin-2-yl)methanol; (S)-(6-(6-(6-(amino(cyclopropyl)methyl)pyridin-2-yl)-4-methoxy-1H-indazol-1-yl)pyrazin-2-yl)methanol; (6-(6-(6-((S)-1-aminobutyl)pyridin-2-yl)-4-(2,6-dimethylmorpholino)-1H-indazol-1-yl)pyridin-2-yl)methanol; (S)-(6-(6-(4-(1-aminobutyl)pyrimidin-2-yl)-1H-indazol-1-yl)pyridin-2-yl)methanol; 3-((6-(6-((S)-1-aminobutyl)pyridin-2-yl)-1-(6-(hydroxymethyl)pyridin-2-yl)-1H-indazol-4-yl) amino)-2-(chloromethyl)propanoic acid; (S)-(6-(6-(6-(1-aminobutyl)pyridin-2-yl)-4-((difluoromethoxy)methyl)-1H-indazol-1-yl)pyridin-2-yl)methanol; (S)-(6-(6-(6-(1-aminobutyl)pyridin-2-yl)-4-(morpholinomethyl)-1H-indazol-1-yl)pyridin-2-yl)methanol; (S)-4-(6-(6-(1-aminobutyl)pyridin-2-yl)-1-(6-(hydroxymethyl)pyridin-2-yl)-1H-indazol-4-yl)thiomorpholine 1,1-dioxide; (S)-(6-(6-(6-(1-amino-4,4,4-trifluorobutyl)pyridin-2-yl)-1H-indazol-1-yl)pyridin-2-yl)methanol; (S)-(6-(6-(6-(1-aminobutyl)pyridin-2-yl)-4-thiomorpholino-1H-indazol-1-yl)pyridin-2-yl)methanol; 1-(6-(6-(6-((S)-1-aminoethyl)pyridin-2-yl)-1H-indazol-1-yl)pyridin-2-yl)ethanol; (S)-(6-(6-(6-(1-aminobutyl)pyridin-2-yl)-4-ethoxy-1H-indazol-1-yl)pyrazin-2-yl)methanol; (S)-(6-(6-(6-(1-aminoethyl)pyridin-2-yl)-4-(1-methyl-1H-pyrazol-3-yl)-1H-indazol-1-yl)pyridin-2-yl)methanol; (S)-(6-(6-(6-(1-aminoethyl)pyridin-2-yl)-4-(2-methylthiazol-4-yl)-1H-indazol-1-yl)pyridin-2-yl)methanol; (S)-(6-(6-(6-(1-aminopropyl)pyridin-2-yl)-4-ethoxy-1H-indazol-1-yl)pyrazin-2-yl)methanol; (S)-(6-(6-(6-(1-aminoethyl)pyridin-2-yl)-4-(3-methoxypropoxy)-1H-indazol-1-yl)pyridin-2-yl)methanol; (S)-(6-(6-(6-(amino(cyclopropyl)methyl)pyridin-2-yl)-4-ethoxy-1H-indazol-1-yl)pyrazin-2-yl)methanol; (S)-(6-(6-(6-(1-aminoethyl)pyridin-2-yl)-4-(1H-1,2,4-triazolyl)H-indazol-1-yl)pyridin-2-yl)methanol; (S)-2-(6-(6-(1-aminoethyl)pyridin-2-yl)-1-(6-(hydroxymethyl)pyridin-2-yl)-1H-indazol-4-yl)thiazole-4-carbonitrile; (S)-(6-(6-(6-(1-aminoethyl)pyridin-2-yl)-4-(isothiazol-3-yl)-1H-indazol-1-yl)pyridin-2-yl)methanol; (S)-(6-(6-(6-(amino(cyclobutyl)methyl)pyridin-2-yl)-1H-indazol-1-yl)pyridin-2-yl)methanol; (S)-(6-(6-(6-(1-aminobutyl)pyridin-2-yl)-4-(tetrahydro-2H-pyran-4-yl)-1H-indazol-1-yl)pyridin-2-yl)methanol; (6-(6-(6-((1R,2S)-1-amino-2-fluorobutyl)pyridin-2-yl)-4-ethoxy-1H-indazol-1-yl)pyridin-2-yl)methanol; (S)-(6-(6-(6-(1-aminobutyl)pyridin-2-yl)-4-morpholino-1H-indazol-1-yl)pyridin-2-yl)methanol; (6-(6-(6-((1R,2R)-1-amino-2-fluorobutyl)pyridin-2-yl)-4-ethoxy-1H-indazol-1-yl)pyridin-2-yl)methanol; 1-(6-(6-(6-((S)-1-aminobutyl)pyridin-2-yl)-1H-indazol-1-yl)pyridin-2-yl)ethanol; (S)-(6-(6-(6-(1-aminobutyl)pyridin-2-yl)-4-(3,3-dimethylazetidin-1-yl)-1H-indazol-1-yl)pyridin-2-yl)methanol; (S)-(6-(6-(6-(1-amino-4,4,4-trifluorobutyl)

pyridin-2-yl)-4-methoxy-1H-indazol-1-yl)pyridin-2-yl)methanol; (S)-(6-(6-(6-(1-aminopropyl)pyridin-2-yl)-4-methoxy-1H-indazol-1-yl)pyrazin-2-yl)methanol; (S)-(6-(6-(6-(1-amino-3,3-difluorobutyl)pyridin-2-yl)-4-ethoxy-1H-indazol-1-yl)pyridin-2-yl)methanol; (S)-1-(6-(4-methoxy-1-(4-(trifluoromethyl)pyrimidin-2-yl)-1H-indazol-6-yl)pyridin-2-yl)butan-1-amine; (6-(6-(6-(amino(oxetan-3-yl)methyl)pyridin-2-yl)-4-ethoxy-1H-indazol-1-yl)pyridin-2-yl)methanol; (S)-1-(6-(4-ethoxy-1-(4-(trifluoromethyl)pyrimidin-2-yl)-1H-indazol-6-yl)pyridin-2-yl)butan-1-amine; (6-{6-[6-((S)-1-Amino-ethyl)-pyridin-2-yl]-4-fluoro-indazol-1-yl}-pyridin-2-yl)-methanol; (S)-(6-(6-(6-(1-aminoethyl)pyridin-2-yl)-4-phenyl-1H-indazol-1-yl)pyridin-2-yl)methanol; (S)-(6-(6-(6-(1-amino-3,3-difluorobutyl)pyridin-2-yl)-1H-indazol-1-yl)pyridin-2-yl)methanol; (S)-(6-(6-(6-(1-aminoethyl)pyridin-2-yl)-4-(5-methylthiazol-2-yl)-1H-indazol-1-yl)pyridin-2-yl)methanol; (6-(6-(6-((S)-1-aminobutyl)pyridin-2-yl)-4-(piperidin-3-ylmethoxy)-1H-indazol-1-yl)pyridin-2-yl)methanol; (6-{6-[6-((S)-1-Amino-butyl)-pyridin-2-yl]-4-isopropoxy-indazol-1-yl}-pyridin-2-yl)-methanol; (S)-(6-(6-(6-(1-aminoethyl)pyridin-2-yl)-4-(pyridin-2-yl)-1H-indazol-1-yl)pyridin-2-yl)methanol; 1-(6-(6-((S)-1-aminobutyl)pyridin-2-yl)-1-(6-(hydroxymethyl)pyridin-2-yl)-1H-indazol-4-yl)pyrrolidine-3-carboxylic acid; (S)-(6-(6-(6-(1-aminobutyl)pyridin-2-yl)-4-(pyrrolidin-1-yl)-1H-indazol-1-yl)pyridin-2-yl)methanol; (6-(6-(6-(amino(oxetan-3-yl)methyl)pyridin-2-yl)-1H-indazol-1-yl)pyridin-2-yl)methanol; (R)-(6-(6-(4-(1-aminobutyl)pyrimidin-2-yl)-1H-indazol-1-yl)pyridin-2-yl)methanol; 1-amino-1-(6-(1-(6-(hydroxymethyl)pyridin-2-yl)-1H-indazol-6-yl)pyridin-2-yl)butan-2-ol; (6-{6-[6-((S)-1-Amino-butyl)-pyridin-2-yl]-4-fluoro-indazol-1-yl}-pyridin-2-yl)-methanol; 4-amino-4-(6-(1-(6-(hydroxymethyl)pyridin-2-yl)-1H-indazol-6-yl)pyridin-2-yl)butan-2-ol; (S)-(6-(6-(6-(1-aminobutyl)pyridin-2-yl)-4-(4-methylpiperazin-1-yl)-1H-indazol-1-yl)pyridin-2-yl)methanol; (S)-(6-(6-(6-(1-amino-4-methoxybutyl)pyridin-2-yl)-4-methoxy-1H-indazol-1-yl)pyridin-2-yl)methanol; (S)-(6-(6-(6-(1-amino-4,4,4-trifluorobutyl)pyridin-2-yl)-4-ethoxy-1H-indazol-1-yl)pyridin-2-yl)methanol; (S)-6-(6-(1-aminobutyl)pyridin-2-yl)-1-(6-(hydroxymethyl)pyridin-2-yl)-1H-indazole-4-carbonitrile; (S)-1-(6-(1-(4-(difluoromethyl)pyrimidin-2-yl)-1H-indazol-6-yl)pyridin-2-yl)propan-1-amine; (S)-(6-(6-(6-(1-amino-4-methoxybutyl)pyridin-2-yl)-4-ethoxy-1H-indazol-1-yl)pyridin-2-yl)methanol; (S)-(6-(6-(6-(1-aminobutyl)pyridin-2-yl)-4-(2,2,2-trifluoroethoxy)-1H-indazol-1-yl)pyridin-2-yl)methanol; (S)-1-(4-(6-(6-(1-aminobutyl)pyridin-2-yl)-1-(6-(hydroxymethyl)pyridin-2-yl)-1H-indazol-4-yl)piperidin-1-yl)ethanone; 1-amino-1-(6-(1-(6-(hydroxymethyl)pyridin-2-yl)-1H-indazol-6-yl)pyridin-2-yl)butan-2-ol; (S)-(6-(6-(6-(1-aminoethyl)pyridin-2-yl)-4-(4-(trifluoromethyl)oxazol-2-yl)-1H-indazol-1-yl)pyridin-2-yl)methanol; (S)-(6-(6-(6-(1-aminobutyl)pyridin-2-yl)-4-((dimethylamino)methyl)-1H-indazol-1-yl)pyridin-2-yl)methanol; (S)-(6-(6-(6-(1-aminobutyl)pyridin-2-yl)-4-((3-chloro-2,2-dimethylpropyl)amino)-1H-indazol-1-yl)pyridin-2-yl)methanol; (S)-(6-(6-(6-(1-aminobutyl)pyridin-2-yl)-4-ethoxy-1H-indazol-1-yl)pyridin-2-yl)methanol; (S)-1-(6-(1-(6-(fluoromethyl)pyridin-2-yl)-1H-indazol-6-yl)pyridin-2-yl)butan-1-amine; (S)-(6-(6-(6-(1-aminobutyl)pyridin-2-yl)-4-(azetidin-1-yl)-1H-indazol-1-yl)pyridin-2-yl)methanol; (S)-(6-(6-(6-(1-aminobutyl)pyridin-2-yl)-4-(4,4-difluoropiperidin-1-yl)-1H-indazol-1-yl)pyridin-2-yl)methanol; (S)-1-(6-(1-(6-(difluoromethyl)pyridin-2-yl)-1H-indazol-6-yl)pyridin-2-yl)butan-1-amine; (S)-(6-(6-(6-(1-aminobutyl)pyridin-2-yl)-4-(3,3-difluoropiperidin-1-yl)-1H-indazol-1-yl)pyridin-2-yl)methanol; (S)-1-(6-(6-(1-aminobutyl)pyridin-2-yl)-1-(6-(hydroxymethyl)pyridin-2-yl)-1H-indazol-4-yl)azetidine-3-carboxylic acid; (6-(6-(6-(1-amino-2-(methylthio)ethyl)pyridin-2-yl)-1H-indazol-1-yl)pyridin-2-yl)methanol; (R)-1-(6-(6-(6-((S)-1-aminobutyl)pyridin-2-yl)-1H-indazol-1-yl)pyridin-2-yl)-2,2,2-trifluoroethanol; (S)-(6-(6-(6-(1-aminoethyl)pyridin-2-yl)-4-(4-methylthiazol-2-yl)-1H-indazol-1-yl)pyridin-2-yl)methanol; (S)-(6-(6-(6-(1-amino-3-methylbutyl)pyridin-2-yl)-1H-indazol-1-yl)pyridin-2-yl)methanol; (R)-(6-(6-(6-(amino(phenyl)methyl)pyridin-2-yl)-4-ethoxy-1H-indazol-1-yl)pyridin-2-yl)methanol; (6-(6-(6-((1R,2R)-1-amino-2-methoxybutyl)pyridin-2-yl)-4-ethoxy-1H-indazol-1-yl)pyridin-2-yl)methanol; (S)-(6-(6-(6-(1-aminobutyl)pyridin-2-yl)-4-(2-cyclopropylethoxy)-1H-indazol-1-yl)pyridin-2-yl)methanol; (S)-(6-(6-(6-(1-aminobutyl)pyridin-2-yl)-4-methoxy-1H-indazol-1-yl)pyridin-2-yl)methanol; (S)-(6-(6-(6-(1-aminobutyl)pyridin-2-yl)-4-(trifluoromethoxy)-1H-indazol-1-yl)pyridin-2-yl)methanol; (S)-(6-(6-(6-(1-aminoethyl)pyridin-2-yl)-4-(4,5-dihydrooxazol-2-yl)-1H-indazol-1-yl)pyridin-2-yl)methanol; 4-amino-4-(6-(1-(6-(hydroxymethyl)pyridin-2-yl)-1H-indazol-6-yl)pyridin-2-yl)butan-2-ol; (S)-(6-(6-(6-(1-aminobutyl)pyridin-2-yl)-4-(difluoromethoxy)-1H-indazol-1-yl)pyrazin-2-yl)methanol; (S)-(6-(6-(6-(1-(methylamino)butyl)pyridin-2-yl)-1H-indazol-1-yl)pyridin-2-yl)methanol; (6-(6-(6-((S)-1-aminoethyl)pyridin-2-yl)-4-(4-methyl-4,5-dihydrooxazol-2-yl)-1H-indazol-1-yl)pyridin-2-yl)methanol; (S)-(6-(6-(6-(1-aininoethyl)pyridin-2-yl)-4-(1-(fluoromethyl)-1H-pyrazol-4-yl)-1H-indazol-1-yl)pyridin-2-yl)methanol; (S)-1-(6-(1-(6-(difluoromethyl)pyridin-2-yl)-1H-indazol-6-yl)pyridin-2-yl)ethanamine; 2-amino-2-(6-(1-(6-(hydroxymethyl)pyridin-2-yl)-1H-indazol-6-yl)pyridin-2-yl)ethanol; (S)-(6-(6-(6-(1-amino-3-methylbut-3-en-1-yl)pyridin-2-yl)-1H-indazol-1-yl)pyridin-2-yl)methanol; (S)-1-(6-(1-(4-(trifluoromethyl)pyrimidin-2-yl)-1H-indazol-6-yl)pyridin-2-yl)butan-1-amine; (6-(6-(6-(1-amino-2-(methylsulfonyl)ethyl)pyridin-2-yl)-1H-indazol-1-yl)pyridin-2-yl)methanol; 1-(6-(6-((S)-1-aminobutyl)pyridin-2-yl)-1-(6-(hydroxymethyl)pyridin-2-yl)-1H-indazol-4-yl)piperidine-3-carboxylic acid; (S)-6-(6-(1-aminopropyl)pyridin-2-yl)-1-(6-(hydroxymethyl)pyridin-2-yl)-1H-indazole-4-carbonitrile; (S)-(6-(6-(6-(1-aminoethyl)pyridin-2-yl)-4-(4,5-dimethylthiazol-2-yl)-1H-indazol-1-yl)pyridin-2-yl)methanol; (S)-(6-(6-(6-(1-aminobutyl)pyridin-2-yl)-4-(piperidin-1-yl)-1H-indazol-1-yl)pyridin-2-yl)methanol; (6-(6-(6-(1-amino-2-cyclopropylethyl)pyridin-2-yl)-1H-indazol-1-yl)pyridin-2-yl)methanol; 1-(6-(6-(6-((S)-1-aminoethyl)pyridin-2-yl)-1H-indazol-1-yl)pyridin-2-yl)ethanol; (6-{6-[6-((S)-1-Amino-butyl)-pyridin-2-yl]-4-fluoro-indazol-1-yl}-pyridin-2-yl)-methanol; 1-(6-(1-(6-methylpyridin-2-yl)-4-(oxazol-5-yl)-1H-indazol-6-yl)pyridin-2-yl)ethanamine; (S)-(6-(6-(4-(1-aminoethyl)pyrimidin-2-yl)-1H-indazol-1-yl)pyridin-2-yl)methanol; (S)-6-(6-(1-aminoethyl)pyridin-2-yl)-1-(6-(hydroxymethyl)pyridin-2-yl)-1H-indazole-4-carbonitrile; (6-(6-(6-(amino(cyclopropyl)methyl)pyridin-2-yl)-1H-indazol-1-yl)pyridin-2-yl)methanol; (S)-1-(6-(1-(6-(difluoromethyl)pyridin-2-yl)-1H-indazol-6-yl)pyridin-2-yl)propan-1-amine; (S)-6-(6-(1-aminoethyl)pyridin-2-yl)-N-(1-hydroxy-2-methylpropan-2-yl)-1-(6-(hydroxymethyl)pyridin-2-yl)-1H-indazole-4-carboxamide; (S)-1-(6-(1-(4-(difluoromethyl)pyrimidin-2-yl)-1H-indazol-6-yl)pyridin-2-yl)ethanamine; 1-(6-(1-(6-methylpyridin-2-yl)-4-(oxazol-2-yl)-1H-indazol-6-yl)pyridin-2-yl)ethanamine; (S)-(6-(6-(6-(1-aminoethyl)pyridin-2-yl)-4-(4-(trifluoromethyl)thiazol-2-yl)-1H-indazol-1-yl)pyridin-2-yl)methanol; (6-(6-(6-(1-amino-2-methoxyethyl)pyridin-2-yl)-1H-indazol-1-yl)pyridin-2-yl) methanol; 2-amino-2-(6-(1-(6-(hydroxymethyl)pyridin-2-yl)-1H-indazol-6-yl)pyridin-2-yl)-N,N-dimethylacetamide; (S)-(6-(6-(6-(1-aminoethyl)pyridin-2-yl)-4-(thiazol-2-yl)-1H-indazol-1-yl)pyridin-2-yl)methanol; (S)-1-(6-(6-(6-((S)-1-aminobutyl)pyridin-2-yl)-1H-indazol-1-yl)pyridin-2-yl)-2,2,2-trifluoroethanol; (S)-(6-(6-(6-(1-aminoethyl)pyridin-2-yl)-4-(5-(trifluoromethyl)thiazol-2-yl)-1H-indazol-1-yl) pyridin-2-yl)methanol; (S)-1-(6-(6-(1-aminobutyl)pyridin-2-yl)-1-(6-(hydroxymethyl)pyridin-2-yl)-1H-indazol-4-yl) piperidine-4-carboxylic acid; (S)-(6-(6-(6-(1-aminoethyl) pyridin-2-yl)-1H-indazol-1-yl)-3-fluoropyridin-2-yl) methanol; (6-(6-(6-((R,2S)-1-amino-2-methoxybutyl) pyridin-2-yl)-4-ethoxy-1H-indazol-1-yl)pyridin-2-yl) methanol; (S)-1-(6-(1-(6-(trifluoromethyl)pyrazin-2-yl)-1H-indazol-6-yl)pyridin-2-yl)butan-1-amine; (S)-6-(6-(6-(1-aminobutyl)pyridin-2-yl)-1H-indazol-1-yl) picolinaldehyde; (S)-(6-(6-(6-(1-aminoethyl)pyridin-2-yl)-4-(3-(trifluoromethyl)-1H-pyrazol-1-yl)-1H-indazol-1-yl) pyridin-2-yl)methanol; 6-(6-((S)-1-aminoethyl)pyridin-2-yl)-N-(2-aminopropyl)-1-(6-(hydroxymethyl)pyridin-2-yl)-1H-indazole-4-carboxamide; (S)-(6-(6-(6-(1-aminoethyl) pyridin-2-yl)-4-(1H-pyrazol-3-yl)-1H-indazol-1-yl)pyridin-2-yl)methanol; 1-(6-(1-(6-(hydroxymethyl)pyridin-2-yl)-1H-indazol-6-yl)pyridin-2-yl)butan-1-ol; 1-(6-(1-(6-(hydroxymethyl)pyridin-2-yl)-1H-indazol-6-yl)pyridin-2-yl)butan-1-ol; (6-(6-(6-(1-amino-2-(3-methyloxetan-3-yl) ethyl)pyridin-2-yl)-1H-indazol-1-yl)pyridin-2-yl)methanol; 3,3,3-trifluoro-1-(6-(1-(6-methylpyridin-2-yl)-1H-indazol-6-yl)pyridin-2-yl)propan-1-amine; 1-(6-(4-(5-methyl-1,3,4-oxadiazol-2-yl)-1-(6-methylpyridin-2-yl)-1H-indazol-6-yl) pyridin-2-yl)ethanamine; 1-(6-(1-(6-methylpyrazin-2-yl)-1H-indazol-6-yl)pyridin-2-yl)ethanamine; 6-{6-[6-((S)-1-Amino-ethyl)-pyridin-2-yl]-indazol-1-yl}-pyridine-2-carboxylic acid; 2-amino-2-(6-(1-(6-(hydroxymethyl) pyridin-2-yl)-1H-indazol-6-yl)pyridin-2-yl)acetonitrile; 2-amino-2-(6-(1-(6-(hydroxymethyl)pyridin-2-yl)-1H-indazol-6-yl)pyridin-2-yl)acetamide; 4-(6-(6-(1-aminoethyl) pyridin-2-yl)-1H-indazol-1-yl)pyrimidine-2-carbonitrile; (6-(6-(3-(1-aminoethyl)phenyl)-1H-indazol-1-yl)pyridin-2-yl)methanol; (6-(6-(6-(1-aminoethyl)-3-fluoropyridin-2-yl)-1H-indazol-1-yl)pyridin-2-yl)methanol; (R)-(6-(6-(4-(1-aminoethyl)pyrimidin-2-yl)-1H-indazol-1-yl)pyridin-2-yl) methanol; (S)-(6-(6-(6-(1-aminoethyl)pyridin-2-yl)-1H-indazol-1-yl)-5-fluoropyridin-2-yl)methanol; (S)-(6-(6-(6-(1-(dimethylamino)butyl)pyridin-2-yl)-1H-indazol-1-yl) pyridin-2-yl)methanol; 1-(6-(6-(6-((S)-1-aminobutyl) pyridin-2-yl)-1H-indazol-1-yl)pyridin-2-yl)ethanol; 2-amino-2-(6-(1-(6-(hydroxymethyl)pyridin-2-yl)-1H-indazol-6-yl)pyridin-2-yl)-N-methylacetamide; (6-(6-(6-(1-amino-2-(methylsulfinyl)ethyl)pyridin-2-yl)-1H-indazol-1-yl)pyridin-2-yl)methanol; (6-(6-(6-((S)-1-aminobutyl) pyridin-2-yl)-4-(1-methoxyethyl)-1H-indazol-1-yl)pyridin-2-yl)methanol; (S)-4-amino-4-(6-(1-(6-(hydroxymethyl) pyridin-2-yl)-1H-indazol-6-yl)pyridin-2-yl)butan-1-ol; (S)-(6-(6-(6-(1-aminobut-3-en-1-yl)pyridin-2-yl)-1H-indazol-1-yl)pyridin-2-yl)methanol; (S)-4-amino-4-(6-(1-(6-(hydroxymethyl)pyridin-2-yl)-1H-indazol-6-yl)pyridin-2-yl)butan-2-one; (S)-1-(6-(4-chloro-1-(4-(difluoromethyl) pyrimidin-2-yl)-1H-indazol-6-yl)pyridin-2-yl)butan-1-amine; (6-(6-(6-(pyrrolidin-2-yl)pyridin-2-yl)-1H-indazol-1-yl)pyridin-2-yl)methanol; (S)-4-(6-(6-(1-aminobutyl) pyridin-2-yl)-1-(6-(hydroxymethyl)pyridin-2-yl)-1H-indazol-4-yl)-2-methylbut-3-yn-2-ol; (S)-(6-(6-(6-(1-aminoethyl)pyridin-2-yl)-4-(2-(trifluoromethyl)thiazol-4-yl)-1H-indazol-1-yl)pyridin-2-yl)methanol; (S)-1-(6-(1-(4-(difluoromethyl)pyrimidin-2-yl)-4-methoxy-1H-indazol-6-yl)pyridin-2-yl)butan-1-amine; (S)-(6-(6-(6-(1-aminopent-3-yn-1-yl)pyridin-2-yl)-4-ethoxy-1H-indazol-1-yl)pyridin-2-yl)methanol; (S)-(6-(6-(6-(amino(phenyl)methyl)pyridin-2-yl)-4-ethoxy-1H-indazol-1-yl)pyridin-2-yl)methanol; (6-(6-(6-((S)-1-aminobutyl)pyridin-2-yl)-4-((S)-pyrrolidin-2-yl)-1H-indazol-1-yl)pyridin-2-yl)methanol; (6-(6-(6-((S)-1-aminobutyl)pyridin-2-yl)-4-(tetrahydrofuran-2-yl)-1H-indazol-1-yl)pyridin-2-yl)methanol; (S)-4-(6-(6-(1-aminobutyl)pyridin-2-yl)-1-(6-(hydroxymethyl)pyridin-2-yl)-1H-indazol-4-yl)morpholin-3-one; (S)-(6-(6-(4-(1-aminobutyl)pyrimidin-2-yl)-4-methoxy-1H-indazol-1-yl) pyridin-2-yl)methanol; (S)-(6-(6-(6-(1-amino-4-methoxybutyl)pyridin-2-yl)-4-(1-methyl-1H-pyrazol-3-yl)-1H-indazol-1-yl)pyridin-2-yl)methanol; (R)-(6-(6-(4-(1-aminobutyl)pyrimidin-2-yl)-4-methoxy-1H-indazol-1-yl) pyridin-2-yl)methanol; (S)-(6-(6-(6-(1-aminoethyl)pyridin-2-yl)-4-(5-(trifluoromethyl)-1H-pyrazol-3-yl)-1H-indazol-1-yl)pyridin-2-yl)methanol; (S)-(6-(6-(6-(1-aminobutyl) pyridin-2-yl)-4-(pyrimidin-2-yl)-1H-indazol-1-yl)pyridin-2-yl)methanol; deutero (S)-(6-(6-(6-(1-aminobutyl)pyridin-2-yl)-1H-indazol-1-yl)pyridin-2-yl)methanol; (S)-(6-(6-(6-(1-aminoethyl)pyridin-2-yl)-4-(5-fluoro-2-yl)methanol; (S)-(4-(6-(6-(1-aminobutyl)pyridin-2-yl)-1H-indazol-1-yl) pyridin-2-yl)methanol; (S)-(3-(6-(6-(1-aminobutyl)pyridin-2-yl)-1H-indazol-1-yl)phenyl)methanol; (S)-(6-(6-(6-(1-aminoethyl)pyridin-2-yl)-4-(5-methyloxazol-2-yl)-1H-indazol-1-yl)pyridin-2-yl)methanol; (S)-(6-(6-(6-(1-aminobutyl)pyridin-2-yl)-4-(1H-1,2,3-triazol-1-yl)-1H-indazol-1-yl)pyridin-2-yl)methanol; (S)-(6-(6-(6-(1-aminobutyl)pyridin-2-yl)-4-((trifluoromethoxy)methyl)-1H-indazol-1-yl)pyridin-2-yl)methanol; (S)-(6-(6-(6-(1-aminoethyl)pyridin-2-yl)-4-(1-(difluoromethyl)-1H-pyrazol-3-yl)-1H-indazol-1-yl)pyridin-2-yl)methanol; (S)-(6-(6-(6-(1-aminoethyl)pyridin-2-yl)-4-(1-(difluoromethyl)-1H-pyrazol-5-yl)-1H-indazol-1-yl)pyridin-2-yl)methanol; (S)-(6-(6-(6-(1-aminoethyl)pyridin-2-yl)-4-(pyrazin-2-yl)-1H-indazol-1-yl)pyridin-2-yl)methanol; (S)-(6-(6-(4-(1-aminopentyl)pyrimidin-2-yl)-1H-indazol-1-yl)pyridin-2-yl) methanol; (R)-3-amino-3-(6-(1-(6-(hydroxymethyl)pyridin-2-yl)-1H-indazol-6-yl)pyridin-2-yl)propanenitrile; (S)-4-amino-4-(6-(1-(6-(hydroxymethyl)pyridin-2-yl)-4-methoxy-1H-indazol-6-yl)pyridin-2-yl)butan-1-ol; (S)-4-amino-4-(6-(4-ethoxy-1-(6-(hydroxymethyl)pyridin-2-yl)-1H-indazol-6-yl)pyridin-2-yl)butan-1-ol; (S)-(6-(6-(6-(1-aminobutyl)pyridin-2-yl)-4-(2-methoxyethoxy)-1H-indazol-1-yl)pyrazin-2-yl)methanol; (S)-(6-(6-(6-(1-aminoethyl)pyridin-2-yl)-4-(2-methoxyethoxy)-1H-indazol-1-yl)pyrazin-2-yl)methanol; (S)-(6-(6-(4-(1-aminobutyl)pyridin-2-yl)-1H-indazol-1-yl)pyridin-2-yl) methanol; (S)-(6-(6-(6-(1-aminobutyl)pyridin-2-yl)-4-(5-methyloxazol-2-yl)-1H-indazol-1-yl)pyridin-2-yl)methanol; (S)-(6-(6-(4-(1-aminobutyl)pyrimidin-2-yl)-4-ethoxy-1H-indazol-1-yl)pyridin-2-yl)methanol; (R)-(6-(6-(4-(1-aminobutyl)pyrimidin-2-yl)-4-ethoxy-1H-indazol-1-yl)pyridin-2-yl)methanol; (S)-2-((6-(6-(1-aminobutyl)pyridin-2-yl)-1-(6-(hydroxymethyl)pyridin-2-yl)-1H-indazol-4-yl)oxy) ethanol; (S)-(6-(6-(6-(1-aminobutyl)pyridin-2-yl)-4-(1,5-dimethyl-1H-pyrazol-3-yl)-1H-indazol-1-yl)pyridin-2-yl) methanol; (S)-(2-(6-(6-(1-aminobutyl)pyridin-2-yl)-1H-indazol-1-yl)pyrimidin-4-yl)methanol; (S)-(6-(6-(6-(1-aminopropyl)pyridin-2-yl)-4-(2-methoxyethoxy)-1H-indazol-1-yl)pyrazin-2-yl)methanol; 2-(6-(6-((S)-1-aminobutyl)pyridin-2-yl)-1-(6-(hydroxymethyl)pyridin-2-yl)-1H-indazol-4-yl)-3-chloropropan-1-ol; (S)-(6-(6-(6-(1-aminoethyl)pyridin-2-yl)-4-(2-methoxyethoxy)-1H-indazol-1-yl)pyridin-2-yl)methanol; (S)-(6-(6-(6-(1- aminopropyl)pyridin-2-yl)-4-(2-methoxyethoxy)-1H-indazol-1-yl)pyridin-2-yl)methanol; (S)-(6-(6-(6-(amino(cyclopropyl)methyl)pyridin-2-yl)-4-(2-methoxyethoxy)-1H-indazol-1-yl)pyridin-2-yl)methanol; (S)-(6-(6-(6-(1-amino-3,3-difluorobutyl)pyridin-2-yl)-4-(2-methoxyethoxy)-1H-indazol-1-yl)pyridin-2-yl)methanol; (S)-4-amino-4-(6-(1-(6-(hydroxymethyl)pyridin-2-yl)-4-(1-methyl-1H-pyrazol-3-yl)-1H-indazol-6-yl)pyridin-2-yl)butan-1-ol; (R)-(6-(6-(6-(1-aminopropyl)pyridin-2-yl)-4-(1,5-dimethyl-1H-pyrazol-3-yl)-1H-indazol-1-yl)pyridin-2-yl)methanol; (R)-(6-(6-(6-(1-amino-2-fluoroethyl)pyridin-2-yl)-1H-indazol-1-yl)pyridin-2-yl)methanol; (S)-1-(6-(1-(6-methylpyrazin-2-yl)-1H-indazol-6-yl)pyridin-2-yl)butan-1-amine; (S)-3-amino-3-(6-(1-(6-(hydroxymethyl)pyridin-2-yl)-1H-indazol-6-yl)pyridin-2-yl)propanenitrile; (S)-4-amino-4-(6-(1-(6-(hydroxymethyl)pyridin-2-yl)-1H-indazol-6-yl)pyridin-2-yl)butanenitrile; (S)-(6-(6-(2-(1-aminobutyl)pyrimidin-4-yl)-1H-indazol-1-yl)pyridin-2-yl)methanol; (4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol; (R)-(6-(6-(6-(1-amino-2-fluoroethyl)pyridin-2-yl)-4-(1,5-dimethyl-1H-pyrazol-3-yl)-1H-indazol-1-yl)pyridin-2-yl)methanol; (S)-4-amino-4-(6-(1-(6-(hydroxymethyl)pyridin-2-yl)-4-(2-methoxyethoxy)-1H-indazol-6-yl)pyridin-2-yl)butan-1-ol; (4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol; (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol; (R)-(6-(6-(2-(1-aminobutyl)pyrimidin-4-yl)-1H-indazol-1-yl)pyridin-2-yl)methanol; (S)-4-amino-4-(6-(4-(1,5-dimethyl-1H-pyrazol-3-yl)-1-(6-(hydroxymethyl)pyridin-2-yl)-1H-indazol-6-yl)pyridin-2-yl)butan-1-ol; (S)-(6-(6-(6-(1-aminoethyl)pyridin-2-yl)-4-(pyrimidin-4-yl)-1H-indazol-1-yl)pyridin-2-yl)methanol; (S)-(6-(6-(6-(1-aminoethyl)pyridin-2-yl)-4-(pyridazin-3-yl)-1H-indazol-1-yl)pyridin-2-yl)methanol; (R)-(6-(6-(6-(1-amino-2-fluoroethyl)pyridin-2-yl)-4-(2-methoxyethoxy)-1H-indazol-1-yl)pyridin-2-yl)methanol; (S)-4-amino-4-(6-(1-(6-(hydroxymethyl)pyrazin-2-yl)-4-(2-methoxyethoxy)-1H-indazol-6-yl)pyridin-2-yl)butan-1-ol; (S)-(6-(6-(4-(1-aminobutyl)pyrimidin-2-yl)-4-(2-methoxyethoxy)-1H-indazol-1-yl)pyridin-2-yl)methanol; (6-(6-(6-(1-aminocyclobutyl)pyridin-2-yl)-4-(2-methoxyethoxy)-1H-indazol-1-yl)pyridin-2-yl)methanol; (R)-(6-(6-(4-(1-aminobutyl)pyrimidin-2-yl)-4-(2-methoxyethoxy)-1H-indazol-1-yl)pyridin-2-yl)methanol; (4S)-4-amino-3-fluoro-4-(6-(1-(6-(hydroxymethyl)pyridin-2-yl)-4-(2methoxyethoxy)-1H-indazol-6-yl)pyridin-2-yl)butan-1-ol; (S)-3-((6-(6-(1-aminobutyl)pyridin-2-yl)-1-(6-(hydroxymethyl)pyridin-2-yl)-1H-indazol-4-yl)oxy)propan-1-ol; (S)-3-((6-(6-(1-aminopropyl)pyridin-2-yl)-1-(6-(hydroxymethyl)pyridin-2-yl)-1H-indazol-4-yl)oxy)propan-1-ol; (S)-3-((6-(6-(1-aminoethyl)pyridin-2-yl)-1-(6-(hydroxymethyl)pyridin-2-yl)-1H-indazol-4-yl) oxy) propan-1-ol ; (6-(6-(6-((S)-1-aminobutyl)pyridin-2-yl)-4-((2S,5R)-5-methyltetrahydrofuran-2-yl)-1H-indazol-1-yl)pyridin-2-yl)methanol; (6-(6-(6-((S)-1-aminobutyl)pyridin-2-yl)-4-((2R,5R)-5-methyltetrahydrofuran-2-yl)-1H-indazol-1-yl)pyridin-2-yl)methanol; (6-(6-(6-((S)-1-aminobutyl)pyridin-2-yl)-4-(tetrahydrofuran-3-yl)-1H-indazol-1-yl)pyridin-2-yl)methanol; (R)-(6-(6-(6-(1-aminobutyl)pyrazin-2-yl)-1H-indazol-1-yl)pyridin-2-yl)methanol; (6-(6-(6-((1R)-1-amino-2-fluoropropyl)pyridin-2-yl)-4-(2-methoxyethoxy)-1H-indazol-1-yl)pyridin-2-yl)methanol; (6-(6-(6-(1-aminocyclobutyl)pyridin-2-yl)-4-(2-methoxyethoxy)-1H-indazol-1-yl)pyrazin-2-yl)methanol; (6-(6-(6-(1-aminocyclopentyl)pyridin-2-yl)-4-(2-methoxyethoxy)-1H-indazol-1-yl)pyridin-2-yl)methanol; (6-(6-(6-(3-aminotetrahydrofuran-3-yl)pyridin-2-yl)-4-(2-methoxyethoxy)-1H-indazol-1-yl)pyridin-2-yl)methanol; (S)-1-((6-(6-(1-aminobutyl)pyridin-2-yl)-1-(6-(hydroxymethyl)pyridin-2-yl)-1H-indazol-4-yl)oxy)-2-methylpropan-2-ol; (S)-(6-(6-(6-(1-aminobutyl)pyrazin-2-yl)-1H-indazol-1-yl)pyridin-2-yl)methanol; (6-(6-(6-((1S)-1-amino-2-fluoropropyl)pyridin-2-yl)-4-(2-methoxyethoxy)-1H-indazol-1-yl)pyridin-2-yl)methanol; (S)-(6-(6-(6-(1-aminoethyl)pyridin-2-yl)-4-(3-methyl-1H-pyrazol-1-yl)-1H-indazol-1-yl)pyridin-2-yl)methanol; (S)-(6-(6-(6-(1-aminoethyl)pyridin-2-yl)-4-(1H-pyrazol-1-yl)-1H-indazol-1-yl)pyridin-2-yl)methanol; (S)-(4-(6-(6-(1-aminobutyl)pyridin-2-yl)-1H-indazol-1-yl)pyrimidin-2-yl)methanol; (6-(6-(8-amino-8-methyl-5,6,7,8-tetrahydroquinolin-2-yl)-1H-indazol-1-yl)pyridin-2-yl)methanol; (6-(6-(8-amino-8-propyl-5,6,7,8-tetrahydroquinolin-2-yl)-1H-indazol-1-yl)pyridin-2-yl)methanol; (6-(6-(6-(3-aminooxetan-3-yl)pyridin-2-yl)-4-(2-methoxyethoxy)-1H-indazol-1-yl)pyridin-2-yl)methanol; (S)-(6-(6-(6-(1-aminobutyl)pyridin-2-yl)-4-(2-(methylsulfonyl)ethoxy)-1H-indazol-1-yl)pyridin-2-yl)methanol; (S)-(6-(6-(6-(1-aminobutyl)pyridin-2-yl)-4-((3,3-difluorocyclobutyl)methoxy)-1H-indazol-1-yl)pyridin-2-yl)methanol; and (S)-(6-(6-(6-(1-aminobutyl)pyridin-2-yl)-4-(1-methylpiperidin-4-yl)-1H-indazol-1-yl)pyridin-2-yl)methanol.

In any aspect or embodiment described herein, the PTM is represented by Formula PTM-X (i.e., Formulas PTM-Xa, PTM-Xb, PTM-Xc, PTM-Xd, PTM-Xe, PTM-Xf, and/or PTM-Xg, which correspond to Formula (I), the first and second structure of paragraph [0042] and the first and second structure of paragraph [0046] of U.S. Patent Application Publication No. 2015/0011532 A1, the structure of paragraph [0046] of U.S. Patent Application Publication No. 2015/0045347 A1, and Formula (I) and the structure of paragraph [0045] of U.S. Patent Application Publication No. 2016/0083375 A1, which is incorporated herein in its entirety for all purposes):

PTM-Xa

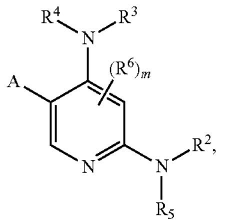

PTM-Xb

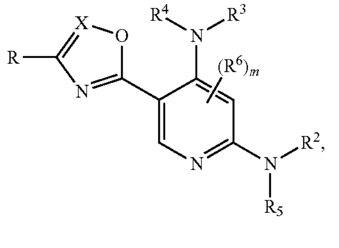

-continued

PTM-Xc

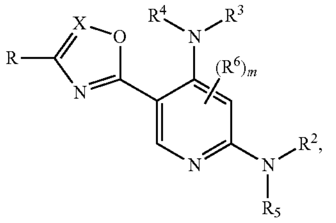

PTM-Xd

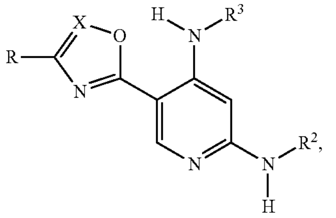

PTM-Xe

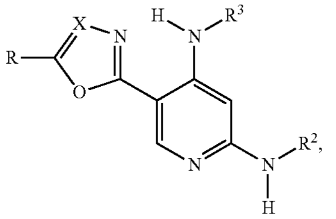

PTM-Xf

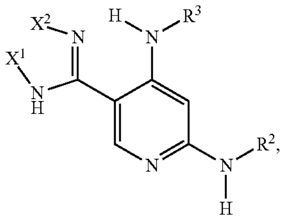

PTM-Xg

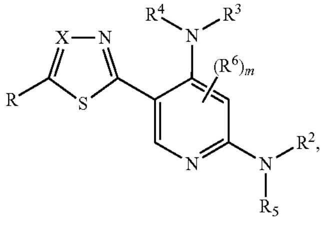

wherein:

A of PTM-X is

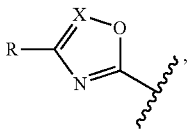, 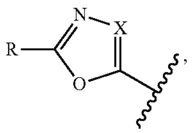, or

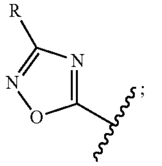;

or A of PTM-X is a triazole optionally substituted by 0-2 R

X of PTM-X is N or C—$R^7$;

R of PTM-X is hydrogen, $R^1$, halogen, cyano, nitro, —OR, —C(═O)—R, —C(═O)O—$R^1$, —C(═O)$NR^{11}$—$R^1$, —S(═O)$_2$—$R^1$, —$NR^{11}$C(═O)—$R^1$, —$NR^1$C(═O)$NR^{11}R^{11}$, —$NR^{11}$C(═O)$NR^{11}R^1$, —$NR^{11}$C(═O)O—$R^1$, —$NR^1$S(═O)$_2R^1$, —$NR^{11}R^{11}$, or —$NR^{11}R^{11}$;

$R^1$ of PTM-X is $C_{1-6}$ alkyl substituted with 0-4 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocycle containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$;

$R^{1a}$ of PTM-X is hydrogen, ═O, F, Cl, Br, $OCF_3$, CN, $NO_2$, —$(CH_2)_r$$OR^b$, —$(CH_2)_r$$SR^b$, —$(CH_2)_r$C(O)$R^b$, —$(CH_2)_r$C(O)O$R^b$, —$(CH_2)_r$OC(O)$R^b$, —$(CH_2)_r$$NR^{11}R^{11}$, —$(CH_2)_r$C(O)$NR^{11}R^{11}$, —$(CH_2)_r$$NR^b$C(O)$R^c$, —$(CH_2)_r$$NR^b$C(O)O$R^c$, —$NR^b$C(O)$NR^{11}R^{11}$, —S(O)$_p$$NR^{11}R^{11}$, —$NR^b$S(O)$_p$$R^c$, —S(O)R, —S(O)$_2$R, $C_{1-6}$ alkyl substituted with 0-2 $R^a$, $C_{1-6}$haloalkyl, —$(CH_2)_r$-3-14 membered carbocycle substituted with 0-3 $R^a$, or —$(CH_2)_r$-5-7 membered heterocycle or heteroaryl, each comprising carbon atoms and 1-4 heteroatoms selected from N, O, and S(O)$_p$ substituted with 0-3 $R^a$;

$R^2$ of PTM-X is $C_{6-10}$ aryl substituted with 0-4 $R^{2a}$, a 5-10 membered heterocycle containing 1-4 heteroatoms selected from N, O, and S, substituted with 1-4 $R^{2a}$, or a 5-10 membered heteroaryl containing 1-4 heteroatoms selected from N, O, and S, substituted with 0-4 $R^{2a}$;

$R^{2a}$ of PTM-X at each occurrence is independently selected from hydrogen, ═O, halo, $OCF_3$, CN, $NO_2$, —$(CH_2)_r$$OR^b$, —$(CH_2)_r$$SR^b$, —$(CH_2)_r$C(O)$R^b$, —$(CH_2)_r$C(O)O$R^b$, —$(CH_2)_r$OC(O)$R^b$, —$(CH_2)_r$$NR^{11}R^{11}$, —$(CH_2)_r$C(O)$NR^{11}R^{11}$, —$(CH_2)_r$$NR^b$C(O)$R^c$, —$(CH_2)_r$$NR^b$C(O)O$R^c$, —$NR^b$C(O)$NR^{11}R^{11}$, —S(O)$_p$$NR^{11}R^{11}$, —$NR^b$S(O)$_p$$R^c$, —S(O)$R^c$, —S(O)$_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and S(O)$_p$ substituted with 0-2 $R^a$;

$R^3$ of PTM-X is $C_{1-6}$alkyl substituted with 0-3 $R^{3a}$, $C_{1-6}$ haloalkyl, $C_{2-6}$ alkenyl substituted with 0-3 $R^{3a}$, $C_{2-6}$ alkynyl substituted with 0-3 $R^{3a}$, $C_{3-10}$ cycloalkyl substituted with 0-3 $R^{3a}$, $C_{6-10}$ aryl substituted with 0-3 $R^{3a}$, a 5-10 membered heterocyclyl containing 1-4 heteroatoms selected from N, O, and S, substituted with 0-3 $R^{3a}$ or a 5-10 membered heteroaryl containing 1-4 heteroatoms selected from N, O, and S, substituted with 0-3 $R^{3a}$;

$R^{3a}$ of PTM-X is hydrogen, ═O, F, Cl, Br, $OCF_3$, CN, $NO_2$, —$(CH_2)_r$$OR^b$, —$(CH_2)_r$$SR^b$, —$(CH_2)_r$C(O)$R^b$, —$(CH_2)_r$C(O)O$R^b$, —$(CH_2)_r$OC(O)$R_b$, —$(CH_2)_r$$NR^{11}R^{11}$, —$(CH_2)_r$C(O)$NR^{11}R^{11}$, —$(CH_2)_r$$NR^b$C(O)$R^c$, —$(CH_2)_r$$NR^b$C(O)O$R^c$, —$NR^b$C(O)$NR^{11}R^{11}$, —S(O)$_p$$NR^{11}R^{11}$, $NR^b$S(O)$_p$$R^c$, —S(O)$R^c$, —S(O)$_2R^c$, $C_{1-6}$ alkyl substituted with 0-2 $R^a$, $C_{1-6}$haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$ substituted with 0-1 $R^a$;

$R^4$ and $R^5$ of PTM-X are independently selected from hydrogen, $C_{1-4}$ alkyl substituted with 0-1 $R^f$, $(CH_2)$-phenyl substituted with 0-3 $R^d$, and a $-(CH_2)$-5-7 membered heterocycle comprising carbon atoms and 1-4 heteroatoms selected from N, O, and $S(O)_p$;

$R^6$ and $R^7$ of PTM-X are independently at each occurrence is selected from hydrogen, =O, F, Cl, Br, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$alkyl substituted with 0-2 $R^a$, $C_{1-6}$haloalkyl, $-(CH_2)_r$-3-14 membered carbocycle substituted with 0-3 $R^a$, or $-(CH_2)_r$-5-7 membered heterocycle or heteroaryl, each comprising carbon atoms and 1-4 heteroatoms selected from N, O, and $S(O)_p$ substituted with 0-3 $R^a$, provided $R^6$ and $R^7$ are not both hydrogen;

$R^{11}$ of PTM-X at each occurrence is independently hydrogen, $R^e$, $C_{1-4}$ alkyl substituted with 0-1 $R^f$, $CH_2$-phenyl substituted with 0-3 $R^d$, or $-(CH_2)$-5-7 membered heterocycle or heteroaryl, each comprising carbon atoms and 1-4 heteroatoms selected from N, O, and $S(O)_p$ substituted with 0-3 $R^d$; or $R^{11}$ and along with another $R^{11}$, $R^1$, or $R^2$ on the same nitrogen atom may join to form an optionally substituted heterocycle;

$R^a$ of PTM-X is hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-1 $R^f$, $C_{1-6}$haloalkyl, $-(CH_2)_r$-3-14 membered carbocycle, or $-(CH_2)_r$-5-7 membered heterocycle or heteroaryl, each comprising carbon atoms and 1-4 heteroatoms selected from N, O, and $S(O)_p$; or two $R^a$ on adjacent or the same carbon atom form a cyclic acetal of the formula $-O-(CH_2)_n-O-$, or $-O-CF_2-O-$, wherein n is selected from 1 or 2;

$R^b$ of PTM-X is hydrogen, $R^e$ of PTM-X, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-3 $R^d$; Re is $C_{1-6}$ alkyl substituted with 0-1 $R_f$, $C_{3-6}$ cycloalkyl, or $(CH_2)_r$-phenyl substituted with 0-3 $R_f$;

$R^c$ of PTM-X is $C_{1-6}$alkyl, $C_{3-6}$cycloalkyl, or $(CH_2)_r$-phenyl substituted with 0-3 $R_f$;

$R^d$ of PTM-X is hydrogen, F, Cl, Br, $OCF_3$, $CF_3$, CN, $NO_2$, $-OR^e$, $-(CH_2)_rC(O)R^e$, $-NR^eR^e$, $-NR^eC(O)OR^c$, $C_{1-6}$alkyl, or $(CH_2)_r$-phenyl substituted with 0-3 $R^f$;

$R^e$ of PTM-X is selected from hydrogen, $C_{1-6}$ alkyl, $C_{3-6}$ cycloalkyl, and $(CH_2)_r$-phenyl substituted with 0-3 $R^f$;

$R^f$ of PTM-X is hydrogen, halo, $NH_2$, OH, or $O(C_{1-6}alkyl)$;

p of PTM-X is 0, 1, or 2;

r of PTM-X is 0, 1, 2, 3, or 4;

m of PTM-X is 0, 1, or 2; and the PTM-X is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-X is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^{1a}$, $R^2$, $R^{2a}$, $R^3$, $R^{3a}$, $R^4$, $R^5$, $R^6$, $R^7$, $R^{11}$, $R^a$, $R^b$, $R^c$, $R^d$, $R^e$, or $R^f$).

In any aspect or embodiment described herein, $R^2$ of PTM-X is phenyl, pyridyl, pyrimidinyl, naphthyl, indolinyl, benzothiazolyl, pyrazolopyridinyl, benzoisothiazolyl, triazolopyridinyl, imidazopyridinyl, benzooxazolyl, triazolopyridinyl, imidazopyridinyl, pyridopyrazinyl, quinazolinyl, pyridopyrazinyl, benzooxadiazolyl, benzothiadiazolyl, benzoimidazolyl, triazolopyridinyl, imdazopyridazinyl, pyridopyrazinyl, naphthyridinyl, quinoxalinyl, phthalazinyl, quinolinyl, indolyl, benzothiazolyl, benzodioxolyl, benzothienyl, isoquinolinyl, benzopyranyl, indolizinyl, benzofuranyl, chromonyl, coumarinyl, benzopyranyl, cinnolinyl, pyrrolopyridyl, furopyridyl, isoindolyl, or quinazolinyl, each group substituted by 1-4 groups selected from $R^{2a}$.

In any aspect or embodiment described herein, $R^2$ of PTM-X is selected from

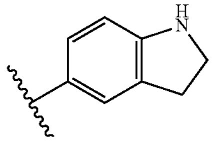 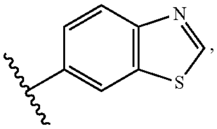,

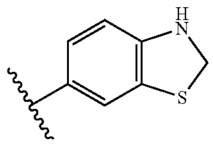, 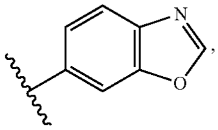,

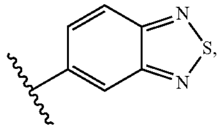, 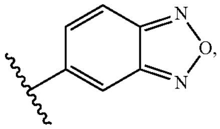,

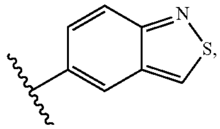, 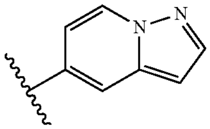,

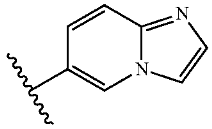, 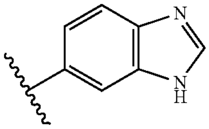,

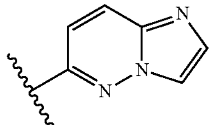, 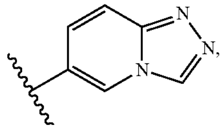,

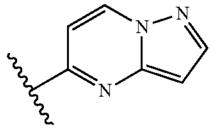, 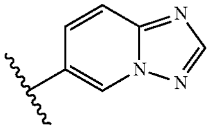,

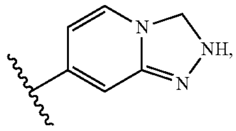, 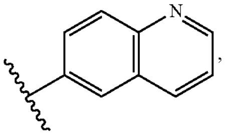,

-continued
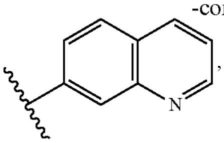, 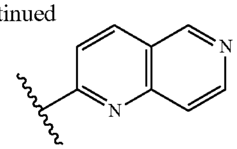,
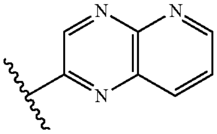, 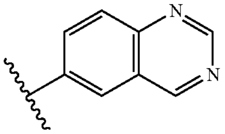,
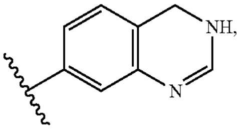 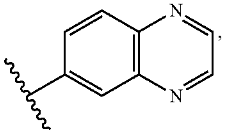,
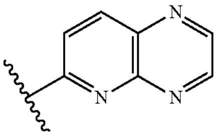, 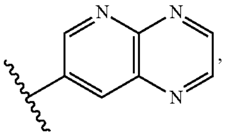,
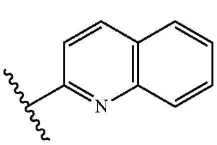, 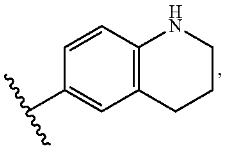,
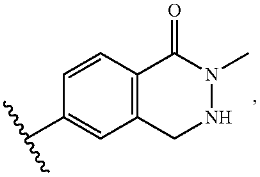, 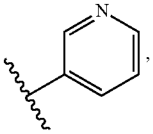,
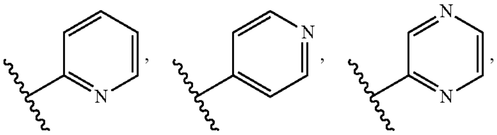
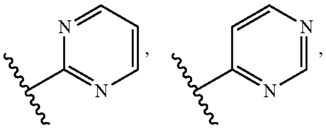
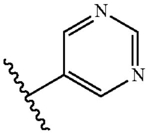, and 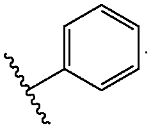.
wherein each group is substituted by 0-4 $R^{2a}$.
In any aspect or embodiment described herein, $R^2$ of PTM-X is selected from
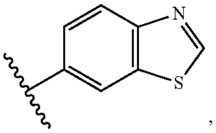, 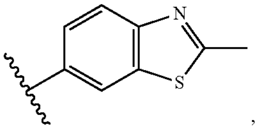,
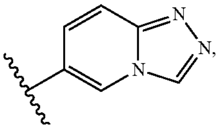 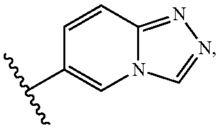
-continued
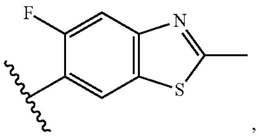, 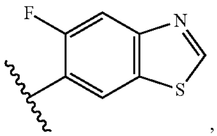,
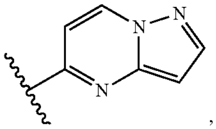, 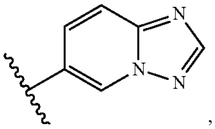,
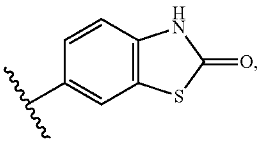
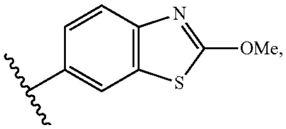 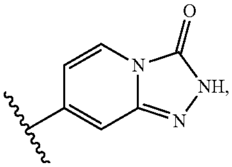
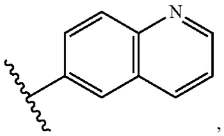,
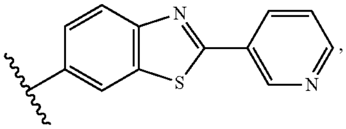
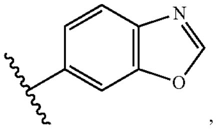, 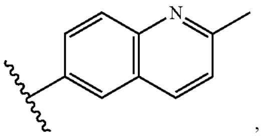,
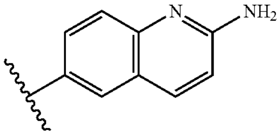,
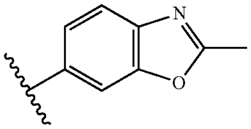, 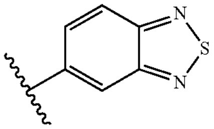,
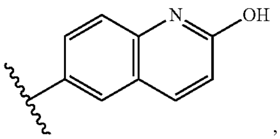,
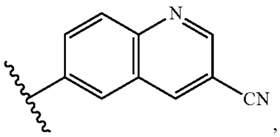, 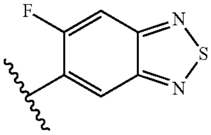,
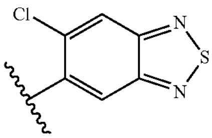, 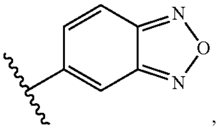, -continued
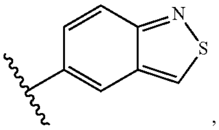
,
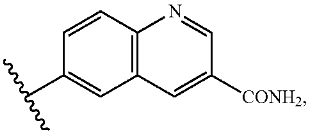
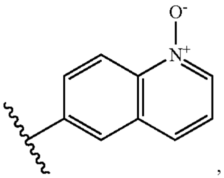
,
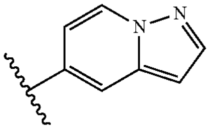
,
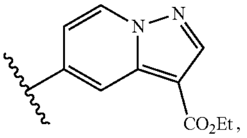
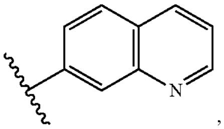
,
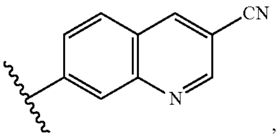
,
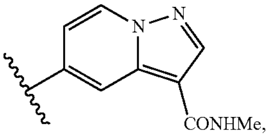
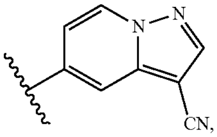
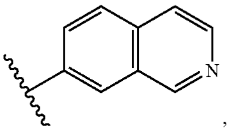
,
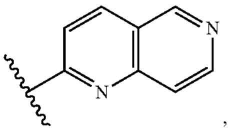
,
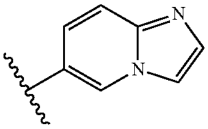
,
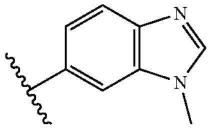
,
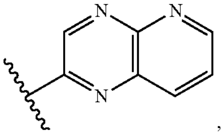
,
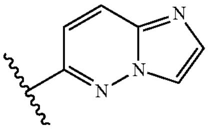
,
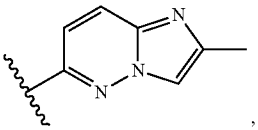
,
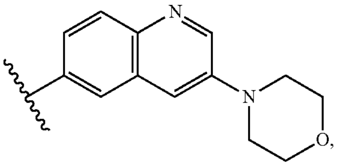
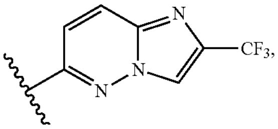
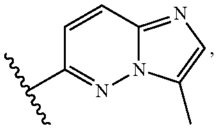
-continued
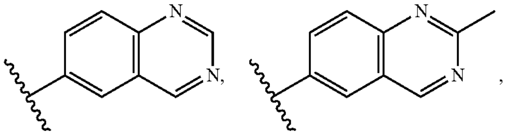
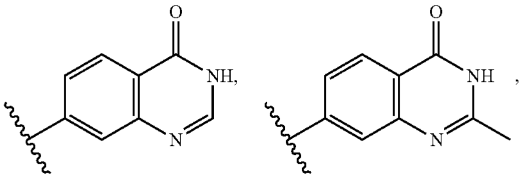
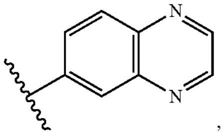
,
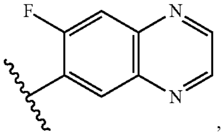
,
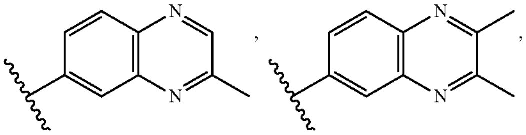
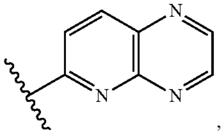
,
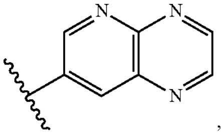
,
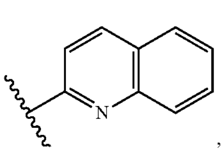
,
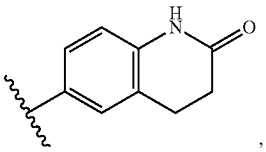
,
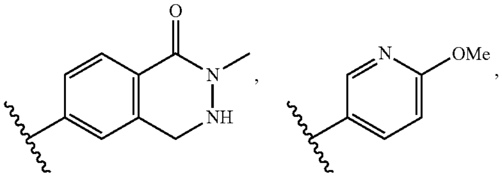
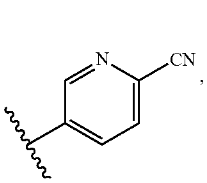
,
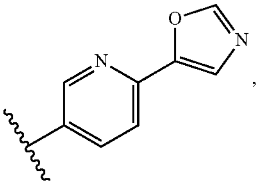
,
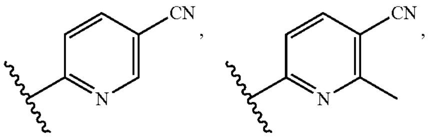
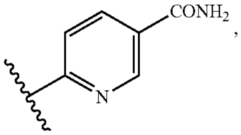
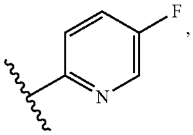
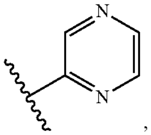
,
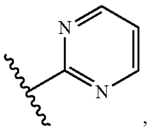
,
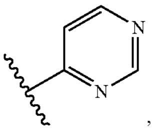
, -continued
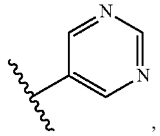, and 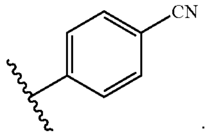.
In any aspect or embodiment described herein, $R^1$ of PTM-X is selected from
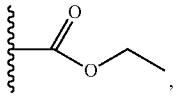, $NH_2$, 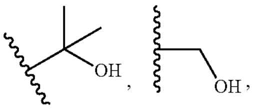,
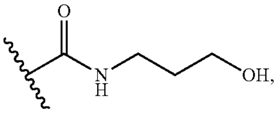 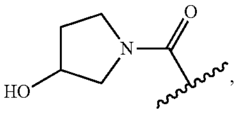,
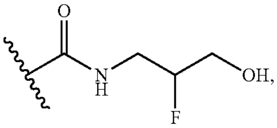
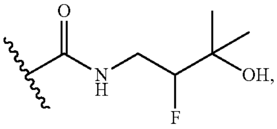 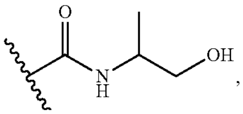,
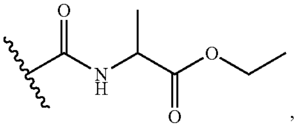,
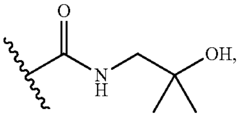 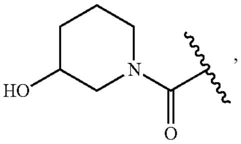,
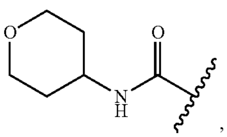, 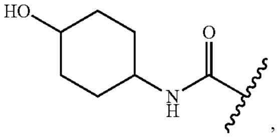,
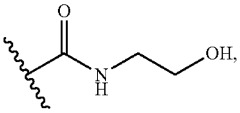
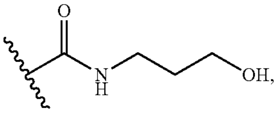 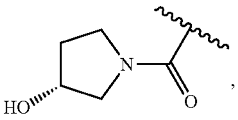,
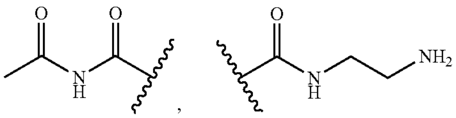,
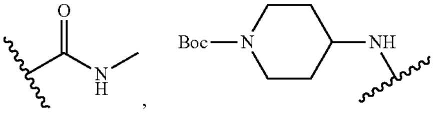,
-continued
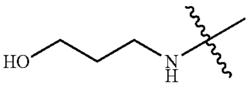, 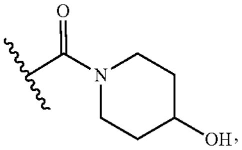
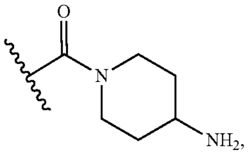 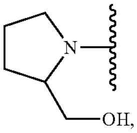
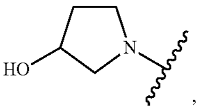, 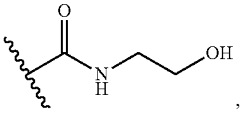,
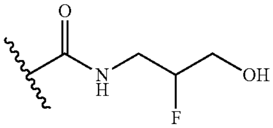, 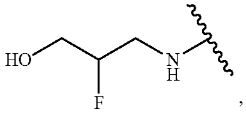,
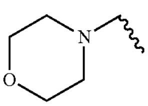, 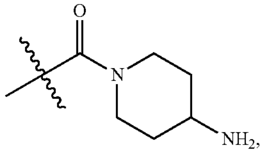
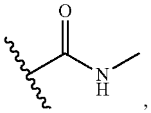, 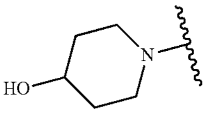,
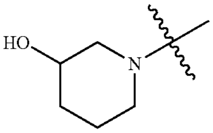, 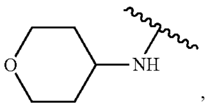,
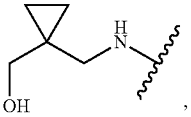, 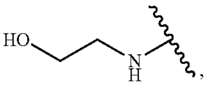
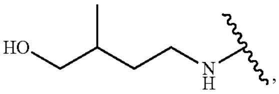
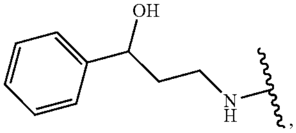
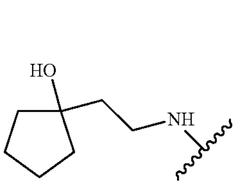, 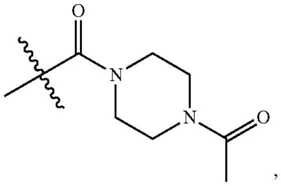,
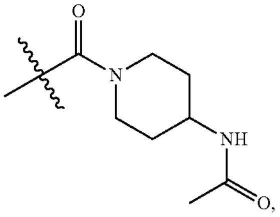 and -continued
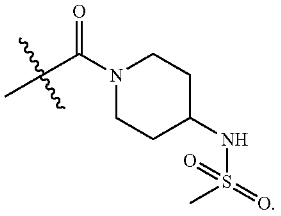
In any aspect or embodiment described herein, R of PTM-X is selected from —$C(O)NH_2$, —$C(O)OC_{1-6}$alkyl, —$C(O)NH(C_{1-6}$alkyl), —$C(O)N(C_{1-6}$alkyl$)_2$,
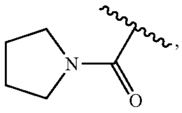,
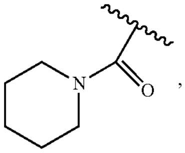,
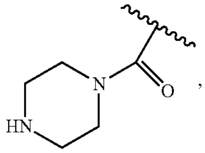,
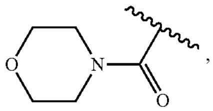,
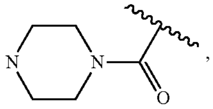,
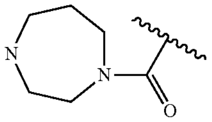, and
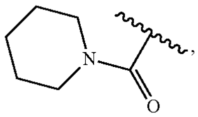,
wherein each group substituted by 0-3 $R^{1a}$.
In any aspect or embodiment described herein, $R^{1a}$ of PTM-X is selected from
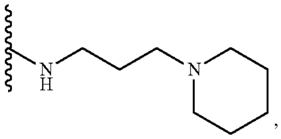,
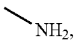,
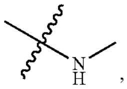,
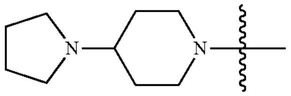,
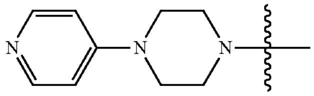,
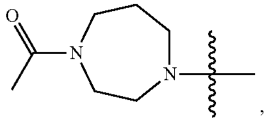,
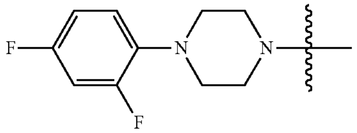,
-continued
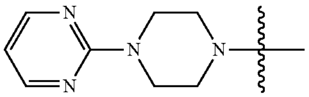,
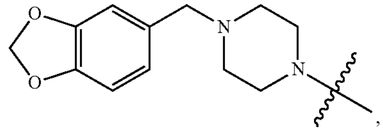,
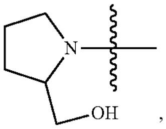,
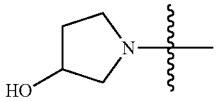,
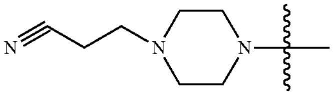,
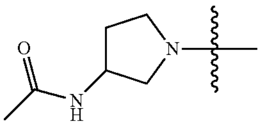,
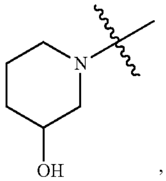,
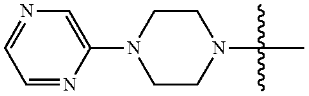,
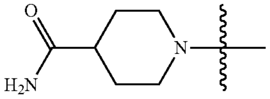,
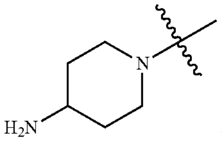,
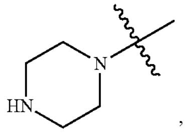,
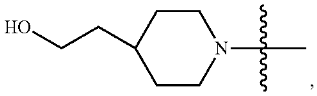,
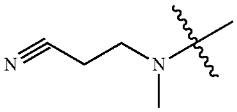,
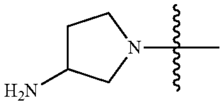,
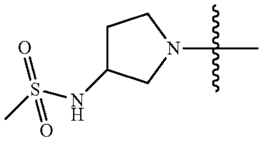,
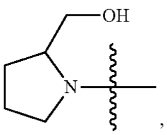,
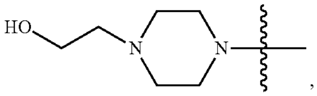,
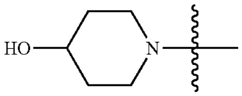,
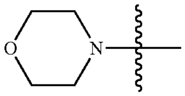,
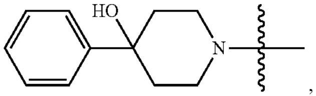, -continued
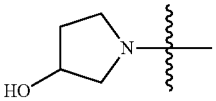, EtO—,
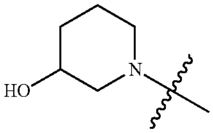,
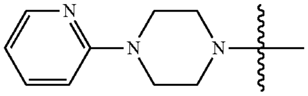,
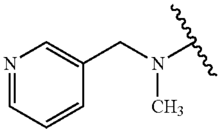,
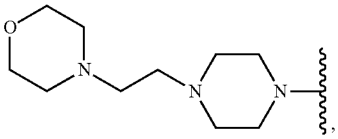,
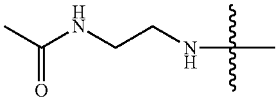,
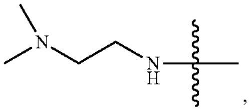,
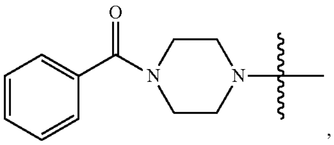, 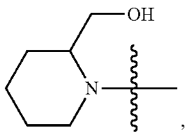,
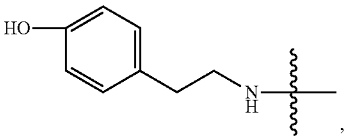,
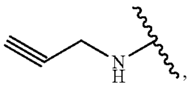, 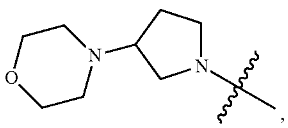,
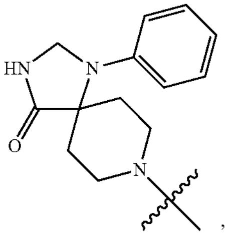, 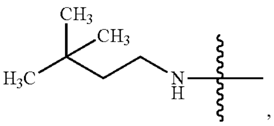,
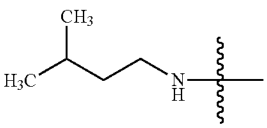,
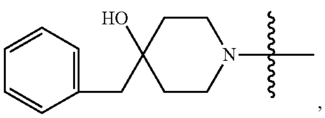,
-continued
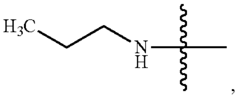,
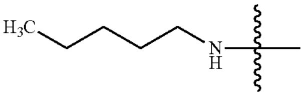,
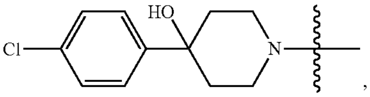,
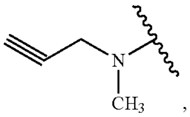, 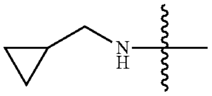,
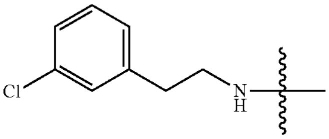,
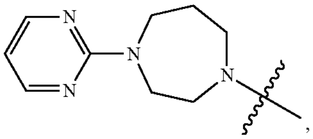,
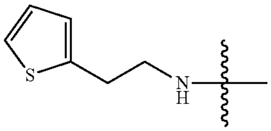,
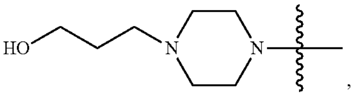,
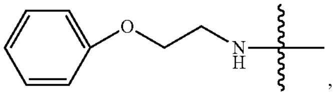,
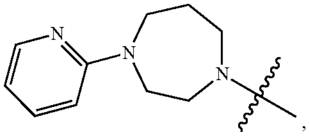,
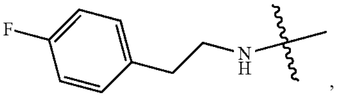,
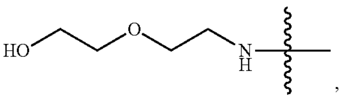,
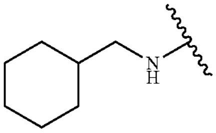, 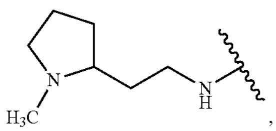,
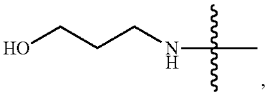,
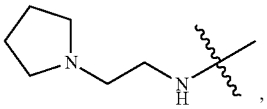, 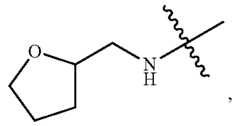, -continued

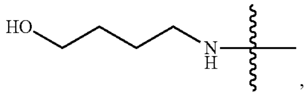
,
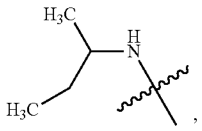
,
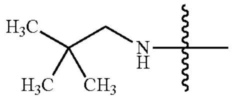
,
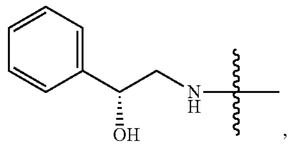
,
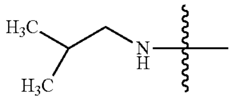
,
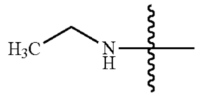
,
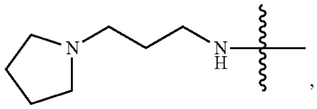
,
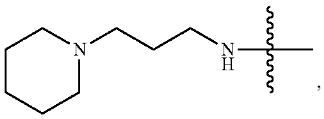
,
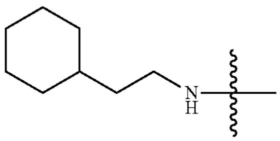
and
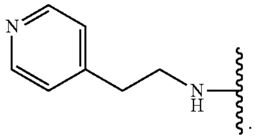
.

In any aspect or embodiment described herein, the PTM is represented by Formula PTM-XI (i.e., Formulas PTM-XIa, PTM-XIb and/or PTM-XIc which correspond to Formulas I and II of International Patent Application Publication WO 2016/053769 A1, Formulas I and II of International Patent Application Publication WO 2016/053770, Formulas I and II of International Patent Application Publication WO 2016/053771 A1 and Formula I of International Patent Application Publication WO 2016/053772 A1, which are incorporated herein in their entirety for all purposes):

PTM-XIa

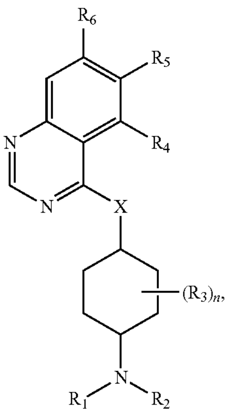

-continued

PTM-XIb

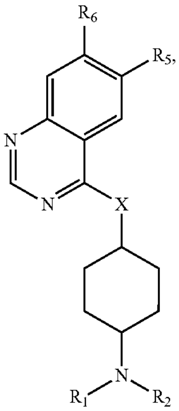
or

PTM-XIc

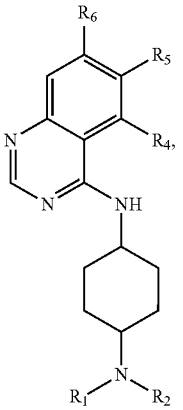

wherein:

X of PTM-XI is NH or O;

b of PTM-XI is 0 or 1;

n of PTM-XI is 0, 1, 2, 3 or 4;

$R_1$ and $R_2$ of PTM-XI are independently H, $(C_1$-$C_4)$alkyl and heterocyclyl, or $R_1$ and $R_2$ can be taken together with the nitrogen to which they are attached to form a monocyclic or bicyclic (fused, bridged or spirocyclic) heterocycle containing 3-8 carbon atoms optionally containing, in addition to the nitrogen, one or two additional heteroatoms selected from N, O and S, said alkyl and heterocycle are optionally substituted with one or more substituents selected from $R_a$;

$R^3$ of PTM-XI is $(C_1$-$C_4)$alkyl wherein two adjacent alkyl groups can join together and form a bridged moiety of 3-6 carbon atoms;

$R_4$ of PTM-XI is absent, halo or $O_b(C_1$-$C_4)$alkyl;

$R_5$ of PTM-XI is selected from halo, CN, $O(C_1$-$C_4)$alkyl, $C_1$-$C_4$ alkyl and $C_2$-$C_4$ alkenyl which are optionally substituted with one or more substituents selected from $R_b$ or $R_5$ is aryl or heteroaryl each optionally substituted with one or more substitutents selected from $R_b$;

$R_6$ of PTM-XI is absent, halo, or $O(C_1$-$C_4)$alkyl;

$R_a$ of PTM-XI is halo, oxo, OH, $O_b(C_1$-$C_4)$alkyl, $C(O)O_b(C_1$-$C_6)$alkyl, $(C{=}O)_b$heterocyclyl, $CF_3$, $SO_2H$, $SO_2(C_1$-$C_4)$alkyl, $C(O)C_1$-$C_4$alkyl, or heterocyclyl, wherein said alkyl can come together with another alkyl to form a bridged moiety and said alkyl and heterocyclyl are optionally substituted with one or more substituents independently selected from F and $(C_1$-$C_4)$alkyl; and $R_b$ of PTM-XI is independently selected from OH, halo, $CHF_2$, $CF_3$, COOH, $SO_2(C_1-C_4)$alkyl, $C(O)C_1-C_4$alkyl, (C═O)$NH_2$, $O_b(C_1-C_4)$alkyl, aryl, heterocyclyl, CN, $C(O)N(R_c)_2$, $N(R_c)_2$, wherein the $R_c$ and alkyl are optionally substituted with OH, $O(C_1-C_4)$alkyl and heterocyclyl; and $R_c$ of PTM-XI is independently selected from H, $SO_2(C_1-C_4)$alkyl, or $C_1-C_4$ alkyl;

the PTM-XI is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-XI is covalently joined to a ULM, a chemical linker group (L), a CLM, an ILM, a VLM, MLM, a ULM', a CLM', a ILM', a VLM', a MLM', or combination thereof via an R group (e.g., $R_1$, $R_2$, $R_3$, $R_4$, $R_5$, $R_6$, $R_a$, $R_b$, or $R_c$).

In any aspect or embodiment described herein, the PTM of PTM-XIb comprises at least one of:

X of PTM-XI is NH or O;

b of PTM-XI is 0 or 1;

$R_1$ and $R_2$ of PTM-X1 are independently H, $(C_1-C_4)$alkyl and tetrahydopyranyl; or $R_1$ and $R_2$ can be taken together with the nitrogen to which they are attached to form morpholinyl, azetidinyl, piperazinyl, pyrrolidinyl, piperidinyl, oxaazaspirooxtyl, oxaazapiroheptanyl and thiomorpholinyl, said alkyl, morpholinyl, azetidinyl, piperazinyl, pyrrolidinyl, piperidinyl, oxaazaspirooxtyl, oxaazapiroheptanyl and thiomorpholinyl are optionally substituted with one or more substituents independently selected from $R_a$;

$R_5$ of PTM-XI is selected from $C_1-C_4$ alkyl and $C_2-C_4$ alkenyl which are optionally substituted with one or more substituents selected from $R_b$;

$R_6$ of PTM-XI is absent, F or methyl;

$R_a$ of PTM-XI is F, oxo, OH, $O_b(C_1-C_4)$alkyl, $CF_3$, $SO_2(C_1-C_4)$alkyl, oxetanyl, pyrazolyl, tetrahydropyranyl and thiophenyl, said oxetanyl, pyrazolyl, tetrahydropyranyl and thiophenyl optionally substituted with one or more substituents independently selected from F, and $(C_1-C_4)$alkyl; and $R_b$ of PTM-XI is independently selected from OH, F, $O_b(C_1-C_4)$alkyl, and CN.

In any aspect or embodiment, the PTM of PTM-XI is selected from: (trans)-N1-(6,7-dimethylquinazolin-4-yl)-N4,N4-dimethylcyclohexane-1,4-diamine (PTM-XI-1); trans-N,N-dimethyl-N'-(6-methylquinazolin-4-yl)cyclohexane-1,4-diamine (PTM-XI-2); 6-methyl-N-(trans-4-morpholin-4-ylcyclohexyl)quinazolin-4-amine (PTM-XI-3); N-(trans-4-morpholin-4-ylcyclohexyl)-6-(trifluoromethyl) quinazolin-4-amine (PTM-XI-4); 7-fluoro-6-methyl-N-(trans-4-morpholin-4-ylcyclohexyl)quinazolin-4-amine (PTM-XI-5); trans-N,N-dimethyl-N'-[6-(trifluoromethyl) quinazolin-4-yl]cyclohexane-1,4-diamine (PTM-XI-6); 4-((trans)-446-methylquinazolin-4-yl)oxy)cyclohexyl)morpholine (PTM-XI-7); 6-methyl-N-((/R,4R)-4-(3-(methylsulfonyl)azetidin-1-yl)cyclohexyl)quinazolin-4-amine (PTM-XI-8); N-[cis-4-(3-fluoroazetidin-1-yl)cyclohexyl]-6-methylquinazolin-4-amine (PTM-XI-9); N-[trans-4-(3-fluoroazetidin-1-yl)cyclohexyl]-6-methylquinazolin-4-amine (PTM-XI-10); 4-{cis-4-[(6-methylquinazolin-4-yl) amino]cyclohexyll piperazin-2-one (PTM-XI-11); 4-{trans-4-[(6-methylquinazolin-4-yl)amino]cyclohexyl}piperazin-2-one (PTM-XI-12); 1-{trans-4-[(6-methylquinazolin-4-yl) amino]cyclohexyl}azetidin-3-ol (PTM-XI-13); 1-{cis-4-[(6-methylquinazolin-4-yl)amino]cyclohexyl}azetidin-3-ol (PTM-XI-14); N-[trans-4-(3,3-difluoropyrrolidin-1-yl)cyclohexyl]-6-methylquinazolin-4-amine (PTM-XI-15); 6-methyl-N-[trans-4-(2-oxa-6-azaspiro[3.4]oct-6-yl)cyclohexyl]quinazolin-4-amine (PTM-XI-16); 6-methyl-N-{cis-4-[3-(methylsulfonyl)azetidin-1-yl]cyclohexyl}quinazolin-4-amine (PTM-XI-17); 6-methyl-N-{4-[4-(trifluoromethyl) piperidin-1-yl]cyclohexyl}quinazolin-4-amine (PTM-XI-18); 6-methyl-N-{4-[4-(trifluoromethyl)piperidin-1-yl] cyclohexyl}quinazolin-4-amine (PTM-XI-19); 6-methyl-N-{4-[3-(trifluoromethyl)piperidin-1-yl] cyclohexyl}quinazolin-4-amine (PTM-XI-20); 6-methyl-N-{4-[2-(trifluoromethyl)piperidin-1-yl] cyclohexyl}quinazolin-4-amine (PTM-XI-21); 6-methyl-N-{4-[2-(trifluoromethyl)piperidin-1-yl] cyclohexyl}quinazolin-4-amine (PTM-XI-22); 6-methyl-N-{4-[3-(trifluoromethyl)piperidin-1-yl] cyclohexyl}quinazolin-4-amine (2-16); (trans)-N1-(6-methylquinazolin-4-yl)-N4-(tetrahydro-2H-pyran-4-yl) cyclohexane-1,4-diamine (PTM-XI-23); trans-N-(6-methylquinazolin-4-yl)-N'-(tetrahydro-2H-pyran-4-ylmethyl)cyclohexane-1,4-diamine (PTM-XI-24); trans-N-[(4S)-2,2-dimethyltetrahydro-2H-pyran-4-yl]-N'-(6-methylquinazolin-4-yl)cyclohexane-1,4-diamine (PTM-XI-25); trans-N-(6-methylquinazolin-4-yl)-N'-(thiophen-2-ylmethyl)cyclohexane-1,4-diamine (PTM-XI-26); trans-N-[(1S)-1-cyclopropylethyl]-N'-(6-methylquinazolin-4-yl) cyclohexane-1,4-diamine (PTM-XI-27); trans-N-(6-methylquinazolin-4-yl)-N-[(1S)-3,3,3-trifluoro-lmethylpropyl]cyclohexane-1,4-diamine (PTM-XI-28); (3S)-2-methyl-3-({trans-4-[(6-methylquinazolin-4-yl) amino]cyclohexyll amino)butan-2-ol (PTM-XI-29); trans-N-(1-methylethyl)-N'-(6-methylquinazolin-4-yl)cyclohexane-1,4-diamine (PTM-XI-30); trans-N-(cyclopropylmethyl)-N'-(6-methylquinazolin-4-yl) cyclohexane-1,4-diamine (PTM-XI-31); trans-N-[(1-methyl-H-pyrazol-5-yl)methyl]-N'-(6-methylquinazolin-4-yl)cyclohexane-1,4-diamine (PTM-XI-32); trans-N-[(3-methyloxetan-3-yl)methyl]-N'-(6-methylquinazolin-4-yl) cyclohexane-1,4-diamine (PTM-XI-33); trans-N-(6-methylquinazolin-4-yl)-N'-(3,3,3-trifluoropropyl) cyclohexane-1,4-diamine (PTM-XI-34); trans-N-(2,2-dimethylpropyl)-N'-(6-methylquinazolin-4-yl)cyclohexane-1,4-diamine (PTM-XI-35); trans-N-[(1S)-2,2-difluoro-1-methylethy 1]-N'-(6-methylquinazolin-4-yl)cyclohexane-1,4-diamine (PTM-XI-36); trans-N-[(1S)-1-methyl-2-(methylsulfonyl)ethyl]-N'-(6-methylquinazolin-4-yl) cyclohexane-1,4-diamine (PTM-XI-37); (trans)-N1-(6-((E)-2-cyclopropylvinyl)quinazolin-4-yl)-N4,N4-dimethylcyclohexane-1,4diamine (PTM-XI-38); N'-(6-ethenylquinazolin-4-yl)-N,N-dimethylcyclohexane-1,4-diamine (PTM-XI-39); trans-N'-{6-[(1E)-3-methoxyprop-1-en-1-yl]quinazolin-4-yl}-N,N-dimethylcyclohexane-1,4-diamine (PTM-XI-40); 6-ethyl-N-(trans-4-morpholin-4-ylcyclohexyl)quinazolin-4-amine (PTM-XI-41); 4-(4-(((trans)-4-morpholinocyclohexyl)amino)quinazolin-6-yl) butanenitrile (PTM-XI-42); (trans)-N1-(6-ethylquinazolin-4-yl)-N4,N4-dimethylcyclohexane-1,4-diamine (PTM-XI-43); N,N-dimethyl-N'-[6-(1-methylethyl)quinazolin-4-yl] cyclohexane-1,4-diamine (PTM-XI-44); 6-butyl-N-(trans-4-morpholin-4-ylcyclohexyl)quinazolin-4-amine (PTM-XI-45); N-(trans-4-morpholin-4-ylcyclohexyl)-6-propylquinazolin-4-amine (PTM-XI-46); 2-(4-(((trans)-4-(dimethylamino)cyclohexyl)amino)quinazolin-6-yl)ethan-1-ol (PTM-XI-47); 3-{4-[(trans-4-morpholin-4-ylcyclohexyl)amino]quinazolin-6-yl}propan-1-ol (PTM-XI-48); 4-{4-[(trans-4-morpholin-4-ylcyclohexyl)amino] quinazolin-6-yl}butan-1-ol (PTM-XI-49); 1-(4-{[trans-4-(dimethylamino)cyclohexyl]aminolquinazolin-6-yl)ethanol (PTM-XI-50); 4-((trans)-446-methylquinazolin-4-yl)amino) cyclohexyl)thiomorpholine-1,1-dioxide (PTM-XI-51); N-((trans)-4-(2-oxa-6-azaspiro[3.3]heptan-6-yl)cyclohexyl)-6-methylquinazolin-4-amine (PTM-XI-52); 4-(4-(((trans)-4-Morpholinocyclohexyl)amino)quinazolin-6-yl) butan-2-ol (PTM-XI-53); (4-(((trans)-4-(dimethylamino) cyclohexyl)amino)quinazolin-6-yl)methanol (PTM-XI-54).

In any aspect or embodiment described herein, the PTM is represented by Formula PTM-XII (i.e., Formulas PTM-XIIa, PTM-XIIb, PTM-XIIc, PTM-XIId, PTM-XIIe, and/or PTM-XIIf, which correspond to Formulas I and II of International Patent Application Publication WO 2016/144844 A1, Formula I of International Patent Application Publication WO 2016/144846 A1, Formula I of International Patent Application Publication WO 2016/144847 A1, Formula I of International Patent Application Publication WO 2016/144848 A1, and Formula I of International Patent Application Publication WO 2016/144849 A1, which are incorporated herein in their entirety for all purposes):

PTM-XIIa

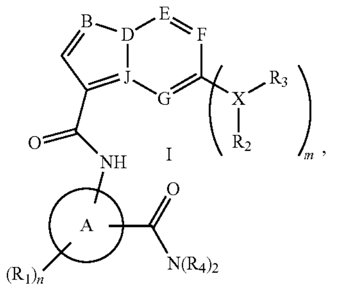

PTM-XIIb

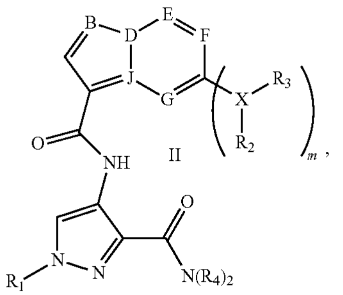

PTM-XIIc

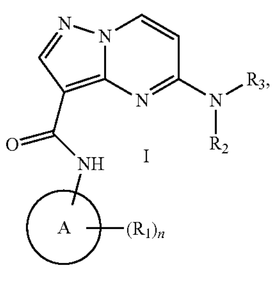

PTM-XIId

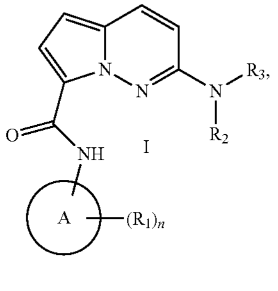

-continued

PTM-XIIe

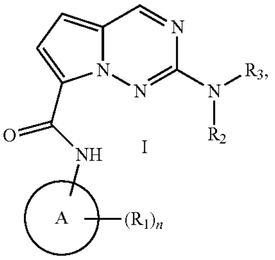

or

PTM-XIIf

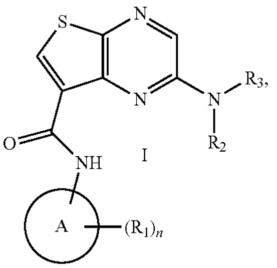

wherein:

B of PTM-XII is CH, N or S; D of PTM-XII is CH or N; E of PTM-XII is CH or N; F of PTM-XII is CH or N; G of PTM-XII is CH or N; and J of PTM-XII is C or N, wherein when B is S then D is CH, E is N, F is CH, G is N and J is C;

X of PTM-XII is O, S, $CH_2$ or N;

m of PTM-XII is 0 or 1;

n of PTM-XII is 0, 1, 2, 3 or 4;

Ring A of PTM-XII is aryl, heterocyclyl, pyridinyl, pyrazolyl, thiophenyl, furanyl or phenyl;

$R_1$ of PTM-XII is independently selected from $(C_1$-$C_4)$alkyl, $(C_3$-$C_6)$cycloalkyl, heterocyclyl, $CF_3$, $CHF_2$, CN, halo, pyrimidine, piperidine and phenyl, each optionally substituted with $(C_1$-$C_4)$alkyl, OH, $CH_3$, $OCH_3$, halo, $O(C_1$-$C_4)$alkyl, methyl-piperidine, $S(O)_2R_c$, $C(O)N(R_b)_2$, or $C(O)O(C_1$-$C_4)$alkyl;

$R_2$ of PTM-XII is absent or H and $R_3$ is independently selected from: $(C_1$-$C_4)$alkyl, $(C_1$-$C_6)$alkyl, $(C_3$-$C_8)$cycloalkyl, heterocyclyl, pyranyl, cyclopentyl, cyclohexyl, cycloheptyl, thiopyranyl, pyrazolyl, piperidinyl, morpholinyl, piperazinyl, each optionally substituted with one or more substituents independently selected from halo, OH, oxo, $N(R_b)_2$, oxopyrrolidinyl, or morpholinyl, or $R_2$ and $R_3$ can be taken together with the nitrogen to which they are attached to form a heterocyclyl, piperazine or morpholine, each optionally substituted with one or more substituents selected from oxo and $R_a$;

$R_4$ of PTM-XII is independently H or methyl;

$R_a$ of PTM-XIIa-f is independently selected from $(C_1$-$C_4)$alkyl, $(C_3$-$C_6)$cycloalkyl, cyclopropyl, $CF_3$, F, $CHF_2$, OH, halo and $NH_2$, said alkyl optionally substituted with $(C_3$-$C_6)$cycloalkyl and $CF_3$; and $R_b$ of PTM-XII is independently selected from H and $(C_1$-$C_4)$alkyl;

$R_c$ of PTM-XII is methyl; and the PTM-XII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-XII is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, $R^a$, $R^b$, $R^c$, or $R^d$).

In any aspect or embodiment described herein, at least one of:

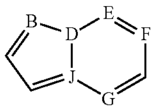

of PTM-XIIa is

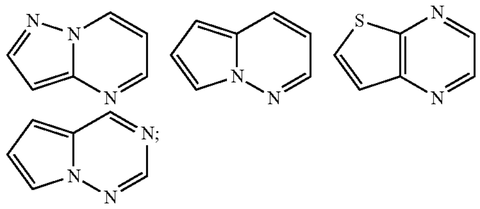

and

X of PTM-XIIa is O, $CH_2$ or N.

In any aspect or embodiment described herein, at least one of:

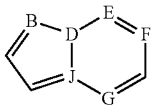

of PTM-XIIa is

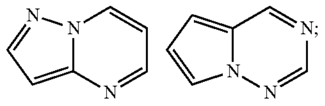

and

X of PTM-XIIa is O, S, $CH_2$ or N.

In any aspect or embodiment described herein, the PTM is represented by Formula PTM-XIII (i.e., Formulas PTM-XIIIa, PTM-XIIIb, PTM-XIIIc, and/or PTM-XIIId, which correspond to Formulas I, IA, IB, and IC of U.S. Patent Application Publication No. 2016/0326151 A1, which is incorporated herein in its entirety for all purposes, and/or PTM-XIIIe, PTM-XIIIf, and/or PTM-XIIIg, which corresponds to Formula(I) of International Patent Application Publication No. WO 2016/174183, which is incorporated herein in its entirety for all purposes, PTM-XIIIi, and/or PTM-XIIIj):

PTM-XIIIa

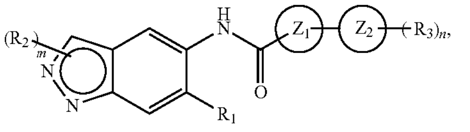

-continued

PTM-XIIIb

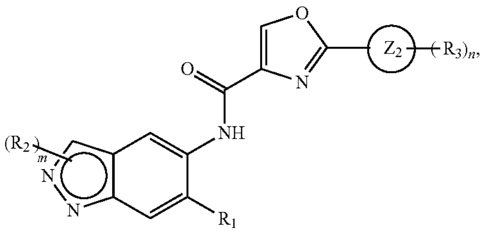

PTM-XIIIc

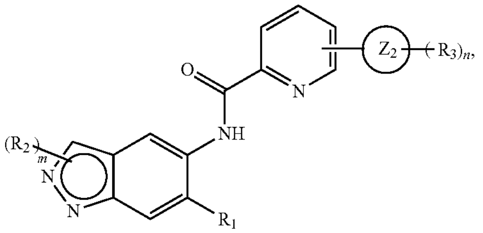

PTM-XIIId

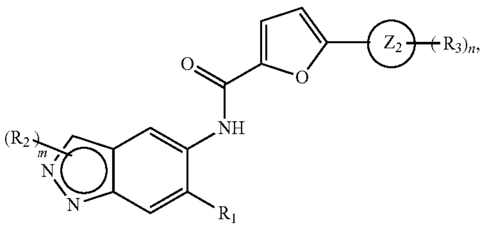

PTM-XIIIe

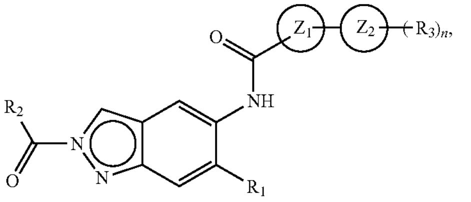

PTM-XIIIf

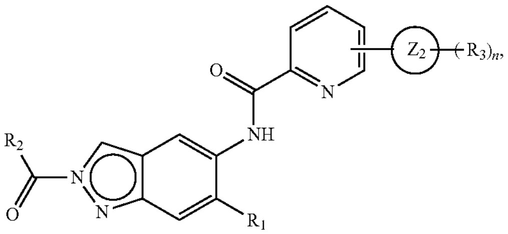

PTM-XIIIg

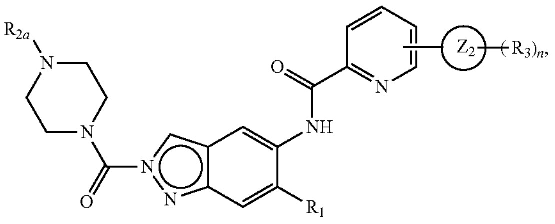

-continued

PTM-XIIIh

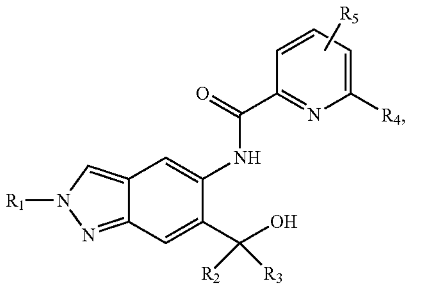

PTM-XIIIi

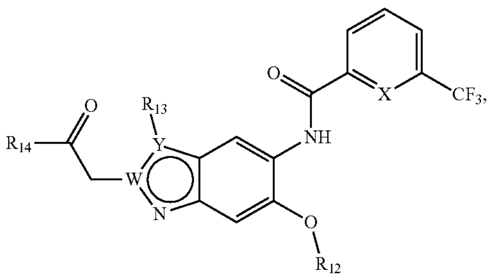

or

PTM-XIIIj

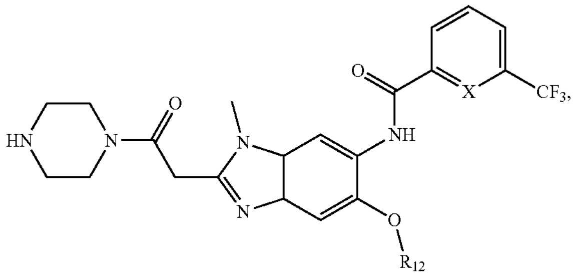

wherein:

Ring $Z_1$ of PTM-XIII is an optionally substituted heteroaryl;

Ring $Z_2$ of PTM-XIII is an optionally substituted heterocycloalkyl, optionally substituted heteroaryl or a direct bond;

$R_1$ of PTM-XIII is optionally substituted alkyl, optionally substituted hydroxy alkyl, cyano, —$NR_aR_b$, optionally substituted cycloalkyl, optionally substituted aryl or optionally substituted heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;

$R_2$ of PTM-XIII, at each occurrence, independently is an optionally substituted group selected from alkyl, cycloalkyl, or cycloheteroalkyl; wherein the substituent, at each occurrence, is independently halogen, alkoxy, hydroxyl, hydroxyalkyl, haloalkyl or haloalkoxy;

$R_{2a}$ of PTM-XIIIa-g is an H or optionally substituted alkyl (e.g., optionally substituted C1-C4 alkyl);

$R_3$ of PTM-XIII, at each occurrence, independently is hydrogen, halogen, alkyl, haloalkyl, haloalkoxy, alkoxy, —$NR_aR_b$, hydroxyl or hydroxyalkyl;

$R_4$ of PTM-XIII at each occurrence is independently is halogen, cyano, an unsubstituted or a singly or multiply, identically or differently substituted C1-C5-alkyl or an unsubstituted or a singly or multiply, identically or differently substituted C3-C6-cycloalkyl (e.g., the substituents of the alkyl or cycloalkyl may be selected from the group of halogen and hydroxyl);

$R_5$ of PTM-XIII at each occurrence is independently is hydrogen, halogen or an unsubstituted or poly-halogen-substituted C1-C5-alkyl;

$R_6$ of PTM-XIII at each occurrence is independently optionally substituted C1-C6-alkyl (e.g., C1-C6-alkyl radical unsubstituted, monobustituted or polysubstituted identically or differently by halogen, hydroxyl, an unsubstituted or mono- or poly-halogen-substituted C3-C6-cycloalkyl, or an $R^9$, $R^{10}SO_2$, $R^{10}SO$ or $R^{11}O$ radical, or a group selected from:

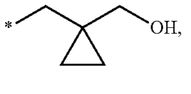 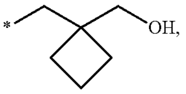 or

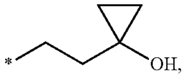

wherein * represents the bonding site of the group to the rest of the molecule);

$R_7$ and $R_8$ of PTM-XIII at each occurrence is independently selected from hydrogen or C1-C6-alkyl (e.g., both may be H or a C1-C6 alkyl, including the same C1-C6 alkyl);

$R_9$ of PTM-XIII is an unsubstituted or mono- or di-methyl-substituted monocyclic saturated heterocycle having 4 to 6 ring atoms, which contains a heteroatom or a heterogroup from the group of O, S, SO and $SO_2$;

$R_{10}$ of PTM-XIII is a C1-C6-alkyl, where the C1-C5-alkyl radical is unsubstituted or mono- or polysubstituted identically or differently by halogen, hydroxyl or C3-C5-cycloalkyl; or $R_{10}$ is C3-C6-cycloalkyl $R_{11}$ of PTM-XIII is an optionally substituted C1-C6-alkyl (e.g., a C1-C6-alkyl radical is unsubstituted or mono- or polysubstituted identically or differently by, e.g., halogen);

$R_a$ of PTM-XIII is hydrogen or alkyl;

$R_b$ of PTM-XIII is hydrogen, alkyl, acyl, hydroxyalkyl, —$SO_2$-alkyl or optionally substituted cycloalkyl;

$R_{12}$ of PTM-XIII is optionally substituted C1-C5 alkyl, optionally substituted methyl, optionally substituted ethyl, optionally substituted cyloalky, or

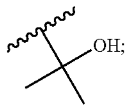 [SMILES: *C(C)(C)O]

$R_{13}$ of PTM-XIII is H or methyl;

$R_{14}$ of PTM-XIII is an optionally substituted linear or branched alkyl (e.g., optionally substituted linear or branched C1-C8 alkyl), optionally substituted amide, carboxylic group, optionally substituted cycloalkyl, optionally substituted heterocycloalkyl, optionally substituted aryl (e.g., optionally substituted C5-C7 aryl), optionally substituted heteroaryl (e.g., optionally substituted C5-C7 heteroaryl), —$SO_2$-alkyl, —$SO_2H$, —O-alkyl, —O-aryl, —O-heteroaryl, optionally substituted urea group;

W and Y of PTM-XIII are selected from C and N with the proviso that one is N and one is C;

X of PTM-XIII is CH or N;

"m" of PTM-XIII is 1 or 2;

"n" of PTM-XIII is 1 or 2; and the PTM-XIII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-XIII is covalently joined to a ULM, a chemical linker group (L), a CLM, an ILM, a VLM, MLM, a ULM', a CLM', a ILM', a VLM', a MLM', or combination thereof via an R group (e.g., $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_a$, $R_b$, or $R_c$).

In any aspect or embodiment described herein, R14 is selected from:

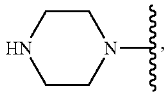,
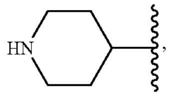,
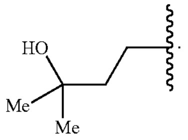.

In any aspect or embodiment described herein, Ring $Z_1$ of PTM-XIII is a 5- or 6-membered optionally substituted heteroaryl.

In any aspect or embodiment described herein, Ring $Z_1$ of the PTM-XIII is selected from the group consisting of tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl and pyrazolyl.

In any aspect or embodiment described herein, Ring $Z_2$ of PTM-XIII is a 5- or 6-membered heteroaryl selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In any aspect or embodiment described herein, Ring $Z_2$ of PTM-XIII is a 5- or 6-membered heterocycloalkyl selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl or 1,4-dioxanyl.

In any aspect or embodiment described herein, the PTM of PTM-XIII is selected from the group consisting of: N-(2-methyl-6-(piperidin-1-yl)-2H-indazol-5-yl)-6-(1H-pyrazol-4-yl) picolinamide; N-(2-methyl-6-(piperidin-1-yl)-2H-indazol-5-yl)-2-(2-methylpyridin-4-yl) oxazole-4-carboxamide; N-(1-methyl-6-(piperidin-1-yl)-1H-indazol-5-yl)-2-(2-methylpyridin-4-yl) oxazole-4-carboxamide; N-(2-cyclopentyl-6-(piperidin-1-yl)-2H-indazol-5-yl)-2-(2-methylpyridin-4-yl)oxazole-4-carboxamide; N-(6-cyano-2-cyclopentyl-2H-indazol-5-yl)-2-(2-methylpyridin-4-yl) oxazole-4-carboxamide; N-(2-cyclopentyl-6-cyclopropyl-2H-indazol-5-yl)-2-(2-methylpyridin-4-yl) oxazole-4-carboxamide; N-(2-cyclopentyl-6-cyclopropyl-2H-indazol-5-yl)-6-(1H-pyrazol-4-yl) picolinamide; N-(2-cyclopentyl-6-morpholino-2H-indazol-5-yl)-2-(2-methylpyridin-4-yl) oxazole-4-carboxamide; 6'-amino-N-(2-cyclopentyl-6-morpholino-2H-indazol-5-yl)-[2,3'-bipyridine]-6-carboxamide 2,2,2-trifluoroacetate; N-(6-(3-fluorophenyl)-2-methyl-2H-indazol-5-yl)-2-(2-methylpyridin-4-yl)oxazole-4-carboxamide; N-(6-cyclohexyl-2-methyl-2H-indazol-5-yl)-2-(2-methylpyridin-4-yl)oxazole-4-carboxamide hydrochloride; 6'-fluoro-N-(2-methyl-6-(piperidin-1-yl)-2H-indazol-5-yl)-[2,3'-bipyridine]-6-carboxamide hydrochloride; N-(6-cyclohexyl-2-methyl-2H-indazol-5-yl)-6-(1H-pyrazol-4-yl)picolinamide hydrochloride; 2'-fluoro-N-(2-methyl-6-(piperidin-1-yl)-2H-indazol-5-yl)-[2,3'-bipyridine]-6-carboxamide; 2-(2-chloropyridin-4-yl)-N-(2-methyl-6-(piperidin-1-yl)-2H-indazol-5-yl)oxazole-4-carboxamide hydrochloride; N-(6-cyclopropyl-2-methyl-2H-indazol-5-yl)-2-(2-methylpyridin-4-yl)oxazole-4-carboxamide hydrochloride; N-(1-cyclopentyl-6-cyclopropyl-1H-indazol-5-yl)-6-(1-methyl-H-pyrazol-4-yl)picolinamide; N-(2-cyclopentyl-6-cyclopropyl-2H-indazol-5-yl)-6-(1-methyl-1H-pyrazol-4-yl)picolinamide; 6-(1-methyl-1H-pyrazol-4-yl)-N-(2-methyl-6-(piperidin-1-yl)-2H-indazol-5-yl) picolinamide; N-(2-cyclopentyl-6-cyclopropyl-2H-indazol-5-yl)-2-(6-methoxypyridin-3-yl)oxazole-4-carboxamide; 2-(6-methoxypyridin-3-yl)-N-(2-methyl-6-(piperidin-1-yl)-2H-indazol-5-yl)oxazole-4-carboxamide; N-(2-methyl-6-(piperidin-1-yl)-2H-indazol-5-yl)-2-(3-methylpyridin-4-yl) oxazole-4-carboxamide; 6-bromo-N-(2-methyl-6-(piperidin-1-yl)-2H-indazol-5-yl)picolinamide; 6-chloro-5-methyl-N-(2-methyl-6-(piperidin-1-yl)-2H-indazol-5-yl) picolinamide N-(2-methyl-6-(piperidin-1-yl)-2H-indazol-5-yl)-2-(6-methylpyridin-3-yl)oxazole-4-carboxamide; N-(2-cyclopentyl-6-cyclopropyl-2H-indazol-5-yl)-2-(2-methylpyridin-3-yl)oxazole-4-carboxamide; N-(2-cyclopentyl-6-cyclopropyl-2H-indazol-5-yl)-2-(3-methylpyridin-4-yl)oxazole-4-carboxamide; N-(2-cyclopentyl-6-cyclopropyl-2H-indazol-5-yl)-2-(6-methylpyridin-3-yl)oxazole-4-carboxamide; 6'-amino-3-methyl-N-(2-methyl-6-(piperidin-1-yl)-2H-indazol-5-yl)-[2,3'-bipyridine]-6-carboxamide hydrochloride; 5-methyl-6-(1-methyl-1H-pyrazol-4-yl)-N-(2-methyl-6-(piperidin-1-yl)-2H-indazol-5-yl)picolinamide; N-(1-cyclopropyl-6-(piperidin-1-yl)-1H-indazol-5-yl)-2-(2-methylpyridin-4-yl) oxazole-4-carboxamide hydrochloride; 2-(2-hydroxypyridin-3-yl)-N-(2-methyl-6-(piperidin-1-yl)-2H-indazol-5-yl)oxazole-4-carboxamide; (S)-6-(3-aminopyrrolidin-1-yl)-N-(2-methyl-6-(piperidin-1-yl)-2H-indazol-5-yl)picolinamide 2,2,2-trifluoroacetate; 34. (S)-6-(1-(2-hydroxypropyl)-1H-pyrazol-4-yl)-N-(2-methyl-6-(piperidin-1-yl)-2H-indazol-5-yl)picolinamide; N-(1,6-dicyclopropyl-1H-indazol-5-yl)-2-(6-methoxypyridin-3-yl) oxazole-4-carboxamide; N-(1,6-dicyclopropyl-1H-indazol-5-yl)-2-(2-methylpyridin-4-yl)oxazole-4-carboxamide hydrochloride; (S)—N-(6-cyclopropyl-1-methyl-1H-indazol-5-yl)-6-(3-hydroxypyrrolidin-1-yl)picolinamide; (R)-6-(3-hydroxypyrrolidin-1-yl)-N-(2-methyl-6-(piperidin-1-yl)-2H-indazol-5-yl)picolinamide; (S)-6-(3-hydroxypyrrolidin-1-yl)-N-(2-methyl-6-(piperidin-1-yl)-2H-indazol-5-yl) picolinamide; 6-(3-hydroxypyrrolidin-1-yl)-N-(2-methyl-6-(piperidin-1-yl)-2H-indazol-5-yl)picolinamide; (S)-6-(3-aminopyrrolidin-1-yl)-N-(6-cyclopropyl-1-methyl-1H-indazol-5-yl)picolinamide; (R)-6-(3-aminopyrrolidin-1-yl)-N-(2-methyl-6-(piperidin-1-yl)-2H-indazol-5-yl) picolinamide; (R)-6-(1-(2-hydroxypropyl)-1H-pyrazol-4-yl)-N-(2-methyl-6-(piperidin-1-yl)-2H-indazol-5-yl) picolinamide; (S)-2-(3-aminopyrrolidin-1-yl)-N-(2-methyl-6-(piperidin-1-yl)-2H-indazol-5-yl)oxazole-4-carboxamide; N-(6-cyclopropyl-1-methyl-1H-indazol-5-yl)-2-(2-methylpyridin-4-yl)oxazole-4-carboxamide; (S)—N-(6-cyclopropyl-1-methyl-1H-indazol-5-yl)-6-(1-(2-hydroxypropyl)-1H-pyrazol-4-yl)picolinamide; (S)—N-(6-cyclopropyl-2- methyl-2H-indazol-5-yl)-6-(1-(2-hydroxypropyl)-1H-pyrazol-4-yl)picolinamide; (S)-6-(3-aminopyrrolidin-1-yl)-N-(6-cyclopropyl-2-methyl-2H-indazol-5-yl)picolinamide; (S)—N-(6-cyclopropyl-2-methyl-2H-indazol-5-yl)-6-(3-hydroxypyrrolidin-1-yl)picolinamide; (S)—N-(6-cyclopropyl-1-methyl-1H-indazol-5-yl)-2-(3-hydroxypyrrolidin-1-yl)oxazole-4-carboxamide; (S)-2-(3-aminopyrrolidin-1-yl)-N-(6-cyclopropyl-1-methyl-1H-indazol-5-yl)oxazole-4-carboxamide; (S)-2-(3-hydroxypyrrolidin-1-yl)-N-(2-methyl-6-(piperidin-1-yl)-2H-indazol-5-yl)oxazole-4-carboxamide; (S)—N-(6-cyclopropyl-1-methyl-1H-indazol-5-yl)-2-(1-(2-hydroxypropyl)-1H-pyrazol-4-yl)oxazole-4-carboxamide; (S)-2-(3-aminopyrrolidin-1-yl)-N-(6-cyclopropyl-2-methyl-2H-indazol-5-yl)oxazole-4-carboxamide; (S)—N-(6-cyclopropyl-2-methyl-2H-indazol-5-yl)-2-(3-hydroxypyrrolidin-1-yl)oxazole-4-carboxamide; (S)-6-(1-(2-hydroxypropyl)-1H-pyrazol-4-yl)-N-(2-methyl-6-(piperidin-1-yl)-2H-indazol-5-yl)picolinamide; 6-((2-hydroxypropyl)amino)-N-(2-methyl-6-(piperidin-1-yl)-2H-indazol-5-yl)picolinamide; N-(6-(4-hydroxypiperidin-1-yl)-2-methyl-2H-indazol-5-yl)-2-(2-methylpyridin-4-yl)oxazole-4-carboxamide; N-(6-(azetidin-1-yl)-1-methyl-1H-indazol-5-yl)-2-(2-methylpyridin-4-yl)oxazole-4-carboxamide; N-(6-(azetidin-1-yl)-2-methyl-2H-indazol-5-yl)-2-(2-methylpyridin-4-yl)oxazole-4-carboxamide; N-(6-(3-hydroxyazetidin-1-yl)-2-methyl-2H-indazol-5-yl)-2-(2-methylpyridin-4-yl)oxazole-4-carboxamide; N-(1-methyl-6-(pyrrolidin-1-yl)-1H-indazol-5-yl)-2-(2-methylpyridin-4-yl)oxazole-4-carboxamide; N-(2-methyl-6-(pyrrolidin-1-yl)-2H-indazol-5-yl)-2-(2-methylpyridin-4-yl)oxazole-4-carboxamide; (S)—N-(6-(3-hydroxypyrrolidin-1-yl)-2-methyl-2H-indazol-5-yl)-2-(2-methylpyridin-4-yl)oxazole-4-carboxamide; (R)—N-(6-(3-hydroxypyrrolidin-1-yl)-2-methyl-2H-indazol-5-yl)-2-(2-methylpyridin-4-yl)oxazole-4-carboxamide; N-(2-methyl-6-(piperidin-1-yl)-2H-indazol-5-yl)-5-(2-methylpyridin-4-yl)furan-2-carboxamide; N-(6-(4-hydroxypiperidin-1-yl)-2-methyl-2H-indazol-5-yl)-5-(2-methylpyridin-4-yl)furan-2-carboxamide; N-(6-(3-hydroxypiperidin-1-yl)-2-methyl-2H-indazol-5-yl)-2-(2-methylpyridin-4-yl)oxazole-4-carboxamide; (R)—N-(6-(3-hydroxypiperidin-1-yl)-2-methyl-2H-indazol-5-yl)-5-(2-methylpyridin-4-yl)furan-2-carboxamide; N-(6-(3-hydroxypiperidin-1-yl)-2-methyl-2H-indazol-5-yl)-5-(2-methylpyridin-4-yl)furan-2-carboxamide; N-(6-(azepan-1-yl)-2-methyl-2H-indazol-5-yl)-2-(2-methylpyridin-4-yl)oxazole-4-carboxamide; N-(6-(azepan-1-yl)-1-methyl-1H-indazol-5-yl)-2-(2-methylpyridin-4-yl)oxazole-4-carboxamide; N-(2,3-dimethyl-6-(piperidin-1-yl)-2H-indazol-5-yl)-2-(2-methylpyridin-4-yl)oxazole-4-carboxamide; N-(1,3-dimethyl-6-(piperidin-1-yl)-1H-indazol-5-yl)-2-(2-methylpyridin-4-yl)oxazole-4-carboxamide; N-(6-(4-hydroxypiperidin-1-yl)-1-(2-methoxyethyl)-1H-indazol-5-yl)-2-(2-methylpyridin-4-yl)oxazole-4-carboxamide; 76. N-(6-(4-hydroxypiperidin-1-yl)-2-(2-methoxyethyl)-2H-indazol-5-yl)-2-(2-methylpyridin-4-yl)oxazole-4-carboxamide; N-(6-(4-hydroxypiperidin-1-yl)-1-methyl-1H-indazol-5-yl)-2-(2-methylpyridin-4-yl)oxazole-4-carboxamide; N-(6-(4-fluoropiperidin-1-yl)-1-methyl-1H-indazol-5-yl)-2-(2-methylpyridin-4-yl)oxazole-4-carboxamide; N-(6-(3-fluoropiperidin-1-yl)-2-methyl-2H-indazol-5-yl)-2-(2-methylpyridin-4-yl)oxazole-4-carboxamide; N-(6-(4-(hydroxymethyl)piperidin-1-yl)-2-methyl-2H-indazol-5-yl)-2-(2-methylpyridin-4-yl)oxazole-4-carboxamide; N-(6-(4-hydroxypiperidin-1-yl)-1,3-dimethyl-1H -indazol-5-yl)-2-(2-methylpyridin-4-yl)oxazole-4-carboxamide; N-(6-(3-(hydroxymethyl)piperidin-1-yl)-2-methyl-2H-indazol-5-yl)-2-(2-methylpyridin-4-yl)oxazole-4-carboxamide; N-(6-(4-hydroxypiperidin-1-yl)-2,3-dimethyl-2H-indazol-5-yl)-2-(2-methylpyridin-4-yl)oxazole-4-carboxamide; 2-(2-acetamidopyridin-4-yl)-N-(2-methyl-6-(piperidin-1-yl)-2H-indazol-5-yl)oxazole-4-carboxamide; 2-(2-acetamidopyridin-4-yl)-N-(6-(3-fluoropiperidin-1-yl)-2-methyl-2H-indazol-5-yl)oxazole-4-carboxamide; 2-(2-aminopyridin-4-yl)-N-(2-methyl-6-(piperidin-1-yl)-2H-indazol-5-yl)oxazole-4-carboxamide hydrochloride; N-(6-(4-fluoropiperidin-1-yl)-1,3-dimethyl-1H-indazol-5-yl)-2-(2-methylpyridin-4-yl)oxazole-4-carboxamide; N-(6-(((1R,4R)-4-hydroxycyclohexyl)amino)-2-methyl-2H-indazol-5-yl)-2-(2-methylpyridin-4-yl)oxazole-4-carboxamide; N-(6-(4-(hydroxymethyl)piperidin-1-yl)-1-methyl-1H-indazol-5-yl)-2-(2-methylpyridin-4-yl)oxazole -carboxamide; 2-(2-aminopyridin-4-yl)-N-(6-(4-fluoropiperidin-1-yl)-2-methyl-2H-indazol-5-yl)oxazole-4-carboxamide hydrochloride; 91. N-(6-(4-fluoropiperidin-1-yl)-2-methyl-2H-indazol-5-yl)-2-(2-methylpyridin-4-yl)oxazole-4-carboxamide hydrochloride; (S)—N-(6-(4-(hydroxymethyl)piperidin-1-yl)-2-methyl-2H-indazol-5-yl)-6-(1-(2-hydroxypropyl)-1H-pyrazol-4-yl)picolinamide; 2-(2-aminopyridin-4-yl)-N-(6-(4-hydroxypiperidin-1-yl)-2-methyl-2H-indazol-5-yl)oxazole-4-carboxamide hydrochloride; 94. N-(6-(4-(hydroxymethyl)piperidin-1-yl)-1-(2-methoxyethyl)-1H-indazol-5-yl)-2-(2-methylpyridin-4-yl)oxazole-4-carboxamide; (S)—N-(6-(4-(hydroxymethyl)piperidin-1-yl)-1-methyl-H-indazol-5-yl)-6-(1-(2-hydroxypropyl)-1H-pyrazol-4-yl)picolinamide; N-(6-(4-(hydroxymethyl)piperidin-1-yl)-2-(2-methoxyethyl)-2H-indazol-5-yl)-2-(2-methylpyridin-4-yl)oxazole-4-carboxamide; 97. N-(6-(4-(hydroxymethyl)piperidin-1-yl)-2-methyl-2H-indazol-5-yl)-2-(2-methoxypyridin-4-yl)oxazole-4-carboxamide; 2-(2-acetamidopyridin-4-yl)-N-(6-(4-(hydroxymethyl)piperidin-1-yl)-2-methyl-2H-indazol-5-yl)oxazole-4-carboxamide; 2-(2-aminopyridin-4-yl)-N-(6-(4-(hydroxymethyl)piperidin-1-yl)-1-methyl-H-indazol-5-yl)oxazole-4-carboxamide hydrochloride; 2-(2-aminopyridin-4-yl)-N-(6-(4-(hydroxymethyl)piperidin-1-yl)-2-methyl-2H-indazol-5-yl)oxazole-4-carboxamide hydrochloride; N-(6-(4-hydroxypiperidin-1-yl)-1-methyl-1H-indazol-5-yl)-2-(2-methoxypyridin-4-yl)oxazole-4-carboxamide; 2-(2-aminopyridin-4-yl)-N-(6-(3-hydroxypiperidin-1-yl)-2-methyl-2H-indazol-5-yl)oxazole-4-carboxamide hydrochloride; 2-(2-methoxypyridin-4-yl)-N-(2-methyl-6-(piperidin-1-yl)-2H-indazol-5-yl)oxazole-4-carboxamide; 2-(2-aminopyridin-4-yl)-N-(6-(3-fluoropiperidin-1-yl)-2-methyl-2H-indazol-5-yl)oxazole-4-carboxamide hydrochloride; (R)-2-(2-aminopyridin-4-yl)-N-(6-(3-hydroxypyrrolidin-1-yl)-2-methyl-2H-indazol-5-yl)oxazole-4-carboxamide hydrochloride; 106. 1-(1,3-dimethyl-5-(2-(2-methylpyridin-4-yl)oxazole-4-carboxamido)-1H-indazol-6-yl)piperidin-4-yl 2-methoxyacetate; N-(6-(4-hydroxypiperidin-1-yl)-2-methyl-2H-indazol-5-yl)-2-(2-methoxypyridin-4-yl)oxazole-4-carboxamide hydrochloride; N-(6-(4-aminopiperidin-1-yl)-1-(2-methoxyethyl)-1H-indazol-5-yl)-2-(2-methylpyridin-4-yl)oxazole-4-carboxamide hydrochloride; N-(6-(4-aminopiperidin-1-yl)-2-methyl-2H-indazol-5-yl)-2-(2-methylpyridin-4-yl)oxazole-4-carboxamide hydrochloride; N-(6-(4-(hydroxymethyl)piperidin-1-yl)-1-(2-methoxyethyl)-3-methyl-1H-indazol-5-yl)-2-(2-methylpyridin-4-yl)oxazole-4-carboxamide; N-(6-(4-(hydroxymethyl)piperidin-1-yl)-1,3-dimethyl-1H-indazol-5-yl)-2-(2-methylpyridin-4-yl)oxazole-4-carboxamide; 2-(2-aminopyridin-4-yl)-N-(6-(4-(hydroxymethyl)piperidin-1-yl)-1,3-dimethyl-1H-indazol-5-yl)oxazole-4-carboxamide; N-(6-(4-hydroxypiperidin-1- yl)-1-methyl-1H-indazol-5-yl)-2-(2-hydroxypyridin-4-yl) oxazole-4-carboxamide; 2-(2,6-dimethylpyridin-4-yl)-N-(6-(4-hydroxypiperidin-1-yl)-1-methyl-1H-indazol-5-yl) oxazole-4-carboxamide; 115. (S)—N-(6-(3-hydroxypyrrolidin-1-yl)-1-methyl-1H-indazol-5-yl)-2-(2-methylpyridin-4-yl)oxazole-4-carboxamide; N-(6-(4-hydroxypiperidin-1-yl)-1-(2-methoxyethyl)-3-methyl-H-indazol-5-yl)-2-(2-methylpyridin-4-yl)oxazole-4-carboxamide; N-(1-(2-hydroxyethyl)-6-(4-hydroxypiperidin-1-yl)-1H-indazol-5-yl)-2-(2-methylpyridin-4-yl)oxazole-4-carboxamide; N-(6-(4-aminopiperidin-1-yl)-2-(2-methoxyethyl)-2H-indazol-5-yl)-2-(2-methylpyridin-4-yl)oxazole-4-carboxamide hydrochloride; 2-(2,6-dimethylpyridin-4-yl)-N-(2-methyl-6-(piperidin-1-yl)-2H-indazol-5-yl)oxazole-4-carboxamide hydrochloride; 2-(2-(dimethylamino)pyridin-4-yl)-N-(2-methyl-6-(piperidin-1-yl)-2H-indazol-5-yl)oxazole-4-carboxamide; N-(6-(4-hydroxypiperidin-1-yl)-1-methyl-1H-indazol-5-yl)-2-(2-(methylamino)pyridin-4-yl)oxazole-4-carboxamide; 122. N-(2-methyl-6-(piperidin-1-yl)-2H-indazol-5-yl)-2-(2-(methylamino)pyridin-4-yl)oxazole-4-carboxamide; N-(6-(4-hydroxypiperidin-1-yl)-2-methyl-2H-indazol-5-yl)-2-(2-(methylsulfonamido) pyridin-4-yl) oxazole-4-carboxamide; 2-(2-(dimethylamino) pyridin-4-yl)-N-(6-(4-hydroxypiperidin-1-yl)-1-methyl-1H-indazol-5-yl)oxazole-4-carboxamide; N-(6-(4-(aminomethyl)piperidin-1-yl)-1-(2-methoxyethyl)-1H-indazol-5-yl)-2-(2-methylpyridin-4-yl)oxazole-4-carboxamide; 2-(2,6-dimethylpyridin-4-yl)-N-(6-(4-hydroxypiperidin-1-yl)-2-methyl-2H-indazol-5-yl)oxazole-4-carboxamide; 2-(2,6-dimethylpyridin-4-yl)-N-(6-(4-fluoropiperidin-1-yl)-2-methyl-2H-indazol-5-yl)oxazole-4-carboxamide; Diethyl(1-(1-methyl-5-(2-(2-methylpyridin-4-yl)oxazole-4-carboxamido)-1H-indazol-6-yl)piperidin-4-yl)phosphate; and Diethyl((1-(2-methyl-5-(2-(2-methylpyridin-4-yl)oxazole-4-carboxamido)-2H-indazol-6-yl) piperidin-4-yl) methyl) phosphate.

In any aspect or embodiment described herein, $R_6$ of PTM-XIIIa-h is a C2-C6-alkyl radical substituted by 1, 2 or 3 fluorine atoms, such as: 2,2,2-trifluoroethyl, 3,3,3-trifluoropropyl, and 4,4,4-trifluorobutyl. In any aspect or embodiment described herein, $R_6$ is a C2-C5-alkyl radical substituted by one or two hydroxyl group(s) or one C1-C3-alkoxy or a tri-fluorine-substituted C1-C3-alkoxy, such as: C2-C5-alkyl radical substituted by hydroxyl or C1-C3-alkoxy or trifluoromethoxy or 2,2,2-trifluoroethoxy or trifluoromethyl, 3-hydroxy-3-methylbutyl, 3-methoxypropyl, 3-hydroxypropyl, 3-trifluoromethoxypropyl, 2-methoxyethyl or 2-hydroxyethyl. In any aspect or embodiment described herein, $R_6$ of PTM-XIIIa-h is a C2-C5-alkyl radical substituted by a C1-C6-alkyl-$SO_2$ group, such as: methyl-$SO_2$-substituted $C_2$-$C_4$-alkyl radical, 2-(methylsulphonyl)ethyl or 3-(methylsulphonyl)propyl.

In any aspect or embodiment described herein, $R_6$ of PTM-XIIIa-h is a $C_1$-$C_3$-alkyl radical substituted by oxetanyl, tetrahydrofuranyl, tetrahydro-2H-pyran-4-yl, 1,1-dioxidotetrahydro-2H-thiopyran-3-yl, 1,1-dioxidotetrahydro-2H-thiopyran-2-yl, 1,1-dioxidotetrahydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl. Particular preference is given to a C1-C3-alkyl radical substituted by an oxetane group. For example, $R^6$ may be a oxetan-3-ylmethyl group In any aspect or embodiment described herein, $R_7$ and $R_8$ are independently selected from hydrogen methyl.

In any aspect or embodiment described herein, $R_4$ of PTM-XIIIa-h is an unsubstituted or mono- or poly-halogen substituted C1-C3-alkyl radical or a C1-C3-alkyl radical, e.g., optionally substituted by one hydroxyl group or a C1-C3-alkyl radical substituted by one hydroxyl group and three fluorine atoms), such as: methyl, trifluoromethyl, difluoromethyl, ethyl, trifluoro-C1-C3-alkyl, difluoro-$C_1$-$C_3$-alkyl, hydroxymethyl, 1-hydroxyethyl, 2-hydroxypropan-2-yl and 2,2,2-trifluoro-1-hydroxyethyl.

In any aspect or embodiment described herein, $R^5$ of PTM-XIIIa-h is hydrogen, fluorine, methyl, chlorine or C1-C3-alkyl.

In any aspect or embodiment described herein, $R_4$ of PTM-XIIIa-h is methyl or trifluoromethyl, and $R^5$ is fluorine (e.g. fluorine in the ortho position to $R^4$).

In any aspect or embodiment described herein, $R_9$ of PTM-XIIIa-h is oxetanyl, oxetan-3-yl, tetrahydrofuranyl, tetrahydro-2H-pyran-4-yl, 1,1-dioxidotetrahydro-2H-thiopyran-3-yl, 1,1-dioxidotetrahydro-2H-thiopyran-2-yl, 1,1-dioxi dotetra hydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl.

In any aspect or embodiment described herein, $R_{10}$ of PTM-XIIIa-h is exclusively connected to the functional groups —$SO_2$— and —SO—, i.e. is an $R_{10}$-substituted —$SO_2$— or SO group. In this connection, $R_{10}$ of PTM-XIIIa-h is preferably C1-C4-alkyl, where the C1-C4-alkyl radical is unsubstituted or monosubstituted by hydroxyl or by cyclopropyl or substituted by three fluorine atoms. In any aspect or embodiment described herein, $R_{10}$ is cyclopropyl radical, methyl, ethyl or hydroxyethyl.

In any aspect or embodiment described herein, $R_{11}$ of PTM-XIIIa-h is an unsubstituted C1-C4-alkyl radical or a tri-fluorine-substituted C1-C4-alkyl radical, such as: methyl, ethyl, trifluoromethyl or 2,2,2-trifluoroethyl.

In any aspect or embodiment described herein, the PTM-XIIIa-h is selected from the group consisting of: N-[6-(2-hyd roxypropa n-2-yl)-2-(2-methoxyethyl)-2H-indazol-5-yl]-6-(trifluoromethyl)pyridine-2-carboxamide; N-[6-(hydroxymethyl)-2-(2-methoxyethyi)-2H-indazol-5-yl]-6-(trifluoromethyl)pyridine-2-carboxamide; N-[6-(2-hydroxypropan-2-yl)-2-(3-methoxypropyi)-2H-indazol-5-yl]-6-(trifluoromethyl)pyridine-2-carboxamide; N-[6-(hydroxymethyl)-2-(3-methoxypropyi)-2H-indazol-5-yl]-6-(trifluoromethyl)pyridine-2-carboxamide; N-[2-(2-hydroxyethyl)-6-(2-hydroxypropan-2-yl)-2H-indazol-5-yl]-6-(trifluoromethyl)pyridine-2-carboxamide; N-[6-(2-hydroxypropa n-2-yl)-2-(3-hydroxypropyl)-2H-indazol-5-yl]-6-(trifluoromethyl)pyridine-2-carboxamide; N-[2-(2-hydroxyethyl)-6-(hydroxymethyi)-2H-indazol-5-yl]-6-(trifluoromethyl)pyridine-2-carboxamide; N-[6-(2-hydroxypropan-2-yl)-2-(oxetan-3-ylmethyl)-2H-indazol-5-yl]-6-(trifluoromethyl)pyridine-2-carboxamide; N-[6-(hydroxymethyl)-2-(oxetan-3-ylmethyi)-2H-indazol-5-yl]-6-(trifluoromethyl)pyridine-2-carboxamide; N-{6-(2-hyd roxypropa n -2-yl )-2-[3-(methyl suI ph onyl) propyl]-2H-ind azol-5-yl}-6-(trifluoromethyl)pyridine-2-carboxamide; N-[2-(3-hydroxy-3-methylbutyl)-6-(2-hydroxypropan-2-yl)-2H-indazol-5-yl]-6-(trifluoromethyl)pyridine-2-carboxamide; N-{6-(2-hyd roxypropan-2-yl)-2-[2-(methyl suI ph onyl)ethyl]-2H-indazol-5-yl}-6-(trifluoromethyl)pyridine-2-carboxamide; 6-(difluoromethyi)-N-[2-(3-hydroxy-3-methylbutyl)-6-(2-hydroxypropan-2-yl)-2Hindazol-5-yl] pyridine-2-carboxamide; 6-(difluoromethyi)-N-{6-(2-hydroxypropan-2-yl)-2-[2-(methylsulphonyl)ethyi]-2Hindazol-5-yl}pyridine-2-carboxamide; 6-(difluoromethyl)-N-[6-(2-hydroxypropan-2-yl)-2-(3-hydroxypropyl)-2H-indazol-5-yl]pyridine-2-carboxamide; N-[6-(2-hydroxypropan-2-yl)-2-(4,4,4-trifluorobutyl)-2H- indazol-5-yl]-6-(trifluoromethyl)pyridine-2-carboxamide; N-{6-(2-hydroxypropan-2-yl)-2-[3-(trifluoromethoxy)propyl]-2H-indazol-5-yl}-6-(trifluoromethyl)pyridine-2-carboxamide; N-{6-(2-hydroxypropan-2-yl)-2-[3-(2,2,2-trifluoroethoxy)propyl]-2H-indazol-5-yl}-6-(trifluoromethyl) pyridine-2-carboxamide; 5-fluoro-N-[2-(3-hydroxy-3-methylbutyl)-6-(2-hydroxypropan-2-yl)-2H-indazol-5-yl]-6-methylpyridine-2-carboxamide; N-[2-(3-hydroxy-3-methylbutyl)-6-(2-hydroxypropan-2-yl)-2H-indazol-5-yl]-6-methylpyridine-2-carboxamide; 6-(2-hydroxypropan-2-yi)-N-[6-(2-hydroxypropan-2-yl)-2-(4,4,4-trifluorobutyi)-2Hindazol-5-yl]pyridine-2-carboxamide.

In any aspect or embodiment described herein, the PTM is selected from the group consisting of:

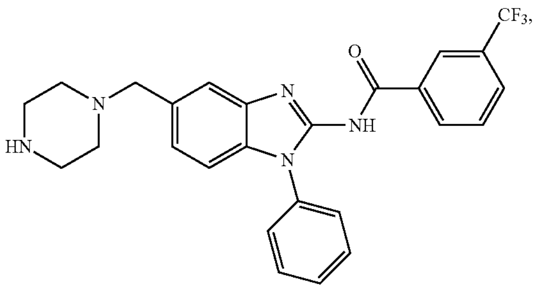

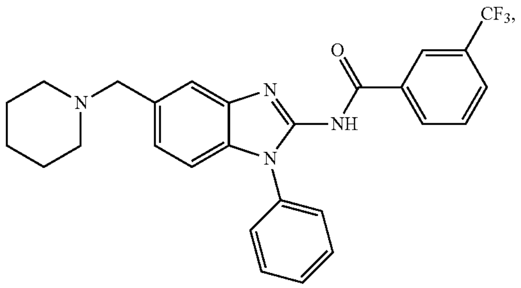

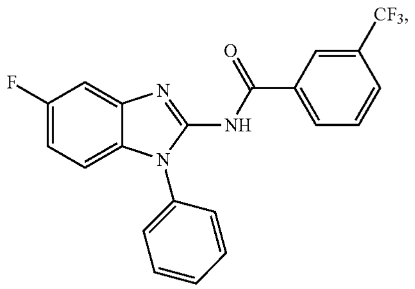

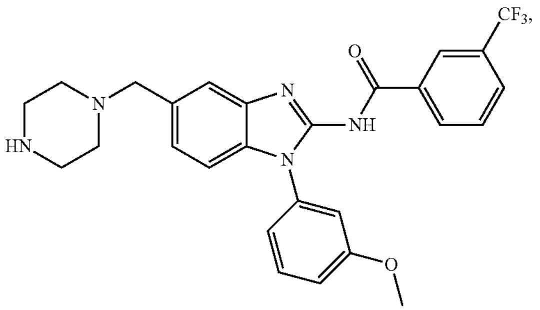

-continued

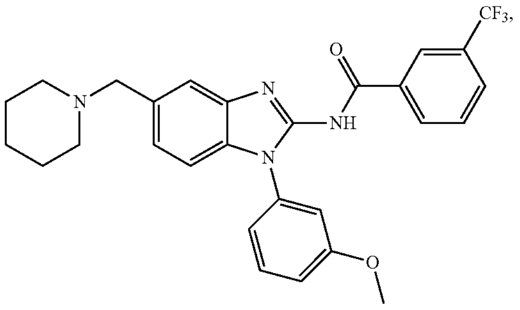

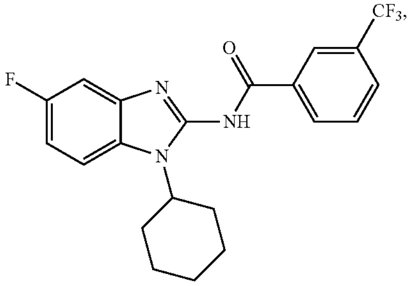

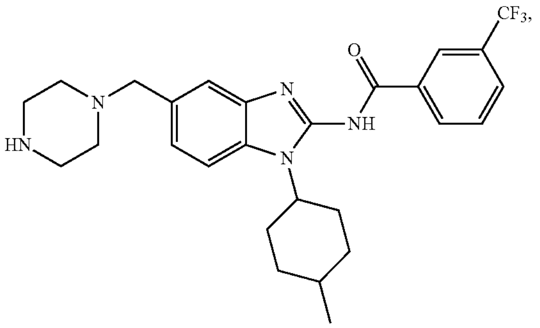

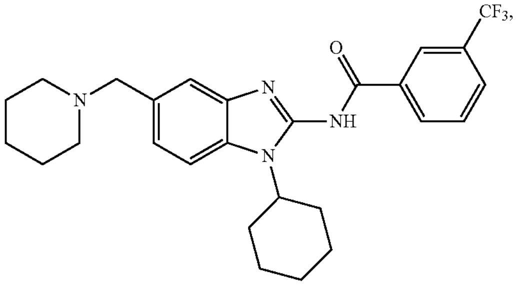

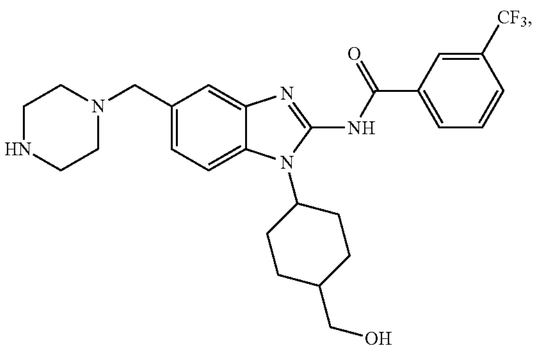

-continued
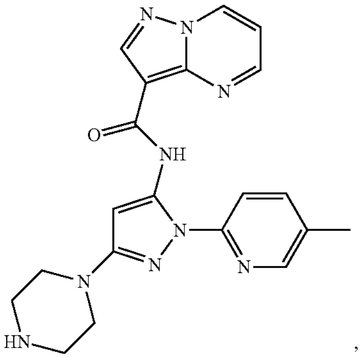
,
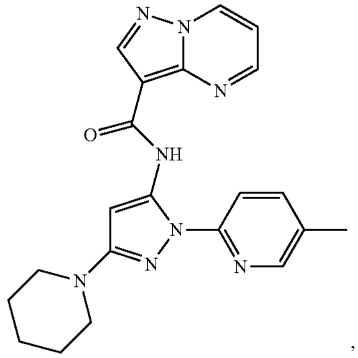
,
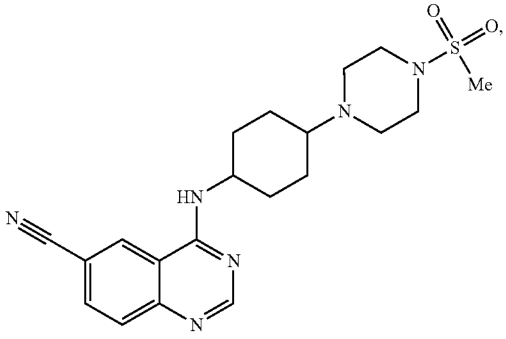
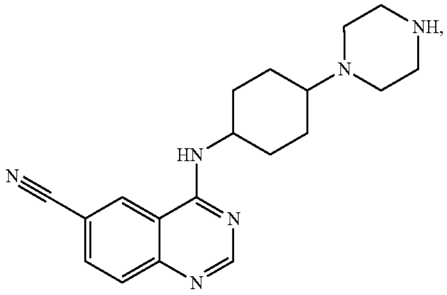
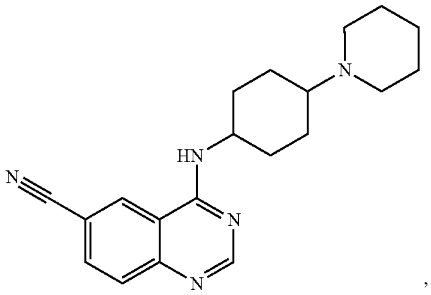
,
-continued
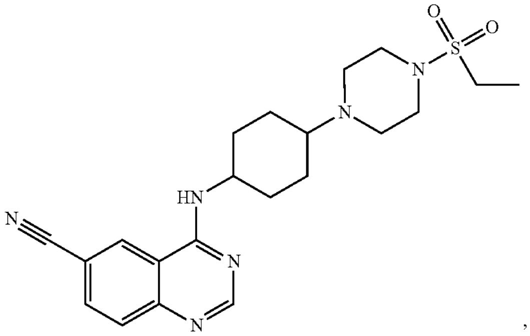
, and
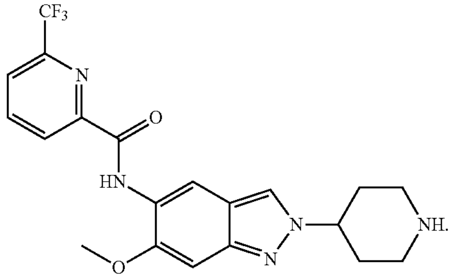
In any aspect or embodiment described herein, the PTM is selected from
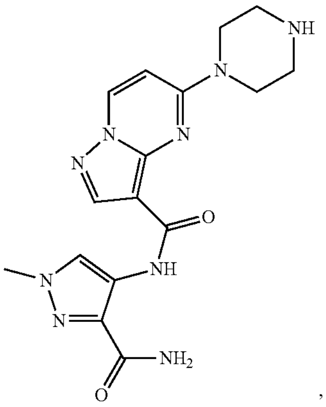
,
(Hanisak J, et al., Bioorg Med Chem Lett, 2016 Sep 1; 26(17): 4150-5)
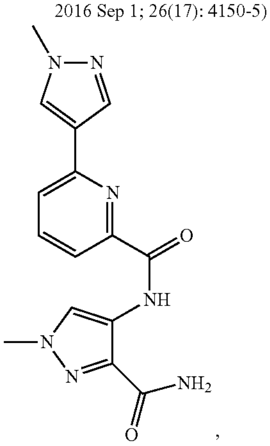
,
(Hanisak J, et al., Bioorg Med Chem Lett, 2016 Sep 1; 26(17): 4150-5)

-continued

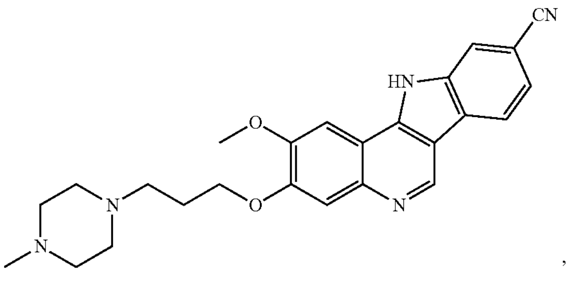

, (Tumey LN, et al. Bioorg Med Chem Lett. 2014 May 1; 24(9): 2066-72)

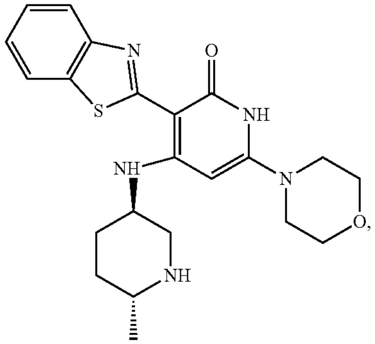

(Seganish WM, et al. ACS Med. Chem. Lett. 2015, 6, 942-947)

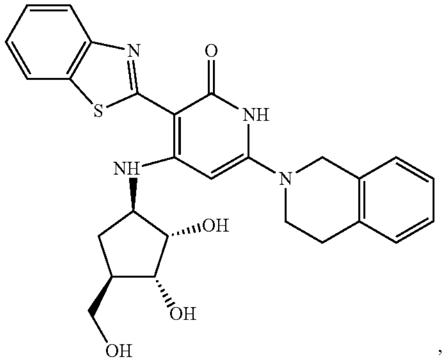

, (Seganish WM, et al. ACS Med. Chem. Lett. 2015, 6, 942-947)

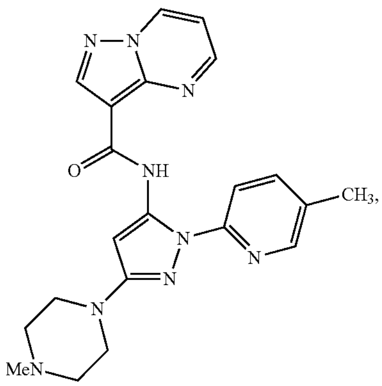

(McElroy WT, et al. ACS Med. Chem. Lett. 2015, 6, 677-682)

-continued

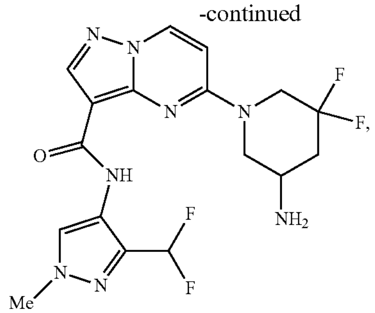

(Lim J, et al. ACS Med. Chem. Lett. 2015, 6, 683-688)

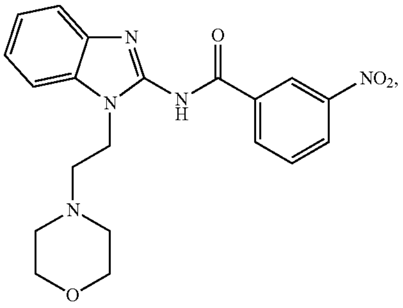

or (pubchem.ncbi.nlm.nih.gov/compound/IRAK-1_4_Inhibitor#section=Top)

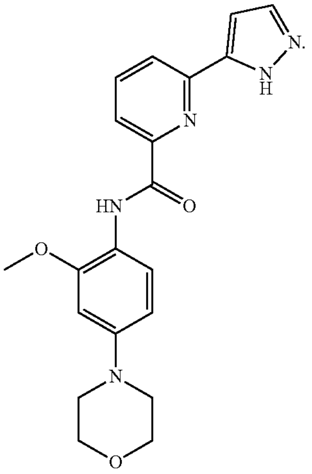

(pubchem.ncbi.nlm.nih.gov/compound/44449334#section=Top)

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosureion may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term “parenteral” as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer’s solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved, in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the disclosure, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, inflammatory diseases/disorders, autoimmune diseases/disorders, neurodegenerative diseases, and/or cardiovascular diseases/disorders, which may be treated using compounds according to the present disclosure are set forth hereinabove.

The description provides therapeutic compositions as described herein for effectuating the degradation of proteins of interest for the treatment or amelioration of a disease, e.g., cancer, inflammatory diseases/disorders, autoimmune diseases/disorders, neurodegenerative diseases, and/or cardiovascular diseases/disorders. In certain additional embodiments, the disease is cancer or an inflammation disorder. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the UM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in that patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

In any aspect or embodiment described herein, the disease states of conditions that may be treated using the composition and/or compound of the present disclosure is at least one of: a cancer, an inflammatory disorder, an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder.

In any aspect or embodiment described herein, the disease states of conditions that may be treated using compounds according to the present disclosure include, for example, at least one of: (A) pulmonary diseases and diseases of the airway including, but not limited to, Adult Respiratory Disease Syndrome (ARDS), Chronic Obstructive Pulmonary Disease (COPD), pulmonary fibrosis, interstitial lung disease, asthma, chronic cough, and allergic rhinitis, (B) transplantation, (C) the autoimmune diseases including, but not limited to, rheumatoid arthritis, systemic lupus erythematosus, multiple sclerosis, and diabetes (e g, type 1 diabetes mellitus), (D) cancer including, but not limited to, solid tumors, skin cancer and lymphoma, (E) cardiovascular diseases including, but not limited to, stroke and atherosclerosis, (F) diseases of the central nervous system including, but not limited to, neurodegenerative diseases, (G) non-CD 14 mediated sepsis, (H) osteoarthritis, (I) osteoporosis, (J) psoriasis and diseases of the skin including, but not limited to, rash and contact and atopic dermatitis, (K) inflammatory disorders; (L) inflammatory bowel disease (including, but not limited to, Crohn's disease and ulcerative colitis), (M) Behcet's syndrome, (N) ankylosing spondylitis, (O) sarcoidosis, (P) gout, (Q) ophthalmic diseases and conditions, and (R) CD14 mediated sepsis. In such patients, the inhibition and/or degradation of IRAK-4 in, e g, IL-1 responsive cells will block the transduction of the IL-1 initiated signal, thereby preventing NF-κB activation and thus providing a treatment for the disorder or disorders.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In any aspect or embodiment described herein, the cancer may be selected from the group consisting of breast cancer, colorectal cancer, non-small cell lung cancer, ovarian, renal, sarcoma, melanoma, head & neck, hepatocellular, thyroid, multidrug-resistant leukemia, lymphoma, multiple myeloma, esophageal, large bowel, pancreatic, mesothelioma, carcinoma (e.g. adenocarcinoma, including esophageal adenocarcinoma), sarcoma (e.g. spindle cell sarcoma, liposarcoma, leiomyosarcoma, abdominal leiomyosarcoma, sclerosing epithelioid sarcoma) and melanoma (e.g. metastatic malignant melanoma).

In any aspect or embodiment described herein, the inflammatory disease/disorder is selected from the group consisting of ocular allergy, conjunctivitis, keratoconjunctivitis sicca, vernal conjunctivitis, allergic rhinitis, autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, primary biliary cirrhosis, uveitis (anterior and posterior), Sjogren's syndrome, interstitial lung fibrosis, psoriatic arthritis, systemic juvenile idiopathic arthritis, nephritis, vasculitis, diverticulitis, interstitial cystitis, glomerulonephritis (e.g. including idiopathic nephrotic syndrome or minimal change nephropathy), chronic granulomatous disease, endometriosis, leptospirosis renal disease, glaucoma, retinal disease, headache, pain, complex regional pain syndrome, cardiac hypertrophy, muscle wasting, catabolic disorders, obesity, fetal growth retardation, hypercholesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma, acute lung injury, acute respiratory distress syndrome, eosinophilia, hypersensitivities, anaphylaxis, fibrositis, gastritis, gastroenteritis, nasal sinusitis, ocular allergy, silica induced diseases, chronic obstructive pulmonary disease (COPD), cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, appendicitis, atopic dermatitis, asthma, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, juvenile rheumatoid arthritis, dermatomyositis, encephalitis, endocarditis, endometritis, enteritis, enterocolitis, epicondylitis, epididymitis, fasciitis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, vasculitis, vulvitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acute and chronic gout, chronic gouty arthritis, psoriasis, psoriatic arthritis, rheumatoid arthritis, Cryopyrin Associated Periodic Syndrome (CAPS) and osteoarthritis.

In any aspect or embodiment described herein, the neurodegenerative disease may be selected from the group consisting of Alzheimer's disease, Parkinson's disease, amyotrophic lateral sclerosis, Huntington's disease, cerebral ischemia and neurodegenerative disease caused by traumatic injury, glutamate neurotoxicity, hypoxia, epilepsy and graft versus host disease.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, anti-inflammatory agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI—R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea (PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Abbreviations

AcOH acetic acid
AcONa sodium acetate
Boc tert-butyloxycarbonyl
$(Boc)_2O$ di-tert-butyl dicarbonate
$CDCl_3$ chloroform-d
DCE 1,2-dichloroethane
DCM dichloromethane
DIAD Diisopropyl azodicarboxylate
DIBAL-H diisobutylaluminium hydride
DIEA N,N-diisopropylethylamine
DMA N,N-dimethylacetamide
DMAP 4-dimethylaminopyridine
DMF N,N-dimethylformamide
DMP Dess-Martin periodinane
DMSO dimethyl sulfoxide
EDCI 1-ethyl-3-(3-dimethylaminopropyl)carbodiimide
eq equivalent(s)
EtOAc ethyl acetate
EtOH ethyl alcohol
h hour(s)
HATU 1-[bis(dimethylamino)methylene]-1H-1,2,3-triazolo[4,5-b]pyridinium 3-oxide hexafluorophosphate
HCl hydrochloric acid
HOBt hydroxybenzotriazole
HPLC high performance liquid chromatography
MeCN acetonitrile
MeOH methanol
M.W. microwave
$NaHCO_3$ sodium bicarbonate
NMR nuclear magnetic resonance
OMs mesylate
OTs tosylate
Pd/C palladium on carbon
$Pd(PPh_3)_4$ tetrakis(triphenylphosphine)palladium(0)
$PhSO_3H$ benzenesulfonic acid
PPTS pyridinium p-toluenesulfonate
Rf retention factor
TEA triethylamine
TFA trifluoroacetic acid
THF tetrahydrofuran
TLC thin-layer chromatography
TosCl 4-toluenesulfonyl chloride Intermediates Intermediate 1: ethyl (1s,4s)-4-aminocyclohexanecarboxylate

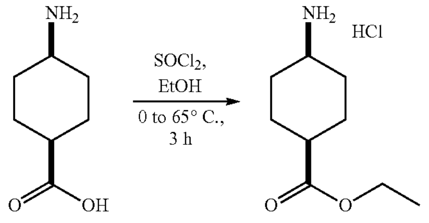

To a solution of (1s,4s)-4-aminocyclohexanecarboxylic acid (10 g, 69.84 mmol, 1 eq) in ethyl alcohol (100 mL) was added thionyl chloride (41.54 g, 349.20 mmol, 25.33 mL, 5 eq) at 0° C. The reaction mixture was heated to 65° C. and allowed to stir for 3 hours. $^1H$ NMR spectroscopy showed desired compound was detected. The reaction mixture was concentrated under reduced pressure. The crude product was triturated with ethyl acetate (50 mL). Ethyl (1s,4s)-4-aminocyclohexanecarboxylate (13.8 g, 66.44 mmol, 95% yield, hydrochloride) was obtained as a white solid. $^1H$ NMR (400 MHz, DMSO-$d_6$) δ: 8.16 (s, 3H), 4.08 (q, J=7.2 Hz, 2H), 3.04 (d, J=4.4 Hz, 1H), 2.62-2.53 (m, 1H), 2.02-1.90 (m, 2H), 1.79 (dd, J=4.4, 10.0 Hz, 2H), 1.63-1.41 (m, 4H), 1.14 (s, 1H), 1.19 (t, J=7.12 Hz, 2H).

Intermediate 2: 2-(2,6-dioxo-3-piperidyl)-5-fluoro-isoindoline-1,3-dione

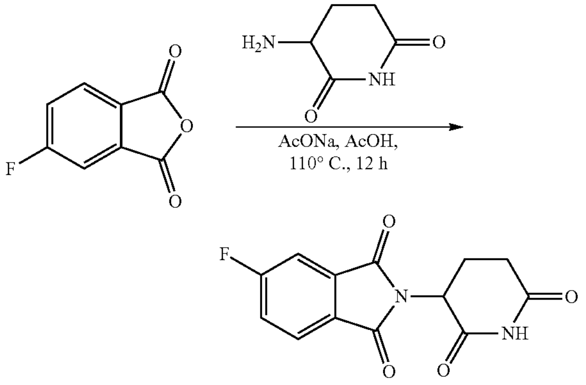

To a solution of 5-fluoroisobenzofuran-1,3-dione (1.00 g, 6.02 mmol, 1.00 eq) in acetic acid (10 mL) was added sodium acetate (987 mg, 12.04 mmol, 2.00 eq) and 3-aminopiperidine-2,6-dione (2.97 g, 18.06 mmol, 3.00 eq, hydrochloric acid). The mixture was stirred at 115° C. for 6 hours. LCMS analysis of the crude reaction mixture indicated complete conversion. The reaction mixture was washed with water (20 mL). The mixture was filtered and concentrated under reduced pressure to afford 2-(2,6-dioxo-3-piperidyl)-5-fluoro-isoindoline-1,3-dione (1.20 g, 4.34 mmol, 72% yield) as a black solid. MS (ESI) m/z: 277.0 $[M+H]^+$. $^1H$ NMR (400 MHz, DMSO-$d_6$) δ: 11.16 (s, 1H), 8.02 (dd, J=3.6, 4.4 Hz, 1H), 7.86 (dd, J=2.4, 7.6 Hz, 1H) 7.65-7.79 (m, 1H), 5.17 (dd, J=5.2, 12.8 Hz, 1H), 2.80-2.96 (m, 1H), 2.53-2.71 (m, 2H), 2.00-2.13 (m, 1H).

Intermediate 3: tert-buty-N-methyl-N-[2-(2-oxoethoxy) ethyl]carbamate

Step 1:

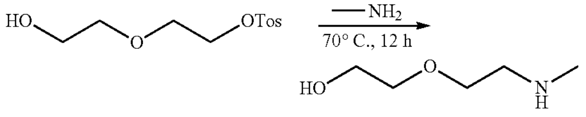

A solution of 2-(2-hydroxyethoxy)ethyl 4-methylbenzenesulfonate (2.50 g, 9.60 mmol, 1 eq) and methanamine (40.0 mL, 1.00 eq) in sealed tube was stirred at 70° C. for 12 hours. Analysis by TLC indicated 2-(2-hydroxyethoxy)

ethyl 4-methylbenzenesulfonate was consumed completely. The reaction mixture was concentrated under reduced pressure to remove methanamine (40.0 mL, 1.00 eq) to give 2-[2-(methylamino)ethoxy]ethanol (1.10 g, crude) as a yellow oil.

Step 2:

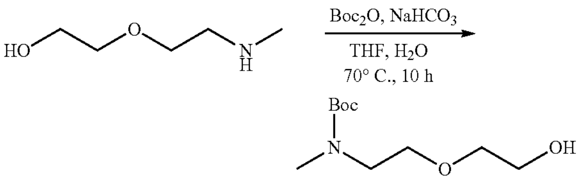

To a solution of 2-[2-(methylamino)ethoxy]ethanol (1.10 g, 9.23 mmol, 1.00 eq) in tetrahydrofuran (20.0 mL) and water (10.0 mL) was added di-tert-butyldicarbonate (3.02 g, 13.85 mmol, 3.2 mL, 1.50 eq) and sodium bicarbonate (1.55 g, 18.46 mmol, 0.7 mL, 2.00 eq). The mixture was stirred at 70° C. for 10 hours. Analysis by TLC and LCMS indicated the reaction was complete. The reaction mixture was quenched by addition of water (100 mL) and extracted with ethyl acetate (100 mL×2). The combined organic layers were concentrated under reduced pressure to give a residue. The residue was purified by column chromatography to give tert-butyl N-[2-(2-hydroxyethoxy)ethyl]-N-methyl-carbamate (400 mg, 1.82 mmol, 19% yield) as a yellow oil. MS (ESI) m/z: 219.9 $[M+H]^+$. $^1H$ NMR (400 MHz, $CDCl_3$) δ: 3.79-3.68 (m, 2H), 3.65-3.54 (m, 4H), 3.50-3.27 (m, 2H), 2.98-2.85 (m, 3H), 1.49-1.37 (m, 9H).

Step 3:

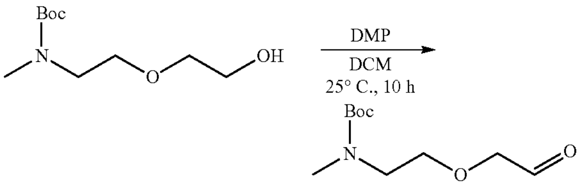

To a solution of tert-butyl N-[2-(2-hydroxyethoxy)ethyl]-N-methyl-carbamate (100 mg, 0.46 mmol, 1.00 eq) in dichloromethane (3.0 mL) was added (1,1,1-triacetoxy)-1,1-dihydro-1,2-benziodoxol-3(1H)-one (232 mg, 0.55 mmol, 0.2 mL, 1.20 eq). The mixture was stirred at 25° C. for 10 hours. The reaction mixture was concentrated under reduced pressure to remove dichloromethane (3.0 mL) to give tert-butyl N-methyl-N-[2-(2-oxoethoxy)ethyl]carbamate (60 mg, crude) as a yellow oil.

Intermediate 4: pyrazolo[1,5-a]pyrimidine-3-carbonyl chloride

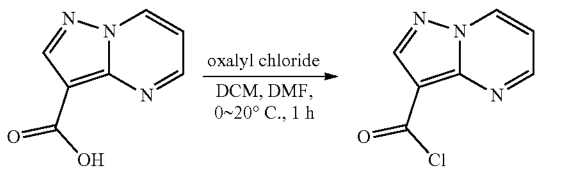 [SMILES: O=C(O)c1cnn2cccnc12 ; O=C(Cl)c1cnn2cccnc12]

To a solution of pyrazolo[1,5-a]pyrimidine-3-carboxylic acid (200 mg, 1.23 mmol, 1 eq) in dichloromethane (8 mL) was added oxalyl chloride (326 mg, 2.57 mmol, 2.1 eq) in dichloromethane (1.3 mL) and N,N-dimethylformamide (0.02 mL) at 0° C. The mixture was stirred at 20° C. for 1 hour. Thin layer chromatography (dichloromethane:methanol=10:1) showed the reaction was complete. The mixture was concentrated under reduced pressure to afford pyrazolo[1,5-a]pyrimidine-3-carbonyl chloride (200 mg, 1.10 mmol, 89% yield) as a brown solid and which was used in the next step without further purification.

Intermediate 5: benzyl 4-(4-aminocyclohexyl)piperazine-1-carboxylate

Step 1:

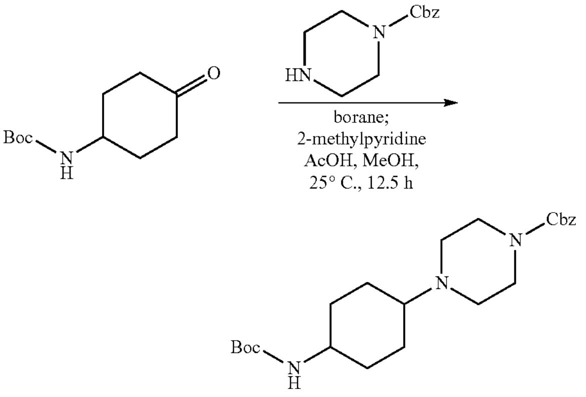

To a solution of tert-butyl N-(4-oxocyclohexyl)carbamate (10 g, 46.89 mmol, 1 eq) in methanol (150 mL) was added acetic acid (15 mL) and benzyl piperazine-1-carboxylate (10.33 g, 46.89 mmol, 1 eq). The mixture was stirred at 30° C. for 0.5 hour. Then 2-methylpyridine borane complex (10.03 g, 93.78 mmol, 2 eq) was added and the mixture was stirred at 30° C. for 12 hours. LCMS analysis of an aliquot indicated completion of the reaction. The reaction mixture was diluted with water (500 mL) and extracted with ethyl acetate (200 mL×3). The combined organic phase was washed with a saturated aqueous solution of sodium bicarbonate (200 mL) and saturated brine (300 mL×2), dried with anhydrous sodium sulfate, filtered and concentrated under reduced pressure. The residue was triturated with petroleum ether:ethyl acetate (V/V=5:1, 150 mL) to give benzyl 4-[4-(tert-butoxycarbonylamino)cyclohexyl]piperazine-1-carboxylate (13 g, 31.1 mmol, 66.4% yield) obtained as a white solid. MS (ESI) m/z: 418.2$[M+H]^+$.

Step 2:

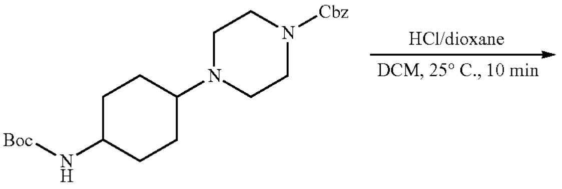

-continued

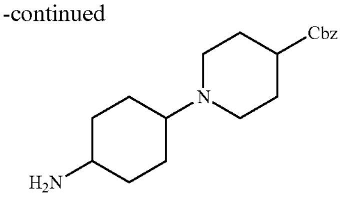

To a solution of benzyl 4-[4-(tert-butoxycarbonylamino)cyclohexyl]piperazine-1-carboxylate (13 g, 31.13 mmol, 1 eq) in dichloromethane (100 mL) was added hydrochloric acid in dioxane (100 mL). The mixture was stirred at 25° C. for 10 minutes. Thin layer chromatography (petroleum ether:ethyl acetate=1:1) confirmed completion of the reaction. The mixture was concentrated under reduced pressure and the resulting residue was used in a subsequent transformation without further purification. Compound benzyl 4-(4-aminocyclohexyl)piperazine-1-carboxylate (10.9 g, 30.80 mmol, 98% yield, hydrochloride) was obtained as a white solid.

Intermediate 6: tert-butyl N-[4-(4-vinylsulfonylpiperazin-1-yl)cyclohexyl]carbamate Step 1:

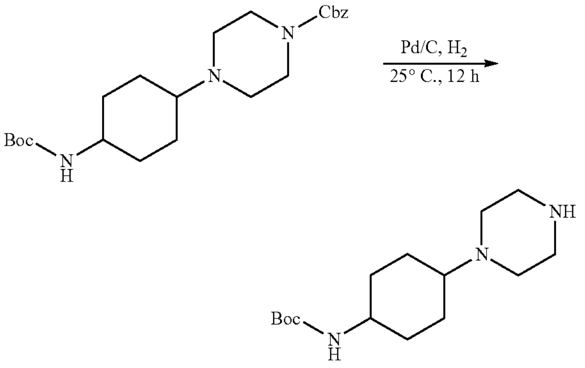

To a solution of benzyl 4-[4-(tert-butoxycarbonylamino)cyclohexyl]piperazine-1-carboxylate (7 g, 16.76 mmol, 1 eq) in tetrahydrofuran (20 mL) and methanol (50 mL) was added palladium on activated carbon catalyst (700 mg, 16.73 mmol, 10% purity, 9.98e-1 eq) under nitrogen. The suspension was degassed under vacuum and purged with an atmosphere of hydrogen several times. The mixture was stirred under hydrogen (15 psi) at 25° C. for 12 hours. Thin layer chromatography (petroleum ether:ethyl acetate=10:1) showed the reaction was complete. The mixture was filtered and concentrated under reduced pressure. The crude product was used in the next step without further purification. Compound tert-butyl N-(4-piperazin-1-ylcyclohexyl) carbamate (4.6 g, 16.23 mmol, 96% yield) was obtained as a white solid. $^1H$ NMR: (400 MHz, DMSO-$d_6$) δ: 6.80-6.60 (m, 1H), 3.18-3.16 (m, 1H), 2.69-2.60 (m, 4H), 2.40-2.31 (m, 4H), 2.07 (t, J=8.7 Hz, 1H), 1.79 (br s, 1H), 1.74 (br d, J=14.5 Hz, 2H), 1.70-1.53 (m, 2H), 1.46-1.38 (m, 2H), 1.38-1.36 (m, 9H), 1.23-1.11 (m, 2H).

Step 2:

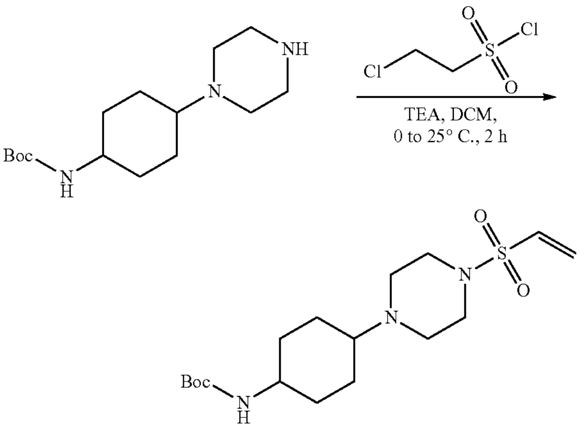

To a solution of tert-butyl N-(4-piperazin-1-ylcyclohexyl) carbamate (4.6 g, 16.23 mmol, 1 eq) in dichloromethane (90 mL) was added triethylamine (8.21 g, 81.15 mmol, 5 eq) and 2-chloroethanesulfonyl chloride (3.97 g, 24.35 mmol, 2.54 mL, 1.5 eq) at 0° C. The mixture was stirred at 25° C. for 2 hours. The mixture was concentrated under reduced pressure. The crude product was purified by silica gel column chromatography (petroleum ether:ethyl acetate=5:1 to 1:1) to give tert-butyl N-[4-(4-vinylsulfonylpiperazin-1-yl)cyclohexyl]carbamate (2.4 g, 6.43 mmol, 39% yield) as a brown solid. $^1H$ NMR: (400 MHz, DMSO-$d_6$) δ: 6.86-6.74 (m, 1H), 6.21-6.05 (m, 2H), 3.54-3.41 (m, 1H), 3.22-3.05 (m, 1H), 3.03-2.93 (m, 4H), 2.59-2.52 (m, 4H), 2.29-2.14 (m, 1H), 1.85-1.56 (m, 4H), 1.47-1.38 (m, 2H), 1.38-1.31 (m, 9H), 1.26-1.15 (m, 2H).

Intermediate 7: 2-[2-(2-oxoethoxy)ethoxy]ethyl 4-methylbenzenesulfonate

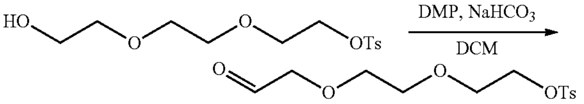

To a solution of 2-[2-(2-hydroxyethoxy)ethoxy]ethyl 4-methylbenzenesulfonate (4 g, 13.14 mmol, 1 eq) in DCM (80 mL) was added Dess-Martin periodinane (7.25 g, 17.10 mmol, 5.29 mL, 1.3 eq) and sodium bicarbonate (11.04 g, 131.42 mmol, 5.11 mL, 10 eq). The mixture was stirred at 23° C. for 1 hour. LCMS analysis confirmed the reaction to be complete. The reaction mixture was poured into water (150 mL) at 0° C. The mixture was extracted with dichloromethane (100 mL×2). The combined organic layers were washed with brine (100 mL×3), dried over anhydrous sodium sulfate, concentrated under vacuum and the resulting residue was purified by column chromatography (petroleum ether/ethyl acetate=10:1 to 0.25:1) to afford 2-[2-(2-oxoethoxy)ethoxy]ethyl4-methylbenzenesulfonate (1.4 g, 4.63 mmol, 35.23% yield) as a yellow oil. MS (ESI) m/z: 303.2 $[M+H]^+$.

Intermediate 8: 2-[2-(2,6-dioxo-3-piperidyl)-1,3-dioxo-isoindolin-5-yl]oxyacetaldehyde Step 1:

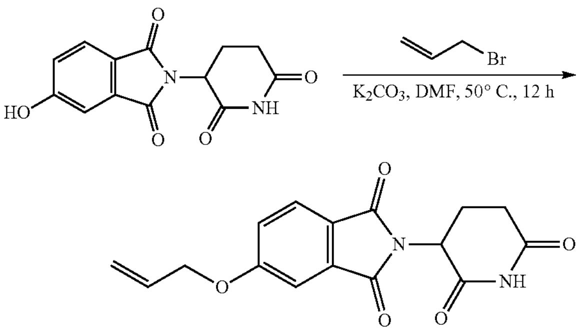

The mixture of 2-(2,6-dioxo-3-piperidyl)-5-hydroxy-isoindoline-1,3-dione (1 g, 3.65 mmol, 1 eq) and potassium carbonate (1.01 g, 7.29 mmol, 2 eq) in dimethylformamide (10 mL)was degassed and refilled with nitrogen 3 times, after which 3-bromoprop-1-ene (470 mg, 3.89 mmol, 1.1 eq) was added to the mixture. The mixture was stirred at 50° C. for 12 hours. The reaction mixture was quenched with water (60 mL) at 0° C., then extracted with ethyl acetate (30 mL×3). The combined organic layers were washed with brine (20 mL×2), dried over anhydrous sodium sulfate, filtered and concentrated to give a residue. The residue was purified by silica gel column chromatography (petroleum ether/ethyl acetate=4/1 to 1/1), to afford 5-allyloxy-2-(2,6-dioxo-3-piperidyl)isoindoline-1,3-dione (0.9 g, 79% yield) obtained as a yellow solid. MS (ESI) m/z: 315.1 $[M+H]^+$.

Step 2:

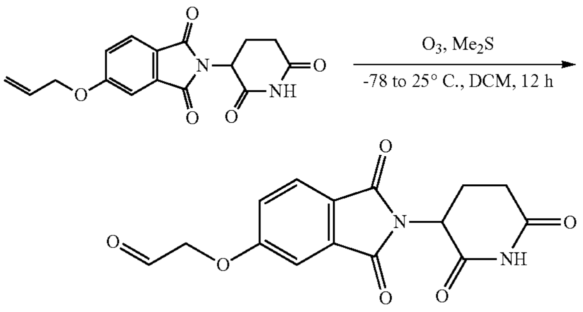

To the mixture of 5-allyloxy-2-(2,6-dioxo-3-piperidyl) isoindoline-1,3-dione (0.7 g, 2.23 mmol, 1 eq) in dichloromethane (200 mL) was bubbled ozone until the mixture turned blue at −78° C. Then nitrogen was bubbled until the solution became colorless. Dimethylsulfide (7.61 g, 123 mmol, 9 mL, 55 eq) was added to the mixture at −78° C. under a nitrogen atmosphere. The mixture was stirred at 25° C. for 12 hours. The reaction mixture was concentrated to give a residue which was purified by silica gel column chromatography (petroleum ether/ethyl acetate=1/1 to 0/1) to afford 2-[2-(2,6-dioxo-3-piperidyl)-1,3-dioxo-isoindolin-5-yl]oxyacetaldehyde (0.7 g, crude), obtained as a light yellow solid. MS (ESI) n/z: 317.0 $[M+H]^+$.

Intermediate 9: 2-[2-[2-(2,6-dioxo-3-piperidyl)-1,3-dioxo-isoindolin-5-yl]oxyethoxy]acetaldehyde Step 1:

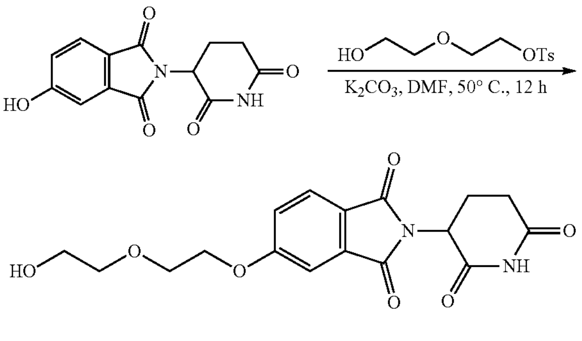

To a mixture of 2-(2,6-dioxo-3-piperidyl)-5-hydroxy-isoindoline-1,3-dione (2 g, 7.29 mmol, 1 eq) and potassium carbonate (3.02 g, 21.9 mmol, 3 eq) in dimethylformamide (10 mL) was added 2-(2-hydroxyethoxy)ethyl 4-methylbenzenesulfonate (2.09 g, 8.02 mmol, 1.1 eq). The mixture was stirred at 50° C. for 12 hours. The reaction mixture was concentrated to give a residue. The residue was purified by silica gel column chromatography (eluted with petroleum ether/ethyl acetate=1/1 to 0:1) to afford 2-(2,6-dioxo-3-piperidyl)-5-[2-(2-hydroxyethoxy)ethoxy]isoindoline-1,3-dione (1.5 g, 54% yield), obtained as a yellow solid. MS (ESI) m/z: 362.9 $[M+H]^+$.

Step 2:

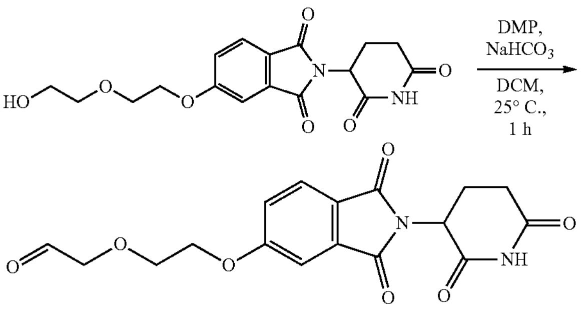

To a solution of 2-(2,6-dioxo-3-piperidyl)-5-[2-(2-hydroxyethoxy)ethoxy]isoindoline-1,3-dione (500 mg, 1.38 mmol, 1 eq) in dichloromethane (20 mL) was added sodium bicarbonate (1.16 g, 13.8 mmol, 0.54 mL, 10 eq), and Dess-Martin periodinane (877 mg, 2 mmol, 1.5 eq) at 0° C. The mixture was stirred at 25° C. for 1 hour. The reaction mixture was quenched with a solution comprised of 50 mL of a saturated aqueous solution of sodium bicarbonate solution and 50 mL of an aqueous sodium thiosulfate solution. The mixture was then extracted with dichloromethane (30 mL×3). The combined organic phase was washed with brine 30 mL, dried over anhydrous sodium sulfate, filtered and concentrated under vacuum. The resulting residue was purified by silica gel chromatography (petroleum ether/ethyl acetate=3/1 to 0/1), to afford crude 2-[2-[2-(2,6-dioxo-3-piperidyl)-1,3-dioxo-isoindolin-5-yl]oxyethoxy]acetaldehyde (400 mg, 80% yield), obtained as a colorless oil.

Intermediate 10: 2-[2-[2-(2,6-dioxo-3-piperidyl)-1,3-dioxo-isoindolin-5-yl]oxyethoxy]ethyl 4-methylbenzenesulfonate

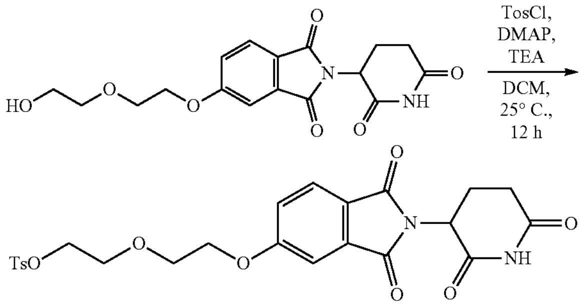

To a solution of 2-(2,6-dioxo-3-piperidyl)-5-[2-(2-hydroxyethoxy)ethoxy]isoindoline-1,3-dione, Intermediate 9 (400 mg, 1.10 mmol, 1 eq) in dichloromethane (5 mL) was added para-toluenesulfonyl chloride (315 mg, 1.66 mmol, 1.5 eq), 4-dimethylaminopyridine (13 mg, 0.11 mmol, 0.1 eq) and triethylamine (335 mg, 3.31 mmol, 3 eq). The mixture was stirred at 25° C. for 12 hours. LCMS analysis confirmed the reaction to be complete. The mixture was diluted with water (10 mL) and extracted with dichloromethane (10 mL×3). The combined organic layers were washed with brine (20 mL×2), dried with anhydrous sodium sulfate, filtered and concentrated under reduced pressure. The residue was purified by preparative reverse phase thin layer chromatography (dichloromethane:methanol=20:1) to give 2-[2-[2-(2,6-dioxo-3-piperidyl)-1,3-dioxo-isoindolin-5-yl]oxyethoxy]ethyl 4-methylbenzenesulfonate (150 mg, 0.29 mmol, 26% yield) as a colorless oil. MS (ESI) m/z: 517.1 $[M+H]^+$.

Intermediate 11: 3-hydroxy-4-methoxybenzenesulfonic acid

Step 1:

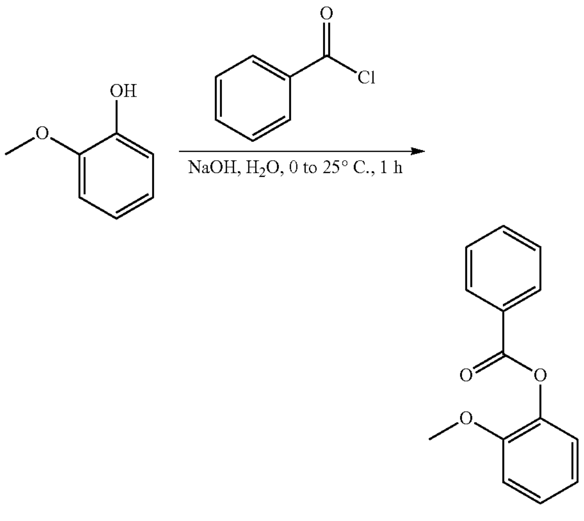

To a solution of sodium hydroxide (80 g, 2.00 mol, 4.97 eq) in water (500 mL) was added 2-methoxyphenol (50 g, 402.78 mmol, 45.05 mL, 1 eq) at 0° C., and then benzoyl chloride (65 g, 462.41 mmol, 53.72 mL, 1.15 eq) was added to above solution. The mixture was stirred at 0-25° C. for 1 hour. The reaction mixture was filtered to afford crude 2-methoxyphenyl benzoate (54 g, 236.59 mmol, 59% yield, 100% purity) as a white solid which was used in the next step without further purification. MS (ESI) m/z: 229.1 $[M+H]^+$.

Step 2:

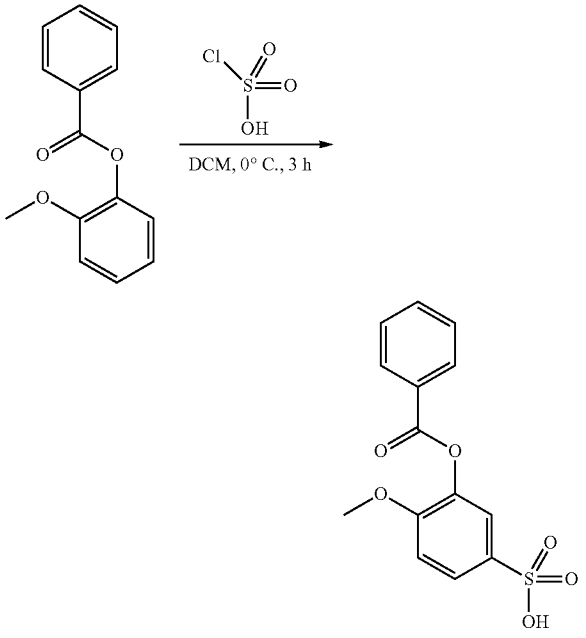

To a solution of 2-methoxyphenyl benzoate (100 g, 438.13 mmol, 1 eq) in dichloromethane (1000 mL) was added chlorosulfonic acid (51 g, 437.68 mmol, 29.14 mL, 0.99 eq) at 0° C. The mixture was stirred at 0° C. for 3 hours. The reaction mixture was filtered and the cake was collected to provide crude product 3-(benzoyloxy)-4-methoxybenzenesulfonic acid (95 g, 308.14 mmol, 70% yield) as a white solid which was used into the next step without further purification. $^1$H NMR (400 MHz, DMSO-$d_6$) δ=8.15-8.09 (m, 2H), 7.78-7.71 (m, 1H), 7.64-7.57 (m, 2H), 7.55 (dd, J=2.0, 8.4 Hz, 1H), 7.40 (d, J=2.0 Hz, 1H), 6.26 (br d, J=16.8 Hz, 5H), 3.76 (s, 3H).

Step 3:

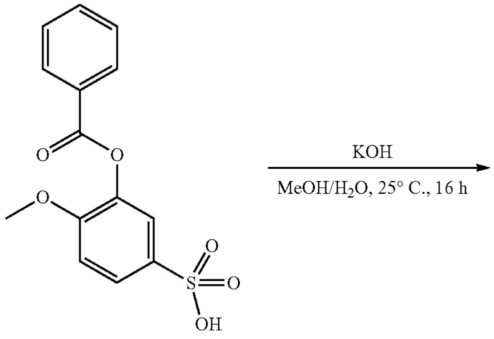

-continued

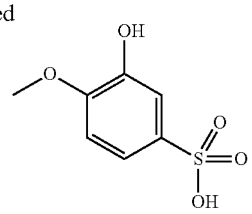

To a solution of 3-(benzoyloxy)-4-methoxybenzenesulfonic acid (90 g, 291.92 mmol, 1 eq) in methanol (450 mL) was added potassium hydroxide (60 g, 1.07 mol, 3.66 eq) in water (450 mL) at 0° C., and then the mixture was stirred at 25° C. for 10 hours. The reaction mixture was concentrated under reduced pressure to remove methanol. The residue was diluted with water (100 mL) and the pH was adjusted to 7 with the addition of a concentrated aqueous solution of hydrochloric acid. The mixture was then extracted with ethyl acetate (100 mL×6). The aqueous layer was concentrated under reduced pressure to give a residue. The residue was washed with ethanol 100 mL, filtered and concentrated under reduced pressure to afford 3-hydroxy-4-methoxybenzenesulfonic acid (50 g, 244.86 mmol, 84% yield) as a brown oil. $^1$H NMR (400 MHz, DMSO-$d_6$) δ=7.07 (d, J=2.0 Hz, 1H), 7.02 (dd, J=2.0, 8.0 Hz, 1H), 6.84 (d, J=8.4 Hz, 1H), 5.81 (br s, 5H), 3.75 (s, 3H).

Scheme 1.

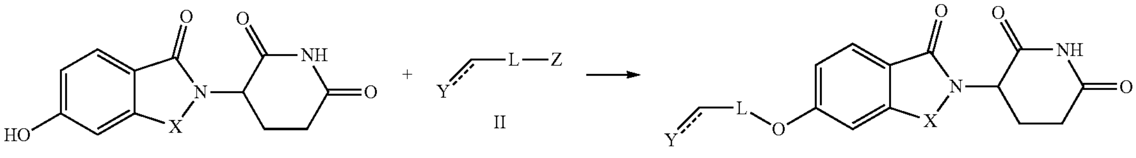

I

II

III

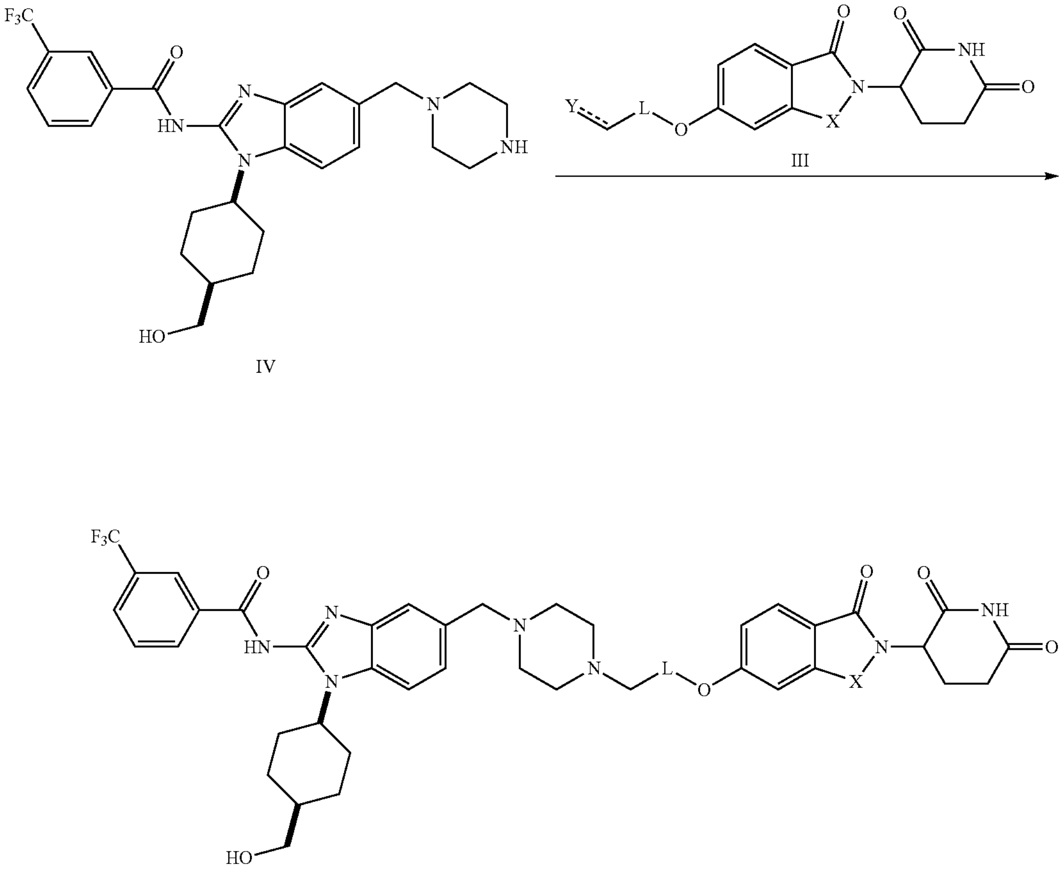

III

IV

V

A compound of formula I may be reacted with a reagent II (commercially available or readily prepared using standard reaction techniques known to one skilled in the art) where Z is an appropriate leaving group (e.g. OMs, OTs, Cl, Br, etc.) under O-alkylation conditions to produce a compound of formula III, wherein L represents an optional linker or portion of a linker and X is $CH_2$ or C═O. Suitable reactions conditions for O-alkylation entail the use of a base, e.g. NaH or potassium carbonate in a solvent such as DMF at 60° C. Compounds of formula III may react with a compound of formula IV through N-alkylation where Y is an appropriate leaving group (e.g. OMs, OTs, Cl, etc.) or through reductive amination where Y is an aldehyde to produce compound of formula V. When Y is a leaving group, suitable reaction conditions are those for an alkylation reaction, e.g. diisopropylethylamine, potassium iodide, DMSO or acetonitrile, 80° C. When Y is an aldehyde, suitable reaction conditions are those for a reductive amination reaction, e.g. sodium cyanoborohydride, methanol, dichloromethane, acetic acid, room temperature.

Exemplary Synthesis of Exemplary Compound 1

N-(5-((4-(2-((2-(2,6-dioxopiperidin-3-yl)-1,3-dioxoisoindolin-5-yl)oxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide Step 1:

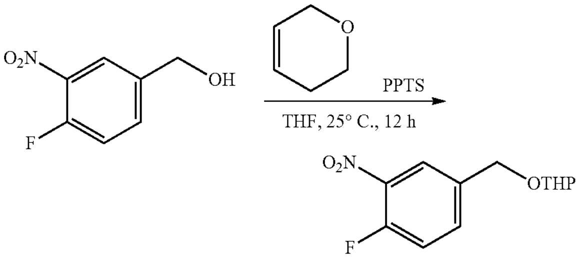

To a solution of (4-fluoro-3-nitro-phenyl)methanol (10 g, 58.44 mmol, 1 eq) in tetrahydrofuran (100 mL) was added pyridinium p-toluenesulfonate (1.47 g, 5.84 mmol, 0.1 eq) and 2,3-dihydropyrane (14.75 g, 175.31 mmol, 16 mL, 3 eq). The mixture was stirred at 25° C. for 12 hours. LCMS analysis showed the reaction was complete. The reaction mixture was diluted with water (300 mL) and extracted with ethyl acetate (100 mL×2). The combined organic phase was washed with saturated brine (100 mL×2), dried with anhydrous sodium sulfate, filtered and concentrated under reduced pressure to give a residue. The residue was purified by silica gel chromatography eluting with a gradient from 20:1 to 10:1 petroleum ether:ethyl acetate to afford 2-[(4-fluoro-3-nitro-phenyl)methoxy]tetrahydropyran (14 g, 54.8 mmol, 93% yield) as a light yellow solid.

Step 2:

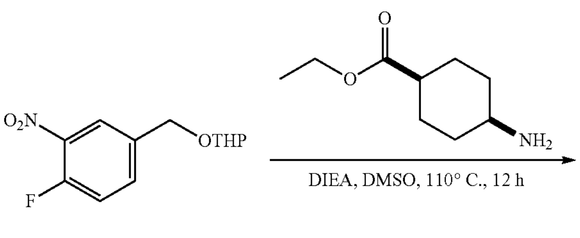

-continued

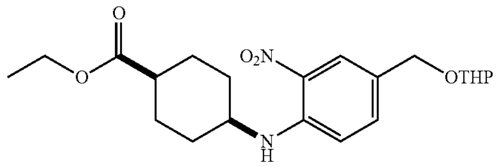

To a solution of 2-[(4-fluoro-3-nitro-phenyl)methoxy]tetrahydropyran (14 g, 54.8 mmol, 1 eq) in dimethylsulfoxide (150 mL) was added diisopropylethylamine (28.36 g, 219.4 mmol, 38.2 mL, 4 eq) and ethyl (1s,4s)-4-aminocyclohexanecarboxylate, Intermediate 1(11.39 g, 54.85 mmol, 1 eq, hydrochloride). The mixture was stirred at 110° C. for 12 hours. Thin layer chromatography (petroleum ether:ethyl acetate=1:1) confirmed the reaction to be complete. The reaction mixture was diluted with water (300 mL) and extracted with ethyl acetate (150 mL×2). The combined organic phase was washed with saturated brine (100 mL×2), dried with anhydrous sodium sulfate, filtered and concentrated under reduced pressure. The residue was purified by silica gel chromatography eluting with a gradient from 10:1 to 5:1 petroleum ether:ethyl acetate to give ethyl (1s,4s)-4-[2-nitro-4-(tetrahydropyran-2-yloxymethyl)anilino]cyclohexanecarboxylate (22 g, 54.12 mmol, 98% yield) as a yellow solid.

$^1H$ NMR (400 MHz, $CDCl_3$) δ: 8.26 (d, J=7.2 Hz, 1H), 8.17 (d, J=1.2 Hz, 1H), 7.44 (dd, J=1.6, 8.8 Hz, 1H), 6.85 (d, J=8.8 Hz, 1H), 4.73-4.62 (m, 2H), 4.38 (d, J=11.6 Hz, 1H), 4.16 (q, J=7.2 Hz, 2H), 3.90 (ddd, J=2.8, 8.4, 11.2 Hz, 1H), 3.71 (s, 1H), 3.60-3.49 (m, 1H), 2.58-2.44 (m, 1H), 2.03-1.93 (m, 2H), 1.90-1.73 (m, 8H), 1.66-1.51 (m, 4H), 1.27 (t, J=7.2 Hz, 3H).

Step 3:

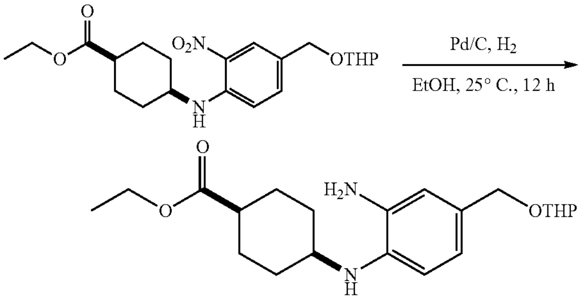

To a solution of ethyl (1s,4s)-4-[2-nitro-4-(tetrahydropyran-2-yloxymethyl)anilino]cyclohexanecarboxylate (22 g, 54.12 mmol, 1 eq) in ethyl alcohol (250 mL) was added palladium on activated carbon catalyst (2 g, 10% purity) under nitrogen atmosphere. The suspension was degassed and purged with an atmosphere of hydrogen 3 times. The mixture was stirred under hydrogen (15 psi) at 25° C. for 12 hours. Thin layer chromatography (petroleum ether:ethyl acetate=1:1) showed the reaction was complete. The reaction mixture was filtered and the filtrate was concentrated to afford ethyl (1s,4s)-4-[2-amino-4-(tetrahydropyran-2-yloxymethyl)anilino] cyclohexanecarboxylate (20 g, 53.12 mmol, 98% yield) as a brown oil which was used in the subsequent reaction without further purification.

Step 4:

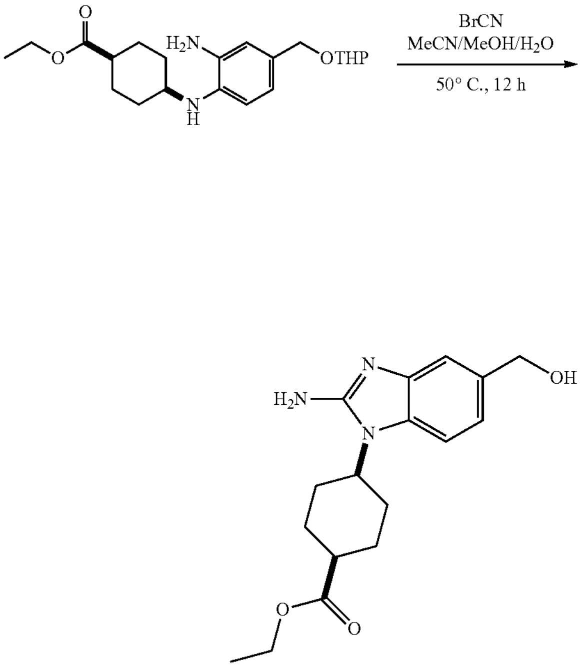

To a solution of ethyl (1s,4s)-4-[2-amino-4-(tetrahydropyran-2-yloxymethyl)anilino]cyclohexanecarboxylate (10 g, 26.56 mmol, 1 eq) in methanol (100 mL) was added a solution of cyanogen bromide (3.38 g, 31.87 mmol, 1.2 eq) in acetonitrile (5.2 mL) and water (5.2 mL) dropwise. The mixture was stirred at 50° C. for 12 hours. LCMS analysis of the reaction mixture indicated the reaction was complete. The pH of the reaction mixture was adjusted to between 9 and 10 with a saturated aqueous solution of sodium bicarbonate. The mixture was diluted with water (200 mL) and extracted with ethyl acetate (80 mL×3). The combined organic phase was washed with a saturated aqueous solution of brine (120 mL×2), dried with anhydrous sodium sulfate, filtered and concentrated under vacuum. The residue was triturated with ethyl acetate (80 mL) to afford ethyl (1s,4s)-4-[2-amino-5-(hydroxymethyl)benzimidazol-1-yl]cyclohexanecarboxylate (8.2 g, 25.84 mmol, 97% yield) as a brown solid. MS (ESI) m/z: 318.1 $[M+H]^+$.

Step 5:

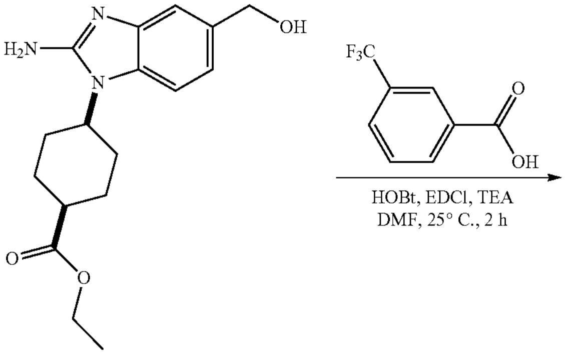

-continued

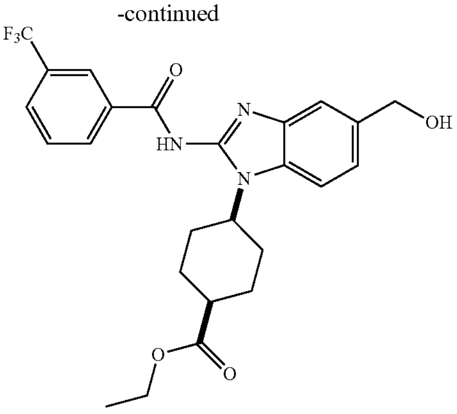

To a solution of ethyl (1s,4s)-4-[2-amino-5-(hydroxymethyl)benzimidazol-1-yl]cyclohexanecarboxylate (5.00 g, 15.75 mmol, 1 eq) and 3-(trifluoromethyl)benzoic acid (3.00 g, 15.75 mmol, 1 eq) in dimethylformamide (80 mL) was added hydroxybenzotriazole (2.55 g, 18.90 mmol, 1.2 eq) and triethylamine (3.19 g, 31.51 mmol, 4.4 mL, 2 eq). The mixture was stirred at 25° C. for 0.5 hour, after which 1-(3-dimethylaminopropyl)-3-ethylcarbodiimide hydrochloride (4.53 g, 23.63 mmol, 1.5 eq) was added, and the mixture was stirred at 25° C. for 1.5 hours. LCMS analysis of the reaction mixture showed the reaction was complete. The reaction mixture was diluted with water (300 mL) and extracted with ethyl acetate (100 mL×3). The combined organic phase was washed with a saturated aqueous brine solution (150 mL×3), dried with anhydrous sodium sulfate, filtered and concentrated under reduced pressure. The residue was purified by silica gel chromatography (petroleum ether:ethyl acetate=10:1 to 2:1) to give ethyl (1s,4s)-4-[5-(hydroxymethyl)-2-[[3-(trifluoromethyl)benzoyl]amino]benzimidazol-1-yl]cyclohexanecarboxylate (2.5 g, 5.11 mmol, 32% yield) as a pink solid. MS (ESI) m/z: 490.0 $[M+H]^+$.

Step 6:

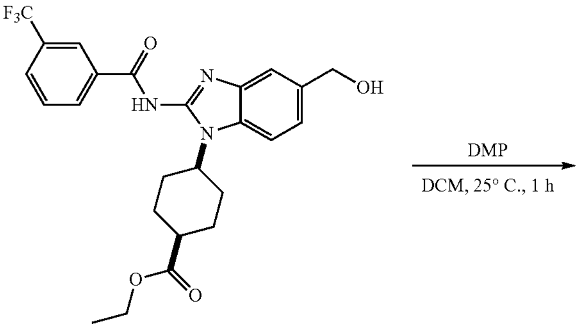

-continued

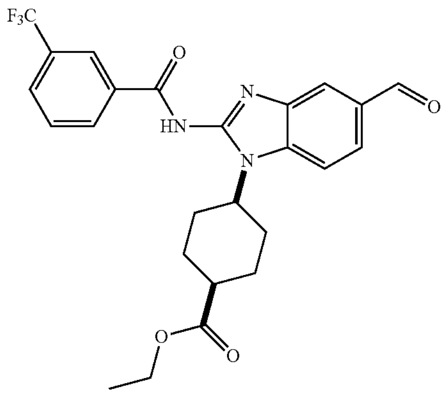

To a solution of ethyl (1s,4s)-4-[5-(hydroxymethyl)-2-[[3-(trifluoromethyl)benzoyl]amino]benzimidazol-1-yl]cyclohexanecarboxylate (300 mg, 0.61 mmol, 1 eq) in dichloromethane (15 mL) was added Dess-Martin periodinane (312 mg, 0.73 mmol, 1.2 eq). The mixture was stirred at 25° C. for 2 hours. Thin layer chromatography (petroleum ether:ethyl acetate=1:1) showed the reaction was complete. The reaction mixture was filtered and the filtrate was adjusted to a pH between 8 and 9 with the addition of a saturated aqueous solution of sodium bicarbonate. The mixture was diluted with water (20 mL) and extracted with dichloromethane (10 mL×3). The combined organic phase was washed with a saturated aqueous brine solution (15 mL×2), dried with anhydrous sodium sulfate, filtered and concentrated under reduced pressure. The residue was purified by silica gel chromatography (petroleum ether:ethyl acetate=30:1 to 10:1) to give ethyl (1s,4s)-4-[5-formyl-2-[[3-(trifluoromethyl)benzoyl]amino]benzimidazol-1-yl]cyclohexanecarboxylate (260 mg, 0.53 mmol, 87% yield) as a purple solid.

Step 7:

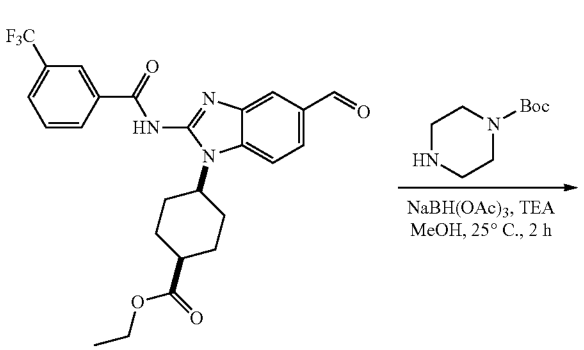

-continued

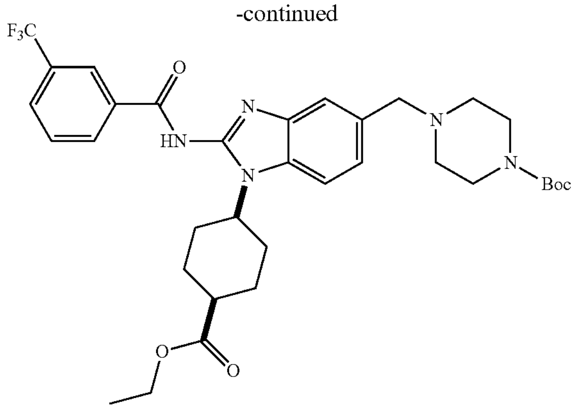

To a solution of tert-butyl piperazine-1-carboxylate (714 mg, 3.84 mmol, 1.1 eq) in 1,2-dichloroethane (20 mL) was added ethyl (1s,4s)-4-[5-formyl-2-[[3-(trifluoromethyl)benzoyl]amino]benzimidazol-1-yl]cyclohexanecarboxylate (1.7 g, 3.49 mmol, 1 eq) and triethylamine (1.46 mL, 3 eq). The mixture was stirred at 25° C. for 0.5 hour. Sodium triacetoxyborohydride (1.48 g, 6.97 mmol, 2 eq) was added, then the mixture was stirred at 25° C. for 1.5 hours. LCMS analysis of the crude reaction mixture showed the reaction was complete. The reaction mixture was diluted with water (50 mL) and extracted with dichloromethane (30 mL×2). The combined organic phase was washed with a saturated brine solution (30 mL×2), dried with anhydrous sodium sulfate, filtered and concentrated. The residue was purified by silica gel chromatography (petroleum ether:ethyl acetate=10:1 to 2:1) to give tert-butyl 4-((1-((1s,4s)-4-(ethoxycarbonyl)cyclohexyl)-2-(3-(trifluoromethyl)benzamido)-1H-benzimidazol-5-yl)methyl)piperazine-1-carboxylate (1.3 g, 1.98 mmol, 56% yield) as a white solid. MS (ESI) m/z: 658.3 $[M+H]^+$.

Step 8:

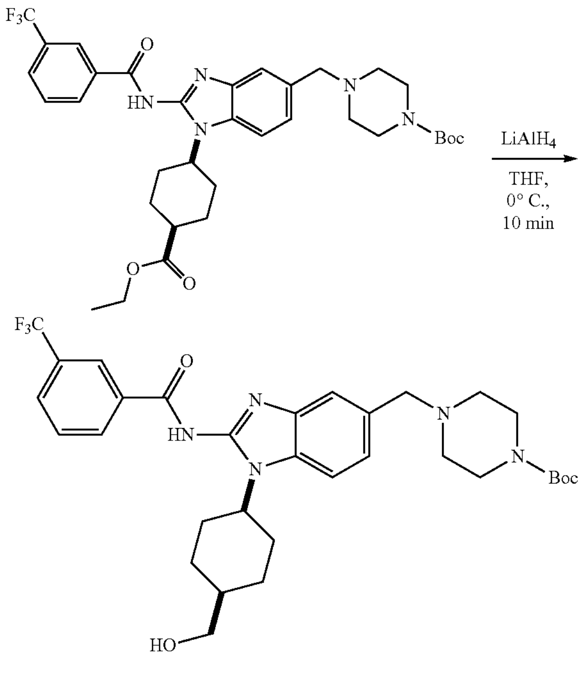

To a solution of tert-butyl 4-((1-((1s,4s)-4-(ethoxycarbonyl)cyclohexyl)-2-(3-(trifluoromethyl)benzamido)-1H-benzimidazol-5-yl)methyl)piperazine-1-carboxylate (1.1 g, 1.67 mmol, 1 eq) in tetrahydrofuran (30 mL) was added lithium aluminum hydride (126 mg, 3.34 mmol, 2 eq) at 0° C. The mixture was stirred at 0° C. for 10 minutes. LCMS analysis of the crude reaction mixture showed the conversion was complete. The reaction mixture was quenched with water (3 mL) at 0° C. and anhydrous sodium sulfate (15 g) was added. The mixture was stirred at 25° C. for 15 minutes and was then filtered. The filtrate was concentrated and the resulting residue was purified by silica gel chromatography (petroleum ether:ethyl acetate=2:1 to 1:4) to give tert-butyl 4-((1-((1s,4s)-4-(hydroxymethyl)cyclohexyl)-2-(3-(trifluoromethyl)benzamido)-1H-benzo[d]imidazol-5-yl)methyl) piperazine-1-carboxylate (380 mg, 0.61 mmol, 36% yield) as a white solid. MS (ESI) m/z: 616.2 $[M+H]^+$. $^1H$ NMR (400 MHz, $CDCl_3$) δ: 12.59 (s, 1H), 8.60 (s, 1H), 8.48 (d, J=8.0 Hz, 1H), 7.75 (d, J=8.0 Hz, 1H), 7.64-7.54 (m, 1H), 7.36-7.30 (m, 2H), 7.22 (dd, J=1.2, 8.4 Hz, 1H), 4.76-4.63 (m, 1H), 3.96 (d, J=7.2 Hz, 2H), 3.58 (s, 2H), 3.49-3.38 (m, 4H), 2.67-2.51 (m, 2H), 2.40 (t, J=5.2 Hz, 4H), 2.12-2.05 (m, 3H), 1.84-1.75 (m, 4H), 1.73-1.71 (m, 1H), 1.46 (s, 9H).

Step 9:

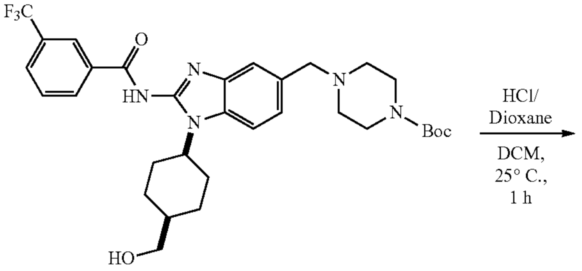

-continued

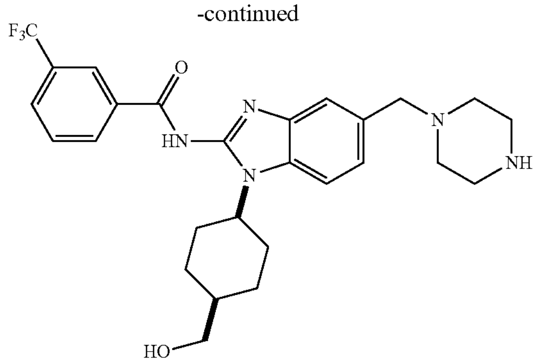

To a solution of tert-butyl 4-((1-((1s,4s)-4-(hydroxymethyl)cyclohexyl)-2-(3-(trifluoromethyl)benzamido)-1H-benzo[d]imidazol-5-yl)methyl)piperazine-1-carboxylate (430 mg, 0.69 mmol, 1 eq) in dichloromethane (5 mL) was added 4 M hydrochloric acid in dioxane (4 M, 5 mL, 28.6 eq). The mixture was stirred at 25° C. for 1 hour. LCMS analysis of the crude reaction mixture showed the reaction was complete. The reaction mixture was concentrated under reduced pressure to remove dioxane. The residue was diluted with water (10 mL) and pH was adjusted to between 9 and 10 with a saturated aqueous solution of sodium bicarbonate. The mixture was extracted with ethyl acetate (10 mL×2). The combined organic phase was washed with a saturated brine solution (10 mL×2), dried with anhydrous sodium sulfate, filtered and concentrated to give N-(1-((1s,4s)-4-(hydroxymethyl)cyclohexyl)-5-(piperazin-1-ylmethyl)-1H-benzo[d]imidazol-2-yl)-3-(trifluoromethyl)benzamide (310 mg, 0.60 mmol, 86% yield) as a white solid. MS (ESI) n/z: 516.2 $[M+H]^+$.

Step 10:

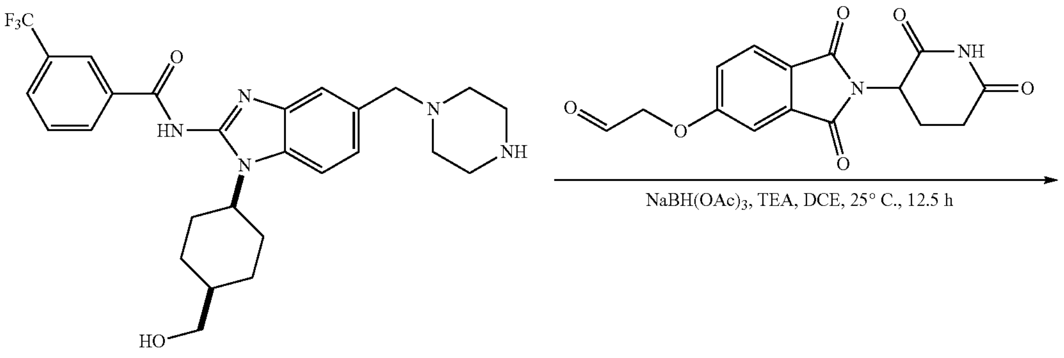

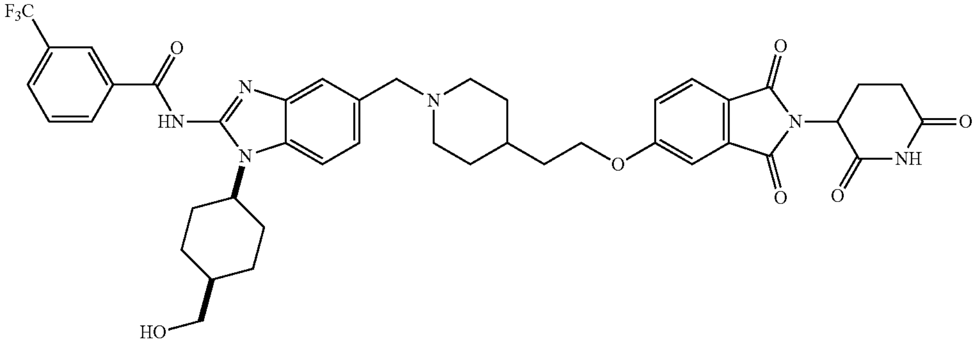

To a solution of N-(1-((1s,4s)-4-(hydroxymethyl)cyclohexyl)-5-(piperazin-1-ylmethyl)-1H-benzo[d]imidazol-2-yl)-3-(trifluoromethyl)benzamide (40 mg, 77.58 umol, 1 eq) in 1,2-dichloroethane (3 mL) was added triethylamine (23 mg, 0.23 mmol, 3 eq) and 2-[2-(2,6-dioxo-3-piperidyl)-1,3-dioxo-isoindolin-5-yl]oxyacetaldehyde, Intermediate 8 (49 mg, 0.15 mmol, 2 eq). The mixture was stirred at 25° C. for 0.5 hour. Sodium triacetoxyborohydride (32 mg, 0.15 mmol, 2 eq) was added, and then the mixture was stirred at 25° C. for 12 hours. LCMS analysis of the crude reaction mixture showed the reaction was complete. The pH of the reaction mixture was adjusted to between 6 and 7 with addition of hydrochloric acid (0.5 mL) and was then concentrated. The residue was purified by semi-preparative reverse phase HPLC to afford N-(5-((4-(2-((2-(2,6-dioxopiperidin-3-yl)-1,3-dioxoisoindolin-5-yl)oxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide (33.8 mg, 0.03 mmol, 46% yield, 96% purity, formate) as a white solid. MS (ESI) m/z: 816.3 $[M+H]^+$. $^1H$ NMR (400 MHz, DMSO-$d_6$) δ: 12.82 (s, 1H), 11.11 (s, 1H), 8.50 (d, J=8.0 Hz, 1H), 8.45 (s, 1H), 8.21 (s, 1H), 7.90 (d, J=8.0 Hz, 1H), 7.82 (d, J=8.4 Hz, 1H), 7.77-7.71 (m, 1H), 7.56-7.51 (m, 2H), 7.45 (d, J=2.0 Hz, 1H), 7.35 (dd, J=2.0, 8.4 Hz, 1H), 7.19 (d, J=8.4 Hz, 1H), 5.11 (dd, J=5.2, 13.2 Hz, 1H), 4.79-4.66 (m, 1H), 4.28 (t, J=5.6 Hz, 2H), 3.68 (d, J=7.6 Hz, 2H), 3.52 (s, 1H), 2.93-2.84 (m, 1H), 2.73 (t, J=5.4 Hz, 2H), 2.64-2.56 (m, 2H), 2.55-2.51 (m, 8H), 2.46-2.35 (m, 4H), 2.10-2.00 (m, 1H), 1.98-1.89 (m, 2H), 1.88-1.80 (m, 1H), 1.74-1.56 (m, 4H).

Exemplary Synthesis of Exemplary Compound 2

N-(5-((4-(2-(2-((2-(2,6-dioxopiperidin-3-yl)-1,3-dioxoisoindolin-5-yl)oxy)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide

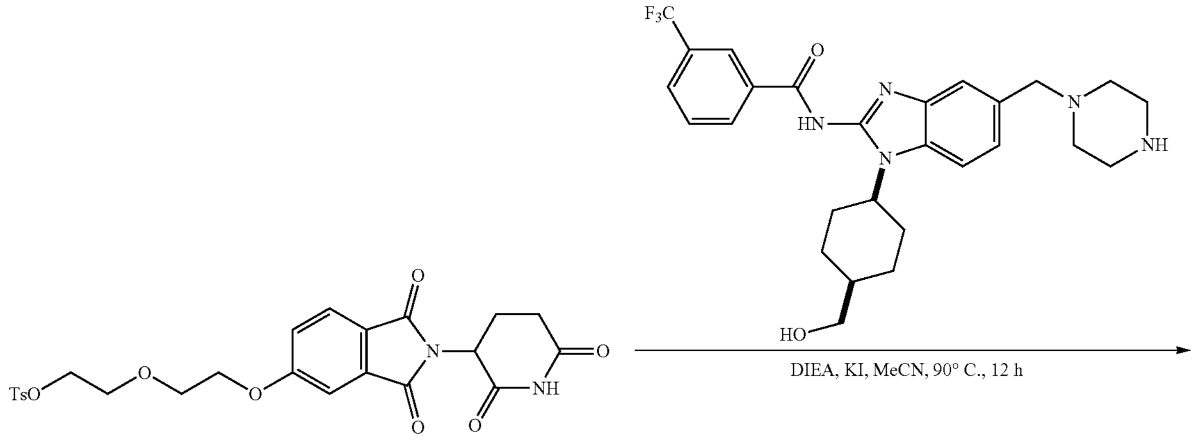

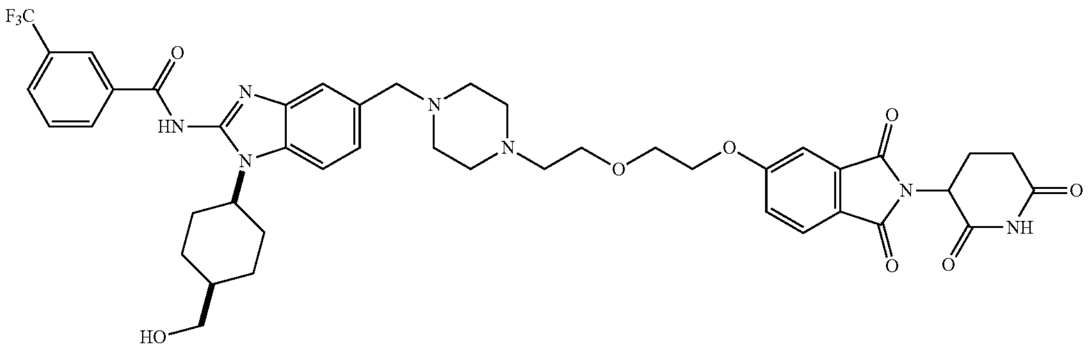

To a solution of 2-[2-[2-(2,6-dioxo-3-piperidyl)-1,3-dioxo-isoindolin-5-yl]oxyethoxy]ethyl 4-methylbenzenesulfonate, Intermediate 10 (50 mg, 0.096 mmol, 1.25 eq) and N-(1-((1s,4s)-4-(hydroxymethyl)cyclohexyl)-5-(piperazin-1-ylmethyl)-1H-benzo[d]imidazol-2-yl)-3-(trifluoromethyl)benzamide (Example 1 intermediate) (40 mg, 0.077 mmol, 1 eq) in acetonitrile (2 mL) was added N,N-diisopropylethylamine (30 mg, 0.23 mmol, 3 eq) and potassium iodide (1.29 mg, 0.007 mmol, 0.1 eq). The mixture was stirred at 90° C. for 12 hours. LCMS analysis indicated completion of the reaction. The reaction mixture was concentrated and the resulting residue was purified by preparative HPLC to afford N-(5-((4-(2-(2-((2-(2,6-dioxopiperidin-3-yl)-1,3-dioxoisoindolin-5-yl)oxy)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide (32.5 mg, 0.034 mmol, 44% yield, 96% purity, formate) as a white solid. MS (ESI) m/z: 860.3 $[M+H]^+$. $^1H$ NMR (400 MHz, DMSO-$d_6$) δ: 12.82 (s, 1H), 11.11 (s, 1H), 8.55-8.38 (m, 2H), 8.21 (s, 1H), 7.90 (d, J=8.4 Hz, 1H), 7.82 (d, J=8.4 Hz, 1H), 7.77-7.70 (m, 1H), 7.56-7.49 (m, 2H), 7.45 (d, J=2.0 Hz, 1H), 7.36 (dd, J=2.4, 8.4 Hz, 1H), 7.18 (d, J=8.4 Hz, 1H), 5.11 (dd, J=5.2, 13.0 Hz, 1H), 4.72 (s, 1H), 4.58 (s, 1H), 4.30 (d, J=4.4 Hz, 2H), 3.76 (s, 2H), 3.68 (d, J=7.2 Hz, 3H), 3.57 (t, J=6.0 Hz, 3H), 3.49 (s, 4H), 2.98-2.79 (m, 2H), 2.63-2.56 (m, 1H), 2.46-2.38 (m, 6H), 2.10-1.99 (m, 2H), 1.94 (d, J=13.6 Hz, 2H), 1.85 (s, 2H), 1.72-1.56 (m, 4H).

The following compounds may be prepared in an analogous fashion as the exemplary synthesis described for Exemplary Compound 2.

| Exemplar Compound | $[M + H]^+$ |
|---|---|
| 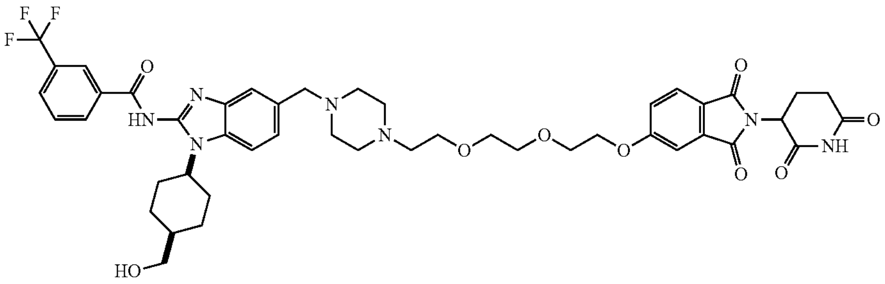 Exemplary Compound 3 | 860.68 |
| 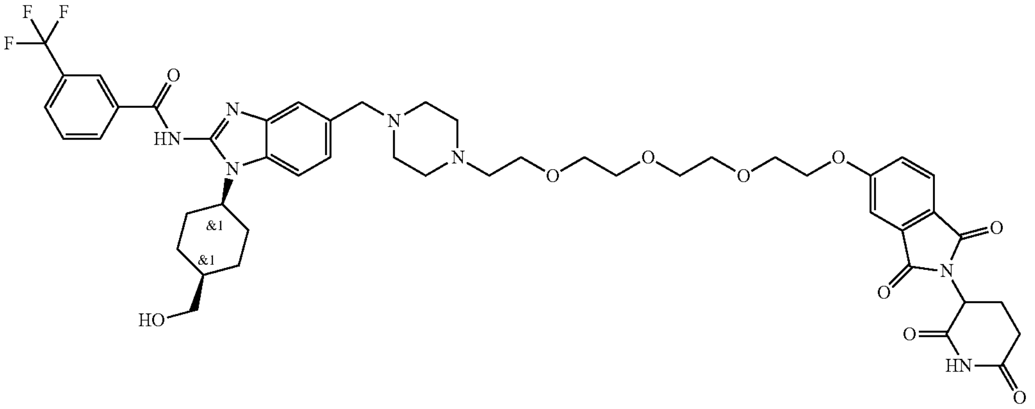 Exemplary Compound 4 | 904.72 |
| 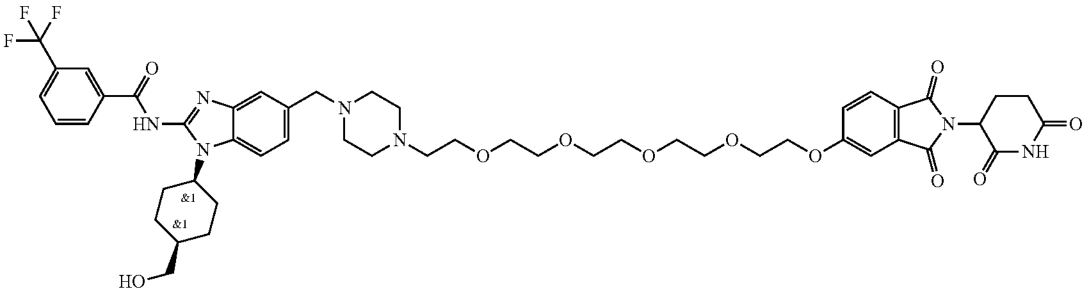 Exemplary Compound 5 | 948.75 |

-continued
| Exemplar Compound | [M + H]+ |
|---|---|
| 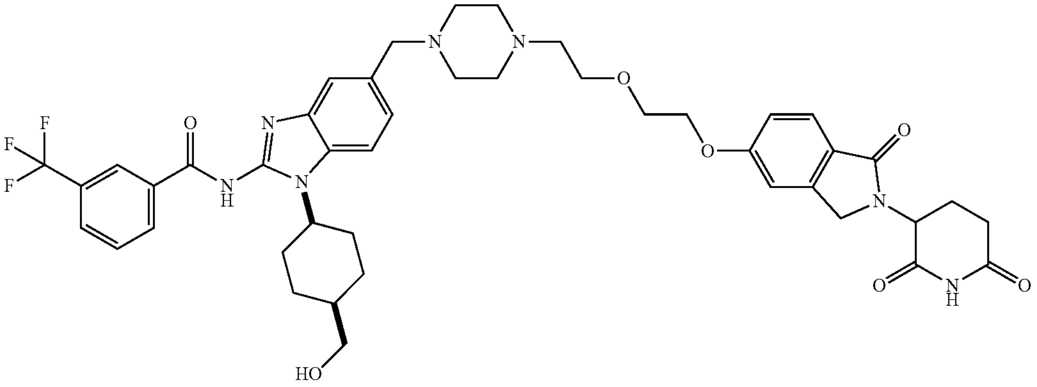 Exemplary Compound 6 | 846.4 |
| 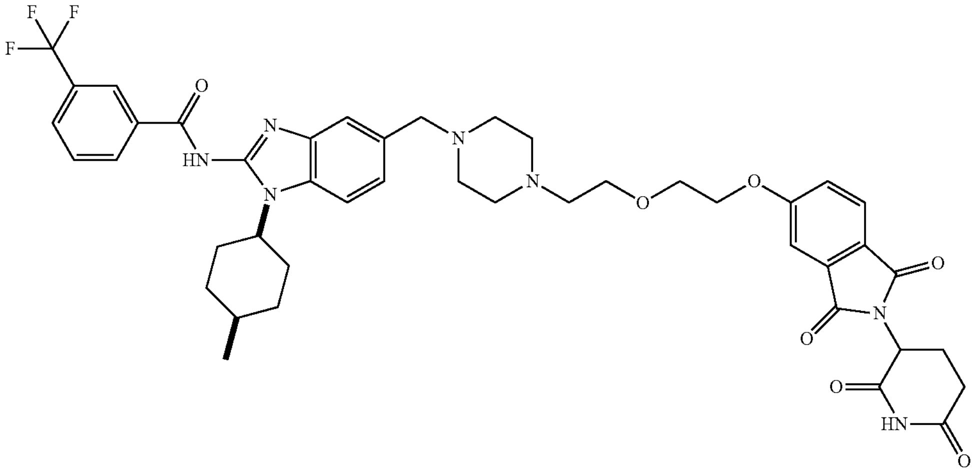 Exemplary Compound 7 | n.d. |
| 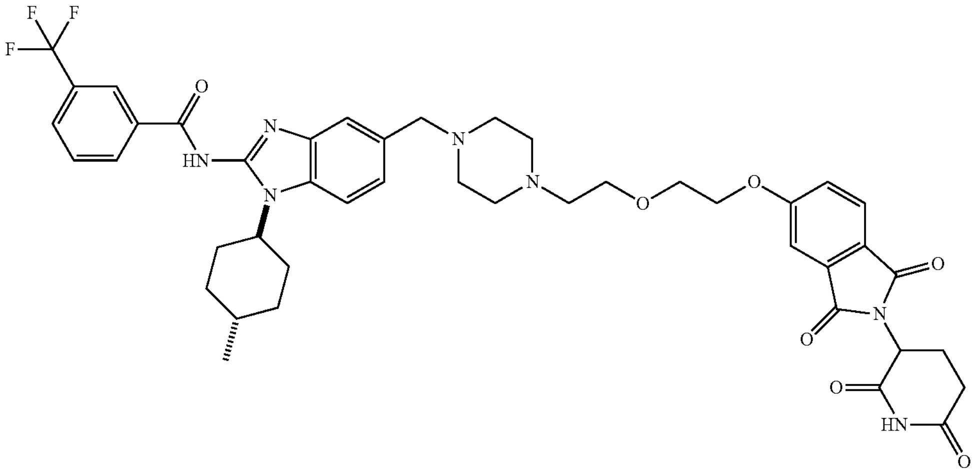 Exemplary Compound 8 | n.d. |

Exemplary Synthesis of Exemplary Compound 9

N-(5-((4-((1-(2-(2,6-dioxopiperidin-3-yl)-1,3-dioxoisoindolin-5-yl)piperidin-4-yl)methyl)piperazin-1-yl)methyl)-1-((1s,4s)-4-(hydroxymethyl)cyclohexyl)-1H-benzo[d]imidazol-2-yl)-3-(trifluoromethyl)benzamide Step 1:

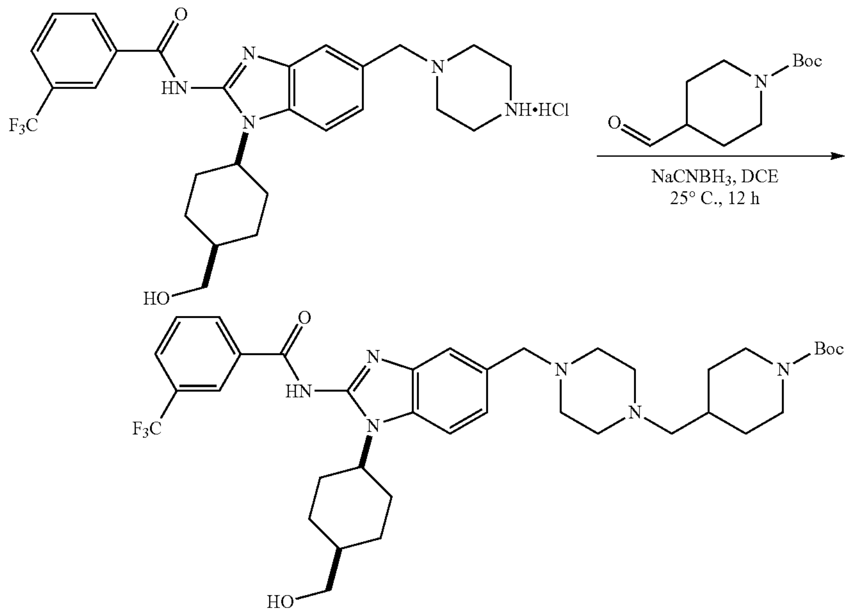

To a solution of N-(1-((1s,4s)-4-(hydroxymethyl)cyclohexyl)-5-(piperazin-1-ylmethyl)-1H-benzo[d]imidazol-2-yl)-3-(trifluoromethyl)benzamide (Example 1 intermediate) (80 mg, 0.14 mmol, 1.00 eq, hydrochloric acid) in 1,2-dichloroethane (2 mL) was added tert-butyl 4-formylpiperidine-1-carboxylate (34 mg, 0.16 mmol, 1.10 eq) sodium cyanoborohydride (18 mg, 0.29 mmol, 2.00 eq) solution. The mixture was stirred at 30° C. for 12 hours. The mixture was concentrated under reduced pressure and the resulting residue was purified by silica gel chromatography eluting with 10% methyl alcohol in dichloromethane. The appropriate fractions were pooled and concentrated to obtain tert-butyl 4-((4-((1-((1s,4s)-4-(hydroxymethyl)cyclohexyl)-2-(3-(trifluoromethyl)benzamido)-1H-benzo[d]imidazol-5-yl)methyl)piperazin-1-yl)methyl)piperidine-1-carboxylate (0.10 g, crude) as a colorless oil. MS (ESI) m/z: 713.2 $[M+H]^+$.

Step 2:

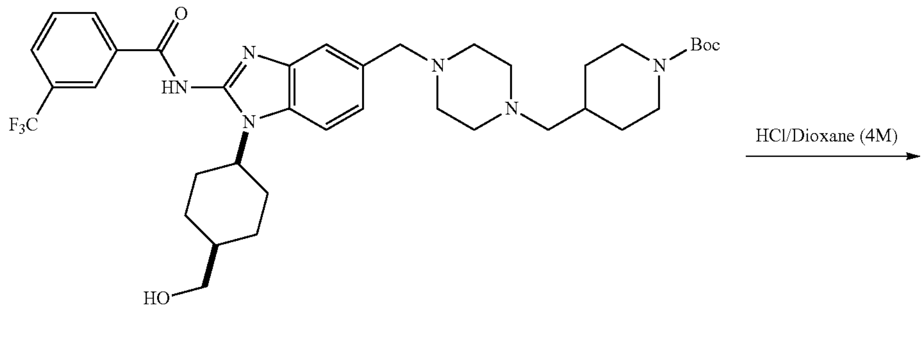

-continued

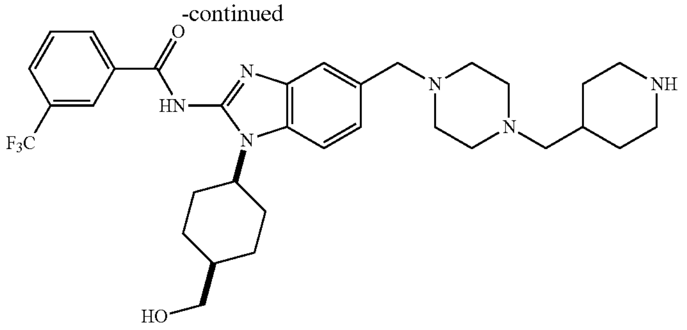

To a solution of tert-butyl 4-((4-((1-((1s,4s)-4-(hydroxymethyl)cyclohexyl)-2-(3-(trifluoromethyl)benzamido)-1H-benzo[d]imidazol-5-yl)methyl)piperazin-1-yl)methyl)piperidine-1-carboxylate (100 mg, 0.14 mmol, 1.00 eq) in ethyl acetate (1 mL) was added a 4 M solution of hydrochloric acid in dioxane (1 mL, 28.5 eq). The mixture was stirred at 25° C. for 0.5 hour. The mixture was concentrated under reduced pressure to afford N-(1-((1s,4s)-4-(hydroxymethyl)cyclohexyl)-5-((4-(piperidin-4-ylmethyl)piperazin-1-yl)methyl)-1H-benzo[d]imidazol-2-yl)-3-(trifluoromethyl)benzamide (85 mg, 0.12 mmol, 88% yield, 2 hydrochloride salt) as a white solid which was used in a subsequent transformation without further purification. MS (ESI) m/z: 613.2 [M+H]$^+$.

Step-3:

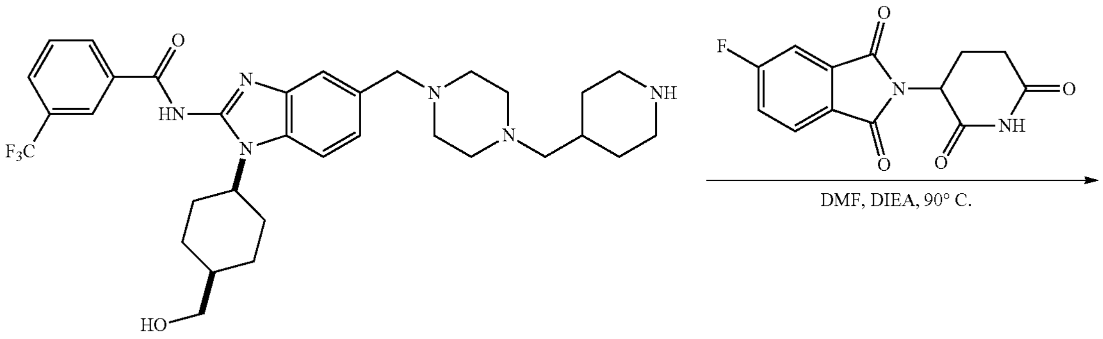

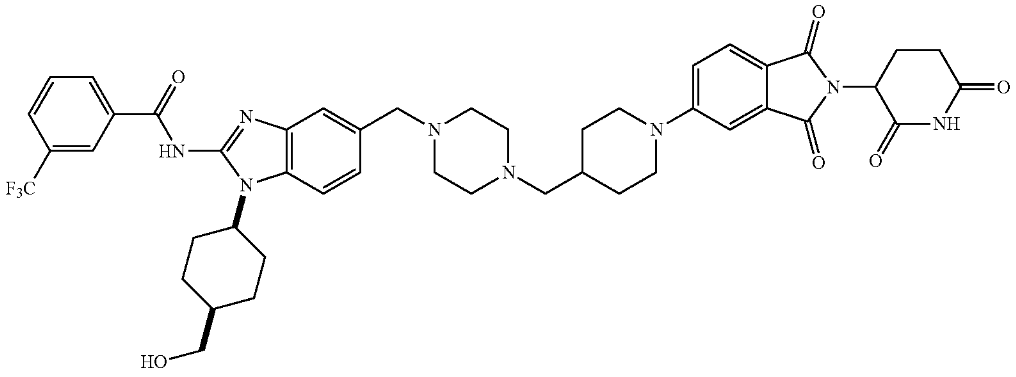

To a solution of N-(1-((1s,4s)-4-(hydroxymethyl)cyclohexyl)-5-((4-(piperidin-4-ylmethyl)piperazin-1-yl)methyl)-1H-benzo[d]imidazol-2-yl)-3-(trifluoromethyl)benzamide (70 mg, 0.11 mmol, 1.00 eq, 2 hydrochloride salt) in dimethylsulfoxide (1 mL) was added diisopropylethylamine (44 mg, 0.34 mmol, 3.00 eq) and 2-(2,6-dioxo-3-piperidyl)-5-fluoro-isoindoline-1,3-dione, Intermediate 2 (32 mg, 0.11 mmol, 1.00 eq). The mixture was stirred at 120° C. for 1 hour. LCMS analysis of the crude reaction mixture indicated complete conversion. The mixture was concentrated under reduced pressure to afford a residue which was purified by preparative HPLC. The appropriate fractions were concentrated to afford N-(5-((4-((1-(2-(2,6-dioxopiperidin-3-yl)-1,3-dioxoisoindolin-5-yl)piperidin-4-yl)methyl)piperazin-1-yl)methyl)-1-((1s,4s)-4-(hydroxymethyl)cyclohexyl)-1H-benzo[d]imidazol-2-yl)-3-(trifluoromethyl)benzamide (13.6 mg, 0.01 mmol, 12% yield, 98% purity, trifluoroacetic acid salt) as a yellow solid. MS (ESI) m/z: 869.4 $[M+H]^+$. $^1H$ NMR (400 MHz, DMSO-$d_6$) δ: 12.21-13.74 (m, 1H), 11.07 (s, 1H), 8.50 (d, J=7.6 Hz, 1H), 8.45 (s, 1H), 7.91 (d, J=8.0 Hz, 1H), 7.75 (t, J=7.6 Hz, 1H), 7.58-7.68 (m, 3H), 7.33 (s, 2H), 7.25 (d, J=8.4 Hz, 1H), 5.06 (dd, J=5.2, 12.8 Hz, 1H), 4.68-4.80 (m, 1H), 4.06 (d, J=12.4 Hz, 4H), 3.69 (d, J=7.2 Hz, 3H), 2.81-3.02 (m, 8H), 2.58-2.69 (m, 2H), 2.33 (br s, 1H), 1.91-2.08 (m, 5H), 1.75-1.90 (m, 4H), 1.58-1.74 (m, 5H), 1.14-1.28 (m, 3H), 1.05 (t, J=7.2 Hz, 2H).

Exemplary Synthesis of Exemplary Compound 10

N-(5-((4-((1-(2-((2-(2,6-dioxopiperidin-3-yl)-1,3-dioxoisoindolin-5-yl)oxy)ethyl)piperidin-4-yl)methyl)piperazin-1-yl)methyl)-1-((1s,4s)-4-(hydroxymethyl)cyclohexyl)-1H-benzo[d]imidazol-2-yl)-3-(trifluoromethyl)benzamide

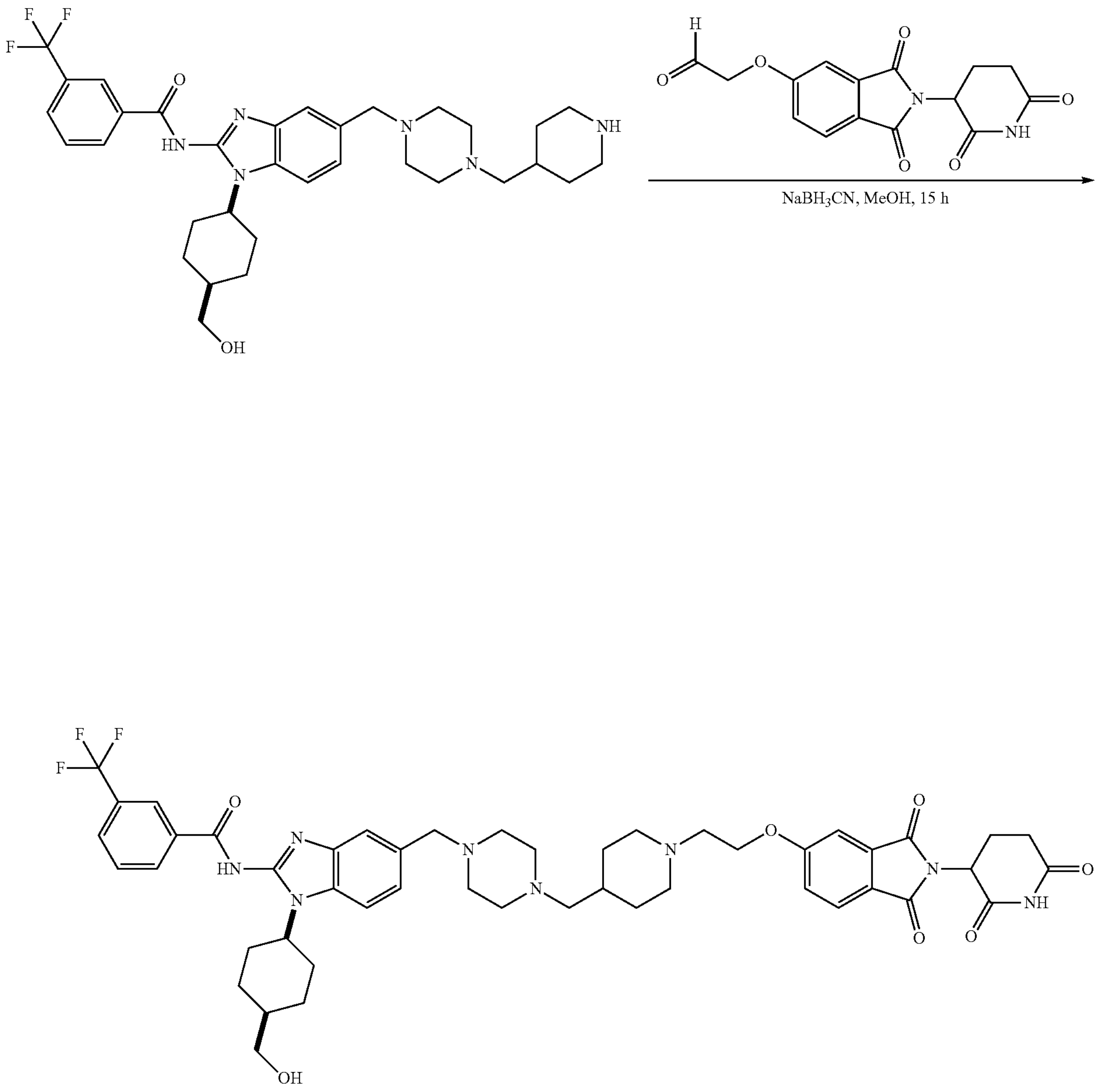

To a solution of N-(1-((1s,4s)-4-(hydroxymethyl)cyclohexyl)-5-((4-(piperidin-4-ylmethyl)piperazin-1-yl)methyl)-1H-benzo[d]imidazol-2-yl)-3-(trifluoromethyl)benzamide (Example 9 intermediate) (50 mg, 0.08 mmol, 1.00 eq, 2 hydrochloride salt) in methyl alcohol (2 mL) was added 2-[2-(2,6-dioxo-3-piperidyl)-1,3-dioxo-isoindolin-5-yl]oxy-acetaldehyde, Intermediate 8 (29 mg, 0.09 mmol, 1.15 eq) and sodium cyanoborohydride (7 mg, 0.11 mmol, 1.27 eq). The mixture was stirred at 25° C. for 15 hours after which the reaction mixture was concentrated under reduced pressure. The residue was purified by preparative HPLC to afford N-(5-((4-((1-(2-((2-(2,6-dioxopiperidin-3-yl)-1,3-dioxoisoindolin-5-yl)oxy)ethyl)piperidin-4-yl)methyl)piperazin-1-yl)methyl)-1-((1s,4s)-4-(hydroxymethyl)cyclohexyl)-1H-benzo[d]imidazol-2-yl)-3-(trifluoromethyl) benzamide (14.8 mg, 0.01 mmol, 17% yield, 99% purity, trifluoroacetic acid) as a white solid. MS (ESI) m/z: 913.2 $[M+H]^+$. $^1H$ NMR (400 MHz, DMSO-$d_6$) δ: 13.30-12.54 (m, 1H), 11.39-11.03 (m, 1H), 10.27-9.80 (m, 1H), 8.69-8.30 (m, 2H), 7.99-7.85 (m, 2H), 7.76 (t, J=8.0 Hz, 1H), 7.72-7.59 (m, 2H), 7.54 (d, J=2.0 Hz, 1H), 7.45-7.28 (m, 2H), 5.14 (dd, J=5.2, 12.8, Hz, 1H), 4.81-4.69 (m, 1H), 4.57 (s, 2H), 4.29-4.08 (m, 3H), 3.70-3.56 (m, 10H), 3.09-2.81 (m, 7H), 2.65-2.54 (m, 6H), 2.10-2.03 (m, 1H), 2.00-1.82 (m, 6H), 1.73-1.60 (m, 4H), 1.41 (d, J=11.6 Hz, 2H).

Scheme 2.

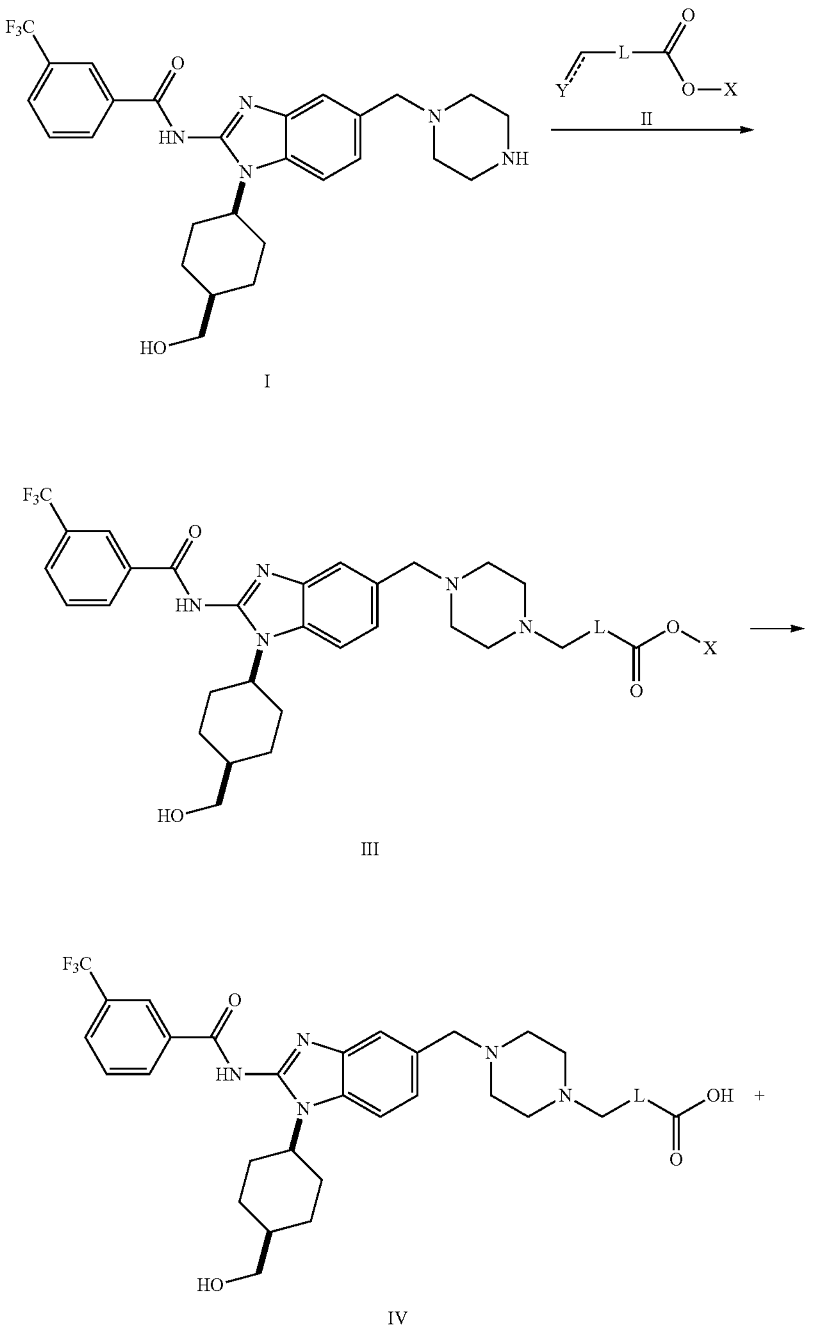

-continued

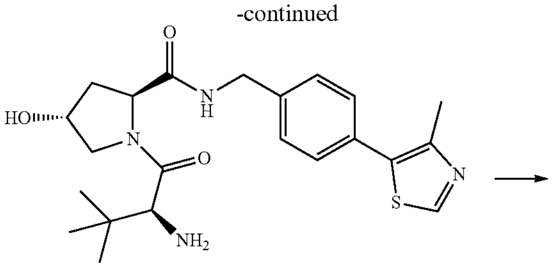

V

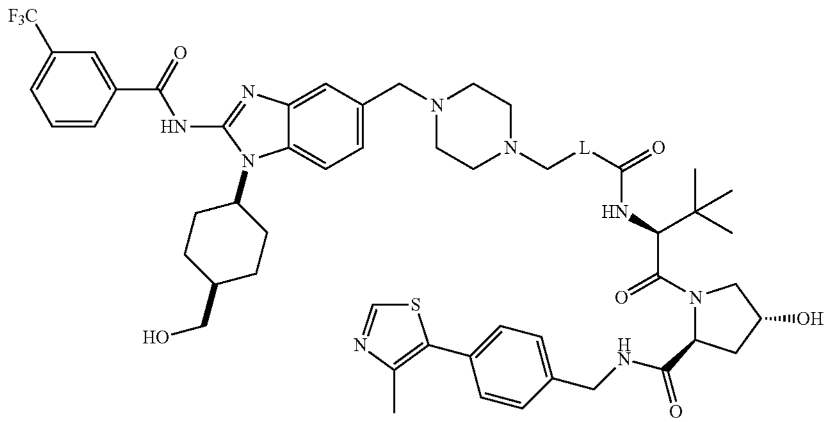

VI

A compound of formula I may be reacted with a reagent II (commercially available or readily prepared using standard reaction techniques known to one skilled in the art) where Y is an appropriate leaving group (e.g. OMs, OTs, Cl, Br etc.) or an aldehyde, under suitable alkylation or reductive amination conditions to produce a compound of formula III, wherein L represents an optional linker or portion of a linker, and X is a protecting group. When Y is a leaving group, suitable reaction conditions are those for an alkylation reaction, e.g. diisopropylethylamine, potassium iodide, DMSO or acetonitrile, 80° C. When Y is an aldehyde, suitable reaction conditions are those for a reductive amination reaction, e.g. sodium cyanoborohydride, methanol, dichloromethane, acetic acid, room temperature. After deprotection of the ester, compounds of formula IV may react with a compound of formula V through amide coupling conditions known to one skilled in the art, e.g. HATU or HOBt, EDCI, TEA, in DMF to provide compounds of formula VI.

Exemplary Synthesis of Exemplary Compound 11

(2S,4R)-4-hydroxy-1-((S)-2-(2-(2-(4-((1-((1SR, 4SR)-4-(hydroxymethyl)cyclohexyl)-2-(3-(trifluoromethyl)benzamido)-1H-benzo[d]imidazol-5-yl) methyl)piperazin-1-yl)ethoxy)acetamido)-3,3-dimethylbutanoyl)-N-(4-(4-methylthiazol-5-yl) benzyl)pyrrolidine-2-carboxamide Step 1:

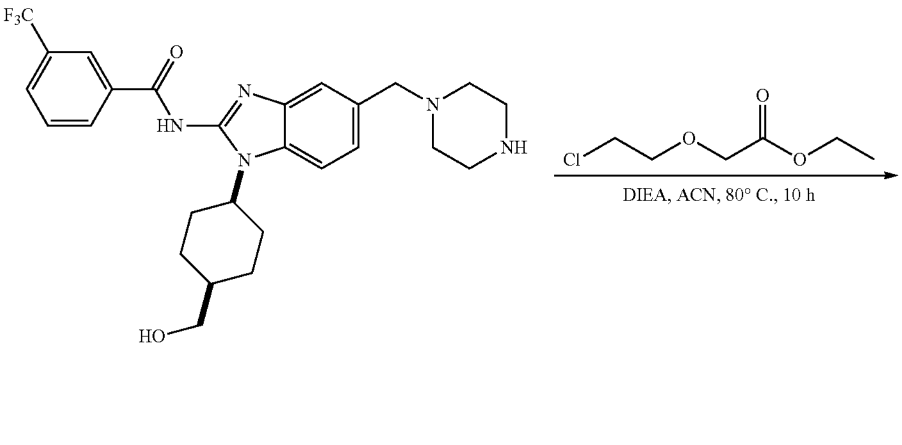

-continued

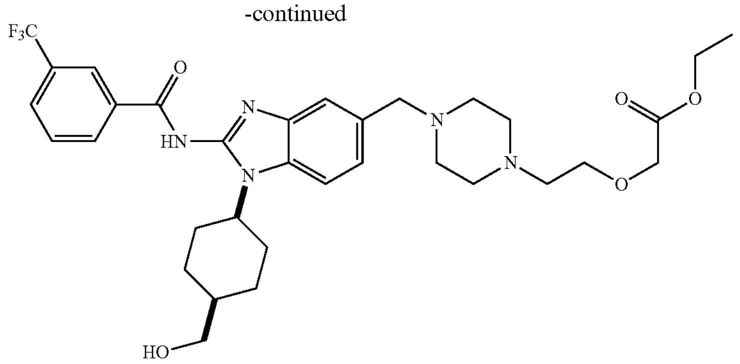

To a solution of N-(1-((1s,4s)-4-(hydroxymethyl)cyclohexyl)-5-(piperazin-1-ylmethyl)-1H-benzo[d]imidazol-2-yl)-3-(trifluoromethyl)benzamide (Example 1 intermediate) (50 mg, 97 μmol, 1.0 eq) in acetonitrile (2 mL) was added ethyl 2-(2-chloroethoxy)acetate (32.3 mg, 194 μmol, 2.0 eq) and diisopropylethylamine (25.1 mg, 194 μmol, 33.8 μL, 2.00 eq). The mixture was stirred for 10 hours at 80° C. LCMS analysis of the crude reaction mixture showed that the reaction was complete. The mixture was filtered. The filtrate was concentrated under reduced pressure and the resulting residue was purified by preparative TLC (dichloromethane:methanol=10:1) to afford ethyl 2-(2-(4-((1-((1s,4s)-4-(hydroxymethyl)cyclohexyl)-2-(3-(trifluoromethyl)benzamido)-1H-benzo[d]imidazol-5-yl)methyl)piperazin-1-yl)ethoxy)acetate (55.0 mg, 85.2 μmol, 87% yield) as a brown oil, which was used in a subsequent reaction without further purification. MS (ESI) m/z: 646.2 [M+H]+.

Step-2

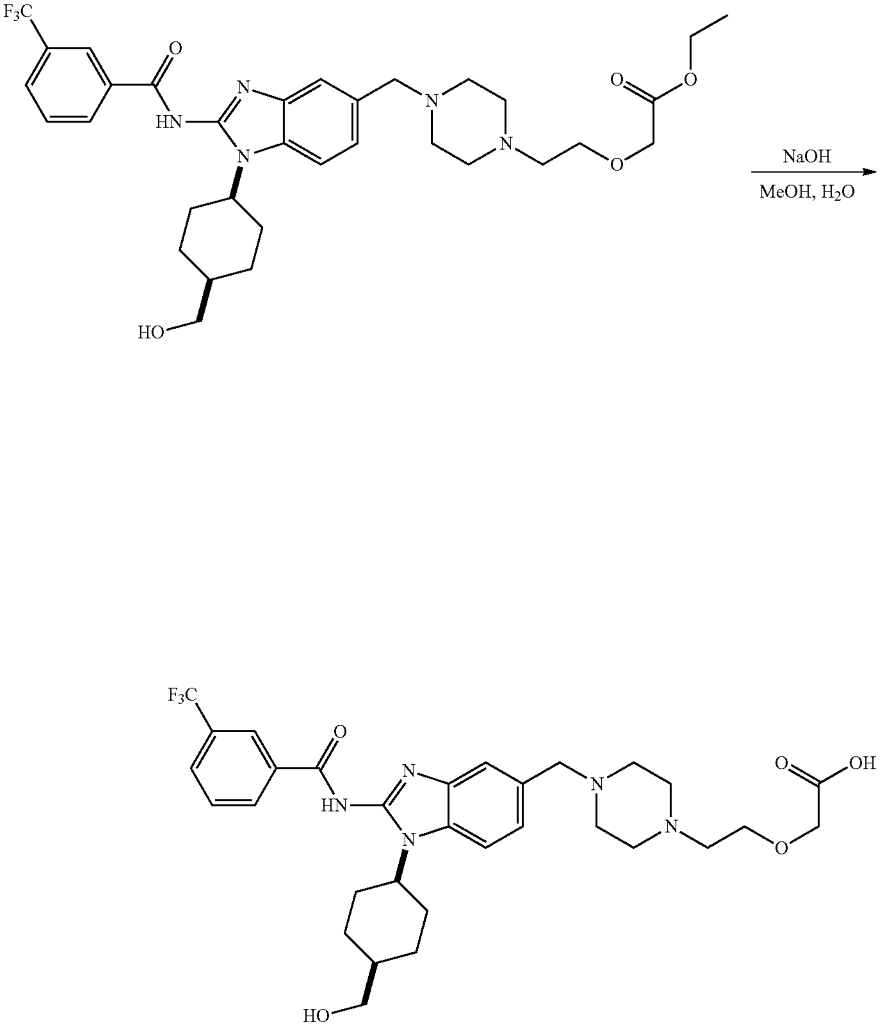

To a solution of ethyl 2-(2-(4-((1-((1s,4s)-4-(hydroxymethyl)cyclohexyl)-2-(3-(trifluoromethyl)benzamido)-1H-benzo[d]imidazol-5-yl)methyl)piperazin-1-yl)ethoxy)acetate (55 mg, 85.2 μmol, 1.00 eq) in methanol (2 mL) and water (1 mL) was added sodium hydroxide (6.81 mg, 170.3 μmol, 2.00 eq). The mixture was stirred for 0.5 hour at 30° C. LCMS analysis of the crude reaction mixture showed that the reaction was complete. The mixture was concentrated under reduced pressure and the resulting residue was diluted with water (1 mL) and the pH was adjusted to 3 with a 1 M aqueous solution of hydrochloride. The mixture was concentrated under reduced pressure to afford a residue which was purified by re-crystallization from 10 mL of dichloromethane to provide 2-(2-(4-((1-((1s,4s)-4-(hydroxymethyl)cyclohexyl)-2-(3-(trifluoromethyl)benzamido)-1H-benzo[d]imidazol-5-yl)methyl)piperazin-1-yl)ethoxy)acetic acid (50.0 mg, 80.9 μmol, 95% yield) as a yellow solid, which was used as is in a subsequent reaction. MS (ESI) m/z: 618.2 $[M+H]^+$.

Step 3:

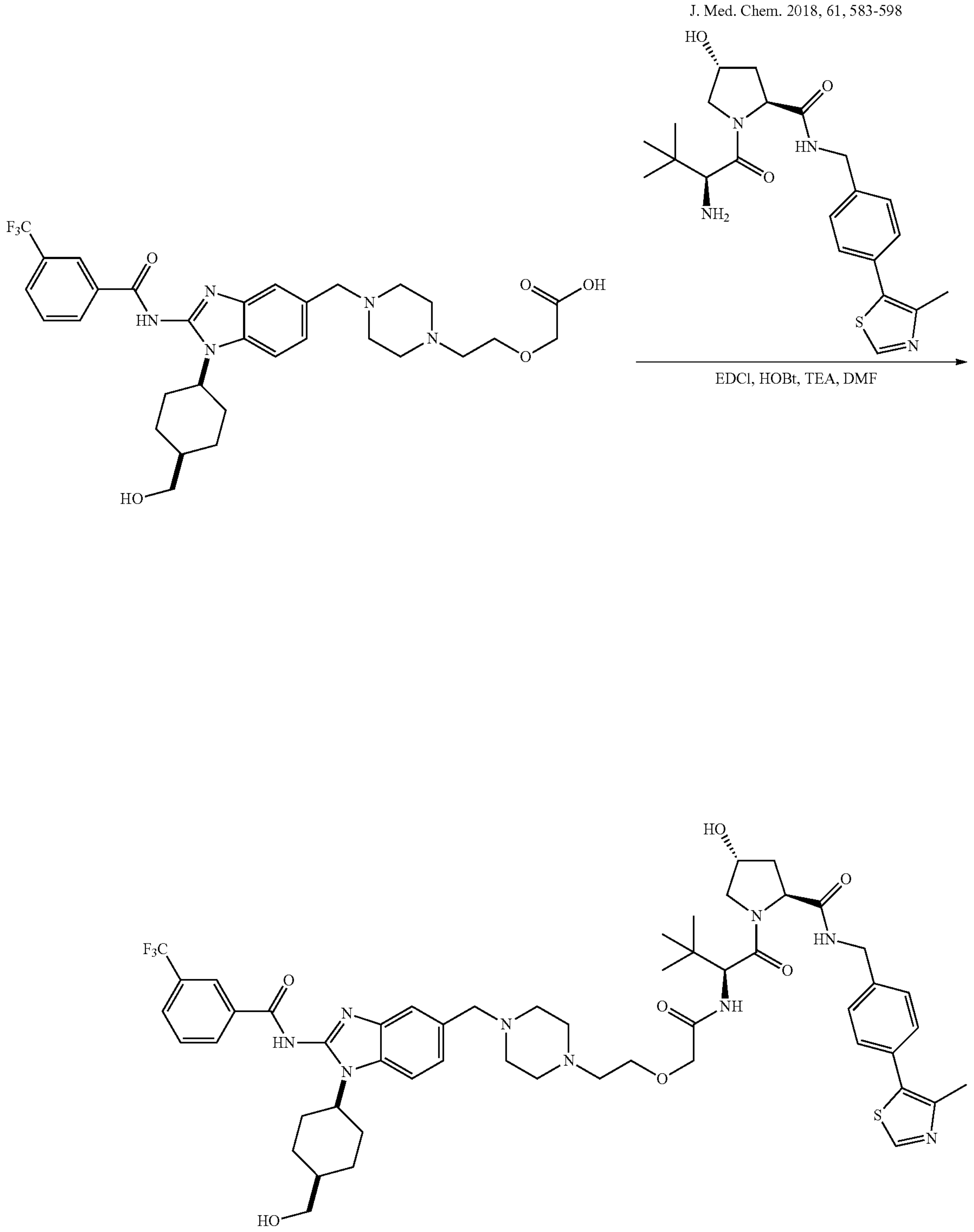

To a solution of 2-(2-(4-((1-((1s,4s)-4-(hydroxymethyl) cyclohexyl)-2-(3-(trifluoromethyl)benzamido)-1H-benzo[d] imidazol-5-yl)methyl)piperazin-1-yl)ethoxy)acetic acid (50.0 mg, 80.9 μmol, 1.00 eq) in N,N-dimethylformamide (1 mL) was added triethylamine (24.57 mg, 242.8 μmol, 33.8 μL, 3.00 eq), hydroxybenzotriazole (16.41 mg, 121.43 μmol, 1.50 eq), 1-(3-dimethylaminopropyl)-3-ethylcarbodiimide hydrochloride (23.28 mg, 121.43 μmol, 1.50 eq) and (2S, 4R)-1-[(2S)-2-amino-3,3-dimethyl-butanoyl]-4-hydroxy-N-[[4-(4-methylthiazol-5-yl)phenyl]methyl]pyrrolidine-2-carboxamide (41.83 mg, 97.14 μmol, 1.20 eq). Then the mixture was stirred for 10 hours at 30° C. LCMS analysis of the crude reaction mixture showed that the reaction was complete. The mixture was filtered and the filtrate was purified by preparative HPLC to give (2S,4R)-4-hydroxy-1-((S)-2-(2-(2-(4-((1-((1SR,4SR)-4-(hydroxymethyl)cyclohexyl)-2-(3-(trifluoromethyl)benzamido)-1H-benzo[d]imidazol-5-yl)methyl)piperazin-1-yl)ethoxy)acetamido)-3,3-dimethylbutanoyl)-N-(4-(4-methylthiazol-5-yl)benzyl) pyrrolidine-2-carboxamide (12.7 mg, 10.8 μmol, 13% yield, 97% purity, trifluoroacetic salt) as a yellow solid. MS(ESI) m/z: 1030.5 $[M+H]^+$. $^1H$ NMR (400 MHz, DMSO-$d_6$) δ: 12.94 (s, 1H), 8.96-9.00 (m, 1H), 8.60 (t, J=6.0 Hz, 11H), 8.50 (d, J=8.0 Hz, 11H), 8.45 (s, 1H), 7.92 (d, J=7.6 Hz, 1H), 7.85 (br d, J=10.0 Hz, 1H), 7.76 (t, J=7.6 Hz, 1H), 7.65 (d, J=8.4 Hz, 1H), 7.60 (s, 1H), 7.35-7.46 (m, 5H), 7.31 (br d, J=8.8 Hz, 1H), 4.72 (br d, J=10.4 Hz, 2H), 4.58 (d, J=9.6 Hz, 1H), 4.33-4.47 (m, 4H), 4.19-4.31 (m, 2H), 3.96-4.15 (m, 7H), 3.71-3.79 (m, 7H), 2.96-3.38 (m, 2H), 2.43 (s, 4H), 2.02-2.12 (m, 1H), 1.81-2.01 (m, 5H), 1.55-1.80 (m, 5H), 0.87-1.01 (m, 11H).

The following compounds may be prepared in an analogous fashion as the exemplary synthesis described for Exemplary Compound 11.

| Exemplary Compound | $[M + H]^+$ |
| --- | --- |
| 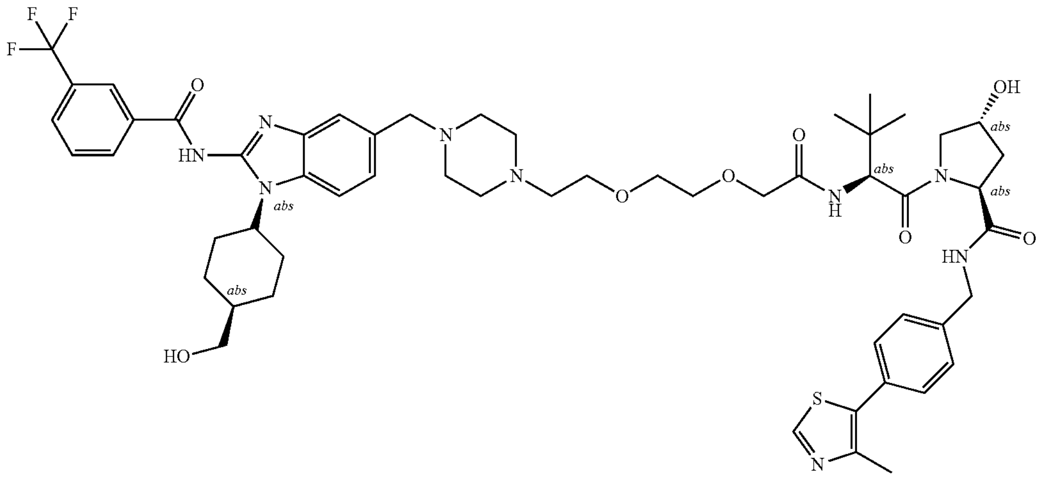 Exemplary Compound 12 | 1074.5 |
| 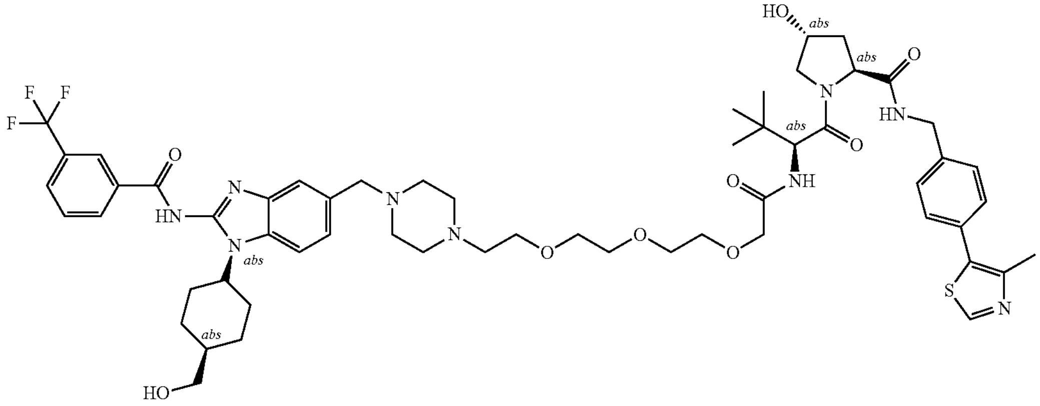 Exemplary Compound 13 | 1118.6 |

-continued

| Exemplary Compound | [M + H]+ |
| --- | --- |
| 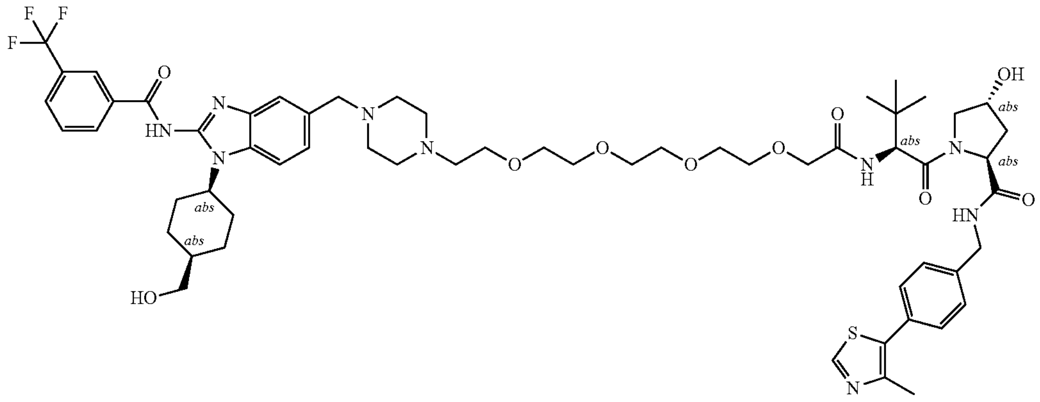 Exemplary Compound 14 | 1162.6 |

Exemplary Synthesis of Exemplary Compound 25

N-(3-(4-(2-(2-(2-((2-(2,6-dioxopiperidin-3-yl)-1,3-dioxoisoindolin-5-yl)oxy)ethoxy)ethoxy)ethyl)piperazin-1-yl)-1-(5-methylpyridin-2-yl)-1H-pyrazol-5-yl)pyrazolo[1,5-a]pyrimidine-3-carboxamide Step 1:

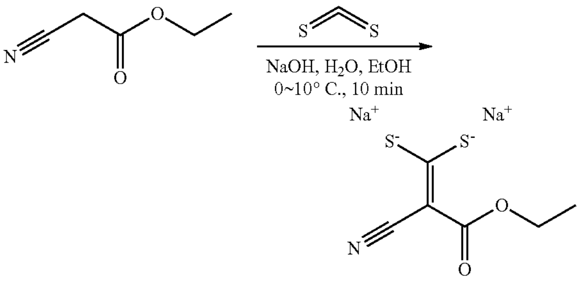

To a solution of ethyl 2-cyanoacetate (100 g, 884.06 mmol, 94.3 mL, 1 eq) and methanedithione (67.31 g, 884.06 mmol, 53.4 mL, 1 eq) in ethanol (1100 mL) was added sodium hydroxide (70.72 g, 1.77 mol, 2 eq) in water (72 mL) at 0° C. dropwise. The mixture was warmed to 10° C. and stirred at 10° C. for 10 minutes. Then the mixture was cooled to 5° C. The mixture was filtered. The filter cake was triturated with petroleum ether and ethanol (300 mL, V:V=5:1 to afford [(Z)-2-cyano-3-ethoxy-3-oxo-1-sodiosulfanuidyl-prop-1-enyl]sulfanylsodium (200 g, 857.56 mmol, 97% yield) as a yellow solid.

Step 2:

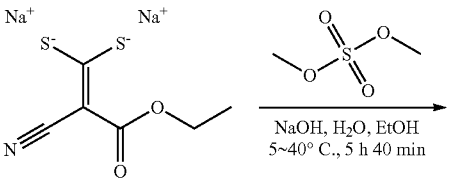

-continued

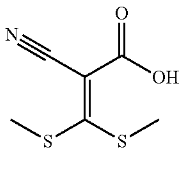

To a solution of sodium hydroxide (59.75 g, 1.49 mol, 1.74 eq) in water (420 mL) was added [(Z)-2-cyano-3-ethoxy-3-oxo-1-sodiosulfanuidyl-prop-1-enyl]sulfanylsodium (200 g, 857.56 mmol, 1 eq). The mixture was stirred at 40° C. for 5 hours. The mixture was cooled to 15° C. and then the mixture was diluted with ethanol (740 mL). The aqueous layer was separated and diluted with water to a total volume of (900 mL). The solution was cooled to 5° C., and dimethyl sulfate (184.96 g, 1.47 mol, 139.07 mL, 1.71 eq) was added at a rate such that the internal temperature was maintained below 15° C. Once the addition was complete, the temperature was maintained between 15 and 30° C. for 40 minutes. The solution was cooled to 15° C. and the mixture was filtered. The pH of the filtrate was adjusted 2 with the addition of a 4 M aqueous solution of hydrochloric acid. The mixture was stirred at 20° C. for 0.5 hour, the solid formed was filtered. The filter cake was dissolved in ethyl acetate (500 mL), dried with anhydrous sodium sulfate, filtered and concentrated under vacuum to provide 2-cyano-3,3-bis (methylsulfanyl)prop-2-enoic acid (80 g, 422.7 mmol, 49% yield) as a yellow solid.

Step 3:

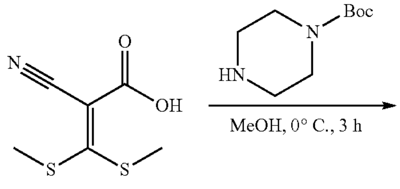

-continued

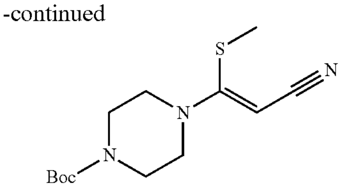

To a solution of 2-cyano-3,3-bis(methylsulfanyl)prop-2-enoic acid (80 g, 422.7 mmol, 1 eq) in methanol (800 mL) was added tert-butyl piperazine-1-carboxylate (157.46 g, 845.42 mmol, 2 eq) and triethylamine (42.77 g, 422.71 mmol, 58.84 mL, 1 eq) at 0° C. The mixture was stirred at 0° C. for 3 hours. The mixture was concentrated under reduced pressure and the resulting residue was used in the next step without further purification. Compound tert-butyl 4-[(Z)-2-cyano-1-methylsulfanyl-vinyl]piperazine-1-carboxylate (120 g, crude) was obtained as a yellow oil.

Step 4:

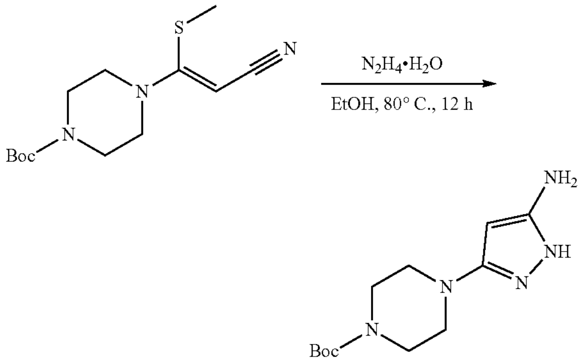

To a solution of tert-butyl 4-[(Z)-2-cyano-1-methylsulfanyl-vinyl]piperazine-1-carboxylate (120 g, 423.45 mmol, 1 eq) in ethanol (960 mL) was added hydrazine hydrate (86.52 g, 1.69 mol, 84 mL, 4 eq). The mixture was stirred at 80° C. for 12 hours. Thin layer chromatography (dichloromethane: methanol=10:1) analysis confirmed the reaction was complete. The mixture was concentrated under vacuum. The residue was purified by silica gel chromatography to afford tert-butyl 4-(5-amino-1H-pyrazol-3-yl)piperazine-1-carboxylate (35 g, 121.76 mmol, 28% yield, 93% purity) as a yellow oil. MS (ESI) m/z: 268.2 $[M+H]^+$.

Step 5:

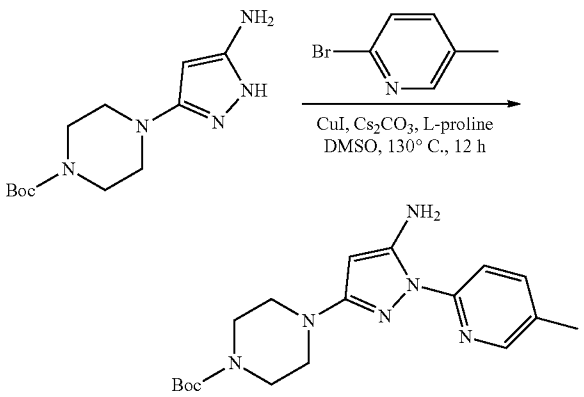

To a solution of tert-butyl 4-(5-amino-1H-pyrazol-3-yl) piperazine-1-carboxylate (649 mg, 1.87 mmol, 1 eq) in dimethylsulfoxide (10 mL) was added 2-bromo-5-methylpyridine (337 mg, 1.96 mmol, 1.05 eq), cuprous iodide (35 mg, 0.19 mmol, 0.1 eq), cesium carbonate (1.22 g, 3.74 mmol, 2 eq) and L-proline (21 mg, 0.19 mmol, 0.1 eq). The mixture was stirred at 130° C. for 12 hours under nitrogen atmosphere. LCMS analysis of an aliquot showed the reaction was complete. The mixture was diluted with water (10 mL) and extracted with ethyl acetate (10 mL×3). The combined organic layers were washed with brine (30 mL×3), dried with anhydrous sodium sulfate, filtered and concentrated under reduced pressure. The resulting residue was purified by column chromatography (petroleum ether: ethyl acetate=20:1) to give tert-butyl 4-[5-amino-1-(5-methyl-2-pyridyl)pyrazol-3-yl]piperazine-1-carboxylate (150 mg, 0.42 mmol, 22% yield) as a white solid. MS (ESI) m/z: 359.2$[M+H]^+$. $^1H$ NMR (400 MHz, DMSO-$d_6$) δ: 8.13 (s, 1H), 7.67 (dd, J=2.0, 8.8 Hz, 1H), 7.60-7.54 (m, 1H), 6.75 (s, 2H), 5.01 (s, 1H), 3.44-3.36 (m, 4H), 3.15-3.05 (m, 4H), 2.26 (s, 3H), 1.41 (s, 9H).

Step 6:

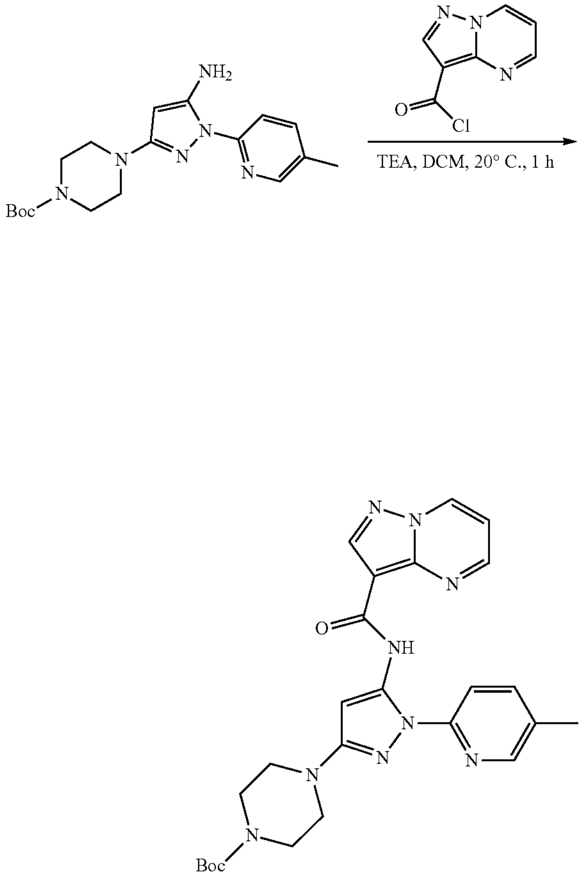

To a solution of tert-butyl 4-[5-amino-1-(5-methyl-2-pyridyl)pyrazol-3-yl]piperazine-1-carboxylate (250 mg, 0.70 mmol, 1 eq) and pyrazolo[1,5-a]pyrimidine-3-carbonyl chloride, Intermediate 4 (200 mg, 1.10 mmol, 1.58 eq) in dichloromethane (8 mL) was added triethylamine (705 mg, 6.97 mmol, 10 eq). The mixture was stirred at 20° C. for 1 hour. LCMS analysis of an aliquot indicated complete conversion. The mixture was concentrated under reduced pressure and the resulting residue was purified by preparative reverse phase HPLC to give tert-butyl 4-[1-(5-methyl-2-pyridyl)-5-(pyrazolo[1,5-a]pyrimidine-3-carbonylamino)pyrazol-3-yl]piperazine-1-carboxylate (60 mg, 0.12 mmol, 17% yield) as a light yellow oil. $^1H$ NMR (400 MHz, DMSO-$d_6$) δ: 13.27 (s, 1H), 9.39 (dd, J=1.6, 7.2 Hz, 1H), 9.15 (dd, J=1.6, 4.0 Hz, 1H), 8.73 (s, 1H), 8.46 (s, 1H), 7.81 (dd, J=2.4, 8.4 Hz, 1H), 7.69 (d, J=8.8 Hz, 1H), 7.38 (dd, J=4.0, 7.2 Hz, 1H), 6.67 (s, 1H), 3.51-3.42 (m, 4H), 3.28-3.20 (m, 4H), 2.38 (s, 3H), 1.43 (s, 9H).

Step 7:

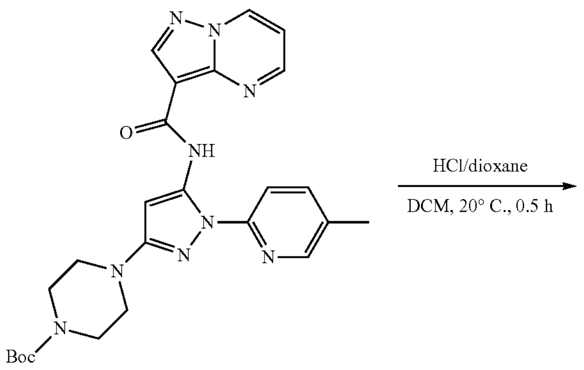

-continued

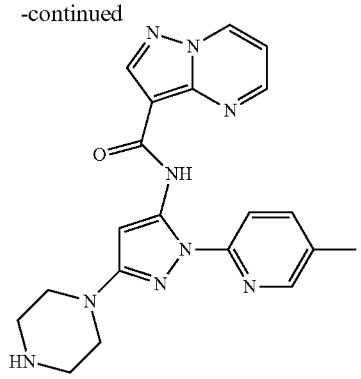

To a solution of tert-butyl 4-[1-(5-methyl-2-pyridyl)-5-(pyrazolo[1,5-a]pyrimidine-3-carbonylamino)pyrazol-3-yl]piperazine-1-carboxylate (60 mg, 0.12 mmol, 1 eq) in dichloromethane (1 mL) was added hydrochloric acid in dioxane (4.0 M, 5 mL). The mixture was stirred at 20° C. for 0.5 hour. Thin layer chromatography (petroleum ether:ethyl acetate=1:1) showed the reaction to be complete. The mixture was concentrated under reduced pressure and the obtained crude product was used in the next step without further purification. Compound N-[2-(5-methyl-2-pyridyl)-5-piperazin-1-yl-pyrazol-3-yl]pyrazolo[1,5-a]pyrimidine-3-carboxamide (50 mg, 0.11 mmol, 95% yield, hydrochloride) was obtained as a yellow solid.

Step 8:

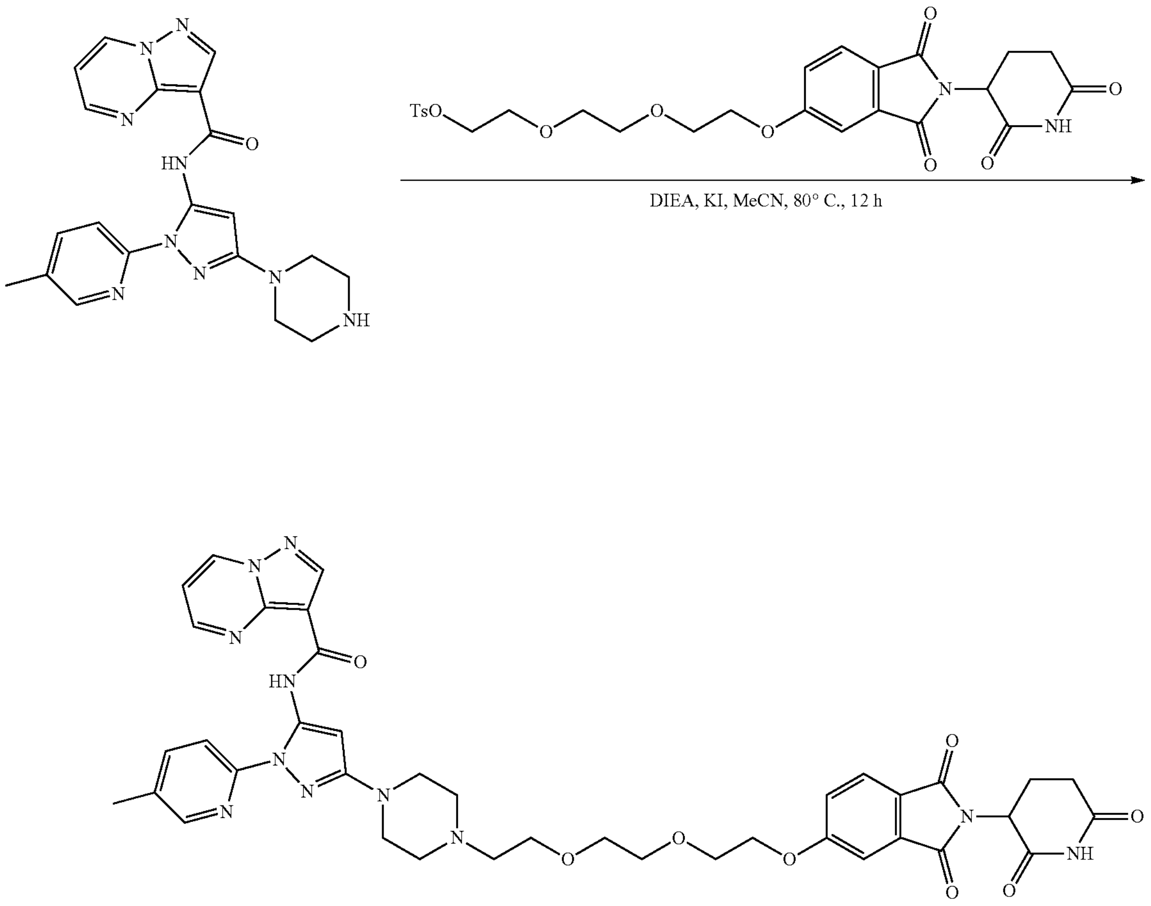

To a solution of N-[2-(5-methyl-2-pyridyl)-5-piperazin-1-yl-pyrazol-3-yl]pyrazolo[1,5-a]pyrimidine-3-carboxamide (47 mg, 0.11 mmol, 1.2 eq, hydrochloride) and 2-[2-[2-[2-(2,6-dioxo-3-piperidyl)-1,3-dioxo-isoindolin-5-yl]oxyethoxy]ethoxy]ethyl 4-methylbenzenesulfonate, prepared in an analogous fashion to Intermediate 10, (50 mg, 0.09 mmol, 1 eq) in acetonitrile (2 mL) was added N,N-diisopropylethylamine (34 mg, 0.27 mmol, 3 eq) and potassium iodide (14 mg, 0.09 mmol, 1 eq). The mixture was stirred at 80° C. for 12 hours. LCMS analysis showed the reaction to be complete. The mixture was adjusted to pH=7 by addition of an aqueous 1 M solution of hydrochloric acid. The mixture was filtered and the residue was purified by preparative reverse phase HPLC to give N-(3-(4-(2-(2-(2-((2-(2,6-dioxopiperidin-3-yl)-1,3-dioxoisoindolin-5-yl)oxy)ethoxy)ethoxy)ethyl)piperazin-1-yl)-1-(5-methylpyridin-2-yl)-1H-pyrazol-5-yl)pyrazolo[1,5-a]pyrimidine-3-carboxamide (19.3 mg, 0.02 mmol, 25% yield, 98% purity, formate) as a yellow solid. MS (ESI) m/z: 792.3 $[M+H]^+$. $^1H$ NMR: (400 MHz, DMSO-$d_6$) δ: 13.27 (s, 1H), 11.11 (s, 1H), 9.38 (dd, J=1.6, 7.2 Hz, 1H), 9.14 (dd, J=1.6, 4.4 Hz, 1H), 8.73 (s, 1H), 8.44 (s, 1H), 8.23 (s, 1H), 7.83 (d, J=8.4 Hz, 1H), 7.79 (dd, J=2.4, 8.8 Hz, 1H), 7.67 (d, J=8.4 Hz, 1H), 7.46 (d, J=2.4 Hz, 1H), 7.40-7.35 (m, 2H), 6.62 (s, 1H), 5.11 (dd, J=5.2, 12.8 Hz, 1H), 4.41-4.27 (m, 2H), 3.83-3.78 (m, 2H), 3.63-3.59 (m, 3H), 3.58-3.53 (m, 6H), 3.24-3.19 (m, 3H), 2.93-2.80 (m, 2H), 2.62-2.56 (m, 2H), 2.55-2.53 (m, 3H), 2.37 (s, 3H), 2.07-2.00 (m, 1H).

The following compounds may be prepared in an analogous fashion as the exemplary synthesis described Exemplary Compound 25.

| Exemplary Compound | $[M + H]^+$ |
| --- | --- |
| 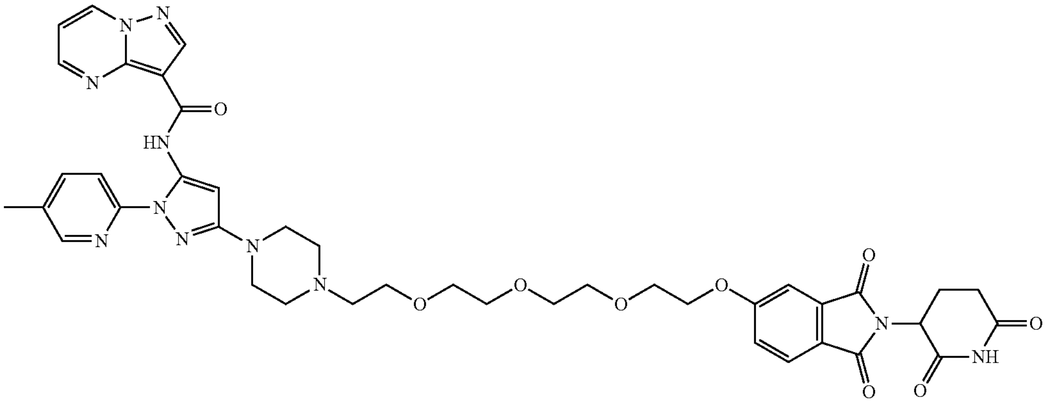 Exemplary Compound 26 | 836.66 |

Scheme 6.

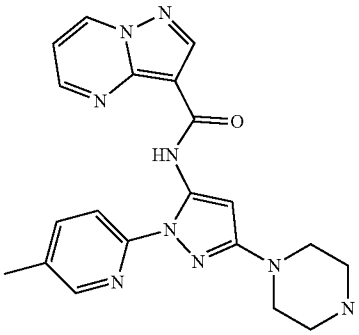

I

+

-continued

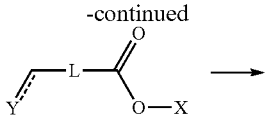

II

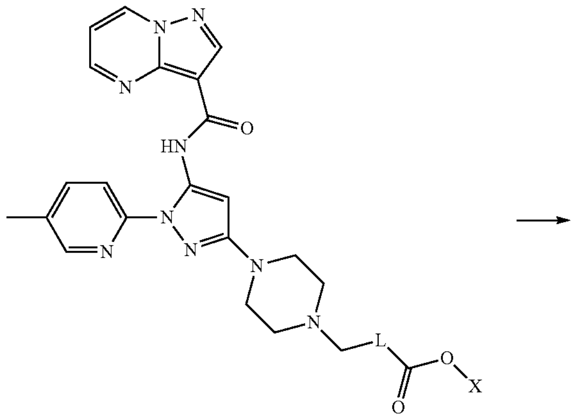

III

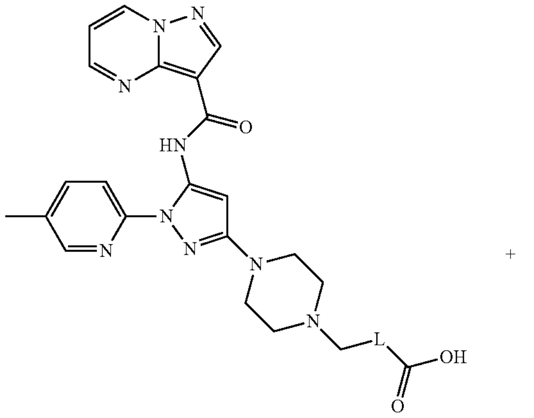

IV

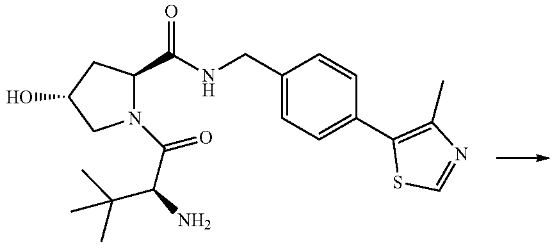

V

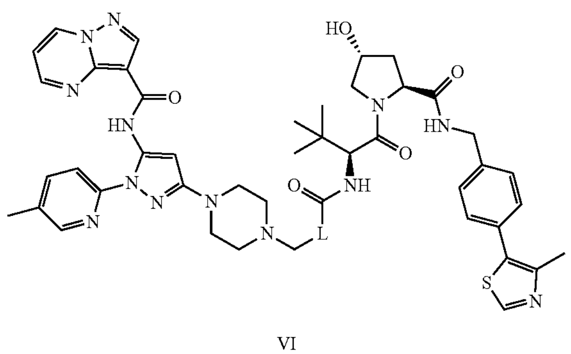

VI

A compound of formula I may be reacted with a reagent II (commercially available or readily prepared using standard reaction techniques known to one skilled in the art) under alkylation or reductive alkylation conditions to produce a compound of formula III, wherein L represents an optional linker or portion of a linker, Y is an appropriate leaving group (e.g. OMs, OTs, Cl, etc.) or an aldehyde, and X is a protecting group. When Y is a leaving group, suitable reaction conditions are those for an alkylation reaction, e.g. diisopropylethylamine, potassium iodide, DMSO or acetonitrile, 80° C. When Y is an aldehyde, suitable reaction conditions are those for a reductive amination reaction, e.g. sodium cyanoborohydride, methanol, dichloromethane, acetic acid, room temperature. Compounds of formula III may be deprotected to reveal a carboxylic acid as in compounds of formula IV. Compounds of formula IV can then be reacted with a compound of formula V using suitable amide coupling conditions, e.g., HOBT or HATU, EDCI, TEA in DMF, to afford compounds of formula VI.

Exemplary Synthesis of Exemplary Compound 27

N-(3-(4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)piperazin-1-yl)-1-(5-methylpyridin-2-yl)-1H-pyrazol-5-yl)pyrazolo[1,5-a]pyrimidine-3-carboxamide Step 1:

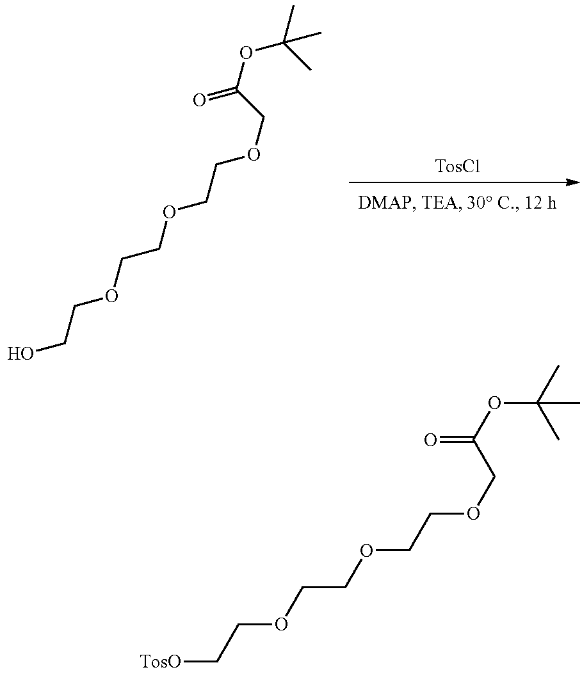

To a solution of tert-butyl 2-[2-[2-(2-hydroxyethoxy)ethoxy]ethoxy]acetate (200 mg, 0.75 mmol, 1 eq), 4-dimethylaminopyridine (9.24 mg, 0.075 mmol, 0.1 eq) and triethylamine (229 mg, 2.27 mmol, 3 eq) in dichloromethane (3 mL) was added tosyl chloride (216 mg, 1.14 mmol, 1.5 eq). The reaction mixture was stirred at 30° C. for 12 hours. LCMS analysis of an aliquot showed formation of the desired compound. The reaction mixture was diluted with water (50 mL) and extracted with ethyl acetate (30 mL×3). The combined organic layers were washed with brine (50 mL×3), dried over anhydrous sodium sulfate, filtered and concentrated under reduced pressure. The residue was purified by silica gel column chromatography (petroleum ether/ethyl acetate=100/1 to 3:1). The appropriate fractions were pooled and concentrated to afford tert-butyl 2-[2-[2-[2-(p-tolylsulfonyloxy)ethoxy]ethoxy]ethoxy]acetate (200 mg, 0.47 mmol, 63% yield) was obtained as a colorless oil. MS (ESI) m/z: 363.1 [M-55]+.

Step 2:

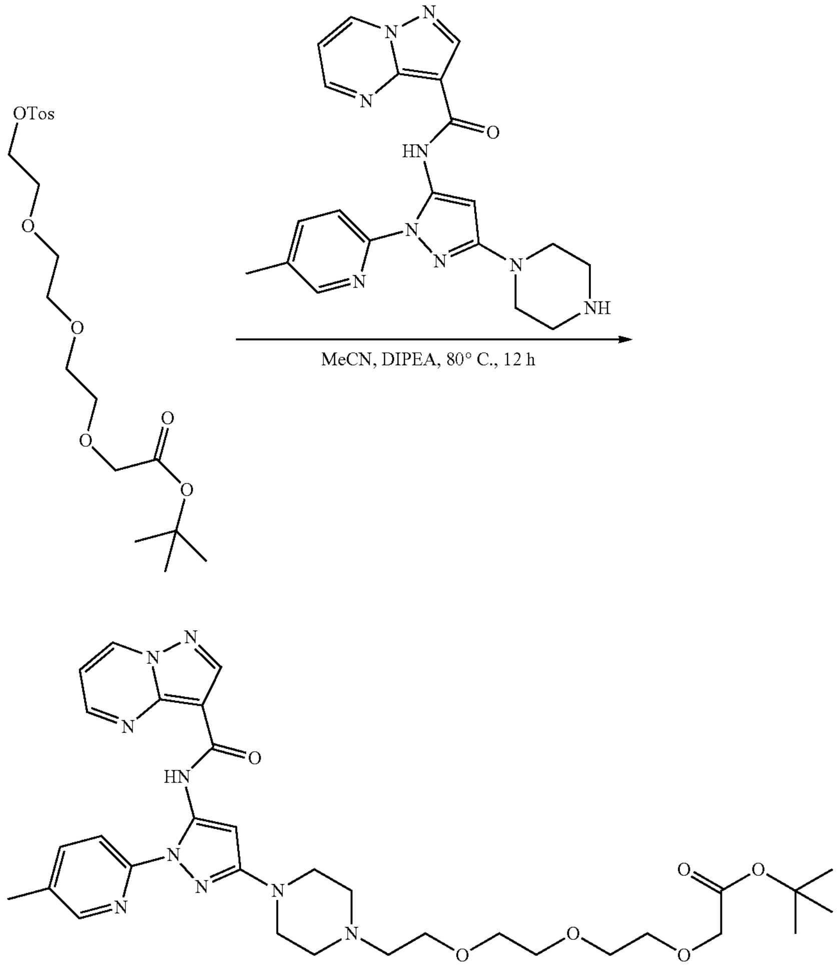

To a solution of N-[2-(5-methyl-2-pyridyl)-5-piperazin-1-yl-pyrazol-3-yl]pyrazolo[1,5-a] pyrimidine-3-carboxamide (100 mg, 0.22 mmol, 1 eq, Hydrochloride), N,N-diisopropylethylamine (88 mg, 0.68 mmol, 3 eq) and tert-butyl 2-[2-[2-[2-(p-tolylsulfonyloxy)ethoxy]ethoxy]ethoxy] acetate (95 mg, 0.22 mmol, 1 eq) in acetonitrile (5 mL) was stirred at 70° C. for 12 hours. LCMS analysis of an aliquot showed formation of the desired compound. The reaction mixture was diluted with water (30 mL) and extracted with ethyl acetate (30 mL×3). The combined organic layers were washed with brine (30 mL×3), dried over anhydrous sodium sulfate, filtered and concentrated under reduced pressure. The residue was purified by preparative TLC (dichloromethane:methanol=10:1) to provide tert-butyl 2-[2-2-[2-[4-[1-(5-methyl-2-pyridyl)-5-(pyrazolo[1,5-a]pyrimidine-3-carbonylamino)pyrazol-3-yl]piperazin-1-yl]ethoxy]ethoxy] ethoxy]acetate (80 mg, 0.12 mmol, 54% yield) as a yellow oil. MS (ESI) m/z: 650.3 [M+H]+.

Step 3:

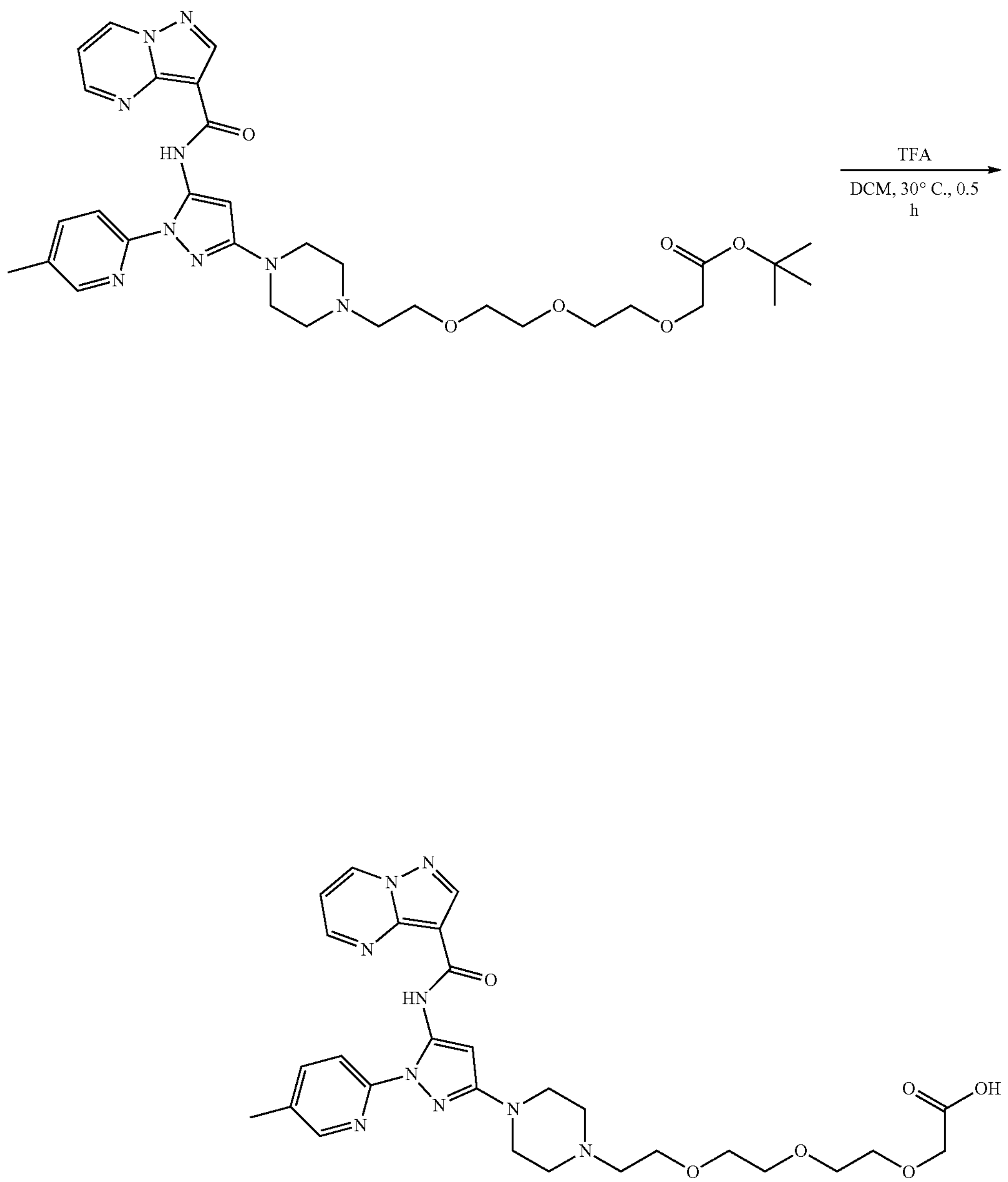

To a solution of tert-butyl 2-[2-[2-[2-[4-[1-(5-methyl-2-pyridyl)-5-(pyrazolo[1,5-a]pyrimidine-3-carbonylamino) pyrazol-3-yl]piperazin-1-yl]ethoxy]ethoxy]ethoxy]acetate (80 mg, 0.12 mmol, 1 eq) in dichloromethane (1 mL) was added trifluoroacetic acid (1.54 g, 13.51 mmol, 1 mL, 109 eq). The reaction mixture was stirred at 30° C. for 0.5 hour. LCMS analysis showed formation of the desired compound. The reaction mixture was concentrated under reduced pressure providing 2-[2-[2-[2-[4-[L-(5-methyl-2-pyridyl)-5-(pyrazolo[1,5-a]pyrimidine-3-carbonylamino)pyrazol-3-yl] piperazin-1-yl]ethoxy]ethoxy]ethoxy]acetic acid (80 mg, 0.11 mmol, 91% yield, trifluoroacetic acid) as a yellow oil which was used directly in the next transformation. MS (ESI) m/z: 594.2 $[M+H]^+$.

Step 4:

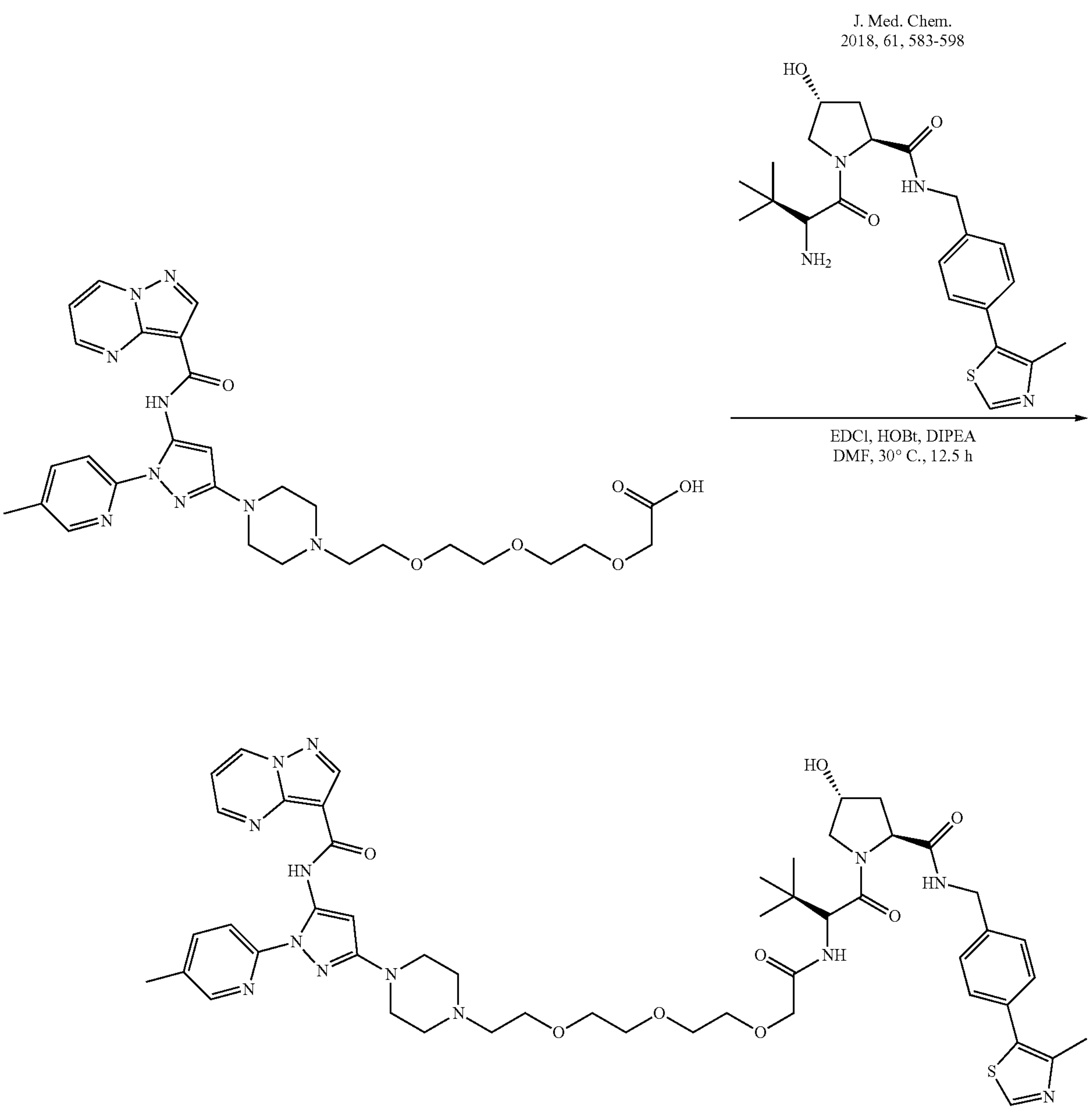

To a solution of 2-[2-[2-[2-[4-[1-(5-methyl-2-pyridyl)-5-(pyrazolo[1,5-a]pyrimidine-3-carbonylamino)pyrazol-3-yl]piperazin-1-yl]ethoxy]ethoxy]ethoxy]acetic acid (80 mg, 0.11 mmol, 1 eq, trifluoroacetic acid), (2S,4R)-1-(2-amino-3,3-dimethyl-butanoyl)-4-hydroxy-N-[[4-(4-methylthiazol-5-yl)phenyl]methyl]pyrrolidine-2-carboxamide (63 mg, 0.13 mmol, 1.2 eq, hydrochloride), hydroxybenzotriazole (18 mg, 0.13 mmol, 1.2 eq) and N,N-diisopropylethylamine (17 mg, 0.13 mmol, 1.2 eq) in N,N-dimethylformamide (5 mL) was stirred at 30° C. for 0.5 hour. Then 1-(3-dimethylaminopropyl)-3-ethylcarbodiimide hydrochloride (26 mg, 0.13 mmol, 1.2 eq) was added. The reaction mixture was stirred at 30° C. for 12 hours. LCMS analysis indicated formation of the desired compound. The reaction mixture was filtered and concentrated under reduced pressure. The residue was purified by preparative HPLC to yield N-(3-(4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)piperazin-1-yl)-1-(5-methylpyridin-2-yl)-1H-pyrazol-5-yl)pyrazolo[1,5-a]pyrimidine-3-carboxamide (44.3 mg, 0.04 mmol, 36% yield, 99% purity, formate) as a yellow solid. MS (ESI) m/z: 594.2 $[M+H]^+$. $^1H$ NMR (400 MHz, DMSO-$d_6$) δ: 13.26 (s, 1H), 9.43-9.33 (m, 1H), 9.16-9.09 (m, 1H), 8.98 (s, 1H), 8.75-8.68 (m, 1H), 8.62 (t, J=6.1 Hz, 1H), 8.43 (s, 1H), 8.19 (s, 1H), 7.81-7.74 (m, 1H), 7.67 (d, J=8.4 Hz, 1H), 7.48-7.33 (m, 6H), 6.63 (s, 1H), 4.58 (d, J=9.5 Hz, 1H), 4.50-4.34 (m, 3H), 4.29-4.21 (m, 1H), 3.99 (s, 2H), 3.69-3.55 (m, 21H), 2.44 (s, 3H), 2.36 (s, 3H), 2.11-2.02 (m, 1H), 1.95-1.86 (m, 1H), 1.04-0.90 (m, 9H).

The following compounds may be prepared in an analogous fashion as the exemplary synthesis described for Exemplary Compound 27.

| Exemplary Compound | $[M + H]^+$ |
| --- | --- |
| 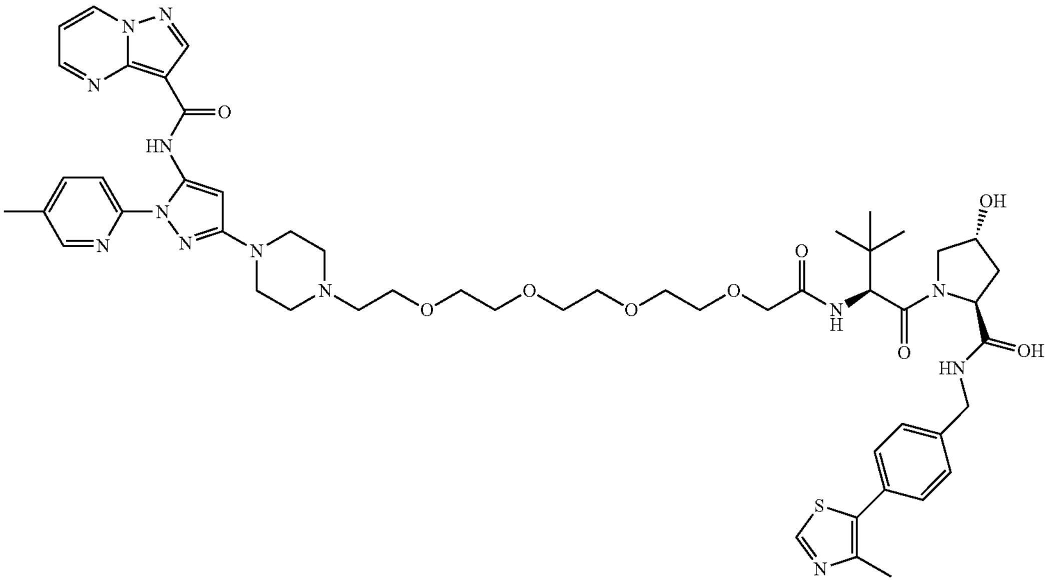 Exemplary Compound 28 | 1050.25 |
Scheme 7.
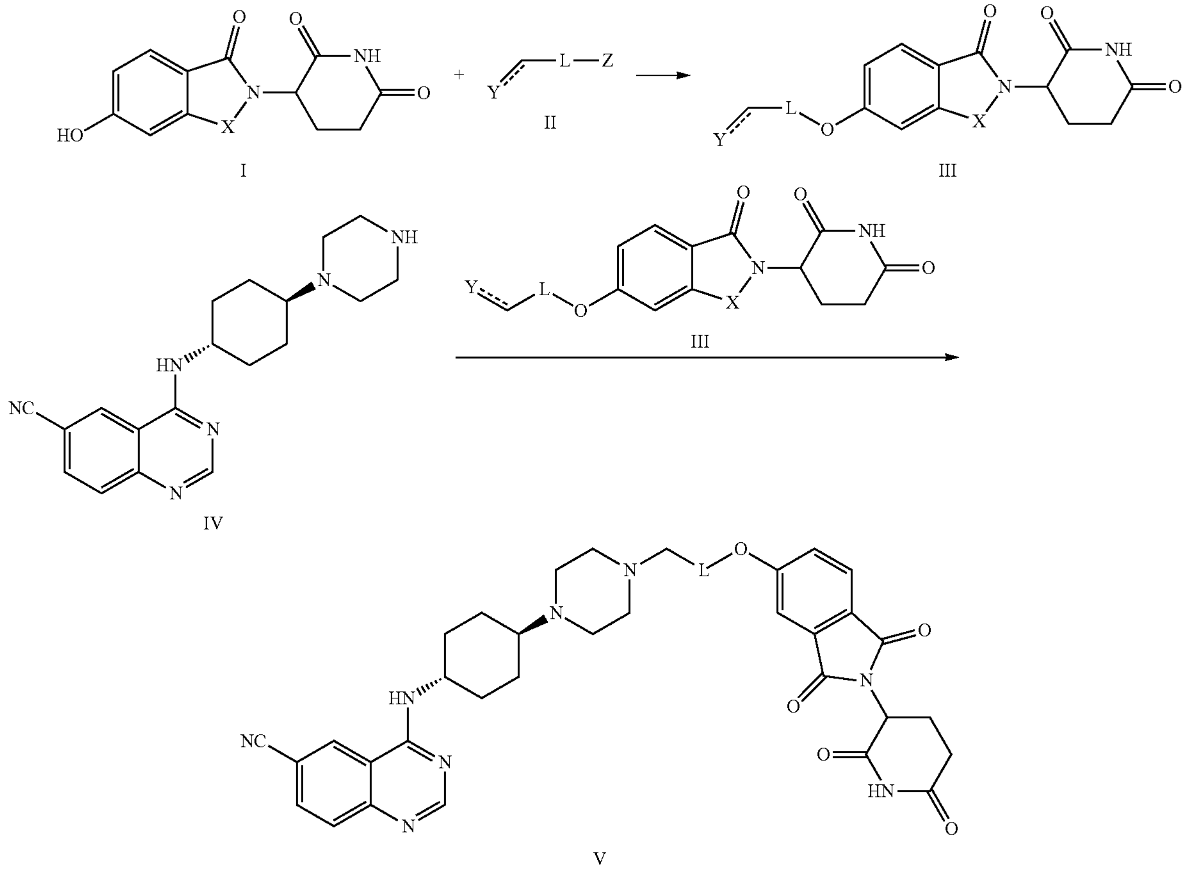

A compound of formula I may be reacted with a reagent II (commercially available or readily prepared using standard reaction techniques known to one skilled in the art) where Z is an appropriate leaving group (e.g. OMs, OTs, Cl, Br, etc.) using O-alkylation conditions to produce a compound of formula III, wherein L represents an optional linker or portion of a linker, X is $CH_2$ or C═O. Compounds of formula III may react with a compound of formula IV through N-alkylation where Y is an appropriate leaving group (e.g. OMs, OTs, Cl, Br, etc.) or through reductive amination where Y is an aldehyde to produce compound of formula V. When Y is a leaving group, suitable reaction conditions are those for an alkylation reaction, e.g. diisopropylethylamine, potassium iodide, DMSO or acetonitrile, 80° C. When Y is an aldehyde, suitable reaction conditions are those for a reductive amination reaction, e.g. sodium cyanoborohydride, methanol, dichloromethane, acetic acid, room temperature.

Exemplary Synthesis of Exemplary Compound 29

4-(((1r,4r)-4-(4-(2-((2-(2,6-dioxopiperidin-3-yl)-1,3-dioxoisoindolin-5-yl)oxy)ethyl)piperazin-1-yl)cyclohexyl)amino)quinazoline-6-carbonitrile Step 1:

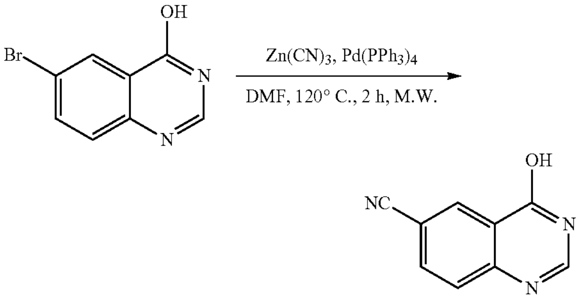

6-bromoquinazolin-4-ol (2 g, 8.89 mmol, 1 eq), zinc cyanide (1.57 g, 13.33 mmol, 1.5 eq) and tetrakis[triphenylphosophine] palladium(0) (1.03 g, 0.88 mmol, 0.1 eq) were charged to a microwave tube in N,N-dimethylformamide (10 mL) under nitrogen atmosphere. The sealed tube was heated at 120° C. for 120 minutes under microwave irradiation. The mixture was filtered and the filtrate was diluted with ethyl acetate (1000 mL). The mixture was washed with brine (500 mL), dried with anhydrous sodium sulfate, filtered and concentrated under vacuum. The crude product was purified by silica gel column chromatography (petroleum ether:ethyl acetate=10:1 to dichloromethane:methanol=10:1) to give 4-hydroxyquinazoline-6-carbonitrile (1.2 g, 7.01 mmol, 39% yield) as a white solid.

Step 2:

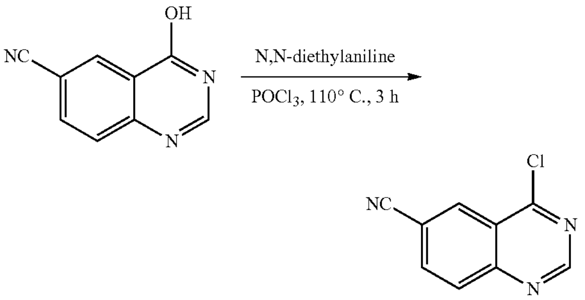

To a solution of 4-hydroxyquinazoline-6-carbonitrile (1 g, 5.84 mmol, 1 eq) in phosphorus oxychloride (107.61 mmol, 10 mL, 18.42 eq) was added N,N-diethylaniline (2.18 g, 14.61 mmol, 2.34 mL, 2.5 eq). The mixture was stirred at 110° C. for 3 hours under nitrogen atmosphere. The mixture was concentrated under reduced pressure and the resulting residue was poured into (100 mL) ice water and stirred for 5 minutes. The mixture was filtered and to the filter cake was added 20 mL methylbenzene. The volatiles were removed under vacuum and 4-chloroquinazoline-6-carbonitrile (600 mg, 3.16 mmol, 54% yield) was thus obtained as a blue solid.

Step 3:

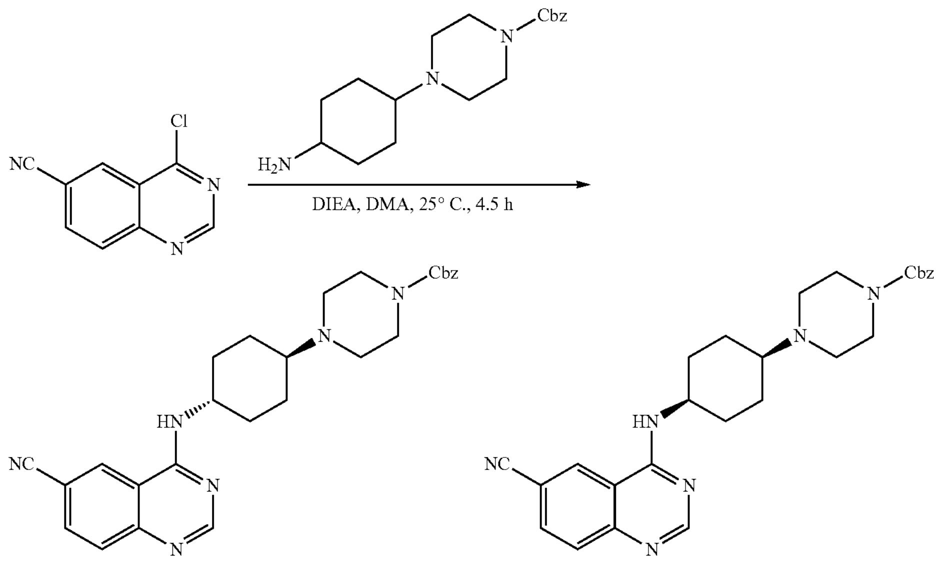

To a solution of benzyl 4-(4-aminocyclohexyl)piperazine-1-carboxylate, Intermediate 5 (10.83 g, 30.59 mmol, 1 eq, hydrochloride) in dimethylacetamide (150 mL) was added N,N-diisopropylethylamine (31.63 g, 244 mmol, 8 eq). The mixture was stirred at 25° C. for 0.5 hour. Then 4-chloroquinazoline-6-carbonitrile (5.8 g, 30.59 mmol, 1 eq) was added to the mixture. The mixture was stirred at 25° C. for 4 hours. LCMS analysis indicated the reaction was complete. The mixture was diluted with water (300 mL) and extracted with ethyl acetate (200 mL×5). The combined organic layers were washed with brine (500 mL×3), dried with anhydrous sodium sulfate, filtered and concentrated in vacuum. The residue was purified by preparative reverse phase HPLC to give benzyl 4-((1r,4r)-4-((6-cyanoquinazolin-4-yl)amino)cyclohexyl)piperazine-1-carboxylate (3.85 g, 8.18 mmol, 27% yield) as a light yellow solid. MS (ESI) m/z: 471.1 $[M+H]^+$. $^1H$ NMR (400 MHz, $CDCl_3$) δ: 8.71 (s, 1H), 8.09 (s, 1H), 7.93-7.85 (m, 2H), 7.41-7.30 (m, 5H), 5.15 (s, 2H), 4.29-4.17 (m, 1H), 3.60-3.46 (m, 4H), 2.57 (s, 4H), 2.48-2.37 (m, 1H), 2.30 (d, J=9.6 Hz, 2H), 2.00 (d, J=14.8 Hz, 2H), 1.58-1.56 (m, 1H), 1.55-1.46 (m, 2H), 1.43-1.31 (m, 2H). The cis isomer, benzyl 4-((1s,4s)-4-((6-cyanoquinazolin-4-yl)amino)cyclohexyl)piperazine-1-carboxylate (6.9 g, 14.66 mmol, 48% yield), was also obtained as a light yellow solid.

Step 4:

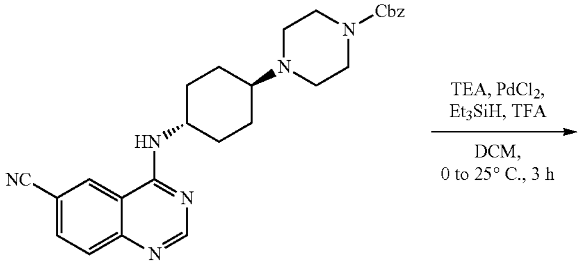

-continued

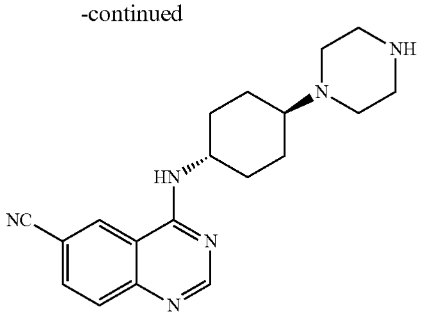

To a solution of benzyl 4-((1r,4r)-4-((6-cyanoquinazolin-4-yl)amino)cyclohexyl)piperazine-1-carboxylate (1.2 g, 2.55 mmol, 1 eq) in dichloromethane (120 mL) was added triethylamine (916 mg, 9.05 mmol, 3.55 eq) and palladium dichloride (452 mg, 2.55 mmol, 1 eq) at 0° C. under nitrogen. Triethylsilane (3.85 g, 33.15 mmol, 13 eq) was added and the mixture was stirred at 25° C. for 2 hours. To the mixture was then added trifluoroacetic acid (5.82 g, 51.00 mmol, 20 eq) and the reaction was allowed to stir at 25° C. for 1 hour. LCMS showed the reaction was complete. The reaction was adjusted to pH between 8 and 9 with the addition of a saturated aqueous solution of sodium bicarbonate. The mixture was concentrated under reduced pressure and the resulting residue was triturated with dichloromethane:methanol (V/V=10:1, 220 mL) and stirred for 10 min. The mixture was filtered, and the filtrate was concentrated to give the crude product. The residue was purified by preparative reverse phase HPLC to give 4-(((1r,4r)-4-(piperazin-1-yl)cyclohexyl)amino)quinazoline-6-carbonitrile (500 mg, 1.49 mmol, 58% yield) as a white solid. MS (ESI) m/z: 337.1 $[M+H]^+$. $^1H$ NMR (400 MHz, DMSO-$d_6$) δ: 8.95 (d, J=1.6 Hz, 1H), 8.56 (s, 1H), 8.27 (d, J=7.6 Hz, 1H), 8.06 (dd, J=1.6, 8.8 Hz, 1H), 7.76 (d, J=8.8 Hz, 1H), 4.12 (td, J=3.6, 7.6 Hz, 1H), 2.68 (t, J=4.4 Hz, 4H), 2.44 (d, J=4.4 Hz, 4H), 2.25 (t, J=11.2 Hz, 1H), 2.04 (d, J=11.2 Hz, 2H), 1.86 (d, J=11.2 Hz, 2H), 1.50-1.30 (m, 4H).

Step 5:

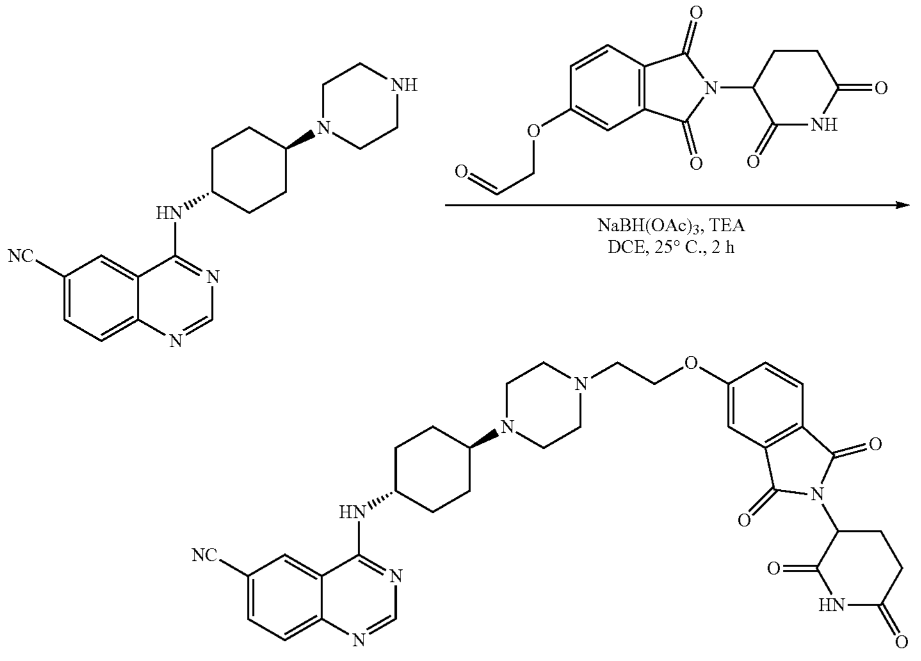

To a solution of 4-(((1r,4r)-4-(piperazin-1-yl)cyclohexyl)amino)quinazoline-6-carbonitrile (40 mg, 0.11 mmol, 1 eq) in 2-dichloroethane (4 mL) was added triethylamine (36 mg, 0.35 mmol, 3 eq) and 2-[2-(2,6-dioxo-3-piperidyl)-1,3-dioxo-isoindolin-5-yl]oxyacetaldehyde, Intermediate 8 (37 mg, 0.11 mmol, 1 eq). The mixture was stirred at 25° C. for 0.5 hour, after which, sodium triacetoxyborohydride (50 mg, 0.23 mmol, 2 eq) was added, the mixture was stirred at 25° C. for 1.5 hours. LCMS showed the reaction was complete. The reaction mixture was concentrated and the resulting residue was purified by semi-preparative reverse phase HPLC to give 4-(((1r,4r)-4-(4-(2-((2-(2,6-dioxopiperidin-3-yl)-1,3-dioxoisoindolin-5-yl)oxy)ethyl)piperazin-1-yl)cyclohexyl)amino)quinazoline-6-carbonitrile (36.5 mg, 0.05 mmol, 44% yield, 98% purity, formate) as a white solid. MS (ESI) m/z: 637.3 $[M+H]^+$. $^1H$ NMR (400 MHz, DMSO-$d_6$) δ: 11.10 (s, 1H), 8.94(d, J=1.6 Hz, 1H), 8.55 (s, 1H), 8.27 (d, J=7.2 Hz, 1H), 8.21 (s, 1H), 8.05 (dd, J=2.0, 8.4 Hz, 1H), 7.83 (d, J=8.4 Hz, 1H), 7.76 (d, J=8.4 Hz, 1H), 7.46 (d, J=2.0 Hz, 1H), 7.37 (dd, J=2.4, 8.4 Hz, 1H), 5.12 (dd, J=5.2, 12.8 Hz, 1H), 4.29 (t, J=5.6 Hz, 2H), 4.12 (d, J=7.2 Hz, 1H), 2.93-2.84(m, 1H), 2.72 (t, J=5.6 Hz, 2H), 2.61 (d, J=2.8 Hz, 2H), 2.55-2.52 (m, 8H), 2.31-2.25 (m, 1H), 2.09-2.00(m, 3H), 1.92-1.83 (m, 2H), 1.49-1.32 (m, 4H).

The following compounds may be prepared in an analogous fashion as the exemplary synthesis described for Exemplary Compound 29.

| Exemplary Compound | $[M + H]^+$ |
|---|---|
| 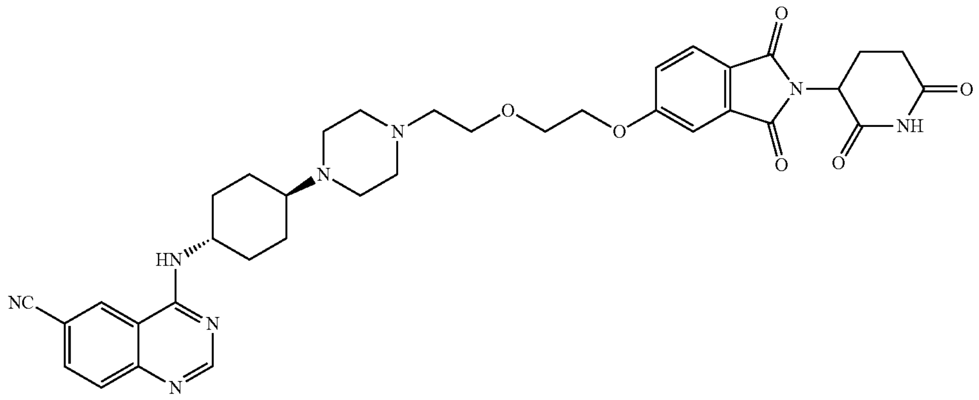 Exemplary Compound 30 | 681.59 |
| 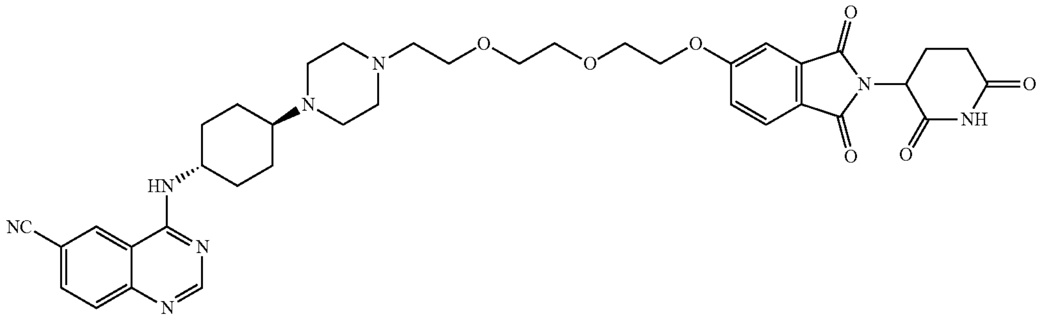 Exemplary Compound 31 | 725.63 |
| 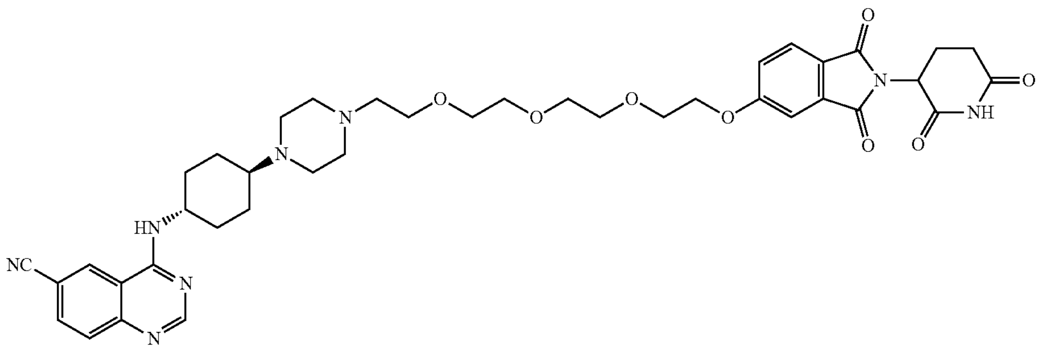 Exemplary Compound 32 | 769.67 |

-continued
| Exemplary Compound | [M + H]+ |
| --- | --- |
| 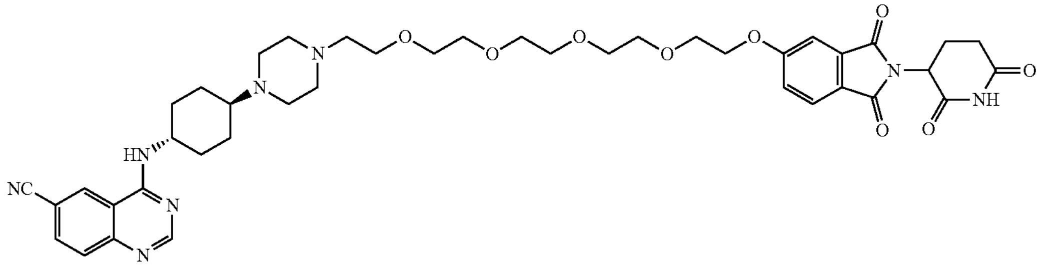<br>Exemplary Compound 33 | 813.7 |
Scheme 8.
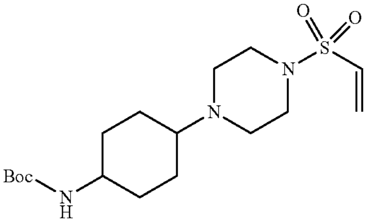
I
+
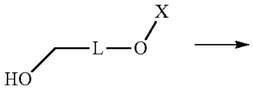
II
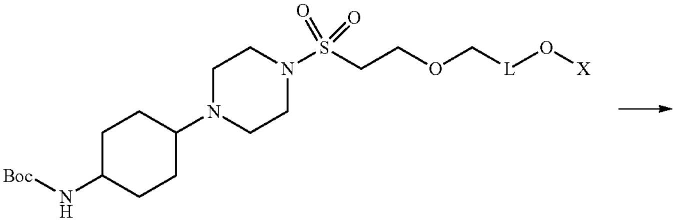
III
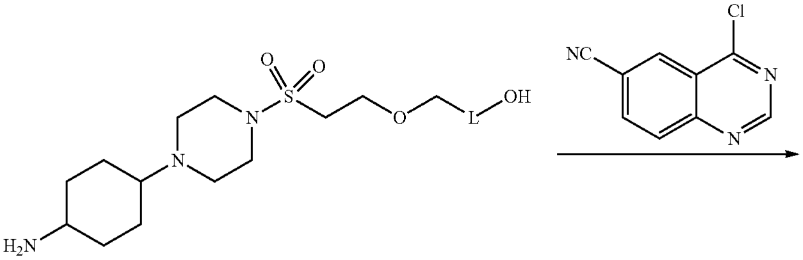
IV
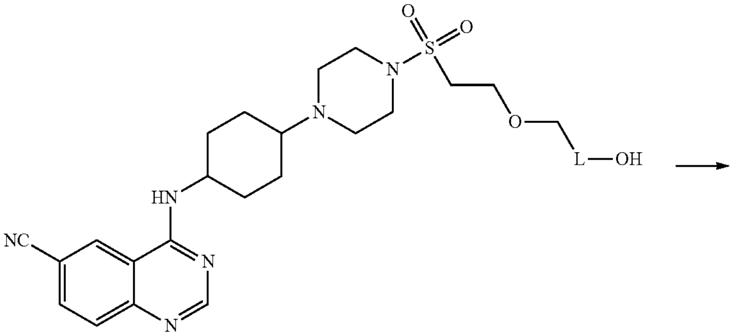
V -continued

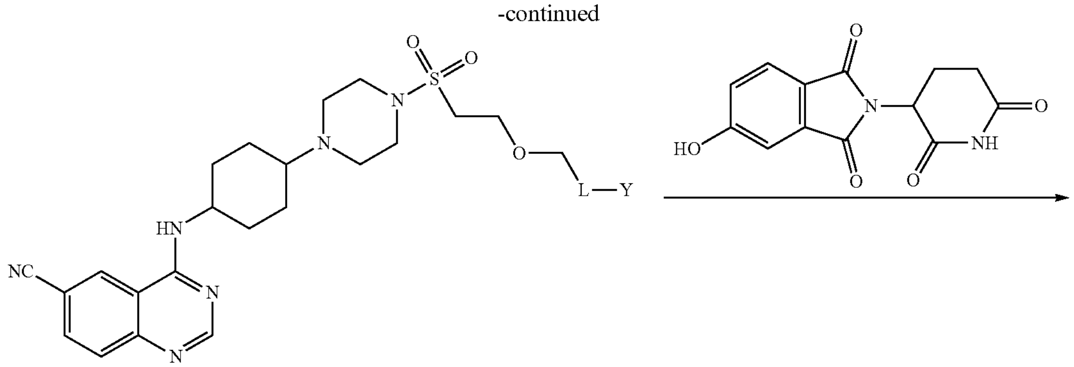

VI

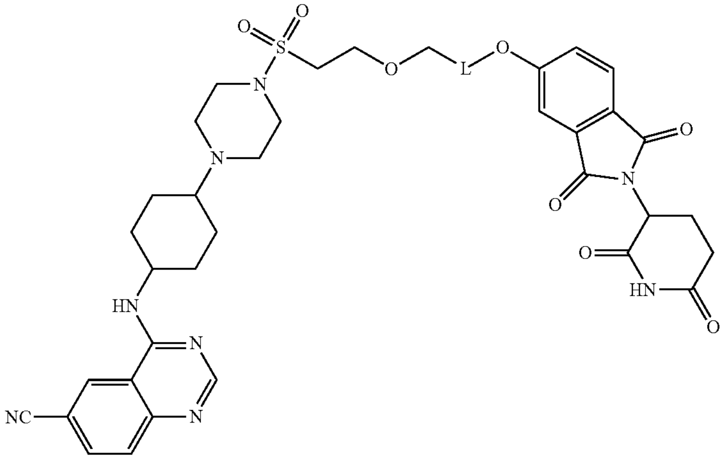

VII

A compound of formula I may be reacted with a reagent II (commercially available or readily prepared using standard reaction techniques known to one skilled in the art) under conjugate addition conditions, e.g. NaH in THE at room temperature, to produce a compound of formula III, wherein L represents an optional linker or portion of a linker and X is a protecting group. Compounds of formula III may be converted to a compound of formula IV through ether deprotection, e.g. using Pd/C, $H_2$, in MeOH or THF, room temperature, followed by N-Boc deprotection, e.g. with TFA or HCl in dioxane. A compound of formula IV may react with 4-chloroquinazoline-6-carbonitrile via suitable nucleophilic aromatic substitution reaction conditions e.g., using a suitable base such as DIEA in DMF, to provide compounds of formula V whose relative stereochemical cis and trans regioisomers may be separated if desired. The alcohol in the compound of formula V may be converted to an appropriate leaving group Y (OTs, OMs, Cl, Br, etc) using standard reaction conditions known to one skilled in the art to provide a compound of formula VI. A compound of formula VI can react via an O-alkylation reaction with 2-(2,6-dioxo-3-piperidyl)-5-hydroxy-isoindoline-1,3-dione to afford compounds of formula VII using a suitable base and solvent, e.g. potassium carbonate in DMF at 60° C.

Exemplary Synthesis of Exemplary Compound 34

4-(((1r,4r)-4-(4-((2-(2-((2-(2,6-dioxopiperidin-3-yl)-1,3-dioxoisoindolin-5-yl)oxy)ethoxy)ethyl)sulfonyl)piperazin-1-yl)cyclohexyl)amino)quinazoline-6-carbonitrile Step 1:

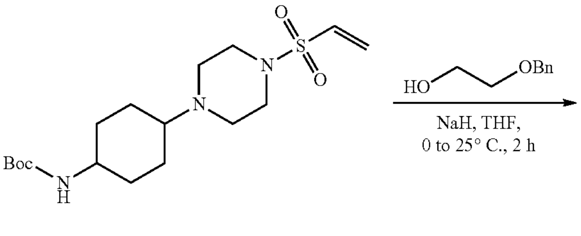

-continued

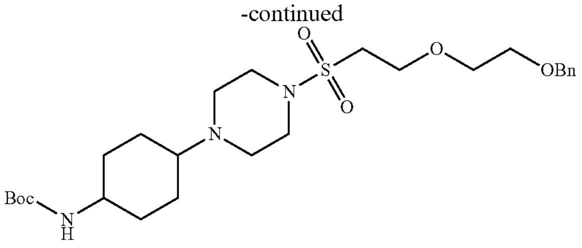

To a solution of 2-benzyloxyethanol (814 mg, 5.35 mmol, 2 eq) in tetrahydrofuran (20 mL) was added sodium hydride (214 mg, 5.35 mmol, 60% purity, 2 eq) at 0° C. The mixture was stirred at 0° C. for 0.5 hour. Then tert-butyl N-[4-(4-vinylsulfonylpiperazin-1-yl)cyclohexyl]carbamate, Intermediate 6 (1 g, 2.68 mmol, 1 eq) in tetrahydrofuran (20 mL) was added dropwise to the mixture at 0° C. The mixture was stirred at 25° C. for 3 hours. LCMS showed the reaction was complete. The mixture was diluted with a saturated aqueous solution of ammonium chloride (50 mL) and extracted with ethyl acetate (30 mL×3). The combined organic layers were washed with brine (60 mL×2), dried with anhydrous sodium sulfate, filtered and concentrated under vacuum. The resulting residue was purified by preparative reverse phase HPLC to give tert-butyl N-[4-[4-[2-(2-benzyloxyethoxy)ethylsulfonyl]piperazin-1-yl]cyclohexyl]carbamate (700 mg, 1.33 mmol, 49% yield) as a colorless oil. MS (ESI) m/z: 526.2 $[M+H]^+$.

Step 2:

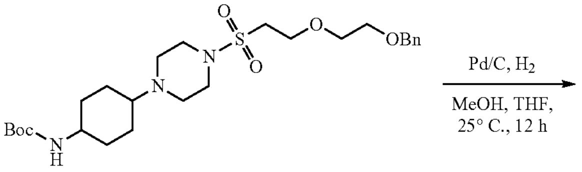

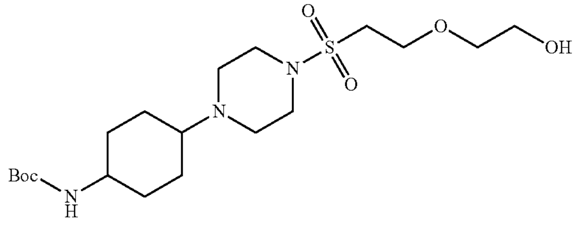

To a solution of tert-butyl N-[4-[4-[2-(2-benzyloxyethoxy)ethylsulfonyl]piperazin-1-yl] cyclohexyl]carbamate (650 mg, 1.24 mmol, 1 eq) in tetrahydrofuran (10 mL) and methanol (10 mL) was added palladium on activated carbon catalyst (100 mg, 1.24 mmol, 10% purity, 1.00 eq) under nitrogen. The suspension was degassed under vacuum and purged with hydrogen several times. The mixture was stirred under hydrogen (15 psi) at 25° C. for 12 hours. Thin layer chromatography (dichloromethane:methanol=10:1) showed the reaction was complete. The mixture was filtered and the filtrate was concentrated under vacuum to afford tert-butyl N-[4-[4-[2-(2-hydroxyethoxy)ethylsulfonyl]piperazin-1-yl] cyclohexyl]carbamate (420 mg, 0.96 mmol, 77% yield) as a colorless oil which was used in the next step without further purification.

Step 3:

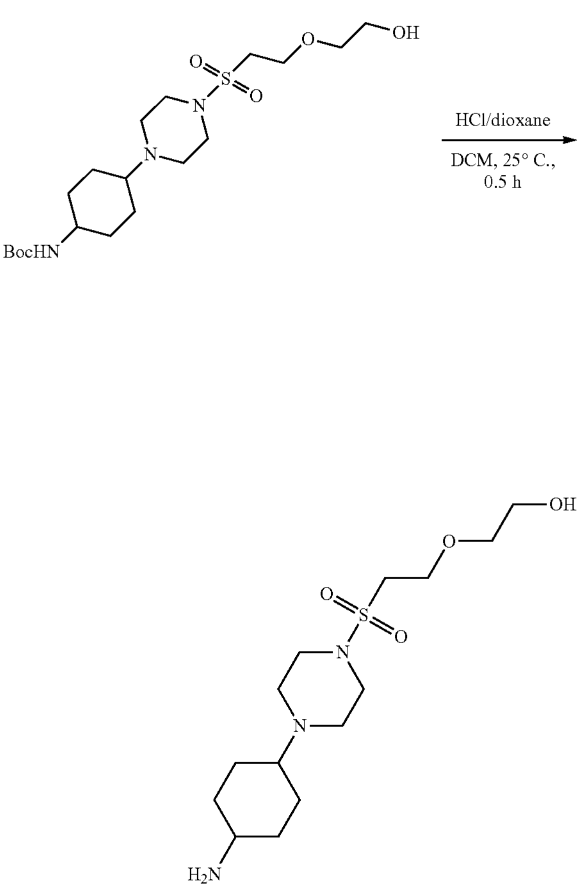

To a solution of tert-butyl N-[4-[4-[2-(2-hydroxyethoxy) ethylsulfonyl]piperazin-1-yl]cyclohexyl]carbamate (450 mg, 1.03 mmol, 1 eq) in dichloromethane (3 mL) was added hydrochloric acid in dioxane (5 mL). The mixture was stirred at 25° C. for 0.5 hour. Thin layer chromatography (dichloromethane:methanol=10:1) indicated completion of the reaction. The mixture was concentrated under reduced pressure to obtain 2-[2-[4-(4-aminocyclohexyl)piperazin-1-yl]sulfonylethoxy]ethanol (320 mg, 0.95 mmol, 92% yield) as a white solid. The crude product was used without further purification in subsequent reactions.

Step 4:

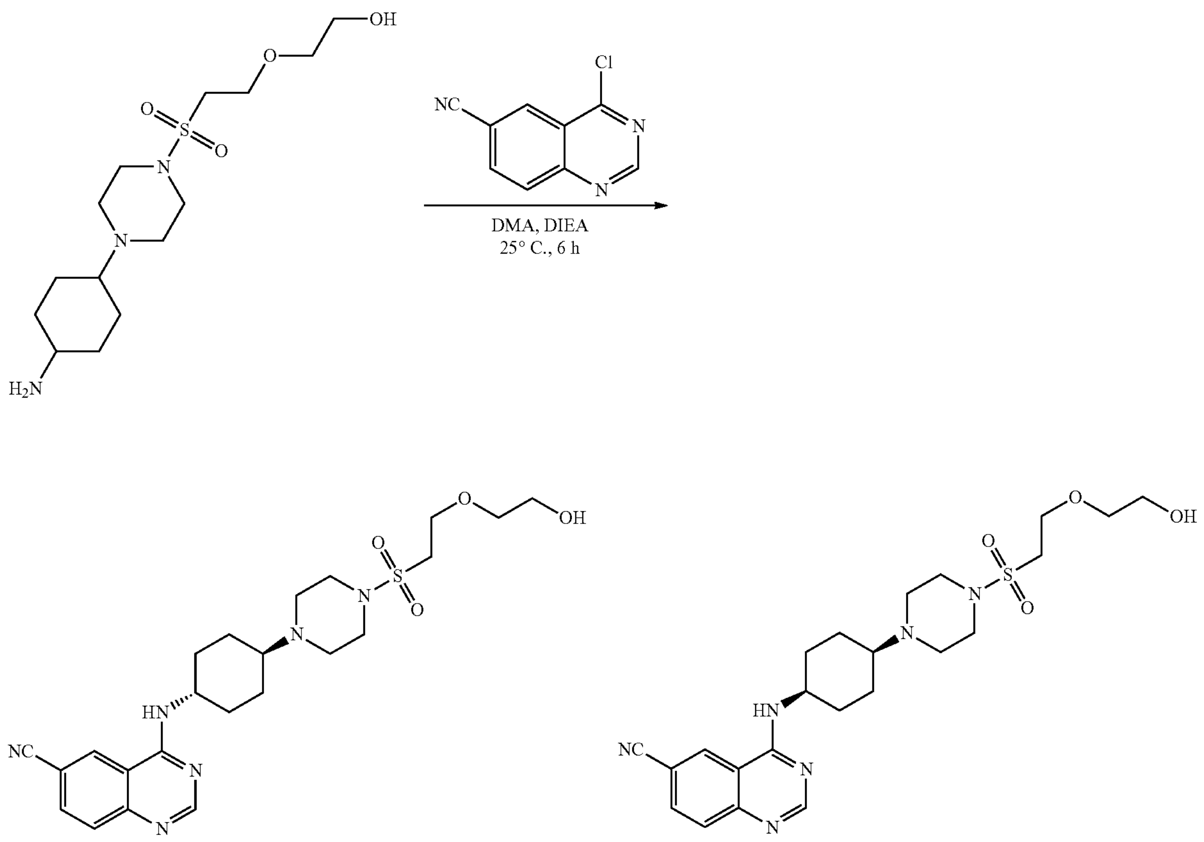 [SMILES: NC1CCC(N2CCN(S(=O)(=O)CCOCCO)CC2)CC1 ; N#Cc1ccc2ncnc(Cl)c2c1 ; N#Cc1ccc2ncnc(N[C@H]3CC[C@H](N4CCN(S(=O)(=O)CCOCCO)CC4)CC3)c2c1 ; N#Cc1ccc2ncnc(N[C@H]3CC[C@@H](N4CCN(S(=O)(=O)CCOCCO)CC4)CC3)c2c1]

To a solution of 2-[2-[4-(4-aminocyclohexyl)piperazin-1-yl]sulfonylethoxy]ethanol (320 mg, 0.95 mmol, 1 eq) in dimethylacetamide (10 mL) was added N,N-diisopropylethylamine (986 mg, 7.63 mmol, 8 eq) and 4-chloroquinazoline-6-carbonitrile (180 mg, 0.95 mmol, 1 eq). The mixture was stirred at 25° C. for 12 hours. LCMS analysis of an aliquot indicated the reaction was complete. The mixture was concentrated under reduced pressure. The residue was purified by preparative reverse phase HPLC to give 4-(((1r,4r)-4-(4-((2-(2-hydroxyethoxy)ethyl)sulfonyl)piperazin-1-yl)cyclohexyl)amino)quinazoline-6-carbonitrile (11 mg, 0.022 mmol, 4.72% yield) as a colorless oil. MS (ESI) m/z: 489.1 $[M+H]^+$. $^1H$ NMR (400 MHz, DMSO-$d_6$) δ: 8.94 (d, J=1.2 Hz, 1H), 8.55 (s, 1H), 8.29 (d, J=7.2 Hz, 1H), 8.05 (dd, J=1.6, 8.8 Hz, 1H), 7.76 (d, J=8.8 Hz, 1H), 4.68-4.57 (m, 1H), 4.19 (s, 1H), 3.74 (t, J=6.0 Hz, 2H), 3.52-3.49 (m, 2H), 3.46 (d, J=4.8 Hz, 2H), 3.29 (s, 2H), 3.15 (d, J=2.4 Hz, 4H), 2.58 (s, 4H), 2.09-2.00 (m, 2H), 1.91-1.80 (m, 2H), 1.46-1.31 (m, 4H), 1.20-1.11 (m, 1H).

4-(((1s,4s)-4-(4-((2-(2-hydroxyethoxy)ethyl)sulfonyl)piperazin-1-yl)cyclohexyl)amino)quinazoline-6-carbonitrile (85 mg, 0.17 mmol, 36.48% yield) was obtained as a white solid. $^1H$ NMR (400 MHz, $CDCl_3$) δ: 8.67 (s, 1H), 8.26 (s, 1H), 7.93-7.80 (m, 2H), 6.60 (d, J=8.0 Hz, 1H), 4.66-4.49 (m, 1H), 4.00-3.93 (m, 2H), 3.90-3.84 (m, 2H), 3.73-3.65 (m, 2H), 3.45 (t, J=4.4 Hz, 4H), 3.36-3.32 (m, 2H), 2.76-2.57 (m, 4H), 2.35 (s, 1H), 1.92-1.74 (m, 8H).

Step 5:

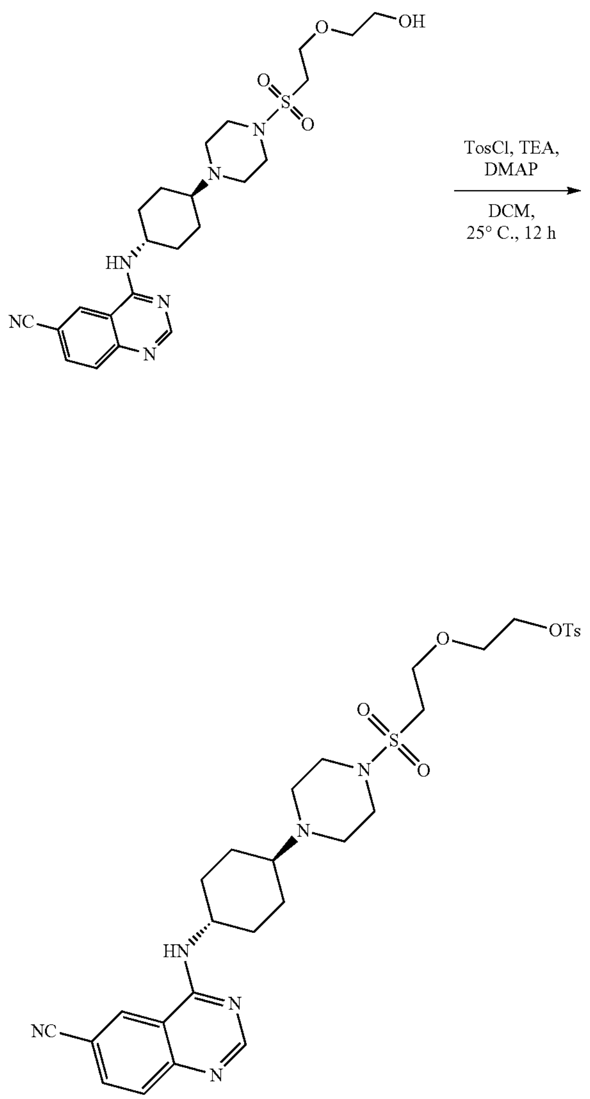

To a solution of 4-(((1r,4r)-4-(4-((2-(2-hydroxyethoxy)ethyl)sulfonyl)piperazin-1-yl) cyclohexyl)amino)quinazoline-6-carbonitrile (300 mg, 0.61 mmol, 1 eq) in dichloromethane (5 mL) was added triethylamine (248 mg, 2.46 mmol, 4 eq), 4-dimethylaminopyridine (7 mg, 0.06 mmol, 0.1 eq) and para-toluensulfonyl chloride (175 mg, 0.09 mmol, 1.5 eq). The mixture was stirred at 25° C. for 12 hours. LCMS showed the reaction was complete. The mixture was diluted with water (10 mL) and extracted with dichloromethane (10 mL×3). Then the combined organic layers were washed with brine (20 mL×2), dried with anhydrous sodium sulfate, filtered and concentrated under vacuum. The crude product was purified by preparative reverse phase thin layer chromatography (dichloromethane: methanol=20:1) to give 2-(2-((4-((1r,4r)-4-((6-cyanoquinazolin-4-yl)amino)cyclohexyl)piperazin-1-yl)sulfonyl)ethoxy)ethyl 4-methylbenzenesulfonate (150 mg, 0.23 mmol, 38% yield) as a colorless oil. MS (ESI) m/z: 643.0 $[M+H]^+$.

Step 6:

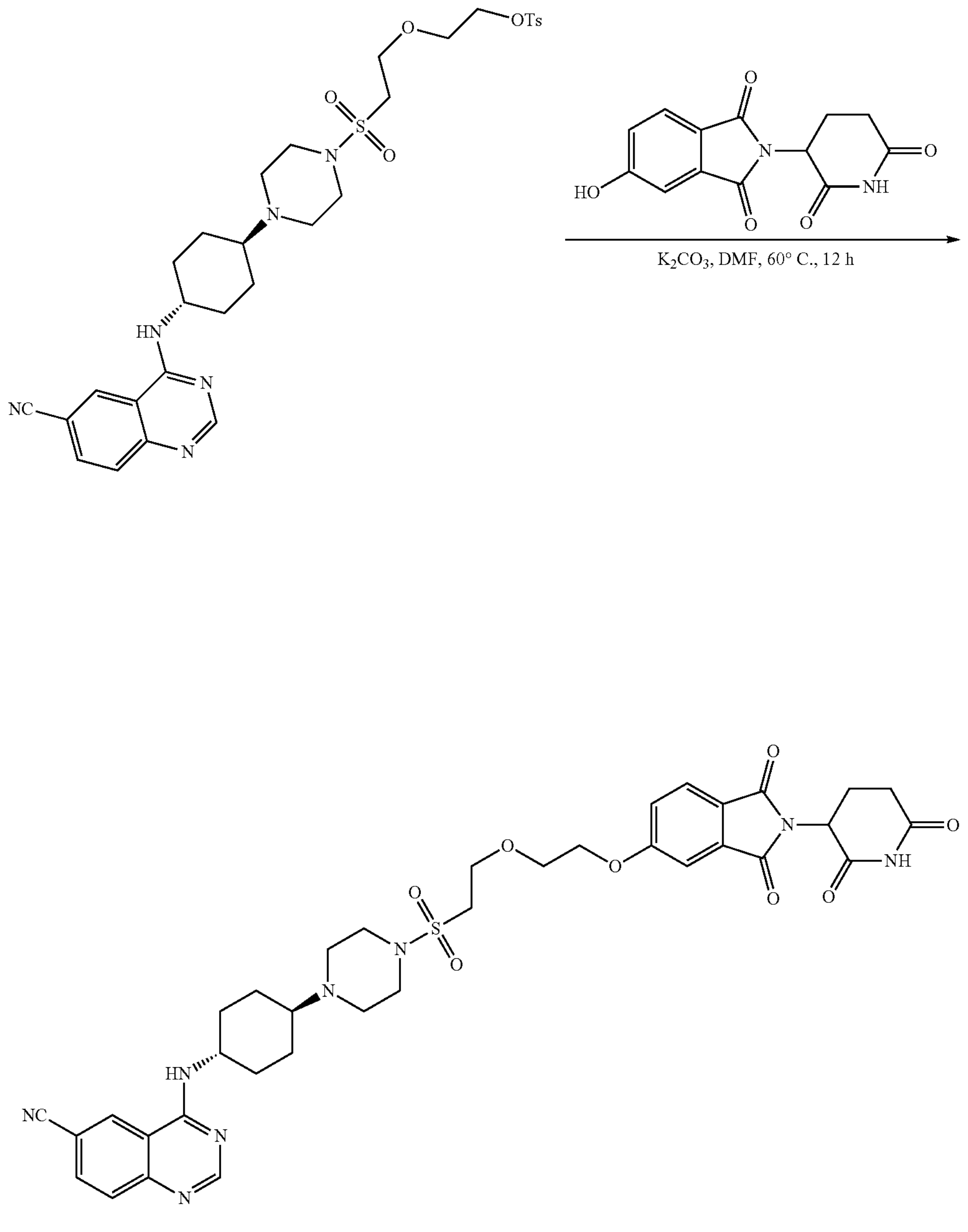

To a solution of 2-(2-((4-((1r,4r)-4-((6-cyanoquinazolin-4-yl)amino)cyclohexyl)piperazin-1-yl)sulfonyl)ethoxy)ethyl 4-methylbenzenesulfonate (150 mg, 0.23 mmol, 1 eq) in N,N-dimethylformamide (3 mL) was added 2-(2,6-dioxo-3-piperidyl)-5-hydroxy-isoindoline-1,3-dione (76 mg, 0.28 mmol, 1.2 eq) and potassium carbonate (64 mg, 0.46 mmol, 2 eq). The mixture was stirred at 60° C. for 2 hours. LCMS showed the reaction was completed. The mixture was diluted with water (10 mL) and extracted with ethyl acetate (10 mL×3). The combined organic layers were washed with brine (20 mL×3), dried with anhydrous sodium sulfate, filtered and concentrated in vacuum. The crude product was purified by preparative reverse phase thin layer chromatography (dichloromethane:methanol=10:1) to give 4-(((1r,4r)-4-(4-((2-(2-((2-(2,6-dioxopiperidin-3-yl)-1,3-dioxoisoindolin-5-yl)oxy)ethoxy)ethyl)sulfonyl)piperazin-1-yl)cyclohexyl)amino)quinazoline-6-carbonitrile (29.9 mg, 0.04 mmol, 16% yield, 96% purity) as a white solid. MS (ESI) m/z: 745.3 $[M+H]^+$. $^1H$ NMR: (400 MHz, DMSO-$d_6$): 11.09 (s, 1H), 8.93 (d, J=1.6 Hz, 1H), 9.02-8.86 (m, 1H), 8.55 (s, 1H), 8.26 (d, J=7.6 Hz, 1H), 8.05 (dd, J=1.6, 8.8 Hz, 1H), 7.84 (d, J=8.4 Hz, 1H), 7.76 (d, J=8.8 Hz, 1H), 7.47 (d, J=2.0 Hz, 1H), 7.39 (dd, J=2.0, 8.4 Hz, 1H), 5.10 (dd, J=5.6, 12.8 Hz, 1H), 4.33 (dd, J=3.2, 5.2 Hz, 2H), 4.19-4.02 (m, 1H), 3.89-3.72 (m, 4H), 3.33 (s, 2H), 3.15 (d, J=4.8 Hz, 4H), 2.91-2.79 (m, 1H), 2.53 (d, J=6.4 Hz, 4H), 2.52 (s, 2H), 2.40-2.28 (m, 1H), 2.05-1.93 (m, 3H), 1.77 (d, J=10.0 Hz, 2H), 1.46-1.28 (m, 4H).

The following compounds may be prepared in an analogous fashion as the exemplary synthesis described for Exemplary Compound 34.

| Exemplary Compound | $[M + H]^+$ |
|---|---|
| 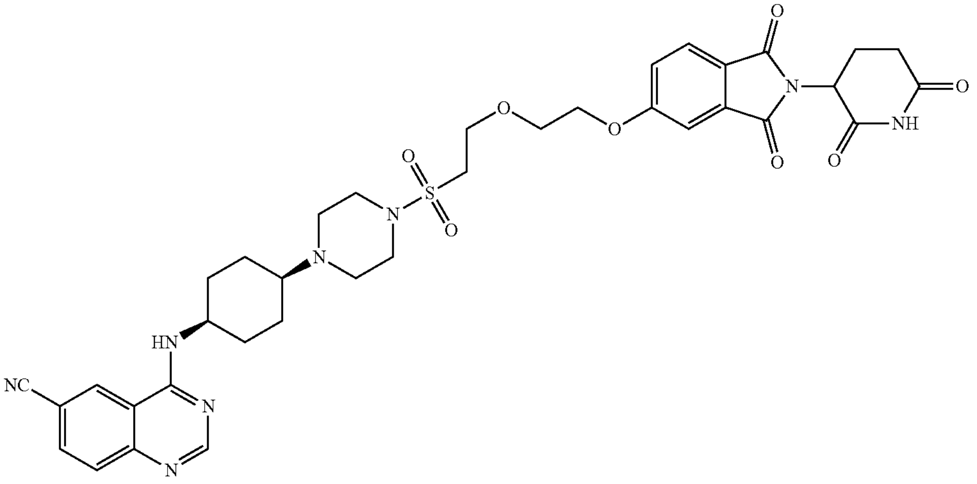 Exemplary Compound 35 | 745.56 |
| 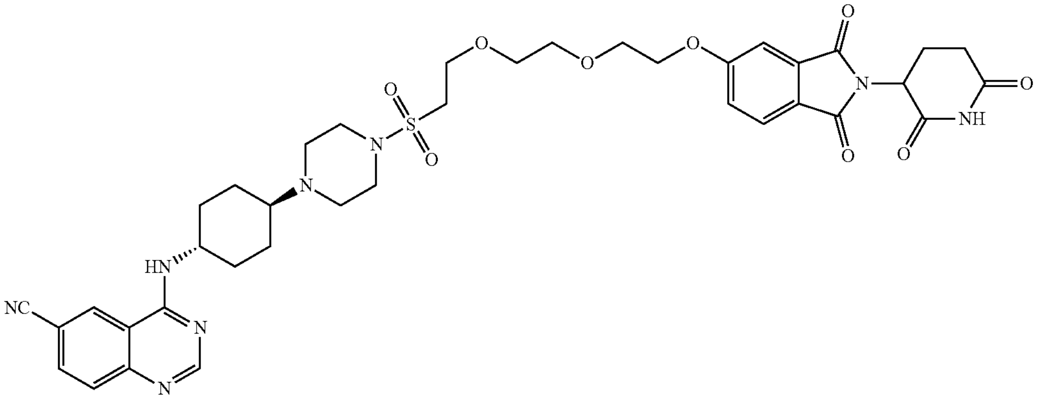 Exemplary Compound 36 | 789.43 |
| 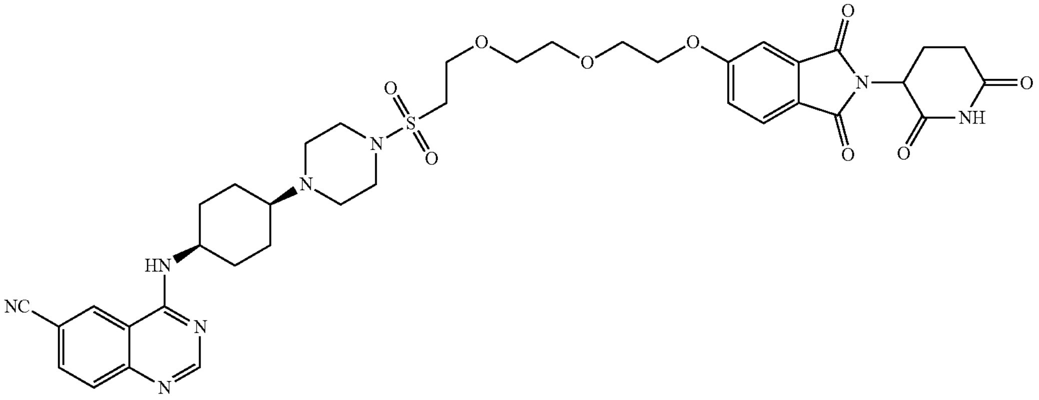 Exemplary Compound 37 | 789.43 |

-continued
| Exemplary Compound | [M + H]+ |
| --- | --- |
| 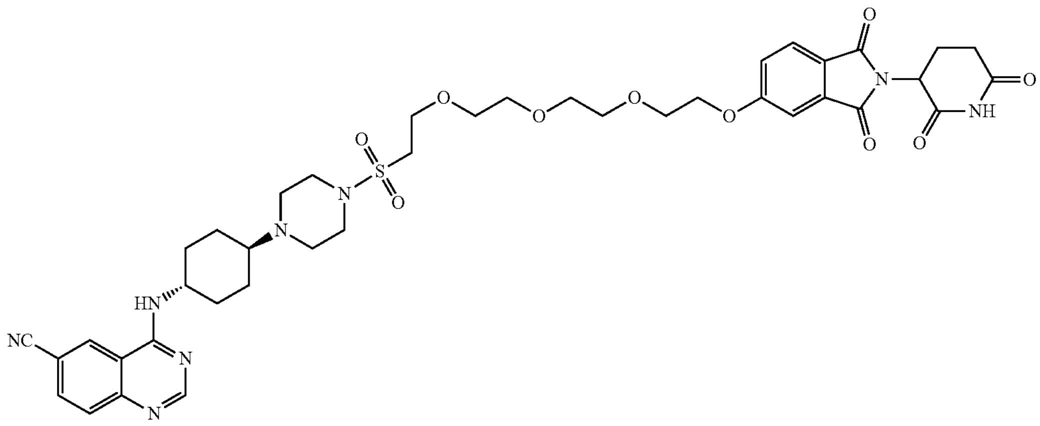 Exemplary Compound 38 | 833.45 |
| 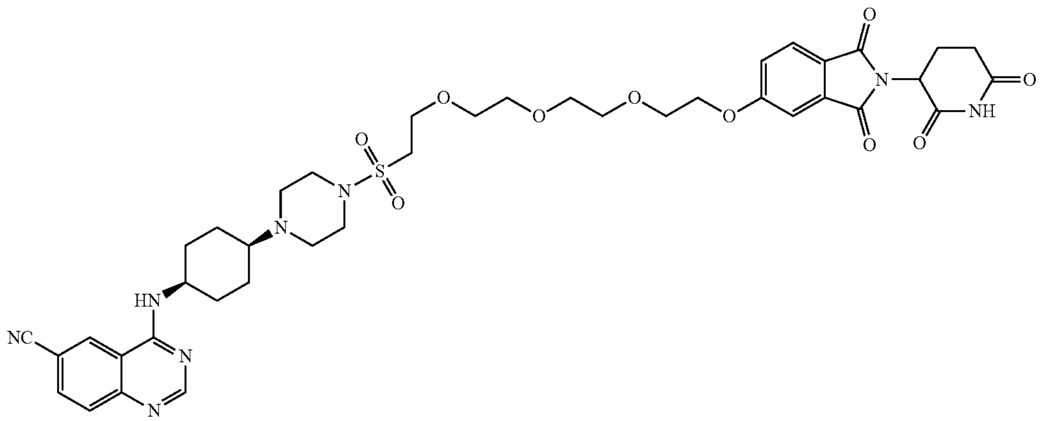 Exemplary Compound 39 | 833.45 |
| 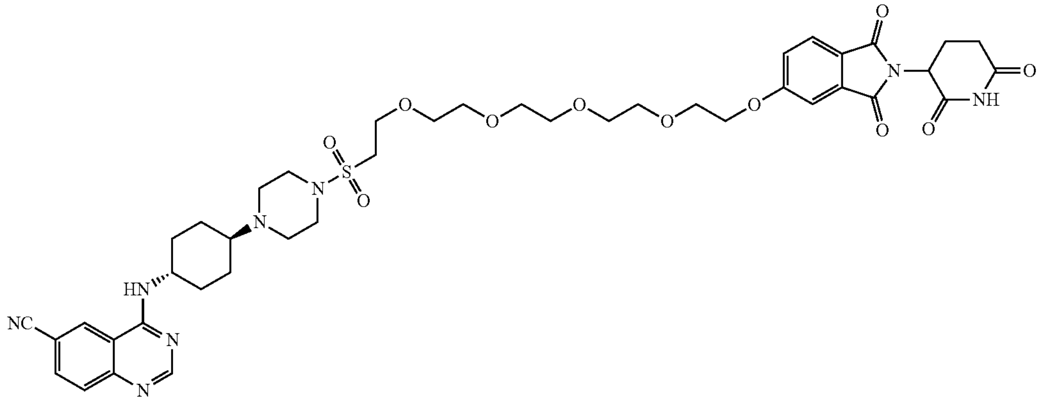 Exemplary Compound 40 | 877.49 |

-continued
| Exemplary Compound | [M + H]+ |
|---|---|
| 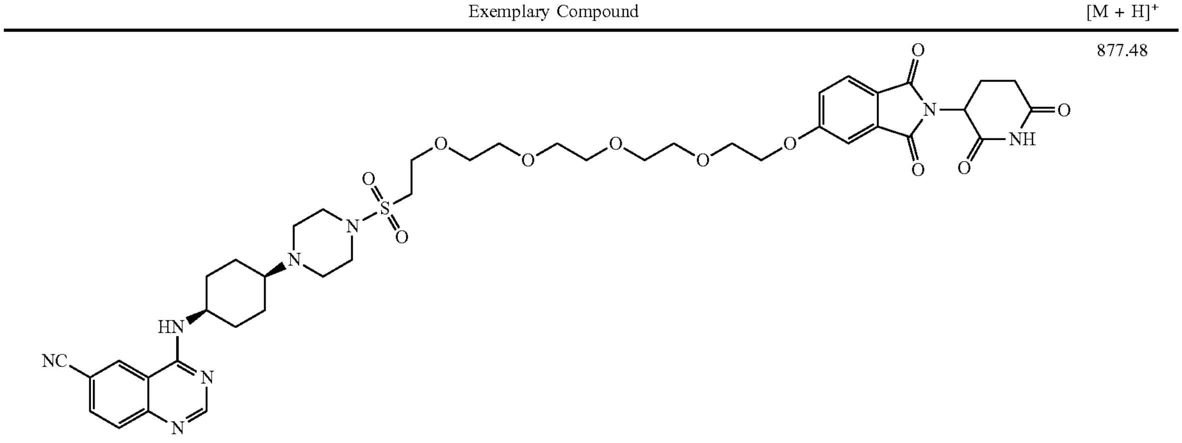<br>Exemplary Compound 41 | 877.48 |
Scheme 9.
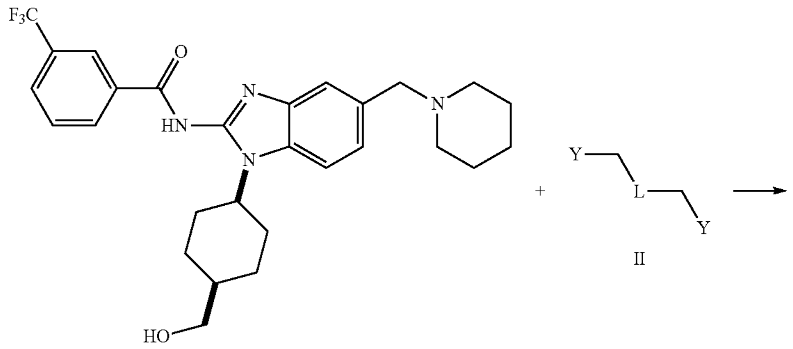
I
II
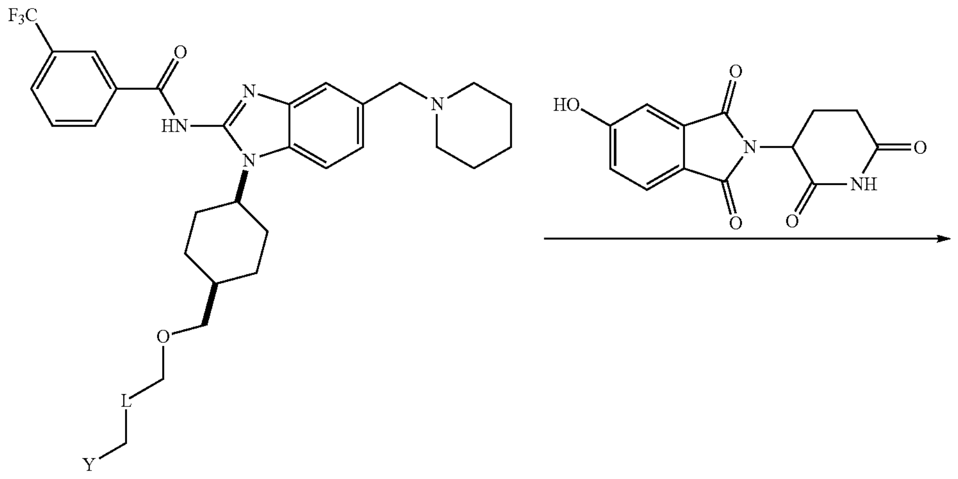
III -continued

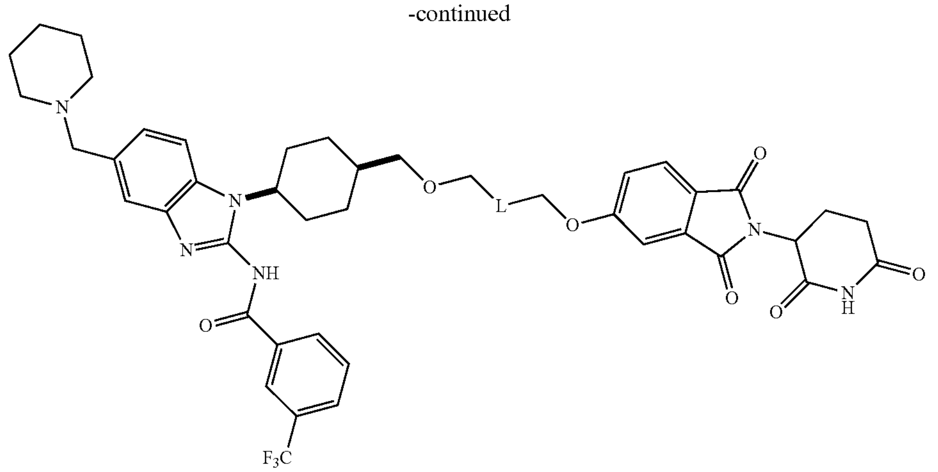

IV

A compound of formula I may be reacted with a reagent II (commercially available or readily prepared using standard reaction techniques known to one skilled in the art) where Y is an appropriate leaving group (e.g. OMs, OTs, Cl, Br, etc.) under etherification conditions to produce a compound of formula III, wherein L represents an optional linker or portion of a linker. Suitable reactions conditions for O-alkylation entail the use of a base, e.g. NaH or potassium carbonate in a solvent such as DMF at 60° C. A compound of formula III can be reacted with 2-(2,6-dioxo-3-piperidyl)-5-hydroxy-isoindoline-1,3-dione to provide compounds of formula IV using suitable reaction conditions for an alkylation reaction, e.g. diisopropylethylamine, potassium iodide, DMSO or acetonitrile, 80° C.

Exemplary Synthesis of Exemplary Compound 42

N-(1-((1s,4s)-4-(13-((2-(2,6-dioxopiperidin-3-yl)-1,3-dioxoisoindolin-5-yl)oxy)-2,5,8,11-tetraoxatridecyl)cyclohexyl)-5-(piperidin-1-ylmethyl)-1H-benzo[d]imidazol-2-yl)-3-(trifluoromethyl)benzamide Step 1:

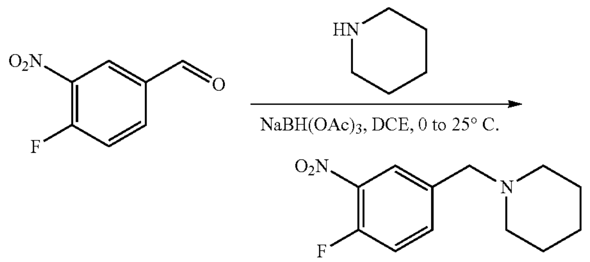

To a solution of 4-fluoro-3-nitro-benzaldehyde (12 g, 70.96 mmol, 1 eq) and acetic acid (12.78 g, 212.88 mmol, 12.18 mL, 3 eq) in 1,2-dichloroethane (200 mL) was added a solution of piperidine (6.65 g, 78.06 mmol, 7.71 mL, 1.1 eq) in 1,2-dichloroethane (50 mL) at 0° C. for 1 hour. Then sodium borohydride acetate (60.16 g, 283.84 mmol, 4 eq) was added to the stirring solution. The mixture was stirred at 0 to 25° C. for 9 hours. The reaction mixture was quenched by addition water (400 mL) at 0° C., and then washed with ethyl acetate (100 mL×2). The aqueous layer was adjusted to pH=8 by the addition of a saturated aqueous solution of sodium bicarbonate, extracted with ethyl acetate (200 mL×2), dried over sodium sulfate, filtered and concentrated under reduced pressure to afford crude 1-[(4-fluoro-3-nitro-phenyl)methyl]piperidine (8 g, 33.58 mmol, 47% yield), obtained as a red oil and used in a subsequent reaction without further purification. MS(ESI) m/z: 239.1 $[M+H]^+$.

Step 2:

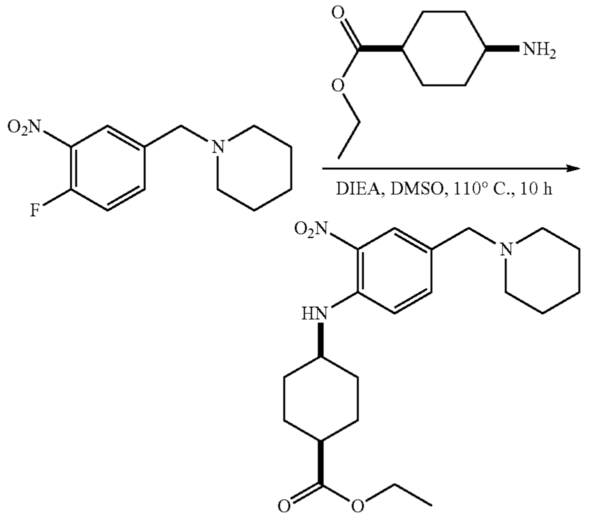

To a solution of 1-[(4-fluoro-3-nitro-phenyl)methyl]piperidine (6.8 g, 28.54 mmol, 1 eq) in dimethyl sulfoxide (35 mL) was added diisopropylethylamine (14.75 g, 114.16 mmol, 19.88 mL, 4 eq) and ethyl (1s,4s)-4-aminocyclohexanecarboxylate, Intermediate 1 (5.93 g, 28.54 mmol, 1 eq, hydrogen chloride). The mixture was stirred at 110° C. for 10 hours. The reaction mixture was quenched by the addition of water (200 mL) at 0° C., and then extracted with ethyl acetate (200 mL×2). The combined organic layers were washed with a brine solution (200 mL×2), dried over anhydrous sodium sulfate, filtered and concentrated under reduced pressure to provide crude ethyl (1s,4s)-4-((2-nitro- 4-(piperidin-1-ylmethyl)phenyl)amino)cyclohexane-1-carboxylate (10 g, 25.67 mmol, 90% yield), obtained as a yellow solid and used as is in the next transformation without further purification. MS (ESI) m/z: 390.2 $[M+H]^+$.

Step 3:

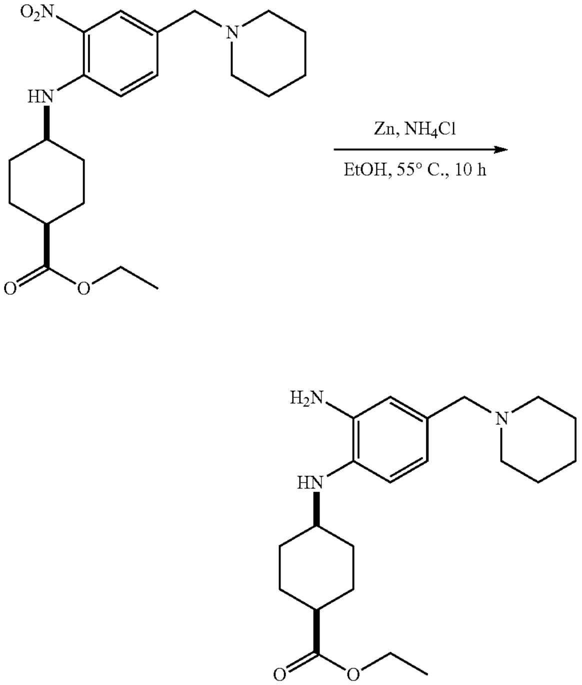

To a solution of ethyl (1s,4s)-4-((2-nitro-4-(piperidin-1-ylmethyl)phenyl)amino)cyclohexane-1-carboxylate (4.5 g, 11.55 mmol, 1 eq) in ethanol (100 mL) was added zinc (15.11 g, 231.07 mmol, 20 eq) and ammonium chloride (12.36 g, 231.07 mmol, 20 eq). The mixture was stirred at 55° C. for 10 hours. The reaction mixture was filtered, the solid was washed with ethanol (50 mL×2), the filtrate was concentrated under reduced pressure to give a residue. The residue was diluted with a saturated aqueous solution of sodium bicarbonate (50 mL) and extracted with ethyl acetate (50 mL×2). The combined organic layers were dried over anhydrous sodium sulfate, filtered and concentrated under reduced pressure to afford crude ethyl (1s,4s)-4-((2-amino-4-(piperidin-1-ylmethyl)phenyl)amino)cyclohexane-1-carboxylate (4 g, 11.13 mmol, 96% yield), obtained as a black oil and used in the subsequent reaction without further purification. MS (ESI) m/z: 275.2 $[M-84]^+$.

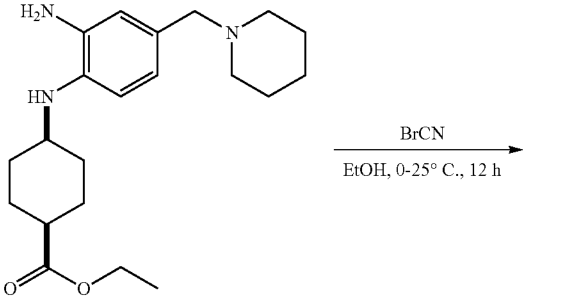

-continued

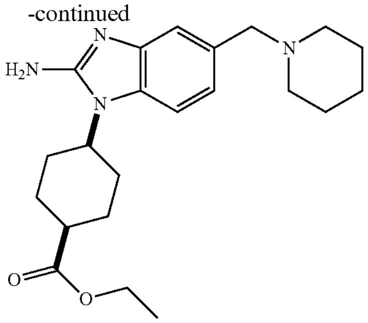

To a solution of cyanic bromide (1.41 g, 13.35 mmol, 982.10 μL, 1.2 eq) in ethanol (20 mL) was added a solution of ethyl (1s,4s)-4-((2-amino-4-(piperidin-1-ylmethyl)phenyl)amino)cyclohexane-1-carboxylate (4 g, 11.13 mmol, 1 eq) in ethanol (40 mL) at 0° C. The mixture was stirred at 0-25° C. for 10 hours. The reaction mixture was quenched by addition of a saturated aqueous solution of sodium bicarbonate (20 mL) at 25° C., and then extracted with ethyl acetate (100 mL×2). The combined organic layers were dried over anhydrous sodium sulfate, filtered and concentrated under reduced pressure to give a residue. The residue was purified by preparative HPLC. The appropriate fractions were pooled and the pH was adjusted to pH=8 by the addition of a saturated aqueous solution of sodium bicarbonate (20 mL) at 25° C. The mixture was extracted with ethyl acetate (100 mL×2), concentrated under reduced pressure to give ethyl (1s,4s)-4-(2-amino-5-(piperidin-1-ylmethyl)-1H-benzo[d]imidazol-1-yl)cyclohexane-1-carboxylate (1 g, 2.60 mmol, 23% yield) as a white solid. MS (ESI) m/z: 385.3. $[M+H]^+$.

Step 5:

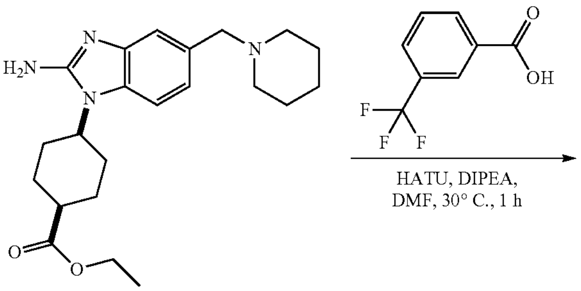

-continued

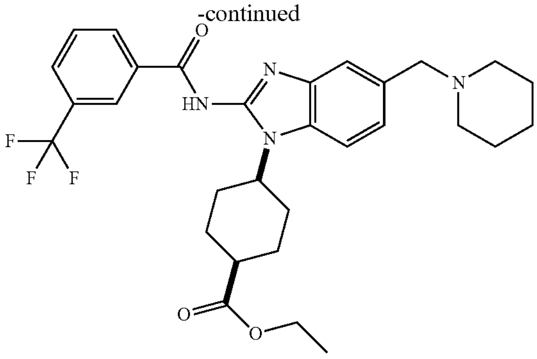

To a solution of 3-(trifluoromethyl)benzoic acid (543.88 mg, 2.86 mmol, 1.1 eq) in N,N-dimethylformamide (10 mL) was added HATU (1.19 g, 3.12 mmol, 1.2 eq) and N,N-diisopropylethylamine (1.34 g, 10.40 mmol, 1.81 mL, 4 eq), ethyl (1s,4s)-4-(2-amino-5-(piperidin-1-ylmethyl)-1H-benzo[d]imidazol-1-yl)cyclohexane-1-carboxylate (1 g, 2.60 mmol, 1 eq). The mixture was stirred at 25° C. for 1 hour. The reaction mixture was quenched by the addition of water (10 mL) at 25° C., and then diluted with ethyl acetate (20 mL) and extracted with ethyl acetate (20 mL×2). The combined organic layers were washed with a brine solution (20 mL×2), dried over anhydrous sodium sulfate, filtered and concentrated under reduced pressure. The resulting residue was purified by silica gel column chromatography (gradient from 50: to 5:1 ethyl acetate:methanol) to afford ethyl (1s,4s)-4-(5-(piperidin-1-ylmethyl)-2-(3-(trifluoromethyl) benzamido)-1H-benzo[d]imidazol-1-yl)cyclohexane-1-carboxylate (1.2 g, 2.16 mmol, 83% yield) as a white solid. MS (ESI) m/z: 557.3. [M+H]+.

Step 6:

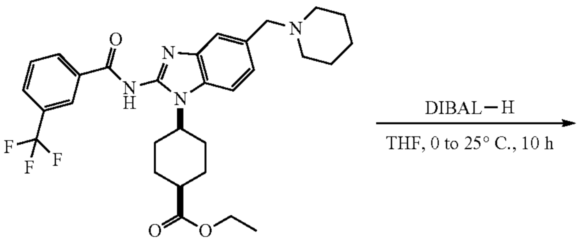

-continued

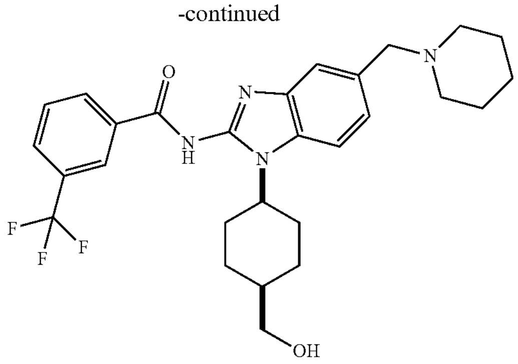

To a solution of ethyl (1s,4s)-4-(5-(piperidin-1-ylmethyl)-2-(3-(trifluoromethyl)benzamido)-1H-benzo[d]imidazol-1-yl)cyclohexane-1-carboxylate (1.2 g, 2.16 mmol, 1 eq) in tetrahydrofuran (10 mL) was added diisobutylaluminumhydride (1 M, 4.74 mL, 2.2 eq) at 0 C. The mixture was stirred at 0 to 25° C. for 12 hours. The reaction mixture was quenched by the addition of a saturated aqueous solution of ammonium chloride (50 mL) at 0° C., and then diluted with ethyl acetate (10 mL) and extracted with ethyl acetate (20 mL×3). The combined organic layers were washed with brine (20 mL×2), dried over anhydrous sodium sulfate, filtered and concentrated under reduced pressure. The resulting residue was purified by silica gel column chromatography (eluted with petroleum ether:ethyl acetate=1:1 to 0:1) to afford N-(1-((1s,4s)-4-(hydroxymethyl)cyclohexyl)-5-(piperidin-1-ylmethyl)-1H-benzo[d]imidazol-2-yl)-3-(trifluoromethyl)benzamide (0.5 g, 777 μmol, 36% yield, 80% purity) as a yellow oil. MS (ESI) m/z: 515.1 [M+H]+.

Step 7:

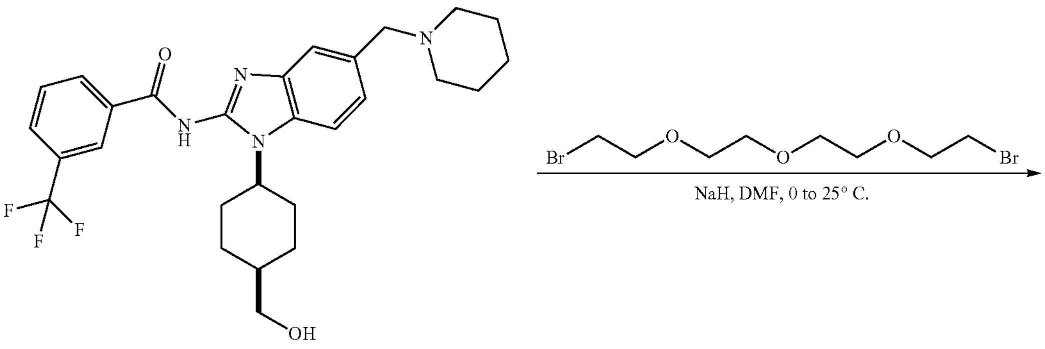

-continued

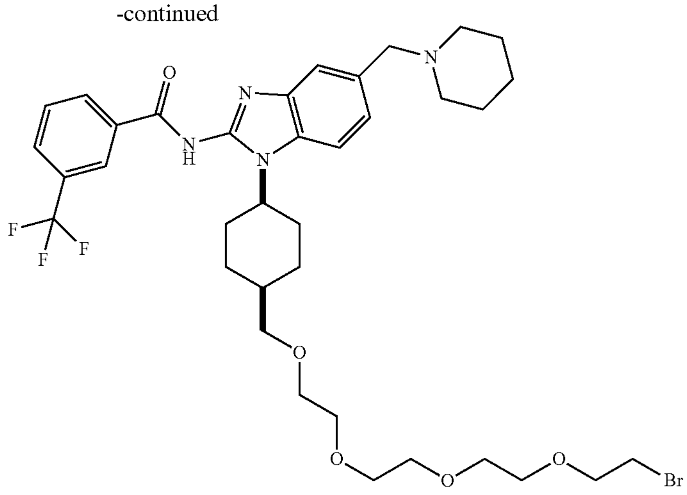

To a solution of N-(1-((1s,4s)-4-(hydroxymethyl)cyclohexyl)-5-(piperidin-1-ylmethyl)-1H-benzo[d]imidazol-2-yl)-3-(trifluoromethyl)benzamide (0.5 g, 971 μmol, 1 eq) in dimethylformamide (2 mL) was added sodium hydride (155.5 mg, 3.89 mmol, 60% purity, 4 eq) at 0° C. After stirring at 0° C. for 0.5 hour, 1-(2-bromoethoxy)-2-[2-(2-bromoethoxy)ethoxy]ethane (932.8 mg, 2.91 mmol, 73.1 μL, 3 eq) was added to the reaction. The mixture was stirred at 0 to 25° C. for 1.5 hours. The reaction mixture was concentrated to give a residue which was purified by preparative HPLC to afford N-(1-((1s,4s)-4-(13-bromo-2,5,8,11-tetraoxatridecyl)cyclohexyl)-5-(piperidin-1-ylmethyl)-1H-benzo[d]imidazol-2-yl)-3-(trifluoromethyl)benzamide (0.2 g, 238.83 μmol, 25% yield, 90% purity) obtained as a yellow oil. MS (ESI) m/z: 753.3 $[M+H]^+$.

Step 8:

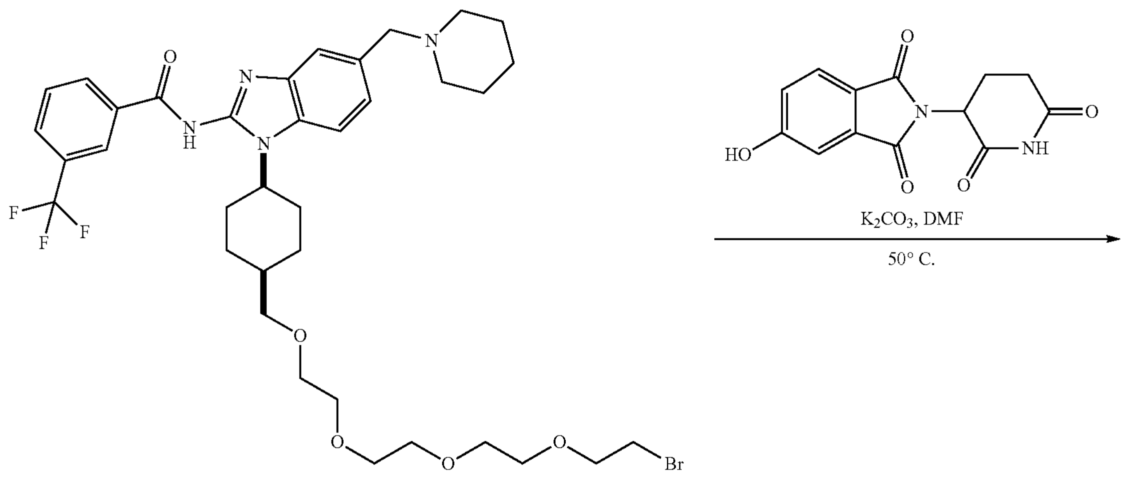

-continued

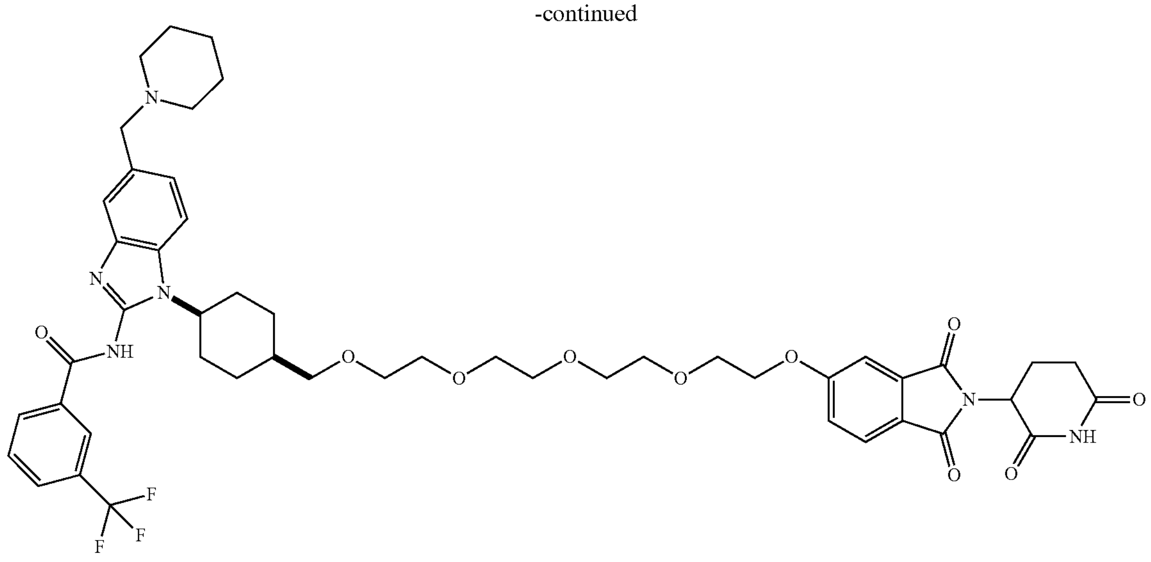

To a solution of N-(1-((1s,4s)-4-(13-bromo-2,5,8,11-tetraoxatridecyl)cyclohexyl)-5-(piperidin-1-ylmethyl)-1H-benzo[d]imidazol-2-yl)-3-(trifluoromethyl)benzamide (0.15 g, 199.02 μmol, 1 eq) in dimethylformamide (3 mL) was added potassium carbonate (82.52 mg, 597.06 mol, 3 eq) and 2-(2,6-dioxo-3-piperidyl)-5-hydroxy-isoindoline-1,3-dione (81.87 mg, 298.53 mol, 1.5 eq). The mixture was allowed to stir at 60° C. for 12 hours. The reaction mixture was concentrated to give a residue which was purified by preparative HPLC to afford N-(1-((1s,4s)-4-(13-((2-(2,6-dioxopiperidin-3-yl)-1,3-dioxoisoindolin-5-yl)oxy)-2,5,8,11-tetraoxatridecyl)cyclohexyl)-5-(piperidin-1-ylmethyl)-1H-benzo[d]imidazol-2-yl)-3-(trifluoromethyl)benzamide (19.1 mg, 19.36 μmol, 10% yield, 96% purity) obtained as a white solid. MS (ESI) m/z: 947.1 $[M+H]^+$. $^1H$ NMR (400 MHz, DMSO-$d_6$) δ ppm 12.83 (br s, 1H) 11.12 (s, 1H) 8.50 (d, J=7.88 Hz, 1H) 8.43 (s, 1H) 8.30 (s, 1H) 7.90 (br d, J=7.64 Hz, 1H) 7.81 (d, J=8.26 Hz, 1H) 7.74 (t, J=7.68 Hz, 1H) 7.56 (d, J=8.38 Hz, 1H) 7.51 (s, 1H) 7.43 (d, J=2.14 Hz, 1H) 7.34 (dd, J=8.32, 2.31 Hz, 1H) 7.15-7.24 (m, 1H) 5.12 (dd, J=12.88, 5.38 Hz, 1H) 4.72 (br s, 1H) 4.24-4.32 (m, 2H) 3.72-3.79 (m, 2H) 3.68 (br d, J=7.50 Hz, 2H) 3.45-3.59 (m, 18H) 1.40 (br s, 2H) 2.89 (ddd, J=17.40, 14.13, 5.50 Hz, 1H) 2.52-2.63 (m, 3H) 2.30-2.35 (m, 4H) 2.00-2.09 (m, 2H) 1.86-1.96 (m, 2H) 1.60-1.77 (m, 4H) 1.49 (br d, J=5.00 Hz, 4H).

The following compounds may be prepared in an analogous fashion as the exemplary synthesis described for Exemplary Compound 42.

| Exemplary Compound | MS |
|---|---|
| 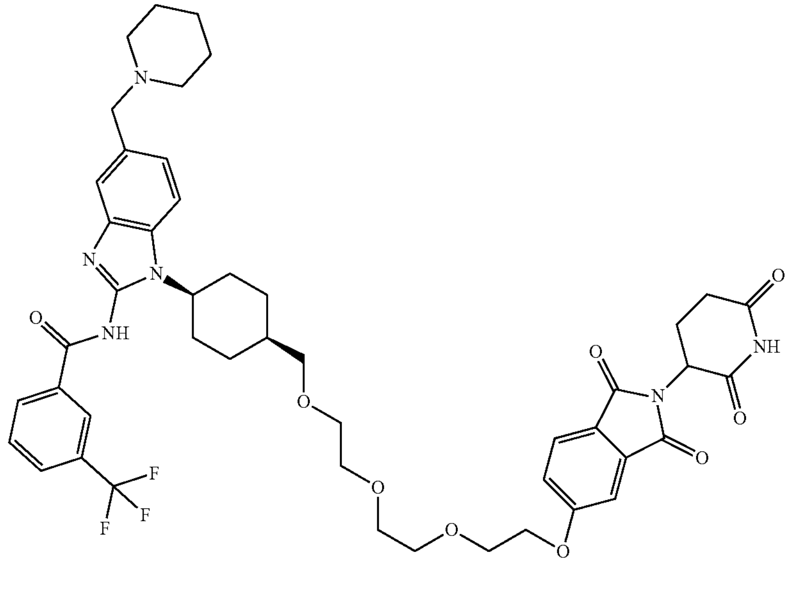 [SMILES: O=C1CCC(N2C(=O)c3ccc(OCCOCCOCCOC[C@H]4CC[C@@H](n5c(NC(=O)c6cccc(C(F)(F)F)c6)nc6cc(CN7CCCCC7)ccc65)CC4)cc3C2=O)C(=O)N1]<br>Exemplary Compound 43 | 903.66 |

-continued

| Exemplary Compound | MS |
| --- | --- |
| 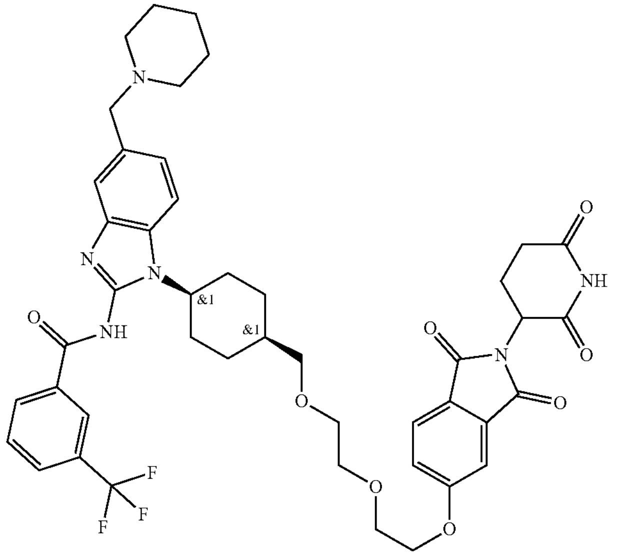 [SMILES: O=C1CCC(N2C(=O)c3ccc(OCCOCCOC[C@H]4CC[C@@H](n5c(NC(=O)c6cccc(C(F)(F)F)c6)nc6cc(CN7CCCCC7)ccc65)CC4)cc3C2=O)C(=O)N1] Exemplary Compound 44 | 859.62 |

Exemplary Synthesis of Exemplary Compound 45

N-(1-((1s,4s)-4-((2-((2-(2,6-dioxopiperidin-3-yl)-1,3-dioxoisoindolin-5-yl)oxy)ethoxy)methyl)cyclohexyl)-5-fluoro-1H-benzo[d]imidazol-2-yl)-3-(trifluoromethyl)benzamide Step 1:

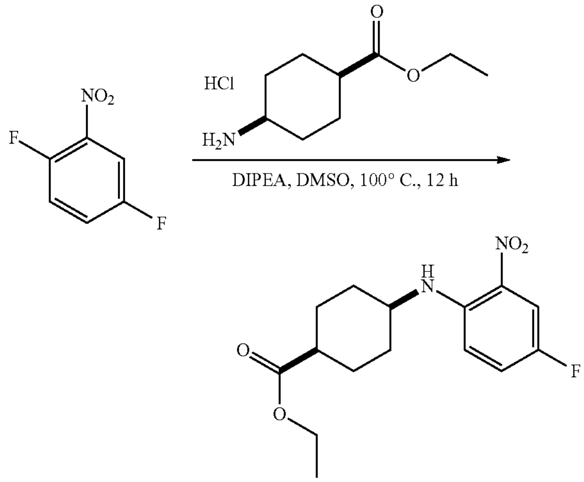

A solution of ethyl (1s,4s)-4-aminocyclohexanecarboxylate, Intermediate 1 (22 g, 105.92 mmol, 1 eq, hydrochloride), 1,4-difluoro-2-nitro-benzene (16.85 g, 105.92 mmol, 11.46 mL, 1.0 eq) and diisopropylethylamine (67.29 g, 520.67 mmol, 90.69 mL, 4.92 eq) in dimethylsulfoxide (200 mL) was stirred at 100° C. for 2.5 hours. LCMS analysis of the crude reaction mixture showed the reaction reached completion. The reaction mixture was poured into water (1000 mL). The mixture was extracted with ethyl acetate (1000 mL×3). The combined organic phase was washed with brine (1000 mL×3), dried over anhydrous sodium sulfate, filtered and concentrated under reduced pressure to afford a residue. The crude product was purified by recrystallization from petroleum ether (100 mL) at 0° C. to afford ethyl (1s,4s)-4-((4-fluoro-2-nitrophenyl)amino)cyclohexane-1-carboxylate (29 g, 93.45 mmol, 88% yield) as a red solid. $^1$H NMR (400 MHz, $CDCl_3$) δ=1.28 (t, J=7.15 Hz, 3H), 1.71-1.90 (m, 6H), 1.93-2.06 (m, 2H), 2.47-2.57 (m, 1H), 3.68 (br s, 1H), 4.17 (q, J=6.8 Hz, 2H), 6.84 (dd, J=9.6, 4.8 Hz, 1 H), 7.23 (ddd, J=9.6, 6.8, 2.8 Hz, 1H), 7.90 (dd, J=9.6, 3.2 Hz, 1H), 8.14 (br d, J=6.4 Hz, 1H).

Step 2:

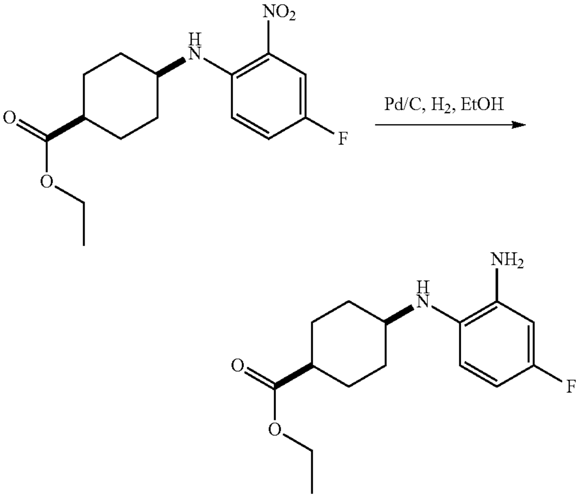

To a solution of ethyl (1s,4s)-4-((4-fluoro-2-nitrophenyl)amino)cyclohexane-1-carboxylate (2 g, 6.44 mmol, 1 eq) in ethyl alcohol (40 mL) was added palladium on carbon (0.2 g, 10% purity) under nitrogen atmosphere. The suspension was degassed and purged with a hydrogen atmosphere 3 times. The mixture was stirred under hydrogen (15 psi) at 25° C. for 3 hours. LCMS analysis indicated the reaction had reached completion. The suspension was filtered, and the filtrate was concentrated under reduced pressure to yield crude ethyl (1s,4s)-4-((2-amino-4-fluorophenyl)amino)cyclohexane-1-carboxylate (1.7 g, 6.06 mmol, 94% yield), obtained as a red oil and used in a subsequent reaction without further purification. $^1$H NMR (400 MHz, $CDCl_3$) δ=1.27 (t, J=7.15 Hz, 3H), 1.59-1.84 (m, 6H), 1.91-2.10 (m, 2H), 2.49 (tt, J=7.6, 3.6 Hz, 1H), 2.60-3.12 (m, 1H), 3.26-3.40 (m, 1H), 3.48-3.82 (m, 2H), 4.11-4.26 (m, 2H), 6.38-6.49 (m, 2H), 6.60 (dd, J=8.4, 5.6 Hz, 1H).

Step 3:

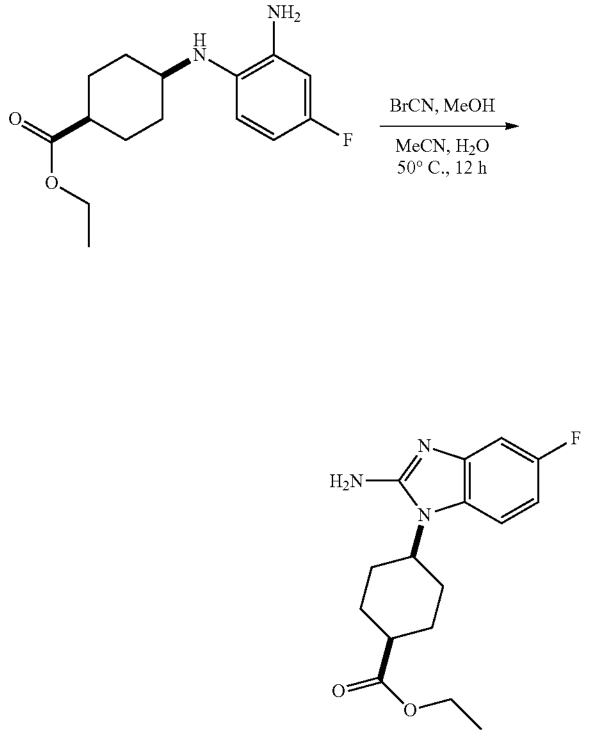

A solution of ethyl (1s,4s)-4-((2-amino-4-fluorophenyl)amino)cyclohexane-1-carboxylate (1.7 g, 6.06 mmol, 1 eq) in methyl alcohol (17 mL) was treated with a solution of bromine ethyl cyanide (963.5 mg, 9.10 mmol, 669.1 μL, 1.5 eq) in acetonitrile (2 mL) and water (2 mL). The reaction mixture was stirred at 50° C. for 12 hours. LCMS analysis of the reaction mixture showed the reaction was complete. The reaction mixture was diluted with water (30 mL). The pH was adjusted to pH=8 with sodium carbonate, and the mixture was extracted with ethyl acetate (30 mL×3). The combined organic layers were washed with brine (20 mL×3), dried over anhydrous sodium sulfate, filtered and concentrated under reduced pressure. The residue was purified by silica gel column chromatography to afford ethyl (1s,4s)-4-(2-amino-5-fluoro-1H-benzo[d]imidazol-1-yl)cyclohexane-1-carboxylate (1.7 g, 5.57 mmol, 91% yield) as a yellow solid. MS (ESI) n/z: 306.1 [M+H]$^+$. $^1$H NMR (400 MHz, $CDCl_3$) δ 1.32 (t, J=6.8 Hz, 3 H), 1.64 (tt, J=14.0, 4.4 Hz, 2H), 1.73-1.85 (m, 2H), 2.27 (br dd, J=14.0, 1.6 Hz, 2H), 2.44 (qd, J=13.2, 4.0 Hz, 2H), 2.65-2.81 (m, 1H), 4.00 (tt, J=12.8, 4.8 Hz, 1H), 4.24 (q, J=7.2 Hz, 2H), 5.28 (br s, 2H), 6.68-6.81 (m, 1H), 7.03-7.17 (m, 2H).

Step 4:

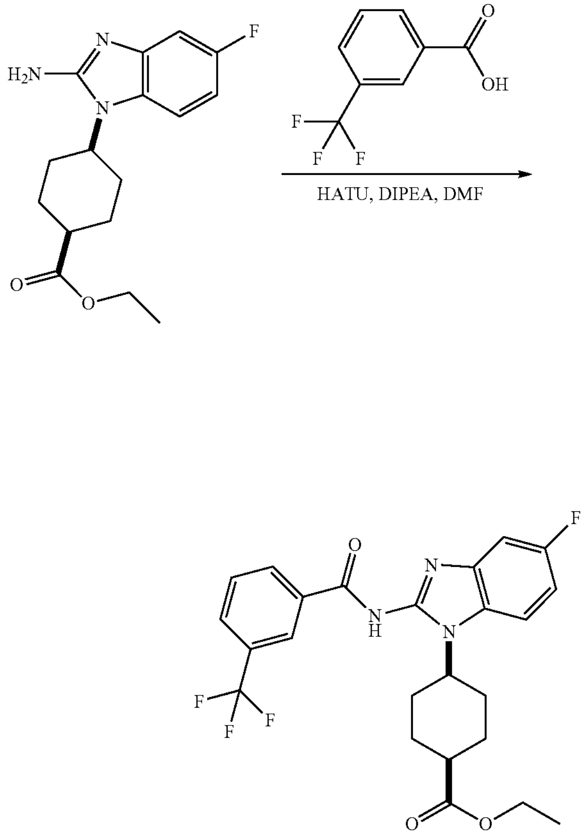

To a solution of 3-(trifluoromethyl)benzoic acid (622.63 mg, 3.27 mmol, 1 eq) in N,N-dimethylformamide (10 mL) was added HATU (1.49 g, 3.93 mmol, 1.2 eq) and N,N-diisopropylethylamine (1.27 g, 9.82 mmol, 1.71 mL, 3 eq). After stirring at 25° C. for 10 min, ethyl (1s,4s)-4-(2-amino-5-fluoro-1H-benzo[d]imidazol-1-yl)cyclohexane-1-carboxylate (1.0 g, 3.27 mmol, 1 eq) was added. The resulting mixture was stirred at 25° C. for 11 hours and 50 minutes. LCMS analysis of an aliquot indicated complete conversion. The mixture was poured into ice-water (60 mL). The aqueous phase was extracted with ethyl acetate (30 mL×3). The combined organic phase was washed with brine (20 mL×2), dried with anhydrous sodium sulfate, filtered and concentrated under vacuum. The residue was purified by silica gel column chromatography (eluted with a gradient from 10 to 5:1 petroleum ether:ethyl acetate) to afford ethyl (1s,4s)-4-(5-fluoro-2-(3-(trifluoromethyl)benzamido)-1H-benzo[d]imidazol-1-yl)cyclohexane-1-carboxylate (1.3 g, 2.72 mmol, 83% yield) as a gray solid. MS (ESI) n/z: 478.1 [M+H]$^+$. $^1$H NMR (400 MHz, $CDCl_3$) δ=1.34 (t, J=7.15 Hz, 3H), 1.79-1.91 (m, 4H), 2.38 (br d, J=13.6 Hz, 2H), 2.47-2.66 (m, 2H), 2.84 (br s, 1H), 4.28 (q, J=7.2 Hz, 2H), 4.97 (ddd, J=12.4, 8.8, 4.0 Hz, 1H), 6.98 (td, J=9.2, 2.4 Hz, 1H), 7.05 (dd, J=8.0, 2.4 Hz, 1H), 7.43 (dd, J=8.8, 4.4 Hz, 1H), 7.58 (t, J=7.6 Hz, 1H), 7.74 (d, J=7.6 Hz, 1H), 8.51 (d, J=8.0 Hz, 1H), 8.57 (s, 1H), 12.70 (br s, 1H).

Step 5:

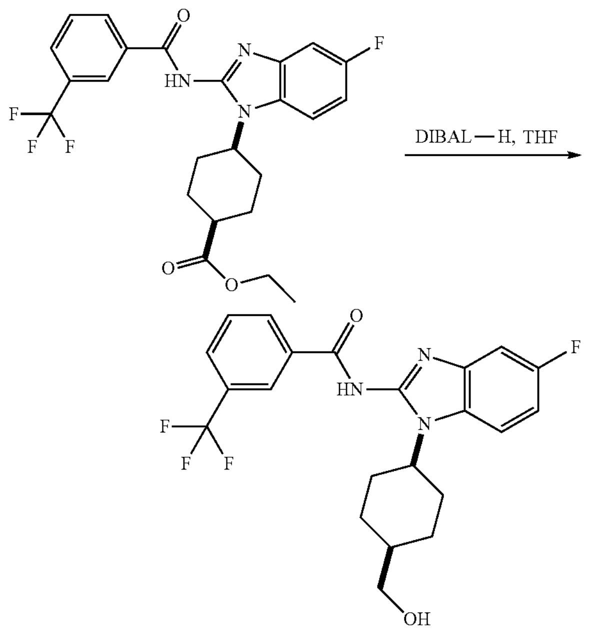

To a solution of ethyl (1s,4s)-4-(5-fluoro-2-(3-(trifluoromethyl)benzamido)-1H-benzo[d]imidazol-1-yl)cyclohexane-1-carboxylate (0.6 g, 1.26 mmol, 1 eq) in tetrahydrofuran (12 mL) was added diisobutylaluminium hydride (1 M, 2.51 mL, 2 eq) at 0° C. The reaction mixture was stirred at 25° C. for 12 hours. LCMS analysis showed the reaction was complete. The reaction mixture was quenched with water (2 mL) at 0° C., diluted with ethyl acetate (80 mL), and anhydrous sodium sulfate (10 g) was added. The mixture was stirred at 25° C. for 15 minutes and filtered. The filtrate was concentrated under reduced pressure. The resulting residue was purified by silica gel column chromatography (eluted with a gradient from 5 to 3:1 petroleum ether: ethyl acetate) to afford N-(5-fluoro-1-((1s,4s)-4-(hydroxymethyl)cyclohexyl)-1H-benzo[d]imidazol-2-yl)-3-(trifluoromethyl)benzamide (0.5 g, 1.14 mmol, 90% yield, 99% purity), obtained as a white solid. MS (ESI) m/z: 436.2 $[M+H]^+$. $^1H$ NMR (400 MHz, $CDCl_3$) δ=1.58-1.87 (m, 5H), 1.97-2.18 (m, 3H), 2.48-2.69 (m, 2H), 3.96 (br d, J=7.2 Hz, 2H), 4.59-4.80 (m, 1H), 6.99 (td, J=9.2, 2.4 Hz, 1H), 7.07 (dd, J=8.0, 2.0 Hz, 1 H), 7.31 (dd, J=8.8, 4.2 Hz, 1 H), 7.53-7.64 (m, 1H), 7.75 (br d, J=7.6 Hz, 1H), 8.47 (br d, J=7.8 Hz, 1H), 8.59 (s, 1H), 12.24-13.35 (m, 1H).

Step 6:

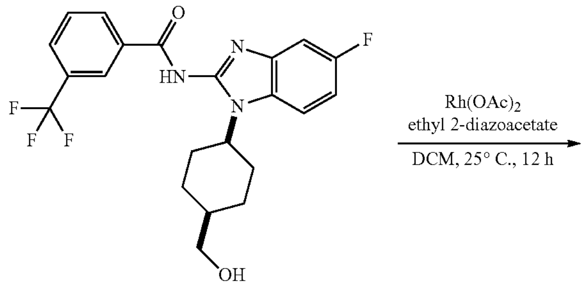

-continued

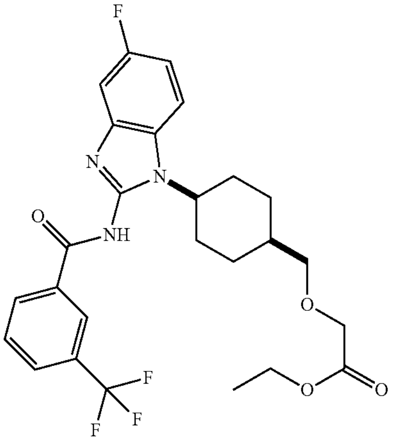

To a solution of N-(5-fluoro-1-((1s,4s)-4-(hydroxymethyl)cyclohexyl)-1H-benzo[d]imidazol-2-yl)-3-(trifluoromethyl)benzamide (0.7 g, 1.61 mmol, 1 eq) and diacetoxyrhodium (53.3 mg, 241.15 μmol, 0.15 eq) in dichloromethane (20 mL) was added ethyl 2-diazoacetate (1.28 g, 11.25 mmol, 7 eq) at 0° C. under nitrogen. The mixture was stirred at 25° C. for 12 hours. LCMS analysis showed the reaction was complete. The mixture was concentrated and the resulting residue was purified by silica gel column chromatography (petroleum ether/ethyl acetate=5/1 to 2/1) to afford ethyl 2-(((1s,4s)-4-(5-fluoro-2-(3-(trifluoromethyl)benzamido)-1H-benzo[d]imidazol-1-yl)cyclohexyl) methoxy)acetate (0.6 g, 1.15 mmol, 71% yield) as a light brown oil. MS (ESI) m/z: 522.2 $[M+H]^+$.

Step 7:

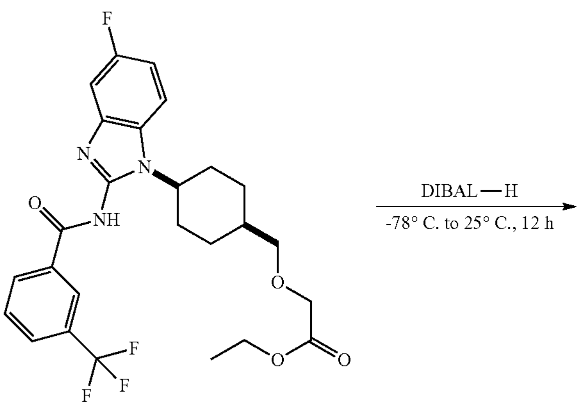

-continued

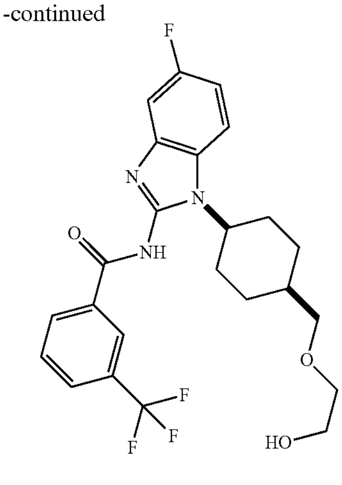

-continued

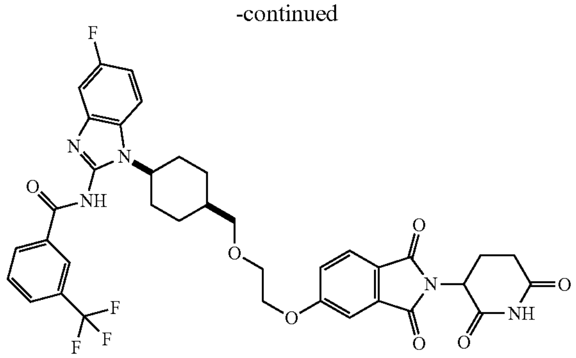

To a solution of ethyl 2-(((1s,4s)-4-(5-fluoro-2-(3-(trifluoromethyl)benzamido)-1H-benzo[d]imidazol-1-yl)cyclohexyl)methoxy)acetate (0.3 g, 575.3 μmol, 1 eq) in dichloromethane (8 mL) was added diisobutylaluminium hydride (1 M, 2.30 mL, 4 eq) dropwise at −78° C. The reaction was stirred at 25° C. for 12 hours. Thin layer chromatography (petroleum ether/ethyl acetate=3:1) analysis indicated the reaction was complete. The reaction mixture was quenched with a saturated aqueous solution of ammonium chloride (3 mL) at −78° C., diluted with ethyl acetate (50 mL), dried over anhydrous sodium sulfate, filtered and concentrated under reduced pressure. The resulting residue was purified by silica gel column chromatography (eluted with a gradient from 10 to 5:1 petroleum ether:ethyl acetate) to afford N-(5-fluoro-1-((1s,4s)-4-((2-hydroxyethoxy)methyl)cyclohexyl)-1H-benzo[d]imidazol-2-yl)-3-(trifluoromethyl)benzamide (0.15 g, 312.8 μmol, 54% yield), obtained as a white solid.

Step 8:

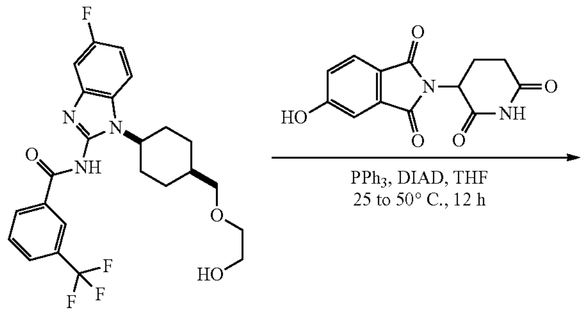

To a mixture of N-(5-fluoro-1-((1s,4s)-4-((2-hydroxyethoxy)methyl)cyclohexyl)-1H-benzo[d]imidazol-2-yl)-3-(trifluoromethyl)benzamide (40 mg, 83.43 μmol, 1 eq), 2-(2,6-dioxo-3-piperidyl)-5-hydroxy-isoindoline-1,3-dione (30 mg, 109.4 μmol, 1.31 eq) and triphenylphosphine (43.76 mg, 166.85 μmol, 2 eq) in tetrahydrofuran (2 mL) was added dropwise diisopropyl azodicarboxylate (33.74 mg, 166.85 μmol, 32.44 μL, 2 eq) in tetrahydrofuran (0.5 mL) at 25° C. The mixture was stirred at 25° C. for 0.5 hour, then heated to 50° C. for 11.5 hours. LCMS analysis of an aliquot indicated formation of the desired compound. The mixture was concentrated under reduced pressure and the resulting residue was purified by semi-preparative reverse phase HPLC to obtain N-(1-((1s,4s)-4-((2-((2-(2,6-dioxopiperidin-3-yl)-1,3-dioxoisoindolin-5-yl)oxy)ethoxy) methyl)cyclohexyl)-5-fluoro-1H-benzo[d]imidazol-2-yl)-3-(trifluoromethyl)benzamide (6.2 mg, 8.26 umol, 9% yield, 98% purity) as a white solid. MS (ESI) m/z: 736.3 $[M+H]^+$. $^1H$ NMR (400 MHz, $CDCl_3$) δ=1.72-1.84 (m, 4H), 2.00-2.11 (m, 2H), 2.12-2.29 (m, 2H), 2.48-2.66 (m, 2H), 2.67-2.98 (m, 3H), 3.83 (d, J=7.2 Hz, 2H), 3.89-3.99 (m, 2H), 4.25-4.36 (m, 2H), 4.57-4.74 (m, 1H), 4.96 (dd, J=12.4, 5.2 Hz, 1H), 6.93-7.02 (m, 1H), 7.09 (dd, J=8.0, 2.4 Hz, 1H), 7.22 (dd, J=8.4, 2.4 Hz, 1H), 7.28-7.33 (m, 1H), 7.38 (d, J=2.4 Hz, 1H), 7.54-7.65 (m, 1H), 7.71-7.80 (m, 2H), 8.04 (s, 1H), 8.48 (d, J=7.6 Hz, 1 H), 8.57 (s, 1 H), 12.55-12.94 (m, 1H).

Scheme 10.

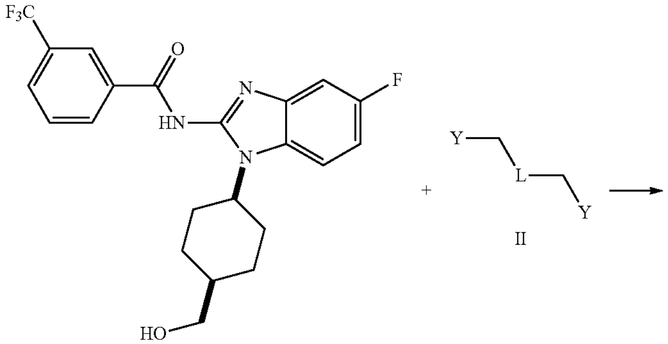

I

II

-continued

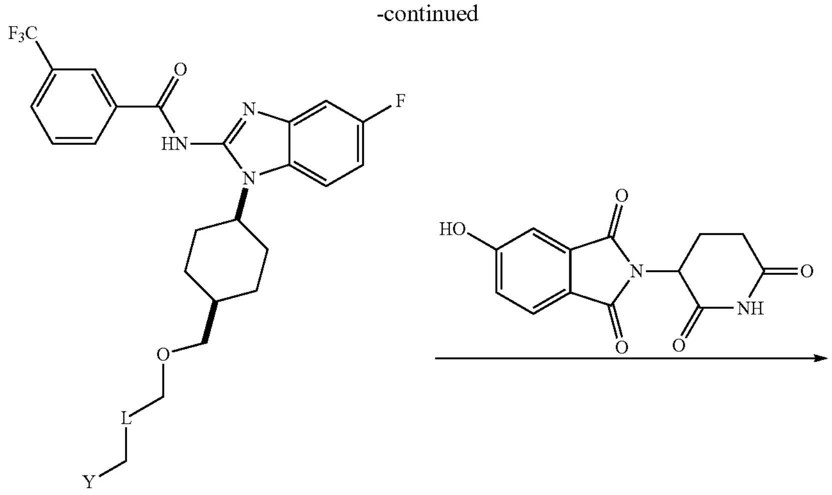

III

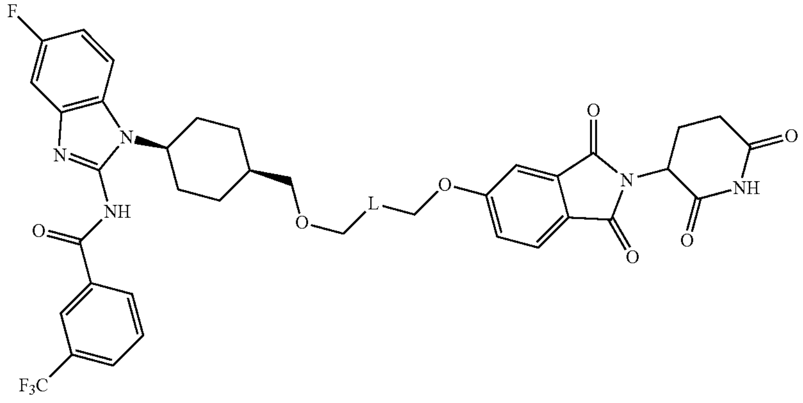

IV

A compound of formula I may be reacted with a reagent II (commercially available or readily prepared using standard reaction techniques known to one skilled in the art) where Y is an appropriate leaving group (e.g. OMs, OTs, Cl, Br, etc.) under O-alkylation conditions to produce a compound of formula III, wherein L represents an optional linker or portion of a linker. A compound of formula III can be reacted with 2-(2,6-dioxo-3-piperidyl)-5-hydroxy-isoindoline-1,3-dione to provide compounds of formula IV using suitable reaction conditions for an alkylation reaction, e.g. diisopropylethylamine, potassium iodide, DMSO or acetonitrile, 80° C.

Exemplary Synthesis of Exemplary Compound 46

N-(1-((1s,4s)-4-((2-(2-((2-(2,6-dioxopiperidin-3-yl)-1,3-dioxoisoindolin-5-yl)oxy)ethoxy)ethoxy)methyl)cyclohexyl)-5-fluoro-1H-benzo[d]imidazol-2-yl)-3-(trifluoromethyl)benzamide Step 1:

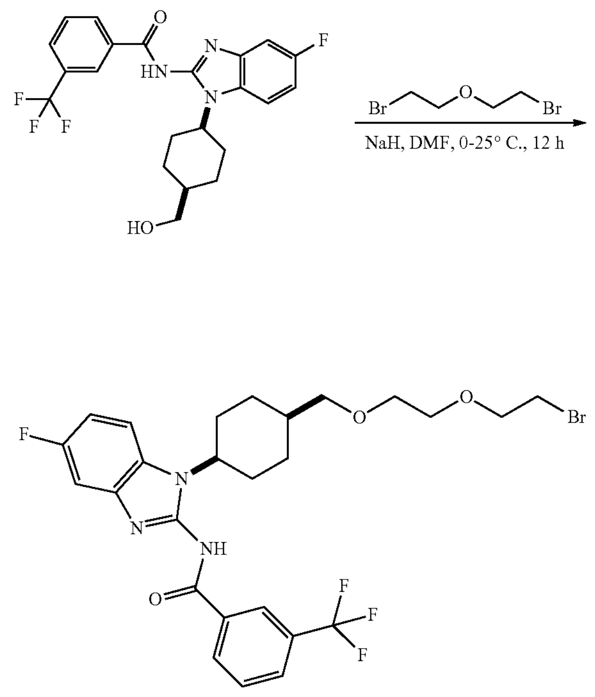

To a stirring mixture of sodium hydride (162.67 mg, 4.07 mmol, 60% purity, 2.21 eq) in N,N-dimethylformamide (8 mL) was added a solution of N-(5-fluoro-1-((1s,4s)-4-(hydroxymethyl)cyclohexyl)-1H-benzo[d]imidazol-2-yl)-3-(trifluoromethyl)benzamide (Example 43 Intermediate) (0.8 g, 1.84 mmol, 1 eq) in N,N-dimethylformamide (0.5 mL) dropwise at 0° C. under nitrogen. After addition, the mixture was stirred at 25° C. for 0.5 hour, after which 1-bromo-2-(2-bromoethoxy)ethane (520.0 mg, 2.24 mmol, 281.1 μL, 1.22 eq) was added to the mixture at 0° C. The mixture was stirred at 25° C. for 11.5 hours. LCMS analysis showed some formation of the desired mass. The reaction mixture was quenched with acetic acid (1.5 mL) at 0° C., diluted with water (30 mL) and extracted with ethyl acetate (3×30 m). The organic layers were combined washed with brine (2×20 mL), dried with anhydrous sodium sulfate, filtered and concentrated under vacuum to give a residue. The residue was purified by silica gel column chromatography (petroleum ether/ethyl acetate=5/1) and then further purified by preparative thin-layer chromatography (petroleum ether/ethyl acetate=2/1) to afford N-(1-((1s,4s)-4-((2-(2-bromoethoxy)ethoxy)methyl)cyclohexyl)-5-fluoro-1H-benzo[d]imidazol-2-yl)-3-(trifluoromethyl) benzamide (62 mg, 105.7 μmol, 5% yield) as a brown oil. MS (ESI) m/z: 588.2 $[M+H]^+$.

Step 2:

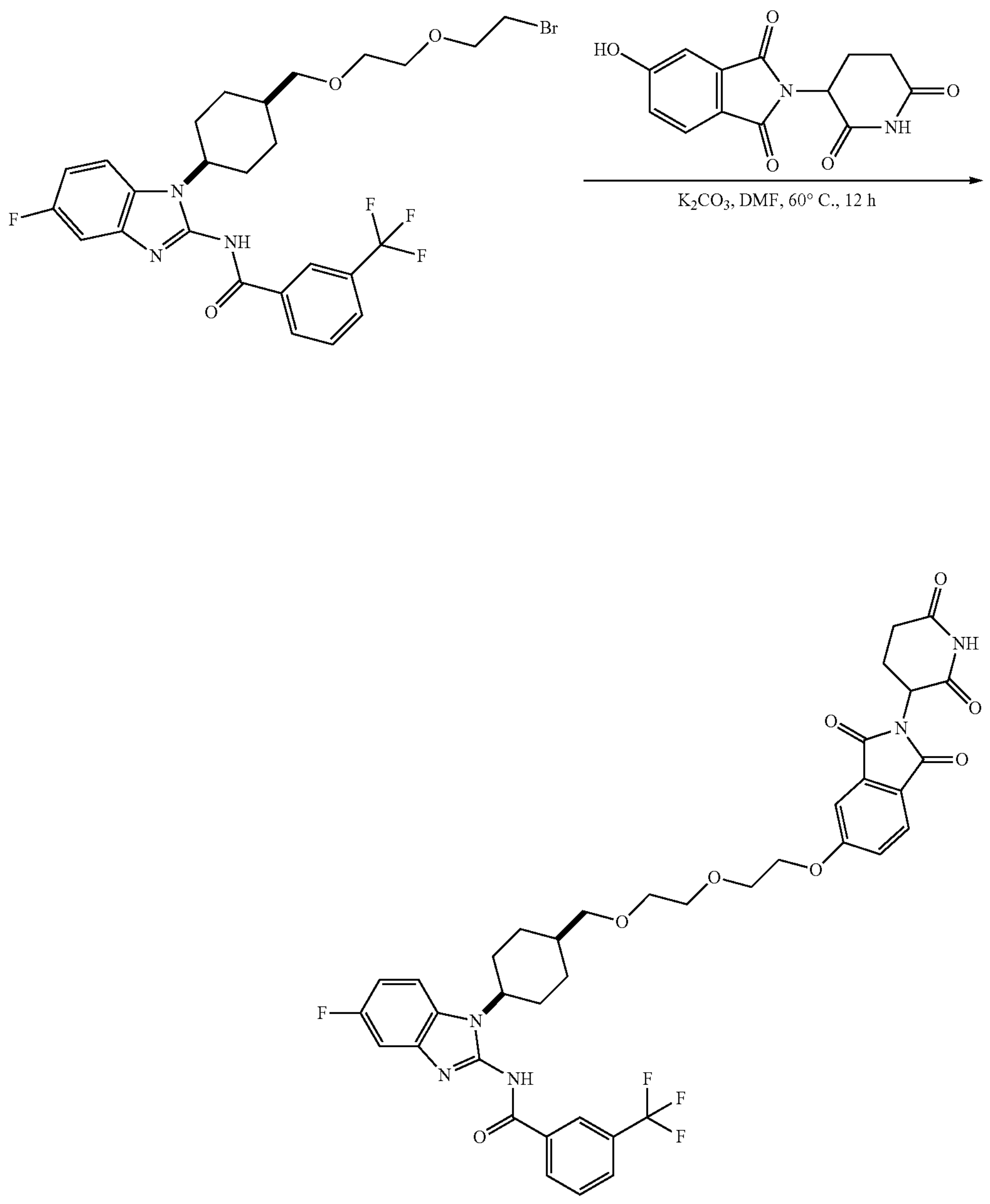

To a mixture of N-(1-((1s,4s)-4-((2-(2-bromoethoxy)ethoxy)methyl)cyclohexyl)-5-fluoro-1H-benzo[d]imidazol-2-yl)-3-(trifluoromethyl)benzamide (60 mg, 102.3 μmol, 1 eq) and 2-(2,6-dioxo-3-piperidyl)-5-hydroxy-isoindoline-1,3-dione (37 mg, 134.9 μmol, 1.32 eq) in N,N-dimethylformamide (2 mL) was added potassium carbonate (56.6 mg, 409.3 μmol, 4 eq). The mixture was stirred at 60° C. for 12 hours. LCMS analysis indicated the reaction to be complete. The mixture was then poured into ice-water (15 mL) and the aqueous phase was extracted with ethyl acetate (20 mL×3). The combined organic phases were washed with brine (20 mL×2), dried with anhydrous sodium sulfate, filtered and concentrated under vacuum. The residue was purified by semi-preparative reverse phase HPLC to afford N-(1-((1s,4s)-4-((2-(2-((2-(2,6-dioxopiperidin-3-yl)-1,3-dioxoisoindolin-5-yl)oxy)ethoxy)ethoxy)methyl)cyclohexyl)-5-fluoro-1H-benzo[d]imidazol-2-yl)-3-(trifluoromethyl)benzamide (9.1 mg, 11.5 μmol, 11% yield, 99% purity) as an off-white solid. MS (ESI) m/z: 780.2 $[M+H]^+$. $^1H$ NMR (400 MHz, $CDCl_3$) δ=1.71-1.84 (m, 4H), 2.02-2.09 (m, 2H), 2.11-2.24 (m, 2H), 2.47-2.64 (m, 2H), 2.68-2.96 (m, 3 H), 3.71-3.82 (m, 6H), 3.87-3.95 (m, 2H), 4.18-4.26 (m, 2H), 4.62-4.80 (m, 1H), 4.97 (dd, J=12.23, 5.2 Hz, 1H), 6.95 (td, J=8.8, 2.4 Hz, 1H), 7.03-7.09 (m, 1H), 7.14 (dd, J=8.4, 2.0 Hz, 1H), 7.23 (d, J=2.0 Hz, 1H), 7.32 (dd, J=8.8, 4.2 Hz, 1H), 7.55-7.62 (m, 1H), 7.68-7.79 (m, 2H), 8.11-8.19 (m, 1H), 8.48 (d, J=8.0 Hz, 1H), 8.56 (s, 1H), 12.43-12.98 (m, 1H).

The following compounds may be prepared in an analogous fashion as the exemplary synthesis described for Exemplary Compound 46.

| Exemplary Compound | [M + H]+ |
|---|---|
| 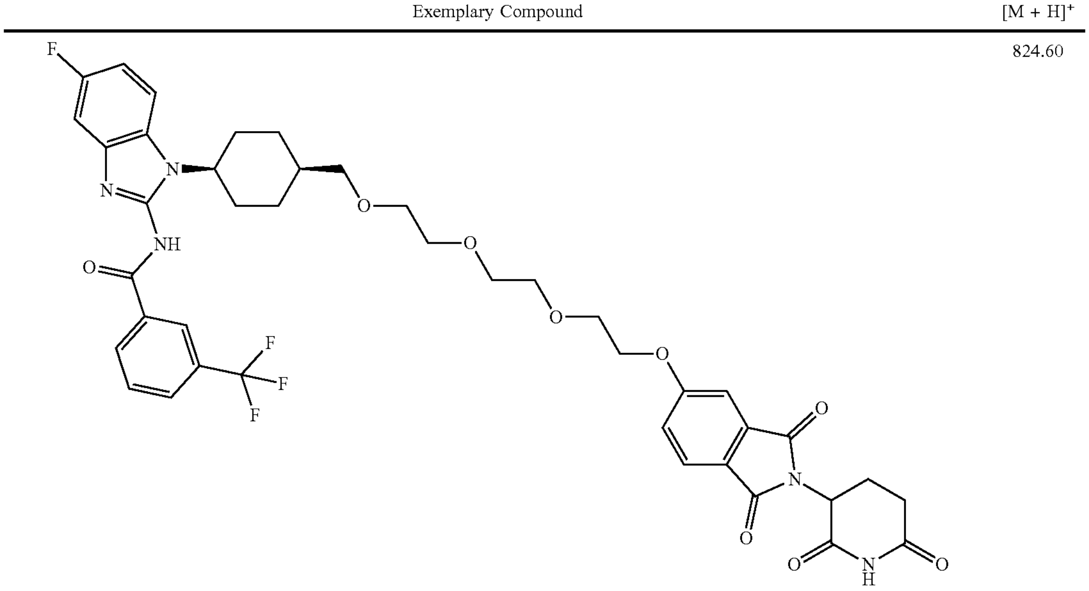 | 824.60 |
| Exemplary Compound 47 | |
| 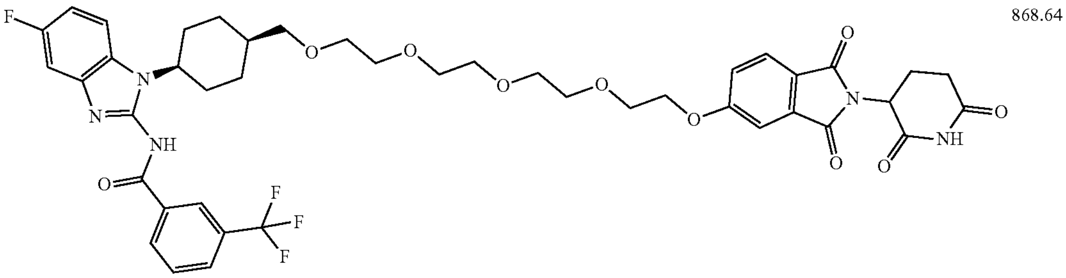 | 868.64 |
| Exemplary Compound 48 | |
Scheme 11.
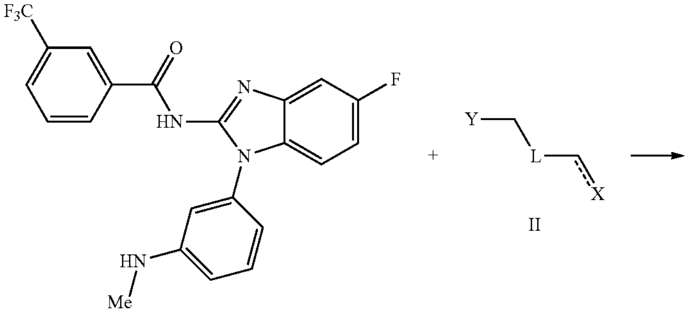
I
II -continued

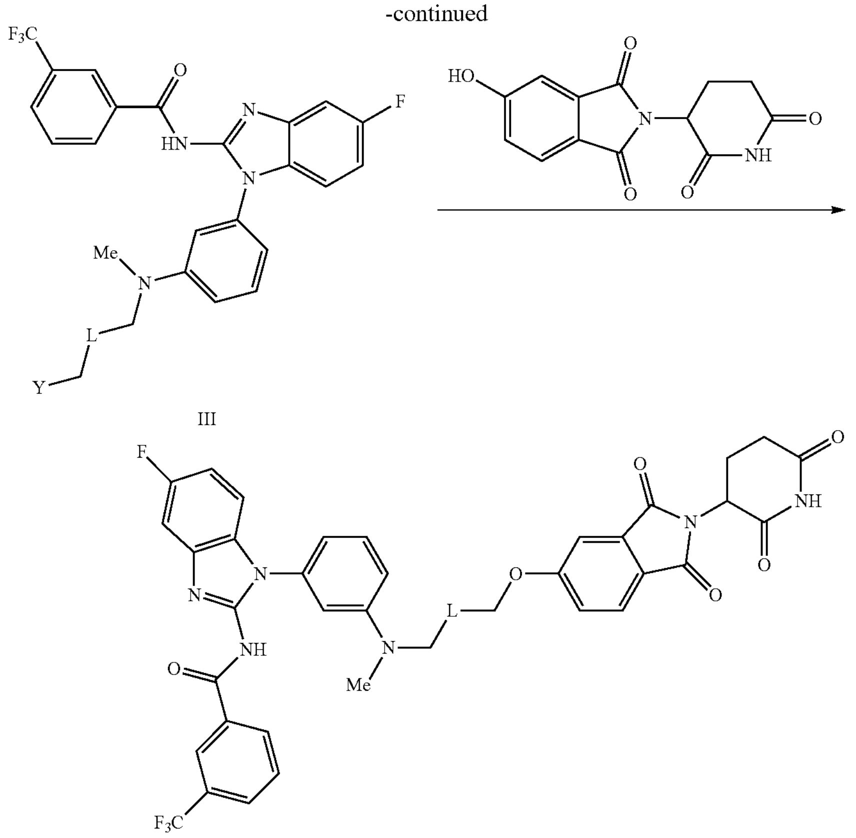

III

IV

A compound of formula I may be reacted with a reagent II (commercially available or readily prepared using standard reaction techniques known to one skilled in the art) where Y is an appropriate leaving group (e.g. OMs, OTs, Cl, Br, etc.) and X is either an appropriate leaving group or an aldehyde and wherein L represents an optional linker or portion of a linker. When X is an aldehyde, suitable reaction conditions to provide a compound of formula III entail reductive amination conditions, e.g. 2-methylpyridine borane complex, acetic acid, methanol, room temperature. A compound of formula III can be reacted with 2-(2,6-dioxo-3-piperidyl)-5-hydroxy-isoindoline-1,3-dione to provide compounds of formula IV using suitable reaction conditions for an alkylation reaction, e.g. diisopropylethylamine, potassium iodide, DMSO or acetonitrile, 80° C.

Exemplary Synthesis of Exemplary Compound 49

N-(1-(3-((2-(2-(2-((2-(2,6-dioxopiperidin-3-yl)-1,3-dioxoisoindolin-5-yl)oxy)ethoxy)ethoxy)ethyl)(methyl)amino)phenyl)-5-fluoro-1H-benzo[d]imidazol-2-yl)-3-(trifluoromethyl)benzamide Step 1:

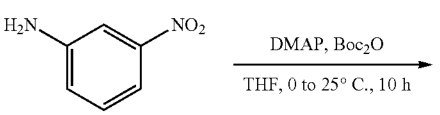

-continued

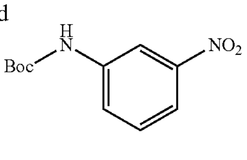

To a mixture of 3-nitroaniline (20 g, 144.80 mmol, 36.36 mL, 1 eq) and di-tert-butyl dicarbonate (31.60 g, 144.80 mmol, 33.26 mL, 1 eq) in tetrahydrofuran (300 mL) was added DMAP (19.46 g, 159.28 mmol, 1.1 eq) in portions at 0° C. The mixture was then stirred at 25° C. for 12 hours. LCMS analysis of an aliquot indicated consumption of the starting material. The reaction mixture was filtered, and the filtrate was concentrated under reduced pressure. The residue was purified by column chromatography (petroleum ether/ethyl acetate=10/1, Rf=0.3) to afford tert-butyl N-(3-nitrophenyl)carbamate (12 g, 50.37 mmol, 35% yield) as a white solid. $^1H$ NMR (400 MHz, DMSO-$d_6$) δ: 10.02-9.83 (m, 1H), 8.56-8.42 (m, 1H), 7.88-7.69 (m, 2H), 7.62-7.47 (m, 1H), 1.57-1.45 (m, 9H).

Step 2:

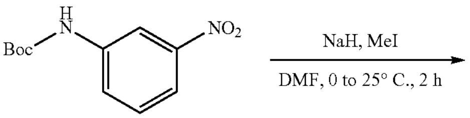

-continued

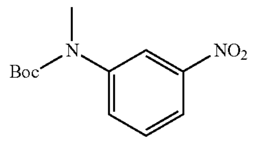

To a mixture of sodium hydride (2.42 g, 60.44 mmol, 60% purity, 1.2 eq) in dimethylformamide (120 mL) was added a solution of tert-butyl N-(3-nitrophenyl)carbamate (12 g, 50.37 mmol, 1 eq) in dimethylformamide (80 mL) portion-wise at 0° C. The mixture was stirred at 0° C. for 30 minutes, followed by portion-wise addition of iodomethane (10.72 g, 75.55 mmol, 4.70 mL, 1.5 eq) at 0° C. The mixture was then allowed to stir for 2.5 hours at 25° C. LCMS analysis confirmed consumption of the starting material. The reaction mixture was quenched by the addition of ice water (1000 mL) and the mixture was extracted with ethyl acetate (500 mL×3). The combined organic phase was concentrated under reduced pressure. The resulting residue was purified by column chromatography (petroleum ether/ethyl acetate=5/1, Rf=0.2) to afford tert-butyl N-methyl-N-(3-nitrophenyl)carbamate (9 g, 35.68 mmol, 71% yield) as a white solid. $^1$H NMR (400 MHz, DMSO-$d_6$) δ: 8.21-8.15 (m, 1H), 8.04-7.98 (m, 1H), 7.80-7.74 (m, 1H), 7.67-7.59 (m, 1H), 3.28-3.22 (m, 3H), 1.46-1.38 (m, 9H).

Step 3:

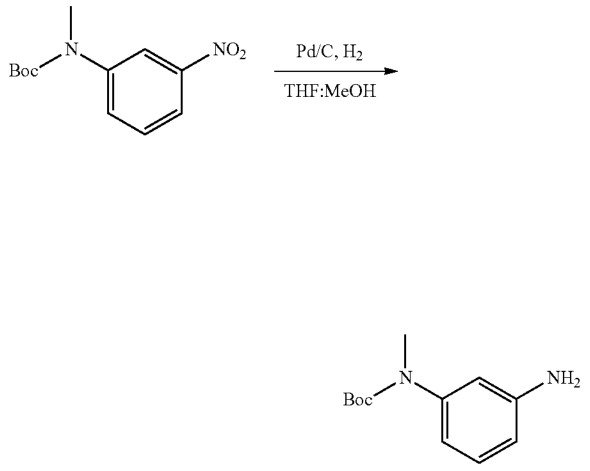

To a solution of tert-butyl N-methyl-N-(3-nitrophenyl) carbamate (9 g, 35.7 mmol, 1 eq) in tetrahydrofuran (70 mL) and methyl alcohol (70 mL) was added Pd/C (1 g, 10% purity). The suspension was degassed under vacuum and purged with hydrogen (1.44 g, 713.53 mmol, 20 eq) several times. The mixture was stirred under hydrogen (15 psi) at 25° C. for 12 hours. LCMS analysis indicated consumption of the starting material. The reaction mixture was filtered and the filtrate was concentrated under vacuum to afford crude tert-butyl N-(3-aminophenyl)-N-methyl-carbamate (7.9 g, 35.54 mmol, 99% yield), obtained as a white solid and used in the next reaction without further purification. $^1$H NMR (400 MHz, DMSO-$d_6$) δ: 7.00-6.91 (m, 1H), 6.47-6.43 (m, 1H), 6.40-6.34 (m, 2H), 5.14-5.02 (m, 2H), 3.12-3.06 (m, 3H), 1.43-1.34 (m, 9H).

Step 4:

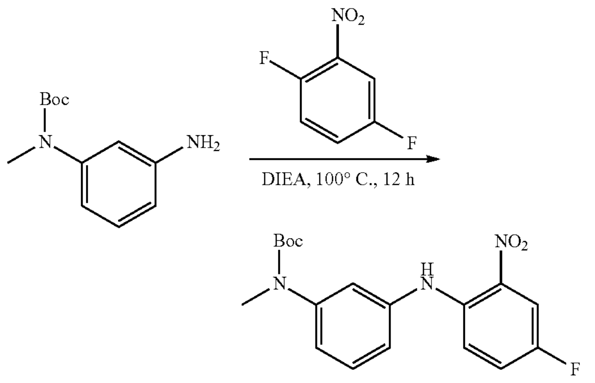

To a mixture of tert-butyl N-(3-aminophenyl)-N-methyl-carbamate (7.9 g, 35.54 mmol, 1 eq) and 1,4-difluoro-2-nitro-benzene (6.22 g, 39.09 mmol, 4.23 mL, 1.1 eq) in dimethylsulfoxide (20 mL) was added diisopropylethylamine (9.19 g, 71.08 mmol, 12.38 mL, 2 eq) in one portion. The mixture was stirred at 100° C. for 12 hours. LCMS analysis showed complete consumption of the starting material. The reaction mixture was quenched by the addition of ice water (100 mL) and the mixture was extracted with ethyl acetate (100 mL×3). The combined organic phase was concentrated under reduced pressure and the resulting residue was purified by column chromatography (petroleum ether/ethyl acetate=5/1, Rf=0.2) to afford tert-butyl N-[3-(4-fluoro-2-nitro-anilino)phenyl]-N-methyl-carbamate (7.5 g, 20.75 mmol, 58% yield) obtained as a white solid. MS (ESI) m/z: 384.1 [M+Na]$^+$.

Step 5:

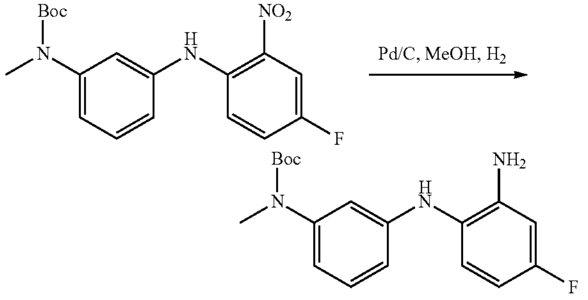

To a solution of tert-butyl N-[3-(4-fluoro-2-nitro-anilino) phenyl]-N-methyl-carbamate (2 g, 5.53 mmol, 1 eq) in methyl alcohol (20 mL) was added Pd/C (0.2 g, 5.53 mmol, 10% purity). The suspension was degassed under vacuum and purged with hydrogen several times. The mixture was stirred under hydrogen (15 psi) at 25° C. for 12 hours. LCMS analysis indicated complete conversion. The reaction mixture was filtered and the filtrate was concentrated under vacuum. The obtained crude tert-butyl N-[3-(2-amino-4-fluoro-anilino)phenyl]-N-methyl-carbamate (1.7 g, 5.13 mmol, 93% yield) was used for the next reaction without further purification and was obtained as a white solid. $^1$H NMR (400 MHz, DMSO-d6) δ: 7.13-7.08 (m, 1H), 7.08-7.02 (m, 1H), 6.97-6.91 (m, 1H), 6.55-6.41 (m, 4H), 6.34-6.26 (m, 1H), 5.13-5.03 (m, 2H), 4.08-4.07 (m, 1H), 3.14-3.06 (m, 3H), 1.39-1.29 (m, 9H).

Step 6:

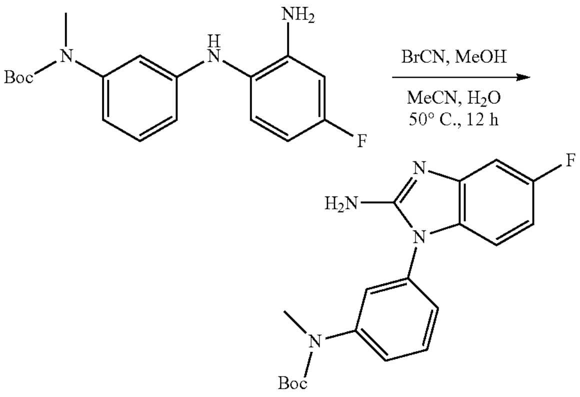

To a mixture of tert-butyl N-[3-(2-amino-4-fluoro-anilino)phenyl]-N-methyl-carbamate (5 g, 15.09 mmol, 1 eq) in methyl alcohol (84 mL) was added a mixture of cyanogen bromide (2.40 g, 22.63 mmol, 1.66 mL, 1.5 eq) in acetonitrile (6 mL) and water (6 mL) in portions. The mixture was heated to 50 C and stirred for 12 hours. LCMS analysis showed consumption of the starting material. The reaction mixture was concentrated under vacuum and the resulting residue was purified by preparative HPLC to afford tert-butyl N-[3-(2-amino-5-fluoro-benzimidazol-1-yl)phenyl]-N-methyl-carbamate (2 g, 5.61 mmol, 37% yield) as a white solid. $^1$H NMR (400 MHz, DMSO-$d_6$): 7.60-7.52 (m, 1H), 7.49-7.42 (m, 1H), 7.42-7.38 (m, 1H), 7.28-7.23 (m, 1H), 7.02-6.97 (m, 1H), 6.85-6.76 (m, 1H), 6.72-6.62 (m, 1H), 6.49-6.38 (m, 2H), 3.29-3.22 (m, 3H), 1.48-1.37 (m, 9H).

Step 7:

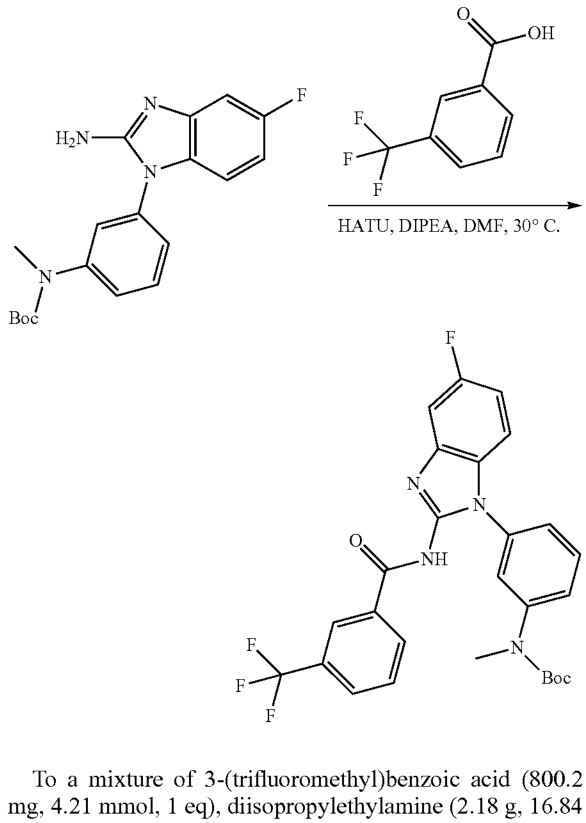

To a mixture of 3-(trifluoromethyl)benzoic acid (800.2 mg, 4.21 mmol, 1 eq), diisopropylethylamine (2.18 g, 16.84 mmol, 2.93 mL, 4 eq) and HATU (1.92 g, 5.05 mmol, 1.2 eq) in dimethylformamide (20 mL) was added tert-butyl N-[3-(2-amino-5-fluoro-benzimidazol-1-yl)phenyl]-N-methyl-carbamate (1.5 g, 4.21 mmol, 1 eq) in one portion. The mixture was stirred at 25° C. for 1 hour. LCMS analysis confirmed the reaction to be complete. The reaction mixture was washed with water (100 mL) and extracted with ethyl acetate (50 mL×3). The combined organic phase was concentrated under vacuum and the resulting residue was purified by column chromatography (Petroleum ether/Ethyl acetate=2/1, Rf=0.3) to afford tert-butyl N-[3-[5-fluoro-2-[[3-(trifluoromethyl)benzoyl]amino]benzimidazol-1-yl]phenyl]-N-methyl-carbamate (2 g, 3.78 mmol, 90% yield) as a white solid. MS (ESI) m/z: 529.2 [M+H]$^+$.

Step 8:

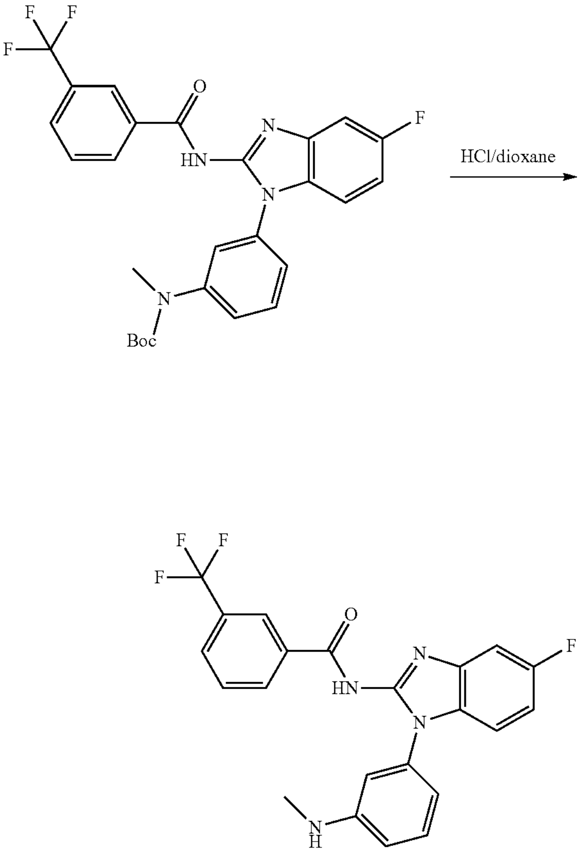

A mixture of tert-butyl N-[3-[5-fluoro-2-[[3-(trifluoromethyl)benzoyl]amino]benzimidazol-1-yl]phenyl]-N-methyl-carbamate (1 g, 1.89 mmol, 1 eq) and a solution of hydrogen chloride in dioxane (4 M, 5 mL, 10.57 eq) was stirred at 25° C. for 1 hour. LCMS analysis confirmed the reaction to be complete. The reaction mixture was concentrated under reduced pressure and the residue was dissolved in ethyl acetate (100 mL), and the mixture was washed with a saturated aqueous solution of sodium bicarbonate to adjust pH to be 8. The organic phase was separated and concentrated under vacuum. Crude N-[5-fluoro-1-[3-(methylamino)phenyl]benzimidazol-2-yl]-3-(trifluoromethyl)benzamide (770 mg, 1.80 mmol, 95% yield) was obtained as a white solid and used as is in the next reaction without further purification. MS (ESI) m/z: 429.1 [M+H]$^+$.

Step 9:

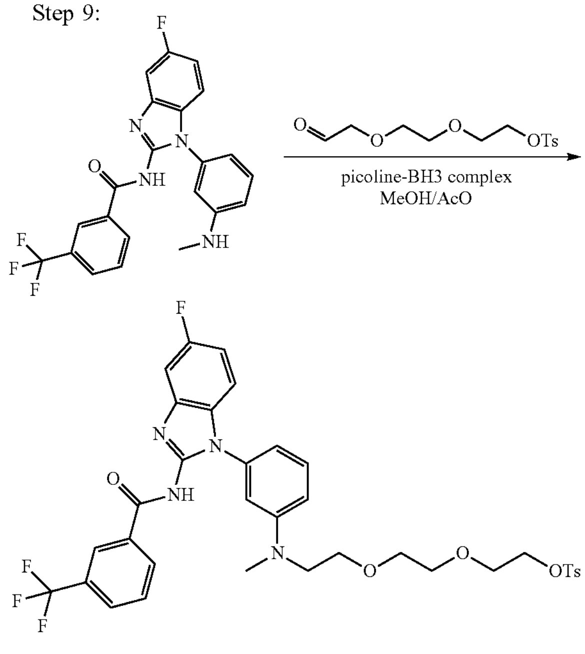

To a mixture of N-[5-fluoro-1-[3-(methylamino)phenyl] benzimidazol-2-yl]-3-(trifluoromethyl) benzamide (300 mg, 700.3 μmol, 1 eq) and 2-[2-(2-oxoethoxy)ethoxy]ethyl 4-methylbenzenesulfonate, Intermediate 7 (317.6 mg, 1.05 mmol, 1.5 eq) in methyl alcohol (5 mL) and acetic acid (0.5 mL) was added 2-methylpyridine borane complex (112.36 mg, 1.05 mmol, 1.5 eq). The mixture was stirred at 25° C. for 12 hours. LCMS analysis confirmed the reaction to be complete. The reaction mixture was concentrated under reduced pressure and 10% aqueous hydrogen chloride (10 mL) was added to the residue. The aqueous solution was stirred for 0.5 hour at room temperature, and sodium carbonate (ca. 2.5 g) and water (10 mL) were added under cooling. The aqueous layer was extracted with ethyl acetate (30 mL×2), and the combined organic layer was washed with brine (15 mL), dried over sodium sulfate, and concentrated. The resulting residue was purified by column chromatography (petroleum ether/ethyl acetate=1/1, Rf=0.2) to afford 2-[2-[2-[3-[5-fluoro-2-[[3-(trifluoromethyl)benzoyl] amino]benzimidazol-1-yl]-N-methyl-anilino]ethoxy] ethoxy]ethyl 4-methylbenzenesulfonate (60 mg, 83.95 μmol, 12% yield) as a white solid. MS (ESI) m/z: 715.2 $[M+H]^+$.

Step 10:

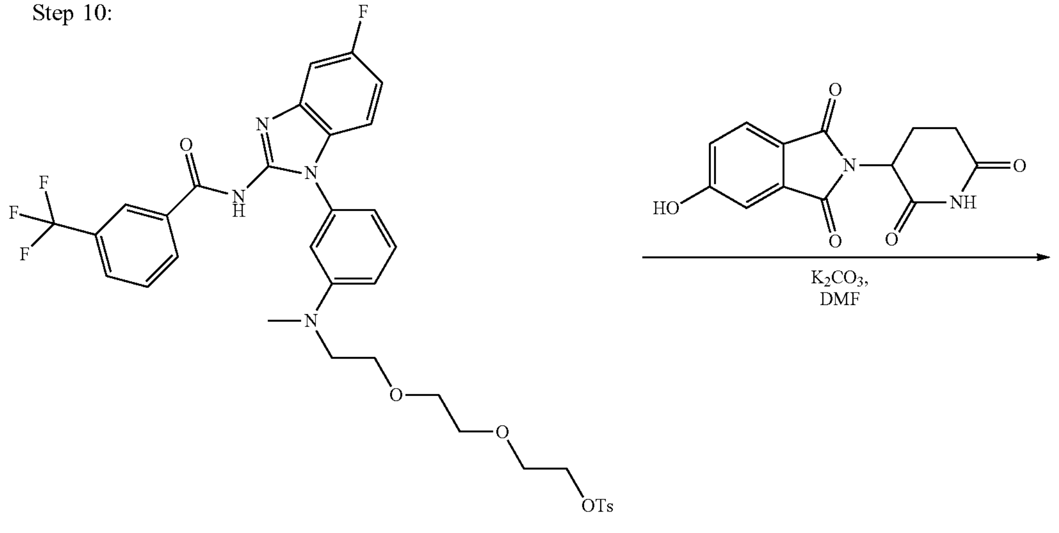

-continued

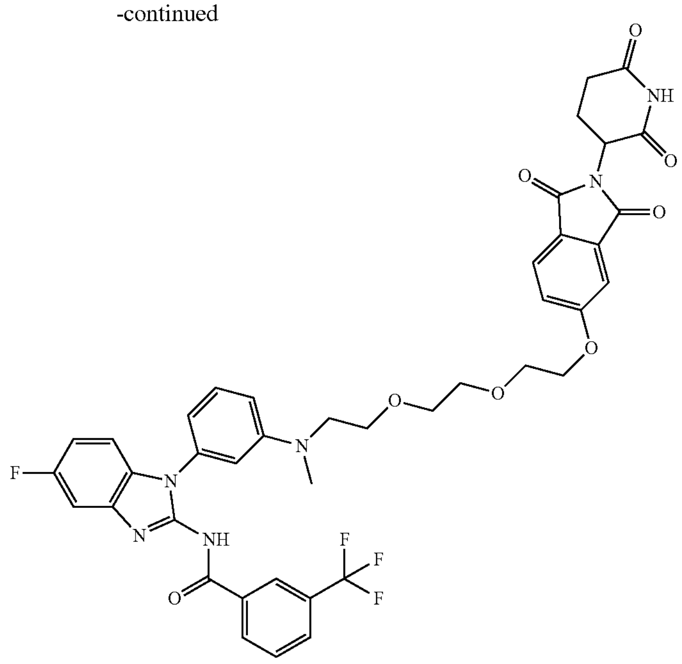

To a mixture of 2-[2-[2-[3-[5-fluoro-2-[[3-(trifluoromethyl)benzoyl]amino]benzimidazol-1-yl]-N-methyl-anilino] ethoxy]ethoxy]ethyl 4-methylbenzenesulfonate (60 mg, 83.95 μmol, 1 eq) and 2-(2,6-dioxo-3-piperidyl)-5-hydroxy-isoindoline-1,3-dione (34.5 mg, 125.9 μmol, 1.5 eq) in dimethylformamide (3 mL) was added potassium carbonate (46.41 mg, 335.79 μmol, 4 eq). The mixture was heated to 50° C. and stirred for 12 hour. LCMS analysis confirmed the reaction to be complete. The reaction mixture was washed with water (30 mL) and extracted with ethyl acetate (20 mL×3). The combined organic phase was concentrated under reduced pressure and the resulting residue was purified by preparative HPLC to afford N-[1-[3-[2-[2-[2-[2-(2,6-dioxo-3-piperidyl)-1,3-dioxo-isoindolin-5-yl]oxyethoxy] ethoxy]ethyl-methyl-amino]phenyl]-5-fluoro-benzimidazol-2-yl]-3-(trifluoromethyl)benzamide (20.4 mg, 24.98 μmol, 30% yield) as an off-white solid. MS (ESI) m/z: 817.2 $[M+H]^+$. $^1H$ NMR (400 MHz, DMSO-$d_6$) δ: 11.10 (s, 1H), 8.35-8.25 (m, 2H), 7.83 (br d, J=7.2 Hz, 1H), 7.76 (d, J=8.3 Hz, 1H), 7.69-7.62 (m, 1H), 7.44-7.34 (m, 3H), 7.29-7.18 (m, 2H), 7.13-7.02 (m, 1H), 6.96 (br d, J=1.1 Hz, 1H), 6.90-6.80 (m, 2H), 5.10 (dd, J=5.4, 12.8 Hz, 1H), 4.25-4.12 (m, 2H), 3.71-3.65 (m, 2H), 3.62-3.45 (m, 10H), 2.96 (s, 3H), 2.91-2.82 (m, 1H), 2.63-2.54 (m, 1H), 2.09-1.96 (m, 1H).

The following compounds may be prepared in an analogous fashion as the exemplary synthesis described for Exemplary Compound 49.

| Exemplary Compound | $[M + H]^+$ |
|---|---|
| 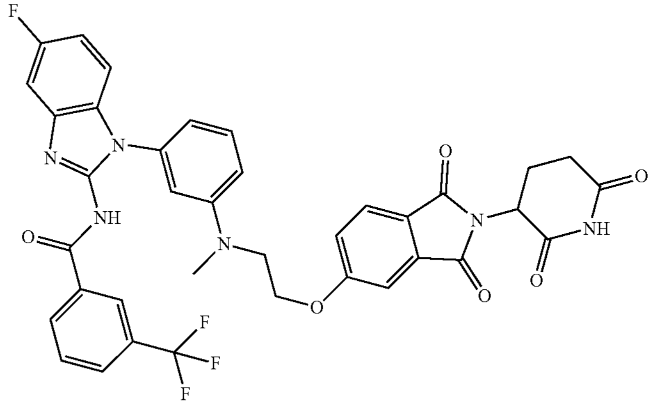 [SMILES: CN(CCOc1ccc2c(c1)C(=O)N(C1CCC(=O)NC1=O)C2=O)c1cccc(-n2c(NC(=O)c3cccc(C(F)(F)F)c3)nc3cc(F)ccc32)c1] Exemplary Compound 50 | 729.49 |

-continued
| Exemplary Compound | [M + H]⁺ |
|---|---|
| 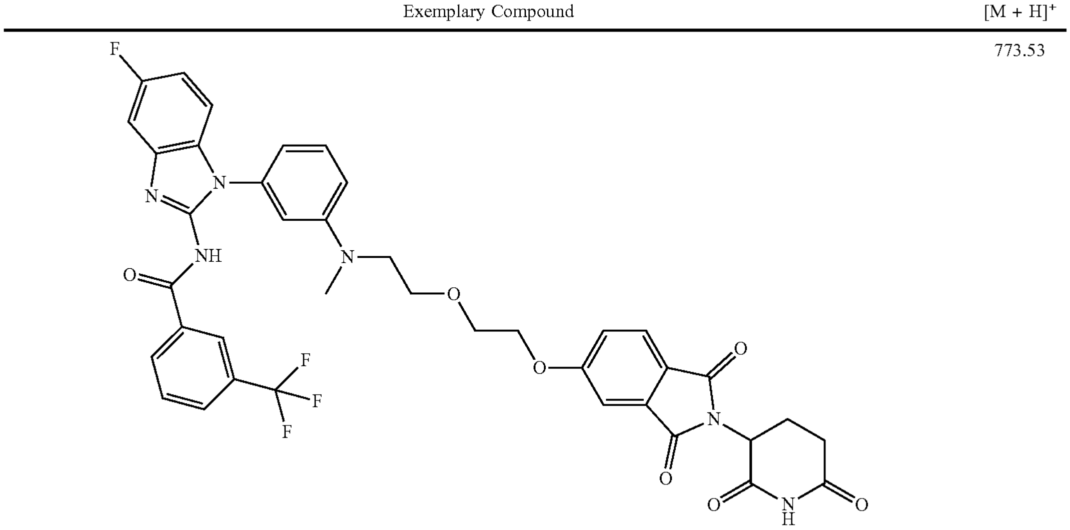 Exemplary Compound 51 | 773.53 |
| 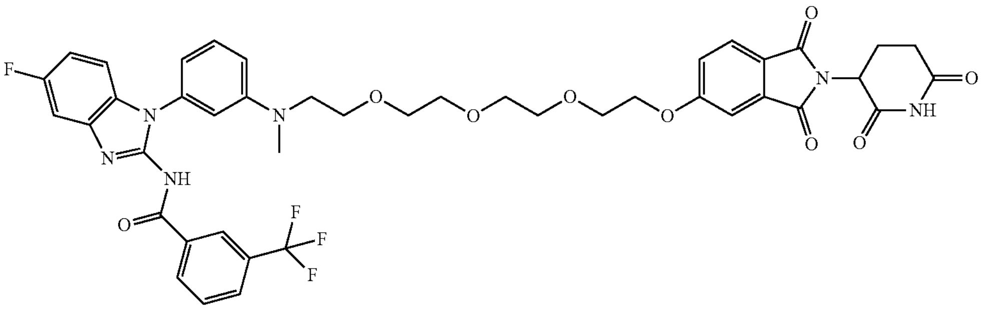 [SMILES: CN(CCOCCOCCOCCOc1ccc2c(c1)C(=O)N(C1CCC(=O)NC1=O)C2=O)c1cccc(-n2c(NC(=O)c3cccc(C(F)(F)F)c3)nc3cc(F)ccc32)c1] Exemplary Compound 52 | 861.62 |
Scheme 12.
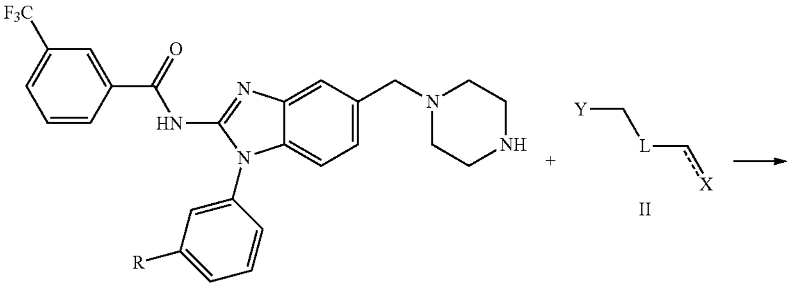
I
II -continued

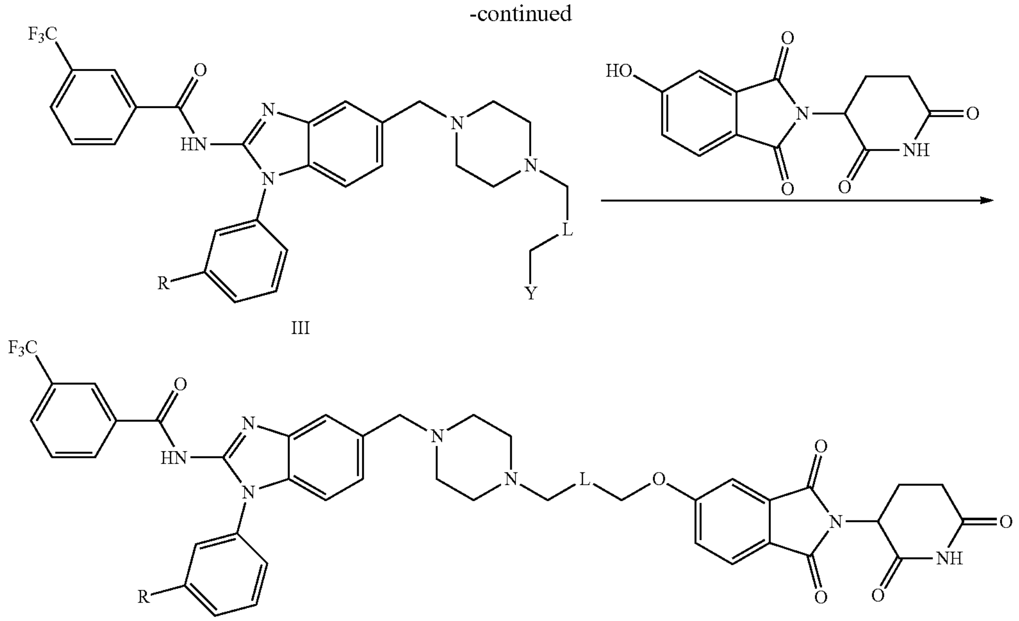

III

IV

A compound of formula I where R may be H or OMe may be reacted with a reagent II (commercially available or readily prepared using standard reaction techniques known to one skilled in the art) where Y is an appropriate leaving group (e.g. OMs, OTs, Cl, Br, etc.) and X is either an appropriate leaving group or an aldehyde and wherein L represents an optional linker or portion of a linker. When X is an aldehyde, suitable reaction conditions to provide a compound of formula III entail reductive amination conditions, e.g. 2-methylpyridine borane complex or sodium acetoxyborohydride, acetic acid, methanol, room temperature. A compound of formula III can be reacted with 2-(2,6-dioxo-3-piperidyl)-5-hydroxy-isoindoline-1,3-dione to provide compounds of formula IV using suitable reaction conditions for an alkylation reaction, e.g. diisopropylethylamine, potassium iodide, DMSO or acetonitrile, 80° C.

Exemplary Synthesis of Exemplary Compound 53

N-(5-((4-(2-(2-(2-((2-(2,6-dioxopiperidin-3-yl)-1,3-dioxoisoindolin-5-yl)oxy)ethoxy)ethoxy)ethyl)piperazin-1-yl)methyl)-1-phenyl-1H-benzo[d]imidazol-2-yl)-3-(trifluoromethyl)benzamide Step 1:

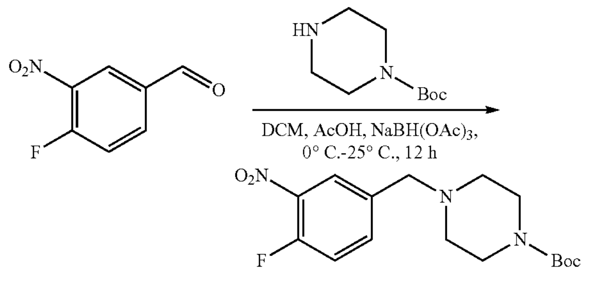

To a solution of 4-fluoro-3-nitro-benzaldehyde (15 g, 88.7 mmol, 1 eq) and acetic acid (16.0 g, 266 mmol, 15.2 mL, 3 eq) in 1,2-dichloroethane (300 mL) was added a solution of tert-butyl piperazine-1-carboxylate (16.5 g, 88.7 mmol, 1 eq) in 1,2-dichloroethane (80 mL) at 0° C. over a period of 1 hour, followed by addition of sodium triacetoxyborohydride (75.2 g, 354 mmol, 4 eq) in portions. The mixture was stirred at 25° C. for 12 hours. LCMS analysis showed formation of the desired compound. The reaction mixture was quenched by addition of a 1M solution of hydrochloric acid to adjust the pH to be 5. The pH was then adjusted to 8 with the addition of an aqueous solution of sodium bicarbonate. The mixture was then extracted with ethyl acetate (300 mL×3). The combined organic phase was dried over sodium sulfate, filtered and concentrated under reduced pressure. The resulting residue was purified by silica gel column chromatography (petroleum ether/ethyl acetate=5/1 to 1/1) to afford tert-butyl 4-[(4-fluoro-3-nitro-phenyl)methyl]piperazine-1-carboxylate (24 g, 80% yield) as a yellow solid. MS (ESI) m/z: 340.1 [M+H]$^+$.

Step 2:

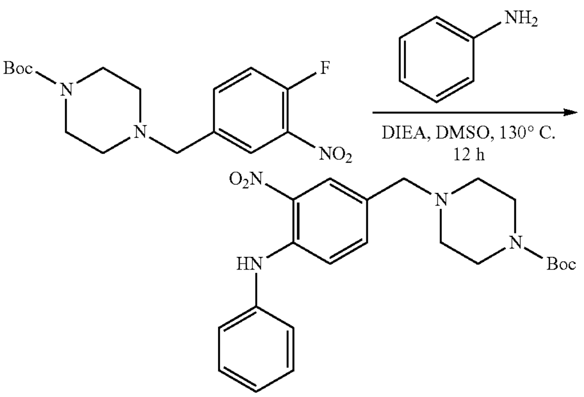

A mixture of tert-butyl 4-[(4-fluoro-3-nitro-phenyl)methyl]piperazine-1-carboxylate (10 g, 29.5 mmol, 1 eq), aniline (11.0 g, 118 mmol, 10.8 mL, 4 eq), N,N-diisopropylethylamine (7.62 g, 58.9 mmol, 10.3 mL, 2 eq) in dimethylsulfoxide (10 mL) was degassed and purged with nitrogen 3 times. The reaction mixture was allowed to stir at 130° C. for 12 hours under a nitrogen atmosphere. The reaction mixture was concentrated to give a residue. To the residue was added water (200 mL) and the mixture was extracted with ethyl acetate (200 mL×3). The combined organic phase was washed with brine (50 mL), dried over anhydrous sodium sulfate, filtered, and concentrated in vacuo. The residue was purified by silica gel column chromatography (petroleum ether/ethyl acetate=3/1 to 1/1), to afford tert-butyl 4-[(4-anilino-3-nitro-phenyl)methyl]piperazine-1-carboxylate (10 g, 82% yield) as a brown oil. MS (ESI) m/z: 413.1 [M+H]+.

Step 3:

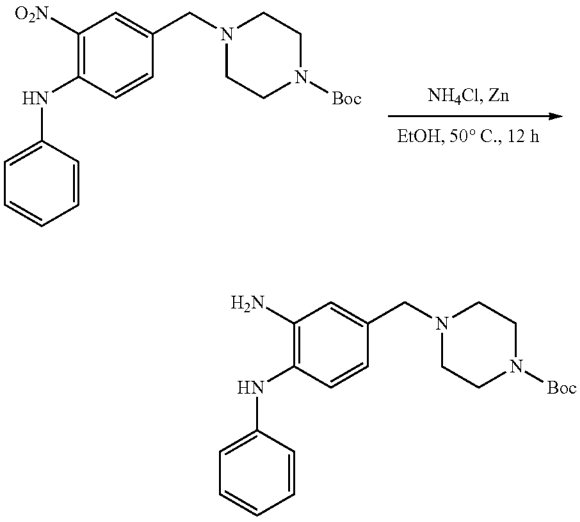

A mixture of tert-butyl 4-[(4-anilino-3-nitro-phenyl)methyl]piperazine-1-carboxylate (10 g, 24.2 mmol, 1 eq), ammonium chloride (25.9 g, 485 mmol, 20 eq), zinc (32 g, 489 mmol, 20.1 eq) in ethyl alcohol (150 mL) was degassed and purged with nitrogen 3 times. The reaction mixture was then heated to 50° C. and allowed to stir for 12 hours under a nitrogen atmosphere. LCMS analysis showed formation of the desired compound. The reaction was filtered and the filtrate was concentrated in vacuo to give the crude product. The residue was purified by silica gel column chromatography (petroleum ether/ethyl acetate=3/1 to 0/1), to afford tert-butyl 4-[(3-amino-4-anilino-phenyl)methyl]piperazine-1-carboxylate (9 g, 97% yield) as a brown oil. MS (ESI) m/z: 405.2 [M+Na]+.

Step 4:

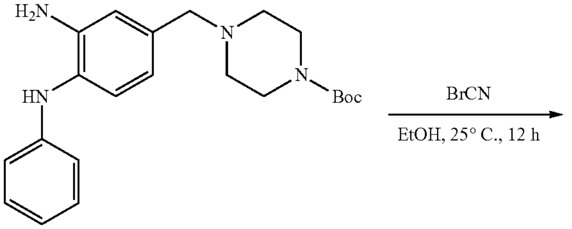

-continued

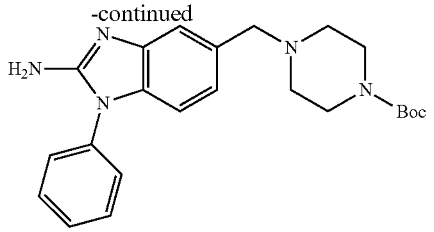

To a solution of cyanogen bromide (3 g, 28.3 mmol, 1.20 eq) in ethyl alcohol (80 mL) was added tert-butyl 4-[(3-amino-4-anilino-phenyl)methyl]piperazine-1-carboxylate (9 g, 23.5 mmol, 1 eq) in ethyl alcohol (50 mL) at 0° C. The reaction mixture was stirred at 25° C. for 12 hours. LCMS showed desired compound was detected. The reaction mixture was concentrated and to the residue was added water (100 mL) and the mixture was extracted with ethyl acetate (100 mL×3). The combined organic phase was washed with brine (20 mL), dried over anhydrous sodium sulfate, filtered and concentrated in vacuo. The crude product was purified by preparative HPLC to yield tert-butyl 4-[(2-amino-1-phenyl-benzimidazol-5-yl)methyl]piperazine-1-carboxylate (1.7 g, 18% yield) obtained as a brown solid. MS (ESI) m/z: 408.3 [M+H]+.

Step 5:

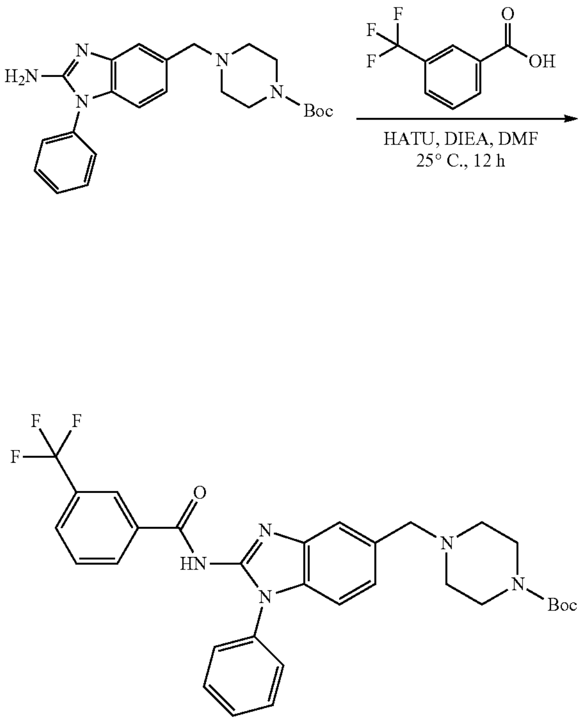

To a solution of 3-(trifluoromethyl)benzoic acid (793 mg, 4.17 mmol, 1 eq) and HATU (1.90 g, 5.01 mmol, 1.2 eq) in dimethylformamide (30 mL) was added N-ethyl-N-propan-2-ylpropan-2-amine (1.62 g, 12.5 mmol, 2.18 mL, 3 eq). After stirring at 25° C. for 10 minutes, a solution of tert-butyl 4-[(2-amino-1-phenyl-benzimidazol-5-yl)methyl]piperazine-1-carboxylate (1.7 g, 4.17 mmol, 1 eq) in dimethylformamide (20 mL) was added. The resulting mixture was allowed to stir at 25° C. for 11 hours and 50 minutes. LCMS analysis showed desired compound was detected. The reaction mixture was concentrated to give a residue. To the reaction mixture was added water (50 mL) and the mixture was extracted with ethyl acetate (50 mL×3). The combined organic phase was washed with brine (30 mL), dried over anhydrous sodium sulfate, filtered and concentrated in vacuo. The residue was purified by silica gel column chromatography (eluting with a gradient from 5 to 1:1 petroleum ether:ethyl acetate) to afford tert-butyl 4-[[1-phenyl-2-[[3-(trifluoromethyl)benzoyl]amino]benzimidazol-5-yl]methyl]piperazine-1-carboxylate (2.3 g, 95% yield) as a brown solid. MS (ESI) m/z: 580.3 [M+H]$^+$.

Step-6:

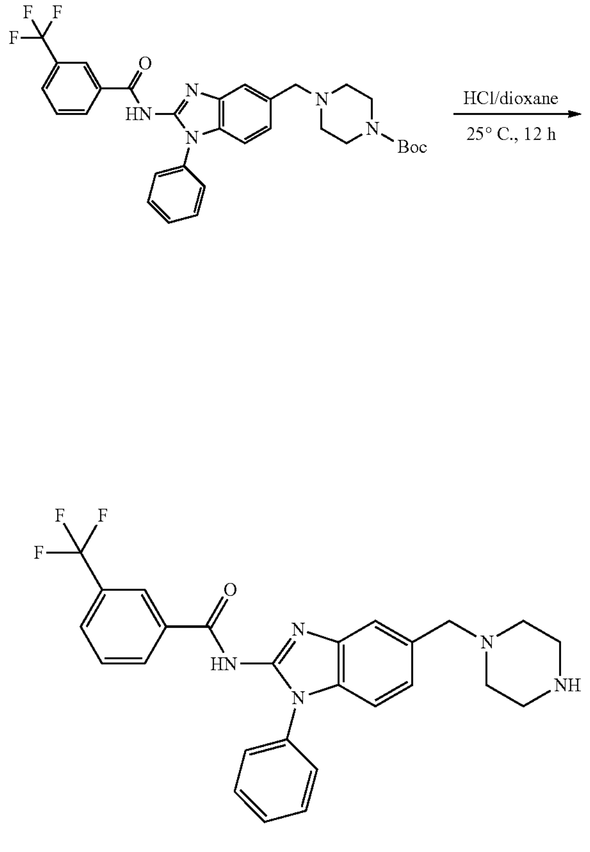

To a solution of tert-butyl 4-[[1-phenyl-2-[[3-(trifluoromethyl)benzoyl]amino]benzimidazol-5-yl]methyl]piperazine-1-carboxylate (2.3 g, 3.97 mmol, 1 eq) in dioxane (10 mL) was added a solution of hydrochloric acid in dioxane (4 M, 0.99 mL, 1 eq). The mixture was stirred at 25° C. for 12 hours. LCMS analysis confirmed the reaction to be complete. The reaction mixture was concentrated to provide crude N-[1-phenyl-5-(piperazin-1-ylmethyl)benzimidazol-2-yl]-3-(trifluoromethyl)benzamide (1 g, crude), obtained as a brown solid used as is in subsequent reactions. MS (ESI) m/z: 480.1 [M+H]$^+$.

Step 7:

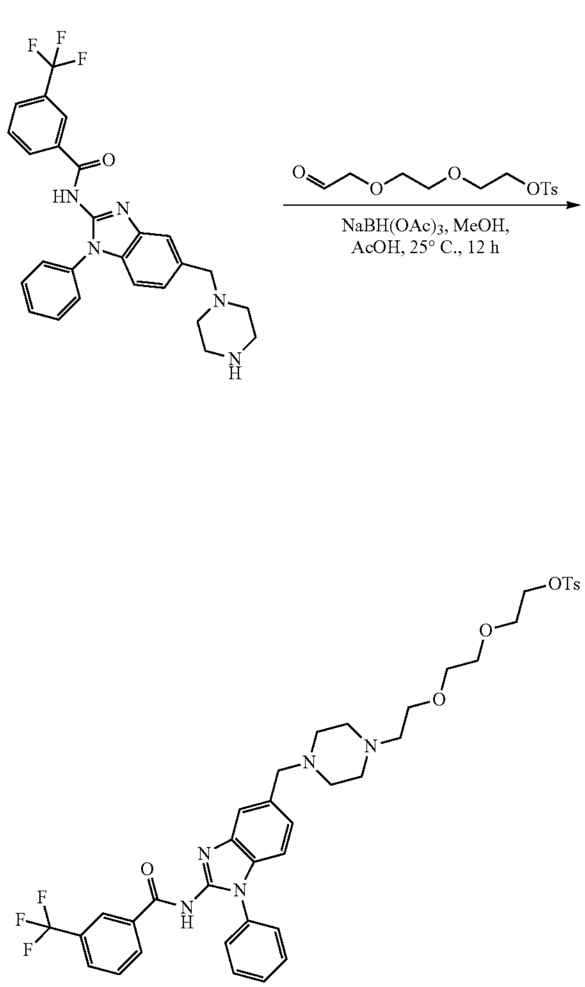

To a solution of N-[-phenyl-5-(piperazin-1-ylmethyl)benzimidazol-2-yl]-3-(trifluoromethyl)benzamide (300 mg, 0.625 mol, 1 eq), 2-[2-(2-oxoethoxy)ethoxy]ethyl 4-methylbenzenesulfonate, Intermediate 7 (283 mg, 0.938 mmol, 1.5 eq) in methanol (5 mL) and acetic acid (0.5 mL) was added 2-methylpyridine borane complex (100 mg, 0.938 mmol, 1.5 eq). The mixture was stirred at 25° C. for 12 hours. LCMS analysis showed the reaction was complete. To the reaction mixture was added water (50 mL) and the mixture was extracted with ethyl acetate (50 mL×3). The combined organic phase was washed with brine (20 mL), dried over anhydrous sodium sulfate, filtered, and concentrated in vacuo. The resulting residue was purified by silica gel column chromatography (dichloromethane/methyl alcohol=20/1 to 5:1), to afford 2-[2-[2-[4-[[1-phenyl-2-[[3-(trifluoromethyl)benzoyl]amino]benzimidazol-5-yl]methyl]piperazin-1-yl]ethoxy]ethoxy]ethyl 4-methylbenzenesulfonate (200 mg, 42% yield) as a brown oil. MS (ESI) m/z: 766.3 [M+H]$^+$.

Step 8:

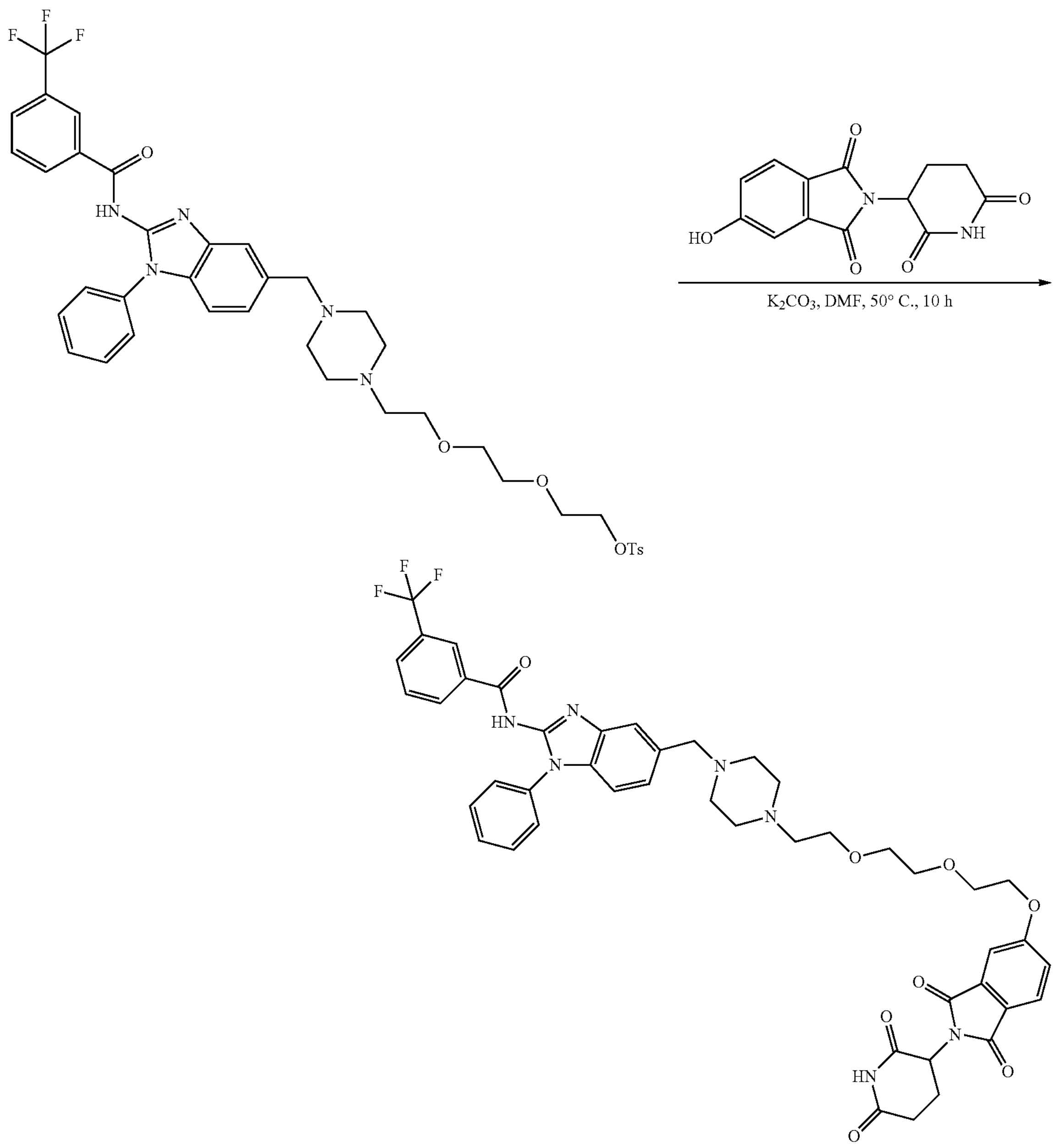

To a mixture of 2-[2-[2-[4-[[1-phenyl-2-[[3-(trifluoromethyl)benzoyl]amino]benzimidazol-5-yl]methyl]piperazin-1-yl]ethoxy]ethoxy]ethyl-4-methylbenzenesulfonate (0.1 g, 0.13 mmol, 1 eq) and 2-(2,6-dioxo-3-piperidyl)-5-hydroxyisoindoline-1,3-dione (60 mg, 0.22 mmol, 1.68 eq) in dimethylformamide (1.5 mL) was added potassium carbonate (80 mg, 0.579 mmol, 4.4 eq). The reaction mixture was stirred at 50° C. for 10 hours. TLC analysis indicated the reaction was complete. The mixture was poured into ice-water (10 mL). The aqueous phase was extracted with ethyl acetate (10 mL×3). The combined organic phase was washed with brine (10 mL), dried with anhydrous sodium sulfate, filtered and concentrated under vacuum. The crude product was purified by preparative HPLC to afford N-(5-((4-(2-(2-(2-((2-(2,6-dioxopiperidin-3-yl)-1,3-dioxoisoindolin-5-yl)oxy)ethoxy)ethoxy)ethyl)piperazin-1-yl)methyl)-1-phenyl-1H-benzo[d]imidazol-2-yl)-3-(trifluoromethyl)benzamide (7.5 mg, 5% yield, 99% purity), obtained as an off-white solid. MS (ESI) m/z: 868.3 $[M+H]^+$. $^1H$ NMR (400 MHz, $CDCl_3$) δ 12.56-12.88 (m, 1H), 9.63-9.98 (m, 1 H), 8.51 (s, 1H), 8.39 (d, J=8.0 Hz, 1H), 7.84 (d, J=8.4 Hz, 1H), 7.69 (d, J=7.6 Hz, 1H), 7.60-7.66 (m, 4H), 7.48-7.56 (m, 2H), 7.44 (d, J=2.4 Hz, 1H), 7.28-7.32 (m, 2H), 7.19 (s, 2 H), 5.05 (dd, J=12.4, 5.2 Hz, 1H), 4.29 (t, J=4.46 Hz, 2H), 3.94 (t, J=4.8 Hz, 2H), 3.65-3.75 (m, 6H), 3.32-3.51 (m, 2H), 2.73-2.99 (m, 4H), 2.67 (s, 4H), 2.46 (s, 4H), 2.00-2.35 (m, 2H).

The following compounds may be prepared in an analogous fashion as the exemplary synthesis described for Exemplary Compound 53.

| Exemplary Compound | [M + H]+ |
| --- | --- |
| 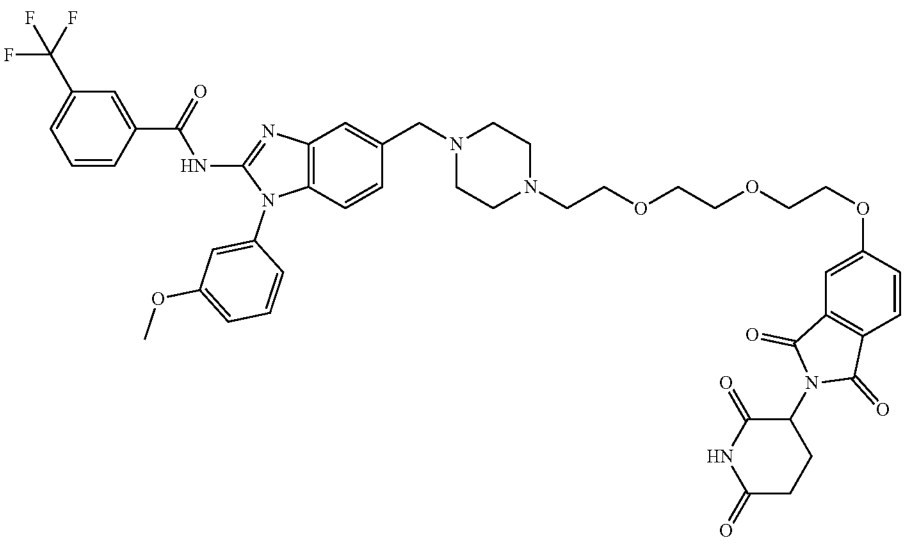 [SMILES: COc1cccc(-n2c(NC(=O)c3cccc(C(F)(F)F)c3)nc3cc(CN4CCN(CCOCCOCCOc5ccc6c(c5)C(=O)N(C5CCC(=O)NC5=O)C6=O)CC4)ccc32)c1] Exemplary Compound 54 | 898.60 |
Exemplary Compound 55
N-(5-((4-(2-((2-(2,6-dioxopiperidin-3-yl)-1,3-dioxoisoindolin-5-yl)oxy)ethyl)piperazin-1-yl)methyl)-1-phenyl-1H-benzo[d]imidazol-2-yl)-3-(trifluoromethyl)benzamide
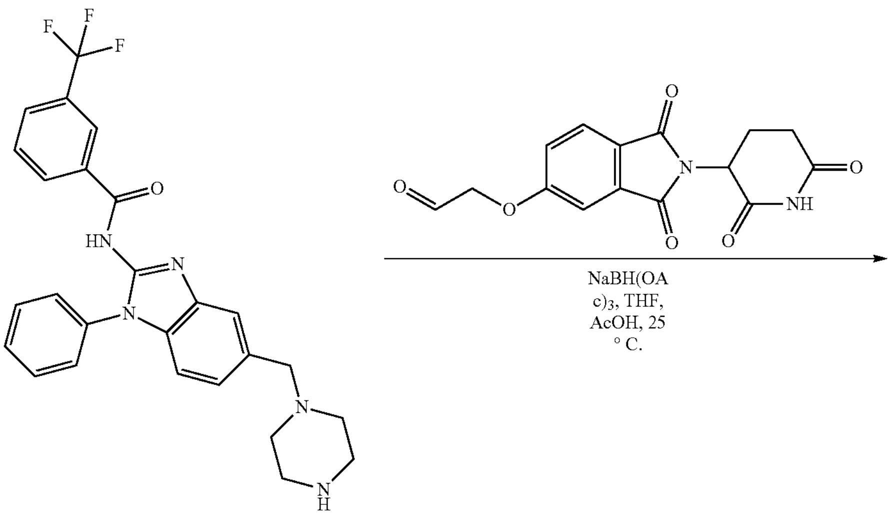

-continued

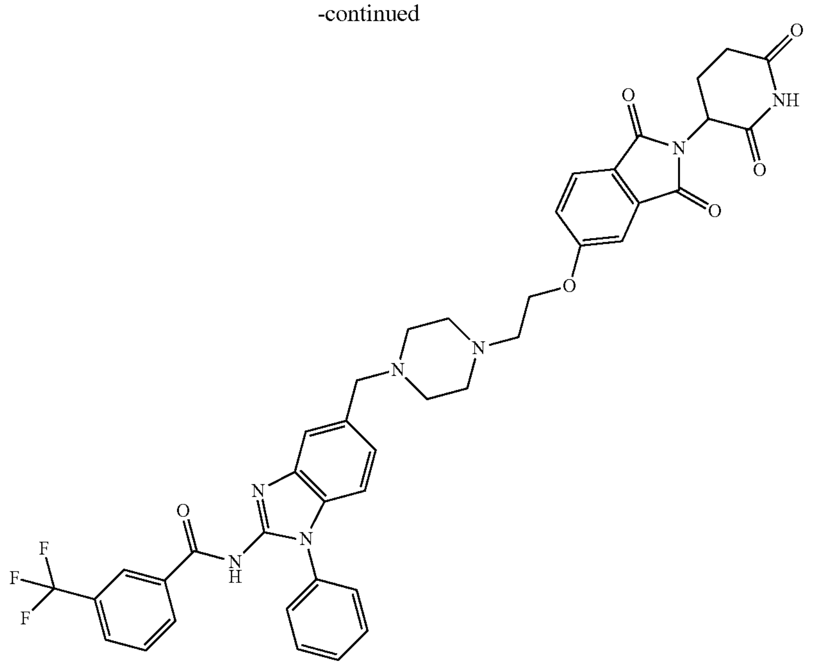

To a mixture of N-[1-phenyl-5-(piperazin-1-ylmethyl) benzimidazol-2-yl]-3-(trifluoromethyl) benzamide (Example 51 Intermediate) (0.15 g, 0.31 mmol, 1 eq) and 2-[2-(2,6-dioxo-3-piperidyl)-1,3-dioxo-isoindolin-5-yl]oxy-acetaldehyde, Intermediate 8 (202 mg, 0.64 mmol, 2.04 eq) in tetrahydrofuran (5 mL) was added acetic acid (10.6 mg, 0.18 mmol, 0.01 mL, 0.6 eq). The mixture was stirred at 25° C. for 0.5 hour, followed by addition of sodium triacetoxy-borohydride (138 mg, 0.65 mmol, 2.08 eq) to the mixture. The mixture was stirred at 25° C. for 9.5 hours. LCMS analysis confirmed the reaction to be complete. To the reaction mixture was added water (20 mL) and the mixture was extracted with ethyl acetate (30 mL×3). The combined organic phase was washed with brine (20 mL), dried over anhydrous sodium sulfate, filtered and concentrated in vacuo. The crude product was purified by preparative HPLC to afford N-(5-((4-(2-((2-(2,6-dioxopiperidin-3-yl)-1,3-di-oxoisoindolin-5-yl)oxy)ethyl)piperazin-1-yl)methyl)-1-phenyl-1H-benzo[d]imidazol-2-yl)-3-(trifluoromethyl)benzamide (82.6 mg, 38% yield, 92% purity) as a white solid. MS (ESI) m/z: 780.3 $[M+H]^+$. $^1H$ NMR (400 MHz, $CDCl_3$) δ 12.64 (s, 1H), 9.20 (s, 1H), 8.49 (s, 1H), 8.37 (d, J=8.0 Hz, 1H), 7.80 (d, J=8.4 Hz, 1H), 7.69 (d, J=8.8 Hz, 1H), 7.62-7.66 (m, 4H), 7.52-7.57 (m, 1H), 7.48-7.52 (m, 1H), 7.39-7.41 (m, 2H), 7.21-7.24 (m, 3H), 4.99 (dd, J=12.4, 5.2 Hz, 1H), 4.26 (t, J=5.2 Hz, 2H), 3.62-3.71 (m, 1H), 3.48-3.59 (m, 1H), 2.82-2.92 (m, 4H), 2.64 (d, J=7.2 Hz, 4H), 2.50 (s, 4H), 2.11-2.20 (m, 2H).

The following compounds may be prepared in an analogous fashion as the exemplary synthesis described for Exemplary Compound 55.

| Exemplary Compound | $[M + H]^+$ |
|---|---|
| 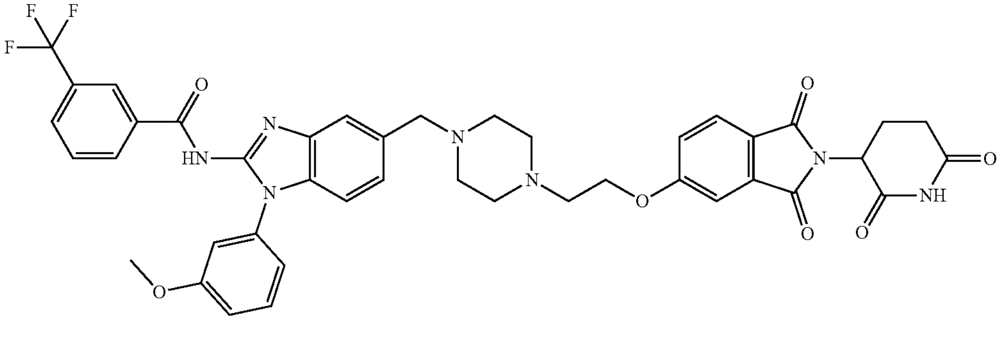 [SMILES: COc1cccc(-n2c(NC(=O)c3cccc(C(F)(F)F)c3)nc3cc(CN4CCN(CCOc5ccc6c(c5)C(=O)N(C5CCC(=O)NC5=O)C6=O)CC4)ccc32)c1] Exemplary Compound 56 | 810.40 |

-continued

| Exemplary Compound | [M + H]+ |
|---|---|
| 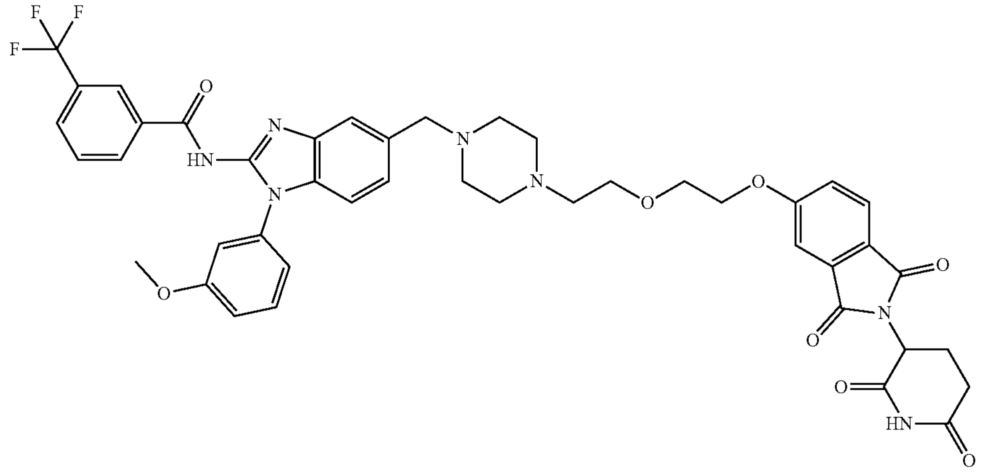 [SMILES: COc1cccc(-n2c(NC(=O)c3cccc(C(F)(F)F)c3)nc3cc(CN4CCN(CCOCCOc5ccc6c(c5)C(=O)N(C5CCC(=O)NC5=O)C6=O)CC4)ccc32)c1] Exemplary Compound 57 | 854.43 |

Scheme 13.

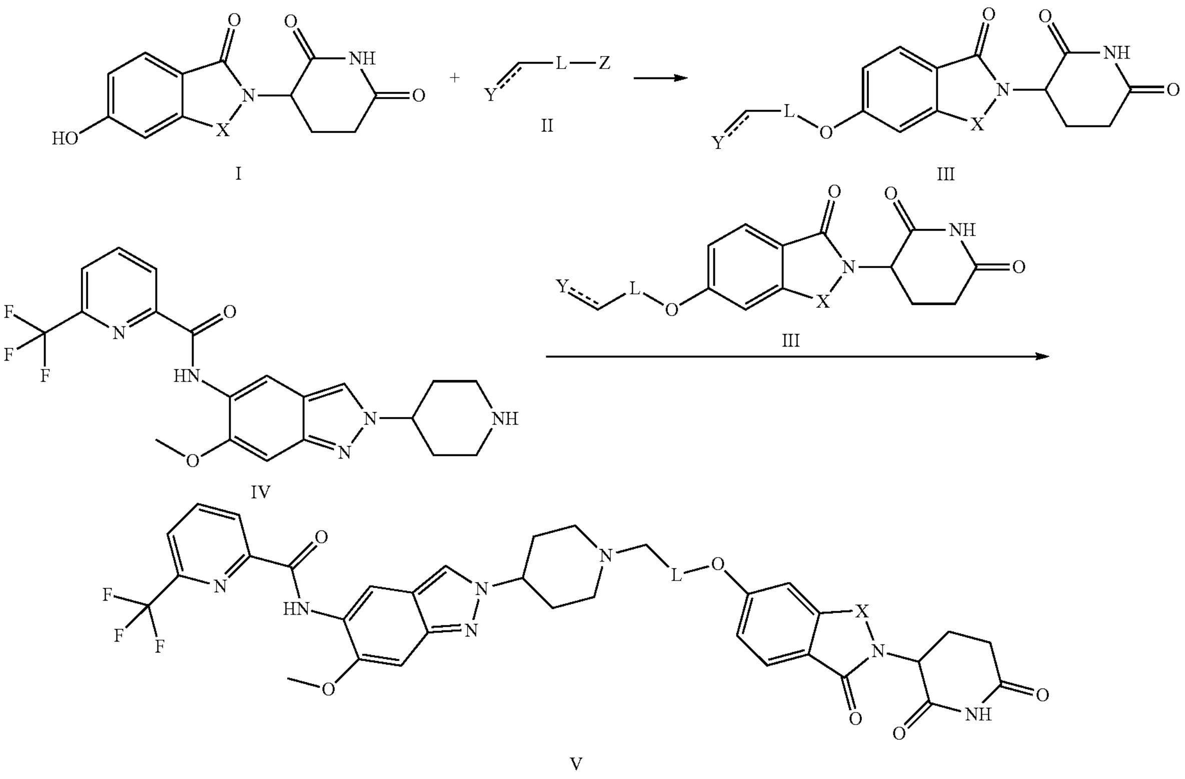

A compound of formula I may be reacted with a reagent II (commercially available or readily prepared using standard reaction techniques known to one skilled in the art) where Z is an appropriate leaving group (e.g. OMs, OTs, Cl, Br, etc.) under O-alkylation conditions to produce a compound of formula III, wherein L represents an optional linker or portion of a linker and X is $CH_2$ or C═O. Suitable reactions conditions for O-alkylation entail the use of a base, e.g. NaH or potassium carbonate in a solvent such as DMF at 60° C. Compounds of formula III may react with a compound of formula IV through N-alkylation where Y is an appropriate leaving group (e.g. OMs, OTs, Cl, etc.) or through reductive amination where Y is an aldehyde to produce compound of formula V. When Y is a leaving group, suitable reaction conditions are those for an alkylation reaction, e.g. diisopropylethylamine, potassium iodide, DMSO or acetonitrile, 80° C. When Y is an aldehyde, suitable reaction conditions are those for a reductive amination reaction, e.g. sodium cyanoborohydride, methanol, dichloromethane, acetic acid, room temperature.

Exemplary Synthesis of Exemplary Compound 58

N-(2-(1-(2-(2-((2-(2,6-dioxopiperidin-3-yl)-1,3-dioxoisoindolin-5-yl)oxy)ethoxy)ethyl)piperidin-4-yl)-6-methoxy-2H-indazol-5-yl)-6-(trifluoromethyl)picolinamide Step 1

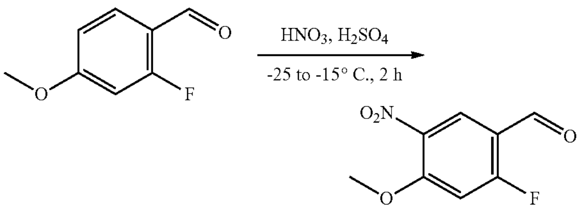

To a solution of 2-fluoro-4-methoxy-benzaldehyde (3 g, 19.46 mmol, 1 eq) in sulfuric acid (15 mL) was added a solution of nitric acid (1.35 mL) in sulfuric acid (2 mL) at −20° C. The mixture was stirred at -20 to −10° C. for 1 hour. The reaction mixture was poured onto ice-water (500 mL) where upon a precipitate formed. The solid was collected by filtration and was washed with water 100 mL (50 mL×2), and dried to give compound 2-fluoro-4-methoxy-5-nitro-benzaldehyde (3.2 g, 16.07 mmol, 82.56% yield) as a white solid. $^1$H NMR (400 MHz, $CDCl_3$) δ: 10.22 (s, 1H), 8.46 (d, J=8 Hz, 1H), 6.88 (d, J=11 Hz, 1H), 4.06 (s, 3 H).

Step 2:

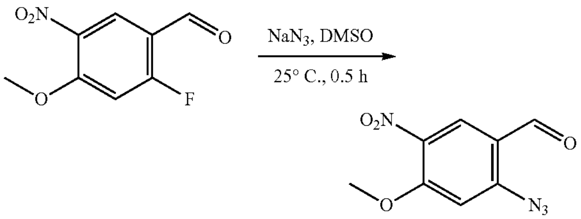

To a solution of 2-fluoro-4-methoxy-5-nitro-benzaldehyde (0.5 g, 2.51 mmol, 1 eq) in dimethylsulfoxide (4 mL) was added sodium azide (326.46 mg, 5.02 mmol, 2 eq). The mixture was stirred at 25° C. for 0.5 hour. The reaction mixture was quenched by the addition of water (20 mL) at 25° C., and then diluted with ethyl acetate (20 mL). The mixture was extracted with ethyl acetate (20 mL×2). The combined organic layers were washed with brine (50 mL×3), dried over anhydrous sodium sulfate, filtered and concentrated under reduced pressure to yield crude 2-azido-4-methoxy-5-nitro-benzaldehyde (0.5 g, 2.25 mmol, 89.64% yield), obtained as a white solid. $^1$H NMR (400 MHz, $CDCl_3$) δ: 10.2 (s, 1H), 8.46 (s, 1H), 6.81 (s, 1H), 4.10 (s, 3 H).

Step 3:

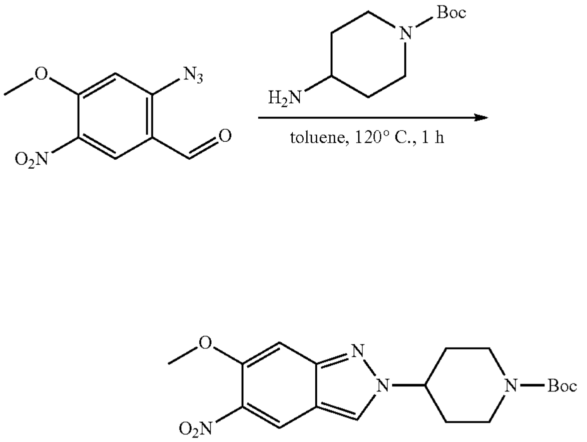

To a solution of 2-azido-4-methoxy-5-nitro-benzaldehyde (0.5 g, 2.25 mmol, 1 eq) in toluene (10 mL) was added tert-butyl 4-aminopiperidine-1-carboxylate (450.76 mg, 2.25 mmol, 1 eq). The mixture was stirred at 120° C. for 1 hour. The reaction mixture was concentrated under reduced pressure to give a residue which was purified by silica gel chromatography to afford tert-butyl 4-(6-methoxy-5-nitro-indazol-2-yl)piperidine-1-carboxylate (0.8 g, 2.13 mmol, 94.4% yield) which was obtained as a white solid. $^1$H NMR (400 MHz, $CDCl_3$) δ: 8.22 (s, 1H), 8.08 (s, 1H), 7.11 (s, 1H), 4.54 (m, 1H), 4.33 (m, 2H), 3.97 (s, 3 H), 2.96 (m, 2H), 2.24 (m, 2H), 2.10 (m, 2H), 1.49 (s, 9H).

Step 4:

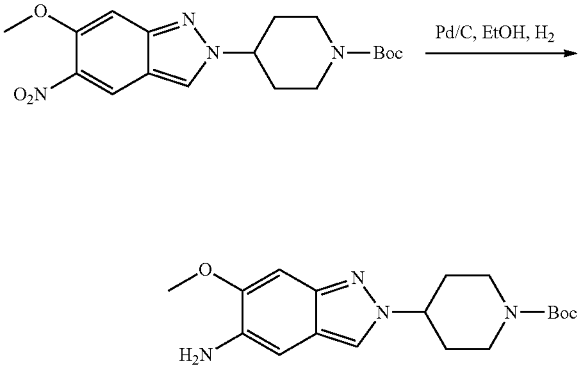

To a solution of tert-butyl 4-(6-methoxy-5-nitro-indazol-2-yl)piperidine-1-carboxylate (0.8 g, 2.13 mmol, 1 eq) in ethanol (10 mL) was added Pd/C (0.5 g, 2.13 mmol, 10% purity, 1 eq) under hydrogen (15 psi). The mixture was stirred at 25° C. for 1 hour. The reaction mixture was concentrated under reduced pressure to give a residue which was purified by silica gel column chromatography to afford tert-butyl 4-(5-amino-6-methoxy-indazol-2-yl)piperidine-1-carboxylate (0.6 g, 1.73 mmol, 81.49% yield), obtained as a white solid. $^1$H NMR (400 MHz, $CDCl_3$) δ: 7.61 (s, 1H), 6.94 (s, 1H), 6.75 (s, 1H), 4.45 (m, 1H), 4.39 (m, 2H), 3.91 (s, 3 H), 2.91 (m, 2H), 2.20 (m, 2H), 2.05 (m, 2H), 1.48 (s, 9H).

Step 5

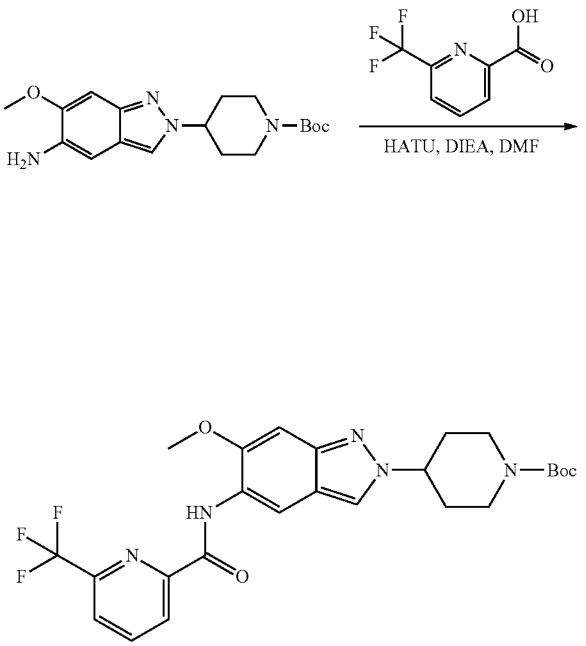

To a solution of 6-(trifluoromethyl)pyridine-2-carboxylic acid (198.60 mg, 1.04 mmol, 1.2 eq) in N,N-dimethylformamide (5 mL) was added HATU (395.1 mg, 1.04 mmol, 1.2 eq), N,N-diisopropylethylamine (335.77 mg, 2.60 mmol, 452.52 μL, 3 eq) and tert-butyl 4-(5-amino-6-methoxy-indazol-2-yl)piperidine-1-carboxylate (0.3 g, 866 μmol, 1 eq). The mixture was stirred at 25° C. for 0.5 hour. The reaction mixture was quenched by the addition of water (20 mL) at 25° C., and then diluted with ethyl acetate (50 mL). The mixture was then extracted with ethyl acetate (50 mL×2). The combined organic layers were washed with brine (50 mL×3), dried over anhydrous sodium sulfate, filtered and concentrated under reduced pressure to give a residue. The residue was purified by silica gel column chromatography to yield tert-butyl 4-[6-methoxy-5-[[6-(trifluoromethyl)pyridine-2-carbonyl]amino]indazol-2-yl]piperidine-1-carboxylate (0.36 g, 693 μmol, 80.0% yield), obtained as a white solid. $^1$H NMR (400 MHz, $CDCl_3$) δ: 10.72 (s, 1H), 8.83 (s, 1H), 8.49 (d, J=10.4, 1H), 8.12 (t, J=10.4, 1H), 7.80 (s, 1H), 7.80 (d, J=10.4, 1H), 7.06 (s, 1H), 4.48 (m, 1H), 4.32 (m, 2H), 4.04 (s, 3 H), 2.96 (m, 2H), 2.20 (m, 2H), 2.10 (m, 2H), 1.49 (s, 9H).

Step 6:

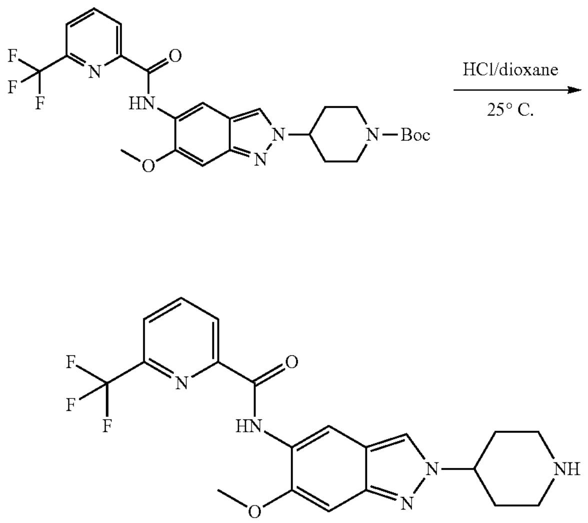 [SMILES: COc1cc2nn(C3CCN(C(=O)OC(C)(C)C)CC3)cc2cc1NC(=O)c1cccc(C(F)(F)F)n1 ; COc1cc2nn(C3CCNCC3)cc2cc1NC(=O)c1cccc(C(F)(F)F)n1]

To a solution of tert-butyl 4-[6-methoxy-5-[[6-(trifluoromethyl)pyridine-2-carbonyl]amino]indazol-2-yl]piperidine-1-carboxylate (0.36 g, 692.95 umol, 1 eq) in methanol (2 mL) was added 4 M hydrochloric acid in dioxane (10 mL). The mixture was stirred at 25° C. for 1 hour. The reaction mixture was concentrated under reduced pressure to yield N-[6-methoxy-2-(4-piperidyl)indazol-5-yl]-6-(trifluoromethyl)pyridine-2-carboxamide (0.31 g, 680 μmol, 98.1% yield, hydrochloric acid). MS (ESI) m/z: 420.2. $[M+H]^+$. $^1$H NMR (400 MHz, DMSO-$d_6$) δ: 10.52 (s, 1H), 9.09 (m, 2H), 8.71 (s, 1H), 8.38 (m, 3H), 8.24 (d, J=8.0, 1H), 7.19 (s, 1H), 4.78 (m, 1H), 3.99 (s, 3 H), 3.46 (m, 2H), 3.13 (m, 2H), 2.28 (m, 4H).

Step 7:

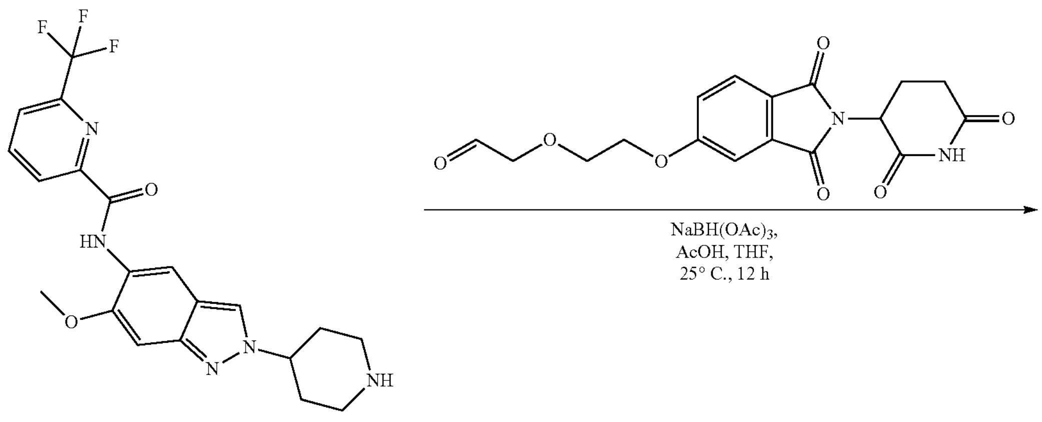

-continued

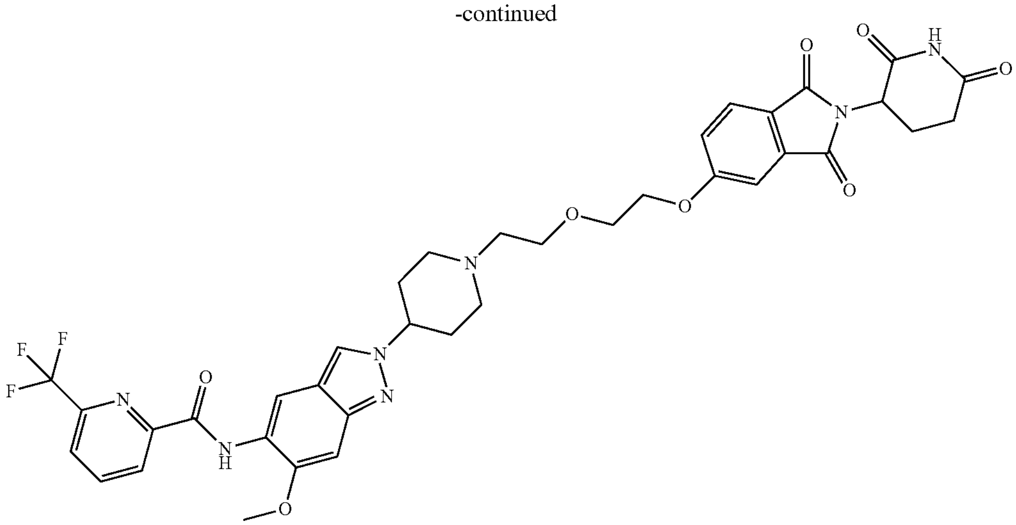

To a mixture of N-[6-methoxy-2-(4-piperidyl)indazol-5-yl]-6-(trifluoromethyl)pyridine-2-carboxamide (150 mg, 0.36 mmol, 1 eq) and 2-[2-[2-(2,6-dioxo-3-piperidyl)-1,3-dioxo-isoindolin-5-yl]oxyethoxy]acetaldehyde, Intermediate 9 (193 mg, 0.54 mmol, 1.5 eq) in tetrahydrofuran (15 mL) was added acetic acid (10.7 mg, 0.18 mmol, 0.01 mL, 0.5 eq). The mixture was stirred at 25° C. for 0.5 hour, followed by addition of sodium triacetoxyborohydride (152 mg, 0.72 mmol, 2 eq) to the mixture. The mixture was stirred at 25° C. for 11.5 hours. LCMS analysis confirmed the reaction to be complete and to the reaction mixture was added water (20 mL). The mixture was extracted with ethyl acetate (30 mL×3). The combined organic phase was washed with brine (20 mL), dried over anhydrous sodium sulfate, filtered and concentrated in vacuo. The crude product was purified by preparative HPLC to yield N-(2-(1-(2-(2-((2-(2,6-dioxopiperidin-3-yl)-1,3-dioxoisoindolin-5-yl)oxy)ethoxy)ethyl)piperidin-4-yl)-6-methoxy-2H-indazol-5-yl)-6-(trifluoromethyl)picolinamide (5.5 mg, 2% yield, 96% purity), obtained as a white solid. MS (ESI) m/z: 764.3 $[M+H]^+$. $^1H$ NMR (400 MHz, $CDCl_3$) δ 10.72 (s, 1H), 8.86 (s, 1H), 8.52 (d, J=8.0 Hz, 2H), 8.13 (t, J=8.0 Hz, 1H), 7.84-7.90 (m, 2H), 7.80 (d, J=8.4 Hz, 1H), 7.42 (d, J=2.4 Hz, 1H), 7.23-7.26 (m, 1H), 7.09 (s, 1H), 4.98 (dd, J=12.4, 5.6 Hz, 1H), 4.42 (s, 1H), 4.25-4.35 (m, 2H), 4.04 (s, 3H), 3.88-3.93 (m, 2H), 3.77 (s, 2H), 3.21 (s, 2H), 2.57-2.99 (m, 6 H), 2.12-2.32 (m, 6H).

The following compounds may be prepared in an analogous fashion as the exemplary synthesis described for Exemplary Compound 58.

| Exemplary Compound | $[M + H]^+$ |
|---|---|
| 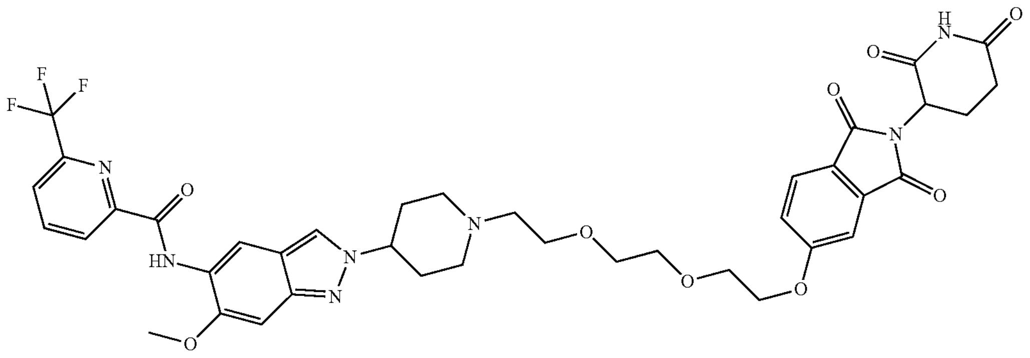 [SMILES: COc1cc2nn(C3CCN(CCOCCOCCOc4ccc5c(c4)C(=O)N(C4CCC(=O)NC4=O)C5=O)CC3)cc2cc1NC(=O)c1cccc(C(F)(F)F)n1]<br>Exemplary Compound 59 | 808.54 |

Scheme 14.
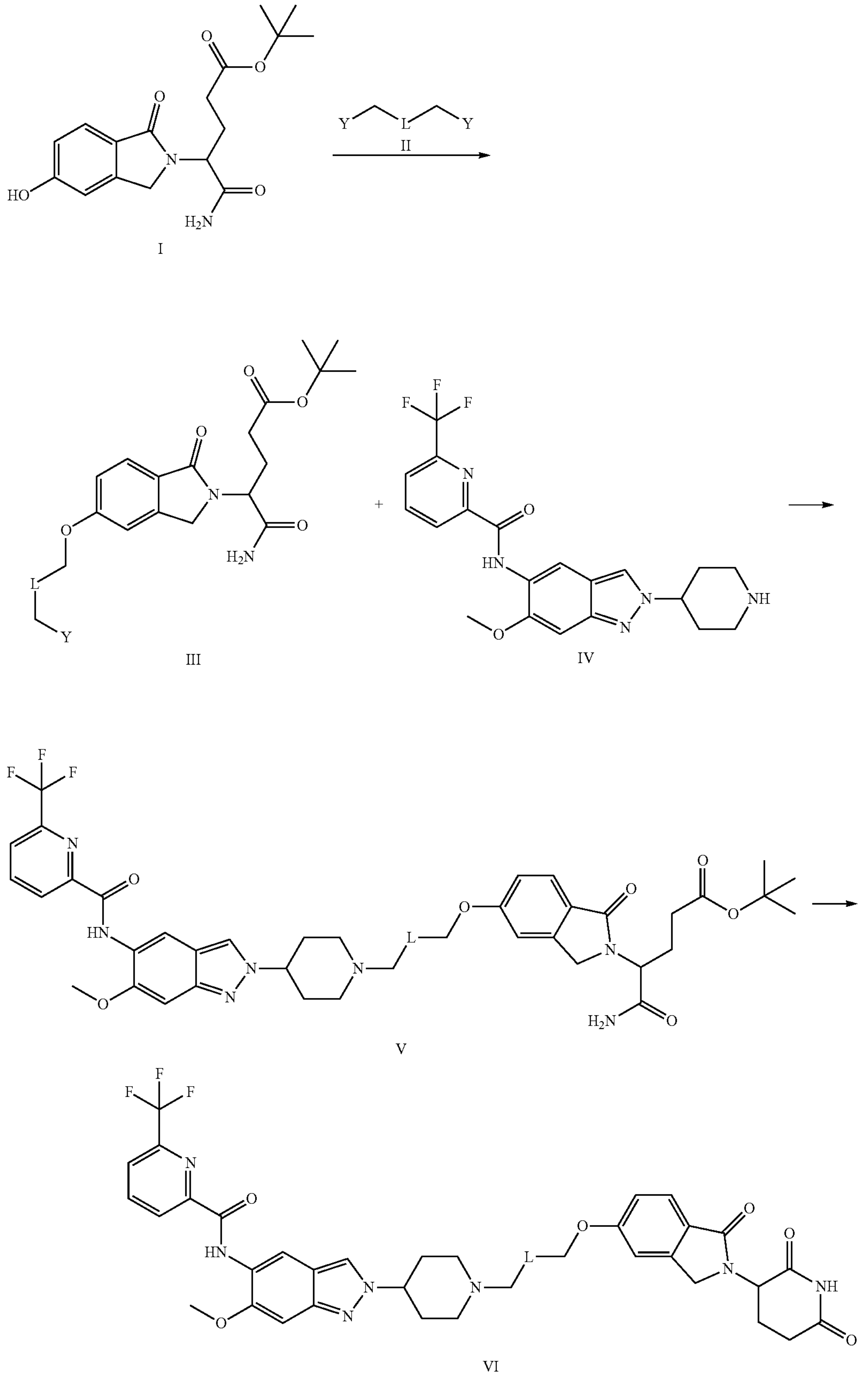
I
II
III
IV
V
VI

A compound of formula I may be reacted with a reagent II (commercially available or readily prepared using standard reaction techniques known to one skilled in the art) where Y is an appropriate leaving group (e.g. OMs, OTs, Cl, Br etc.) under etherification or alkylation conditions to produce a compound of formula III, wherein L represents an optional linker or portion of a linker. Suitable reaction conditions for O-alkylation entail use of an appropriate base e.g., potassium carbonate in acetonitrile or DMF at 60° C. Compounds of formula III may react with a compound of formula IV through N-alkylation where Y is an appropriate leaving group (e.g. OMs, OTs, Cl, Br etc.) to produce a compound of formula V. Suitable reaction conditions are those for an alkylation reaction, e.g. diisopropylethylamine, potassium iodide, DMSO or acetonitrile, 80° C. A compound of formula V can then undergo a cyclization reaction to afford compounds of formula VI.

Exemplary Synthesis of Exemplary Compound 60

N-(2-(1-(2-(2-((2-(2,6-dioxopiperidin-3-yl)-1-oxoisoindolin-5-yl)oxy)ethoxy)ethyl)piperidin-4-yl)-6-methoxy-2H-indazol-5-yl)-6-(trifluoromethyl)picolinamide Step 1:

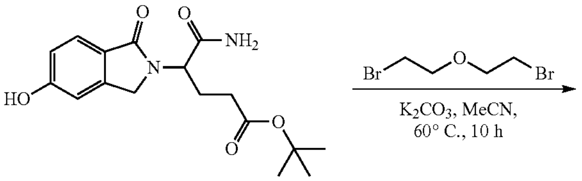

-continued

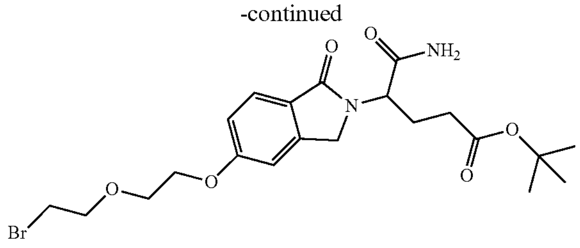

To a solution of tert-butyl 5-amino-4-(5-hydroxy-1-oxo-isoindolin-2-yl)-5-oxo-pentanoate (0.5 g, 1.50 mmol, 1 eq) in acetonitrile (10 mL) was added potassium carbonate (268.67 mg, 1.94 mmol, 1.3 eq) and 1-bromo-2-(2-bromoethoxy)ethane (693.59 mg, 2.99 mmol, 374.9 μL, 2 eq). The mixture was stirred at 60° C. for 12 hours. The reaction mixture was concentrated to give a residue which was purified by silica gel column chromatography (petroleum ether/ethyl acetate=1/1 to 0:1) to afford tert-butyl 5-amino-4-[5-[2-(2-bromoethoxy) ethoxy]-1-oxo-isoindolin-2-yl]-5-oxo-pentanoate (0.53 g, 982.76 umol, 66% yield, 90% purity) obtained as a yellow oil. MS (ESI) m/z: 487.0 $[M+H]^+$.

Step 2:

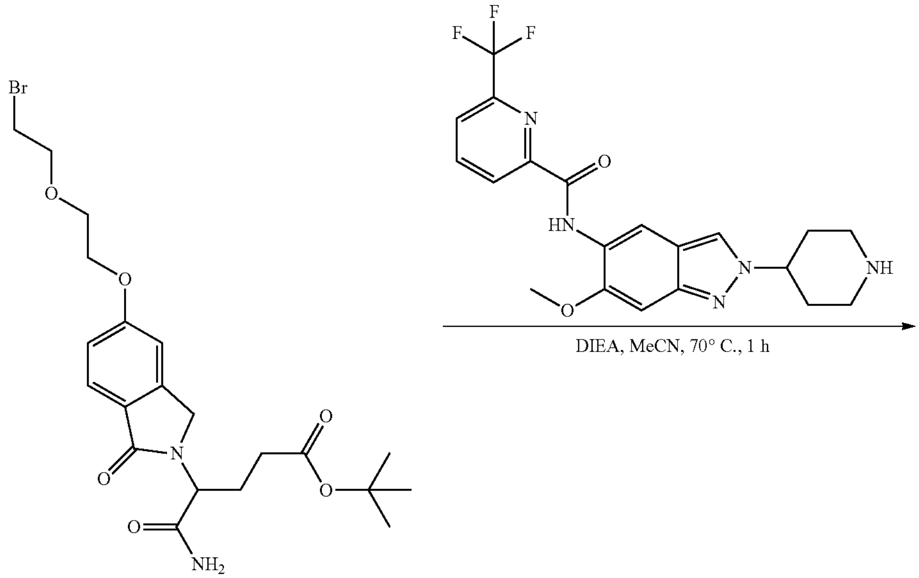

-continued

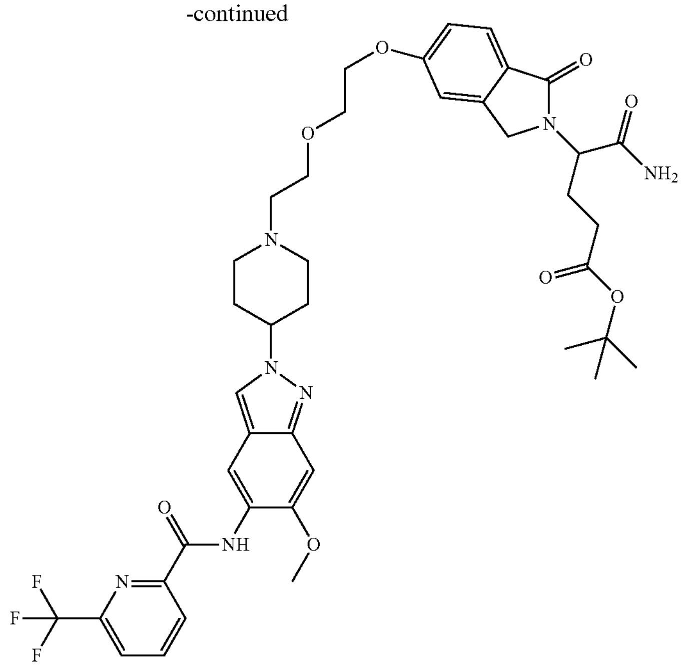

To a solution of tert-butyl 5-amino-4-[5-[2-(2-bromoethoxy)ethoxy]-1-oxo-isoindolin-2-yl]-5-oxo-pentanoate (0.25 g, 515.07 umol, 1 eq) in acetonitrile (10 mL) was added N-ethyl-N-isopropylpropan-2-amine (133.14 mg, 1.03 mmol, 179.4 uL, 2.0 eq) and N-[6-methoxy-2-(4-piperidyl)indazol-5-yl]-6-(trifluoromethyl)pyridine-2-carboxamide (Example 56 Intermediate) (216.0 mg, 515.1 μmol, 1 eq). The mixture was stirred at 70° C. for 12 hours. The reaction mixture was concentrated to give a residue which was purified by silica gel column chromatography (petroleum ether/ethyl acetate=1/1 to 0:1) to yield tert-butyl 5-amino-4-[5-[2-[$^{2}$-[4-[6-methoxy-5-[[6-(trifluoromethyl)pyridine-2-carbonyl]amino]indazol-2-yl]-1-piperidyl]ethoxy]ethoxy]-1-oxo-isoindolin-2-yl]-5-oxo-pentanoate (0.4 g, 466.1 μmol, 90% yield, 96% purity), obtained as a white solid. MS (ESI) m/z: 823.86 [M+H]$^+$.

Step 3:

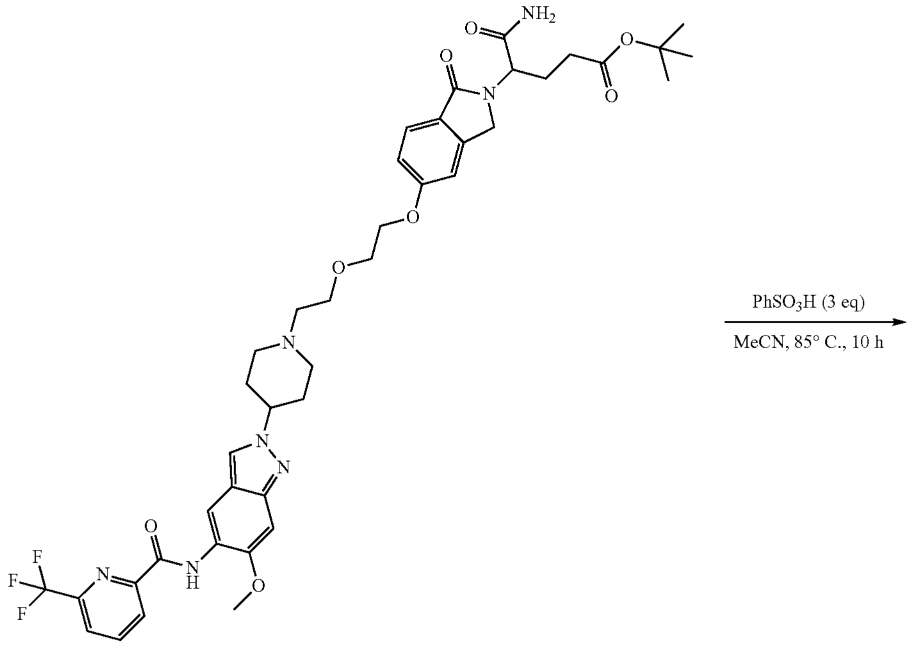

-continued

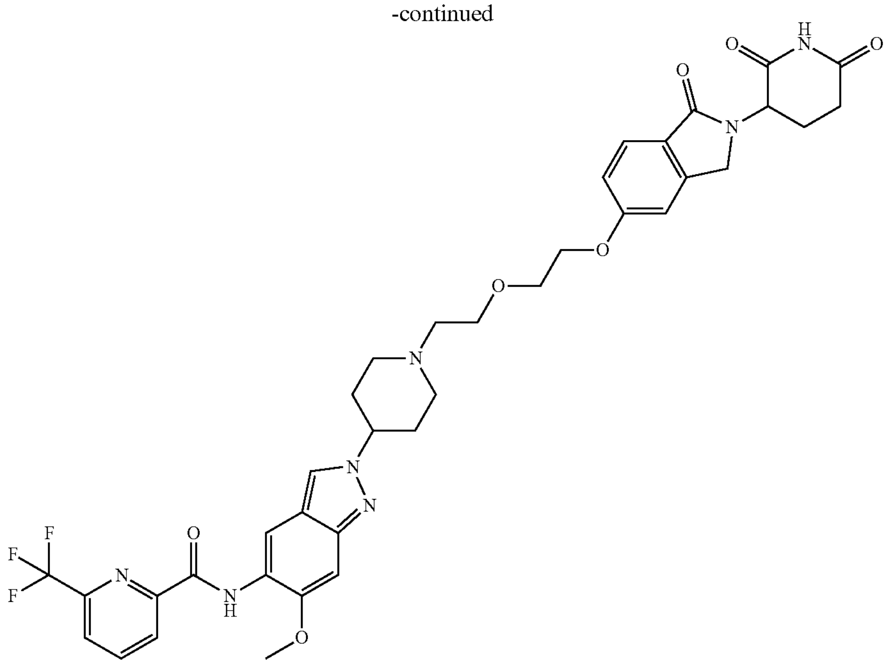

To a solution of tert-butyl 5-amino-4-[5-[2-[2-[4-[6-methoxy-5-[[6-(trifluoromethyl)pyri dine-2-carbonyl] amino]indazol-2-yl]-1-piperidyl]ethoxy]ethoxy]-1-oxo-isoindolin-2-yl]-5-oxo-pentanoate (0.15 g, 182.07 μmol, 1 eq) in acetonitrile (5 mL) was added benzenesulfonic acid (86.4 mg, 546.2 μmol, 3 eq). The mixture was stirred at 80° C. for 20 hours. The reaction mixture was concentrated to give a residue which was purified by preparative HPLC to afford N-(2-(1-(2-(2-((2-(2,6-dioxopiperidin-3-yl)-1-oxoisoindolin-5-yl)oxy)ethoxy)ethyl)piperidin-4-yl)-6-methoxy-2H-indazol-5-yl)-6-(trifluoromethyl)picolinamide (48.8 mg, 63.14 μmol, 35% yield, 97% purity), obtained as a white solid. MS (ESI) m/z: 748.4 $[M+H]^+$. $^1H$ NMR (400 MHz, DMSO-$d_6$) δ ppm 10.98 (s, 1H) 10.51 (s, 1H) 8.69 (s, 1H) 8.33-8.52 (m, 3H) 8.23 (d, J=7.70 Hz, 1H) 7.64 (d, J=8.30 Hz, 1H) 7.15-7.24 (m, 2H) 7.08 (dd, J=8.38, 2.14 Hz, 1H) 5.08 (dd, J=13.34, 5.01 Hz, 1H) 4.18-4.43 (m, 5H) 3.99 (s, 3H) 3.74-3.85 (m, 2H) 3.63 (t, J=5.76 Hz, 2H) 2.83-3.12 (m, 3H) 2.57 (brt, J=5.82 Hz, 3H) 2.30-2.44 (m, 2H) 1.90-2.26 (m, 7H).

The following compounds may be prepared in an analogous fashion as the exemplary synthesis described for Exemplary Compound 60.

| Exemplary Compound | $[M + H]^+$ |
|---|---|
| 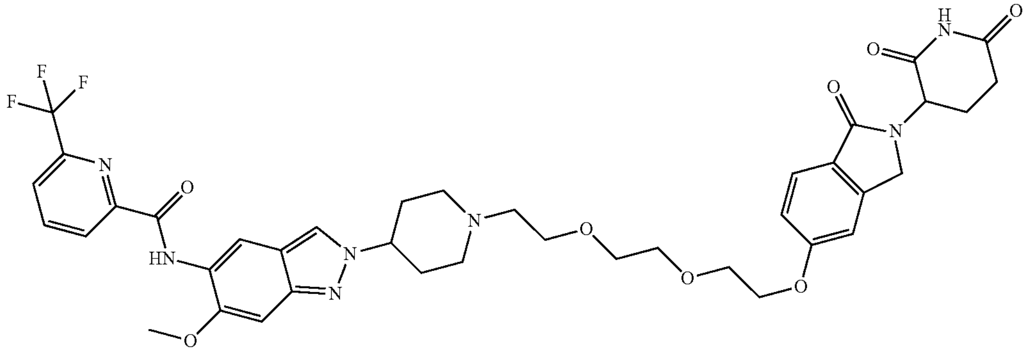 [SMILES: COc1cc2nn(C3CCN(CCOCCOCCOc4ccc5c(c4)CN(C4CCC(=O)NC4=O)C5=O)CC3)cc2cc1NC(=O)c1cccc(C(F)(F)F)n1] Exemplary Compound 61 | 794.56 |

Examples

Biochemical Assay for IRAK4 Kinase Inhibition.

A Z'-Lyte assay based on a fluorescence resonance energy transfer (FRET) readout was developed for measuring IRAK4-dependent phosphorylation of a FRET-peptide substrate as described by Thermo Fisher Scientific (Grand Island, N.Y.). At a starting concentration of 1.5 mM, the identified compounds were serially diluted with 100% dimethyl sulfoxide (DMSO) in 3-fold increments, into Greiner bio-one 96-well plates (cat. #: 650201, Greiner bio-one, Monroe, N.C.). Compounds were then transferred to intermediate Greiner bio-one 96-well plates and diluted 10-fold with Kinase assay buffer (25 mM HEPES, pH 7.5, 10 mM $MgCl_2$, 10 mM $MnCl_2$, 1 mM EGTA, and 0.01% Brij-35, 2 mM DTT). Three μL of the serially diluted compounds were then transferred in duplicate to low-volume 384-well black proxiplates (cat. #: 6008269; Perkin Elmer, Akron, Ohio), to give duplicate twelve-point concentration curves. Six μl of a 2.5× solution of IRAK4 enzyme (cat #: 40064, BPS Bioscience, San Diego, Calif.) in kinase buffer was added to each well, followed by a 10 minutes pre-incubation step. Reactions were initiated by adding 6 μl of a 2.5× substrate mix of ATP and Z'-Lyte Ser/Thr 7 peptide (cat. #: PV3180, Thermo Fisher Scientific, Grand Island, N.Y.) and proceeded at room temperature for 1 hour. The final concentration of key reagents in the 15 uL kinase reactions were 2 μM substrate, 2 nM enzyme, and 1 mM ATP, with dose responses starting at 30 μM compound. At the end of the kinase reactions, 5 μl of developing solution (as instructed in for cat. #: PV3180, Thermo Fisher Scientific, Grand Island, N.Y.) was added to each well and incubated at room temperature for 1 hour. All wells were read on an Envision 2105 Multilabel fluorescence plate reader (Perkin Elmer, Waltham, Mass.) at 400 nm excitation and 460 nm/530 nm emission. Plus and minus 100% inhibition controls were used to calculate percent inhibition and IC50 curves were generated using Graphpad Prism (La Jolla, Calif.).

Western Blot Assay for Assessing Degradation of IRAK4.

MCF7 cells, purchased from ATCC (Manassas, Va.), were used at a passage range of 2-19. Cells were seeded at 50% confluency in 96-well plates at 180 μl/well in cell media (Dulbecco's Modified Eagle medium/nutrient F-12 Ham-10% Fetal Bovine Serum) and incubated overnight. The next morning, compounds were serially diluted and added (20 μl into 180 μl media) at a final DMSO concentration of 0.1%. Cells were rinsed with cell media and replaced with compounds in media, followed by incubation overnight. After a 24 hour incubation with compound, cell were harvested (90-100% confluent at harvest). Cells were then washed once with 100 μl of Dulbecco's hosphate-buffered saline and then lysed with 40 μl of lysis buffer (1×RIPA+HALT protease inhibitor+HALT phosphatase inhibitor) on ice for 10 minutes. Lysates were then cleaned by filtration in 1.2 m filter plates followed by western blotting. For each sample, 30 μl of lysate were added to 10 μl of 4×LDS sample buffer, then denatured at 95° C. for 5 minutes in the thermal cycler and placed on ice. Fifteen μL of each sample were then loaded on 4-15% Tris/Glycine gels and run for 25 minutes at 250 (constant) volts in 1× Tris/Glycine buffer. Protein was transferred from gels to nitrocellulose using a BioRad Turbo dry-transfer unit with the Turbo/midi default program. All blots were rinsed with $ddH_2O$ and blocked for 1 hour at room temperature in 5% bovine serum albumin (BSA) in tris-buffered saline-Tween 20 (TBS-T) (0.1%) on rocker. Blots were exposed to primary antibody in 5% BSA in TBS-T (0.1%) overnight at 4° C. on rocker. Primary antibodies, diluted 1:1000 in cell media, were as follows: anti-IRAK4 (cat. #: ab119942, Abcam, Cambridge, Mass.), anti-IRAK1 (cat. #: CST 4504S, Cell Signaling Technology, Danvers, Mass.), and anti-Beta-actin (Cat. #: ab8227, Abcam, Cambridge, Mass.). Blots were then washed with TBS-T (0.1%) three times for 5 minutes on a rocker at room temperature. Secondary antibody (1:18,000 anti-rabbit-HRP and/or anti-mouse-HRP in 5% BSA in TBST (0.1%) was then added, and blots incubated at room temperature rocker for 1 hour. Blots were washed 3 times in TBS-T (0.1%) for 5 minutes at room temperature on the rocker. Signal was developed with Femto Max substrate for 5 minutes and blots read on a ChemiDoc. Percent degradation was assessed by comparing IRAK4 signal in compound vs. DMSO treated lysates.

Figure 2A:
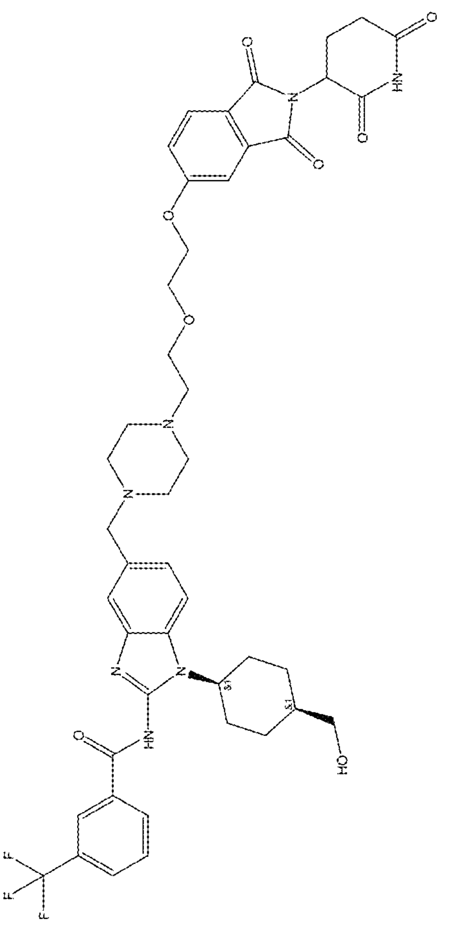
FIGS. 2A, 2B, and 2C. (A) Chemical structure of Exemplary Compound 2. (B) Western blots of IRAK4 and IRAK1 protein degradation by Exemplary Compound 2. (C) Percent degradation of IRAK 4 from the western blots of FIG. 2B (percent remaining is shown). Graphs of percent degradation of IRAK1 by Exemplary Compound 2 is not provided as no significant degradation was observed, as is demonstrated in the blots of FIG. 2B. Exemplary Compound 2 demonstrated a Dmax of 71% and a DC50 of 9.7 nM.
Figure 2B:
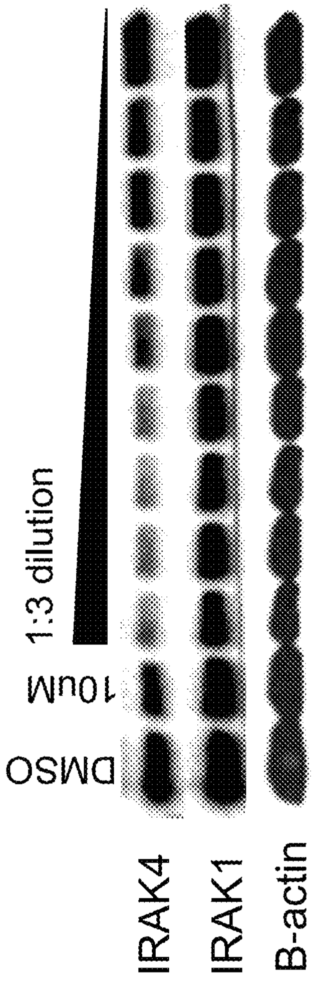
Figure 2C:
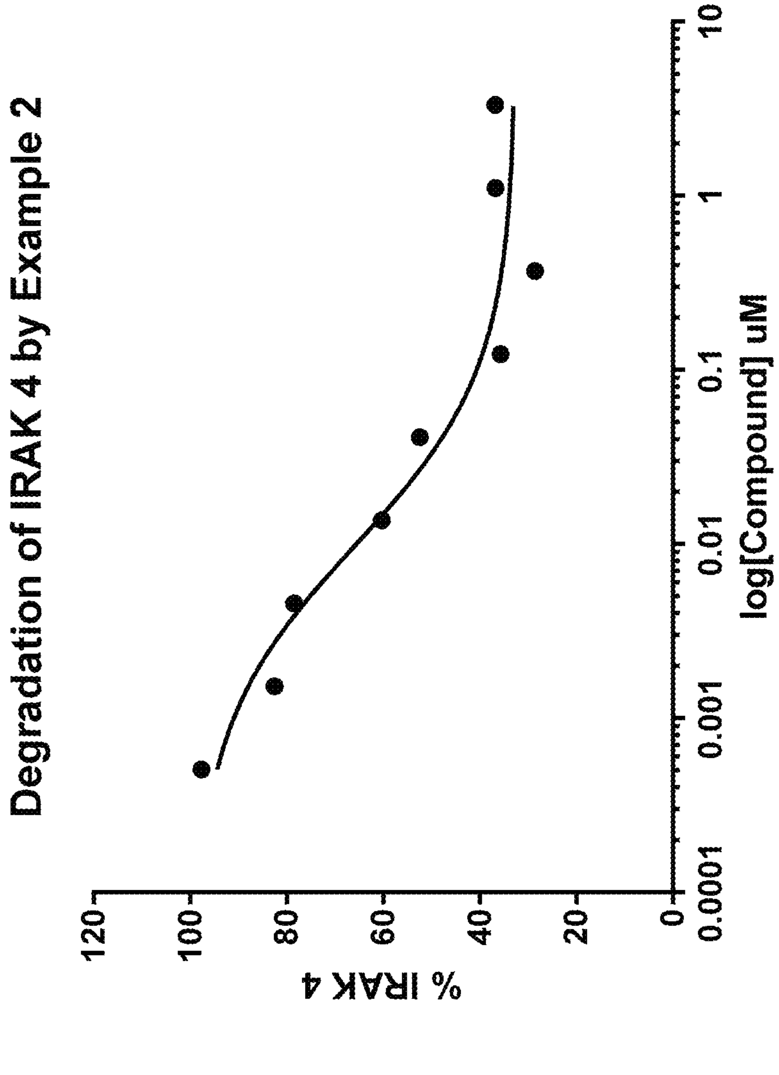
Figure 3A:
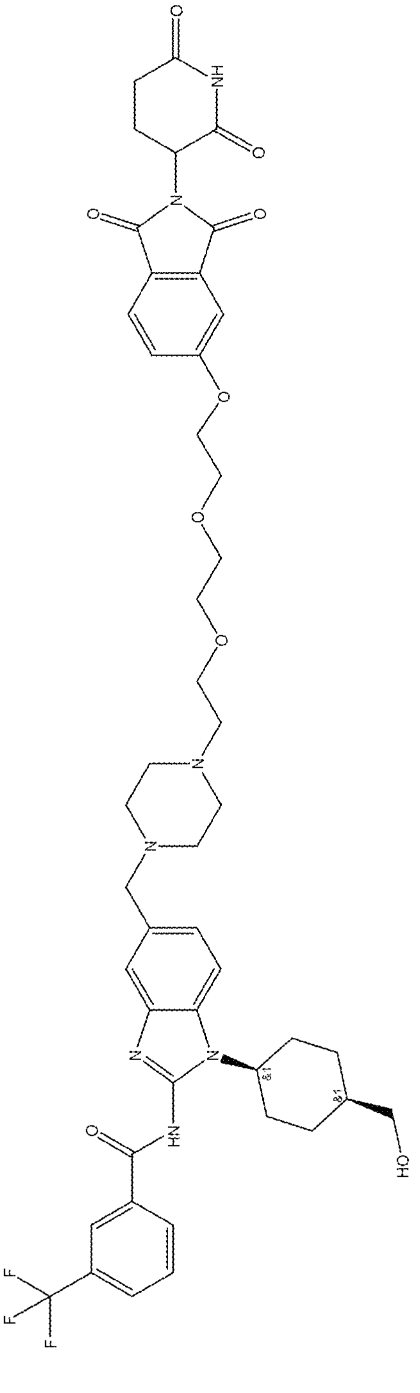
FIGS. 3A, 3B, and 3C. (A) Chemical structure of exemplary compound 3. (B) Western blots of IRAK4 and IRAK1 protein degradation by Exemplary Compound 3. (C) Percent degradation of IRAK 4 from the western blots of FIG. 3B (percent remaining is shown). Graphs of percent degradation of IRAK1 by Exemplary Compound 3 is not provided as no significant degradation was observed, as is demonstrated in the blots of FIG. 3B. Exemplary Compound 3 demonstrated a Dmax of 80% and a DC50 of 23 nM.
Figure 3B:
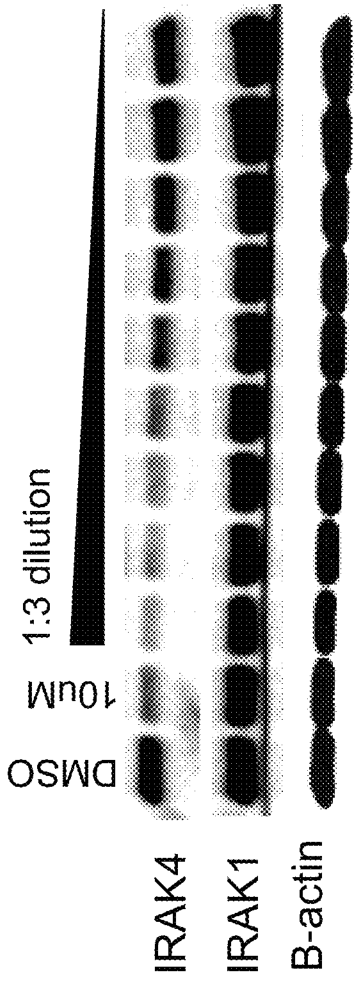
Figure 3C:
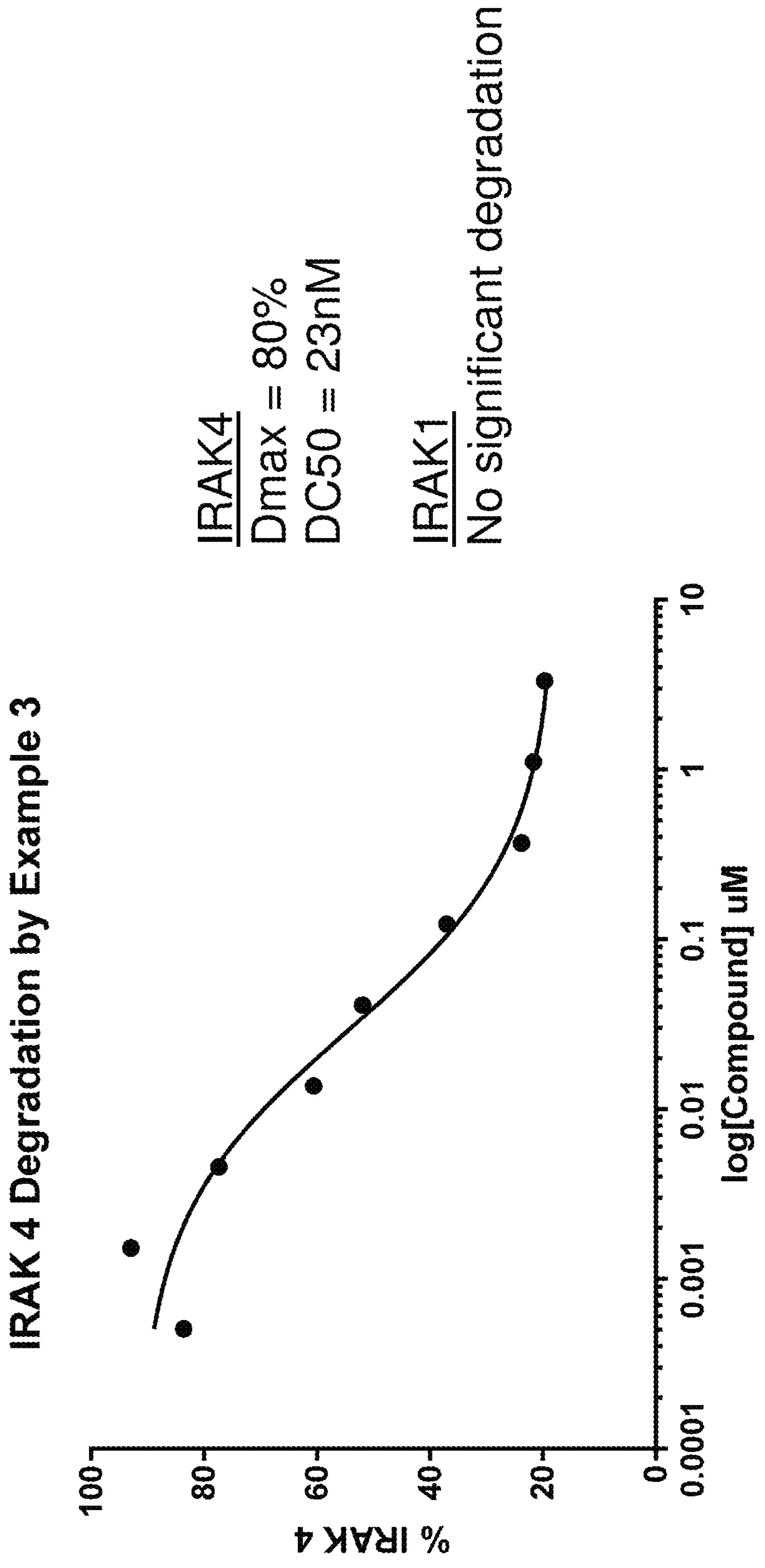

IRAK4 and IRAK1 protein degradation by Example 2 and Example 3 was examined and illustrated in the blots of FIGS. 2B and 3B, respectively. The percent degradation of IRAK 4 by Example 2 and Example 3 are shown in FIGS. 2C and 3C (percent remaining is shown). Graphs of percent degradation of IRAK1 by Examples 2 and 3 is not provided as no significant degradation was observed, as is demonstrated in the blots of FIGS. 2B and 3B, respectively. Example 2 demonstrated a Dmax of 71% and a DC50 of 9.7 nM. Example 3 demonstrate a Dmax of 80% and a DC50 of 23 nM.

Figure 4A:
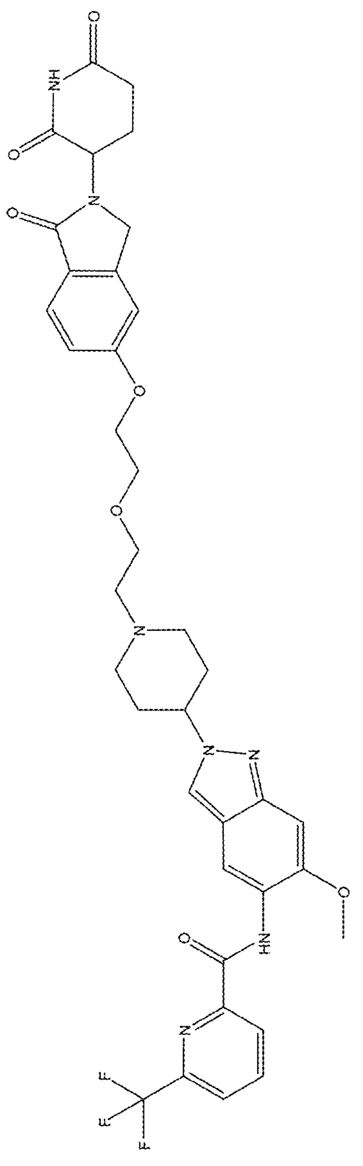
FIGS. 4A, 4B, and 4C. (A) Chemical structure of exemplary compound 60. (B) Western blots of IRAK 4 protein degradation by Exemplary Compound 60. (C) Percent degradation of IRAK4 from the western blots of FIG. 4B (percent remaining is shown). Exemplary Compound 60 demonstrated a Dmax of 73% and a DC50 of 3.5 nM.
Figure 4B:
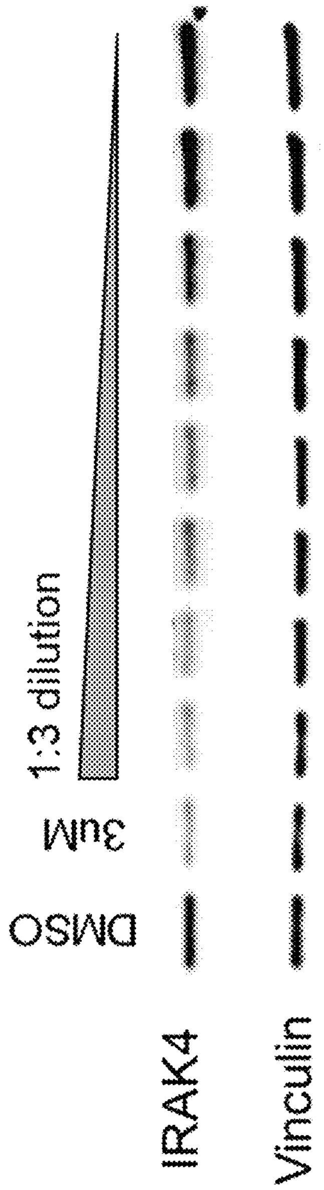
Figure 4C:
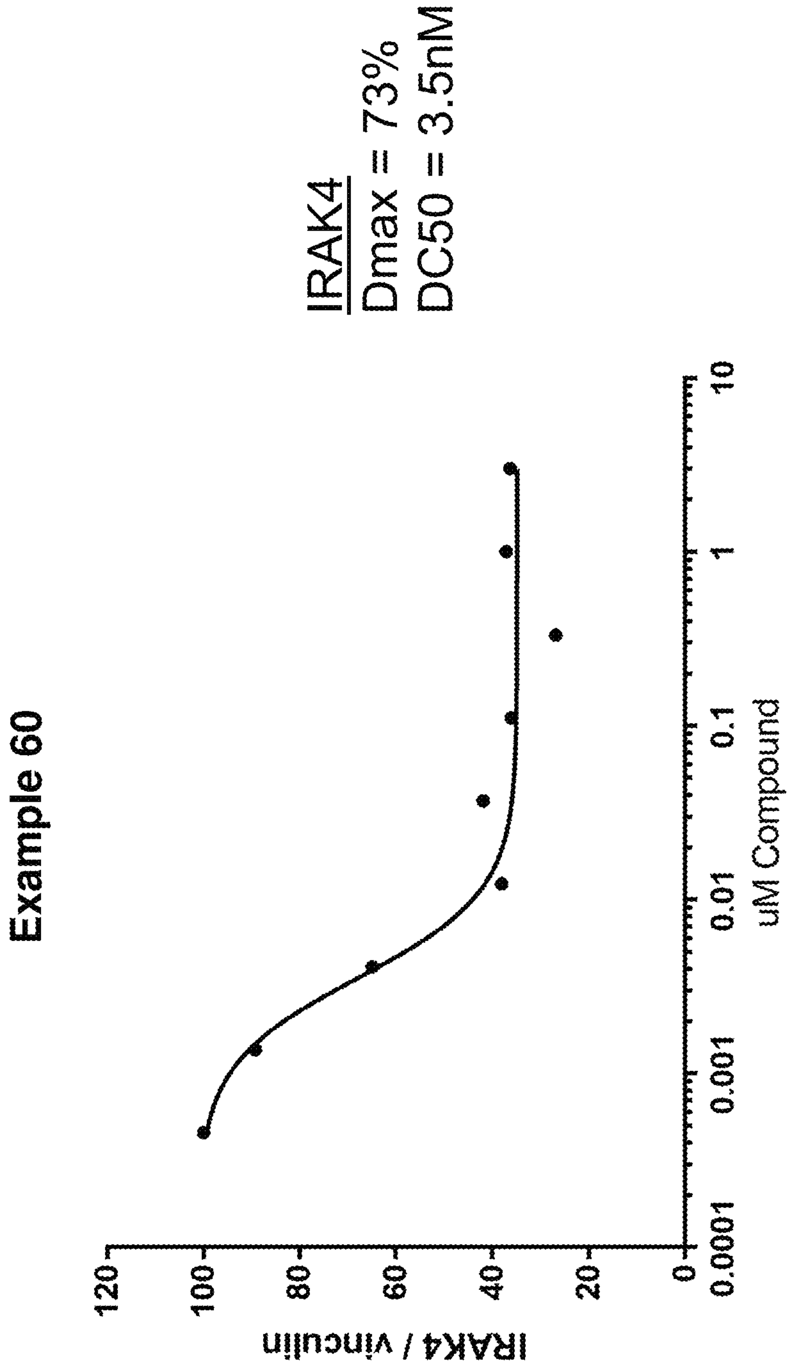

IRAK 4 protein degradation by Example 60 was examined and is illustrated in the blots of FIG. 4B with vinculin as a loading control. The percent of IRAK4 degradation by Example 60 is shown in FIG. 4C (percent remaining is shown). Example 60 demonstrated a Dmax of 73% and a DC50 of 3.5 nM.

Enzyme-Linked Immunosorbent Assay (ELISA) Assay for IRAK4 Degradation.

Figure 5:
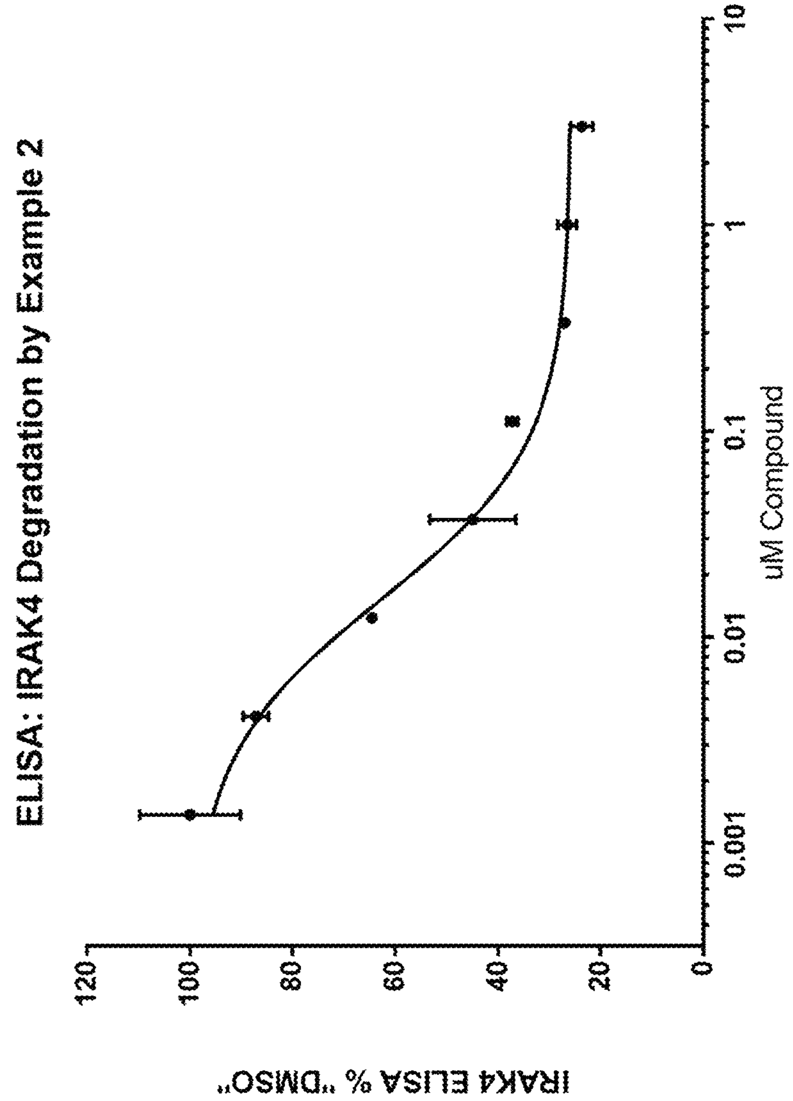
FIG. 5. IRAK4 degradation enzyme-linked immunosorbent assay data for Exemplary Compound 2.

MCF7 cells, purchased from ATCC (Manassas, Va.), were used at a passage range of 2-19. Cells were prepared and treated with compounds for 24 hours, exactly as described above for the Western blots. The ELISA assay was performed using the kit and instructions described by Abcam (cat. #: ab213472, Abcam Biotechnology, Cambridge, Mass.). Table 1 below provides and compares the ELISA IRAK4 degradation data to the western blot IRAK 4 degradation data for Examples 2, 3, 4, and 5. Furthermore, FIG. 5 is a graph illustrating the ELISA IRAK4 degradation data.

TABLE 1

IRAK4 and IRAK 1 protein degradation by Examples 2-5.

| | IRAK4 by western | | IRAK4 by ELISA | |
|---|---|---|---|---|
| | DC50 | % degraded | DC50 | % degraded |
| Example 2 | 10 | 71 | 15 | 76 |
| Example 3 | 23 | 80 | 15 | 86 |
| Example 4 | 25 | 87 | 25 | 89 |
| Example 5 | 40 | 76 | 29 | 80 |

As shown in Table 1, as well as FIGS. 2C and 5, the western blot and ELISA provided similar data for Examples 2-5.

Cell Proliferation Assay Using CellTiter-Glo.

Cells were lifted, washed and counted. White, clear-bottom 96-well plates were seeded with 1801 growth media per well. To allow sub-confluent growth for 3-5 days, seeding densities were as follows: OCI-Ly3 (from DSMZ, Braunschweig, Germany)=10000 cells/well; OCI-Ly19 (from DSMZ, Braunschweig, Germany)=2000 cells/well;

DHL-6 (from ATCC, Manassas, Va.)=2000 cells/well; MCF-7 (from ATCC, Manassas, Va.)=2000 cells/well. One extra plate was seeded for a "time zero" CellTiter-Glo reading. Cells were allowed to adhere/incubate overnight at 37° C./5% $CO_2$. The next day, cells were treated in technical duplicate with 20 μl of 10 μl compound (1% DMSO) was added as appropriate. Plates were returned to incubator for 3 or 5 days. The "time zero" plate was spun down at 300×g, media flicked out and replaced with 100 μl fresh media and 100 μl CellTiter-Glo 2.0 (Promega, Madison, Wis.; plate was then read on Envision 2105 with luminescence setting. At the end point (3 or 5 days), the compound treated plates were spun down at 300×g for 5 minutes, media flicked out, then replaced with 100 μl fresh media and 100 μl CellTiter-Glo 2.0. Plates were then read on the Envision with the luminescence setting.

TABLE 4

| Exemplary compounds of the present disclosure | | |
|---|---|---|
| Ex # | Structure | Chemical Name |
| 1 | 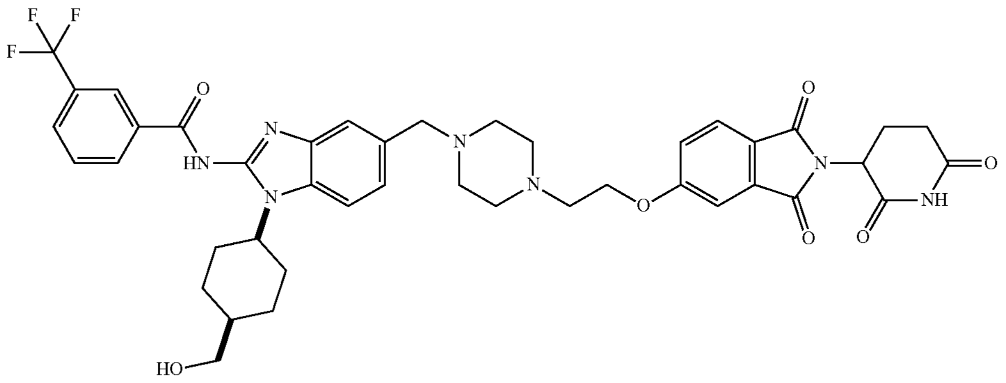 $C_{42}H_{44}F_3N_7O_7$ | N-(5-((4-(2-((2-(2,6-dioxopiperidin-3-yl)-1,3-dioxoisoindolin-5-yl)oxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide |
| 2 | 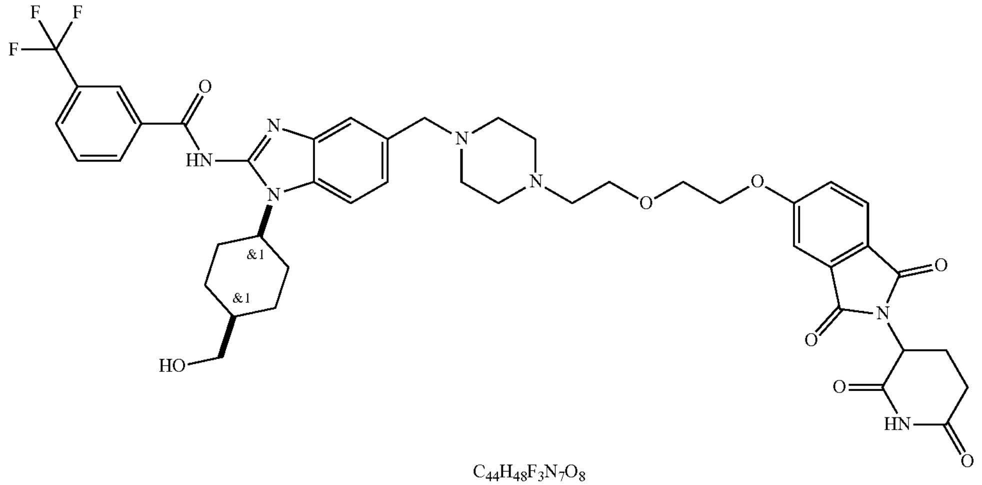 $C_{44}H_{48}F_3N_7O_8$ | N-(5-((4-(2-(2-((2-(2,6-dioxopiperidin-3-yl)-1,3-dioxoisoindolin-5-yl)oxy)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 3 | 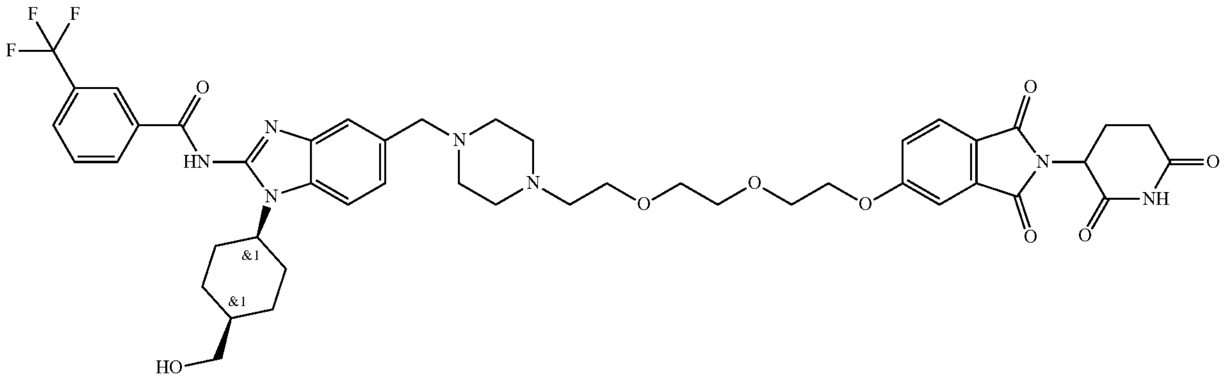 $C_{46}H_{52}F_3N_7O_9$ | N-(5-((4-(2-(2-(2-((2-(2,6-dioxopiperidin-3-yl)-1,3-dioxoisoindolin-5-yl)oxy)ethoxy)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide |
| 4 | 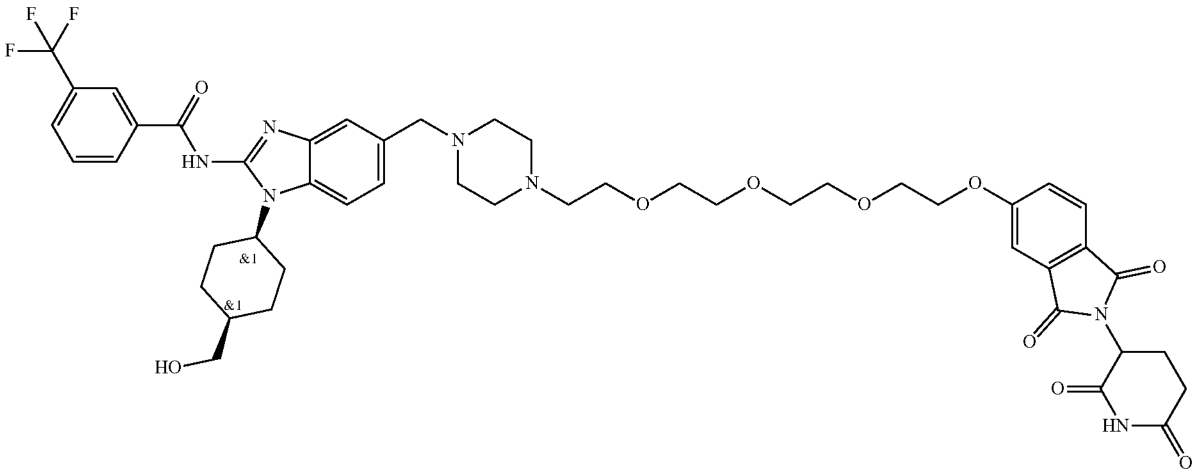 $C_{48}H_{56}F_3N_7O_{10}$ | N-(5-((4-(2-(2-(2-(2-((2-(2,6-dioxopiperidin-3-yl)-1,3-dioxoisoindolin-5-yl)oxy)ethoxy)ethoxy)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 5 | 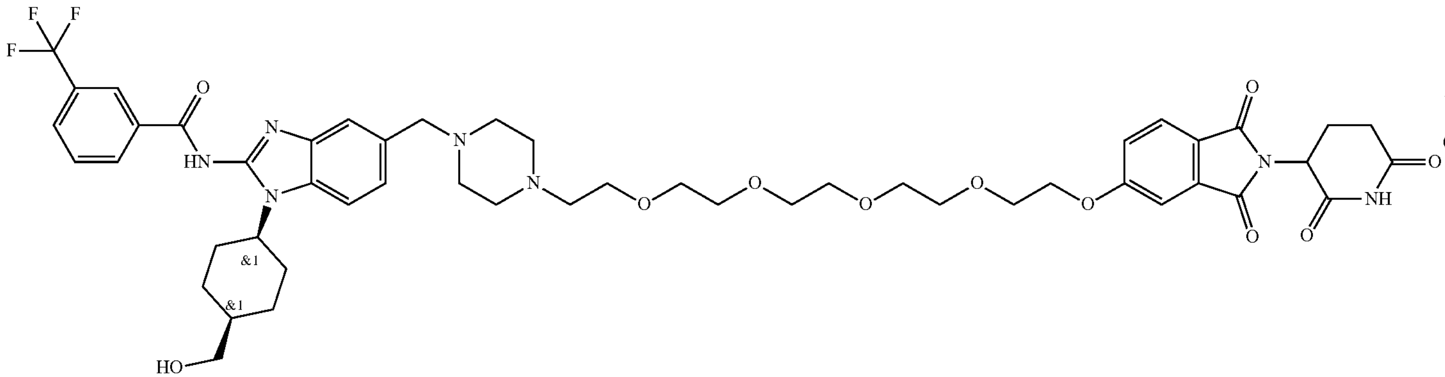 $C_{50}H_{60}F_3N_7O_{11}$ | N-(5-((4-(14-((2-(2,6-dioxopiperidin-3-yl)-1,3-dioxoisoindolin-5-yl)oxy)-3,6,9,12-tetraoxatetradecyl)piperazin-1-yl)methyl)-1-((1s,4s)-4-(hydroxymethyl)cyclohexyl)-1H-benzo[d]imidazol-2-yl)-3-(trifluoromethyl)benzamide |
| 6 | 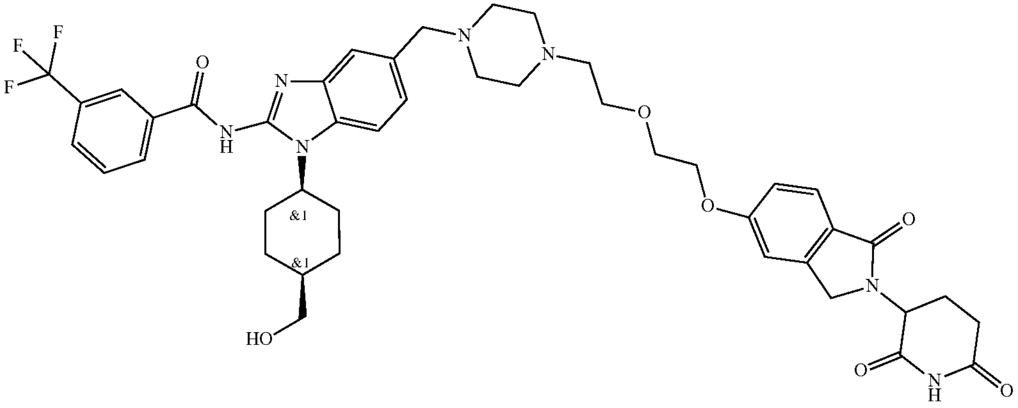 $C_{44}H_{50}F_3N_7O_7$ | N-(5-((4-(2-(2-((2-(2,6-dioxopiperidin-3-yl)-1-oxoisoindolin-5-yl)oxy)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 7 | 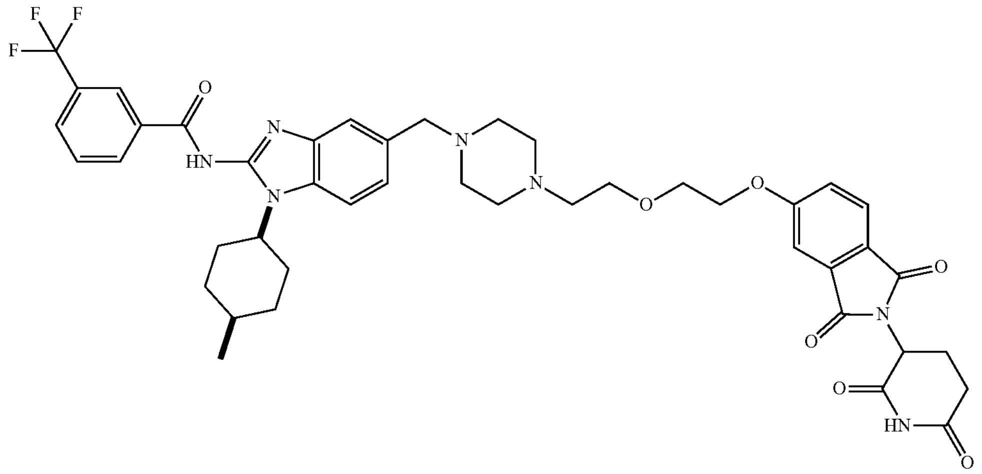 $C_{44}H_{48}F_3N_7O_7$ | N-(5-((4-(2-(2-((2-(2,6-dioxopiperidin-3-yl)-1,3-dioxoisoindolin-5-yl)oxy)ethoxy)ethyl)piperazin-1-yl)methyl)-1-((1s,4s)-4-methylcyclohexyl)-1H-benzo[d]imidazol-2-yl)-3-(trifluoromethyl)benzamide |
| 8 | 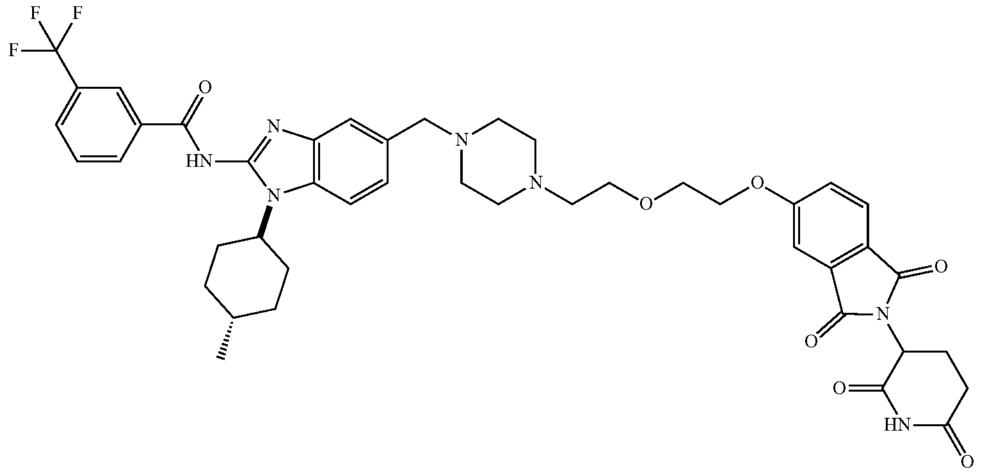 $C_{44}H_{48}F_3N_7O_7$ | N-(5-((4-(2-(2-((2-(2,6-dioxopiperidin-3-yl)-1,3-dioxoisoindolin-5-yl)oxy)ethoxy)ethyl)piperazin-1-yl)methyl)-1-((1r,4r)-4-methylcyclohexyl)-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 9 | 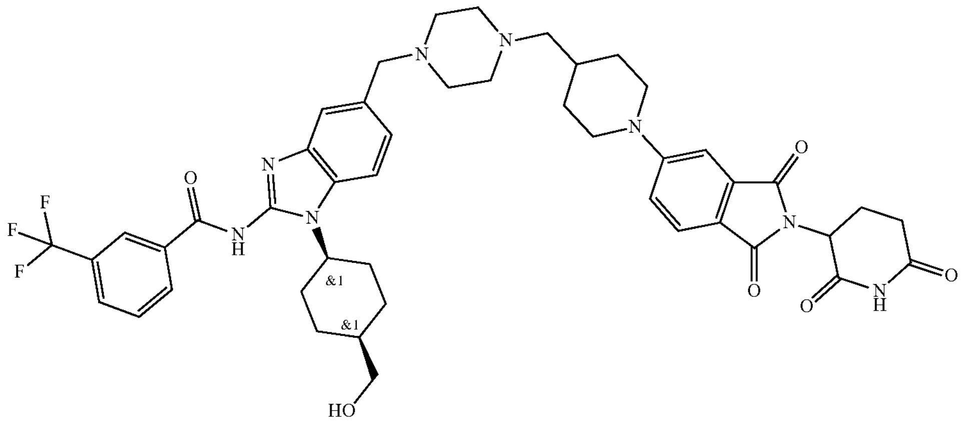 $C_{46}H_{51}F_3N_8O_6$ | N-(5-((4-((1-(2-(2,6-dioxopiperidin-3-yl)-1,3-dioxoisoindolin-5-yl)piperazin-4-yl)methyl)piperzin-1-yl)methyl)-1-((1s,4s)-4-(hydroxymethyl)cyclohexyl)-1H-benzo[d]imidazol-2-yl)-3-(trifluoromethyl)benzamide |
| 10 | 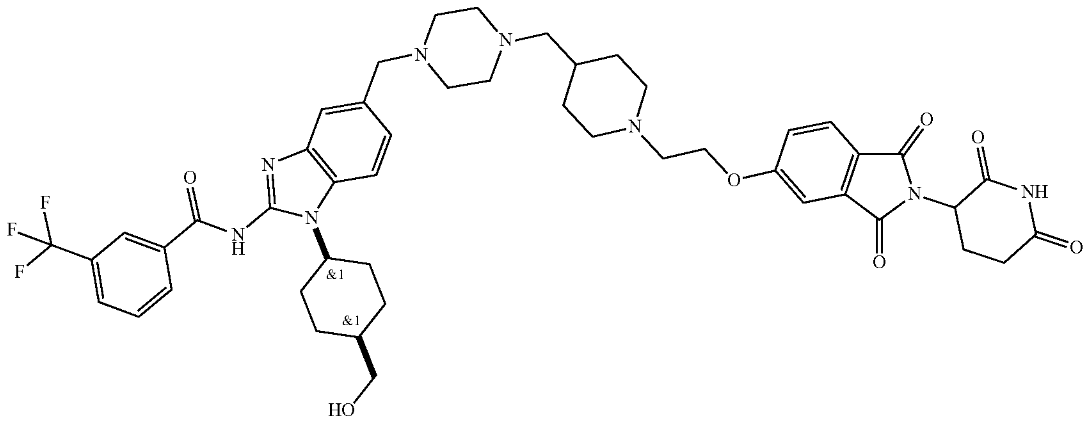 $C_{48}H_{55}F_3N_8O_7$ | N-(5-((4-((1-(2-((2-(2,6-dioxopiperidin-3-yl)-1,3-dioxoisoindolin-5-yl)oxy)ethyl)piperazin-4-yl)methyl)piperzin-1-yl)methyl)-1-((1s,4s)-4-(hydroxymethyl)cyclohexyl)-1H-benzo[d]imidazol-2-yl)-3-(trifluoromethyl)benzamide |

TABLE 4-continued
| Exemplary compounds of the present disclosure | | |
|---|---|---|
| Ex # | Structure | Chemical Name |
| 11 | 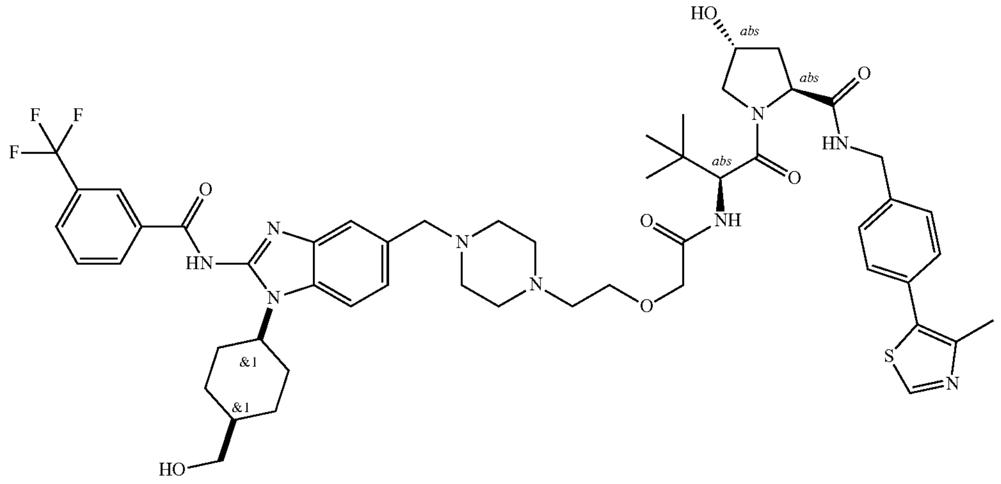 $C_{53}H_{66}F_3N_9O_7S$ | (2S,4R)-4-hydroxy-1-((S)-2-(2-(2-(4-((1-((1SR,4SR)-4-(hydroxymethyl)cyclohexyl)-2-(3-(trifluoromethyl)benzamido)-1H-benzo[d]imidazol-5-yl)methyl)piperazin-1-yl)ethoxy)acetamido)-3,3-dimethylbutanoyl)-N-(4-(4-methylthiazol-5-yl)benzyl)pyrrolidine-2-carboxamide |

TABLE 4-continued
| Exemplary compounds of the present disclosure | | |
|---|---|---|
| Ex # | Structure | Chemical Name |
| 12 | 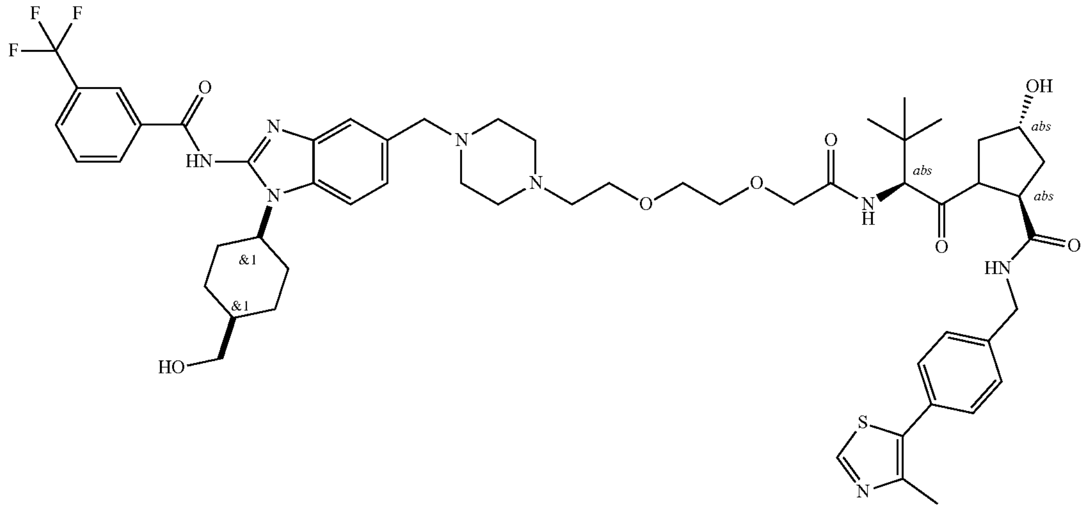 $C_{55}H_{70}F_3N_9O_8S$ | (2S,4R)-4-hydroxy-1-((S)-2-(2-(2-(2-(4-((1-((1SR,4SR)-4-(hydroxymethyl)cyclohexyl)-2-(3-(trifluoromethyl)benzamido)-1H-benzo[d]imidazol-5-yl)methyl)piperazin-1-yl)ethoxy)ethoxy)acetamido)-3,3-dimethylbutanoyl)-N-(4-(4-methylthiazol-5-yl)benzyl)pyrrolidine-2-carboxamide |

TABLE 4-continued

| Exemplary compounds of the present disclosure | | |
|---|---|---|
| Ex # | Structure | Chemical Name |
| 13 | 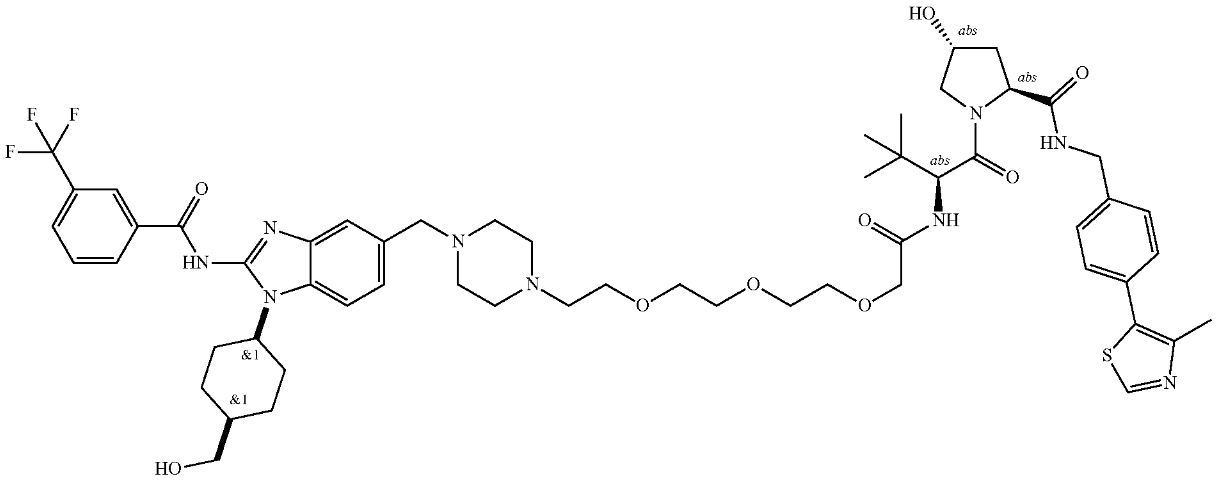 $C_{57}H_{74}F_3N_9O_9S$ | (2S,4R)-1-((S)-2-(tert-butyl)-14-(4-((1-((1SR,4SR)-4-(hydroxymethyl)cyclohexyl)-2-(3-(trifluoromethyl)benzamido)-1H-benzo[d]imidazol-5-yl)methyl)piperazin-1-yl)-4-oxo-6,9,12-trioxa-3-azatetradecanoyl)-4-hydroxy-N-(4-(4-methylthiazol-5-yl)benzyl)pyrrolidine-2-carboxamide |
| 14 | 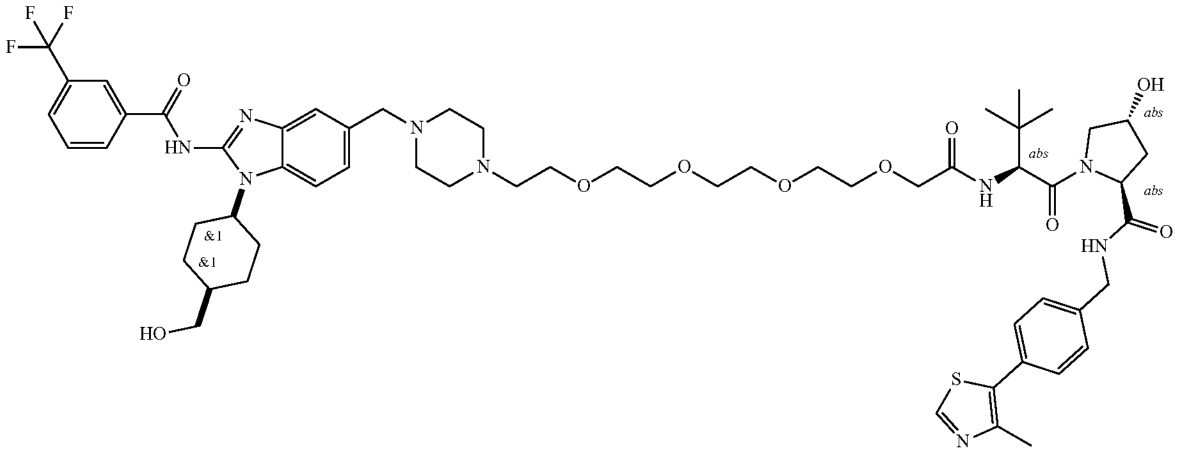 $C_{59}H_{78}F_3N_9O_{10}S$ | (2S,4R)-1-((S)-2-(tert-butyl)-17-(4-((1-((1SR,4SR)-4-(hydroxymethyl)cyclohexyl)-2-(3-(trifluoromethyl)benzamido)-1H-benzo[d]imidazol-5-yl)methyl)piperazin-1-yl)-4-oxo-6,9,12-tetraoxa-3-azatetradecanoyl)-4-hydroxy-N-(4-(4-methylthiazol-5-yl)benzyl)pyrrolidine-2-carboxamide |

TABLE 4-continued

| Exemplary compounds of the present disclosure | | |
|---|---|---|
| Ex # | Structure | Chemical Name |
| 25 | 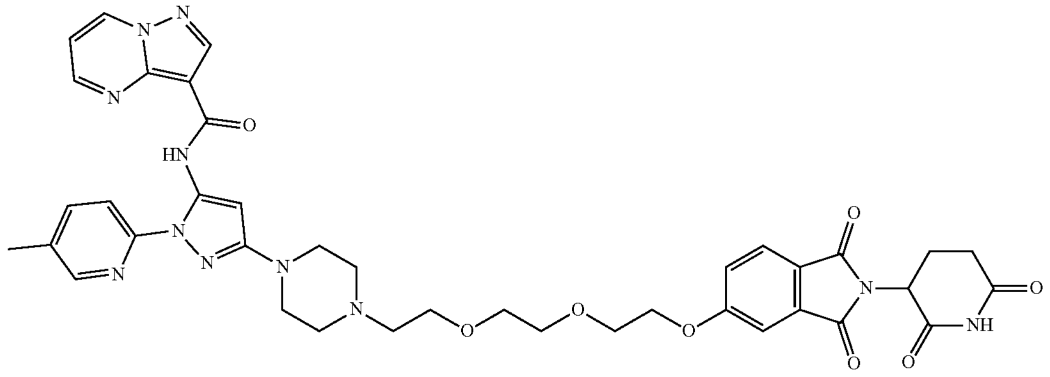<br>$C_{39}H_{41}N_{11}O_8$ | N-(3-(4-(2-(2-(2-((2-(2,6-dioxopiperidin-3-yl)-1,3-dioxoisoindolin-5-yl)oxy)ethoxy)ethoxy)ethyl)piperazin-1-yl)-1-(5-methylpyridin-2-yl)-1H-pyrazol-5-yl)pyrazolo[1,5-a]pyrimidine-3-caboxamide |
| 26 | 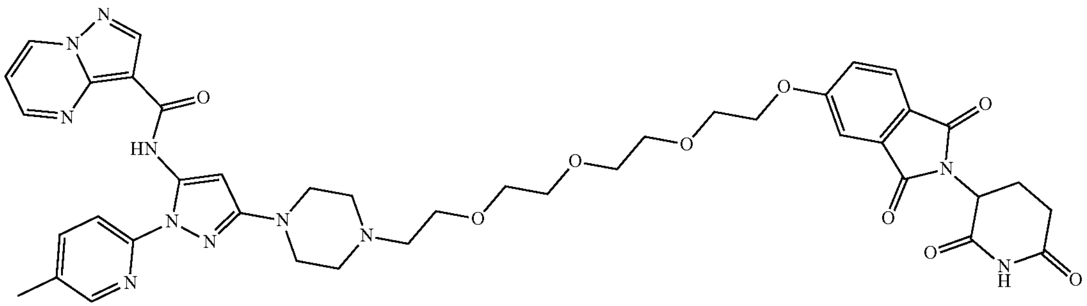<br>$C_{41}H_{45}N_{11}O_9$ | N-(3-(4-(2-(2-(2-(2-((2-(2,6-dioxopiperidin-3-yl)-1,3-dioxoisoindolin-5-yl)oxy)ethoxy)ethoxy)ethoxy)ethyl)piperazin-1-yl)-1-(5-methylpyridin-2-yl)-1H-pyrazol-5-yl)pyrazolo[1,5-a]pyrimidine-3-caboxamide |

TABLE 4-continued

| Exemplary compounds of the present disclosure | | |
|---|---|---|
| Ex # | Structure | Chemical Name |
| 27 | 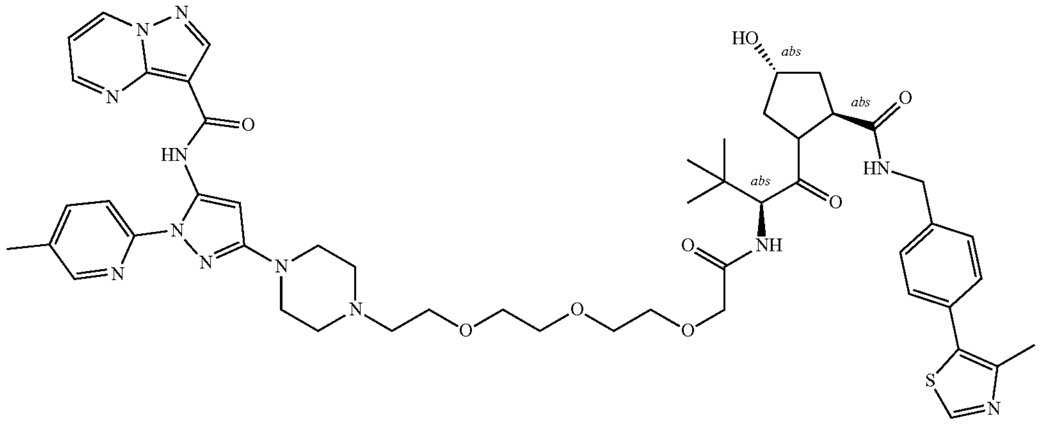 $C_{50}H_{63}N_{13}O_8S$ | N-(3-(4-((S)-13-((2S,4R)-4-hydroxy-2-((4-(4-methylthiazol-5-yl)benzyl)carbamoyl) pyrrolidine-1-carbonyl)-14,14-dimethyl-11-oxo-3,6,9-trioxa-12-azapentadecyl)piperazin-1-yl)-1-(5-methylpyridin-2-yl)-1H-pyrazol-5-yl)pyrazolo[1,5-a]pyrimidine-3-carboxamide |
| 28 | 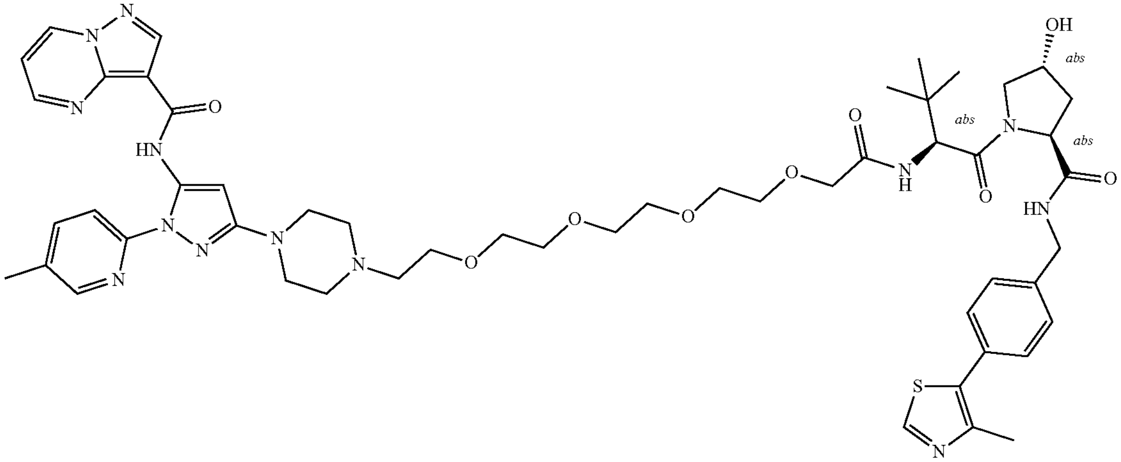 $C_{52}H_{67}N_{13}O_9S$ | N-(3-(4-((S)-16-((2S,4R)-4-hydroxy-2-((4-(4-methylthiazol-5-yl)benzyl)carbamoyl) pyrrolidine-1-carbonyl)-17,17-dimethyl-14-oxo-3,6,9,12-tetraoxa-15-azapentadecyl)piperazin-1-yl)-1-(5-methylpyridin-2-yl)-1H-pyrazol-5-yl)pyrazolo[1,5-a]pyrimidine-3-carboxamide |

TABLE 4-continued
| Ex # | Structure | Chemical Name |
| --- | --- | --- |
| | Exemplary compounds of the present disclosure | |
| 29 | 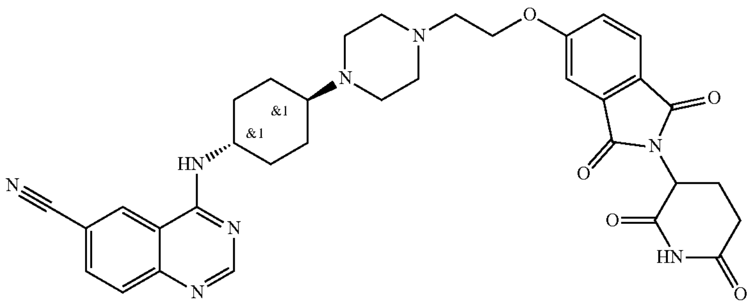 [SMILES: N#Cc1ccc2ncnc(N[C@H]3CC[C@H](N4CCN(CCOc5ccc6c(c5)C(=O)N(C5CCC(=O)NC5=O)C6=O)CC4)CC3)c2c1] | 4-((1r,4r)-4-(4-(2-((2-(2,6-dioxopiperidin-3-yl)-1,3-dioxoisoindolin-5-yl)oxy)ethyl)piperazin-1-yl)cyclohexyl)amino) quinazoline-6-carbonitrile |
| 30 | 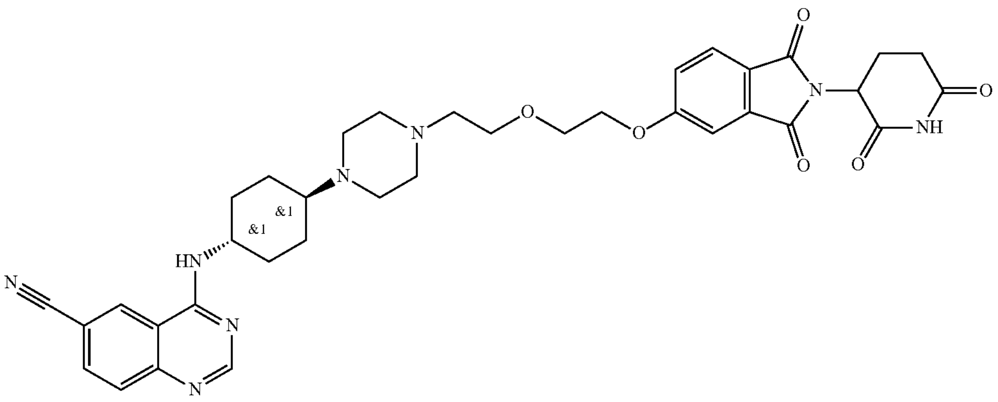 $C_{36}H_{40}N_8O_6$ | 4-((1r,4r)-4-(4-(2-(2-((2-(2,6-dioxopiperidin-3-yl)-1,3-dioxoisoindolin-5-yl)oxy)ethoxy)ethyl)piperazin-1-yl)cyclohexyl)amino) quinazoline-6-carbonitrile |

TABLE 4-continued

| Exemplary compounds of the present disclosure | | |
|---|---|---|
| Ex # | Structure | Chemical Name |
| 31 | 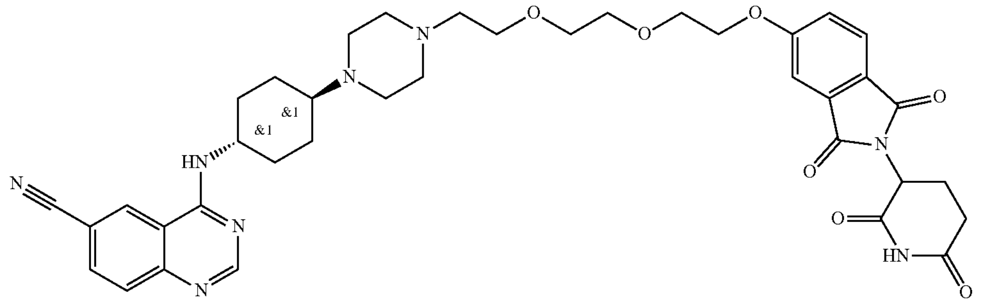 $C_{38}H_{44}N_8O_7$ | 4-((1r,4r)-4-(4-(2-(2-(2-((2-(2,6-dioxopiperidin-3-yl)-1,3-dioxoisoindolin-5-yl)oxy)ethoxy)ethoxy)ethyl) piperazin-1-yl)cyclohexyl)amino) quinazoline-6-carbonitrile |
| 32 | 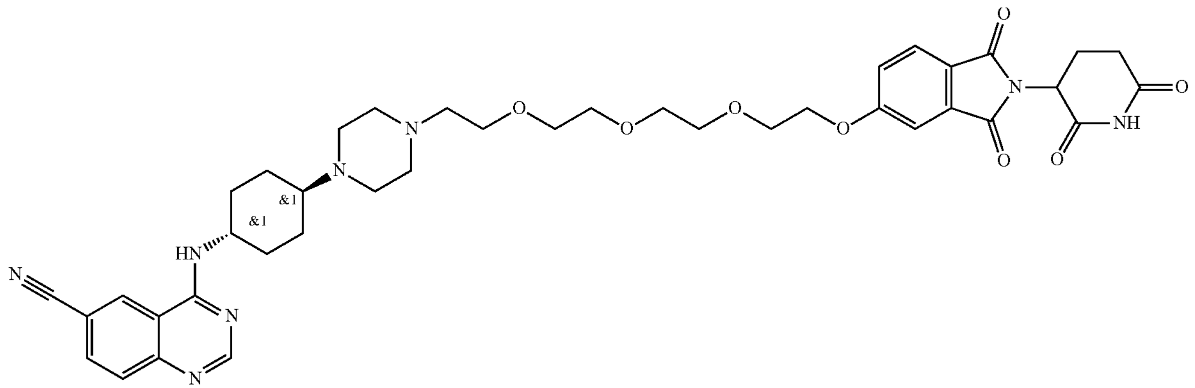 $C_{40}H_{48}N_8O_8$ | 4-((1r,4r)-4-(4-(2-(2-(2-(2-((2-(2,6-dioxopiperidin-3-yl)-1,3-dioxoisoindolin-5-yl)oxy)ethoxy)ethoxy)ethoxy) ethyl)piperazin-1-yl)cyclohexyl)amino) quinazoline-6-carbonitrile |

TABLE 4-continued

| Exemplary compounds of the present disclosure | | |
|---|---|---|
| Ex # | Structure | Chemical Name |
| 33 | 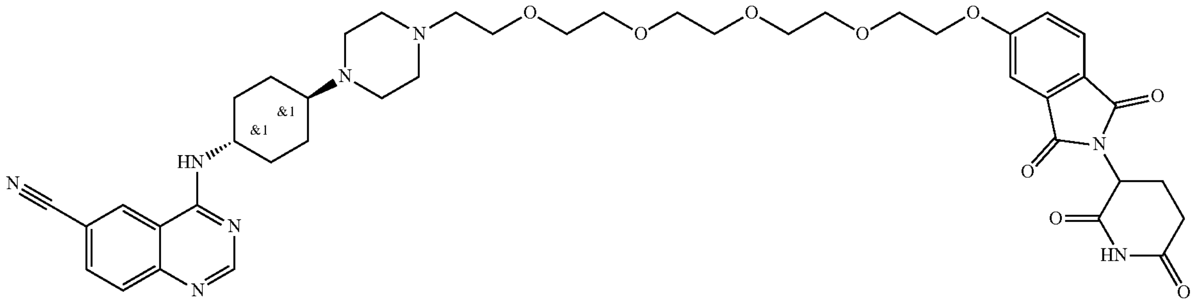 $C_{42}H_{52}N_8O_9$ | 4-((1r,4r)-4-(4-(14-((2-(2,6-dioxopiperidin-3-yl)-1,3-dioxoisoindolin-5-yl)oxy)-3,6,9,12-tetraoxatetradecyl)piperazin-1-yl)cyclohexyl)amino) quinazoline-6-carbonitrile |
| 34 | 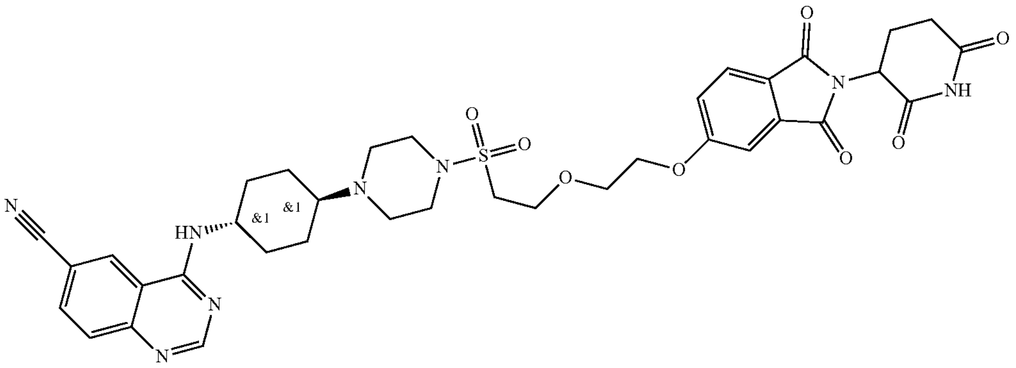 $C_{36}H_{40}N_8O_8S$ | 4-((1r,4r)-4-(4-((2-(2-((2-(2,6-dioxopiperidin-3-yl)-1,3-dioxoisoindolin-5-yl)oxy)ethoxy)ethyl)sulfonyl) piperazin-1-yl)cyclohexyl)amino) quinazoline-6-carbonitrile |

TABLE 4-continued

| Exemplary compounds of the present disclosure | | |
|---|---|---|
| Ex # | Structure | Chemical Name |
| 35 | 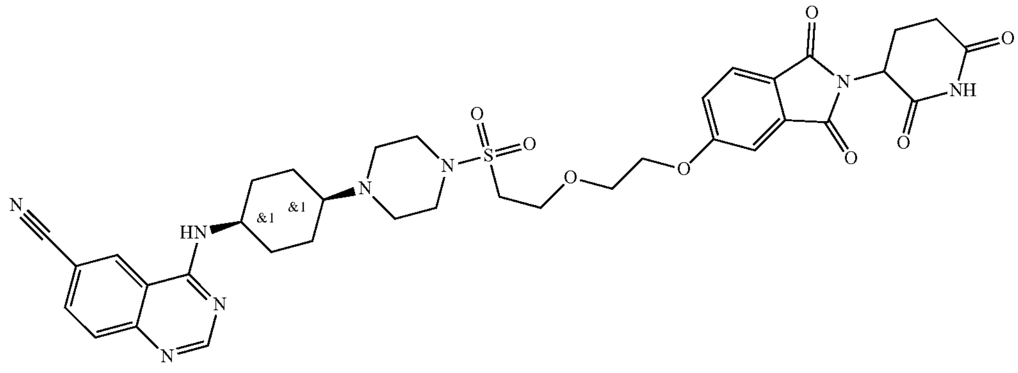 $C_{36}H_{40}N_8O_8S$ | 4-((1s,4s)-4-(4-((2-(2-((2-(2,6-dioxopiperidin-3-yl)-1,3-dioxoisoindolin-5-yl)oxy)ethoxy)ethyl)sulfonyl)piperazin-1-yl)cyclohexyl)amino)quinazoline-6-carbonitrile |
| 36 | 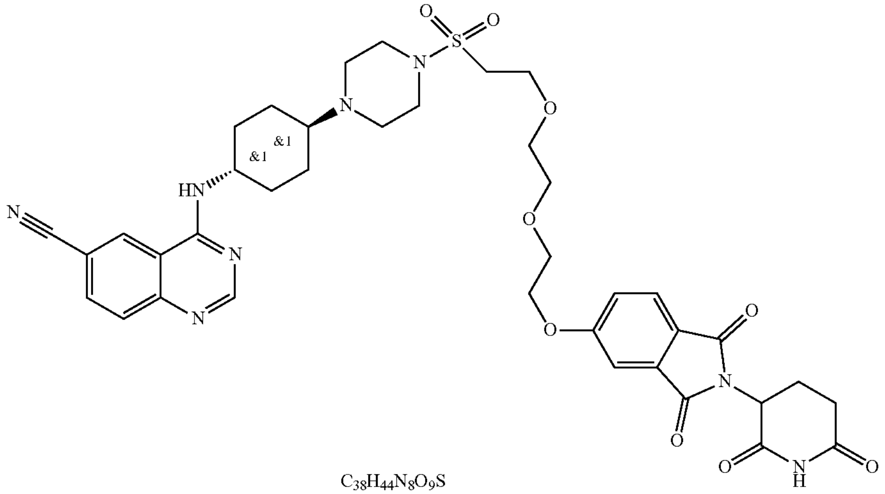 [SMILES: N#Cc1ccc2ncnc(N[C@H]3CC[C@H](N4CCN(S(=O)(=O)CCOCCOCCOc5ccc6c(c5)C(=O)N(C5CCC(=O)NC5=O)C6=O)CC4)CC3)c2c1 ; "C38H44N8O9S"] $C_{38}H_{44}N_8O_9S$ | 4-((1r,4r)-4-(4-((2-(2-(2-((2-(2,6-dioxopiperidin-3-yl)-1,3-dioxoisoindolin-5-yl)oxy)ethoxy)ethoxy)ethyl)sulfonyl)piperazin-1-yl)cyclohexyl)amino)quinazoline-6-carbonitrile |

TABLE 4-continued

| Exemplary compounds of the present disclosure | | |
|---|---|---|
| Ex # | Structure | Chemical Name |
| 37 | 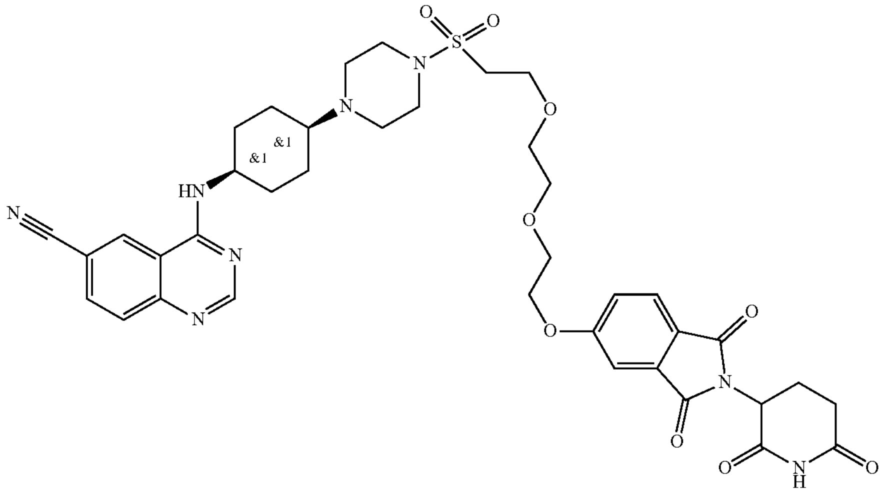 $C_{38}H_{44}N_8O_9S$ | 4-((1s,4s)-4-(4-((2-(2-(2-((2-(2,6-dioxopiperidin-3-yl)-1,3-dioxoisoindolin-5-yl)oxy)ethoxy)ethoxy)ethyl)sulfonyl)piperazin-1-yl)cyclohexyl)amino)quinazoline-6-carbonitrile |
| 38 | 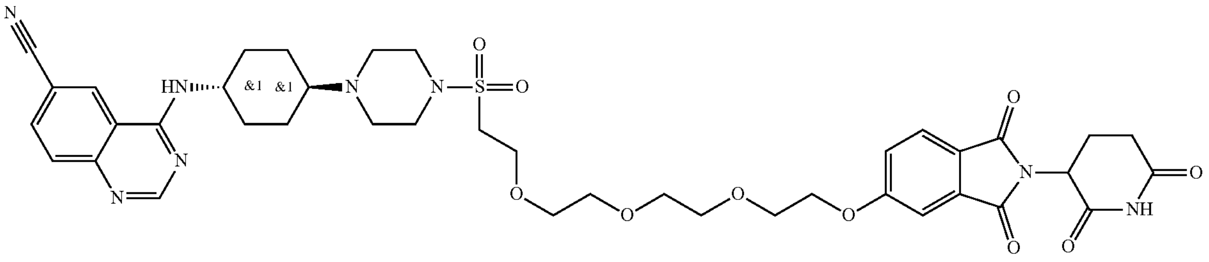 $C_{40}H_{48}N_8O_{10}S$ | 4-((1r,4r)-4-(4-((2-(2-(2-(2-((2-(2,6-dioxopiperidin-3-yl)-1,3-dioxoisoindolin-5-yl)oxy)ethoxy)ethoxy)ethoxy)ethyl)sulfonyl)piperazin-1-yl)cyclohexyl)amino)quinazoline-6-carbonitrile |

TABLE 4-continued

| Exemplary compounds of the present disclosure | | |
|---|---|---|
| Ex # | Structure | Chemical Name |
| 39 | 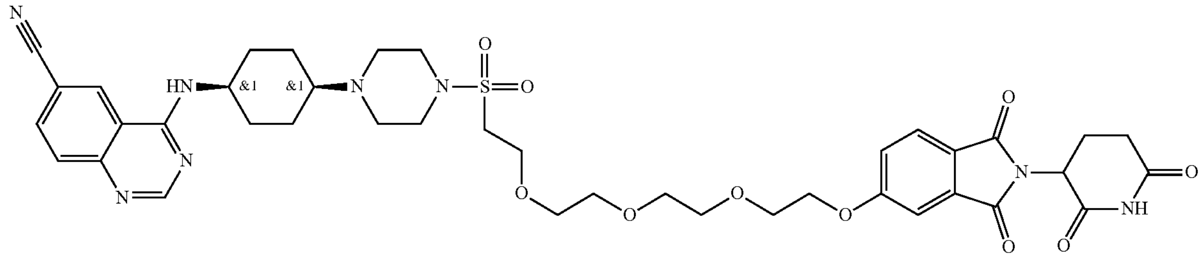 $C_{40}H_{48}N_8O_{10}S$ | 4-((1s,4s)-4-(4-((2-(2-(2-(2-((2-(2,6-dioxopiperidin-3-yl)-1,3-dioxoisoindolin-5-yl)oxy)ethoxy)ethoxy)ethoxy)ethyl)sulfonyl)piperazin-1-yl)cyclohexyl)amino)quinazoline-6-carbonitrile |
| 40 | 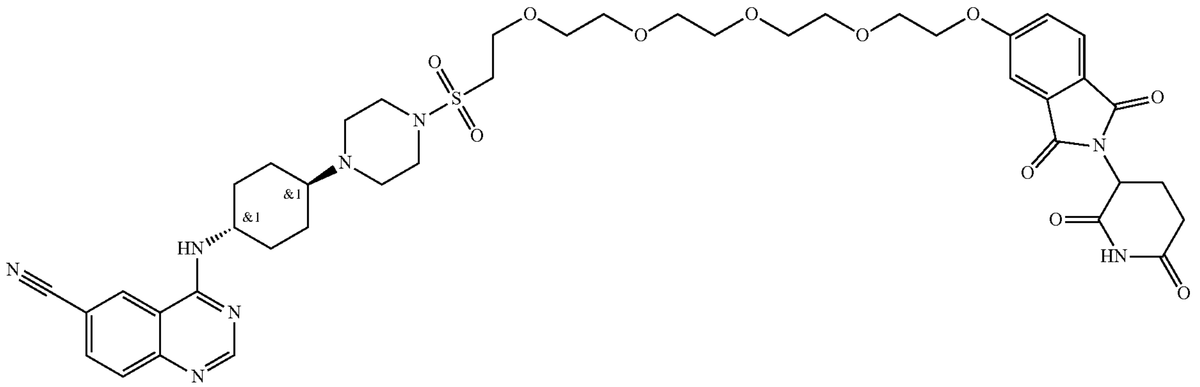 $C_{42}H_{52}N_8O_{11}S$ | 4-((1r,4r)-4-(4-((14-((2-(2,6-dioxopiperidin-3-yl)-1,3-dioxoisoindolin-5-yl)oxy)-3,6,8,12-tetraoxatetradecyl)sulfonyl)piperazin-1-yl)cyclohexyl)amino)quinazoline-6-carbonitrile |

TABLE 4-continued

Exemplary compounds of the present disclosure

| Ex # | Structure | Chemical Name |
| --- | --- | --- |
| 41 | 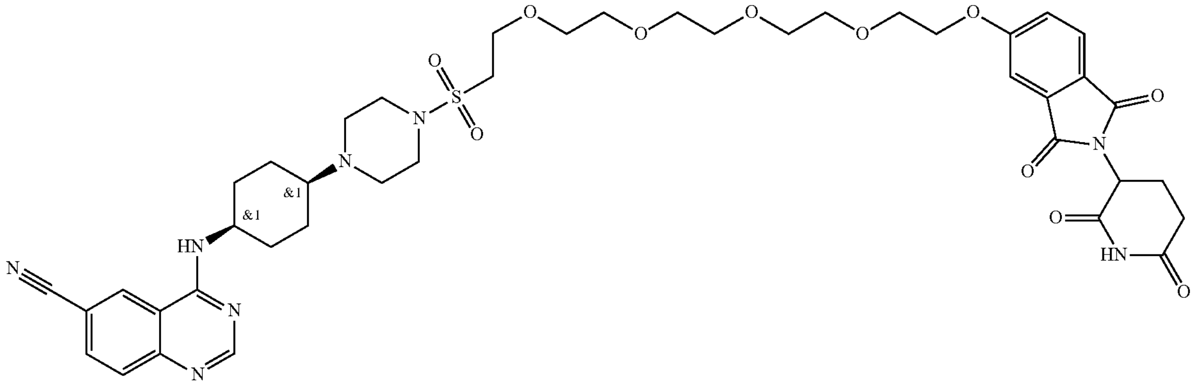 $C_{42}H_{52}N_8O_{11}S$ | 4-((1s,4s)-4-(4-((14-((2-(2,6-dioxopiperidin-3-yl)-1,3-dioxoisoindolin-5-yl)oxy)-3,6,8,12-tetraoxatetradecyl)sulfonyl) piperazin-1-yl)cyclohexyl)amino) quinazoline-6-carbonitrile |
| 42 | 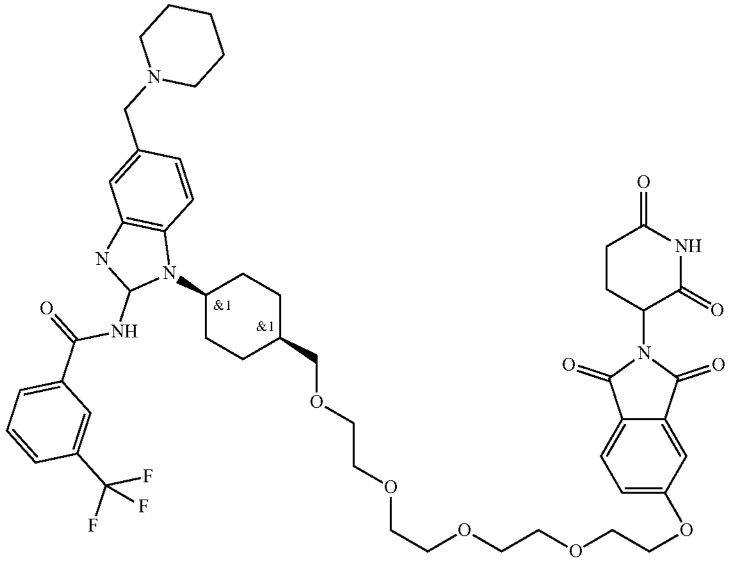 $C_{49}H_{57}F_3N_6O_{10}$ | N-(1-((1s,4s)-4-(13-((2-(2,6-dioxopiperidin-3-yl)-1,3-dioxoisoindolin-5-yl)oxy)-2,5,8,11-tetraoxatetradecyl)cyclohexyl)-5-(piperidin-1-ylmethyl)-1H-benzo[d]imidazol-2-yl)-3-(trifluoromethyl)benzamide |

TABLE 4-continued
| Exemplary compounds of the present disclosure | | |
|---|---|---|
| Ex # | Structure | Chemical Name |
| 43 | 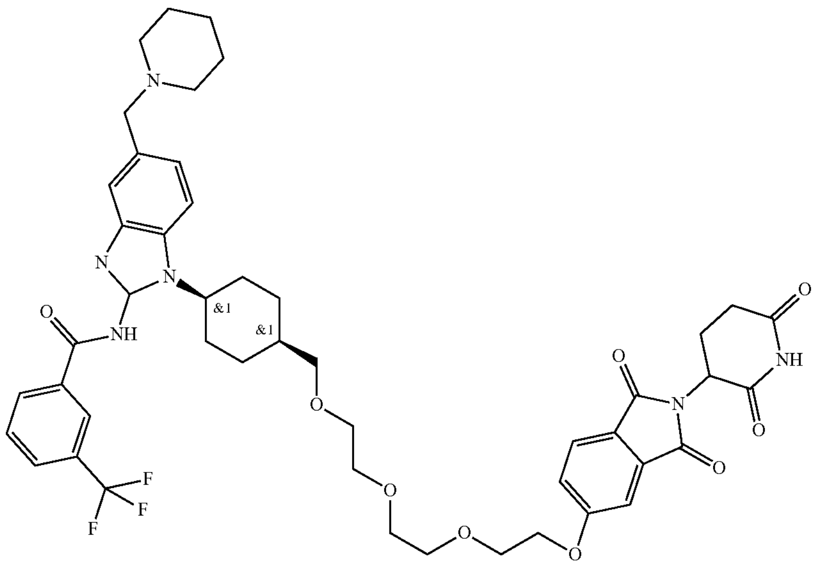 $C_{47}H_{53}F_3N_6O_9$ | N-(1-((1s,4s)-4-((2-(2-(2-((2-(2,6-dioxopiperidin-3-yl)-1,3-dioxoisoindolin-5-yl)oxy)ethoxy)ethoxy)ethoxy)methyl)cyclohexyl)-5-(piperidin-1-ylmethyl)-1H-benzo[d]imidazol-2-yl)-3-(trifluoromethyl)benzamide |

TABLE 4-continued
| Exemplary compounds of the present disclosure | | |
|---|---|---|
| Ex # | Structure | Chemical Name |
| 44 | 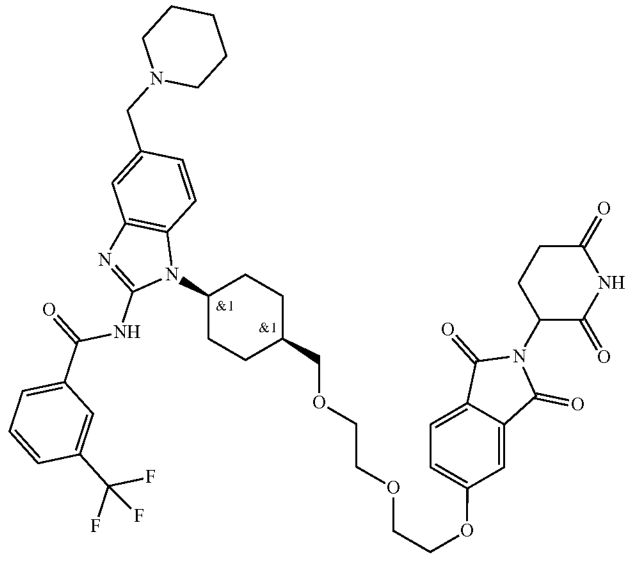 $C_{45}H_{49}F_3N_6O_8$ | N-(1-((1s,4s)-4-((2-(2-((2-(2,6-dioxopiperidin-3-yl)-1,3-dioxoisoindolin-5-yl)oxy)ethoxy)ethoxy)methyl)cyclohexyl)-5-(piperidin-1-ylmethyl)-1H-benzo[d]imidazol-2-yl)-3-(trifluoromethyl)benzamide |

TABLE 4-continued
| Exemplary compounds of the present disclosure | | |
|---|---|---|
| Ex # | Structure | Chemical Name |
| 45 | 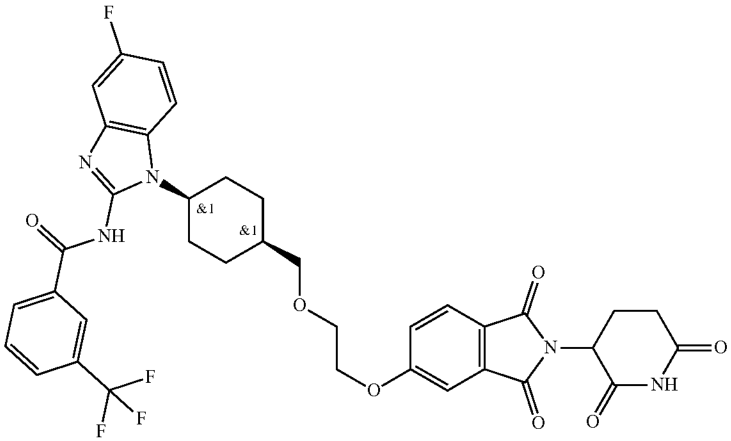 $C_{37}H_{33}F_4N_5O_7$ | N-(1-((1s,4s)-4-((2-((2-(2,6-dioxopiperidin-3-yl)-1,3-dioxoisoindolin-5-yl)oxy)ethoxy)methyl) cyclohexyl)-5-(piperidin-1-ylmethyl)-1H-benzo[d]imidazol-2-yl)-3-(trifluoromethyl)benzamide |

TABLE 4-continued
| Exemplary compounds of the present disclosure | | |
| --- | --- | --- |
| Ex # | Structure | Chemical Name |
| 46 | 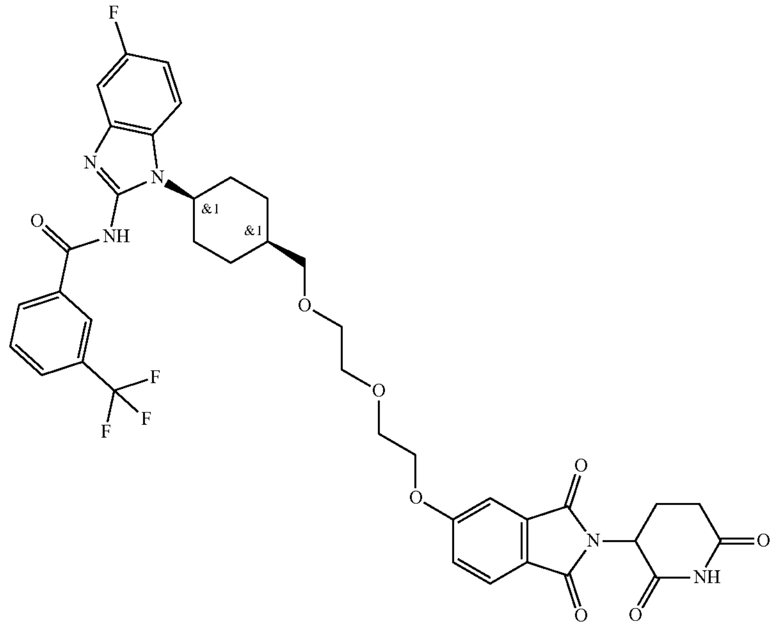 $C_{39}H_{37}F_4N_5O_8$ | N-(1-((1s,4s)-4-((2-(2-((2-(2,6-dioxopiperidin-3-yl)-1,3-dioxoisoindolin-5-yl)oxy)ethoxy)ethoxy)methyl)cyclohexyl)-5-fluoro-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 47 | 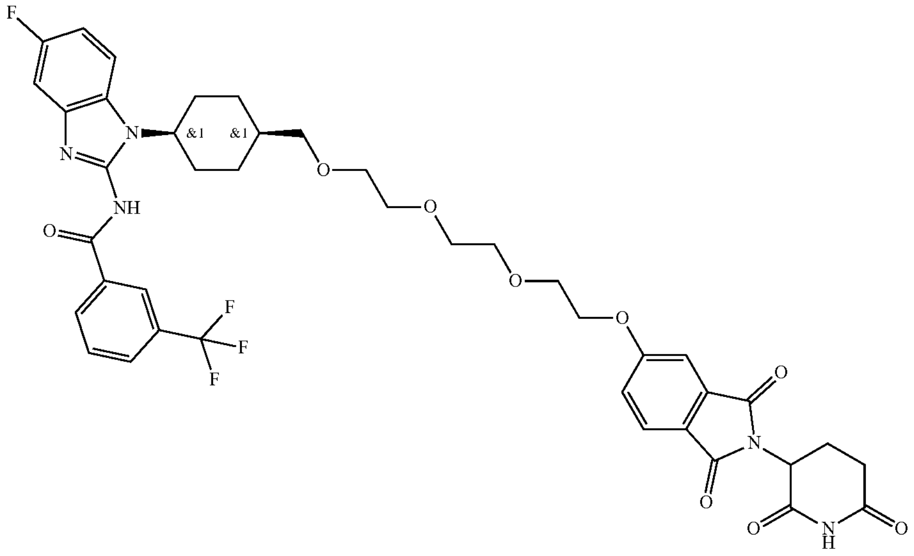 $C_{41}H_{41}F_4N_5O_9$ | N-(1-((1s,4s)-4-((2-(2-(2-((2-(2,6-dioxopiperidin-3-yl)-1,3-dioxoisoindolin-5-yl)oxy)ethoxy)ethoxy)ethoxy)methyl)cyclohexyl)-5-fluoro-1H-benzo[d]imidazol-2-yl)-3-(trifluoromethyl)benzamide |
| 48 | 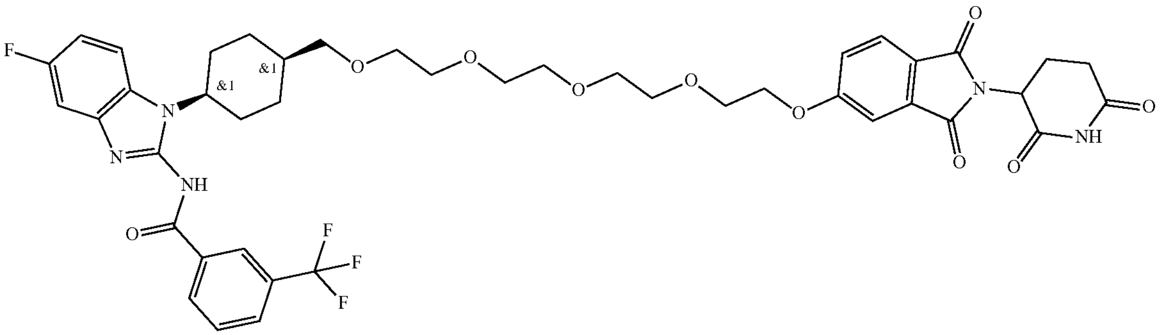 $C_{43}H_{45}F_4N_5O_{10}$ | N-(1-((1s,4s)-4-(13-((2-(2,6-dioxopiperidin-3-yl)-1,3-dioxoisoindolin-5-yl)oxy)-2,5,8,11-tetraoxatridecyl)cyclohexyl)-5-fluoro-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 49 | 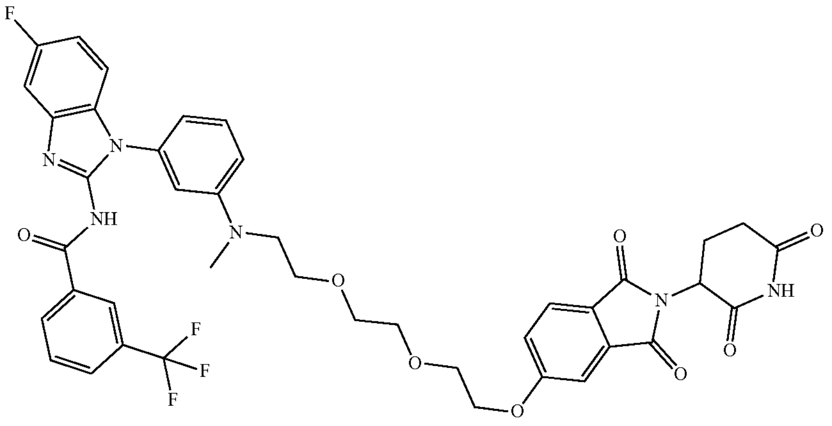<br>$C_{41}H_{36}F_4N_6O_8$ | N-(1-(3-((2-(2-(2-((2-(2,6-dioxopiperidin-3-yl)-1,3-dioxoisoindolin-5-yl)oxy)ethoxy)ethoxy)ethyl)(methyl)amino)phenyl)-5-fluoro-1H-benzo[d]imidazol-2-yl)-3-(trifluoromethyl)benzamide |
| 50 | 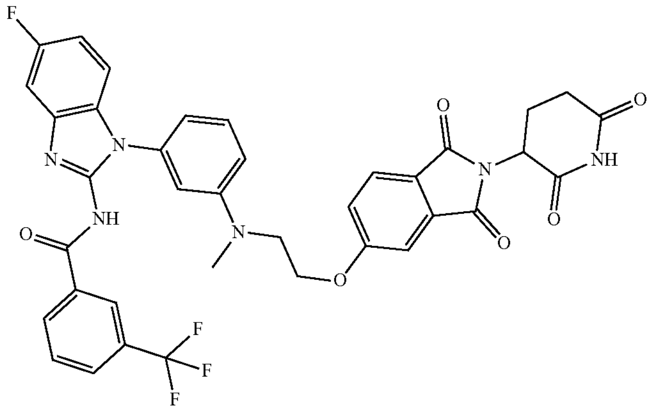<br>$C_{37}H_{28}F_4N_6O_6$ | N-(1-(3-((2-((2-(2,6-dioxopiperidin-3-yl)-1,3-dioxoisoindolin-5-yl)oxy)ethyl)(methyl)amino)phenyl)-5-fluoro-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 51 | 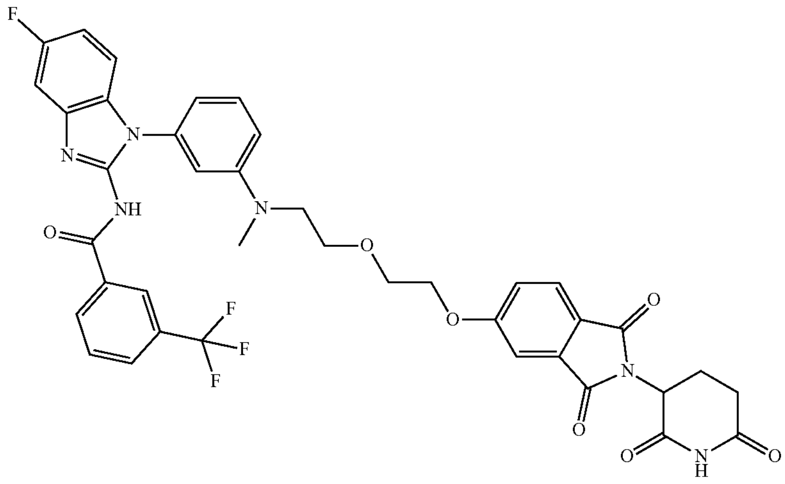 $C_{39}H_{32}F_4N_6O_7$ | N-(1-(3-((2-(2-((2-(2,6-dioxopiperidin-3-yl)-1,3-dioxoisoindolin-5-yl)oxy)ethoxy)ethyl)(methyl)amino)phenyl)-5-fluoro-1H-benzo[d]imidazol-2-yl)-3-(trifluoromethyl)benzamide |
| 52 | 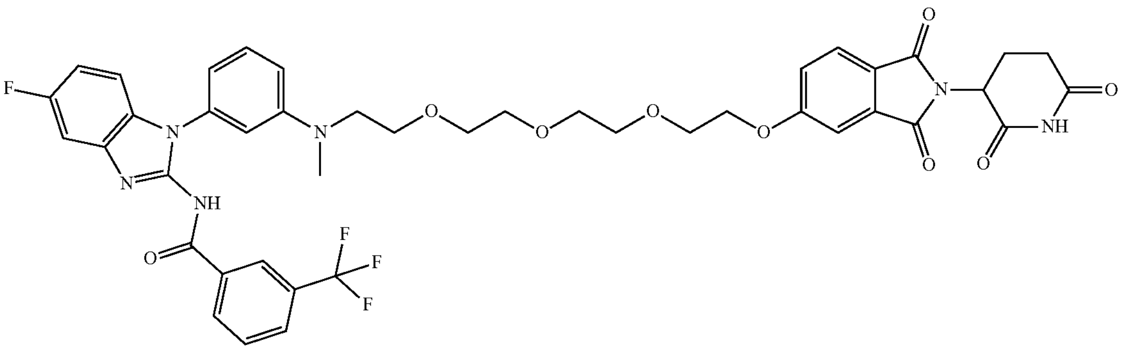 $C_{43}H_{40}F_4N_6O_9$ | N-(1-(3-((2-(2-(2-(2-((2-(2,6-dioxopiperidin-3-yl)-1,3-dioxoisoindolin-5-yl)oxy)ethoxy)ethoxy)ethoxy)ethyl)(methyl)amino)phenyl)-5-fluoro-1H-benzo[d]imidazol-2-yl)-3-(trifluoromethyl)benzamide |

TABLE 4-continued
| Exemplary compounds of the present disclosure | | |
|---|---|---|
| Ex # | Structure | Chemical Name |
| 53 | 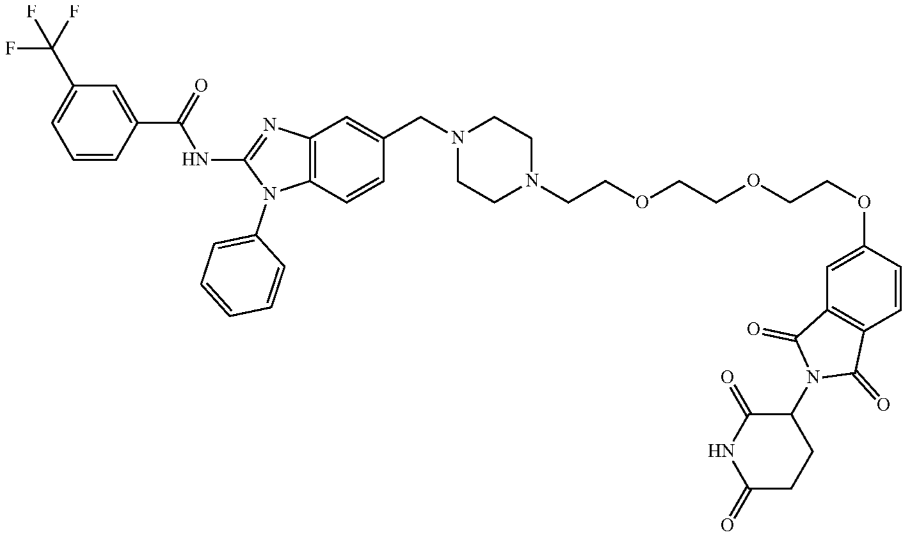 $C_{45}H_{44}F_3N_7O_8$ | N-(5-((4-(2-(2-(2-((2-(2,6-dioxopiperidin-3-yl)-1,3-dioxoisoindolin-5-yl)oxy)ethoxy)ethoxy)ethyl)piperazin-1-yl)methyl)-1-phenyl-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 54 | 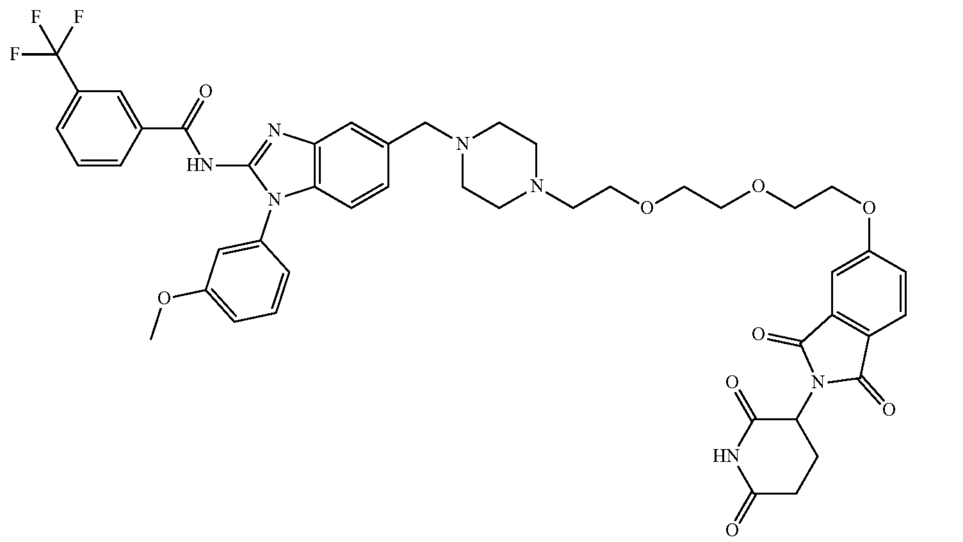<br>$C_{46}H_{46}F_3N_7O_9$ | N-(5-((4-(2-(2-(2-((2-(2,6-dioxopiperidin-3-yl)-1,3-dioxoisoindolin-5-yl)oxy)ethoxy)ethoxy)ethyl)piperazin-1-yl)methyl)-1-(3-methoxyphenyl)-1H-benzo[d]imidazol-2-yl)-3-(trifluoromethyl)benzamide |
| 55 | 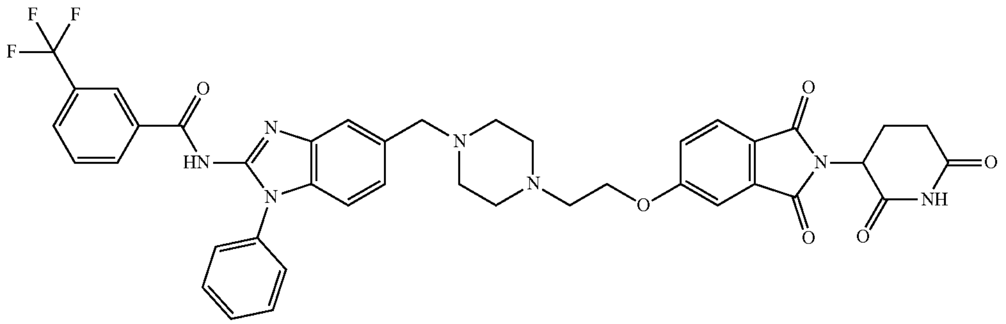<br>$C_{41}H_{36}F_3N_7O_6$ | N-(5-((4-(2-((2-(2,6-dioxopiperidin-3-yl)-1,3-dioxoisoindolin-5-yl)oxy)ethyl)piperazin-1-yl)methyl)-1-phenyl-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 56 | 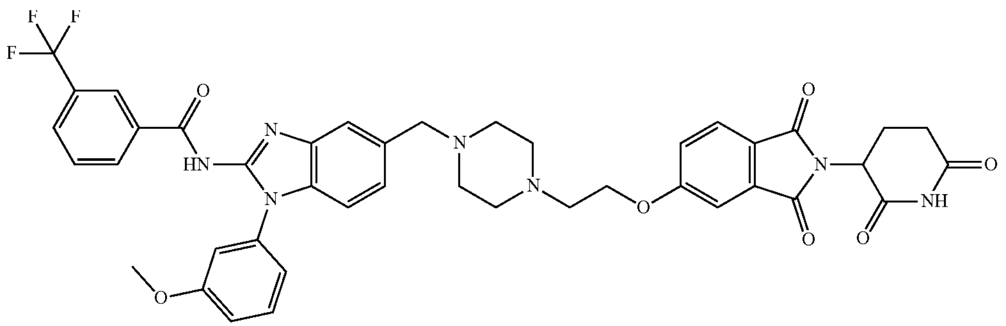 $C_{42}H_{38}F_3N_7O_7$ | N-(5-((4-(2-((2-(2,6-dioxopiperidin-3-yl)-1,3-dioxoisoindolin-5-yl)oxy)ethyl)piperazin-1-yl)methyl)-1-(3-methoxyphenyl)-1H-benzo[d]imidazol-2-yl)-3-(trifluoromethyl)benzamide |
| 57 | 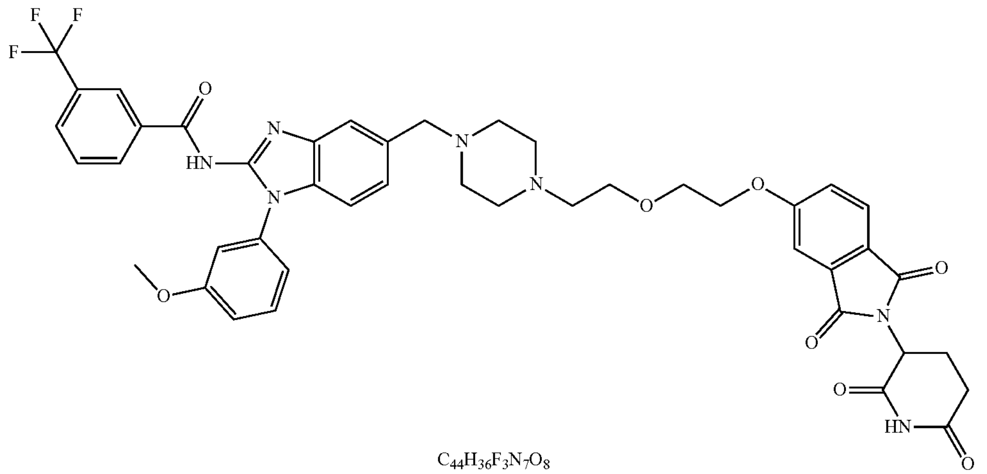 [SMILES: COc1cccc(-n2c(NC(=O)c3cccc(C(F)(F)F)c3)nc3cc(CN4CCN(CCOCCOc5ccc6c(c5)C(=O)N(C5CCC(=O)NC5=O)C6=O)CC4)ccc32)c1 ; "C44H36F3N7O8"] $C_{44}H_{36}F_3N_7O_8$ | N-(5-((4-(2-(2-((2-(2,6-dioxopiperidin-3-yl)-1,3-dioxoisoindolin-5-yl)oxy)ethoxy)ethyl)piperazin-1-yl)methyl)-1-(3-methoxyphenyl)-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 58 | 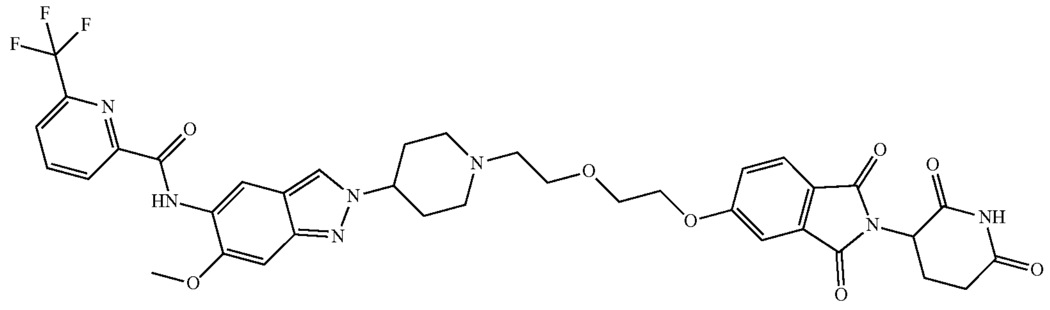 $C_{37}H_{36}F_3N_7O_8$ | N-(2-(1-(2-(2-((2-(2,6-dioxopiperidin-3-yl)-1,3-dioxoisoindolin-5-yl)oxy)ethoxy)ethyl)piperidin-4-yl)-6-methoxy-2H-indazol-5-yl)-6-(trifluoromethyl)picolinamide |
| 59 | 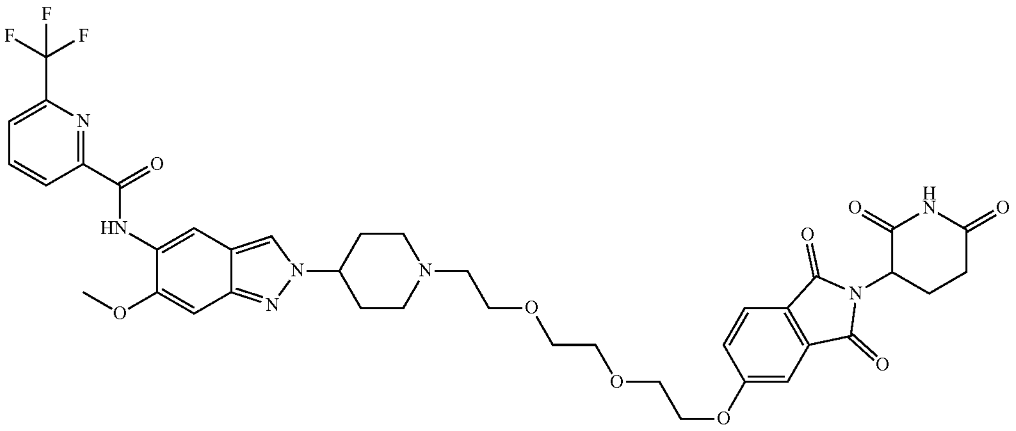 $C_{39}H_{40}F_3N_7O_9$ | N-(2-(1-(2-(2-(2-((2-(2,6-dioxopiperidin-3-yl)-1,3-dioxoisoindolin-5-yl)oxy)ethoxy)ethoxy)ethyl)piperidin-4-yl)-6-methoxy-2H-indazol-5-yl)-6-(trifluoromethyl)picolinamide |

TABLE 4-continued
| Exemplary compounds of the present disclosure | | |
|---|---|---|
| Ex # | Structure | Chemical Name |
| 60 | 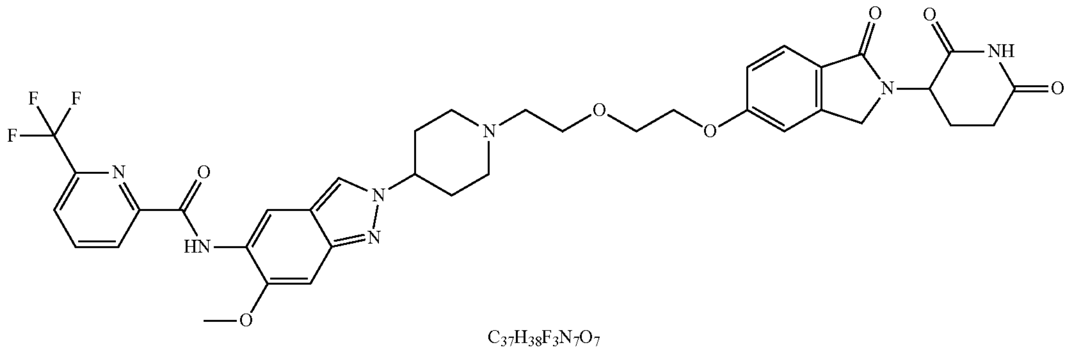 [SMILES: COc1cc2nn(C3CCN(CCOCCOc4ccc5c(c4)CN(C4CCC(=O)NC4=O)C5=O)CC3)cc2cc1NC(=O)c1cccc(C(F)(F)F)n1 ; "C37H38F3N7O7"] $C_{37}H_{38}F_3N_7O_7$ | N-(2-(1-(2-(2-((2-(2,6-dioxopiperidin-3-yl)-1-oxoisoindolin-5-yl)oxy)ethoxy)ethyl)piperadin-4-yl)-6-methoxy-2H-indazol-5-yl)-6-(trifluoromethyl)picolinamide |
| 61 | 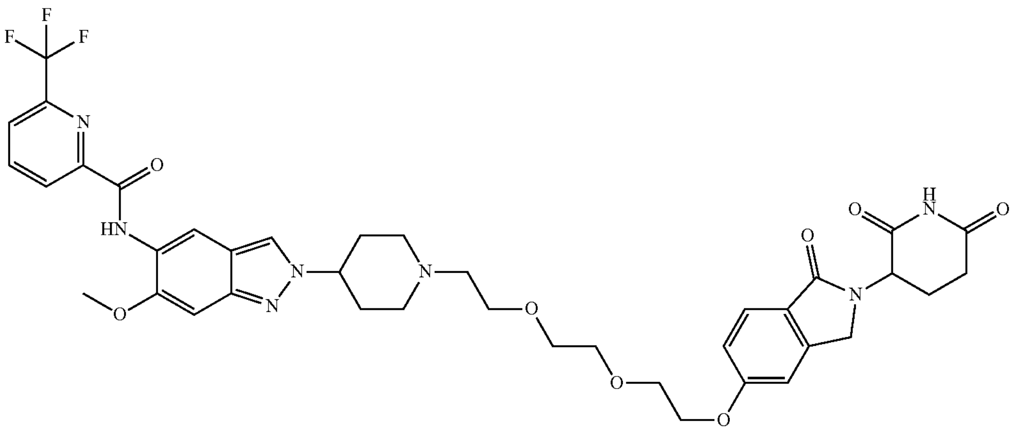 $C_{39}H_{41}F_3N_8O_8$ | N-(2-(1-(2-(2-(2-((2-(2,6-dioxopiperidin-3-yl)-1-oxoisoindolin-5-yl)oxy)ethoxy)ethoxy)ethyl)piperadin-4-yl)-6-methoxy-2H-indazol-5-yl)-6-(trifluoromethyl)picolinamide |

TABLE 4-continued

| Exemplary compounds of the present disclosure | | |
|---|---|---|
| Ex # | Structure | Chemical Name |
| 62 | 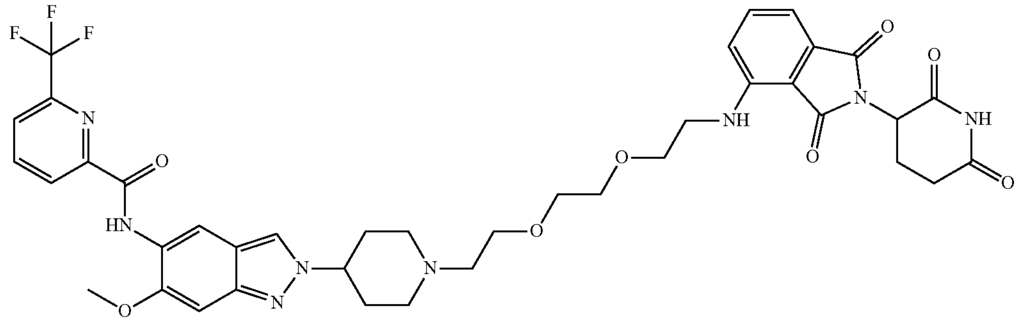 $C_{39}H_{41}F_3N_8O_8$ | N-(2-(1-(2-(2-(2-((2-(2,6-dioxopiperidin-3-yl)-1,3-dioxoisoindolin-4-yl)amino)ethoxy)ethoxy)ethyl)piperadin-4-yl)-6-methoxy-2H-indazol-5-yl)-6-(trifluoromethyl)picolinamide |
| 63 | 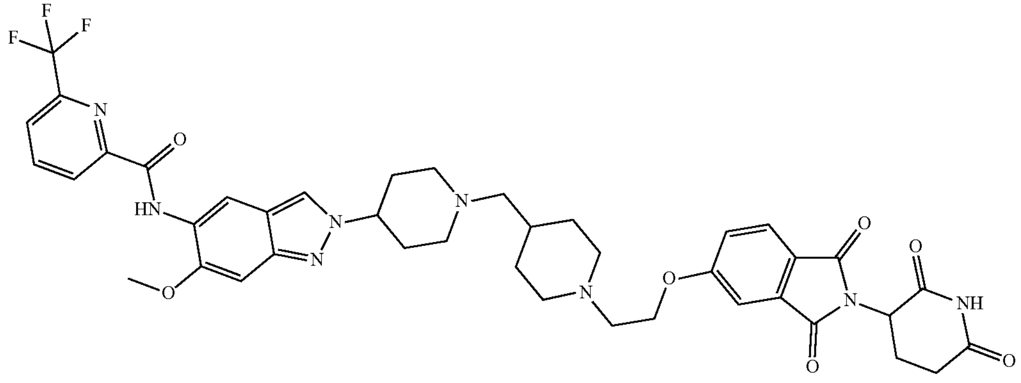 $C_{41}H_{43}F_3N_8O_7$ | N-(2-(1-((1-(2-((2-(2,6-dioxopiperidin-3-yl)-1,3-dioxoisoindolin-5-yl)oxy)ethyl)piperadin-4-yl)methyl)piperidin-4-yl)-6-methoxy-2H-indazol-5-yl)-6-(trifluoromethyl)picolinamide |

TABLE 4-continued

| Exemplary compounds of the present disclosure | | |
|---|---|---|
| Ex # | Structure | Chemical Name |
| 64 | 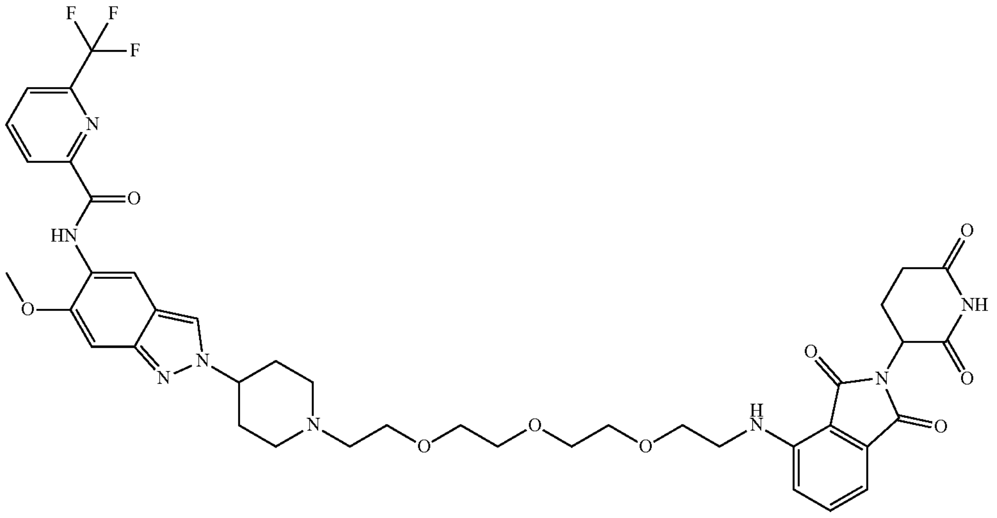 $C_{41}H_{45}F_3N_8O_9$ | N-(2-(1-(2-(2-(2-(2-((2-(2,6-dioxopiperidin-3-yl)-1,3-dioxoisoindolin-4-yl)amino)ethoxy)ethoxy)ethoxy)ethyl)piperadin-4-yl)-6-methoxy-2H-indazol-5-yl)-6-(trifluoromethyl)picolinamide |
| 65 | 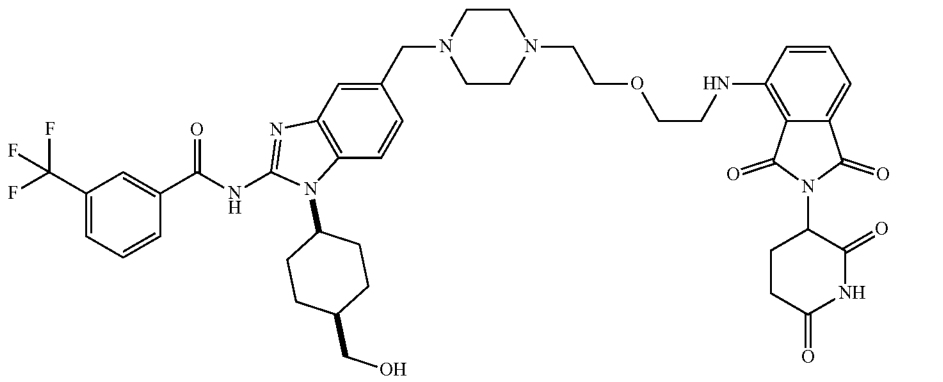 $C_{44}H_{49}F_3N_8O_7$ | N-(5-((4-(2-(2-((2-(2,6-dioxopiperidin-3-yl)-1,3-dioxoisoindolin-4-yl)amino)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide |

TABLE 4-continued

| Exemplary compounds of the present disclosure | | |
|---|---|---|
| Ex # | Structure | Chemical Name |
| 66 | 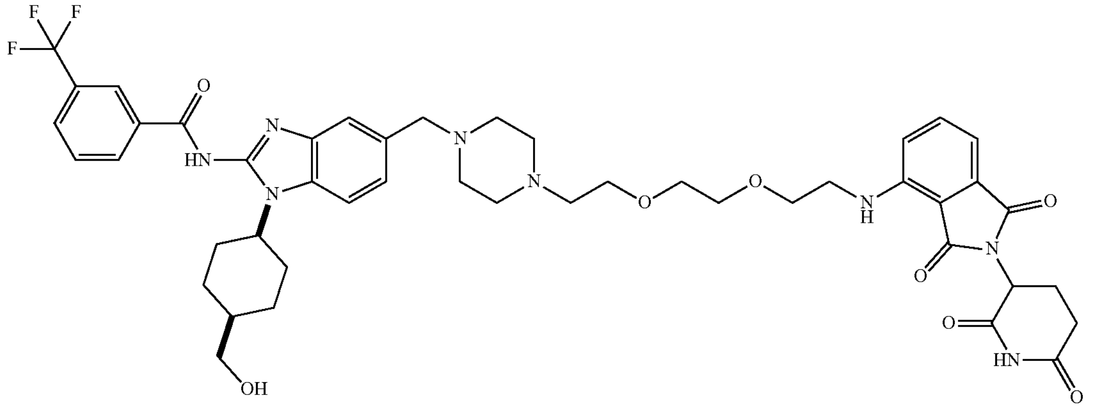 $C_{46}H_{53}F_3N_8O_8$ | N-(5-((4-(2-(2-(2-((2-(2,6-dioxopiperidin-3-yl)-1,3-dioxoisoindolin-4-yl)amino)ethoxy)ethoxy)ethyl)piperazin-1-yl)methyl)-1-((1s,4s)-4-(hydroxymethyl)cyclohexyl)-1H-benzo[d]imidazol-2-yl)-3-(trifluoromethyl)benzamide |
| 67 | 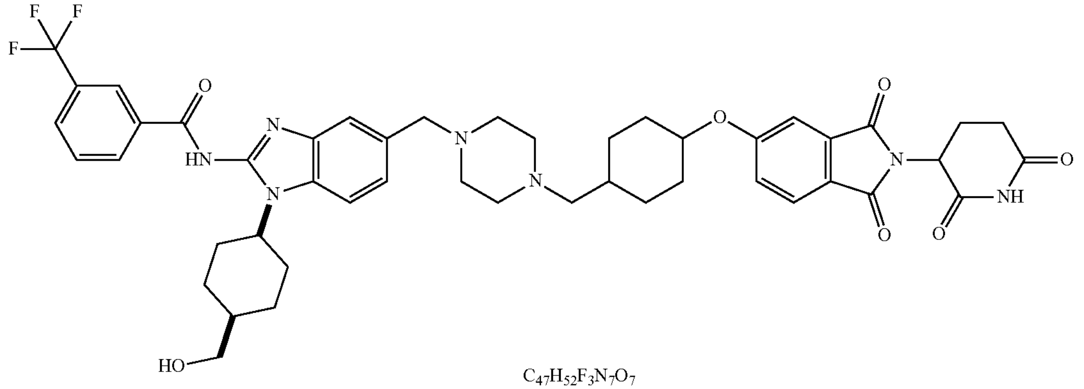 $C_{47}H_{52}F_3N_7O_7$ | N-(5-((4-((4-((2-(2,6-dioxopiperidin-3-yl)-1,3-dioxoisoindolin-5-yl)oxy)cycloethyl)methyl)piperazin-1-yl)methyl)-1-((1s,4s)-4-(hydroxymethyl)cyclohexyl)-1H-benzo[d]imidazol-2-yl)-3-(trifluoromethyl)benzamide |

TABLE 4-continued
| Exemplary compounds of the present disclosure | | |
|---|---|---|
| Ex # | Structure | Chemical Name |
| 68 | 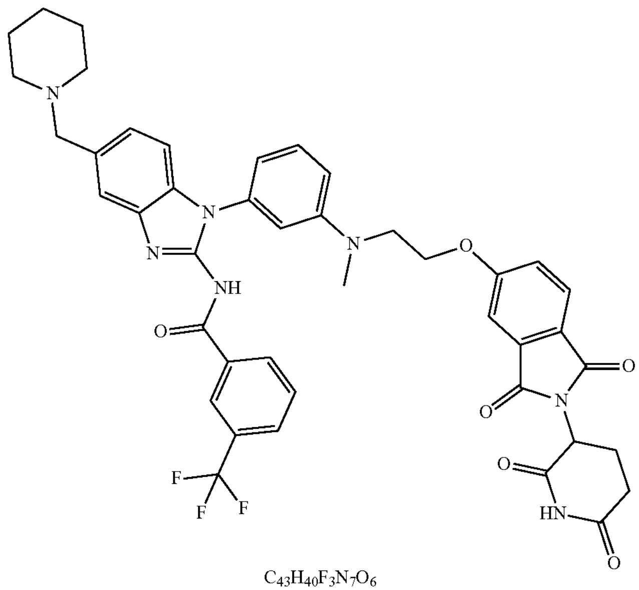 [SMILES: CN(CCOc1ccc2c(c1)C(=O)N(C1CCC(=O)NC1=O)C2=O)c1cccc(-n2c(NC(=O)c3cccc(C(F)(F)F)c3)nc3cc(CN4CCCCC4)ccc32)c1 ; "C43H40F3N7O6"] $C_{43}H_{40}F_3N_7O_6$ | N-(1-(3-((2-(2,6-dioxopiperidin-3-yl)-1,3-dioxoisoindolin-5-yl)oxy)ethyl)(methyl)amino)phenyl)-5-(piperadin-1-yl)methyl)-1H-benzo[d]imidazol-2-yl)-3-(trifluoromethyl)benzamide |

TABLE 5

| Characterization data for exemplary compounds of the present disclosure | | | | | |
|---|---|---|---|---|---|
| Ex # | MW; [M + H] + 1 (2) | IRAK4 Dmax (%)* | IRAK4 DC50** (nM) | IRAK4 IC50*** (nM) | Proton NMR data |
| 1 | 815.851; 816.64 | C | C | A | (400 MHz, DMSO-d6) δ: 12.82 (s, 1H), 11.11 (s, 1H), 8.50 (d, J = 8.0 Hz, 1H), 8.45 (s, 1H), 8.21 (s, 1H), 7.90 (d, J = 8.0 Hz, 1H), 7.82 (d, J = 8.4 Hz, 1H), 7.77-7.71 (m, 1H), 7.56-7.51 (m, 2H), 7.45 (d, J = 2.0 Hz, 1H), 7.35 (dd, J = 2.0, 8.4 Hz, 1H), 7.19 (d, J = 8.4 Hz, 1H), 5.11 (dd, J = 5.2, 13.2 Hz, 1H), 4.79-4.66 (m, 1H), 4.28 (t, J = 5.6 Hz, 2H), 3.68 (d, J = 7.6 Hz, 2H), 3.52 (s, 1H), 2.93-2.84 (m, 1H), 2.73 (t, J = 5.4 Hz, 2H), 2.64-2.56 (m, 2H), 2.55-2.51 (m, 8H), 2.46-2.35 (m, 4H), 2.10-2.00 (m, 1H), 1.98-1.89 (m, 2H), 1.88-1.80 (m, 1H), 1.74-1.56 (m, 4H) |
| 2 | 860.68 | B | A | A | (400 MHz, DMSO-d6) δ: 12.82 (s, 1H), 11.11 (s, 1H), 8.55-8.38 (m, 2H), 8.21 (s, 1H), 7.90 (d, J = 8.4 Hz, 1H), 7.82 (d, J = 8.4 Hz, 1H), 7.77-7.70 (m, 1H), 7.56-7.49 (m, 2H), 7.45 (d, J = 2.0 Hz, 1H), 7.36 (dd, J = 2.4, 8.4 Hz, 1H), 7.18 (d, J = 8.4 Hz, 1H), 5.11 (dd, J = 5.2, 13.0 Hz, 1H), 4.72 (s, 1H), 4.58 (s, 1H), 4.30 (d, J = 4.4 Hz, 2H), 3.76 (s, 2H), 3.68 (d, J = 7.2 Hz, 3H), 3.57 (t, J = 6.0 Hz, 3H), 3.49 (s, 4H), 2.98-2.79 (m, 2H), 2.63-2.56 (m, 1H), 2.46-2.38 (m, 6H), 2.10-1.99 (m, 2H), 1.94 (d, J = 13.6 Hz, 2H), 1.85 (s, 2H), 1.72-1.56 (m, 4H) |
| 3 | 904.72 | A | A | A | (400 MHz, DMSO-d6) δ: 12.83 (s, 1H), 11.12 (s, 1H), 8.50 (d, J = 8.0 Hz, 1H), 8.45 (s, 1H), 8.26 (s, 1H), 7.90 (d, J = 8.0 Hz, 1H), 7.82 (d, J = 8.0 Hz, 1H), 7.77-7.71 (m, 1H), 7.56-7.49 (m, 2H), 7.45 (d, J = 2.0 Hz, 1H), 7.36 (dd, J = 2.0, 8.4 Hz, 1H), 7.17 (d, J = 8.4 Hz, 1H), 5.12 (dd, J = 5.6, 13.2 Hz, 1H), 4.78-4.65 (m, 2H), 4.33-4.29 (m, 2H), 3.80-3.76 (m, 2H), 3.68 (br d, J = 7.6 Hz, 3H), 3.62-3.55 (m, 4H), 3.54-3.44 (m, 10H), 2.91-2.85 (m, 1H), 2.62-2.58 (m, 2H), 2.46-2.34 (m, 6H), 2.09-1.99 (m, 1H), 1.94 (d, J = 12.8 Hz, 2H), 1.85 (s, 1H), 1.73-1.57 (m, 4H) |
| 4 | 948.75 | A | A | A | (400 MHz, DMSO-d6) δ: 12.83 (s, 1H), 11.12 (s, 1H), 8.49 (d, J = 8.0 Hz, 1H), 8.44 (s, 1H), 8.26 (s, 1H), 7.90 (d, J = 7.2 Hz, 1H), 7.82 (d, J = 8.0 Hz, 1H), 7.74 (t, J = 8.0 Hz, 1H), 7.56-7.49 (m, 2H), 7.44 (d, J = 2.0 Hz, 1H), 7.35 (dd, J = 2.0, 8.4 Hz, 1H), 7.17 (d, J = 8.4 Hz, 1H), 5.12 (dd, J = 5.6, 13.2 Hz, 1H), 4.72 (s, 1H), 4.32-4.27 (m, 2H), 3.78-3.75 (m, 2H), 3.68 (d, J = 7.6 Hz, 3H), 3.62-3.56 (m, 4H), 3.55-3.51 (m, 4H), 3.51-3.44 (m, 10H), 2.92-2.85 (m, 1H), 2.62-2.57 (m, 2H), 2.47-2.34 (m, 6H), 2.07-1.99 (m, 1H), 1.94 (d, J = 13.2 Hz, 2H), 1.84 (s, 1H), 1.73-1.55 (m, 4H) |
| 5 | 992.79 | B | B | A | (400 MHz, DMSO-d6) δ: 12.84 (s, 1H), 11.13 (s, 1H), 8.50 (d, J = 8.0 Hz, 1H), 8.45 (s, 1H), 8.25 (s, 1H), 7.90 (d, J = 8.0 Hz, 1H), 7.82 (d, J = 8.4 Hz, 1H), 7.74 (t, J = 8.0 Hz, 1H), 7.57-7.50 (m, 2H), 7.45 (d, J = 2.4 Hz, 1H), 7.36 (dd, J = 2.4, 8.4 Hz, 1H), 7.19 (d, J = 8.4 Hz, 1H), 5.12 (dd, J = 5.6, 12.8 Hz, 1H), 4.73 (s, 1H), 4.33-4.27 (m, 2H), 3.78-3.75 (m, 2H), 3.69 (d, J = 7.6 Hz, 3H), 3.62-3.56 (m, 4H), 3.55-3.44 (m, 18H), 2.93-2.85 (m, 1H), 2.63-2.57 (m, 2H), 2.47-2.38 (m, 6H), 2.09-2.01 (m, 1H), 1.94 (d, J = 12.8 Hz, 2H), 1.85 (s, 1H), 1.71-1.59 (m, 4H) |
| 6 | 846.5 | N.D. | E | A | (400 MHz, CD3OD) δ: 8.59-8.49 (m, 3H), 7.83 (br d, J = 7.6 Hz, 1H), 7.76-7.66 (m, 2H), 7.56 (br d, J = 8.4 Hz, 1H), 7.50 (s, 1H), 7.30 (br d, J = 7.6 Hz, 1H), 7.16 (s, 1H), 7.10 (br d, J = 8.6 Hz, 1H), 5.17 (br dd, J = 5.2, 13.2 Hz, 1H), 4.54-4.38 (m, 2H), 4.27 (br s, 2H), 3.94- |

TABLE 5-continued

Characterization data for exemplary compounds of the present disclosure

| Ex # | MW; [M + H] + 1 (2) | IRAK4 Dmax (%)* | IRAK4 DC50** (nM) | IRAK4 IC50*** (nM) | Proton NMR data |
|---|---|---|---|---|---|
| | | | | | 3.84 (m, 4H), 3.78 (br t, J = 4.8 Hz, 2H), 3.73-3.63 (m, 2H), 2.99-2.45 (m, 15H), 2.23-1.96 (m, 5H), 1.89-1.71 (m, 4H). |
| 7 | 422.83 | C | E | C | |
| 8 | 422.83 | N.D. | N.D. | N.D. | |
| 9 | 869.65 | A | A | A | (400 MHz, DMSO-d6) δ: 12.21-13.74 (m, 1H), 11.07 (s, 1H), 8.50 (d, J = 7.6 Hz, 1H), 8.45 (s, 1 H), 7.91 (d, J = 8.0 Hz, 1H), 7.75 (t, J = 7.6 Hz, 1H), 7.58-7.68 (m, 3 H), 7.33 (s, 2 H), 7.25 (d, J = 8.4 Hz, 1H), 5.06 (dd, J = 5.2, 12.8 Hz, 1H), 4.68-4.80 (m, 1H), 4.06 (d, J = 12.4 Hz, 4H), 3.69 (d, J = 7.2 Hz, 3H), 2.81-3.02 (m, 8H), 2.58-2.69 (m, 2H), 2.33 (br s, 1H), 1.91-2.08 (m, 5H), 1.75-1.90 (m, 4H), 1.58-1.74 (m, 5 H), 1.14-1.28 (m, 3H), 1.05 (t, J = 7.2 Hz, 2H). |
| 10 | 913.7 | A | B | A | (400 MHz, DMSO-d6) δ: 13.30-12.54 (m, 1H), 11.39-11.03 (m, 1H), 10.27-9.80 (m, 1H), 8.69-8.30 (m, 2H), 7.99-7.85 (m, 2H), 7.76 (t, J = 8.0 Hz, 1H), 7.72-7.59 (m, 2H), 7.54 (d, J = 2.0 Hz, 1H), 7.45-7.28 (m, 2H), 5.14 (dd, J = 5.2, 12.8, Hz, 1H), 4.81-4.69 (m, 1H), 4.57 (s, 2H), 4.29-4.08 (m, 3H), 3.70-3.56 (m, 10H), 3.09-2.81 (m, 7H), 2.65-2.54 (m, 6H), 2.10-2.03 (m, 1H), 2.00-1.82 (m, 6H), 1.73-1.60 (m, 4H), 1.41 (d, J = 11.6 Hz, 2H). |
| 11 | 1030.84 | A | E | D | (400 MHz, DMSO-d6) δ: 12.94 (s, 1H), 8.96-9.00 (m, 1H), 8.60 (t, J = 6.0 Hz, 1H), 8.50 (d, J = 8.0 Hz, 1H), 8.45 (s, 1H), 7.92 (d, J = 7.6 Hz, 1H), 7.85 (br d, J = 10.0 Hz, 1H), 7.76 (t, J = 7.6 Hz, 1H), 7.65 (d, J = 8.4 Hz, 1H), 7.60 (s, 1H), 7.35-7.46 (m, 5H), 7.31 (br d, J = 8.8 Hz, 1H), 4.72 (br d, J = 10.4 Hz, 2H), 4.58 (d, J = 9.6 Hz, 1H), 4.33-4.47 (m, 4H), 4.19-4.31 (m, 2H), 3.96-4.15 (m, 7H), 3.71-3.79 (m, 7H), 2.96-3.38 (m, 2H), 2.43 (s, 4H), 2.02-2.12 (m, 1H), 1.81-2.01 (m, 5H), 1.55-1.80 (m, 5H), 0.87-1.01 (m, 11H). |
| 12 | 1074.88 | N.D. | E | B | (400 MHz, DMSO-d6) δ: 8.96 (s, 1H), 8.59 (t, J = 6.0 Hz, 1H), 8.49 (d, J = 7.6 Hz, 1H), 8.44 (s, 1H), 8.21-8.16 (m, 1H), 7.89 (d, J = 8.0 Hz, 1H), 7.74 (t, J = 7.6 Hz, 1H), 7.55-7.49 (m, 2H), 7.38 (s, 4H), 7.17 (d, J = 8.4 Hz, 1H), 4.72 (s, 1H), 4.56 (d, J = 9.6 Hz, 1H), 4.43 (t, J = 8.0 Hz, 1H), 4.40-4.32 (m, 2H), 4.28-4.18 (m, 1H), 3.96 (s, 2H), 3.72-3.62 (m, 4H), 3.62-3.57 (m, 4H), 3.56-3.51 (m, 5H), 3.48 (s, 3H), 2.52 (d, J = 1.6 Hz, 8H), 2.43 (s, 3H), 2.40-2.35 (m, 2H), 2.11-2.00 (m, 1H), 1.98-1.79 (m, 4H), 1.74-1.54 (m, 4H), 0.98-0.86 (m, 9H) |
| 13 | 1118.92 | N.D. | E | D | (400 MHz, DMSO-d6) δ: 8.97 (s, 1H), 8.60 (t, J = 6.0 Hz, 1H), 8.50 (d, J = 7.6 Hz, 1H), 8.45 (s, 1H), 8.21-8.12 (m, 1H), 7.89 (d, J = 7.6 Hz, 1H), 7.74 (t, J = 7.6 Hz, 1H), 7.57-7.47 (m, 2H), 7.41 (d, J = 9.2 Hz, 1H), 7.39 (s, 3H), 7.18 (d, J = 9.2 Hz, 1H), 4.78-4.67 (m, 1H), 4.56 (d, J = 9.6 Hz, 1H), 4.47-4.40 (m, 2H), 4.39-4.30 (m, 2H), 4.29-4.15 (m, 2H), 3.96 (s, 2H), 3.70-3.64 (m, 4H), 3.61-3.53 (m, 8H), 3.50-3.44 (m, 7H), 2.52 (d, J = 2.0 Hz, 8H), 2.43 (s, 3H), 2.37 (s, 2H), 2.08-2.02 (m, 1H), 1.96-1.83 (m, 4H), 1.70-1.58 (m, 4H), 0.96-0.91 (m, 9H) |
| 14 | 1162.95 | N.D. | E | A | (400 MHz, DMSO-d6) δ: 8.99 (s, 1H), 8.60 (t, J = 6.0 Hz, 1H), 8.50 (d, J = 7.6 Hz, 1H), 8.45 (s, 1H), 7.92 (br d, J = 8.0 Hz, 1H), 7.76 (t, J = 7.6 Hz, 1H), 7.65 (d, J = 8.4 Hz, 1H), 7.59 (s, 1H), 7.35-7.50 (m, 6H), 7.31 (br d, J = 8.0 Hz, 1H), 4.73 (br d, J = 10.6 Hz, 2H), 4.56 (d, J = 9.4 Hz, 1H), 4.33-4.46 (m, 4H), 4.20-4.31 (m, 2H), 3.90-4.12 (m, 7H), 3.59-3.73 (m, 19H), 2.98-3.35 (m, 2H), 2.44 (s, 4H), 2.02-2.12 (m, |

TABLE 5-continued

Characterization data for exemplary compounds of the present disclosure

| Ex # | MW; [M + H] + 1 (2) | IRAK4 Dmax (%)* | IRAK4 DC50** (nM) | IRAK4 IC50*** (nM) | Proton NMR data |
|---|---|---|---|---|---|
| | | | | | 1H), 1.81-2.01 (m, 5H), 1.57-1.77 (m, 5H), 0.85-1.00 (m, 11H). |
| 25 | 792.62 | N.D. | E | B | (400 MHz, DMSO-d6) δ: 13.27 (s, 1H), 11.11 (s, 1H), 9.38 (dd, J = 1.6, 7.2 Hz, 1H), 9.14 (dd, J = 1.6, 4.4 Hz, 1H), 8.73 (s, 1H), 8.44 (s, 1H), 8.23 (s, 1H), 7.83 (d, J = 8.4 Hz, 1H), 7.79 (dd, J = 2.4, 8.8 Hz, 1H), 7.67 (d, J = 8.4 Hz, 1H), 7.46 (d, J = 2.4 Hz, 1H), 7.40-7.35 (m, 2H), 6.62 (s, 1H), 5.11 (dd, J = 5.2, 12.8 Hz, 1H), 4.41-4.27 (m, 2H), 3.83-3.78 (m, 2H), 3.63-3.59 (m, 3H), 3.58-3.53 (m, 6H), 3.24-3.19 (m, 3H), 2.93-2.80 (m, 2H), 2.62-2.56 (m, 2H), 2.55-2.53 (m, 3H), 2.37 (s, 3H), 2.07-2.00 (m, 1H) |
| 26 | 836.66 | N.D. | E | D | (400 MHz, DMSO-d6) δ: 13.25 (s, 1H), 11.11 (s, 1H), 9.38 (dd, J = 1.6, 7.2 Hz, 1H), 9.14 (dd, J = 1.6, 4.2 Hz, 1H), 8.72 (s, 1H), 8.43 (s, 1H), 8.22 (s, 1H), 7.81-7.75 (m, 2H), 7.67 (d, J = 8.8 Hz, 1H), 7.43 (d, J = 2.0 Hz, 1H), 7.39-7.32 (m, 2H), 6.62 (s, 1H), 5.10 (dd, J = 5.6, 13.2 Hz, 1H), 4.35-4.25 (m, 2H), 3.82-3.78 (m, 2H), 3.62-3.59 (m, 3H), 3.56-3.51 (m, 10H), 3.30-3.16 (m, 3H), 2.85 (d, J = 11.6 Hz, 2H), 2.63-2.57 (m, 2H), 2.55-2.54 (m, 3H), 2.37 (s, 3H), 2.07-1.99 (m, 1H) |
| 27 | 1006.83 | N.D. | E | D | (400 MHz, DMSO-d6) δ: 13.26 (s, 1H), 9.43-9.33 (m, 1H), 9.16-9.09 (m, 1H), 8.98 (s, 1H), 8.75-8.68 (m, 1H), 8.62 (t, J = 6.1 Hz, 1H), 8.43 (s, 1H), 8.19 (s, 1H), 7.81-7.74 (m, 1H), 7.67 (d, J = 8.4 Hz, 1H), 7.48-7.33 (m, 6H), 6.63 (s, 1H), 4.58 (d, J = 9.5 Hz, 1H), 4.50-4.34 (m, 3H), 4.29-4.21 (m, 1H), 3.99 (s, 2H), 3.69-3.55 (m, 21H), 2.44 (s, 3H), 2.36 (s, 3H), 2.11-2.02 (m, 1H), 1.95-1.86 (m, 1H), 1.04-0.90 (m, 9H) |
| 28 | 1050.86 | N.D. | E | D | (400 MHz, DMSO-d6) δ: 13.25 (s, 1H), 9.43-9.32 (m, 1H), 9.16-9.08 (m, 1H), 8.97 (s, 1H), 8.74-8.67 (m, 1H), 8.59 (t, J = 5.9 Hz, 1H), 8.43 (s, 1H), 8.18 (s, 1H), 7.80-7.74 (m, 1H), 7.67 (d, J = 8.6 Hz, 1H), 7.47-7.32 (m, 6H), 6.63 (s, 1H), 4.60-4.53 (m, 1H), 4.48-4.37 (m, 2H), 4.26-4.20 (m, 1H), 4.01-3.93 (m, 2H), 3.77-3.47 (m, 24H), 2.54 (br d, J = 5.3 Hz, 4H), 2.43 (s, 3H), 2.36 (s, 3H), 2.10-2.03 (m, 1H), 1.95-1.87 (m, 1H), 0.97-0.91 (m, 9H) |
| 29 | 637.55 | N.D. | E | D | (400 MHz, DMSO-d6) δ: 11.10 (s, 1H), 8.94 (d, J = 1.6 Hz, 1H), 8.55 (s, 1H), 8.27 (d, J = 7.2 Hz, 1H), 8.21 (s, 1H), 8.05 (dd, J = 2.0, 8.4 Hz, 1H), 7.83 (d, J = 8.4 Hz, 1H), 7.76 (d, J = 8.4 Hz, 1H), 7.46 (d, J = 2.0 Hz, 1H), 7.37 (dd, J = 2.4, 8.4 Hz, 1H), 5.12 (dd, J = 5.2, 12.8 Hz, 1H), 4.29 (t, 7 = 5.6 Hz, 2H), 4.12 (d, J = 7.2 Hz, 1H), 2.93-2.84 (m, 1H), 2.72 (t, J = 5.6 Hz, 2H), 2.61 (d, J = 2.8 Hz, 2H), 2.55-2.52 (m, 8H), 2.31-2.25 (m, 1H), 2.09-2.00 (m, 3H), 1.92-1.83 (m, 2H), 1.49-1.32 (m, 4H) |
| 30 | 681.59 | N.D. | E | D | (400 MHz, DMSO-d6) δ: 11.19-11.01 (m, 1H), 8.94 (d, J = 1.6 Hz, 1H), 8.55 (s, 1H), 8.27 (d, J = 7.6 Hz, 1H), 8.19 (s, 1H), 8.05 (dd, J = 1.6, 8.8 Hz, 1H), 7.84 (d, J = 8.4 Hz, 1H), 7.76 (d, J = 8.8 Hz, 1H), 7.45 (d, J = 2.4 Hz, 1H), 7.37 (dd, J = 2.4, 8.4 Hz, 1H), 5.11 (dd, J = 5.6, 12.8 Hz, 1H), 4.38-4.26 (m, 2H), 4.18-4.05 (m, 1H), 3.79-3.75 (m, 2H), 3.60-3.56 (m, 6H), 2.95-2.85 (m, 1H), 2.63-2.55 (m, 2H), 2.47-2.36 (m, 6H), 2.31-2.25 (m, 1H), 2.10-1.98 (m, 3H), 1.87 (d, J = 11.6 Hz, 2H), 1.48-1.29 (m, 4H) |
| 31 | 725.63 | N.D. | E | E | (400 MHz, DMSO-d6) δ: 11.15-11.05 (m, 1H), 8.94 (d, J = 1.6 Hz, 1H), 8.55 (s, 1H), 8.26 (d, J = 7.6 Hz, 1H), 8.19 (s, 1H), 8.05 (dd, J = 1.6, 8.8 Hz, 1H), 7.84 (d, J = 8.4 Hz, 1H), 7.76 (d, J = 8.8 Hz, 1H), 7.46 (d, J = 2.4 |

TABLE 5-continued

Characterization data for exemplary compounds of the present disclosure

| Ex # | MW; [M + H] + 1 (2) | IRAK4 Dmax (%)* | IRAK4 DC50** (nM) | IRAK4 IC50*** (nM) | Proton NMR data |
|---|---|---|---|---|---|
| | | | | | Hz, 1H), 7.38 (dd, J = 2.4, 8.4 Hz, 1H), 5.11 (dd, J = 5.6, 12.8 Hz, 1H), 4.36-4.25 (m, 2H), 4.18-4.03 (m, 1H), 3.82-3.78 (m, 2H), 3.63-3.56 (m, 6H), 3.54-3.52 (m, 4H), 2.94-2.85 (m, 1H), 2.60-2.54 (m, 2H), 2.46-2.41 (m, 6H), 2.30-2.23 (m, 1H), 2.07-1.98 (m, 3H), 1.90-1.80 (m, 2H), 1.48-1.26 (m, 4H) |
| 32 | 769.67 | N.D. | E | E | (400 MHz, DMSO-d6) δ: 11.11 (s, 1H), 8.93 (d, J = 1.6 Hz, 1H), 8.54 (s, 1H), 8.27 (d, J = 7.6 Hz, 1H), 8.20 (s, 1H), 8.05 (dd, J = 1.6, 8.8 Hz, 1H), 7.84 (d, J = 8.4 Hz, 1H), 7.76 (d, J = 8.8 Hz, 1H), 7.46 (d, J = 2.0 Hz, 1H), 7.38 (dd, J = 2.0, 8.4 Hz, 1H), 5.11 (dd, J = 5.6, 13.2 Hz, 1H), 4.36-4.28 (m, 2H), 4.16-4.06 (m, 1H), 3.82-3.78 (m, 2H), 3.62-3.59 (m, 6H), 3.55 (d, J = 2.8 Hz, 4H), 3.49-3.48 (m, 4H), 2.94-2.86 (m, 1H), 2.62-2.55 (m, 2H), 2.47-2.37 (m, 6H), 2.31-2.25 (m, 1H), 2.08-1.98 (m, 3H), 1.86 (d, J = 11.2 Hz, 2H), 1.49-1.27 (m, 4H) |
| 33 | 813.7 | N.D. | E | E | (400 MHz, DMSO-d6) δ: 11.11 (s, 1H), 8.93 (d, J = 1.2 Hz, 1H), 8.54 (s, 1H), 8.27 (d, J = 7.2 Hz, 1H), 8.19 (s, 1H), 8.05 (dd, J = 1.6, 8.8 Hz, 1H), 7.83 (d, J = 8.4 Hz, 1H), 7.76 (d, J = 8.8 Hz, 1H), 7.45 (d, J = 2.2 Hz, 1H), 7.37 (dd, J = 2.4, 8.4 Hz, 1H), 5.11 (dd, J = 5.6, 12.8 Hz, 1H), 4.35-4.29 (m, 2H), 4.16-4.07 (m, 1H), 3.81-3.78 (m, 2H), 3.62-3.59 (m, 4H), 3.57-3.54 (m, 6H), 3.52-3.51 (m, 4H), 3.48-3.47 (m, 4H), 2.91-2.82 (m, 1H), 2.63-2.55 (m, 2H), 2.44 (t, J = 6.0 Hz, 6H), 2.31-2.27 (m, 1H), 2.08-1.98 (m, 3H), 1.87 (d, J = 11.2 Hz, 2H), 1.48-1.28 (m, 4H) |
| 34 | 745.38 | N.D. | E | E | (400 MHz, DMSO-d6) δ: 11.09 (s, 1H), 8.93 (d, J = 1.6 Hz, 1H), 9.02-8.86 (m, 1H), 8.55 (s, 1H), 8.26 (d, J = 7.6 Hz, 1H), 8.05 (dd, J = 1.6, 8.8 Hz, 1H), 7.84 (d, J = 8.4 Hz, 1H), 7.76 (d, J = 8.8 Hz, 1H), 7.47 (d, J = 2.0 Hz, 1H), 7.39 (dd, J = 2.0, 8.4 Hz, 1H), 5.10 (dd, J = 5.6, 12.8 Hz, 1H), 4.33 (dd, J = 3.2, 5.2 Hz, 2H), 4.19-4.02 (m, 1H), 3.89-3.72 (m, 4H), 3.33 (s, 2H), 3.15 (d, J = 4.8 Hz, 4H), 2.91-2.79 (m, 1H), 2.53 (d, J = 6.4 Hz, 4H), 2.52 (s, 2H), 2.40-2.28 (m, 1H), 2.05-1.93 (m, 3H), 1.77 (d, J = 10.0 Hz, 2H), 1.46-1.28 (m, 4H) |
| 35 | 745.56 | N.D. | E | E | (400 MHz, DMSO-d6) δ: 11.13-11.07 (m, 1H), 9.05 (s, 1H), 8.55 (s, 1H), 8.09 (d, J = 7.2 Hz, 1H), 8.04 (dd, J = 1.6, 8.8 Hz, 1H), 7.85-7.72 (m, 2H), 7.42 (s, 1H), 7.40-7.33 (m, 1H), 5.11-5.05 (m, 1H), 4.36-4.32 (m, 2H), 4.31-4.22 (m, 2H), 3.87-3.79 (m, 6H), 3.52-3.50 (m, 2H), 3.17 (s, 3H), 2.61-2.56 (m, 2H), 2.54-2.53 (m, 3H), 2.24-2.16 (m, 1H), 2.04-1.94 (m, 1H), 1.90-1.77 (m, 4H), 1.67-1.56 (m, 2H), 1.53-1.44 (m, 2H) |
| 36 | 789.43 | N.D. | E | E | (400 MHz, DMSO-d6) δ: 11.10 (s, 1H), 8.93 (d, J = 1.2 Hz, 1H), 8.58-8.52 (m, 1H), 8.26 (d, J = 7.6 Hz, 1H), 8.05 (dd, J = 1.6, 8.8 Hz, 1H), 7.84 (d, J = 8.4 Hz, 1H), 7.76 (d, J = 8.8 Hz, 1H), 7.46 (d, J = 2.4 Hz, 1H), 7.38 (dd, J = 2.4, 8.4 Hz, 1H), 5.11 (dd, J = 5.2, 12.8 Hz, 1H), 4.39-4.26 (m, 2H), 4.19-4.03 (m, 1H), 3.84-3.78 (m, 2H), 3.74 (t, J = 6.0 Hz, 2H), 3.66-3.61 (m, 2H), 3.60-3.55 (m, 2H), 3.30-3.28 (m, 2H), 3.15 (s, 4H), 2.94-2.81 (m, 1H), 2.61-2.53 (m, 6H), 2.42-2.35 (m, 1H), 2.09-1.96 (m, 3H), 1.83 (d, J = 10.0 Hz, 2H), 1.51-1.25 (m, 4H) |
| 37 | 789.43 | | | E | (400 MHz, DMSO-d6) δ: 11.10 (s, 1H), 9.06 (d, J = 1.6 Hz, 1H), 8.55 (s, 1H), 8.09 (d, J = 6.8 Hz, 1H), 8.03 (dd, J = 1.6, 8.8 Hz, 1H), 7.77 (dd, J = 8.4, 18.0 Hz, 2H), 7.41 (d, J = 2.0 Hz, 1H), 7.36-7.28 (m, 1H), 5.11 (dd, J = |

TABLE 5-continued

| Characterization data for exemplary compounds of the present disclosure | | | | | |
|---|---|---|---|---|---|
| Ex # | MW; [M + H] + 1 (2) | IRAK4 Dmax (%)* | IRAK4 DC50** (nM) | IRAK4 IC50*** (nM) | Proton NMR data |
| | | | | | 5.2, 12.8 Hz, 1H), 4.36-4.21 (m, 3H), 3.83-3.78 (m, 2H), 3.76 (t, J = 6.0 Hz, 2H), 3.65-3.61 (m, 2H), 3.61-3.57 (m, 2H), 3.34 (s, 2H), 3.18 (s, 4H), 2.96-2.82 (m, 1H), 2.64-2.55 (m, 2H), 2.55-2.52 (m, 4H), 2.29-2.19 (m, 1H), 2.07-2.00 (m, 1H), 1.95-1.80 (m, 4H), 1.65 (dd, J = 3.6, 8.0 Hz, 2H), 1.58-1.47 (m, 2H) |
| 38 | 833.45 | | | E | (400 MHz, DMSO-d6) δ: 1.31-1.46 (m, 4 H), 1.85 (d, J = 10.4 Hz, 2 H), 1.99-2.08 (m, 3 H), 2.57 (s, 3 H), 2.83-2.95 (m, 1 H), 3.14 (d, J = 4.8 Hz, 4 H), 3.30 (s, 3 H), 3.52-3.58 (m, 8 H), 3.59-3.64 (m, 3 H), 3.72-3.83 (m, 4 H), 4.12 (d, J = 7.6 Hz, 1 H), 4.30-4.34 (m, 2 H), 5.11 (m, 1 H), 7.38 (m, 1 H), 7.46 (d, J = 2.4 Hz, 1 H), 7.76 (d, J = 8.8 Hz, 1 H), 7.83 (d, J = 8.4 Hz, 1 H), 8.06 (m, 1 H), 8.28 (d, J = 7.6 Hz, 1 H), 8.34 (s, 1 H), 8.55 (s, 1 H), 8.94 (s, 1 H), 11.11 (s, 1 H) |
| 39 | 833.45 | | | E | (400 MHz, DMSO-d6) δ: 1.50-1.69 (m, 5 H), 1.88 (d, J = 8.8 Hz, 5 H), 2.00-2.11 (m, 2 H), 2.25 (s, 2 H), 2.31-2.36 (m, 3 H), 2.66-2.69 (m, 2 H), 2.88 (d, J = 12.0 Hz, 1 H), 3.19 (s, 5 H), 3.55 (s, 6 H), 3.58-3.61 (m, 2 H), 3.73-3.79 (m, 4 H), 4.30 (d, J = 3.6 Hz, 3 H), 5.12 (m, 1 H), 7.34 (m, 1 H), 7.43 (d, J = 2.0 Hz, 1 H), 7.76 (d, J = 8.8 Hz, 1 H), 7.81 (d, J = 8.4 Hz, 1 H), 8.05 (m, 1 H), 8.12 (d, J = 6.8 Hz, 1 H), 8.56 (s, 1 H), 9.08 (s, 1 H), 11.11 (s, 1 H) |
| 40 | 877.49 | N.D. | E | E | (400 MHz, DMSO-d6) δ: 11.11 (s, 1H), 9.08 (s, 1H), 8.56 (s, 1H), 8.28 (s, 1H), 8.12 (d, J = 6.8 Hz, 1H), 8.05 (m, 1H), 7.86-7.72 (m, 2H), 7.44 (d, J = 2.0 Hz, 1H), 7.35 (m, 1H), 5.12 (m, 1H), 4.33-4.27 (m, 3H), 3.79-3.72 (m, 4H), 3.58-3.51 (m, 14H), 3.19 (s, 4H), 2.93-2.85 (m, 1H), 2.64-2.57 (m, 4H), 2.25 (s, 1H), 2.08-1.82 (m, 6H), 1.70-1.46 (m, 5H) |
| 41 | 877.48 | N.D. | E | E | (400 MHz, DMSO-d6) δ: 8.63 (s, 1H), 8.04 (s, 1H), 7.84-7.77 (m, 2H), 7.73-7.67 (m, 1H), 7.30 (d, J = 2.4 Hz, 1H), 7.19-7.15 (m, 2H), 5.73-5.61 (m, 1H), 4.89 (m, 1H), 4.25-4.09 (m, 3H), 3.89-3.77 (m, 4H), 3.68-3.51 (m, 13H), 3.16 (t, J = 6.4 Hz, 6H), 2.88-2.56 (m, 8H), 2.38 (s, 1H), 2.24-2.17 (m, 2H), 2.13-2.07 (m, 1H), 1.93-1.85 (m, 2H), 1.26-1.17 (m, 2H) |
| 42 | 947.69 | N.D. | E | D | (400 MHz, DMSO-d6) δ: ppm 12.83 (br s, 1 H) 11.12 (s, 1 H) 8.50 (d, J = 7.88 Hz, 1 H) 8.43 (s, 1 H) 8.30 (s, 1 H) 7.90 (br d, J = 7.64 Hz, 1 H) 7.81 (d, J = 8.26 Hz, 1 H) 7.74 (t, J = 7.68 Hz, 1 H) 7.56 (d, J = 8.38 Hz, 1 H) 7.51 (s, 1 H) 7.43 (d, J = 2.14 Hz, 1 H) 7.34 (dd, J = 8.32, 2.31 Hz, 1 H) 7.15-7.24 (m, 1 H) 5.12 (dd, J = 12.88, 5.38 Hz, 1 H) 4.72 (br s, 1 H) 4.24-4.32 (m, 2 H) 3.72-3.79 (m, 2 H) 3.68 (br d, J = 7.50 Hz, 2 H) 3.45-3.59 (m, 18 H)1.40 (br s, 2 H) 2.89 (ddd, J = 17.40, 14.13, 5.50 Hz, 1 H) 2.52-2.63 (m, 3 H) 2.30-2.35 (m, 4 H) 2.00-2.09 (m, 2 H) 1.86-1.96 (m, 2 H) 1.60-1.77 (m, 4 H) 1.49 (br d, J = 5.00 Hz, 4H) |
| 43 | 903.66 | N.D. | E | N.D. | (400 MHz, DMSO-d6) δ: δ ppm 12.83 (br s, 1 H) 11.12 (s, 1 H) 8.50 (d, J = 7.88 Hz, 1 H) 8.43 (s, 1 H) 8.30 (s, 1 H) 7.90 (br d, J = 7.64 Hz, 1 H) 7.81 (d, J = 8.26 Hz, 1 H) 7.74 (t, J = 7.68 Hz, 1 H) 7.56 (d, J = 8.38 Hz, 1 H) 7.51 (s, 1 H) 7.43 (d, J = 2.14 Hz, 1 H) 7.34 (dd, J = 8.32, 2.31 Hz, 1 H) 7.15-7.24 (m, 1 H) 5.12 (dd, J = 12.88, 5.38 Hz, 1 H) 4.72 (br s, 1 H) 4.24-4.32 (m, 2 H) 3.72-3.79 (m, 2 H) 3.68 (br d, J = 7.50 Hz, 2 H) 3.45-3.59 (m, 18 H) 2.89 (ddd, J = 17.40, 14.13, 5.50 Hz, 1 H)1.37 (br s, 1 H) 2.52-2.63 (m, 3 H) 2.67- |

TABLE 5-continued

| Characterization data for exemplary compounds of the present disclosure | | | | | |
|---|---|---|---|---|---|
| Ex # | MW; [M + H] + 1 (2) | IRAK4 Dmax (%)* | IRAK4 DC50** (nM) | IRAK4 IC50*** (nM) | Proton NMR data |
| | | | | | 2.67 (m, 3 H) 2.56-2.67 (m, 2 H) 2.33-2.35 (m, 2H) 1.64-2.01 (m, 12 H) |
| 44 | 859.62 | N.D. | E | E | (400 MHz, DMSO-d6) δ ppm 12.83 (br s, 1 H) 11.12 (s, 1 H) 8.50 (d, J = 7.88 Hz, 1 H) 8.43 (s, 1 H) 8.30 (s, 1 H) 7.90 (br d, J = 7.64 Hz, 1 H) 7.81 (d, J = 8.26 Hz, 1 H) 7.74 (t, J = 7.68 Hz, 1 H) 7.56 (d, J = 8.38 Hz, 1 H) 7.51 (s, 1 H) 7.43 (d, J = 2.14 Hz, 1 H) 7.34 (dd, J = 8.32, 2.31 Hz, 1 H) 7.15-7.24 (m, 1 H) 5.12 (dd, J = 12.88, 5.38 Hz, 1 H) 4.72 (br s, 1 H) 4.24-4.32 (m, 2 H)1.39-1.49 (br d, J = 5.00 Hz, 6 H) 3.72-3.79 (m, 2 H) 3.68 (br d, J = 7.50 Hz, 2 H) 3.45-3.59 (m, 10 H) 2.89 (ddd, J = 17.40, 14.13, 5.50 Hz, 1 H) 2.52-2.63 (m, 3 H) 2.30-2.35 (m, 4 H) 2.00-2.09 (m, 2 H) 1.86-1.96 (m, 2 H) 1.66-1.77 (m, 4 H) |
| 45 | 736.35 | N.D. | N.D. | E | (400 MHz, DMSO-d6) δ = 1.72-1.84 (m, 4 H), 2.00-2.11 (m, 2 H), 2.12-2.29 (m, 2 H), 2.48-2.66 (m, 2 H), 2.67-2.98 (m, 3 H), 3.83 (d, J = 7.2 Hz, 2 H), 3.89-3.99 (m, 2 H), 4.25-4.36 (m, 2 H), 4.57-4.74 (m, 1 H), 4.96 (dd, J = 12.4, 5.2 Hz, 1 H), 6.93-7.02 (m, 1 H), 7.09 (dd, J = 8.0, 2.4 Hz, 1 H), 7.22 (dd, J = 8.4, 2.4 Hz, 1 H), 7.28-7.33 (m, 1 H), 7.38 (d, J = 2.4 Hz, 1 H), 7.54-7.65 (m, 1 H), 7.71-7.80 (m, 2 H), 8.04 (s, 1 H), 8.48 (d, J = 7.6 Hz, 1 H), 8.57 (s, 1 H), 12.55-12.94 (m, 1 H). |
| 46 | 780.56 | N.D. | E | E | (400 MHz, DMSO-d6) δ = 1.71-1.84 (m, 4 H), 2.02-2.09 (m, 2 H), 2.11-2.24 (m, 2 H), 2.47-2.64 (m, 2 H), 2.68-2.96 (m, 3 H), 3.71-3.82 (m, 6 H), 3.87-3.95 (m, 2 H), 4.18-4.26 (m, 2 H), 4.62-4.80 (m, 1 H), 4.97 (dd, J = 12.23, 5.2 Hz, 1 H), 6.95 (td, J = 8.8, 2.4 Hz, 1 H), 7.03-7.09 (m, 1 H), 7.14 (dd, J = 8.4, 2.0 Hz, 1 H), 7.23 (d, J = 2.0 Hz, 1 H), 7.32 (dd, J = 8.8, 4.2 Hz, 1 H), 7.55-7.62 (m, 1 H), 7.68-7.79 (m, 2 H), 8.11-8.19 (m, 1 H), 8.48 (d, J = 8.0 Hz, 1 H), 8.56 (s, 1 H), 12.43-12.98 (m, 1 H). |
| 47 | 824.6 | N.D. | E | E | (400 MHz, DMSO-d6) δ = 1.69-1.85 (m, 4 H), 1.97-2.09 (m, 2 H), 2.11-2.23 (m, 2 H), 2.45-2.63 (m, 2 H), 2.66-2.98 (m, 3 H), 3.67-3.79 (m, 10 H), 3.85-3.93 (m, 2 H), 4.16-4.25 (m, 2 H), 4.64-4.81 (m, 1 H), 4.92-5.01 (m, 1 H), 6.95-7.03 (m, 1 H), 7.04-7.12 (m, 1 H), 7.14-7.21 (m, 1 H), 7.31-7.37 (m, 1 H), 7.55-7.62 (m, 1 H), 7.75 (d, J = 8.4 Hz, 2 H), 8.08-8.15 (m, 1 H), 8.45-8.51 (m, 1 H), 8.56 (s, 1 H), 12.35-12.98 (m, 1 H) |
| 48 | 868.64 | N.D. | E | E | (400 MHz, DMSO-d6) δ = 1.71-1.87 (m, 4 H), 1.99-2.10 (m, 2 H), 2.12-2.22 (m, 2 H), 2.43-2.60 (m, 2 H), 2.69-3.01 (m, 3 H), 3.58-3.76 (m, 14 H), 3.84-3.93 (m, 2 H), 4.18-4.28 (m, 2 H), 4.64-4.79 (m, 1 H), 4.87-5.02 (m, 1 H), 6.94-7.14 (m, 2 H), 7.18-7.26 (m, 1 H), 7.32-7.39 (m, 2 H), 7.55-7.62 (m, 1 H), 7.73-7.80 (m, 2 H), 8.24-8.35 (m, 1 H), 8.45-8.51 (m, 1 H), 8.54-8.59 (m, 1 H), 12.29-12.92 (m, 1 H). |
| 49 | 817.58 | N.D. | E | E | (400 MHz, DMSO-d6) δ: 11.10 (s, 1H), 8.35-8.25 (m, 2H), 7.83 (br d, J = 7.2 Hz, 1H), 7.76 (d, J = 8.3 Hz, 1H), 7.69-7.62 (m, 1H), 7.44-7.34 (m, 3H), 7.29-7.18 (m, 2H), 7.13-7.02 (m, 1H), 6.96 (br d, J = 1.1 Hz, 1H), 6.90-6.80 (m, 2H), 5.10 (dd, J = 5.4, 12.8 Hz, 1H), 4.25-4.12 (m, 2H), 3.71-3.65 (m, 2H), 3.62-3.45 (m, 10H), 2.96 (s, 3H), 2.91-2.82 (m, 1H), 2.63-2.54 (m, 1H), 2.09-1.96 (m, 1H) |
| 50 | 729.49 | N.D. | E | E | (300 MHz, DMSO-d6) δ ppm 11.11 (br s, 1 H) 8.24-8.37 (m, 2 H) 7.81 (br d, J = 7.96 Hz, 1 H) 7.73 (d, J = 8.24 Hz, 1 H) 7.62 (t, J = 7.82 Hz, 1 H) 7.40-7.48 (m, 2 H) 7.37 (d, J = 2.28 Hz, 1 H) 7.19-7.30 (m, 2 H) 7.02-7.15 (m, 2 H) 6.85-7.00 (m, 2 H) 5.11 (dd, J = 12.94, |

TABLE 5-continued

| Ex # | MW; [M + H] + 1 (2) | IRAK4 Dmax (%)* | IRAK4 DC50** (nM) | IRAK4 IC50*** (nM) | Proton NMR data |
|---|---|---|---|---|---|
| Characterization data for exemplary compounds of the present disclosure | | | | | |
| | | | | | 5.26 Hz, 1 H) 4.38 (br s, 2 H) 3.05 (s, 3 H) 3.83 (br s, 2 H) 2.80-2.98 (m, 2 H) 2.73 (s, 1 H) 2.24-2.32 (m, 1 H) 2.06 (br d, J = 11.62 Hz, 1 H) |
| 51 | 773.53 | N.D. | E | E | (400 MHz, DMSO-d6) δ ppm 11.11 (br s, 1 H) 8.28-8.35 (m, 2 H) 7.84 (br d, J = 7.58 Hz, 1 H) 7.76 (d, J = 8.30 Hz, 1 H) 7.66 (t, J = 7.76 Hz, 1 H) 7.36-7.44 (m, 3 H) 7.19-7.28 (m, 2 H) 7.05-7.14 (m, 2 H) 6.99 (br s, 1 H) 6.83-6.91 (m, 2 H) 5.11 (dd, J = 12.84, 5.50 Hz, 1 H) 4.24 (br s, 2 H) 3.74 (br s, 2 H) 3.65-3.69 (m, 2 H) 3.58 (br d, J = 5.14 Hz, 2 H) 2.98 (s, 4 H) 2.88 (br d, J = 13.94 Hz, 1 H) 2.68 (s, 2 H) 2.33 (s, 2 H) 2.00-2.07 (m, 1 H). |
| 52 | 861.62 | N.D. | E | E | (400 MHz, DMSO-d6) δ: 11.10 (br s, 1H), 8.34-8.24 (m, 2H), 7.87-7.80 (m, 1H), 7.80-7.75 (m, 1H), 7.72-7.62 (m, 1H), 7.46-7.34 (m, 3H), 7.32-7.26 (m, 1H), 7.25-7.16 (m, 1H), 7.15-7.04 (m, 1H), 6.95 (br s, 1H), 6.89-6.79 (m, 2H), 5.16-5.03 (m, 1H), 4.31-4.16 (m, 1H), 3.73-3.68 (m, 2H), 3.44 (s, 16H), 3.00-2.92 (m, 3H), 2.08-1.97 (m, 1H) |
| 53 | 868.59 | N.D. | E | E | (400 MHz, CDCl3) δ 12.56-12.88 (m, 1 H), 9.63-9.98 (m, 1 H), 8.51 (s, 1 H), 8.39 (d, J = 8.0 Hz, 1 H), 7.84 (d, J = 8.4 Hz, 1 H), 7.69 (d, J = 7.6 Hz, 1 H), 7.60-7.66 (m, 4 H), 7.48-7.56 (m, 2 H), 7.44 (d, J = 2.4 Hz, 1 H), 7.28-7.32 (m, 2 H), 7.19 (s, 2 H), 5.05 (dd, J = 12.4, 5.2 Hz, 1 H), 4.29 (t, J = 4.46 Hz, 2 H), 3.94 (t, J = 4.8 Hz, 2 H), 3.65-3.75 (m, 6 H), 3.32-3.51 (m, 2 H), 2.73-2.99 (m, 4 H), 2.67 (s, 4 H), 2.46 (s, 4 H), 2.00-2.35 (m, 2 H). |
| 54 | 898.6 | N.D. | E | E | (400 MHz, CDCl3)δ 12.42-12.92 (m, 1 H), 9.90 (s, 1 H), 8.54 (s, 1 H), 8.42 (d, J = 8.0 Hz, 1 H), 7.84 (d, J = 8.4 Hz, 1 H), 7.70 (d, J = 7.2 Hz, 1 H), 7.52 (t, J = 8.4 Hz, 2 H), 7.45 (d, J = 2.0 Hz, 1 H), 7.28-7.32 (m, 2 H), 7.16-7.24 (m, 4 H), 7.05-7.10 (m, 1 H), 5.05 (dd, J = 12.4, 5.2 Hz, 1 H). 4.29 (s, 2 H), 3.93 (t, J = 4.4 Hz, 2 H), 3.89 (s, 3 H), 3.72 (t, J = 4.4 Hz, 4 H), 3.66 (d, J = 4.4 Hz, 2 H), 3.34-3.52 (m, 2 H), 2.77-2.97 (m, 4 H), 2.73 (s, 4 H), 2.49 (s, 4 H), 2.11-2.26 (m, 2 H). |
| 55 | 780.39 | N.D. | E | E | (400 MHz, CDCl3) δ: δ 12.64 (s, 1 H), 9.20 (s, 1 H), 8.49 (s, 1 H), 8.37 (d, J = 8.0 Hz, 1 H), 7.80 (d, J = 8.4 Hz, 1 H), 7.69 (d, J = 8.8 Hz, 1 H), 7.62-7.66 (m, 4 H), 7.52-7.57 (m, 1 H), 7.48-7.52 (m, 1 H), 7.39-7.41 (m, 2 H), 7.21-7.24 (m, 3 H), 4.99 (dd, J = 12.4, 5.2 Hz, 1 H), 4.26 (t, J = 5.2 Hz, 2 H), 3.62-3.71 (m, 1 H), 3.48-3.59 (m, 1 H), 2.82-2.92 (m, 4 H), 2.64 (d, J = 7.2 Hz, 4 H), 2.50 (s, 4 H), 2.11-2.20 (m, 2 H). |
| 56 | 810.4 | N.D. | E | E | (400 MHz, CDCl3) δ 12.67 (s, 1 H), 9.07 (s, 1 H), 8.47-8.56 (m, 1 H), 8.39 (d, J = 8.0 Hz, 1 H), 7.77-7.83 (m, 1 H), 7.70 (d, J = 8.0 Hz, 1 H), 7.48-7.57 (m, 2 H), 7.35-7.44 (m, 2 H), 7.20-7.26 (m, 5 H), 7.05-7.12 (m, 1 H), 4.99 (dd, J = 12.4, 5.2 Hz, 1 H), 4.19-4.32 (m, 2 H), 3.90 (s, 3 H), 3.63-3.73 (m, 1 H), 3.55 (d, J = 12.8 Hz, 1 H), 2.74-2.96 (m, 4 H), 2.64 (d, J = 8.0 Hz, 4 H), 2.51 (s, 4 H), 2.12-2.20 (m, 2 H). |
| 57 | 854.43 | N.D. | N.D. | E | (400 MHz, CDCl3) δ = 12.49-12.87 (m, 1 H), 9.71-9.88 (m, 1 H), 8.54 (s, 1 H), 8.43 (d, J = 7.6 Hz, 1 H), 7.84 (d, J = 8.4 Hz, 1 H), 7.70 (d, J = 8.0 Hz, 1 H), 7.48-7.57 (m, 2 H), 7.28-7.43 (m, 3 H), 7.17-7.25 (m, 4 H), 7.04-7.12 (m, 1 H), 4.99-5.16 (m, 1 H), 4.20-4.40 (m, 2 H), 3.84-3.95 (m, 5 H), 3.66-3.77 (m, 2 H), 3.53-3.64 (m, 1 H), 3.31-3.45 (m, 1 H), 2.84-2.97 (m, 2 H), 2.13-2.78 (m, 12 H). |
| 58 | 764.5 | B | A | A | (400 MHz, CDCl3) δ 10.72 (s, 1 H), 8.86 (s, 1 H), 8.52 (d, J = 8.0 Hz, 2 H), 8.13 (t, J = 8.0 |

TABLE 5-continued

Characterization data for exemplary compounds of the present disclosure

| Ex # | MW; [M + H] + 1 (2) | IRAK4 Dmax (%)* | IRAK4 DC50** (nM) | IRAK4 IC50*** (nM) | Proton NMR data |
|---|---|---|---|---|---|
| | | | | | Hz, 1 H), 7.84-7.90 (m, 2 H), 7.80 (d, J = 8.4 Hz, 1 H), 7.42 (d, J = 2.4 Hz, 1 H), 7.23-7.26 (m, 1 H), 7.09 (s, 1 H), 4.98 (dd, J = 12.4, 5.6 Hz, 1 H), 4.42 (s, 1 H), 4.25-4.35 (m, 2 H), 4.04 (s, 3 H), 3.88-3.93 (m, 2 H), 3.77 (s, 2 H), 3.21 (s, 2 H), 2.57-2.99 (m, 6 H), 2.12-2.32 (m, 6 H). |
| 59 | 808.54 | B | D | A | (400 MHz, CDCl3) δ ppm δ 10.71 (s, 1 H), 8.83 (s, 1 H), 8.42-8.55 (m, 2 H), 8.13 (t, J = 8.0 Hz, 1 H), 7.89 (s, 1 H), 7.86 (d, J = 7.6 Hz, 1 H), 7.79 (d, J = 8.4 Hz, 1 H), 7.40 (d, J = 2.4 Hz, 1 H), 7.24 (dd, J = 8.4, 2.31 Hz, 1 H), 7.07 (s, 1 H), 4.97 (dd, J = 12.4, 5.2 Hz, 1 H), 4.35-4.45 (m, 1 H), 4.24-4.32 (m, 2 H), 4.04 (s, 3 H), 3.88-3.96 (m, 2 H), 3.67-3.76 (m, 6 H), 3.19 (d, J = 11.6 Hz, 2 H), 2.71-2.86 (m, 4 H), 2.10-2.47 (m, 8 H). |
| 60 | 750.53 | B | A | A | (400 MHz, CDCl3) δ ppm 10.98 (s, 1 H) 10.51 (s, 1 H) 8.69 (s, 1 H) 8.33-8.52 (m, 3 H) 8.23 (d, J = 7.70 Hz, 1 H) 7.64 (d, J = 8.30 Hz, 1 H) 7.15-7.24 (m, 2 H) 7.08 (dd, J = 8.38, 2.14 Hz, 1 H) 5.08 (dd, J = 13.34, 5.01 Hz, 1 H) 4.18-4.43 (m, 5 H) 3.99 (s, 3 H) 3.74-3.85 (m, 2 H) 3.63 (t, J = 5.76 Hz, 2 H) 2.83-3.12 (m, 3 H) 2.57 (br t, J = 5.82 Hz, 3 H) 2.30-2.44 (m, 2 H) 1.90-2.26 (m, 7 H) |
| 61 | 794.56 | N.D. | E | A | (400 MHz, DMSO-d6) δ ppm 10.97 (br s, 1 H) 10.51 (s, 1 H) 8.69 (s, 1 H) 8.33-8.51 (m, 3 H) 8.22 (d, J = 7.58 Hz, 1 H) 7.63 (d, J = 8.44 Hz, 1 H) 7.13-7.22 (m, 2 H) 7.08 (dd, J = 8.38, 2.14 Hz, 1 H) 5.07 (dd, J = 13.34, 5.14 Hz, 1 H) 4.14-4.44 (m, 5 H) 3.98 (s, 3 H) 3.74-3.85 (m, 2 H) 3.51-3.66 (m, 6 H) 2.83-3.07 (m, 3 H) 2.53-2.62 (m, 3 H) 2.31-2.45 (m, 1 H) 1.91-2.24 (m, 7 H) |
| 62 | 807.55 | N.D. | N.D. | A | |
| 63 | 817.57 | A | B | A | |
| 64 | 851.59 | N.D. | N.D. | A | (400 MHz, DMSO-d6) δ ppm δ 11.09 (s, 1 H), 10.50 (s, 1 H), 8.68 (s, 1 H), 8.33-8.50 (m, 3 H), 8.22 (d, J = 7.2 Hz, 1 H), 7.54-7.61 (m, 1 H), 7.11-7.19 (m, 2 H), 7.03 (d, J = 6.8 Hz, 1 H), 6.61 (t, J = 5.6 Hz, 1 H), 5.04 (dd, J = 12.4, 4.8 Hz, 1 H), 4.35 (bt, J = 7.6 Hz, 1 H), 3.98 (s, 3 H), 3.63 (t, J = 5.2 Hz, 2 H), 3.46-3.59 (m, 12 H), 2.78-3.13 (m, 4 H), 2.60 (s, 2 H), 1.92-2.23 (m, 8H). |
| 65 | 859.63 | N.D. | N.D. | N.D. | |
| 66 | 903.66 | B | D | A | |
| 67 | 442.86 | A | B | A | (400 MHz, CDCl3) δ ppm δ: 9.62 (s, 1H), 7.72 (d, J = 8.4 Hz, 1H), 6.97 (d, J = 2.8 Hz, 1H), 6.89 (dd, J = 2.8, 8.8 Hz, 1H), 4.27-4.22 (m, 1H), 3.84 (s, 3H), 3.80 (s, 3H), 2.29-2.07 (m, 1H), 2.06-2.02 (m, 4H), 1.53-1.44 (m, 4H). |
| 68 | 442.86 | C | D | E | |

N.D. = Not Determined
*IRAK4 Dmax Ranges:
A > 70
70 ≥ B > 50
50 ≥ C > 30
D ≤ 30
**IRAK4 DC50 Ranges:
A < 30
30 ≤ B < 100
100 ≤ C < 300
300 ≤ D < 1000
E ≥ 1000
***IRAK4 IC50 Ranges:
A < 30
30 ≤ B < 100
100 ≤ C < 300
300 ≤ D < 1000
E ≥ 1000

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present invention, but should not be seen as limiting the present invention in any way.

Specific Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative.

In certain embodiments, the description provides the following exemplary IRAK PROTAC molecules, including salts, prodrugs, polymorphs, analogs, derivatives, and deuterated forms thereof.

In certain other embodiments, the bifunctional compounds is selected from exemplary compounds 1-14 and 25-68.

In certain other embodiments, the description provides exemplary IRAK PROTAC molecules by selecting a PTM from Table 6(e.g., a PTM selected from the group consisting of PTM1through PTM91), a linker from Table 7(e.g., a linker selected from the group consisting of Linker1 through Linker18), and a ULM from Table 8(e.g., a linker selected from the group consisting of ULM1 through ULM25), including salts, prodrugs, polymorphs, analogs, derivatives, and deuterated forms thereof:

TABLE 6

| Exemplary PTMs | |
|---|---|
| PTM Number | Chemical Structure |
| PTM1 | 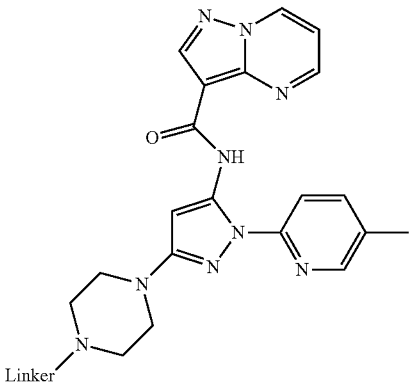 |
| PTM2 | 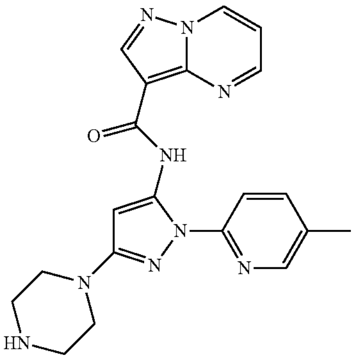 [SMILES: Cc1ccc(-n2nc(N3CCNCC3)cc2NC(=O)c2cnn3cccnc23)nc1] |
| PTM3 | 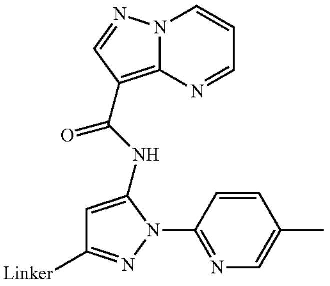 |

TABLE 6-continued
| Exemplary PTMs | |
|---|---|
| PTM Number | Chemical Structure |
| PTM4 | 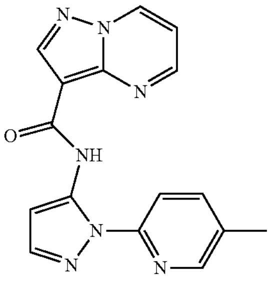 [SMILES: Cc1ccc(-n2nccc2NC(=O)c2cnn3cccnc23)nc1] |
| PTM5 | 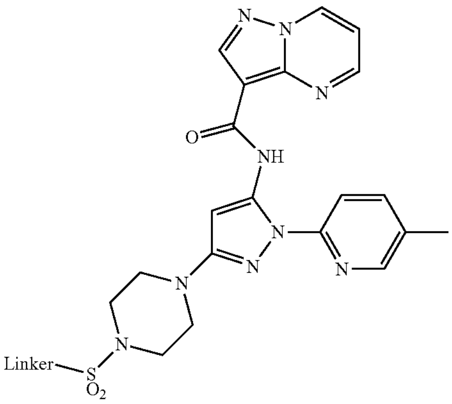 |
| PTM6 | 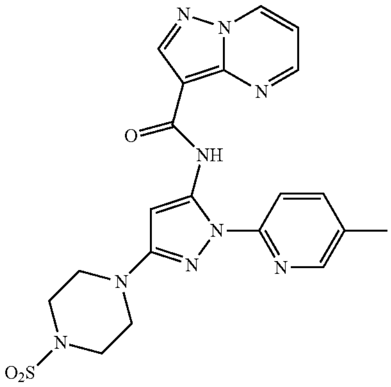 |
| PTM7 | 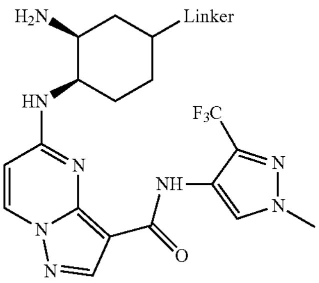 |

TABLE 6-continued
| Exemplary PTMs | |
|---|---|
| PTM Number | Chemical Structure |
| PTM8 | 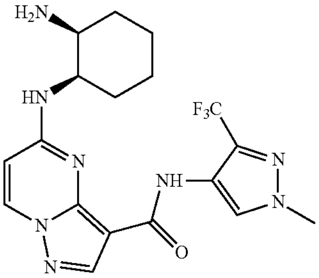 [SMILES: Cn1cc(NC(=O)c2cnn3ccc(N[C@@H]4CCCC[C@@H]4N)nc23)c(C(F)(F)F)n1] |
| PTM9 | 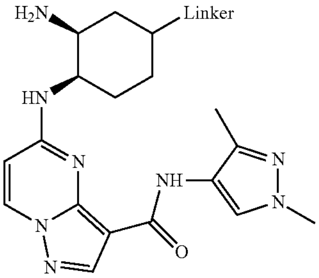 |
| PTM10 | 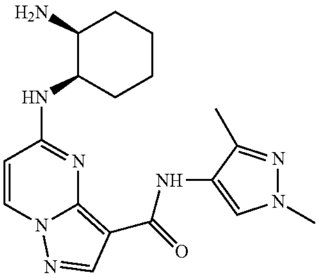 [SMILES: Cc1nn(C)cc1NC(=O)c1cnn2ccc(N[C@@H]3CCCC[C@@H]3N)nc12] |
| PTM11 | 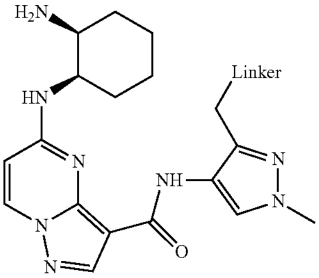 |
| PTM12 | 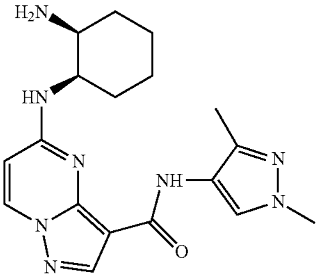 [SMILES: Cc1nn(C)cc1NC(=O)c1cnn2ccc(N[C@@H]3CCCC[C@@H]3N)nc12] |

TABLE 6-continued
| Exemplary PTMs | |
|---|---|
| PTM Number | Chemical Structure |
| PTM13 | 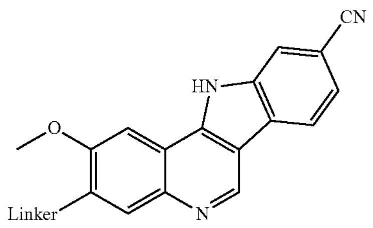 |
| PTM14 | 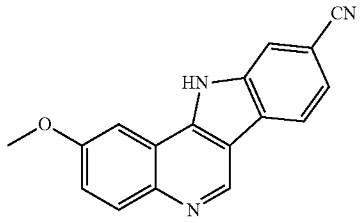 [SMILES: COc1ccc2ncc3c4ccc(C#N)cc4[nH]c3c2c1] |
| PTM15 | 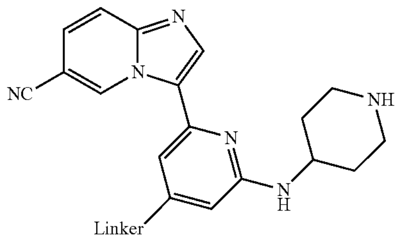 |
| PTM16 | 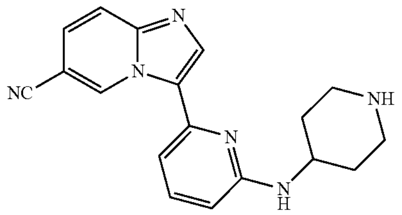 [SMILES: N#Cc1ccc2ncc(-c3cccc(NC4CCNCC4)n3)n2c1] |
| PTM17 | 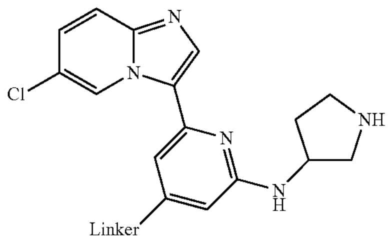 |
| PTM18 | 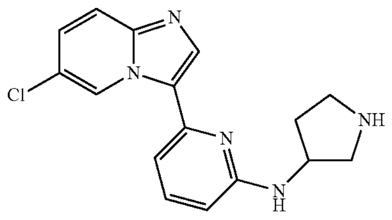 [SMILES: Clc1ccc2ncc(-c3cccc(NC4CCNC4)n3)n2c1] |

TABLE 6-continued
| Exemplary PTMs | |
| --- | --- |
| PTM Number | Chemical Structure |
| PTM19 | 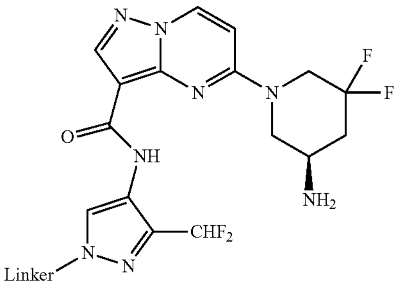 |
| PTM20 | 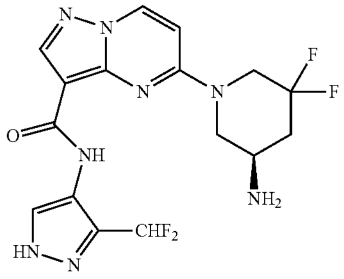 [SMILES: N[C@H]1CN(c2ccn3ncc(C(=O)Nc4c[nH]nc4C(F)F)c3n2)CC(F)(F)C1] |
| PTM21 | 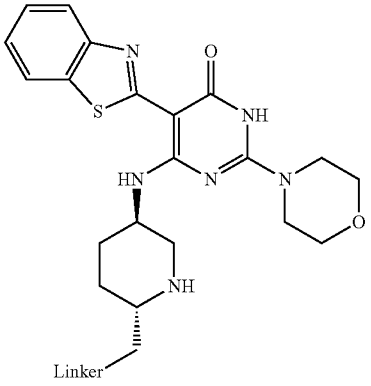 |
| PTM22 | 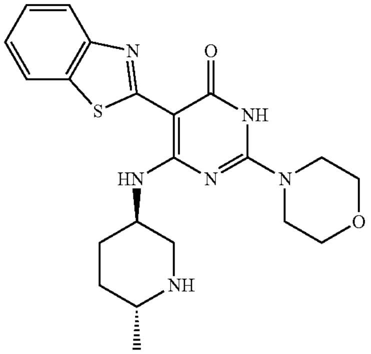 [SMILES: C[C@@H]1CC[C@@H](Nc2nc(N3CCOCC3)[nH]c(=O)c2-c2nc3ccccc3s2)CN1] |

TABLE 6-continued
| Exemplary PTMs | |
|---|---|
| PTM Number | Chemical Structure |
| PTM23 | 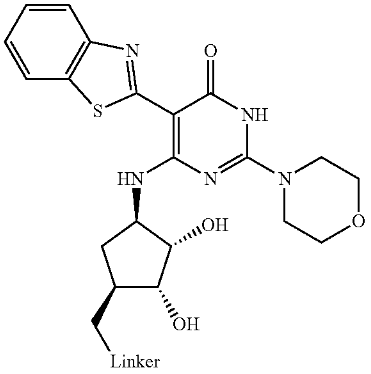 |
| PTM24 | 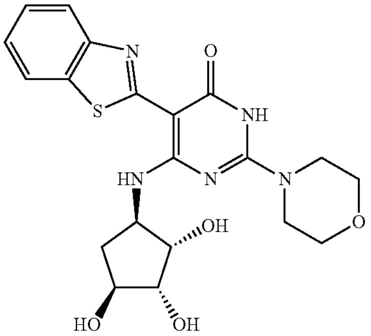 [SMILES: O=c1[nH]c(N2CCOCC2)nc(N[C@@H]2C[C@H](O)[C@@H](O)[C@H]2O)c1-c1nc2ccccc2s1] |
| PTM25 | 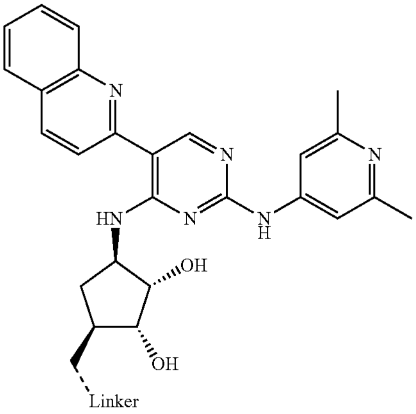 |
| PTM26 | 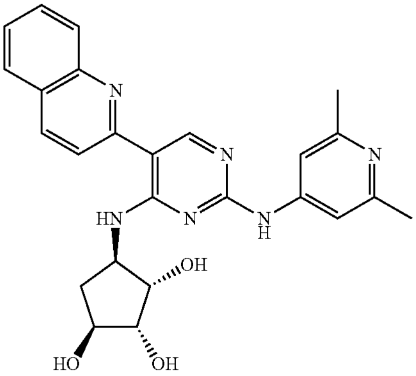 [SMILES: Cc1cc(Nc2ncc(-c3ccc4ccccc4n3)c(N[C@@H]3C[C@H](O)[C@@H](O)[C@H]3O)n2)cc(C)n1] |

TABLE 6-continued
| Exemplary PTMs | |
|---|---|
| PTM Number | Chemical Structure |
| PTM27 | 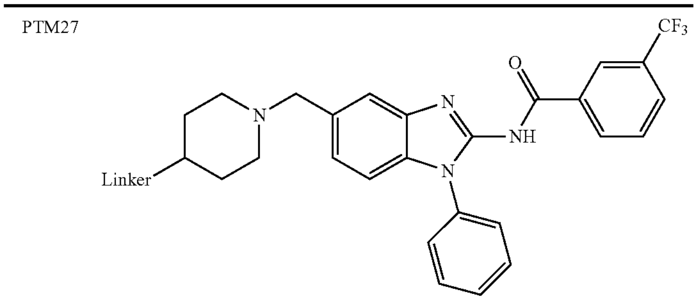 |
| PTM33 | 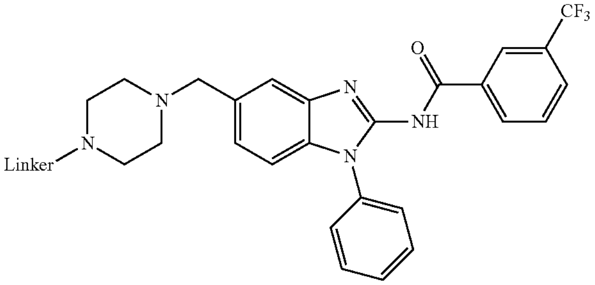 |
| PTM28 | 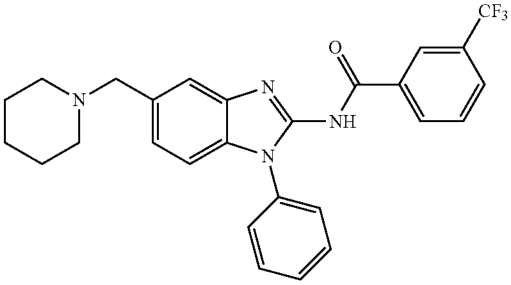 [SMILES: O=C(Nc1nc2cc(CN3CCCCC3)ccc2n1-c1ccccc1)c1cccc(C(F)(F)F)c1] |
| PTM34 | 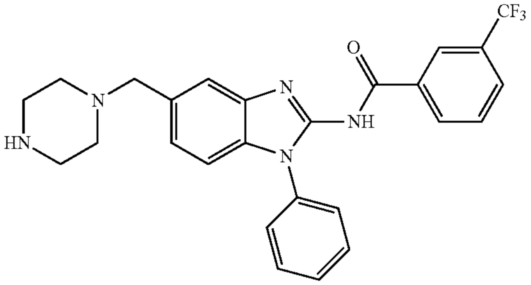 [SMILES: O=C(Nc1nc2cc(CN3CCNCC3)ccc2n1-c1ccccc1)c1cccc(C(F)(F)F)c1] |
| PTM29 | 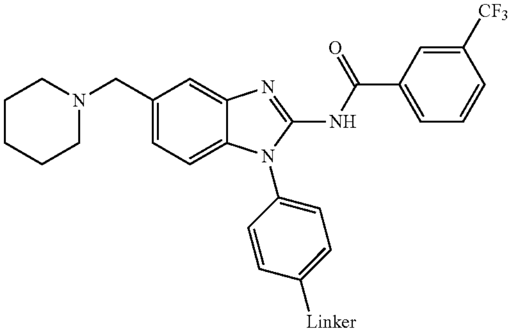 |

TABLE 6-continued
| Exemplary PTMs | |
|---|---|
| PTM Number | Chemical Structure |
| PTM35 | 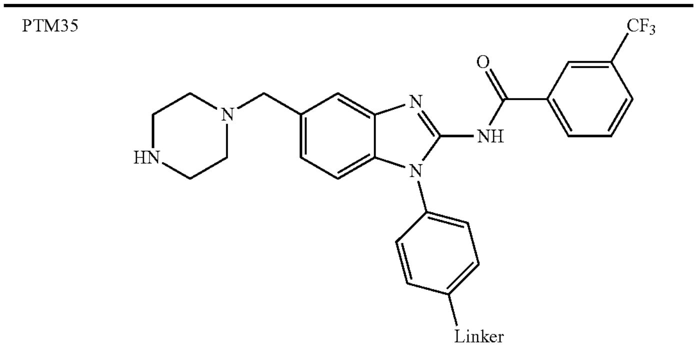 |
| PTM30 | 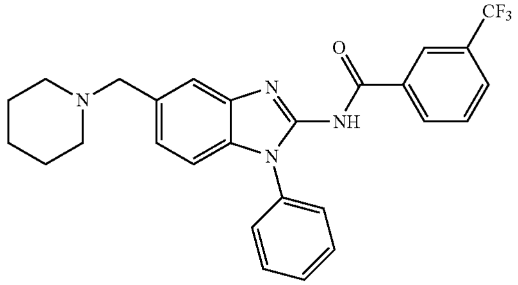 [SMILES: O=C(Nc1nc2cc(CN3CCCCC3)ccc2n1-c1ccccc1)c1cccc(C(F)(F)F)c1] |
| PTM36 | 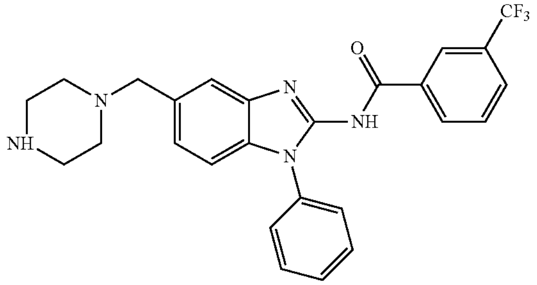 [SMILES: O=C(Nc1nc2cc(CN3CCNCC3)ccc2n1-c1ccccc1)c1cccc(C(F)(F)F)c1] |
| PTM31 | 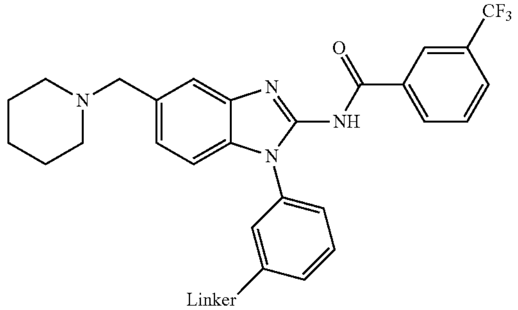 |
| PTM37 | 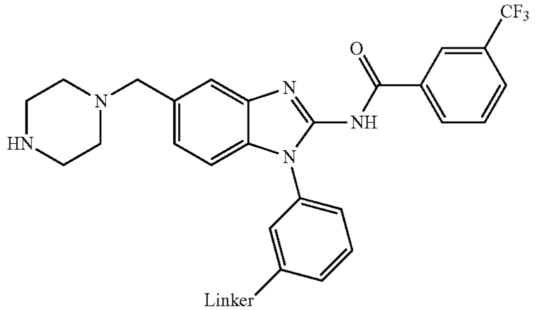 |

TABLE 6-continued
| Exemplary PTMs | |
|---|---|
| PTM Number | Chemical Structure |
| PTM32 | 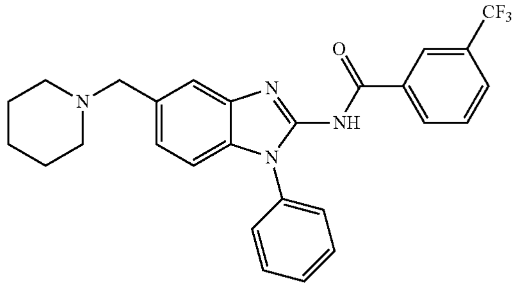 [SMILES: O=C(Nc1nc2cc(CN3CCCCC3)ccc2n1-c1ccccc1)c1cccc(C(F)(F)F)c1] |
| PTM38 | 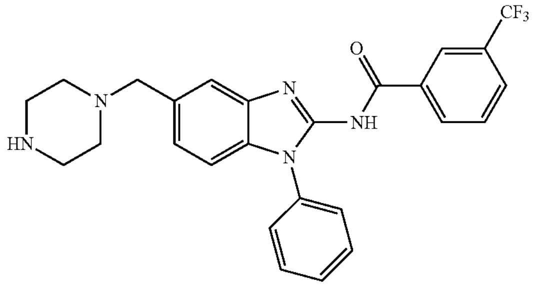 [SMILES: O=C(Nc1nc2cc(CN3CCNCC3)ccc2n1-c1ccccc1)c1cccc(C(F)(F)F)c1] |
| PTM39 | 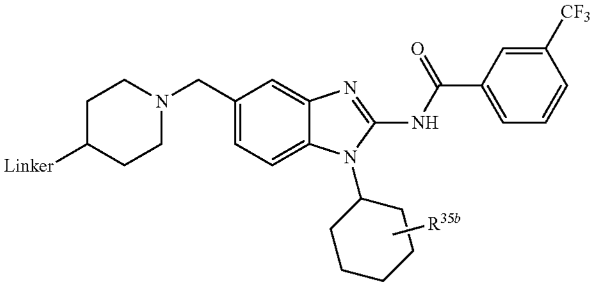 |
| PTM40 | 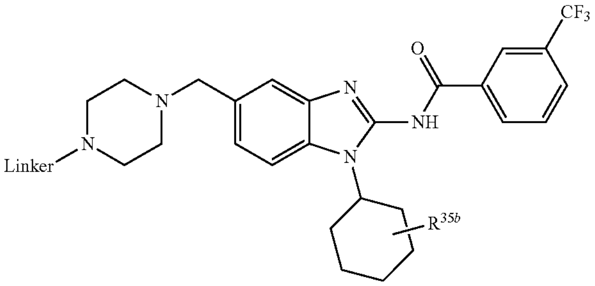 |
| PTM41 | 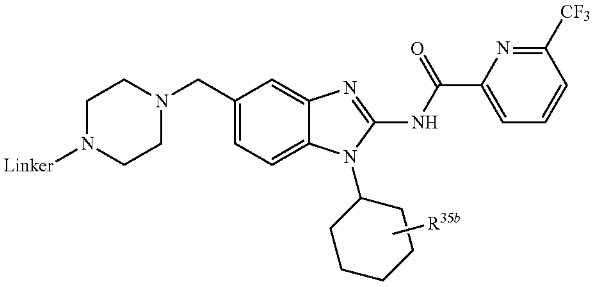 |

TABLE 6-continued
| PTM Number | Chemical Structure |
|---|---|
| Exemplary PTMs | |
| PTM42 | 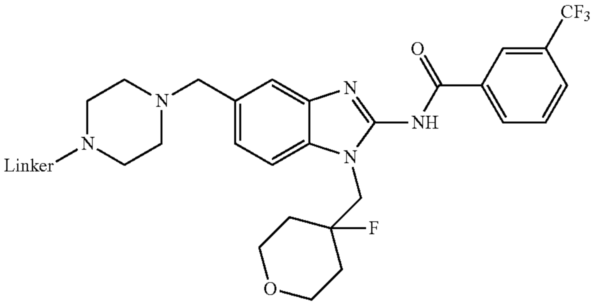 |
| PTM43 | 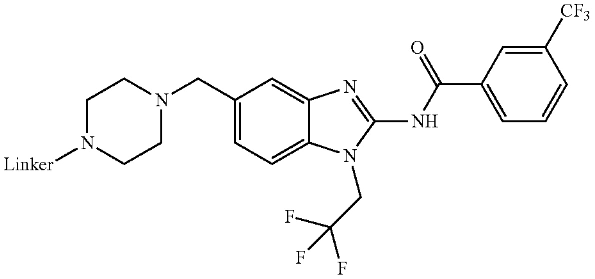 |
| PTM44 | 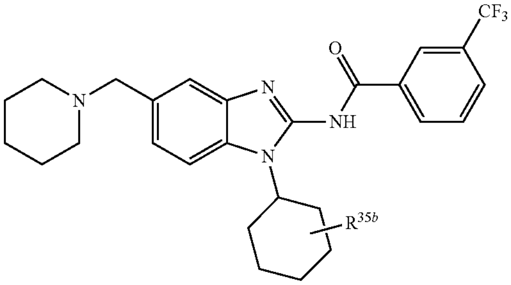 |
| PTM45 | 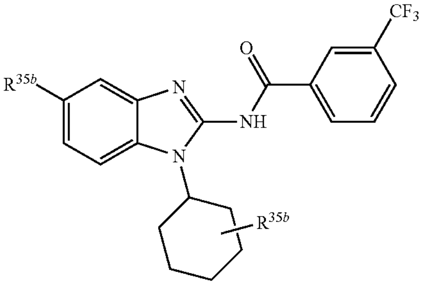 |
| PTM46 | 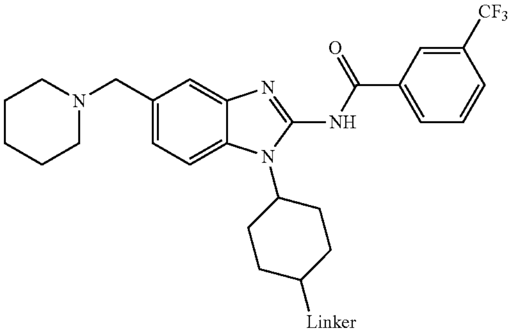 |

TABLE 6-continued
| Exemplary PTMs | |
|---|---|
| PTM Number | Chemical Structure |
| PTM47 | 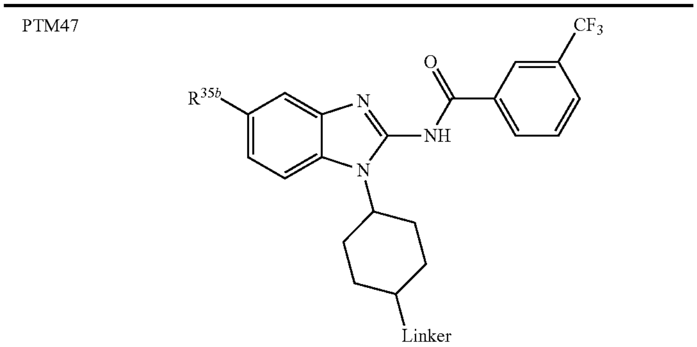 |
| PTM48 | 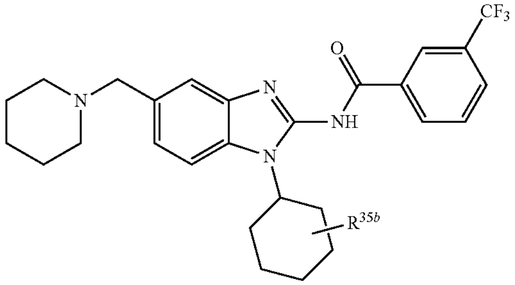 |
| PTM49 | 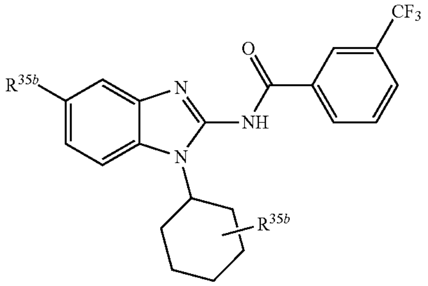 |
| PTM50 | 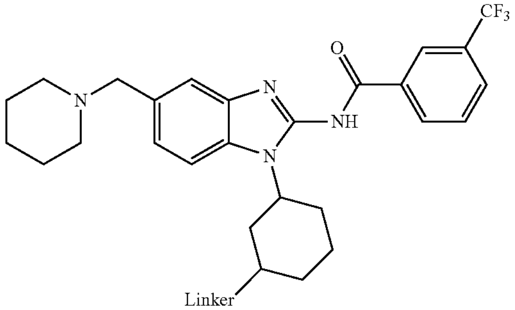 |
| PTM51 | 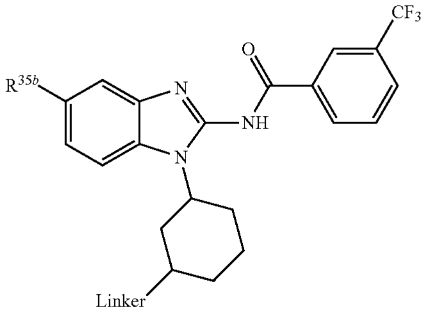 |

TABLE 6-continued
| PTM Number | Chemical Structure |
| --- | --- |
| | Exemplary PTMs |
| PTM52 | 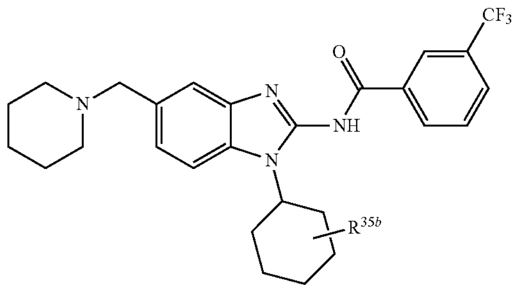 |
| PTM53 | 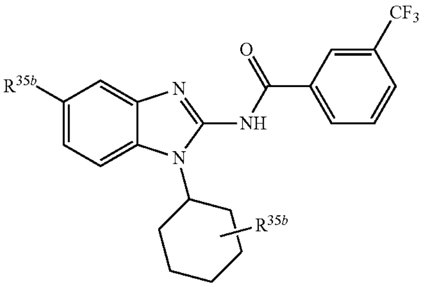 |
| PTM54 | 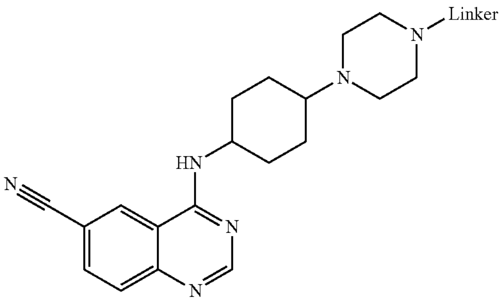 |
| PTM55 | 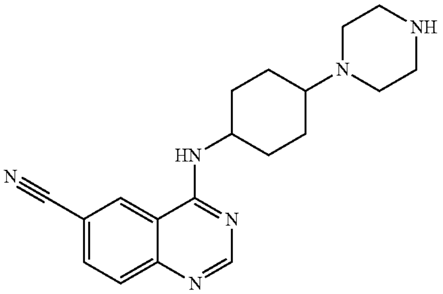 [SMILES: N#Cc1ccc2ncnc(NC3CCC(N4CCNCC4)CC3)c2c1] |
| PTM56 | 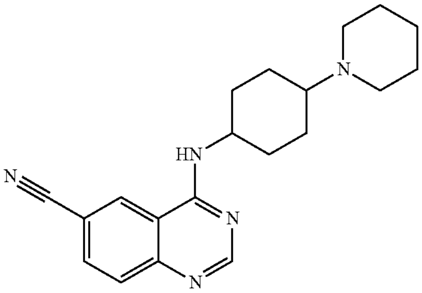 [SMILES: N#Cc1ccc2ncnc(NC3CCC(N4CCCCC4)CC3)c2c1] |

TABLE 6-continued
| Exemplary PTMs | |
|---|---|
| PTM Number | Chemical Structure |
| PTM57 | 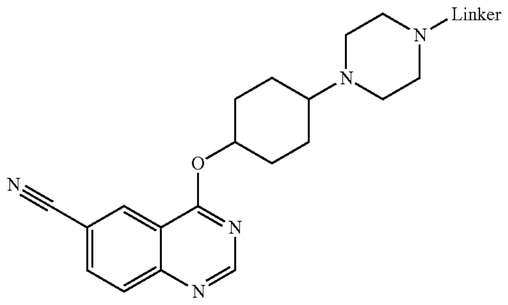 |
| PTM58 | 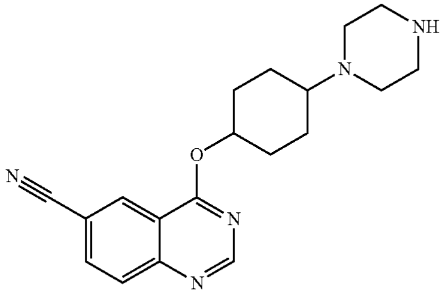 [SMILES: N#Cc1ccc2ncnc(OC3CCC(N4CCNCC4)CC3)c2c1] |
| PTM59 | 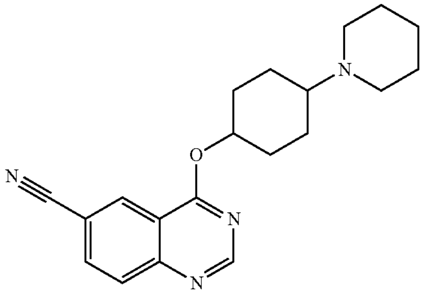 [SMILES: N#Cc1ccc2ncnc(OC3CCC(N4CCCCC4)CC3)c2c1] |
| PTM60 | 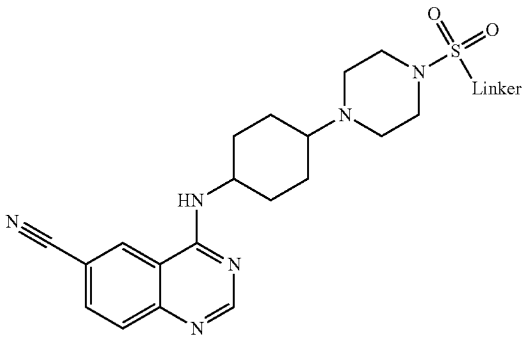 |

TABLE 6-continued
| Exemplary PTMs | |
|---|---|
| PTM Number | Chemical Structure |
| PTM61 | 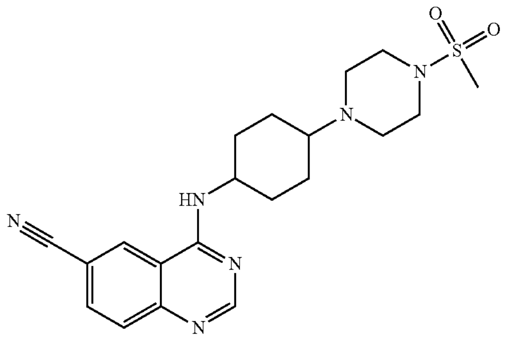 [SMILES: CS(=O)(=O)N1CCN(C2CCC(Nc3ncnc4ccc(C#N)cc34)CC2)CC1] |
| PTM62 | 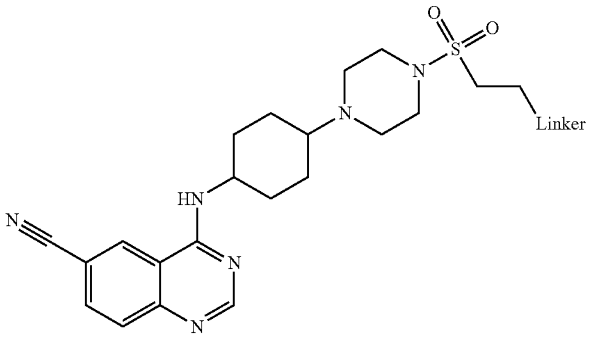 |
| PTM63 | 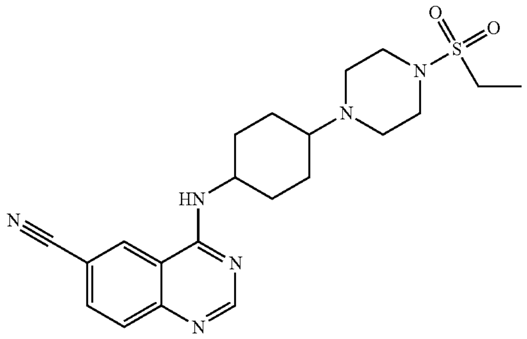 [SMILES: CCS(=O)(=O)N1CCN(C2CCC(Nc3ncnc4ccc(C#N)cc34)CC2)CC1] |
| PTM64 | 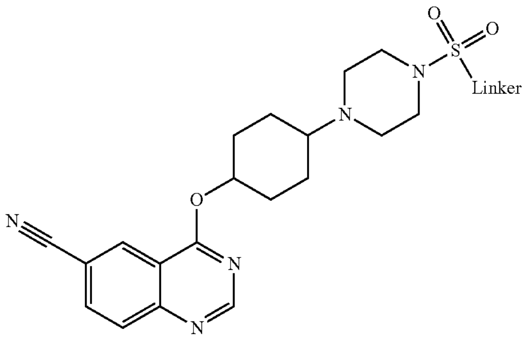 |

TABLE 6-continued
| Exemplary PTMs | |
|---|---|
| PTM Number | Chemical Structure |
| PTM65 | 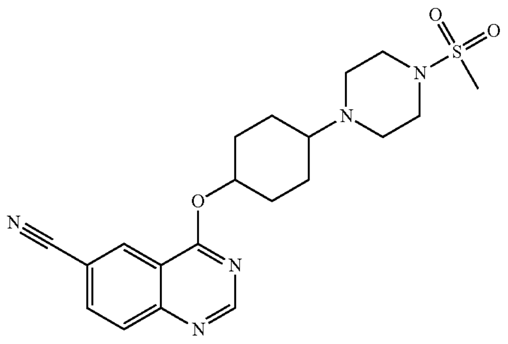 [SMILES: CS(=O)(=O)N1CCN(C2CCC(Oc3ncnc4ccc(C#N)cc34)CC2)CC1] |
| PTM66 | 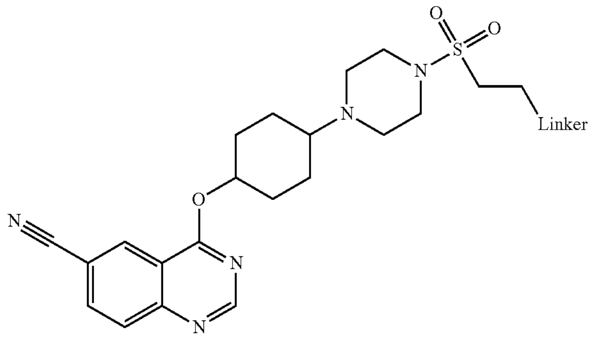 |
| PTM67 | 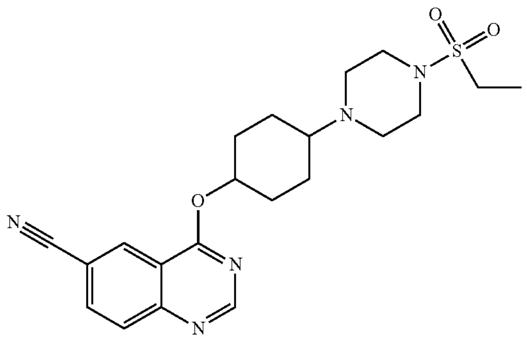 [SMILES: CCS(=O)(=O)N1CCN(C2CCC(Oc3ncnc4ccc(C#N)cc34)CC2)CC1] |
| PTM68 | 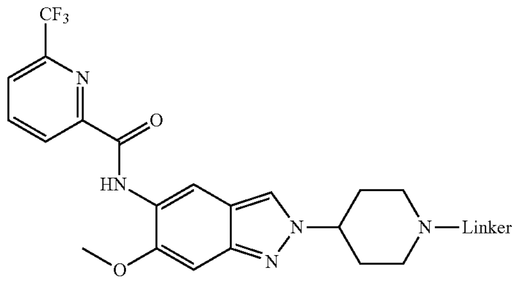 |

TABLE 6-continued
| Exemplary PTMs | |
|---|---|
| PTM Number | Chemical Structure |
| PTM69 | 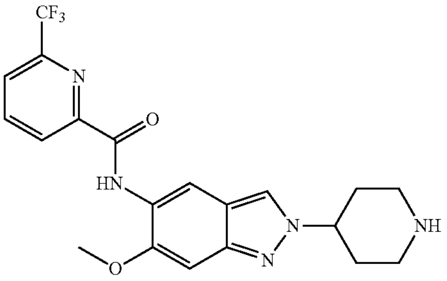 [SMILES: COc1cc2nn(C3CCNCC3)cc2cc1NC(=O)c1cccc(C(F)(F)F)n1] |
| PTM70 | 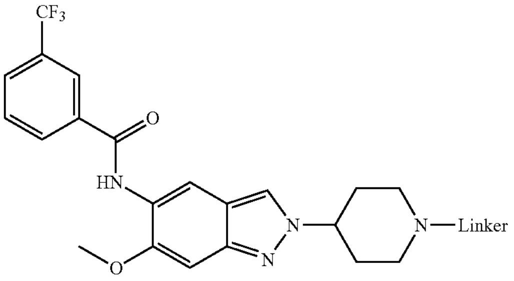 |
| PTM71 | 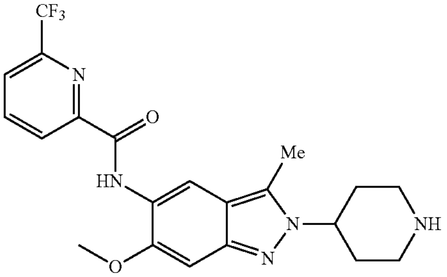 [SMILES: COc1cc2nn(C3CCNCC3)c(C)c2cc1NC(=O)c1cccc(C(F)(F)F)n1] |
| PTM72 | 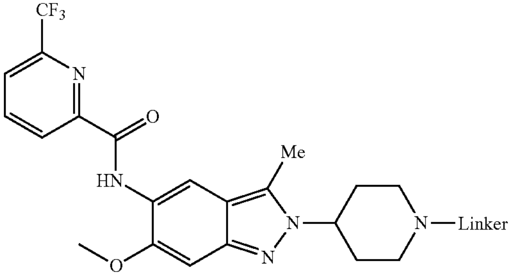 |
| PTM73 | 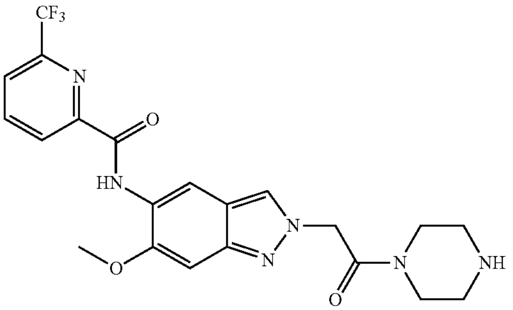 [SMILES: COc1cc2nn(CC(=O)N3CCNCC3)cc2cc1NC(=O)c1cccc(C(F)(F)F)n1] |

TABLE 6-continued
| Exemplary PTMs | |
|---|---|
| PTM Number | Chemical Structure |
| PTM74 | 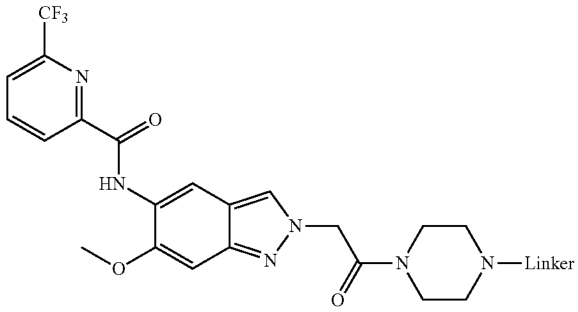 |
| PTM75 | 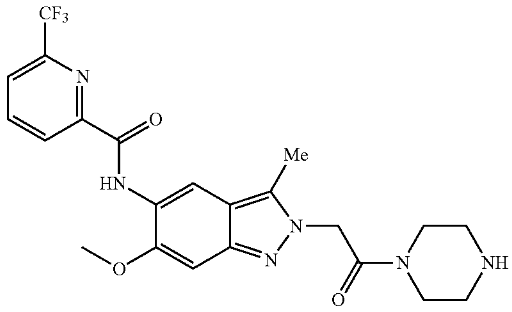 [SMILES: COc1cc2nn(CC(=O)N3CCNCC3)c(C)c2cc1NC(=O)c1cccc(C(F)(F)F)n1] |
| PTM76 | 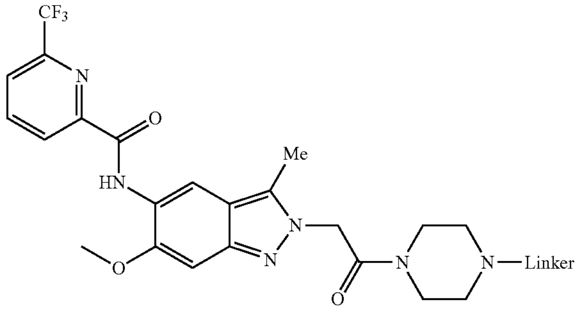 |
| PTM77 | 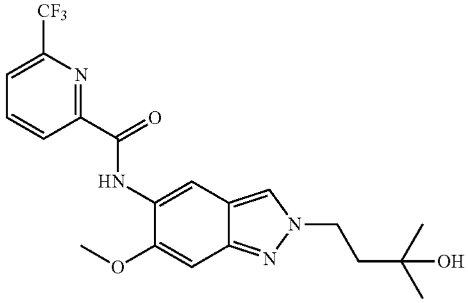 [SMILES: COc1cc2nn(CCC(C)(C)O)cc2cc1NC(=O)c1cccc(C(F)(F)F)n1] |

TABLE 6-continued
| Exemplary PTMs | |
|---|---|
| PTM Number | Chemical Structure |
| PTM78 | 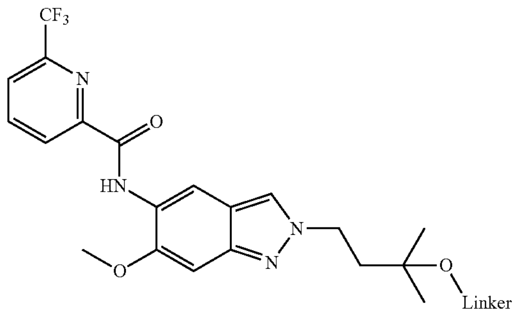 |
| PTM79 | 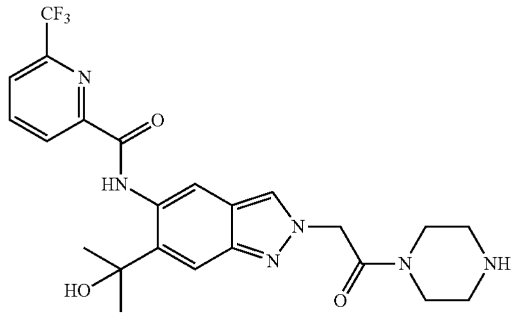 [SMILES: CC(C)(O)c1cc2nn(CC(=O)N3CCNCC3)cc2cc1NC(=O)c1cccc(C(F)(F)F)n1] |
| PTM80 | 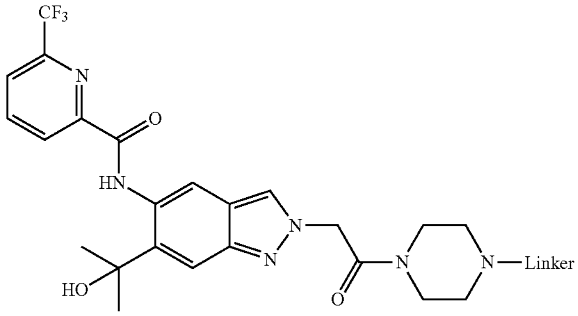 |
| PTM81 | 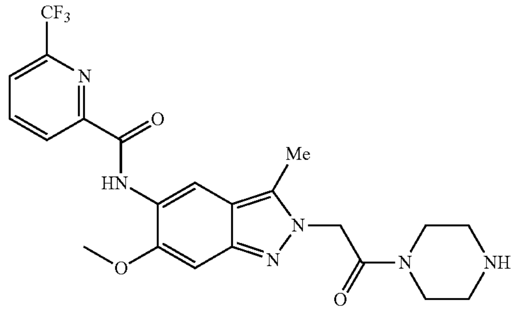 [SMILES: COc1cc2nn(CC(=O)N3CCNCC3)c(C)c2cc1NC(=O)c1cccc(C(F)(F)F)n1] |

TABLE 6-continued
| Exemplary PTMs | |
| --- | --- |
| PTM Number | Chemical Structure |
| PTM82 | 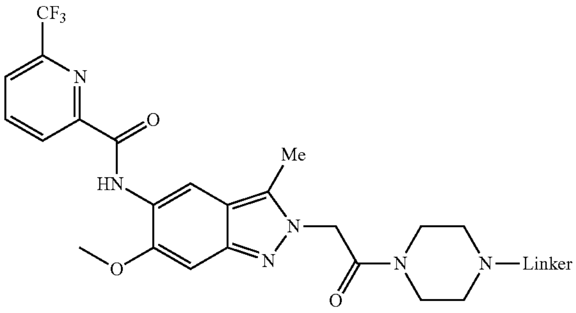 |
| PTM83 | 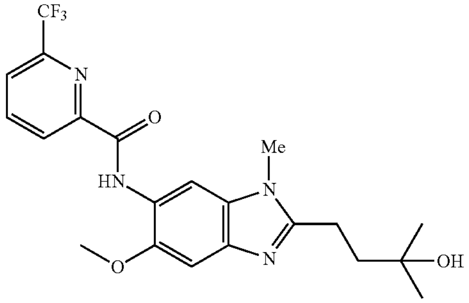 [SMILES: COc1cc2nc(CCC(C)(C)O)n(C)c2cc1NC(=O)c1cccc(C(F)(F)F)n1] |
| PTM84 | 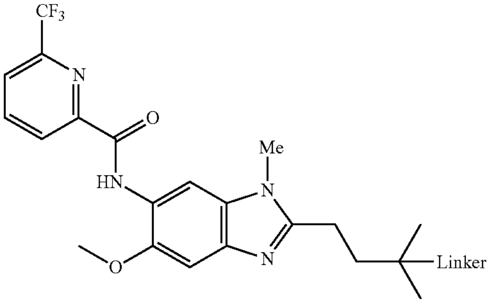 |
| PTM85 | 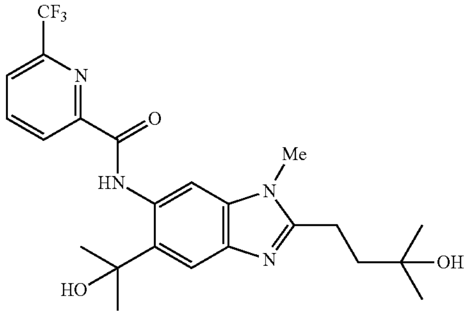 [SMILES: Cn1c(CCC(C)(C)O)nc2cc(C(C)(C)O)c(NC(=O)c3cccc(C(F)(F)F)n3)cc21] |

TABLE 6-continued
| Exemplary PTMs | |
|---|---|
| PTM Number | Chemical Structure |
| PTM86 | 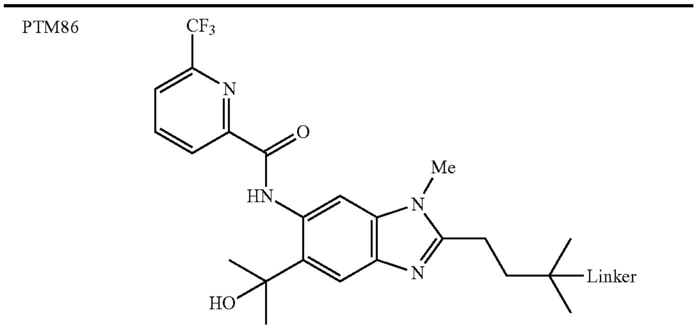 |
| PTM87 | 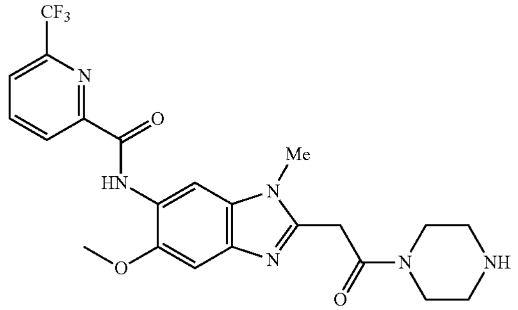 [SMILES: COc1cc2nc(CC(=O)N3CCNCC3)n(C)c2cc1NC(=O)c1cccc(C(F)(F)F)n1] |
| PTM88 | 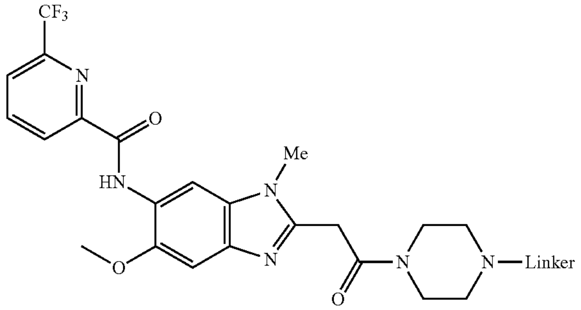 |
| PTM89 | 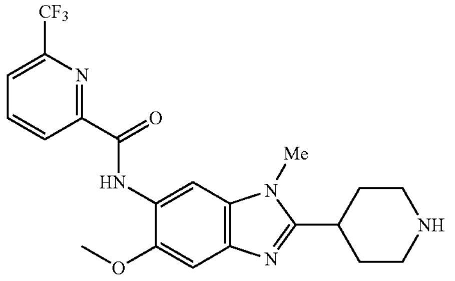 [SMILES: COc1cc2nc(C3CCNCC3)n(C)c2cc1NC(=O)c1cccc(C(F)(F)F)n1] |
| PTM90 | 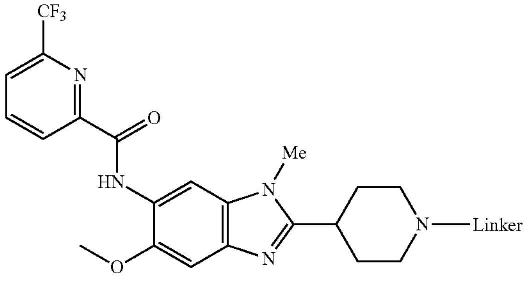 |

TABLE 6-continued
| Exemplary PTMs | |
|---|---|
| PTM Number | Chemical Structure |
| PTM91 | 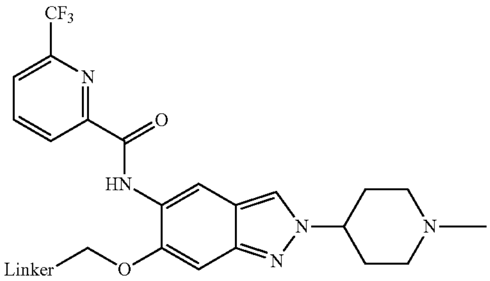 |
TABLE 7
| Exemplary Linkers | |
|---|---|
| Linker Number | Chemical Structure |
| Linker1 | 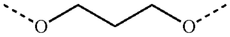 |
| Linker2 | 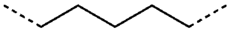 |
| Linker3 | 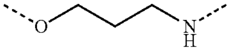 |
| Linker4 | 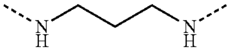 |
| Linker5 | 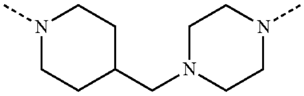 |
| Linker6 | 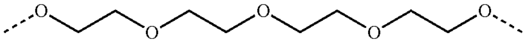 |
| Linker7 | 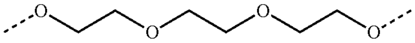 |
| Linker8 | 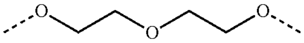 |
| Linker9 | 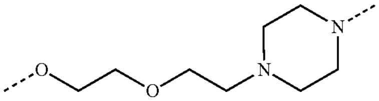 |
| Linker10 | 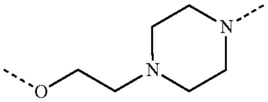 |
| Linker 11 | 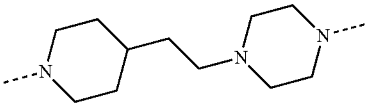 |
| Linker 12 | 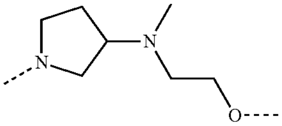 |

TABLE 7-continued
| Exemplary Linkers | |
|---|---|
| Linker Number | Chemical Structure |
| Linker 13 | 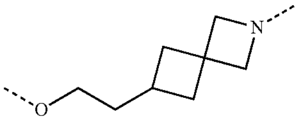 |
| Linker 14 | 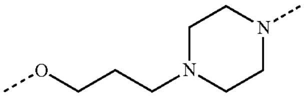 |
| Linker 15 | 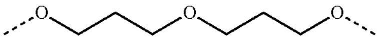 |
| Linker 16 | 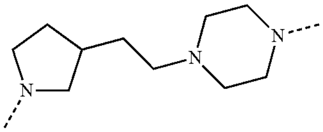 |
| Linker 17 | 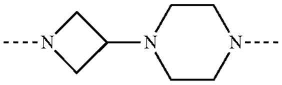 |
| Linker 18 | 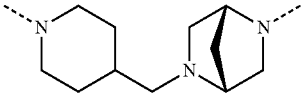 |
TABLE 8
| Exemplary ULMs | |
|---|---|
| ULM Number | Structure |
| ULM1 | 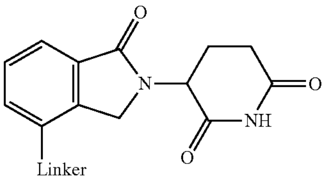 |
| ULM2 | 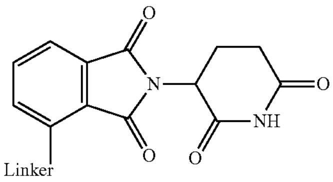 |
| ULM3 | 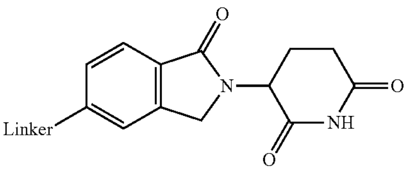 |
TABLE 8-continued
| Exemplary ULMs | |
|---|---|
| ULM Number | Structure |
| ULM4 | 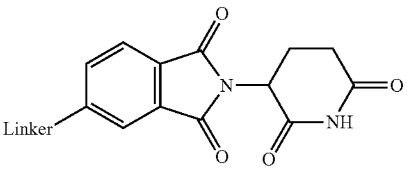 |
| ULM5 | 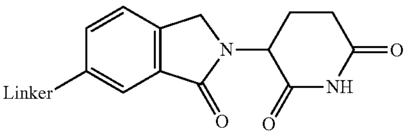 |
| ULM6 | 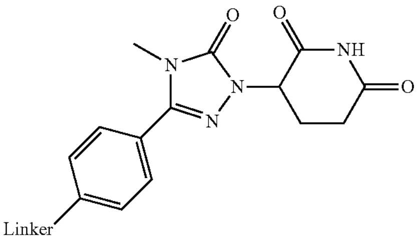 |

TABLE 8-continued
| Exemplary ULMs | |
|---|---|
| ULM Number | Structure |
| ULM7 | 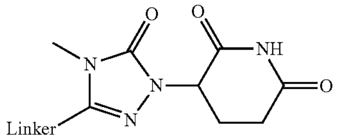 |
| ULM8 | 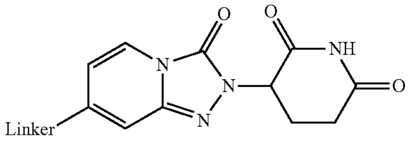 |
| ULM9 | 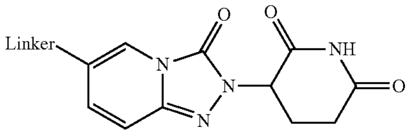 |
| ULM10 | 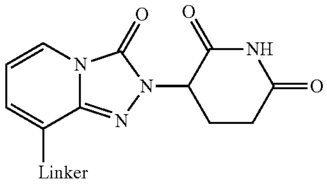 |
| ULM11 | 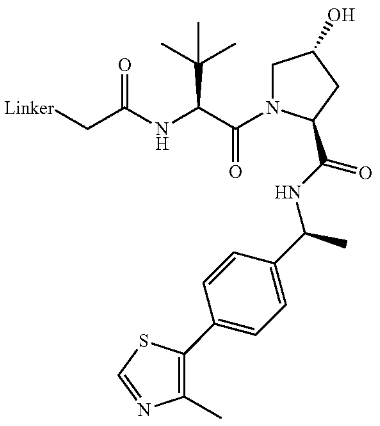 |
| ULM12 | 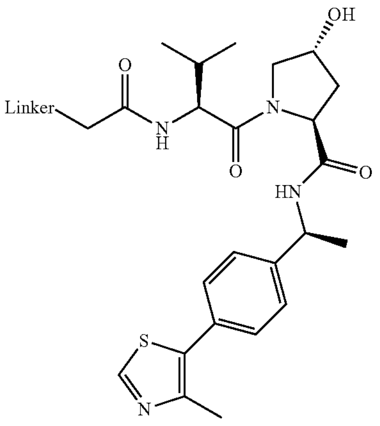 |
TABLE 8-continued
| Exemplary ULMs | |
|---|---|
| ULM Number | Structure |
| ULM13 | 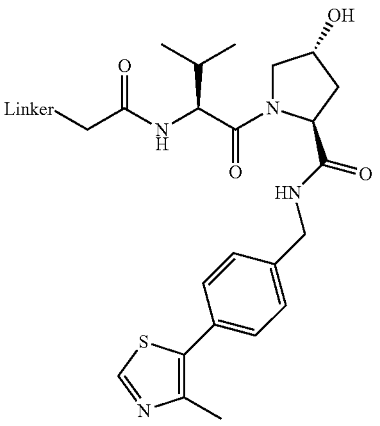 |
| ULM14 | 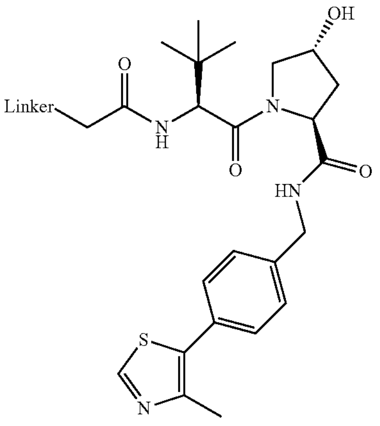 |
| ULM15 | 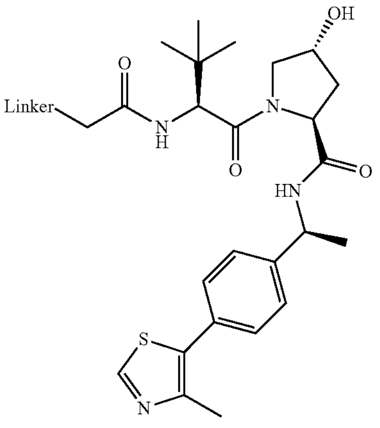 |
| ULM16 | 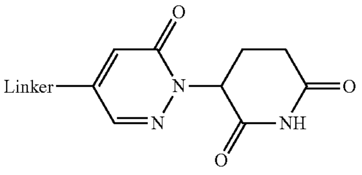 |

TABLE 8-continued

| Exemplary ULMs | |
|---|---|
| ULM Number | Structure |
| ULM17 | 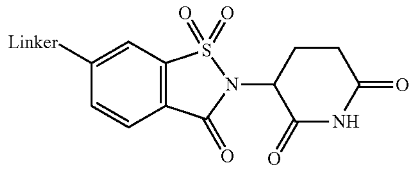 |
| ULM18 | 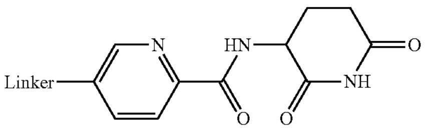 |
| ULM19 | 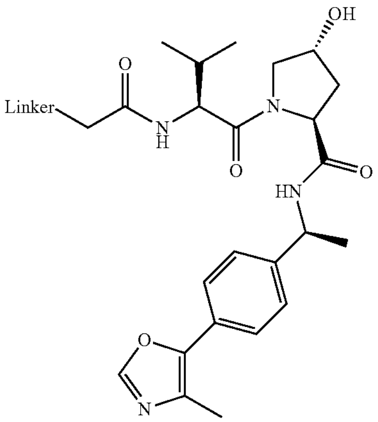 |
| ULM20 | 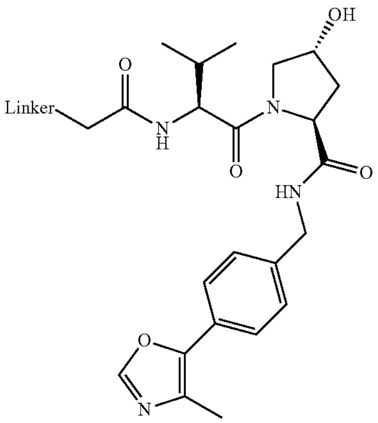 |

TABLE 8-continued

| Exemplary ULMs | |
|---|---|
| ULM Number | Structure |
| ULM21 | 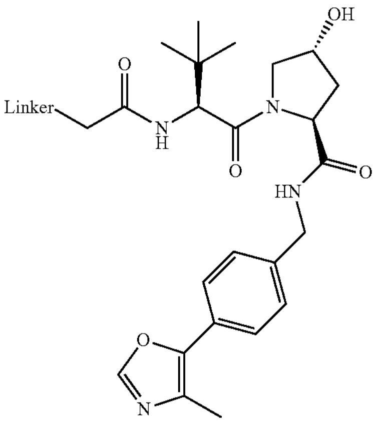 |
| ULM22 | 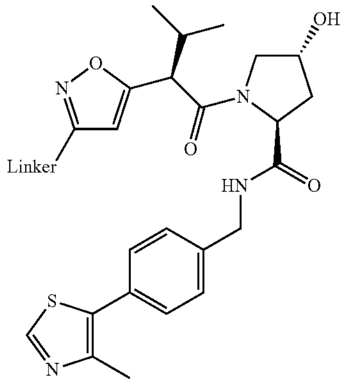 |
| ULM23 | 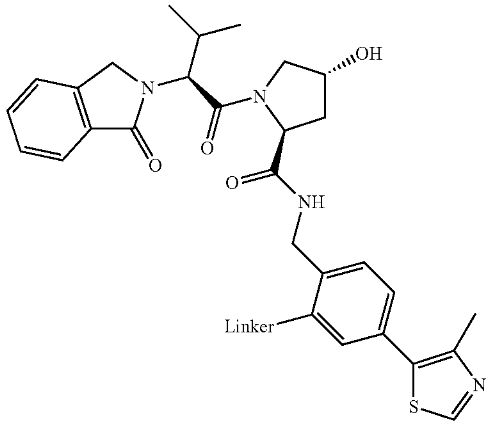 |

Additionally, the description provides a compound comprising a PTM from Table 6 (i.e., a PTM selected from the group consisting of PTM1-PTM91), a linker from Table 7 (i.e., a linker selected from the group consisting of Linker1-Linker18), and a ULM from Table 8 (i.e., a ULM selected from the group consisting of ULM1-ULM23), including salts, prodrugs, polymorphs, analogs, derivatives, and deuterated forms thereof.

In other embodiments, the description provides a composition comprising a compound having a PTM from Table 6 (i.e., a PTM selected from the group consisting of PTM1-PTM91), a linker from Table 7 (i.e., a linker selected from the group consisting of Linker1-Linker18), and a ULM from Table 8 (i.e., a ULM selected from the group consisting of ULM1-ULM23), including salts, prodrugs, polymorphs, analogs, derivatives, and deuterated forms thereof.

In an aspect, the present disclosure provides a bifunctional compound having the chemical structure:

ULM-L-PTM, or a pharmaceutically acceptable salt, enantiomer, stereoisomer, solvate, polymorph or prodrug thereof, wherein: the ULM is a small molecule E3 ubiquitin ligase binding moiety that binds an E3 ubiquitin ligase; the PTM is a small molecule comprising an Interleukin-1 Receptor-Associated Kinase 4 (IRAK-4) targeting moiety; and the L is a bond or a chemical linking moiety connecting the ULM and the PTM.

In any aspect or embodiment described herein, at least one of: the PTM is selected from Table 6, the linker (L) is selected from Table 7, the ULM is selected from Table 8, or a combination thereof.

In any aspect or embodiment described herein, the E3 ubiquitin ligase binding moiety that targets an E3 ubiquitin ligase selected from the group consisting of Von Hippel-Lindau (VLM), cereblon (CLM), mouse double-minute homolog2 (MLM), and IAP (ILM).

In any aspect or embodiment described herein, the PTM is represented by Formula PTM-I:

PTM-I

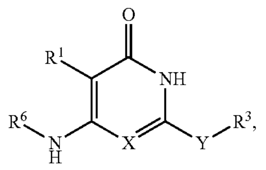

wherein:

X of PTM-I is —N═ or —CH═;

Y of PTM-I is selected from the group consisting of —$NR^2$—, —$CH_2$ and —O—; or when Y is —$NR^2$—, $R^2$ and $R^3$ together with the nitrogen to which they are attached optionally form a 4- to 6-membered heterocyclic ring, wherein the 4- to 6-membered heterocyclic ring is optionally substituted with 1 to 3 substituents independently selected from $R^7$ groups;

$R^1$ of PTM-I is selected from the group consisting of: hydrogen, $C_{1-10}$ alkyl, $C_{3-8}$ cycloalkyl, aryl, heterocyclyl, halogen, —COOR, —NR, —$SR^7$, —$OR^7$, —$SO_2R^7$, —$COR^7$, —$NCOR^7$, and —$CONR^7$;

$R^2$ of PTM-I is selected from the group consisting of: hydrogen, $C_{1-10}$ alkyl, and $C_{3-4}$ cycloalkyl;

$R^3$ of PTM-I is selected from the group consisting of: hydrogen, $C_{1-10}$ alkyl, $C_{3-4}$ cycloalkyl, aryl, heterocyclyl, and —$COOR^7$;

$R^6$ of PTM-I is selected from the group consisting of: $C_{1-10}$ alkyl, $C_{3-4}$ cycloalkyl, aryl, heterocyclyl, —$COOR^7$, —$SO_2R^7$, —$COR^7$; and $R^7$ of PTM-I is selected from the group consisting of: hydrogen, $C_{1-10}$ alkyl, $C_{3-4}$ cycloalkyl, aryl, and heteroaryl;

wherein each of the $C_{1-10}$ alkyl, $C_{3-4}$ cycloalkyl, aryl and heterocyclyl of $R^1$, $R^3$, $R^6$ and $R^7$ is optionally substituted with 1-4 substituents independently selected from the group consisting of $C_{1-4}$ alkyl, $C_{1-4}$ alkoxy, halogen, —$SO_2R^8$ and —$OR^8$;

$R^8$ of PTM-I is selected from the group consisting of hydrogen, and $C_{1-6}$ alkyl; and the PTM-I is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-II:

PTM-II

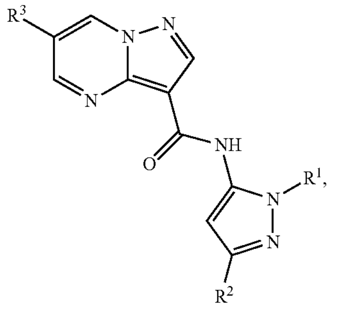

wherein:

$R^1$ of PTM-II is aryl, heteroaryl, heterocyclyl or ($C_{1-6}$ alkyl)$R^6$, wherein said aryl, heteroaryl, and heterocyclyl groups are optionally substituted with one or two substituents selected from the group consisting of halo, cyano, $R^4$, $C_{1-3}$ aminoalkyl, $C_{1-3}$ hydroxyalkyl, $C_{3-4}$ cycloalkyl, $OR^4$, $NR^4R^5$, $NR^4COR^6$, $NR^4SO_2R^6$, $SO_2NR^4R'$, $CONR^4R^5$;

$R^2$ of PTM-II of PTM-II is aryl, heteroaryl, $C_{3-8}$ cycloalkyl, heterocyclyl or ($C_{1-6}$ alkyl)$R^6$, wherein said aryl, heteroaryl, cycloalkyl and heterocyclyl groups are optionally substituted with one or two substituents selected from the group consisting of halo, cyano, oxo, hydroxyl, imino, hydroxyimino, $R^4$, $OR^4$, O($C_{3-8}$ cycloalkyl), (C═O)$OR^4$, $SO_mR^6$, $SO_mR^4$, $NR^4R^5$, $SO_2NR^4R^5$ and $NR^4SO_2R^6$;

$R^3$ of PTM-II is a halo, cyano, oxo, hydroxyl, imino, hydroxyimino, $R^4$, $OR^4$, $C_{3-8}$ cycloalkyl, $SO_mR^6$, $SO_mR^4NR^4R^5$, or (C═O)$NR^4R^5$, $NR^4$(CO)$R^6$, $SO_mNR^4R^5$and $NR^4SO_2R^6$;

$R^4$ of PTM-II is independently hydrogen or $C_{1-6}$ alkyl, wherein said alkyl is optionally substituted with one to three halo or hydroxyl;

$R^5$ of PTM-II is independently hydrogen or $C_{1-6}$ alkyl, wherein said alkyl is optionally substituted with halo or hydroxyl;

$R^6$ of PTM-II is independently aryl, heteroaryl, $C_{3-8}$ cycloalkyl or heterocyclyl;

m of PTM-II is an integer from zero to two; and the PTM-II is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-III:

PTM-III

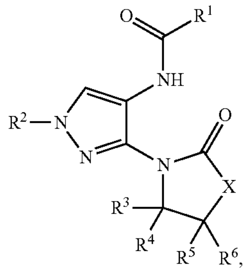

wherein:

- $R^1$ of PTM-III is an optionally substituted aromatic heterocyclic group or an optionally substituted $C_{6-14}$ aryl group;
- $R^2$ of PTM-III is a hydrogen atom or a substituent;
- $R^3$ and $R^4$ of PTM-III are independently a hydrogen atom or a substituent, or $R^3$ and $R^4$ in combination optionally form an optionally substituted ring;
- $R^5$ and $R^6$ of PTM-III are independently a hydrogen atom or a substituent, or $R^5$ and $R^6$ in combination optionally form an optionally substituted ring;
- X of PTM-III is $CR^7R^8$, $NR^9$, O or S;
- $R^7$ and $R^8$ of PTM-III are independently a hydrogen atom or a substituent, or $R^7$ and $R^8$ in combination optionally form an optionally substituted ring;
- $R_9$ of PTM-III is a hydrogen atom or a substituent; and
- the PTM-III is covalently joined to a ULM, a chemical linker group (L), a CLM, an ILM, a VLM, MLM, a ULM', a CLM', a ILM', a VLM', a MLM', or combination thereof In any aspect or embodiment described herein, the PTM is represented by Formula PTM-IV:

PTM-IV

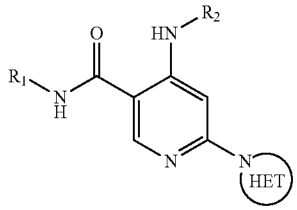

, wherein:

- HET of PTM-IV is a heteroaryl selected from pyrazolyl, indolyl, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$;
- $R_a$ of PTM-IV is H, F, Cl, Br, —CN, —OH, C alkyl, $C_{1-4}$ fluoroalkyl, $C_{1-4}$ hydroxyalkyl, $C_{1-4}$ alkoxy, $—NH_2$, $—NH(C_{1-4}$ alkyl), $—N(C_{1-4}$ alkyl$)_2$, $—NH(C_{1-4}$ hydroxyalkyl), $—NH(C_{1-4}$ fluoroalkyl), $—NH(C_{1-6}$ hydroxy-fluoroalkyl), $—C(O)NH_2$, $—CH_2NHC(O)(C_{1-6}$ alkyl), $—CH_2NHC(O)(C_{1-6}$ hydroxyalkyl), $—CH_2NHC(O)NH(C_{1-6}$ alkyl), $—CH_2NHC(O)NHCH_2$(phenyl), $—CH_2NHC(O)N(C_{1-4}$ alkyl$)_2$, $—CH_2NHC(O)O(C_{1-4}$ alkyl), $—CH_2NHC(O)(C_{3-6}$ cycloalkyl), $—CH_2NHC(O)$(tetrahydrofuranyl), $—CH_2NHC(O)CH_2(C_{3-6}$ cycloalkyl), $—CH_2NHC(O)CH_2$(tetrahydropyranyl), $—CH_2NHC(O)CH_2$(phenyl), $—NHC(O)(C_{1-4}$ alkyl), pyrrolidinyl, hydroxypyrrolidinyl, or pyridazinyl;
- $R_b$ of PTM-IV is H or $—NH_2$;
- $R_1$ of PTM-IV is: (i) $C_{1-6}$ alkyl, $C_{1-6}$ fluoroalkyl, $C_{1-6}$ hydroxyalkyl, $C_{1-8}$ hydroxy-fluoroalkyl, $—(C_{1-6}$ alkylenyl)$O(C_{1-4}$ alkyl), $—(C_{1-6}$ alkylenyl)$O(C_{1-4}$ fluoroalkyl), $—(C_{1-6}$ fluoroalkylenyl)$O(C_{1-4}$ alkyl), $—(C_{1-6}$ fluoroalkylenyl)$O(C_{1-4}$ deuteroalkyl), $—(C_{1-6}$ fluoroalkylenyl)$O(C_{1-4}$ fluoroalkyl), $—(C_{1-4}$ fluoroalkylenyl)$C(C_{3-6}$ cycloalkyl$)_2$(OH), $—(C_{1-4}$ alkylenyl)$NHC(O)(C_{1-4}$ alkylenyl)$OC(O)(C_{1-3}$ alkyl), $—(C_{1-6}$ alkylenyl)$NHS(O)_2(C_{1-4}$ alkyl), $—(C_{1-6}$ alkylenyl)$P(O)(C_{1-4}$ alkoxy$)_2$, $—(C_{1-6}$ fluoroalkylenyl)$NH(C_{1-4}$ alkyl), $—(C_{1-6}$ alkylenyl)$C(O)NH(C_{1-4}$ alkyl), $—(C_{1-6}$ fluoroalkylenyl)$C(O)NH(C_{1-4}$ alkyl), $—(C_{1-6}$ fluoroalkylenyl)$C(O)NH(C_{1-4}$ hydroxyalkyl), or $—(C_{1-6}$ fluoroalkylenyl)$OP(O)(OH)_2$; (ii) $—(C_{1-3}$ alkylenyl)$R_x$, $—(C_{1-3}$ fluoroalkylenyl)$R_x$, $—(C_{1-3}$ alkylenyl)$C(O)R_x$, $—(C_{1-3}$ alkylenyl)$C(O)NHR_x$, $—(C_{1-3}$fluoroalkylenyl)$C(O)R_x$,or $—CH_2CF=$ (tetrahydropyranyl), wherein $R_x$ is a cyclic group selected from $C_{3-6}$ cycloalkyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, $—CH_3$, $—C(CH_2)_2OH$, $—OCH_3$, $—C(O)CH_2CN$, $—S(O)_2CH_3$, $—S(O)_2NH_2$, $—NHC(O)CH_3$, $—N(S(O)_2CH_3)_2$, $—CH_2CH_2$(acetamidophenyl), $—CH_2CH_2$(methoxyphenyl), $—CH_2CH_2$ (sulfamoylphenyl), oxetanyl, benzyl, and morpholinyl; (iii) C3-6 cycloalkyl or C4-6 cycloalkenyl, each substituted with zero to 3 substituents independently selected from F, —OH, —CN, C1-3 alkyl, C1-3 alkoxy, —S(C1-3 alkyl), —NO2, —S(O)2(C1-3 alkyl), C1-4 hydroxyalkyl, —C(C1-3 alkyl)(OH)(C3-6 cycloalkyl), —CH2C(O)NH(C1-3 alkyl), —NHC(O)(C1-3 alkyl), —NHC(O)(C1-4 hydroxyalkyl), —C(O)NH(C1-3 alkyl), —C(O)NH(C1-3 deuteroalkyl), —C(O)NH(C3-6 cycloalkyl), —NHC(O)O(C1-3 alkyl), —NHS(O)2(C1-3 alkyl), pyridinyl, imidazolyl, pyrazolyl, methylimidazolyl, methylpyrazolyl, and thiazolyl; (iv) tetrahydropyranyl, piperidinyl, pyrazolyl, phenyl, pyridinyl, or pyrimidinyl, each substituted with zero to 1 substituent selected from —OH, C1-3 alkyl, C1-3 fluoroalkyl, C1-4 hydroxyalkyl, C1-3 alkoxy, —C(O)(C1-4 alkyl), —S(O)2(C1-4 alkyl), S(O)2NH (C1-4 alkyl), —NH(C1-3 alkyl), —N(C1-3 alkyl)2, —O(C1-3 alkylenyl)N(C1-3 alkyl)2, —CH2(morpholinyl), azetidinyl, oxetanyl, tetrahydropyranyl, morpholinyl, piperazinyl, piperidinyl, methylpiperazinyl, methoxypiperidinyl, pyridinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione;
- $R_2$ of PTM-IV is: (i) $C_{1-7}$ alkyl or $C_{2-6}$ alkenyl, each substituted with zero to three substituents independently selected from F, —OH, and —CN; $—(C_{1-4}$ alkylenyl)$O(C_{1-4}$ alkyl), $—(C_{1-4}$ alkylenyl)$O(C_{1-4}$ fluoroalkyl), $—(C_{1-6}$ alkylenyl)$NH_2$, $—(C_{1-6}$ alkylenyl)$S(O)_2(C_{1-3}$ alkyl), $—(C_{1-6}$ fluoroalkylenyl)$NH(C_{1-3}$ alkyl), or $—(C_{1-6}$ alkylenyl)$NHC(O)(C_{1-3}$ fluoroalkyl);

(ii) —($C_{1-4}$ alkylenyl)$R_y$, wherein $R_y$ is $C_{3-6}$ cycloalkyl, azetidinyl, oxetanyl, oxazolyl, pyridinyl, tetrahydropyranyl, or morpholinyl, each substituted with zero to 2 substituents independently selected from F, —OH, and $C_{1-3}$ alkyl; (iii) $C_{3-6}$ cycloalkyl, azetidinyl, oxetanyl, furanyl, tetrahydrofuranyl, pyrrolidinyl, piperidinyl, or tetrahydropyranyl, each substituted with zero to 3 substituents independently selected from F, —OH, $C_{1-3}$ alkyl, $C_{1-3}$ hydroxyalkyl, —C(O)($C_{1-3}$ alkyl), —C(O)($C_{1-3}$ fluoroalkyl), —C(O)($C_{1-3}$ cyanoalkyl), —C(O)O($C_{1-3}$ alkyl), —C(O)$NH_2$, —C(O)NH($C_{1-3}$ alkyl), —C(O)(difluorophenyl), —$NH_2$, —NH($C_{1-3}$ alkyl), —NH($C_{1-3}$ fluoroalkyl), —NH(oxetanyl), —NHC(O)($C_{1-3}$ alkyl), —NHC(O)($C_{1-3}$ fluoroalkyl), —NHC(O)($C_{3-6}$ cycloalkyl), —NHC(O)(fluorophenyl), —$S(O)_2$($C_{1-3}$ alkyl), imidazolyl, phenyl, pyrimidinyl, fluoropyrimidinyl, chloropyrimidinyl, and methoxypyrimidinyl; (iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxybicyclo[2.2.1]heptanyl; or (v) phenyl, pyrazolyl, thiazolyl, thiadiazolyl, or indazolyl, each substituted with 0 to 2 substituents independently selected from F, Cl, —OH, —CN, $C_{1-4}$ alkyl, $C_{1-4}$ hydroxyalkyl, $C_{1-4}$ fluoroalkyl, $C_{1-4}$ cyanoalkyl, $C_{1-3}$ alkoxy, $C_{3-6}$ cycloalkyl, —($C_{1-3}$ alkylenyl)O($C_{1-3}$ alkyl), —($C_{1-3}$ alkylenyl)O($C_{1-3}$ fluoroalkyl), —C(O)$NH_2$, —C(O)NH($C_{1-3}$ alkyl), —NHC(O)($C_{1-3}$ alkyl), —NHC(O)$S(O)_2$($C_{1-3}$ alkyl), —$S(O)_2NH_2$, —$S(O)_2$($C_{1-3}$ alkyl), pyrazolyl, methyl pyrazolyl, imidazolyl, triazolyl, methyl tetrazolyl, ethyl tetrazolyl, phenyl, pyrimidinyl, fluoropyrimidinyl, and tetrahydropyranyl; and the PTM-IV is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-Va or PTM-Vb:

PTM-Va

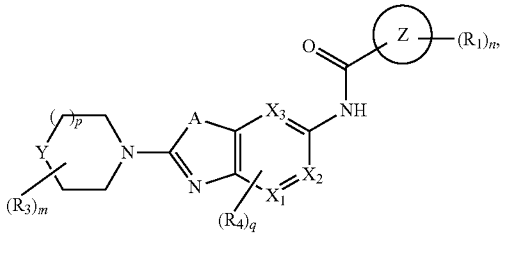

or

PTM-Vb

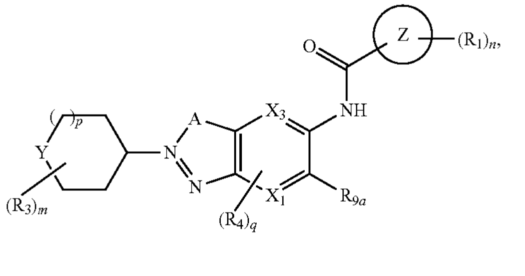

wherein:

$X_1$ and $X_3$ of PTM-Va or PTM-Vb independently are CH or N; $X_2$ of PTM-V is $CR_2$ or N; provided one and not more than one of $X_1$, $X_2$ or $X_3$ is N;

Y of PTM-Va or PTM-Vb is —$CH_2$— or O;

Ring Z of PTM-Va or PTM-Vb is aryl, heteroaryl, or heterocyclyl;

A of PTM-Va or PTM-Vb is O, S, or NH;

$R_1$ of PTM-Va or PTM-Vb at each occurrence, is independently hydrogen, cyano, halo, hydroxy, —NO2, —$NR_5R_6$, optionally substituted alkyl, optionally substituted aryl, optionally substituted cycloalkyl, optionally substituted heterocycloalkyl, optionally substituted heterocyclyl or optionally substituted heteroaryl, wherein the substituent, in each occurrence, is independently selected from alkyl, alkoxy, haloalkyl, cyano, aminoalkyl, halo, hydroxyl, hydroxyalkyl, —$NR^7R^8$, or $COOR^9$;

$R_2$ of PTM-Va or PTM-Vb is hydrogen, optionally substituted cycloalkyl, optionally substituted aryl, optionally substituted heterocyclyl or —$NR_aR_b$; wherein the substituent is alkyl, amino, halo or hydroxyl;

$R_3$ of PTM-Va or PTM-Vb, at each occurrence, is independently selected from hydrogen, carboxy, cyano, hydroxy, hydroxyalkyl, alkyl, aryl, heteroaryl, —$SO_2R_7$, hydroxyl or oxo;

$R_4$ of PTM-Va or PTM-Vb at each occurrence is independently selected from hydrogen, halogen, alkyl, aryl, heterocycloalkyl, heterocycloalkylalkyl, heteroaryl, Y-arylalkyl or —Y-cycloalkyl; wherein cycloalkyl, aryl, heterocycloalkyl, heterocycloalkylalkyl, heteroaryl and arylalkyl can be optionally substituted with hydroxy, alkyl, haloalkyl, cyano or halo;

$Y_1$ of PTM-Va or PTM-Vb is selected from direct bond, O, —C(O)— or $NR^9$;

$R_5$ and $R_6$ of PTM-Va or PTM-Vb are independently selected from hydrogen, hydroxyalkyl, aminoalkyl, acyl, optionally substituted alkyl, optionally substituted heterocyclyl, optionally substituted aryl; wherein the optional substituent, in each occurrence, is independently selected from halo, haloalkyl or —$COOR_9$;

$R_7$ and $R_8$ of PTM-Va or PTM-Vb are independently hydrogen, alkyl, acyl, heterocyclyl, —$COR_9$ or —$COOR_9$;

$R_9$ of PTM-Va or PTM-Vb at each occurrence is independently selected from hydrogen or alkyl;

$R_{9a}$ of PTM-Vb is selected from hydrogen, halo, optionally substituted alkoxy (e.g., optionally substituted C1-C4 alkoxy), optionally substituted alkyl (e.g., C1-C4 alkyl optionally substituted with halo or hydroxy), hydroxyalkyl (e.g. C1-C4 hydroxyalkyl), or haloalkyl (e.g., $C_1$-$C_4$ haloalkyl);

"m", "n" and "q" of PTM-Va or PTM-Vb are independently selected from 0, 1, 2, or 3;

"p" of PTM-Va or PTM-Vb is 0 or 1;

the PTM-Va or PTM-Vb is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-VIa, PTM-VIb, or PTM-VIc:

PTM-VIa

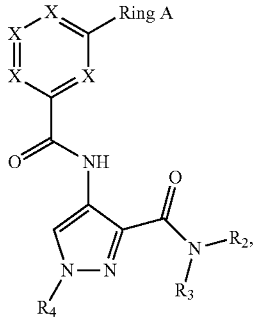

PTM-VIb

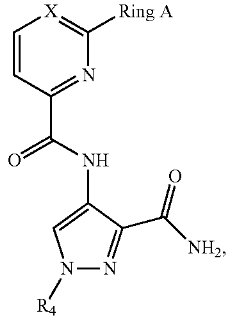

or

PTM-VIc

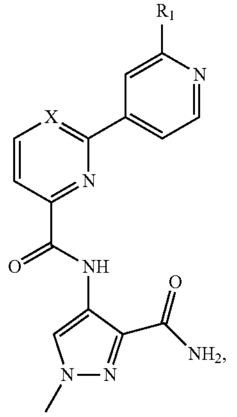

wherein:

X of PTM-VIa-c is CH or N;

a of PTM-VIa-c is 0 or 1;

b of PTM-VIa-c is 0 or 1;

m of PTM-VIa-c is 0, 1 or 2;

Ring A of PTM-VIa-c is $(C_3\text{-}C_8)$cycloalkyl, $(C_3\text{-}C_8)$cycloalkenyl, aryl or heterocycle optionally substituted with one to three substituents independently selected from $R_1$;

$R_1$ of PTM-VIa-c is selected from: H, oxo, $(C{=}O)_aO_b(C_1\text{-}C_{10})$alkyl, $(C{=}O)_aO_b$-aryl, $(C{=}O)_aO_b(C_2\text{-}C_{10})$alkenyl, $(C{=}O)_aO_b(C_2\text{-}C_{10})$alkynyl, $CO_2H$, halo, OH, $O_b(C_1\text{-}C_6)$fluoroalkyl, $(C{=}O)_aNR_5R_6$, CN, $(C{=}O)_aO_b(C_3\text{-}C_8)$cycloalkyl, $S(O)_mNR_5R_6$, SH, $S(O)_m$—$(C_1\text{-}C_{10})$alkyl and $(C{=}O)_aO_b$-heterocyclyl, said alkyl, aryl, alkenyl, alkynyl, cycloalkyl, and heterocyclyl are optionally substituted with one or more substituents selected from $R_a$;

$R_2$ and $R_3$ of PTM-VIa-c are independently selected from: H, $(C{=}O)_aO_bC_1\text{-}C_{10}$ alkyl, $(C{=}O)_aO_b$aryl, $C_2\text{-}C_{10}$ alkenyl, $C_2\text{-}C_{10}$ alkynyl, $(C{=}O)_aO_b$ heterocyclyl, $CO_2H$, CN, $O_bC_1\text{-}C_6$ fluoroalkyl, $O_a(C{=}O)_bNR_5R_6$, CHO, $(N{=}O)R_5R_6$, $S(O)_mNR_5R_6$, SH, $S(O)_m$—$(C_1\text{-}C_{10})$alkyl, $(C{=}O)_aO_bC_3\text{-}C_8$ cycloalkyl, optionally substituted with one or more substituents selected from $R_1$; or $R_2$ and $R_3$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R_1$;

$R_4$ of PTM-VIa-c is selected from: $(C_1\text{-}C_6)$alkyl and $(C_3\text{-}C_6)$cycloalkyl, optionally substituted with $R_a$;

$R_5$ and $R_6$ of PTM-VIa-c are independently selected from: H, oxo, $(C{=}O)_aO_b(C_1\text{-}C_{10})$alkyl, $(C{=}O)_aO_b$-aryl, $(C{=}O)_aO_b(C_2\text{-}C_{10})$alkenyl, $(C{=}O)_aO_b(C_2\text{-}C_{10})$alkynyl, $CO_2H$, $O_b(C_1\text{-}C_6)$fluoroalkyl, $(C{=}O)_aN(R_a)_2$, CN, $(C{=}O)_aO_b(C_3\text{-}C_8)$cycloalkyl, $S(O)_m$ $N(R_a)_2$, SH, $S(O)_m$—$(C_1\text{-}C_{10})$alkyl and $(C{=}O)_aO_b$-heterocyclyl, said alkyl, aryl, alkenyl, alkynyl, cycloalkyl, and heterocyclyl are optionally substituted with one or more substituents selected from $R_a$;

$R_a$ of PTM-VIa-c is independently selected from $R_b$, OH, $(C_1\text{-}C_6)$alkoxy, halogen, cyclopropyl, $CO_2H$, CN, $O_a(C{=}O)_b(C_1\text{-}C_6)$alkyl, oxo, and $N(R_b)_2$;

$R_b$ of PTM-VIa-c is independently selected from H and $(C_1\text{-}C_6)$alkyl; and the PTM-Via-c is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-VIIa, PTM-VIIb, PTM-VIIc, PTM-VIId, PTM-VIIe, PTM-VIIf, PTM-VIIg, PTM-VIIh, PTM-VIIi, PTM-VIIj, PTM-VIIk, or PTM-VIIm:

PTM-VIIa

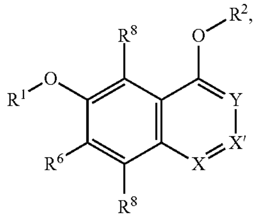

PTM-VIIb

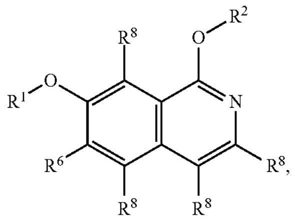

PTM-VIIc

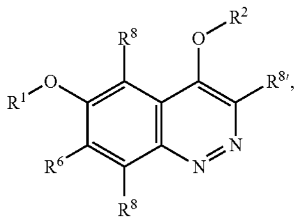

-continued

PTM-VIId

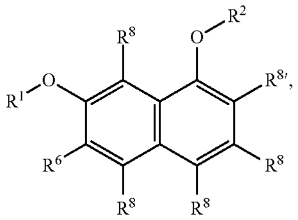

PTM-VIIe

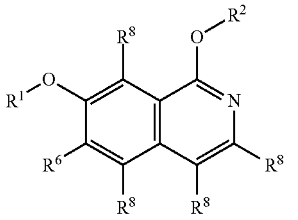

PTM-VIIf

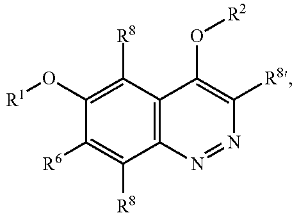

PTM-VIIg

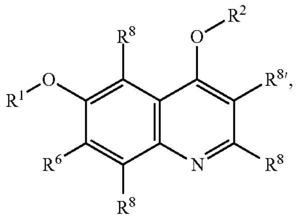

PTM-VIIh

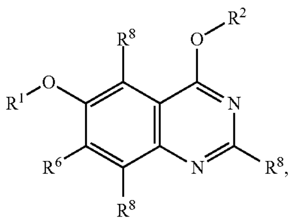

PTM-VIIi

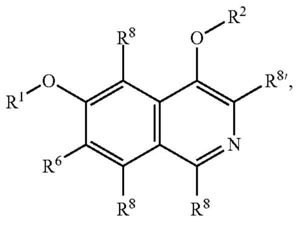

PTM-VIIj

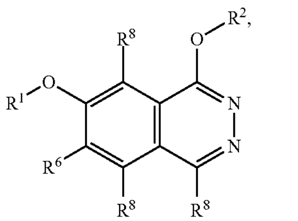

-continued

PTM-VIIk

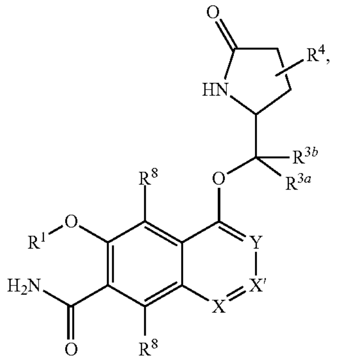

or

PTM-VIIm

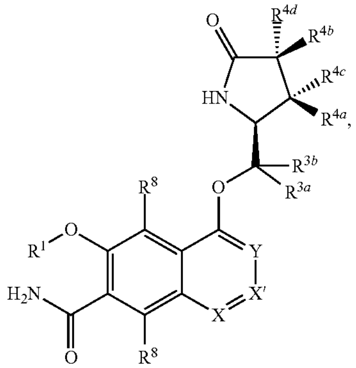

wherein:

X and X' of PTM-VIIa-k or PTM-VIIm are each independently $CR^8$, N or $—N^+—O^-$; Y is independently N, $—N^+—O—$ or CR'; provided that at least one of X, X' or Y is neither N nor $—N^+—O^-$ and that no more than one of X, X' or Y is $—N^+—O^-$;

$R^1$ of PTM-VIIa-k or PTM-VIIm is $C_1$-$C_6$alkyl; $C_2$-$C_6$alkenyl; $C_2$-$C_6$alkynyl; $—(CR^{3a}R^{3b})_m$-(3- to 7-membered cycloalkyl); $—(CR^{3a}R^{3b})_m$-(3- to 7-membered heterocycloalkyl) having one to three heteroatoms; $—(CR^{3a}R^{3b})_m$-(5- to 10-membered heteroaryl), having one to three heteroatoms; or $—(CR^{3a}R^{3b})_m—C_6$-$C_{12}$aryl; wherein said alkyl, alkenyl, alkynyl, cycloalkyl, heterocycloalkyl, heteroaryl or aryl is optionally substituted with one to five halogen, deuterium, $—OR^5$, $—SR^5$, $—NR^{11a}R^{11b}$, cyano, $C_1$-$C_6$alkyl, C3-$C_6$cycloalkyl or $—C_1$-$C_6$alkoxy;

$R^2$ of PTM-VIIa-k or PTM-VIIm is $—(CR^{3a}R^{3b})_m$-(3- to 10-membered cycloalkyl); $—(CR^{3a}R^{3b})_m$-(3- to 10-membered heterocycloalkyl) having one to three heteroatoms; $—(CR^{3a}R^{3b})_m$-(5- to 10 membered heteroaryl) having one to three heteroatoms; or $—(CR^{3a}R^{3b})_m—C_6$-$C_{12}$aryl; wherein said cycloalkyl, heterocycloalkyl, heteroaryl or aryl is optionally substituted with one to five $R^4$; and wherein, if the heteroatom on said heterocycloalkyl and heteroaryl is N, said N is optionally substituted with $R^{4'}$; or $R^2$ is $C_1$-$C_6$alkyl, wherein said alkyl is optionally substituted with $NH_2$, OH or cyano;

$R^{3a}$ and $R^{3b}$ of PTM-VIIa-k or PTM-VIIm for each occurrence are independently hydrogen or $C_1$-$C_3$alkyl;

$R^4$ of PTM-VIIa-k or PTM-VIIm for each occurrence is independently a bond, deuterium, halogen, cyano, $C_1$-$C_6$alkyl, $C_2$-$C_6$alkenyl, oxo, $—OR^5$, $—SR^5$, —S(O)$R_9$, $—S(O)_2R_9$, $—NR^{11a}R^{11b}$, $—C(O)R^{10}$, $—(CR^{3a}R^{3b})_n$-(3- to 7-membered cycloalkyl), $—(CR^{3a}R_b)_n$-(4- to 10-membered heterocycloalkyl), having one to three heteroatoms, $—(CR^{3a}R^{3b})_n$-(5- to 10 membered heteroaryl), having one to three heteroatoms, or $—(CR^{3a}R^{3b})_n—C_6$-$C_{12}$aryl wherein said alkyl, cycloalkyl, heterocycloalkyl, heteroaryl or aryl is each optionally and independently substituted with one to five deuterium, halogen, $OR^5$, $—SR^5$, $—NR^{11a}R^{11b}$, cyano, $C_1$-$C_6$alkyl, $C_3$-$C_6$cycloalkyl or $C_1$-$C_6$alkoxy; or two $R^4$ taken together with the respective carbons to which each are bonded form a 3- to 6-membered cycloalkyl or 4- to 6-membered heterocycloalkyl, wherein said cycloalkyl or heterocycloalkyl is optionally substituted with one to three halogen, deuterium, $—OR^5$, $—SR^5$, $—NR^{11a}R^{11b}$, cyano or $C_1$-$C_6$alkyl or $C_1$-$C_6$alkoxy, wherein the alkyl or alkoxy is optionally substituted with halogen, deuterium, $—OR^5$, $—SR^5$, $—NR^{11a}R^{11b}$ or cyano; and wherein, if a heteroatom on said heterocycloalkyl is N, said N is optionally substituted with $R^{4'}$;

$R^{4'}$ of PTM-VIIa-k or PTM-VIIm is independently $C_1$-$C_6$alkyl, $C_2$-$C_6$alkenyl, $—C(O)R^{10}$, $—S(O)_2R^9$, $—(CR^{3a}R^{3b})_n$-(3- to 7-membered cycloalkyl), $—(CR^{3a}R^{3b})_n$-(4- to 10-membered heterocycloalkyl) or $C(O)(CH_2)_tCN$; wherein said alkyl, alkenyl, cycloalkyl, or heterocycloalkyl is each optionally and independently substituted with one to five deuterium, halogen, OH, cyano or $C_1$-$C_6$alkoxy; or $R^4$ and $R^{4'}$ taken together with the respective atoms to which each are bonded form a 3- to 6-membered cycloalkyl or 4- to 6-membered heterocycloalkyl, wherein said cycloalkyl or heterocycloalkyl is optionally substituted with one to three halogen, deuterium, $OR^5$, $—SR^5$, cyano, $C_1$-$C_6$alkyl or $C_1$-$C_6$alkoxy, wherein the alkyl or alkoxy is optionally substituted with halogen, deuterium, $—OR^5$, $—SR^5$, $—NR^{11a}R^{11b}$, or cyano;

$R^{4a}$ and $R^{4b}$ of PTM-VIIa-k or PTM-VIIm are each independently hydrogen, deuterium, fluoro, OH, $—OR^5$, methyl, ethyl, vinyl, cyclopropyl or propyl, optionally substituted with one to five deuterium, fluoro, methoxy or OH;

$R^{4c}$ and $R^{4d}$ of PTM-VIIa-k or PTM-VIIm for each occurrence are independently and optionally halogen, OH, deuterium, $C_1$-$C_6$alkyl, $C_2$-$C_6$alkenyl, $—OR^5$, $—(CR^{3a}R^{3b})_n$-(3- to 6-membered cycloalkyl), or $—(CR^{3a}R^{3b})_n$-(4- to 6-membered heterocycloalkyl) wherein said alkyl, cycloalkyl and heterocycloalkyl are each optionally and independently substituted with one to five deuterium, halogen, OH, cyano, or $C_1$-$C_6$alkoxy; $NH_2$; or $R^{4c}$ and $R^{4d}$ taken together with the carbons to which they are bonded form a 4- to 7-membered heterocycloalkyl or a 3- to 7-membered cycloalkyl, wherein said heterocycloalkyl or cycloalkyl is optionally substituted with one to three fluoro, $C_1$-$C_3$alkyl or $C_1$-$C_3$fluoroalkyl;

or $R^{4a}$ and $R^{4c}$ of PTM-VIIa-k or PTM-VIIm taken together with the carbon to which they are bonded form a 4- to 7-membered heterocycloalkyl or a 3- to 7-membered cycloalkyl, wherein said heterocycloalkyl or cycloalkyl is optionally substituted with one to three fluoro, $C_1$-$C_3$alkyl or $C_1$-$C_3$fluoroalkyl;

$R^5$ of PTM-VIIa-k or PTM-VIIm is independently hydrogen or $C_1$-$C_6$alkyl, wherein said alkyl is optionally substituted with halogen, deuterium, $C_1$-$C_6$alkoxy, $C_1$-$C_6$alkylthiolyl, $—NR^{11a}R^{11b}$, cyano, $C_1$-$C_6$alkyl or $C_3$-$C_6$cycloalkyl; or two $R^5$ taken together with the oxygen atoms to which they are bonded form a 5- or 6-membered heterocycloalkyl;

$R^6$ of PTM-VIIa-k or PTM-VIIm is $—C(O)NHR^7$, $CO_2R^7$ or cyano;

$R^7$ of PTM-VIIa-k or PTM-VIIm is hydrogen or $C_1$-$C_6$alkyl;

each $R^8$ of PTM-VIIa-k or PTM-VIIm is independently hydrogen, halogen, cyano, —OR, $—SR^5$, $—C_1$-$C_6$alkyl, $C_3$-$C_6$cycloalkyl, 3- to 10-membered heterocycloalkyl or 5- to 6-membered heteroaryl or aryl, wherein said alkyl, cycloalkyl, heterocycloalkyl, heteroaryl or aryl is optionally substituted with one to three halogen, $—NR^{11a}R^{11b}$, $—OR^5$, $—SR^5$, cyano, $C_1$-$C_3$ alkyl, $—C(O)R^{10}$ or oxo;

$R^{8'}$ of PTM-VIIa-k or PTM-VIIm is hydrogen, deuterium, halogen, cyano, $—OR^8$, $—SR^5$ or $—NR^{11a}NR^{11b}$.

$R^9$ of PTM-VIIa-k or PTM-VIIm is $—(CR^{3a}R^{3b})_p(C_1$-$C_3$alkyl), $—(CR^{3a}R^{3b})_p$(4- to 6-membered cycloalkyl), $—(CR^{3a}R^{3b})_p$(4- to 6-membered heterocycloalkyl) or $—(CR^{3a}R^{3b})_p(C_5$-$C_9$aryl), wherein said alkyl, cycloalkyl, heterocycloalkyl or aryl is each optionally substituted with fluoro or $C_1$-$C_3$alkyl;

$R^{10}$ of PTM-VIIa-k or PTM-VIIm is $C_1$-$C_6$alkyl, wherein said alkyl is optionally substituted with deuterium, halogen, OH, $C_1$-$C_6$alkoxy or cyano;

$R^{11a}$ and $R^{11b}$ of PTM-VIIa-k or PTM-VIIm are each independently hydrogen or $C_1$-$C_6$alkyl, wherein said alkyl is optionally substituted with deuterium, $C_1$-$C_6$alkoxy or cyano; and if $C_2$-$C_6$alkyl, said alkyl is optionally substituted with deuterium, $C_1$-$C_6$alkoxy, cyano, halogen or OH;

m of PTM-VIIa-k or PTM-VIIm is independently 0, 1, 2 or 3;

n of PTM-VIIa-k or PTM-VIIm is independently 0, 1, 2 or 3;

p of PTM-VIIa-k or PTM-VIIm is independently 0 or 1;

t of PTM-VIIa-k or PTM-VIIm is 1, 2 or 3; and the PTM-VIIa-k is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-VIIIa, PTM-VIIIb, PTM-VIIIc, PTM-VIIId, PTM-VIIIe, or PTM-VIIIf:

PTM-VIIIa

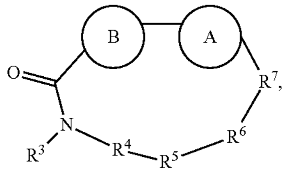

PTM-VIIIb

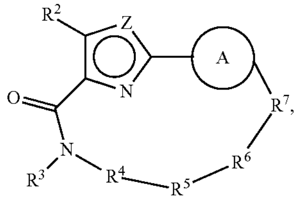

-continued

PTM-VIIIc

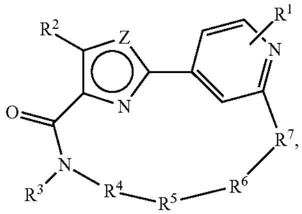

PTM-VIIId

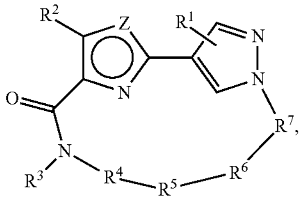

PTM-VIIIe

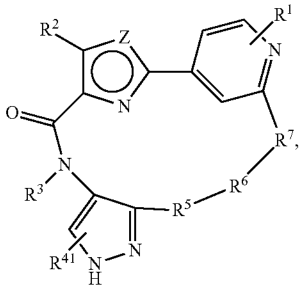

or

PTM-VIIIf

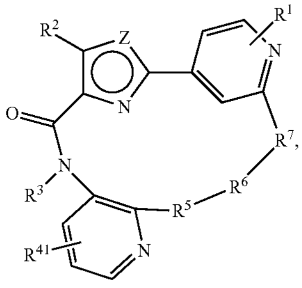

wherein:

Ring A of PTM-VIIIa-f is phenylene or 5- to 6-membered heteroarylene containing 1-3 heteroatoms chosen from O, S, and N, wherein ring A is optionally substituted with lower alkyl that is further optionally substituted;

Ring B of PTM-VIIIa-f is phenylene, 5- to 6-membered heterocycloalkylene containing 1-3 heteroatoms chosen from O, S, and N, or 5- to 6-membered heteroarylene containing 1-3 heteroatoms chosen from O, S, and N, wherein ring B is optionally substituted with lower alkyl or lower alkyloxyalkyl, either of which is further optionally substituted;

$R^2$ of PTM-VIIIa-f is chosen from hydrogen and lower alkyl;

$R^3$ of PTM-VIIIa-f is chosen from hydrogen, lower alkyl optionally substituted with alkoxy, amino, N-(alkyl)amino, N,N-(dialkyl)amino, or phenyl, heterocycloalkyl, and heteroaryl, wherein phenyl, heterocycloalkyl, and heteroaryl are optionally substituted with one or two groups independently chosen from lower alkyl and wherein alkoxy is optionally substituted with tri(alkyl)silyl;

$R^4$ of PTM-VIIIa-f is chosen from heteroarylene and arylene, each of which is optionally substituted, or $R^4$ and $R^3$ of PTM-VIIIa-f taken together with the nitrogen to which they are bound, form an optionally substituted 3- to 7-membered heterocycloalkyl ring, or $R^4$ of PTM-VIIIa-f is an alkylene chain having 1-3 carbon atoms that is optionally substituted with one or two groups independently chosen from lower alkyl and cycloalkyl, each of which groups is optionally substituted with hydroxyl or alkoxy, or $R^4$ of PTM-VIIIa-f is absent;

$R^5$ of PTM-VIIIa-f is chosen from $C(O)NR^{51}$, $NR^{52}$, and O, or $R^5$ is absent, provided that if $R^4$ is absent, then $R^5$ is absent;

$R^6$ of PTM-VIIIa-f is an alkylene or alkenylene chain having one or two double bonds, wherein the alkylene or alkenylene chain has 2 to 10 carbon atoms, the alkylene or alkenylene chain is optionally substituted with one or two groups independently chosen from lower alkyl, cycloalkyl and phenyl, each of which groups is optionally substituted with hydroxyl, alkoxy, $—C(O)OR^{85}$, $—C(O)NR^{82}R^{83}$, benzoyl, and benzyl, further wherein one or two of the carbon atoms in the alkylene or alkenylene chain is optionally replaced by an O, S, SO, $SO_2$, $C(O)NR^{51}$, or $NR^{61}$, and wherein one of the carbon atoms in the alkylene or alkenylene chain, is optionally connected by the nitrogen atom of $C(O)NR^{51}$ or $NR^{61}$ to form a 5- to 7-membered ring, which may further be substituted with oxo, wherein two of the carbon atoms in the alkylene or alkenylene chain, are optionally connected by a two or three carbon atom alkylene or alkenylene chain to form a 5- to 7-membered ring;

$R^7$ of PTM-VIIIa-f is chosen from $NR^{71}$ and O, or $R^7$ is absent;

$R^{21}$ of PTM-VIIIa-f is chosen from hydrogen and lower alkyl optionally substituted with lower alkoxy, wherein lower alkoxy is optionally substituted with tri(alkyl)silyl;

$R^{41}$ of PTM-VIIIa-f is independently chosen from heterocycloalkyl, lower alkyl optionally substituted with $—C(O)OR^9$, amino, N-(alkyl)amino, N,N-(dialkyl)amino, cycloalkyl, or heterocycloalkyl, $—C(O)OR^9$, hydroxyl, and $—C(O)NR^{10}R^{11}$, wherein $R^9$ is chosen from hydrogen and lower alkyl, $R^{10}$ and $R^{11}$ are independently hydrogen and lower alkyl, or $R^{10}$ and $R^{11}$, together with the nitrogen to which they are bound form a heterocycloalkyl, and each lower alkyl, cycloalkyl and heterocycloalkyl is optionally substituted with one, two, or three groups independently chosen from $—C(O)OR^9$, lower alkyl, lower alkoxy, hydroxyl, halogen, amino, N-(alkyl)amino, N,N-(dialkyl)amino, and heterocycloalkyl;

$R^{51}$ of PTM-VIIIa-f is chosen from hydrogen and lower alkyl;

$R^{52}$ of PTM-VIIIa-f is chosen from hydrogen, lower alkyl, and $—C(O)OR^{81}$;

$R^{61}$ of PTM-VIIIa-f is chosen from hydrogen, lower alkyl, $—(CH_2)_nC(O)OR^{81}$, $—(CH_2)_nC(O)NR^{82}R^{83}$, $—C(O)R^{84}$, $—C(O)(CH_2)_pNR^2C(O)OR^{81}$, $—C(O)(CH_2)_pNR^{82}R^{83}$;

$R^{71}$ of PTM-VIIIa-f is chosen from hydrogen, lower alkyl, and $—C(O)OR^{81}$;

$R^{81}$ of PTM-VIIIa-f is hydrogen or lower alkyl;

$R^{82}$ of PTM-VIIIa-f is hydrogen or lower alkyl, $R^{83}$ of PTM-VIIIa-f is hydrogen or lower alkyl, $R^{84}$ of PTM-VIIIa-f is hydrogen, lower alkyl, $C_3$-$C_6$cycloalkyl or tetrahydropyran, wherein the lower alkyl is optionally substituted with hydroxy or $—C(O)OR^{81}$;

$R^{85}$ of PTM-VIIIa-f is hydrogen, lower alkyl, or benzyl, n of PTM-VIIIa-f is 0, 1, 2, or 3;

p of PTM-VIIIa-f is 1 or 2;

Z of PTM-VIIIa-f is chosen from O, S, and $NR^{21}$; and the PTM-VIIIa-f is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-IXa, PTM-IXb, PTM-IXc, PTM-IXd, PTM-IXe, PTM-IXf, PTM-IXg, PTM-IXh, PTM-IXi, PTM-IXj, PTM-IXk, PTM-IXl, or PTM-IXm:

PTM-IXa

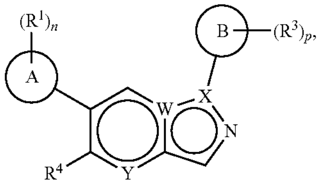

PTM-IXb

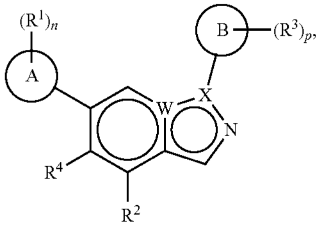

PTM-IXc

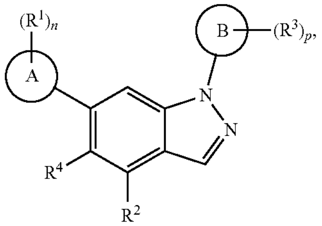

PTM-IXd

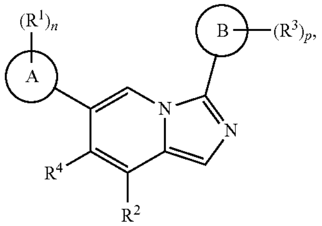

or

PTM-IXe

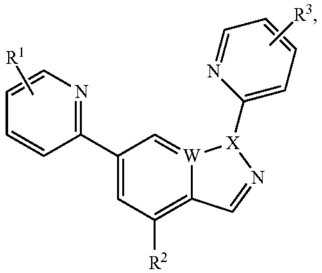

-continued

PTM-IXf

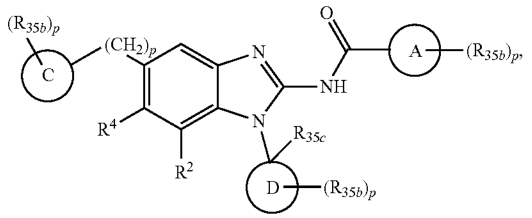

PTM-IXg

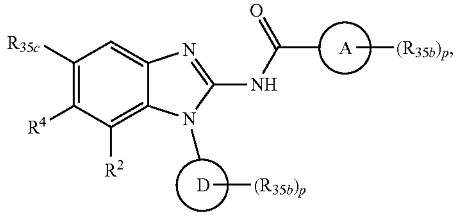

PTM-IXh

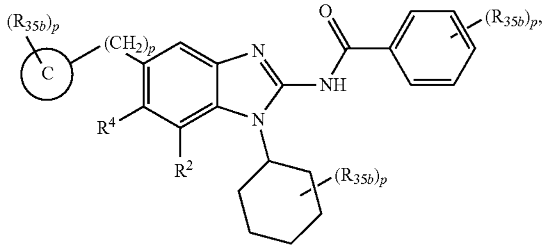

PTM-IXi

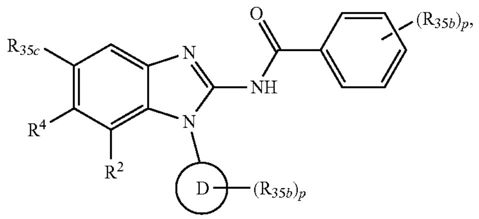

PTM-IXj

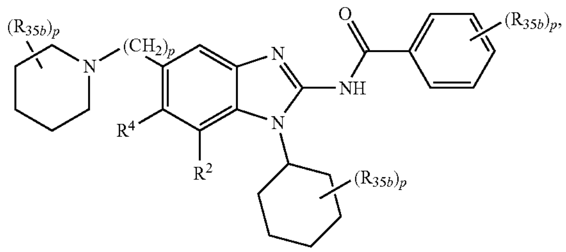

PTM-IXk

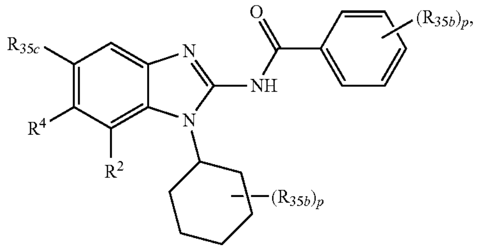

-continued

PTM-IXl

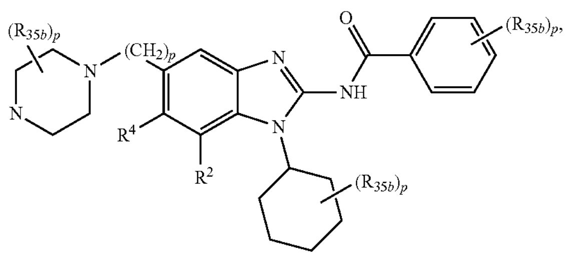

PTM-IXm

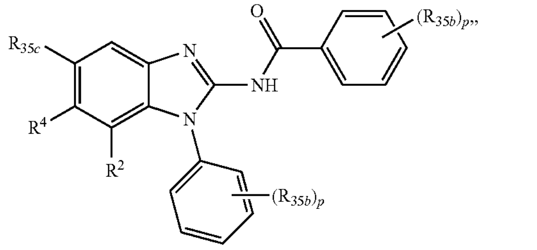

PTM-IXn

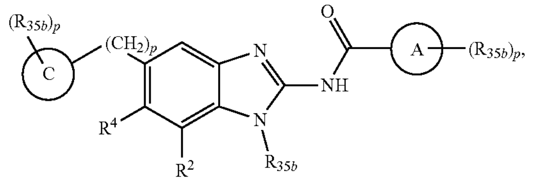

wherein:

Ring A of PTM-IXa-m is selected from phenyl and 5- or 6-membered heteroaryl;

Ring B of PTM-IXa-m is selected from phenyl and 5- or 6-membered heteroaryl;

Ring C of PTM-IXa-m is selected from a 5- or 6-membered cycloalkyl or cycloheteroalkyl;

Rind D of PTM-IXa-m selected from phenyl, 5-membered aryl or heteroaryl, 6-member aryl or heteroaryl, 5-membered cycloalkyl or cycloheteroalkyl, or 6-membered cycloalkyl or cycloheteroalkyl;

n of PTM-IXa-e is 0, 1, or 2;

p of PTM-IXa-m is 0, 1, or 2;

one of W and X of PTM-IXa-m is N, and the other of W and X is C;

Y of PTM-IXa-m is N or C—$R^2$ $R^1$ of PTM-IXa-m is selected from $C_{1-6}$alkyl, $C_{2-6}$alkenyl, C26alkynyl, $C_{3-6}$cycloalkyl, 3- to 6-membered saturated heterocyclyl, halo, —CN, —C($R^{1a}$)═NR($OR^{1a}$), —C($R^{1a}$)═N($R^{1a}$), —C(O)$R^{1a}$, —C(O)$_2R^{1a}$, —C(O)N($R^{1a}$)$_2$, —$NO_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —$OR^{1a}$, —OC(O)$R^{1a}$, —OC(O)N($R^{1a}$)$_2$, —$SR^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^{15}$;

$R^{1a}$ of PTM-IXa-m in each occurrence is independently selected from H, $C_{1-6}$alkyl, $C_{2-6}$alkenyl, $C_{2-6}$alkynyl, 3- to 6-membered monocyclic carbocyclyl, and 3- to 6-membered monocyclic heterocyclyl wherein said $C_{1-6}$alkyl, $C_{2-6}$alkenyl, $C_{2-6}$alkynyl, 3- to 6-membered monocyclic carbocyclyl, and 3- to 6-membered monocyclic heterocyclyl in each occurrence are optionally and independently substituted with one or more $R^{10}$;

$R^{10}$ of PTM-IXa-m in each occurrence is independently selected from C^aUcyl, $C_{2-6}$alkenyl, $C_{2-6}$alkynyl, 3- to 6-membered carbocyclyl, 3- to 6-membered heterocyclyl, halo, —CN, —C($R^{10a}$)═NR($OR^{10a}$), —C($R^{10a}$)═N($R^{10a}$), —C(O)$R^{10a}$, —C(O)$_2R^{10a}$, —C(O)N($R^{10a}$)$_2$, —N0$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —$OR^{10a}$, —OC(O)$R^{10a}$, —OC(O)N($R^{10a}$)$_2$, —$SR^{10a}$, —S(O)$R^{10a}$, —S(O)$_2R^{10a}$, —S(O)N(R)$_2$, and S(O)$_2$N($R^{10a}$)$_2$;

$R^{10a}$ of PTM-IXa-m in each occurrence is independently selected from H and $C_{1-6}$alkyl, wherein said $C_{1-6}$alkyl is optionally substituted with one or more halo;

$R^{15}$ of PTM-IXa-m in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{15a}$)═NR($OR^{15a}$), —C($R^{15a}$)═N($R^{15a}$), —C(O)$R^{15a}$, —C(O)$_2R^{15a}$, —C(O)N($R^{15a}$)$_2$, —$NO_2$, —N($R^{15a}$)$_2$, —N($R^{15a}$)C(O)$R^{15a}$, —N($R^{15a}$)C(O)$_2R^{15a}$, —N($R^{15a}$)C(O)N($R^{15a}$)$_2$, —N($R^{15a}$)S(O)$_2R^{15a}$, —$OR^{15a}$, —OC(O)$R^{15a}$, —OC(O)N($R^{15a}$)$_2$, —$SR^{15a}$, —S(O)$R^{15a}$, —S(O)$_2R^{15a}$, —S(O)N($R^{15a}$)$_2$, and —S(O)$_2$N($R^{15a}$)$_2$;

$R^{15a}$ of PTM-IXa-m in each occurrence is independently selected from H and $C_{1-6}$alkyl, wherein said $C_{1-6}$alkyl is optionally substituted with one or more halo;

$R^2$ of PTM-IXa-m is selected from H, $C_{1-6}$alkyl, $C_{2-6}$alkenyl, $C_{2-6}$alkynyl, 3- to 7-membered carbocyclyl, 3- to 7-membered heterocyclyl, halo, —CN, —C($R^{2a}$)═NR($OR^{2a}$), —C($R^{2a}$)═N($R^{2a}$), —C(O)$R^{2a}$, —C(O)$_2R^{2a}$, —C(O)N($R^{2a}$)$_2$, —$NO_2$, —N($R^{2a}$)$_2$, —N($R^{2a}$)C(O)$R^2$, —N($R^{2a}$)C(O)$_2R^{2a}$, —N($R^{2a}$)C(O)N($R^{2a}$)$_2$, —N($R^{2a}$)S(O)$_2R^{2a}$, —$OR^{2a}$, —OC(O)$R^2$, —OC(O)N($R^{2a}$)$_2$, —$SR^{2a}$, —S(O)$R^2$, —S(O)$_2R^{2a}$, —S(O)N($R^{2a}$)$_2$, and —S(O)$_2$N($R^{2a}$)$_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one or more $R^{20}$;

$R^{2a}$ of PTM-IXa-m in each occurrence is independently selected from H and $C_{1-6}$alkyl, wherein said $C_{1-6}$alkyl in each occurrence is optionally and independently substituted with one or more $R^{20}$;

$R^{20}$ of PTM-IXa-m in each occurrence is independently selected from $C_{1-6}$alkyl, $C_{2-6}$alkenyl, $C_{2-6}$alkynyl, $C_{3-7}$cycloalkyl, 3- to 7-membered saturated heterocyclyl, halo, —CN, —C($R^{20a}$)═NR($OR^{20a}$), —C($R^{20a}$)═N($R^{20a}$), —C(O)$R^{2a}$, —C(O)$_2R^{20a}$, —C(O)N($R^{2a}$)$_2$, —N0$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R^{20a}$, —$OR^{20a}$, —OC(O)$R^{20a}$, —OC(O)N($R^{20a}$)$_2$, —$SR^{20a}$, —S(O)$R^{20a}$, —S(O)$_2R^{20a}$, S(O)N($R^{20a}$)$_2$, and —S(0)$_2$N(R)$_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one or more $R^2$;

$R^{20a}$ of PTM-IXa-m in each occurrence is independently selected from H and $C_{1-6}$alkyl, wherein said $C_{1-6}$alkyl is optionally substituted with $R^{25}$;

$R^{25}$ of PTM-IXa-m is selected from halo and —$OR^{25a}$;

$R^{25a}$ of PTM-IXa-m is selected from H and $C_{1-6}$alkyl;

$R^3$ of PTM-IXa-m is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —$C(R^{3a})$═$NR(OR^{3a})$, —$C(R^{3a})$═$N(R^{3a})$, —$C(O)R^{3a}$, —$C(O)_2R^{3a}$, —$C(O)N(R^{3a})_2$, —$NO_2$, —$N(R^{3a})_2$, —$N(R^{3a})C(O)R^{3a}$, —$N(R^{3a})C(O)_2R^{3a}$, —$N(R^{3a})C(O)N(R^{3a})_2$, —$N(R^{3a})S(O)_2R^{3a}$, —$OR^{3a}$, —$OC(O)R^{3a}$, —$OC(O)N(R^{3a})_2$, —$SR^{3a}$, —$S(O)R^{3a}$, —$S(O)_2R^{3a}$, —$S(O)N(R^{3a})_2$, and —$S(O)_2N(R^{3a})_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{30}$.

$R^{3a}$ of PTM-IXa-m in each occurrence is independently selected from H, $C_{1-6}$alkyl, 3- to 6-membered carbocyclyl, and 3- to 6-membered heterocyclyl, wherein said $C_{1-6}$alkyl, 3- to 6-membered carbocyclyl, and 3- to 6-membered heterocyclyl in each occurrence are optionally and independently substituted with one or more $R^{30}$;

$R^{30}$ of PTM-IXa-m in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —$C(R^{30a})$═$NR(OR^{30a})$, —$C(R^{30a})$═$N(R^{30a})$, —$C(O)R^{30a}$, —$C(O)_2R^{30a}$, —$C(O)N(R^{30a})_2$, —$NO_2$, —$N(R^{30a})_2$, —$N(R^{30a})C(O)R^{3a}$, —$N(R^{30a})C(O)_2R^{30a}$, —$N(R^{30a})C(O)N(R^{30a})_2$, —$N(R^{30a})S(O)_2R^{30a}$, —$OR^{30a}$, —$OC(O)R^{30a}$, —$OC(O)N(R^{30a})_2$, —$SR^{30a}$, —$S(O)R^{30a}$, —$S(O)_2R^{30a}$, —$S(O)N(R^{30a})_2$, and —$S(O)_2N(R^{30a})_2$, wherein said $C_{1-3}$alkyl, $C_{2-6}$alkenyl, $C_{2-6}$alkynyl, 3-6 membered carboyclyl, 3- to 6-membered heterocyclyl in each occurrence are optionally and independently substituted with one or more $R^{35}$;

$R^{30a}$ of PTM-IXa-m in each occurrence is independently selected from H and $C_{1-6}$alkyl, wherein said $C_{1-6}$alkyl is optionally substituted with one or more $R^{35}$;

$R^{35}$ of PTM-IXa-m in each occurrence is independently selected from halo and —$OR^{35a}$;

$R^{35a}$ of PTM-IXa-m in each occurrence is independently selected from H and $C_{1-6}$alkyl;

$R^{35b}$ of PTM-IXa-m in each occurrence is independently selected from H, halo, optionally substituted alkoxy (e.g., optionally substituted C1-C4 alkoxy), optionally substituted alkyl (e.g., C1-C4 alkyl optionally substituted with halo or hydroxy), hydroxyalkyl (e.g. C1-C4 hydroxyalkyl), or haloalkyl (e.g., C1-C4 haloalkyl);

$R^{35c}$ of PTM-IXa-m in each occurrence is independently selected from halo or haloalkyl (e.g., $C_1$-$C_4$ haloalkyl);

$R^4$ of PTM-IXa-m is selected from H, halo, $C_{1-6}$alkyl, $N(R^{4a})_2$, and —$OR^{4a}$;

$R^{4a}$ of PTM-IXa-m in each occurrence is independently selected from H and $C_{1-6}$alkyl; and the PTM-Ixa-m is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-Xa, PTM-Xb, PTM-Xc, PTM-Xd, PTM-Xe, PTM-Xf, or PTM-Xg:

PTM-Xa

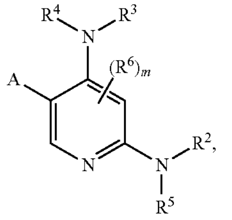

PTM-Xb

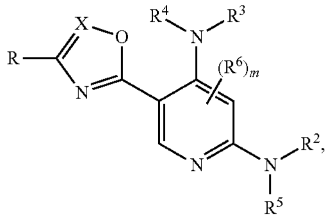

PTM-Xc

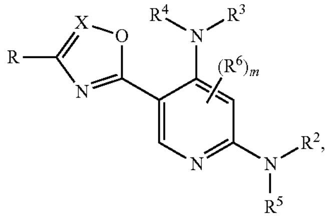

PTM-Xd

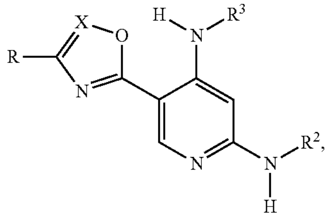

PTM-Xe

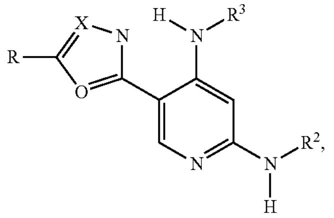

PTM-Xf

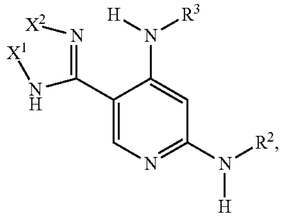

PTM-Xg

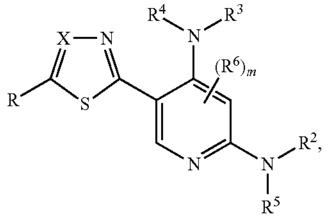

wherein:

-continued

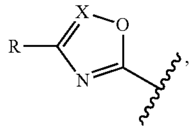, 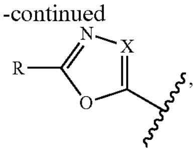, or

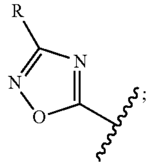;

A of PTM-Xa-g is or A of PTM-X is a triazole optionally substituted by 0-2 R

X of PTM-Xa-g is N or C—$R^7$;

R of PTM-Xa-g is hydrogen, $R^1$, halogen, cyano, nitro, —$OR^1$, —C(═O)—$R^1$, —C(═O)O—$R^1$, —C(═O)$NR^{11}$—$R^1$, —S(═O)$_2$—$R^1$, —$NR^{11}$C(═O)—$R^{11}$, —$NR^{11}$C(═O)$NR^{11}R^{11}$, —$NR^{11}$C(═O)$NR^{11}R^1$, —$NR^{11}$C(═O)O—$R^1$, —$NR^{11}$S(═O)$_2R^1$, —$NR^{11}R^{11}$, or —$NR^{11}R^1$;

$R^1$ of PTM-Xa-g is $C_{1-6}$ alkyl substituted with 0-4 $R^{1a}$, $C_{1-6}$haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocycle containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$;

$R^{1a}$ of PTM-Xa-g is hydrogen, ═O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^b S(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle or heteroaryl, each comprising carbon atoms and 1-4 heteroatoms selected from N, O, and $S(O)_p$ substituted with 0-3 $R^a$;

$R^2$ of PTM-Xa-g is $C_{6-10}$ aryl substituted with 0-4 $R^{2a}$, a 5-10 membered heterocycle containing 1-4 heteroatoms selected from N, O, and S, substituted with 1-4 $R^{2a}$, or a 5-10 membered heteroaryl containing 1-4 heteroatoms selected from N, O, and S, substituted with 0-4 $R^{2a}$;

$R^{2a}$ of PTM-Xa-g at each occurrence is independently selected from hydrogen, ═O, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R_b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^b S(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$substituted with 0-2 $R^{3a}$;

$R^3$ of PTM-Xa-g is $C_1$-6alkyl substituted with 0-3 $R^{3a}$, $C_{1-6}$haloalkyl, $C_{2-6}$ alkenyl substituted with 0-3 $R^{3a}$, $C_{2-6}$ alkynyl substituted with 0-3 $R^{3a}$, $C_{3-10}$ cycloalkyl substituted with 0-3 $R^{3a}$, C6-i aryl substituted with 0-3 $R^{3a}$, a 5-10 membered heterocyclyl containing 1-4 heteroatoms selected from N, O, and S, substituted with 0-3 $R^{3a}$ or a 5-10 membered heteroaryl containing 1-4 heteroatoms selected from N, O, and S, substituted with 0-3 $R^{3a}$;

$R^{3a}$ of PTM-Xa-g is hydrogen, ═O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, $NR^bS(O)_pR^c$, —$S(O)R^c$, —$S(O)_2R^c$, $C_{1-6}$ alkyl substituted with 0-2 $R_a$, $C_{1-6}$haloalkyl, —$(CH_2)_r$-3-14 membered carbocycle substituted with 0-1 $R_a$, or —$(CH_2)_r$-5-7 membered heterocycle or heteroaryl, each comprising carbon atoms and 1-4 heteroatoms selected from N, O, and $S(O)_p$ substituted with 0-1 $R^a$;

$R^4$ and $R^5$ of PTM-Xa-g are independently selected from hydrogen, $C_{1-4}$ alkyl substituted with 0-1 $R^f$, $(CH_2)$-phenyl substituted with 0-3 $R^d$, and a —$(CH_2)$-5-7 membered heterocycle comprising carbon atoms and 1-4 heteroatoms selected from N, O, and $S(O)_p$;

$R^6$ and $R^7$ of PTM-Xa-g are independently at each occurrence is selected from hydrogen, ═O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^b S(O)_pR^c$, —$S(O)R^c$, —$S(O)_2R^c$, $C_{1-6}$alkyl substituted with 0-2 $R^a$, C1-6haloalkyl, —$(CH_2)_r$-3-14 membered carbocycle substituted with 0-3 $R_a$, or —$(CH_2)_r$-5-7 membered heterocycle or heteroaryl, each comprising carbon atoms and 1-4 heteroatoms selected from N, O, and $S(O)_p$ substituted with 0-3 $R^a$, provided $R^6$ and $R^7$ are not both hydrogen;

$R^{11}$ of PTM-Xa-g at each occurrence is independently hydrogen, $R^c$, $C_{1-4}$ alkyl substituted with 0-1 $R^f$, $CH_2$-phenyl substituted with 0-3 $R^d$, or —$(CH_2)$-5-7 membered heterocycle or heteroaryl, each comprising carbon atoms and 1-4 heteroatoms selected from N, O, and $S(O)_p$ substituted with 0-3 $R^d$; or $R^{11}$ and along with another $R^{11}$, $R^1$, or $R^2$ on the same nitrogen atom may join to form an optionally substituted heterocycle;

$R^a$ of PTM-Xa-g is hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R_b$, —$(CH_2)_rC(O)OR^b$, —$(CH_2)_rOC(O)R_b$, —$(CH_2)_rNR^{11}R^{11}$, —$(CH_2)_rC(O)NR^{11}R^{11}$, $(CH_2)_rNR^bC(O)R^c$, $(CH_2)_rNR^bC(O)ORC$, —$NR^bC(O)NR^{11}R^{11}$, —$S(O)_pNR^{11}R^{11}$, —$NR^bS(O)_pR^c$, —$S(O)R^C$, —$S(O)_2R'$, $C_{1-6}$ alkyl substituted with 0-1 $R^f$, $C_{1-6}$haloalkyl, —$(CH_2)_r$-3-14 membered carbocycle, or —$(CH_2)$-5-7 membered heterocycle or heteroaryl, each comprising carbon atoms and 1-4 heteroatoms selected from N, O, and $S(O)_p$; or two $R^a$ on adjacent or the same carbon atom form a cyclic acetal of the formula —O—$(CH_2)_n$—O—, or —O—$CF_2$—O—, wherein n is selected from 1 or 2;

$R^b$ of PTM-Xa-g is hydrogen, $R^c$ of PTM-X, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-3 $R^d$; $R_e$ is $C_{1-6}$ alkyl substituted with 0-1 $R^f$, $C_{3-6}$ cycloalkyl, or $(CH_2)_r$-phenyl substituted with 0-3 $R_f$;

$R^c$ of PTM-Xa-g is $C_{1-6}$alkyl, $C_{3-6}$cycloalkyl, or $(CH_2)_r$-phenyl substituted with 0-3 $R^f$;

$R^d$ of PTM-Xa-g is hydrogen, F, Cl, Br, $OCF_3$, $CF_3$, CN, $NO_2$, —$OR^e$, —$(CH_2)_rC(O)R^e$, —$NR^eR^e$, —$NR^eC(O)OR^c$, $C_{1-6}$ alkyl, or $(CH_2)_r$-phenyl substituted with 0-3 $R^f$;

$R^e$ of PTM-Xa-g is selected from hydrogen, $C_{1-6}$ alkyl, $C_{3-6}$ cycloalkyl, and $(CH_2)_r$-phenyl substituted with 0-3 $R^f$;

$R^f$ of PTM-Xa-g is hydrogen, halo, $NH_2$, OH, or $O(C_{1-6}alkyl)$;

p of PTM-Xa-g is 0, 1, or 2;

r of PTM-Xa-g is 0, 1, 2, 3, or 4;

m of PTM-Xa-g is 0, 1, or 2; and the PTM-Xa-g is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-XIa, PTM-XIb, or PTM-XIc:

PTM-XIa

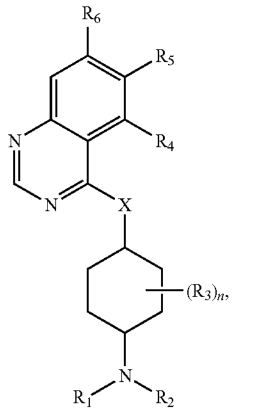

PTM-XIb

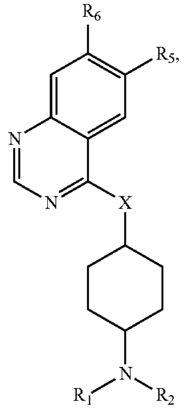

or

-continued

PTM-XIc

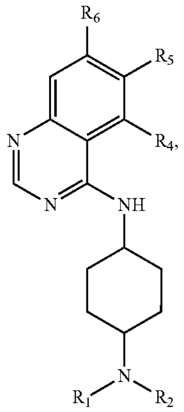

wherein:

X of PTM-XIa-c is NH or 0;

b of PTM-XIa-c is 0 or 1;

n of PTM-XIa-c is 0, 1, 2, 3 or 4;

$R_1$ and $R_2$ of PTM-XIa-c are independently H, $(C_1-C_4)$ alkyl and heterocyclyl, or $R_1$ and $R_2$ can be taken together with the nitrogen to which they are attached to form a monocyclic or bicyclic (fused, bridged or spirocyclic) heterocycle containing 3-8 carbon atoms optionally containing, in addition to the nitrogen, one or two additional heteroatoms selected from N, O and S, said alkyl and heterocycle are optionally substituted with one or more substituents selected from $R_a$;

$R^3$ of PTM-XIa-c is $(C_1-C_4)$alkyl wherein two adjacent alkyl groups can join together and form a bridged moiety of 3-6 carbon atoms;

$R_4$ of PTM-XIa-c is absent, halo or $O_b(C_1-C_4)$alkyl;

$R_5$ of PTM-XIa-c is selected from halo, CN, $O(C_1-C_4)$ alkyl, $C_1-C_4$ alkyl and $C_2-C_4$ alkenyl which are optionally substituted with one or more substituents selected from $R_b$ or $R_5$ is aryl or heteroaryl each optionally substituted with one or more substitutents selected from $R_b$;

$R_6$ of PTM-XIa-c is absent, halo, or $O(C_1-C_4)$alkyl;

$R_a$ of PTM-XIa-c is halo, oxo, OH, $O_b(C_1-C_4)$alkyl, $C(O)O_b(C_1-C_6)$alkyl, $(C{=}O)_b$heterocyclyl, $SO_2H$, $CF_3$, $SO_2(C_1-C_4)$alkyl, $C(O)C_1-C_4$alkyl, or heterocyclyl, wherein said alkyl can come together with another alkyl to form a bridged moiety and said alkyl and heterocyclyl are optionally substituted with one or more substituents independently selected from F and $(C_1-C_4)$alkyl; and $R_b$ of PTM-XIa-c is independently selected from OH, halo, $CHF_2$, $CF_3$, COOH, $SO_2(C_1-C_4)$alkyl, $C(O)C_1-C_4$alkyl, $(C{=}O)NH_2$, $O_b(C_1-C_4)$alkyl, aryl, heterocyclyl, CN, $C(O)N(R_c)_2$, $N(R_c)_2$, wherein the $R_c$ and alkyl are optionally substituted with OH, $O(C_1-C_4)$alkyl and heterocyclyl;

$R_c$ of PTM-XIa-c is independently selected from H, $SO_2(C_1-C_4)$alkyl, or $C_1-C_4$ alkyl;

the PTM-XIa-c is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-XIIa, PTM-XIIb, PTM-XIIc, PTM-XIId, PTM-XIIe, or PTM-XIIf:

PTM-XIIa

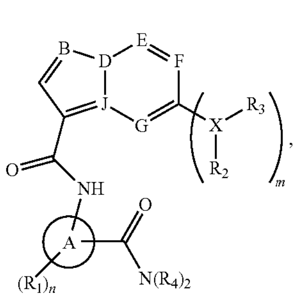

,

PTM-XIIb

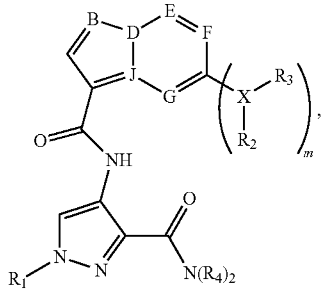

,

PTM-XIIc

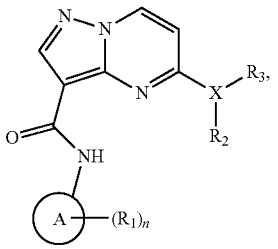

PTM-XIId

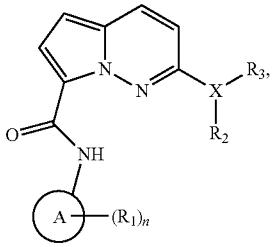

PTM-XIIe

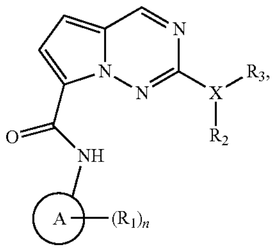

or

PTM-XIIf

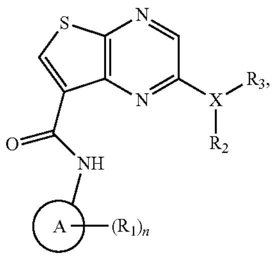

wherein:

B of PTM-XIIa-f is CH, N or S; D of PTM-XII is CH or N; E of PTM-XII is CH or N; F of PTM-XII is CH or N; G of PTM-XII is CH or N; and J of PTM-XII is C or N, wherein when B is S then D is CH, E is N, F is CH, G is N and J is C;

X of PTM-XIIa-f is O, S, $CH_2$ or N;

m of PTM-XIIa-f is 0 or 1;

n of PTM-XIIa-f is 0, 1, 2, 3 or 4;

Ring A of PTM-XIIa-f is aryl, heterocyclyl, pyridinyl, pyrazolyl, thiophenyl, furanyl or phenyl;

$R_1$ of PTM-XIIa-f is independently selected from ($C_1$-$C_4$) alkyl, ($C_3$-$C_6$)cycloalkyl, heterocyclyl, $CF_3$, $CHF_2$, CN, halo, pyrimidine, piperidine and phenyl, each optionally substituted with ($C_1$-$C_4$)alkyl, OH, $CH_3$, $OCH_3$, halo, O($C_1$-$C_4$)alkyl, methyl-piperidine, $S(O)_2R_c$, $C(O)N(R_b)_2$, or C(O)O($C_1$-$C_4$)alkyl;

$R_2$ of PTM-XIIa-f is absent or H and $R_3$ is independently selected from: ($C_1$-$C_4$)alkyl, ($C_1$-$C_6$)alkyl, ($C_3$-$C_8$)cycloalkyl, heterocyclyl, pyranyl, cyclopentyl, cyclohexyl, cycloheptyl, thiopyranyl, pyrazolyl, piperidinyl, morpholinyl, piperazinyl, each optionally substituted with one or more substituents independently selected from halo, OH, oxo, $N(R_b)_2$, oxopyrrolidinyl, or morpholinyl, or $R_2$ and $R_3$ can be taken together with the nitrogen to which they are attached to form a heterocyclyl, piperazine or morpholine, each optionally substituted with one or more substituents selected from oxo and $R_a$;

$R_4$ of PTM-XIIa-f is independently H or methyl;

$R_a$ of PTM-XIIa-f is independently selected from ($C_1$-$C_4$) alkyl, ($C_3$-$C_6$)cycloalkyl, cyclopropyl, $CF_3$, F, $CHF_2$, OH, halo and $NH_2$, said alkyl optionally substituted with ($C_3$-$C_6$)cycloalkyl and $CF_3$; and $R_b$ of PTM-XIIa-f is independently selected from H and ($C_1$-$C_4$)alkyl;

$R_c$ of PTM-XIIa-f is methyl; and the PTM-XIIa-f is covalently joined to a ULM, a chemical linker group (L), a CLM, an ILM, a VLM, MLM, a ULM', a CLM', a ILM', a VLM', a MLM', or combination thereof.

In any aspect or embodiment described, the PTM is represented by Formula PTM-XIIIa, PTM-XIIIb, PTM-XIIIc, PTM-XIIId, PTM-XIIIe, PTM-XIIIf, PTM-XIIIg, PTM-XIIIh, PTM-XIIIi, or PTM-XIIIj:

PTM-XIIIa

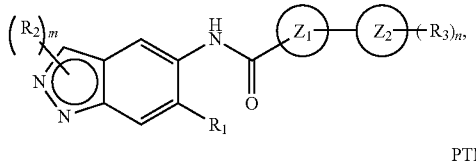

PTM-XIIIb

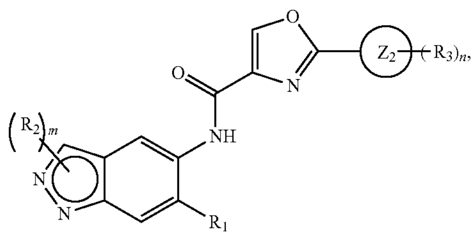

-continued

PTM-XIIIc

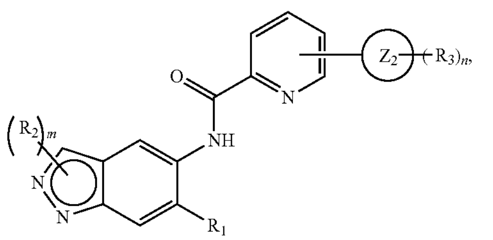

PTM-XIIId

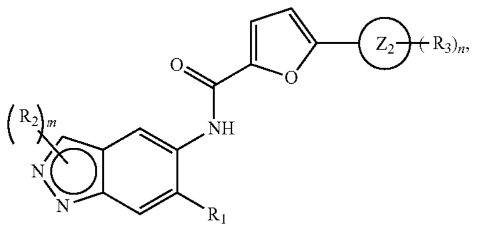

PTM-XIIIe

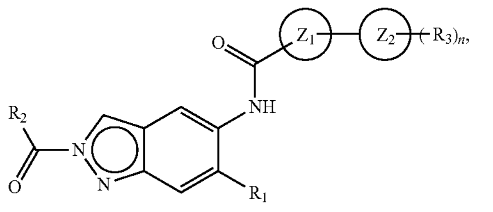

PTM-XIIIf

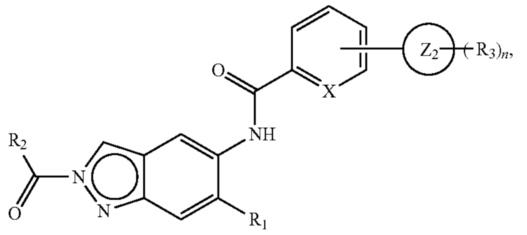

PTM-XIIIg

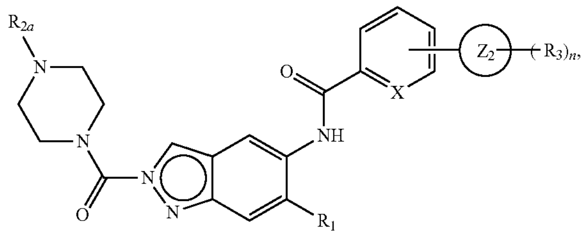

PTM-XIIIh

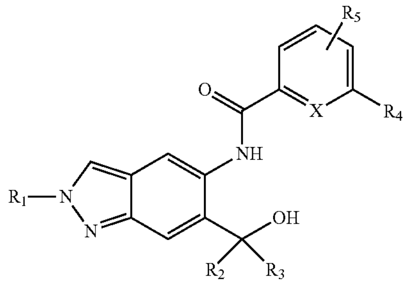

-continued

PTM-XIIIi

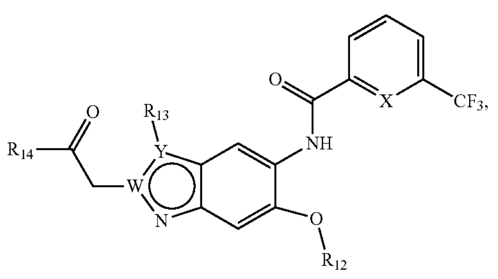

or

PTM-XIIIj

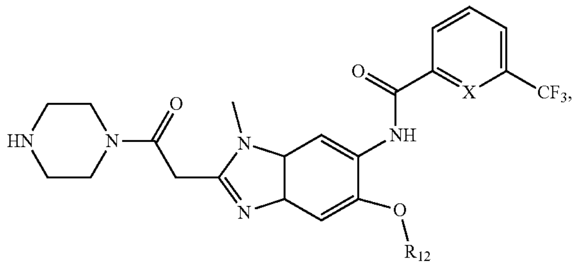

wherein:

Ring $Z_1$ of PTM-XIIIa-j is an optionally substituted heteroaryl;

Ring $Z_2$ of PTM-XIIIa-j is a optionally substituted heterocycloalkyl, optionally substituted heteroaryl or a direct bond;

$R_1$ of PTM-XIIIa-j is optionally substituted alkyl, optionally substituted hydroxyalkyl cyano, —$NR_aR_b$, optionally substituted cycloalkyl, optionally substituted aryl or optionally substituted heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;

$R_2$ of PTM-XIIIa-j, at each occurrence, independently is an optionally substituted group selected from alkyl, cycloalkyl, or cycloheteroalkyl; wherein the substituent, at each occurrence, is independently halogen, alkoxy, hydroxyl, hydroxyalkyl, haloalkyl or haloalkoxy;

$R_{2a}$ of PTM-XIIIa-j is an H or optionally substituted alkyl (e.g., optionally substituted $C_1$-$C_4$ alkyl);

$R_3$ of PTM-XIIIa-j, at each occurrence, independently is hydrogen, halogen, alkyl, haloalkyl, haloalkoxy, alkoxy, —$NR_aR_b$, hydroxyl or hydroxyalkyl;

$R_4$ of PTM-XIIIa-j at each occurrence is independently is halogen, cyano, an unsubstituted or a singly or multiply, identically or differently substituted $C_1$-$C_5$-alkyl or an unsubstituted or a singly or multiply, identically or differently substituted $C_3$-$C_6$-cycloalkyl (e.g., the substituents of the alkyl or cycloalkyl may be selected from the group of halogen and hydroxyl);

$R_5$ of PTM-XIIIa-j at each occurrence is independently is hydrogen, halogen or an unsubstituted or poly-halogen-substituted C1-C5-alkyl;

$R_6$ of PTM-XIIIa-j at each occurrence is independently optionally substituted C1-C6-alkyl (e.g., C1-C6-alkyl radical unsubstituted, monobustituted or polysubstituted identically or differently by halogen, hydroxyl, an unsubstituted or mono- or poly-halogen-substituted C3-C6-cycloalkyl, or an $R^9$, $R^{10}SO_2$, $R^{10}SO$ or $R^{11}O$ radical, or a group selected from:

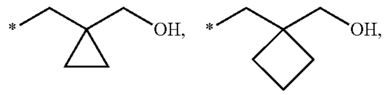

or

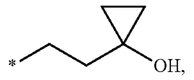

wherein * represents the bonding site of the group to the rest of the molecule);

- $R_7$ and $R_8$ of PTM-XIIIa-j at each occurrence is independently selected from hydrogen or C1-C6-alkyl (e.g., both may be H or a C1-C6 alkyl, including the same C1-C6 alkyl);
- $R_9$ of PTM-XIIIa-j is an unsubstituted or mono- or dimethyl-substituted monocyclic saturated heterocycle having 4 to 6 ring atoms, which contains a heteroatom or a heterogroup from the group of O, S, SO and $SO_2$;
- $R_{10}$ of PTM-XIIIa-j is a C1-C6-alkyl, where the C1-C5-alkyl radical is unsubstituted or mono- or polysubstituted identically or differently by halogen, hydroxyl or C3-C5-cycloalkyl; or $R_{10}$ is C3-C6-cycloalkyl
- $R_{11}$ of PTM-XIIIa-j is an optionally substituted C1-C6-alkyl (e.g., a C1-C6-alkyl radical is unsubstituted or mono- or polysubstituted identically or differently by, e.g., halogen);
- $R_a$ of PTM-XIIIa-j is hydrogen or alkyl;
- $R_b$ of PTM-XIIIa-j is hydrogen, alkyl, acyl, hydroxyalkyl, —$SO_2$-alkyl or optionally substituted cycloalkyl;
- $R_{12}$ of PTM-XIIIa-j is optionally substituted C1-C5 alkyl, optionally substituted methyl, optionally substituted ethyl, optionally substituted cyloalky, or

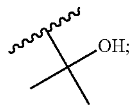 [SMILES: *C(C)(C)O]

- $R_{13}$ of PTM-XIIIa-j is H or methyl;
- $R_{14}$ of PTM-XIIIa-j is an optionally substituted linear or branched alkyl (e.g., optionally substituted linear or branched C1-C8 alkyl), optionally substituted amide, carboxylic group, optionally substituted cycloalkyl, optionally substituted heterocycloalkyl, optionally substituted aryl (e.g., optionally substituted C5-C7 aryl), optionally substituted heteroaryl (e.g., optionally substituted C5-C7 heteroaryl), —$SO_2$-alkyl, —$SO_2H$, —O-alkyl, —O-aryl, —O-heteroaryl, optionally substituted urea group;
- W and Y of PTM-XIIIa-j are selected from C and N with the proviso that one is N and one is C;
- X of PTM-XIIIa-j is CH or N;
- "m" of PTM-XIIIa-j is 1 or 2;
- "n" of PTM-XIIIa-j is 1 or 2; and
- the PTM-XIIIa-j is covalently joined to a ULM, a chemical linker group (L), a CLM, an ILM, a VLM, MLM, a ULM', a CLM', a ILM', a VLM', a MLM', or combination thereof.

In aspect or embodiment described herein, the ULM is a Von Hippel-Lindau (VHL) ligase-binding moiety (VLM) with a chemical structure represented by:

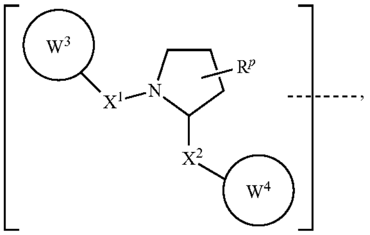

wherein:

- $X^1$, $X^2$ are each independently selected from the group of a bond, O, $NR^{Y3}$, $CR^{Y3}R^{Y4}$, C═O, C═S, SO, and $SO_2$;
- $R^{Y3}$, $R^{Y4}$ are each independently selected from the group of H, linear or branched $C_{1-6}$ alkyl, optionally substituted by 1 or more halo, optionally substituted $C_{1-6}$ alkoxyl (e.g., optionally substituted by 1-3 $R^P$ groups);
- $R^P$ is 0, 1, 2, or 3 groups, each independently selected from the group H, halo, —OH, $C_{1-3}$ alkyl, C═O;
- $W^3$ is selected from the group of an optionally substituted T, an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR^1$-T-Aryl, an optionally substituted —$NR^1$-T-Heteroaryl or an optionally substituted —$NR^1$-T-Heterocycle;
- $X^3$ is C═O, $R^1$, $R^{1a}$, $R^{1b}$;
- each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C═O, $R^{Y3}$C═S, $R^3$SO, $R^3SO_2$, N($R^{Y3}R^{Y4}$)C═O, N($R^{Y3}R^{Y4}$)C═S, N($R^{Y3}R^{Y4}$)SO, and N($R^{Y3}R^{Y4}$)$SO_2$;
- T is selected from the group of an optionally substituted alkyl, —$(CH_2)_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocycle, or —OH groups or an amino acid side chain optionally substituted; and
- n is 0 to 6,
- $W^4$ is

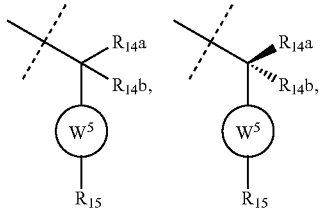

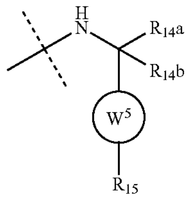

or

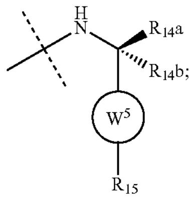

$R_{14a}$, $R_{14b}$, are each independently selected from the group of H, haloalkyl, or optionally substituted alkyl;

$W^5$ is selected from the group of a phenyl or a 5-10 membered heteroaryl, $R_{15}$ is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

and wherein the dashed line indicates the site of attachment of at least one PTM, another ULM (ULM') or a chemical linker moiety coupling at least one PTM or a ULM' or both to ULM.

In aspect or embodiment described herein, the ULM is a Von Hippel-Lindau (VHL) ligase-binding moiety (VLM) with a chemical structure represented by:

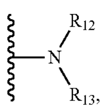

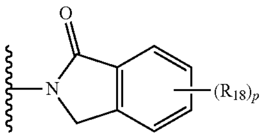

or

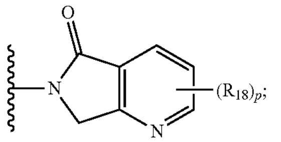

wherein:

$W^3$ is selected from the group of an optionally substituted aryl, optionally substituted heteroaryl, or

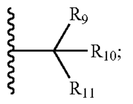

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclic, optionally substituted alkoxy, optionally substituted heteroaryl, optionally substituted aryl,

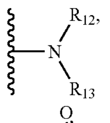

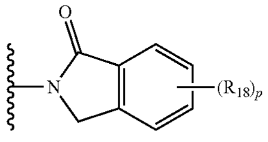

or

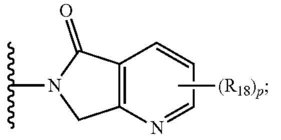

$R_{12}$ is selected from the group of H or optionally substituted alkyl;

$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, are each independently selected from the group of H, haloalkyl, or optionally substituted alkyl;

$W^5$ is selected from the group of a phenyl or a 5-10 membered heteroaryl, $R_{15}$ is selected from the group consisting of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted cycloheteroalkyl;

$R_{16}$ is independently selected from the group consisting of halo, optionally substituted alkyl, optionally substituted haloalkyl, hydroxy, or optionally substituted haloalkoxy;

o is 0, 1, 2, 3, or 4;

$R_{18}$ is independently selected from the group consisting of H, halo, optionally substituted alkoxy, cyano, optionally substituted alkyl, haloalkyl, haloalkoxy or a linker; and p is 0, 1, 2, 3, or 4, and wherein the dashed line indicates the site of attachment of at least one PTM, another ULM (ULM') or a chemical linker moiety coupling at least one PTM or a ULM' or both to ULM.

In aspect or embodiment described herein, the ULM has a chemical structure selected from the group of:

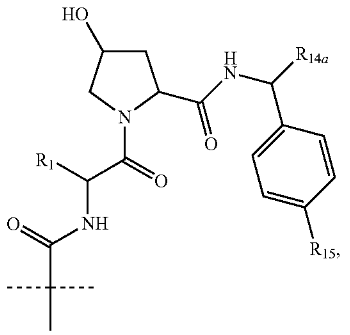

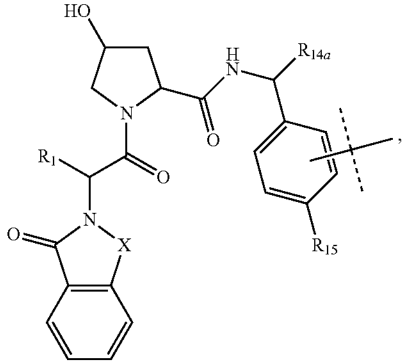

and

-continued

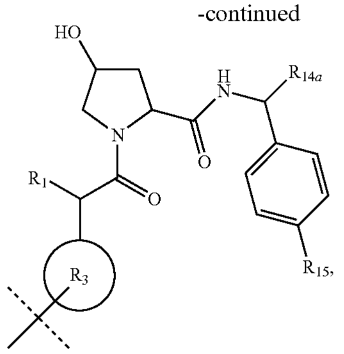

wherein:

$R_1$ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ is H, haloalkyl, optionally substituted alkyl, methyl, fluoromethyl, hydroxymethyl, ethyl, isopropyl, or cyclopropyl;

$R_{15}$ is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, optionally substituted cycloalkyl, or optionally substituted cycloheteroalkyl;

X is C, $CH_2$, or C═O $R_3$ is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to the ULM.

In aspect or embodiment described herein, the ULM comprises a group according to the chemical structure:

ULM-f

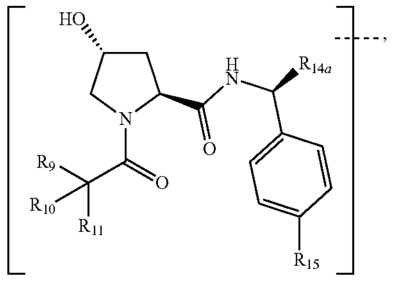

wherein:

$R_{14a}$ is H, haloalkyl, optionally substituted alkyl, methyl, fluoromethyl, hydroxymethyl, ethyl, isopropyl, or cyclopropyl;

R9 is H;

R10 is H, ethyl, isopropyl, tert-butyl, sec-butyl, cyclopropyl, cyclobutyl, cyclopentyl, or cyclohexyl;

R11 is

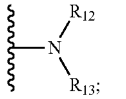

optionally substituted heteroaryl,

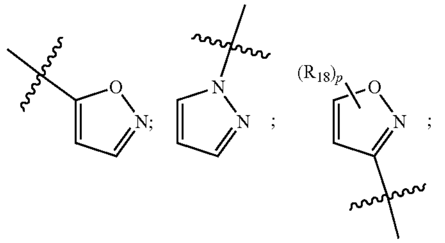

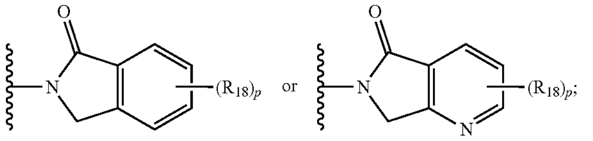

p is 0, 1, 2, 3, or 4; and each $R_{18}$ is independently halo, optionally substituted alkoxy, cyano, optionally substituted alkyl, haloalkyl, haloalkoxy or a linker;

R12 is H, C═O

R13 is H, optionally substituted alkyl, optionally substituted alkylcarbonyl, optionally substituted (cycloalkyl) alkylcarbonyl, optionally substituted aralkylcarbonyl, optionally substituted arylcarbonyl, optionally substituted (heterocyclyl)carbonyl, or optionally substituted aralkyl, $R_{15}$ is selected from the group consisting of H, halogen, Cl, CN, OH, $NO_2$, optionally substituted heteroaryl, optionally substituted aryl;

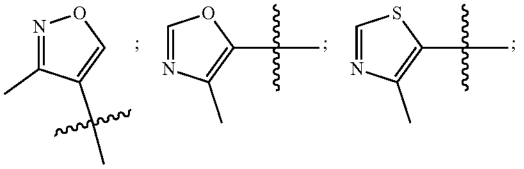

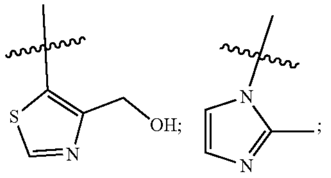

and wherein the dashed line indicates the site of attachment of at least one PTM, another ULM (ULM') or a chemical linker moiety coupling at least one PTM or a ULM' or both to the ULM.

In aspect or embodiment described herein, the ULM is a cereblon E3 ligase-binding moiety (CLM) selected from the group consisting of a thalidomide, lenalidomide, pomalidomide, analogs thereof, isosteres thereof, or derivatives thereof.

In aspect or embodiment described herein, the CLM has a chemical structure represented by:

(a)

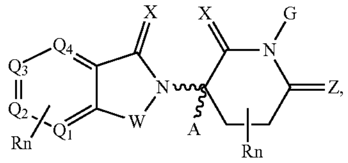

(b)

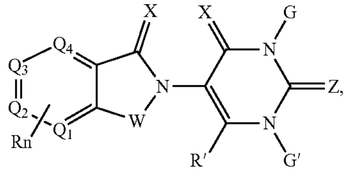

(c)

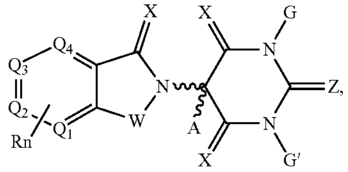

(d)

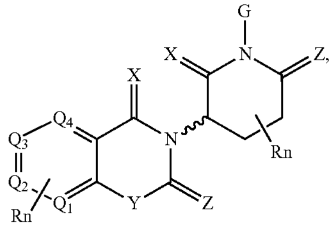

(e)

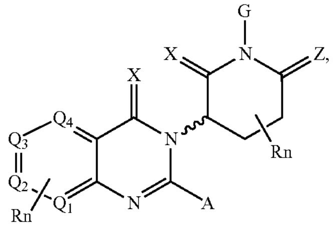

or (f)

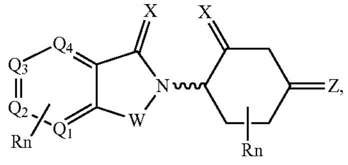

wherein:

- W is selected from the group consisting of $CH_2$, CHR, C═O, $SO_2$, NH, and N-alkyl; each X is independently selected from the group consisting of O, S, and $H_2$;
- Y is selected from the group consisting of $CH_2$, —C═CR', NH, N-alkyl, N-aryl, N-hetaryl, N-cycloalkyl, N-heterocyclyl, O, and S;
- Z is selected from the group consisting of O, S, and $H_2$;
- G and G' are independently selected from the group consisting of H, optionally substituted linear or branched alkyl, OH, R'OCOOR, R'OCONRR", $CH_2$-heterocyclyl optionally substituted with R', and benzyl optionally substituted with R';
- $Q_1$, $Q_2$, $Q_3$, and $Q_4$ represent a carbon C substituted with a group independently selected from R', N or N-oxide;
- A is independently selected from the group H, optionally substituted linear or branched alkyl, cycloalkyl, Cl and F;
- R comprises —CONR'R", —OR', —NR'R", —SR', —$SO_2$R', —$SO_2$NR'R", —CR'R"—, —CR'NR'R"—, (—CR'O)$_{n'}$R", -aryl, -hetaryl, optionally substituted linear or branched -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", -$SF_5$and —$OCF_3$;
- R' and R" are independently selected from the group consisting of a bond, H, alkyl, cycloalkyl, aryl, heteroaryl, heterocyclic, —C(═O)R, heterocyclyl, each of which is optionally substituted;
- ⌇ represents a bond that may be stereospecific ((R) or (S)) or non-stereospecific; and
- $R_n$ comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy,
- n' is an integer from 1-10 (e.g., 1-4, 1, 2, 3, 4, 5, 6, 7, 8, 9, or 10), and wherein
- when n is 1, R is modified to be covalently joined to the linker group (L), and
- when n is 2, 3, or 4, then one $R_n$ is modified to be covalently joined to the linker group (L), and any other R is optionally modified to be covalently joined to a PTM, a CLM, a second CLM having the same chemical structure as the CLM, a CLM', a second linker, or any multiple or combination thereof.

In aspect or embodiment described herein, the CLM has a chemical structure represented by:

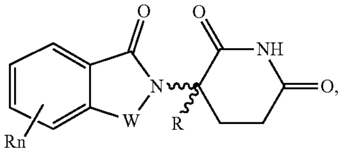

wherein:

- W is independently selected from the group CH2, C═O, NH, and N-alkyl;
- R is independently selected from a H, methyl, or optionally substituted linear or branched alkyl (e.g., optionally substituted linear or branched C1-C6 alkyl );
- ⌇ represents a bond that may be stereospecific ((R) or (S)) or non-stereospecific; and
- Rn comprises from 1 to 4 independently selected functional groups or atoms, for example, O, OH, N, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, and optionally, one of which is modified to be covalently joined to a PTM, a chemical linker group (L), a CLM (or CLM') or combination thereof.

In aspect or embodiment described herein, the ULM is a (MDM2) binding moiety (MLM) with a chemical moiety selected from the group consisting of a substituted imidazolines, a substituted spiro-indolinones, a substituted pyrrolidines, a substituted piperidinones, a substituted morpholinones, a substituted pyrrolopyrimidines, a substituted imidazolopyridines, a substituted thiazoloimidazoline, a substituted pyrrolopyrrolidinones, and a substituted isoquinolinones.

In aspect or embodiment described herein, the ULM is a IAP E3 ubiquitin ligase binding moiety (ILM) comprising the amino acids alanine (A), valine (V), proline (P), and isoleucine (I) or their unnatural mimetics.

In aspect or embodiment described herein, the ULM is a IAP E3 ubiquitin ligase binding moiety (ILM) comprising a AVPI tetrapeptide fragment or derivative thereof.

In aspect or embodiment described herein, the linker (L) comprises a chemical structural unit represented by the formula:

$$-(A^L)_q-,$$

wherein:

- $(A^L)_q$ is a group which is connected to at least one of a ULM moiety, a PTM moiety, or a combination thereof;
- q is an integer greater than or equal to 1; and
- each A is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups;
- $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)\ SO_2N(C_{1-8}alkyl)_2$, $NH\ SO_2NH(C_{1-8}alkyl)$, $NH\ SO_2N(C_{1-8}alkyl)_2$, $NH\ SO_2NH_2$.

In aspect or embodiment described herein, the linker (L) comprises a group represented by a general structure selected from the group consisting of:

—N(R)—$(CH2)_m$-$O(CH2)_n$-$O(CH2)_o$-$O(CH2)_p$-$O(CH2)_q$-$O(CH2)_r$-OCH2-,

—O—$(CH2)_m$-$O(CH2)_n$-$O(CH2)_o$-$O(CH_2)_p$-$O(CH2)_q$-O$(CH2)_r$-OCH2-,

—O—$(CH2)_m$-$O(CH2)_n$-$O(CH2)_o$-$O(CH2)_p$-$O(CH2)_q$-O$(CH2)_r$-O—;

—N(R)—$(CH2)_m$-$O(CH2)_n$-$O(CH2)_o$-$O(CH2)_p$-$O(CH2)_q$-$O(CH2)_r$-O—;

—$(CH2)_m$-$O(CH2)_n$-$O(CH2)_o$-$O(CH2)_p$-$O(CH2)_q$-$O(CH2)_r$-O—;

—$(CH2)_m$-$O(CH2)_n$-$O(CH2)_o$-$O(CH2)_p$-$O(CH2)_q$-$O(CH2)_r$-OCH2-;

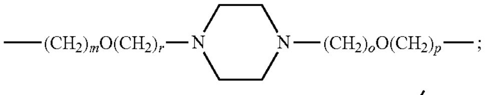

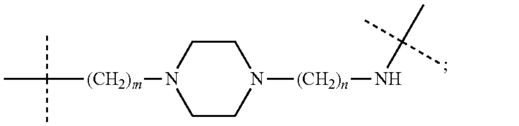

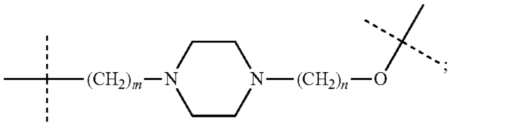

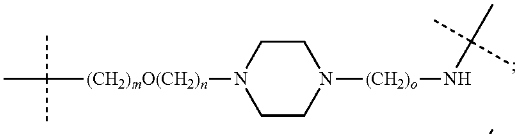

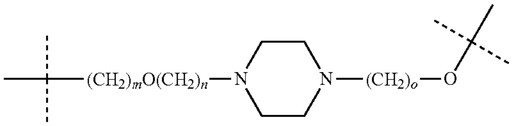

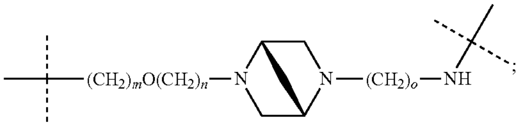

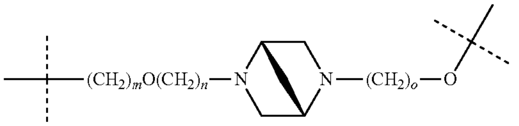

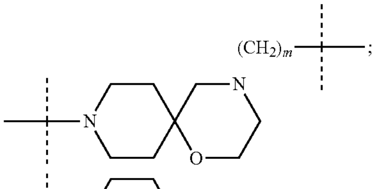

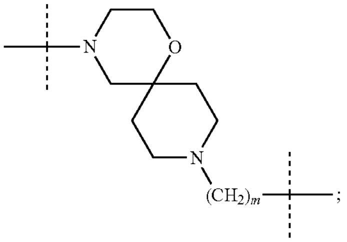

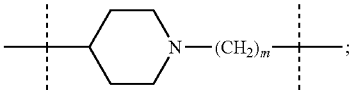

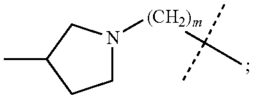

;

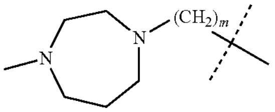

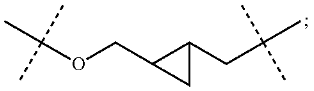

-continued
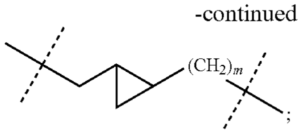
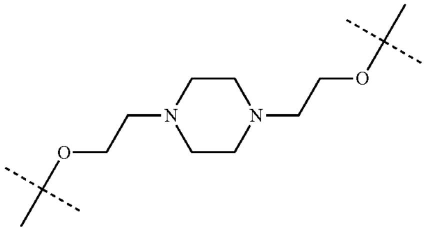
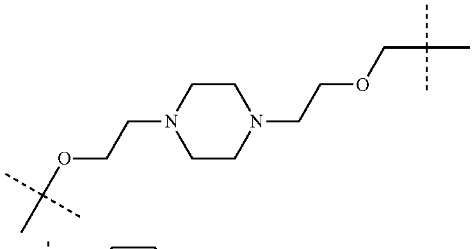
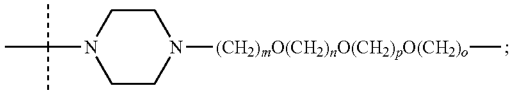
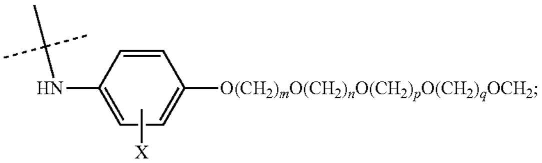
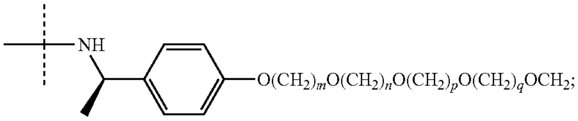
-continued
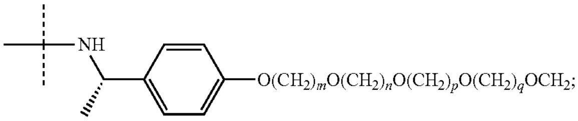
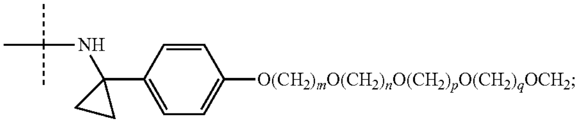
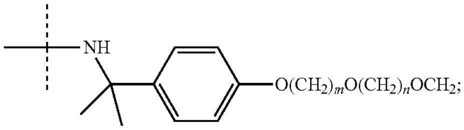
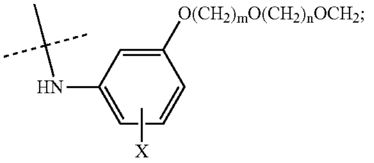
and
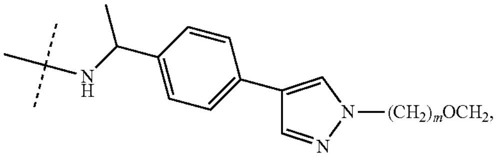
wherein each m, n, o, p, q, and r is independently 0, 1, 2, 3, 4, 5, 6 with the proviso that when the number is zero, there is no N—C or O—O bond, R is selected from the group H, methyl and ethyl, and X is selected from the group H and F;
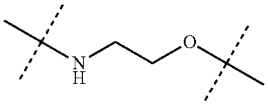
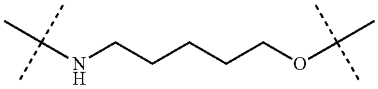
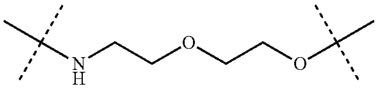
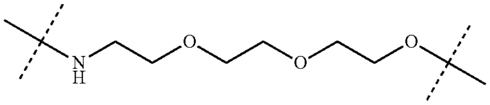
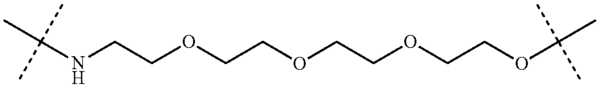
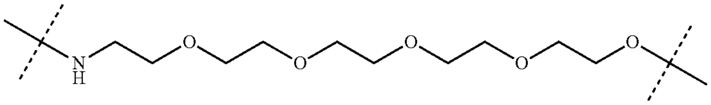
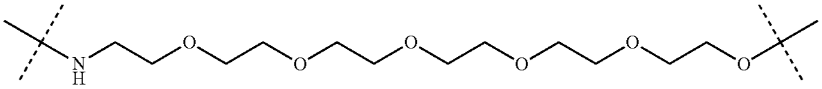
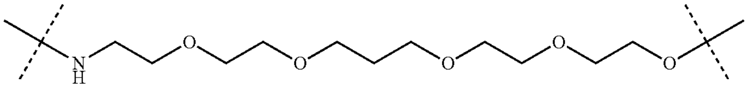
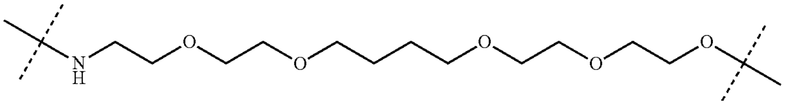
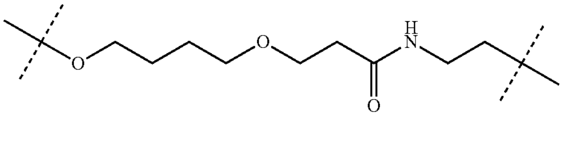
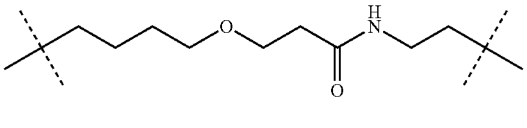

-continued
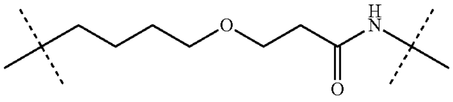
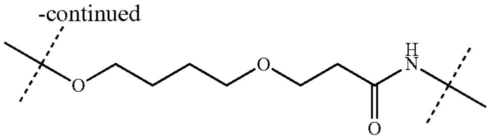
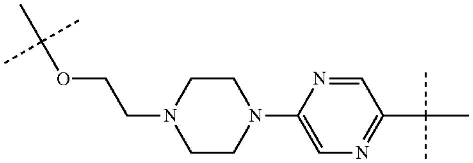
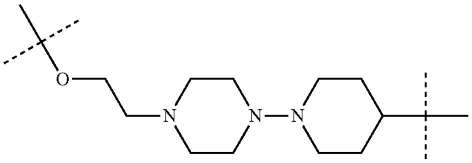
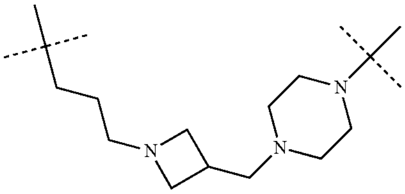
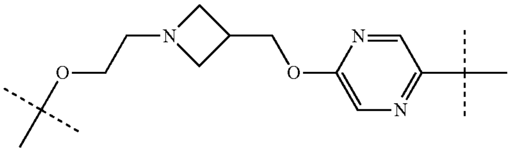
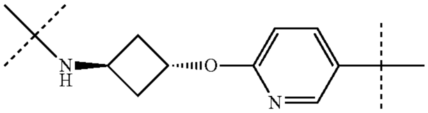
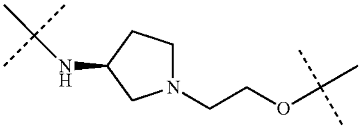
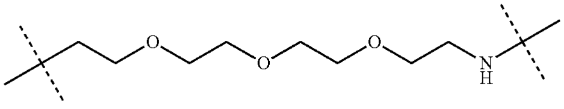
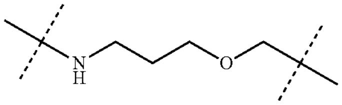
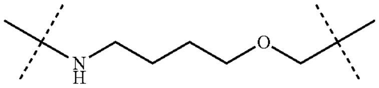
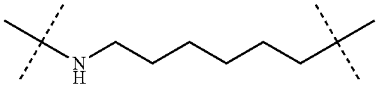
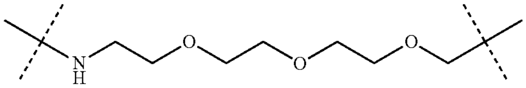
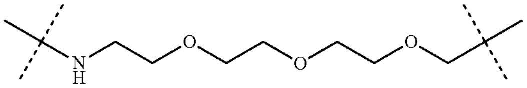
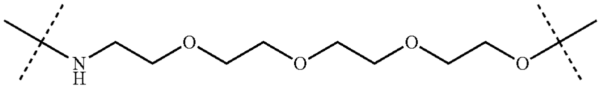
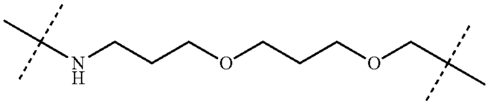
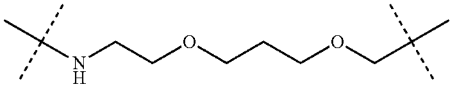
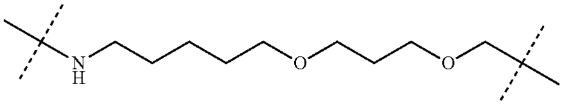
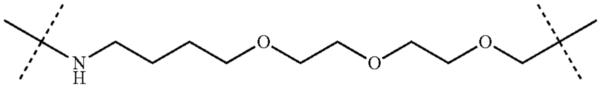
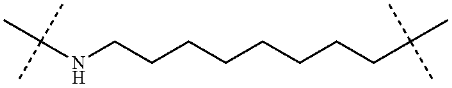
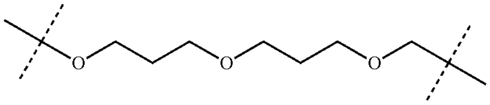
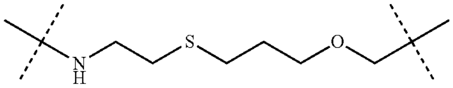
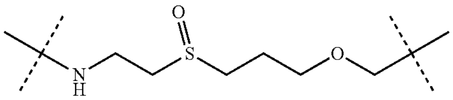
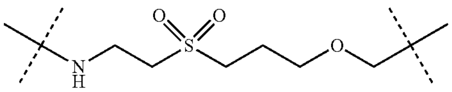
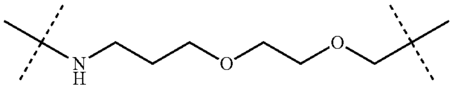
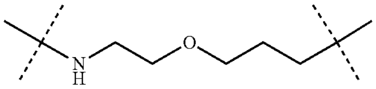
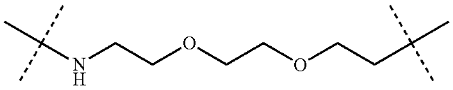
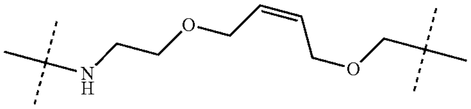
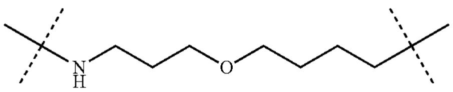
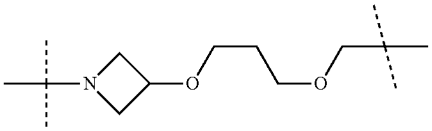

-continued
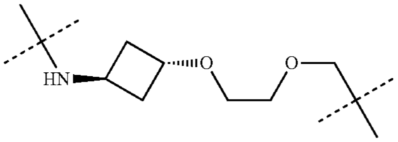
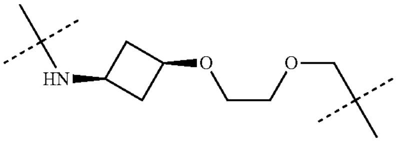
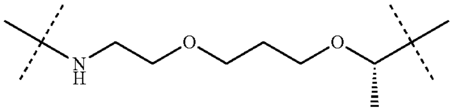
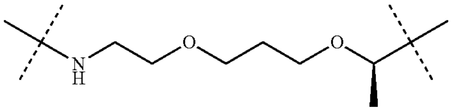
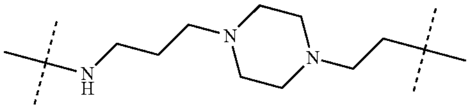
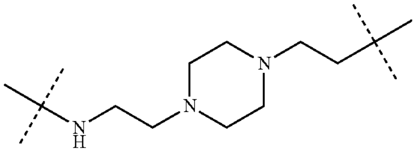
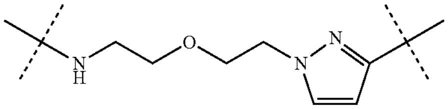
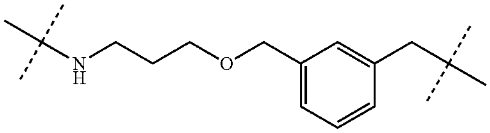
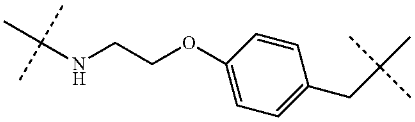
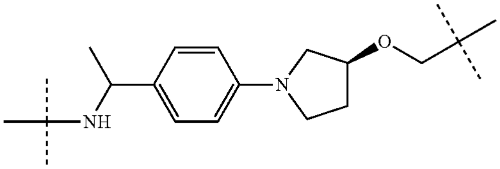
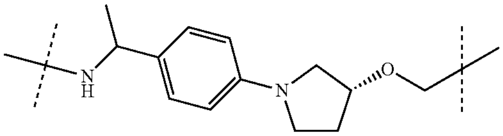
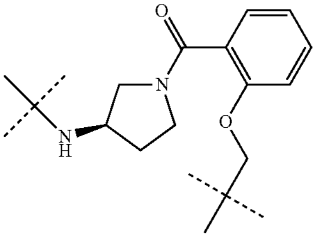
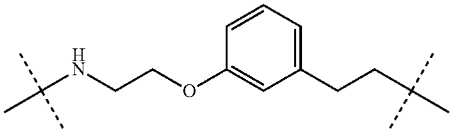
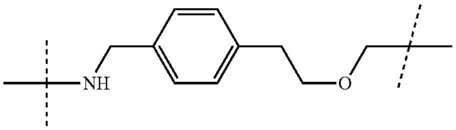
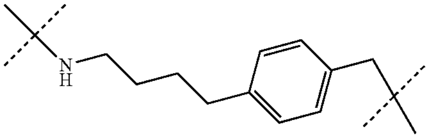
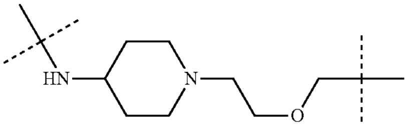
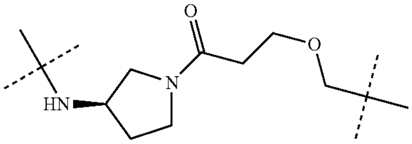
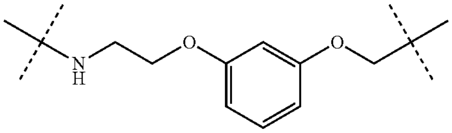
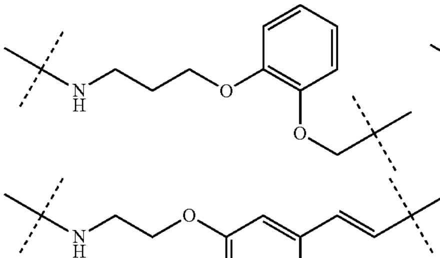
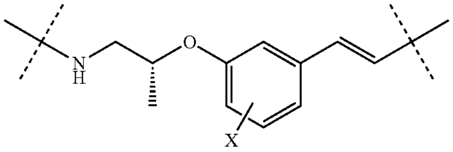
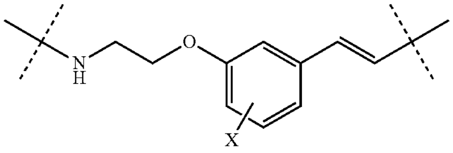
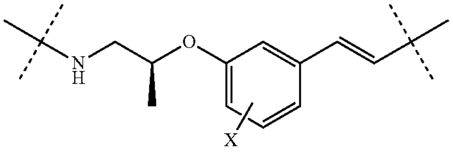
X = H, F -continued
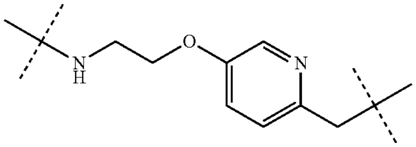
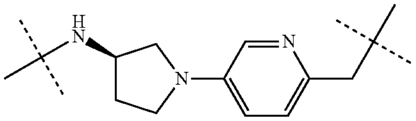
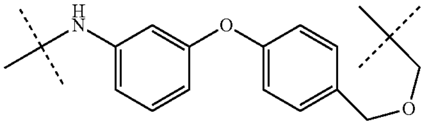
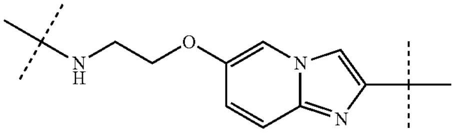
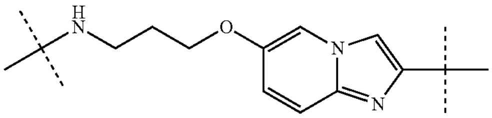
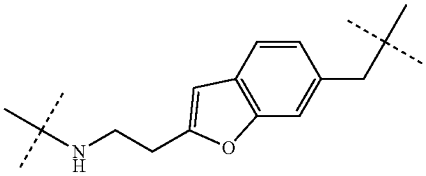
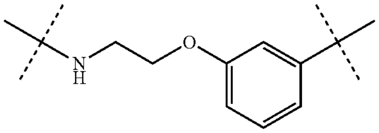
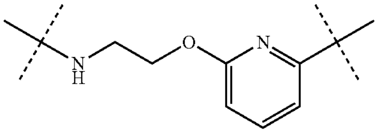
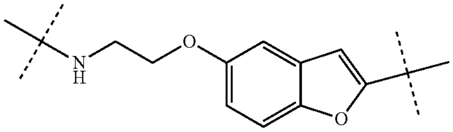
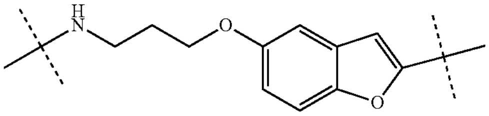
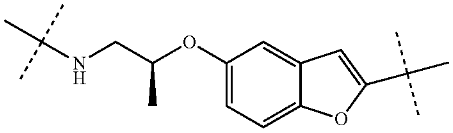
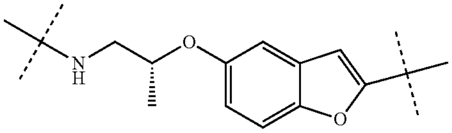
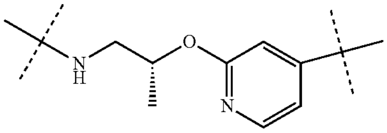
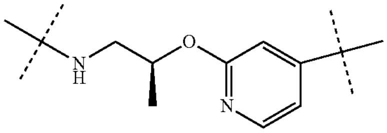
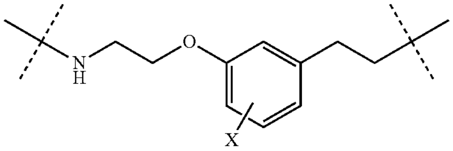
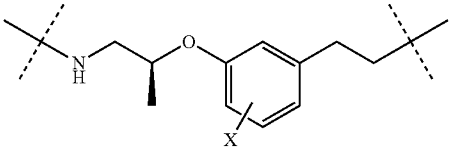
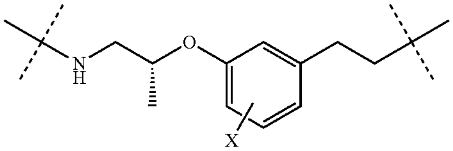
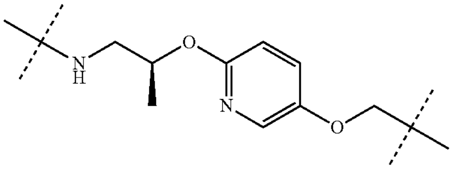
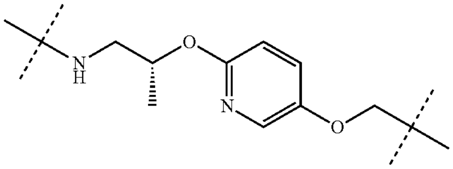
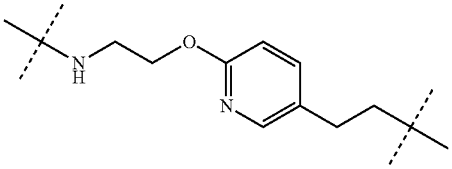
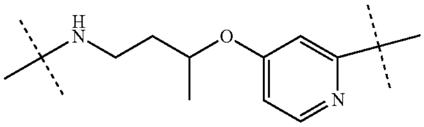
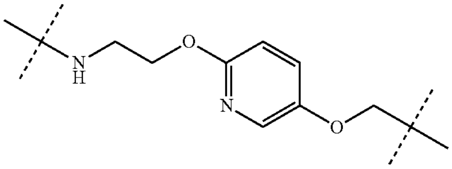

-continued
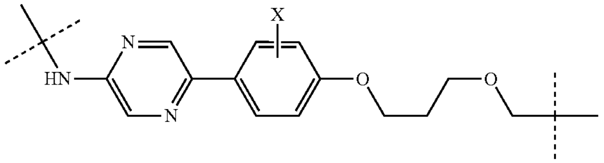
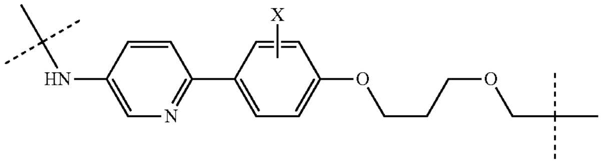
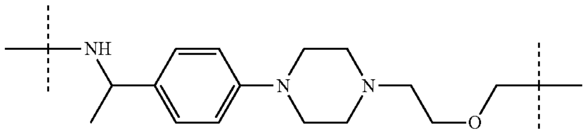
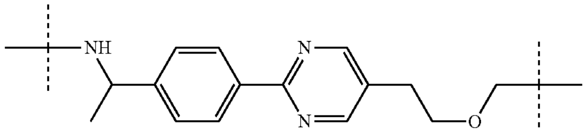
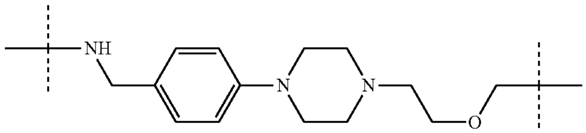
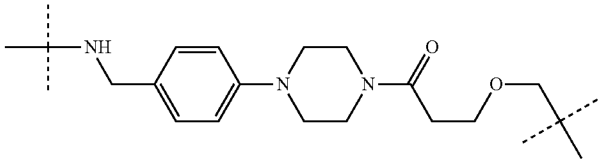
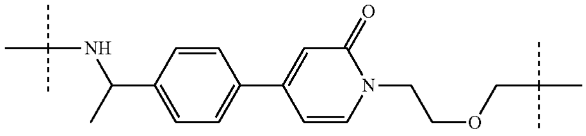
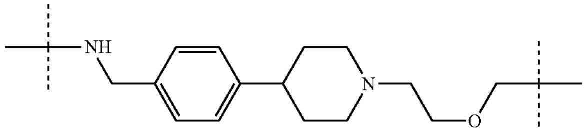
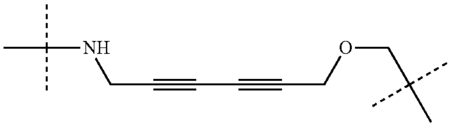
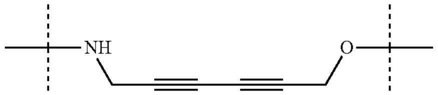
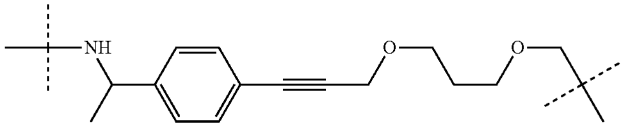
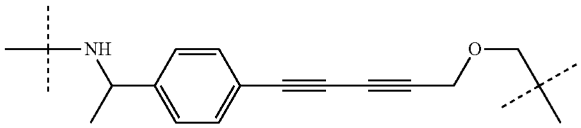
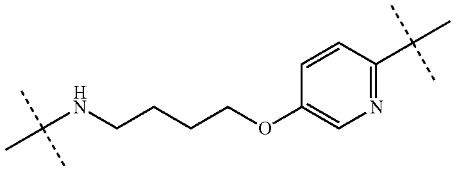
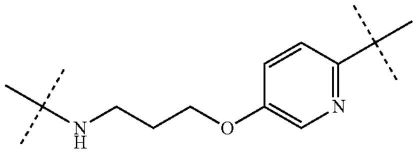
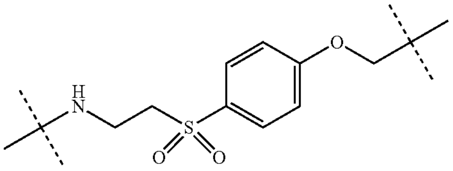

-continued
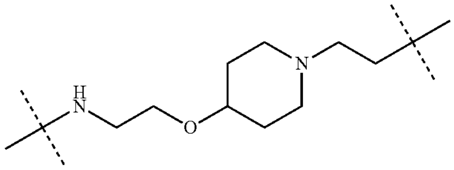
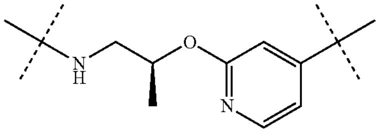
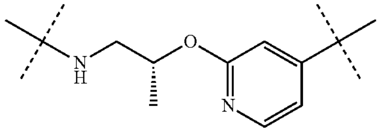
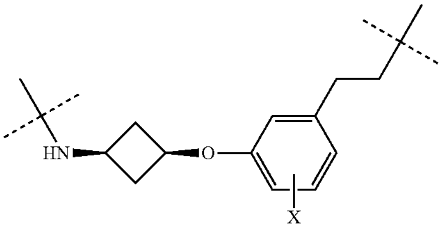
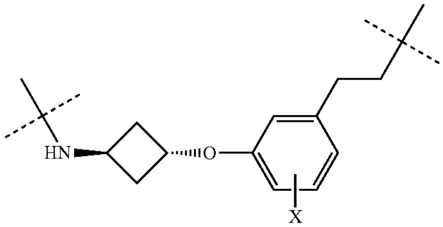
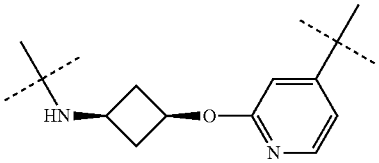
X = H, F
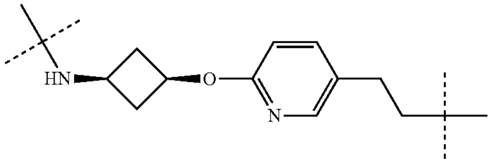
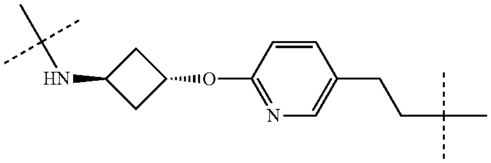
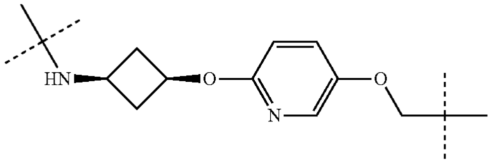
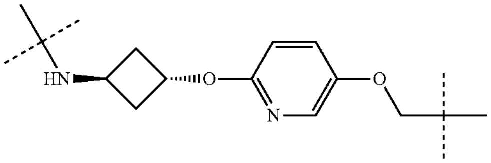
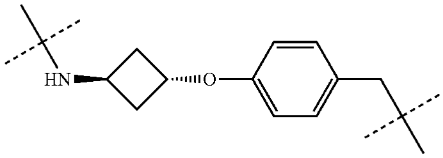
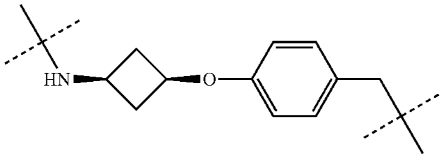
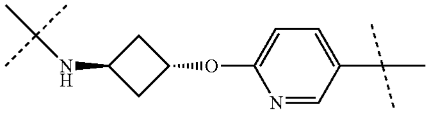
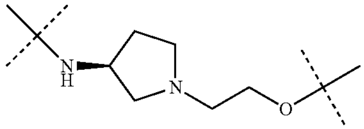
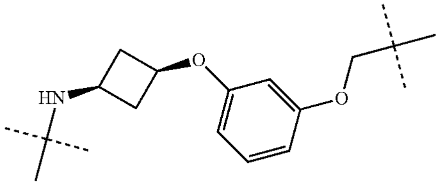
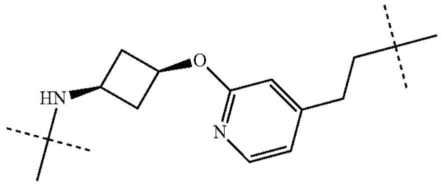
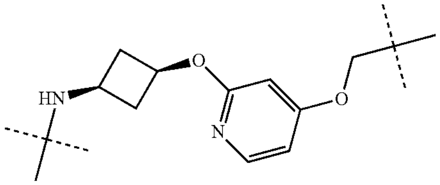
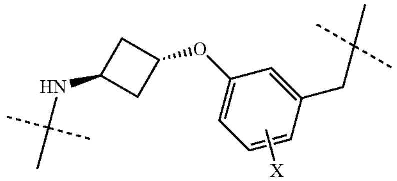

-continued
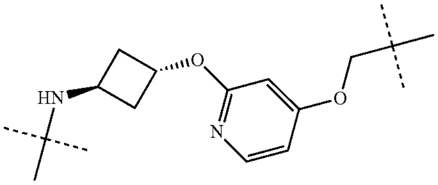
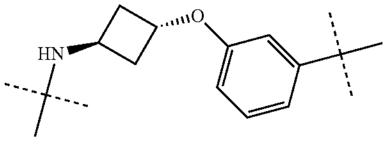
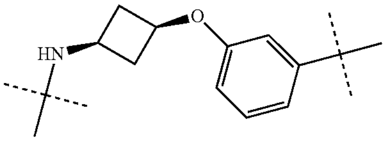
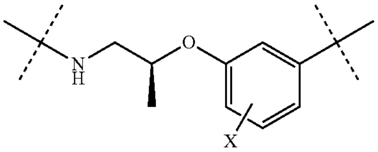
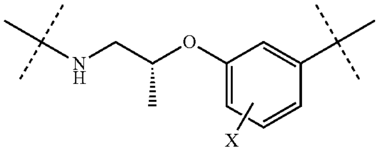
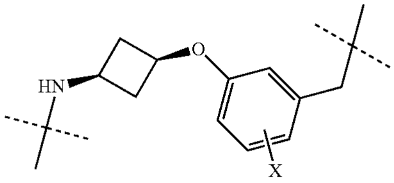
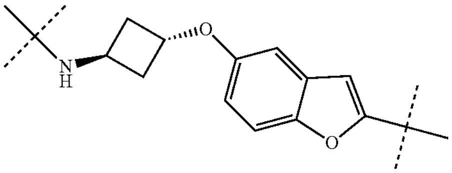
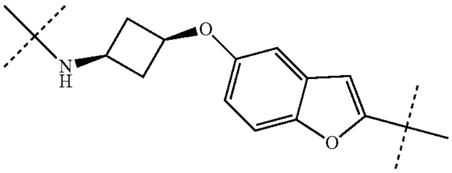
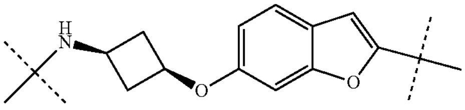
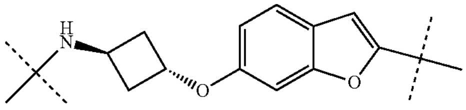
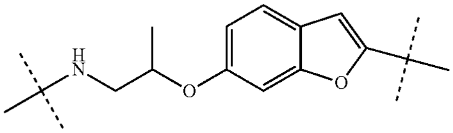
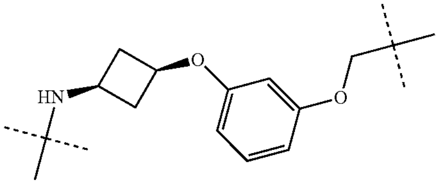
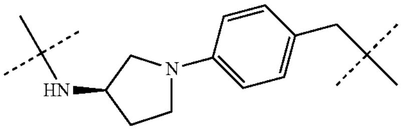
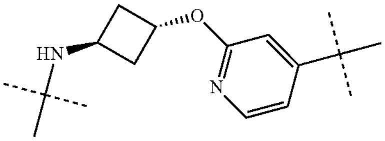
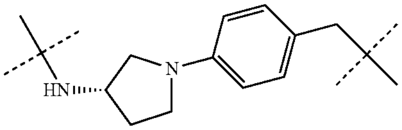
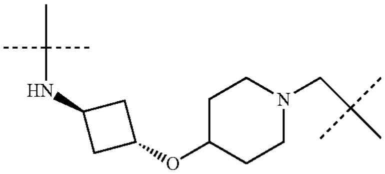
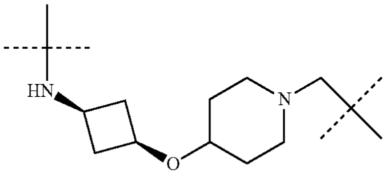
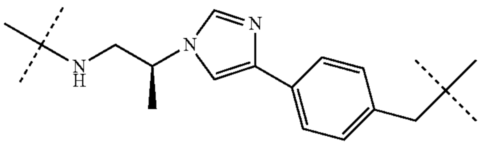
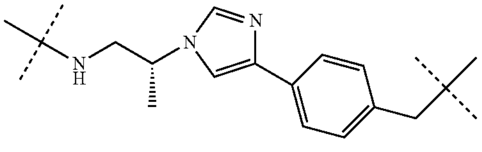
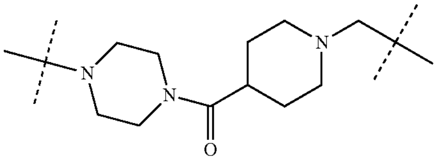

-continued
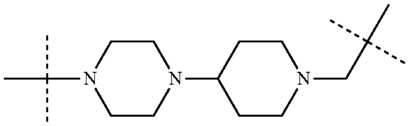
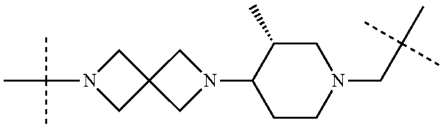
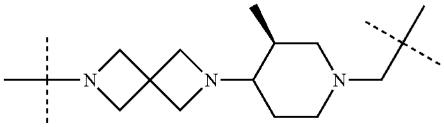
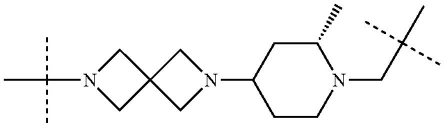
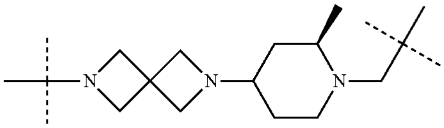
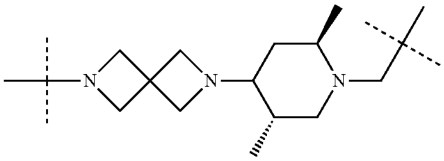
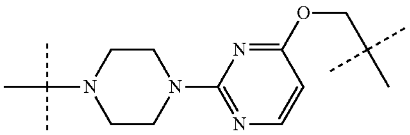
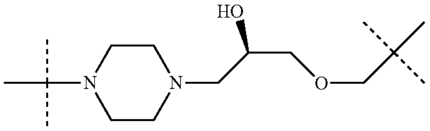
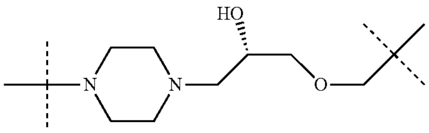
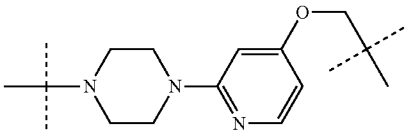
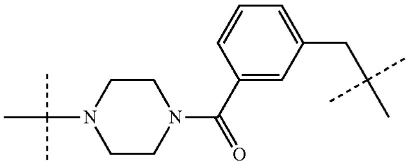
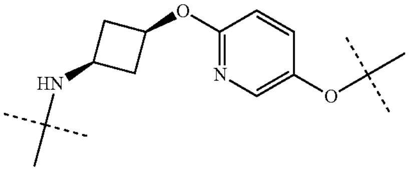
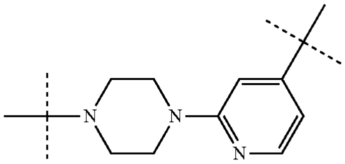
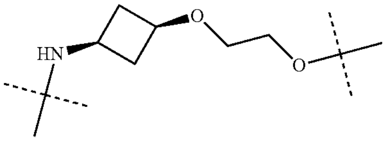
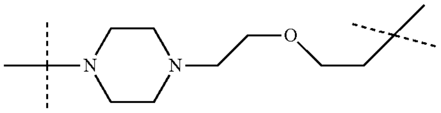
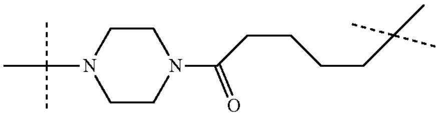
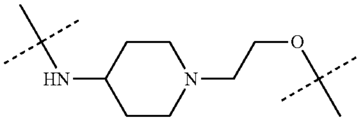
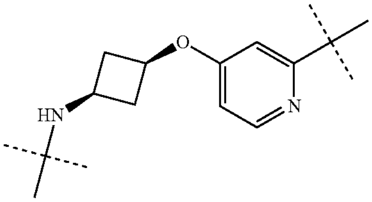
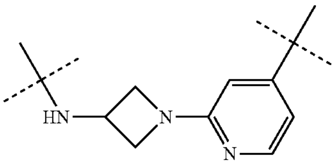
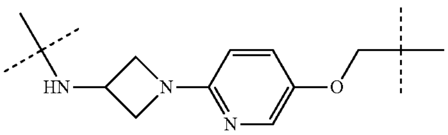
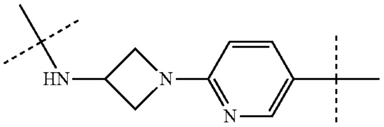
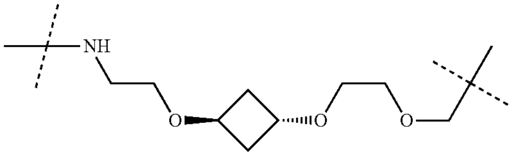
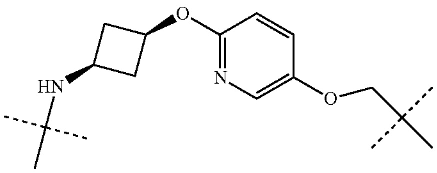

-continued
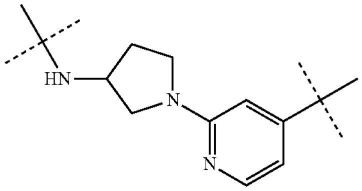
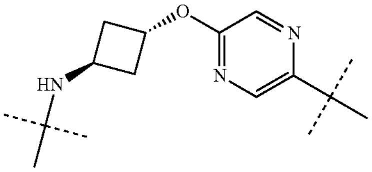
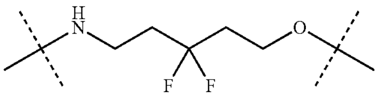
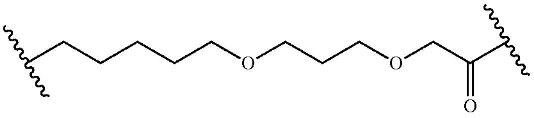;
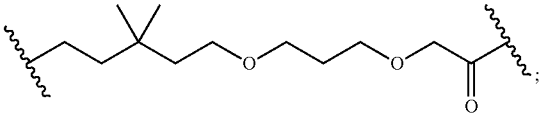;
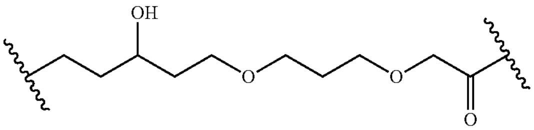;
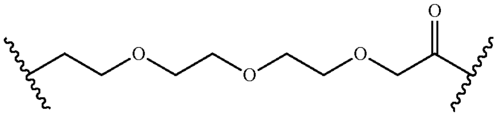;
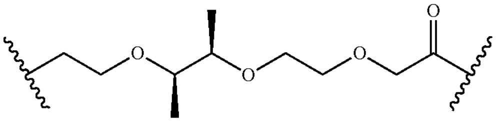;
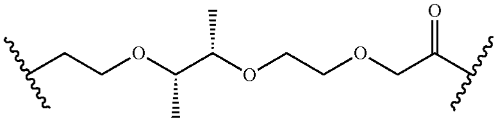;
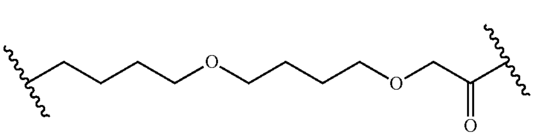;
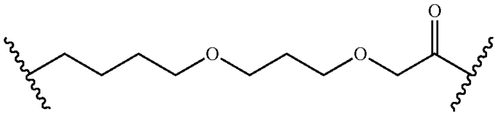;
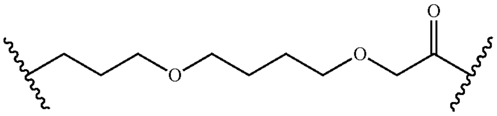;
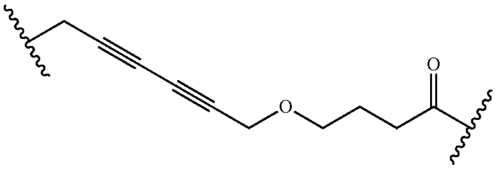;
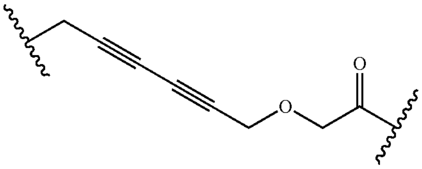;
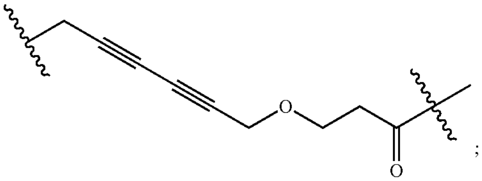;
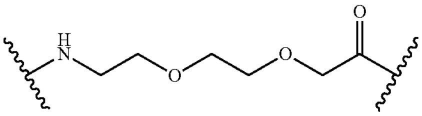;
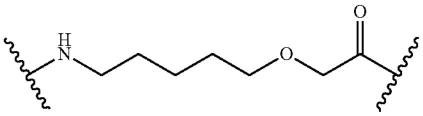;
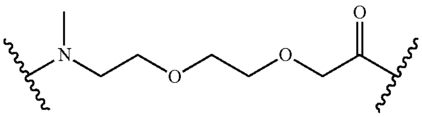;
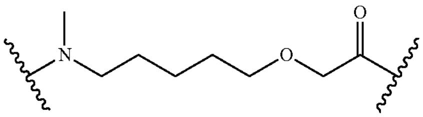;
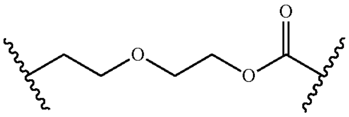;
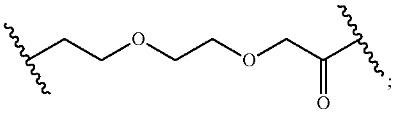;
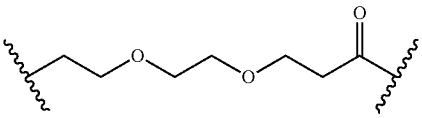;
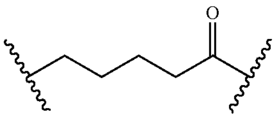;
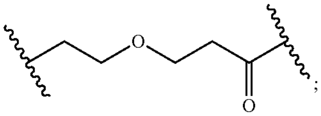;
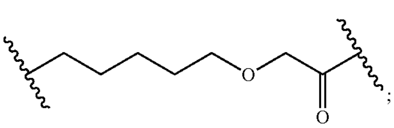;
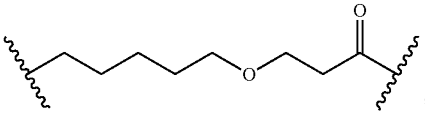;

-continued
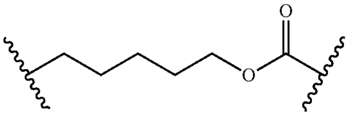
;
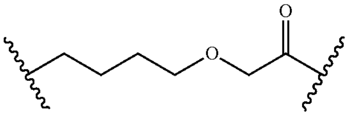
;
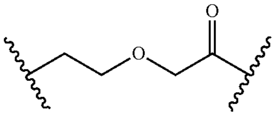
;
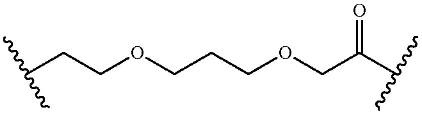
;
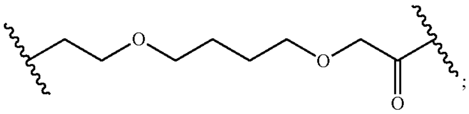
;
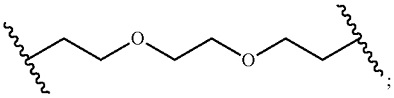
;
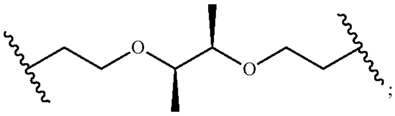
;
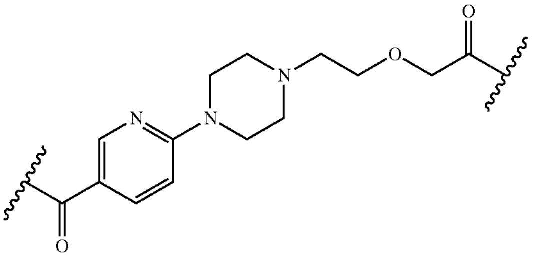
;
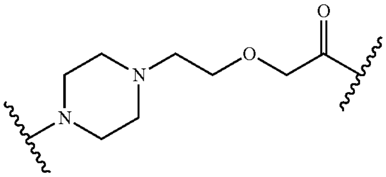
;
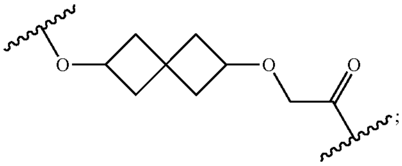
;
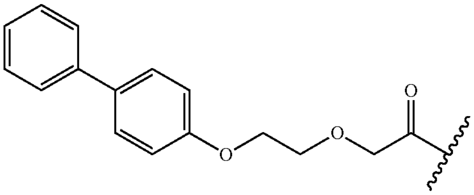
;
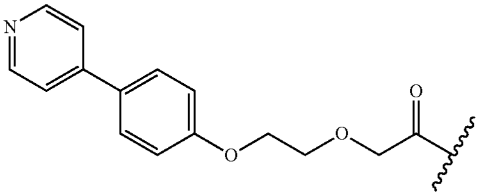
;
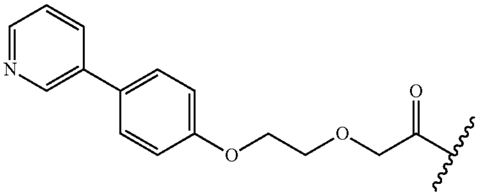
;
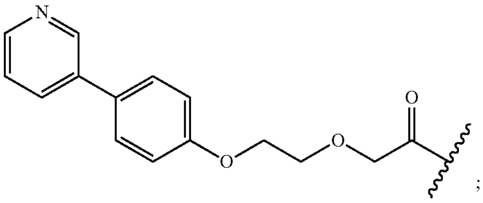
;
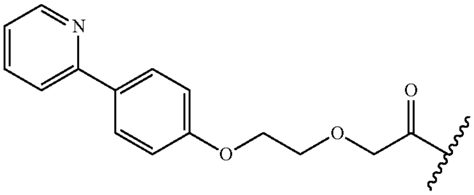
;
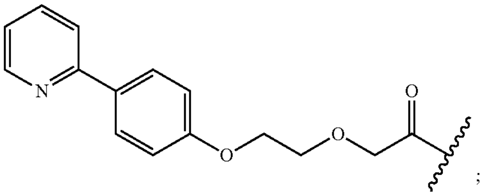
;
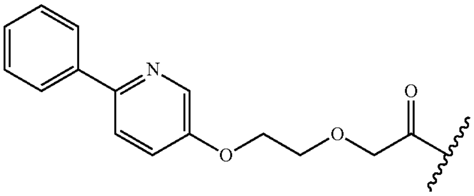
;
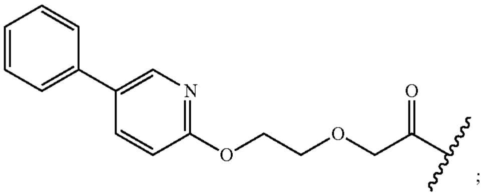
;
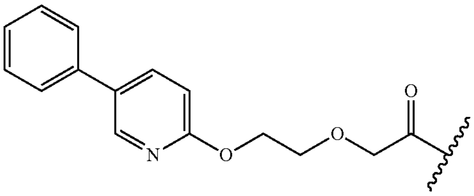
;

-continued
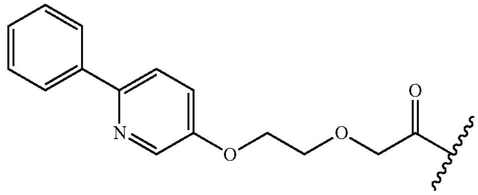
;
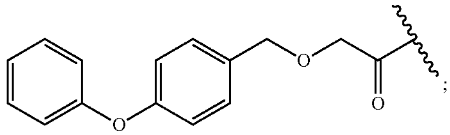
;
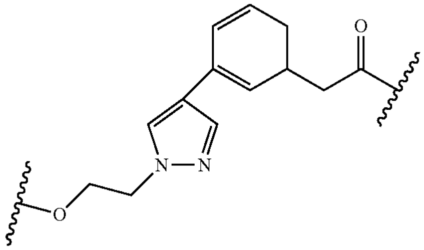
;
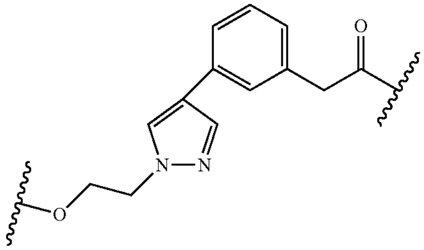
;
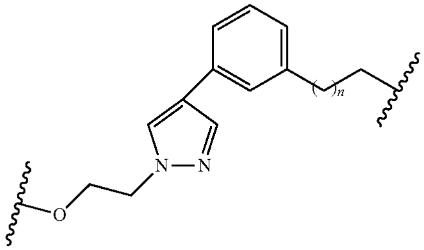
;
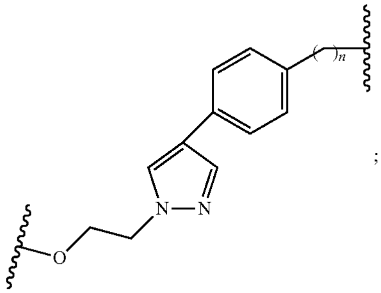
;
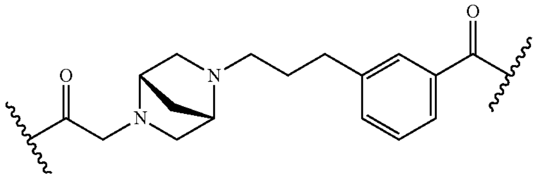
;
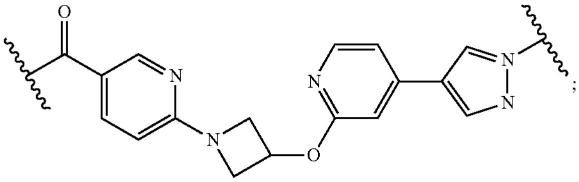
;
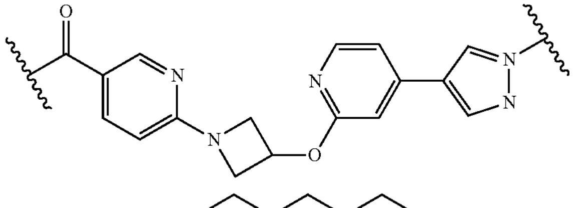
;
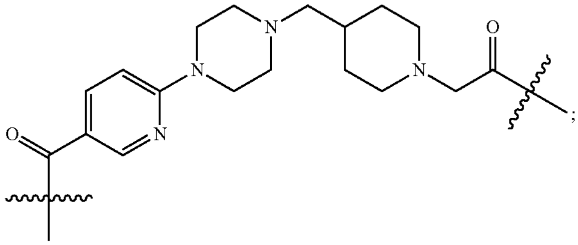
;
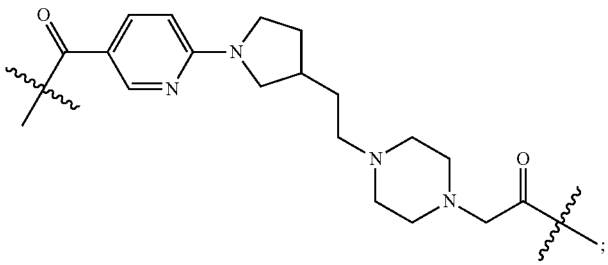
;

-continued
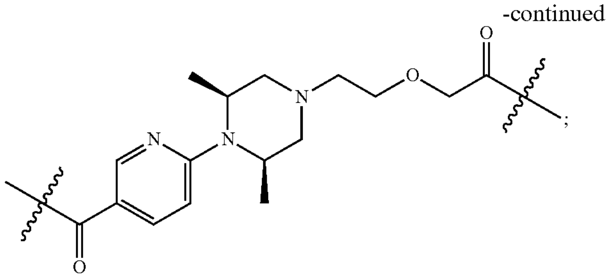
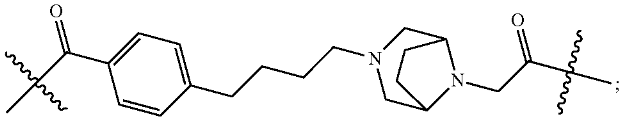
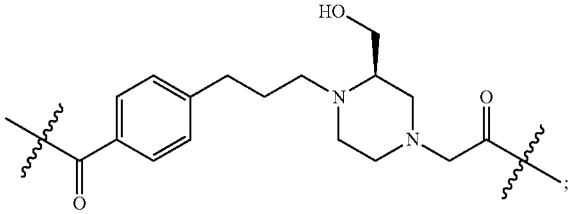
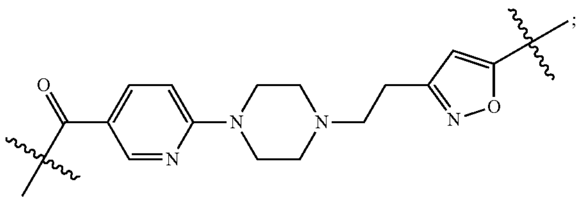
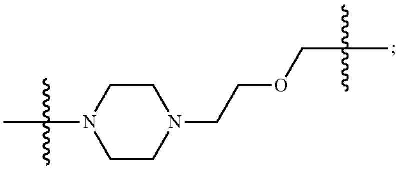
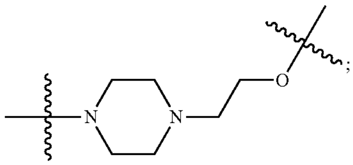
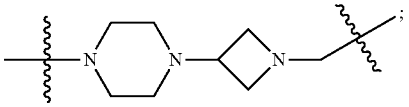
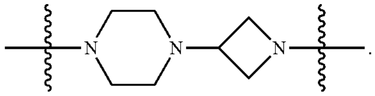
In aspect or embodiment described herein, the linker (L) is selected from the group consisting of:
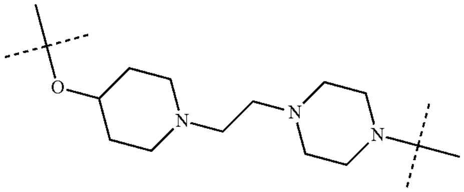
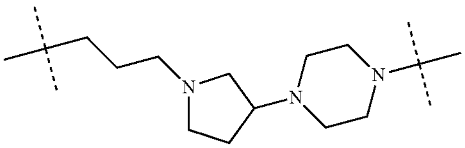
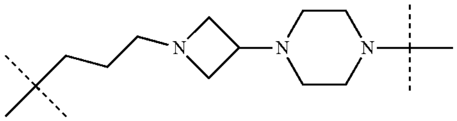
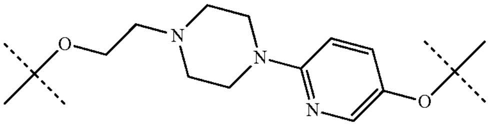
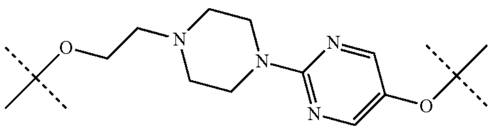
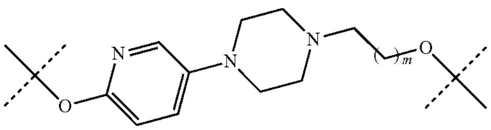

-continued
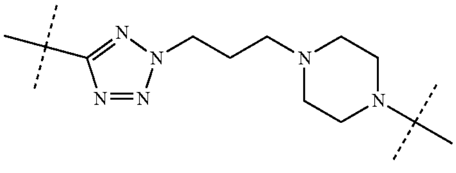
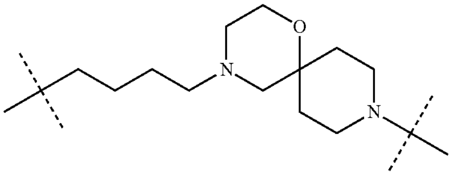
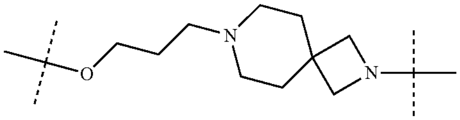
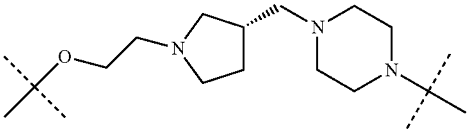
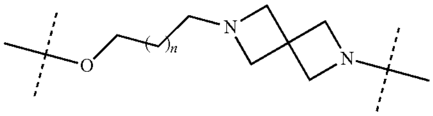
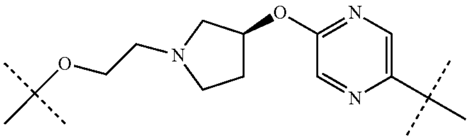
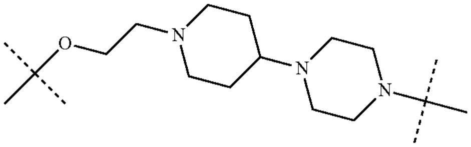
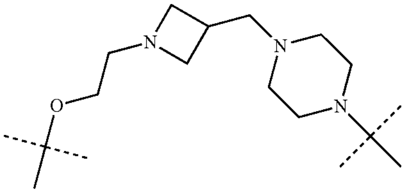
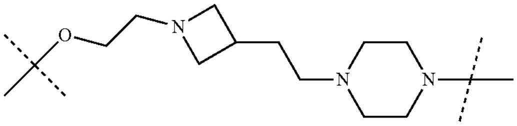
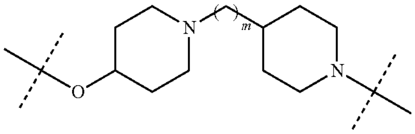
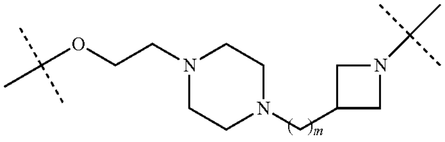
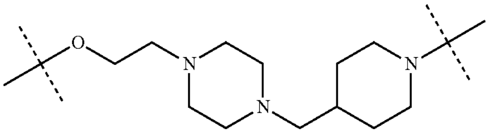
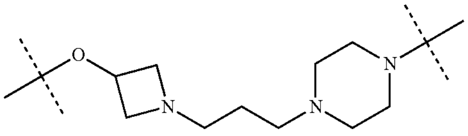
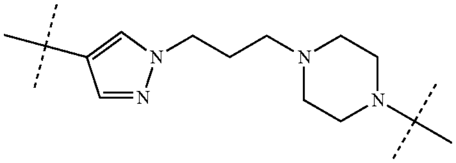
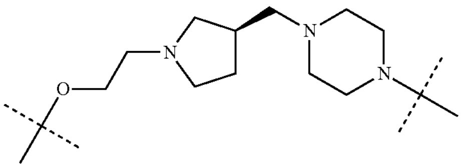
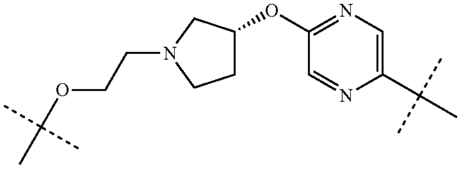
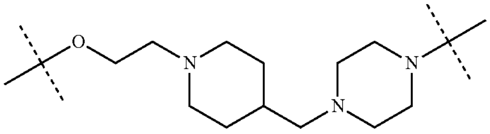
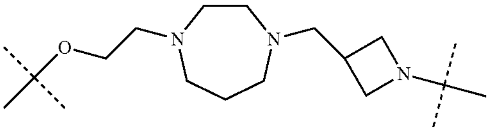
m = 1, 2; n = 0, 1
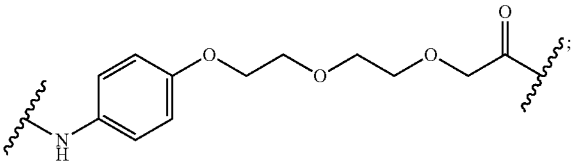;

-continued
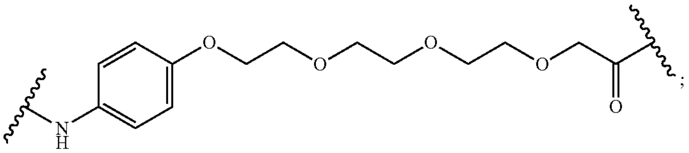
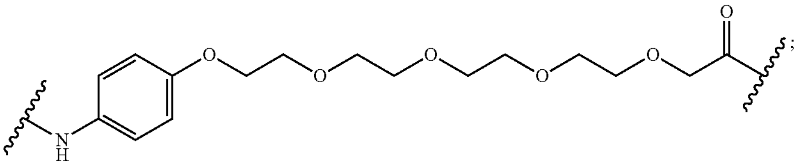
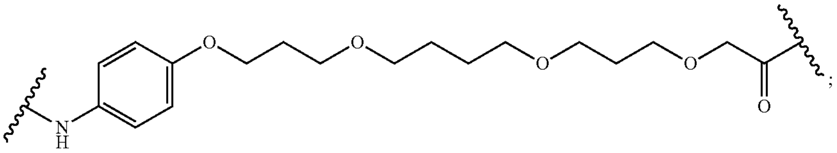
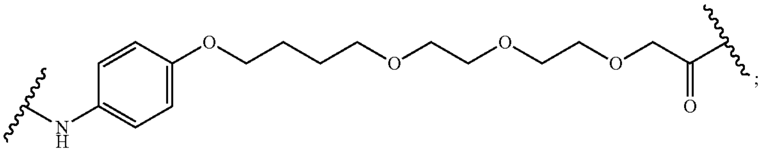
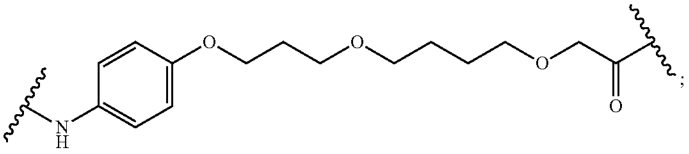
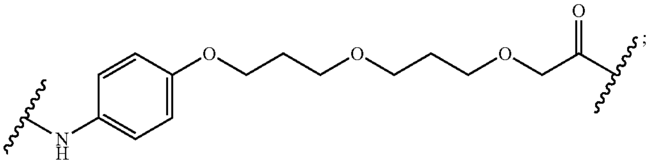
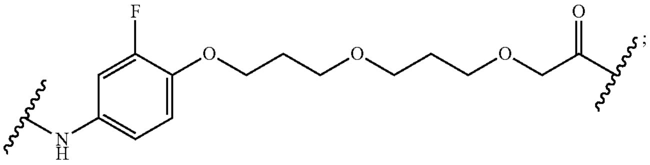
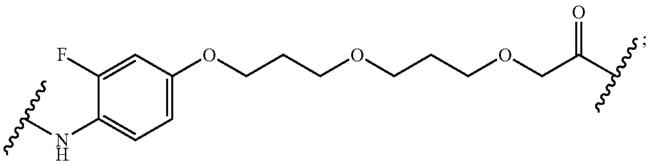
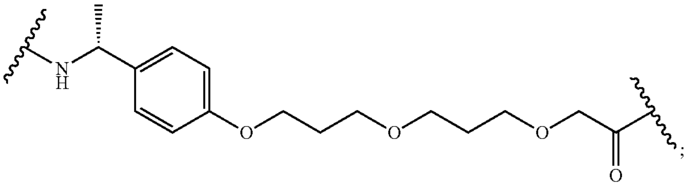
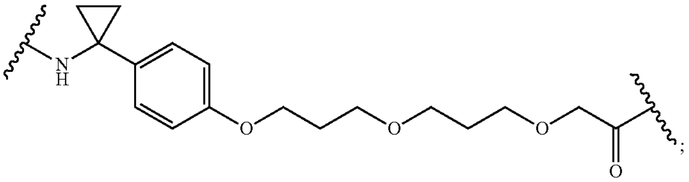

-continued
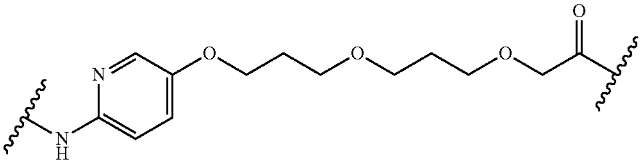
;
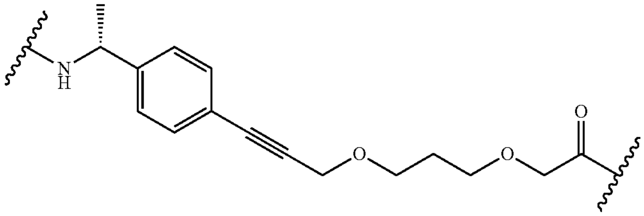
;
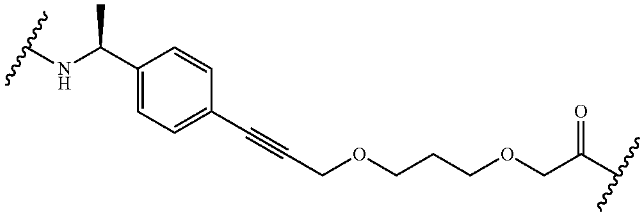
;
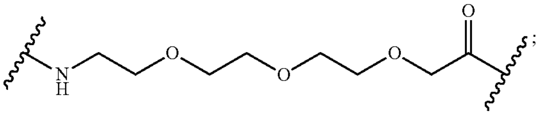
;
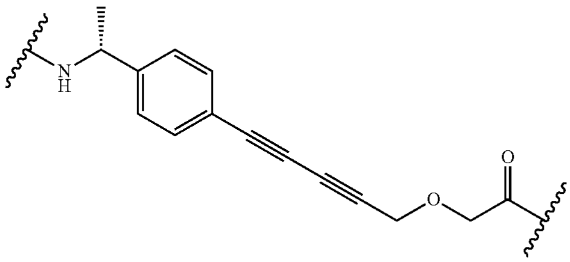
;
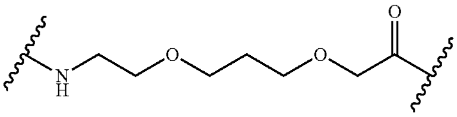
;
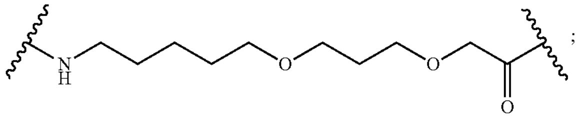
;
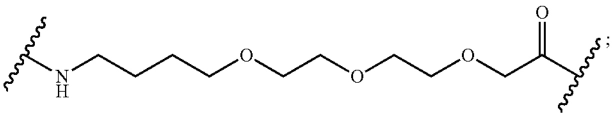
;
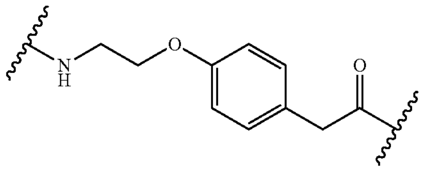
;
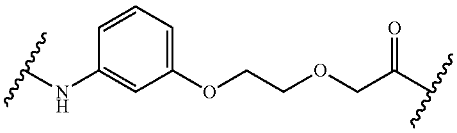
;
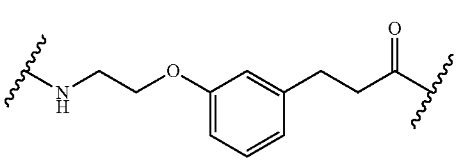
;
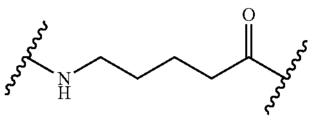
;
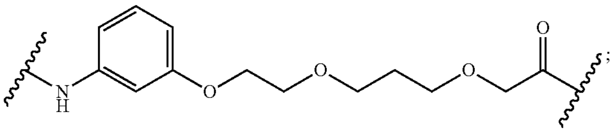
;
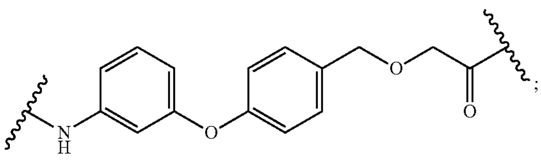
;
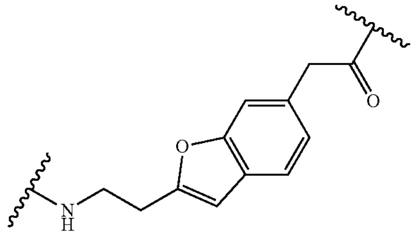
;

-continued
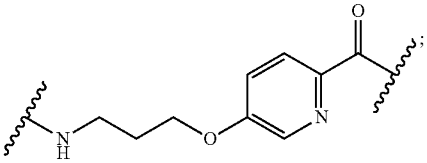
;
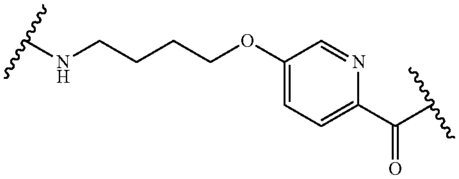
;
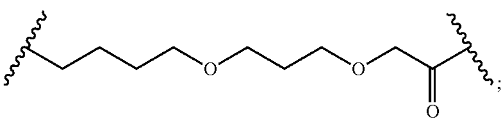
;
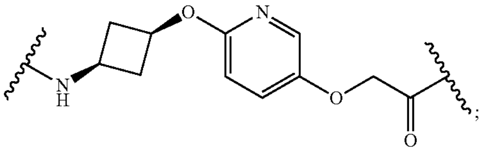
;
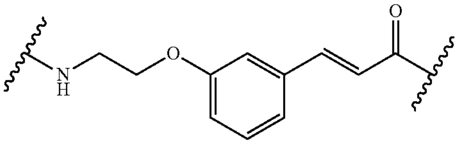
;
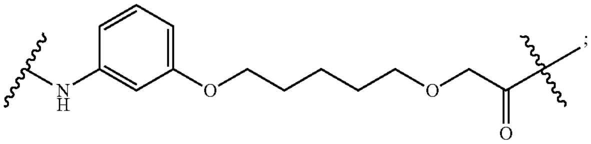
;
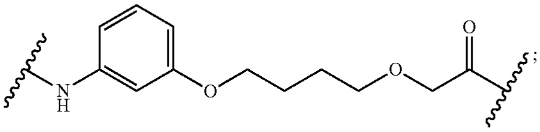
;
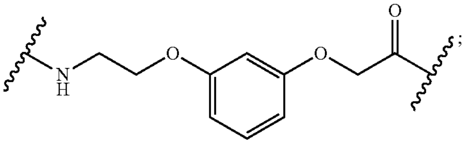
;
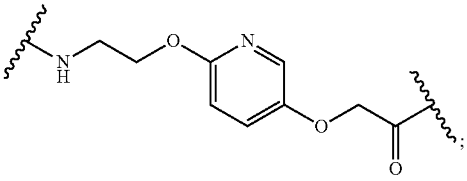
;
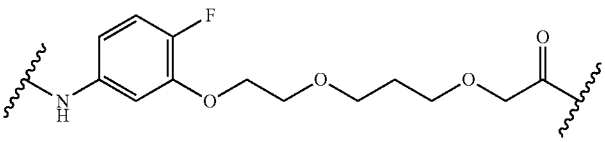
;
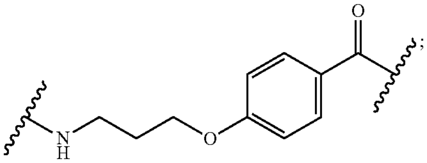
;
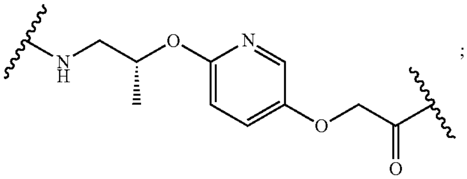
;
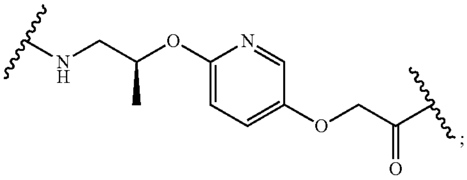
;
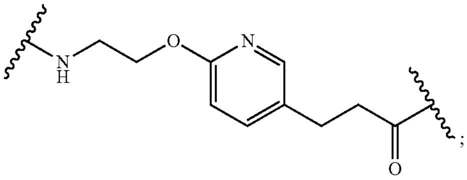
;
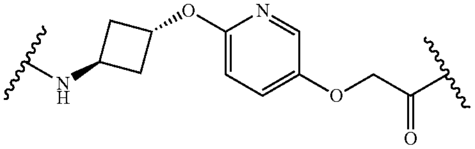
;
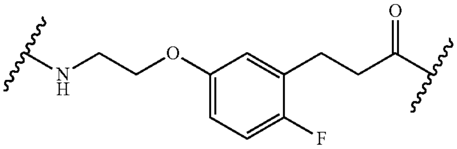
;
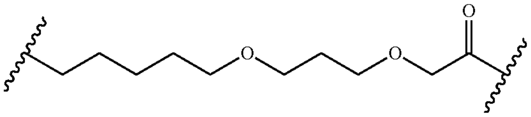
;
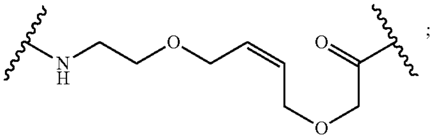
;
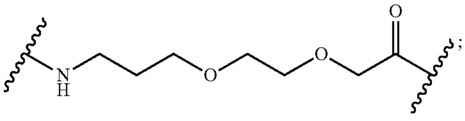
;
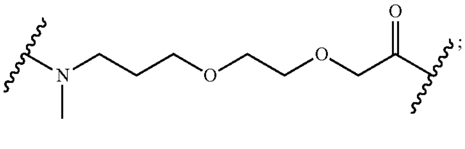
;

-continued
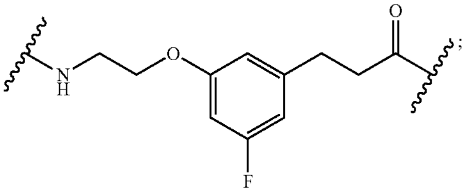
;
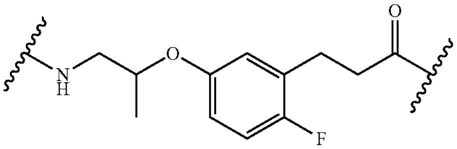
;
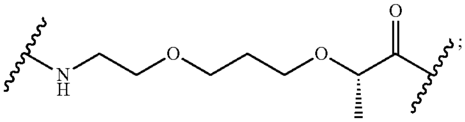
;
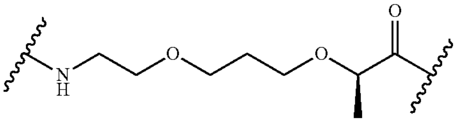
;
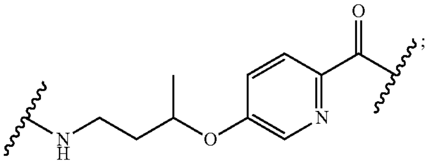
;
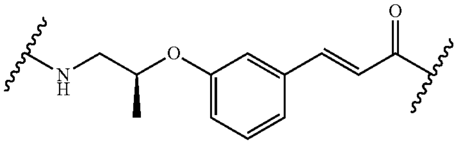
;
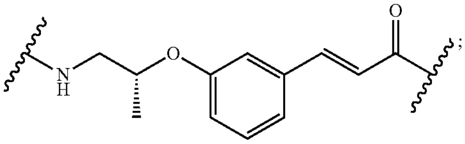
;
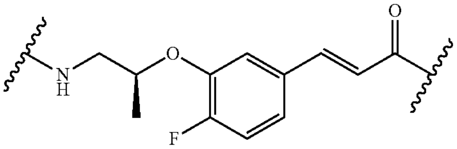
;
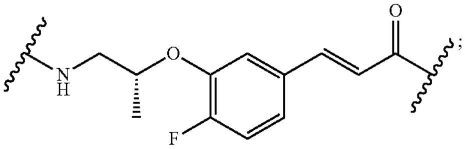
;
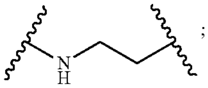
;
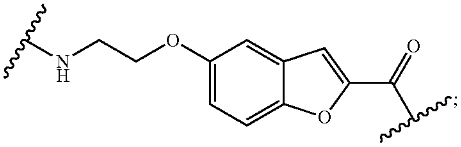
;
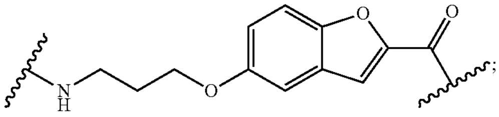
;
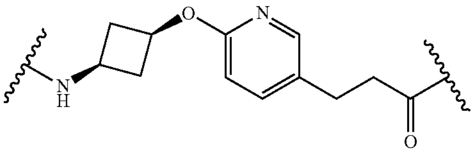
;
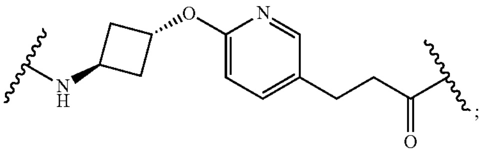
;
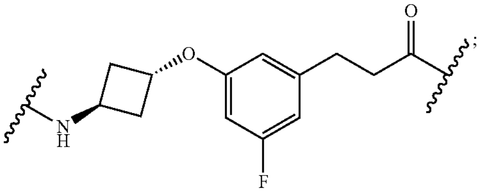
;
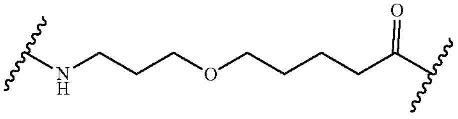
;
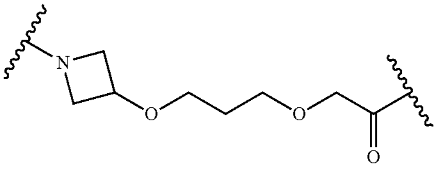
;
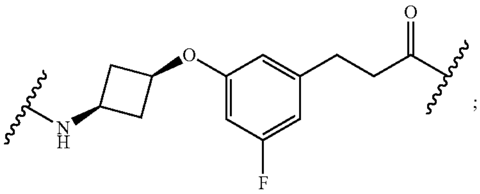
;
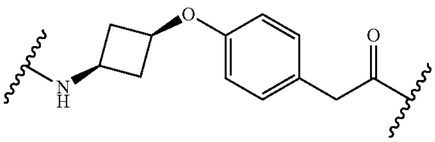
;
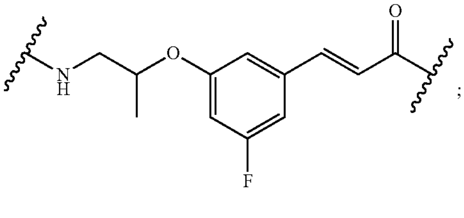
;

-continued
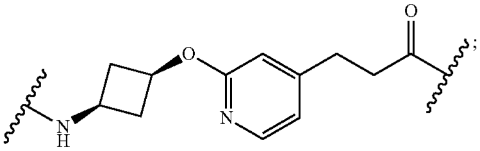
;
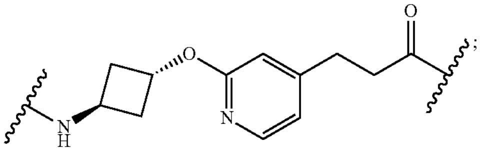
;
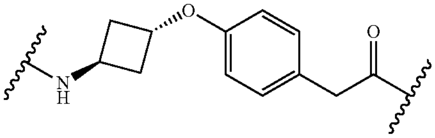
;
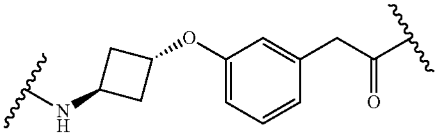
;
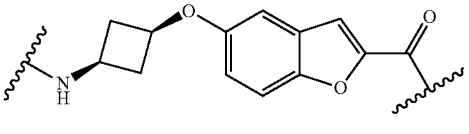
;
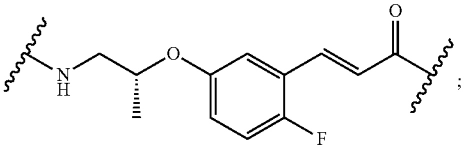
;
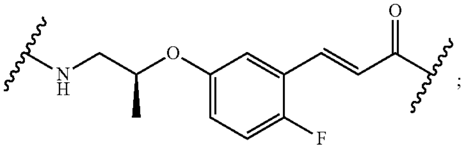
;
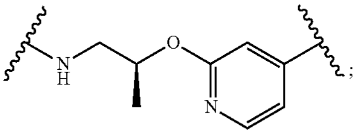
;
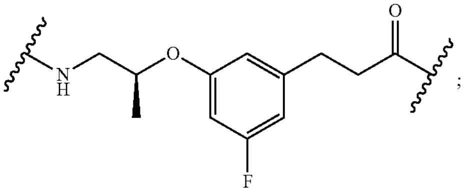
;
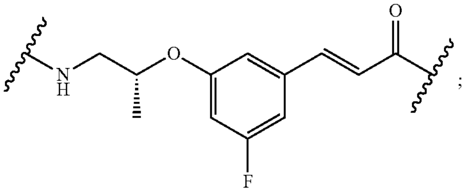
;
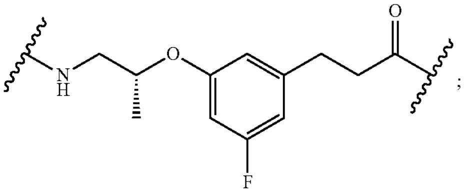
;
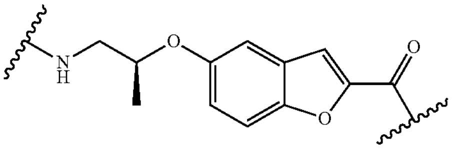
;
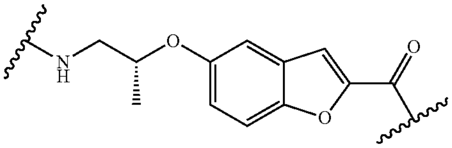
;
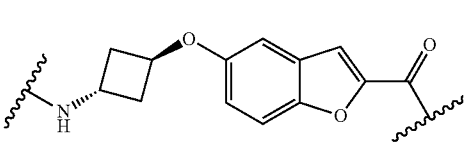
;
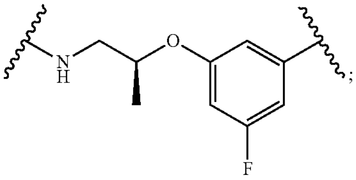
;
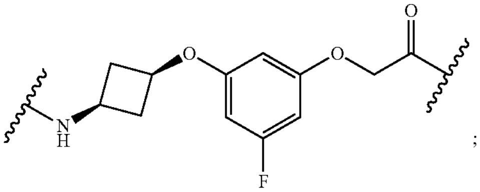
;
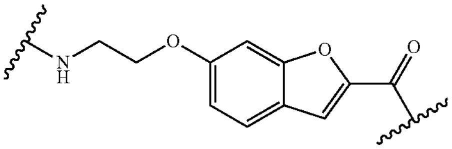
;
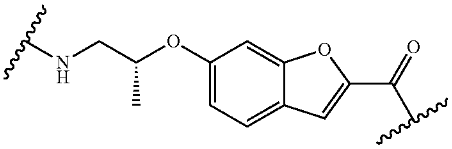
;
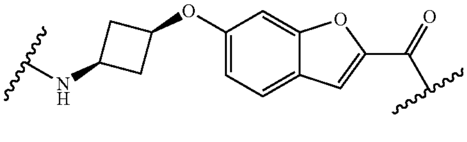
;
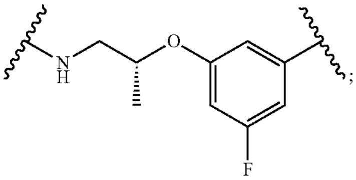
;

-continued
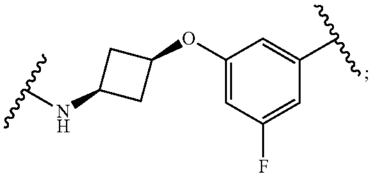
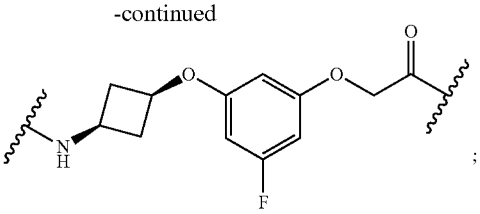
;
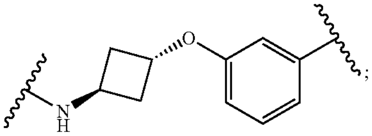
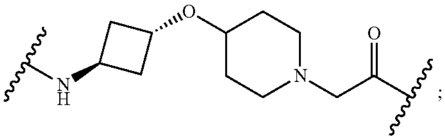
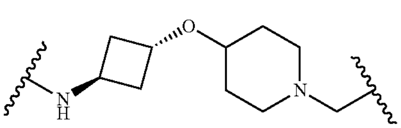
and
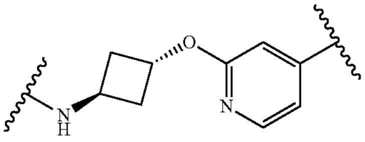
.
In aspect or embodiment described herein, the linker (L) is selected from the group consisting of:
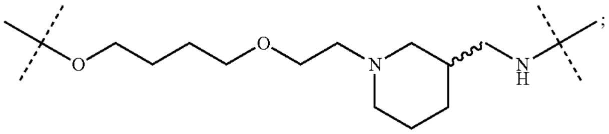
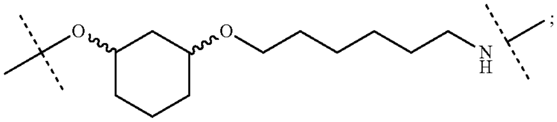
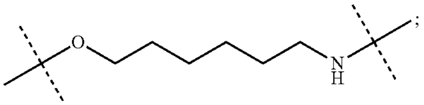
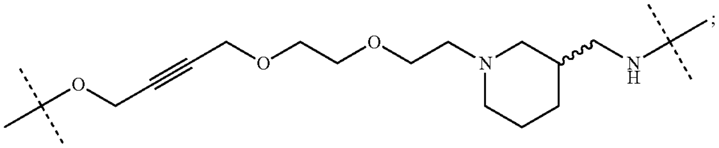
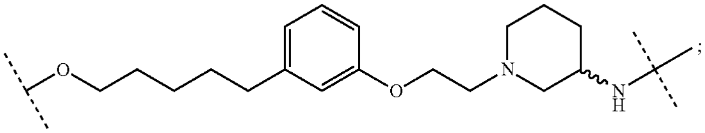
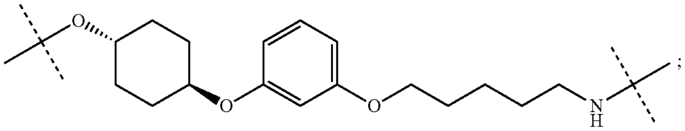
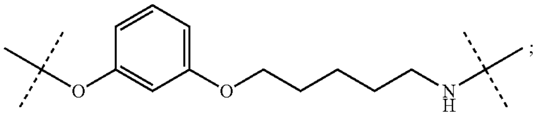
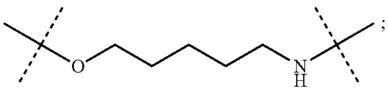
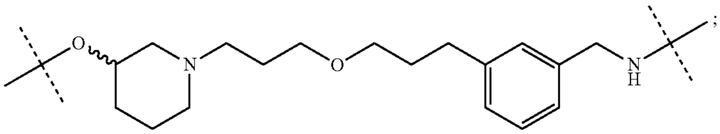

-continued
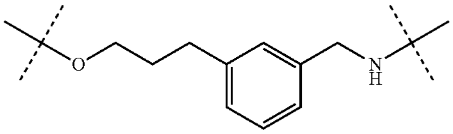
;
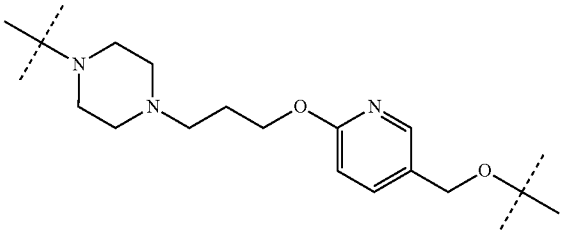
;
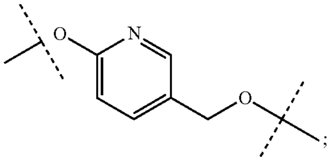
;
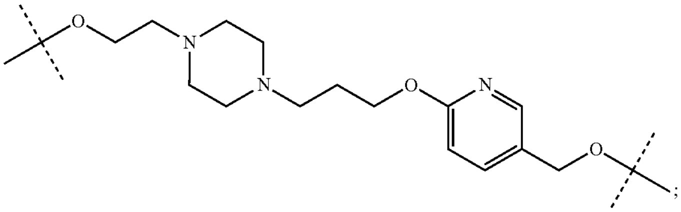
;
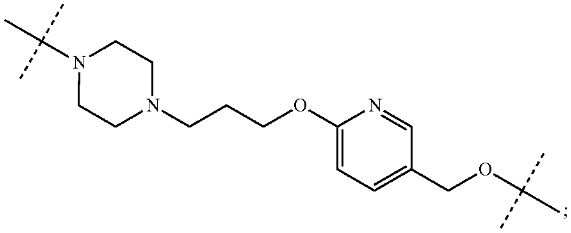
;
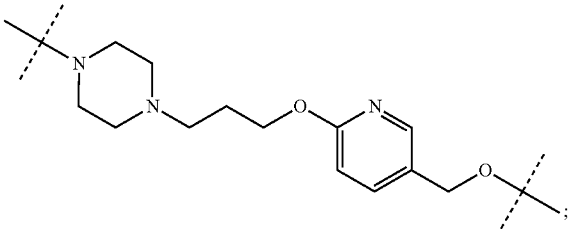
;
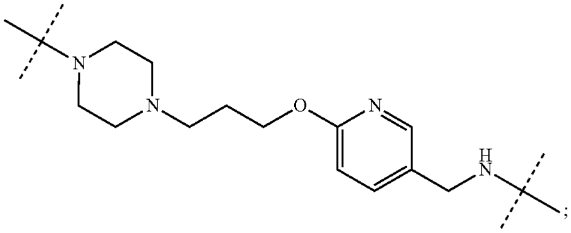
;
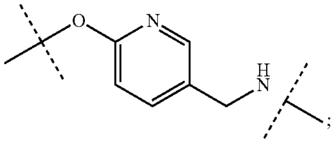
;
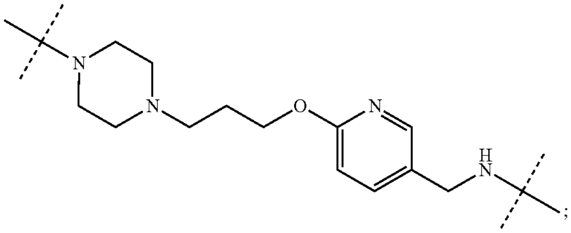
;
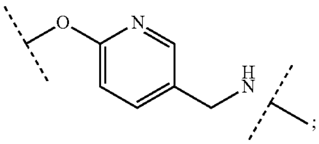
;
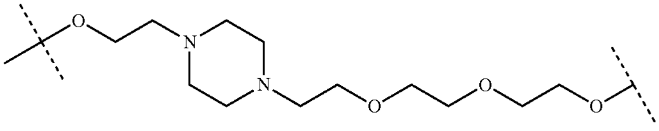
;
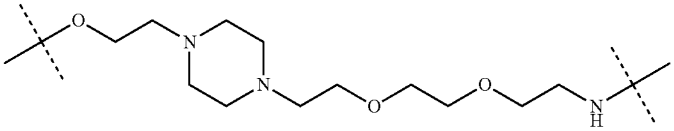
;

-continued
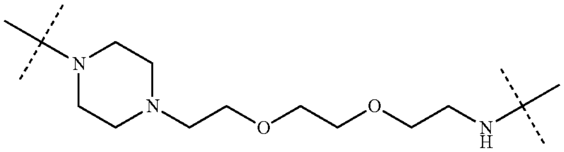
;
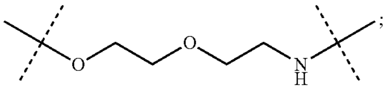
;
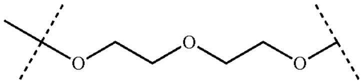
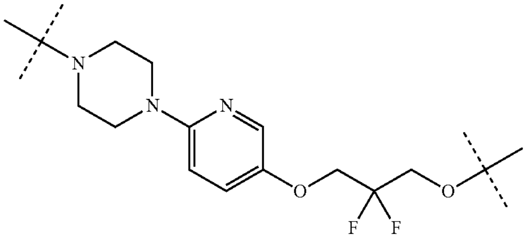
;
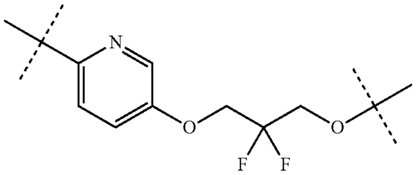
;
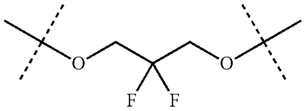
;
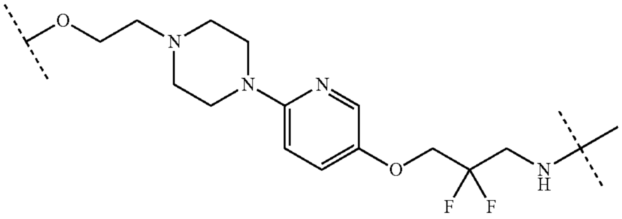
;
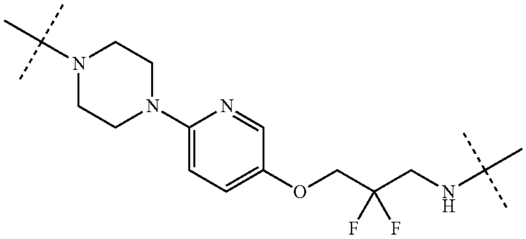
;
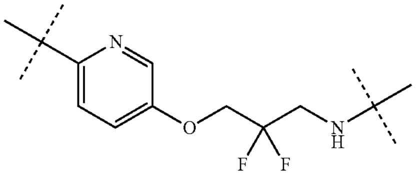
;
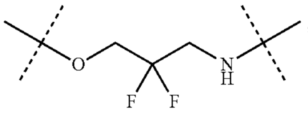
;
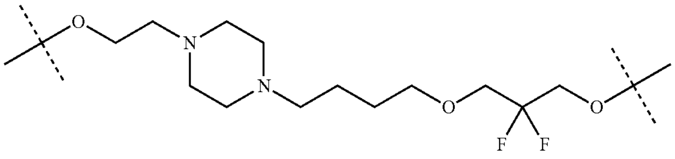
;
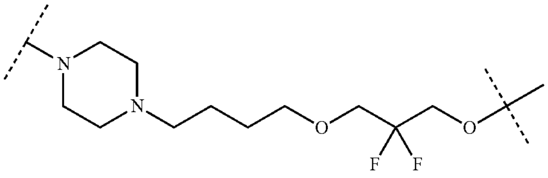
;
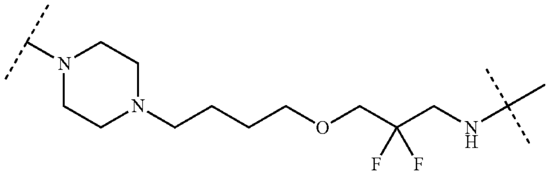
;
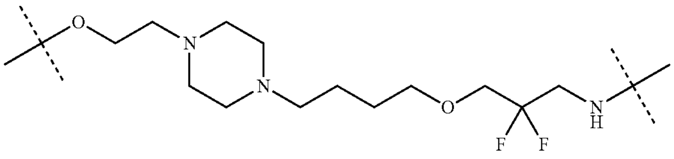
;
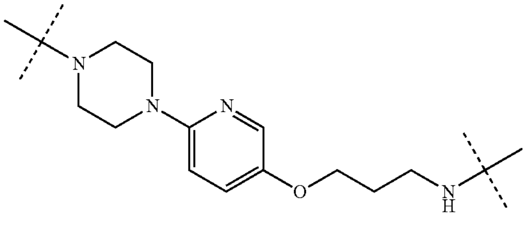
;
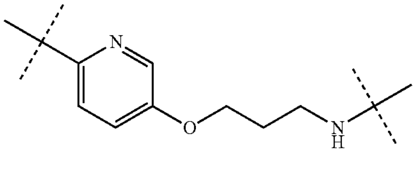
;

-continued
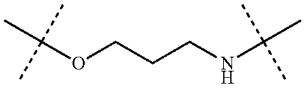;
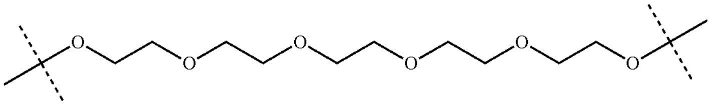;
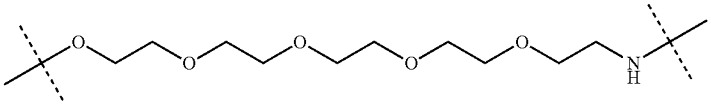
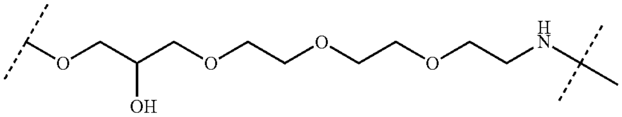;
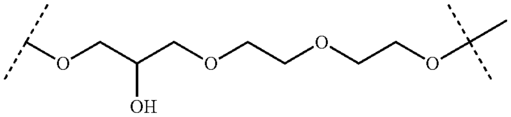;
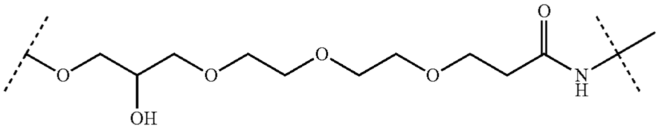;
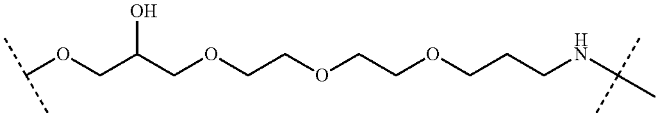;
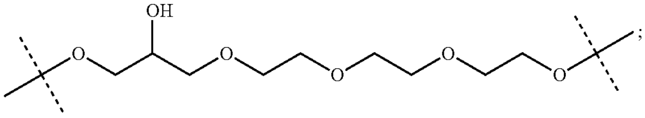;
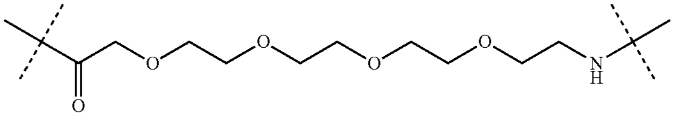;
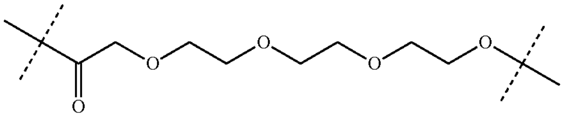;
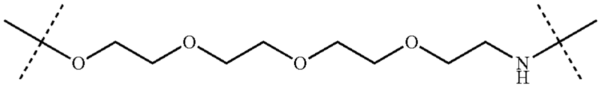;
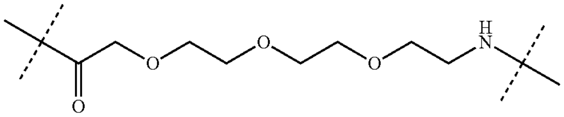;
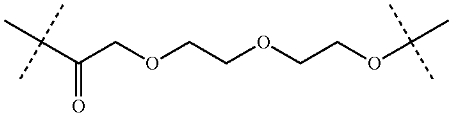;
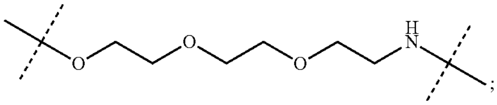;
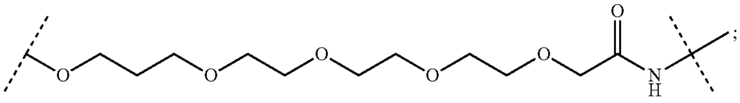;
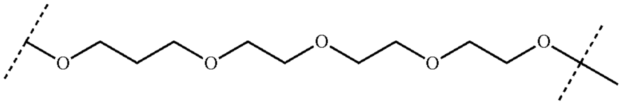;
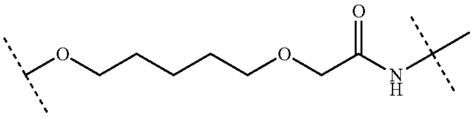;
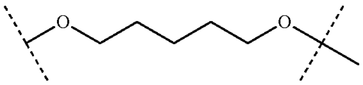;
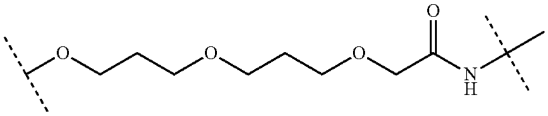;

-continued
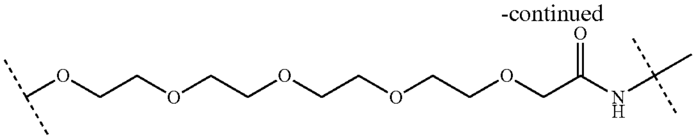
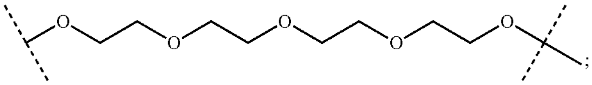 ; 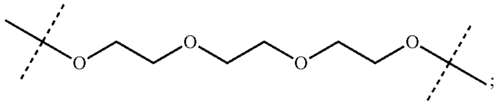 ;
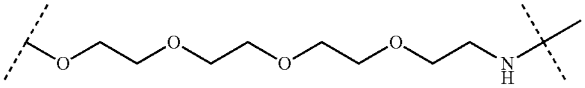 ; 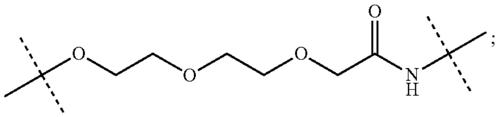 ;
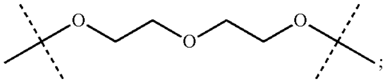 ; 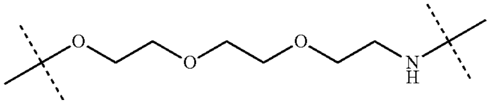 ;
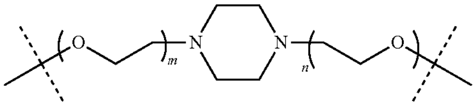 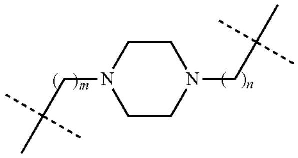
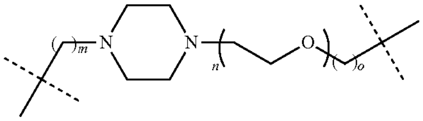 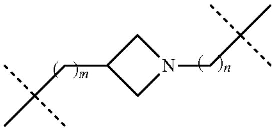
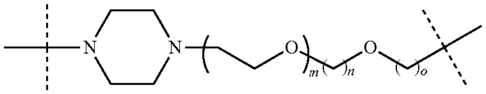 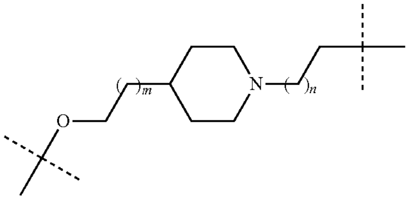
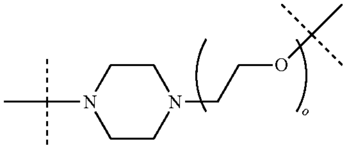 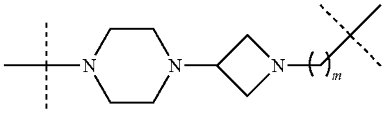
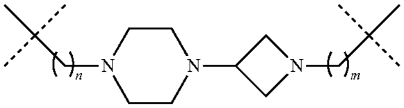 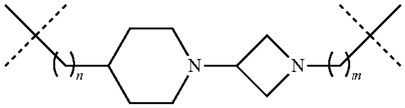
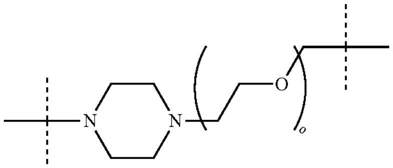 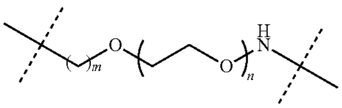 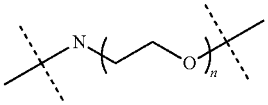
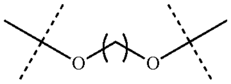 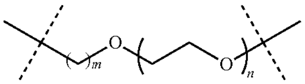 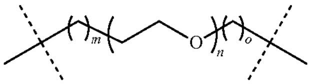
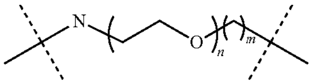 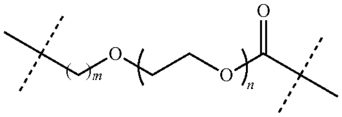 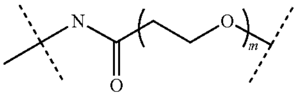
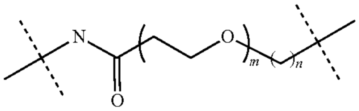 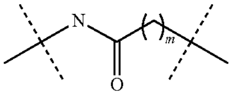 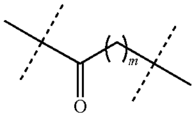

-continued
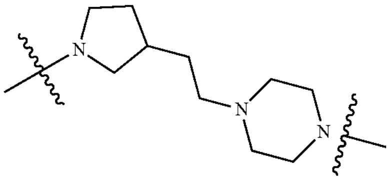 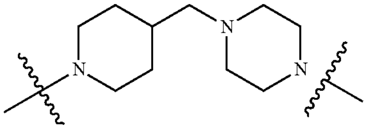
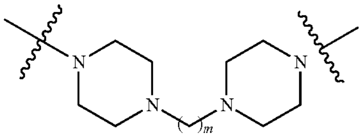 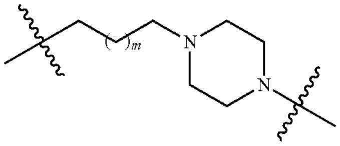 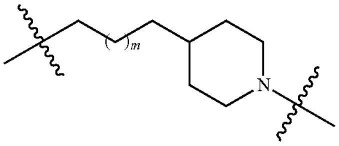
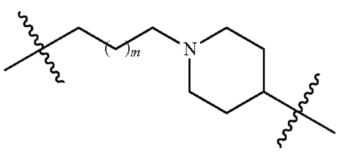 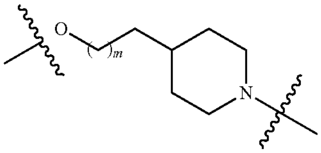 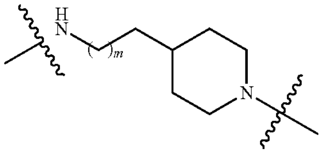
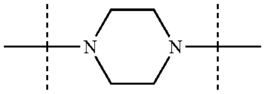 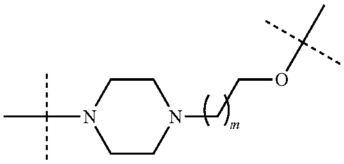 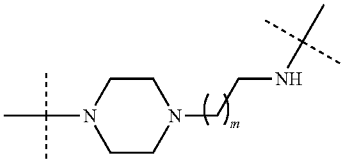
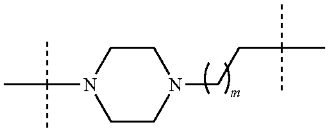 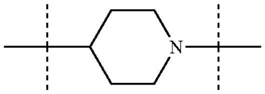 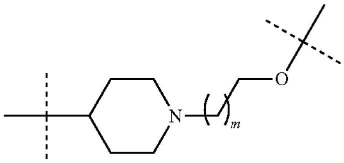
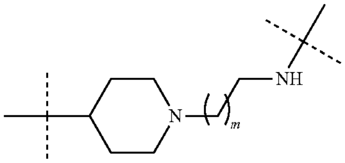 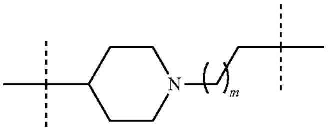
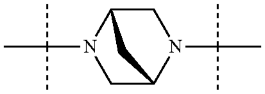 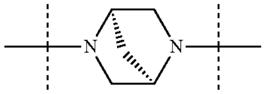 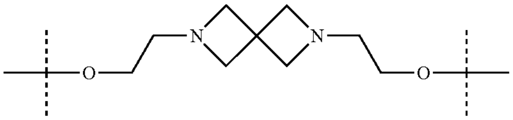
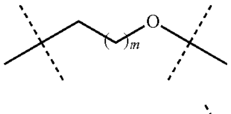 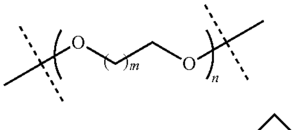 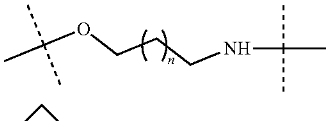
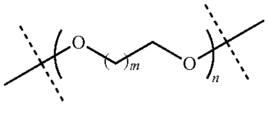 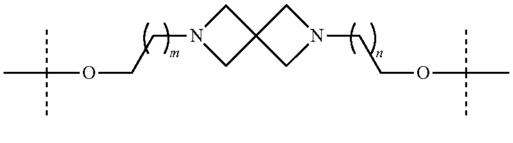
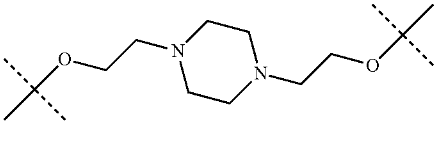 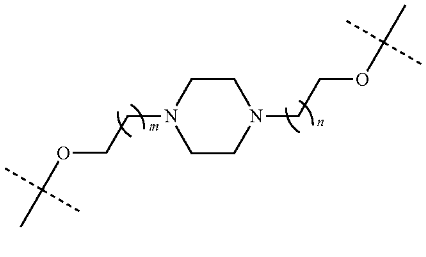

-continued
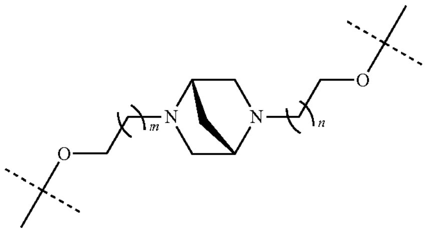
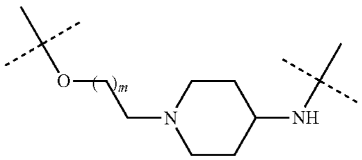
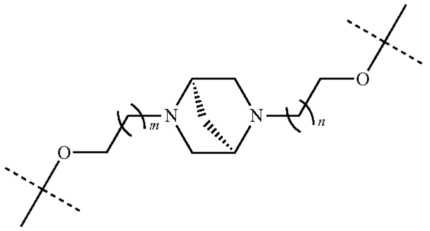
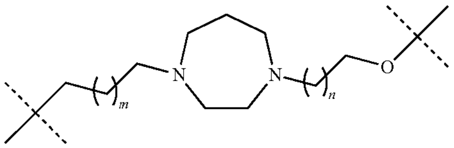
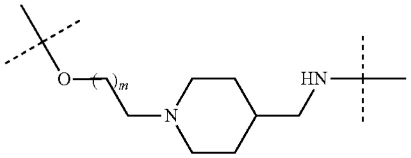
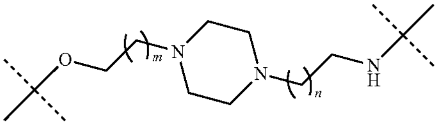
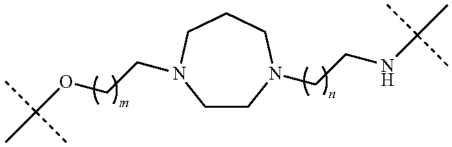
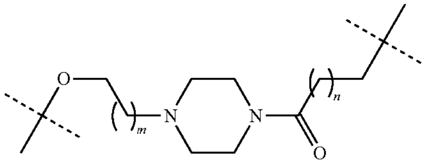
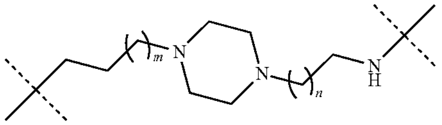
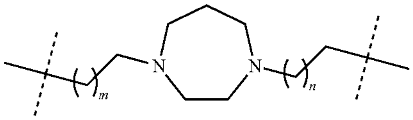
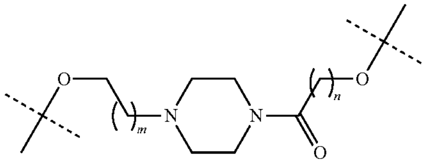
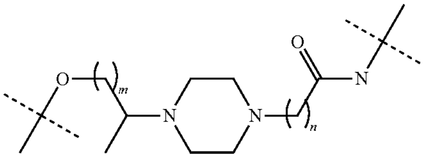
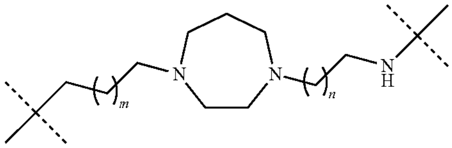
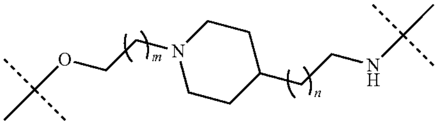
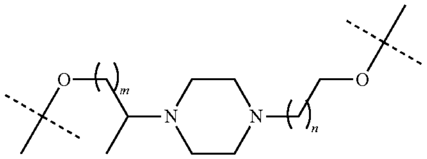
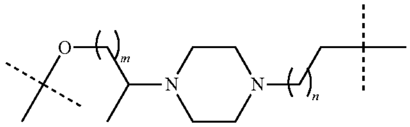
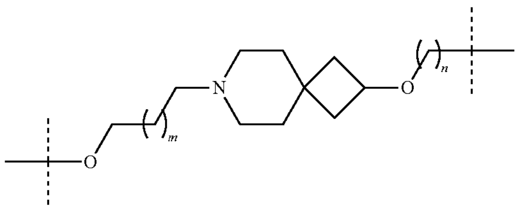
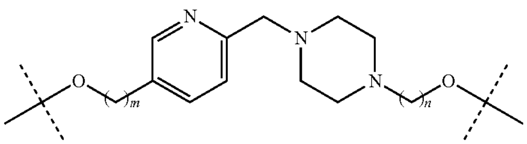

-continued
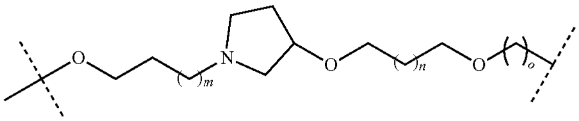
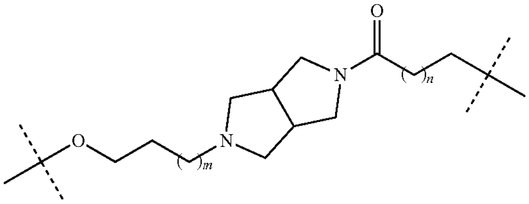
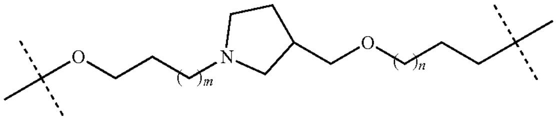
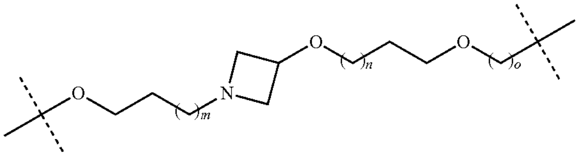
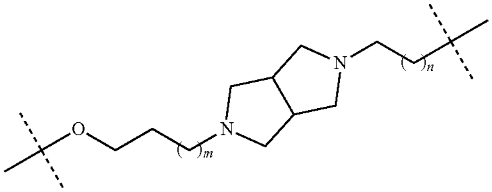
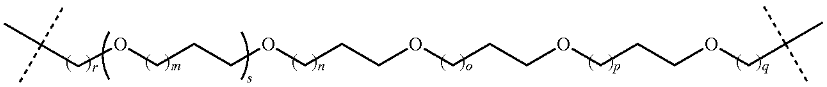
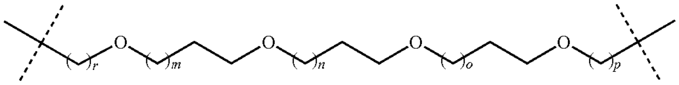
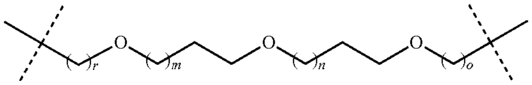
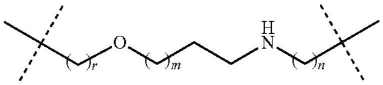
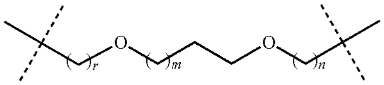
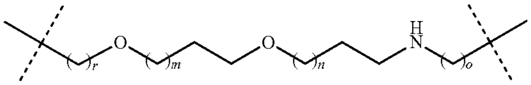
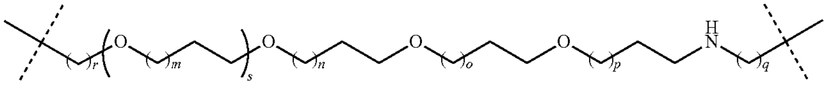
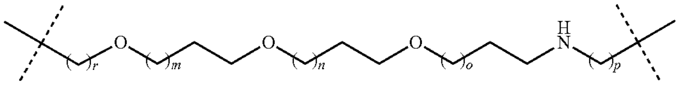
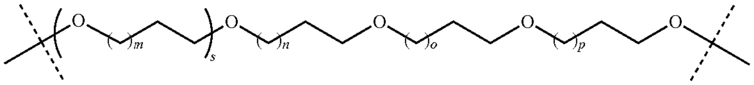
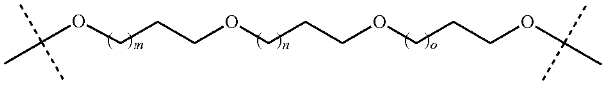
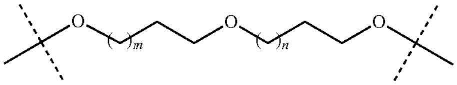
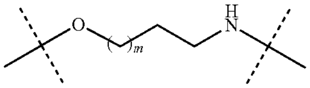
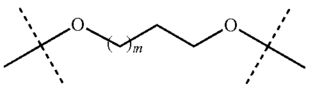
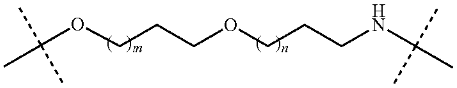
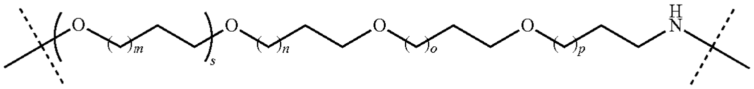
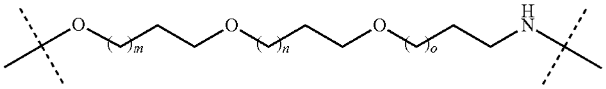
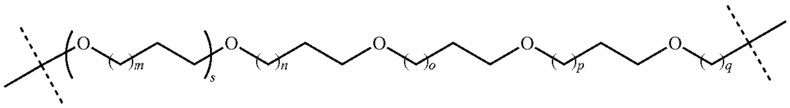
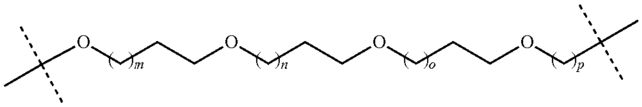

-continued
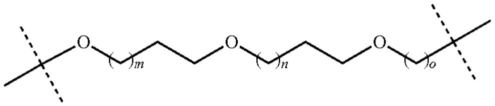
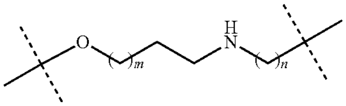
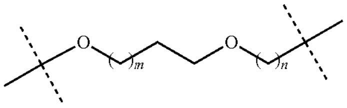
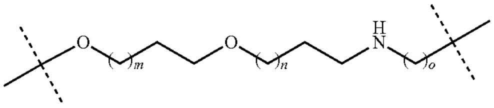
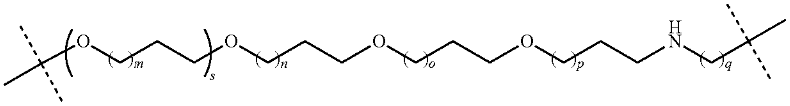
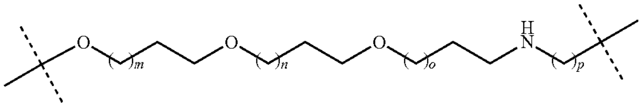
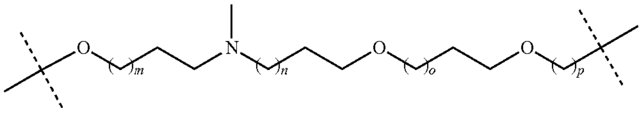
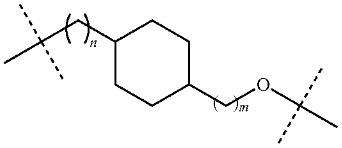
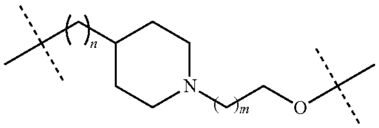
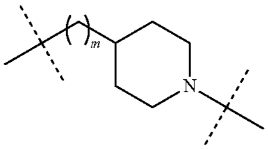
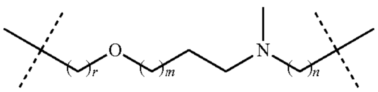
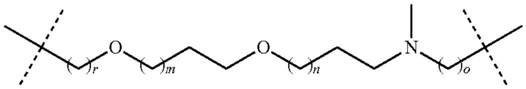
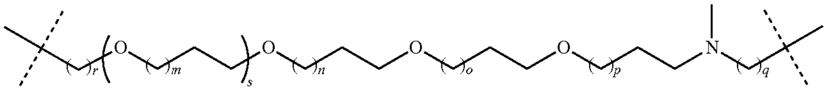
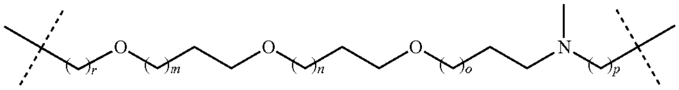
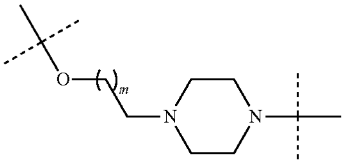
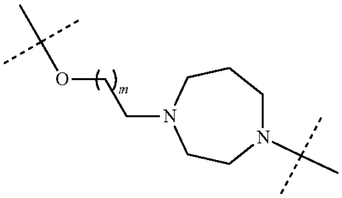
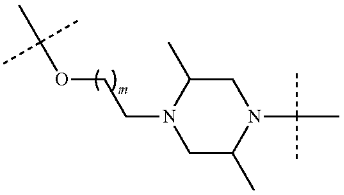
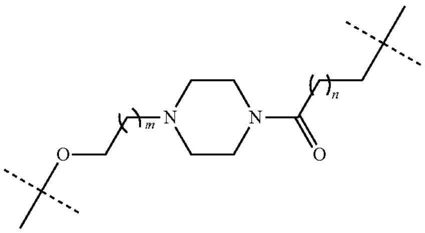
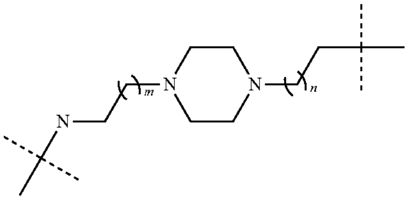
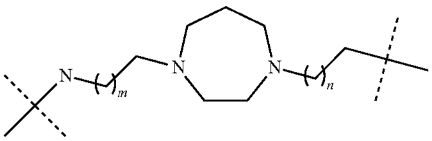
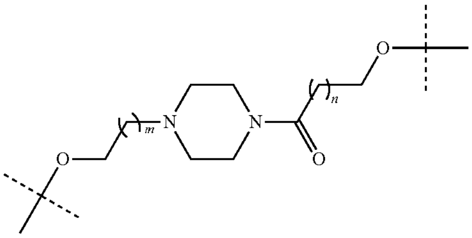

-continued
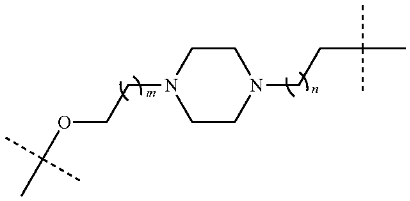
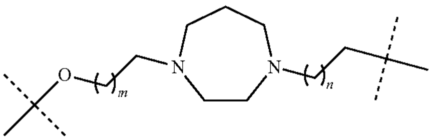
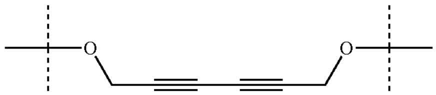
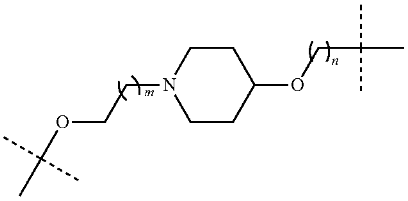
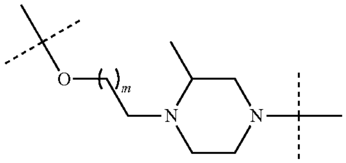
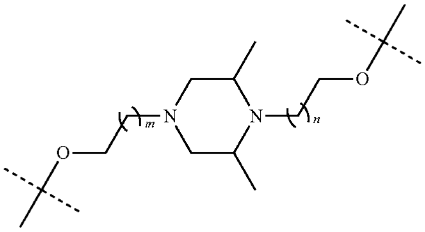
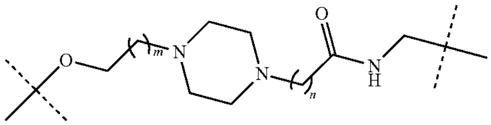
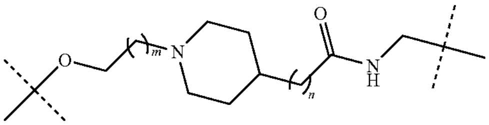
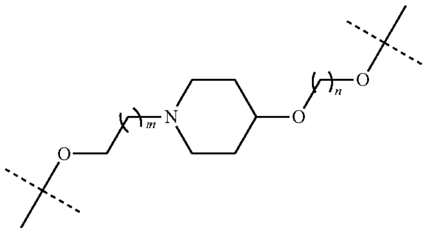
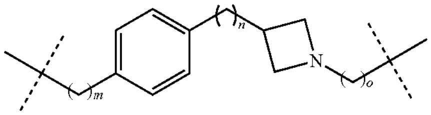
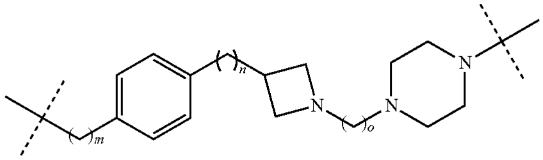
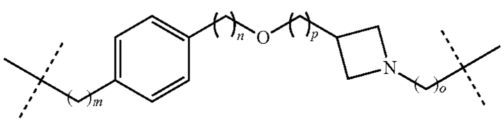
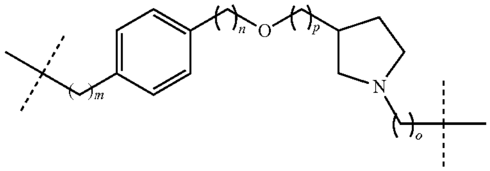
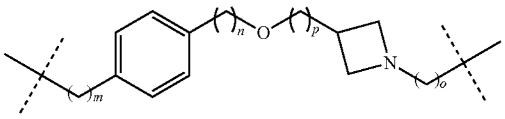
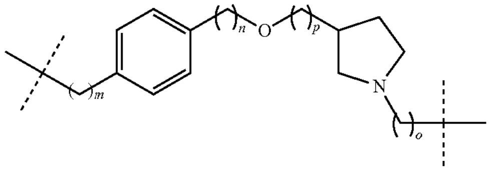
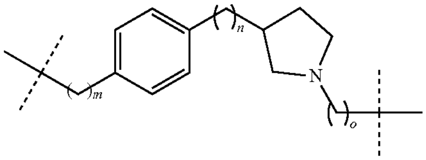
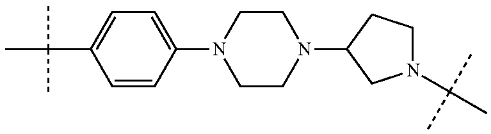
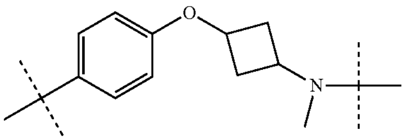

-continued
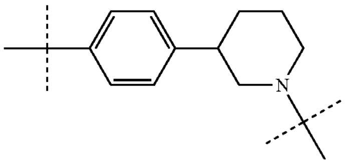
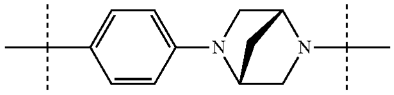
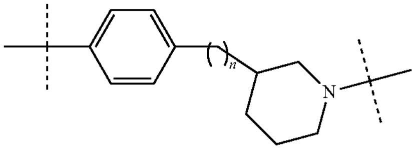
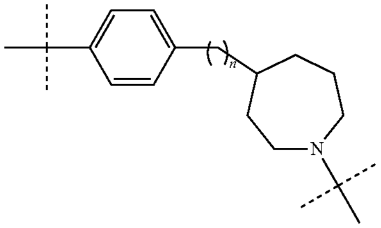
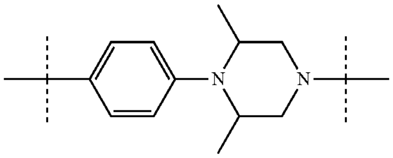
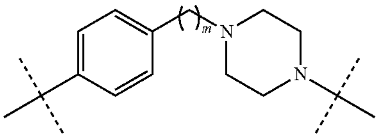
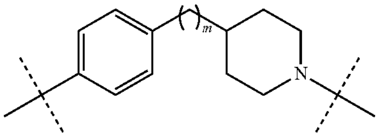
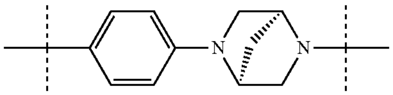
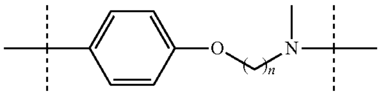
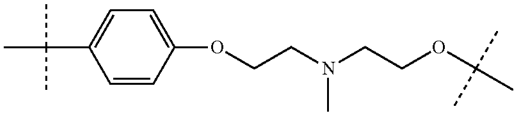
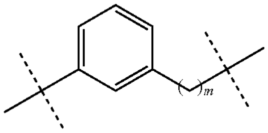
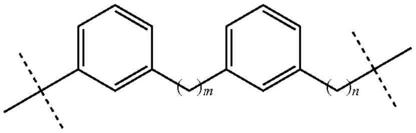
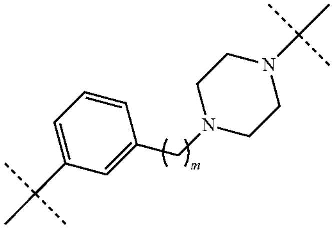
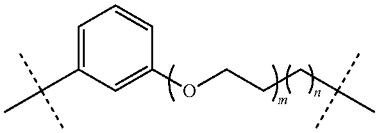
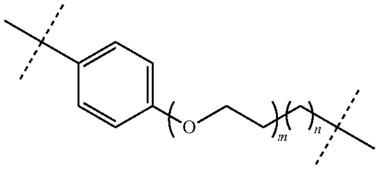
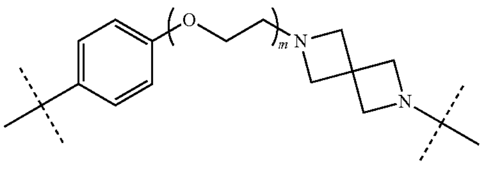
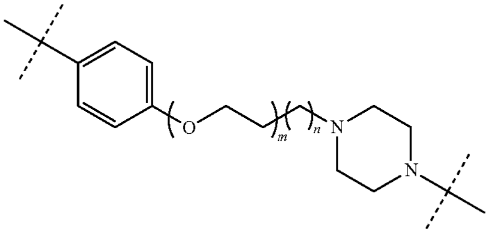
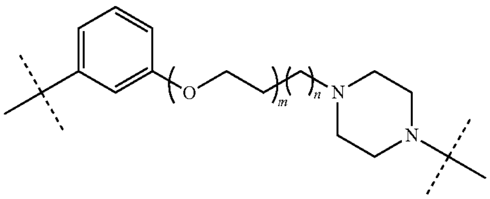
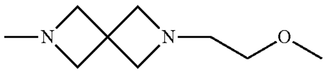

-continued
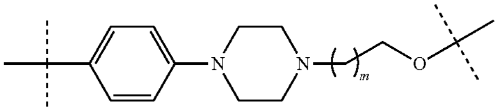
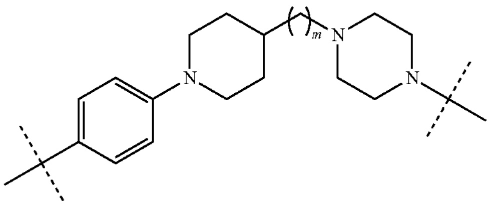
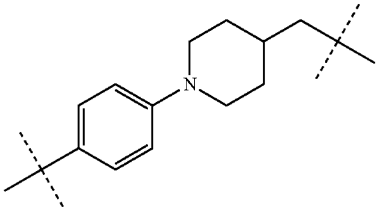
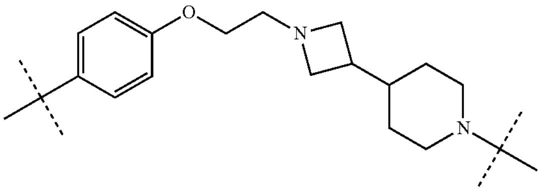
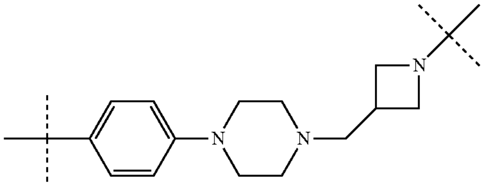
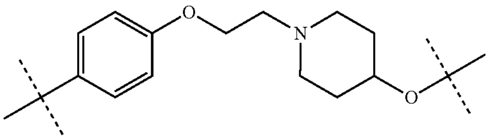
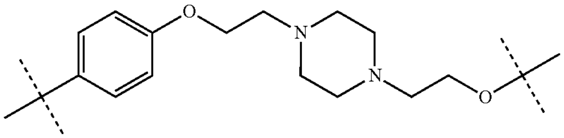
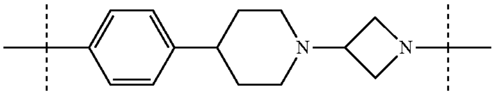
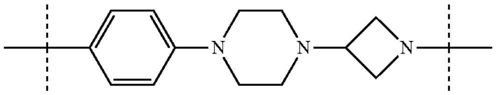
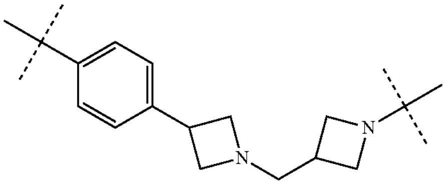
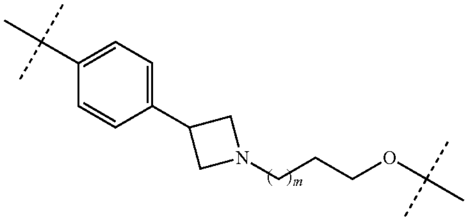
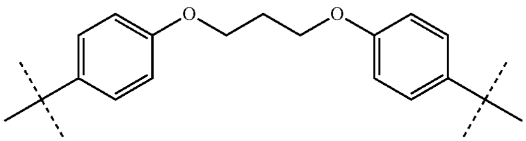
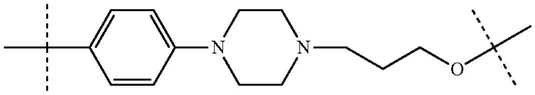
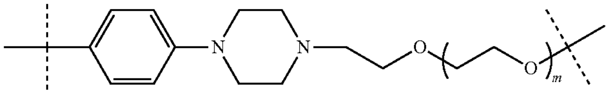
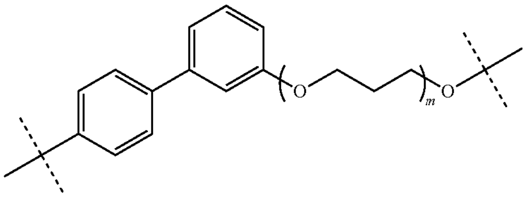
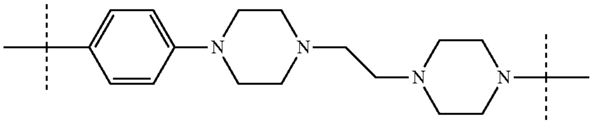
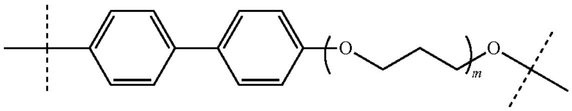

-continued
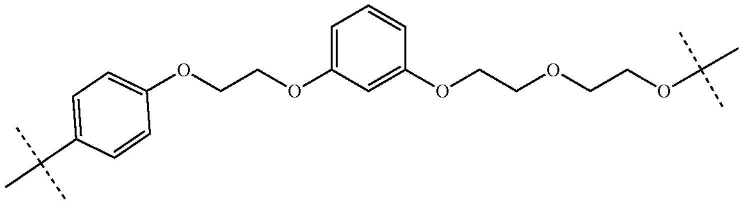
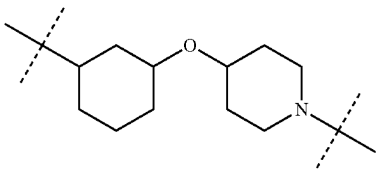
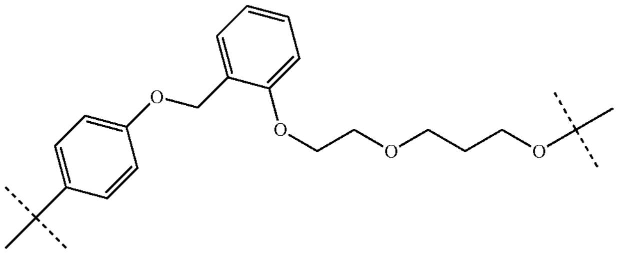
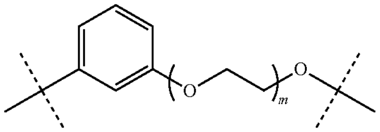
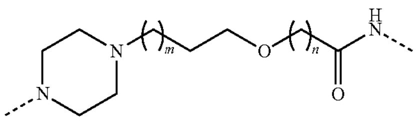
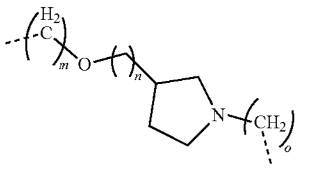
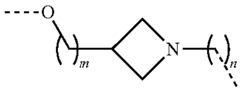
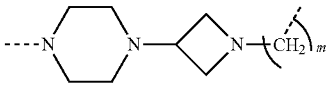
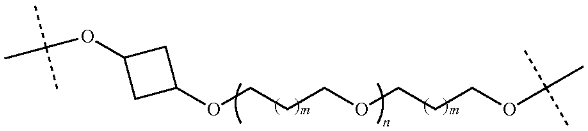
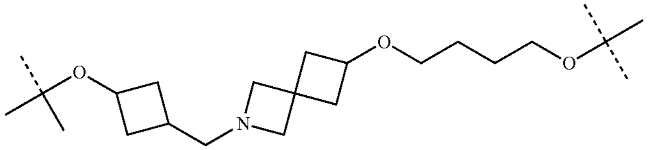
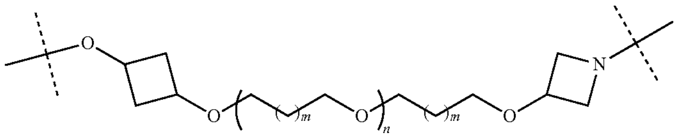
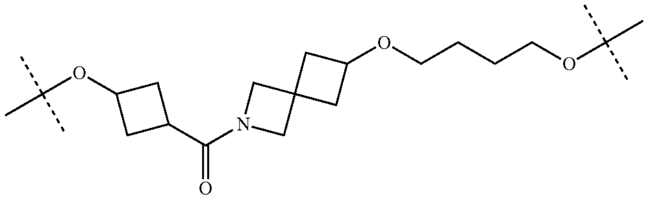
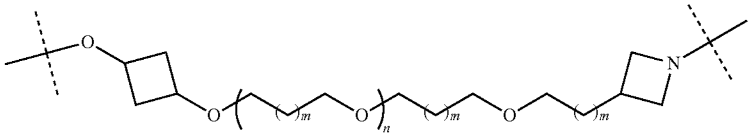
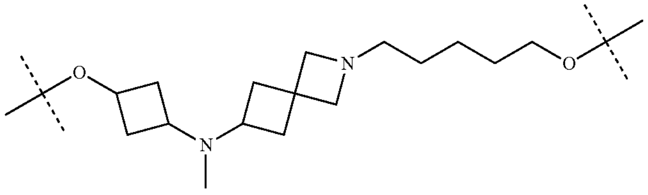
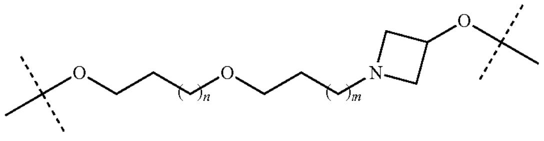

-continued
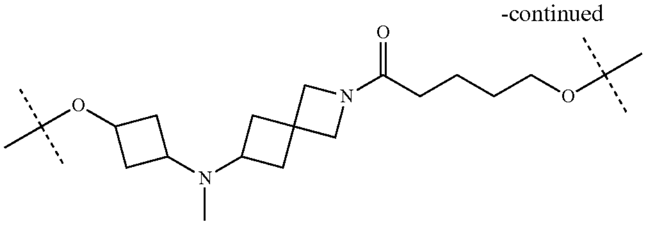
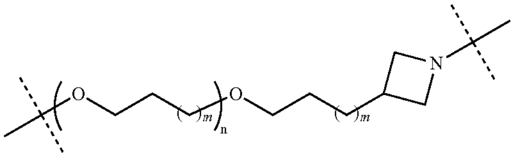
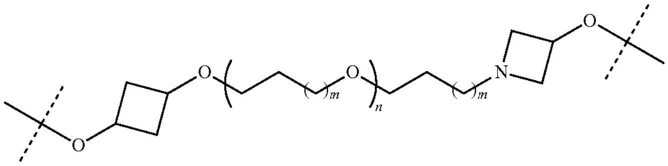
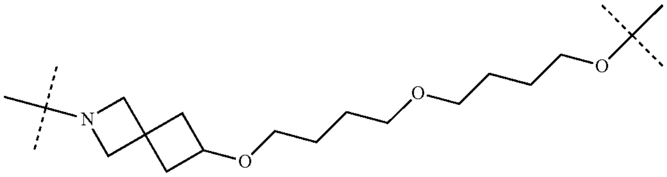
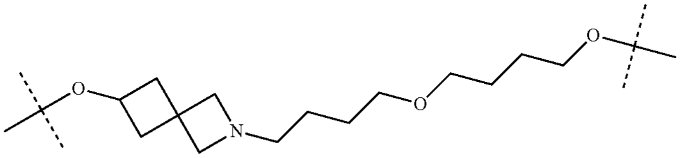
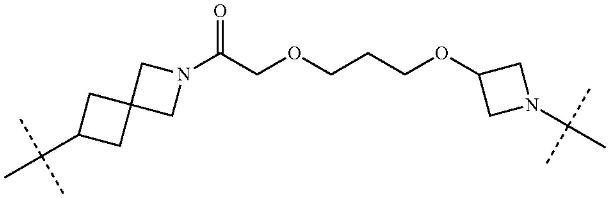
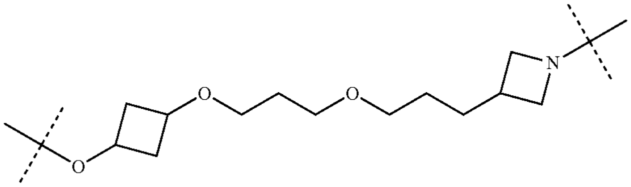
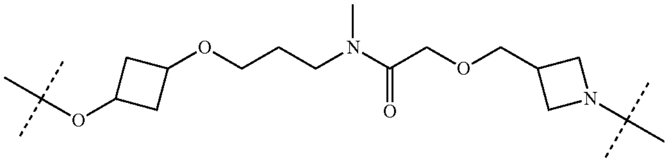
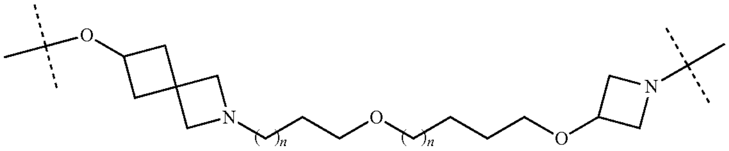
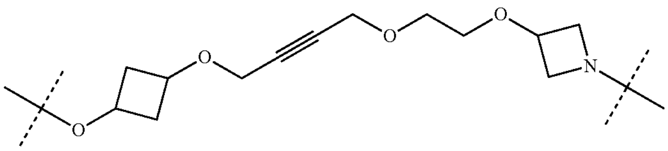

-continued
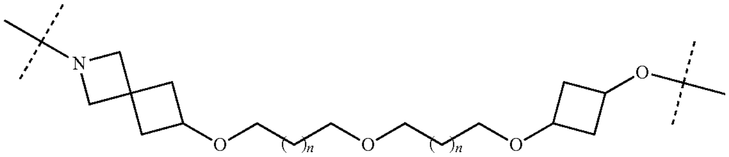
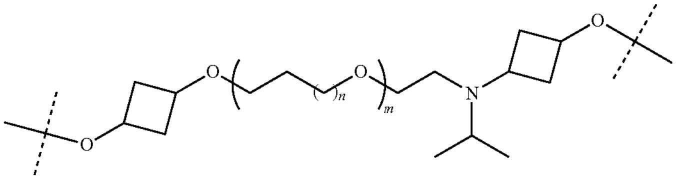
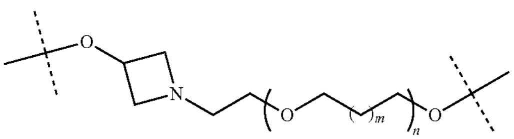
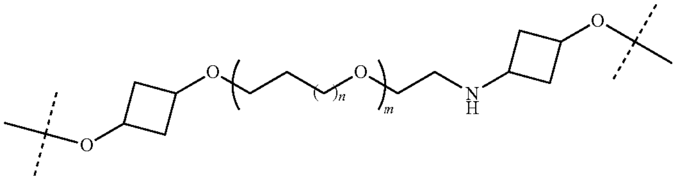
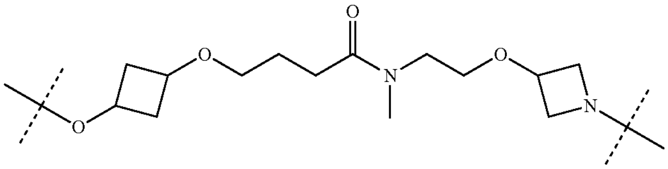
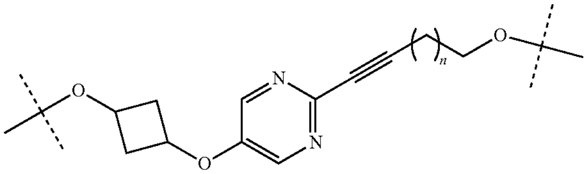
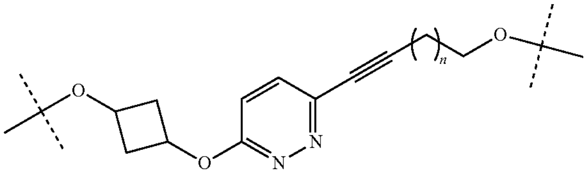
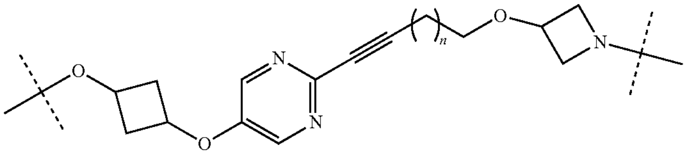
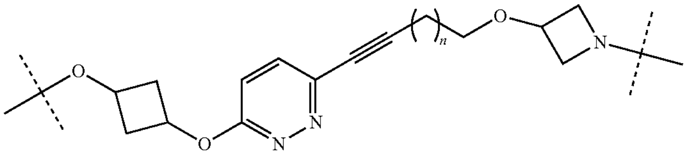
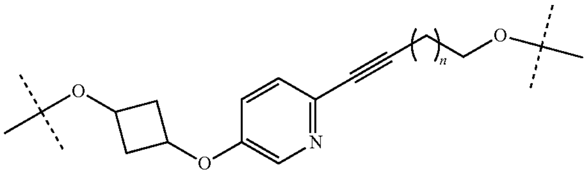

-continued
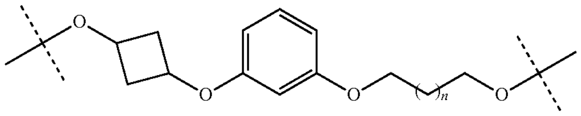
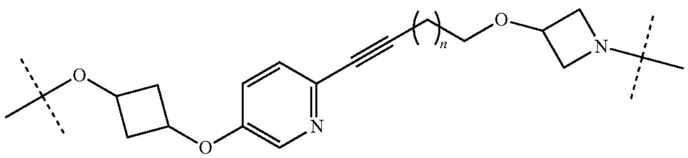
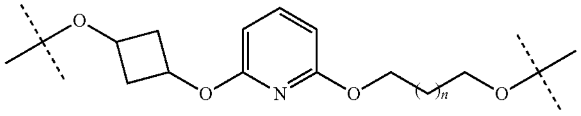
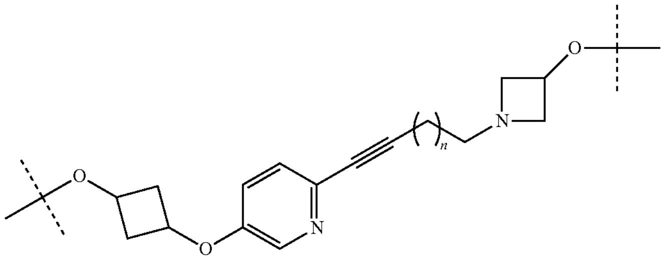
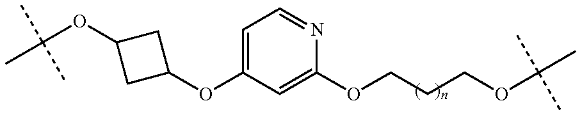
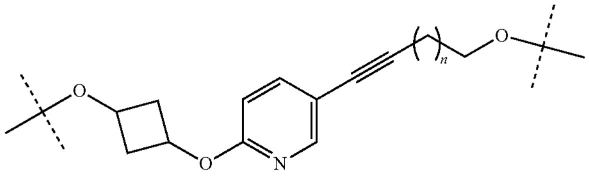
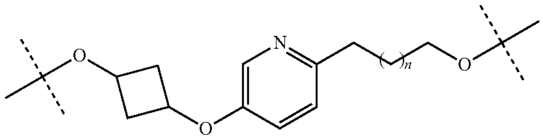
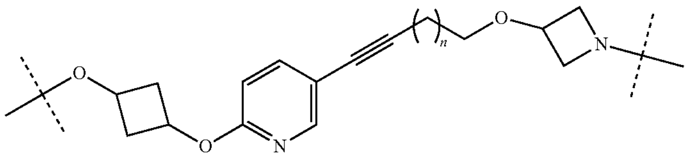
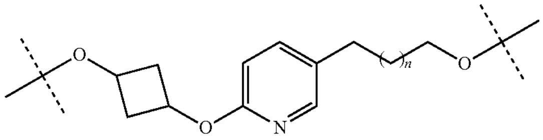
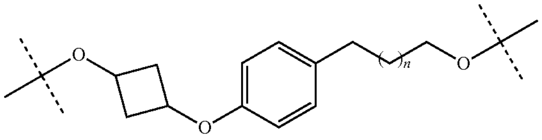
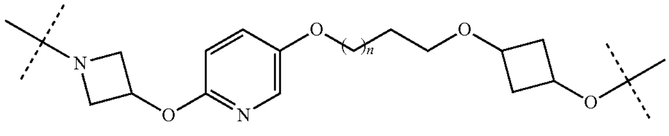
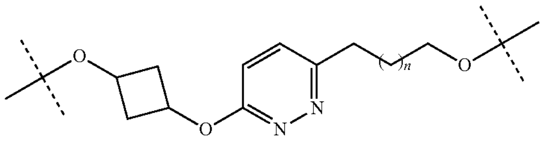

-continued
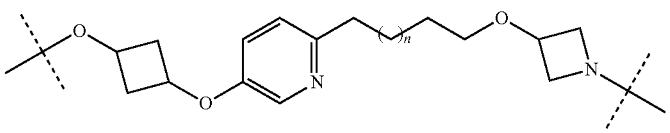
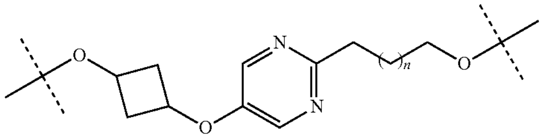
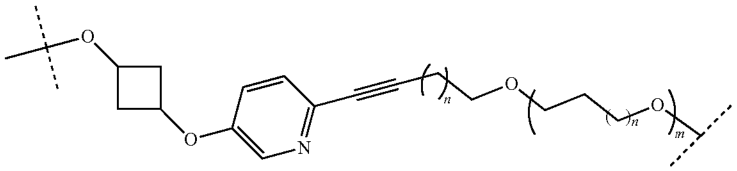
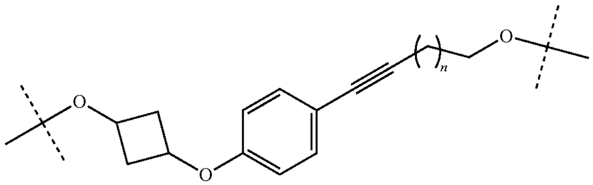
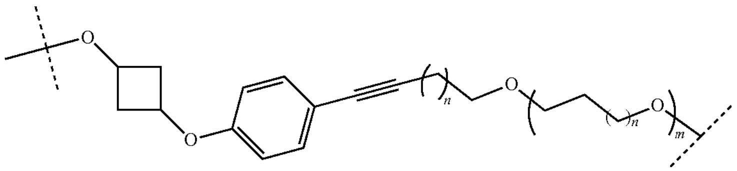
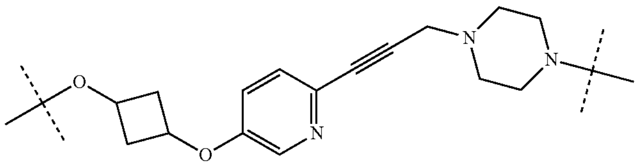
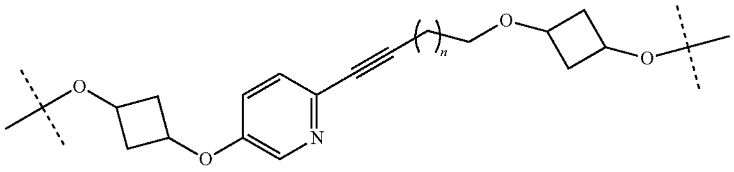
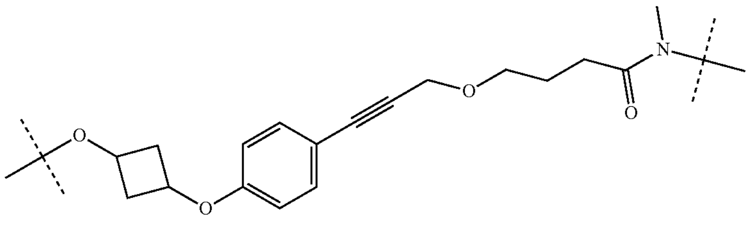
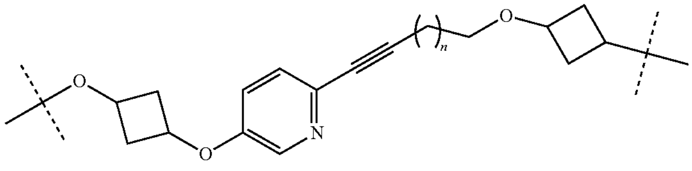
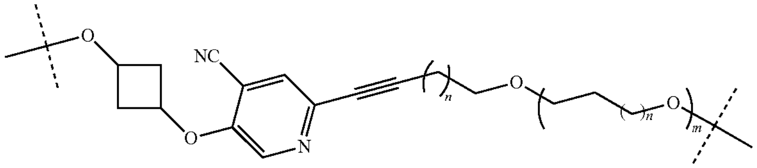

-continued
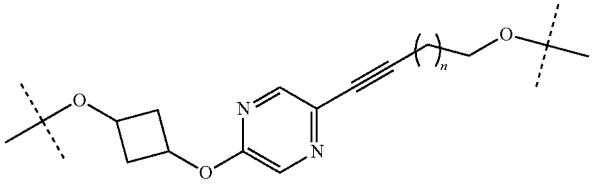
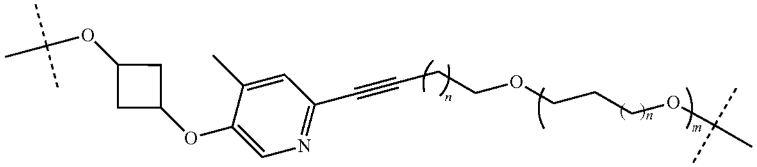
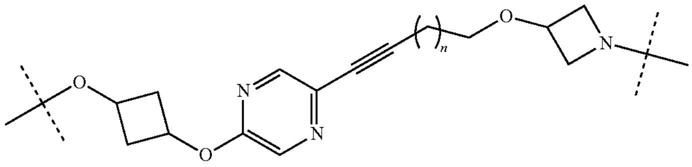
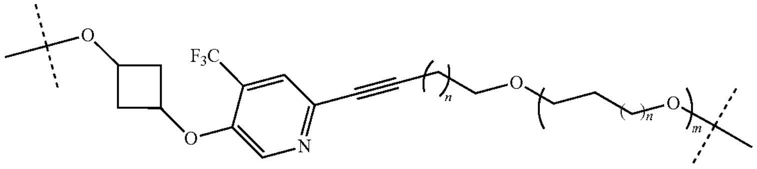
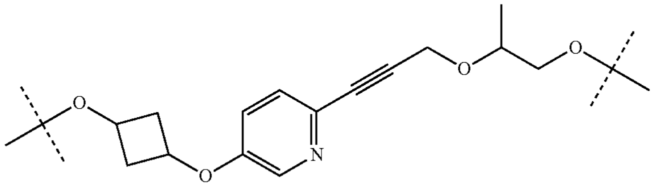
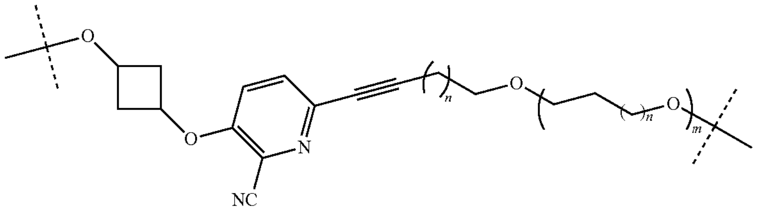
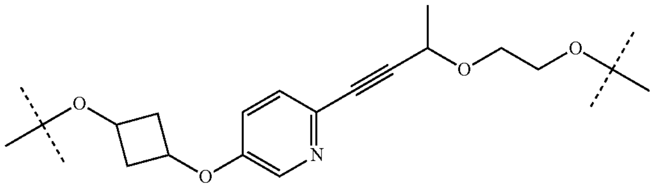
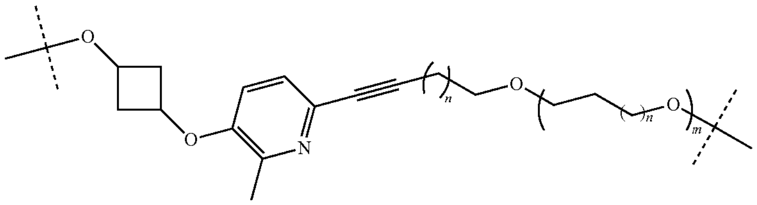
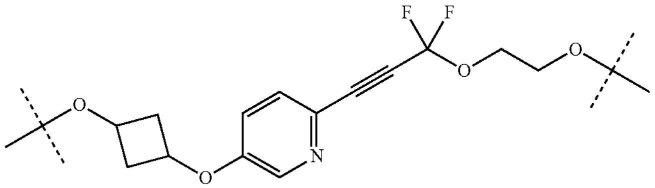

-continued
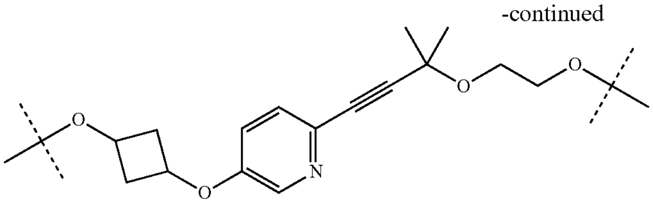
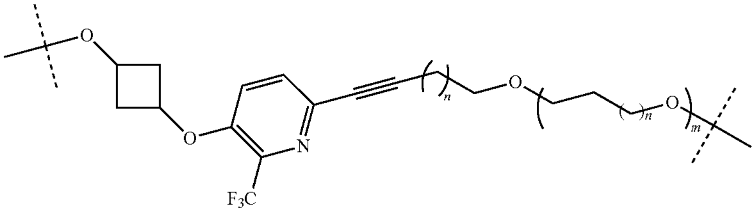
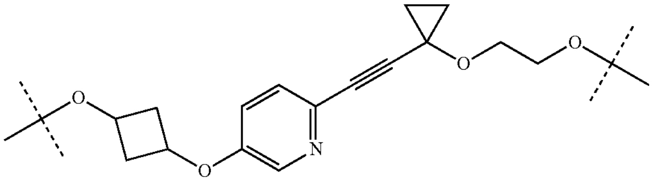
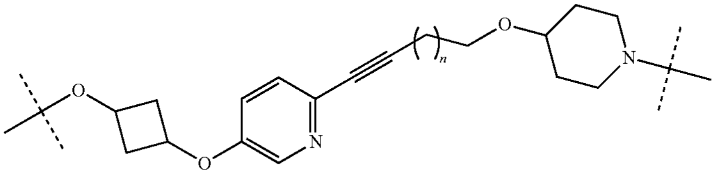
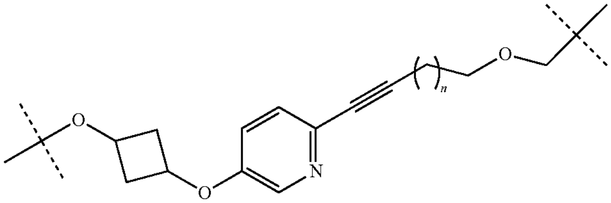
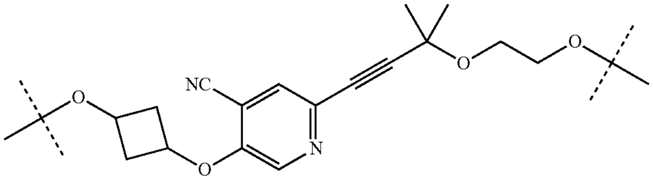
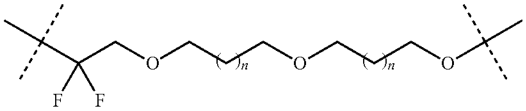
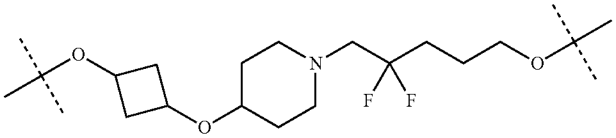
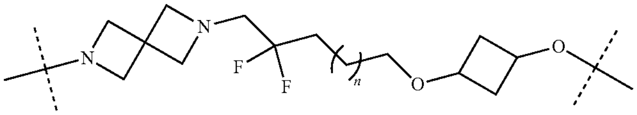
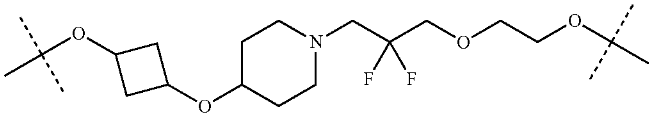
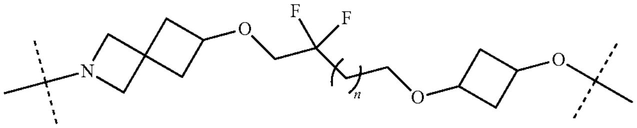

-continued
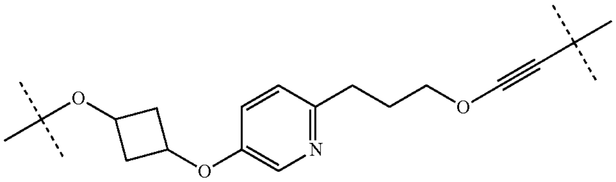
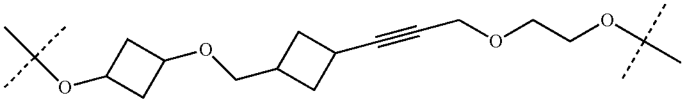
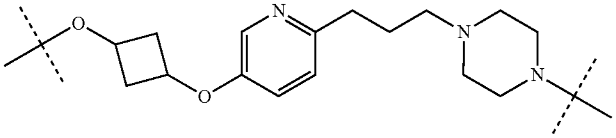
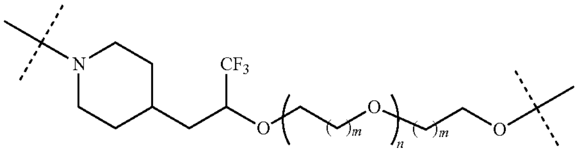
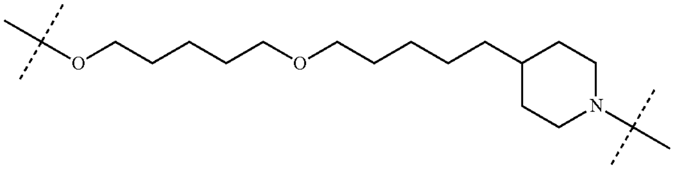
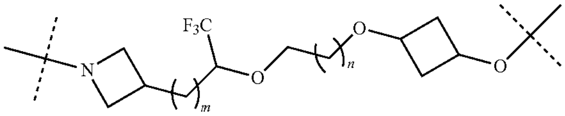
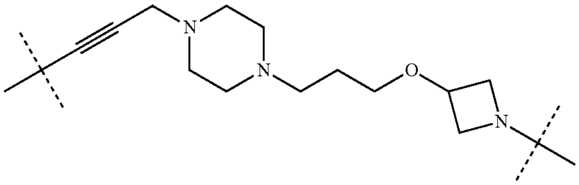
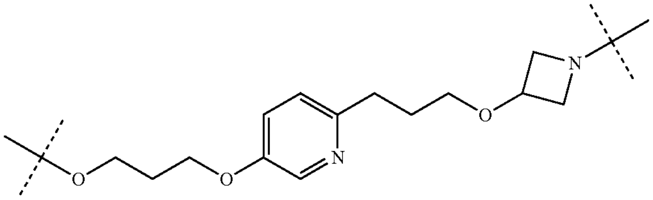
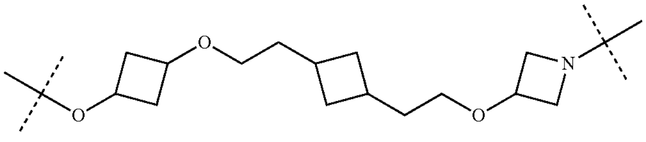
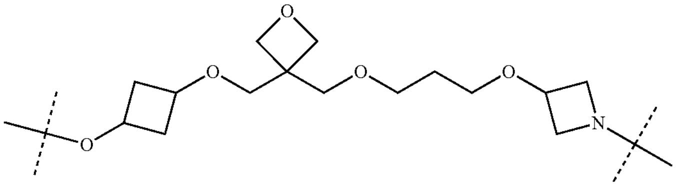
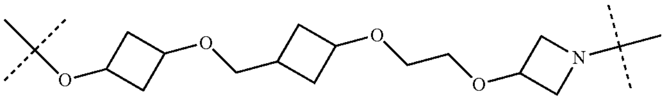

-continued
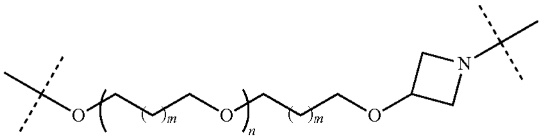
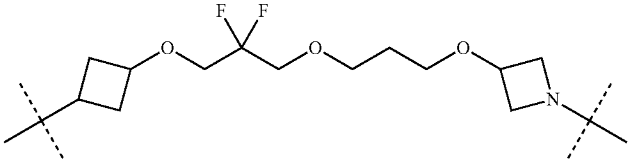
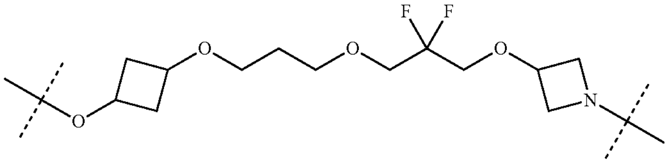
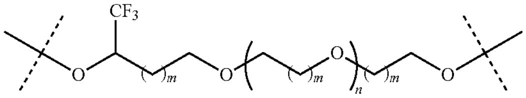
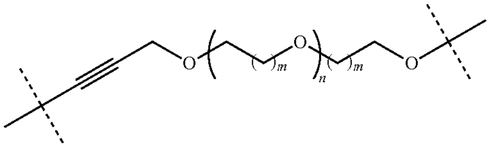
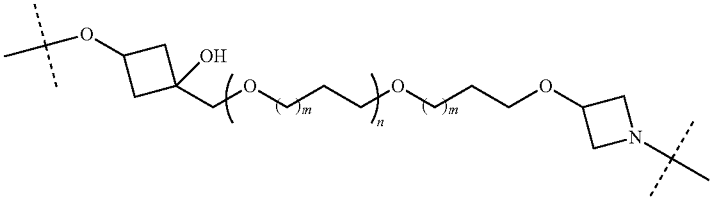
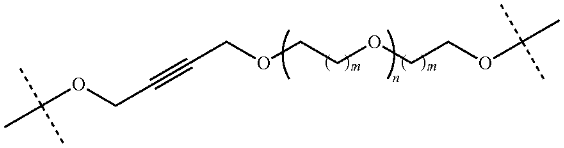
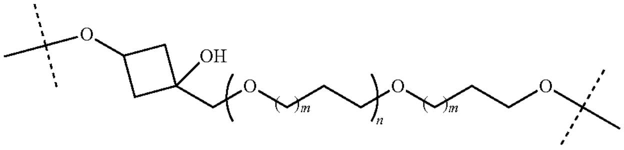
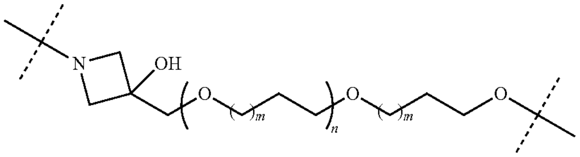
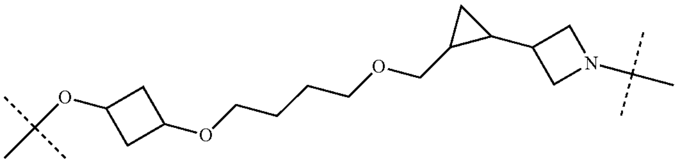
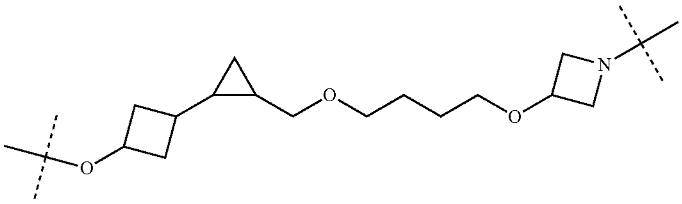

-continued
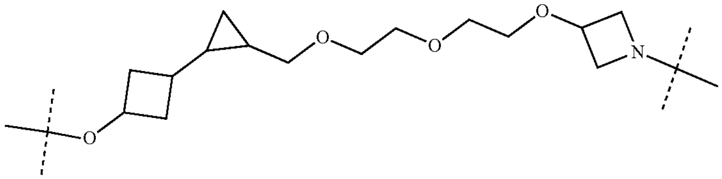
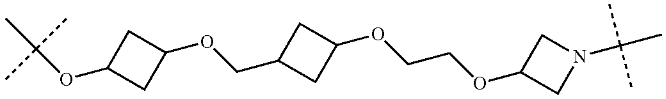
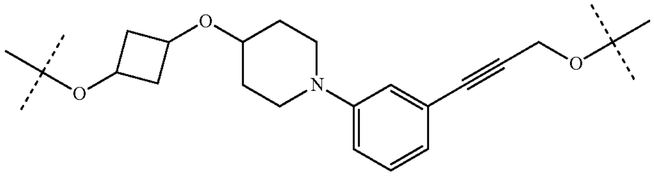
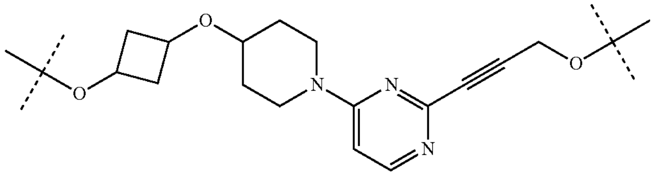
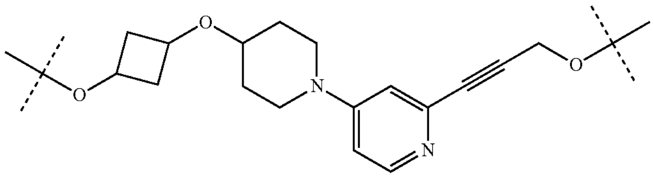
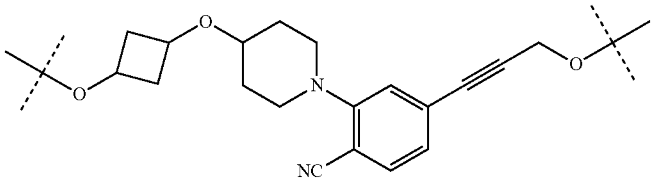
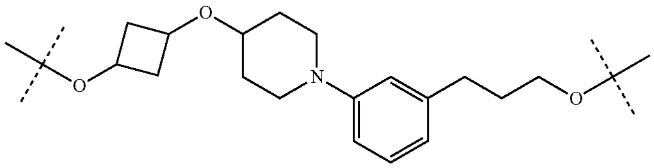
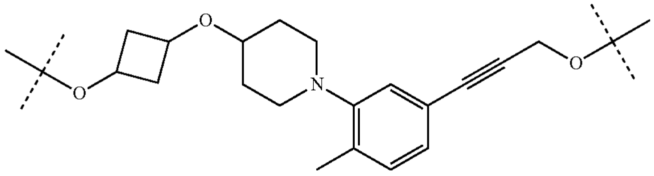
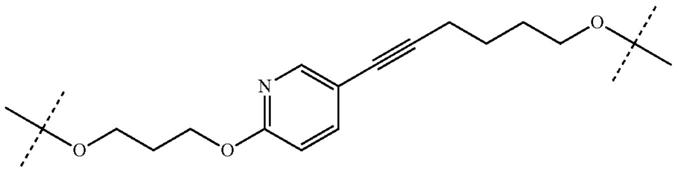
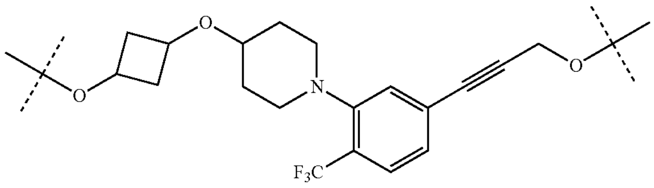

-continued
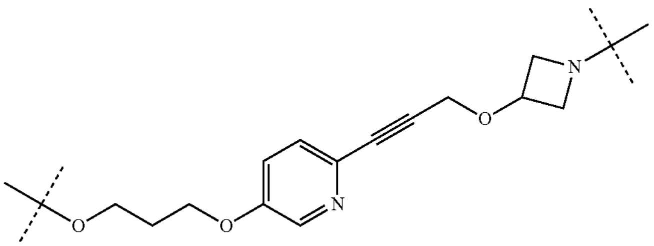
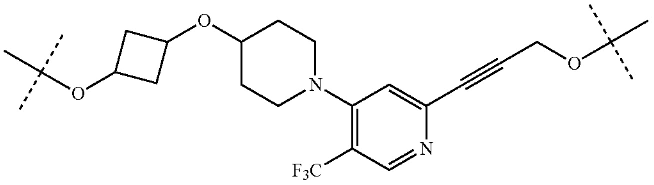
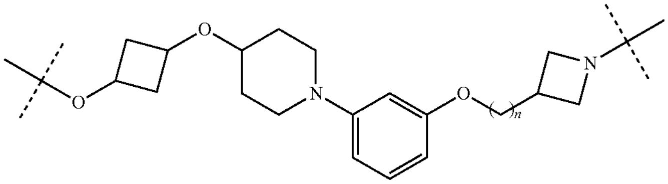
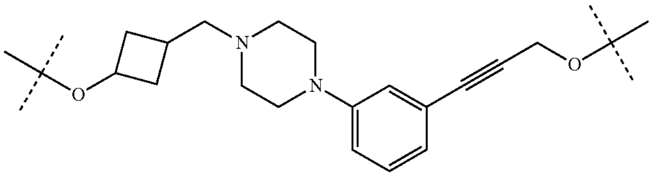
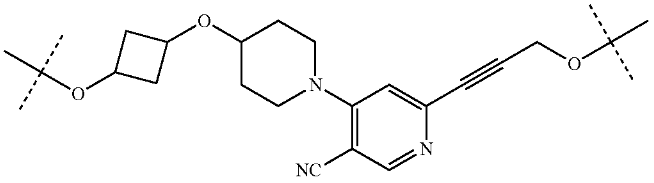
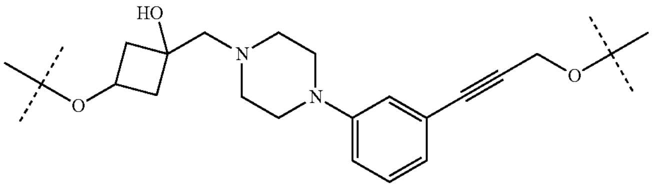
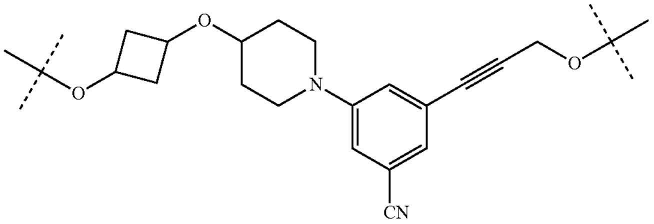
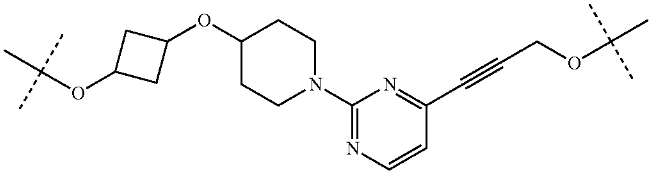

-continued
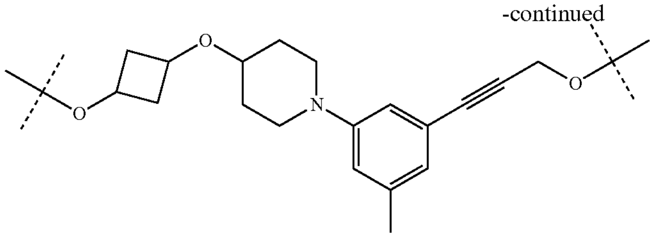
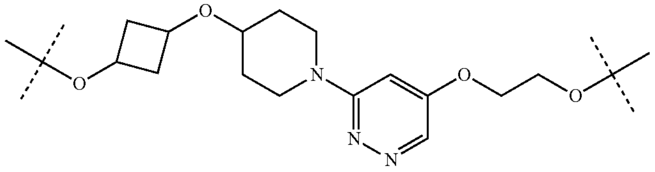
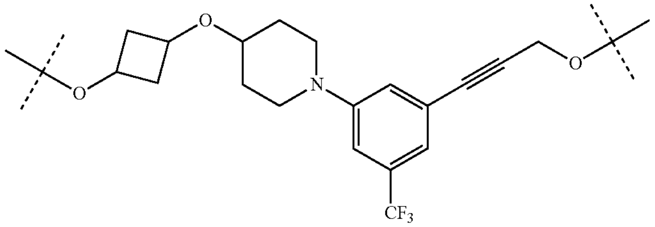
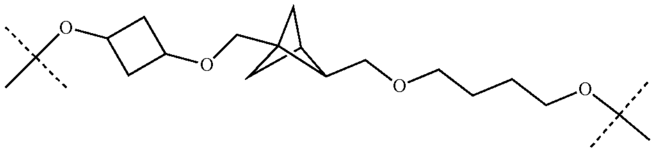
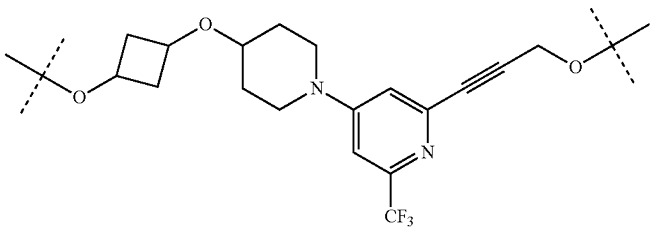
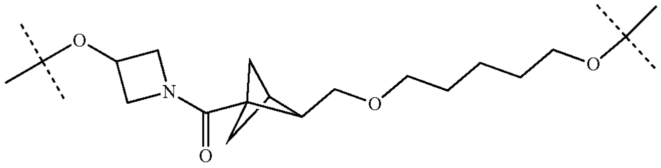
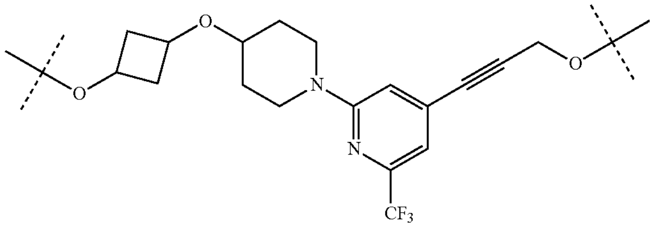
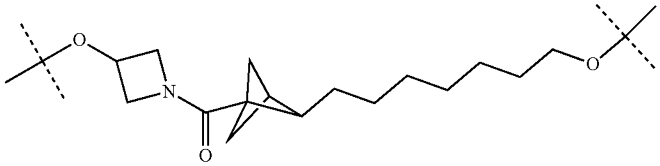
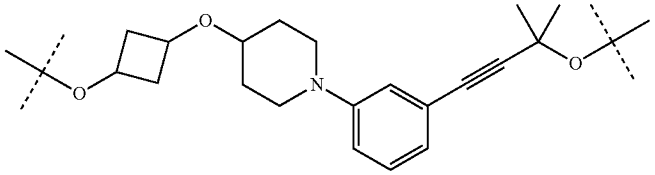

-continued
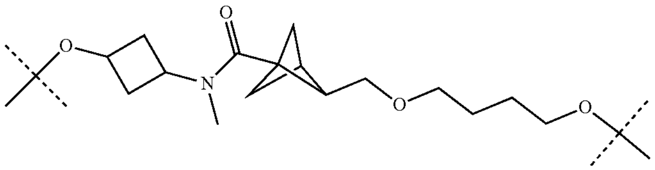
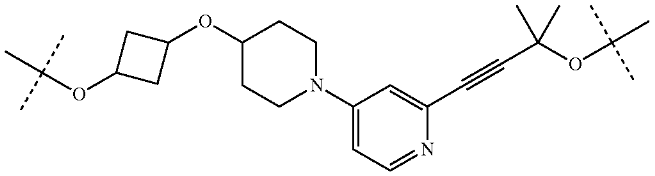
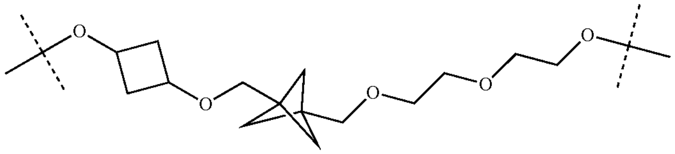
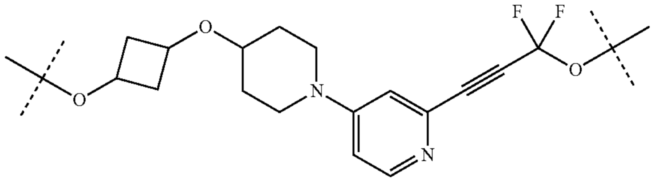
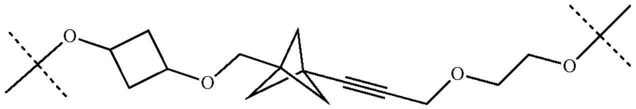
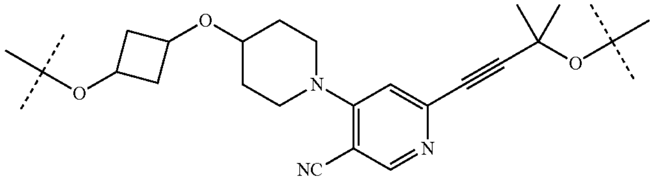
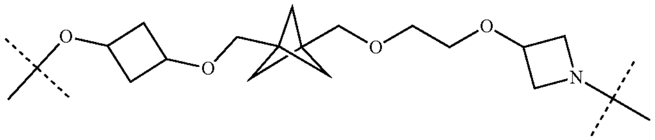
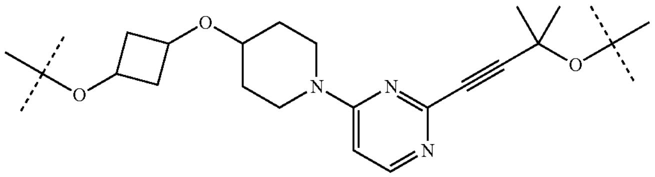
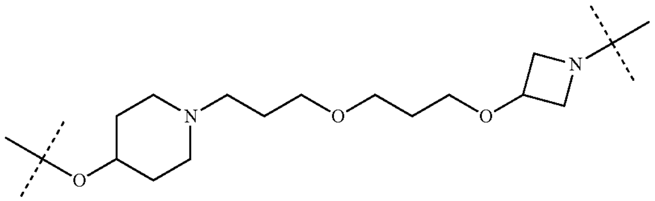
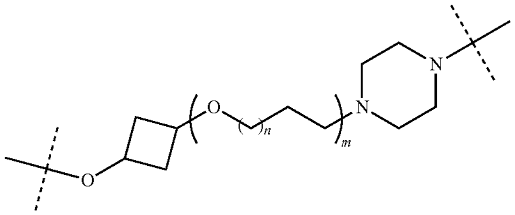

-continued
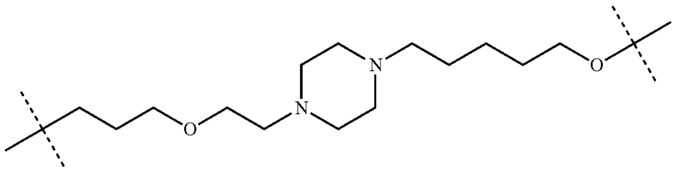
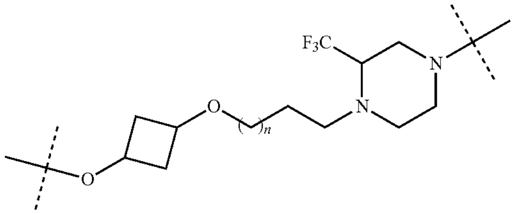
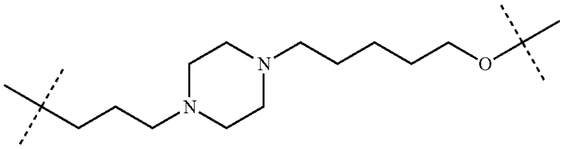
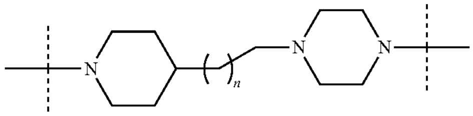
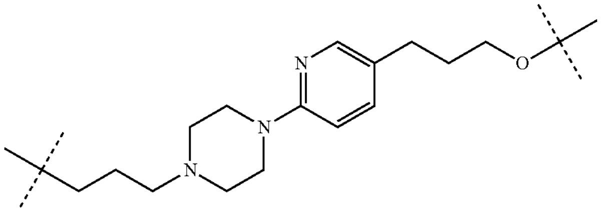
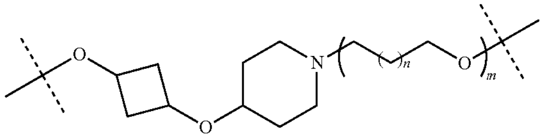
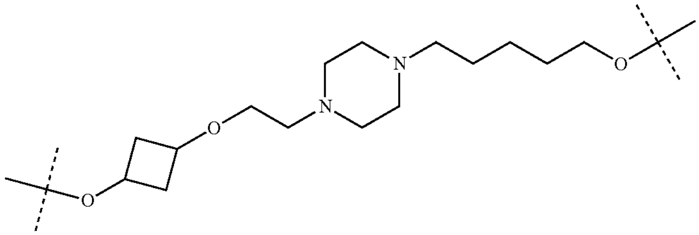
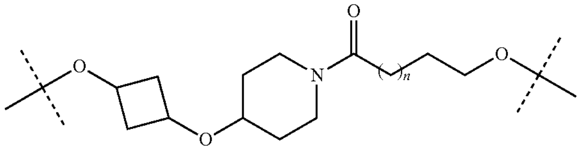
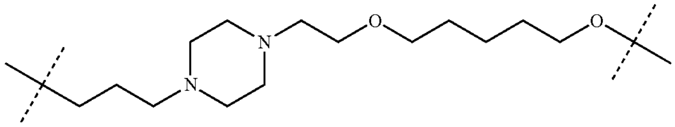
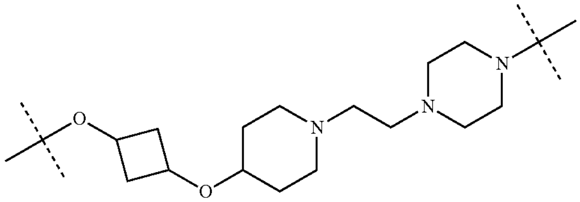
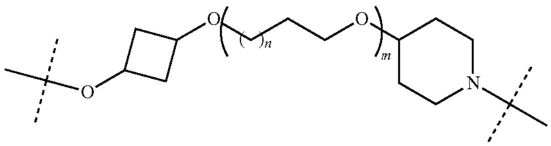
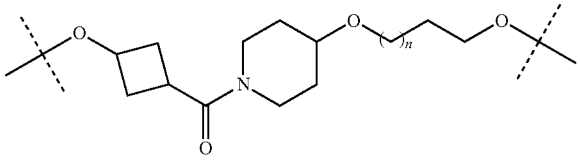
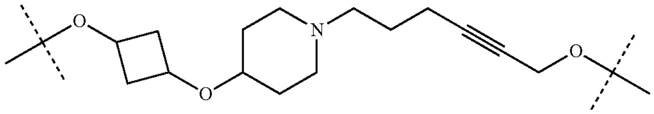

-continued
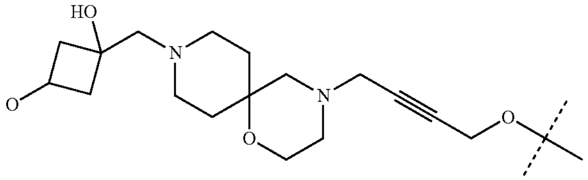
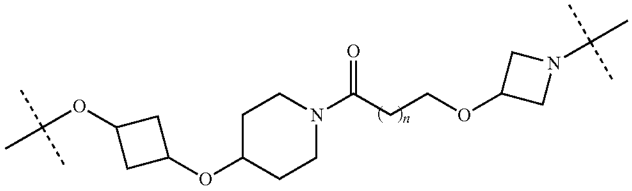
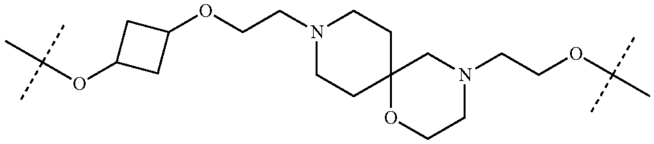
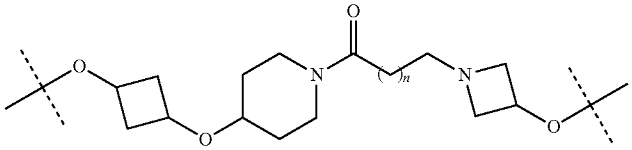
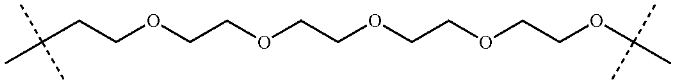
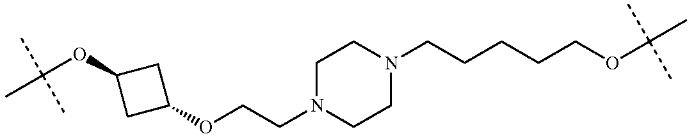
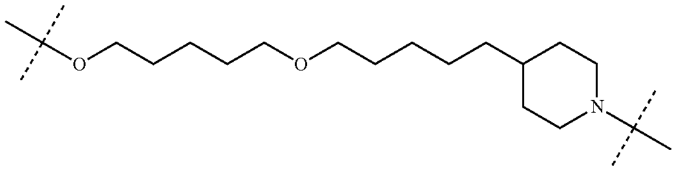
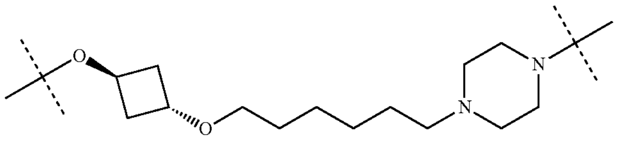
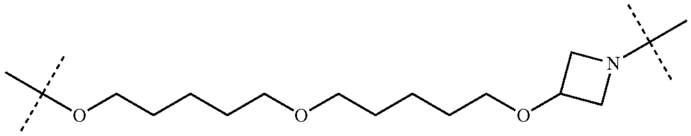
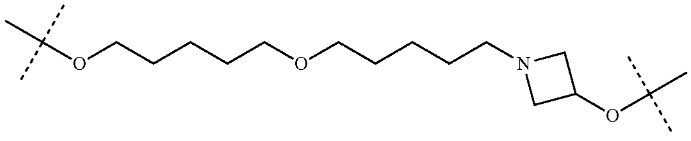

-continued
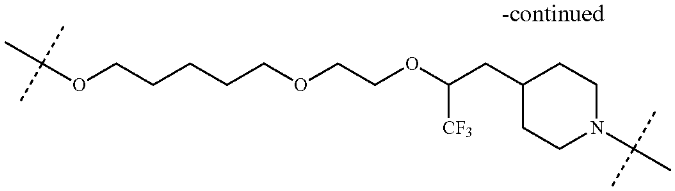
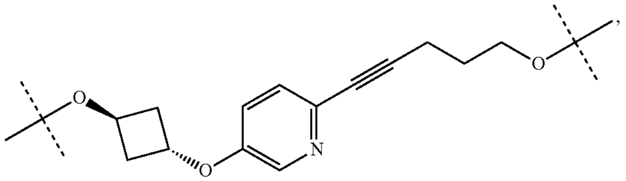
wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, the linker (L) is selected from:
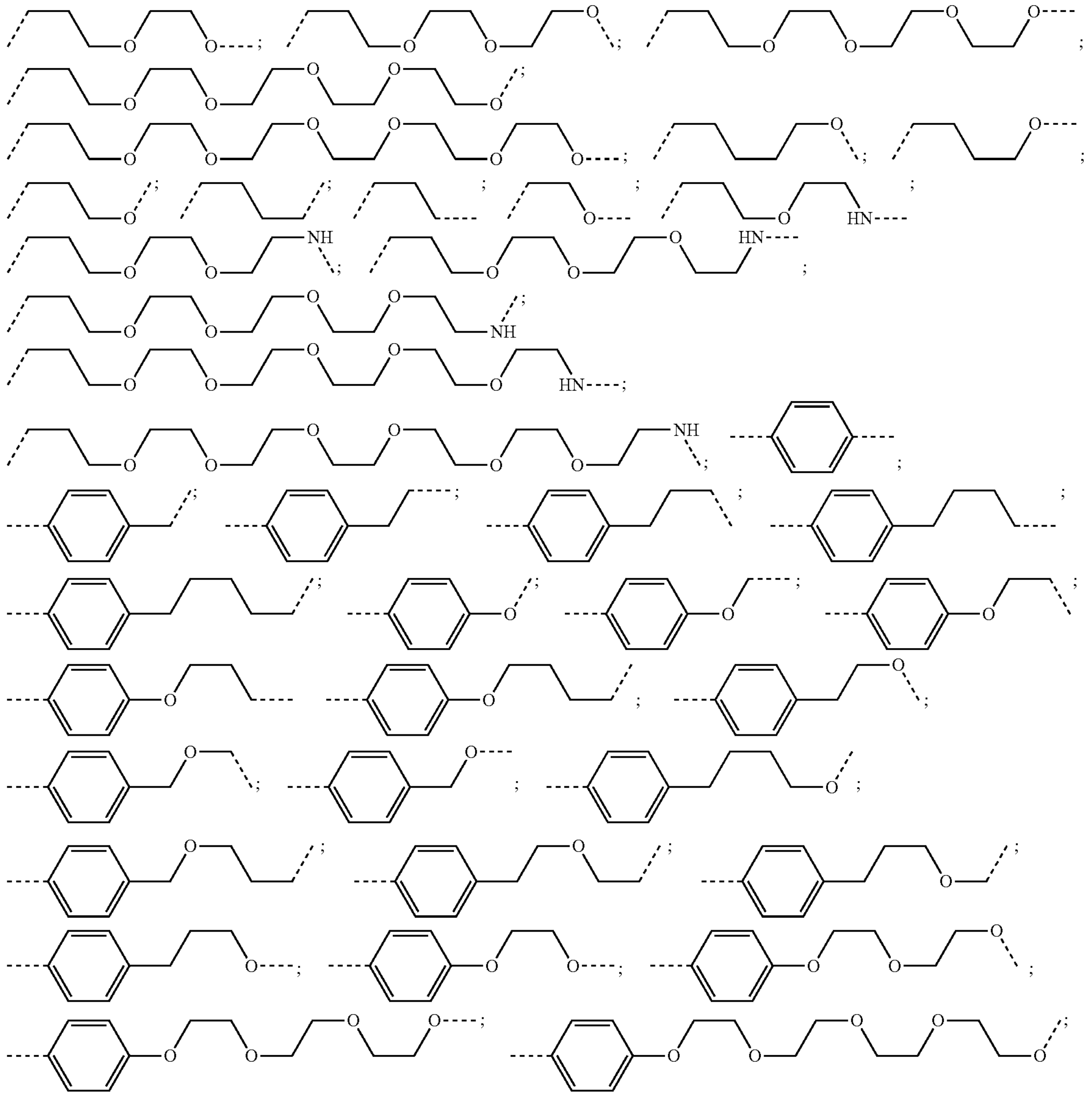

-continued
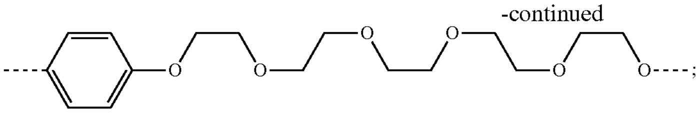;
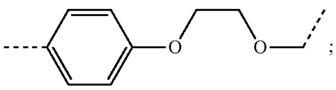;
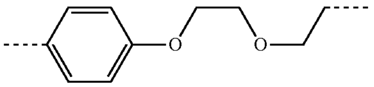;
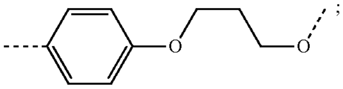;
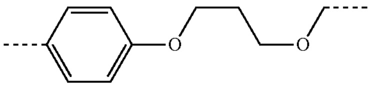;
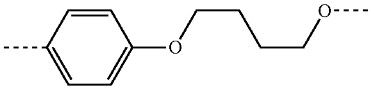;
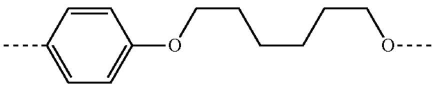;
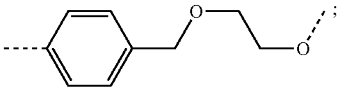;
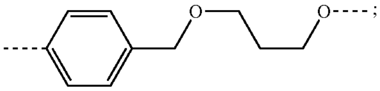;
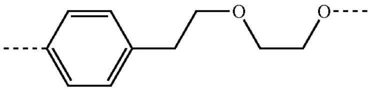;
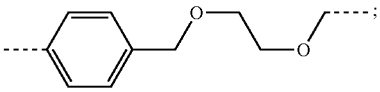;
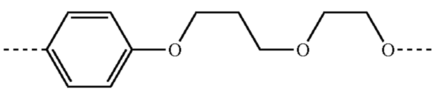;
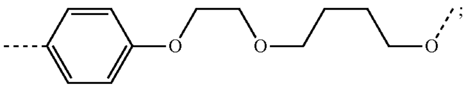;
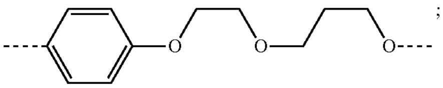;
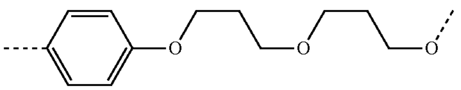;
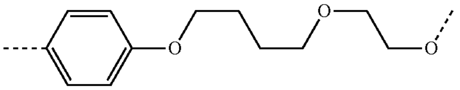;
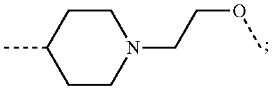;
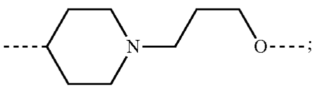;
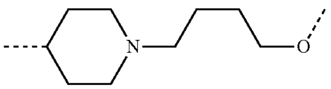;
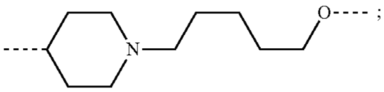;
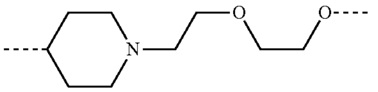;
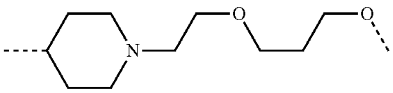;
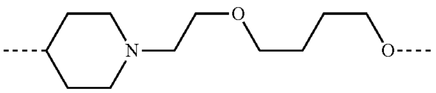;
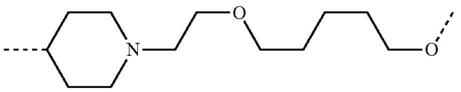;
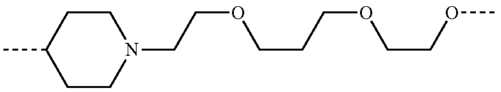;
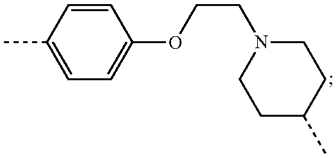;
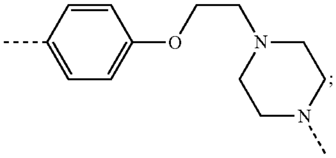;
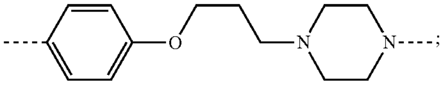;
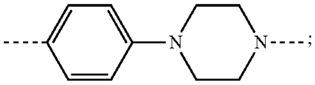;
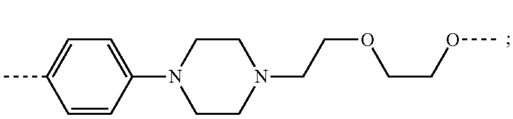;
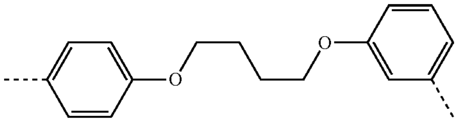;
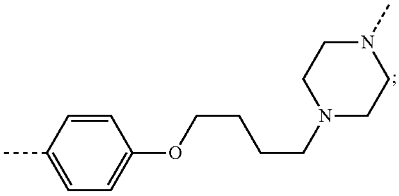;
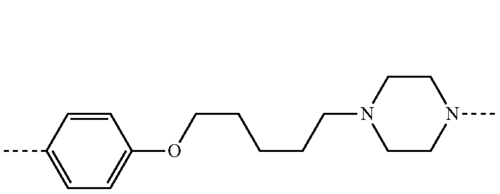;
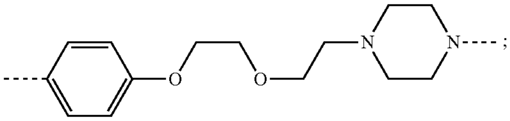;
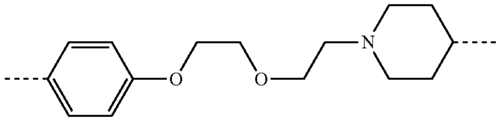;

-continued
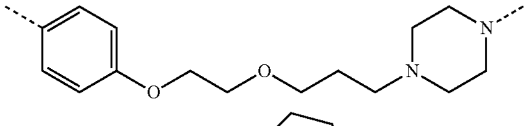;
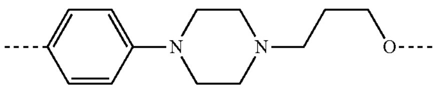;
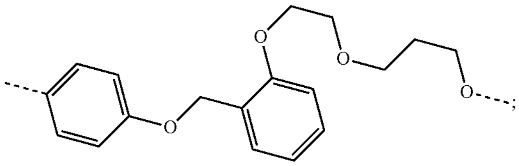;
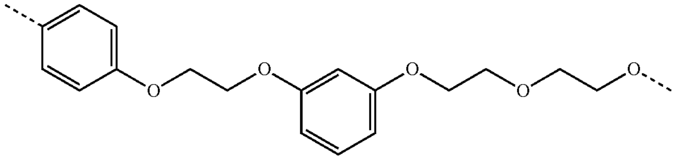;
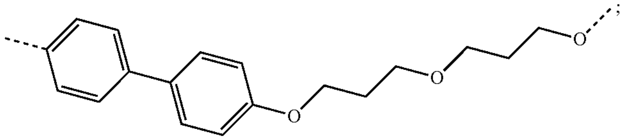;
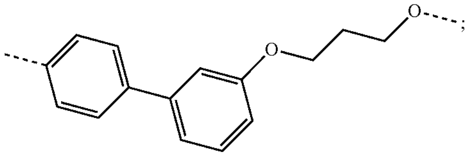;
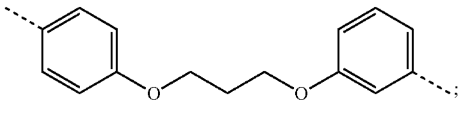;
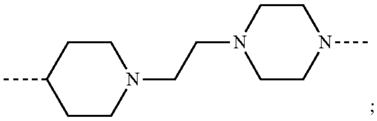;
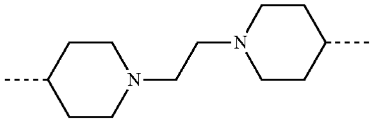;
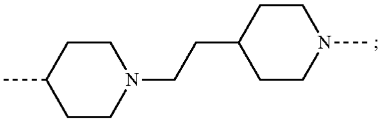;
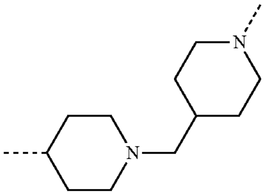;
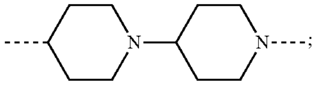;
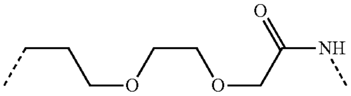;
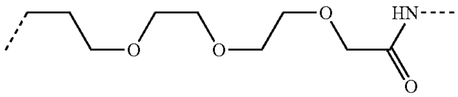;
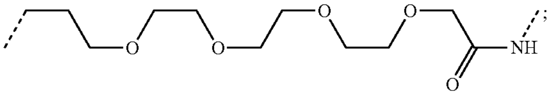;
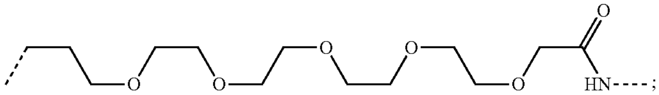;
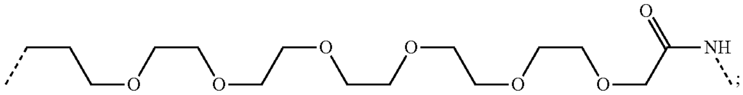;
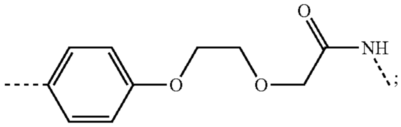;
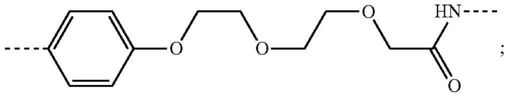;
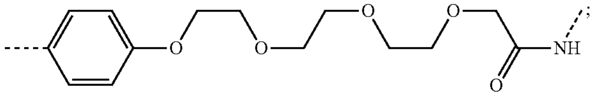;
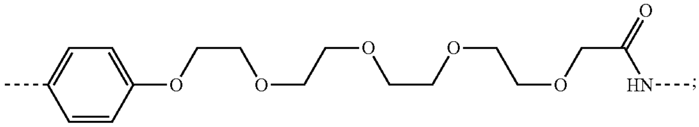;

-continued
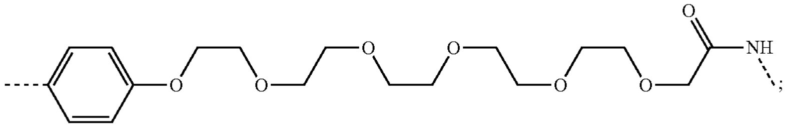
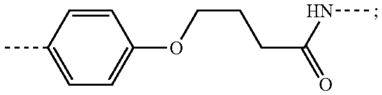
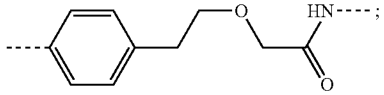
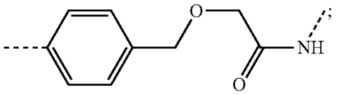
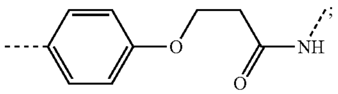
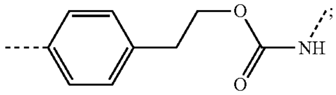
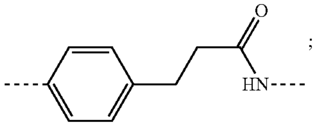
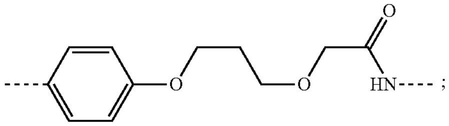
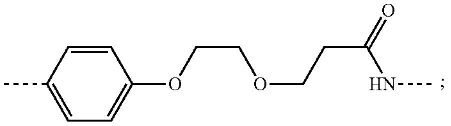
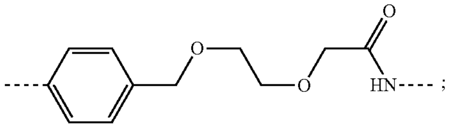
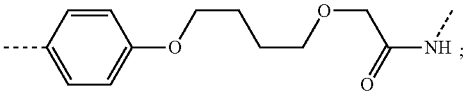
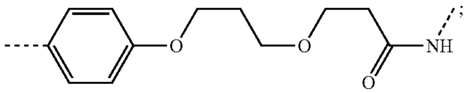
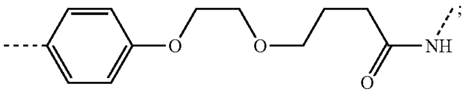
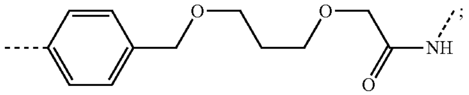
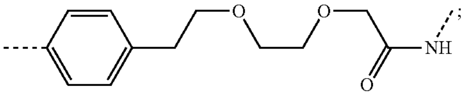
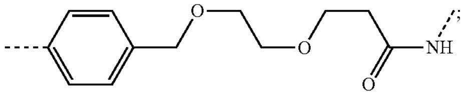
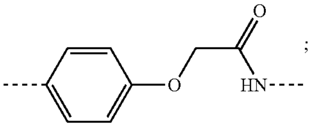
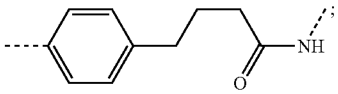
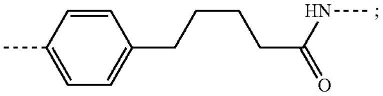
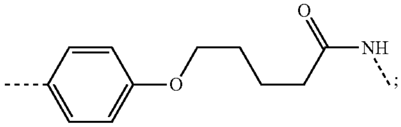
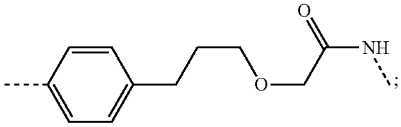
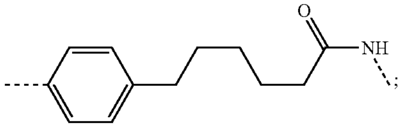
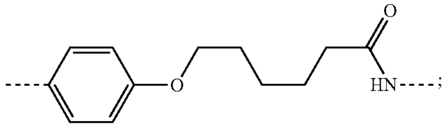
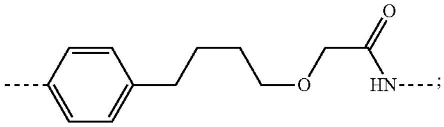
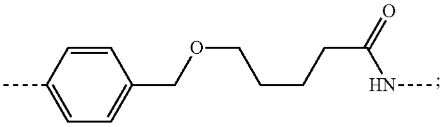
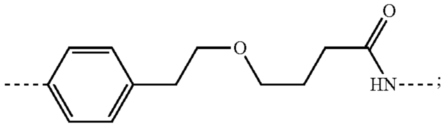
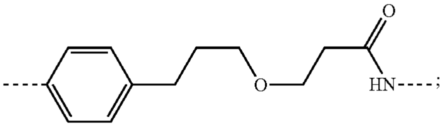
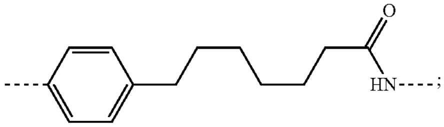
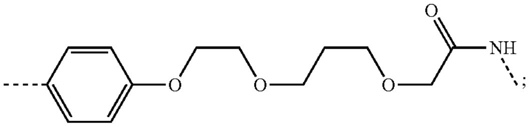

-continued
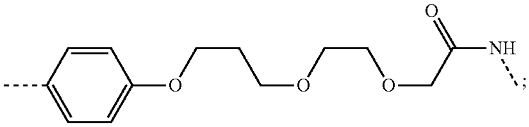;
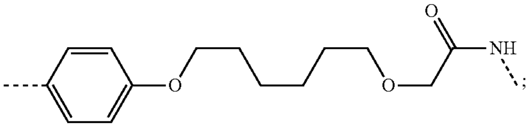;
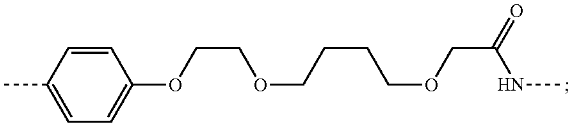;
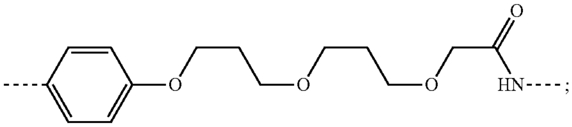;
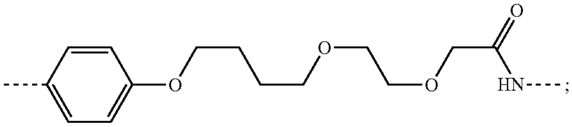;
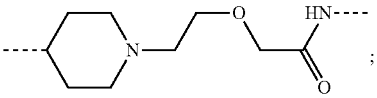;
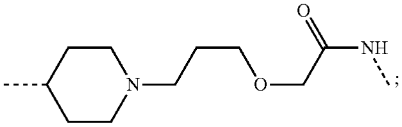;
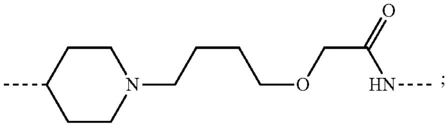;
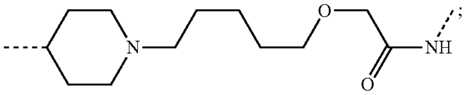;
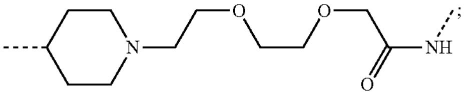;
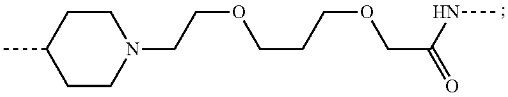;
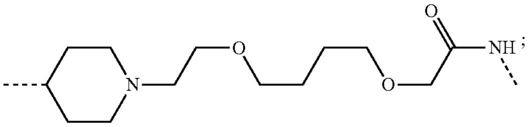;
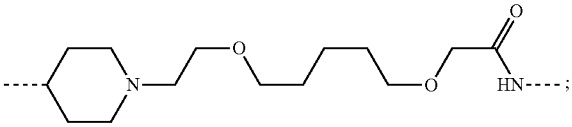;
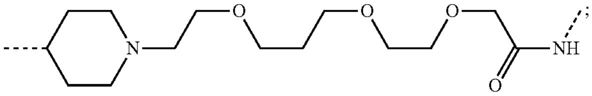;
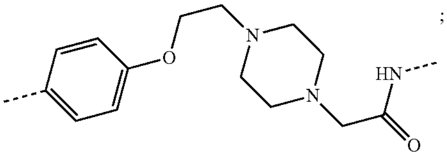;
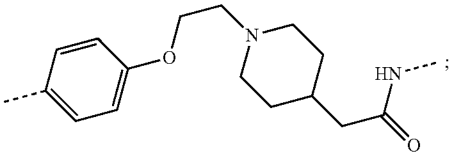;
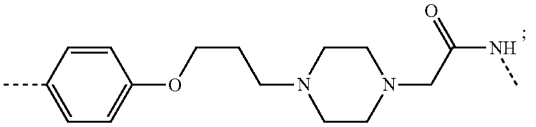;
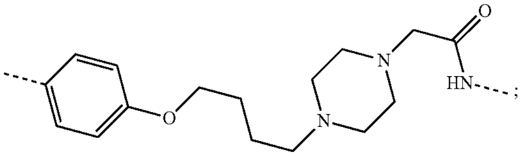;
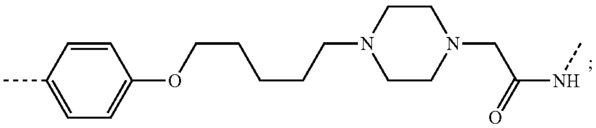;
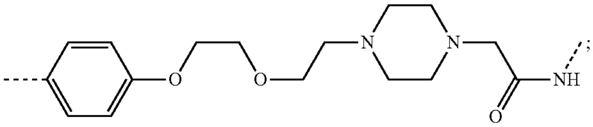;
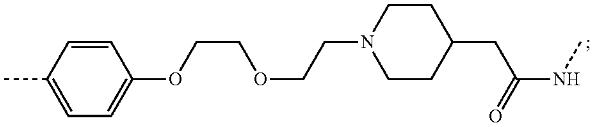;
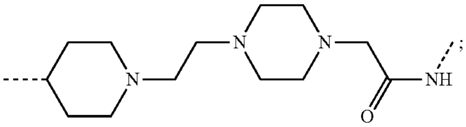;

-continued
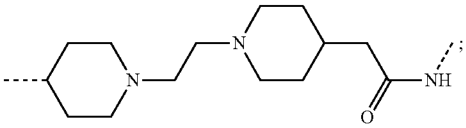;
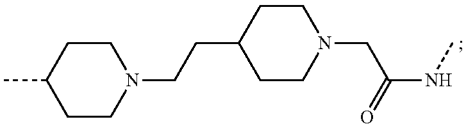;
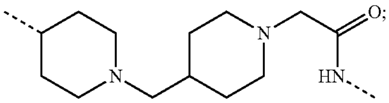;
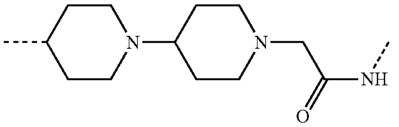;
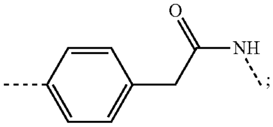;
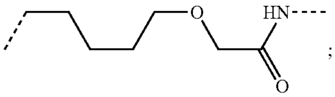;
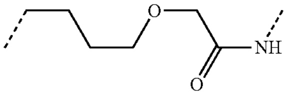;
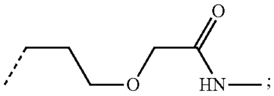;
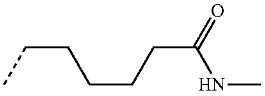;
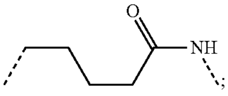;
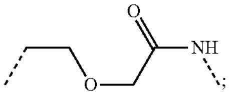;
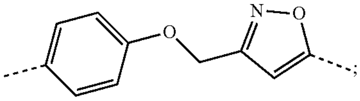;
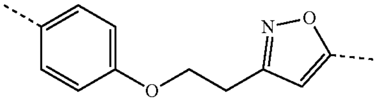;
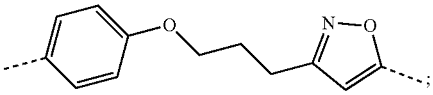;
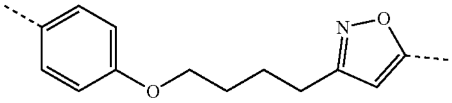;
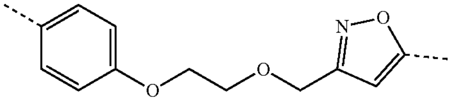;
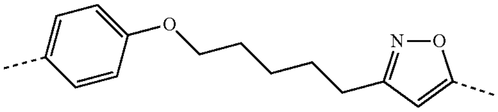;
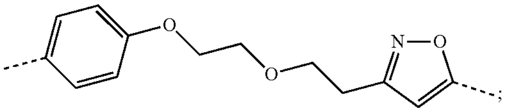;
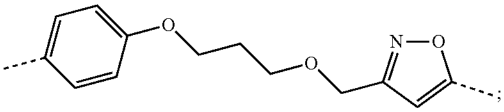;
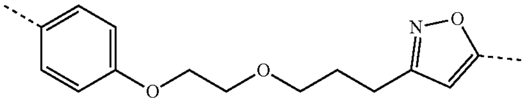;
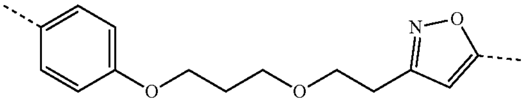;
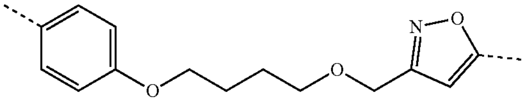;
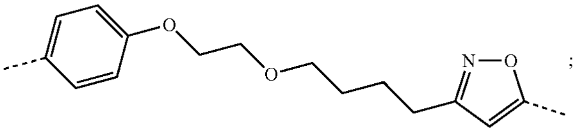;
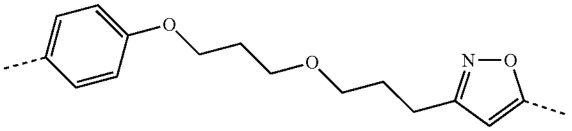;
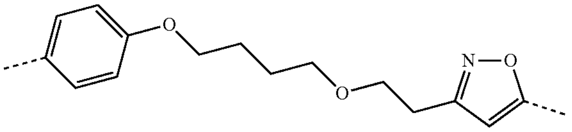;
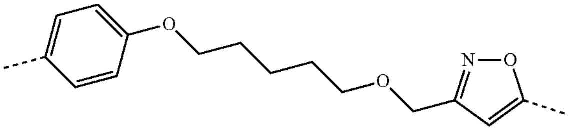;
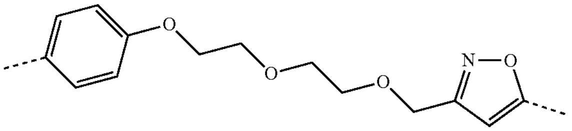;

-continued
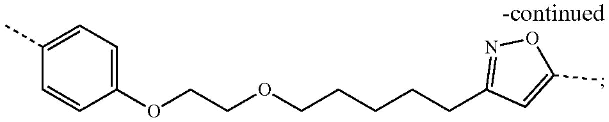;
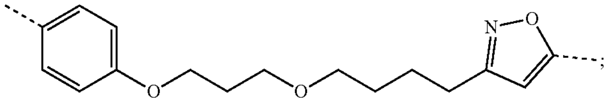;
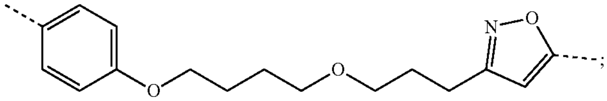;
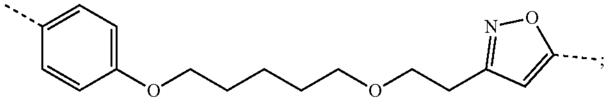;
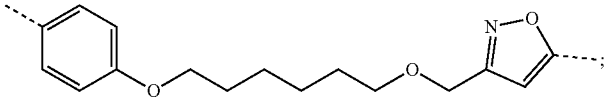;
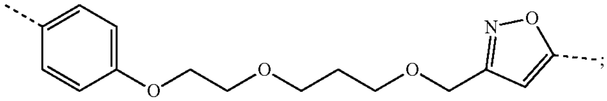;
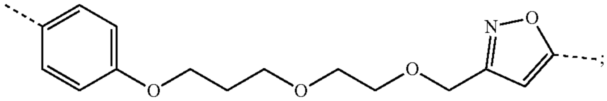;
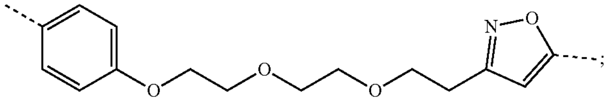; 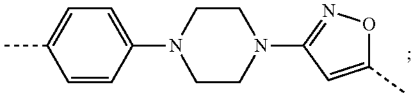;
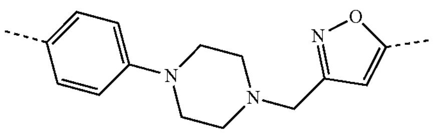; 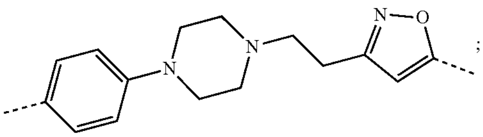;
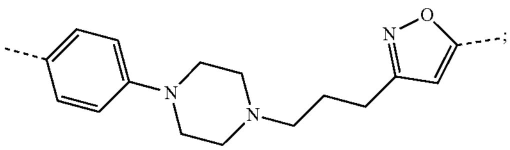; 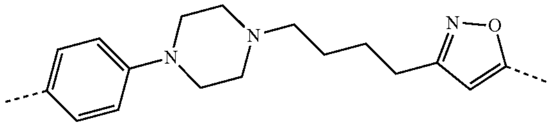;
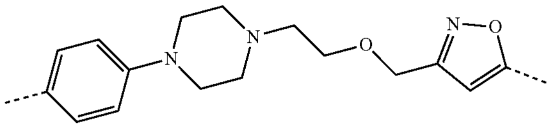;
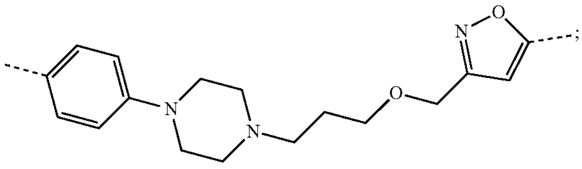;
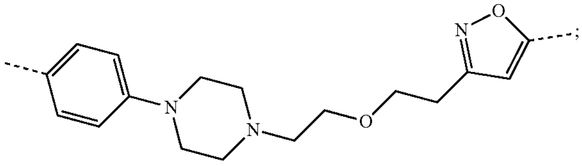;
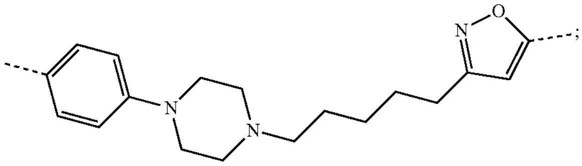;

-continued
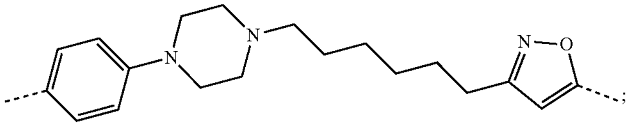
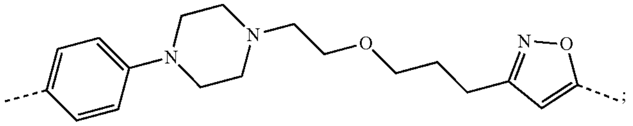
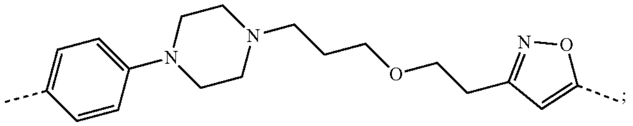
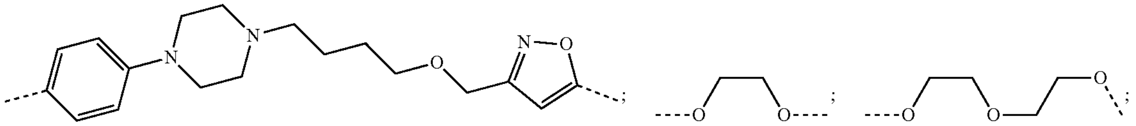
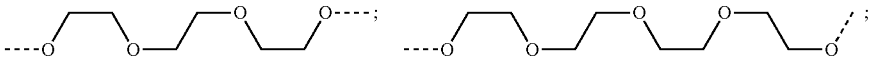
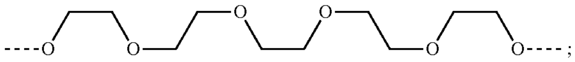
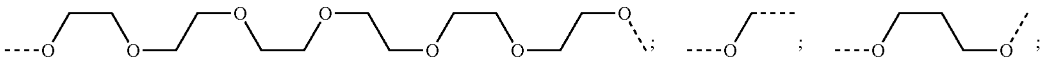
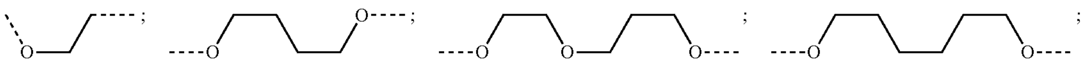
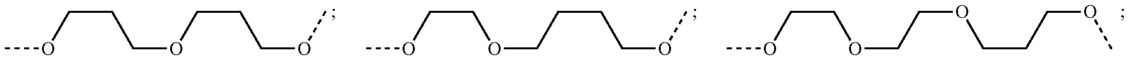
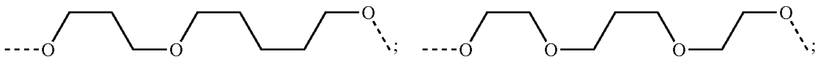
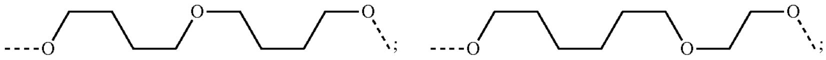
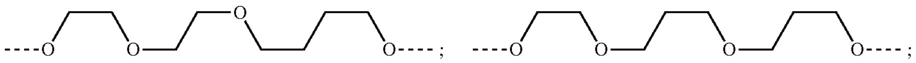
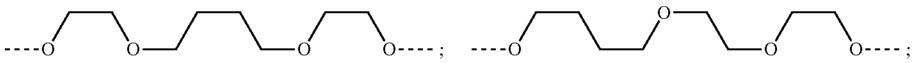
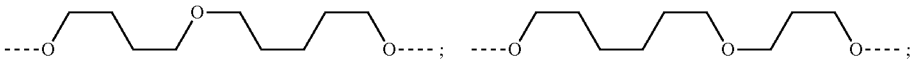
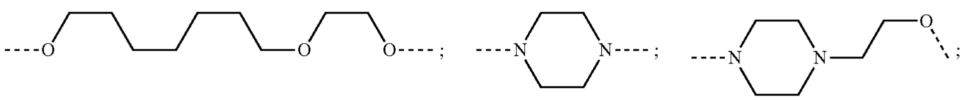
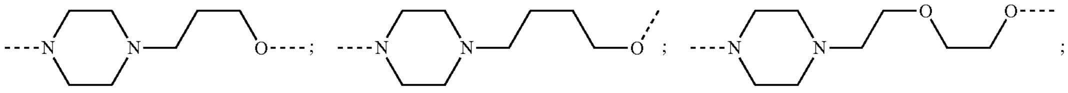
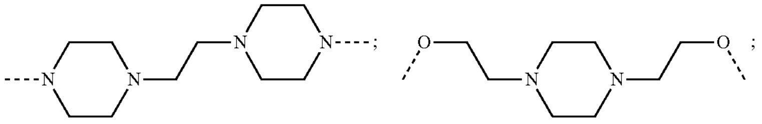
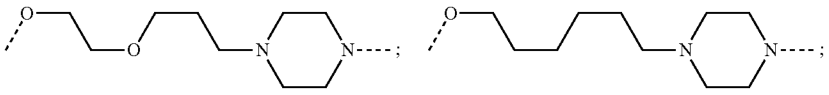
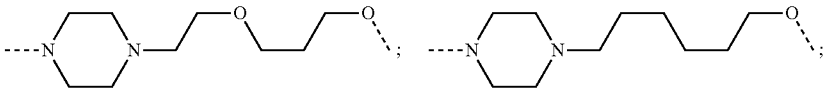

-continued
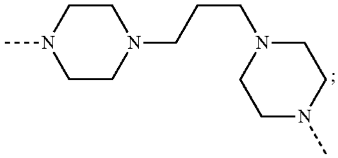;
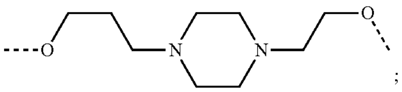;
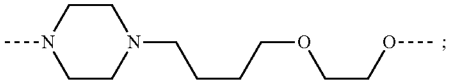;
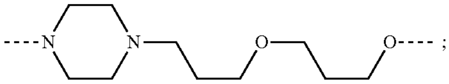;
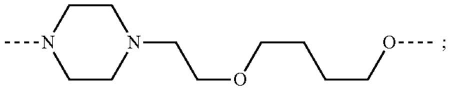;
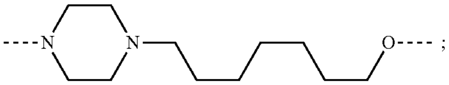;
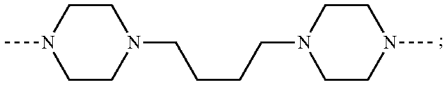;
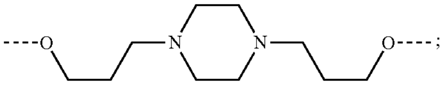;
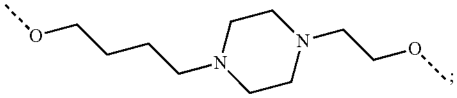;
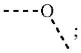;
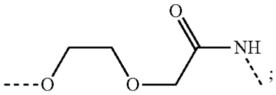;
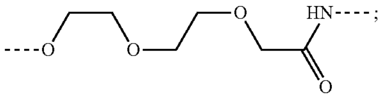;
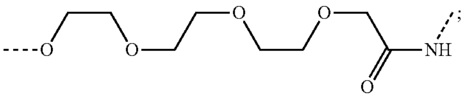;
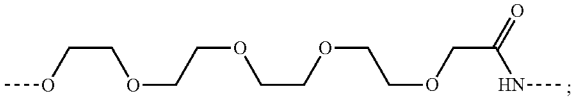;
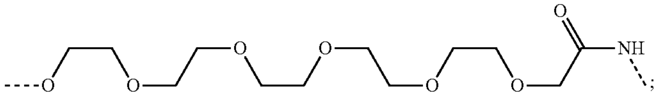;
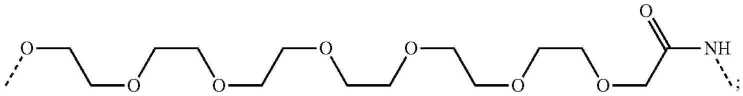;
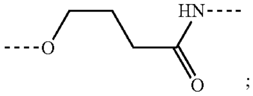;
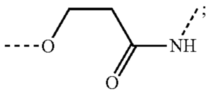;
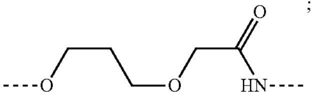;
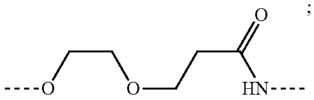;
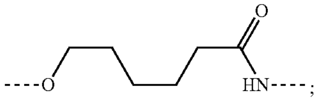;
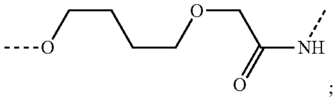;
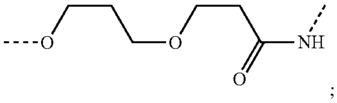;
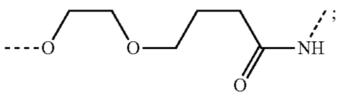;
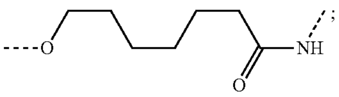;
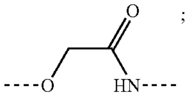;
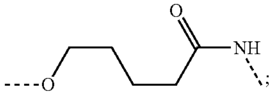;
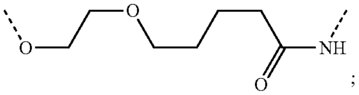;
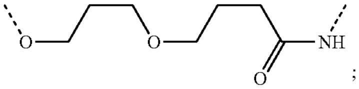;
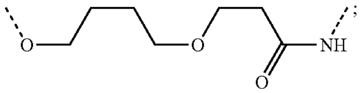;
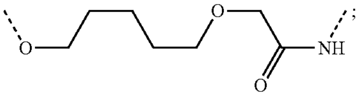;
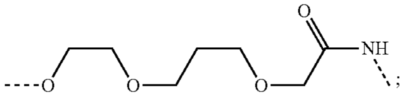;
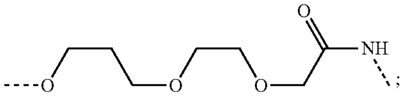;
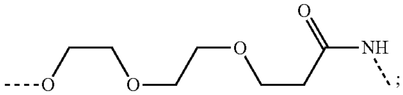;
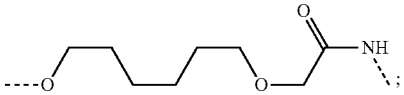;
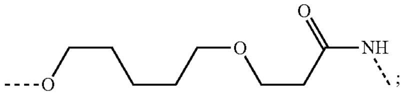;
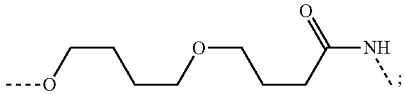;

-continued
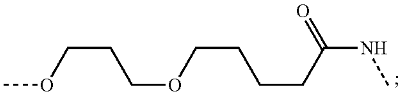
;
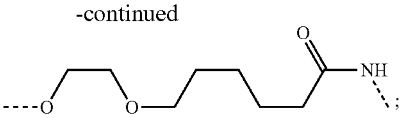
;
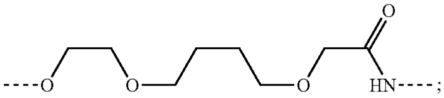
;
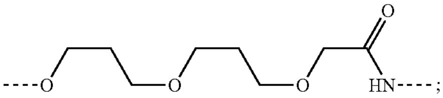
;
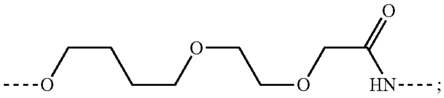
;
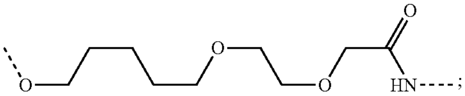
;
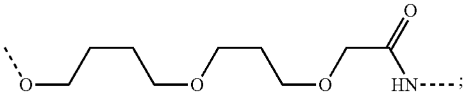
;
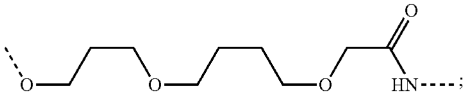
;
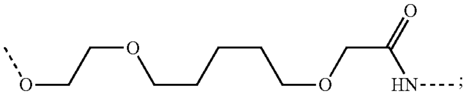
;
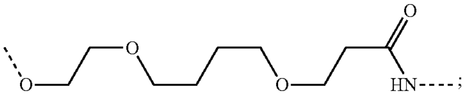
;
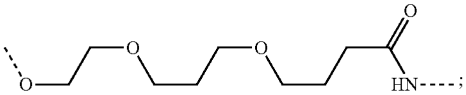
;
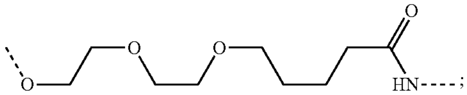
;
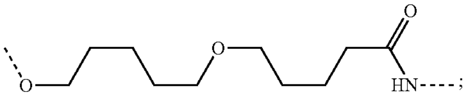
;
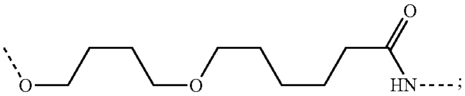
;
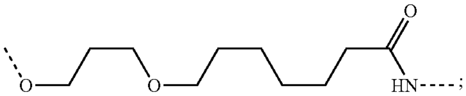
;
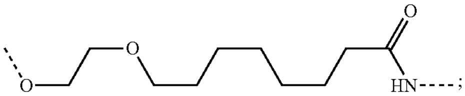
;
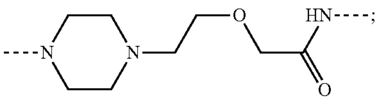
;
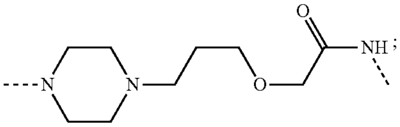
;
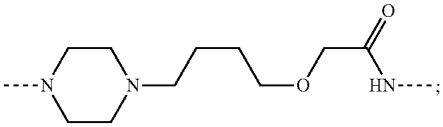
;
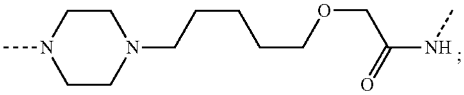
;
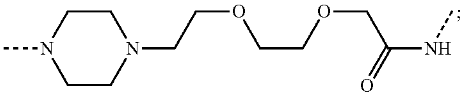
;
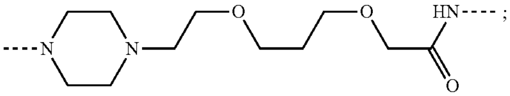
;
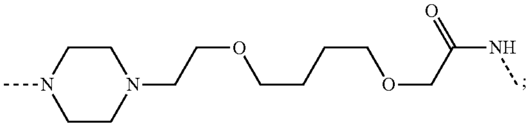
;
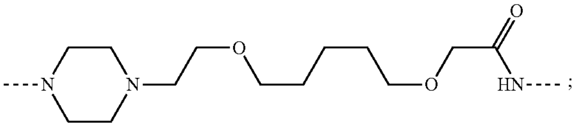
;
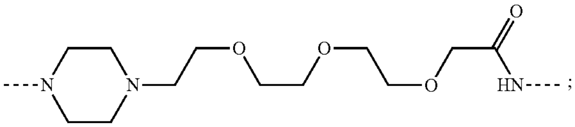
;
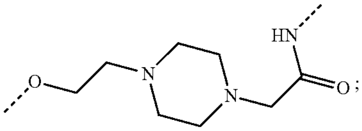
;
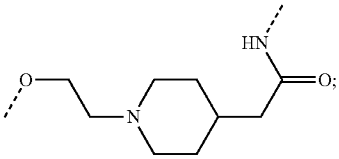
;
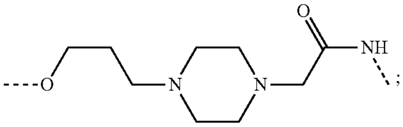
;
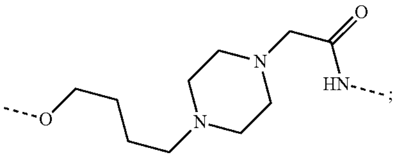
;
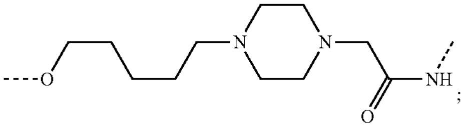
;

-continued
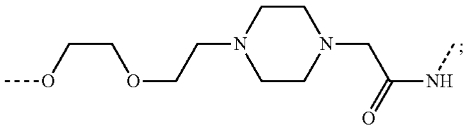;
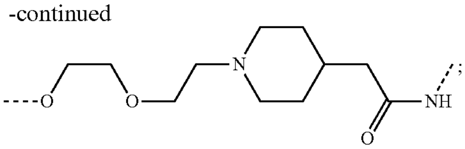;
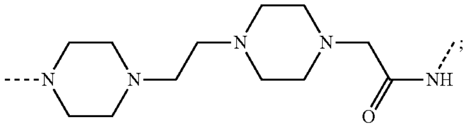;
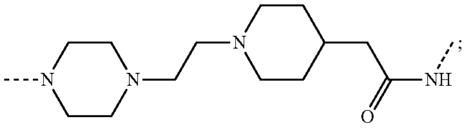;
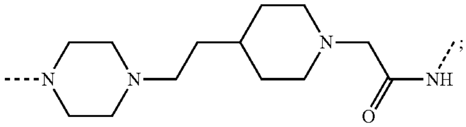;
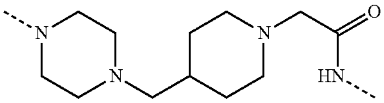;
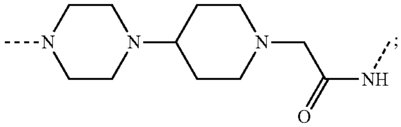;
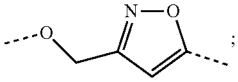;
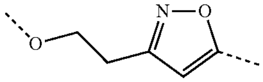;
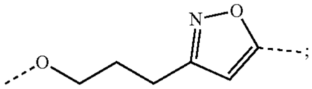;
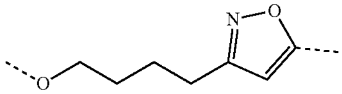;
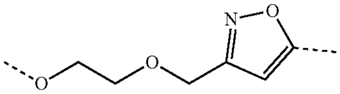;
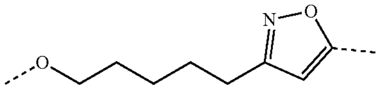;
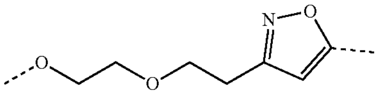;
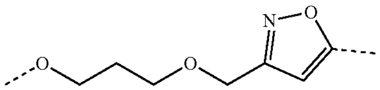;
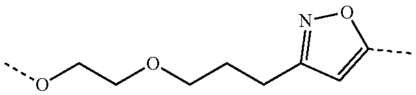;
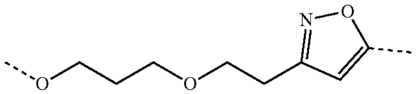;
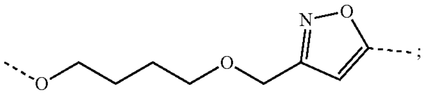;
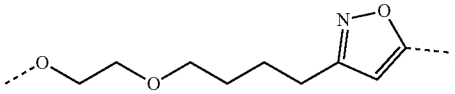;
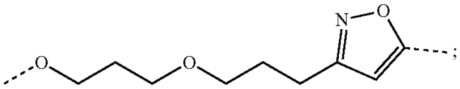;
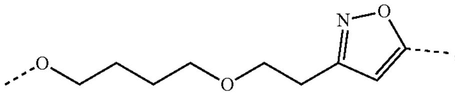;
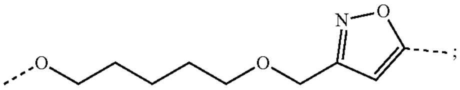;
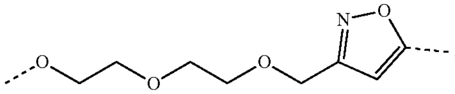;
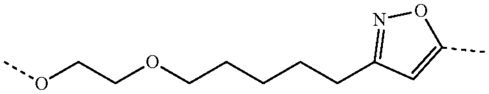;
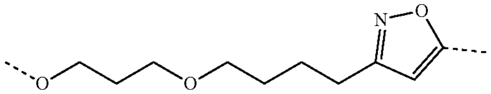;
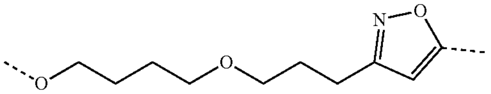;
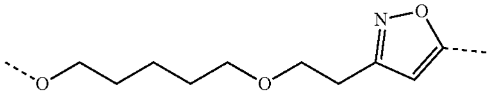;
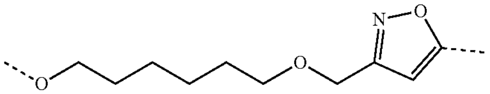;
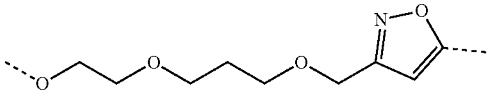;
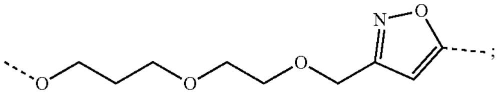;
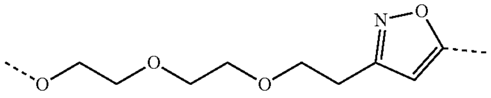;
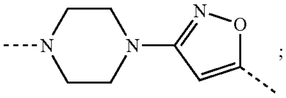;
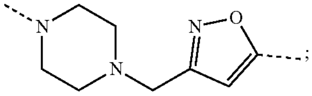;
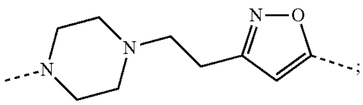;
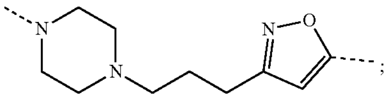;
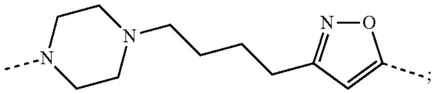;
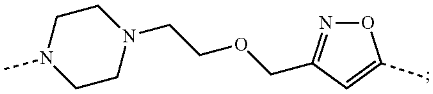;

-continued

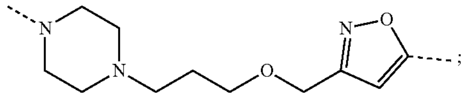

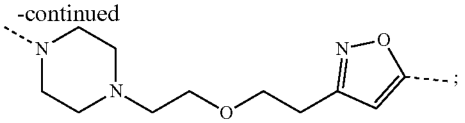

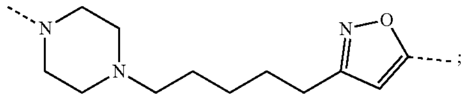

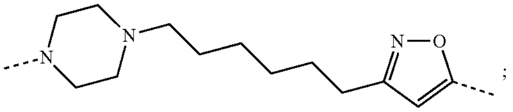

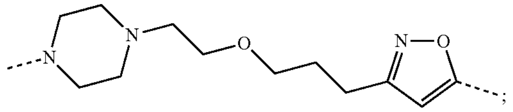

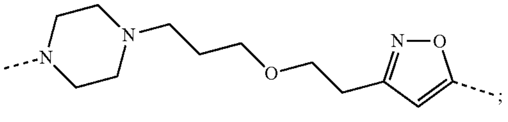

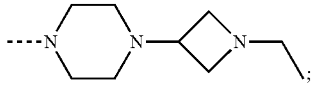

and

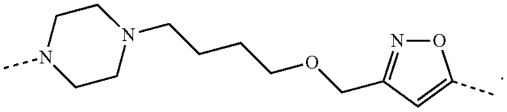

In any aspect or embodiment described herein, the linker (L) comprises the following chemical structure:

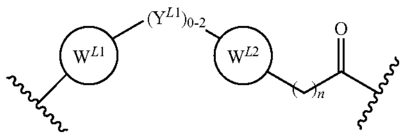

or

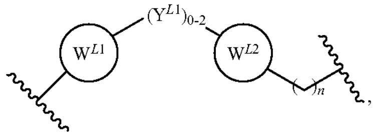

wherein:

$W^{L1}$ and $W^{L2}$ are each independently a 4-8 membered ring with 0-4 heteroatoms, optionally substituted with RQ, each RQ is independently a H, halo, OH, CN, CF3, C1-C6 alkyl (linear, branched, optionally substituted), C1-C6 alkoxy (linear, branched, optionally substituted), or 2 RQ groups taken together with the atom they are attached to, form a 4-8 membered ring system containing 0-4 heteroatoms;

$Y^{L1}$ is each independently a bond, C1-C6 alkyl (linear, branched, optionally substituted) and optionally one or more C atoms are replaced with O; or C1-C6 alkoxy (linear, branched, optionally substituted);

n is 0-10; and a dashed line indicates the attachment point to the PTM or ULM moieties.

In any aspect or embodiment described herein, the linker (L) comprises the following chemical structure:

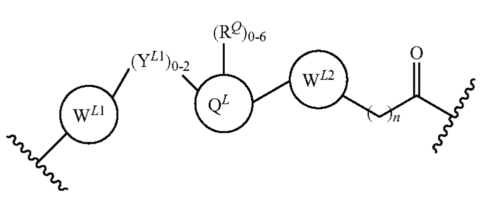

or

-continued

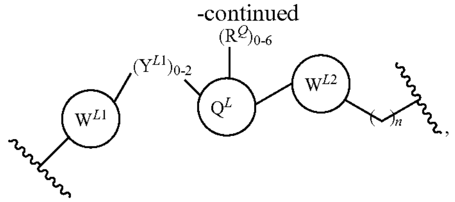

wherein:

$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In any aspect or embodiment described herein, the linker (L) is selected from the group consisting of:

-continued
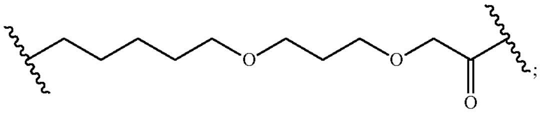;
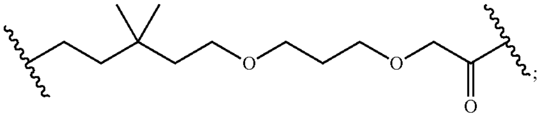;
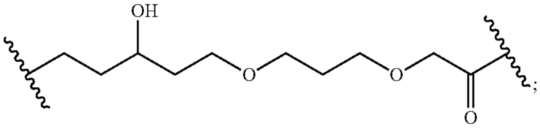;
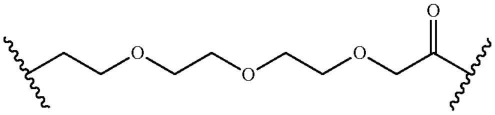;
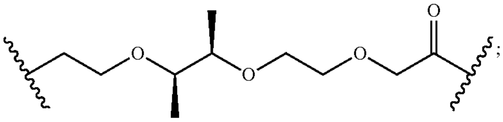;
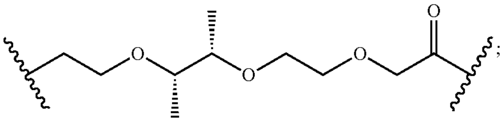;
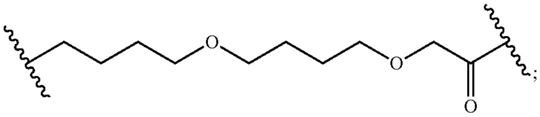;
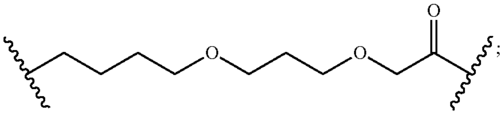;
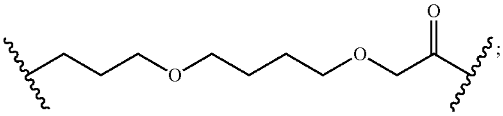;
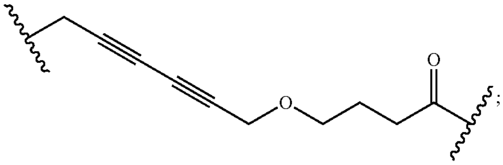;
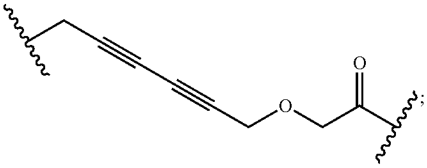;
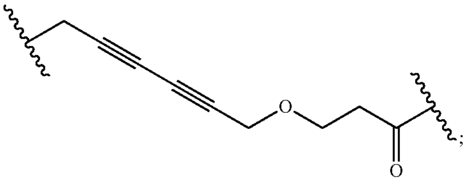;
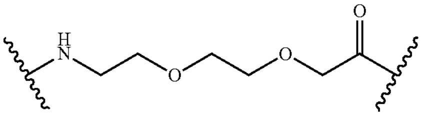;
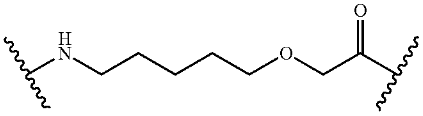;
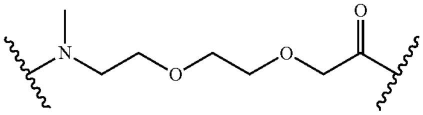;
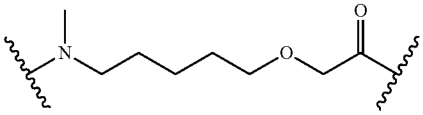;
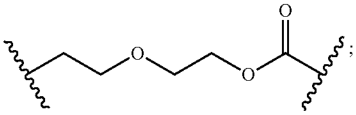;
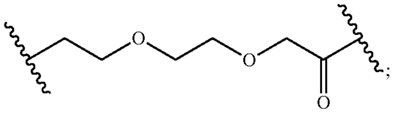;
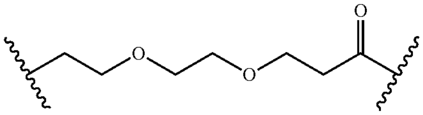;
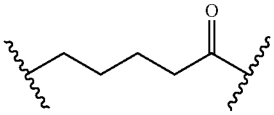;
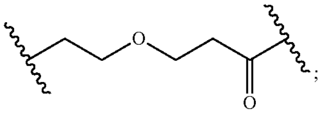;
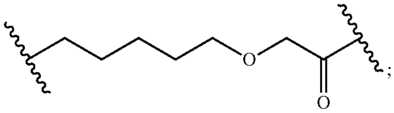;
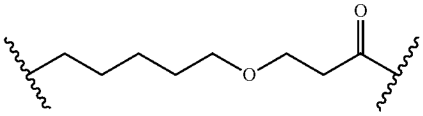;
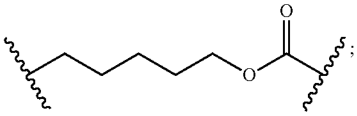;
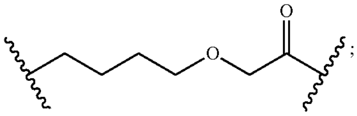;
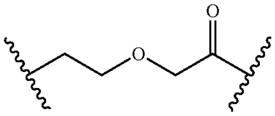;
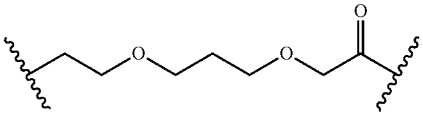;

-continued
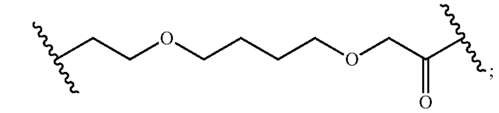
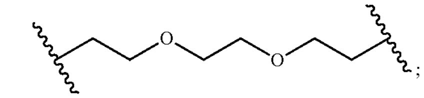
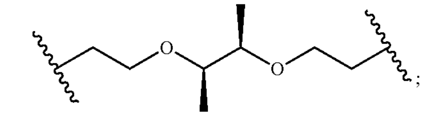
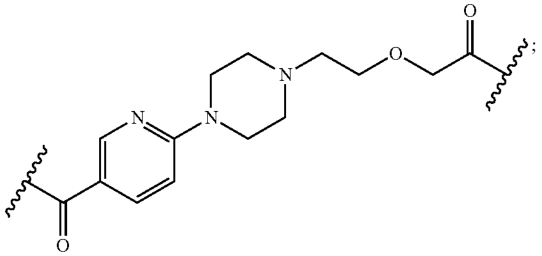
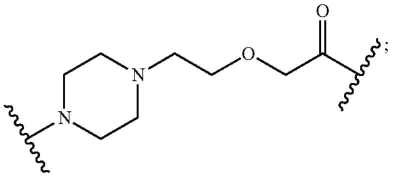
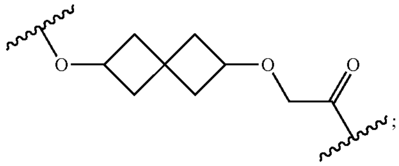
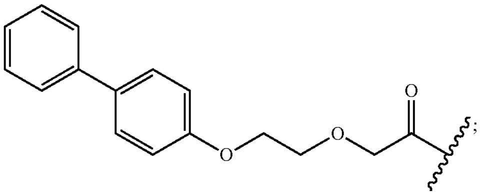
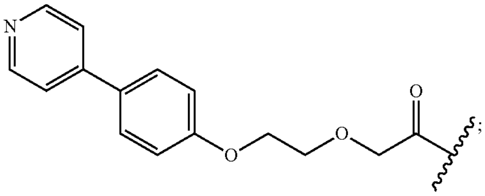
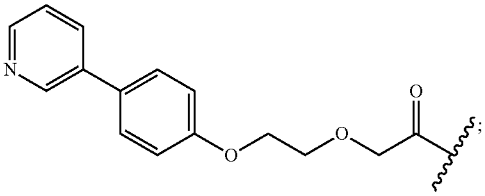
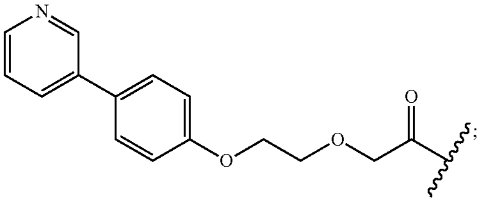
-continued
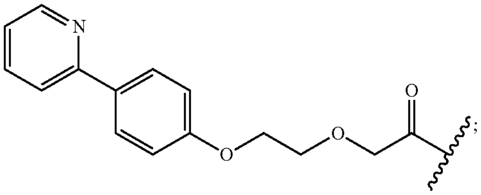
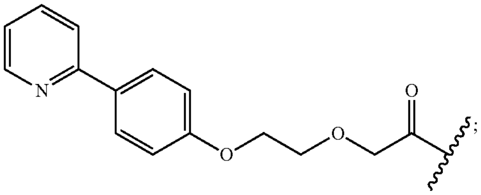
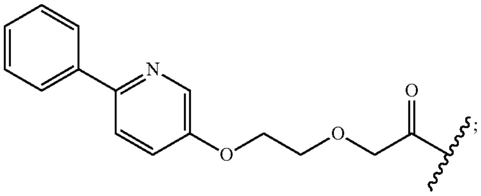
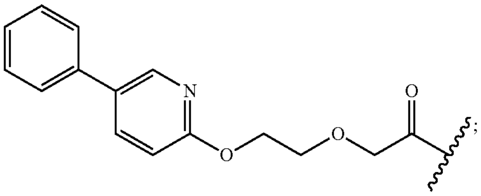
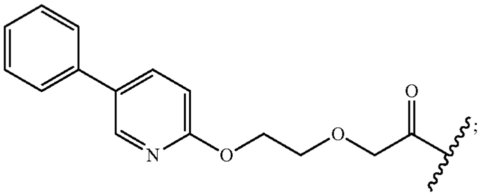
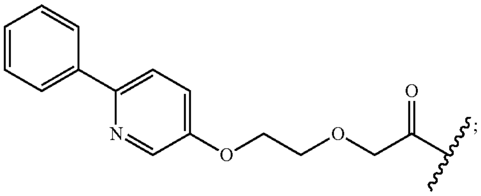
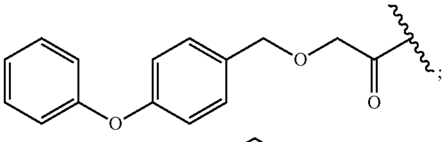
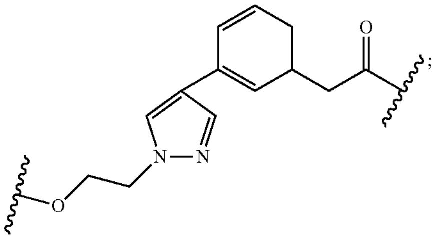
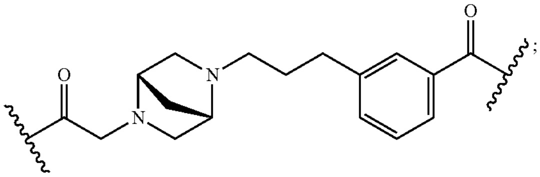

-continued
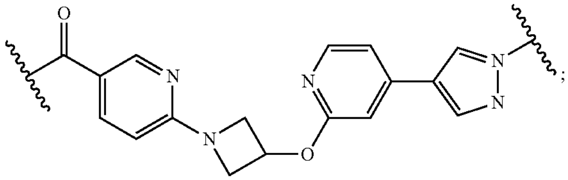
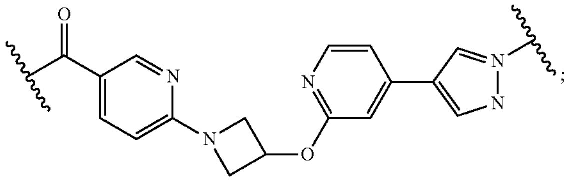
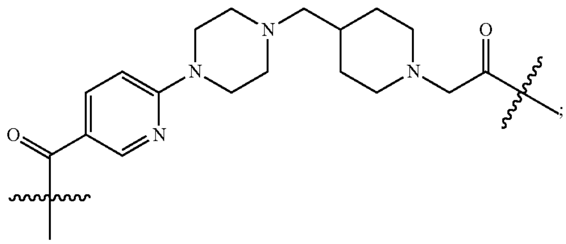
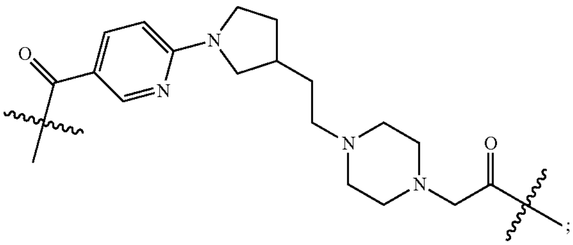
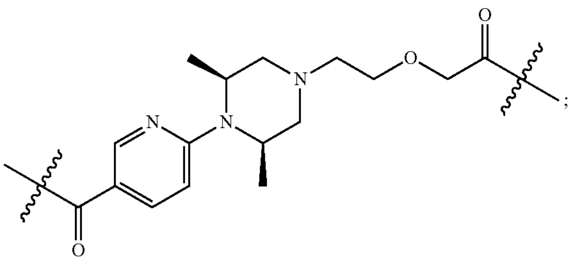
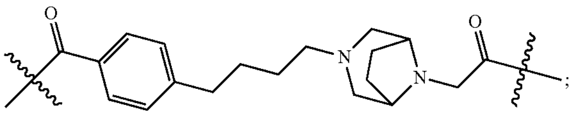
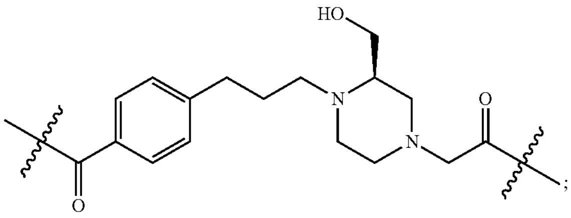
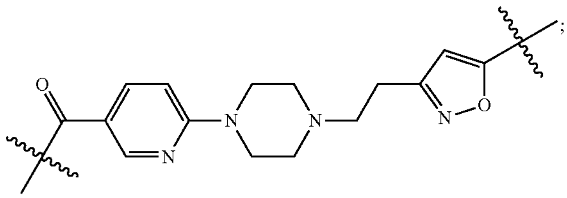
-continued
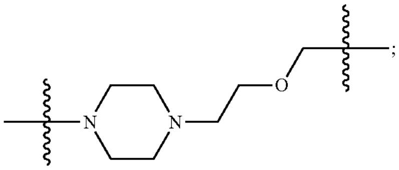
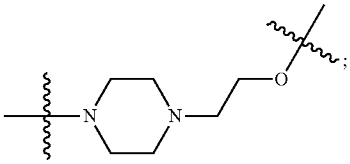
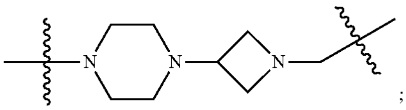
; and
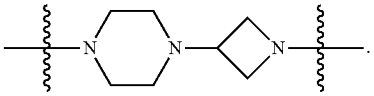
In any aspect or embodiment described herein, the linker (L) is a polyethylenoxy group optionally substituted with aryl or phenyl comprising from 1 to 10 ethylene glycol units.
In any aspect or embodiment described herein, the PTM is selected from the group consisting of:
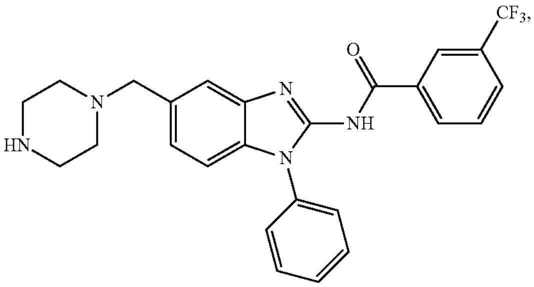
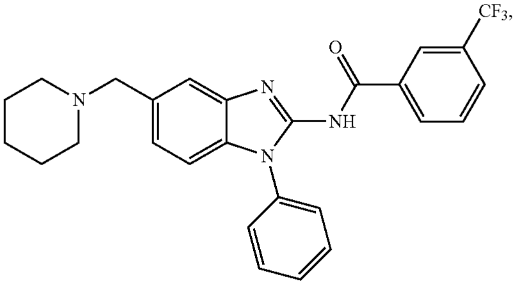
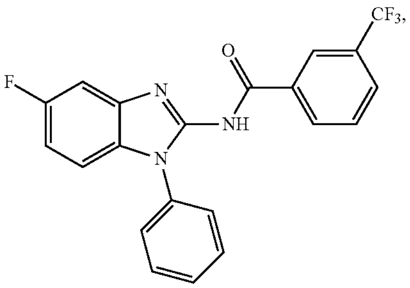

-continued
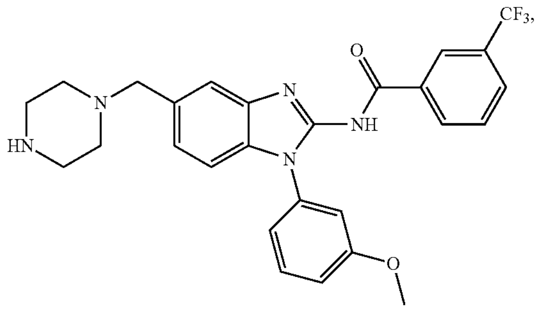
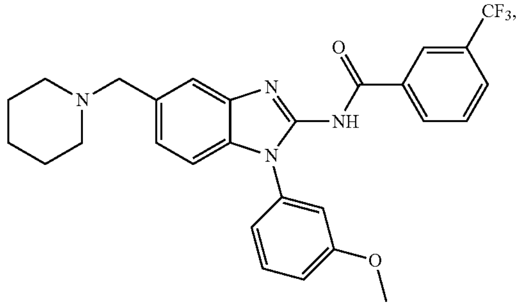
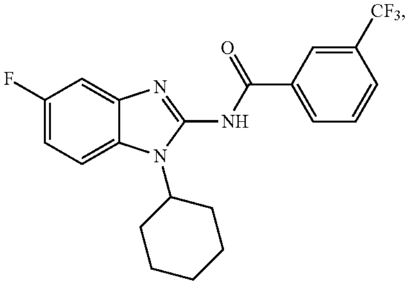
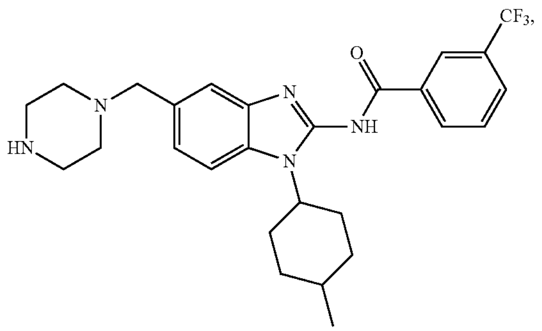
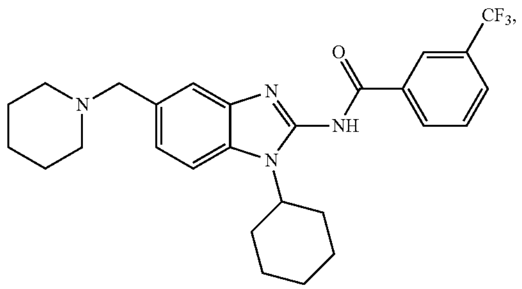
-continued
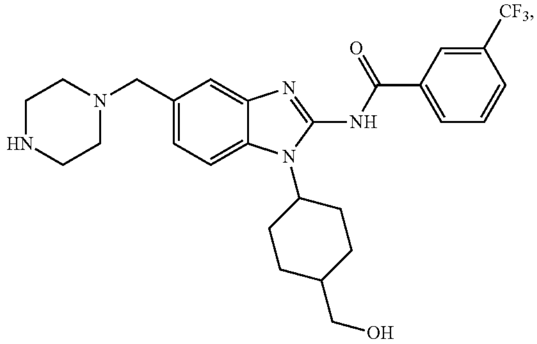
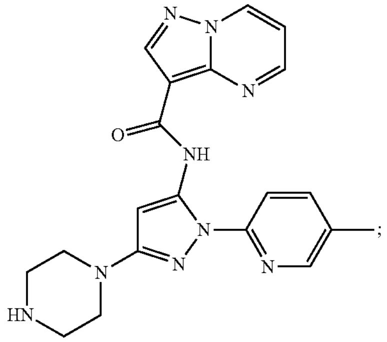
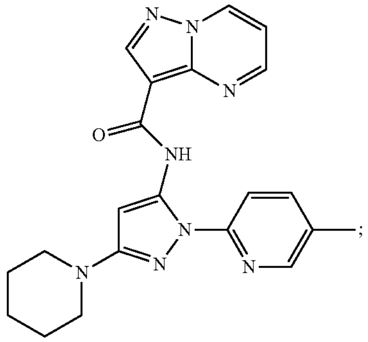
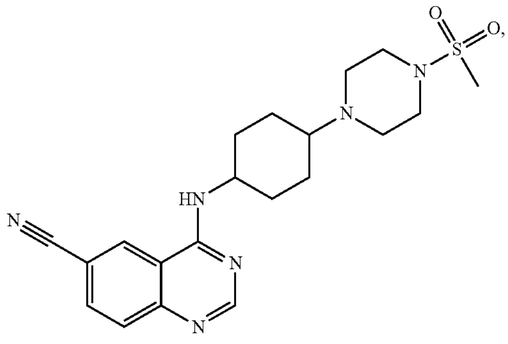
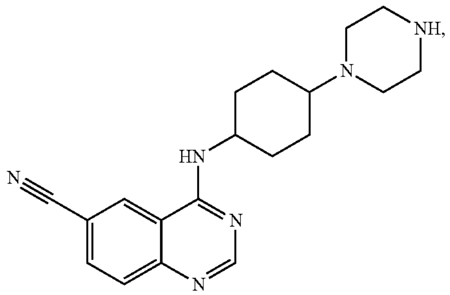

-continued

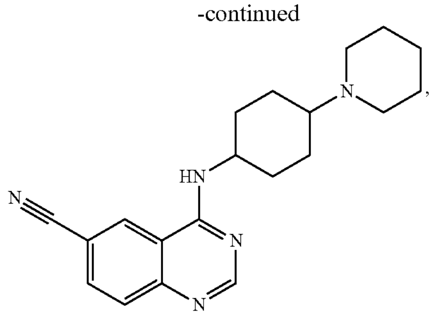

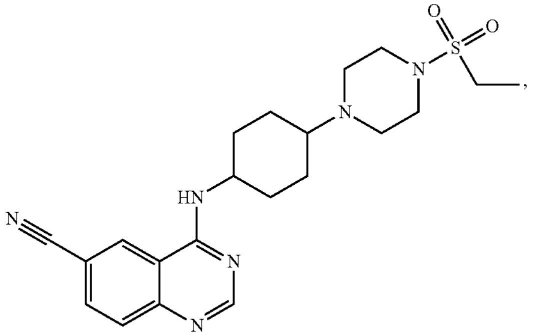

and

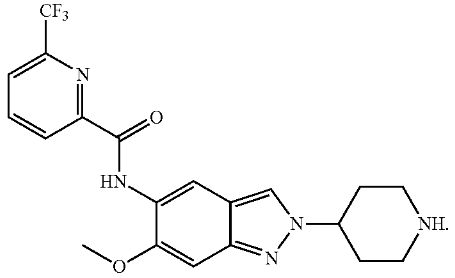

In any aspect or embodiment described herein, the compound comprises multiple ULMs, multiple PTMs, multiple linkers or any combinations thereof.

In another aspect, the present disclosure provides for a composition. The composition comprises an effective amount of a bifunctional compound of present disclosure, and a pharmaceutically acceptable carrier.

In aspect or embodiment described herein, the composition further comprises at least one of additional bioactive agent or another bifunctional compound of the present disclosure.

In aspect or embodiment described herein, the additional bioactive agent is anti-neurodegenerative agent, an anti-inflammatory agent, and/or an anti-cancer agent.

A composition comprising a pharmaceutically acceptable carrier and an effective amount of at least one compound of the present disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with tau accumulation and aggregation.

In any aspect or embodiment described herein, the disease or disorder is a neurodegenerative disease or disorder, an inflammatory disease or disorder and/or a cancer associated with IRAK-4 accumulation and aggregation.

In any aspect or embodiment described herein, the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In any aspect or embodiment described herein, the inflammatory disease or disorder is selected from the group consisting of ocular allergy, conjunctivitis, keratoconjunctivitis sicca, vernal conjunctivitis, allergic rhinitis, autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, primary biliary cirrhosis, uveitis (anterior and posterior), Sjogren's syndrome, interstitial lung fibrosis, psoriatic arthritis, systemic juvenile idiopathic arthritis, nephritis, vasculitis, diverticulitis, interstitial cystitis, glomerulonephritis (e.g. including idiopathic nephrotic syndrome or minimal change nephropathy), chronic granulomatous disease, endometriosis, leptospirosis renal disease, glaucoma, retinal disease, headache, pain, complex regional pain syndrome, cardiac hypertrophy, muscle wasting, catabolic disorders, obesity, fetal growth retardation, hypercholesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma, acute lung injury, acute respiratory distress syndrome, eosinophilia, hypersensitivities, anaphylaxis, fibrositis, gastritis, gastroenteritis, nasal sinusitis, ocular allergy, silica induced diseases, chronic obstructive pulmonary disease (COPD), cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, appendicitis, atopic dermatitis, asthma, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, juvenile rheumatoid arthritis, dermatomyositis, encephalitis, endocarditis, endometritis, enteritis, enterocolitis, epicondylitis, epididymitis, fasciitis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, vasculitis, vulvitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acute and chronic gout, chronic gouty arthritis, psoriasis, psoriatic arthritis, rheumatoid arthritis, Cryopyrin Associated Periodic Syndrome (CAPS) and osteoarthritis.

Cell Proliferation Assay Using CellTiter-Glo.

Cells were lifted, washed and counted. White, clear-bottom 96-well plates were seeded with 180 μl growth media per well. To allow sub-confluent growth for 3-5 days, seeding densities were as follows: OCI-Ly3 (from DSMZ, Braunschweig, Germany)=10000 cells/well; OCI-Ly19 (from DSMZ, Braunschweig, Germany)=2000 cells/well; DHL-6 (from ATCC, Manassas, Va.)=2000 cells/well; MCF-7 (from ATCC, Manassas, Va.)=2000 cells/well. One extra plate was seeded for a "time zero" CellTiter-Glo reading. Cells were allowed to adhere/incubate overnight at 37° C./5% $CO_2$. The next day, cells were treated in technical duplicate with 20 μl of 10X compound (1% DMSO) was added as appropriate. Plates were returned to incubator for 3 or 5 days. The "time zero" plate was spun down at 300×g, media flicked out and replaced with 100 μl fresh media and 100 μl CellTiter-Glo 2.0 (Promega, Madison, Wis.; plate was then read on Envision 2105 with luminescence setting. At the end point (3 or 5 days), the compound treated plates were spun down at 300×g for 5 minutes, media flicked out, then replaced with 100 μl fresh media and 100 μl CellTiter-Glo 2.0. Plates were then read on the Envision with the luminescence setting.

In certain other embodiments, the description provides exemplary IRAK PROTAC molecules by selecting a PTM from Table 6(e.g., a PTM selected from the group consisting of PTM1 through PTM91), a linker from Table 7(e.g., a linker selected from the group consisting of Linker1 through Linker18), and a ULM from Table 8 (e.g., a linker selected from the group consisting of ULM1 through ULM25), including salts, prodrugs, polymorphs, analogs, derivatives, and deuterated forms thereof:

Additionally, the description provides a compound comprising a PTM from Table 6 (i.e., a PTM selected from the group consisting of PTM1-PTM91), a linker from Table 7 (i.e., a linker selected from the group consisting of Linker1-Linker18), and a ULM from Table 8 (i.e., a ULM selected from the group consisting of ULM1-ULM23), including salts, prodrugs, polymorphs, analogs, derivatives, and deuterated forms thereof.

In other embodiments, the description provides a composition comprising a compound having a PTM from Table 6 (i.e., a PTM selected from the group consisting of PTM1-PTM91), a linker from Table 7 (i.e., a linker selected from the group consisting of Linker1-Linker18), and a ULM from Table 8 (i.e., a ULM selected from the group consisting of ULM1-ULM23), including salts, prodrugs, polymorphs, analogs, derivatives, and deuterated forms thereof.

In an aspect, the present disclosure provides a bifunctional compound having the chemical structure:

ULM-L-PTM, or a pharmaceutically acceptable salt, enantiomer, stereoisomer, solvate, polymorph or prodrug thereof, wherein: the ULM is a small molecule E3 ubiquitin ligase binding moiety that binds an E3 ubiquitin ligase; the PTM is a small molecule comprising an Interleukin-1 Receptor-Associated Kinase 4 (IRAK-4) targeting moiety; and the L is a bond or a chemical linking moiety connecting the ULM and the PTM.

In any aspect or embodiment described herein, at least one of: the PTM is selected from Table 6, the linker (L) is selected from Table 7, the ULM is selected from Table 8, or a combination thereof.

What is claimed is:

1. A bifunctional compound having the chemical structure:

PTM-L-ULM, or a pharmaceutically acceptable salt, enantiomer, stereoisomer, solvate, or polymorph thereof, wherein:

(a) the L is a chemical linker group that covalently couples the ULM to the PTM;

(b) the ULM is a cereblon E3 ubiquitin ligase binding moiety (CLM) that has a chemical structure represented by (a)

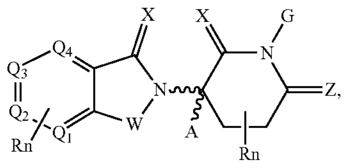

(b)

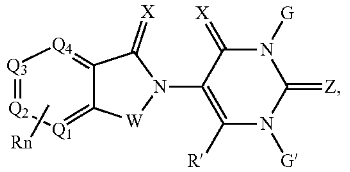

(c)

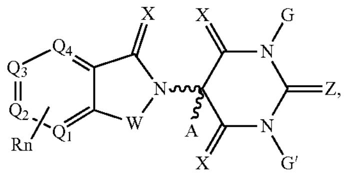

(d)

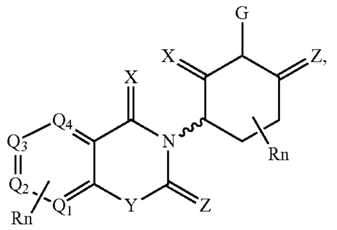

-continued (e)

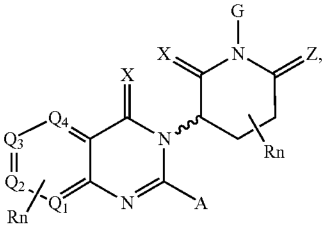

or (f)

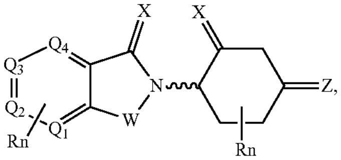

wherein:

W is selected from the group consisting of $CH_2$, CHR, C═O, $SO_2$, NH, and N-alkyl;

each X is independently selected from the group consisting of absent, O, and S;

Y is selected from the group consisting of $CH_2$, —C═CR', NH, N-alkyl, N-aryl, N-hetaryl, N-cycloalkyl, N-heterocyclyl, O, and S;

Z is selected from the group consisting of absent, O, and S;

G and G' are independently selected from the group consisting of H, optionally substituted linear or branched alkyl, OH, R'OCOOR, R'OCONRR", $CH_2$-heterocyclyl optionally substituted with R', and benzyl optionally substituted with R';

$Q_1$, $Q_2$, $Q_3$, and $Q_4$ represent a carbon C substituted with a group independently selected from H, R, N or N-oxide;

A is independently selected from the group H, optionally substituted linear or branched alkyl, cycloalkyl, Cl and F;

n is an integer from 1 to 4, wherein one $R_a$ is modified to be covalently joined to the PTM or the chemical linker group;

R comprises —CONR'R", —OR', —NR'R", —SR', —$SO_2$R', —$SO_2$NR'R", —CR'R"—, —CR'NR'R"—, $(—CR'O)_{n'}R"$, -aryl, -hetaryl, optionally substituted linear or branched -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", -alkyl-aryl, —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$and —$OCF_3$;

R' and R" are independently selected from the group consisting of a bond, H, alkyl, cycloalkyl, aryl, heteroaryl, heterocyclic, —C(═O)R, heterocyclyl, each of which is optionally substituted;

∿∿ represents a bond that may be stereospecific ((R) or (S)) or non-stereospecific; and n' is an integer from 1-10;

(c) the PTM is a small molecule comprising an Interleukin-1 Receptor-Associated Kinase 4 (IRAK-4) targeting moiety represented by PTM-Va or PTM-Vb:

PTM-Va

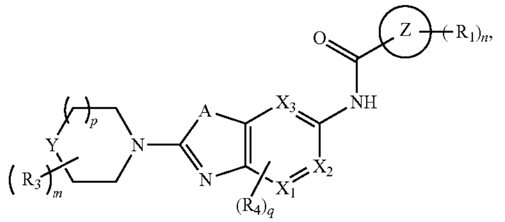

or

PTM-Vb

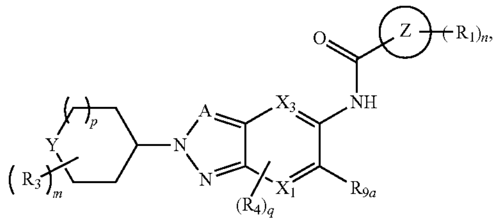

wherein:

$X_1$ and $X_3$ of PTM-Va or PTM-Vb independently are CH or N; $X_2$ of PTM-Va is $CR_2$ or N; provided one and not more than one of $X_1$, $X_2$ or $X_3$ is N;

Y of PTM-Va or PTM-Vb is —$CH_2$—, NH, or O;

Ring Z of PTM-Va or PTM-Vb is aryl, heteroaryl, or heterocyclyl;

A of PTM-Va is O, S, or NH;

A of PTM-Vb is —CH or —$CCH_3$;

$R_1$ of PTM-Va or PTM-Vb at each occurrence, is independently hydrogen, cyano, halo, hydroxy, —$NO_2$, —$NR_5R_6$, optionally substituted alkyl, optionally substituted aryl, optionally substituted cycloalkyl, optionally substituted heterocycloalkyl, optionally substituted heterocyclyl or optionally substituted heteroaryl, wherein the substituent, in each occurrence, is independently selected from alkyl, alkoxy, haloalkyl, cyano, aminoalkyl, halo, hydroxyl, hydroxyalkyl, —$NR_7R_8$, or $COOR^9$;

$R_2$ of PTM-Va or PTM-Vb is hydrogen, optionally substituted cycloalkyl, optionally substituted aryl, or optionally substituted heterocyclyl; wherein the substituent is alkyl, amino, halo or hydroxyl;

$R_3$ of PTM-V, at each occurrence, is independently selected from hydrogen, carboxy, cyano, hydroxy, hydroxyalkyl, alkyl, aryl, heteroaryl, —$SO_2R_7$, hydroxyl or oxo;

$R_4$ of PTM-Va or PTM-Vb at each occurrence is independently selected from hydrogen, halogen, alkyl, aryl, heterocycloalkyl, heterocycloalkylalkyl, heteroaryl, $Y_1$-arylalkyl or —$Y_1$-cycloalkyl; wherein cycloalkyl, aryl, heterocycloalkyl, heterocycloalkylalkyl, heteroaryl and arylalkyl can be optionally substituted with hydroxy, alkyl, haloalkyl, cyano or halo;

$Y_1$ of PTM-Va or PTM-Vb is selected from direct bond, O, —C(O)— or $NR_9$;

$R_5$ and $R_6$ of PTM-Va or PTM-Vb are independently selected from hydrogen, hydroxyalkyl, aminoalkyl, acyl, optionally substituted alkyl, optionally substituted heterocyclyl, optionally substituted aryl; wherein the optional substituent, in each occurrence, is independently selected from halo, haloalkyl or —$COOR_9$;

$R_7$ and $R_8$ of PTM-Va or PTM-Vb are independently hydrogen, alkyl, acyl, heterocyclyl, —$COR_9$ or —$COOR^9$;

$R_9$ of PTM-V or PTM-Vb at each occurrence is independently selected from hydrogen or alkyl;

$R_{9a}$ of PTM-Vb is selected from hydrogen, halo, optionally substituted alkoxy, optionally substituted alkyl, hydroxyalkyl, or haloalkyl;

"m", "n" and "q" of PTM-Va or PTM-Vb are independently selected from 0, 1, 2, or 3;

"p" of PTM-Va or PTM-Vb is 0 or 1; and

Y, $R_1$, $R_2$, $R_3$, $R_4$, $R_5$, $R_6$, $R_7$, $R_8$, $R_9$, or $R_{9a}$ is modified to be covalently joined to the chemical linker group.

2. The compound of claim 1, wherein the PTM is represented by Formula PTM-Vb.

3. The compound according to claim 1, wherein the CLM has a chemical structure represented by:

(a)

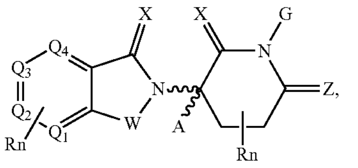

or (f)

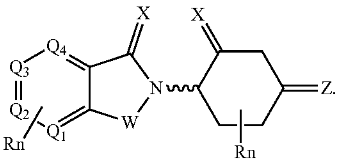

4. The compound according to claim 1, wherein the CLM has a chemical structure represented by:

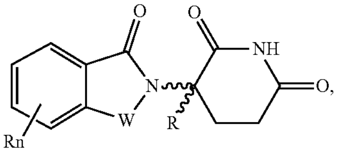

wherein:

W is independently selected from the group CH2, C═O, NH, and N-alkyl;

A is H, methyl, or optionally substituted linear or branched C1-C6 alkyl;

〰 represents a bond that may be stereospecific ((R) or (S)) or non-stereospecific; and n is an integer from 1 to 4, wherein one $R_n$ is modified to be covalently joined to the PTM, or the chemical linker group (L).

5. The compound according to claim 1, wherein the linker (L) comprises a chemical structural unit represented by the formula:

$$-(A^L)_q-,$$

wherein:

$(A^L)_q$ is a group which is connected to at least one of ULM moiety, PTM moiety, or a combination thereof;

q is an integer greater than or equal to 1, each A is independently selected from the group consisting of $CR^{L1}R^{L2}$, O, S, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 1-6 $R^{L1}$ and/or $R^{L2}$ groups, $C_{3-11}$heteocyclyl optionally substituted with 1-6 $R^{L1}$ and/or $R^{L2}$ groups, aryl optionally substituted with 1-6 $R^{L1}$ and/or $R^{L2}$ groups, and heteroaryl optionally substituted with 1-6 $R^{L1}$ and/or $R^{L2}$ groups, where $R^{L1}$ or $R^{L2}$, each independently are optionally linked to another atom of the linker (L) to form a cycloalkyl and/or heterocyclyl moiety, and optionally substituted with 1-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC{-}C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)SO_2N(C_{1-8}alkyl)_2$, NH $SO_2NH(C_{1-8}alkyl)$, NH $SO_2N(C_{1-8}alkyl)_2$, or NH $SO_2NH_2$.

6. The compound according to claim 5, wherein the linker (L) is selected from the group consisting of:

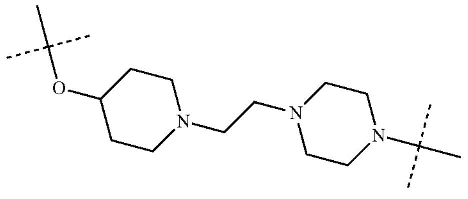

;

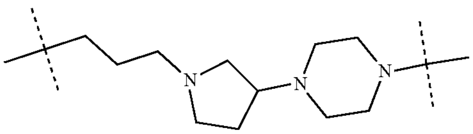

;

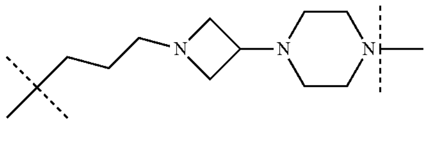

;

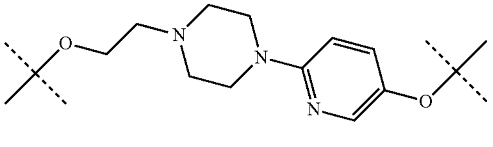

;

-continued
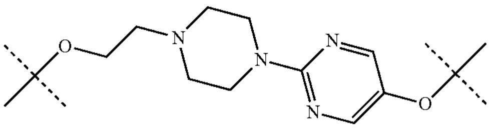 ; 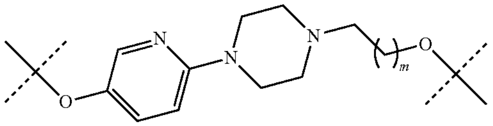 ;
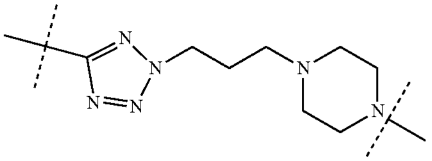 ; 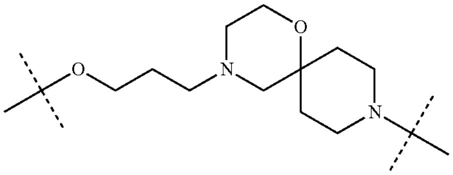 ;
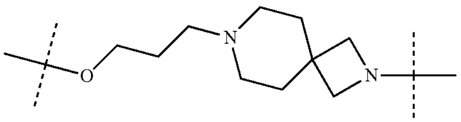 ; 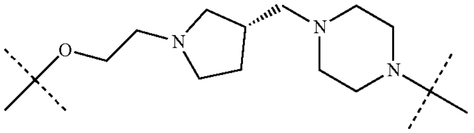 ;
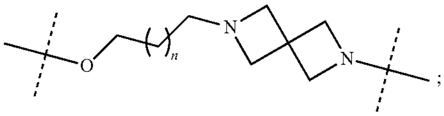 ; 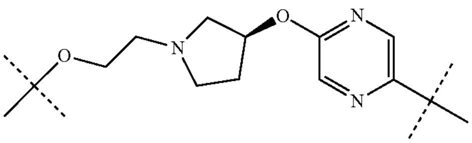 ;
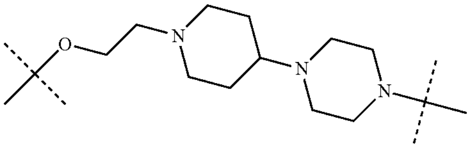 ; 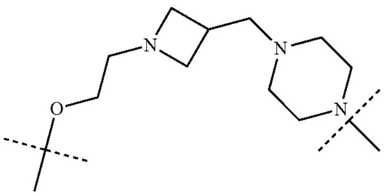 ;
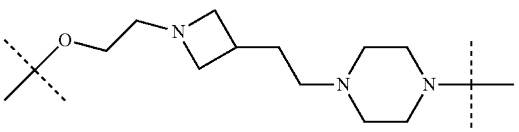 ; 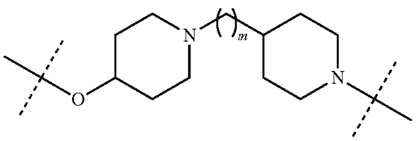 ;
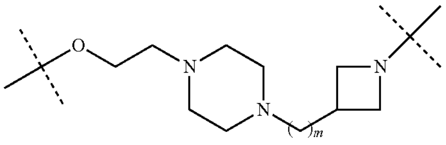 ; 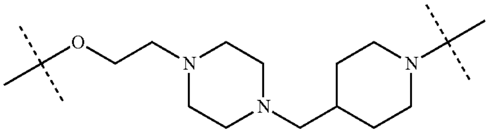 ;
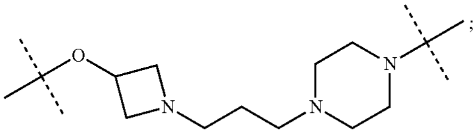 ; 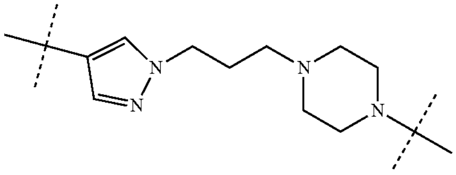 ;
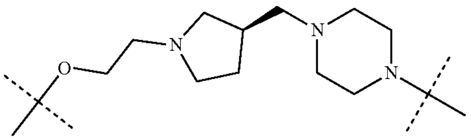 ; 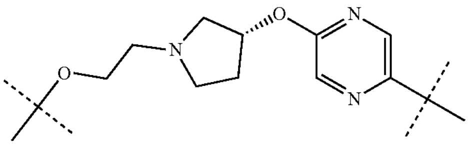 ;
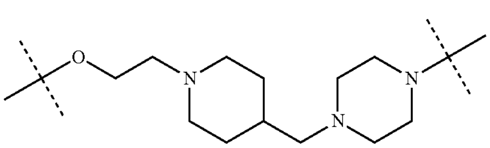 ; 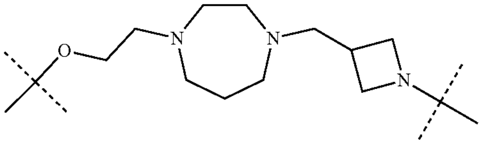 ;
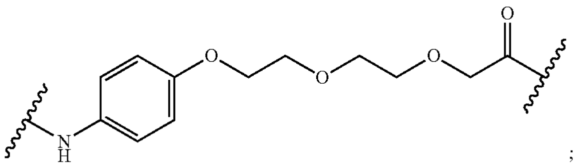 ;

-continued
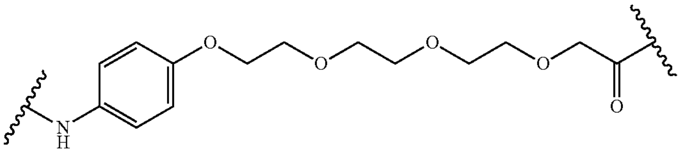
;
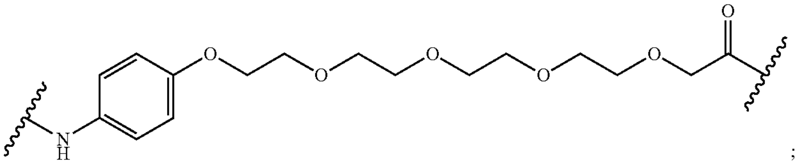
;
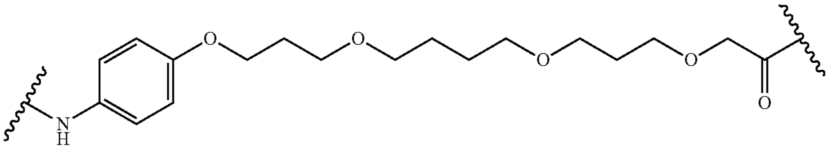
;
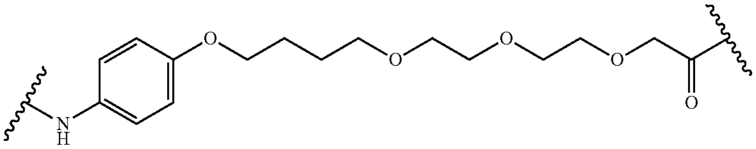
;
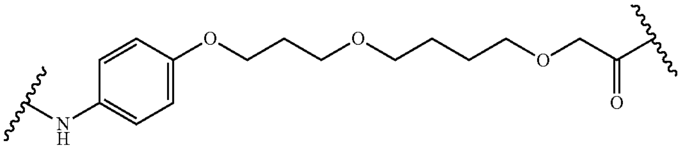
;
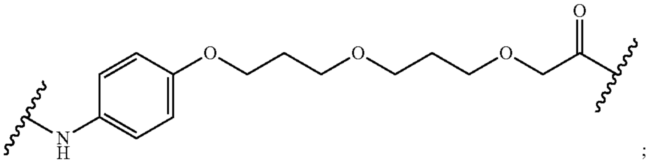
;
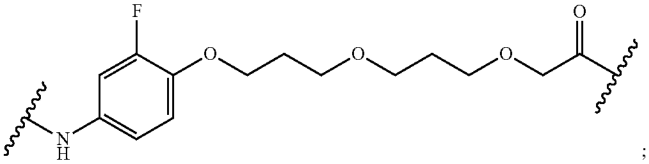
;
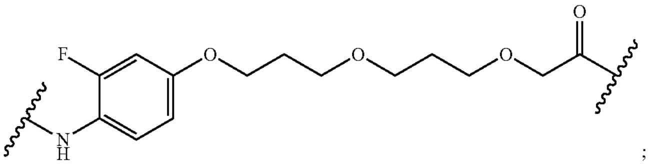
;
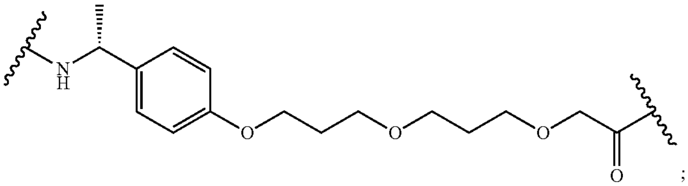
;
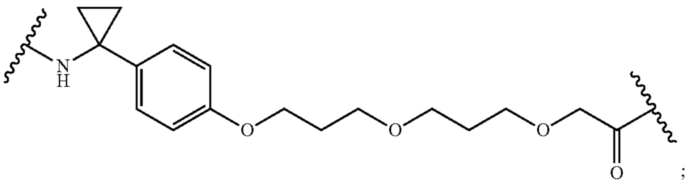
;

-continued
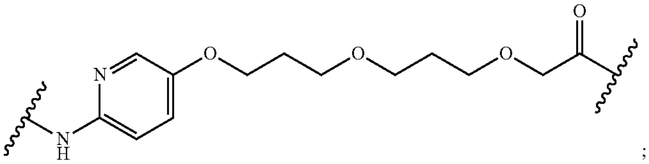
;
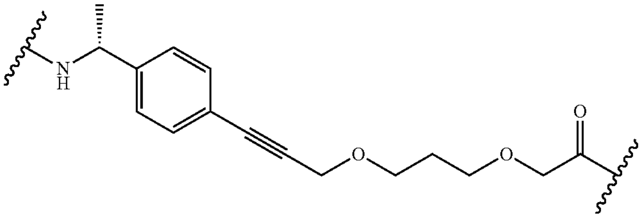
;
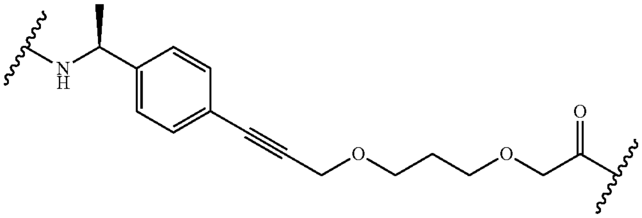
;
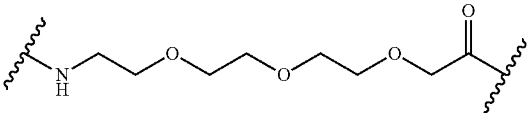
;
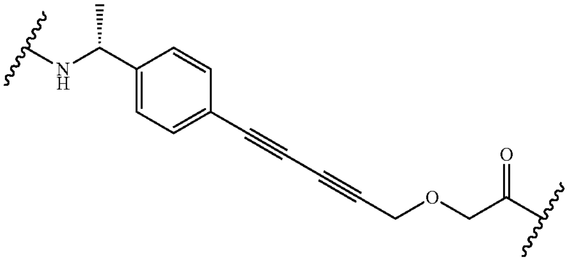
;
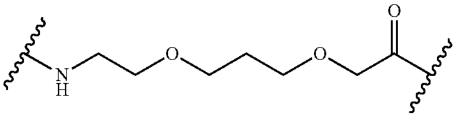
;
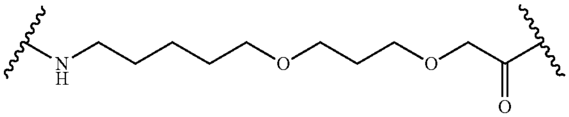
;
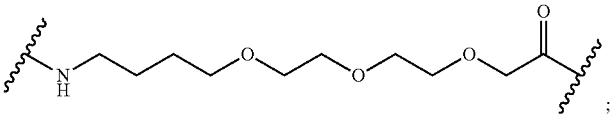
;
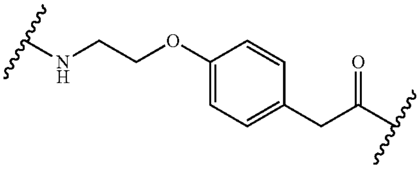
;
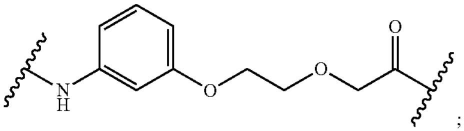
;
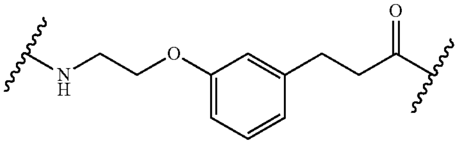
;
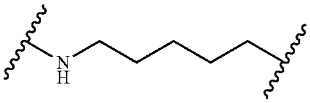
;
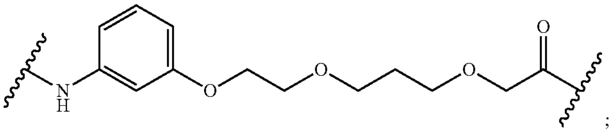
;
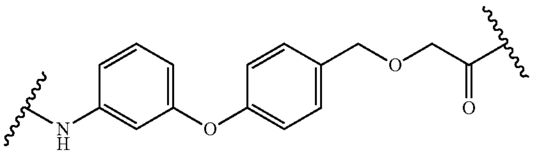
;
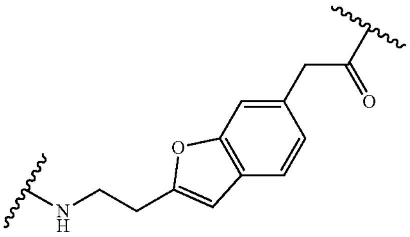
;

-continued
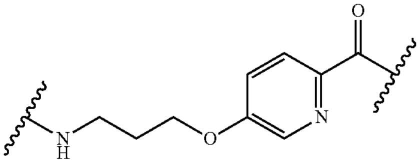
;
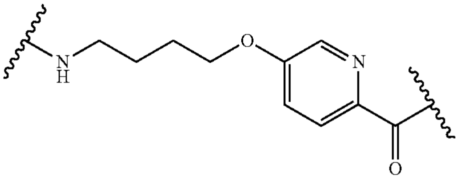
;
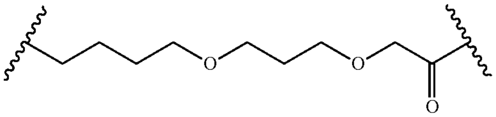
;
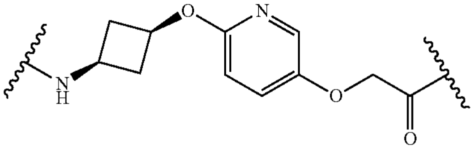
;
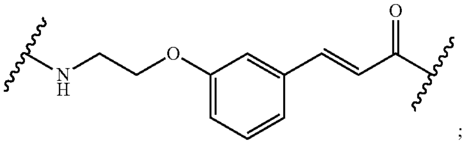
;
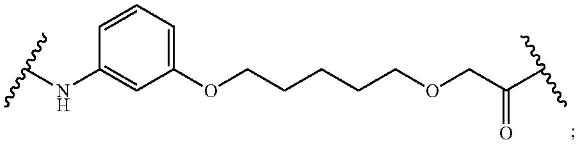
;
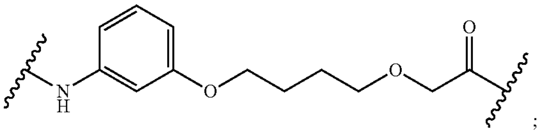
;
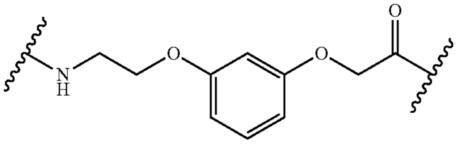
;
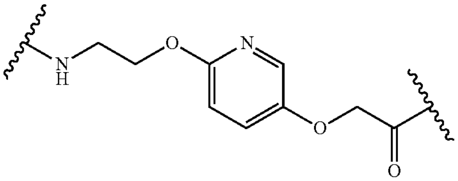
;
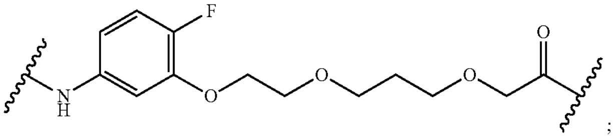
;
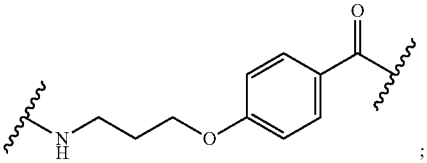
;
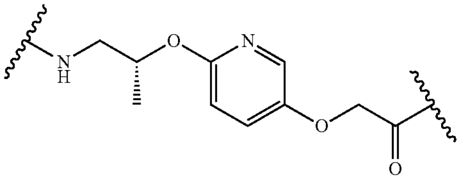
;
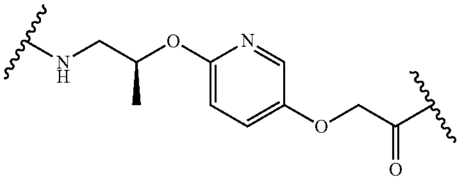
;
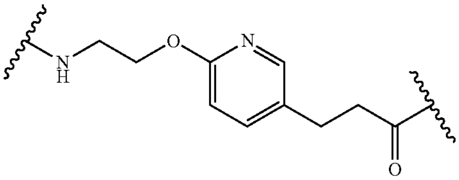
;
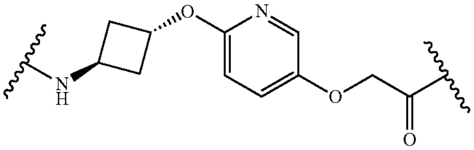
;
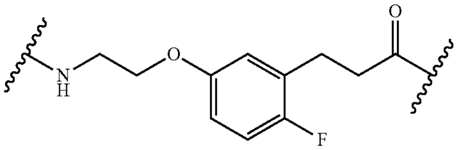
;
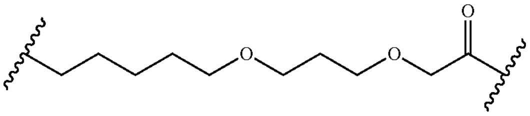
;
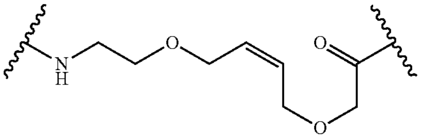
;
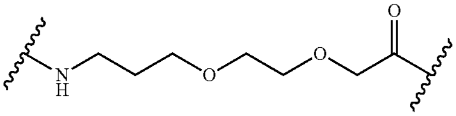
;
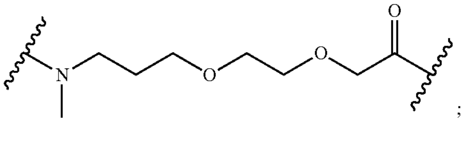
;

-continued
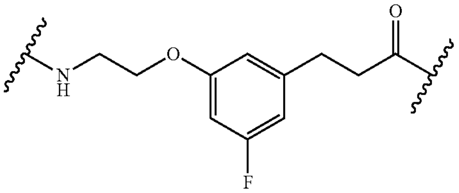 ; 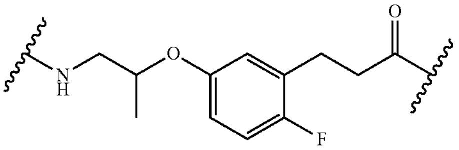 ;
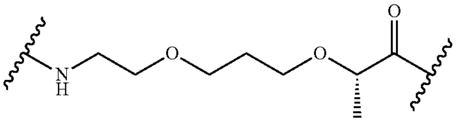 ; 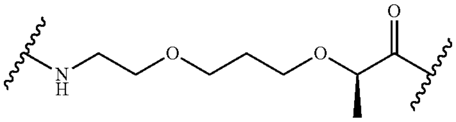 ;
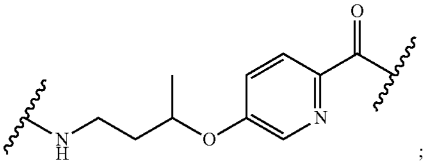 ; 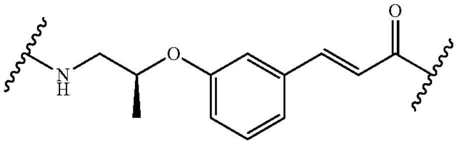 ;
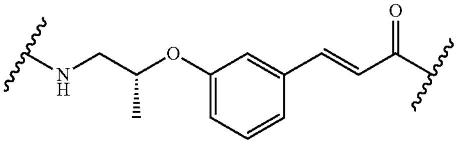 ; 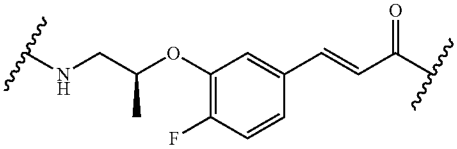 ;
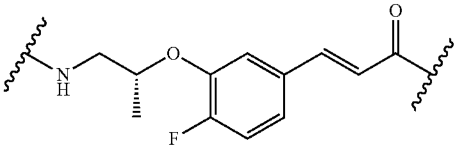 ; 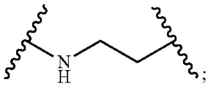 ; 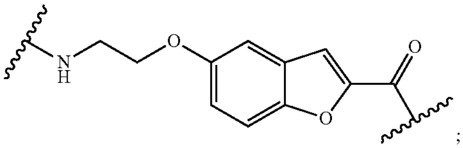 ;
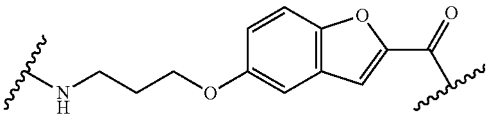 ; 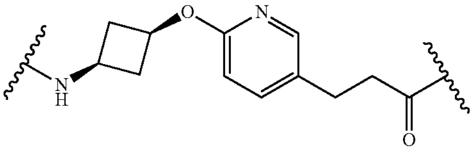 ;
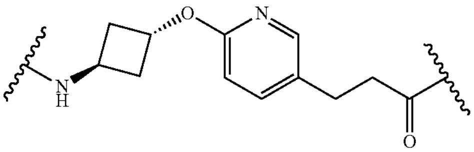 ; 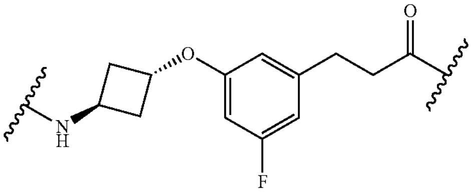 ;
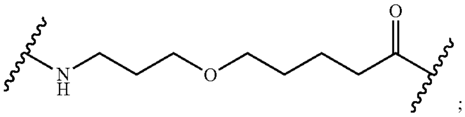 ; 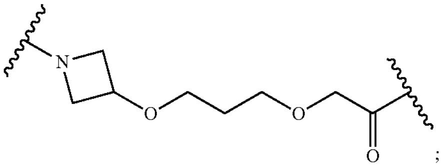 ;
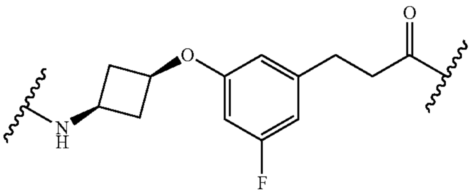 ; 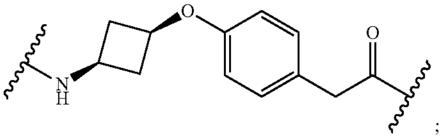 ;
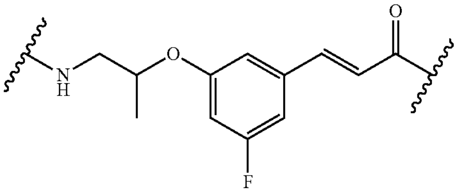 ; 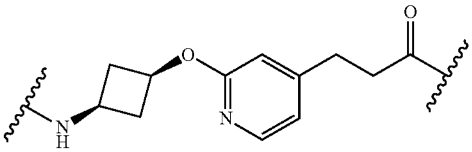 ;

-continued
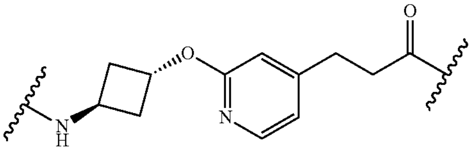;
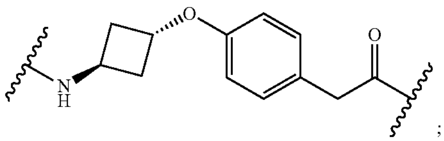;
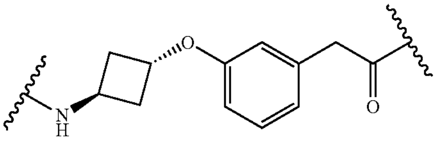;
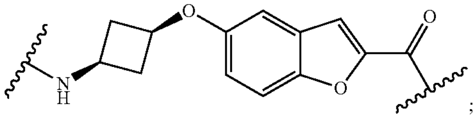;
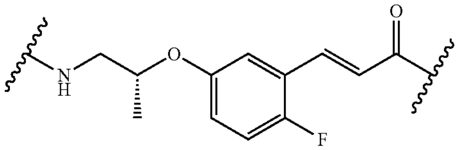;
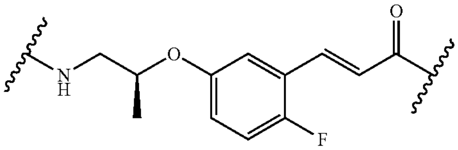;
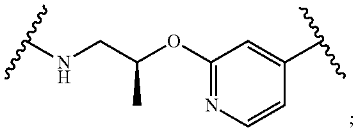;
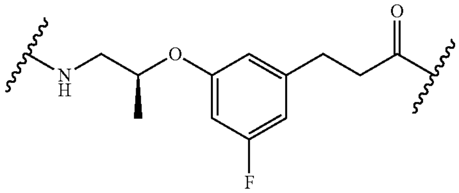;
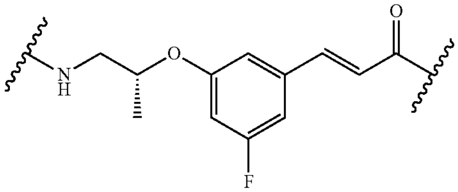;
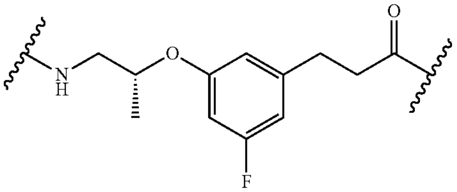;
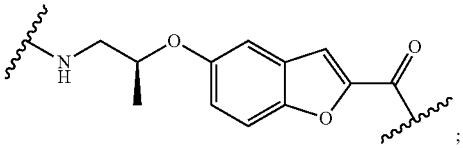;
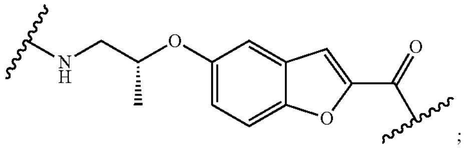;
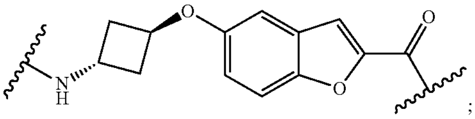;
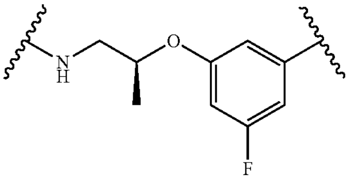;
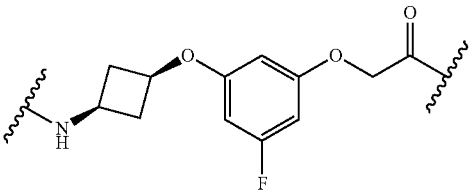;
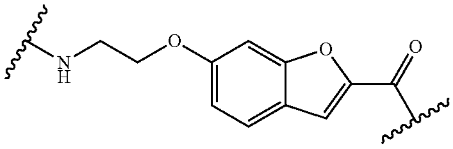;
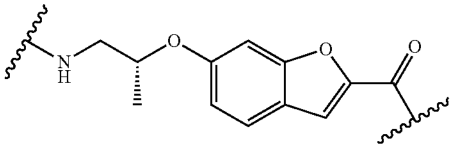;
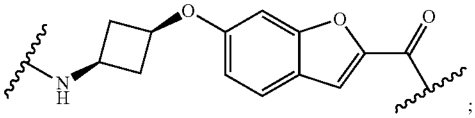;
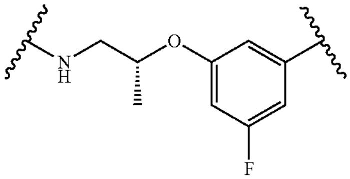;
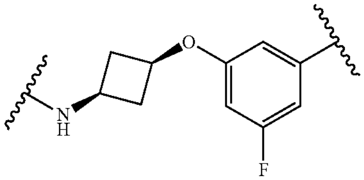;

-continued
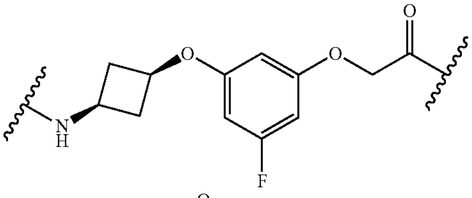
;
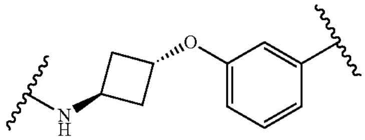
;
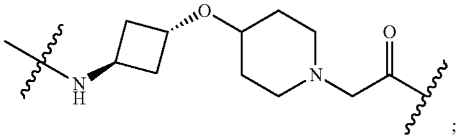
;
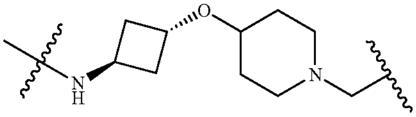
and
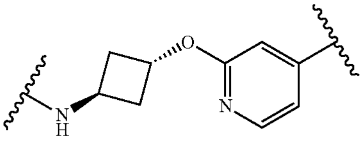
,
wherein: m is 1 or 2; and n is 0 or 1.
7. The compound according to claim 5, wherein the linker (L) is selected from the group consisting of:
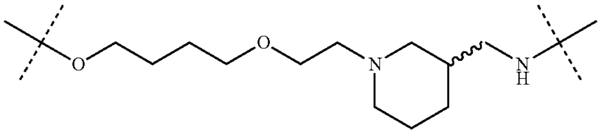
;
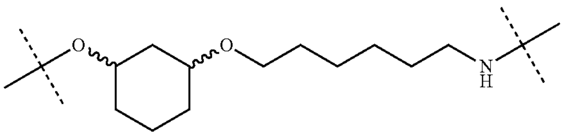
;
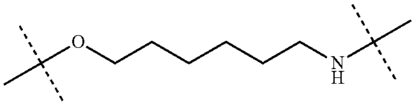
;
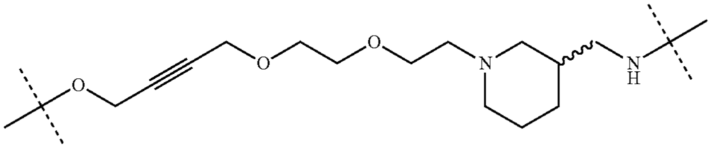
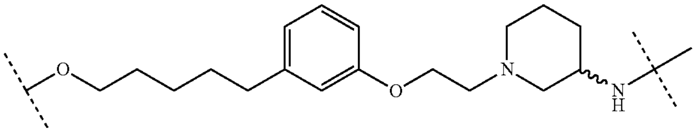
;
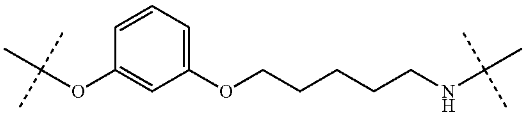
;
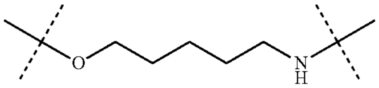
;
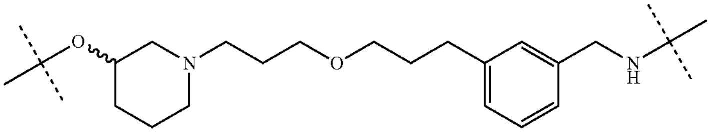
;
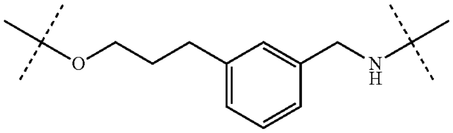
;
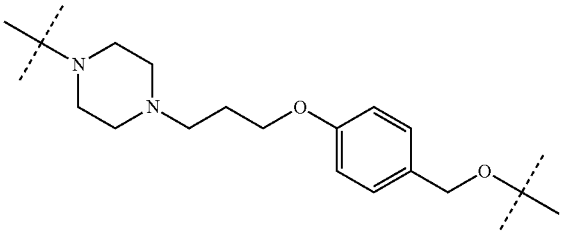
;

-continued
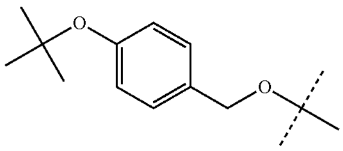 ;
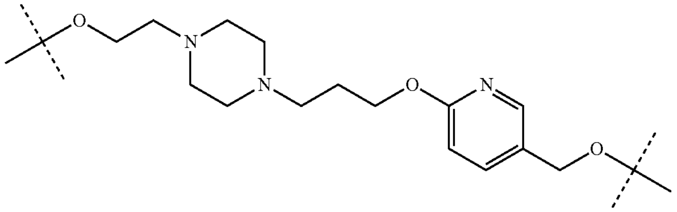 ;
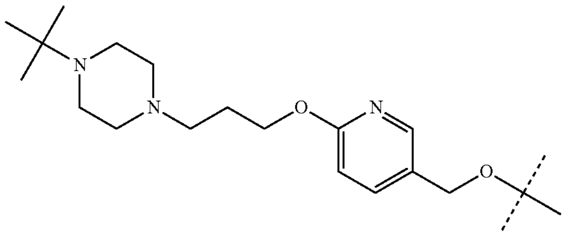 ;
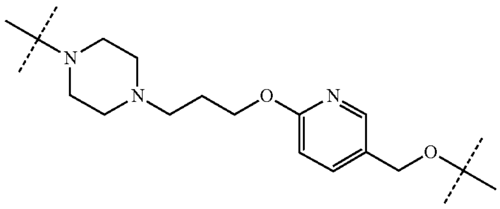 ;
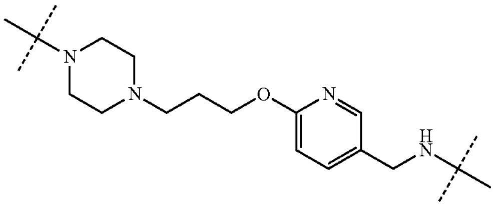 ;
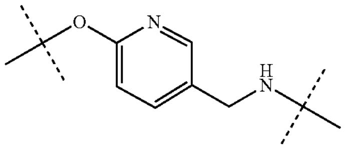 ;
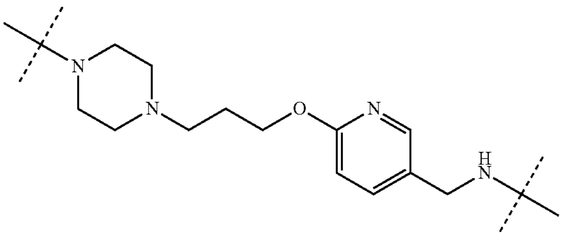 ;
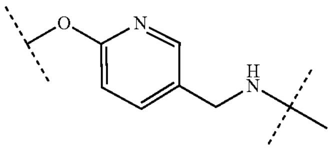 ;
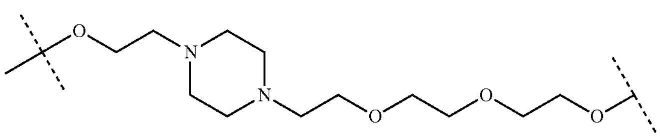 ;
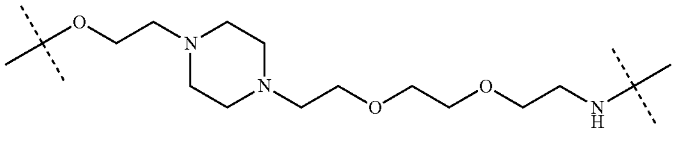 ;
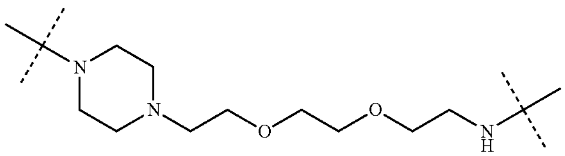 ;
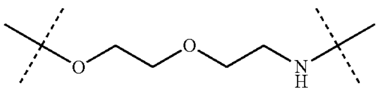 ;

-continued
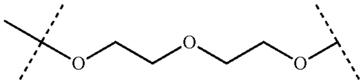
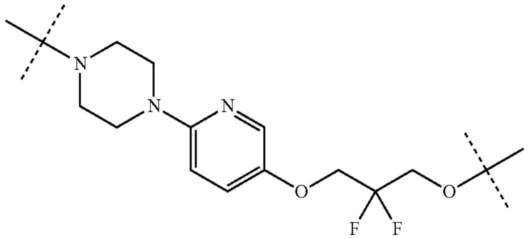 ;
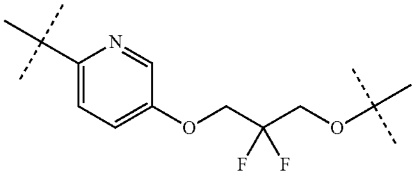 ; 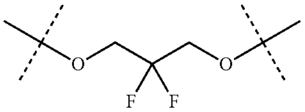 ;
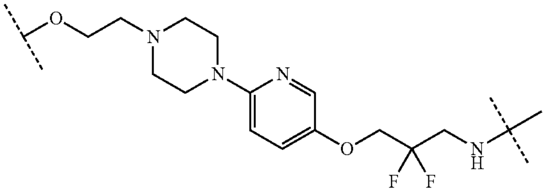 ; 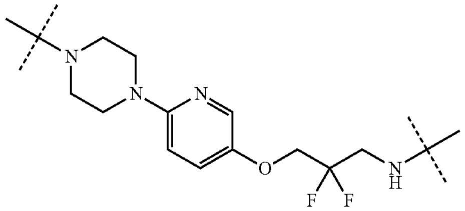 ;
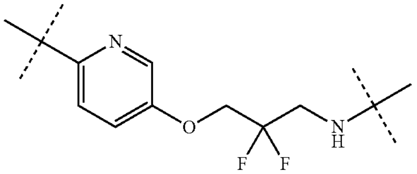 , 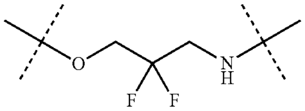 ;
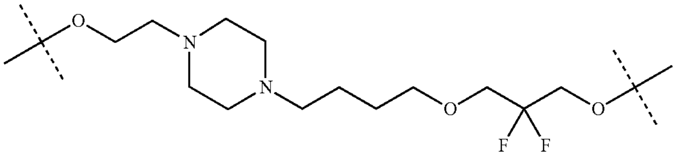 ;
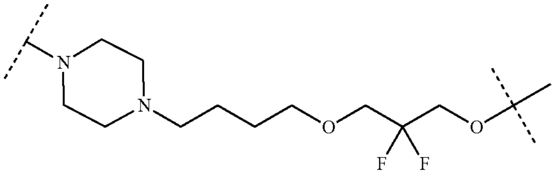 ; 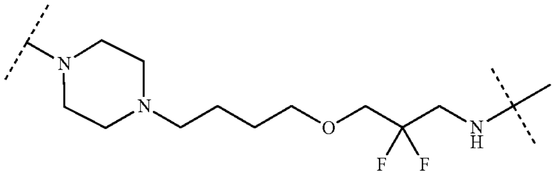 ;
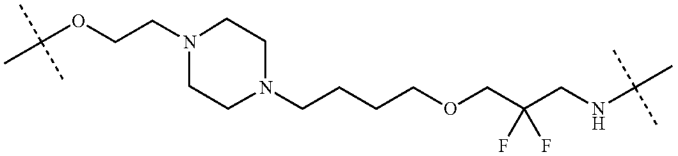 ;
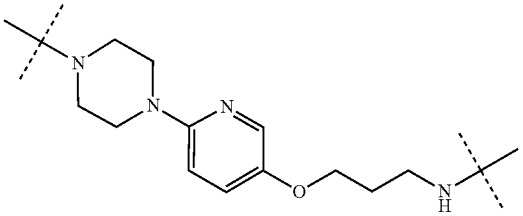 ; 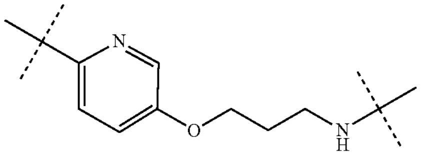 ;
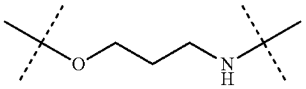 ; 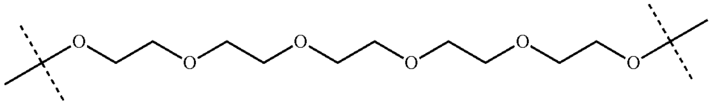 ;

-continued
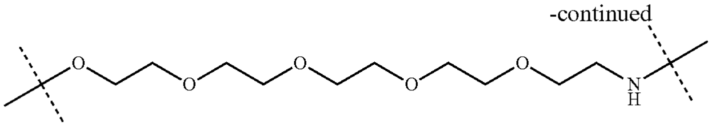 ;
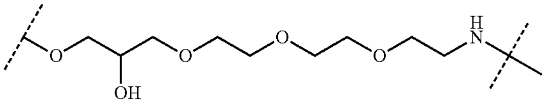 ; 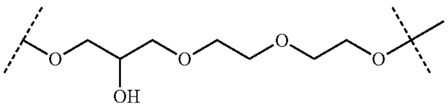 ;
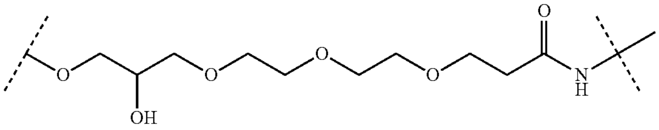 ;
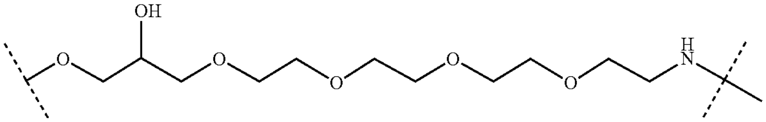 ;
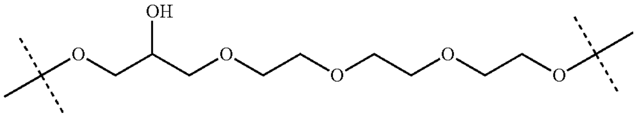 ;
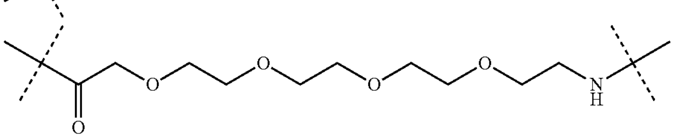 ;
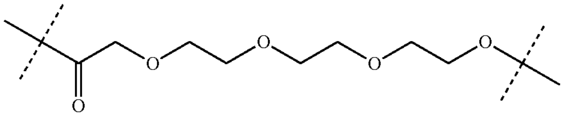 ;
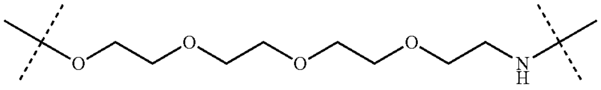 ;
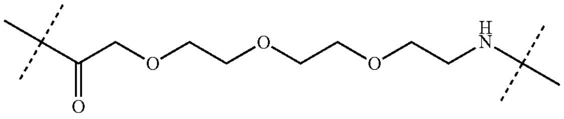 ; 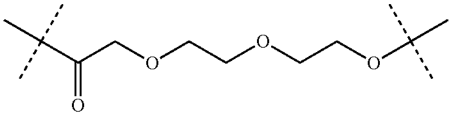 ;
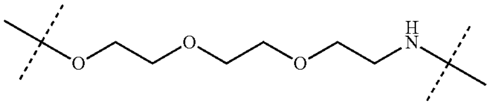 ;
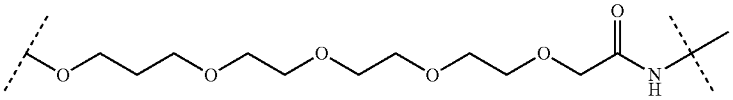 ;
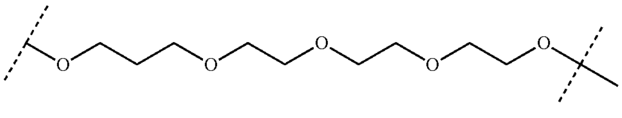 ; 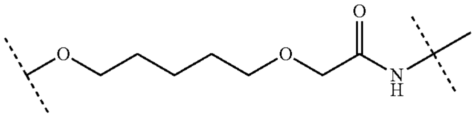 ;
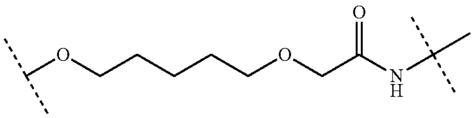 ; 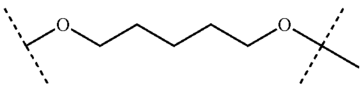 ;
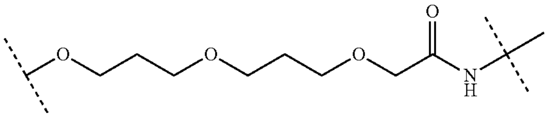 ;
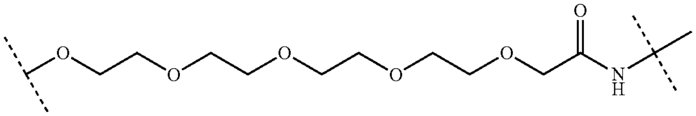 ;

-continued
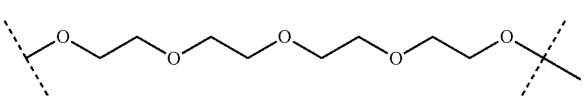 ; 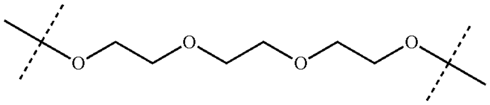 ;
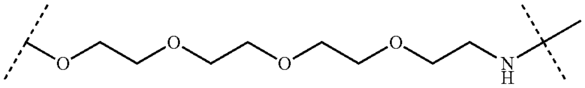 ; 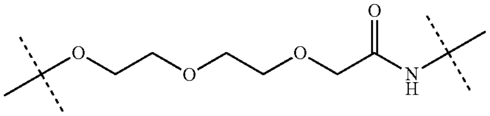 ;
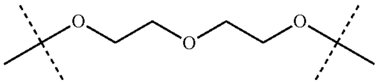 ; 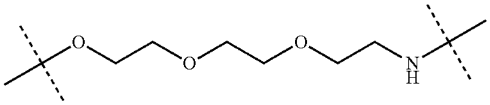 ;
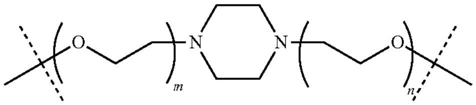 ; 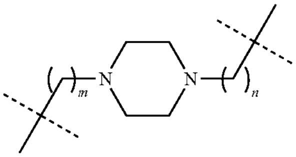 ;
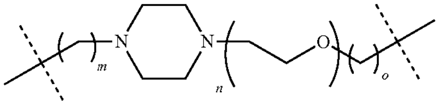 ; 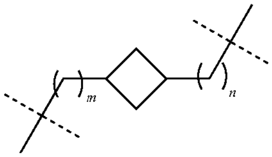 ;
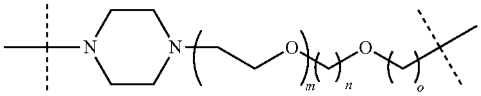 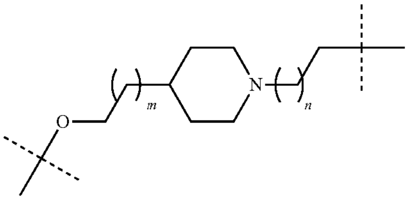 ;
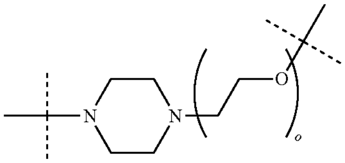 ; 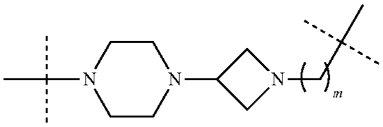 ;
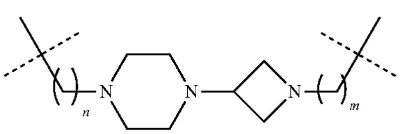 ; 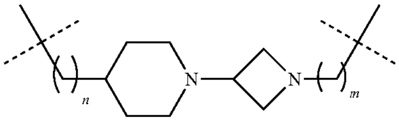 ;
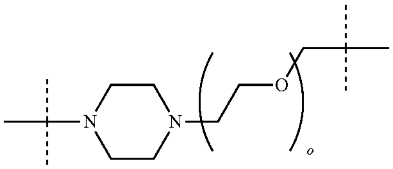 ;
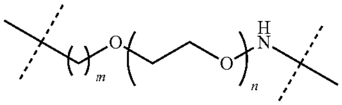 ; 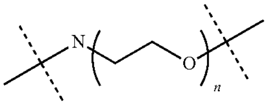 ; 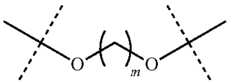 ;
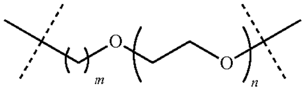 ; 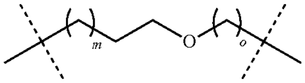 ; 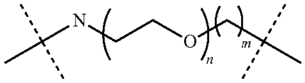 ;
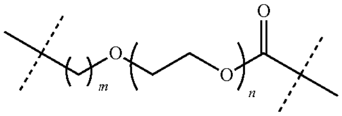 ; 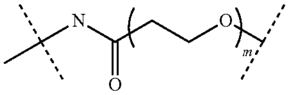 ; 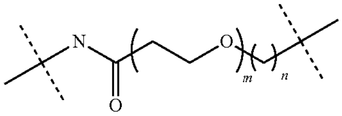 ;

-continued
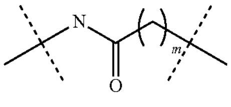 ; 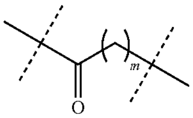 ; 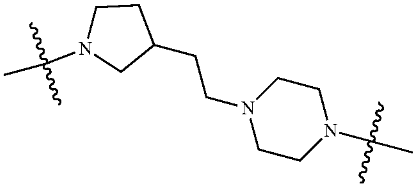 ;
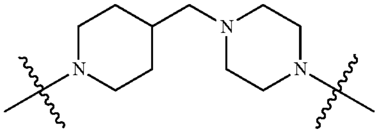 ; 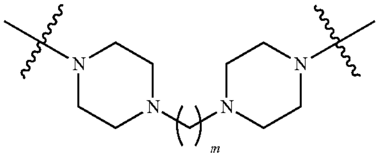 ;
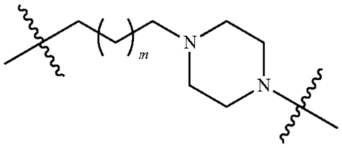 ; 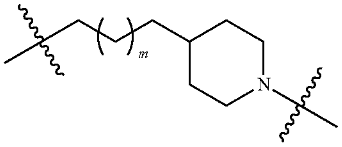 ; 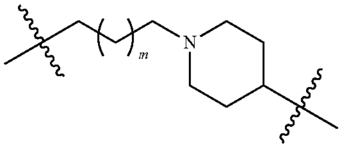 ;
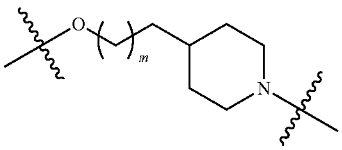 ; 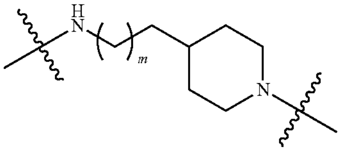 ; 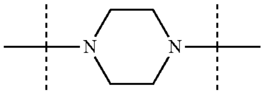 ;
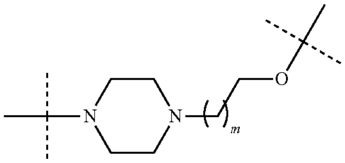 ; 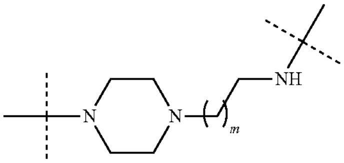 ; 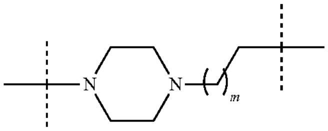 ;
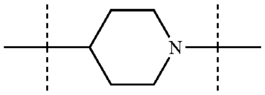 ; 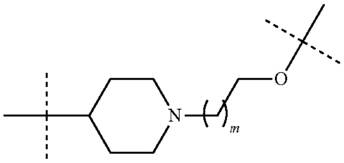 ; 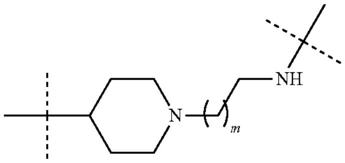 ;
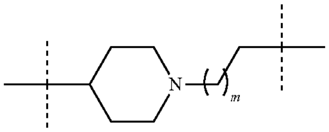 ; 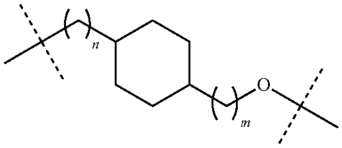 ; 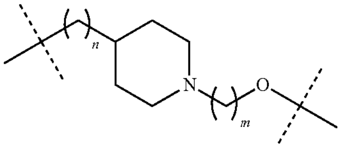 ;
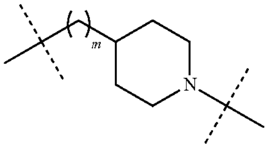 ; 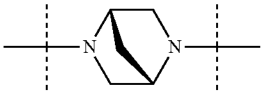 ; 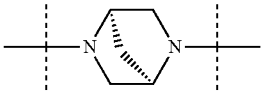 ;
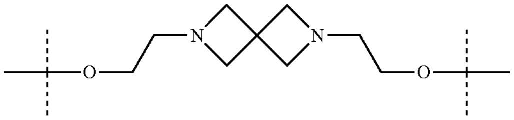 ; 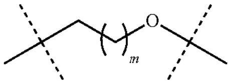 ; 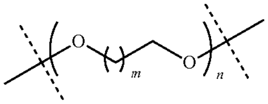 ;
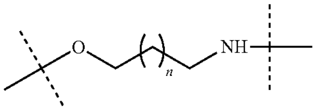 ; 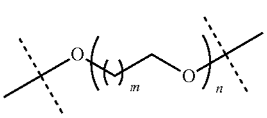 ; 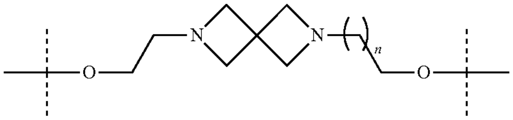 ;

-continued
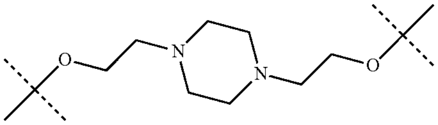
;
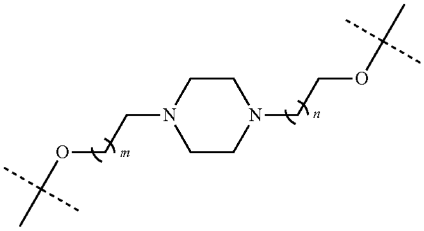
;
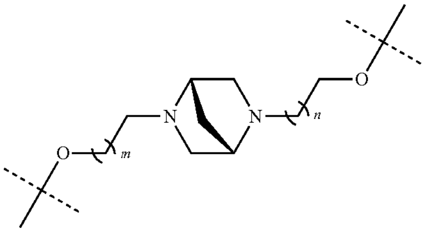
;
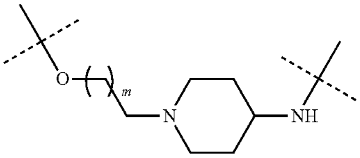
;
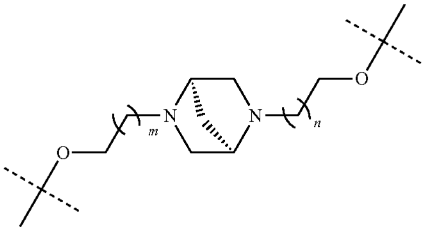
;
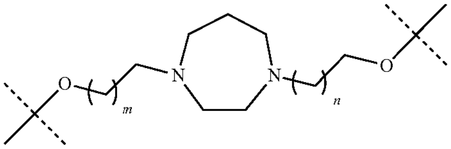
;
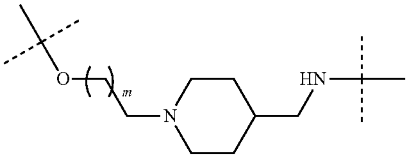
;
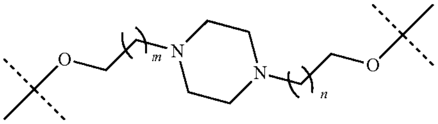
;
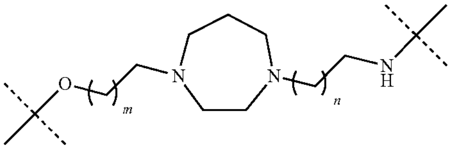
;
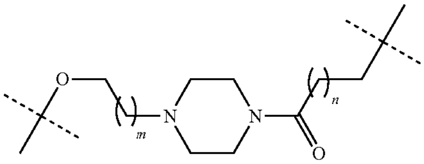
;
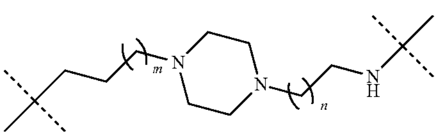
;
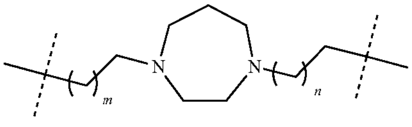
;
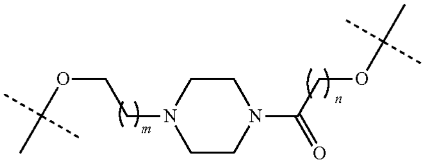
;
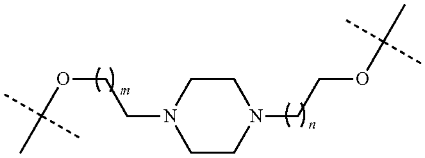
;
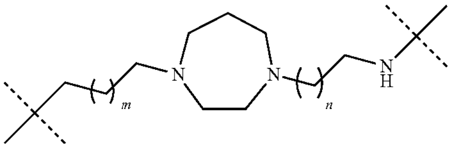
;
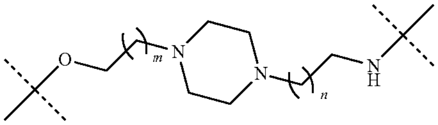
;
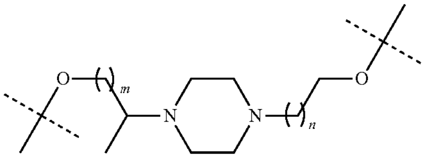
;
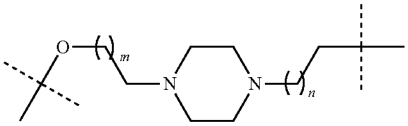
;

-continued
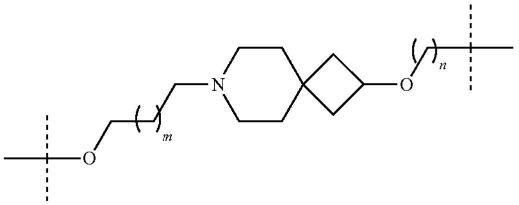 ;
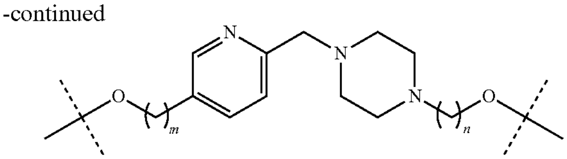 ;
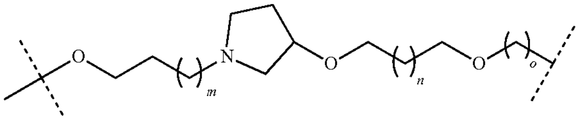 ;
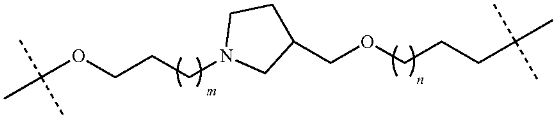 ;
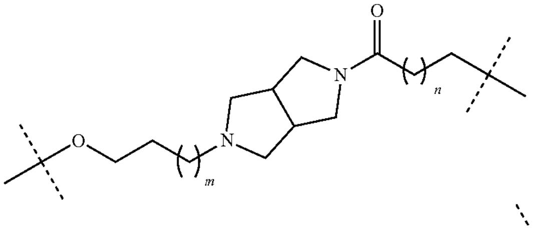 ;
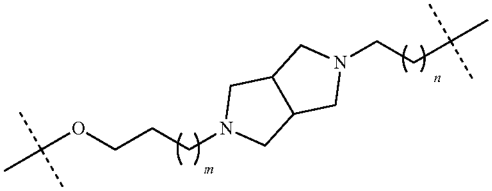 ;
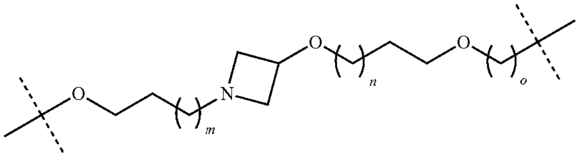 ;
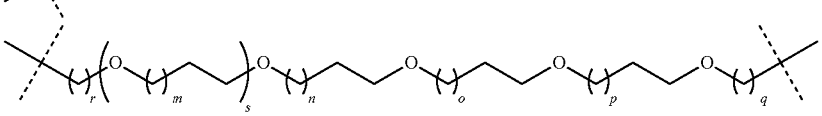 ;
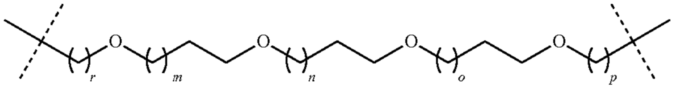 ;
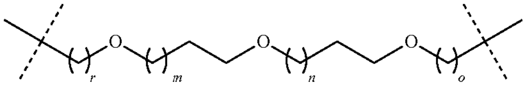 ;
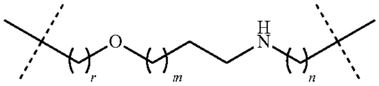 ;
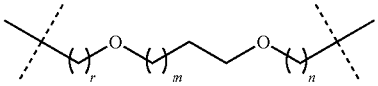 ;
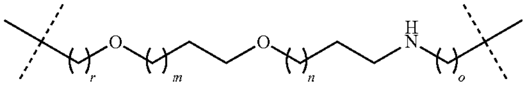 ;
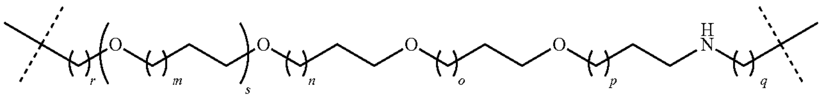 ;
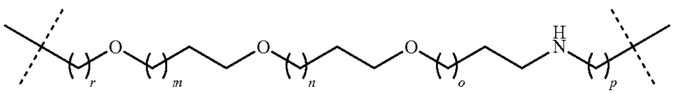 ;
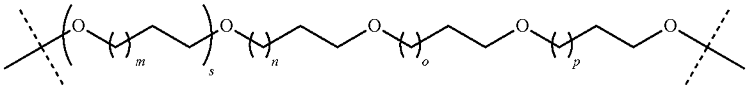 ;
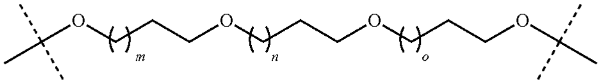 ;
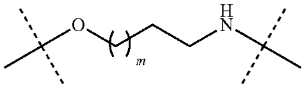 ;
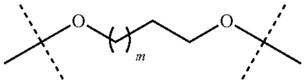 ;
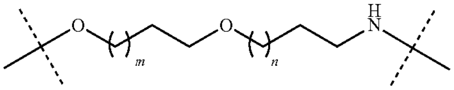 ;
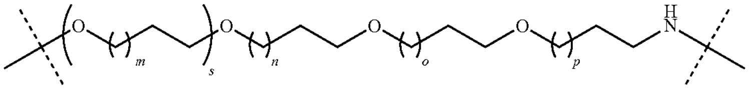 ;
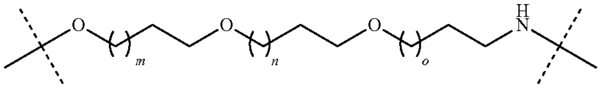 ;

-continued
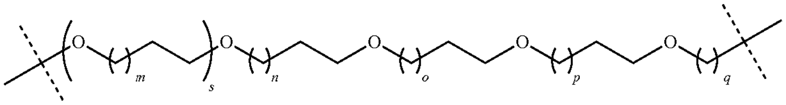
;
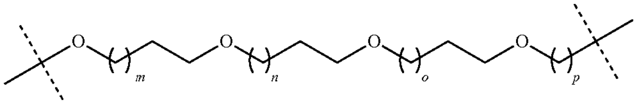
;
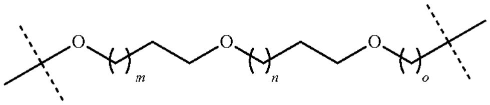
;
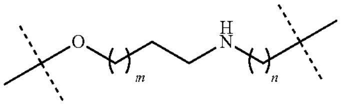
;
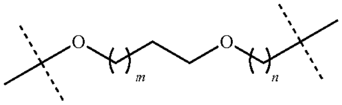
;
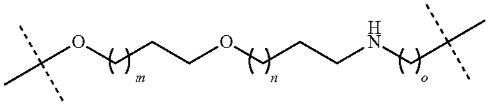
;
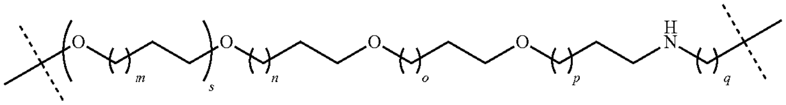
;
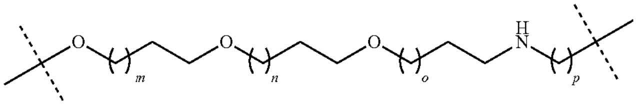
;
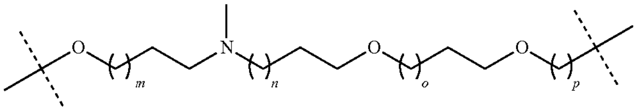
;
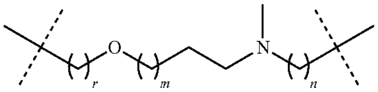
;
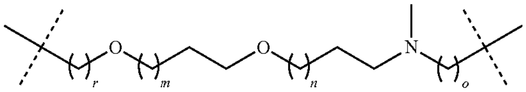
;
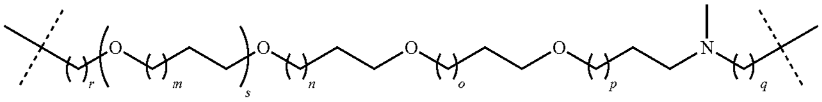
;
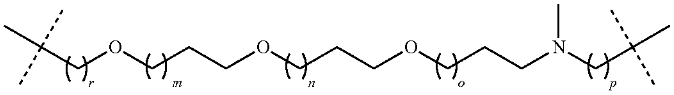
;
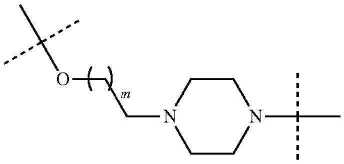
;
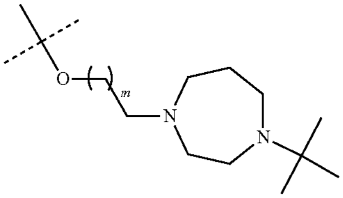
;
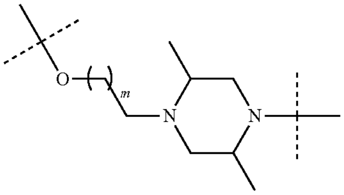
;
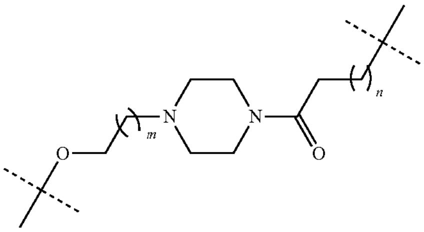
;
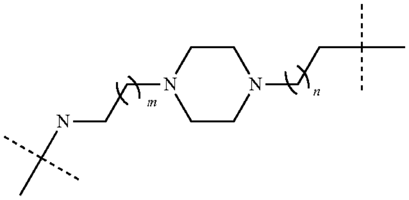
;
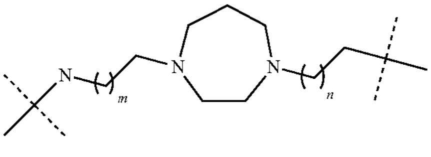
;

-continued
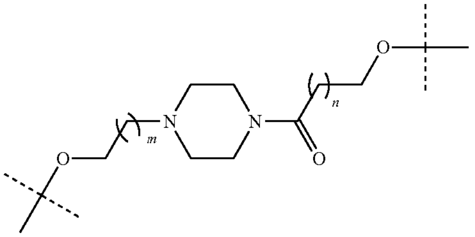
;
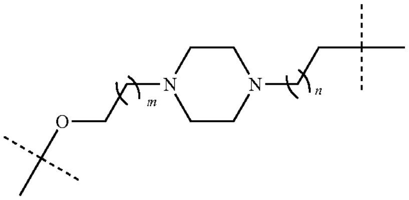
;
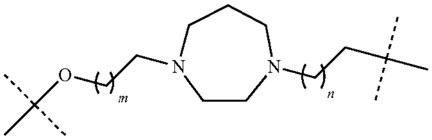
;
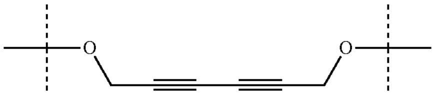
;
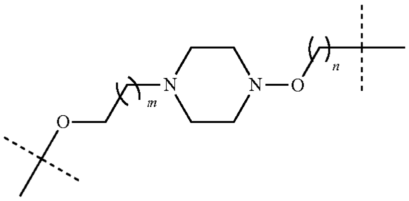
;
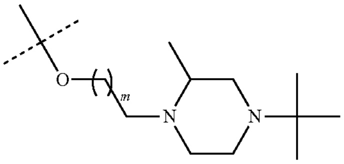
;
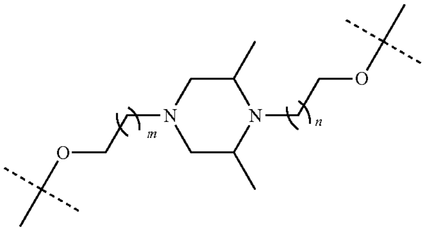
;
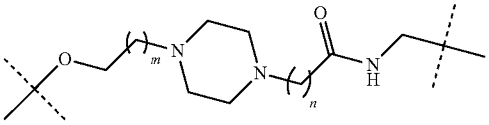
;
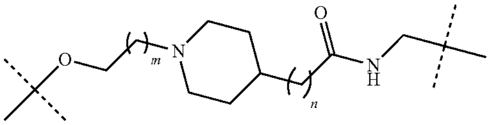
;
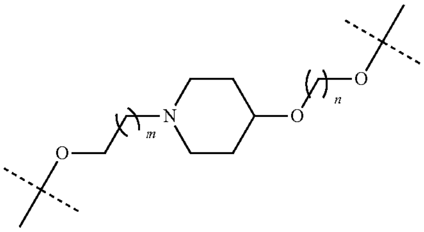
;
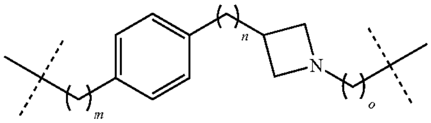
;
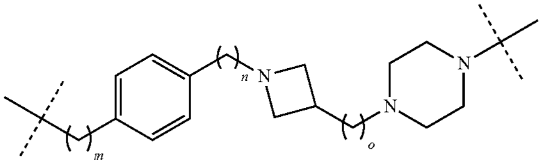
;
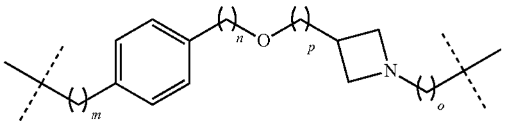
;
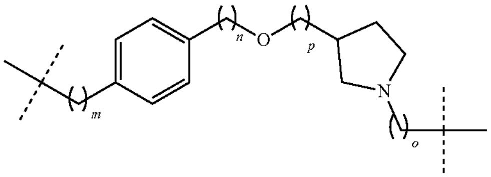
;
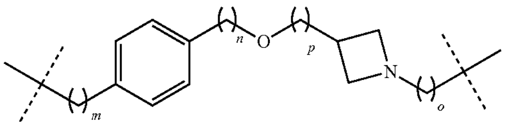
;
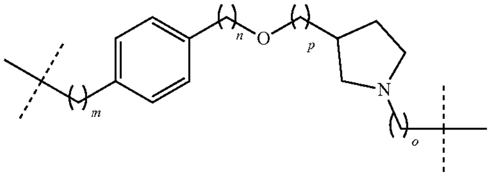
;
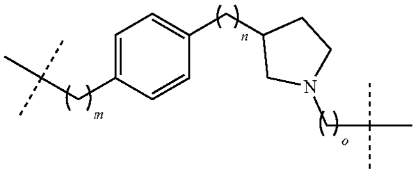
;
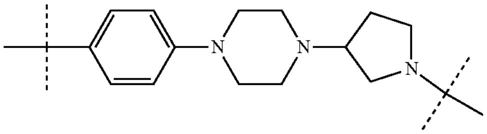
;

-continued
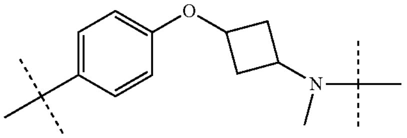 ;
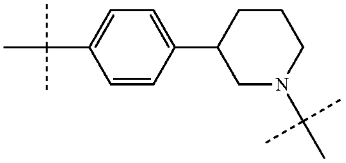 ;
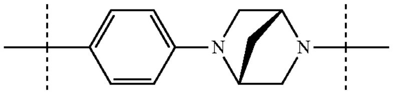 ;
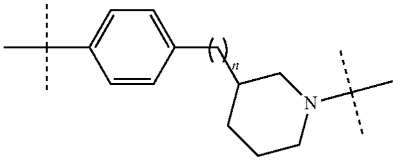 ;
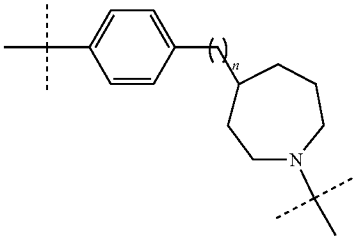 ;
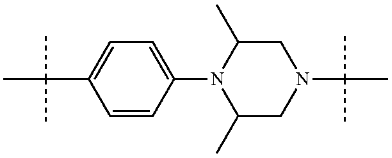 ;
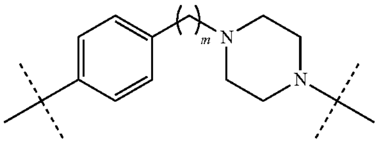 ;
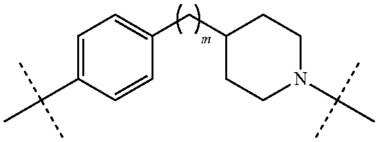 ;
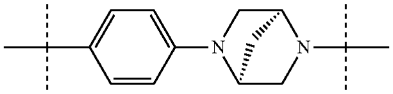 ;
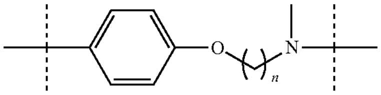 ;
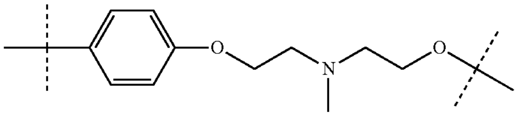 ;
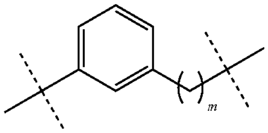 ;
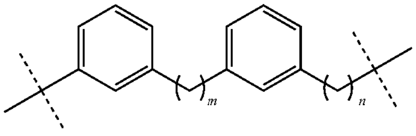 ;
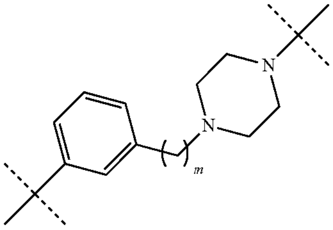 ;
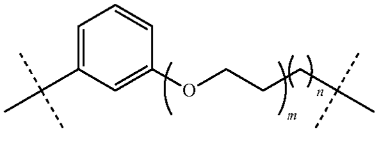 ;
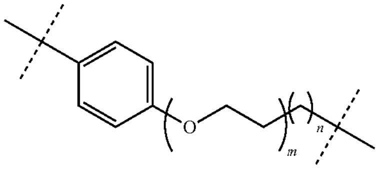 ;
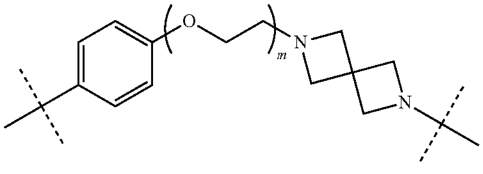 ;
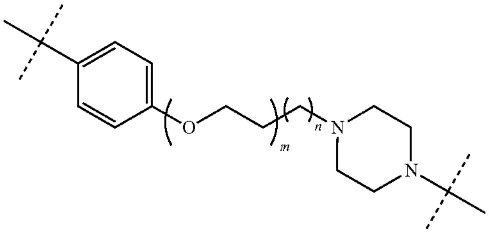 ;

-continued
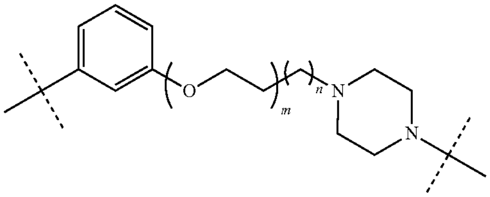 ; 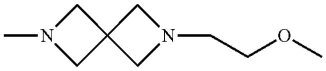 ;
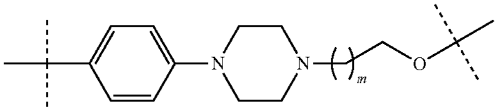 ; 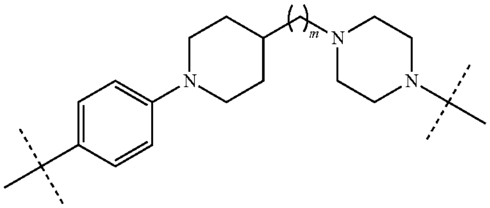 ;
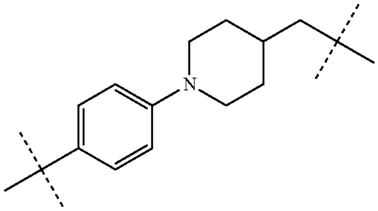 ; 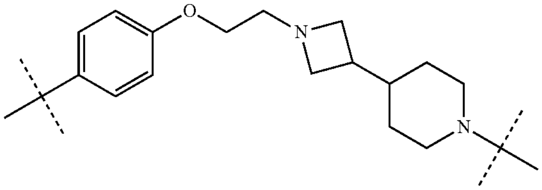 ;
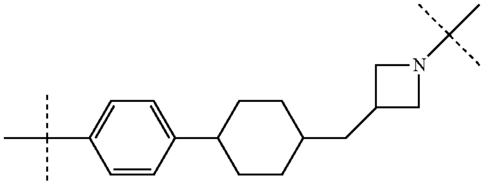 ; 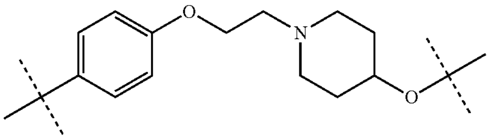 ;
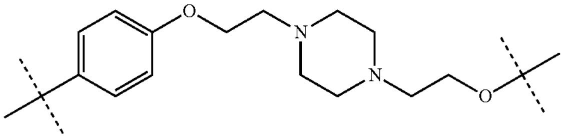 ; 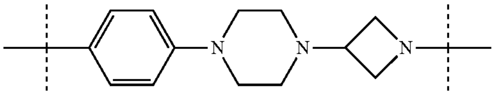 ;
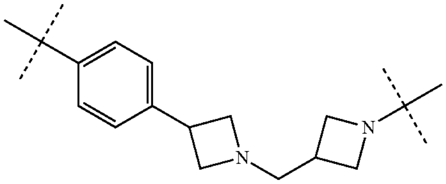 ; 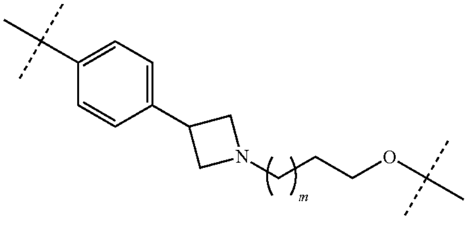 ;
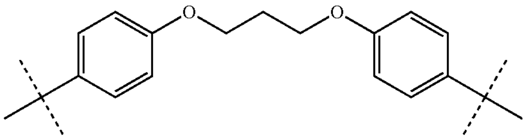 ; 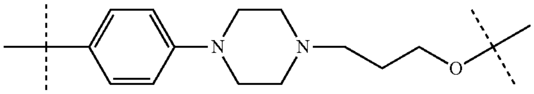 ;
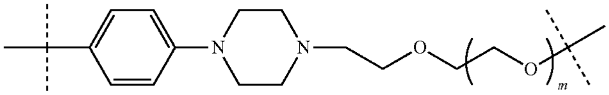 ;
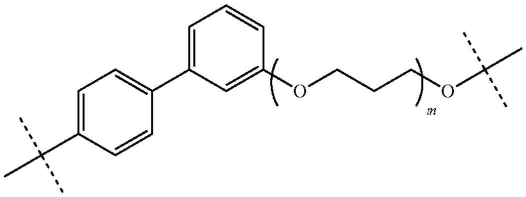 ; 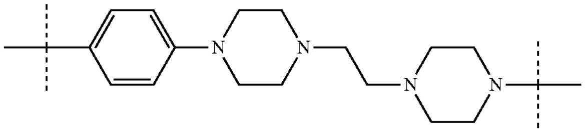 ;
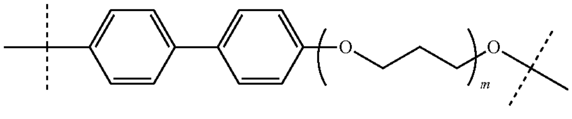 ;

-continued
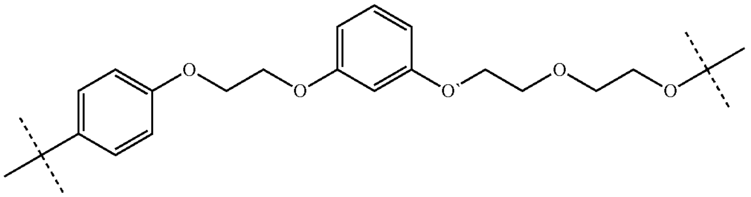 ; 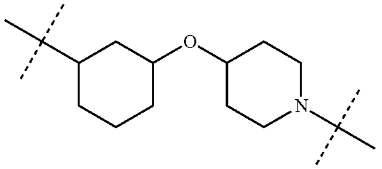 ;
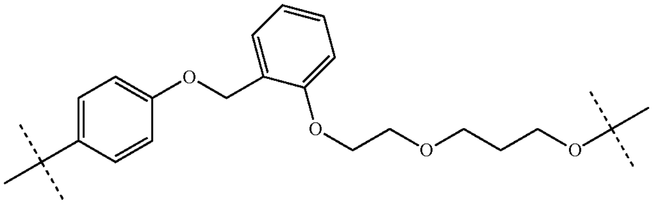 ; 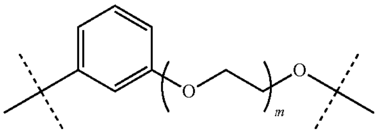 ;
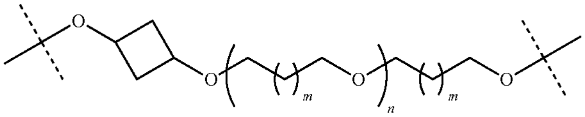 ;
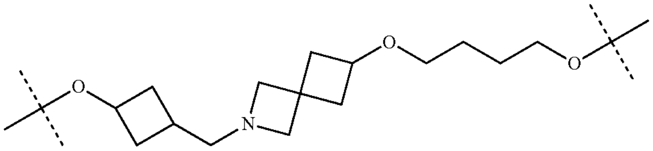 ;
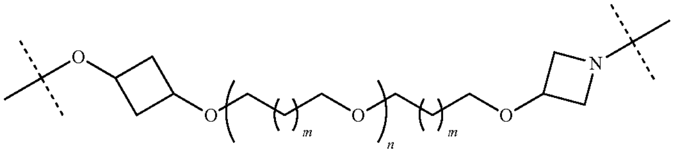 ;
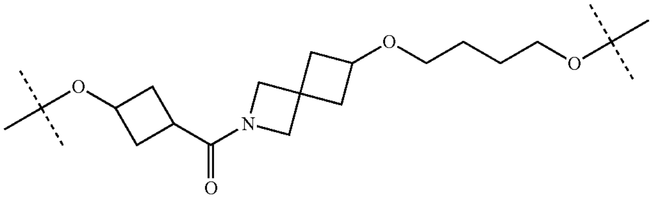 ;
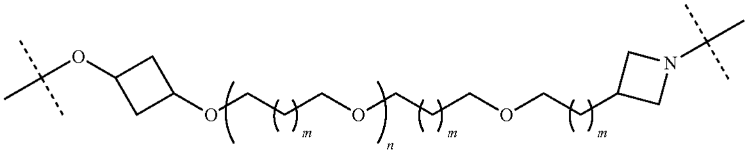 ;
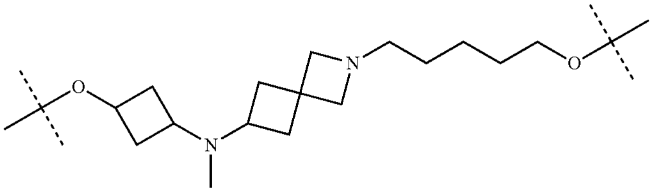 ;
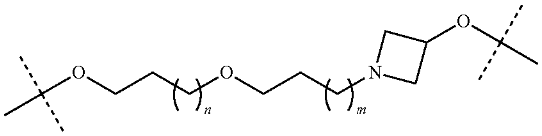 ;
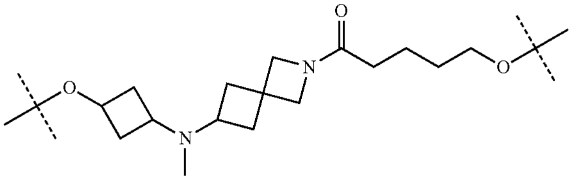 ; 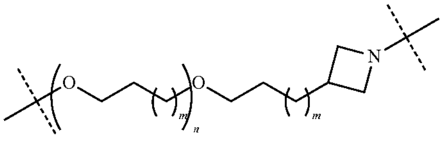 ;

-continued
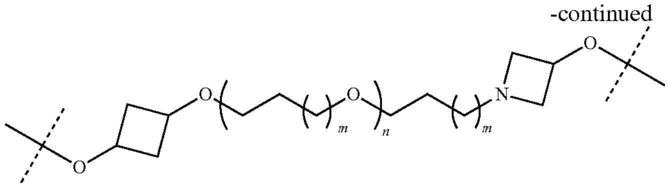
;
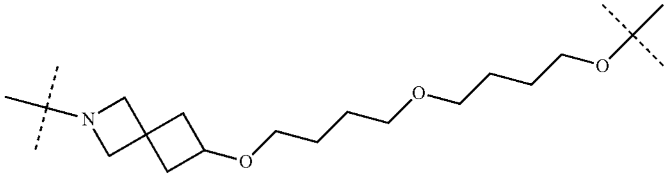
;
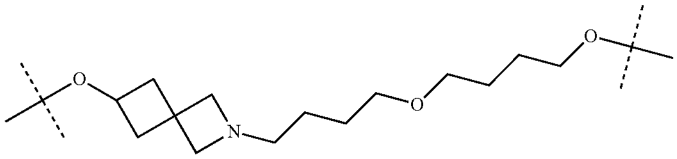
;
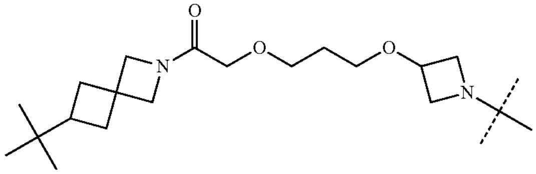
;
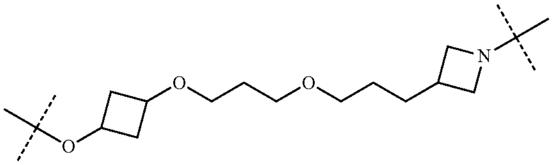
;
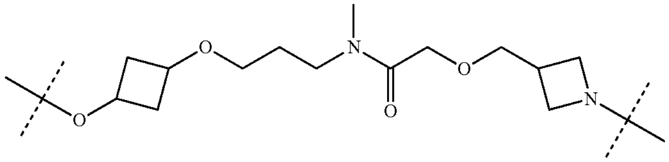
;
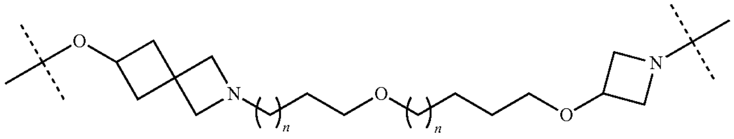
;
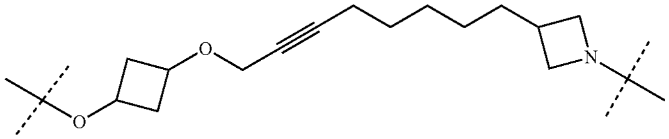
;
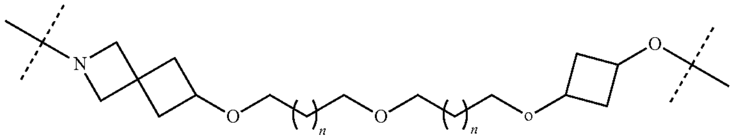
;
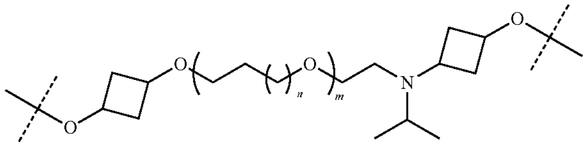
;
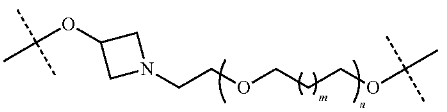
;
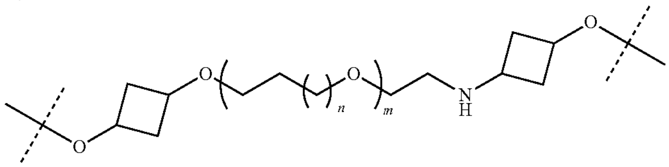
;
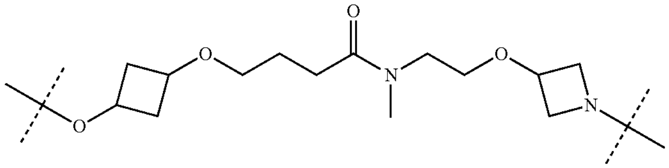
;

-continued
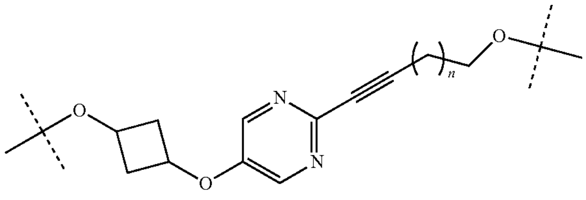
;
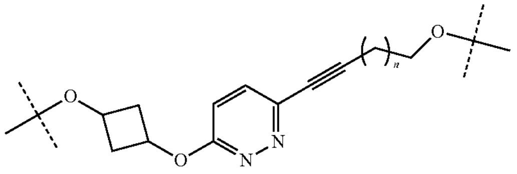
;
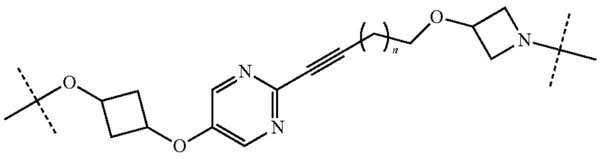
;
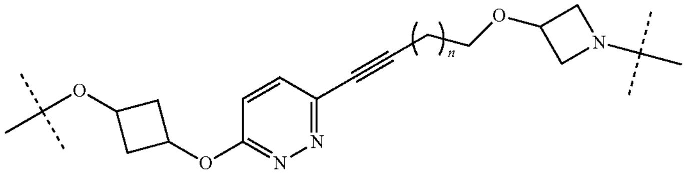
;
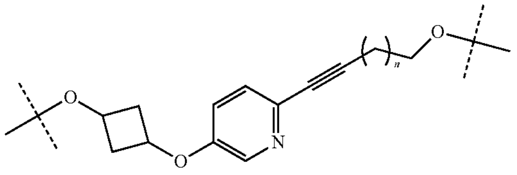
;
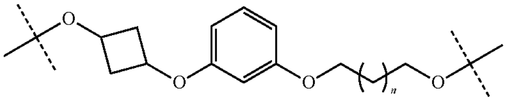
;
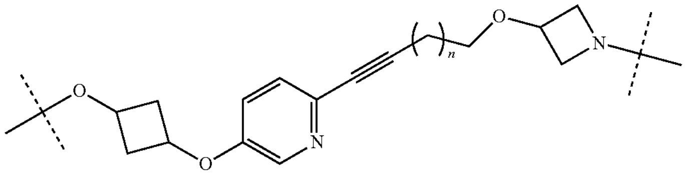
;
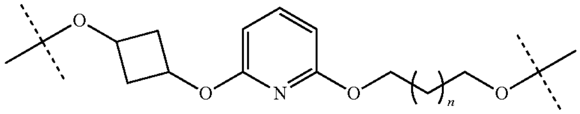
;
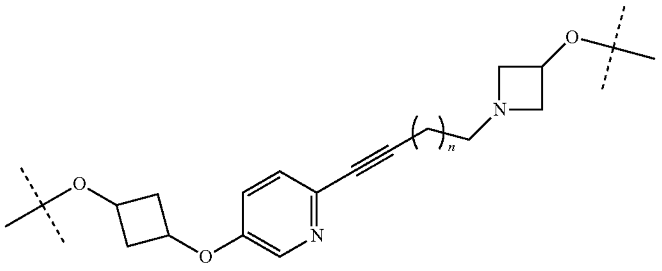
;
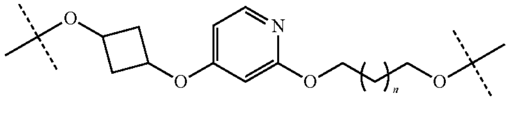
;
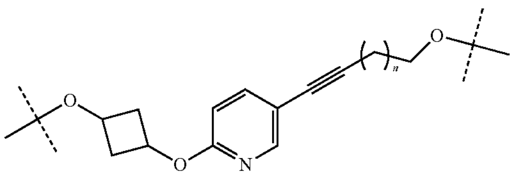
;
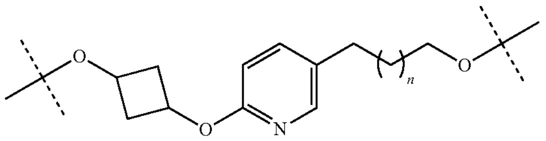
;

-continued
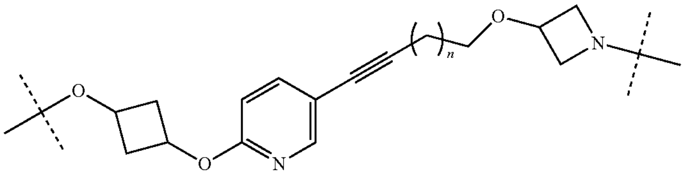
;
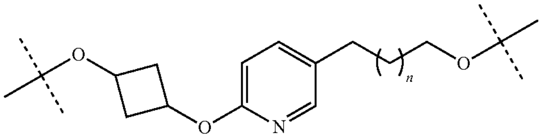
;
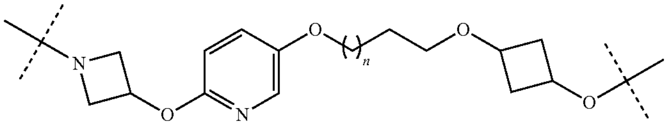
;
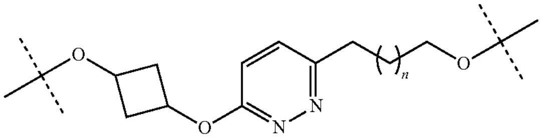
;
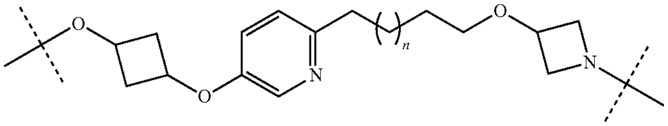
;
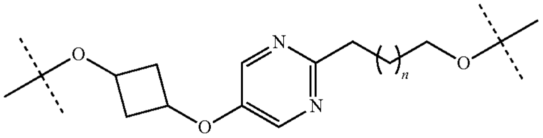
;
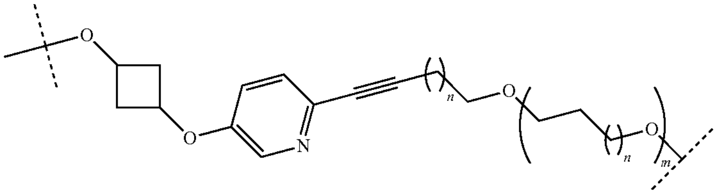
;
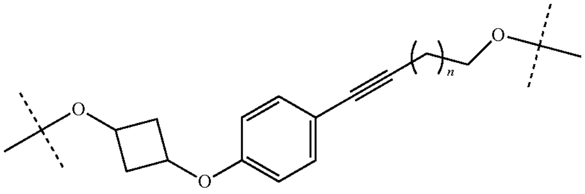
;
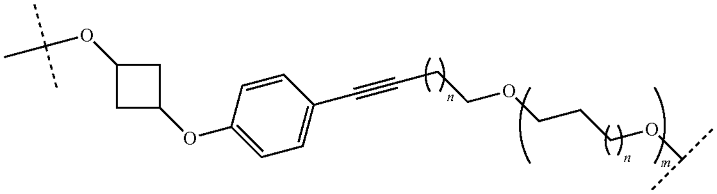
;
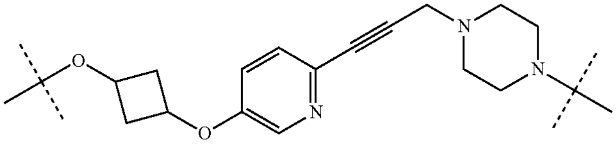
;

-continued
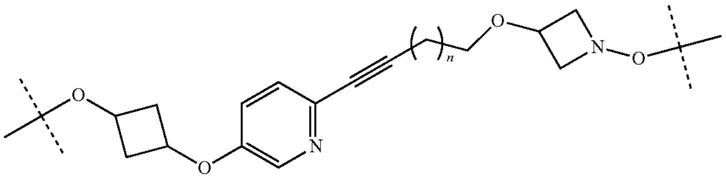
;
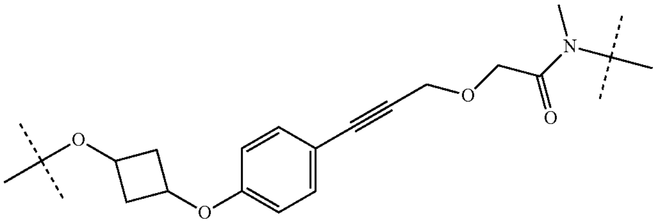
;
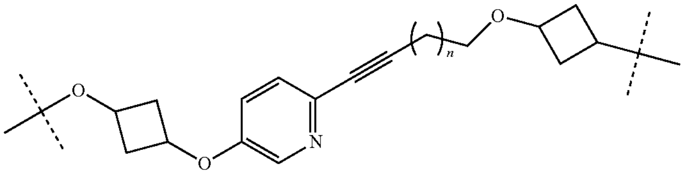
;
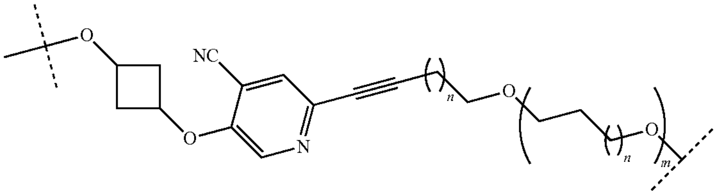
;
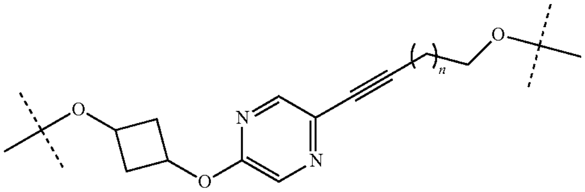
;
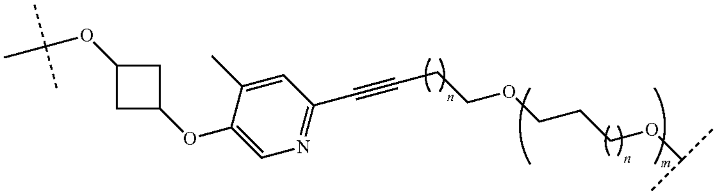
;
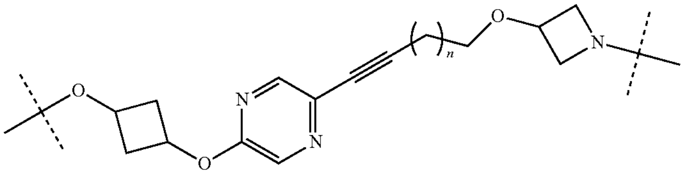
;
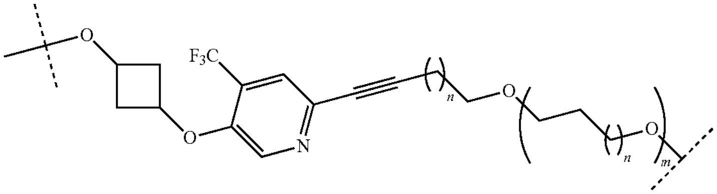
;
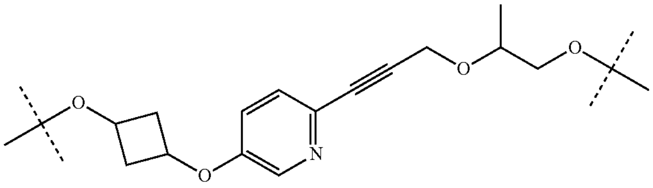
;

-continued
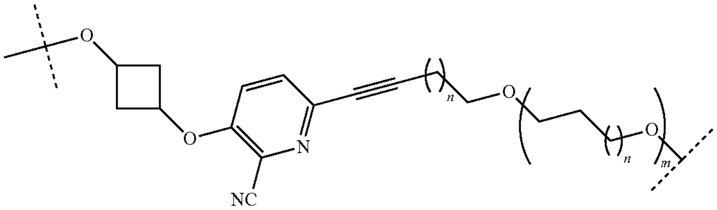
;
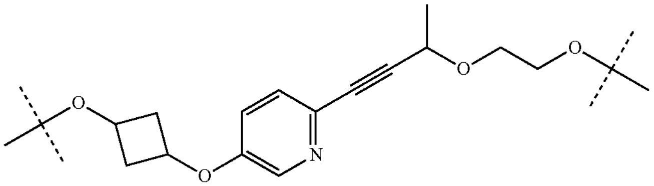
;
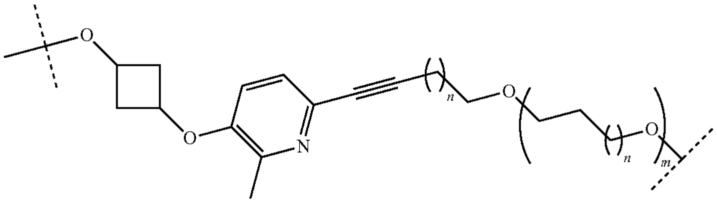
;
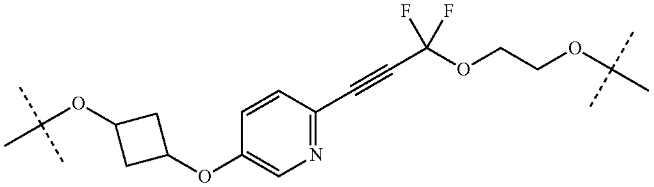
;
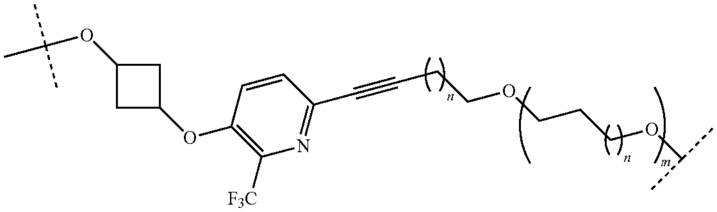
;
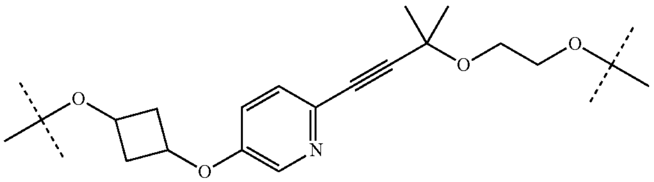
;
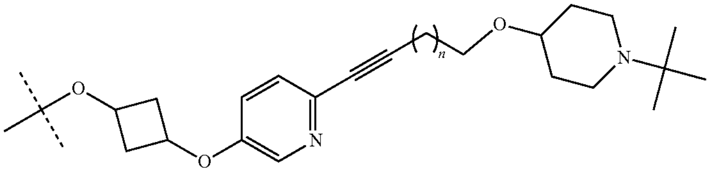
;
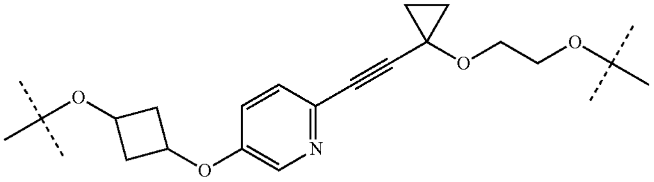
;
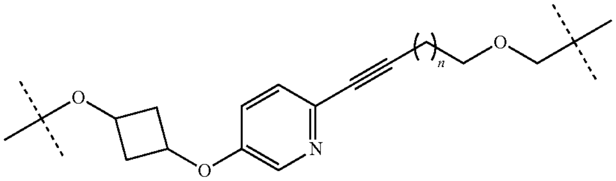
;

-continued
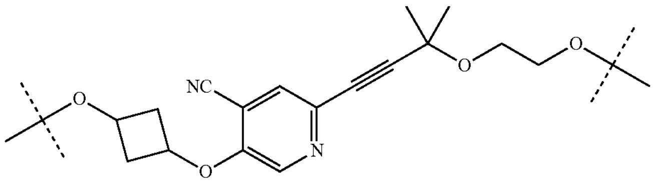 ;
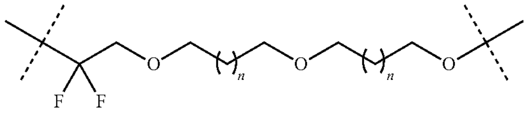 ; 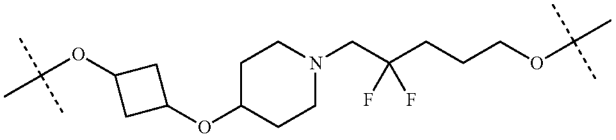 ;
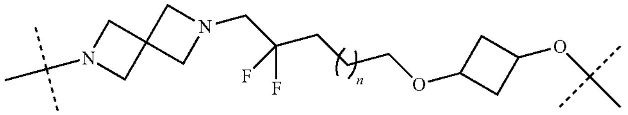 ;
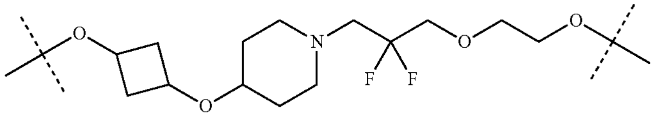 ;
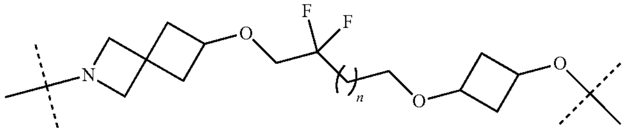 ;
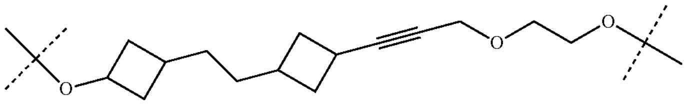 ;
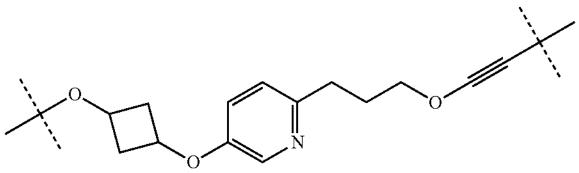 ; 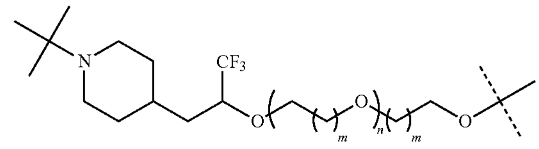 ;
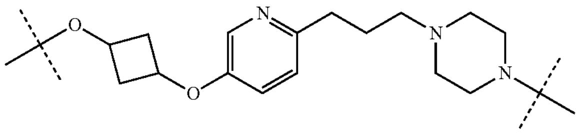 ; 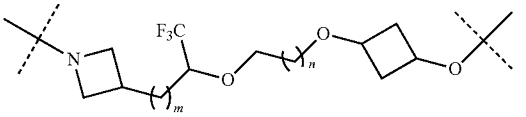 ;
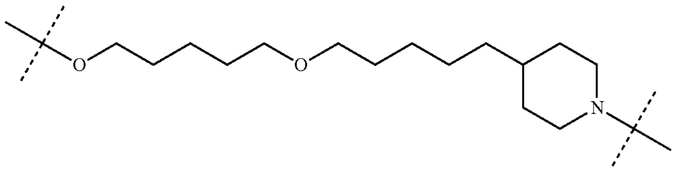 ;
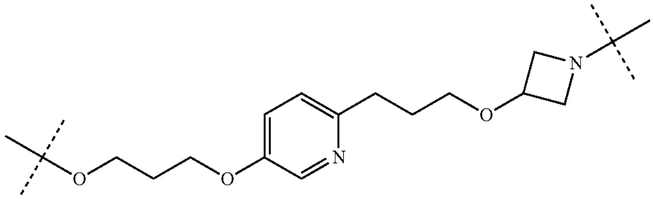 ;
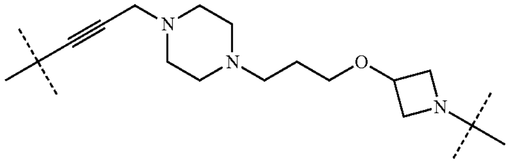 ; 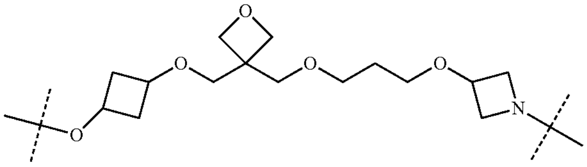 ;

-continued
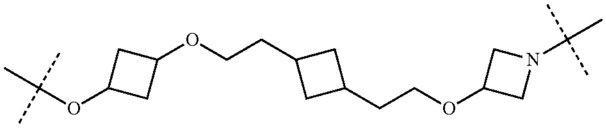
;
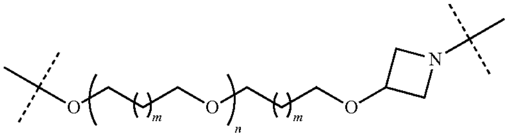
;
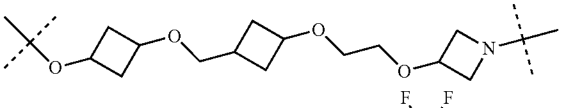
;
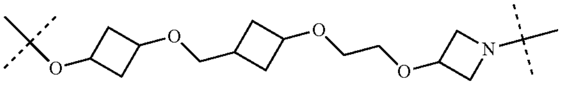
;
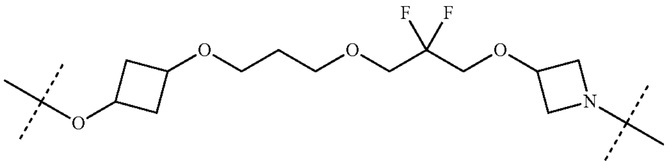
;
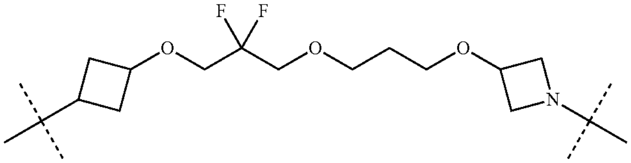
;
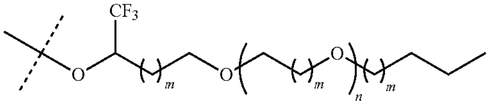
;
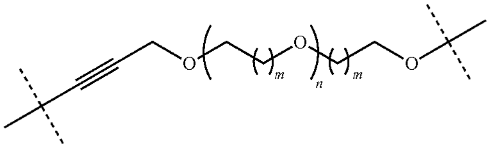
;
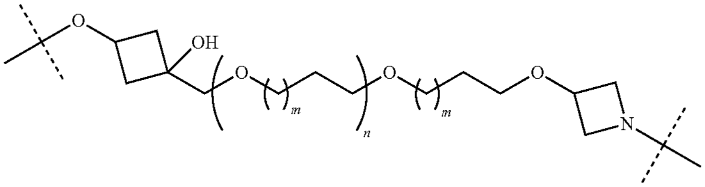
;
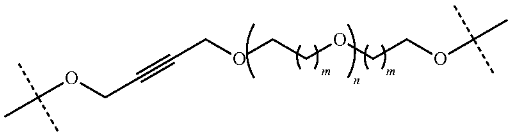
;
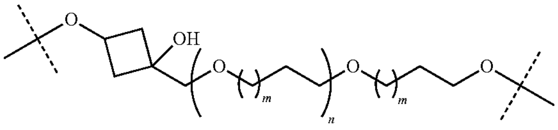
;
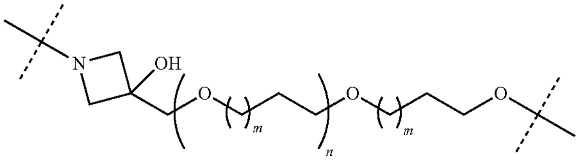
;
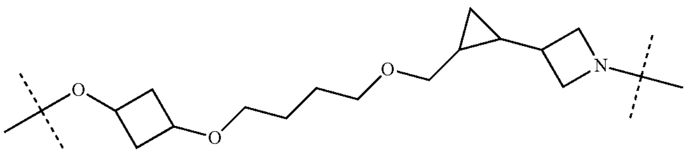
;
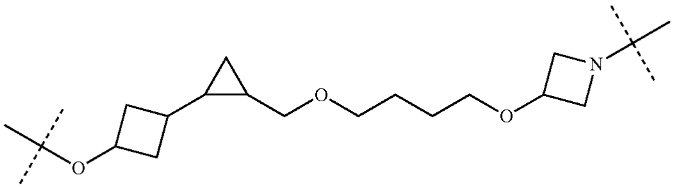
;
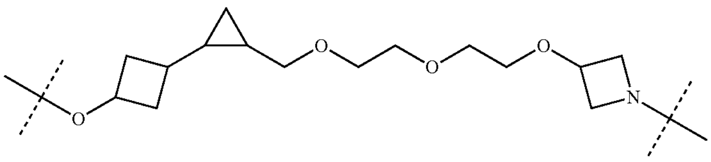
;

-continued
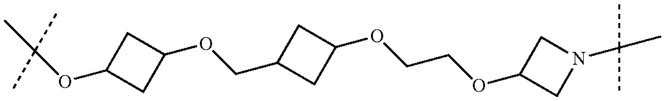 ; 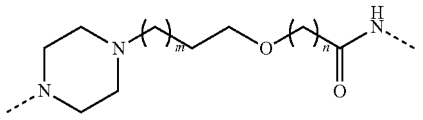 ;
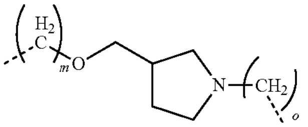 ; 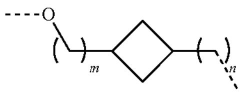 ; 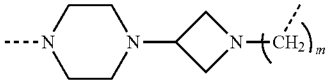
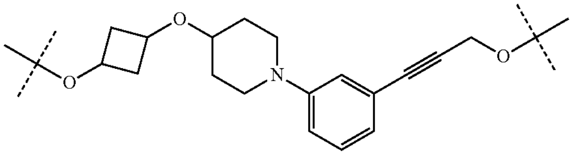 ; 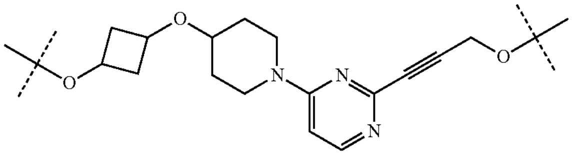 ;
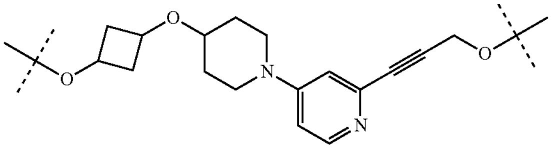 ; 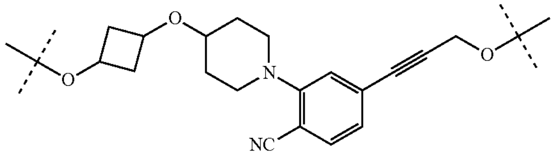 ;
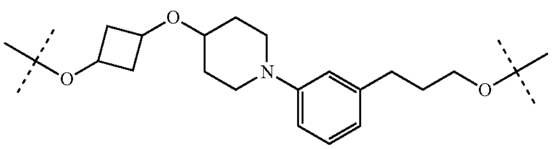 ; 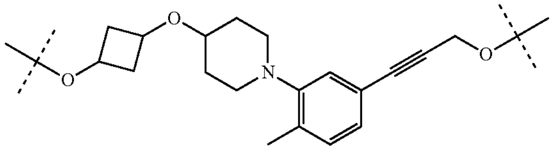 ;
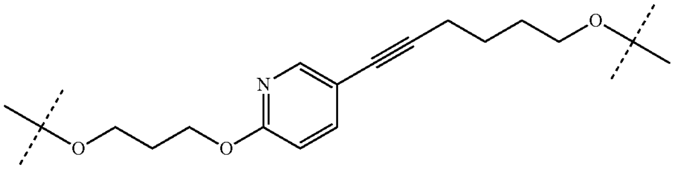 ;
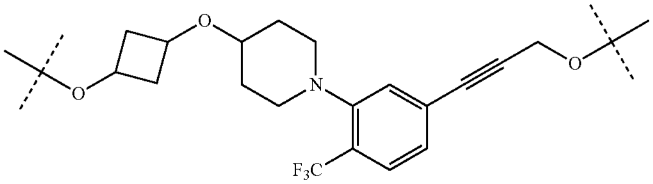 ;
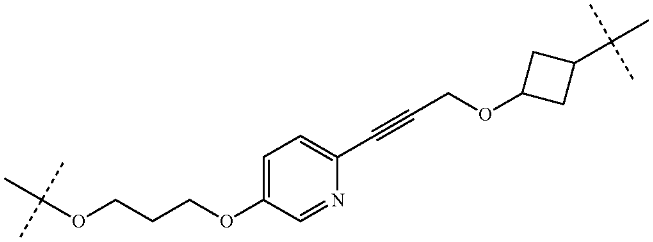 ;
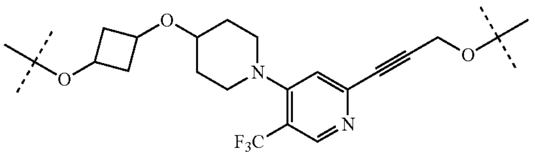 ; 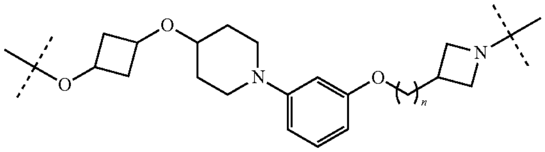 ;
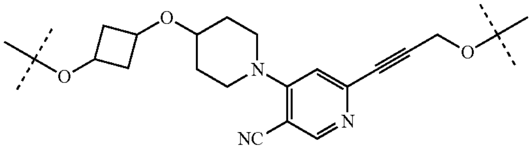 ; 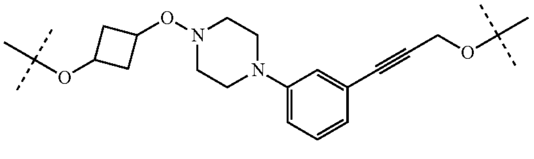 ;

-continued
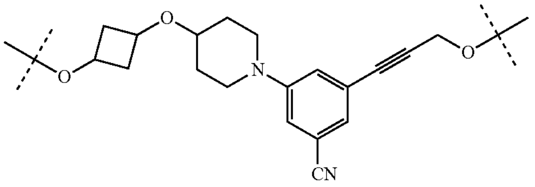
;
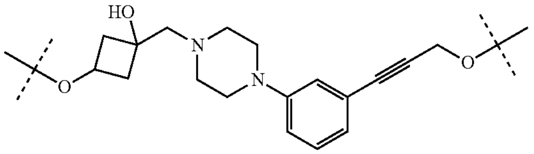
;
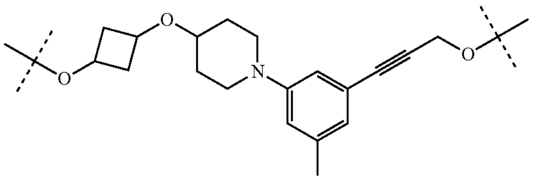
;
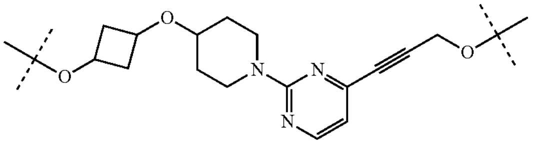
;
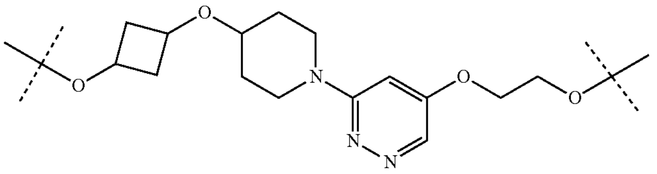
;
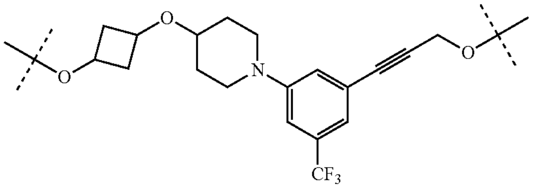
;
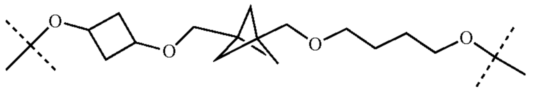
;
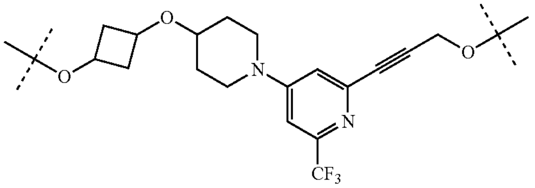
;
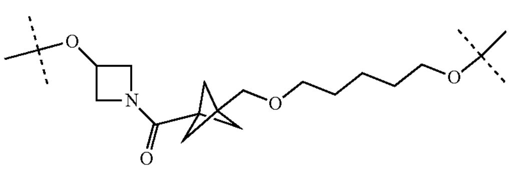
;
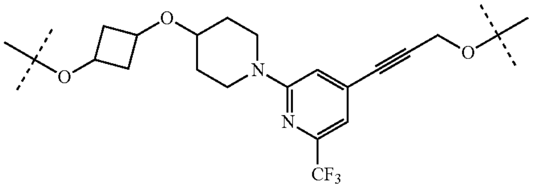
;
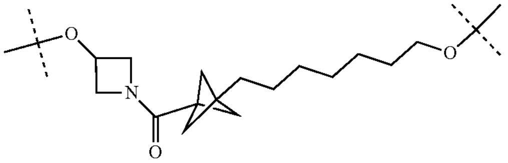
;
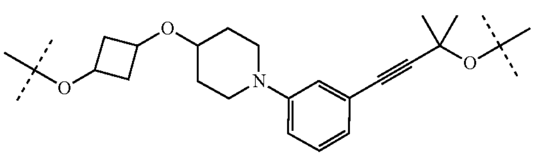
;
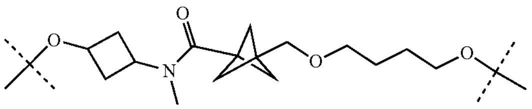
;
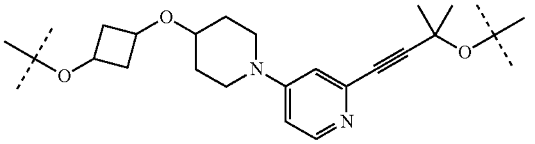
;
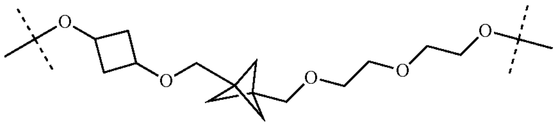
;
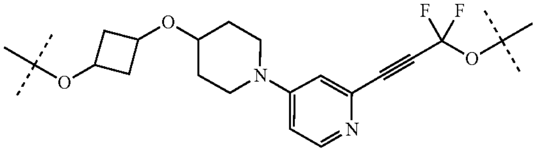
;
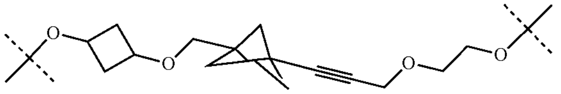
;
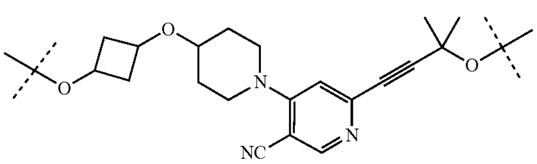
;
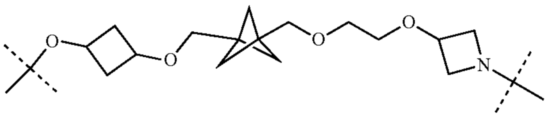
;

-continued
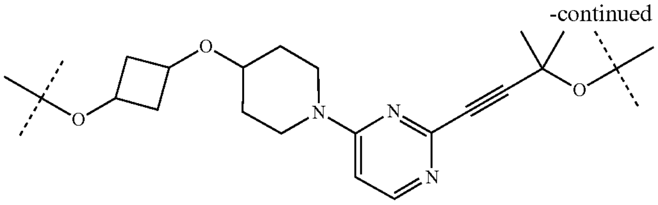 ;
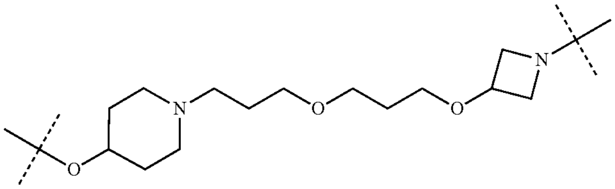 ;
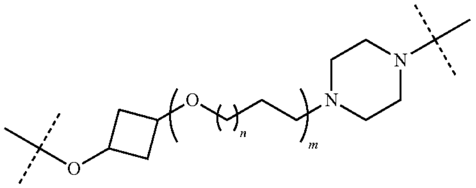 ;
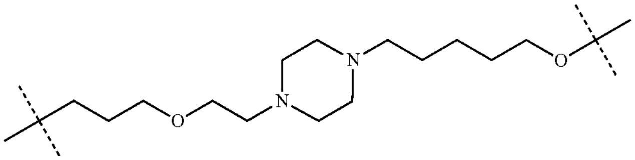 ;
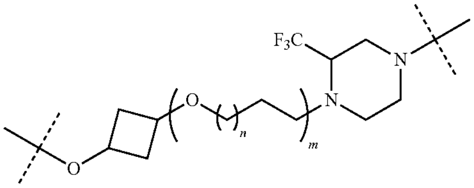 ;
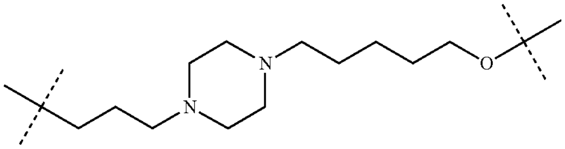 ;
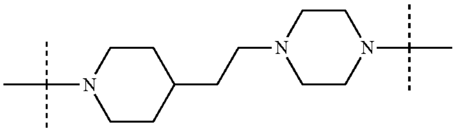 ;
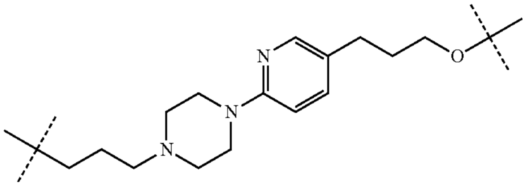 ;
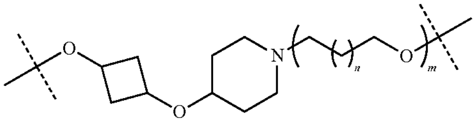 ;
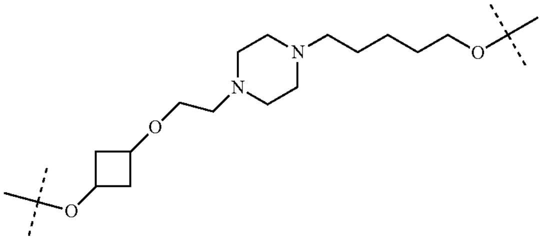 ;
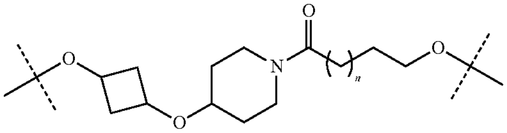 ;
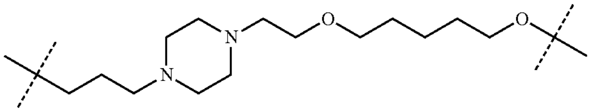 ;
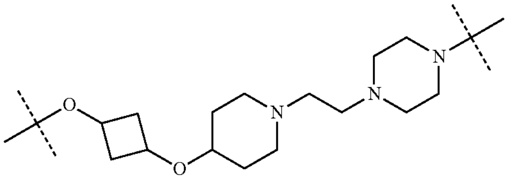 ;
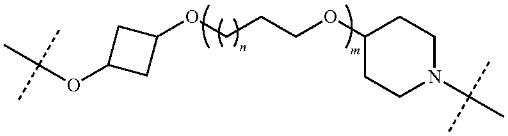 ;
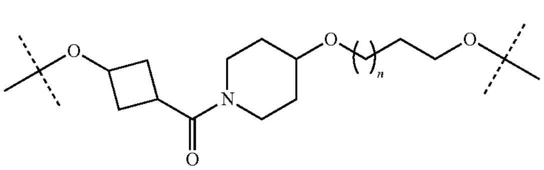 ;
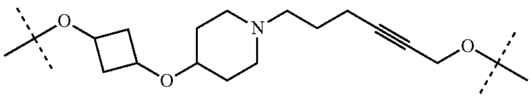 ;
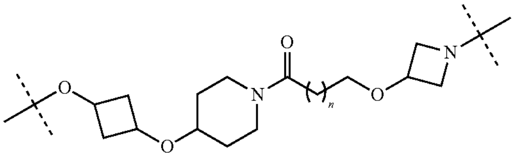 ;

-continued
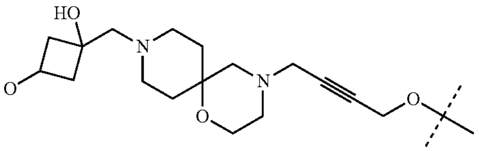 ; 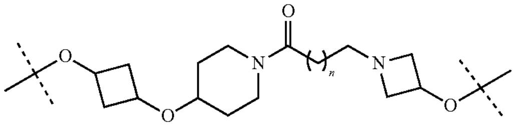 ;
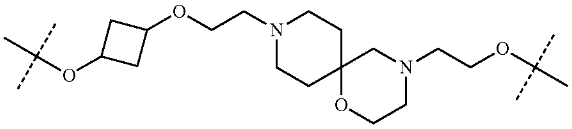 ; 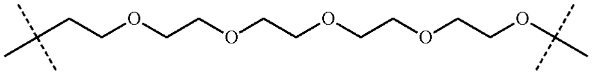 ;
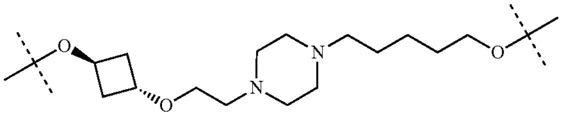 ; 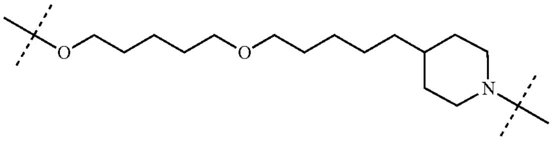 ;
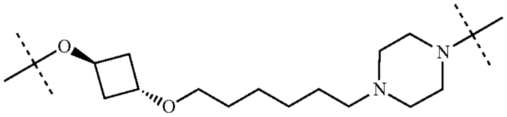 ; 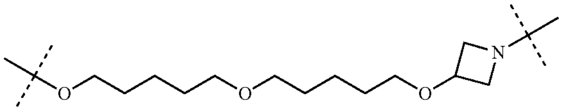 ;
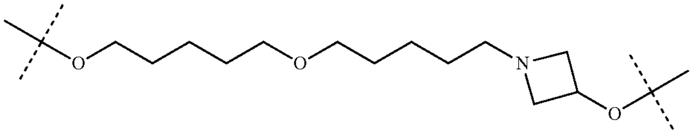 ;
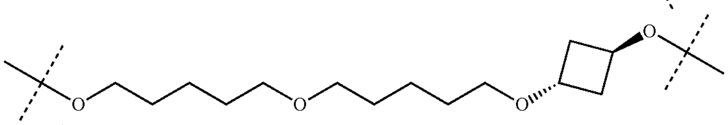 ;
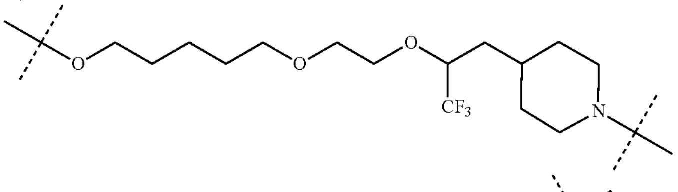 ; and
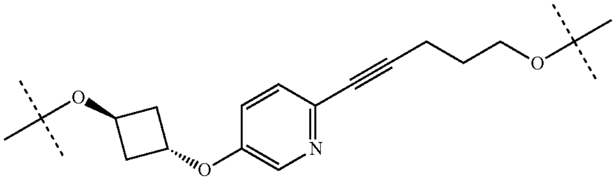 .
wherein each m, n, o, p, q, r, and s is independently 0, 1, 2, 3, 4, 5, 6, 7, 8, 9, 10, 11, 12, 13, 14, 15, 16, 17, 18, 19, or 20.
8. The compound according to claim 5, wherein the linker is selected from:
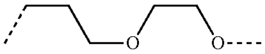 ; 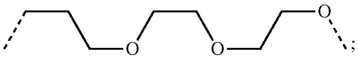 ; 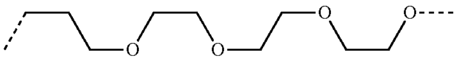 ;
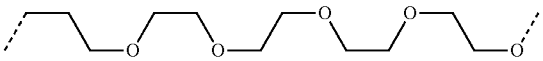 ;
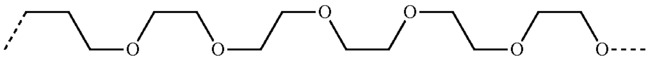 ; 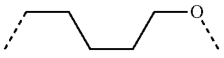 ; 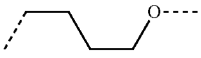 ;
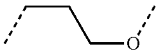 ; 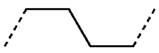 ; 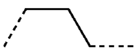 ; 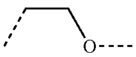 ; 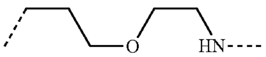 ;
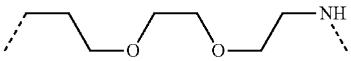 ; 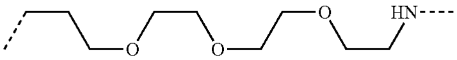 ;
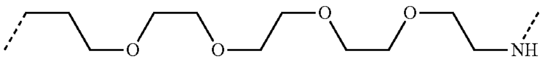 ;

-continued
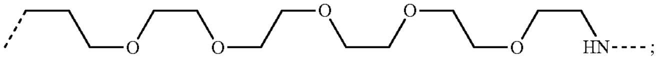
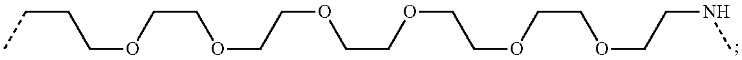
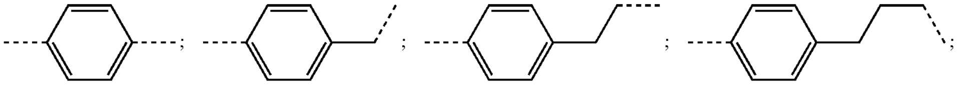
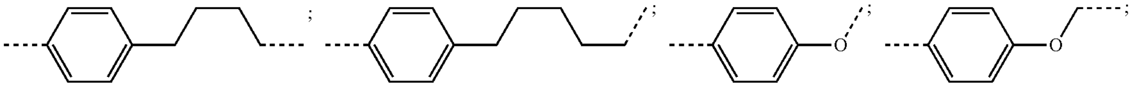
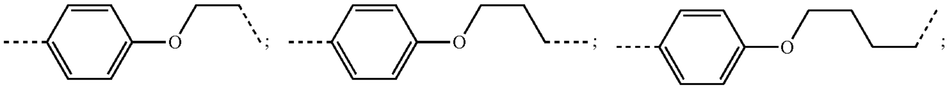
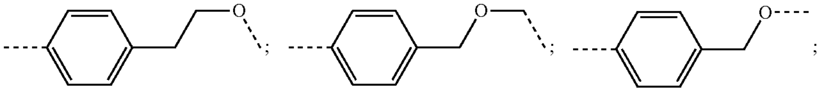
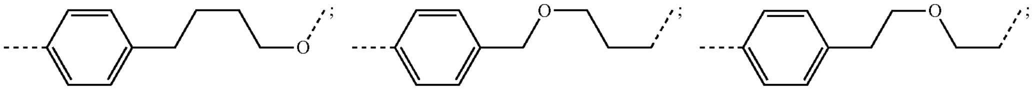
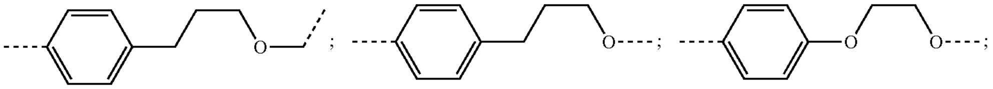
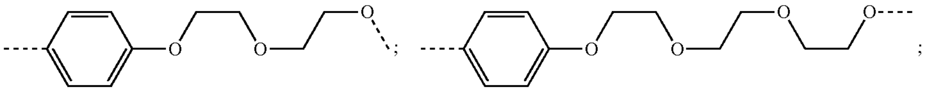
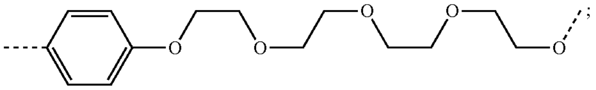
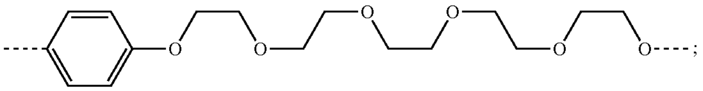
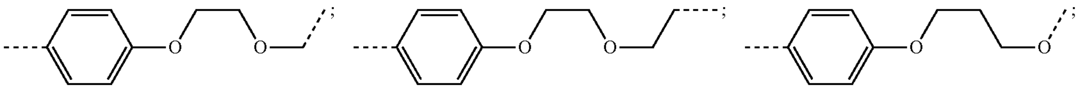
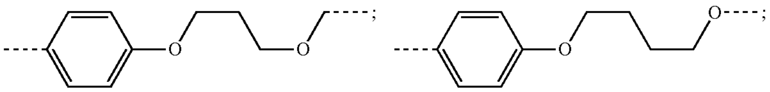
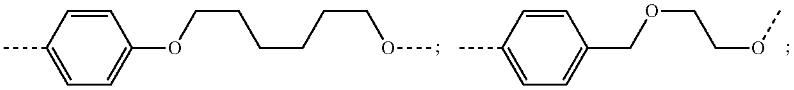
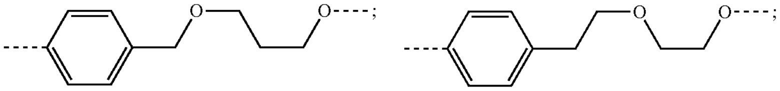
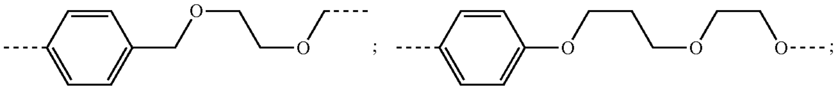
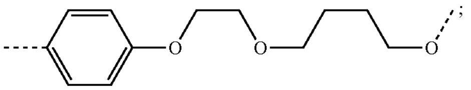
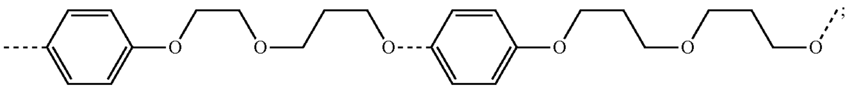
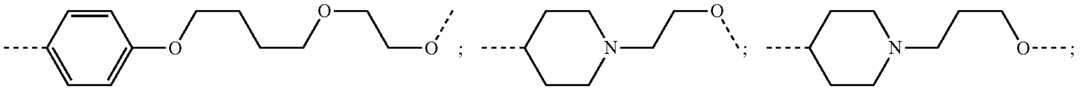

-continued
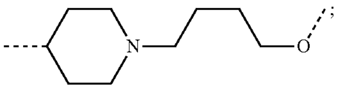;
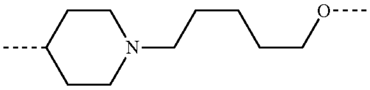;
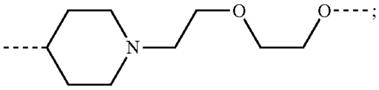;
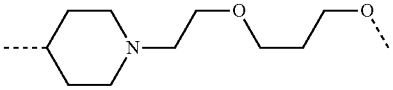;
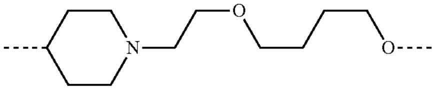;
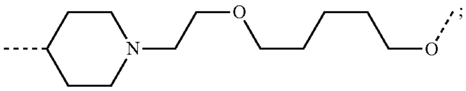;
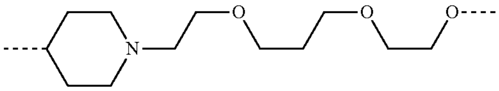;
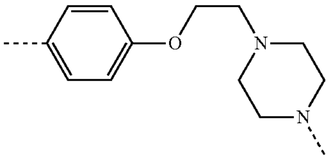;
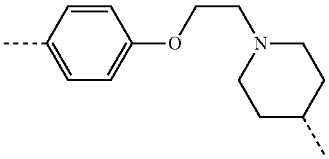;
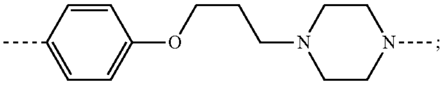;
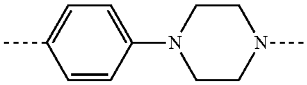;
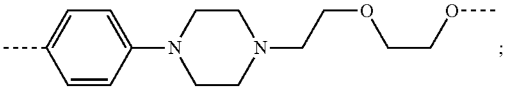;
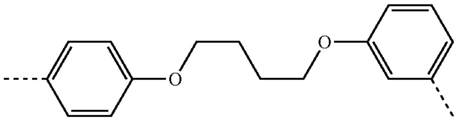;
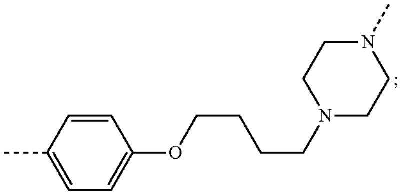;
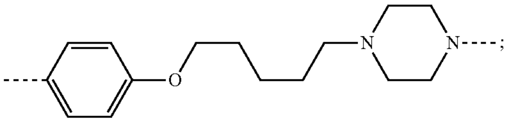;
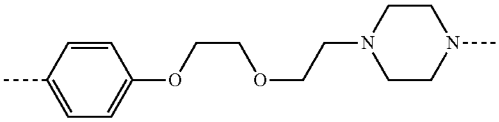;
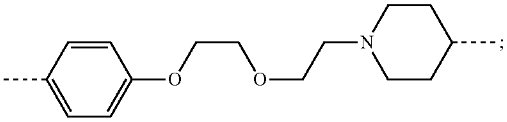;
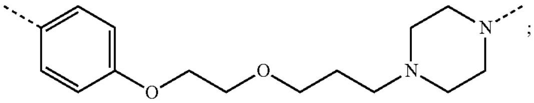;
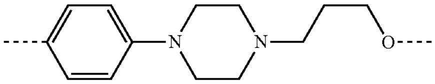;
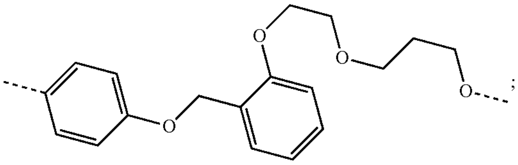;
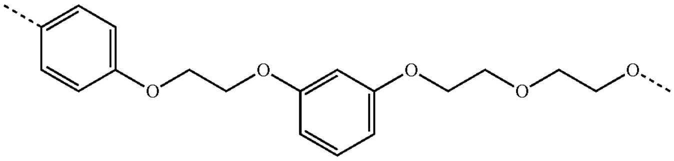;
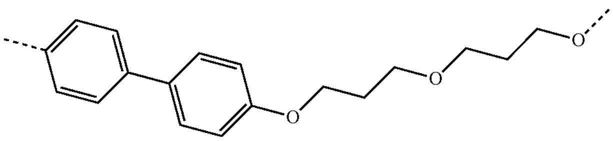;
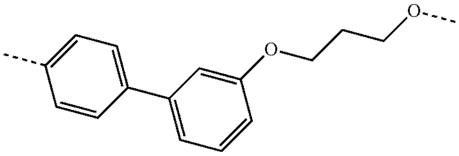;
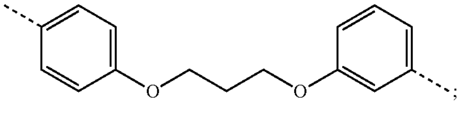;
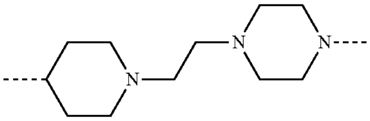;
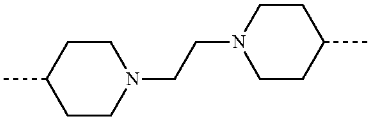;
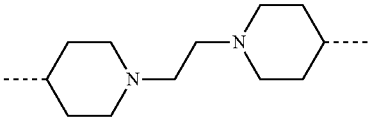;

-continued
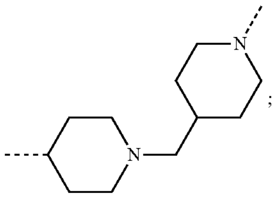
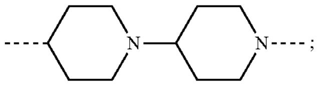
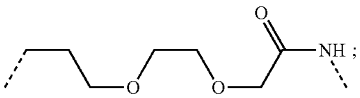
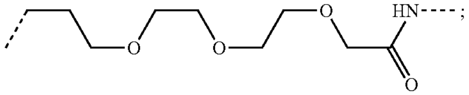
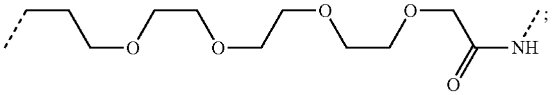
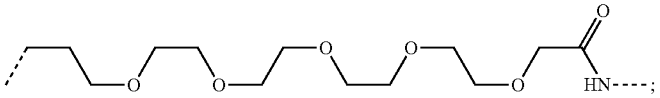
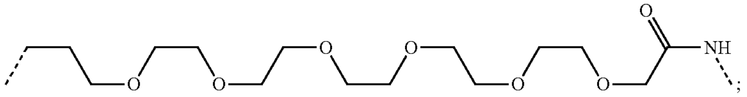
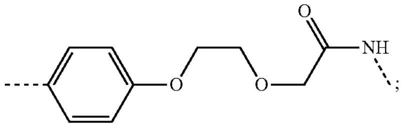
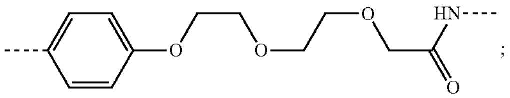
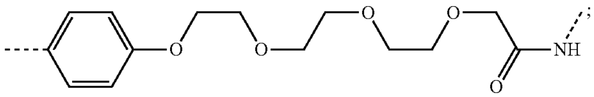
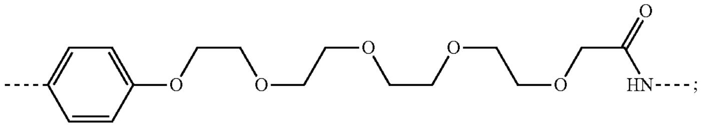
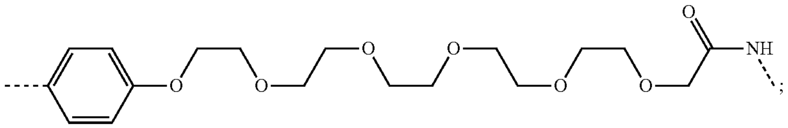
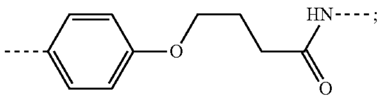
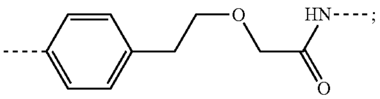
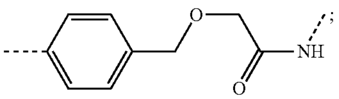
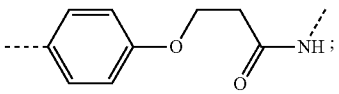
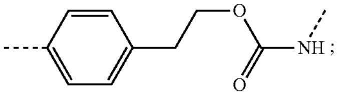
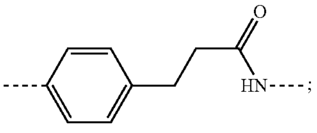
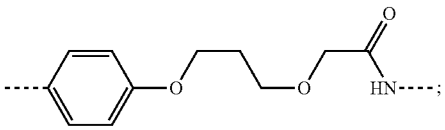
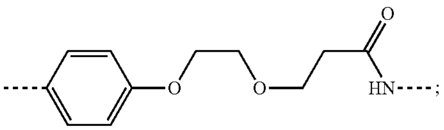
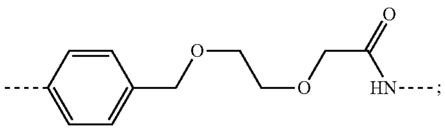
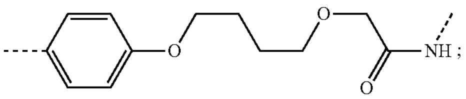
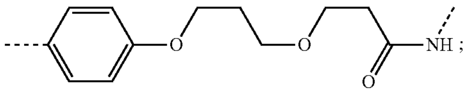
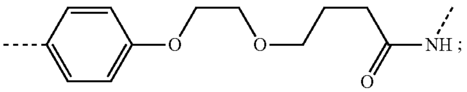
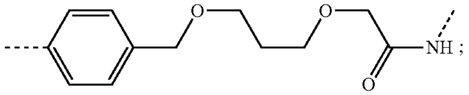
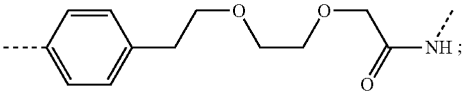

-continued
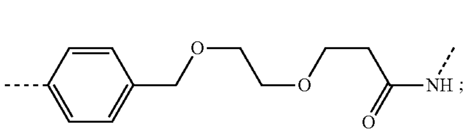
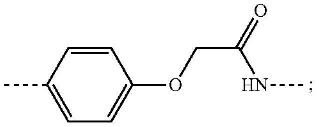
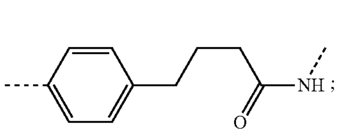
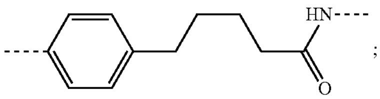
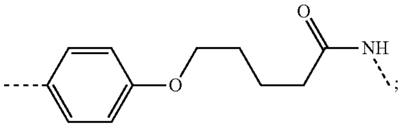
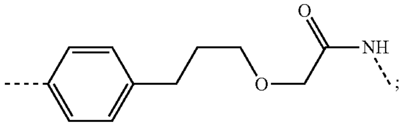
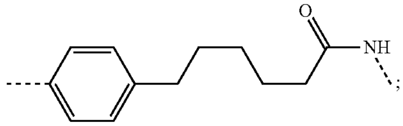
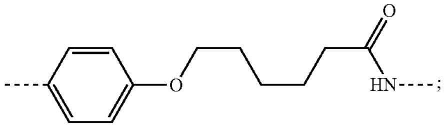
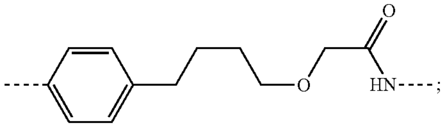
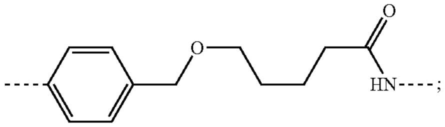
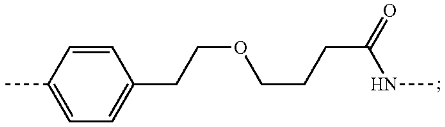
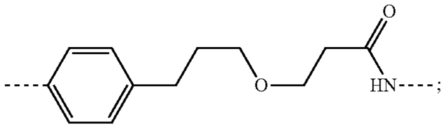
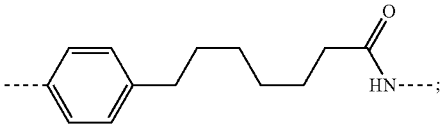
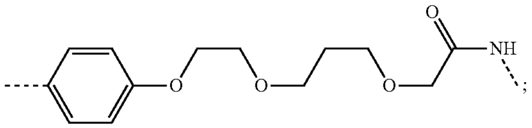
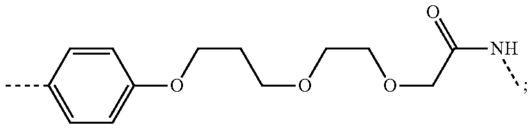
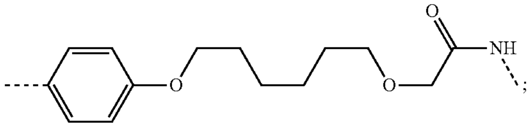
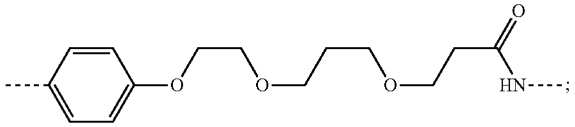
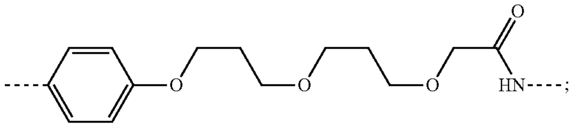
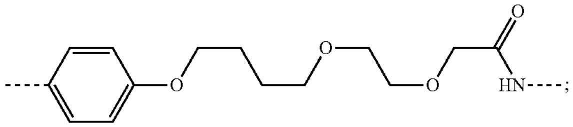
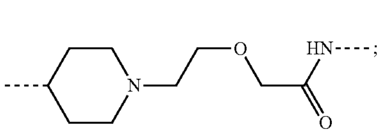
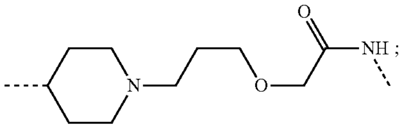
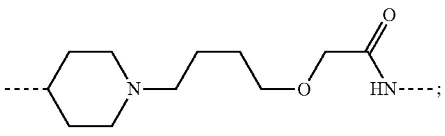
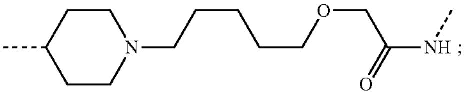
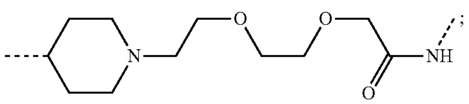
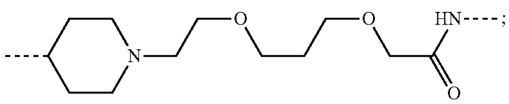
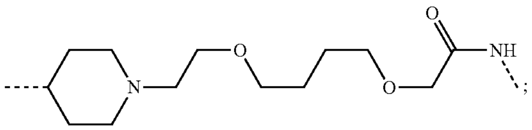
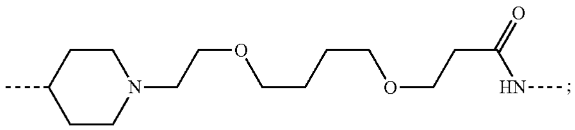

-continued
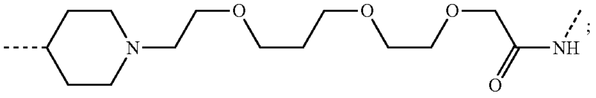;
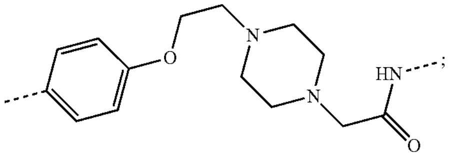;
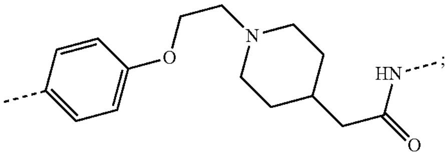;
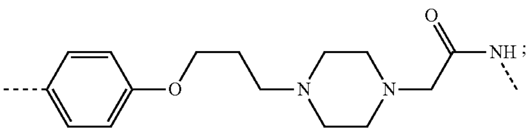;
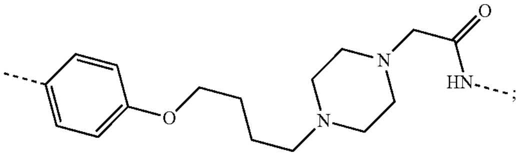;
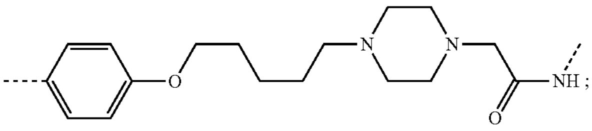;
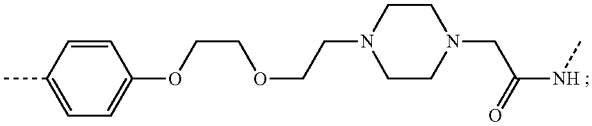;
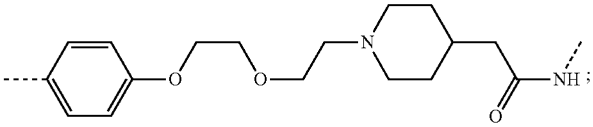;
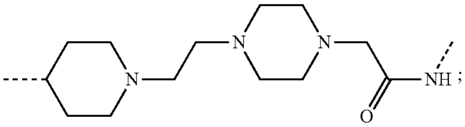;
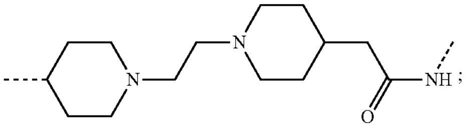;
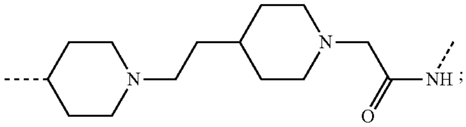;
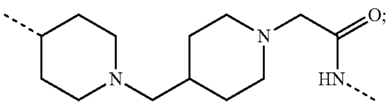;
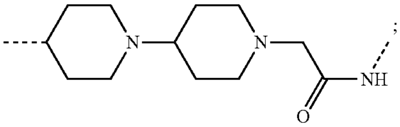;
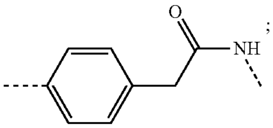;
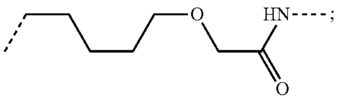;
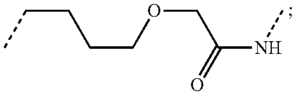;
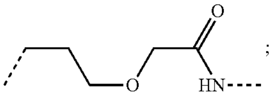;
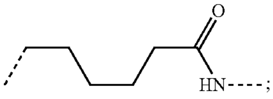;
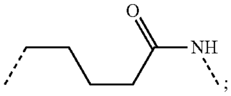;
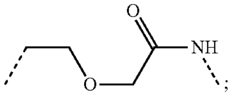;
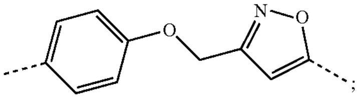;
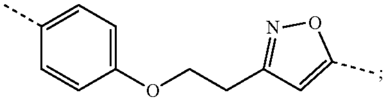;
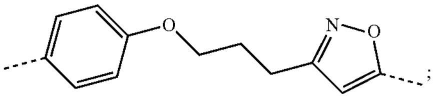;
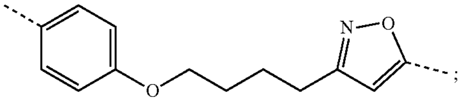;
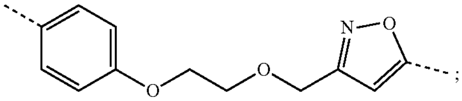;
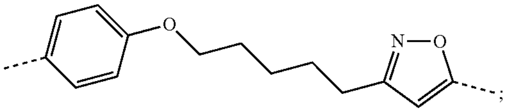;
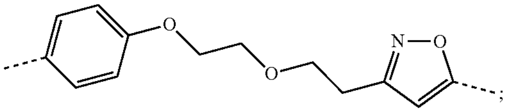;
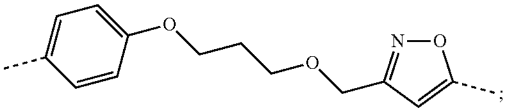;
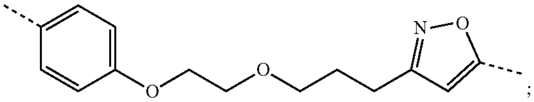;
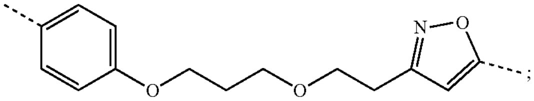;
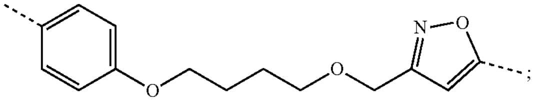;

-continued
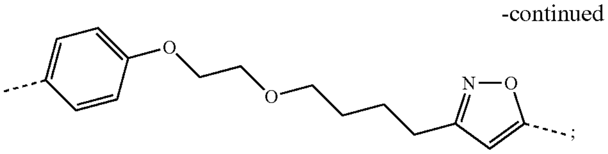
;
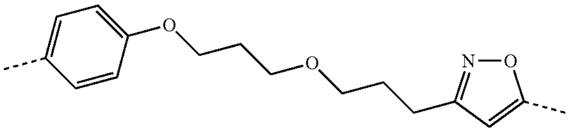
;
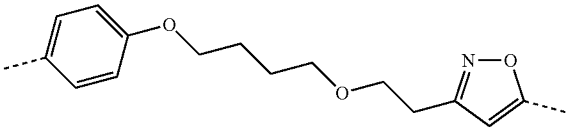
;
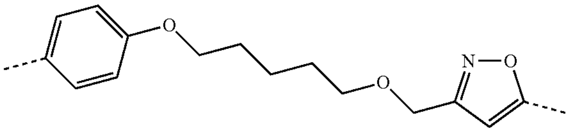
;
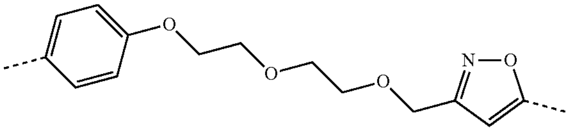
;
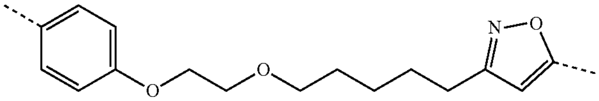
;
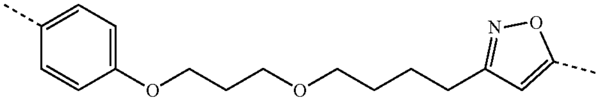
;
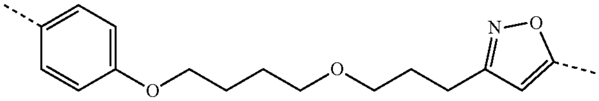
;
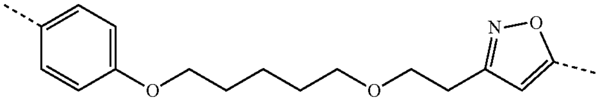
;
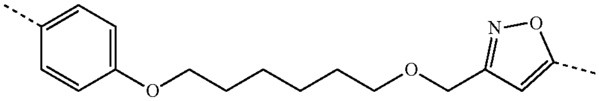
;
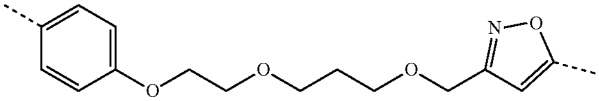
;
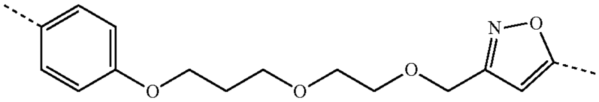
;
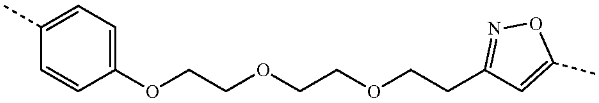
;
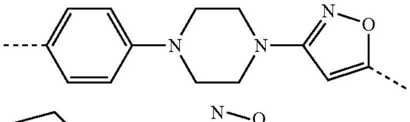
;
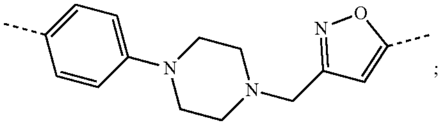
;
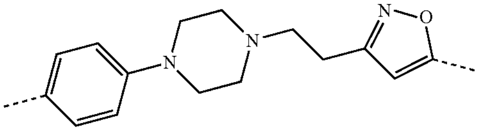
;
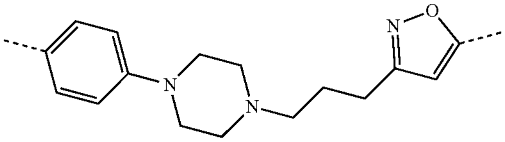
;
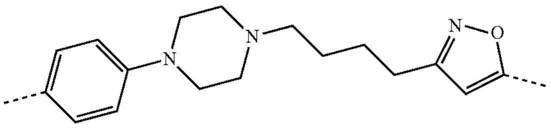
;

-continued
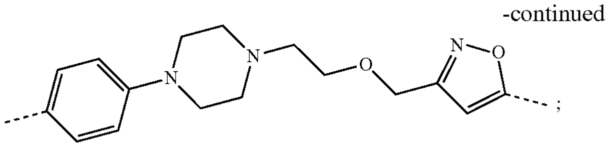
;
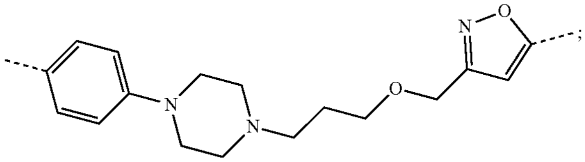
;
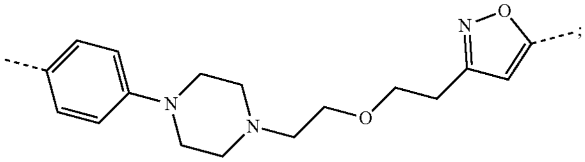
;
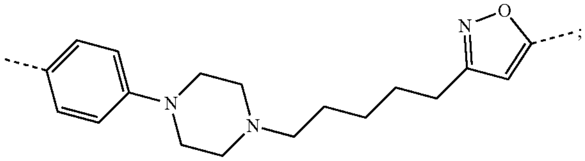
;
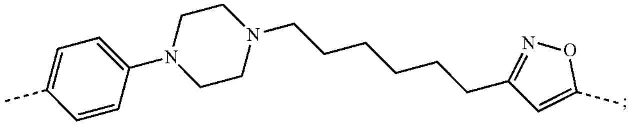
;
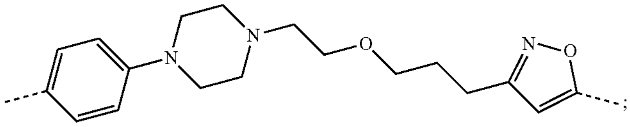
;
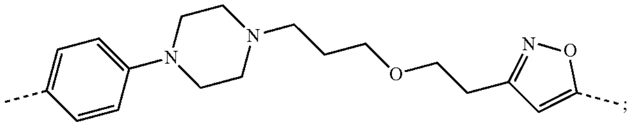
;
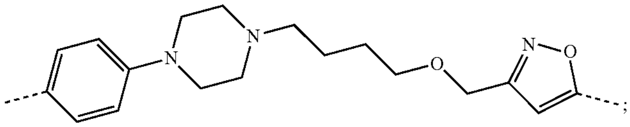
; 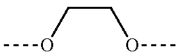
; 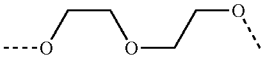
;
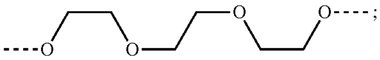
; 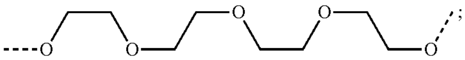
;
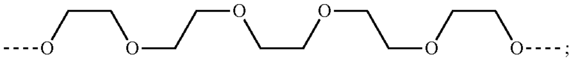
;
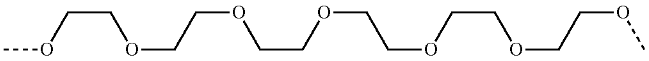
; 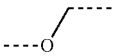
; 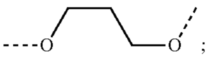
;
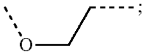
; 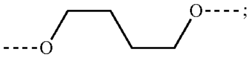
; 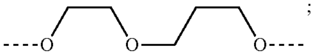
; 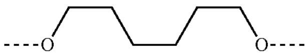
;
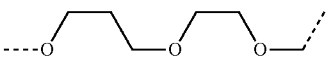
; 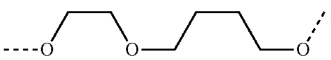
; 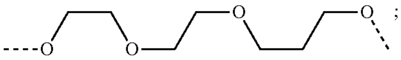
;
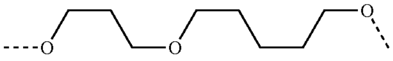
; 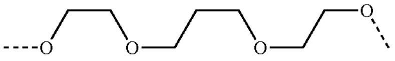
;
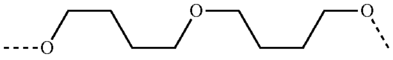
; 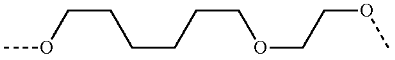
;
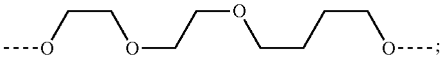
; 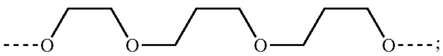
;
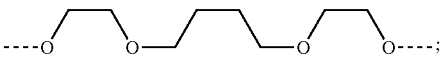
; 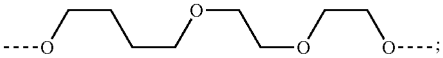
;
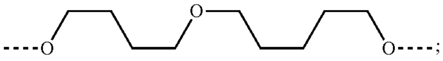
; 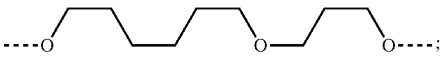
;

-continued
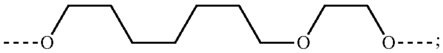; 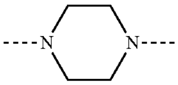; 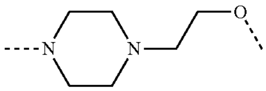;
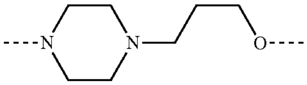; 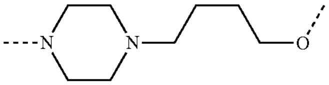; 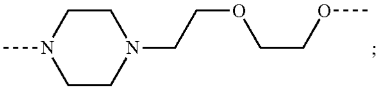;
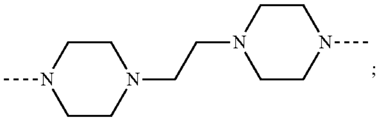; 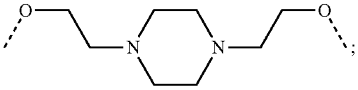;
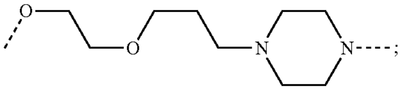; 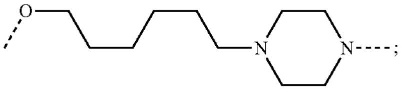;
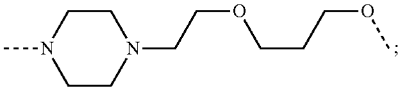; 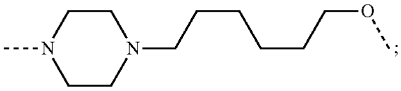;
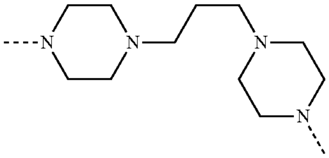; 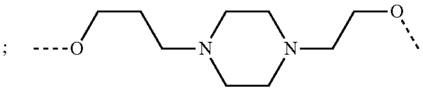;
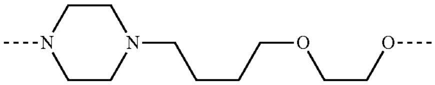; 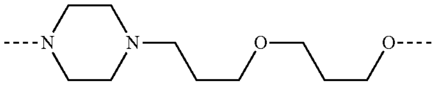;
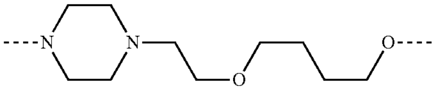; 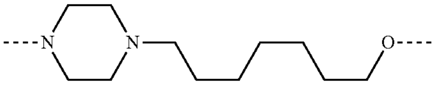;
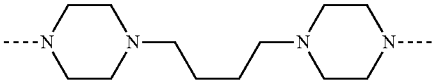; 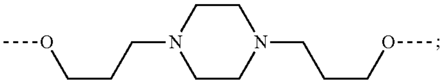;
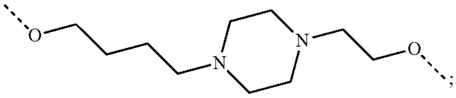; 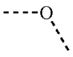; 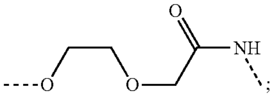;
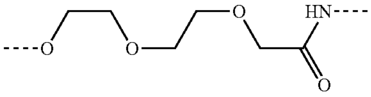; 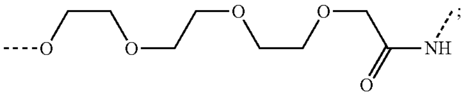;
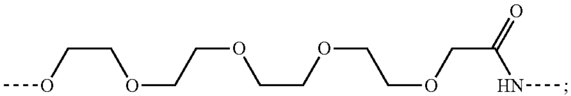;
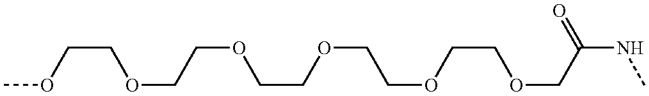;
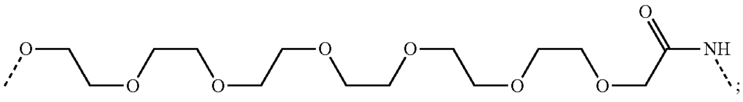; 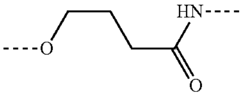;
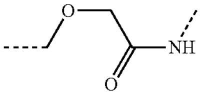; 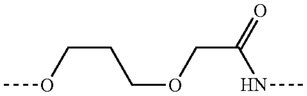; 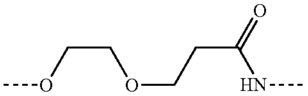;
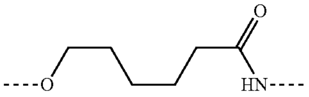; 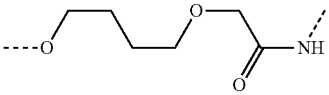; 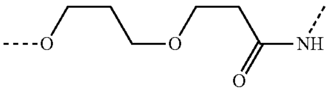;

-continued
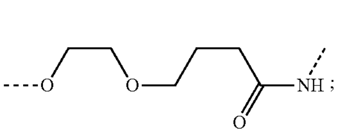 ; 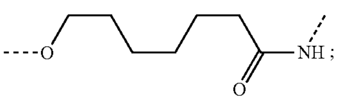 ; 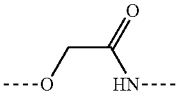 ;
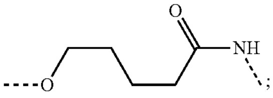 ; 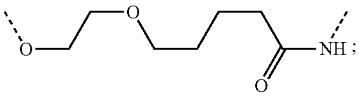 ; 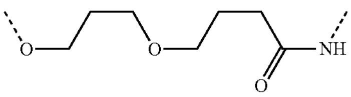 ;
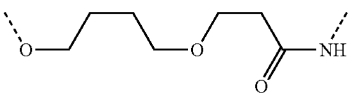 ; 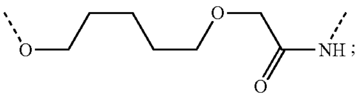 ; 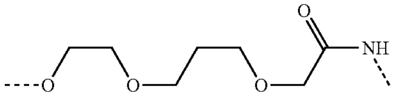 ;
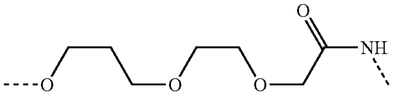 ; 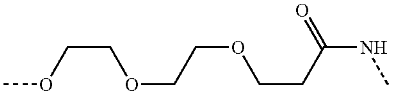 ;
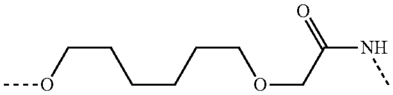 ; 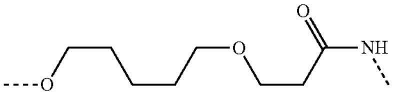
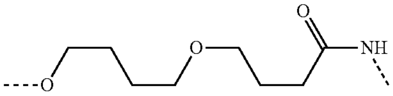 ; 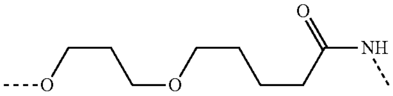
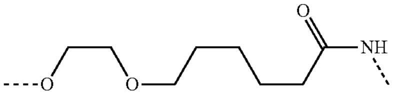 ; 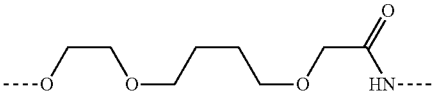 ;
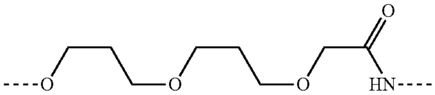 ; 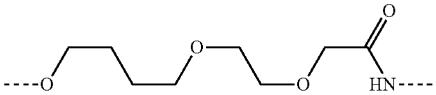 ;
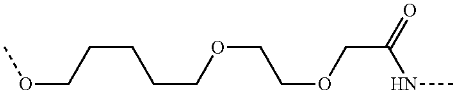 ; 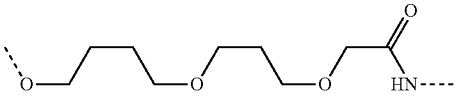 ;
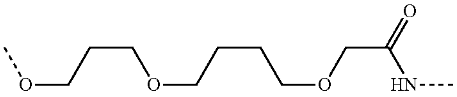 ; 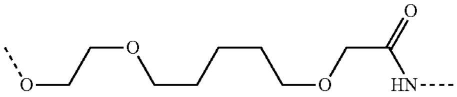 ;
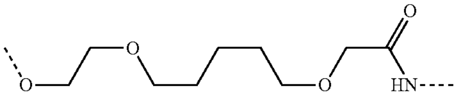 ; 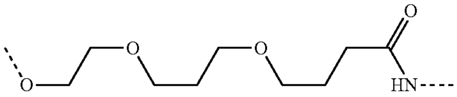 ;
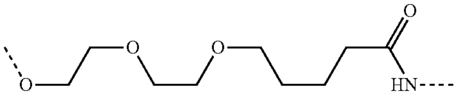 ; 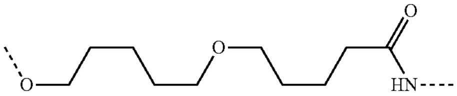 ;
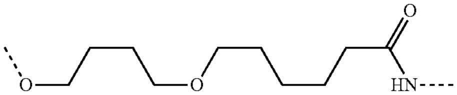 ; 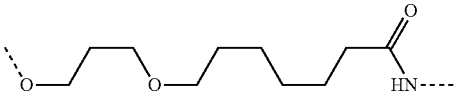 ;
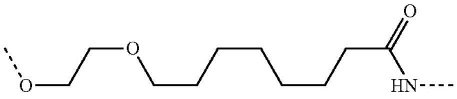 ; 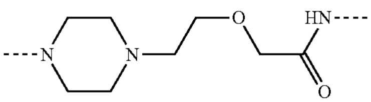 ;
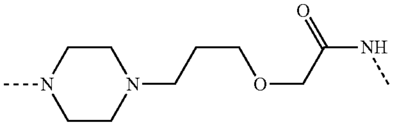 ; 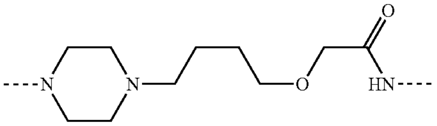 ;
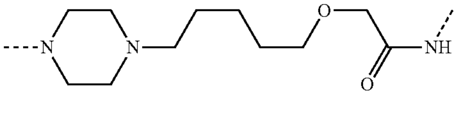 ; 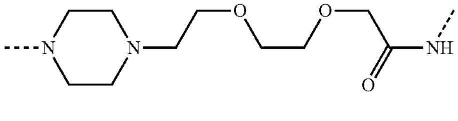 ;

-continued
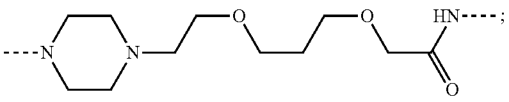;
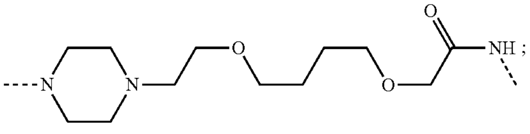;
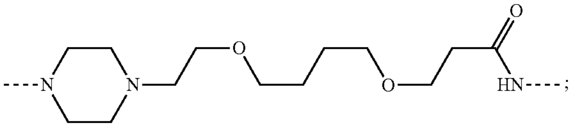;
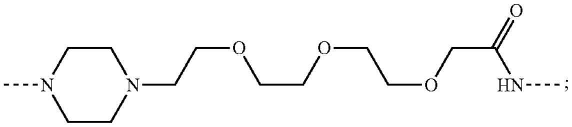;
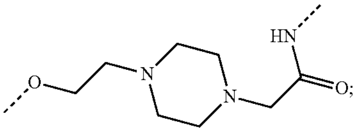;
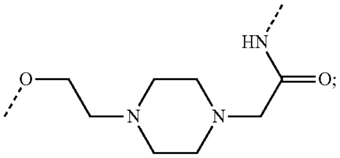;
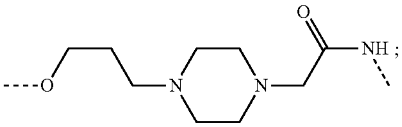;
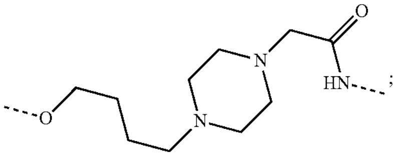;
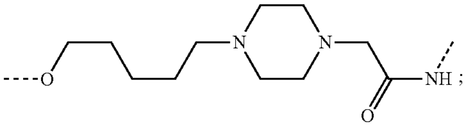;
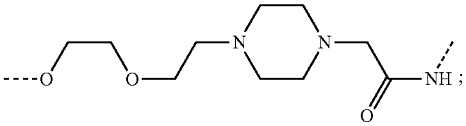;
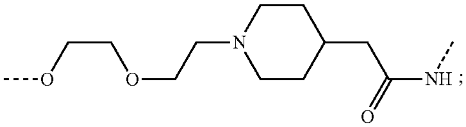;
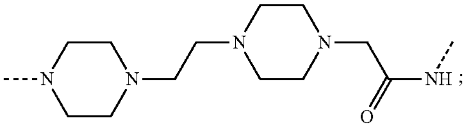;
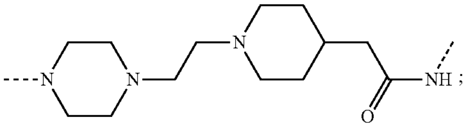;
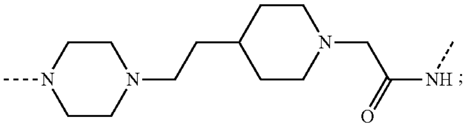;
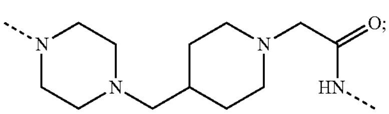;
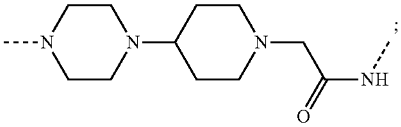;
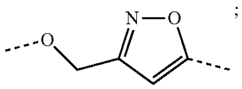;
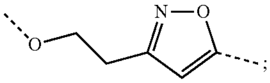;
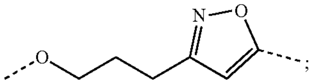;
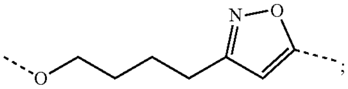;
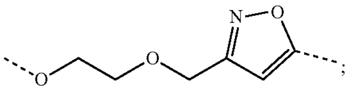;
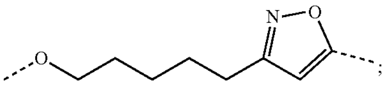;
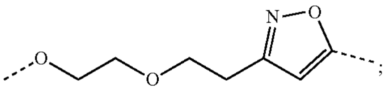;
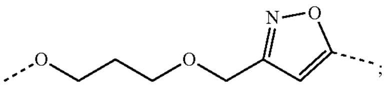;
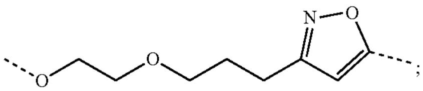;
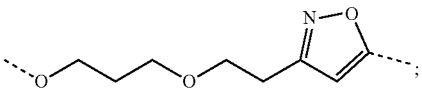;
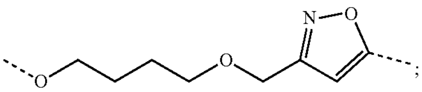;
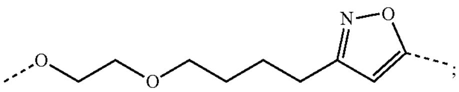;
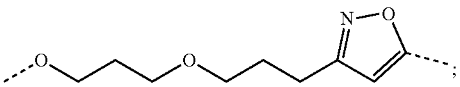;
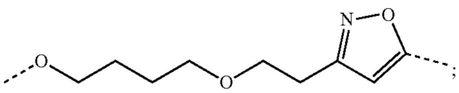;
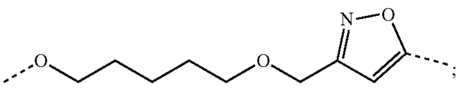;
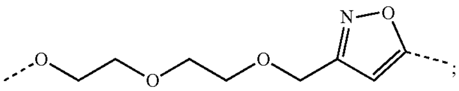;
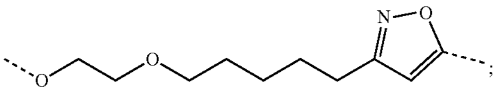;

-continued

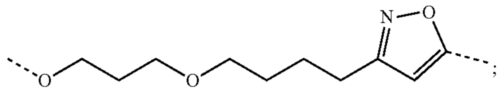
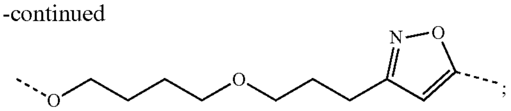
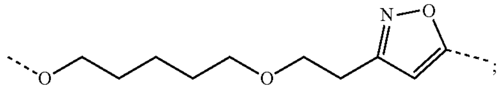
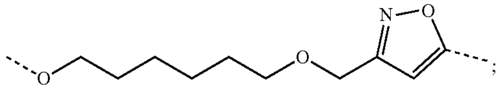
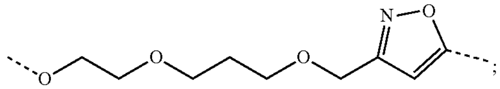
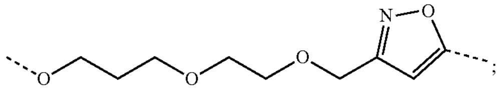
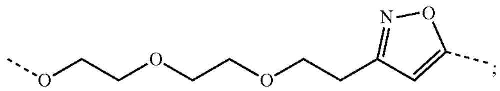
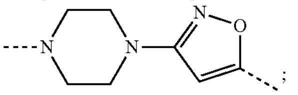
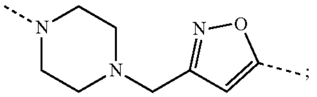
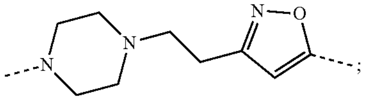
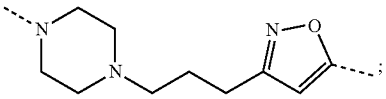
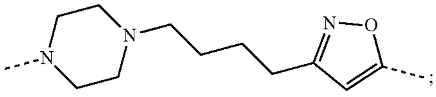
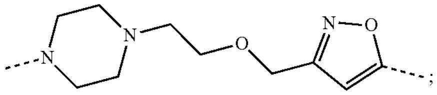
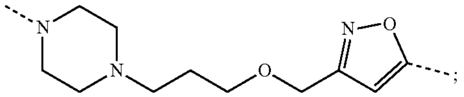
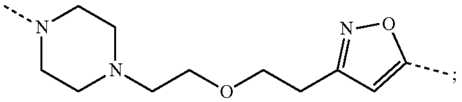
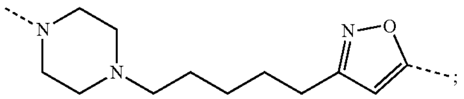
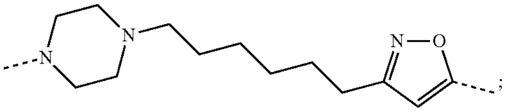
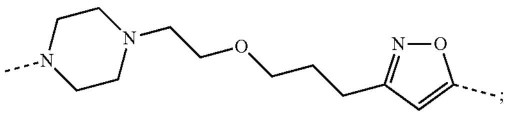
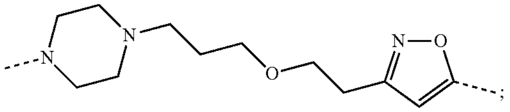
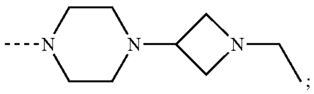

and

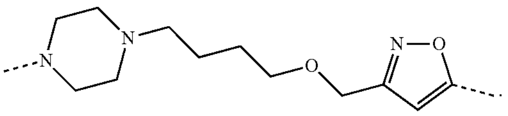

9. The compound according to claim 1, wherein the linker (L) comprises the following chemical structure:

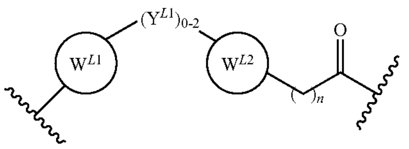

or

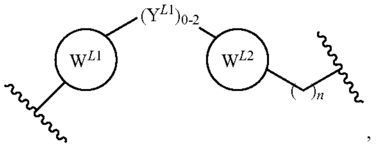

, wherein:

$W^{L1}$ and $W^{L2}$ are each independently a 4-8 membered ring with 0-4 heteroatoms, optionally substituted with RQ, each RQ is independently a H, halo, OH, CN, CF3, optionally substituted linear or branched C1-C6 alkyl, optionally substituted linear or branched C1-C6 alkoxy, or 2 RQ groups taken together with the atom they are attached to, form a 4-8 membered ring system containing 0-4 heteroatoms;

$Y^{L1}$ is each independently a bond, optionally substituted linear or branched C1-C6 alkyl and optionally one or more C atoms are replaced with O; or optionally substituted linear or branched C1-C6 alkoxy;

n is 0-10; and

indicates the attachment point to the PTM or the ULM.

10. The compound according to claim 1, wherein the linker (L) comprises the following chemical structure:

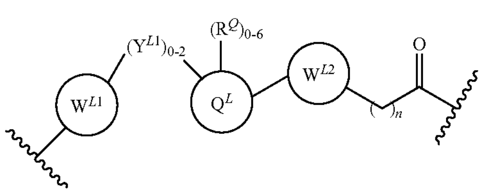

or

-continued

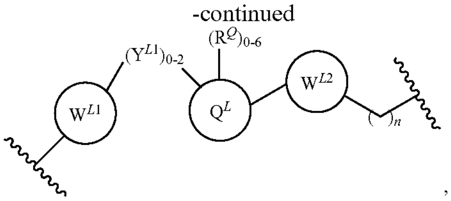

, wherein:

$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with RQ, each RQ is independently a H, halo, OH, $NR^{YL1}R^{YL2}$, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, $OC_{1-3}$alkyl optionally substituted by 1 or more F, or 2 RQ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, optionally substituted linear or branched $C_1$-$C_6$ alkyl and optionally one or more C atoms are replaced with O; optionally substituted linear or branched $C_1$-$C_6$ alkoxy;

$Q^L$ is a 3-6 membered alicyclic or aromatic ring with 0-4 heteroatoms, optionally bridged, optionally substituted with 0-6 $R^Q$, each $R^Q$ is independently: H, linear or branched $C_{1-6}$ alkyl optionally substituted by 1 or more halo or $C_{1-6}$ alkoxyl, or 2 $R^Q$ groups taken together with the atom they are attached to, form a 3-8 membered ring system containing 0-2 heteroatoms;

$R^{YL1}$, $R^{YL2}$ are each independently H, OH, linear or branched $C_{1-6}$ alkyl optionally substituted by 1 or more halo or $C_{1-6}$ alkoxyl, or $R^{YL1}$, $R^{YL2}$ together with the atom they are attached to, form a 3-8 membered ring system containing 0-2 heteroatoms;

n is 0-10; and

indicates the attachment point to the PTM or the ULM.

11. The compound according to claim 9, wherein the linker (L) is selected from the group consisting of:

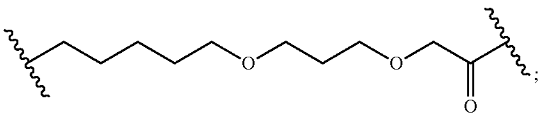

;

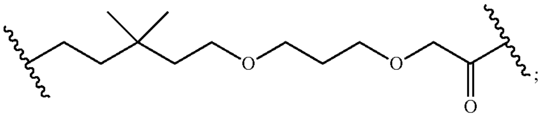

;

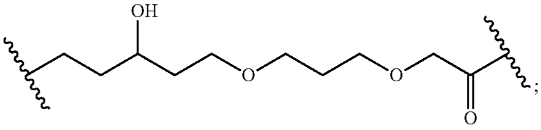

;

-continued

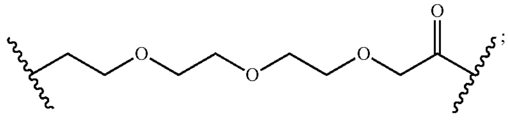

;

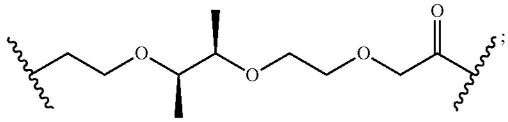

;

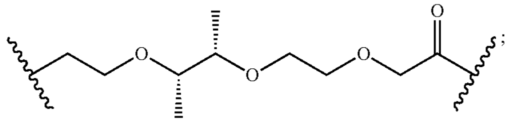

;

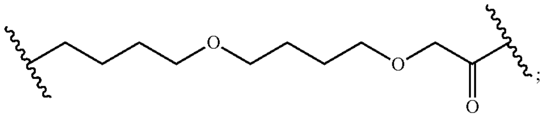

;

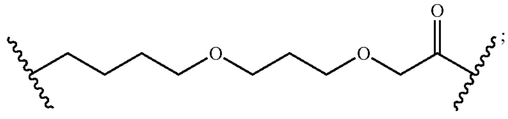

;

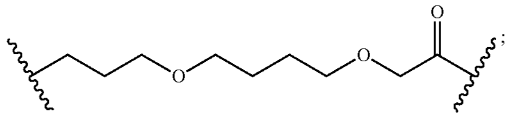

;

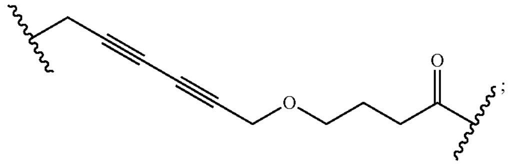

;

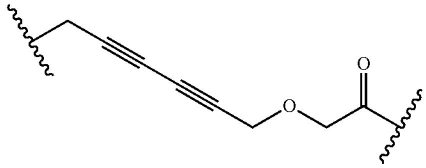

;

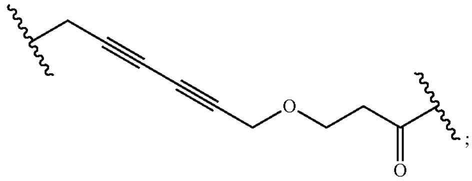

;

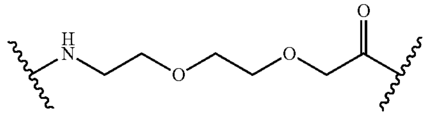

;

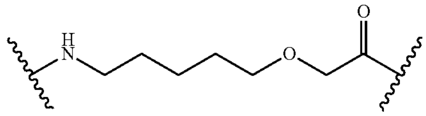

;

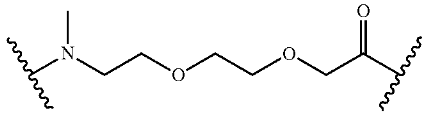

;

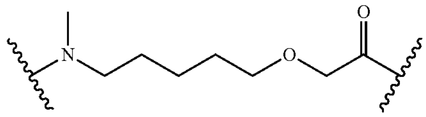

;

-continued
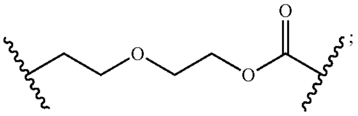
;
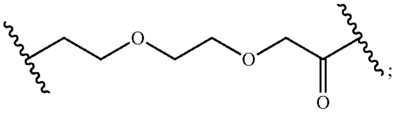
;
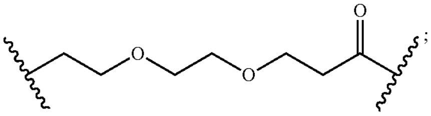
;
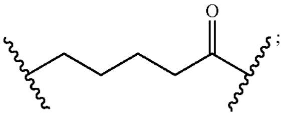
;
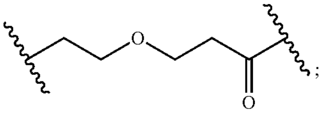
;
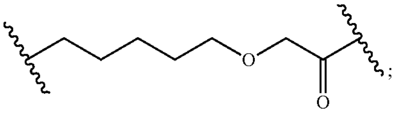
;
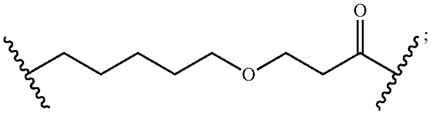
;
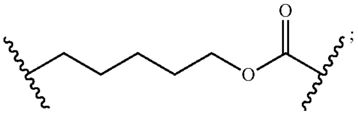
;
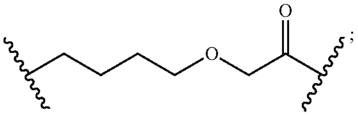
;
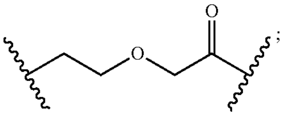
;
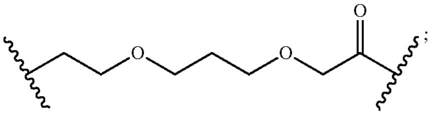
;
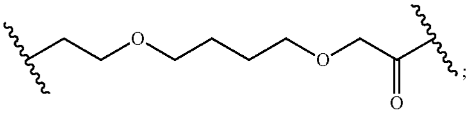
;
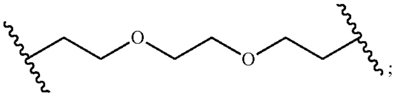
;
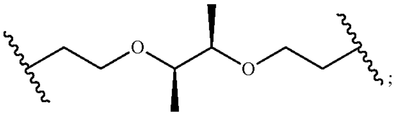
;
-continued
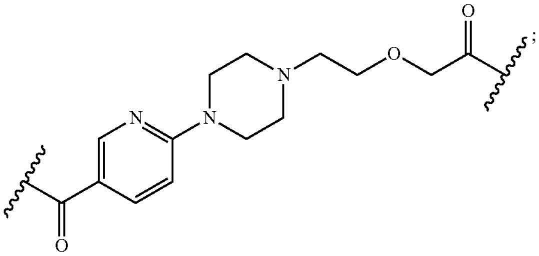
;
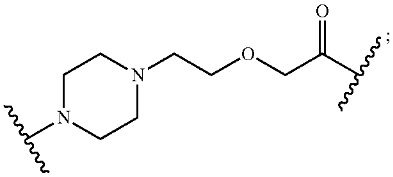
;
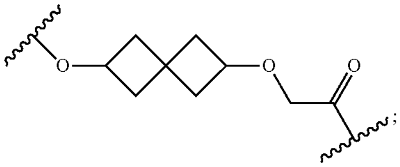
;
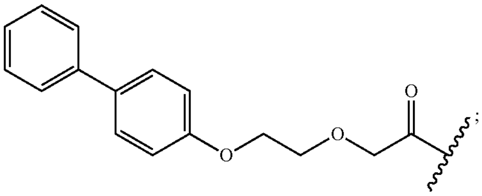
;
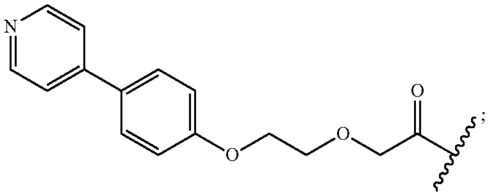
;
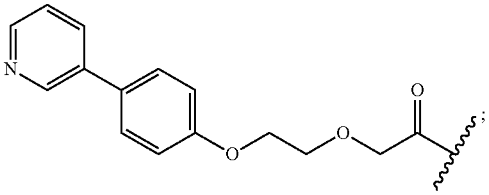
;
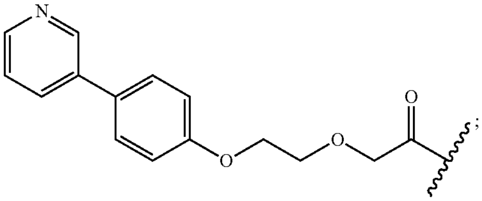
;
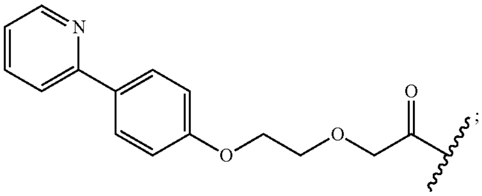
;

-continued
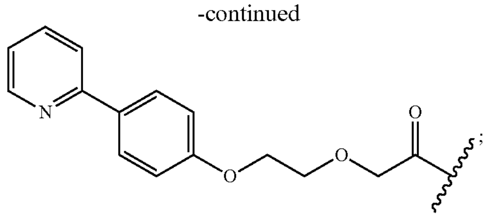
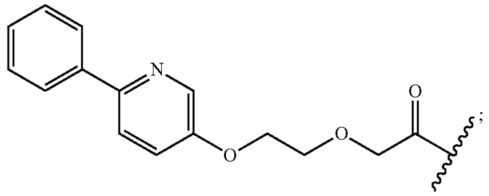
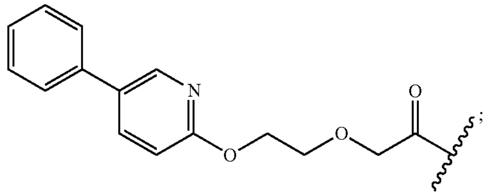
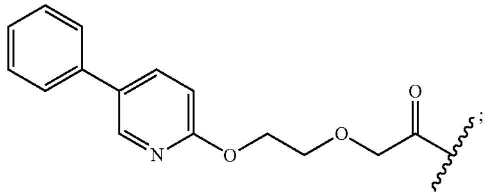
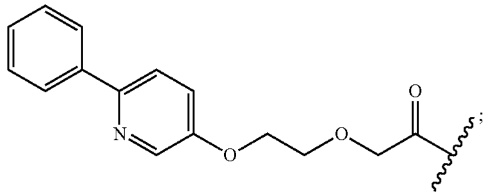
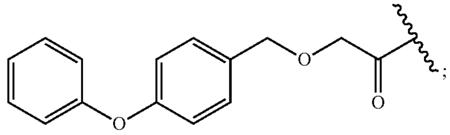
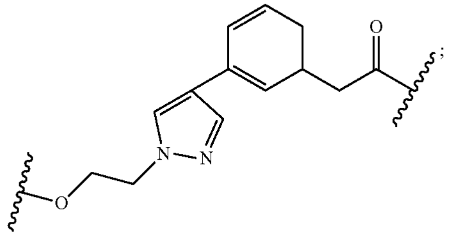
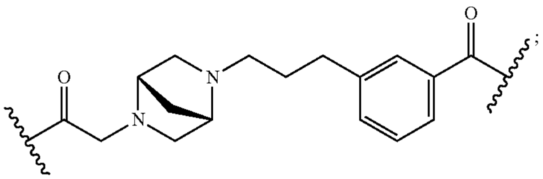
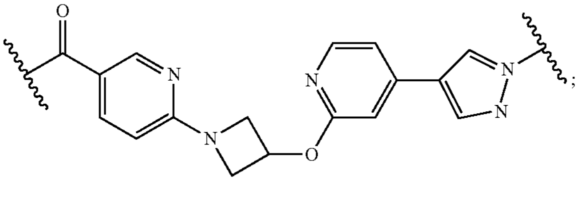
-continued
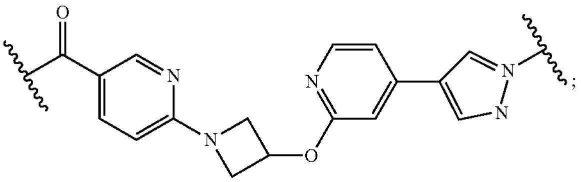
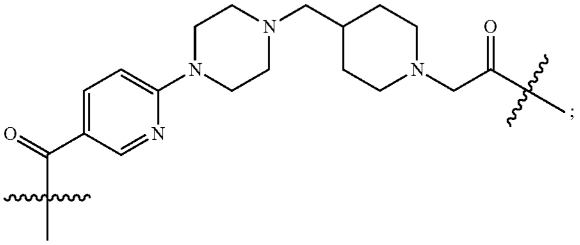
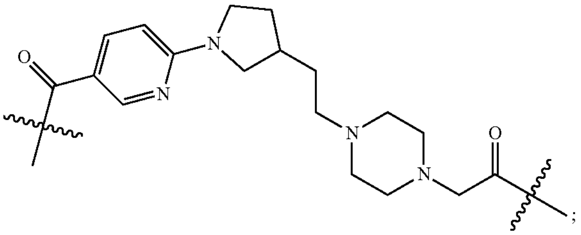
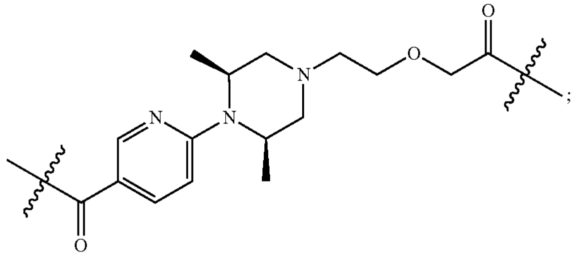
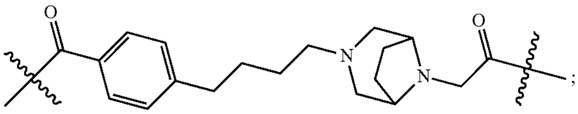
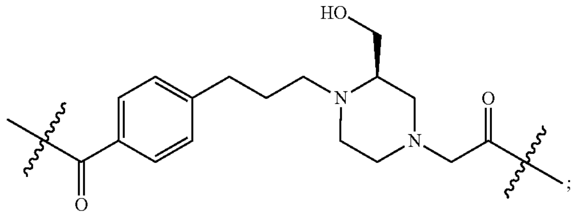
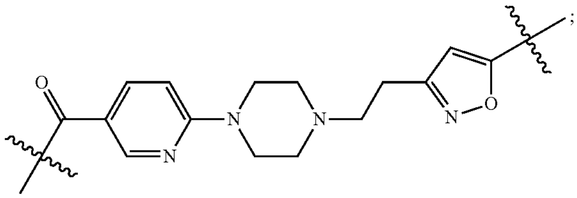
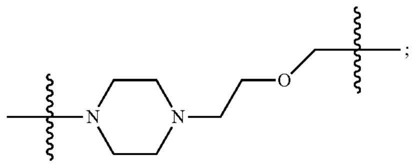

-continued
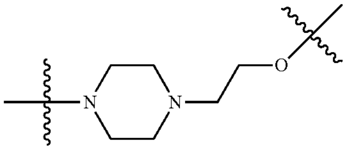
;
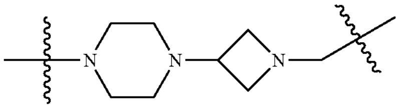
; and
-continued
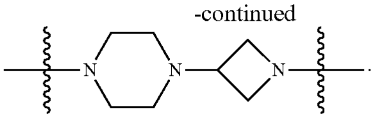
.
12. The compound according to claim 1, wherein the linker (L) is a polyethylenoxy group optionally substituted with aryl or phenyl comprising from 1 to 10 ethylene glycol units.
13. The compound according to claim 1, wherein the compound is selected from:
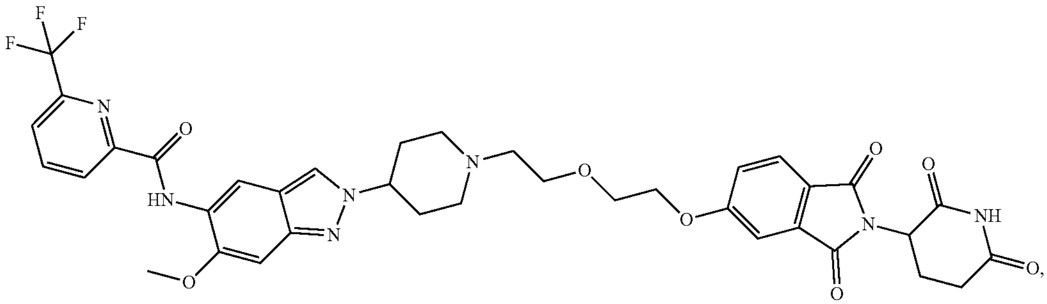
,
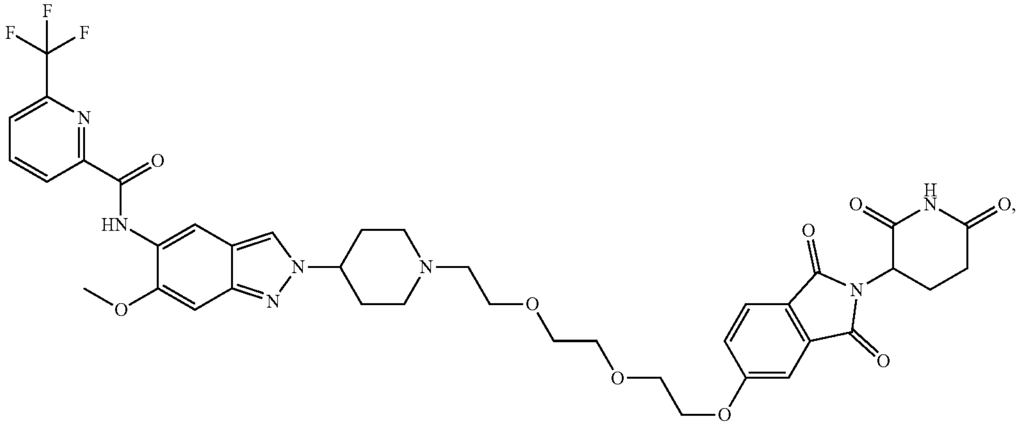
,
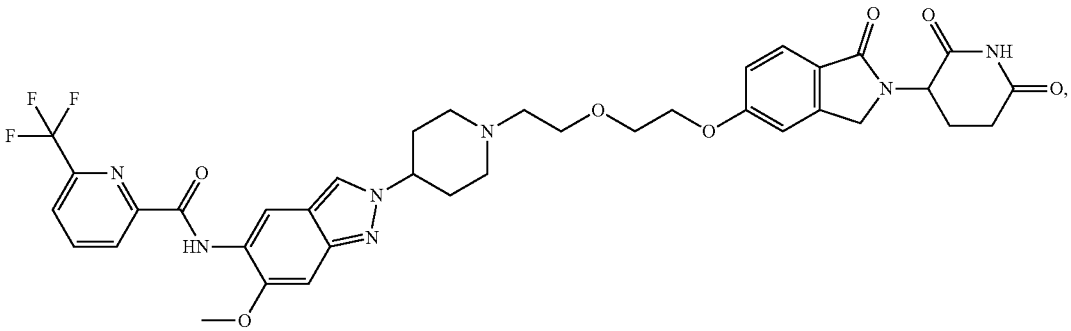
, -continued
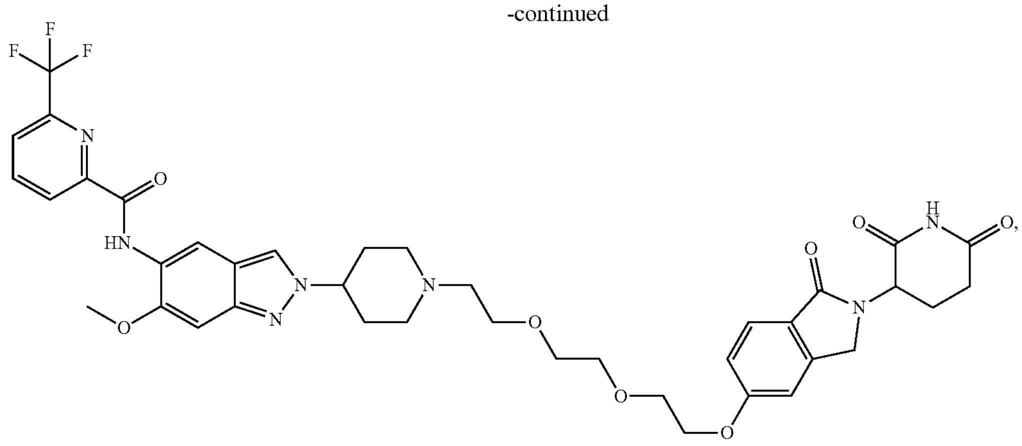
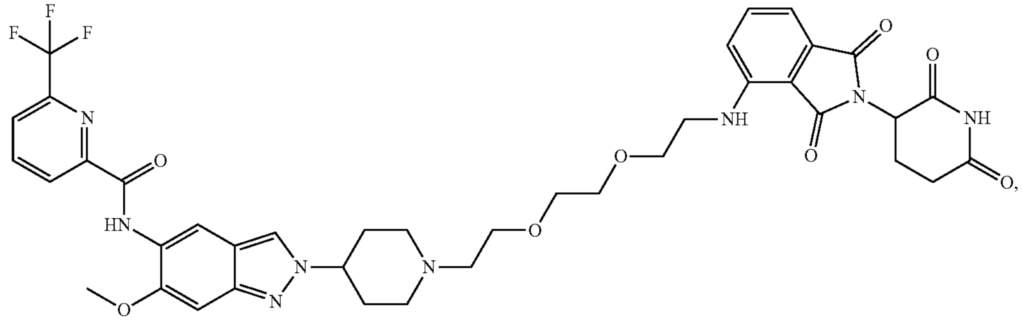
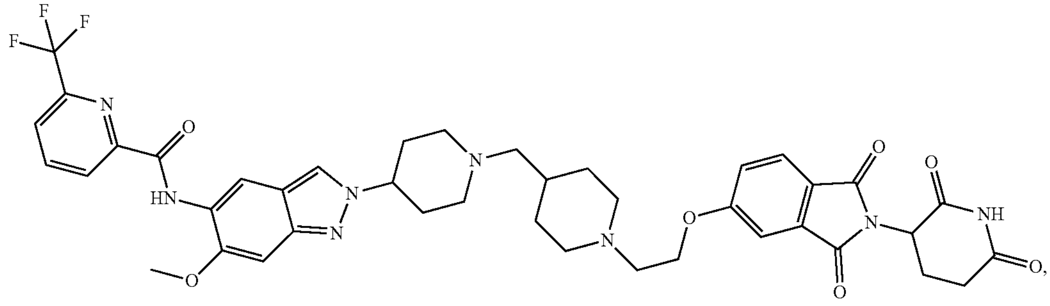
and
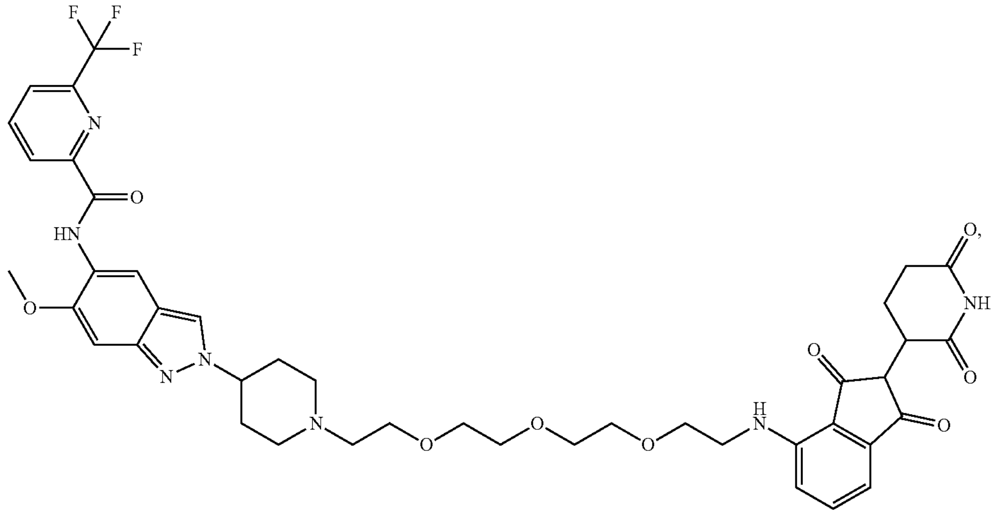
including salts, enantiomer, stereoisomer, solvates, and polymorphs thereof.

14. The compound according to claim 1, wherein at least one of:
(a) the PTM is selected from
(PTM-68)
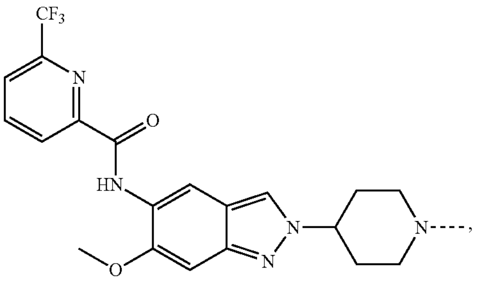
(PTM-69)
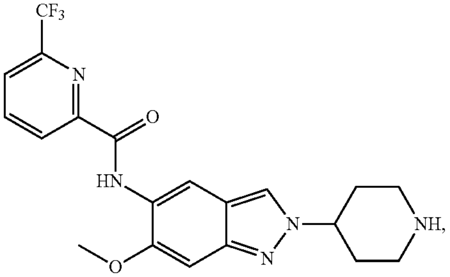
(PTM-70)
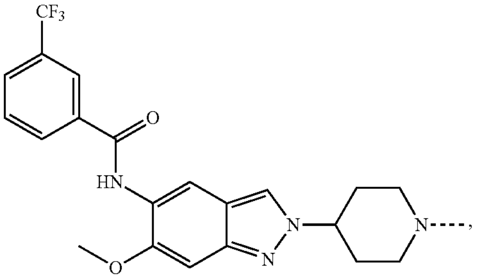
(PTM-71)
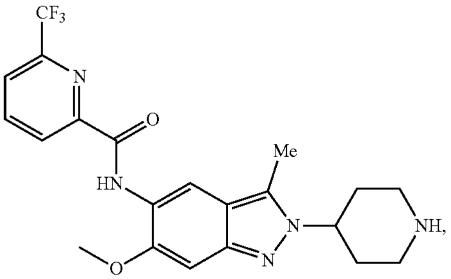
and
(PTM72)
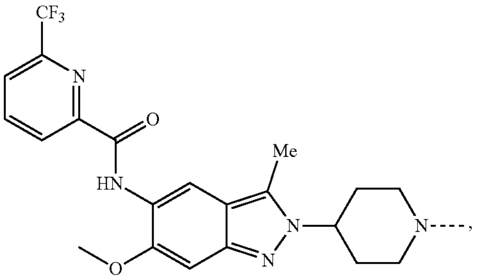
wherein the ⁄ is the point of attachment of the PTM to the L;
(b) the linker is selected from
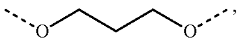
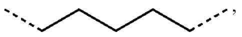
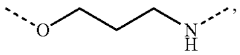
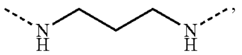
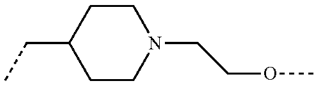
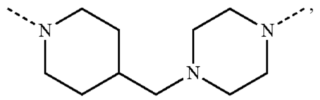
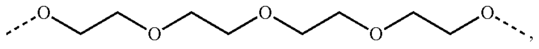
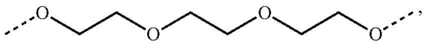
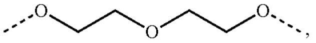
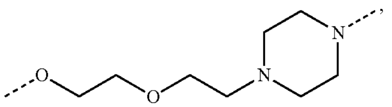
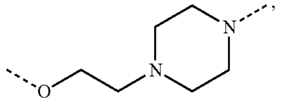
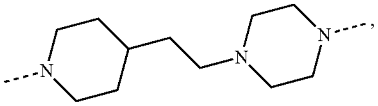
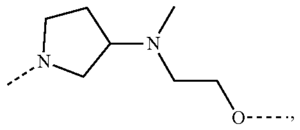
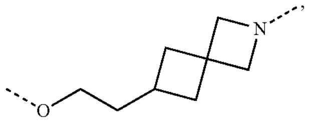
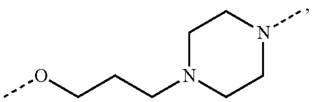
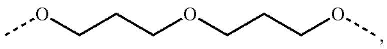
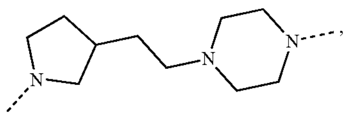
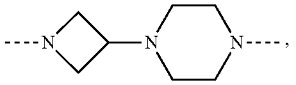
and
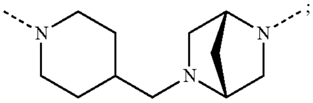

(c) the ULM is selected from
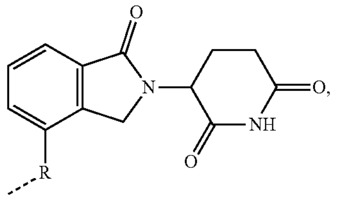
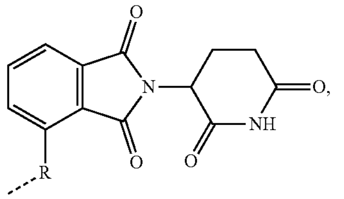
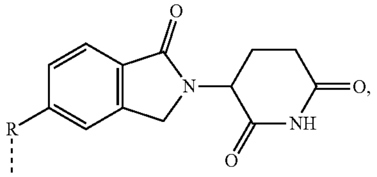
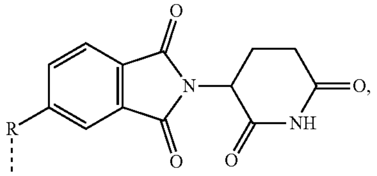
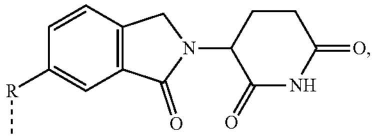
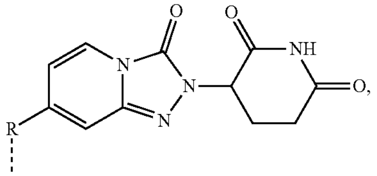
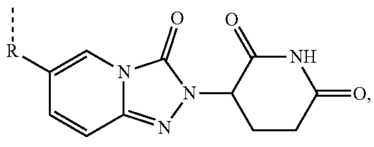 and
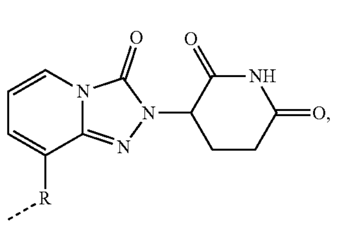
wherein  is the point of attachment of the CLM to the L; or
(d) a combination thereof.
15. The compound according to claim 1, wherein the PTM is
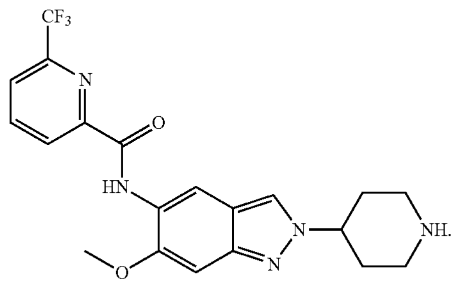 [SMILES: COc1cc2nn(C3CCNCC3)cc2cc1NC(=O)c1cccc(C(F)(F)F)n1]
16. The compound according to claim 5, wherein the linker (L) comprises a group represented by a general structure selected from the group consisting of:
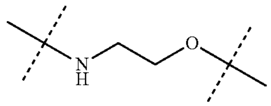;
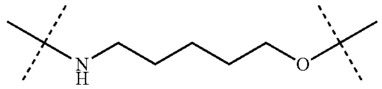;
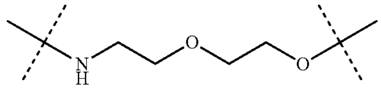;
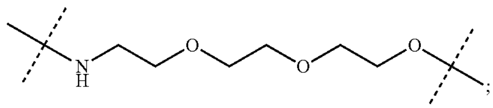;
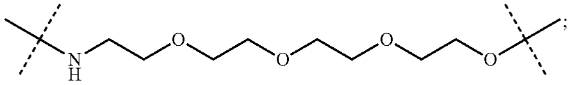;
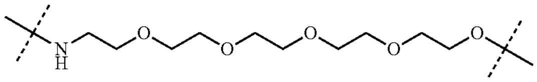;
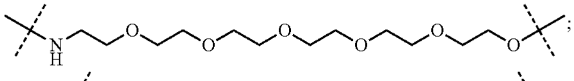;
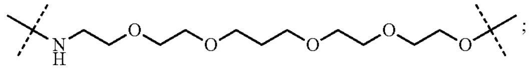;
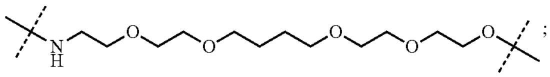;
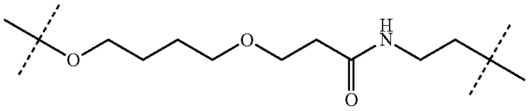;
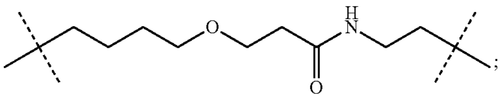;
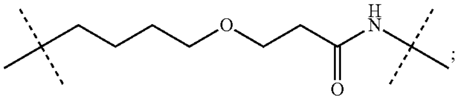;
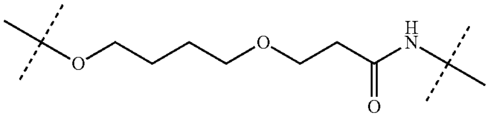;

-continued
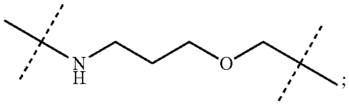
;
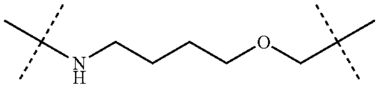
;
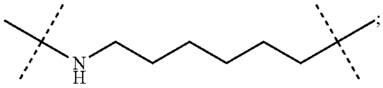
;
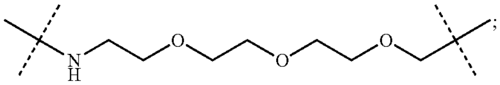
;
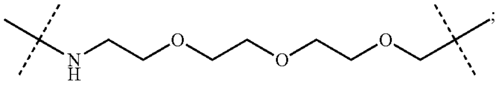
;
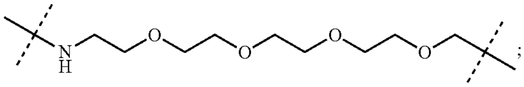
;
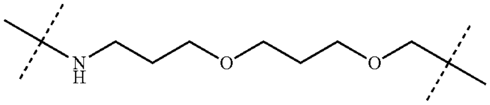
;
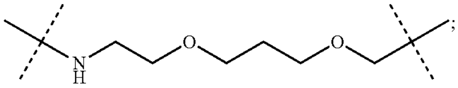
;
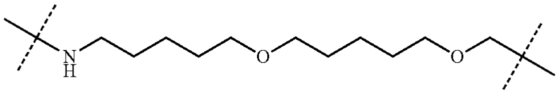
;
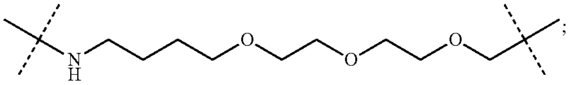
;
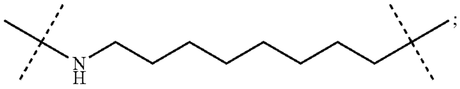
;
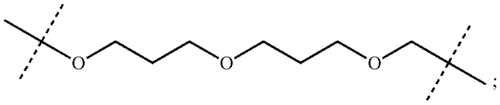
;
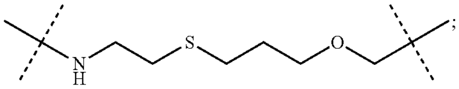
;
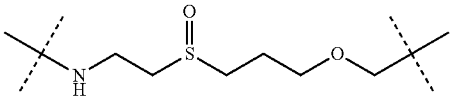
;
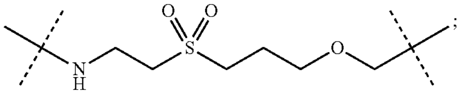
;
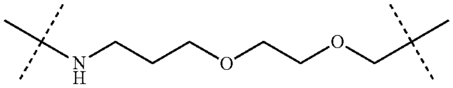
;
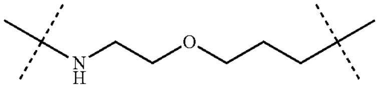
;
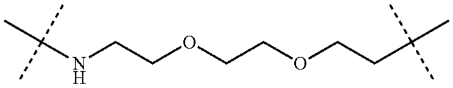
;
-continued
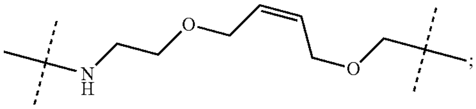
;
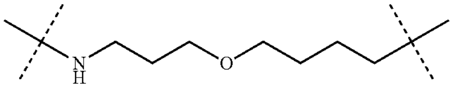
;
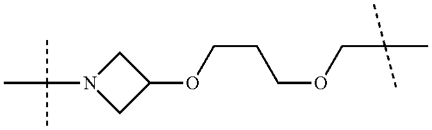
;
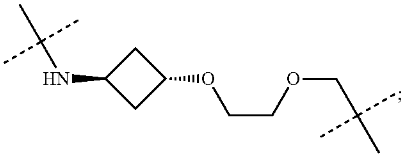
;
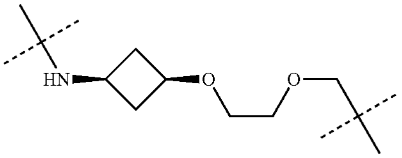
;
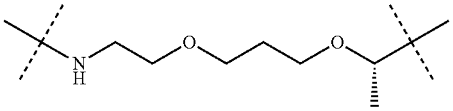
;
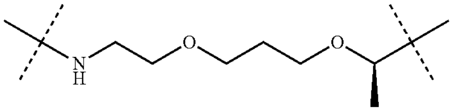
;
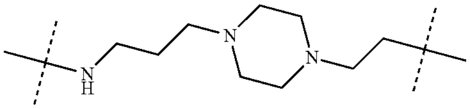
;
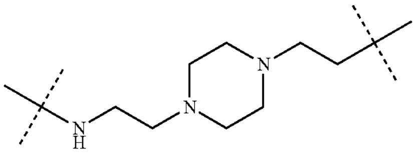
;
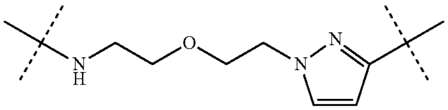
;
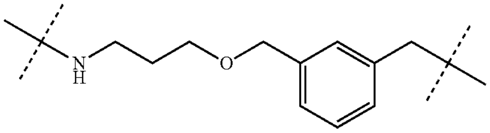
;
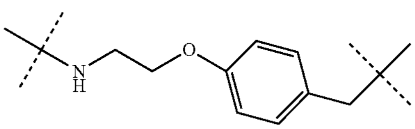
;
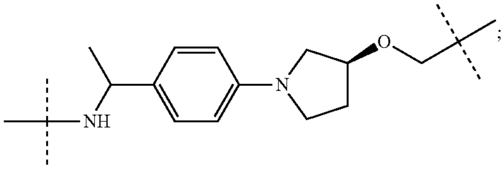
;

-continued
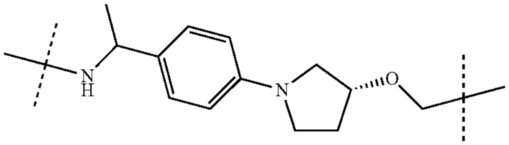
;
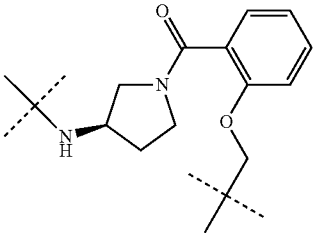
;
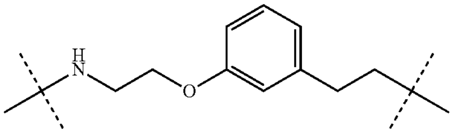
;
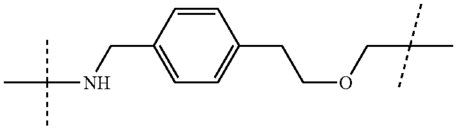
;
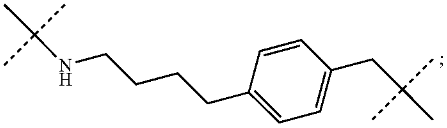
;
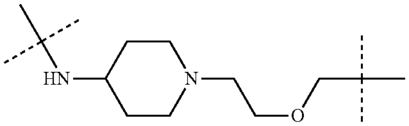
;
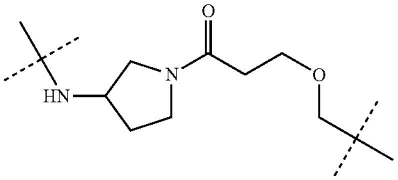
;
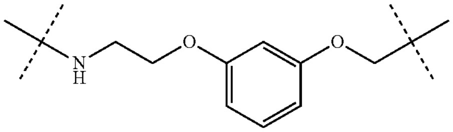
;
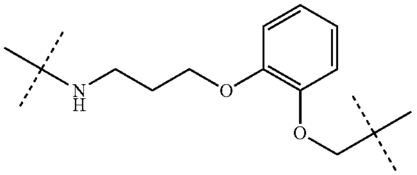
;
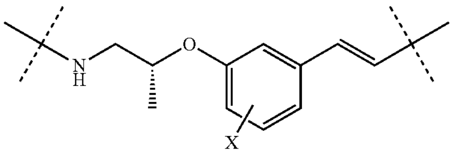
;
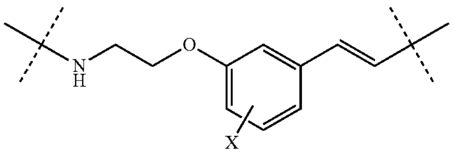
;
-continued
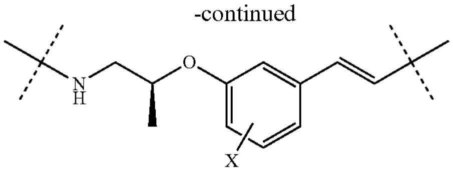
;
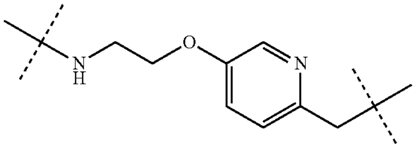
;
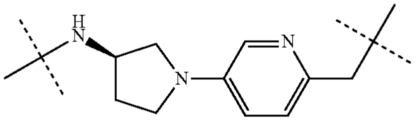
;
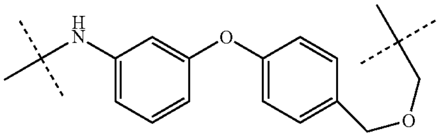
;
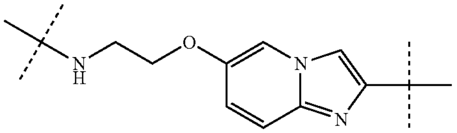
;
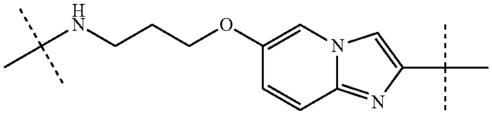
;
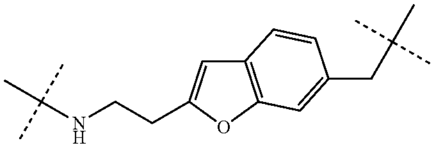
;
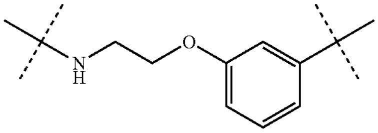
;
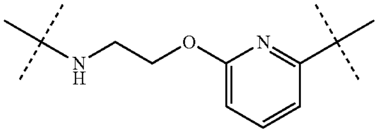
;
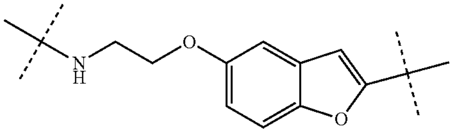
;
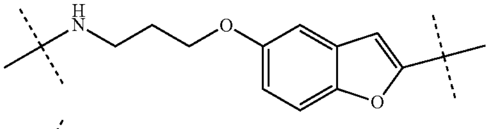
;
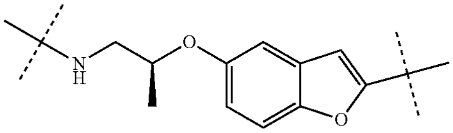
;
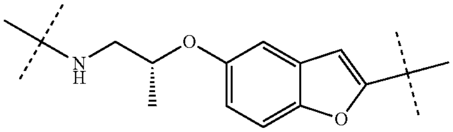
;

-continued
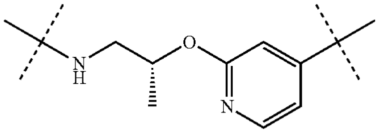
;
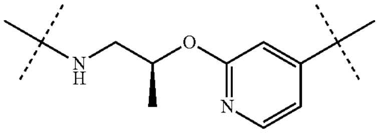
;
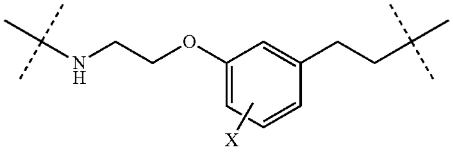
;
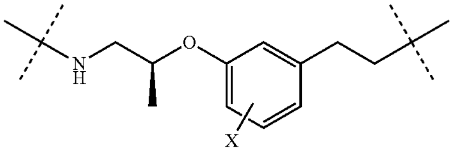
;
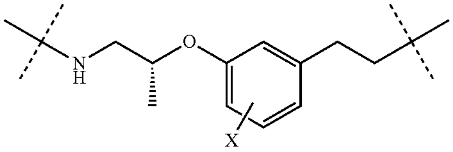
;
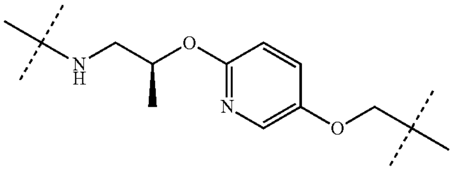
;
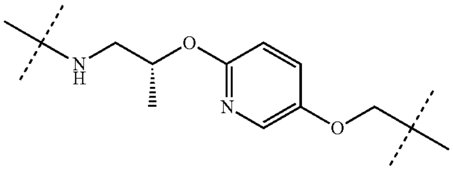
;
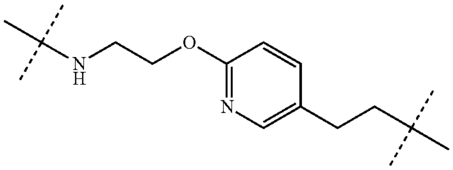
;
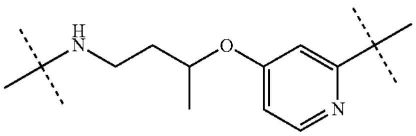
;
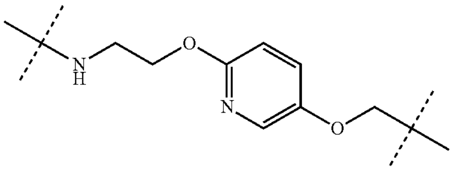
;
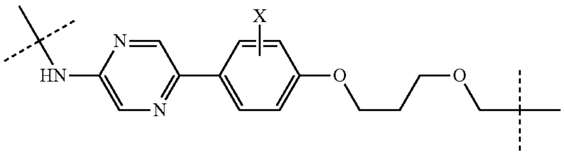
;
-continued
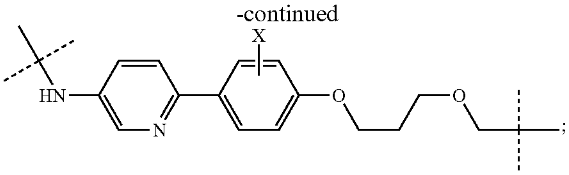
;
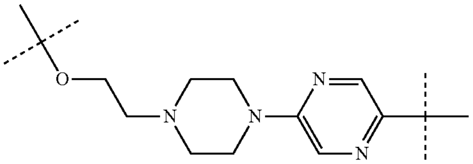
;
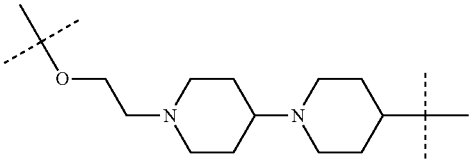
;
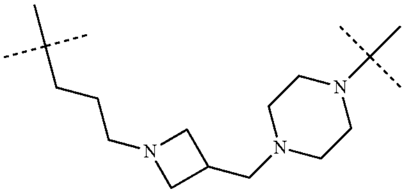
;
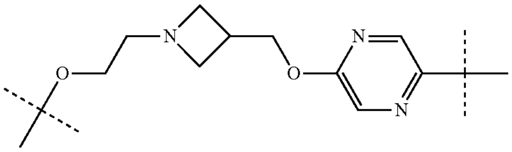
;
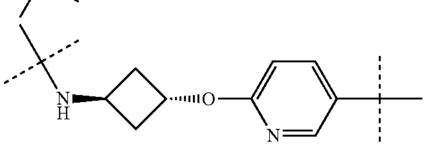
;
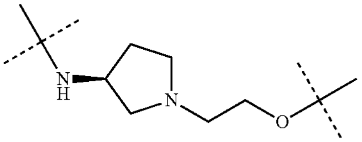
;
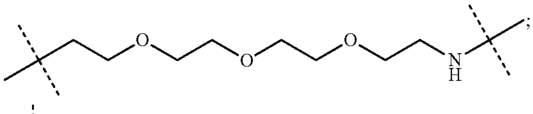
;
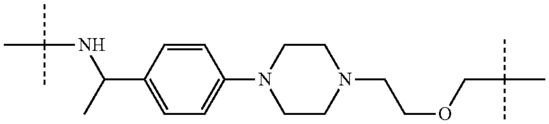
;
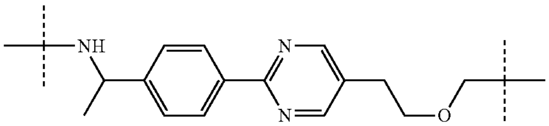
;
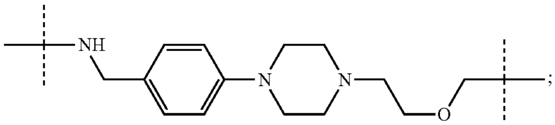
;
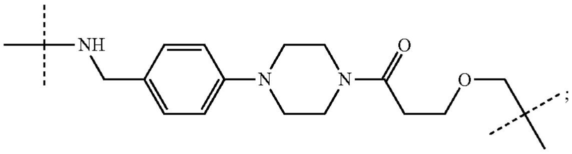
;

-continued
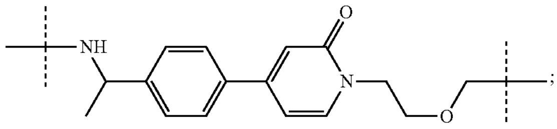
;
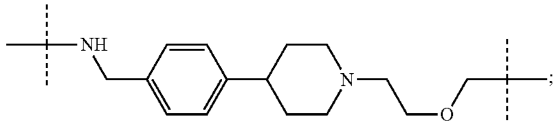
;
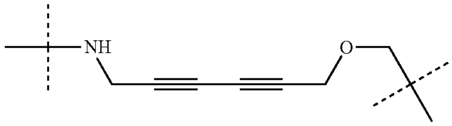
;
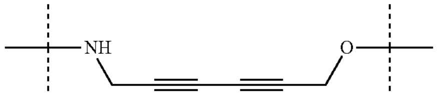
;
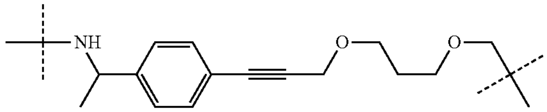
;
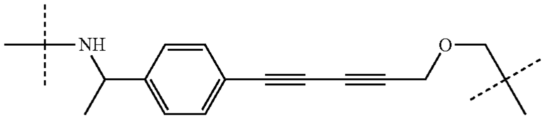
;
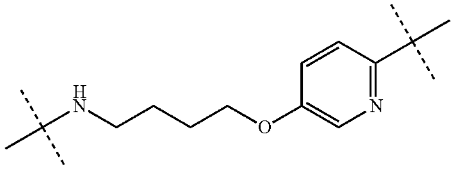
;
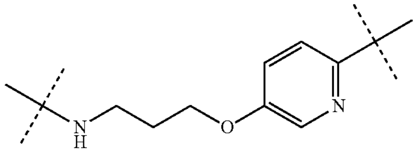
;
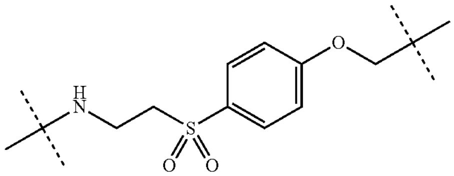
;
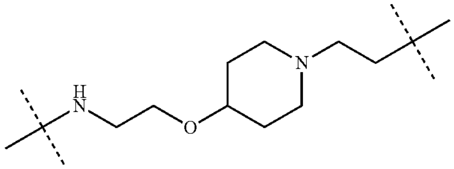
;
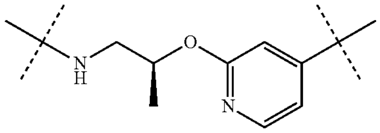
;
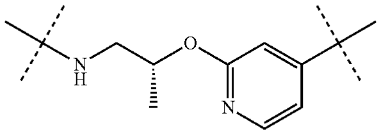
;
-continued
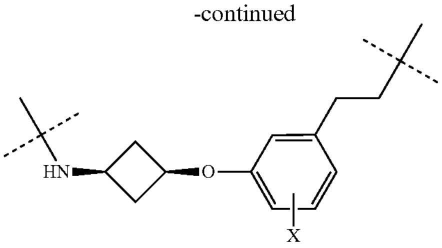
;
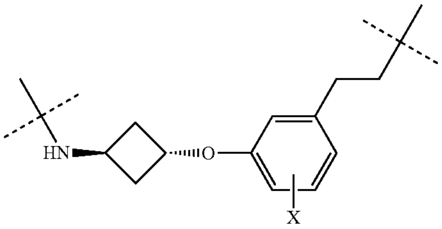
;
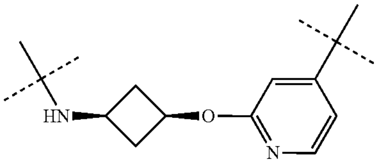
;
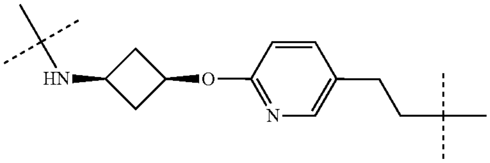
;
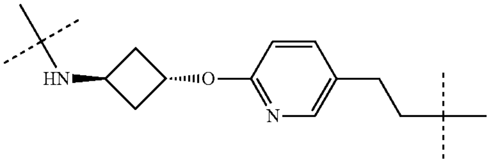
;
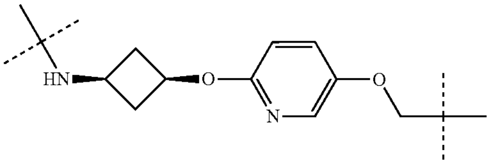
;
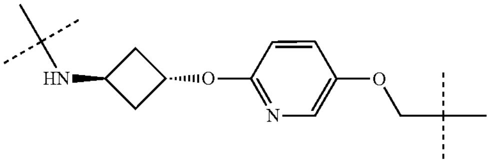
;
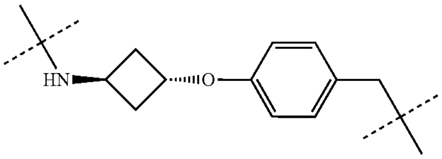
;
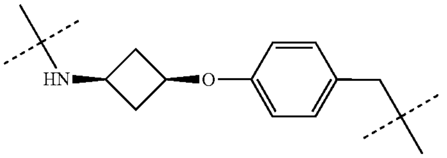
;
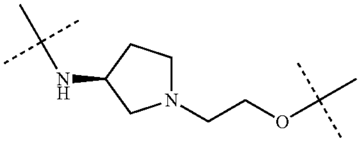
;

-continued
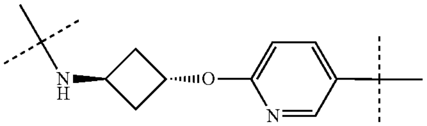
;
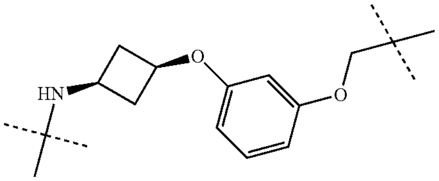
;
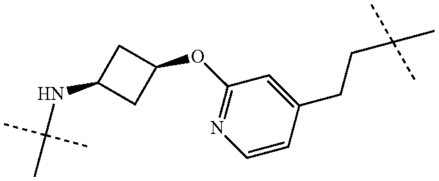
;
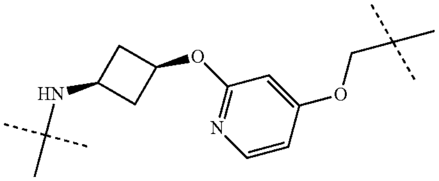
;
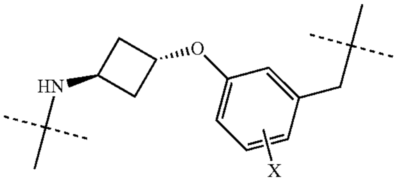
;
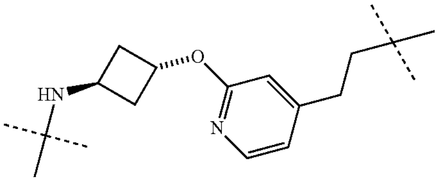
;
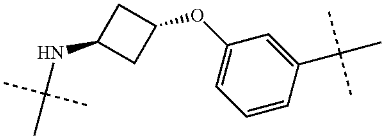
;
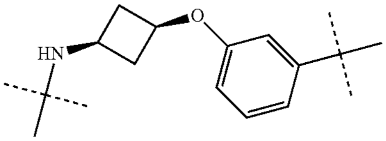
;
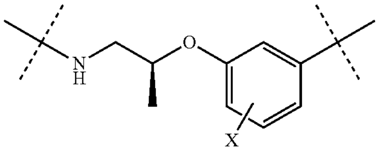
;
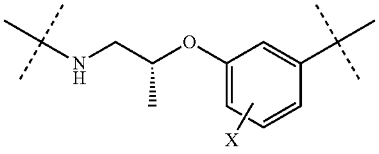
;
-continued
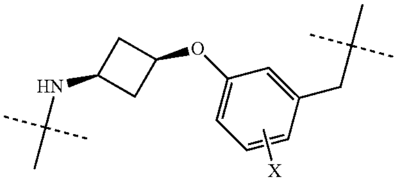
;
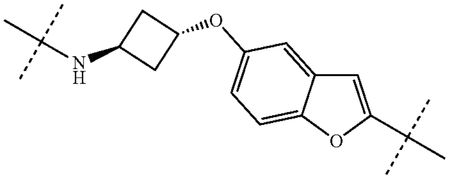
;
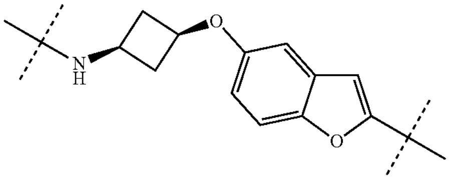
;
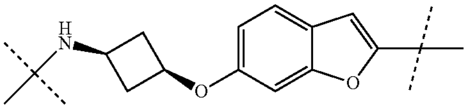
;
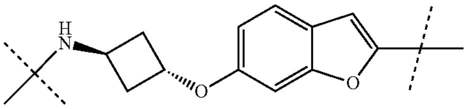
;
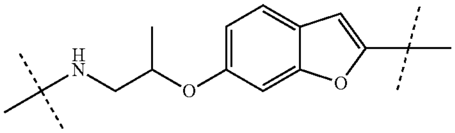
;
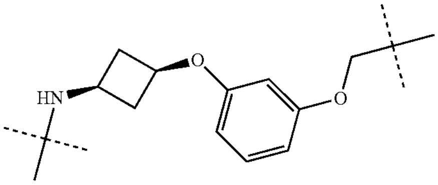
;
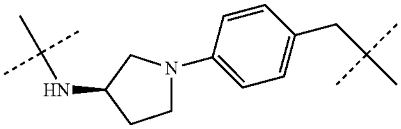
;
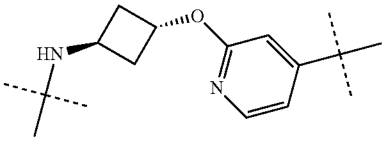
;
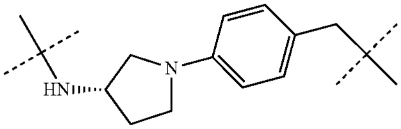
;
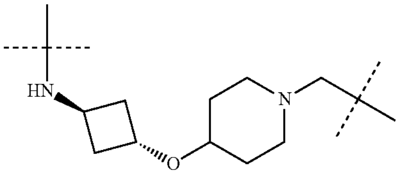
;

1119
-continued
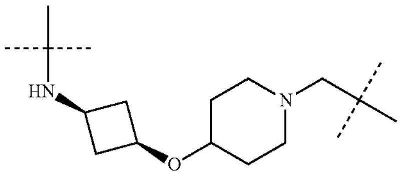
;
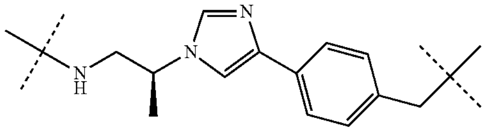
;
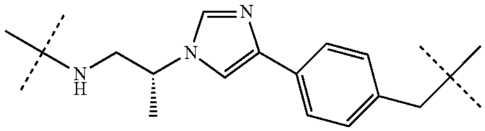
;
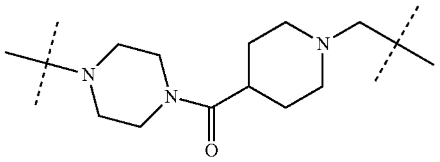
;
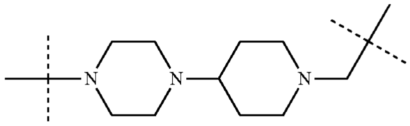
;
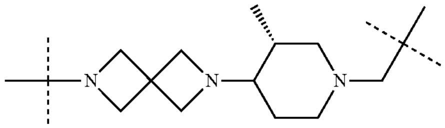
;
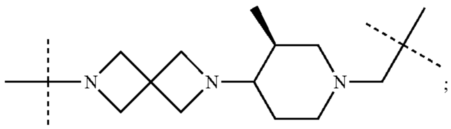
;
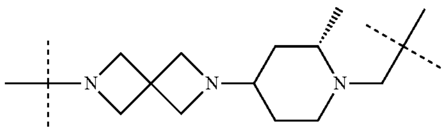
;
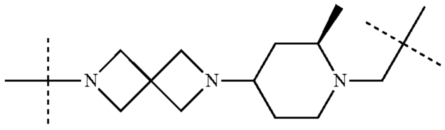
;
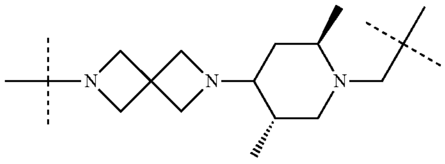
;
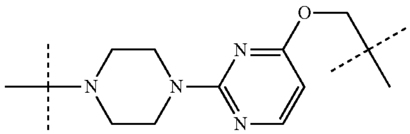
;
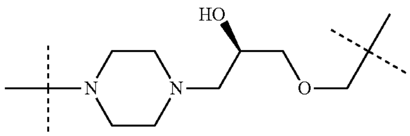
;
1120
-continued
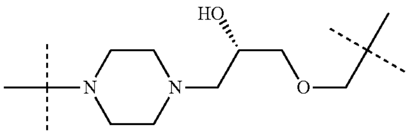
;
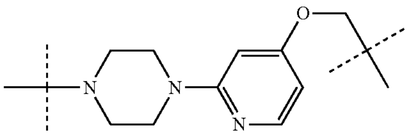
;
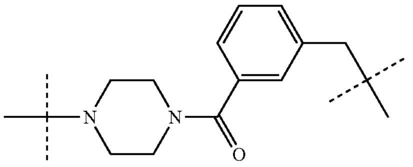
;
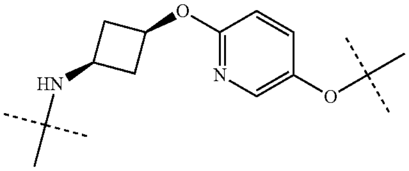
;
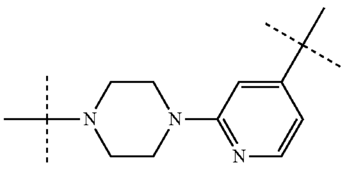
;
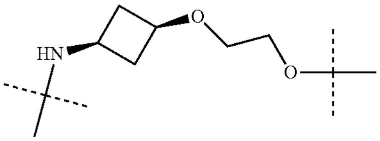
;
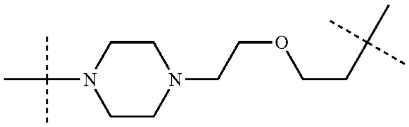
;
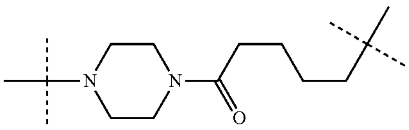
;
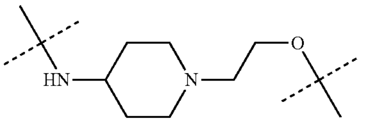
;
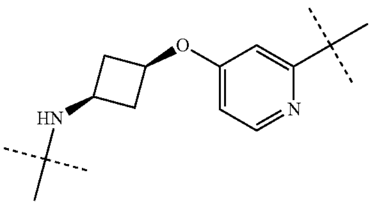
;
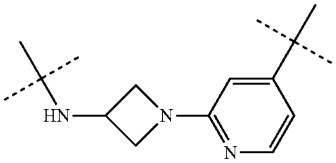
;

-continued
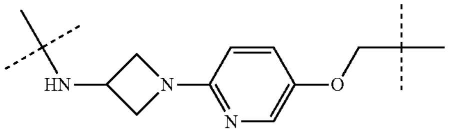
;
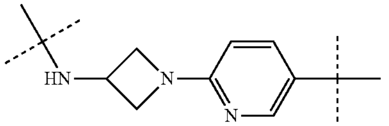
;
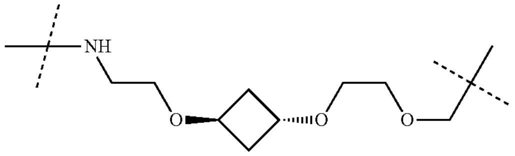
;
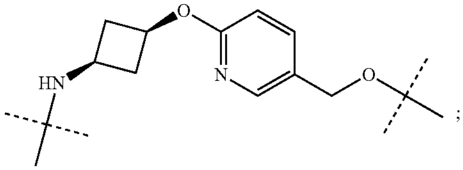
;
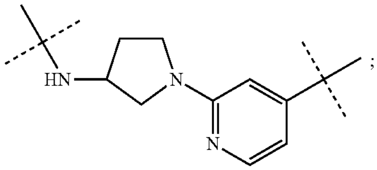
;
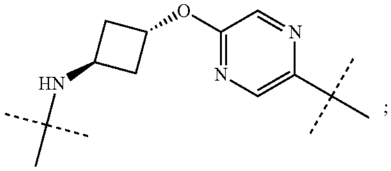
;
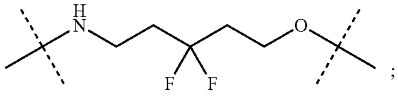
;
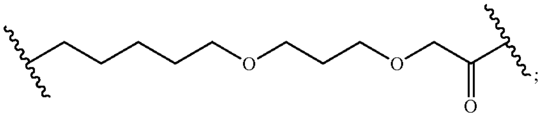
;
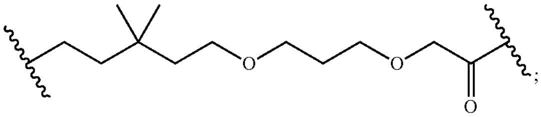
;
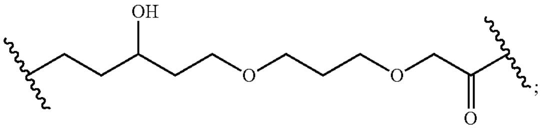
;
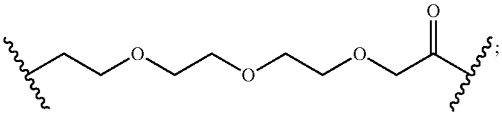
;
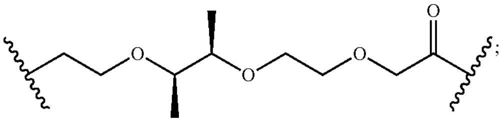
-continued
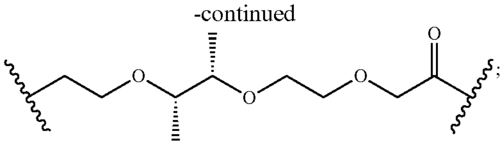
;
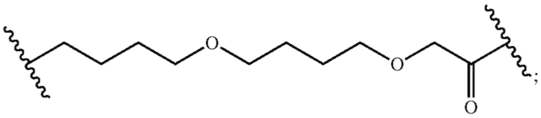
;
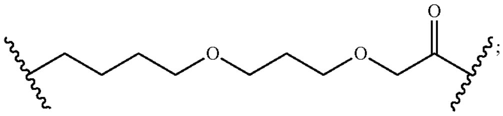
;
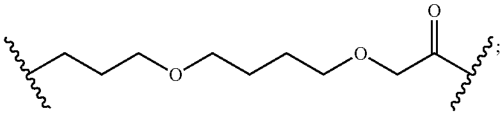
;
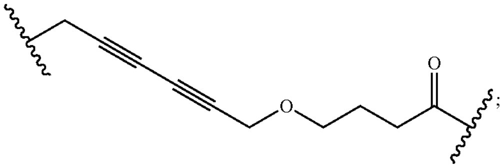
;
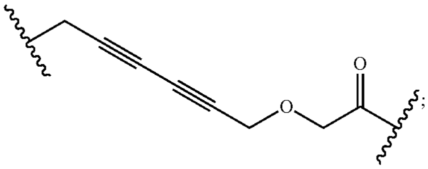
;
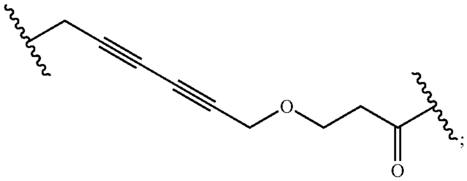
;
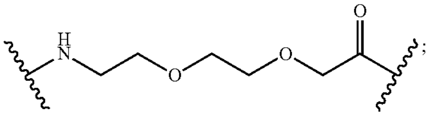
;
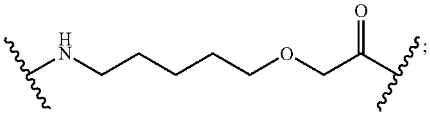
;
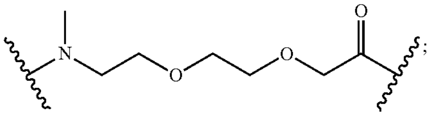
;
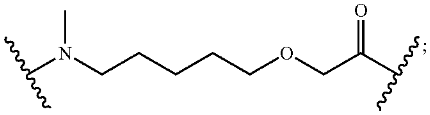
;
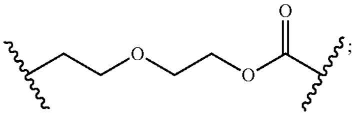
;
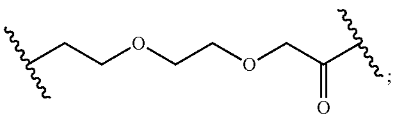
;

-continued
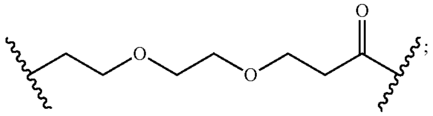
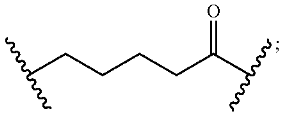
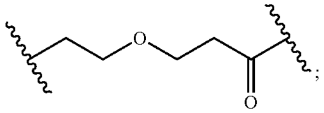
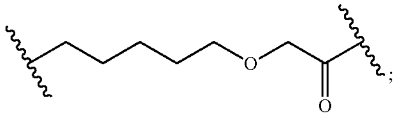
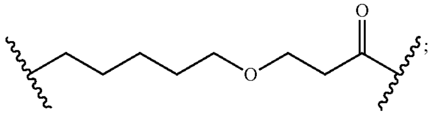
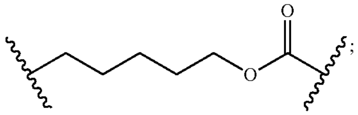
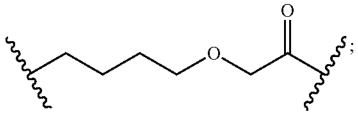
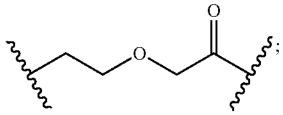
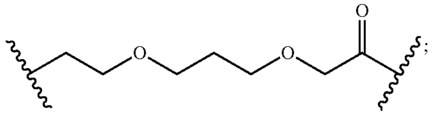
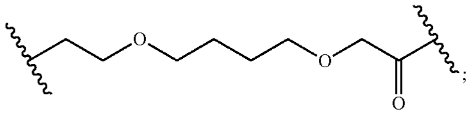
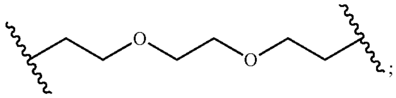
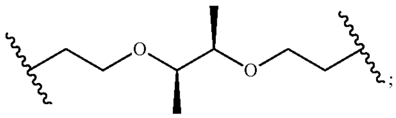
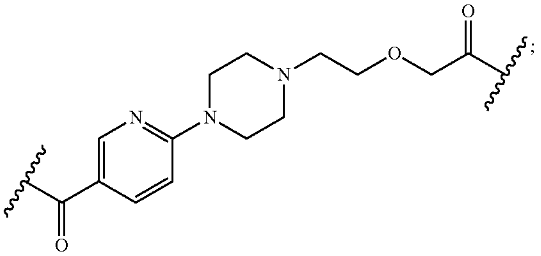
-continued
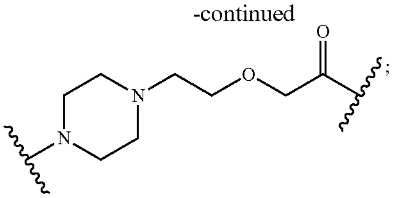
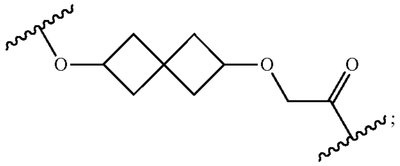
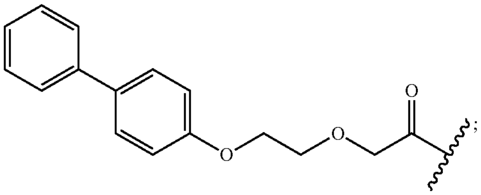
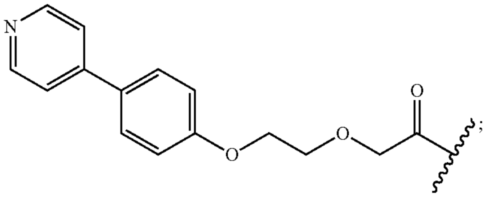
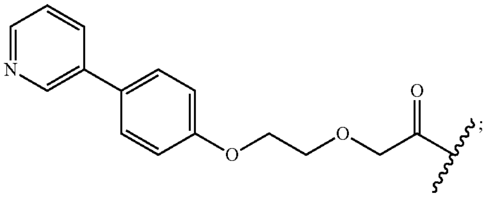
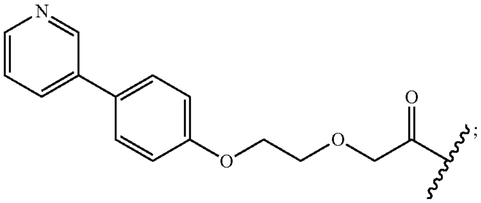
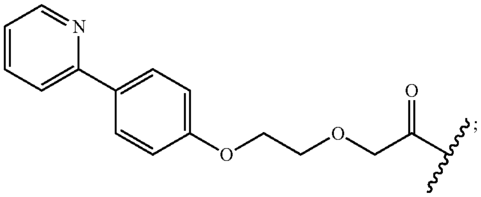
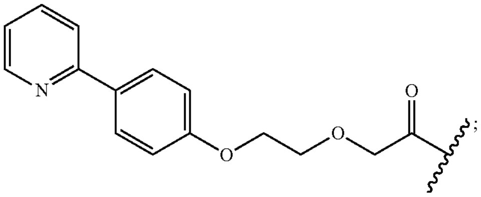
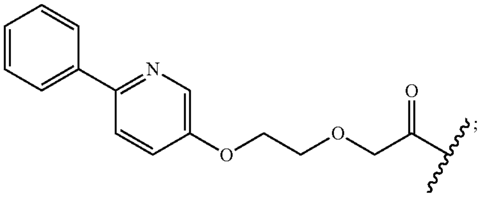

-continued
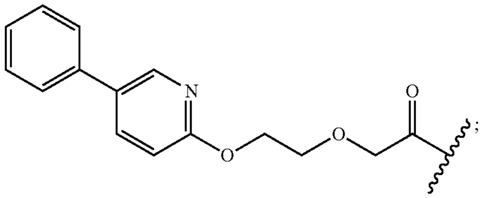
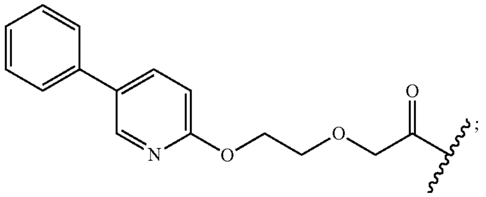
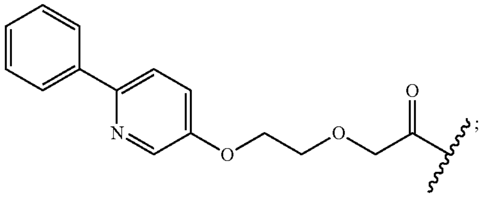
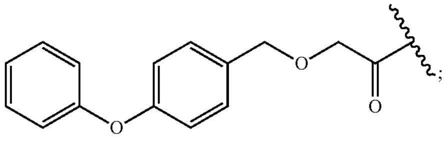
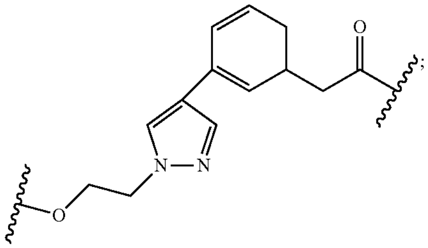
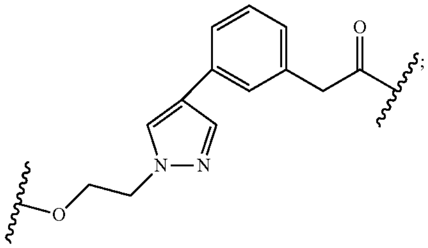
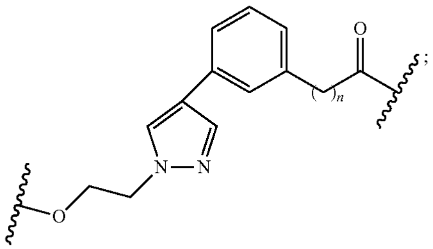
-continued
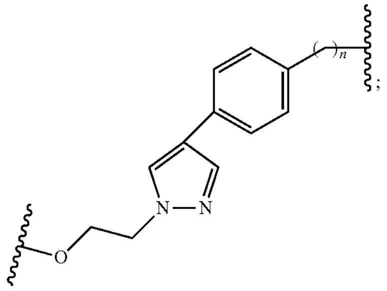
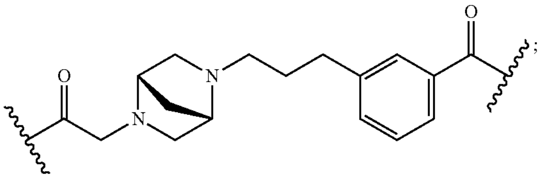
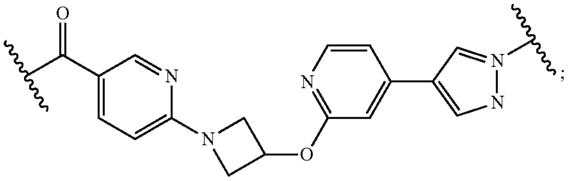
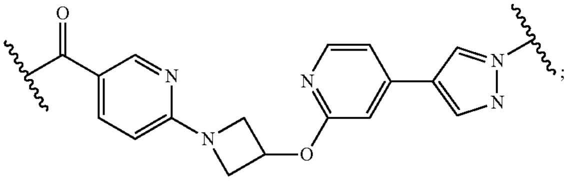
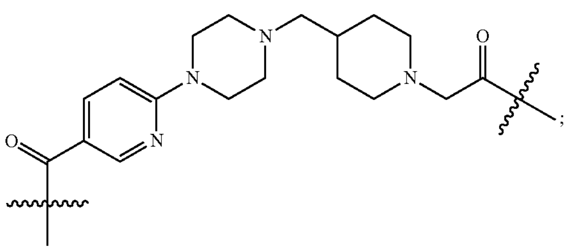
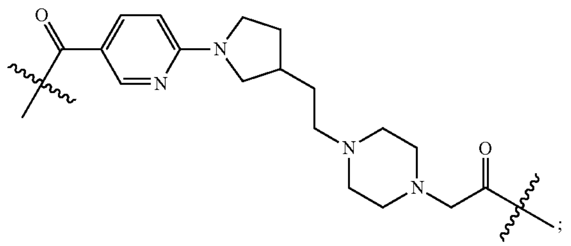
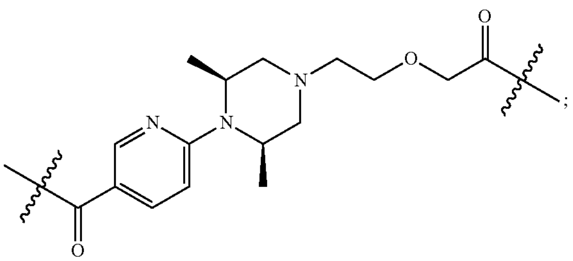
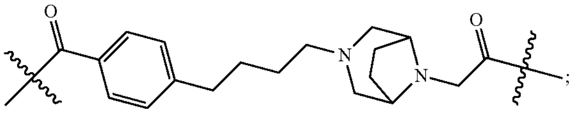

-continued
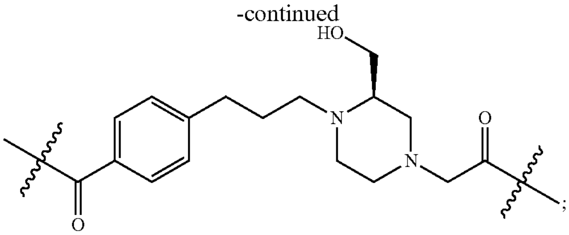
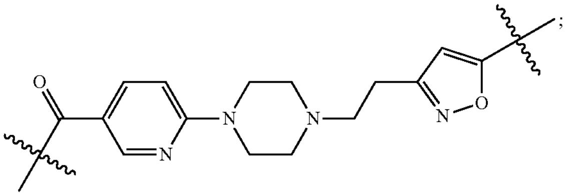
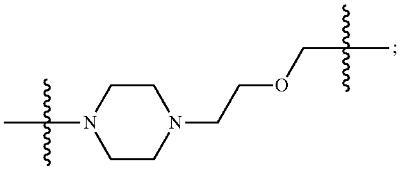
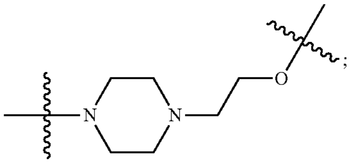
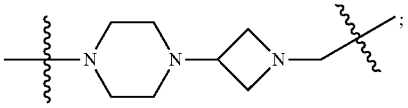
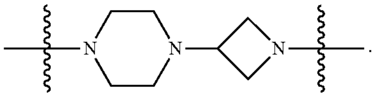
—N(R)—(CH2)$_m$O(CH2)$_n$-O(CH2)$_o$-O(CH2)$_p$-O(CH2)$_q$-O(CH2)$_r$-OCH2-,
—O—(CH2)$_m$-O(CH2)$_n$-O(CH2)$_o$-(CH2)$_p$-O(CH2)$_q$-O(CH2)$_r$-OCH2-,
—O—(CH2)$_m$-O(CH2)$_n$-O(CH2)$_o$-O(CH2)$_p$-O(CH2)$_q$-O(CH2)$_r$-O—;
—N(R)—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-OCH2-;
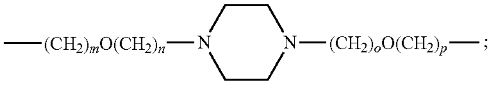
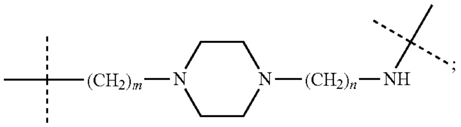
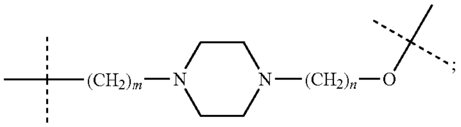
-continued
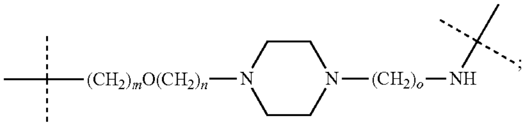
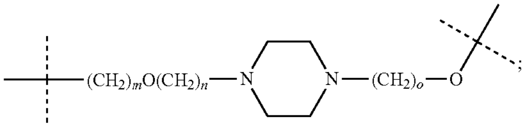
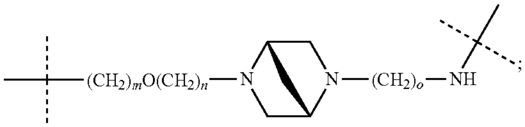
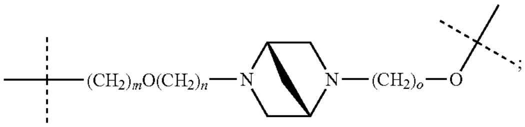
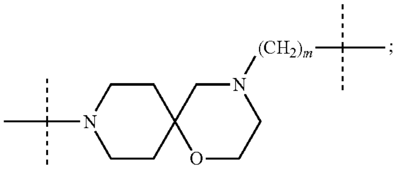
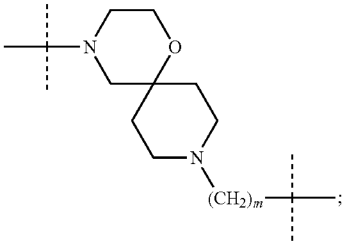
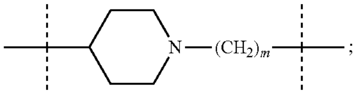
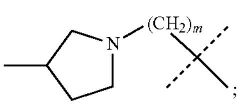
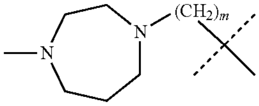
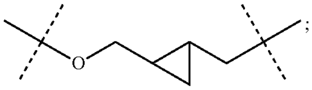
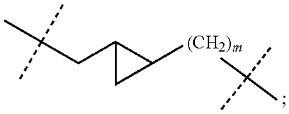
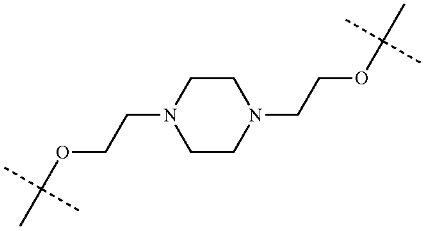

-continued

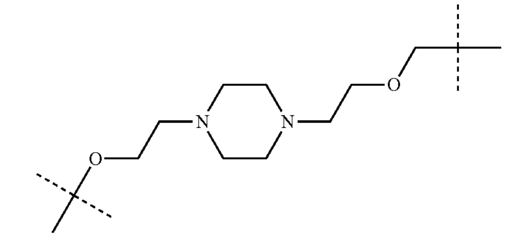

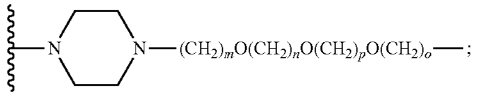

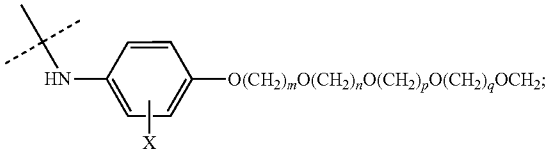

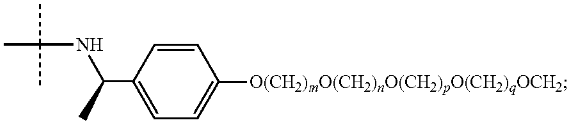

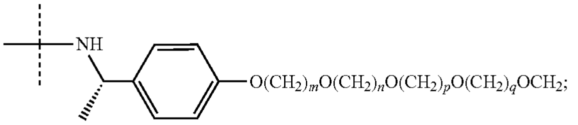

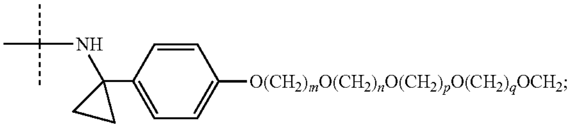

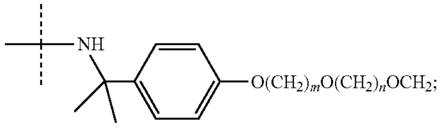

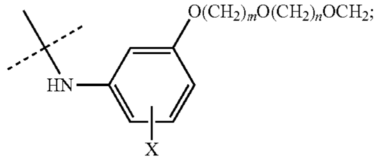

and

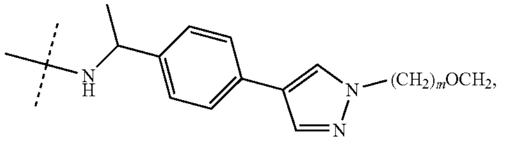

wherein:

each m, n, o, p, q, and r is independently 0, 1, 2, 3, 4, 5, 6, with the proviso that when the number is zero, there is no N—O or O—O bond;

R is selected from the group H, methyl and ethyl; and

X is selected from the group H and F.

17. A composition comprising an effective amount of a bifunctional compound of claim 1, and a pharmaceutically acceptable carrier.

18. The composition of claim 17, wherein the composition further comprises at least one of additional bioactive agent or another bifunctional compound of claim 1.

19. The composition of claim 18, wherein the additional bioactive agent is anti-neurodegenerative agent, an anti-inflammatory agent, and/or an anti-cancer agent.

20. A method for treating a disease or disorder in a subject, the method comprising administering a composition comprising a pharmaceutically acceptable carrier and an effective amount of at least one compound of claim 1 to a subject in need thereof, wherein the compound is effective in treating or ameliorating at least one symptom of the disease or disorder.

21. The method of claim 20, wherein the disease or disorder is associated with IRAK-4 accumulation and aggregation.

22. The method of claim 20, wherein the disease or disorder is a neurodegenerative disease or disorder, an inflammatory disease or disorder and/or a cancer associated with IRAK-4 accumulation and aggregation.

23. The method of claim 22, wherein the cancer is squamous-cell carcinoma, basal cell carcinoma, adenocarcinoma, hepatocellular carcinomas, and renal cell carcinomas, cancer of the bladder, cancer of the head, cancer of the kidney, cancer of the neck, leukemia, benign and malignant lymphomas, Burkitt's lymphoma, Non-Hodgkin's lymphoma, benign and malignant melanomas, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, Schwannomas, bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma, carcinosarcoma, Hodgkin's disease, Wilms' tumor, teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL, and Philadelphia chromosome positive CML.

24. The method of claim 23, wherein the inflammatory disease or disorder is selected from the group consisting of ocular allergy, conjunctivitis, keratoconjunctivitis sicca, vernal conjunctivitis, allergic rhinitis, autoimmune hematological disorders, hemolytic anemia, aplastic anemia, pure red cell anemia and idiopathic thrombocytopenia, systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease, ulcerative colitis, Crohn's disease, irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, primary biliary cirrhosis, uveitis (anterior and posterior), Sjogren's syndrome, interstitial lung fibrosis, psoriatic arthritis, systemic juvenile idiopathic arthritis, nephritis, vasculitis, diverticulitis, interstitial cystitis, glomerulonephritis, idiopathic nephrotic syndrome, minimal change nephropathy, chronic granulomatous disease, endometriosis, leptospirosis renal disease, glaucoma, retinal disease, headache, pain, complex regional pain syndrome, cardiac hypertrophy, muscle wasting, catabolic disorders, obesity, fetal growth retardation, hypercholesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma, acute lung injury, acute respiratory distress syndrome, eosinophilia, hypersensitivities, anaphylaxis, fibrositis, gastritis, gastroenteritis, nasal sinusitis, ocular allergy, silica induced diseases, chronic obstructive pulmonary disease (COPD), cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, appendicitis, atopic dermatitis, asthma, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, juvenile rheumatoid arthritis, dermatomyositis, encephalitis, endocarditis, endometritis, enteritis, enterocolitis, epicondylitis, epididymitis, fasciitis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, vasculitis, vulvitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acute and chronic gout, chronic gouty arthritis, psoriasis, psoriatic arthritis, rheumatoid arthritis, Cryopyrin Associated Periodic Syndrome (CAPS), and osteoarthritis.

* * * * *